US011142523B2

(12) United States Patent
Davenport et al.

(10) Patent No.: US 11,142,523 B2
(45) Date of Patent: *Oct. 12, 2021

(54) 1,3-THIAZOL-2-YL SUBSTITUTED BENZAMIDES

(71) Applicant: Bayer Aktiengesellschaft, Leverkusen (DE)

(72) Inventors: Adam James Davenport, Abingdon (GB); Nico Bräuer, Falkensee (DE); Oliver Martin Fischer, Berlin (DE); Andrea Rotgeri, Berlin (DE); Antje Rottmann, Berlin (DE); Ioana Neagoe, Hamburg (DE); Jens Nagel, Daxweiler (DE); Anne-Marie Godinho-Coelho, Hamburg (DE); Jürgen Klar, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/589,838

(22) Filed: Oct. 1, 2019

(65) Prior Publication Data

US 2020/0131169 A1    Apr. 30, 2020

Related U.S. Application Data

(63) Continuation of application No. 16/192,314, filed on Nov. 15, 2018, now Pat. No. 10,472,354, which is a continuation of application No. 15/534,855, filed as application No. PCT/EP2015/078765 on Dec. 7, 2015, now Pat. No. 10,174,016.

(30) Foreign Application Priority Data

Dec. 9, 2014    (EP) .................................... 14196954

(51) Int. Cl.
| | |
|---|---|
| *A61K 31/506* | (2006.01) |
| *A61P 13/00* | (2006.01) |
| *A61P 13/10* | (2006.01) |
| *A61P 25/16* | (2006.01) |
| *A61P 25/28* | (2006.01) |
| *A61P 29/00* | (2006.01) |
| *A61P 31/04* | (2006.01) |
| *A61P 31/18* | (2006.01) |
| *C07D 417/14* | (2006.01) |
| *C07D 417/12* | (2006.01) |
| *C07D 471/08* | (2006.01) |
| *C07D 498/08* | (2006.01) |
| *A61K 31/5377* | (2006.01) |

(52) U.S. Cl.
CPC ........ *C07D 417/12* (2013.01); *A61K 31/5377* (2013.01); *A61P 13/00* (2018.01); *A61P 13/10* (2018.01); *A61P 25/16* (2018.01); *A61P 25/28* (2018.01); *A61P 29/00* (2018.01); *A61P 31/04* (2018.01); *A61P 31/18* (2018.01); *C07D 417/14* (2013.01); *C07D 471/08* (2013.01); *C07D 498/08* (2013.01); *Y02P 20/582* (2015.11)

(58) Field of Classification Search
CPC ... C07D 417/12; C07D 417/14; A61K 31/506
See application file for complete search history.

(56) References Cited

U.S. PATENT DOCUMENTS

| | | | | |
|---|---|---|---|---|
| 10,174,016 | B2 * | 1/2019 | Davenport | .............. A61P 13/00 |
| 10,183,937 | B2 * | 1/2019 | Davenport | ........... C07D 498/08 |
| 10,202,369 | B2 * | 2/2019 | Davenport | .............. A61P 31/04 |
| 10,472,354 | B2 * | 11/2019 | Davenport | .............. A61P 13/00 |
| 2009/0317360 | A1 * | 12/2009 | Rai | ...................... C07D 277/46 |
| | | | | 424/85.4 |
| 2010/0152203 | A1 | 6/2010 | Chen | |
| 2010/0324056 | A1 | 12/2010 | Broka | |
| 2010/0324069 | A1 | 12/2010 | Chen | |
| 2011/0065681 | A1 | 3/2011 | Wei | |
| 2011/0206783 | A1 | 8/2011 | Burgey et al. | |
| 2013/0059883 | A1 | 3/2013 | Baloglu | |
| 2013/0296310 | A1 * | 11/2013 | Chen | ................... A61K 31/501 |
| | | | | 514/227.8 |
| 2015/0239842 | A1 | 8/2015 | Edwards | |

FOREIGN PATENT DOCUMENTS

| | | | |
|---|---|---|---|
| EP | | 3381917 A1 | 10/2018 |
| WO | WO2006119504 | A2 | 11/2006 |
| WO | WO2008000645 | A1 | 1/2008 |
| WO | WO2008055840 | A1 | 5/2008 |
| WO | WO2008123963 | A1 | 10/2008 |

(Continued)

OTHER PUBLICATIONS

Abdulqawi et al. (2015). "P2X3 receptor antagonist (AF-219) in refractory chronic cough: A randomised, double-blind, placebo-controlled phase 2 study", Lancet 385: 1198-1205.
Burnstock (1993). "Physiological and pathological roles of purines: An update", Drug Dev. Res. 28: 195-206.
Burnstock (2013). "Introduction and perspective, historical note", Front. Cell. Neurosci. 7:227, 13 pages.
Burnstock (2013). "Purinergic mechanisms and pain—An update", Eur. J. Pharmacol. 716:24-40.
Burnstock (2014). "Purinergic signalling in the gastrointestinal tract and related organs in health and disease", Purinergic Signal. 10:3-50.
Burnstock et al. (2011). "Purinergic signalling: From normal behaviour to pathological brain function", Prog. Neurobiol. 95:229-274.
Chizh et al. (2000). "P2X receptors and nociception", Pharmacol. Rev. 53: 553-568.

(Continued)

*Primary Examiner* — Amanda L. Aguirre
(74) *Attorney, Agent, or Firm* — Morrison & Foerster LLP

(57) ABSTRACT

The present invention relates to 1,3-thiazol-2-yl substituted benzamide compounds of general formula (I) as described and defined herein, to pharmaceutical compositions and combinations comprising said compounds and to the use of said compounds for manufacturing a pharmaceutical composition for the treatment or prophylaxis of a disease, in particular of neurogenic disorder, as a sole agent or in combination with other active ingredients.

16 Claims, No Drawings

(56) References Cited

FOREIGN PATENT DOCUMENTS

| | | | |
|---|---|---|---|
| WO | WO2008130481 A1 | 10/2008 | |
| WO | 2008136756 A1 | 11/2008 | |
| WO | WO2009058298 A1 | 5/2009 | |
| WO | WO2009058299 A1 | 5/2009 | |
| WO | WO2009077365 A1 | 6/2009 | |
| WO | WO2009077366 A1 | 6/2009 | |
| WO | WO2009077367 A1 | 6/2009 | |
| WO | WO2009077371 A1 | 6/2009 | |
| WO | WO2009110985 A2 | 9/2009 | |
| WO | WO2010033168 A2 | 3/2010 | |
| WO | WO2013009810 A1 | 1/2013 | |
| WO | WO-2013173441 A2 * | 11/2013 | ........... C07D 417/12 |
| WO | WO2013173441 A2 | 11/2013 | |
| WO | 2019219672 A1 | 11/2019 | |
| WO | 2019219674 A1 | 11/2019 | |
| WO | 2020260463 A1 | 12/2020 | |

OTHER PUBLICATIONS

Cockayne et al. (2000). "Urinary bladder hyporeflexia and reduced pain-related behaviour in P2X3-deficient mice", Nature 407: 1011-1015.

Cross et al. (1976). "International Union of Pure and Applied Chemistry: Organic Chemistry Division Commission on Nomenclature of Organic Chemistry", Pure & Appl. Chem. 45:11-30.

Fabbretti (2013). "ATP P2X3 receptors and neuronal sensitization", Front. Cell. Neurosci. 7:236, six pages.

Finger et al. (2005). "ATP signaling is crucial for communication from taste buds to gustatory nerves", Science 310: 1495-1498.

Ford (2012). "In pursuit of P2X3 antagonists: Novel therapeutics for chronic pain and afferent sensitization", Purinergic Signal. 8 (suppl 1):53-526.

Ford (2012). "P2X3 antagonists: Novel therapeutics for afferent sensitization and chronic pain", Pain Manag. 2:267-277.

Ford (2014). "P2X3 antagonism for sensitization-driven signs and symptoms of common diseases: POC results in distressing respiratory, somatosensory and visceral conditions", abstract at Pain & Migraine Therapeutics Summit, p. 7.

Ford (2014). "P2X3 antagonism with AF-219: Clinical potential and findings", abstract at Purines 2014, International Conference on Nucleotides, Nucleosides and Nucleobases, published in Purinergic Signal. 10:657-854 at 662-663.

Ford et al. (2013). "Inhibition of ATP-gated P2X3 channels by AF-219: An effective anti-tussive mechanism in chronic cough", abstract 7026 at European Respiratory Society Annual Congress, one page.

Ford et al. (2013). "The therapeutic promise of ATP antagonism at P2X3 receptors in respiratory and urological disorders", Front. Cell. Neurosci. 7:267, ten pages.

Garcia-Guzman et al. (1997). "Molecular characterization and pharmacological properties of the human P2X3 purinoceptor", Mol. Brain Res. 47:59-66.

International Preliminary Report on Patentability dated Jun. 13, 2017 for PCT Application No. PCT/EP2015/078765, filed Dec. 7, 2015, 8 pages.

International Search report dated Feb. 4, 2016 for PCT Application No. PCT/EP2015/078765, filed Dec. 7, 2015, 3 pages.

Jiang (2012). "P2X receptor-mediated ATP purinergic signaling in health and disease", Cell Health Cytoskeleton 4:83-101.

Joseph et al. (2013). "Role of endothelial cells in antihyperalgesia induced by a triptan and β-blocker", Neurosci. 232:83-89.

Kinnamon et al. (2013). "A taste for ATP: Neurotransmission in taste buds", Front. Cell. Neurosci. 7:264, seven pages.

North (2003). "P2X3 receptors and peripheral pain mechanisms", J. Physiol. 554:301-308.

Prado et al. (2013). "Neuronal P2X3 receptor activation is essential to the hyperalgesia induced by prostaglandins and sympathomimetic amines released during inflammation", Neuropharm. 67:252-258.

Saul et al. (2013). "Heteromeric assembly of P2X subunits", Front. Cell. Neurosci. 7:250, 20 pages.

Souslova et al. (2000). "Warm-coding deficits and aberrant inflammatory pain in mice lacking P2X3 receptors", Nature 407:1015-1017.

Strand et al. (2014). "An exploratory 4-week study of a P2X3 antagonist AF-219 in the treatment of patients with osteoarthritis (OA) of the knee", abstract 2240 at ACR/ARHP Annual Meeting, two pages.

Vandenbeuch et al. (2015). "Postsynaptic P2X3-containing receptors in gustatory nerve fibres mediate responses to all taste qualities in mice", J. Physiol. 593:1113-1125.

Written Opinion of the ISA dated Feb. 4, 2016 for PCT Application No. PCT/EP2015/078765, filed Dec. 7, 2015, 4 pages.

Morice, A.H. (2019). "The effect of gefapixant, a P2X3 antagonist, on cough reflex sensitivity: a randomised placebo-controlled study," Eur Respir J 54: 1-10.

Richards, D. et al. (2019). "Action of MK-7264 (gefapixant) at human P2X3 and P2X2/3 receptors and in vivo efficacy in models of sensitisation," Br J Pharmacol. 176: 2279-2291.

Smith, J.A. et al. (2020). "Gefapixant in two randomised dose-escalation studies in chronic cough," Eur Respir J 55: 1-10.

Smith, J.A. et al. (2020). "Gefapixant, a P2X3 receptor antagonist, for the treatment of refractory or unexplained chronic cough: a randomised, double-blind, controlled, parallel-group, phase 2b trial," Lancet Respir Med, https://doi.org/10.1016/S2213-2600(19)30471-0.

U.S. Appl. No. 17/055,482, filed Nov. 13, 2020, for Lucas Hudson Hofmeisi et al.

U.S. Appl. No. 17/055,488, filed Nov. 13, 2020, for Christian Friedrich et al.

* cited by examiner

1,3-THIAZOL-2-YL SUBSTITUTED BENZAMIDES

CROSS REFERENCE TO RELATED APPLICATIONS

This application is a continuation application of U.S. patent application Ser. No. 16/192,314, filed Nov. 15, 2018, which is a continuation application of U.S. patent application Ser. No. 15/534,855, which adopts the international filing date of Dec. 7, 2015, now U.S. Pat. No. 10,174,016, which is the National Phase application under 35 U.S.C. § 371 of International Application No. PCT/EP2015/078765, filed Dec. 7, 2015, which claims priority benefit to European Application No. 14196954.3, filed Dec. 9, 2014.

The present invention relates to 1,3-thiazol-2-yl substituted benzamide compounds of general formula (I) as described and defined herein, to pharmaceutical compositions and combinations comprising said compounds and to the use of said compounds for manufacturing a pharmaceutical composition for the treatment or prophylaxis of a disease, in particular of neurogenic disorder, as a sole agent or in combination with other active ingredients.

BACKGROUND OF THE INVENTION

The present invention relates to chemical compounds that inhibit P2X3 receptor. P2X purinoceptor 3 is a protein that in humans is encoded by the P2RX3 gene (Garcia-Guzman M, Stuhmer W, Soto F (September 1997). "Molecular characterization and pharmacological properties of the human P2X3 purinoceptor". Brain Res. Mol. Brain Res. 47 (1-2): 59-66). The product of this gene belongs to the family of purinoceptors for ATP. This receptor functions as a ligand-gated ion channel and transduces ATP-evoked nociceptor activation.

P2X purinoreceptors are a family of ligand-gated ion channels that are activated by ATP. To date, seven members of this family have been cloned, comprising P2X1-7 [Burnstock 2013, front Cell. Neurosci. 7:227]. These channels can exist as homomers and heteromers [Saul 2013, front Cell Neurosci. 7:250]. Purines, such as ATP, have been recognized as important neurotransmitters and by acting via their respective receptors they have been implicated in various physiological and pathophysiological roles [Burnstock 1993, Drug Dev. Res. 28:196-206; Burnstock 2011, Prog. Neurobiol. 95:229-274; Jiang 2012, Cell Health Cytoskeleton 4:83-101].

Among the P2X family members, in particular the P2X3 receptor has been recognized as an important mediator of nociception [Burnstock 2013, Eur J Pharmacol 716:24-40; North 2003, J. Phyiol. 554:301-308; Chizh 2000, Pharmacol. Rev. 53:553-568]. It is mainly expressed in dorsal root ganglia in a subset of nociceptive sensory neurons. During inflammation the expression of the P2X3 receptor is increased, and activation of P2X3 receptor has been described to sensitize peripheral nerves [Fabretti 2013, front Cell Neurosci. 7:236].

The prominent role of the P2X3 receptor in nociception has been described in various animal models, including mouse and rat models for acute, chronic and inflammatory pain. P2X3 receptor knock-out mice show a reduced pain response [Cockayne 2000, Nature 407:1011-1015; Souslova 2000, Nature 407:1015-1017]. P2X3 receptor antagonists have been shown to act anti-nociceptive in different models of pain and inflammatory pain [Ford 2012, Purin Signal 8 (Suppl. 1):S3-S26]. The P2X3 receptor has also been shown to integrate different nociceptive stimuli. Hyperalgesia induced by PGE2, ET-1 and dopamine have all been shown to be mediated via release of ATP and activation of the P2X3 receptor [Prado 2013, Neuropharm. 67:252-258; Joseph 2013, Neurosci. 232C: 83-89].

Besides its prominent role in nociception and in pain-related diseases involving both chronic and acute pain, the P2X3 receptor has been shown to be involved in genitourinary, gastrointestinal and respiratory conditions and disorders, including overactive bladder and chronic cough [Ford 2013, front Cell Neurosci. 7:267; Burnstock 2014, Purin. Signal 10(1):3-50]. ATP-release occurs in these 2 examples from epithelial cells, which in turn activates the P2X3 receptor and induces contraction of bladder and lung muscles respectively leading to premature voiding or cough.

P2X3 subunits do not only form homotrimers but also heterotrimers with P2X2 subunits. P2X3 subunits and P2X2 subunits are also expressed on nerve fibres innervating the tongue, therein taste buds [Kinnamon 2013, front Cell Neurosci. 7:264]. In a phyiosological setting, receptors containing P2X3 and/or P2X2 subunits are involved in the transmission of taste from the tongue (bitter, sweet, salty, umami and sour). Recent data show that while blocking the P2X3 homomeric receptor alone is important to achieve anti-nociceptive efficacy, non-selective blockade of both the P2X3 homomeric receptor and the P2X2/3 heteromeric receptor leads to changes in taste perception which might limit the therapeutic use of non-selective P2X3 and P2X2/3 receptor antagonists [Ford 2014, purines 2014, abstract book p15]. Therefore, compounds that differentiate between P2X3 and P2X2/3 receptors are highly desirable.

Compounds blocking both the exclusively P2X3 subunit containing ion channel (P2X3 homomer) as well as the ion channel composed of P2X2 and P2X3 subunit (P2X2/3 heterotrimer) are called P2X3 and P2X2/3 nonselective receptor antagonists [Ford, Pain Manag. 2012]. Clinical Phil trials demonstrated that AF-219, a P2X3 antagonist, leads to taste disturbances in treated subjects by affecting taste sensation via the tongue [e.g. Abdulqawi et al, Lancet 2015; Strand et al, 2015 ACR/ARMP Annual Meeting, Abstract 2240]. This side effect has been attributed to the blockade of P2X2/3 channels, i.e. the heterotrimer [A. Ford, London 2015 Pain Therapeutics Conference, congress report]. Both P2X2 and P2X3 subunits are expressed on sensory nerve fibers innervating the tongue. Knock-out animals deficient for P2X2 and P2X3 subunits show reduced taste sensation and even taste loss [Finger et al, Science 2005], whereas P2X3 subunit single knock-outs exhibit a mild or no change in phenotype with respect to taste. Moreover, 2 distinct populations of neurons have been described in the geniculate ganglion expressing either P2X2 and P2X3 subunits or P2X3 subunit alone. In an in vivo setting assessing taste preference towards an artificial sweetener via a lickometer, only at very high free plasma levels (>100 µM) effects on taste were observed, indicating that rather the P2X2 and P2X3 subunits expressing population plays a major role in taste sensation than the P2X3 subunit expressing population [Vandenbeuch et al, J. Physiol. 2015]. Hence, as a modified taste perception has profound effects on the quality of life of patients, P2X3-homomeric receptor-selective antagonists are deemed to be superior towards non-selective receptor antagonists and are considered to represent a solution towards the problem of insufficient patient compliance during chronic treatment as indicated by increased drop-out rates during Phil trials [Strand et al, 2015 ACR/ARMP Annual Meeting, Abstract 2240 and A. Ford, London 2015 Pain Therapeutics Conference, congress report].

Benzamide derivative compounds have been disclosed in prior art for the treatment or prophylaxis of different diseases:

WO2009/058298 and WO2009/058299 (Merck) disclose novel P2X3 type receptor antagonists which have a benzamide core structure substituted with a phenyl or pyridyl moiety, but not a thiazole, rendering said compounds different from the compounds of the present invention.

WO2008/000645 (Roche) addresses P2X3 and/or P2X2/3 receptor antagonist compounds useful for the treatment of diseases associated with P2X purinergic receptors.

According to the general formula of claim 1, the benzamide compounds are substituted with tetrazole. Furthermore, they may be having substituents like phenyl, pyridinyl, pyrimidinyl, pyridazinyl or thiophenyl. However, there is no thiazolyl substituent disclosed.

WO2009/077365, WO2009/077366, WO2009/077367 and WO2009/077371 (Roche) disclose a series of benzamide derivatives either substituted with imidazole, triazole, pyrazole or tetrazole which are stated to be useful for treatment of diseases associated with P2X purinergic receptors, and more particularly to P2X3 receptor and/or P2X2/3 receptor antagonists. According to the general formula of claim 1, the benzamide compounds may have additional substituents $R^6$, $R^7$ and $R^8$ being $C_1$-$C_6$-alkyl, $C_1$-$C_6$-alkoxy, $C_1$-$C_6$-haloalkyl, halogen atoms or cyano. However, ethers substituted with the functional groups like —$C_2$-$C_6$-alkyl-$OR^4$, —$(CH_2)_q$—$(C_3$-$C_7$-cyclo-alkyl), —$(CH_2)_q$-(6- to 12-membered heterobicycloalkyl), —$(CH_2)_q$-(4- to 7-membered heterocycloalkyl), —$(CH_2)_q$-(5- to 10-membered heteroaryl) or —$C_2$-$C_6$-alkynyl are not disclosed.

US20100152203 (Roche) discloses substituted benzamides with $R^1$ being thiadiazolyl and $R^2$ being phenyl, pyridinyl, pyrimidinyl, pyridazinyl, or thiophenyl as compounds useful for treatment of diseases associated with P2X purinergic receptors, and more particularly relates to P2X3 receptor and/or P2X2/3 receptor antagonists usable for treatment of genitourinary, pain, inflammatory, gastrointestinal and respiratory diseases, conditions and disorders. More specifically, the benzamide compounds may be additionally substituted with $C_1$-$C_6$-alkyl, $C_1$-$C_6$-alkoxy, $C_1$-$C_6$-haloalkyl, halogen atoms or cyano. However, ethers substituted with the functional groups like —$C_2$-$C_6$-alkyl-$OR^4$, —$(CH_2)_q$—$(C_3$-$C_7$-cycloalkyl), —$(CH_2)_q$-(6- to 12-membered heterobicycloalkyl), —$(CH_2)_q$-(4- to 7-membered heterocycloalkyl), —$(CH_2)_q$-(5- to 10-membered heteroaryl) or —$C_2$-$C_6$-alkynyl are not disclosed.

US20100324056 (Roche) discloses substituted benzamides with $R^1$ being phenyl, thienyl, pyrimidinyl, pyridazinyl, or pyridinyl as compounds useful for treatment of diseases associated with P2X purinergic receptors, and more particularly relates to P2X3 receptor and/or P2X2/3 receptor antagonists usable for treatment of genitourinary, pain, inflammatory, gastrointestinal and respiratory diseases, conditions and disorders. Ethers substituted with the functional groups like —$C_2$-$C_6$-alkyl-$OR^4$, —$(CH_2)_q$—$(C_3$-$C_7$-cycloalkyl), —$(CH_2)_q$-(6- to 12-membered heterobicycloalkyl), —$(CH_2)_q$-(4- to 7-membered heterocycloalkyl), —$(CH_2)_q$-(5- to 10-membered heteroaryl) or —$C_2$-$C_6$-alkynyl are not disclosed.

US20100324069 (Genentech) discloses oxazolone- and pyrrolidinone-substituted benzamides and their use for the prophylaxis and/or treatment of diseases which are associated with P2X3 receptor and/or P2X2/3 receptor antagonists. According to the general formula of claim 1 the benzamide compounds are additional substituted with a pyridine or phenyl. Ether-bearing groups at the benzamide core structure are not disclosed.

WO2006119504 (Renovis) relates to fused heterocyclic compounds of the class tetrahydronaphthyridines and tetrahydropyrido[4,3-d]pyrimidines and to pharmaceutical compositions containing such compounds.

WO2008123963 (Renovis) relates to fused heterocyclic compounds of the class tetrahydropyrido[4,3-d]pyrimidines and pharmaceutical compositions comprising such compounds. Also provided are methods for preventing and/or treating conditions in mammals, such as (but not limited to) arthritis, Parkinson's disease, Alzheimer's disease, asthma, myocardial infarction, pain syndromes (acute and chronic or neuropathic), neurodegenerative disorders, schizophrenia, cognitive disorders, anxiety, depression, inflammatory bowel disease and autoimmune disorders, and promoting neuroprotection, using the fused heterocyclic compounds and pharmaceutical compositions thereof.

WO2008130481 (Renovis) discloses 2-cyanophenyl fused heterocyclic compounds of the class tetrahydropyrido[4,3-d]pyrimidines and pharmaceutical compositions comprising such compounds.

WO2010033168 (Renovis) discloses a series of benzamides substituted with phenyl or pyridyl which are stated to be useful for treatment of diseases associated with P2X purinergic receptors, and more particularly to P2X3 receptor and/or P2X2/3 receptor antagonists. However, benzamides with additional ether groups are not disclosed.

WO2009110985 (Renovis) relates to phenyl- and pyridyl-substituted benzamide compounds and pharmaceutical compositions comprising such compounds, but not thiazole-substituted benzamides, rendering said compounds different from the compounds of the present invention.

WO2008/055840 (Roche) relates to thiazol- and oxazole-substituted benzamides substituted with $R^2$ being phenyl, pyridinyl, pyrimidinyl, pyridazinyl or thiophenyl that can be used for treating diseases associated with P2X purinergic receptors, and more particularly as P2X3 and/or P2X2/3 receptor antagonists. However, the thiazole substituted benzamides have in fact $C_1$-$C_6$-alkyl, $C_1$-$C_6$-alkoxy, $C_1$-$C_6$-haloalkyl, halo-$C_1$-$C_6$-alkoxy groups, halogen atoms or cyano, but ethers substituted with the functional groups like —$C_2$-$C_6$-alkyl-$OR^4$, —$(CH_2)_q$—$(C_3$-$C_7$-cyclo-alkyl), —$(CH_2)_q$-(6- to 12-membered heterobicycloalkyl), —$(CH_2)_q$-(4- to 7-membered heterocycloalkyl), —$(CH_2)_q$-(5- to 10-membered heteroaryl) or —$C_2$-$C_6$-alkynyl are not disclosed.

So, the state of the art described above does not describe the specific thiazole substituted benzamide compounds of general formula (I) of the present invention as defined herein or an isomer, enantiomer, diastereomer, racemate, hydrate, solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit the P2X3 receptor and may therefore be used for the treatment or prophylaxis of following diseases:

genitourinary, gastrointestinal, respiratory and pain-related diseases, conditions and disorders;
gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular Interstitial cystitis; idiopathic bladder hypersensitivity [Ford 2014, purines 2014, abstract book p15];

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis);

Epilepsy, partial and generalized seizures;

Respiratory disorders including chronic obstructive pulmonary disorder (COPD) [Ford 2013, European Respiratory Society Annual Congress 2013], asthma [Ford 2014, 8th Pain&Migraine Therapeutics Summit], bronchospasm, pulmonary fibrosis, acute cough, chronic cough including chronic idiopathic and chronic refractory cough;

Gastrointestinal disorders including irritable bowel syndrome (IBS), inflammatory bowel disease (IBD), biliary colic and other biliary disorders, renal colic, diarrhea-dominant IBS, gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

myocardial infarction, lipid disorders;

pain-associated diseases or disorders selected from the group consisting of hyperalgesia, allodynia, functional bowel disorders (such as irritable bowel syndrome), gout, arthritis (such as osteoarthritis [Ford 2014, 8$^{th}$ Pain&Migraine Therapeutics Summit], rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints pruritus.

The compounds of the present invention show high P2X3 receptor inhibition and furthermore selectivity over the P2X2/3 receptor. Selective inhibition of the P2X3 receptor over the P2X2/3 receptor means at least 3-fold selectivity over the P2X2/3 receptor. Preferred compounds of the present invention show at least 10-fold selectivity over the P2X2/3 receptor. In addition to that, more preferred compounds of the present invention show further advantageous properties that are beneficial for their use as medicaments, such as desirable pharmacokinetic profiles that provide suitable metabolic stability and oral bioavailability. In addition to that, even more preferred compounds of the present invention show further advantageous properties that are beneficial for their use as medicaments, such as desirable pharmacokinetic profiles that provide suitable metabolic stability and oral bioavailability, and at least one additional advantageous property chosen from an advantageous cardiovascular profile and a suitable CYP inhibition profile.

SUMMARY OF THE INVENTION

The present invention covers compounds of general formula (I):

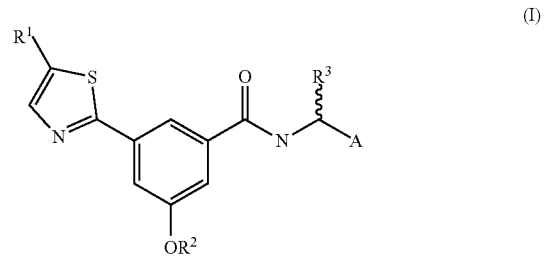

in which $R^1$ represents a halogen atom, $C_1$-$C_4$-alkyl or $C_3$-$C_6$-cycloalkyl, wherein $C_1$-$C_4$-alkyl is optionally substituted with 1-5 halogen atoms which are the same or different;

$R^2$ represents —$C_2$-$C_6$-alkyl-$OR^4$, —$(CH_2)_q$—($C_3$-$C_7$-cycloalkyl), —$(CH_2)_q$-(6- to 12-membered heterobicycloalkyl), —$(CH_2)_q$-(4- to 7-membered heterocycloalkyl), —$(CH_2)_q$-(5- to 10-membered heteroaryl) or —$C_2$-$C_6$-alkynyl; and
wherein said —$(CH_2)_q$—($C_3$-$C_7$-cycloalkyl), —$(CH_2)_q$-(6- to 12-membered heterobicycloalkyl) and —$(CH_2)_q$-(4- to 7-membered heterocycloalkyl) are optionally substituted with one or more substituents which are the same or different, at any ring carbon atom and selected from the group consisting of $C_1$-$C_4$ alkyl, optionally substituted with 1-5 halogen atoms which are the same or different, a halogen atom, —NR$^a$R$^b$, COOR$^5$ and oxo (=O); and wherein independently any ring nitrogen atom, if present in said —(CH$_2$)$_q$-(6- to 12-membered heterobicycloalkyl) and —(CH$_2$)$_q$-(4- to 7-membered heterocycloalkyl) is substituted with R$^c$; and wherein said —(CH$_2$)$_q$-(5- to 10-membered heteroaryl) is optionally substituted with one or more substituents which are the same or different, and selected from the group consisting of C$_1$-C$_4$-alkyl, optionally substituted with 1-5 halogen atoms which are the same or different, a halogen atom, —NR$^a$R$^b$ and —COOR$^5$;

R$^3$ represents hydrogen or C$_1$-C$_4$-alkyl, which is optionally substituted with 1-5 halogen atoms which are the same or different;

R$^4$ and R$^5$ represent hydrogen or C$_1$-C$_4$-alkyl;

R$^a$ and R$^b$ represent hydrogen or C$_1$-C$_4$-alkyl;

R$^c$ represents hydrogen, C$_1$-C$_4$-alkyl, optionally substituted with 1-5 halogen atoms which are the same or different, —C(O)O—C$_1$-C$_4$-alkyl, or —C(O)—C$_1$-C$_4$-alkyl;

A represents 5- to 10-membered heteroaryl which is optionally substituted with one or more substituents, which are the same or different, and selected from the group consisting of a halogen atom, C$_1$-C$_3$-alkyl, and C$_1$-C$_3$-alkoxy, wherein C$_1$-C$_3$-alkyl and C$_1$-C$_3$-alkoxy are optionally substituted with 1-5 halogen atoms which are the same or different;

q represents an integer of 0, 1, or 2;

or an isomer, enantiomer, diastereomer, racemate, hydrate, solvate, or a salt thereof, or a mixture of same.

The present invention further relates to compounds of general formula (Ia),

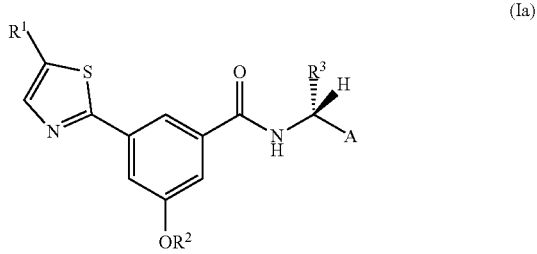

(Ia)

in which A, R$^1$, R$^2$ and R$^3$ have the meanings as defined in formula (I), preferably R$^3$ represents C$_1$-C$_4$-alkyl, more preferably methyl;

or an isomer, enantiomer, diastereomer, racemate, hydrate, solvate, or a salt thereof, or a mixture of same.

The present invention further relates to pharmaceutical compositions and combinations comprising said compounds, to use of said compounds for manufacturing a medicament for the treatment or prophylaxis of diseases or disorders and for the treatment of pains which are associated with such diseases.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine or a chlorine atom.

The term "alkyl" is to be understood as meaning a linear or branched, saturated, monovalent hydrocarbon group with the number of carbon atoms as specified and having as a rule, 2 to 6 in case of R$^2$, and 1 to 4 for all other alkyl substituents, preferably 1 to 3, carbon atoms, by way of example and by preference a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("C$_1$-C$_4$-alkyl"), e.g. a methyl, ethyl, n-propyl, n-butyl, iso-propyl, iso-butyl, sec-butyl, tert-butyl group, more particularly 1, 2 or 3 carbon atoms ("C$_1$-C$_3$-alkyl"), e.g. a methyl, ethyl, n-propyl- or iso-propyl group, and even more particularly 1 or 2 carbon atoms ("C$_1$-C$_2$-alkyl"), e.g. a methyl or ethyl group.

The term "C$_1$-C$_4$-alkyl, optionally substituted with 1-5 halogen atoms", or in analogy "C$_1$-C$_3$-alkyl, optionally substituted with 1-5 halogen atoms" or "C$_1$-C$_2$-alkyl which are optionally substituted with 1-5 halogen atoms", is to be understood as meaning a linear or branched, saturated, monovalent hydrocarbon group in which the term "C$_1$-C$_4$-alkyl", "C$_1$-C$_3$-alkyl" or "C$_1$-C$_2$-alkyl" is defined supra, and in which one or more hydrogen atoms is replaced by a halogen atom, which are the same or different, i.e. one halogen atom being independent from another. In particular, halogen is fluorine or chlorine.

The term "C$_1$-C$_4$-alkyl, optionally substituted with 1-5 fluorine atoms", or in analogy "C$_1$-C$_3$-alkyl, optionally substituted with 1-5 fluorine atoms" or "C$_1$-C$_2$-alkyl, optionally substituted with 1-5 fluorine atoms", is to be understood as meaning a linear or branched, saturated, monovalent hydrocarbon group in which the term "C$_1$-C$_4$-alkyl", "C$_1$-C$_3$-alkyl" or "C$_1$-C$_2$-alkyl" is defined supra, and in which one or more hydrogen atoms is replaced by a fluorine atom.

Said "C$_1$-C$_4$-alkyl, optionally substituted with 1-5 fluorine atoms" or "C$_1$-C$_4$-alkyl group, optionally substituted with 1-5 halogen atoms" is, for example,

—CH$_2$CH$_2$CH$_2$CF$_3$.

Similarly, the above-mentioned applies to "C$_1$-C$_3$-alkyl, optionally substituted with 1-5 halogen atoms", or "C$_1$-C$_2$-alkyl, optionally substituted with 1-5 halogen atoms", or "C$_1$-C$_3$-alkyl, optionally substituted with 1-5 fluorine atoms", or "C$_1$-C$_2$-alkyl, optionally substituted with 1-5 fluorine atoms". Thus said "C$_1$-C$_3$-alkyl optionally substituted with 1-5 halogen atoms" or "C$_1$-C$_3$-alkyl optionally substituted with 1-5 fluorine atoms" is, for example,

—CH$_2$CH$_2$CF$_3$.

Said "C$_1$-C$_2$-alkyl optionally substituted with 1-5 halogen atoms" or "C$_1$-C$_2$-alkyl optionally substituted with 1-5 fluorine atoms" is, for example, —CF$_3$, —CHF$_2$, —CH$_2$F, —CF$_2$CF$_3$, —CH$_2$CHF$_2$, or —CH$_2$CF$_3$.

Under the proviso, that R$^2$ in formula (I) or (Ia) is —C$_2$-C$_6$-alkyl-OR$^4$, "C$_2$-C$_6$-alkyl" is to be understood as C$_1$-C$_5$-alkylene which is bound to the phenolic oxygen via —CH$_2$— group. For example C$_1$-C$_5$-alkylene is methylene, ethylene, propylene, butylene, pentylene, iso-propylene, iso-butylene, sec-butylene, tert-butylene, iso-pentylene, 2-methylbutylene, 1-methylbutylene, 1-ethylpropylene, 1,2-dimethyl-propylene, neo-pentylene, 1,1-dimethylpropylene.

Under the proviso, that $R^2$ in formula (I) or (Ia) is —$C_2$-$C_6$-alkyl-$OR^4$, "$C_2$-$C_6$-alkyl" is also to be understood as $C_1$-$C_4$-alkylene which is bound to the phenolic oxygen via —CH—CH$_3$ group.

Under the proviso, that $R^2$ in formula (I) or (Ia) is —$C_2$-$C_4$-alkyl-$OR^4$, "$C_2$-$C_4$-alkyl" is to be understood as $C_1$-$C_3$-alkylene which is bound to the phenolic oxygen via —CH$_2$— group. Under the proviso that $R^2$ in formula (I) or (Ia) is —$C_2$-$C_4$-alkyl-$OR^4$, "$C_2$-$C_4$-alkyl" is also to be understood as $C_1$-$C_2$-alkylene which is bound to the phenolic oxygen via —CH—CH$_3$ group.

Under the proviso, that $R^2$ in formula (I) or (Ia) is —$C_2$-$C_4$-alkyl-OH, "$C_2$-$C_4$-alkyl" is to be understood as $C_1$-$C_3$-alkylene which is bound to the phenolic oxygen via —CH$_2$— group.

Under the proviso that $R^2$ in formula (I) or (Ia) is —$C_2$-$C_4$-alkyl-OH, "$C_2$-$C_4$-alkyl" is also to be understood as $C_1$-$C_2$-alkylene which is bound to the phenolic oxygen via —CH—CH$_3$ group.

Under the proviso, that $R^2$ in formula (I) or (Ia) is —$C_2$-$C_6$-alkyl-$OR^4$, "—$OR^4$" is either at a tertiary, secondary or primary carbon atom of the —$C_2$-$C_6$-alkyl chain.

Under the proviso, that $R^2$ in formula (I) or (Ia) is —$C_2$-$C_4$-alkyl-$OR^4$, "—$OR^4$" is either at a tertiary, secondary or primary carbon atom of the —$C_2$-$C_4$-alkyl chain.

Under the proviso, that $R^2$ in formula (I) or (Ia) is —$C_2$-$C_4$-alkyl-OH, "—OH" is either at a tertiary, secondary or primary carbon atom of the —$C_2$-$C_4$-alkyl chain.

For example, said —$C_2$-$C_6$-alkyl-$OR^4$ is 3-hydroxybutan-2-yl, (2R,3R)-3-hydroxybutan-2-yl, (2S,3S)-3-hydroxybutan-2-yl, (2R,3S)-3-hydroxybutan-2-yl, (2S,3R)-3-hydroxybutan-2-yl, (2R,3R)-3-methoxybutan-2-yl, (2S,3S)-3-methoxybutan-2-yl, (2R,3S)-3-methoxybutan-2-yl, (2S,3R)-3-methoxybutan-2-yl, 3-methoxybutan-2-yl, 2-hydroxy-2-methylpropan-1-yl, 2-methoxy-2-methylpropan-1-yl, 3-hydroxpropan1-yl, 3-hydroxybutan-1-yl, 3-hydroxy-3-methylbutan-1-yl, 3-hydroxy-2-methylbutan-1-yl, 3-hydroxy-2,2-dimethylpropan-1-yl, 4-hydroxy-3-methylbutan-2-yl, 4-hydroxy-3-methylpent-1-yl, 4-hydroxy-4-methylpent-1-yl, 2-hydroxy-2-methylpropan-1-yl, 2-methoxy-2-methyl-propan-1-yl, 2-methoxyethan-1-yl, 3-methoxypropan-1-yl, 4-methoxybutan-1-yl, 2-ethoxyethan-1-yl, 3-ethoxypropan-1-yl, 4-ethoxybutan-1-yl, 2-iso-propoxyethan-1-yl, 3-iso-propoxypropan-1-yl, 4-iso-propoxybutan-1-yl, 2-hydroxyethan-1-yl, 3-hydroxypropan-1-yl, 4-hydroxybutan-1-yl, preferably 3-hydroxybutan-2-yl, (2R,3R)-3-hydroxybutan-2-yl, (2S,3S)-3-hydroxybutan-2-yl, (2R,3S)-3-hydroxybutan-2-yl, (2S,3R)-3-hydroxybutan-2-yl, more preferably (2R,3R)-3-hydroxybutan-2-yl, (2S,3S)-3-hydroxybutan-2-yl.

For example, said —$C_2$-$C_4$-alkyl-$OR^4$ or —$C_2$-$C_4$-alkyl-OH is preferably 3-hydroxybutan-2-yl, (2R,3R)-3-hydroxybutan-2-yl, (2S,3S)-3-hydroxybutan-2-yl, (2R,3S)-3-hydroxybutan-2-yl, (2S,3R)-3-hydroxybutan-2-yl, more preferably (2R,3R)-3-hydroxybutan-2-yl, (2S,3S)-3-hydroxybutan-2-yl.

The term "alkoxy" is to be understood as meaning a linear or branched, saturated, monovalent, hydrocarbon group of formula —O-alkyl, in which the term "alkyl" is defined as meaning a linear or branched, saturated, monovalent hydrocarbon group with the number of carbon atoms atoms as specified and having as a rule, 1 to 3, preferably 1 to 2 alkyl substituents, especially preferably 1, carbon atoms. Particularly, said group has 1, 2 or 3 carbon atoms ("$C_1$-$C_3$-alkoxy"), e.g. a methoxy, ethoxy, n-propoxy or iso-propoxy group, and even more particularly 1 or 2 carbon atoms ("$C_1$-$C_2$-alkoxy"), e.g. a methoxy or ethoxy group.

The term "$C_1$-$C_3$-alkoxy optionally substituted with 1-5 halogen atoms" is to be understood as meaning a linear or branched, saturated, monovalent hydrocarbon group in which the term "$C_1$-$C_3$-alkoxy" is defined supra, and in which one or more hydrogen atoms is replaced by a halogen atom, which are the same or different, i.e. one halogen atom being independent from another. In particular, halogen is fluorine or chlorine.

Said "$C_1$-$C_3$-alkoxy" group is optionally substituted with 1 to 5 fluorine atoms, for example, —$OCF_3$, —$OCHF_2$, —$OCH_2F$, —$OCF_2CF_3$, —$OCH_2CHF_2$, —$OCH_2CF_3$, —$OCH_2CH_2CF_3$, or —$OCH_2CF_2CF_3$. In particular, said "$C_1$-$C_3$-alkoxy" group optionally substituted with fluorine is —$OCF_3$.

The term "$C_2$-$C_6$-alkynyl" is to be understood as meaning a linear or branched, monovalent hydrocarbon group which contains one or more triple bonds, preferably one triple bond, and which contains 2, 3, 4, 5 or 6 carbon atoms, particularly 3 or 4 carbon atoms ("$C_3$-$C_4$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent2-ynyl, 1-methyl-pent-2-ynyl, 4-methylpent-1-ynyl, 3-methylpent-1-ynyl, 2-ethylbut-3-ynyl, 1-ethyl-but-3-ynyl, 1-ethylbut-2-ynyl, 1-propylprop-2-ynyl, 1-isopropylprop-2-ynyl, 2,2-di-methylbut-3-ynyl, 1,1-dimethylbut-3-ynyl, 1,1-dimethylbut-2-ynyl, or 3,3-dimethyl-but-1-ynyl group. Particularly, said alkynyl group is prop-1-ynyl or prop-2-ynyl.

The term "cycloalkyl" is to be understood as meaning a saturated, monovalent, monocyclic hydrocarbon ring with the number of carbon atoms as specified and having as a rule, 3 to 7 or 3 to 6 ring carbon atoms, preferably 3 to 4 ring carbon atoms.

"$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Each hydrogen of a cycloalkyl carbon may be replaced by a substituent as further specified. Particularly, said ring contains 3, 4, 5 or 6 carbon atoms ("$C_3$-$C_6$-cycloalkyl"), preferably 3 or 4 carbon atoms ("$C_3$-$C_4$-cycloalkyl").

In case of $R^2$ in formula (I) or (Ia), said "$C_3$-$C_7$-cycloalkyl" in "$(CH_2)_q$—($C_3$-$C_7$-cycloalkyl)" is, unless indicated otherwise, optionally substituted with one or more substituents which are the same or different, at any ring carbon atom and selected from the group consisting of $C_1$-$C_4$ alkyl, optionally substituted with 1-5 halogen atoms which are the same or different, a halogen atom, —$NR^aR^b$, $COOR^5$ and oxo (=O). In case of Rein formula (I) or (Ia), said "$C_3$-$C_4$-cycloalkyl" as such or "$C_3$-$C_4$-cycloalkyl" in "$CH_2$—($C_3$-$C_4$-cycloalkyl)" is, unless indicated otherwise, optionally substituted with one or more substituents which are the same or different, at any ring carbon atom and selected from a group consisting of $C_1$-$C_4$-alkyl, optionally substituted with 1-5 halogen atoms which are the same or different, a halogen atom, —$NR^aR^b$, —$COOR^5$ and oxo (=O).

The term "heterocycloalkyl" is to be understood as meaning a saturated, monovalent, monocyclic hydrocarbon ring with the number of ring atoms as specified in which one, two or three ring atoms of the hydrocarbon ring is/are replaced by one, two or three heteroatoms or heteroatom-containing groups independently selected from O, S, S(=O), S(=O)$_2$, or N.

"4- to 7-membered heterocycloalkyl" is to be understood as meaning a saturated, monovalent, monocyclic "heterocycloalkyl" ring as defined supra which contains 4, 5, 6 or 7 ring atoms.

Similarly, "4- to 6-membered heterocycloalkyl" is to be understood as meaning a saturated, monovalent, monocyclic "heterocycloalkyl" ring as defined supra which contains 4, 5 or 6 ring atoms.

In case of R$^2$ in formula (I) or (Ia), said 4- to 7-membered heterocycloalkyl or 4- to 6-membered heterocycloalkyl is, unless indicated otherwise, optionally substituted with one or more substituents which are the same or different, at any ring carbon atom and selected from the group consisting of C$_1$-C$_4$ alkyl, optionally substituted with 1-5 halogen atoms which are the same or different, a halogen atom, —NR$^a$R$^b$, COORS and oxo (=O); and wherein independently any ring nitrogen atom, if present in said 4- to 7-membered or 4- to 6-membered heterocycloalkyl is substituted with R$^c$; it being possible for said 4- to 7-membered or 4- to 6-membered heterocycloalkyl group to be attached to the rest of the molecule via any one of the carbon atoms or, if present, a nitrogen atom. Accordingly, any ring nitrogen atom if present in said 4- to 7-membered or 4- to 6-membered heterocycloalkyl group is only substituted with R$^c$, if the designated atom's normal valency under the existing circumstances is not exceeded.

Particularly, said 4- to 7-membered heterocycloalkyl can contain 3, 4, 5 or 6 carbon atoms, and one or two of the above-mentioned heteroatoms or heteroatom-containing groups provided that the total number of ring atoms is not greater than 7, more particularly said heterocycloalkyl can contain 3, 4 or 5 carbon atoms, and one or two of the above-mentioned heteroatoms or heteroatom-containing groups provided that the total number of ring atoms is not greater than 6 (a "4- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or a 7-membered ring, such as a diazepanyl ring, for example.

Particularly, without being limited thereto, said heterocycloalkyl can be in a more preferred embodiment (3R)-tetrahydrofuran-3-yl, (3S)-tetrahydrofuran-3-yl, 4-methylmorpholin-2-yl, (2R)-4-methylmorpholin-2-yl, (2S)-4-methylmorpholin-2-yl, 4-methylmorpholin-3-yl, (3R)-4-methylmorpholin-3-yl, or (3S)-4-methylmorpholin-3-yl, most preferred (2R)-4-methylmorpholin-2-yl.

The term "6- to 12-membered heterobicycloalkyl" is to be understood as meaning a saturated, monovalent bicyclic hydrocarbon radical in which the two rings share one or two common ring atoms, and wherein said bicyclic hydrocarbon radical contains 5, 6, 7, 8, 9 or 10 carbon atoms and one, two or three heteroatoms or heteroatom-containing groups independently selected from O, S, S(=O), S(=O)$_2$, or N, provided that the total number of ring atoms is not greater than 12. Said 6- to 12-membered heterobicycloalkyl is, unless indicated otherwise, optionally substituted with one or more substituents, which are the same or different, at any ring carbon atom and selected from the group consisting of C$_1$-C$_4$ alkyl, optionally substituted with 1-5 halogen atoms which are the same or different, a halogen atom, —NR$^a$R$^b$, COOR$^S$ and oxo (=O); and wherein independently any ring nitrogen atom, if present in said 6- to 12-membered heterobicycloalkyl is substituted with R$^c$; it being possible for said 6- to 12-membered heterobicycloalkyl to be attached to the rest of the molecule via any one of the carbon atoms or, if present, a nitrogen atom. Accordingly, any ring nitrogen atom if present in said 6- to 12-membered heterobicycloalkyl is only substituted with R$^c$, if the designated atom's normal valency under the existing circumstances is not exceeded. Said 6- to 12-membered heterobicycloalkyl is, for example, azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl.

Heterospirocycloalkyl and bridged heterocycloalkyl, as defined below, are also included within the scope of this definition.

The term "heterospirocycloalkyl" is to be understood as meaning a saturated, monovalent bicyclic hydrocarbon radical in which the two rings share one common ring atom, and wherein said bicyclic hydrocarbon radical contains 5, 6, 7, 8, 9 or 10 carbon atoms, and one, two or three heteroatoms or heteroatom-containing groups independently selected from O, S, S(=O), S(=O)$_2$, or N, provided that the total number of ring atoms is not greater than 12. It is possible for said heterospirocycloalkyl to be attached to the rest of the molecule via any one of the carbon atoms or, if present, a nitrogen atom. Said heterospirocycloalkyl is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, oxazaspiro[5.5]undecyl, diazaspiro[3.3]heptyl, thiazaspiro[3.3]heptyl, thiazaspiro-[4.3]octyl, or azaspiro[5.5]decyl.

The term "bridged heterocycloalkyl" is to be understood as meaning a saturated, monovalent bicyclic hydrocarbon radical in which the two rings share two common ring atoms which are not immediately adjacent, and wherein said bicyclic hydrocarbon radical contains 5, 6, 7, 8, 9 or 10 carbon atoms, and one, two or three heteroatoms or heteroatom-containing groups independently selected from O, S, S(=O), S(=O)$_2$, or N, provided that the total number of ring atoms is not greater than 12. It is possible for said bridged heterocycloalkyl to be attached to the rest of the molecule via any one of the carbon atoms or, if present, a nitrogen atom. Said bridged heterocycloalkyl is, for example, azabicyclo[2.2.1]heptyl, oxazabicyclo[2.2.1]heptyl, thiazabicyclo[2.2.1]heptyl, diazabicyclo[2.2.1]heptyl, azabicyclo[2.2.2]octyl, diazabicyclo[2.2.2]octyl, oxazabicyclo[2.2.2]octyl, thiazabicyclo[2.2.2]octyl, azabicyclo[3.2.1]octyl, diazabicyclo[3.2.1]octyl, oxazabicyclo-[3.2.1]octyl, thiazabicyclo[3.2.1]octyl, azabicyclo[3.3.1]nonyl, diazabicyclo[3.3.1]-nonyl, oxazabicyclo[3.3.1]nonyl, thiazabicyclo[3.3.1]nonyl, azabicyclo[4.2.1]nonyl, diazabicyclo[4.2.1]nonyl, oxazabicyclo[4.2.1]nonyl, thiazabicyclo[4.2.1]nonyl, azabicyclo[3.3.2]decyl, diazabicyclo[3.3.2]decyl, oxazabicyclo[3.3.2]decyl, thiazabicyclo[3.3.2]decyl, or azabicyclo[4.2.2]decyl.

The term "heteroaryl" is understood as meaning a monovalent, monocyclic or bicyclic hydrocarbon ring system with at least one aromatic ring with the number of ring system atoms as specified and wherein one, two or three ring atoms of the monovalent, monocyclic or bicyclic hydrocarbon ring system is/are replaced by one, two or three heteroatoms or heteroatom-containing groups independently selected from O, S, S(=O), S(=O)$_2$, or N.

"5- to 10-membered heteroaryl" is understood as meaning a heteroaryl having 5, 6, 7, 8, 9 or 10 ring atoms (a "5- to 10-membered heteroaryl") and wherein one, two or three ring atoms of the monovalent, monocyclic or bicyclic hydrocarbon ring system is/are replaced by one, two or three heteroatoms or heteroatom-containing groups independently selected from O, S, S(=O), S(=O)$_2$, or N. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc. and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridinyl, pyridazinyl, pyrimidinyl, pyrazinyl, triazinyl, etc., and benzo derivatives thereof, such as, for example, quinolinyl, quinazolinyl, isoquinolinyl, etc.; indolizinyl, and benzo derivatives thereof; or cinnolinyl, phthalazinyl, quinazolinyl, quinoxalinyl, etc.

In case of $R^2$ of formula (I) or (Ia), said 5- to 10-membered heteroaryl is, unless indicated otherwise, optionally substituted with one or more substituents which are the same or different, and selected from the group consisting of $C_1$-$C_4$-alkyl, optionally substituted with 1-5 halogen atoms which are the same or different, a halogen atom, —NR$^a$R$^b$ and —COOR$_5$.

In case of $R^2$ of formula (I) or (Ia), said 5- to 10-membered heteroaryl optionally substituted as described above, can be in particular substituted with $C_1$-$C_2$-alkyl at any ring N, if present.

In case of A of formula (I) or (Ia), said 5- to 10-membered heteroaryl is, unless indicated otherwise, optionally substituted with one or more substituents, which are the same or different, and selected from the group consisting of a halogen atom, $C_1$-$C_3$-alkyl, and $C_1$-$C_3$-alkoxy, wherein $C_1$-$C_3$-alkyl and $C_1$-$C_3$-alkoxy are optionally substituted with 1-5 halogen atoms which are the same or different.

In case of A of formula (I) or (Ia), a "5- or 6-membered heteroaryl" is understood as meaning a heteroaryl having 5 or 6 ring atoms and wherein one, two or three ring atoms of the hydrocarbon ring system is/are replaced by one, two or three heteroatoms or heteroatom-containing groups independently selected from O, S, S(=O), S(=O)$_2$, or N. Said "5- or 6-membered heteroaryl" is, unless indicated otherwise, optionally substituted with one or more substituents, which are the same or different, and selected from the group consisting of a halogen atom, $C_1$-$C_3$-alkyl, and $C_1$-$C_3$-alkoxy, wherein $C_1$-$C_3$-alkyl and $C_1$-$C_3$ alkoxy are optionally substituted with 1-5 halogen atoms which are the same or different A 5-membered heteroaryl group is preferably selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl.

A 6-membered heteroaryl group is preferably selected from pyridinyl, pyridazinyl, pyrimidinyl, pyrazinyl, triazinyl.

In particular, said 5- or 6-membered heteroaryl is, optionally substituted with preferably one or two substituents, which are the same or different, and selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms.

In particular, said 5- or 6-membered heteroaryl is a 6-membered heteroaryl with one or two nitrogen atom(s) and is optionally substituted with one or two substituents, which are the same or different, and selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms.

Preferably said 6-membered heteroaryl is $CF_3$-pyrimidinyl, most preferably 2-$CF_3$-pyrimidin-5-yl. Also preferred is $CF_3$-pyridazinyl, most preferably 6-$CF_3$-pyridazin-3-yl.

In general, and unless otherwise mentioned, the term "heteroaryl" includes all possible isomeric forms thereof, e.g. the positional isomers thereof. Thus, for some illustrative non-restricting example, the term pyridyl includes pyridin-2-yl, pyridin-3-yl, and pyridin-4-yl; or the term pyrimidinyl includes pyrimidin-2-yl, pyrimidin-4-yl and pyrimidin-5-yl; or the term pyridazinyl includes pyridazin-3-yl and pyridazin-4-yl; or the term thiazolyl includes 1,3-thiazol-5-yl, 1,3-thiazol-4-yl and 1,3-thiazol-2-yl.

The term "$C_1$-$C_4$" as used throughout this text is to be understood as meaning a group having a finite number of carbon atoms of 1 to 4, i.e. 1, 2, 3 or 4 carbon atoms, e.g. in the context of the definition of "$C_1$-$C_4$-alkyl", it is to be understood as meaning an alkyl group having a finite number of carbon atoms of 1 to 4, i.e. 1, 2, 3 or 4 carbon atoms.

The term "$C_2$-$C_6$" as used throughout this text is to be understood as meaning a group having a finite number of carbon atoms of 2 to 6, i.e. 2, 3, 4, 5 or 6 carbon atoms, e.g. in the context of the definition of "$C_2$-$C_6$-alkyl", it is to be understood as meaning an alkyl group having a finite number of carbon atoms of 2 to 6, i.e. 2, 3, 4, 5 or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

The term "$C_1$-$C_3$" as used in the context of the definition "$C_1$-$C_3$-alkoxy" is to be understood as meaning an alkoxy group, having a finite number of carbon atoms of 1 to 3, i.e. 1, 2 or 3 carbon atoms.

The same applies to other mentioned "alkyl", alkynyl or "alkoxy" as mentioned herein and as it is to be understood by a skilled person.

It is to be understood further that for example a term "$C_1$-$C_6$" is to be interpreted as any sub-range comprised therein, e.g. $C_1$-$C_6$, $C_2$-$C_3$, $C_2$-$C_6$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$.

Similarly, the mentioned above applies to "$C_1$-$C_4$-alkyl", "$C_1$-$C_3$-alkyl", "$C_1$-$C_3$-alkoxy", "$C_1$-$C_2$-alkyl" or "$C_1$-$C_2$-alkoxy" optionally substituted with 1-5 halogen which are the same or different.

Similarly, as used herein, the term "$C_2$-$C_6$", as used throughout this text, e.g. in the context of the definitions of "$C_2$-$C_6$-alkynyl", is to be understood as meaning an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$ and $C_2$-$C_4$.

Further, as used herein, the term "$C_3$-$C_7$", as used throughout this text, is to be understood as meaning a group having a finite number of carbon atoms of 3 to 7, i.e. 3, 4, 5, 6 or 7 carbon atoms, e.g. in the context of the definition of "$C_3$-$C_7$-cycloalkyl", it is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 5, in particular from 1 to 3.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, sulphur, fluorine and chlorine such as $^2$H (deuterium), $^3$H (tritium), $^{11}$C, $^{13}$C, $^{14}$C, $^{15}$N, $^{17}$O, $^{18}$O, $^{33}$S, $^{34}$S, $^{35}$S, $^{36}$S, $^{18}$F and $^{36}$Cl, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel O D and Chiracel O J among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl. Chem. 45, 11-30, 1976).

Further, the compounds of the present invention may exist as tautomers.

The present invention includes all possible tautomers of the compounds of the present invention as single tautomers, or as any mixture of said tautomers, in any ratio.

The present invention also relates to useful forms of the compounds as disclosed herein, such as metabolites, hydrates, solvates, prodrugs, salts, in particular pharmaceutically acceptable salts, and co-precipitates.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et at. "Pharmaceutical Salts," J. Pharm. Sci. 1977, 66, 1-19. A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Unless otherwise indicated, the compounds of the present invention are also referred to isomers, enantiomers, diastereomers, racemates, hydrates, solvates, or a salt thereof, or a mixture of same.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorph, in any ratio.

In accordance with a first aspect, the present invention covers compounds of general formula (Ia):

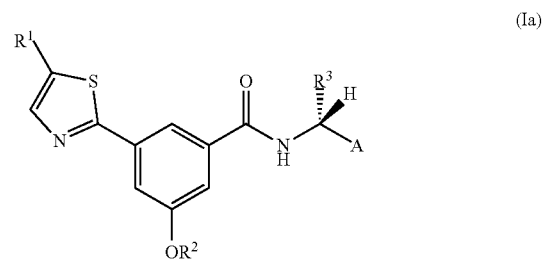

(Ia)

in which A, $R^1$, $R^2$ and $R^3$ have the meanings as defined in formula (I), preferably $R^3$ represents $C_1$-$C_4$-alkyl, more preferably methyl;

or an isomer, enantiomer, diastereomer, racemate, hydrate, solvate, or a salt thereof, or a mixture of same.

Also preferred are compounds of general formula (I), wherein

A represents an optionally substituted 5- or 6-membered heteroaryl, preferably an optionally substituted 6-membered heteroaryl; and in which $R^1$, $R^2$ and $R^3$ have the same meaning as defined in general formula (I), or an isomer, enantiomer, diastereomer, racemate, hydrate, solvate, or a salt thereof, or a mixture of same.

Also preferred are compounds of general formula (Ia), wherein

A represents an optionally substituted 5- or 6-membered heteroaryl, preferably an optionally substituted 6-membered heteroaryl; and in which $R^1$, $R^2$ and $R^3$ have the same meaning as defined in general formula (Ia), or an isomer, enantiomer, diastereomer, racemate, hydrate, solvate, or a salt thereof, or a mixture of same.

Additionally preferred are compounds of general formula (I), wherein $R^1$ represents $C_1$-$C_4$-alkyl, preferably methyl or ethyl; and in which A, $R^2$ and $R^3$ have the same meaning as defined in general formula (I), or an isomer, enantiomer, diastereomer, racemate, hydrate, solvate, or a salt thereof, or a mixture of same.

Additionally preferred are compounds of general formula (Ia), wherein $R^1$ represents $C_1$-$C_4$-alkyl, preferably methyl or ethyl; and in which A, $R^2$ and $R^3$ have the same meaning as defined in general formula (Ia), or an isomer, enantiomer, diastereomer, racemate, hydrate, solvate, or a salt thereof, or a mixture of same.

Additionally preferred are compounds of general formula (I), wherein $R^1$ represents a halogen atom, preferably chloro; and in which A, $R^2$ and $R^3$ have the same meaning as defined in general formula (I), or an isomer, enantiomer, diastereomer, racemate, hydrate, solvate, or a salt thereof, or a mixture of same.

Additionally preferred are compounds of general formula (Ia), wherein $R^1$ represents a halogen atom, preferably chloro; and in which A, $R^2$ and $R^3$ have the same meaning as defined in general formula (Ia), or an isomer, enantiomer, diastereomer, racemate, hydrate, solvate, or a salt thereof, or a mixture of same.

Also preferred are compounds of general formula (I), more preferably compounds of general formula (Ia), wherein R³ represents $C_1$-$C_4$-alkyl, preferably methyl; and
in which R¹, R² and A have the same meaning as defined in general formula (I),
or an isomer, enantiomer, diastereomer, racemate, hydrate, solvate, or a salt thereof, or a mixture of same.

In another preferred embodiment, the invention relates to compounds of general formula (I), wherein
R² represents —$C_2$-$C_4$-alkyl-OR⁴, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$;
q represents an integer of 0; and
in which A, $R^c$, R¹ and R³ have the same meaning as defined in general formula (I),
or an isomer, enantiomer, diastereomer, racemate, hydrate, solvate, or a salt thereof, or a mixture of same.

In another preferred embodiment, the invention relates to compounds of general formula (I), wherein
R² represents —$C_2$-$C_3$-alkyl-OR⁴, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$;
q represents an integer of 0; and
in which A, $R^c$, R¹ and R³ have the same meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
R² represents —$C_2$-$C_4$-alkyl-OR⁴, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$;
q represents an integer of 0; and
in which A, $R^c$, R¹ and R³ have the same meaning as defined in general formula (Ia),
or an isomer, enantiomer, diastereomer, racemate, hydrate, solvate, or a salt thereof, or a mixture of same.

In another preferred embodiment, the invention relates to compounds of general formula (Ia), wherein
R² represents —$C_2$-$C_3$-alkyl-OR⁴, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$;
q represents an integer of 0; and in which A, $R^c$, R¹ and R³ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of general formula (I), wherein
R² represents —$(CH_2)_q$-(4- to 6-membered heterocycloalkyl); and wherein $(CH_2)_q$-(4- to 6-membered heterocycloalkyl) is optionally substituted with one or more substituents which are the same or different, at any ring carbon atom; and
wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl; and
q represents an integer of 1; and
in which A, $R^c$, R¹ and R³ have the same meaning as defined in general formula (I),
or an isomer, enantiomer, diastereomer, racemate, hydrate, solvate, or a salt thereof, or a mixture of same.

In yet another preferred embodiment, the invention relates to compounds of general formula (I), wherein
R² represents-$(CH_2)_q$-morpholinyl, wherein the ring nitrogen atom is substituted with $R^c$; and
$R^c$ represents methyl;
q represents an integer of 1; and
in which A, R¹ and R³ have the same meaning as defined in general formula (I),
or an isomer, enantiomer, diastereomer, racemate, hydrate, solvate, or a salt thereof, or a mixture of same.

In yet another preferred embodiment, the invention relates to compounds of general formula (Ia), wherein
R² represents —$(CH_2)_q$-(4- to 6-membered heterocycloalkyl); and wherein $(CH_2)_q$-(4- to 6-membered heterocycloalkyl) is optionally substituted with one or more substituents which are the same or different, at any ring carbon atom; and
wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl; and
q represents an integer of 1; and
in which A, $R^c$, R¹ and R³ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of general formula (Ia), wherein
R² represents-$(CH_2)_q$-morpholinyl, wherein the ring nitrogen atom is substituted with $R^c$; and
$R^c$ represents methyl;
q represents an integer of 1; and
in which A, R¹ and R³ have the same meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein $R^2$ represents —$C_2$-$C_4$-alkyl-OH; and
in which A, $R^1$ and $R^3$ have the same meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
$R^2$ represents —$C_2$-$C_4$-alkyl-OH; and
in which A, $R^1$ and $R^3$ have the same meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein
A represents an optionally substituted 5- or 6-membered heteroaryl, preferably an optionally substituted 6-membered heteroaryl; and
$R^1$ represents $C_1$-$C_4$-alkyl, preferably methyl or ethyl; and
in which $R^2$ and $R^3$ have the same meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
A represents an optionally substituted 5- or 6-membered heteroaryl, preferably an optionally substituted 6-membered heteroaryl; and
$R^1$ represents $C_1$-$C_4$-alkyl, preferably methyl or ethyl; and
in which $R^2$ and $R^3$ have the same meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein
A represents an optionally substituted 5- or 6-membered heteroaryl, preferably an optionally substituted 6-membered heteroaryl; and
$R^1$ represents a halogen atom, preferably chloro; and
in which $R^2$ and $R^3$ have the same meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
A represents an optionally substituted 5- or 6-membered heteroaryl, preferably an optionally substituted 6-membered heteroaryl; and
$R^1$ represents a halogen atom, preferably chloro; and
in which $R^2$ and $R^3$ have the same meaning as defined in general formula (Ia),
or an isomer, enantiomer, diastereomer, racemate, hydrate, solvate, or a salt thereof, or a mixture of same.

Also preferred are compounds of general formula (I), more preferably compounds of general formula (Ia), wherein
A represents an optionally substituted 5- or 6-membered heteroaryl, preferably an optionally substituted 6-membered heteroaryl; and
$R^3$ represents $C_1$-$C_4$-alkyl, preferably methyl; and
in which $R^1$ and $R^2$ have the same meaning as defined in general formula (I),
or an isomer, enantiomer, diastereomer, racemate, hydrate, solvate, or a salt thereof, or a mixture of same.

Additionally preferred are compounds of general formula (I), more preferably compounds of general formula (Ia), wherein
A represents an optionally substituted 5- or 6-membered heteroaryl, preferably an optionally substituted 6-membered heteroaryl;
$R^1$ represents $C_1$-$C_4$-alkyl, preferably methyl or ethyl; and
$R^3$ represents $C_1$-$C_4$-alkyl, preferably methyl; and
in which $R^2$ has the same meaning as defined in general formula (I),
or an isomer, enantiomer, diastereomer, racemate, hydrate, solvate, or a salt thereof, or a mixture of same.

Additionally preferred are compounds of general formula (I), more preferably compounds of general formula (Ia), wherein
A represents an optionally substituted 5- or 6-membered heteroaryl, preferably an optionally substituted 6-membered heteroaryl;
$R^1$ represents a halogen atom, preferably chloro; and
$R^3$ represents $C_1$-$C_4$-alkyl, preferably methyl; and
in which $R^2$ has the same meaning as defined in general formula (I),
or an isomer, enantiomer, diastereomer, racemate, hydrate, solvate, or a salt thereof, or a mixture of same.

A preferred embodiment relates to compounds of general formula (I), more preferably compounds of general formula (Ia), wherein
A represents an optionally substituted 5- or 6-membered heteroaryl, preferably an optionally substituted 6-membered heteroaryl;
$R^1$ represents $C_1$-$C_4$-alkyl, preferably methyl or ethyl;
$R^2$ represents —$C_2$-$C_4$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$;
$R^3$ represents $C_1$-$C_4$-alkyl, preferably methyl; and
q represents an integer of 0,
wherein $R^c$ is defined as in formula (I),
or an isomer, enantiomer, diastereomer, racemate, hydrate, solvate, or a salt thereof, or a mixture of same.

A preferred embodiment relates to compounds of general formula (I), more preferably compounds of general formula (Ia), wherein
A represents an optionally substituted 5- or 6-membered heteroaryl, preferably an optionally substituted 6-membered heteroaryl;
$R^1$ represents $C_1$-$C_4$-alkyl, preferably methyl or ethyl;
$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl; and
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$; and
$R^3$ represents $C_1$-$C_4$-alkyl, preferably methyl; and
q represents an integer of 0,
wherein $R^c$ is defined as in formula (I),
or an isomer, enantiomer, diastereomer, racemate, hydrate, solvate, or a salt thereof, or a mixture of same.

A preferred embodiment relates to compounds of general formula (I), more preferably compounds of general formula (Ia), wherein A represents an optionally substituted 5- or 6-membered heteroaryl, preferably an optionally substituted 6-membered heteroaryl;
$R^1$ represents $C_1$-$C_4$-alkyl, preferably methyl or ethyl;
$R^2$ represents —$(CH_2)_q$-(4- to 6-membered heterocycloalkyl); and wherein $(CH_2)_q$-(4- to 6-membered heterocycloalkyl) is optionally substituted with one or more substituents which are the same or different, at any ring carbon atom; and
wherein independently any ring nitrogen atom, if present in said —$(CH_2)_q$-(4 to 6-membered heterocycloalkyl) is substituted with $R^c$; wherein —$(CH_2)_q$-(4- to 6-membered heterocycloalkyl) is preferably —$(CH_2)_q$-morpholinyl;
$R^3$ represents $C_1$-$C_4$-alkyl, preferably methyl; and
q represents an integer of 1;
wherein $R^c$ is defined as in formula (I),
or an isomer, enantiomer, diastereomer, racemate, hydrate, solvate, or a salt thereof, or a mixture of same.

A preferred embodiment relates to compounds of general formula (I), more preferably compounds of general formula (Ia), wherein A represents an optionally substituted 5- or 6-membered heteroaryl, preferably an optionally substituted 6-membered heteroaryl;
$R^1$ represents $C_1$-$C_4$-alkyl, preferably methyl or ethyl;
$R^2$ represents —$(CH_2)_q$-morpholinyl, wherein the ring nitrogen atom is substituted with $R^c$; and
$R^c$ represents methyl;
$R^3$ represents $C_1$-$C_4$-alkyl, preferably methyl; and
q represents an integer of 1;
or an isomer, enantiomer, diastereomer, racemate, hydrate, solvate, or a salt thereof, or a mixture of same.

A preferred embodiment relates to compounds of general formula (I), more preferably compounds of general formula (Ia), wherein A represents an optionally substituted 5- or 6-membered heteroaryl, preferably an optionally substituted 6-membered heteroaryl;
$R^1$ represents a halogen atom, preferably chloro;
$R^2$ represents —$C_2$-$C_4$-alkyl-OH, preferably 3-hydroxybutan-2-yl;
$R^3$ represents $C_1$-$C_4$-alkyl, preferably methyl;
or an isomer, enantiomer, diastereomer, racemate, hydrate, solvate, or a salt thereof, or a mixture of same.

Another preferred embodiment relates to compounds of general formula (I), more preferably compounds of general formula (Ia), wherein A represents 5- or 6-membered heteroaryl at least containing one or two nitrogen atom(s), preferably a 6-membered heteroaryl with one or two nitrogen atom(s),
wherein said 5- or 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^1$ represents methyl or ethyl;
$R^2$ represents —$C_2$-$C_3$-alkyl-$OR^4$, unsubstituted —$CH_2$—($C_3$-$C_4$-cycloalkyl), unsubstituted $C_3$-$C_4$-cycloalkyl, unsubstituted $(CH_2)_q$-(4- to 6-membered heterocycloalkyl), or —$C_2$-$C_4$-alkynyl;
$R^3$ represents methyl; and
q represents an integer of 0,
or an isomer, enantiomer, diastereomer, racemate, hydrate, solvate, or a salt thereof, or a mixture of same.

Another preferred embodiment relates to compounds of general formula (I), more preferably compounds of general formula (Ia), wherein A represents 5- or 6-membered heteroaryl at least containing one or two nitrogen atom(s), preferably a 6-membered heteroaryl with one or two nitrogen atom(s),
wherein said 5- or 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^1$ represents methyl or ethyl;
$R^2$ represents optionally substituted $(CH_2)_q$-(4- to 6-membered heterocycloalkyl), wherein —$(CH_2)_q$-(4- to 6-membered heterocycloalkyl) is optionally substituted with one or more substituents which are the same or different, at any ring carbon atom; and
wherein independently any ring nitrogen atom, if present in said —$(CH_2)_q$-(4- to 6-membered heterocycloalkyl) is substituted with $R^c$; wherein —$(CH_2)_q$-(4- to 6-membered heterocycloalkyl) is preferably —$(CH_2)_q$-morpholinyl;
$R^3$ represents methyl; and
q represents an integer of 1,
wherein $R^c$ is defined as in formula (I),
or an isomer, enantiomer, diastereomer, racemate, hydrate, solvate, or a salt thereof, or a mixture of same.

Another preferred embodiment relates to compounds of general formula (I), more preferably compounds of general formula (Ia), wherein A represents 5- or 6-membered heteroaryl at least containing one or two nitrogen atom(s), preferably a 6-membered heteroaryl with one or two nitrogen atom(s),
wherein said 5- or 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^1$ represents methyl or ethyl;
$R^2$ represents —$(CH_2)_q$-morpholinyl, wherein the ring nitrogen atom is substituted with $R^c$ as defined in formula (I), preferably substituted with methyl;
$R^3$ represents methyl; and
q represents an integer of 1,
or an isomer, enantiomer, diastereomer, racemate, hydrate, solvate, or a salt thereof, or a mixture of same.

Another preferred embodiment relates to compounds of general formula (I), more preferably compounds of general formula (Ia), wherein A represents 5- or 6-membered heteroaryl at least containing one or two nitrogen atom(s), preferably a 6-membered heteroaryl with one or two nitrogen atom(s),
wherein said 5- or 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;

$R^1$ represents a chloro atom;

$R^2$ represents —$C_2$-$C_4$-alkyl-OH, preferably 3-hydroxybutan-2-yl; and $R^3$ represents methyl, or an isomer, enantiomer, diastereomer, racemate, hydrate, solvate, or a salt thereof, or a mixture of same.

In another preferred embodiment, the invention relates to compounds of general formula (I), wherein A represents pyrimidinyl, pyridazinyl, pyridinyl, pyrazinyl, thiazolyl or thiadiazolyl, preferably pyrimidinyl, pyridazinyl, thiazolyl or thiadiazolyl, more preferably pyrimidinyl, pyridazinyl or thiadiazolyl, wherein said pyrimidinyl, pyridazinyl, pyridinyl, pyrazinyl, thiazolyl and thiadiazolyl are optionally substituted; and in which $R^1$, $R^2$ and $R^3$ have the same meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents pyrimidinyl, pyridazinyl, pyridinyl, pyrazinyl, thiazolyl or thiadiazolyl, preferably pyrimidinyl, pyridazinyl, thiazolyl or thiadiazolyl, more preferably pyrimidinyl, pyridazinyl or thiadiazolyl, wherein said pyrimidinyl, pyridazinyl, pyridinyl, pyrazinyl, thiazolyl and thiadiazolyl are optionally substituted; and in which $R^1$, $R^2$ and $R^3$ have the same meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents $CF_3$-pyrimidinyl, preferably 2-$CF_3$-pyrimidin-5-yl; and in which $R^1$, $R^2$ and $R^3$ have the same meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents $CF_3$-pyrimidinyl, preferably 2-$CF_3$-pyrimidin-5-yl; and in which $R^1$, $R^2$ and $R^3$ have the same meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents $CF_3$-pyridazinyl, preferably 6-$CF_3$-pyridazin-3-yl; and in which $R^1$, $R^2$ and $R^3$ have the same meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents $CF_3$-pyridazinyl, preferably 6-$CF_3$-pyridazin-3-yl; and in which $R^1$, $R^2$ and $R^3$ have the same meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein $R^2$ represents cyclopropylmethyl, tetrahydrofuran-3-yl, tetrahydrofuran-2-ylmethyl, tetrahydrofuran-3-ylmethyl, prop-2-yn-1-yl, but-2-yn-1-yl, oxetan-3-yl, tetrahydropyran-4-yl, tetrahydro-2H-pyran-4-ylmethyl, pyridin-4-yl, pyridin-3-yl, 1,3,4-thiadiazol-2-yl, 1,3-thiazol-2-yl, 2,2-dimethyl-2-methoxyethyl, methoxyethyl, piperidin-4-yl, pyrrolidin-3-yl or azetidin-3-yl which are optionally substituted, preferably unsubstituted cyclopropylmethyl, unsubstituted oxetan-3-yl, unsubstituted tetrahydrofuran-3-yl; and in which $R^1$, A and $R^3$ have the same meaning as defined in general formula (I), or an isomer, enantiomer, diastereomer, racemate, hydrate, solvate, or a salt thereof, or a mixture of same.

In another preferred embodiment, the invention relates to compounds of general formula (I), wherein $R^2$ represents 3-hydroxybutan-2-yl, prop-2-yn-1-yl, but-2-yn-1-yl, 2,2-dimethyl-2-methoxyethyl, methoxyethyl; or cyclopropylmethyl, tetrahydrofuran-3-yl, tetrahydrofuran-2-ylmethyl, tetrahydrofuran-3-ylmethyl, oxetan-3-yl, tetrahydropyran-4-yl, tetrahydro-2H-pyran-4-ylmethyl, (4-methylmorpholin-2-yl)methyl, pyridin-4-yl, pyridin-3-yl, 1,3,4-thiadiazol-2-yl, 1,3-thiazol-2-yl, piperidin-4-yl, pyrrolidin-3-yl or azetidin-3-yl which are optionally substituted, preferably unsubstituted cyclopropylmethyl, unsubstituted oxetan-3-yl, unsubstituted (3R)-tetrahydrofuran-3-yl, unsubstituted (3S)-tetrahydrofuran-3-yl, [(2R)-4-methylmorpholin-2-yl]methyl, [(2S)-4-methylmorpholin-2-yl]methyl, (2R,3R)-3-hydroxybutan-2-yl, (2S,3S)-3-hydroxybutan-2-yl, (2S,3R)-3-hydroxybutan-2-yl or (2R,3S)-3-hydroxybutan-2-yl; and in which $R^1$, A and $R^3$ have the same meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein $R^2$ represents cyclopropylmethyl, tetrahydrofuran-3-yl, tetrahydrofuran-2-ylmethyl, tetrahydrofuran-3-ylmethyl, prop-2-yn-1-yl, but-2-yn-1-yl, oxetan-3-yl, tetrahydropyran-4-yl, tetrahydro-2H-pyran-4-ylmethyl, pyridin-4-yl, pyridin-3-yl, 1,3,4-thiadiazol-2-yl, 1,3-thiazol-2-yl, 2,2-dimethyl-2-methoxyethyl, methoxyethyl, piperidin-4-yl, pyrrolidin-3-yl or azetidin-3-yl which are optionally substituted, preferably unsubstituted cyclopropylmethyl, unsubstituted oxetan-3-yl, unsubstituted tetrahydrofuran-3-yl; and in which $R^1$, A and $R^3$ have the same meaning as defined in general formula (Ia), or an isomer, enantiomer, diastereomer, racemate, hydrate, solvate, or a salt thereof, or a mixture of same.

In another preferred embodiment, the invention relates to compounds of general formula (Ia), wherein $R^2$ represents 3-hydroxybutan-2-yl, prop-2-yn-1-yl, but-2-yn-1-yl, 2,2-dimethyl-2-methoxyethyl, methoxyethyl; or cyclopropylmethyl, tetrahydrofuran-3-yl, tetrahydrofuran-2-ylmethyl, tetrahydrofuran-3-ylmethyl, oxetan-3-yl, tetrahydropyran-4-yl, tetrahydro-2H-pyran-4-ylmethyl, (4-methylmorpholin-2-yl)methyl, pyridin-4-yl, pyridin-3-yl, 1,3,4-thiadiazol-2-yl, 1,3-thiazol-2-yl, piperidin-4-yl, pyrrolidin-3-yl or azetidin-3-yl which are optionally substituted, preferably unsubstituted cyclopropylmethyl, unsubstituted oxetan-3-yl, unsubstituted (3R)-tetrahydrofuran-3-yl, unsubstituted (3S)-tetrahydrofuran-3-yl, [(2R)-4-methylmorpholin-2-yl]methyl, [(2S)-4-methylmorpholin-2-yl]methyl, (2R,3R)-3-hydroxybutan-2-yl, (2S,3S)-3-hydroxybutan-2-yl, (2S,3R)-3-hydroxybutan-2-yl or (2R,3S)-3-hydroxybutan-2-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (I), wherein
$R^2$ represents unsubstituted tetrahydrofuran-3-yl or unsubstituted oxetan-3-yl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (I), wherein
$R^2$ represents unsubstituted (3R)-tetrahydrofuran-3-yl, (3S)-tetrahydrofuran-3-yl or unsubstituted oxetan-3-yl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (I), wherein
$R^2$ represents unsubstituted (3R)-tetrahydrofuran-3-yl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (I), wherein
$R^2$ represents [(2R)-4-methylmorpholin-2-yl]methyl, (2R,3R)-3-hydroxybutan-2-yl, or (2S,3S)-3-hydroxybutan-2-yl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (I), wherein
$R^2$ represents [(2R)-4-methylmorpholin-2-yl]methyl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (I), wherein
$R^2$ represents (2R,3R)-3-hydroxybutan-2-yl, or (2S,3S)-3-hydroxybutan-2-yl; and
in which $R^1$, A and $R^3$ have the same meaning as defined in general formula (I),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents unsubstituted tetrahydrofuran-3-yl or unsubstituted oxetan-3-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents unsubstituted (3R)-tetrahydrofuran-3-yl, (3S)-tetrahydrofuran-3-yl or unsubstituted oxetan-3-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents unsubstituted (3R)-tetrahydrofuran-3-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents [(2R)-4-methylmorpholin-2-yl]methyl, (2R,3R)-3-hydroxybutan-2-yl or (2S,3S)-3-hydroxybutan-2-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents [(2R)-4-methylmorpholin-2-yl]methyl; and
in which $R^1$, A and $R^3$ have the same meaning as defined in general formula (Ia),
or an isomer, enantiomer, diastereomer, racemate, hydrate, solvate, or a salt thereof, or a mixture of same.

In yet another preferred embodiment, the invention relates to compounds of formula (Ia), wherein
$R^2$ represents (2R,3R)-3-hydroxybutan-2-yl, or (2S,3S)-3-hydroxybutan-2-yl; and
in which $R^1$, A and $R^3$ have the same meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein
A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^1$ represents methyl or ethyl; and
in which $R^2$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^1$ represents methyl or ethyl; and
in which $R^2$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^3$ represents a methyl group; and
in which $R^1$ and $R^2$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (I), wherein
A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_4$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl;
  wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and
q represents an integer of 0; and
in which $R^c$, $R^1$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (I), wherein
A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl;
  wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and
q represents an integer of 0; and
in which $R^c$, $R^1$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein
A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_4$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl;
  wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and
q represents an integer of 0; and
in which $R^c$, $R^1$ and $R^3$ have the meaning as defined in general formula (Ia),
or an isomer, enantiomer, diastereomer, racemate, hydrate, solvate, or a salt thereof, or a mixture of same.

In another preferred embodiment, the invention relates to compounds of general formula (Ia), wherein
A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl;
  wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and
q represents an integer of 0; and
in which $R^c$, $R^1$ and $R^3$ have the meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and
  wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl; and
q represents an integer of 1; and
in which $R^c$, $R^1$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$(CH_2)_q$-morpholinyl, wherein the ring nitrogen atom is substituted with $R^c$; and
$R^c$ represents methyl; and
q represents an integer of 1; and
in which $R^1$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and
  wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl; and
q represents an integer of 1; and
in which $R^c$, $R^1$ and $R^3$ have the meaning as defined in general formula (Ia),
or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$(CH_2)_q$-morpholinyl, wherein the ring nitrogen atom is substituted with $R^c$; and
$R^c$ represents methyl; and
q represents an integer of 1; and
in which $R^1$ and $R^3$ have the meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_4$-alkyl-OH; and
in which $R^1$ and $R^3$ have the meaning as defined in general formula (I),
or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, $C_1$-$C_2$-alkyl, optionally substituted with 1-5 fluorine atoms, or $C_1$-$C_2$-alkoxy, optionally substituted with 1-5 fluorine atoms;
$R^2$ represents —$C_2$-$C_4$-alkyl-OH; and
in which $R^1$ and $R^3$ have the meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl;
  wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl; and in which $R^2$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl; and in which $R^2$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^3$ represents methyl; and in which $R^1$ and $R^2$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$C_2$-$C_3$-alkyl-$OR^4$, —$CH_2$—($C_3$-$C_4$-cycloalkyl), $C_3$-$C_4$-cycloalkyl, —$(CH_2)q$-(4- to 6-membered heterocycloalkyl), or —$C_2$-$C_4$-alkynyl;
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and q represents an integer of 0; and in which $R^c$, $R^1$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$C_2$-$C_3$-alkyl-$OR^4$, —$CH_2$—($C_3$-$C_4$-cycloalkyl), $C_3$-$C_4$-cycloalkyl, $(CH_2)q$-(4- to 6-membered heterocycloalkyl), or —$C_2$-$C_4$-alkynyl;
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and q represents an integer of 0; and in which $R^c$, $R^1$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and
wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl;

q represents an integer of 1; and in which $R^c$, $R^1$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl;

q represents an integer of 1; and in which $R^c$, $R^1$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$C_2$-$C_4$-alkyl-OH; and in which $R^1$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl;
wherein said 5-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$C_2$-$C_4$-alkyl-OH; and in which $R^1$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^3$ represents methyl; and in which $R^2$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents chloro;

$R^3$ represents methyl; and in which $R^2$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^3$ represents methyl;

$R^2$ represents —$C_2$-$C_4$-alkyl-$OR^4$, $CH_2$—($C_3$-$C_4$-cycloalkyl), $C_3$-$C_4$-cycloalkyl, —$(CH_2)_q$-(4 to 6-membered heterocycloalkyl), or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted one or two times, identically or differently, at any ring carbon atom with a substituent selected from $C_1$-$C_4$-alkyl, optionally substituted with 1-5 halogen atoms which are the same or different, a halogen atom, —$NR^aR^b$ or —$COOR^5$; and wherein independently any ring nitrogen atom, if present in said —$(CH_2)_q$-(4- to 6-membered heterocycloalkyl) is substituted with $R^c$; and q represents an integer of 0; and in which $R^c$ and $R^1$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^3$ represents methyl;

$R^2$ represents —$C_2$-$C_3$-alkyl-$OR^4$, $CH_2$—($C_3$-$C_4$-cycloalkyl), $C_3$-$C_4$-cycloalkyl, —$(CH_2)_q$-(4 to 6-membered heterocycloalkyl), or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted one or two times, identically or differently, at any ring carbon atom with a substituent selected from $C_1$-$C_4$-alkyl, optionally substituted with 1-5 halogen atoms which are the same or different, a halogen atom, —$NR^aR^b$ or —COOR$^5$; and wherein independently any ring nitrogen atom, if present in said —(CH$_2$)$_q$-(4- to 6-membered heterocycloalkyl) is substituted with R$^c$; and q represents an integer of 0; and in which R$^c$ and R$^1$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, C$_1$-C$_2$-alkyl, optionally substituted with 1 to 5 fluorine atoms, or C$_1$-C$_2$-alkoxy, optionally substituted with 1 to 5 fluorine atoms;

R$^3$ represents methyl;

R$^2$ represents —(CH$_2$)$_q$-(4- to 6-membered heterocycloalkyl); and wherein (CH$_2$)$_q$-(4- to 6-membered heterocycloalkyl) is optionally substituted with one or two substituents which are the same or different, at any ring carbon atom and selected from the group consisting of C$_1$-C$_4$-alkyl, optionally substituted with 1-5 halogen atoms which are the same or different, a halogen atom, —NR$^a$R$^b$ and —COOR$^5$; and
  wherein independently any ring nitrogen atom, if present in said —(CH$_2$)q-(4 to 6-membered heterocycloalkyl) is substituted with R$^c$; and wherein said —(CH$_2$)$_q$-(4 to 6-membered heterocycloalkyl) is preferably —(CH$_2$)$_q$-morpholinyl;

q represents an integer of 1; and in which R$^c$ and R$^1$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, C$_1$-C$_2$-alkyl, optionally substituted with 1 to 5 fluorine atoms, or C$_1$-C$_2$-alkoxy, optionally substituted with 1 to 5 fluorine atoms;

R$^3$ represents methyl;

R$^2$ represents —(CH$_2$)$_q$-morpholinyl, wherein the ring nitrogen atom is substituted with R$^c$; and R$^c$ represents methyl;

q represents an integer of 1; and in which R$^1$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 6-membered heteroaryl, in particular pyrimidinyl or pyridazinyl;
  wherein said 6-membered heteroaryl is optionally substituted one or two times, identically or differently, with a substituent selected from a fluorine or chlorine atom, C$_1$-C$_2$-alkyl, optionally substituted with 1 to 5 fluorine atoms, or C$_1$-C$_2$-alkoxy, optionally substituted with 1 to 5 fluorine atoms;

R$^3$ represents methyl;

R$^2$ represents C$_2$-C$_4$-alkyl-OH, preferably 3-hydroxybutan-2-yl; and in which R$^1$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl,
  wherein said 6-membered heteroaryl is optionally substituted one or two times, identically or differently, with a substituent selected from a fluorine or chlorine atom, C$_1$-C$_2$-alkyl, optionally substituted with 1 to 5 fluorine atoms, or C$_1$-C$_2$-alkoxy, optionally substituted with 1 to 5 fluorine atoms;

R$^1$ represents methyl or ethyl;

R$^2$ represents —C$_2$-C$_4$-alkyl-OR$^4$, —CH$_2$—(C$_3$-C$_4$-cycloalkyl), C$_3$-C$_4$-cycloalkyl, —(CH$_2$)$_q$-(4 to 6-membered heterocycloalkyl) or —C$_2$-C$_4$-alkynyl,
  wherein said —CH$_2$—(C$_3$-C$_4$-cycloalkyl), C$_3$-C$_4$-cycloalkyl and —(CH$_2$)$_q$-(4- to 6-membered heterocycloalkyl) are optionally substituted with one or two substituents which are the same or different, at any ring carbon atom and selected from the group consisting of C$_1$-C$_4$-alkyl, optionally substituted with 1-5 halogen atoms which are the same or different, a halogen atom, —NR$^a$R$^b$ and —COOR$^5$; and wherein independently any ring nitrogen atom, if present in said —(CH$_2$)$_q$-(4- to 6-membered heterocycloalkyl) is substituted with R$^c$; and q represents an integer of 0; and in which R$^c$ and R$^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl,
  wherein said 6-membered heteroaryl is optionally substituted one or two times, identically or differently, with a substituent selected from a fluorine or chlorine atom, C$_1$-C$_2$-alkyl, optionally substituted with 1 to 5 fluorine atoms, or C$_1$-C$_2$-alkoxy, optionally substituted with 1 to 5 fluorine atoms;

R$^1$ represents methyl or ethyl;

R$^2$ represents —C$_2$-C$_4$-alkyl-OR$^4$, —CH$_2$—(C$_3$-C$_4$-cycloalkyl), C$_3$-C$_4$-cycloalkyl, —(CH$_2$)$_q$-(4 to 6-membered heterocycloalkyl) or —C$_2$-C$_4$-alkynyl,
  wherein said —CH$_2$—(C$_3$-C$_4$-cycloalkyl), C$_3$-C$_4$-cycloalkyl and —(CH$_2$)$_q$-(4- to 6-membered heterocycloalkyl) are optionally substituted with one or two substituents which are the same or different, at any ring carbon atom and selected from the group consisting of C$_1$-C$_4$-alkyl, optionally substituted with 1-5 halogen atoms which are the same or different, a halogen atom, —NR$^a$R$^b$ and —COOR$^5$; and wherein independently any ring nitrogen atom, if present in said —(CH$_2$)$_q$-(4- to 6-membered heterocycloalkyl) is substituted with R$^c$; and q represents an integer of 0; and in which $R^c$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4 to 6-membered heterocycloalkyl) or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and q represents an integer of 0; and in which $R^c$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4 to 6-membered heterocycloalkyl) or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$; and q represents an integer of 0; and in which $R^c$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl;

q represents an integer of 1; and in which $R^c$ and $R^3$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-morpholinyl, wherein the ring nitrogen atom is substituted with $R^c$; and $R^c$ represents methyl;

q represents an integer of 1; and in which $R^3$ has the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; and wherein said —$(CH_2)_q$-(4 to 6-membered heterocycloalkyl) is preferably —$(CH_2)_q$-morpholinyl;

q represents an integer of 1; and in which $R^c$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl; $R^2$ represents —$(CH_2)_q$-morpholinyl, wherein the ring nitrogen atom is substituted with $R^c$; and $R^c$ represents methyl;

q represents an integer of 1; and in which $R^3$ has the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents chloro;

$R^2$ represents $C_2$-$C_4$-alkyl-OH, preferably 3-hydroxybutan-2-yl; and in which $R^3$ has the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 6-membered heteroaryl, in particular pyrimidinyl or pyridazinyl, wherein said 6-membered heteroaryl is optionally substituted one or two times, identically or differently, with a substituent selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents chloro;

$R^2$ represents $C_2$-$C_4$-alkyl-OH, preferably 3-hydroxybutan-2-yl; and in which $R^3$ has the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular thiazolyl or thiadiazolyl, wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^3$ represents methyl; and in which $R^2$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular thiazolyl or thiadiazolyl,
wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents chloro;

$R^3$ represents methyl;

in which $R^2$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular thiazolyl or thiadiazolyl,
wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$C_2$-$C_3$-alkyl-$OR^4$, —$CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl;
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4- to 6-membered heterocycloalkyl) is substituted with $R^c$;

$R^3$ represents methyl;

q represents an integer of 0; and in which $R^c$ and $R^1$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular thiazolyl or thiadiazolyl,
wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; wherein said —$(CH_2)_q$-(4- to 6-membered heterocycloalkyl) is preferably —$(CH_2)_q$-morpholinyl;

$R^3$ represents methyl;

q represents an integer of 1; and in which $R^c$ and $R^1$ have the meaning as defined in general formula (I), or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl, wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$C_2$-$C_3$-alkyl-$OR^4$, $CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted one or two times, identically or differently, at any ring carbon atom with a substituent selected from $C_1$-$C_4$-alkyl, optionally substituted with 1-5 halogen atoms which are the same or different, a halogen atom, —$NR^aR^b$ or —$COOR^5$; and wherein independently any ring nitrogen atom of said —$(CH_2)_q$-(4- to 6-membered heterocycloalkyl) is substituted with $R^c$; and q represents an integer of 0;

in which $R^c$ and $R^3$ have the meaning as defined in general formula (I), and or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl, wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$C_2$-$C_3$-alkyl-$OR^4$, $CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl, wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted one or two times, identically or differently, at any ring carbon atom with a substituent selected from $C_1$-$C_4$-alkyl, optionally substituted with 1-5 halogen atoms which are the same or different, a halogen atom, —$NR^aR^b$ or —$COOR^5$; and wherein independently any ring nitrogen atom of said —$(CH_2)_q$-(4- to 6-membered heterocycloalkyl) is substituted with $R^c$;

q represents an integer of 0; and in which $R^c$ and $R^3$ have the meaning as defined in general formula (Ia), or an isomer, enantiomer, diastereomer, racemate, hydrate, solvate, or a salt thereof, or a mixture of same.

In another preferred embodiment, the invention relates to compounds of general formula (I), wherein A represents a 5-membered heteroaryl, in particular thiazolyl or thiadiazolyl, wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl;

q represents an integer of 1; and in which $R^c$ and $R^3$ have has the meaning as defined in general formula (I), or an isomer, enantiomer, diastereomer, racemate, hydrate, solvate, or a salt thereof, or a mixture of same.

In another preferred embodiment, the invention relates to compounds of general formula (Ia), wherein A represents a 5-membered heteroaryl, in particular thiazolyl or thiadiazolyl, wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl;

q represents an integer of 1; and
in which $R^c$ and $R^3$ have has the meaning as defined in general formula (Ia),
or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 6-membered heteroaryl, in particular pyrimidinyl or pyridazinyl;
wherein said 6-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;
$R^1$ represents methyl or ethyl;
$R^2$ represents —$C_2$-$C_3$-alkyl-OR$^4$, $CH_2$—($C_3$-$C_4$-cycloalkyl), $C_3$-$C_4$-cycloalkyl, —$(CH_2)_q$-(4- to 6-membered heterocycloalkyl), or —$C_2$-$C_4$-alkynyl,
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or two substituents which are the same or different, at any ring carbon atom and selected from the group consisting of $C_1$-$C_4$-alkyl, optionally substituted with 1-5 halogen atoms which are the same or different, a halogen atom, —NR$^a$R$^b$ and —COOR$^5$; and wherein independently any ring nitrogen atom, if present in said —$(CH_2)_q$-(4- to 6-membered heterocycloalkyl) is substituted with $R^c$; and
$R^3$ represents methyl; and
q represents an integer of 0,
in which $R^c$ has the meaning as defined in general formula (I), or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 6-membered heteroaryl, in particular pyrimidinyl or pyridazinyl;
wherein said 6-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;
$R^1$ represents methyl or ethyl;
$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —NR$^a$R$^b$ and —COOR$^5$; and
wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl;
$R^3$ represents methyl; and
q represents an integer of 1,
in which $R^c$ has the meaning as defined in general formula (I),
or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 6-membered heteroaryl, in particular pyrimidinyl or pyridazinyl;
wherein said 6-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;
$R^1$ represents methyl or ethyl;
$R^2$ represents —$(CH_2)_q$-morpholinyl, wherein the ring nitrogen atom is substituted with $R^c$; and
$R^c$ represents methyl;
$R^3$ represents methyl; and
q represents an integer of 1,
or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 6-membered heteroaryl, in particular pyrimidinyl or pyridazinyl;
wherein said 6-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;
$R^1$ represents chloro;
$R^2$ represents —$C_2$-$C_4$-alkyl-OH, preferably 3-hydroxybutan-2-yl; and
$R^3$ represents methyl,
or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein
A represents a 5-membered heteroaryl, in particular a thiazolyl or thiadiazolyl;
wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;
$R^1$ represents methyl or ethyl;
$R^2$ represents —$C_2$-$C_3$-alkyl-OR$^4$, $CH_2$—($C_3$-$C_4$-cycloalkyl), $C_3$-$C_4$-cycloalkyl, —$(CH_2)_q$-(4 to 6-membered heterocycloalkyl), or —$C_2$-$C_4$-alkynyl
wherein said —$CH_2$—($C_3$-$C_4$-cycloalkyl), $C_3$-$C_4$-cycloalkyl and —$(CH_2)_q$-(4- to 6-membered heterocycloalkyl) are optionally substituted with one or more substituents which are the same or different, at any ring carbon atom and selected from the group consisting of $C_1$-$C_4$-alkyl, optionally substituted with 1-5 halogen atoms which are the same or different, a halogen atom, —NR$^a$R$^b$ and —COOR$^5$; and wherein independently any ring nitrogen atom if present in said —$(CH_2)_q$-(4- to 6-membered heterocycloalkyl) is substituted with $R^c$; and
$R^3$ represents methyl; and
q represents an integer of 0,
in which $R^c$ has the meaning as defined in formula (I),
or an isomer, enantiomer, diastereomer, racemate, hydrate, solvate, or a salt thereof, or a mixture of same.

In another preferred embodiment, the invention relates to compounds of general formula (I), more preferably to compounds of general formula (Ia), wherein A represents a 5-membered heteroaryl, in particular a thiazolyl or thiadiazolyl;
  wherein said 5-membered heteroaryl is optionally substituted with one or two substituents which are the same or different, and selected from a fluorine or chlorine atom, $C_1$-$C_2$-alkyl, optionally substituted with 1 to 5 fluorine atoms, or $C_1$-$C_2$-alkoxy, optionally substituted with 1 to 5 fluorine atoms;

$R^1$ represents methyl or ethyl;

$R^2$ represents —$(CH_2)_q$-(4- to 6-membered heterocycloalkyl); and wherein $(CH_2)_q$-(4- to 6-membered heterocycloalkyl) is optionally substituted with one or two substituents which are the same or different, at any ring carbon atom and selected from the group consisting of $C_1$-$C_4$-alkyl, optionally substituted with 1-5 halogen atoms which are the same or different, a halogen atom, —$NR^aR^b$ and —$COOR^5$; and
  wherein independently any ring nitrogen atom, if present in said —$(CH_2)_q$-(4 to 6-membered heterocycloalkyl) is substituted with $R^c$; and wherein —$(CH_2)_q$-(4- to 6-membered heterocycloalkyl) is preferably —$(CH_2)_q$-morpholinyl;
and $R^3$ represents methyl; and q represents an integer of 1,
in which $R^c$ has the meaning as defined in formula (I), or an isomer, enantiomer, diastereomer, racemate, hydrate, solvate, or a salt thereof, or a mixture of same.

The following compounds are disclosed, namely
1) 3-(cyclopropylmethoxy)-5-(5-methyl-1,3-thiazol-2-yl)-N-{(1R)-1-[2-(trifluoromethyl)pyrimidin-5-yl]ethyl}benzamide
2) 3-(cyclopropylmethoxy)-N-[(6-methylpyridazin-3-yl)methyl]-5-(5-methyl-1,3-thiazol-2-yl)benzamide
3) 3-(cyclopropylmethoxy)-N-[(5-methylpyrazin-2-yl)methyl]-5-(5-methyl-1,3-thiazol-2-yl)benzamide
4) 3-(cyclopropylmethoxy)-N-[(1R)-1-(5-methylpyrazin-2-yl)ethyl]-5-(5-methyl-1,3-thiazol-2-yl)benzamide
5) N-[1-(3-chloro-5-fluoropyridin-2-yl)ethyl]-3-(cyclopropylmethoxy)-5-(5-methyl-1,3-thiazol-2-yl)benzamide
6) N-[1-(5-chloro-3-fluoropyridin-2-yl)ethyl]-3-(cyclopropylmethoxy)-5-(5-methyl-1,3-thiazol-2-yl)benzamide
7) 3-(cyclopropylmethoxy)-N-[(1R)-1-(5-methyl-1,3,4-thiadiazol-2-yl)ethyl]-5-(5-methyl-1,3-thiazol-2-yl)benzamide
8) 3-(cyclopropylmethoxy)-N-[(1R)-1-(6-methylpyridazin-3-yl)ethyl]-5-(5-methyl-1,3-thiazol-2-yl)benzamide
9) 3-(cyclopropylmethoxy)-5-(5-methyl-1,3-thiazol-2-yl)-N-{(1R)-1-[6-(trifluoromethyl)pyridazin-3-yl]ethyl}benzamide
10) 3-(cyclopropylmethoxy)-N-[(1R)-1-(2-methylpyrimidin-5-yl)ethyl]-5-(5-methyl-1,3-thiazol-2-yl)benzamide
11) 3-(5-methyl-1,3-thiazol-2-yl)-5-[(3R)-tetrahydrofuran-3-yloxy]-N-{(1R)-1-[2-(trifluoromethyl)pyrimidin-5-yl]ethyl}benzamide
12) N-[(5-methylpyrazin-2-yl)methyl]-3-(5-methyl-1,3-thiazol-2-yl)-5-[(3R)-tetrahydrofuran-3-yloxy]benzamide
13) N-[1-(3-chloro-5-fluoropyridin-2-yl)ethyl]-3-(5-methyl-1,3-thiazol-2-yl)-5-[(3R)-tetrahydrofuran-3-yloxy]benzamide
14) N-[1-(5-chloro-3-fluoropyridin-2-yl)ethyl]-3-(5-methyl-1,3-thiazol-2-yl)-5-[(3R)-tetrahydrofuran-3-yloxy]benzamide
15) N-[(1R)-1-(5-chloropyridin-2-yl)ethyl]-3-(5-methyl-1,3-thiazol-2-yl)-5-[(3R)-tetrahydrofuran-3-yloxy]benzamide
16) N-[(1R)-1-(5-methylpyrazin-2-yl)ethyl]-3-(5-methyl-1,3-thiazol-2-yl)-5-[(3R)-tetrahydrofuran-3-yloxy]benzamide
17) N-[(6-methylpyridazin-3-yl)methyl]-3-(5-methyl-1,3-thiazol-2-yl)-5-[(3R)-tetrahydrofuran-3-yloxy]benzamide
18) N-[(1R)-1-(6-methylpyridazin-3-yl)ethyl]-3-(5-methyl-1,3-thiazol-2-yl)-5-[(3R)-tetrahydrofuran-3-yloxy]benzamide
19) 3-(5-methyl-1,3-thiazol-2-yl)-5-[(3R)-tetrahydrofuran-3-yloxy]-N-{(1R)-1-[6-(trifluoromethyl)pyridazin-3-yl]ethyl}benzamide
20) N-[(1R)-1-(5-methyl-1,3,4-thiadiazol-2-yl)ethyl]-3-(5-methyl-1,3-thiazol-2-yl)-5-[(3R)-tetrahydrofuran-3-yloxy]benzamide
21) 3-(5-methyl-1,3-thiazol-2-yl)-5-[(3R)-tetrahydrofuran-3-yloxy]-N-{[6-(trifluoromethyl)pyridazin-3-yl]methyl}benzamide
22) 3-(5-methyl-1,3-thiazol-2-yl)-5-[(3R)-tetrahydrofuran-3-yloxy]-N-{(1R)-1-[2-(trifluoromethyl)pyrimidin-5-yl]propyl}benzamide
23) N-[(1R)-1-(2-methylpyrimidin-5-yl)ethyl]-3-(5-methyl-1,3-thiazol-2-yl)-5-[(3R)-tetrahydrofuran-3-yloxy]benzamide
24) N-[(1R)-1-(6-methylpyridin-3-yl)ethyl]-3-(5-methyl-1,3-thiazol-2-yl)-5-[(3R)-tetrahydrofuran-3-yloxy]benzamide
25) N-[(1R)-1-(6-methylpyridazin-3-yl)ethyl]-3-(5-methyl-1,3-thiazol-2-yl)-5-[(3S)-tetrahydrofuran-3-yloxy]benzamide
26) 3-(5-methyl-1,3-thiazol-2-yl)-5-[(3S)-tetrahydrofuran-3-yloxy]-N-{(1R)-1-[2-(trifluoromethyl)pyrimidin-5-yl]ethyl}benzamide
27) N-[(1R)-1-(5-chloropyridin-2-yl)ethyl]-3-(5-methyl-1,3-thiazol-2-yl)-5-[(3S)-tetrahydrofuran-3-yloxy]benzamide
28) N-[(1R)-1-(5-methylpyrazin-2-yl)ethyl]-3-(5-methyl-1,3-thiazol-2-yl)-5-[(3S)-tetrahydrofuran-3-yloxy]benzamide
29) N-[(1R)-1-(5-methylpyrazin-2-yl)ethyl]-3-(5-methyl-1,3-thiazol-2-yl)-5-[(3S)-tetrahydrofuran-3-yloxy]benzamide
30) N-[(1R)-1-(6-methylpyridin-3-yl)ethyl]-3-(5-methyl-1,3-thiazol-2-yl)-5-[(3S)-tetrahydrofuran-3-yloxy]benzamide
31) N-[(6-methylpyridazin-3-yl)methyl]-3-(5-methyl-1,3-thiazol-2-yl)-5-(prop-2-yn-1-yloxy)benzamide
32) N-[(5-chloro-3-fluoropyridin-2-yl)methyl]-3-(5-methyl-1,3-thiazol-2-yl)-5-(prop-2-yn-1-yloxy)benzamide
33) N-[(1R)-1-(6-methylpyridin-3-yl)ethyl]-3-(5-methyl-1,3-thiazol-2-yl)-5-(prop-2-yn-1-yloxy)benzamide
34) N-[(1R)-1-(5-methylpyrazin-2-yl)ethyl]-3-(5-methyl-1,3-thiazol-2-yl)-5-(prop-2-yn-1-yloxy)benzamide
35) N-[(5-methylpyrazin-2-yl)methyl]-3-(5-methyl-1,3-thiazol-2-yl)-5-(prop-2-yn-1-yloxy)benzamide
36) 3-(5-methyl-1,3-thiazol-2-yl)-5-(prop-2-yn-1-yloxy)-N-{(1R)-1-[2-(trifluoromethyl)pyrimidin-5-yl]ethyl}benzamide
37) N-[(1R)-1-(6-methylpyridazin-3-yl)ethyl]-3-(5-methyl-1,3-thiazol-2-yl)-5-(prop-2-yn-1-yloxy)benzamide
38) 3-(5-methyl-1,3-thiazol-2-yl)-5-(prop-2-yn-1-yloxy)-N-{(1R)-1-[6-(trifluoromethyl)pyridazin-3-yl]ethyl}benzamide
39) N-[(1R)-1-(2-methylpyrimidin-5-yl)ethyl]-3-(5-methyl-1,3-thiazol-2-yl)-5-(prop-2-yn-1-yloxy)benzamide 40) 3-(but-2-yn-1-yloxy)-5-(5-methyl-1,3-thiazol-2-yl)-N-{(1R)-1-[2-(trifluoromethyl)pyrimidin-5-yl]ethyl}benzamide
41) 3-(but-2-yn-1-yloxy)-N-[(1R)-1-(5-methyl-1,3,4-thiadiazol-2-yl)ethyl]-5-(5-methyl-1,3-thiazol-2-yl)benzamide
42) N-[(1R)-1-(5-methylpyrazin-2-yl)ethyl]-3-(5-methyl-1,3-thiazol-2-yl)-5-(oxetan-3-yloxy)benzamide
43) N-[(1R)-1-(2-methylpyrimidin-5-yl)ethyl]-3-(5-methyl-1,3-thiazol-2-yl)-5-(oxetan-3-yloxy)benzamide
44) N-[1-(5-chloro-3-fluoropyridin-2-yl)ethyl]-3-(5-methyl-1,3-thiazol-2-yl)-5-(oxetan-3-yloxy)benzamide
45) N-[(6-methylpyridazin-3-yl)methyl]-3-(5-methyl-1,3-thiazol-2-yl)-5-(oxetan-3-yloxy)benzamide
46) N-[(1R)-1-(5-chloropyridin-2-yl)ethyl]-3-(5-methyl-1,3-thiazol-2-yl)-5-(oxetan-3-yloxy)benzamide
47) N-[(1R)-1-(6-methylpyridazin-3-yl)ethyl]-3-(5-methyl-1,3-thiazol-2-yl)-5-(oxetan-3-yloxy)benzamide
48) 3-(5-methyl-1,3-thiazol-2-yl)-5-(oxetan-3-yloxy)-N-{(1R)-1-[2-(trifluoromethyl)pyrimidin-5-yl]ethyl}benzamide
49) N-[1-(3-chloro-5-fluoropyridin-2-yl)ethyl]-3-(5-methyl-1,3-thiazol-2-yl)-5-(oxetan-3-yloxy)benzamide
50) N-[(1R)-1-(5-methyl-1,3,4-thiadiazol-2-yl)ethyl]-3-(5-methyl-1,3-thiazol-2-yl)-5-(oxetan-3-yloxy)benzamide
51) N-[(1R)-1-(6-methylpyridin-3-yl)ethyl]-3-(5-methyl-1,3-thiazol-2-yl)-5-(oxetan-3-yloxy)benzamide
52) 3-(5-methyl-1,3-thiazol-2-yl)-5-(oxetan-3-yloxy)-N-{[6-(trifluoromethyl)pyridazin-3-yl]methyl}benzamide
53) 3-(5-methyl-1,3-thiazol-2-yl)-5-(oxetan-3-yloxy)-N-{(1R)-1-[2-(trifluoromethyl)pyrimidin-5-yl]propyl}benzamide
54) N-[(6-methylpyridazin-3-yl)methyl]-3-(5-methyl-1,3-thiazol-2-yl)-5-[(2S)-tetrahydrofuran-2-ylmethoxy]benzamide
55) N-[(5-chloro-3-fluoropyridin-2-yl)methyl]-3-(5-methyl-1,3-thiazol-2-yl)-5-[(2S)-tetrahydrofuran-2-ylmethoxy]benzamide
56) N-[(5-methylpyrazin-2-yl)methyl]-3-(5-methyl-1,3-thiazol-2-yl)-5-[(2S)-tetrahydrofuran-2-ylmethoxy]benzamide
57) N-[(1R)-1-(5-methylpyrazin-2-yl)ethyl]-3-(5-methyl-1,3-thiazol-2-yl)-5-[(2S)-tetrahydrofuran-2-ylmethoxy]benzamide
58) 3-(5-methyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide
59) N-[(1R)-1-(6-methylpyridazin-3-yl)ethyl]-3-(5-methyl-1,3-thiazol-2-yl)-5-[(2S)-tetrahydrofuran-2-ylmethoxy]benzamide
60) 3-(5-methyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide
61) N-[(1R)-1-(6-methylpyridazin-3-yl)ethyl]-3-(5-methyl-1,3-thiazol-2-yl)-5-[(2R)-tetrahydrofuran-2-ylmethoxy]benzamide
62) N-[(6-methylpyridazin-3-yl)methyl]-3-(5-methyl-1,3-thiazol-2-yl)-5-[(2R)-tetrahydrofuran-2-ylmethoxy]benzamide
63) 3-(5-methyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide
64) N-[(1R)-1-(5-methylpyrazin-2-yl)ethyl]-3-(5-methyl-1,3-thiazol-2-yl)-5-[(2R)-tetrahydrofuran-2-ylmethoxy]benzamide
65) N-[1-(5-chloro-3-fluoropyridin-2-yl)ethyl]-3-(5-methyl-1,3-thiazol-2-yl)-5-[(3S)-tetrahydrofuran-3-ylmethoxy]benzamide
66) N-[(6-methylpyridazin-3-yl)methyl]-3-(5-methyl-1,3-thiazol-2-yl)-5-[(3S)-tetrahydrofuran-3-ylmethoxy]benzamide
67) N-[(5-methylpyrazin-2-yl)methyl]-3-(5-methyl-1,3-thiazol-2-yl)-5-[(3S)-tetrahydrofuran-3-ylmethoxy]benzamide
68) N-[(1R)-1-(5-methylpyrazin-2-yl)ethyl]-3-(5-methyl-1,3-thiazol-2-yl)-5-[(3S)-tetrahydrofuran-3-ylmethoxy]benzamide
69) N-[1-(3-chloro-5-fluoropyridin-2-yl)ethyl]-3-(5-methyl-1,3-thiazol-2-yl)-5-[(3R)-tetrahydrofuran-3-ylmethoxy]benzamide
70) 3-(5-methyl-1,3-thiazol-2-yl)-5-[(3S)-tetrahydrofuran-3-ylmethoxy]-N-{(1R)-1-[2-(trifluoromethyl)pyrimidin-5-yl]ethyl}benzamide
71) N-[(1R)-1-(6-methylpyridazin-3-yl)ethyl]-3-(5-methyl-1,3-thiazol-2-yl)-5-[(3S)-tetrahydrofuran-3-ylmethoxy]benzamide
72) 3-(5-methyl-1,3-thiazol-2-yl)-5-[(3S)-tetrahydrofuran-3-ylmethoxy]-N-{(1R)-1-[6-(trifluoromethyl)pyridazin-3-yl]ethyl}benzamide
73) 3-(5-methyl-1,3-thiazol-2-yl)-5-[(3R)-tetrahydrofuran-3-ylmethoxy]-N-{(1R)-1-[2-(trifluoromethyl)pyrimidin-5-yl]ethyl}benzamide
74) N-[(1R)-1-(5-methylpyrazin-2-yl)ethyl]-3-(5-methyl-1,3-thiazol-2-yl)-5-[(3R)-tetrahydrofuran-3-ylmethoxy]benzamide
75) N-[(6-methylpyridazin-3-yl)methyl]-3-(5-methyl-1,3-thiazol-2-yl)-5-[(3R)-tetrahydrofuran-3-ylmethoxy]benzamide
76) N-[(5-methylpyrazin-2-yl)methyl]-3-(5-methyl-1,3-thiazol-2-yl)-5-[(3R)-tetrahydrofuran-3-ylmethoxy]benzamide
77) N-[(1R)-1-(6-methylpyridazin-3-yl)ethyl]-3-(5-methyl-1,3-thiazol-2-yl)-5-[(3R)-tetrahydrofuran-3-ylmethoxy]benzamide
78) N-[1-(5-chloro-3-fluoropyridin-2-yl)ethyl]-3-(5-methyl-1,3-thiazol-2-yl)-5-[(3R)-tetrahydrofuran-3-ylmethoxy]benzamide
79) 3-(5-methyl-1,3-thiazol-2-yl)-5-[(3R)-tetrahydrofuran-3-ylmethoxy]-N-{(1R)-1-[6-(trifluoromethyl)pyridazin-3-yl]ethyl}benzamide
80) N-[1-(3-chloro-5-fluoropyridin-2-yl)ethyl]-3-(5-methyl-1,3-thiazol-2-yl)-5-(tetrahydro-2H-pyran-4-yloxy)benzamide
81) N-[1-(5-chloro-3-fluoropyridin-2-yl)ethyl]-3-(5-methyl-1,3-thiazol-2-yl)-5-(tetrahydro-2H-pyran-4-yloxy)benzamide
82) N-[(6-methylpyridazin-3-yl)methyl]-3-(5-methyl-1,3-thiazol-2-yl)-5-(tetrahydro-2H-pyran-4-yloxy)benzamide
83) N-[(5-methylpyrazin-2-yl)methyl]-3-(5-methyl-1,3-thiazol-2-yl)-5-(tetrahydro-2H-pyran-4-yloxy)benzamide
84) N-[(1R)-1-(5-methylpyrazin-2-yl)ethyl]-3-(5-methyl-1,3-thiazol-2-yl)-5-(tetrahydro-2H-pyran-4-yloxy)benzamide
85) 3-(5-methyl-1,3-thiazol-2-yl)-5-(tetrahydro-2H-pyran-4-yloxy)-N-{(1R)-1-[2-(trifluoromethyl)pyrimidin-5-yl]ethyl}benzamide
86) N-[(1R)-1-(6-methoxypyridin-3-yl)ethyl]-3-(5-methyl-1,3-thiazol-2-yl)-5-(tetrahydro-2H-pyran-4-yloxy)benzamide
87) N-[(1R)-1-(6-methylpyridazin-3-yl)ethyl]-3-(5-methyl-1,3-thiazol-2-yl)-5-(tetrahydro-2H-pyran-4-yloxy)benzamide
88) N-[(6-methoxypyridazin-3-yl)methyl]-3-(5-methyl-1,3-thiazol-2-yl)-5-(tetrahydro-2H-pyran-4-yloxy)benzamide 89) 3-(5-methyl-1,3-thiazol-2-yl)-5-(tetrahydro-2H-pyran-4-yloxy)-N-{(1R)-1-[6-(trifluoromethyl)pyridazin-3-yl]ethyl}benzamide
90) 3-(5-methyl-1,3-thiazol-2-yl)-5-(tetrahydro-2H-pyran-4-yloxy)-N-{(1R)-1-[2-(trifluoromethyl)pyrimidin-5-yl]propyl}benzamide
91) N-[(1R)-1-(6-methylpyridin-3-yl)ethyl]-3-(5-methyl-1,3-thiazol-2-yl)-5-(tetrahydro-2H-pyran-4-yloxy)benzamide
92) N-[(1R)-1-(5-methyl-1,3,4-thiadiazol-2-yl)ethyl]-3-(5-methyl-1,3-thiazol-2-yl)-5-(tetrahydro-2H-pyran-4-yloxy)benzamide
93) N-[(6-methylpyridazin-3-yl)methyl]-3-(5-methyl-1,3-thiazol-2-yl)-5-(tetrahydro-2H-pyran-4-ylmethoxy)benzamide
94) N-[(1R)-1-(5-methylpyrazin-2-yl)ethyl]-3-(5-methyl-1,3-thiazol-2-yl)-5-(tetrahydro-2H-pyran-4-ylmethoxy)benzamide
95) N-[1-(5-chloro-3-fluoropyridin-2-yl)ethyl]-3-(5-methyl-1,3-thiazol-2-yl)-5-(tetrahydro-2H-pyran-4-ylmethoxy)benzamide
96) N-[1-(3-chloro-5-fluoropyridin-2-yl)ethyl]-3-(5-methyl-1,3-thiazol-2-yl)-5-(tetrahydro-2H-pyran-4-ylmethoxy)benzamide
97) N-[(5-methylpyrazin-2-yl)methyl]-3-(5-methyl-1,3-thiazol-2-yl)-5-(tetrahydro-2H-pyran-4-ylmethoxy)benzamide
98) 3-(5-methyl-1,3-thiazol-2-yl)-5-(tetrahydro-2H-pyran-4-ylmethoxy)-N-{(1R)-1-[2-(trifluoromethyl)pyrimidin-5-yl]ethyl}benzamide
99) N-[(1R)-1-(6-methylpyridazin-3-yl)ethyl]-3-(5-methyl-1,3-thiazol-2-yl)-5-(tetrahydro-2H-pyran-4-ylmethoxy)benzamide
100) N-[(1R)-1-(6-methylpyridazin-3-yl)ethyl]-3-[(2-methylpyridin-4-yl)oxy]-5-(5-methyl-1,3-thiazol-2-yl)benzamide
101) N-[(6-methylpyridazin-3-yl)methyl]-3-[(2-methylpyridin-4-yl)oxy]-5-(5-methyl-1,3-thiazol-2-yl)benzamide
102) N-[(1R)-1-(5-methylpyrazin-2-yl)ethyl]-3-[(2-methylpyridin-4-yl)oxy]-5-(5-methyl-1,3-thiazol-2-yl)benzamide
103) 3-[(2-methylpyridin-4-yl)oxy]-5-(5-methyl-1,3-thiazol-2-yl)-N-{(1R)-1-[2-(trifluoromethyl)pyrimidin-5-yl]ethyl}benzamide
104) N-[(5-methylpyrazin-2-yl)methyl]-3-[(2-methylpyridin-4-yl)oxy]-5-(5-methyl-1,3-thiazol-2-yl)benzamide
105) 3-[(2-methylpyridin-4-yl)oxy]-5-(5-methyl-1,3-thiazol-2-yl)-N-{(1R)-1-[6-(trifluoromethyl)pyridazin-3-yl]ethyl}benzamide
106) 3-[(2-methylpyridin-4-yl)oxy]-N-[(1R)-1-(2-methylpyrimidin-5-yl)ethyl]-5-(5-methyl-1,3-thiazol-2-yl)benzamide
107) N-[(1R)-1-(6-methylpyridin-3-yl)ethyl]-3-[(2-methylpyridin-4-yl)oxy]-5-(5-methyl-1,3-thiazol-2-yl)benzamide
108) 3-[(6-methylpyridin-3-yl)oxy]-5-(5-methyl-1,3-thiazol-2-yl)-N-{(1R)-1-[2-(trifluoromethyl)pyrimidin-5-yl]ethyl}benzamide
109) N-[(1R)-1-(5-methylpyrazin-2-yl)ethyl]-3-[(5-methyl-1,3,4-thiadiazol-2-yl)oxy]-5-(5-methyl-1,3-thiazol-2-yl)benzamide
110) N-[(1R)-1-(6-methylpyridazin-3-yl)ethyl]-3-[(5-methyl-1,3,4-thiadiazol-2-yl)oxy]-5-(5-methyl-1,3-thiazol-2-yl)benzamide
111) 3-[(5-methyl-1,3,4-thiadiazol-2-yl)oxy]-5-(5-methyl-1,3-thiazol-2-yl)-N-{(1R)-1-[2-(trifluoromethyl)pyrimidin-5-yl]ethyl}benzamide
112) N-[(1R)-1-(5-methylpyrazin-2-yl)ethyl]-3-(5-methyl-1,3-thiazol-2-yl)-5-(1,3-thiazol-2-yloxy)benzamide
113) N-[(1R)-1-(6-methylpyridazin-3-yl)ethyl]-3-(5-methyl-1,3-thiazol-2-yl)-5-(1,3-thiazol-2-yloxy)benzamide
114) N-[(1R)-1-(6-methylpyridin-3-yl)ethyl]-3-(5-methyl-1,3-thiazol-2-yl)-5-(1,3-thiazol-2-yloxy)benzamide
115) N-[(1R)-1-(5-chloropyridin-2-yl)ethyl]-3-(5-chloro-1,3-thiazol-2-yl)-5-(2-methoxy-2-methylpropoxy)benzamide
116) 3-(5-chloro-1,3-thiazol-2-yl)-5-(2-methoxy-2-methylpropoxy)-N-{(1R)-1-[2-(trifluoromethyl)pyrimidin-5-yl]ethyl}benzamide
117) 3-(5-chloro-1,3-thiazol-2-yl)-5-(2-methoxy-2-methylpropoxy)-N-[(1R)-1-(5-methylpyrazin-2-yl)ethyl]benzamide
118) N-[(6-methylpyridazin-3-yl)methyl]-3-(tetrahydro-2H-pyran-4-ylmethoxy)-5-[5-(trifluoromethyl)-1,3-thiazol-2-yl]benzamide
119) 3-(5-cyclobutyl-1,3-thiazol-2-yl)-N-[(6-methylpyridazin-3-yl)methyl]-5-(tetrahydro-2H-pyran-4-ylmethoxy)benzamide
120) 3-(5-cyclobutyl-1,3-thiazol-2-yl)-5-(tetrahydro-2H-pyran-4-ylmethoxy)-N-{(1R)-1-[2-(trifluoromethyl)pyrimidin-5-yl]ethyl}benzamide
121) 3-(5-cyclobutyl-1,3-thiazol-2-yl)-N-[(1R)-1-(5-methylpyrazin-2-yl)ethyl]-5-[(3S)-tetrahydrofuran-3-ylmethoxy]benzamide
122) 3-(5-cyclobutyl-1,3-thiazol-2-yl)-N-[(6-methylpyridazin-3-yl)methyl]-5-[(3S)-tetrahydrofuran-3-ylmethoxy]benzamide
123) 3-(5-cyclobutyl-1,3-thiazol-2-yl)-5-[(3S)-tetrahydrofuran-3-ylmethoxy]-N-{(1R)-1-[2-(trifluoromethyl)pyrimidin-5-yl]ethyl}benzamide
124) 3-(5-cyclobutyl-1,3-thiazol-2-yl)-N-[(1R)-1-(2-methylpyrimidin-5-yl)ethyl]-5-(tetrahydro-2H-pyran-4-ylmethoxy)benzamide
125) 3-(5-ethyl-1,3-thiazol-2-yl)-N-[(1R)-1-(2-methylpyrimidin-5-yl)ethyl]-5-(tetrahydro-2H-pyran-4-ylmethoxy)benzamide
126) N-[(1R)-1-(2-methylpyrimidin-5-yl)ethyl]-3-[5-(propan-2-yl)-1,3-thiazol-2-yl]-5-(tetrahydro-2H-pyran-4-ylmethoxy)benzamide
127) 3-(5-cyclobutyl-1,3-thiazol-2-yl)-N-[(1R)-1-(6-methylpyridazin-3-yl)ethyl]-5-(tetrahydro-2H-pyran-4-yloxy)benzamide
128) 3-(5-ethyl-1,3-thiazol-2-yl)-N-[(1R)-1-(6-methylpyridazin-3-yl)ethyl]-5-(tetrahydro-2H-pyran-4-yloxy)benzamide
129) 3-(5-ethyl-1,3-thiazol-2-yl)-5-(tetrahydro-2H-pyran-4-yloxy)-N-{(1R)-1-[2-(trifluoromethyl)pyrimidin-5-yl]ethyl}benzamide
130) N-[(1R)-1-(2-methylpyrimidin-5-yl)ethyl]-3-(5-methyl-1,3-thiazol-2-yl)-5-[(3S)-tetrahydrofuran-3-yloxy]benzamide
131) N-[(1R)-1-(5-methylpyrazin-2-yl)ethyl]-3-[(6-methylpyridin-3-yl)oxy]-5-(5-methyl-1,3-thiazol-2-yl)benzamide
132) N-[1-(3-chloro-5-fluoropyridin-2-yl)ethyl]-3-(5-methyl-1,3-thiazol-2-yl)-5-[(3S)-tetrahydrofuran-3-yloxy]benzamide
133) N-[(6-methylpyridazin-3-yl)methyl]-3-(5-methyl-1,3-thiazol-2-yl)-5-[(3S)-tetrahydrofuran-3-yloxy]benzamide
134) N-[1-(5-chloro-3-fluoropyridin-2-yl)ethyl]-3-(5-methyl-1,3-thiazol-2-yl)-5-[(3S)-tetrahydrofuran-3-yloxy]benzamide 135) 3-(5-cyclobutyl-1,3-thiazol-2-yl)-N-[(1R)-1-(6-methylpyridazin-3-yl)ethyl]-5-[(3S)-tetrahydrofuran-3-ylmethoxy]benzamide
136) 3-(2-methoxyethoxy)-N-[(1R)-1-(2-methylpyrimidin-5-yl)ethyl]-5-(5-methyl-1,3-thiazol-2-yl)benzamide
137) tert-butyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate
138) 3-(5-methyl-1,3-thiazol-2-yl)-5-(piperidin-4-yloxy)-N-{(1R)-1-[2-(trifluoromethyl)pyrimidin-5-yl]ethyl}benzamide
139) 3-[(1-methylpiperidin-4-yl)oxy]-5-(5-methyl-1,3-thiazol-2-yl)-N-{(1R)-1-[2-(trifluoromethyl)pyrimidin-5-yl]ethyl}benzamide
140) 3-(5-methyl-1,3-thiazol-2-yl)-5-{[1-(propan-2-yl)piperidin-4-yl]oxy}-N-{(1R)-1-[2-(trifluoromethyl)pyrimidin-5-yl]ethyl}benzamide
141) 3-{[(3R)-1-methylpyrrolidin-3-yl]oxy}-5-(5-methyl-1,3-thiazol-2-yl)-N-{(1R)-1-[2-(trifluoromethyl)pyrimidin-5-yl]ethyl}benzamide
142) 3-{[(3S)-1-methylpyrrolidin-3-yl]oxy}-5-(5-methyl-1,3-thiazol-2-yl)-N-{(1R)-1-[2-(trifluoromethyl)pyrimidin-5-yl]ethyl}benzamide
143) 3-[(1-methylazetidin-3-yl)oxy]-5-(5-methyl-1,3-thiazol-2-yl)-N-{(1R)-1-[2-(trifluoromethyl)pyrimidin-5-yl]ethyl}benzamide
144) 3-(5-methyl-1,3-thiazol-2-yl)-5-(prop-2-yn-1-yloxy)-N-{(1S)-1-[2-(trifluoromethyl)pyrimidin-5-yl]ethyl}benzamide
145) 3-(5-methyl-1,3-thiazol-2-yl)-5-(tetrahydro-2H-pyran-4-yloxy)-N-{(1S)-1-[2-(trifluoromethyl)pyrimidin-5-yl]ethyl}benzamide
146) tert-butyl 6-[3-(5-methyl-1,3-thiazol-2-yl)-5-({(1R)-1-[2-(trifluoromethyl)pyrimidin-5-yl]ethyl}carbamoyl)phenoxy]-2-azaspiro[3.3]heptane-2-carboxylate
147) 3-(5-methyl-1,3-thiazol-2-yl)-5-[(3R)-tetrahydrofuran-3-yloxy]-N-{(1R)-1-[5-(trifluoromethyl)pyrazin-2-yl]ethyl}benzamide
148) 3-(5-methyl-1,3-thiazol-2-yl)-5-(oxetan-3-yloxy)-N-{(1R)-1-[6-(trifluoromethyl)pyridin-3-yl]ethyl}benzamide Also disclosed are the following compounds, namely:
149) 3-(1-azabicyclo[2.2.2]oct-4-yloxy)-5-(5-methyl-1,3-thiazol-2-yl)-N-{(1R)-1-[2-(trifluoromethyl)pyrimidin-5-yl]ethyl}benzamide
150) 3-[(1-acetylpiperidin-4-yl)oxy]-5-(5-methyl-1,3-thiazol-2-yl)-N-{(1R)-1-[2-(trifluoromethyl)pyrimidin-5-yl]ethyl}benzamide
151) N-{(1R)-1-[2-(difluoromethyl)pyrimidin-5-yl]ethyl}-3-(5-methyl-1,3-thiazol-2-yl)-5-[(3S)-tetrahydrofuran-3-yloxy]benzamide
152) N-{(1R)-1-[2-(difluoromethyl)pyrimidin-5-yl]ethyl}-3-(5-methyl-1,3-thiazol-2-yl)-5-(oxetan-3-yloxy)benzamide
153) N-{(1R)-1-[2-(difluoromethyl)pyrimidin-5-yl]ethyl}-3-(5-methyl-1,3-thiazol-2-yl)-5-[(3R)-tetrahydrofuran-3-yloxy]benzamide
154) N-{(1R)-1-[2-(difluoromethyl)pyrimidin-5-yl]ethyl}-3-(5-methyl-1,3-thiazol-2-yl)-5-(tetrahydro-2H-pyran-4-yloxy)benzamide
155) 3-{[(3S)-1-methylpiperidin-3-yl]oxy}-5-(5-methyl-1,3-thiazol-2-yl)-N-{(1R)-1-[2-(trifluoromethyl)pyrimidin-5-yl]ethyl}benzamide
156) 3-[(3-methyloxetan-3-yl)oxy]-5-(5-methyl-1,3-thiazol-2-yl)-N-{(1R)-1-[2-(trifluoromethyl)pyrimidin-5-yl]ethyl}benzamide
157) 3-(5-methyl-1,3-thiazol-2-yl)-5-[(3R)-tetrahydrofuran-3-yloxy]-N-{(1R)-1-[6-(trifluoromethyl)pyridin-3-yl]ethyl}benzamide
158) 3-{[(3R)-1-methylpiperidin-3-yl]oxy}-5-(5-methyl-1,3-thiazol-2-yl)-N-{(1R)-1-[2-(trifluoromethyl)pyrimidin-5-yl]ethyl}benzamide
159) 3-(5-methyl-1,3-thiazol-2-yl)-5-[2-(1H-1,2,4-triazol-1-yl)ethoxy]-N-{(1R)-1-[2-(trifluoromethyl)pyrimidin-5-yl]ethyl}benzamide
160) 3-(5-methyl-1,3-thiazol-2-yl)-5-[2-(1H-1,2,4-triazol-1-yl)ethoxy]-N-{(1R)-1-[6-(trifluoromethyl)pyridin-3-yl]ethyl}benzamide
161) 3-(5-methyl-1,3-thiazol-2-yl)-5-(oxetan-3-yloxy)-N-{(1R)-1-[6-(trifluoromethyl)pyridazin-3-yl]ethyl}benzamide
162) Trans Isomer 1; 3-{[3-hydroxybutan-2-yl]oxy}-5-(5-methyl-1,3-thiazol-2-yl)-N-{(1R)-1-[2-(trifluoromethyl)pyrimidin-5-yl]ethyl}benzamide
163) Trans Isomer 2; 3-{[3-hydroxybutan-2-yl]oxy}-5-(5-methyl-1,3-thiazol-2-yl)-N-{(1R)-1-[2-(trifluoromethyl)pyrimidin-5-yl]ethyl}benzamide
164) N-{(1R)-1-[6-(difluoromethyl)pyridin-3-yl]ethyl}-3-(5-methyl-1,3-thiazol-2-yl)-5-(oxetan-3-yloxy)benzamide
165) 3-{[trans-3-(dimethylamino)cyclobutyl]oxy}-5-(5-methyl-1,3-thiazol-2-yl)-N-{(1R)-1-[2-(trifluoromethyl)pyrimidin-5-yl]ethyl}benzamide
166) 3-(5-methyl-1,3-thiazol-2-yl)-5-[(3R)-tetrahydrofuran-3-yloxy]-N-{[2-(trifluoromethyl)pyrimidin-5-yl]methyl}benzamide
167) 3-(5-methyl-1,3-thiazol-2-yl)-5-(oxetan-3-yloxy)-N-{[2-(trifluoromethyl)pyrimidin-5-yl]methyl}benzamide
168) 3-[(3R)-1-azabicyclo[2.2.2]oct-3-yloxy]-5-(5-methyl-1,3-thiazol-2-yl)-N-{(1R)-1-[2-(trifluoromethyl)pyrimidin-5-yl]ethyl}benzamide
169) 3-(5-ethyl-1,3-thiazol-2-yl)-5-(oxetan-3-yloxy)-N-{(1R)-1-[2-(trifluoromethyl)pyrimidin-5-yl]ethyl}benzamide
170) 3-[(6-methylpyridazin-3-yl)oxy]-5-(5-methyl-1,3-thiazol-2-yl)-N-{(1R)-1-[2-(trifluoromethyl)pyrimidin-5-yl]ethyl}benzamide
171) N-{(1R)-1-[6-(difluoromethyl)pyridin-3-yl]ethyl}-3-(5-methyl-1,3-thiazol-2-yl)-5-[(3R)-tetrahydrofuran-3-yloxy]benzamide
172) 3-[(3R)-1-azabicyclo[2.2.2]oct-3-yloxy]-5-(5-methyl-1,3-thiazol-2-yl)-N-{(1R)-1-[6-(trifluoromethyl)pyridin-3-yl]ethyl}benzamide
173) 3-[(3S)-1-azabicyclo[2.2.2]oct-3-yloxy]-5-(5-ethyl-1,3-thiazol-2-yl)-N-{(1R)-1-[2-(trifluoromethyl)pyrimidin-5-yl]ethyl}benzamide
174) 3-[(3R)-1-azabicyclo[2.2.2]oct-3-yloxy]-5-(5-ethyl-1,3-thiazol-2-yl)-N-{(1R)-1-[2-(trifluoromethyl)pyrimidin-5-yl]ethyl}benzamide
175) 3-[(3S)-1-azabicyclo[2.2.2]oct-3-yloxy]-5-(5-methyl-1,3-thiazol-2-yl)-N-{(1R)-1-[6-(trifluoromethyl)pyridin-3-yl]ethyl}benzamide
176) 3-[(5-methyl-1,3,4-thiadiazol-2-yl)oxy]-5-(5-methyl-1,3-thiazol-2-yl)-N-{(1R)-1-[6-(trifluoromethyl)pyridin-3-yl]ethyl}benzamide
177) 3-[(2R)-1,4-dioxan-2-ylmethoxy]-5-(5-methyl-1,3-thiazol-2-yl)-N-{(1R)-1-[6-(trifluoromethyl)pyridin-3-yl]ethyl}benzamide
178) 3-[(2R)-1,4-dioxan-2-ylmethoxy]-5-(5-methyl-1,3-thiazol-2-yl)-N-{(1R)-1-[2-(trifluoromethyl)pyrimidin-5-yl]ethyl}benzamide 179) 3-[(2R)-1,4-dioxan-2-ylmethoxy]-5-(5-methyl-1,3-thiazol-2-yl)-N-{(1R)-1-[6-(trifluoromethyl)pyridazin-3-yl]ethyl}benzamide
180) 3-[(2S)-1,4-dioxan-2-ylmethoxy]-5-(5-methyl-1,3-thiazol-2-yl)-N-{(1R)-1-[6-(trifluoromethyl)pyridin-3-yl]ethyl}benzamide 181) 3-[(2S)-1,4-dioxan-2-ylmethoxy]-5-(5-methyl-1,3-thiazol-2-yl)-N-{(1R)-1-[2-(trifluoromethyl)pyrimidin-5-yl]ethyl}benzamide
182) 3-[(2S)-1,4-dioxan-2-ylmethoxy]-5-(5-methyl-1,3-thiazol-2-yl)-N-{(1R)-1-[6-(trifluoromethyl)pyridazin-3-yl]ethyl}benzamide
183) Trans Isomer 1; 3-{[3-hydroxybutan-2-yl]oxy}-5-(5-methyl-1,3-thiazol-2-yl)-N-{(1R)-1-[6-(trifluoromethyl)pyridazin-3-yl]ethyl}benzamide
184) Trans Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide
185) Cis Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide
186) Trans Isomer 1; 3-(5-chloro-1,3-thiazol-2-yl)-5-{[3-hydroxybutan-2-yl]oxy}-N-{(1R)-1-[6-(trifluoromethyl)pyridin-3-yl]ethyl}benzamide
187) Cis Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide
188) Trans Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide
189) Trans Isomer 2; 3-(5-chloro-1,3-thiazol-2-yl)-5-{[3-hydroxybutan-2-yl]oxy}-N-{(1R)-1-[6-(trifluoromethyl)pyridin-3-yl]ethyl}benzamide
190) tert-Butyl (3R)-3-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate, as a mixture of diastereoisomers
191) 3-(but-2-yn-1-yloxy)-N-[(1R)-1-(6-methylpyridazin-3-yl)ethyl]-5-(5-methyl-1,3-thiazol-2-yl)benzamide 192) 3-[(3S)-1-azabicyclo[2.2.2]oct-3-yloxy]-5-(5-methyl-1,3-thiazol-2-yl)-N-{(1R)-1-[2-(trifluoromethyl)pyrimidin-5-yl]benzamide
193) Enantiomer 1; 3-(5-methyl-1,3-thiazol-2-yl)-5-(oxetan-3-yloxy)-N-{-1-[5-(trifluoromethyl)-1,3,4-thiadiazol-2-yl]ethyl}benzamide
194) Enantiomer 2; 3-(5-methyl-1,3-thiazol-2-yl)-5-(oxetan-3-yloxy)-N-{-1-[5-(trifluoromethyl)-1,3,4-thiadiazol-2-yl]ethyl}benzamide
195) Enantiomer 1; 3-(5-methyl-1,3-thiazol-2-yl)-5-(tetrahydro-2H-pyran-4-yloxy)-N-{1-[5-(trifluoromethyl)-1,3,4-thiadiazol-2-yl]ethyl}benzamide
196) Enantiomer 2; 3-(5-methyl-1,3-thiazol-2-yl)-5-(tetrahydro-2H-pyran-4-yloxy)-N-{1-[5-(trifluoromethyl)-1,3,4-thiadiazol-2-yl]ethyl}benzamide
197) Diastereoisomer 1; 3-(5-methyl-1,3-thiazol-2-yl)-5-[(3R)-tetrahydrofuran-3-yloxy]-N-{1-[5-(trifluoromethyl)-1,3,4-thiadiazol-2-yl]ethyl}benzamide
198) Diastereoisomer 1; 3-(5-methyl-1,3-thiazol-2-yl)-5-[(3R)-tetrahydrofuran-3-yloxy]-N-{1-[5-(trifluoromethyl)-1,3,4-thiadiazol-2-yl]ethyl}benzamide
199) Diastereoisomer 2; 1; 3-(5-methyl-1,3-thiazol-2-yl)-5-[(3R)-tetrahydrofuran-3-yloxy]-N-{(1R)-1-[5-(trifluoromethyl)-1,3,4-thiadiazol-2-yl]ethyl}benzamide
200) Diastereoisomer 2; 3-(5-methyl-1,3-thiazol-2-yl)-5-[(3S)-tetrahydrofuran-3-yloxy]-N-{(1R)-1-[5-(trifluoromethyl)-1,3,4-thiadiazol-2-yl]ethyl}benzamide
201) 3-(5-methyl-1,3-thiazol-2-yl)-5-(piperidin-4-yloxy)-N-{(1R)-1-[6-(trifluoromethyl)pyridazin-3-yl]ethyl}benzamide
202) 3-(2-azaspiro[3.3]hept-6-yloxy)-5-(5-methyl-1,3-thiazol-2-yl)-N-{(1R)-1-[2-(trifluoromethyl)pyrimidin-5-yl]ethyl}benzamide
203) 3-(5-methyl-1,3-thiazol-2-yl)-5-[(3S)-pyrrolidin-3-yloxy]-N-{(1R)-1-[2-(trifluoromethyl)pyrimidin-5-yl]ethyl}benzamide
204) 3-{[3-fluoropiperidin-4-yl]oxy}-5-(5-methyl-1,3-thiazol-2-yl)-N-{(1R)-1-[2-(trifluoromethyl)pyrimidin-5-yl]ethyl}benzamide, as a mixture of cis isomers
205) Diastereoisomer 1; 3-(5-methyl-1,3-thiazol-2-yl)-5-(piperidin-3-yloxy)-N-{(1R)-1-[2-(trifluoromethyl)pyrimidin-5-yl]ethyl}benzamide
206) Diastereoisomer 2; 3-(5-methyl-1,3-thiazol-2-yl)-5-(piperidin-3-yloxy)-N-{(1R)-1-[2-(trifluoromethyl)pyrimidin-5-yl]ethyl}benzamide
207) Cis Isomer 1; 3-(5-methyl-1,3-thiazol-2-yl)-5-{[2-(trifluoromethyl)piperidin-4-yl]oxy}-N-{(1R)-1-[2-(trifluoromethyl)pyrimidin-5-yl]ethyl}benzamide
208) Cis Isomer 2; 3-(5-methyl-1,3-thiazol-2-yl)-5-{[2-(trifluoromethyl)piperidin-4-yl]oxy}-N-{(1R)-1-[2-(trifluoromethyl)pyrimidin-5-yl]ethyl}benzamide
209) 3-{[2-methyl-2-azabicyclo[2.2.1]hept-5-yl]oxy}-5-(5-methyl-1,3-thiazol-2-yl)-N-{(1R)-1-[2-(trifluoromethyl)pyrimidin-5-yl]ethyl}benzamide
210) 3-[(1-methylpiperidin-4-yl)oxy]-5-(5-methyl-1,3-thiazol-2-yl)-N-{(1R)-1-[6-(trifluoromethyl)pyridazin-3-yl]ethyl}benzamide
211) 3-[(1-methylazetidin-3-yl)oxy]-5-(5-methyl-1,3-thiazol-2-yl)-N-{(1R)-1-[6-(trifluoromethyl)pyridazin-3-yl]ethyl}benzamide
212) 3-[(3-fluoro-1-methylpiperidin-4-yl)oxy]-5-(5-methyl-1,3-thiazol-2-yl)-N-{(1R)-1-[2-(trifluoromethyl)pyrimidin-5-yl]ethyl}benzamide, as a single unknown isomer
213) 3-{[1-(dimethylamino)cyclo propyl]methoxy}-5-(5-methyl-1,3-thiazol-2-yl)-N-{(1R)-1-[2-(trifluoromethyl)pyrimidin-5-yl]ethyl}benzamide
214) 3-[(2-methyl-2-azaspiro[3.3]hept-6-yl)oxy]-5-(5-methyl-1,3-thiazol-2-yl)-N-{(1R)-1-[2-(trifluoromethyl)pyrimidin-5-yl]ethyl}benzamide
215) N-{(1R)-1-[2-(difluoromethyl)pyrimidin-5-yl]ethyl}-3-[(1-methylpiperidin-4-yl)oxy]-5-(5-methyl-1,3-thiazol-2-yl)benzamide
216) 3-{[(3-endo)-8-methyl-8-azabicyclo[3.2.1]oct-3-yl]oxy}-5-(5-methyl-1,3-thiazol-2-yl)-N-{(1R)-1-[2-(trifluoromethyl)pyrimidin-5-yl]ethyl}benzamide
217) 3-{[(3-exo)-8-methyl-8-azabicyclo[3.2.1]oct-3-yl]oxy}-5-(5-methyl-1,3-thiazol-2-yl)-N-{(1R)-1-[2-(trifluoromethyl)pyrimidin-5-yl]ethyl}benzamide
218) 3-{[(4aS,7R,7aR)-4-methyloctahydrocyclopenta[b][1,4]oxazin-7-yl]oxy}-5-(5-methyl-1,3-thiazol-2-yl)-N-{(1R)-1-[2-(trifluoromethyl)pyrimidin-5-yl]ethyl}benzamide
219) 3-{[(4aS,7S,7aR)-4-methyloctahydrocyclopenta[b][1,4]oxazin-7-yl]oxy}-5-(5-methyl-1,3-thiazol-2-yl)-N-{(1R)-1-[2-(trifluoromethyl)pyrimidin-5-yl]ethyl}benzamide
220) Diastereoisomer 1; 3-[(1-methylpiperidin-3-yl)oxy]-5-(5-methyl-1,3-thiazol-2-yl)-N-{(1R)-1-[2-(trifluoromethyl)pyrimidin-5-yl]ethyl}benzamide
221) Diastereoisomer 2; 3-[(1-methylpiperidin-3-yl)oxy]-5-(5-methyl-1,3-thiazol-2-yl)-N-{(1R)-1-[2-(trifluoromethyl)pyrimidin-5-yl]ethyl}benzamide 222) Cis Isomer 1; 3-(5-methyl-1,3-thiazol-2-yl)-5-{[1-methyl-2-(trifluoromethyl)piperidin-4-yl]oxy}-N-{(1R)-1-[2-(trifluoromethyl)pyrimidin-5-yl]ethyl}benzamide
223) Cis Isomer 2; 3-(5-methyl-1,3-thiazol-2-yl)-5-{[1-methyl-2-(trifluoromethyl)piperidin-4-yl]oxy}-N-{(1R)-1-[2-(trifluoromethyl)pyrimidin-5-yl]ethyl}benzamide
224) 3-(5-methyl-1,3-thiazol-2-yl)-5-{[1-(propan-2-yl)piperidin-4-yl]oxy}-N-{(1R)-1-[6-(trifluoromethyl)pyridazin-3-yl]ethyl}benzamide
225) 3-(5-methyl-1,3-thiazol-2-yl)-5-{[(3S)-1-(propan-2-yl)pyrrolidin-3-yl]oxy}-N-{(1R)-1-[2-(trifluoromethyl)pyrimidin-5-yl]ethyl}benzamide
226) methyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate
227) ethyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate
228) ethyl (3S)-3-[3-(5-methyl-1,3-thiazol-2-yl)-5-({(1R)-1-[2-(trifluoromethyl)pyrimidin-5-yl]ethyl}carbamoyl)phenoxy]pyrrolidine-1-carboxylate
229) 3-(5-methyl-1,3-thiazol-2-yl)-5-{[1-(propan-2-yl)azetidin-3-yl]oxy}-N-{(1R)-1-[2-(trifluoromethyl)pyrimidin-5-yl]ethyl}benzamide
230) Cis Isomer 1; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide
231) Cis Isomer 2; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide
232) 3-[(1,1-dioxidotetrahydro-2H-thiopyran-4-yl)oxy]-5-(5-methyl-1,3-thiazol-2-yl)-N-{(1R)-1-[2-(trifluoromethyl)pyrimidin-5-yl]ethyl}benzamide
233) 3-[(1,1-dioxidotetrahydro-2H-thiopyran-4-yl)oxy]-5-(5-methyl-1,3-thiazol-2-yl)-N-{(1R)-1-[6-(trifluoromethyl)pyridin-3-yl]ethyl}benzamide
234) 3-(5-ethyl-1,3-thiazol-2-yl)-N-[(1R)-1-(5-methylpyrazin-2-yl)ethyl]-5-(tetrahydro-2H-pyran-4-yloxy)benzamide
235) 3-(5-ethyl-1,3-thiazol-2-yl)-N-[(6-methylpyridazin-3-yl)methyl]-5-(tetrahydro-2H-pyran-4-yloxy)benzamide
236) 3-(5-cyclobutyl-1,3-thiazol-2-yl)-N-[(1R)-1-(5-methylpyrazin-2-yl)ethyl]-5-(tetrahydro-2H-pyran-4-yloxy)benzamide
237) 3-(5-cyclobutyl-1,3-thiazol-2-yl)-N-[(6-methylpyridazin-3-yl)methyl]-5-(tetrahydro-2H-pyran-4-yloxy)benzamide
238) 3-(5-cyclobutyl-1,3-thiazol-2-yl)-5-(tetrahydro-2H-pyran-4-yloxy)-N-{(1R)-1-[2-(trifluoromethyl)pyrimidin-5-yl]ethyl}benzamide
239) 3-(5-cyclobutyl-1,3-thiazol-2-yl)-5-[(3S)-tetrahydrofuran-3-ylmethoxy]-N-{(1S)-1-[2-(trifluoromethyl)pyrimidin-5-yl]ethyl}benzamide
240) 3-(5-ethyl-1,3-thiazol-2-yl)-N-[(1R)-1-(6-methylpyridazin-3-yl)ethyl]-5-[(3R)-tetrahydrofuran-3-yloxy]benzamide
241) 3-(5-ethyl-1,3-thiazol-2-yl)-N-[(1R)-1-(5-methylpyrazin-2-yl)ethyl]-5-[(3R)-tetrahydrofuran-3-yloxy]benzamide
242) 3-(5-ethyl-1,3-thiazol-2-yl)-5-[(3R)-tetrahydrofuran-3-yloxy]-N-{(1R)-1-[2-(trifluoromethyl)pyrimidin-5-yl]ethyl}benzamide
243) 3-(5-cyclobutyl-1,3-thiazol-2-yl)-N-[(1R)-1-(6-methylpyridazin-3-yl)ethyl]-5-[(3R)-tetrahydrofuran-3-yloxy]benzamide
244) 3-(5-cyclobutyl-1,3-thiazol-2-yl)-N-[(1R)-1-(5-methylpyrazin-2-yl)ethyl]-5-[(3R)-tetrahydrofuran-3-yloxy]benzamide
245) 3-(5-cyclobutyl-1,3-thiazol-2-yl)-5-[(3R)-tetrahydrofuran-3-yloxy]-N-{(1R)-1-[2-(trifluoromethyl)pyrimidin-5-yl]ethyl}benzamide
246) N-[(1R)-1-(6-methylpyridazin-3-yl)ethyl]-3-[5-(propan-2-yl)-1,3-thiazol-2-yl]-5-[(3R)-tetrahydrofuran-3-yloxy]benzamide
247) N-[(1R)-1-(5-methylpyrazin-2-yl)ethyl]-3-[5-(propan-2-yl)-1,3-thiazol-2-yl]-5-[(3R)-tetrahydrofuran-3-yloxy]benzamide
248) 3-[5-(propan-2-yl)-1,3-thiazol-2-yl]-5-[(3R)-tetrahydrofuran-3-yloxy]-N-{(1R)-1-[2-(trifluoromethyl)pyrimidin-5-yl]ethyl}benzamide
249) 3-(5-ethyl-1,3-thiazol-2-yl)-N-[(1R)-1-(6-methylpyridazin-3-yl)ethyl]-5-[(3S)-tetrahydrofuran-3-yloxy]benzamide
250) 3-(5-ethyl-1,3-thiazol-2-yl)-N-[(1R)-1-(5-methylpyrazin-2-yl)ethyl]-5-[(3S)-tetrahydrofuran-3-yloxy]benzamide
251) 3-(5-ethyl-1,3-thiazol-2-yl)-5-[(3S)-tetrahydrofuran-3-yloxy]-N-{(1R)-1-[2-(trifluoromethyl)pyrimidin-5-yl]ethyl}benzamide
252) 3-(5-cyclobutyl-1,3-thiazol-2-yl)-N-[(1R)-1-(6-methylpyridazin-3-yl)ethyl]-5-[(3S)-tetrahydrofuran-3-yloxy]benzamide
253) 3-(5-cyclobutyl-1,3-thiazol-2-yl)-N-[(1R)-1-(5-methylpyrazin-2-yl)ethyl]-5-[(3S)-tetrahydrofuran-3-yloxy]benzamide
254) 3-(5-cyclobutyl-1,3-thiazol-2-yl)-5-[(3S)-tetrahydrofuran-3-yloxy]-N-{(1R)-1-[2-(trifluoromethyl)pyrimidin-5-yl]ethyl}benzamide
255) N-[(1R)-1-(6-methylpyridazin-3-yl)ethyl]-3-[5-(propan-2-yl)-1,3-thiazol-2-yl]-5-[(3S)-tetrahydrofuran-3-yloxy]benzamide
256) N-[(1R)-1-(5-methylpyrazin-2-yl)ethyl]-3-[5-(propan-2-yl)-1,3-thiazol-2-yl]-5-[(3S)-tetrahydrofuran-3-yloxy]benzamide
257) 3-[5-(propan-2-yl)-1,3-thiazol-2-yl]-5-[(3S)-tetrahydrofuran-3-yloxy]-N-{(1R)-1-[2-(trifluoromethyl)pyrimidin-5-yl]ethyl}benzamide
258) 3-(5-ethyl-1,3-thiazol-2-yl)-N-[(1R)-1-(6-methylpyridazin-3-yl)ethyl]-5-[(3R)-tetrahydrofuran-3-ylmethoxy]benzamide
259) 3-(5-ethyl-1,3-thiazol-2-yl)-N-[(1R)-1-(5-methylpyrazin-2-yl)ethyl]-5-[(3R)-tetrahydrofuran-3-ylmethoxy]benzamide
260) 3-(5-ethyl-1,3-thiazol-2-yl)-5-[(3R)-tetrahydrofuran-3-ylmethoxy]-N-{(1R)-1-[2-(trifluoromethyl)pyrimidin-5-yl]ethyl}benzamide
261) 3-(5-cyclobutyl-1,3-thiazol-2-yl)-N-[(1R)-1-(6-methylpyridazin-3-yl)ethyl]-5-[(3R)-tetrahydrofuran-3-yl-methol]benzamide
262) 3-(5-cyclobutyl-1,3-thiazol-2-yl)-N-[(1R)-1-(5-methylpyrazin-2-yl)ethyl]-5-[(3R)-tetrahydrofuran-3-ylmethoxy]benzamide
263) 3-(5-cyclobutyl-1,3-thiazol-2-yl)-5-[(3R)-tetrahydrofuran-3-ylmethoxy]-N-{(1R)-1-[2-(trifluoromethyl)pyrimidin-5-yl]ethyl}benzamide
264) N-[(1R)-1-(6-methylpyridazin-3-yl)ethyl]-3-[5-(propan-2-yl)-1,3-thiazol-2-yl]-5-[(3R)-tetrahydrofuran-3-ylmethoxy]benzamide
265) N-[(1R)-1-(5-methylpyrazin-2-yl)ethyl]-3-[5-(propan-2-yl)-1,3-thiazol-2-yl]-5-[(3R)-tetrahydrofuran-3-ylmethoxy]benzamide 266) 3-[5-(propan-2-yl)-1,3-thiazol-2-yl]-5-[(3R)-tetrahydrofuran-3-ylmethoxy]-N-{(1R)-1-[2-(trifluoromethyl)pyrimidin-5-yl]ethyl}benzamide
267) 3-(5-ethyl-1,3-thiazol-2-yl)-N-[(1R)-1-(6-methylpyridazin-3-yl)ethyl]-5-[(2R)-tetrahydrofuran-2-ylmethoxy]benzamide
268) 3-(5-ethyl-1,3-thiazol-2-yl)-N-[(1R)-1-(5-methylpyrazin-2-yl)ethyl]-5-[(2R)-tetrahydrofuran-2-ylmethoxy]benzamide
269) 3-(5-ethyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide
270) 3-(5-cyclobutyl-1,3-thiazol-2-yl)-N-[(1R)-1-(6-methylpyridazin-3-yl)ethyl]-5-[(2R)-tetrahydrofuran-2-ylmethoxy]benzamide
271) 3-(5-cyclobutyl-1,3-thiazol-2-yl)-N-[(1R)-1-(5-methylpyrazin-2-yl)ethyl]-5-[(2R)-tetrahydrofuran-2-ylmethoxy]benzamide
272) 3-(5-cyclobutyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide
273) N-[(1R)-1-(6-methylpyridazin-3-yl)ethyl]-3-[5-(propan-2-yl)-1,3-thiazol-2-yl]-5-[(2R)-tetrahydrofuran-2-ylmethoxy]benzamide
274) N-[(1R)-1-(5-methylpyrazin-2-yl)ethyl]-3-[5-(propan-2-yl)-1,3-thiazol-2-yl]-5-[(2R)-tetrahydrofuran-2-ylmethoxy]benzamide
275) 3-[5-(propan-2-yl)-1,3-thiazol-2-yl]-5-[(2R)-tetrahydrofuran-2-ylmethoxy]-N-{(1R)-1-[2-(trifluoromethyl)pyrimidin-5-yl]ethyl}benzamide
276) 3-(5-ethyl-1,3-thiazol-2-yl)-N-[(1R)-1-(6-methylpyridazin-3-yl)ethyl]-5-[(3S)-tetrahydrofuran-3-ylmethoxy]benzamide
277) 3-(5-ethyl-1,3-thiazol-2-yl)-N-[(1R)-1-(5-methylpyrazin-2-yl)ethyl]-5-[(3S)-tetrahydrofuran-3-ylmethoxy]benzamide
278) 3-(5-ethyl-1,3-thiazol-2-yl)-5-[(3S)-tetrahydrofuran-3-ylmethoxy]-N-{(1R)-1-[2-(trifluoromethyl)pyrimidin-5-yl]ethyl}benzamide
279) N-[(1R)-1-(6-methylpyridazin-3-yl)ethyl]-3-[5-(propan-2-yl)-1,3-thiazol-2-yl]-5-[(3S)-tetrahydrofuran-3-ylmethoxy]benzamide
280) N-[(1R)-1-(5-methylpyrazin-2-yl)ethyl]-3-[5-(propan-2-yl)-1,3-thiazol-2-yl]-5-[(3S)-tetrahydrofuran-3-ylmethoxy]benzamide
281) 3-[5-(propan-2-yl)-1,3-thiazol-2-yl]-5-[(3S)-tetrahydrofuran-3-ylmethoxy]-N-{(1R)-1-[2-(trifluoromethyl)pyrimidin-5-yl]ethyl}benzamide
282) 3-(5-ethyl-1,3-thiazol-2-yl)-N-[(1R)-1-(6-methylpyridazin-3-yl)ethyl]-5-[(2S)-tetrahydrofuran-2-ylmethoxy]benzamide
283) 3-(5-ethyl-1,3-thiazol-2-yl)-N-[(1R)-1-(5-methylpyrazin-2-yl)ethyl]-5-[(2S)-tetrahydrofuran-2-ylmethoxy]benzamide
284) 3-(5-ethyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide
285) 3-(5-cyclobutyl-1,3-thiazol-2-yl)-N-[(1R)-1-(6-methylpyridazin-3-yl)ethyl]-5-[(2S)-tetrahydrofuran-2-ylmethoxy]benzamide
286) 3-(5-cyclobutyl-1,3-thiazol-2-yl)-N-[(1R)-1-(5-methylpyrazin-2-yl)ethyl]-5-[(2S)-tetrahydrofuran-2-ylmethoxy]benzamide
287) 3-(5-cyclobutyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide
288) N-[(1R)-1-(6-methylpyridazin-3-yl)ethyl]-3-[5-(propan-2-yl)-1,3-thiazol-2-yl]-5-[(2S)-tetrahydrofuran-2-ylmethoxy]benzamide
289) N-[(1R)-1-(5-methylpyrazin-2-yl)ethyl]-3-[5-(propan-2-yl)-1,3-thiazol-2-yl]-5-[(2S)-tetrahydrofuran-2-ylmethoxy]benzamide
290) 3-[5-(propan-2-yl)-1,3-thiazol-2-yl]-5-[(2S)-tetrahydrofuran-2-ylmethoxy]-N-{(1R)-1-[2-(trifluoromethyl)pyrimidin-5-yl]ethyl}benzamide
291) 3-(5-methyl-1,3-thiazol-2-yl)-5-[(3R)-tetrahydrofuran-3-yloxy]-N-{(1S)-1-[2-(trifluoromethyl)pyrimidin-5-yl]ethyl}benzamide
292) 3-(5-ethyl-1,3-thiazol-2-yl)-5-[(3R)-tetrahydrofuran-3-ylmethoxy]-N-{(1R)-1-[6-(trifluoromethyl)pyridazin-3-yl]ethyl}benzamide
293) 3-[5-(propan-2-yl)-1,3-thiazol-2-yl]-5-[(3R)-tetrahydrofuran-3-ylmethoxy]-N-{(1R)-1-[6-(trifluoromethyl)pyridazin-3-yl]ethyl}benzamide
294) 3-[5-(propan-2-yl)-1,3-thiazol-2-yl]-5-[(3R)-tetrahydrofuran-3-yloxy]-N-{(1R)-1-[6-(trifluoromethyl)pyridazin-3-yl]ethyl}benzamide
295) 3-(5-cyclobutyl-1,3-thiazol-2-yl)-5-[(3S)-tetrahydrofuran-3-yloxy]-N-{(1R)-1-[6-(trifluoromethyl)pyridazin-3-yl]ethyl}benzamide
296) 3-(5-ethyl-1,3-thiazol-2-yl)-5-[(3S)-tetrahydrofuran-3-ylmethoxy]-N-{(1R)-1-[6-(trifluoromethyl)pyridazin-3-yl]ethyl}benzamide
297) 3-(5-cyclobutyl-1,3-thiazol-2-yl)-5-[(3R)-tetrahydrofuran-3-ylmethoxy]-N-{(1R)-1-[6-(trifluoromethyl)pyridazin-3-yl]ethyl}benzamide
298) 3-[5-(propan-2-yl)-1,3-thiazol-2-yl]-5-[(3S)-tetrahydrofuran-3-ylmethoxy]-N-{(1R)-1-[6-(trifluoromethyl)pyridazin-3-yl]ethyl}benzamide
299) 3-[5-(propan-2-yl)-1,3-thiazol-2-yl]-5-[(2R)-tetrahydrofuran-2-ylmethoxy]-N-{(1R)-1-[6-(trifluoromethyl)pyridazin-3-yl]ethyl}benzamide
300) 3-(5-cyclobutyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide
301) 3-[5-(propan-2-yl)-1,3-thiazol-2-yl]-5-[(2S)-tetrahydrofuran-2-ylmethoxy]-N-{(1R)-1-[6-(trifluoromethyl)pyridazin-3-yl]ethyl}benzamide
302) 3-(5-ethyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide
303) 3-(5-methyl-1,3-thiazol-2-yl)-5-{[1-(2,2,2-trifluoroethyl)piperidin-4-yl]oxy}-N-{(1R)-1-[2-(trifluoromethyl)pyrimidin-5-yl]ethyl}benzamide
304) 3-{[1-(2,2-difluoroethyl)piperidin-4-yl]oxy}-5-(5-methyl-1,3-thiazol-2-yl)-N-{(1R)-1-[2-(trifluoromethyl)pyrimidin-5-yl]ethyl}benzamide
305) 3-{[1-(2,2-difluoroethyl)piperidin-4-yl]oxy}-N-[(1R)-1-(6-methylpyridazin-3-yl)ethyl]-5-(5-methyl-1,3-thiazol-2-yl)benzamide
306) 3-{[1-(2,2-difluoroethyl)piperidin-4-yl]oxy}-N-[(1R)-1-(5-methylpyrazin-2-yl)ethyl]-5-(5-methyl-1,3-thiazol-2-yl)benzamide
307) 3-{[1-(2,2-difluoroethyl)piperidin-4-yl]oxy}-N-[(6-methylpyridazin-3-yl)methyl]-5-(5-methyl-1,3-thiazol-2-yl)benzamide
308) 3-{[1-(2,2-difluoroethyl)piperidin-4-yl]oxy}-5-(5-methyl-1,3-thiazol-2-yl)-N-{(1S)-1-[2-(trifluoromethyl)pyrimidin-5-yl]ethyl}benzamide
309) 3-{[1-(2,2-difluoroethyl)piperidin-4-yl]oxy}-N-[(1R)-1-(2-methylpyrimidin-5-yl)ethyl]-5-(5-methyl-1,3-thiazol-2-yl)benzamide 310) 3-(5-methyl-1,3-thiazol-2-yl)-5-{[1-(2,2,2-trifluoroethyl)piperidin-4-yl]oxy}-N-{(1S)-1-[2-(trifluoromethyl)pyrimidin-5-yl]ethyl}benzamide
311) N-[(1R)-1-(6-methylpyridazin-3-yl)ethyl]-3-(5-methyl-1,3-thiazol-2-yl)-5-{[1-(2,2,2-trifluoroethyl)piperidin-4-yl]oxy}benzamide
312) 3-(5-methyl-1,3-thiazol-2-yl)-5-{[1-(2,2,2-trifluoroethyl)piperidin-4-yl]oxy}-N-{(1R)-1-[6-(trifluoromethyl)pyridazin-3-yl]ethyl}benzamide
313) N-[(1R)-1-(5-methylpyrazin-2-yl)ethyl]-3-(5-methyl-1,3-thiazol-2-yl)-5-{[1-(2,2,2-trifluoroethyl)piperidin-4-yl]oxy}benzamide
314) N-[(6-methylpyridazin-3-yl)methyl]-3-(5-methyl-1,3-thiazol-2-yl)-5-{[1-(2,2,2-trifluoroethyl)piperidin-4-yl]oxy}benzamide
315) N-[(1R)-1-(2-methylpyrimidin-5-yl)ethyl]-3-(5-methyl-1,3-thiazol-2-yl)-5-{[1-(2,2,2-trifluoroethyl)piperidin-4-yl]oxy}benzamide
316) 3-(5-chloro-1,3-thiazol-2-yl)-N-[(1R)-1-(6-methylpyridazin-3-yl)ethyl]-5-[(3S)-tetrahydrofuran-3-ylmethoxy]benzamide
317) 3-(5-chloro-1,3-thiazol-2-yl)-N-[(1R)-1-(6-methylpyridazin-3-yl)ethyl]-5-[(3R)-tetrahydrofuran-3-yloxy]benzamide
318) 3-(5-chloro-1,3-thiazol-2-yl)-5-[(3R)-tetrahydrofuran-3-yloxy]-N-{(1R)-1-[6-(trifluoromethyl)pyridazin-3-yl]ethyl}benzamide
319) 3-(5-chloro-1,3-thiazol-2-yl)-N-[(1R)-1-(5-methylpyrazin-2-yl)ethyl]-5-[(3R)-tetrahydrofuran-3-yloxy]benzamide
320) 3-(5-chloro-1,3-thiazol-2-yl)-5-[(3S)-tetrahydrofuran-3-yloxy]-N-{(1R)-1-[6-(trifluoromethyl)pyridazin-3-yl]ethyl}benzamide
321) 3-(5-chloro-1,3-thiazol-2-yl)-N-[(1R)-1-(5-methylpyrazin-2-yl)ethyl]-5-[(3S)-tetrahydrofuran-3-yloxy]benzamide
322) 3-(5-chloro-1,3-thiazol-2-yl)-N-[(1R)-1-(6-methylpyridazin-3-yl)ethyl]-5-[(3S)-tetrahydrofuran-3-yloxy]benzamide
323) 3-(5-chloro-1,3-thiazol-2-yl)-5-[(3S)-tetrahydrofuran-3-ylmethoxy]-N-{(1R)-1-[2-(trifluoromethyl)pyrimidin-5-yl]ethyl}benzamide
324) 3-(5-chloro-1,3-thiazol-2-yl)-N-[(1R)-1-(5-methylpyrazin-2-yl)ethyl]-5-(tetrahydro-2H-pyran-4-yloxy)benzamide
325) 3-(5-chloro-1,3-thiazol-2-yl)-N-[(1R)-1-(6-methylpyridazin-3-yl)ethyl]-5-(tetrahydro-2H-pyran-4-yloxy)benzamide
326) 3-(5-chloro-1,3-thiazol-2-yl)-5-(tetrahydro-2H-pyran-4-yloxy)-N-{(1R)-1-[6-(trifluoromethyl)pyridazin-3-yl]ethyl}benzamide
327) 3-[(3-methyloxetan-3-yl)methoxy]-5-(5-methyl-1,3-thiazol-2-yl)-N-{(1R)-1-[2-(trifluoromethyl)pyrimidin-5-yl]ethyl}benzamide
328) 3-(2-hydroxy-2-methylpropoxy)-5-(5-methyl-1,3-thiazol-2-yl)-N-{(1R)-1-[2-(trifluoromethyl)pyrimidin-5-yl]ethyl}benzamide
329) 3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide, as a mixture of two diastereoisomers
330) Diastereoisomer 1; 3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide
331) Diastereoisomer 2; 3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide
332) 3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide, as a mixture of two diastereoisomers
333) Diastereoisomer 1; 3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide
334) Diastereoisomer 2; 3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide
335) 3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide, as a mixture of two diastereoisomers
336) Diastereoisomer 1; 3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide
337) Diastereoisomer 2; 3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide
338) 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide, as a mixture of cis isomers
339) Cis Isomer 1; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide
340) Cis Isomer 2; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide
341) 3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide, as a mixture of two stereoisomers
342) Stereoisomer 1; 3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide
343) Stereoisomer 2; 3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide
344) 3-[(7-isopropyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide, as a mixture of two stereoisomers
345) methyl 9-[3-(5-methyl-1,3-thiazol-2-yl)-5-({(1R)-1-[2-(trifluoromethyl)pyrimidin-5-yl]ethyl}carbamoyl)phenoxy]-3-oxa-7-azabicyclo[3.3.1]nonane-7-carboxylate, as a mixture of two stereoisomers
346) tert-butyl (2R)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate
347) 3-(5-methyl-1,3-thiazol-2-yl)-5-[(2R)-morpholin-2-ylmethoxy]-N-{(1R)-1-[2-(trifluoromethyl)pyrimidin-5-yl]ethyl}benzamide
348) 3-{[(2R)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide
349) tert-butyl (2S)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate
350) 3-(5-methyl-1,3-thiazol-2-yl)-5-[(2S)-morpholin-2-ylmethoxy]-N-{(1R)-1-[2-(trifluoromethyl)pyrimidin-5-yl]ethyl}benzamide 351) 3-{[(2S)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide
352) 3-(5-methyl-1,3-thiazol-2-yl)-5-[morpholin-2-ylmethoxy]-N-{(1R)-1-[2-(trifluoromethyl)pyrimidin-5-yl]ethyl}benzamide, as a mixture of diastereoisomers
353) 3-{[4-methylmorpholin-2-yl]methoxy}-5-(5-methyl-1,3-thiazol-2-yl)-N-{(1R)-1-[2-(trifluoromethyl)pyrimidin-5-yl]ethyl}benzamide, as a mixture of diastereoisomers
354) Diastereoisomer 1; 3-(fluoropiperidin-3-yl)methoxy}-5-(5-methyl-1,3-thiazol-2-yl)-N-{(1R)-1-[2-(trifluoromethyl)pyrimidin-5-yl]ethyl}benzamide
355) Diastereoisomer 2; 3-(fluoropiperidin-3-yl)methoxy}-5-(5-methyl-1,3-thiazol-2-yl)-N-{(1R)-1-[2-(trifluoromethyl)pyrimidin-5-yl]ethyl}benzamide
356) Diastereoisomer 1; 3-{[3-fluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide
357) Diastereoisomer 2; 3-{[3-fluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide
358) 3-[(3-fluoroazetidin-3-yl)methoxy]-5-(5-methyl-1,3-thiazol-2-yl)-N-{(1R)-1-[2-(trifluoromethyl)pyrimidin-5-yl]ethyl}benzamide
359) 3-{[4,4-difluoropiperidin-3-yl]methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers
360) 3-{[(3R)-4-methylmorpholin-3-yl]methoxy}-5-(5-methyl-1,3-thiazol-2-yl)-N-{(1R)-1-[2-(trifluoromethyl)pyrimidin-5-yl]ethyl}benzamide
361) 3-{[(3S)-4-methylmorpholin-3-yl]methoxy}-5-(5-methyl-1,3-thiazol-2-yl)-N-{(1R)-1-[6-(trifluoromethyl)pyridin-3-yl]ethyl}benzamide
362) 3-{[(3S)-4-methylmorpholin-3-yl]methoxy}-5-(5-methyl-1,3-thiazol-2-yl)-N-{(1R)-1-[2-(trifluoromethyl)pyrimidin-5-yl]ethyl}benzamide
363) 3-{[(3R)-4-methylmorpholin-3-yl]methoxy}-5-(5-methyl-1,3-thiazol-2-yl)-N-{(1R)-1-[6-(trifluoromethyl)pyridin-3-yl]ethyl}benzamide
364) 3-{[4-fluoro-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide, as a mixture of stereoisomers
365) 3-{[4-fluoro-1-methylpyrrolidin-2-yl]methoxy}-5-(5-methyl-1,3-thiazol-2-yl)-N-{(1R)-1-[6-(trifluoromethyl)pyridin-3-yl]ethyl}benzamide, as a mixture of stereoisomers
366) 3-{[(2R)-4-methylmorpholin-2-yl]methoxy}-5-(5-methyl-1,3-thiazol-2-yl)-N-{(1R)-1-[6-(trifluoromethyl)pyridin-3-yl]ethyl}benzamide
367) 3-(5-chloro-1,3-thiazol-2-yl)-5-{[(2R)-4-methylmorpholin-2-yl]methoxy}-N-{(1R)-1-[2-(trifluoromethyl)pyrimidin-5-yl]ethyl}benzamide
368) 3-{[(2S)-4-methylmorpholin-2-yl]methoxy}-5-(5-methyl-1,3-thiazol-2-yl)-N-{[2-(trifluoromethyl)pyrimidin-5-yl]methyl}benzamide
369) N-{(1R)-1-[6-(difluoromethyl)pyridin-3-yl]ethyl}-3-{[(2R)-4-methylmorpholin-2-yl]methoxy}-5-(5-methyl-1,3-thiazol-2-yl)benzamide
370) 3-{[(2S)-4-methylmorpholin-2-yl]methoxy}-5-(5-methyl-1,3-thiazol-2-yl)-N-{(1R)-1-[6-(trifluoromethyl)pyridin-3-yl]ethyl}benzamide
371) 3-[(3-fluoro-1-methylazetidin-3-yl)methoxy]-5-(5-methyl-1,3-thiazol-2-yl)-N-{(1R)-1-[2-(trifluoromethyl)pyrimidin-5-yl]ethyl}benzamide
372) 3-{[(2R)-4-methylmorpholin-2-yl]methoxy}-5-(5-methyl-1,3-thiazol-2-yl)-N-{[2-(trifluoromethyl)pyrimidin-5-yl]methyl}benzamide
373) 3-{[(2R)-4-methylmorpholin-2-yl]methoxy}-5-(5-methyl-1,3-thiazol-2-yl)-N-{(1R)-1-[6-(trifluoromethyl)pyridazin-3-yl]ethyl}benzamide
374) 3-{[(2S)-4-methylmorpholin-2-yl]methoxy}-5-(5-methyl-1,3-thiazol-2-yl)-N-{(1R)-1-[6-(trifluoromethyl)pyridazin-3-yl]ethyl}benzamide
375) 3-(5-ethyl-1,3-thiazol-2-yl)-5-{[(2S)-4-methylmorpholin-2-yl]methoxy}-N-{(1R)-1-[2-(trifluoromethyl)pyrimidin-5-yl]ethyl}benzamide
376) 3-(5-chloro-1,3-thiazol-2-yl)-5-{[(2S)-4-methylmorpholin-2-yl]methoxy}-N-{(1R)-1-[2-(trifluoromethyl)pyrimidin-5-yl]ethyl}benzamide
377) 3-(5-ethyl-1,3-thiazol-2-yl)-5-{[(2R)-4-methylmorpholin-2-yl]methoxy}-N-{(1R)-1-[2-(trifluoromethyl)pyrimidin-5-yl]ethyl}benzamide
378) 3-{[(2S)-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide
379) 3-{[(2R)-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide
380) 3-[(1-methylpiperidin-4-yl)methoxy]-5-(5-methyl-1,3-thiazol-2-yl)-N-{(1R)-1-[2-(trifluoromethyl)pyrimidin-5-yl]ethyl}benzamide
381) 3-(5-methyl-1,3-thiazol-2-yl)-5-{[(2R)-4-(propan-2-yl)morpholin-2-yl]methoxy}-N-{(1R)-1-[2-(trifluoromethyl)pyrimidin-5-yl]ethyl}benzamide
382) 3-(5-methyl-1,3-thiazol-2-yl)-5-{[(2S)-4-(propan-2-yl)morpholin-2-yl]methoxy}-N-{(1R)-1-[2-(trifluoromethyl)pyrimidin-5-yl]ethyl}benzamide
383) 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers
384) Diastereoisomer 1; 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide
385) Diastereoisomer 2; 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide
386) 3-[(3-fluoro-1-methylazetidin-3-yl)methoxy]-5-(5-methyl-1,3-thiazol-2-yl)-N-{(1R)-1-[6-(trifluoromethyl)pyridin-3-yl]ethyl}benzamide
387) 3-(5-ethyl-1,3-thiazol-2-yl)-5-[(3-fluoro-1-methylazetidin-3-yl)methoxy]-N-{(1R)-1-[6-(trifluoromethyl)pyridin-3-yl]ethyl}benzamide
388) 3-{[(3R)-4-methylmorpholin-3-yl]methoxy}-5-(5-methyl-1,3-thiazol-2-yl)-N-{(1R)-1-[6-(trifluoromethyl)pyridazin-3-yl]ethyl}benzamide
389) 3-{[(3S)-4-methylmorpholin-3-yl]methoxy}-5-(5-methyl-1,3-thiazol-2-yl)-N-{(1R)-1-[6-(trifluoromethyl)pyridazin-3-yl]ethyl}benzamide
390) 3-{[(2R)-4-ethylmorpholin-2-yl]methoxy}-5-(5-methyl-1,3-thiazol-2-yl)-N-{(1R)-1-[2-(trifluoromethyl)pyrimidin-5-yl]ethyl}benzamide
391) 3-{[(2R)-4-(2,2-difluoroethyl)morpholin-2-yl]methoxy}-5-(5-methyl-1,3-thiazol-2-yl)-N-{(1R)-1-[2-(trifluoromethyl)pyrimidin-5-yl]ethyl}benzamide
392) methyl (2R)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate 393) methyl (2S)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate
394) 3-(azetidin-3-ylmethoxy)-5-(5-methyl-1,3-thiazol-2-yl)-N-{(1R)-1-[2-(trifluoromethyl)pyrimidin-5-yl]ethyl}benzamide
395) 3-{[(3R)-4-methyl-5-oxomorpholin-3-yl]methoxy}-5-(5-methyl-1,3-thiazol-2-yl)-N-{(1R)-1-[2-(trifluoromethyl)pyrimidin-5-yl]ethyl}benzamide
396) 3-(5-methyl-1,3-thiazol-2-yl)-5-{[(3R)-5-oxomorpholin-3-yl]methoxy}-N-{(1R)-1-[2-(trifluoromethyl)pyrimidin-5-yl]ethyl}benzamide
397) 3-{[(5S)-3-methyl-2-oxo-1,3-oxazolidin-5-yl]methoxy}-5-(5-methyl-1,3-thiazol-2-yl)-N-{(1R)-1-[2-(trifluoromethyl)pyrimidin-5-yl]ethyl}benzamide
398) 3-{[(5R)-3-methyl-2-oxo-1,3-oxazolidin-5-yl]methoxy}-5-(5-methyl-1,3-thiazol-2-yl)-N-{(1R)-1-[2-(trifluoromethyl)pyrimidin-5-yl]ethyl}benzamide
399) 3-{[(2R)-4-methyl-5-oxomorpholin-2-yl]methoxy}-5-(5-methyl-1,3-thiazol-2-yl)-N-{(1R)-1-[2-(trifluoromethyl)pyrimidin-5-yl]ethyl}benzamide
400) 3-(5-methyl-1,3-thiazol-2-yl)-5-{[(2S)-5-oxomorpholin-2-yl]methoxy}-N-{(1R)-1-[2-(trifluoromethyl)pyrimidin-5-yl]ethyl}benzamide
401) 3-{[(2S)-4-methyl-5-oxomorpholin-2-yl]methoxy}-5-(5-methyl-1,3-thiazol-2-yl)-N-{(1R)-1-[2-(trifluoromethyl)pyrimidin-5-yl]ethyl}benzamide
402) 3-{[(3S)-4-methyl-5-oxomorpholin-3-yl]methoxy}-5-(5-methyl-1,3-thiazol-2-yl)-N-{(1R)-1-[2-(trifluoromethyl)pyrimidin-5-yl]ethyl}benzamide
403) 3-(5-methyl-1,3-thiazol-2-yl)-5-{[(3S)-5-oxomorpholin-3-yl]methoxy}-N-{(1R)-1-[2-(trifluoromethyl)pyrimidin-5-yl]ethyl}benzamide
404) tert-butyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers
405) 3-[(5-isopropyl-2-oxa-5-azabicyclo[2.2.1]hept-1-yl)methoxy]-5-(5-methyl-1,3-thiazol-2-yl)-N-{(1R)-1-[2-(trifluoromethyl)pyrimidin-5-yl]ethyl}benzamide, as a mixture of 2 diastereoisomers
406) 3-[(5-methyl-2-oxa-5-azabicyclo[2.2.1]hept-1-yl)methoxy]-5-(5-methyl-1,3-thiazol-2-yl)-N-{(1R)-1-[2-(trifluoromethyl)pyrimidin-5-yl]ethyl}benzamide, as a mixture of 2 diastereoisomers
407) 3-(5-methyl-1,3-thiazol-2-yl)-5-[(1S,4S)-2-oxa-5-azabicyclo[2.2.1]hept-1-ylmethoxy]-N-{(1R)-1-[2-(trifluoromethyl)pyrimidin-5-yl]ethyl}benzamide, as a mixture of 2 diastereoisomers
408) 3-(5-methyl-1,3-thiazol-2-yl)-5-[(5-propyl-2-oxa-5-azabicyclo[2.2.1]hept-1-yl)methoxy]-N-{(1R)-1-[2-(trifluoromethyl)pyrimidin-5-yl]ethyl}benzamide, as a mixture of 2 diastereoisomers
409) methyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers
410) ethyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers
411) 3-{[(2S)-4-ethylmorpholin-2-yl]methoxy}-5-(5-methyl-1,3-thiazol-2-yl)-N-{(1R)-1-[2-(trifluoromethyl)pyrimidin-5-yl]ethyl}benzamide
412) tert-butyl (2R)-2-{[3-(5-methyl-1,3-thiazol-2-yl)-5-({(1S)-1-[2-(trifluoromethyl)pyrimidin-5-yl]ethyl}carbamoyl)phenoxy]methyl}morpholine-4-carboxylate
413) 3-(5-methyl-1,3-thiazol-2-yl)-5-[(2R)-morpholin-2-ylmethoxy]-N-{(1S)-1-[2-(trifluoromethyl)pyrimidin-5-yl]ethyl}benzamide
414) 3-(5-ethyl-1,3-thiazol-2-yl)-5-[(2S)-morpholin-2-ylmethoxy]-N-{(1R)-1-[6-(trifluoromethyl)pyridazin-3-yl]ethyl}benzamide
415) 3-(5-ethyl-1,3-thiazol-2-yl)-5-[(2R)-morpholin-2-ylmethoxy]-N-{(1R)-1-[6-(trifluoromethyl)pyridazin-3-yl]ethyl}benzamide
416) 3-{[(2R)-4-methylmorpholin-2-yl]methoxy}-5-(5-methyl-1,3-thiazol-2-yl)-N-{(1S)-1-[2-(trifluoromethyl)pyrimidin-5-yl]ethyl}benzamide
417) 3-{[(2S)-4-methylmorpholin-2-yl]methoxy}-5-(5-methyl-1,3-thiazol-2-yl)-N-{(1S)-1-[2-(trifluoromethyl)pyrimidin-5-yl]ethyl}benzamide
418) 3-(5-ethyl-1,3-thiazol-2-yl)-5-{[(2S)-4-methylmorpholin-2-yl]methoxy}-N-{(1R)-1-[6-(trifluoromethyl)pyridazin-3-yl]ethyl}benzamide
419) 3-(5-ethyl-1,3-thiazol-2-yl)-5-{[(2R)-4-methylmorpholin-2-yl]methoxy}-N-{(1R)-1-[6-(trifluoromethyl)pyridazin-3-yl]ethyl}benzamide Also disclosed are compounds, namely
3-(5-Methyl-1,3-thiazol-2-yl)-5-[(3R)-tetrahydrofuran-3-yloxy]-N-{(1R)-1-[2-(trifluoromethyl)pyrimidin-5-yl]ethyl}benzamide;
3-(5-Methyl-1,3-thiazol-2-yl)-5-[(3S)-tetrahydrofuran-3-yloxy]-N-{(1R)-1-[2-(trifluoromethyl)pyrimidin-5-yl]ethyl}benzamide;
3-(5-Methyl-1,3-thiazol-2-yl)-5-(oxetan-3-yloxy)-N-{(1R)-1-[2-(trifluoromethyl)pyrimidin-5-yl]ethyl}benzamide;
3-(5-Ethyl-1,3-thiazol-2-yl)-5-[(3R)-tetrahydrofuran-3-yloxy]-N-{(1R)-1-[2-(trifluoromethyl)pyrimidin-5-yl]ethyl}benzamide;
3-(5-Ethyl-1,3-thiazol-2-yl)-5-[(3S)-tetrahydrofuran-3-yloxy]-N-{(1R)-1-[2-(trifluoromethyl)pyrimidin-5-yl]ethyl}benzamide;
3-(5-Ethyl-1,3-thiazol-2-yl)-5-(oxetan-3-yloxy)-N-{(1R)-1-[2-(trifluoromethyl)pyrimidin-5-yl]ethyl}benzamide;
3-(5-Methyl-1,3-thiazol-2-yl)-5-[(3R)-tetrahydrofuran-3-yloxy]-N-{(1R)-1-[6-(trifluoromethyl)pyridazin-3-yl]ethyl}benzamide;
3-(5-Methyl-1,3-thiazol-2-yl)-5-[(3S)-tetrahydrofuran-3-yloxy]-N-{(1R)-1-[6-(trifluoromethyl)pyridazin-3-yl]ethyl}benzamide.

Preferred compounds are, namely
3-(5-methyl-1,3-thiazol-2-yl)-5-[(3R)-tetrahydrofuran-3-yloxy]-N-{(1R)-1-[2-(trifluoromethyl)pyrimidin-5-yl]ethyl}benzamide;
3-(5-methyl-1,3-thiazol-2-yl)-5-[(3S)-tetrahydrofuran-3-yloxy]-N-{(1R)-1-[2-(trifluoromethyl)pyrimidin-5-yl]ethyl}benzamide.

An even more preferred compound is 3-(5-methyl-1,3-thiazol-2-yl)-5-[(3R)-tetra-hydrofuran-3-yloxy]-N-{(1R)-1-[2-(trifluoromethyl)pyrimidin-5-yl]ethyl}benzamide.

Also preferred compounds are, namely
3-(5-ethyl-1,3-thiazol-2-yl)-5-{[(2R)-4-methylmorpholin-2-yl]methoxy}-N-{(1R)-1-[2-(trifluoromethyl)pyrimidin-5-yl]ethyl}benzamide;
3-{[(2R)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide;

3-(5-ethyl-1,3-thiazol-2-yl)-5-{[(2R)-4-methylmorpholin-2-yl]methoxy}-N-{(1R)-1-[6-(trifluoromethyl)pyridazin-3-yl]ethyl}benzamide.

An even more preferred compound is 3-{[(2R)-4-methylmorpholin-2-yl]methoxy}-5-(5-methyl-1,3-thiazol-2-yl)-N-{(1R)-1-[2-(trifluoromethyl)pyrimidin-5-yl]ethyl}-benzamide.

Also preferred compounds are, namely

Trans Isomer 2; 3-{[3-hydroxybutan-2-yl]oxy}-5-(5-methyl-1,3-thiazol-2-yl)-N-{(1R)-1-[2-(trifluoromethyl)pyrimidin-5-yl]ethyl}benzamide;

Trans Isomer 1; 3-{[3-hydroxybutan-2-yl]oxy}-5-(5-methyl-1,3-thiazol-2-yl)-N-{(1R)-1-[6-(trifluoromethyl)pyridazin-3-yl]ethyl}benzamide;

Trans Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide;

Cis Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide;

Cis Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide;

Trans Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide;

Cis Isomer 1; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide;

Cis Isomer 2; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide;

Cis Isomer 1; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide;

Cis Isomer 2; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide.

An even more preferred compound is Cis Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}-benzamide.

It is to be understood that the present invention relates also to any combination of the preferred embodiments described above.

Synthesis of Compounds of General Formula (I)/(Ia) of the Present Invention

Compounds of general formula (I) with the meaning of $R^1$-$R^3$ and A as defined in general formula (I), can be synthesized according to a general procedure depicted in Scheme 1 starting from synthons of the formula (II) or (IV) respectively.

In analogy, compounds of general formula (Ia) with the meaning of $R^1$-$R^3$ and A as defined in general formula (Ia), can be synthesized according to a general procedure depicted in Scheme 1 starting from synthons of the formula (II) or (IVa) respectively. Intermediates depicted in Schemes 2 and 3 having an ester moiety —C(O)OR' are referred to as methyl, ethyl or propyl ester, respectively (R': methyl, ethyl, propyl).

A carboxylic acid of formula (II) may react with an amine of formula (III) by methods known to those skilled in the art to give the compounds of the general formula (I).

The reaction takes place in that for example, a carboxylic acid of formula (II) is activated with reagents such as dicyclohexylcarbodiimide (DCC), 1-(3-dimethylaminopropyl)-3-ethylcarbodiimide (EDCl), N-hydroxybenzotriazole (HOBT), N-[(dimethylamino)-(3H-[1,2,3]triazolo[4,5-b]pyridin-3-yloxy)methylidene]-N-methylmethanaminium hexafluorophosphate (HATU) or propylphosphonic anhydride (T3P). For example, the reaction with HATU takes place in an inert solvent, such as N,N-dimethylformamide, dichloromethane or dimethyl sulfoxide in the presence of the appropriate amine formula (III) and a tertiary amine (such as triethylamine or diisopropylethylamine) at temperatures between −30° C. and +60° C.

It is also possible to convert a carboxylic acid of the formula (II) into the corresponding carboxylic acid chloride with an inorganic acid chloride (such as phosphorus pentachloride, phosphorus trichloride or thionyl chloride) and then into the target compounds of the general formula (I), in pyridine or an inert solvent (such as N,N-dimethylformamide), in the presence of the appropriate amine formula (III) and a tertiary amine (for example triethylamine) at temperatures between −30° C. and +60° C.

In full analogy, a carboxylic acid of formula (II) may react with an amine of formula (IIIa) by methods known to those skilled in the art to give the compounds of the general formula (Ia).

In the same manner, the compounds of the general formula (I) can be obtained from boronic acid pinacol esters of the general formula (IV) by reaction with bromo-thiazoles of the formula (V) by methods known to those skilled in the art in a suitable solvent (for example N,N-dimethylformamide, tetrahydrofuran, 1,4-dioxane, dimethoxyethane and optionally water) and addition of a base (such as triethylamine, potassium carbonate, caesium carbonate) and a catalyst-ligand mixture, for example of palladium(II) acetate/triphenylphosphine, tetrakis-(triphenylphosphine)palladium(O), bis(diphenylphosphino)ferrocenedichloro-palladium (II), at temperatures between 10° C. and 120° C.

In analogy, the compounds of the general formula (Ia) can be obtained from boronic acid pinacol esters of the general formula (IVa) by reaction with bromo-thiazoles of the formula (V).

The carboxylic acids of the general formula (II) can for example be obtained from esters of the formula (VI) by ester saponification in a suitable solvent or solvent mixture (for example methanol, ethanol or tetrahydrofuran) with addition of an aqueous solution of an alkali metal hydroxide, for example sodium hydroxide or lithium hydroxide, at temperatures between 10° C. and 60° C. (Scheme 2).

In the same manner, carboxylic acids formula (XII) can be obtained from esters formula (X) (Scheme 3), and carboxylic acids formula (XX) from esters formula (XXI) (Scheme 4).

Alternatively, carboxylic acids of the formula (II) can be obtained from nitrites of the formula (XXXIV) by nitrite hydrolysis in a suitable solvent or solvent mixture (for example dimethyl sulfoxide or ethanol) with addition of an aqueous solution of an alkali metal hydroxide, for example sodium hydroxide, at temperatures between 80° C. and 130° C. (Scheme 5).

The compounds of the general formula (VI) can be obtained from boronic acid pinacol esters of the general formula (IX) by reaction with bromo-thiazoles of the general formula (V) (Scheme 2), analogously to the synthesis of the compounds of formula (I) from the compounds formula (IV).

In the same manner, compounds of the formula (VII) can be obtained from boronic pinacol esters formula (VIII) and bromo-thiazoles formula (V) (Scheme 2).

Alternatively, compounds of the general formula (VI) can be obtained from phenols of the general formula (VII) by reaction with electrophiles $R^2$-LG (LG: leaving group) of the general formula (XXIV) (Scheme 2), by methods known to those skilled in the art in a suitable solvent (for example N,N-dimethylformamide, acetonitrile, acetone, dimethyl sulfoxide) in the presence of a base (for example potassium carbonate and caesium carbonate) at temperatures between 10° C. and 120° C.

A suitable leaving group may include, for example chloro, bromo, iodo, methanesulfonyloxy, p-toluenesulfonyloxy, trifluoromethanesulfonyloxy or nonafluorobutanesulfonyloxy.

Additionally, phenols of the general formula (VII) may react with alcohols $R^2$-LG (LG: OH) to give compounds of the general formula (VI) (Scheme 2), by methods known to those skilled in the art in a suitable solvent (for example dichloromethane or tetrahydrofuran) in the presence of triphenylphosphine and diisopropyl azodicarboxylate, at temperatures between –20° C. and 40° C.

Alternatively, compounds of the general formula (VI) can be obtained from phenols of the general formula (VII) by reaction with oxiranes of the general formula (XXV) (Scheme 2) as electrophiles (wherein R" R'" can independently be H or $C_1$-$C_4$-alkyl), by methods known to those skilled in the art in a suitable solvent (for example N,N-dimethylformamide, acetonitrile or dimethyl sulfoxide) in the presence of a base (for example potassium carbonate or caesium carbonate) at temperatures between 10° C. and 120° C.

In the same manner as described above, compounds of the formula (X) can be obtained from 3-bromo-5-hydroxybenzoic acid ester of the formula (XXVI) and compounds of the formula (XXIV) or formula (XXV), respectively (Scheme 2).

In addition, compounds of the formula (VI) can also be obtained from aryl bromides of the general formula (XXVIII) by reaction with a heteroaromatic alcohol of the formula (XXIV) (LG: OH, $R^2$: 5-10-membered heteroaromatic system), by methods known to those skilled in the art in a suitable solvent (for example N-methyl-2-pyrrolidinone) in the presence of a base (for example potassium carbonate or caesium carbonate) and copper(I) chloride, by heating the reaction mixture in a microwave, at temperatures between 100° C. and 220° C. (Scheme 2).

After workup and purification it may occur that by following the described procedure a carboxylic acid of the general formula (II) instead of the before mentioned ester of formula (VI) is obtained.

The compounds of the general formula (XXXIV) can be obtained from aryl fluorides of the formula (XXXII) by reaction with alcohols $R_2$—OH of the general formula (XXXIII) (Scheme 5), by methods known to those skilled in the art in a suitable solvent (for example N,N-dimethylformamide) in the presence of a base (for example sodium hydride) at temperatures between 10° C. and 80° C.

Compounds of the general formula (XXXII) can be obtained from boronic acid pinacol esters of the general formula (XXXI) by reaction with bromo-thiazoles of the formula (V) (Scheme 5), analogously to the synthesis of the compounds of formula (I) from the compounds formula (IV).

The compounds of the general formula (IV) can be obtained from aryl bromides of the general formula (XI) by reaction with bis(pinacolato)diborane (Scheme 3) in a suitable solvent (for example 1,4-dioxane) in the presence of potassium acetate and a catalyst (for example 1,1'-bis(diphenylphosphino)ferrocene-palladium(II)dichloride dichloromethane complex or [1,1'-bis(diphenylphosphino)ferrocene]dichloro-palladium(II)) at temperatures between 60° C. and 100° C.

In analogy, the compounds of the general formula (IVa) can be obtained from aryl bromides of the general formula (XIa).

In the same manner, compounds of the formula (IX) can be obtained from aryl bromides of general formula (X) and likewise compounds of the general formula (VIII) can be obtained from 3-bromo-5-hydroxybenzoic acid esters of formula (XXVI) (Scheme 2).

Similarly, compounds of the general formula (XXXI) can be obtained from aryl bromides of the general formula (XXX) (Scheme 5).

The compounds of the general formula (XI) can be obtained from carboxylic acids of the general formula (XII) by reaction with amines of the general formula (III) (Scheme 3), analogously to the synthesis of the compounds of formula (I) from carboxylic acids formula (II) and amines formula (III).

In analogy, the compounds of the general formula (XIa) can be obtained from carboxylic acids of the general formula (XII) by reaction with amines of the general formula (IIIa).

Compounds of the general formula (XXVIII) can be obtained from aryl bromides of the general formula (XXVII) by reaction with thiazoles of the formula (XXIX) (Met: e.g. tributylstannanyl) by methods known to those skilled in the art in a suitable solvent (for example N,N-dimethylformamide) and addition of a base (for example potassium carbonate or caesium carbonate) and a catalyst-ligand mixture (for example of palladium(II) acetate/triphenylphosphine, tetrakis(triphenylphosphine)-palladium(0)) at temperatures between 40° C. and 120° C. (Scheme 2).

Amines of the general formula (IIIa) can be obtained from sulfinamides of the general formula (XIII) or (XIV) by methods known to those skilled in the art in a suitable solvent (for example methanol, 2-propanol, diethyl ether) and addition of an acid (for example hydrochloric acid) at appropriate concentrations (e.g. 4M in dioxane, 3M in 2-propanol, 2M in diethyl ether, 12M in water) at temperatures between 0° C. and 40° C. (Scheme 4). The amines of the general formula (IIIa) may be obtained as the mono, bis or tris salt (for example the hydrochloric/dihydrochloric salts). Alternatively, the amine salt can be converted into the free base by methods known to those skilled in the art.

Amines of the general formula (III) and (IIIa) can be used as the free base or salt of undefined stoichiometry according to, but not limited to, the synthetic disclosure herein to obtain compounds of the general formula (I)/(Ia) and general formula (XI)/(XIa).

Sulfinamides of the general formula (XIII) can be obtained from ketones of the general formula (XVII) which are converted in situ to sulfinimides of the general formula (XV) by methods known to those skilled in the art in a suitable solvent (for example diethyl ether, tetrahydrofuran) and addition of titanium(IV) ethoxide and (S)-2-tert-butylsulfinamide, at temperatures between 10° C. and 80° C. The sulfinimides (XV) can be directly converted to sulfinamides of the formula (XIII) by methods known to those skilled in the art in a suitable solvent (for example tetrahydrofuran) and the addition of L-selectride, at temperatures between –80° C. and –70° C. (Scheme 4).

Sulfinamides of the general formula (XIV) can be obtained from aldehydes of the general formula (XVIII) which are converted to sulfinimides of the general formula (XVI) by methods known to those skilled in the art in a suitable solvent (for example dichloroethane) and addition of Copper(II) sulfate and (R)-2-tert-butylsulfinamide, at temperatures between 10° C. and 80° C. The sulfinimides (XVI) can be converted to sulfinamides of the formula (XIV) by methods known to those skilled in the art in a suitable solvent (for example tetrahydrofuran, diethyl ether) and the addition of a Grignard reagent $R^3MgX$ (X: Cl, Br), at temperatures between −70° C. and −20° C. (Scheme 4).

Amines having the opposite stereochemistry to the stereochemistry described for amines of the general formula (IIIa) can be synthesized in analogous fashion as described for amines (IIIa) starting from ketone (XVII) and using (R)-2-tert-butylsulfinamide instead of (S)-2-tert-butylsulfinamide. In a similar fashion, starting from aldehyde (XVIII) and using using (S)-2-tert-butylsulfinamide instead of (R)-2-tert-butylsulfinamide.

Ketones of the general formula (XVII) can be obtained from Weinreb amides of the general formula (XIX) by methods known to those skilled in the art in a suitable solvent (for example tetrahydrofuran, diethyl ether, tert-butyl methyl ether or toluene) and the addition of a Grignard reagent $R^3MgX$ (X: Cl, Br, I), at temperatures between −20° C. and 0° C. (Scheme 4).

Likewise, ketones of the general formula (XVII) can be obtained from nitrites of the general formula (XXII) and a Grignard reagent $R^3MgX$ (X: Cl, Br, I).

In addition, ketones of the general formula (XVII) can be obtained from halides of the general formula (XXIII) (Hal: Cl, Br) by methods known to those skilled in the art in a suitable solvent (for example N,N-dimethylformamide), tributyl(1-ethoxyvinyl)-stannane and a catalyst (for example dichlorobis(triphenylphosphine)palladium(II)), at temperatures between 40° C. and 100° C. and subsequent cleavage of the enol ether intermediate under acidic conditions (for example aqueous hydrochloric acid), in a suitable solvent (for example tetrahydrofuran) at temperatures between 10° C. and 40° C. (Scheme 4).

Weinreb amides of the general formula (XIX) can be obtained from carboxylic acids of the general formula (XX) and N-methoxymethaneamine in analogous fashion as described for amides of formula (I) from carboxylic acids of formula (II).

Aldehydes of the general formula (XVIII) can be obtained from amides of the formula (XIX) by reduction methods known to those skilled in the art in a suitable solvent (for example tetrahydrofuran) and a reducing agent (for example lithium aluminium hydride) at temperatures between −80° C. and −70° C. (Scheme 4).

Bromo-thiazoles of the general formula (V) can be generated from amino-thiazoles of the formula (XXXV) by methods known to those skilled in the art in a suitable reaction medium (for example aqueous hydrobromic acid/ sodium nitrite, copper(II) bromide/tert-butyl nitrite) in acetonitrile or N,N-dimethylformamide at temperatures between 0° C. and 40° C. (Scheme 4).

Additionally, compounds of the general formula Ia, IIIa, IVa and XIa can be obtained directly from their racemic respectively diastereoisomeric mixtures of the general formula I, III, IV and XI through separation of said mixtures using methods known to someone skilled in the art (e.g. preparative chiral HPLC).

Scheme 1

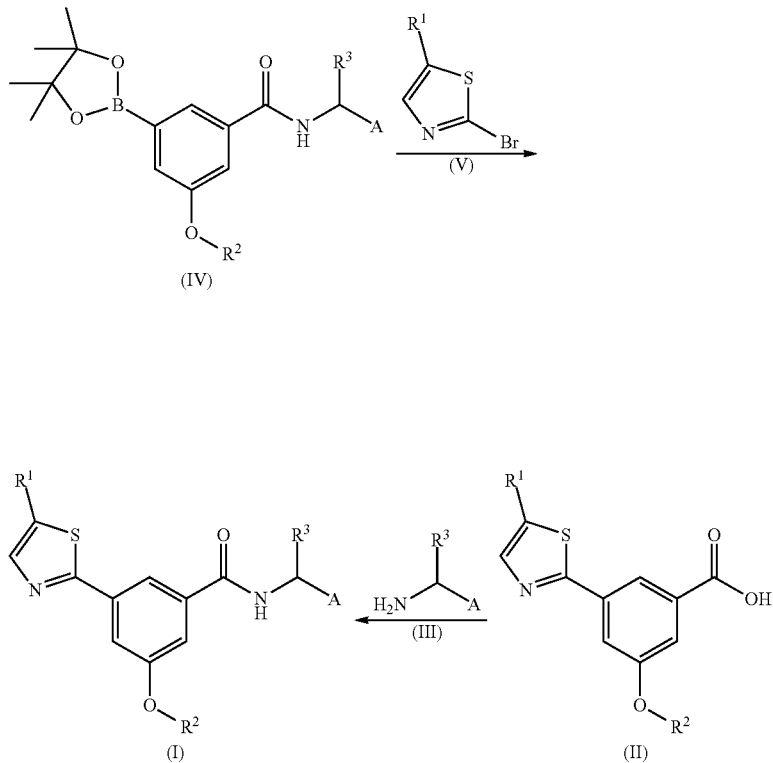

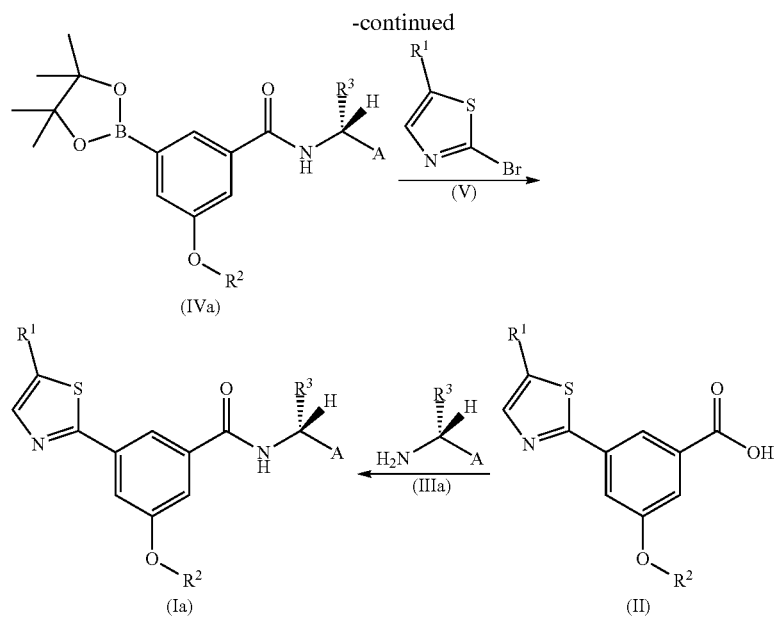
Scheme 2
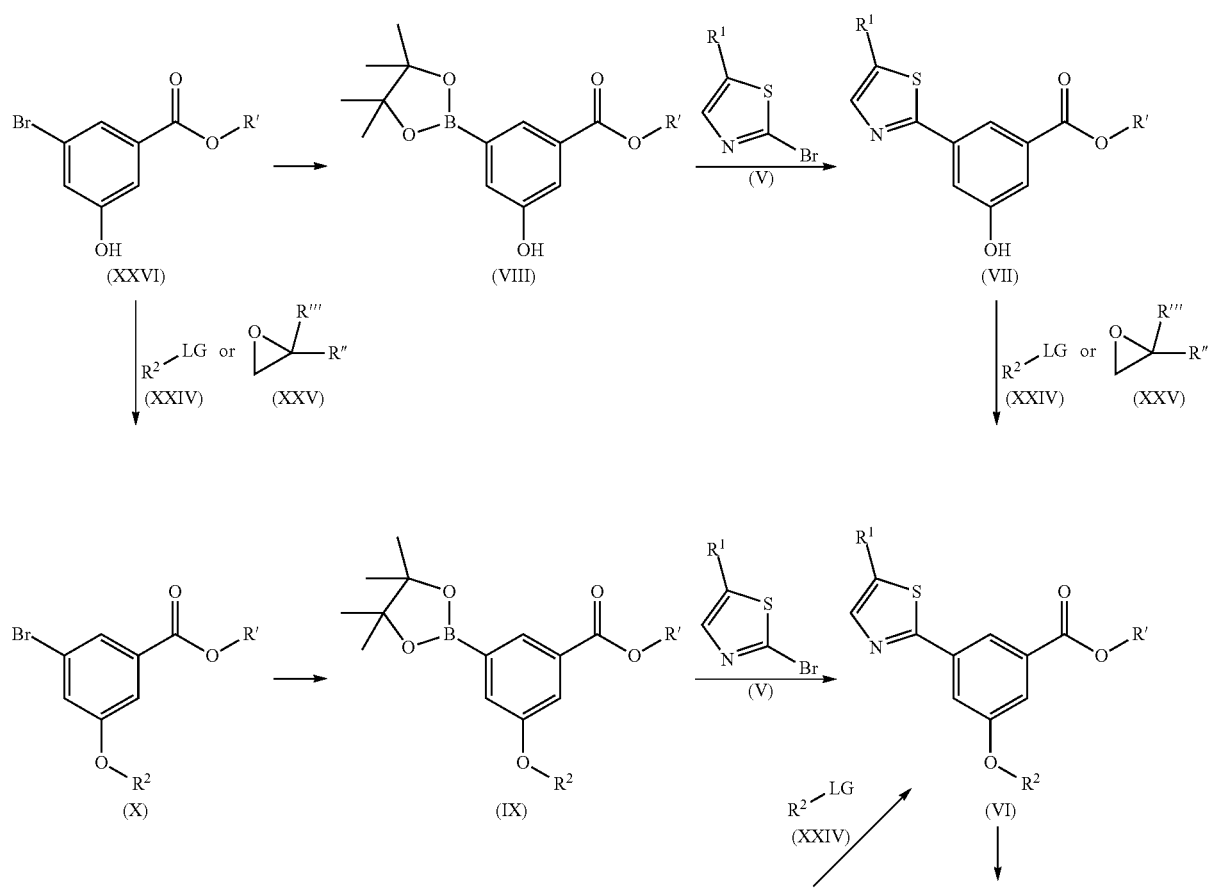

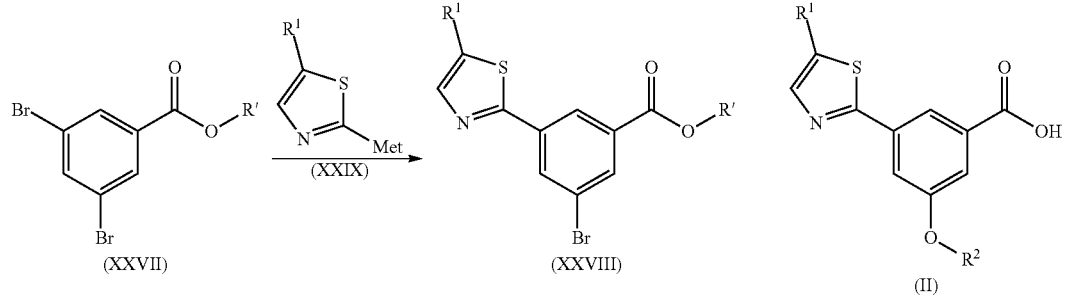
Scheme 3
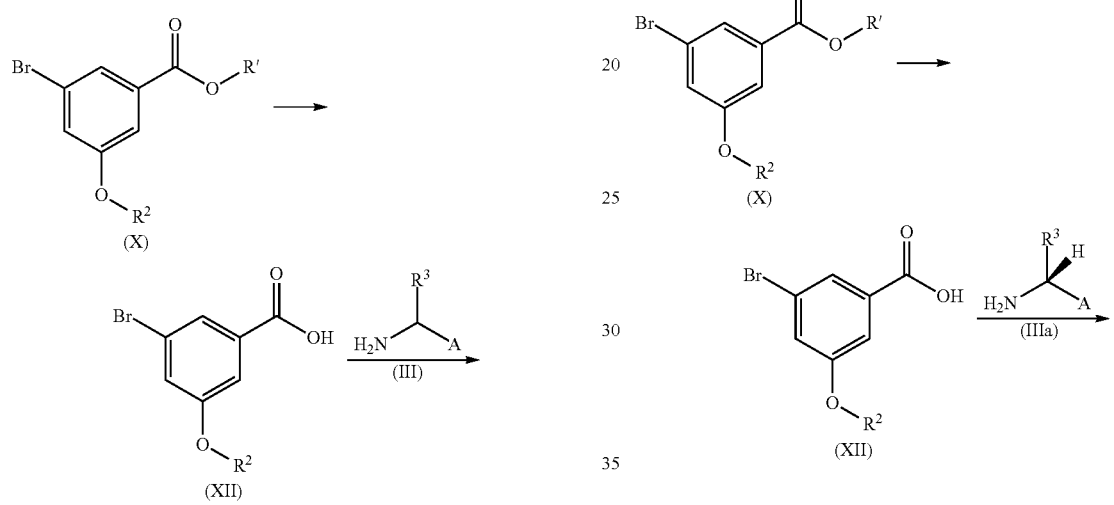
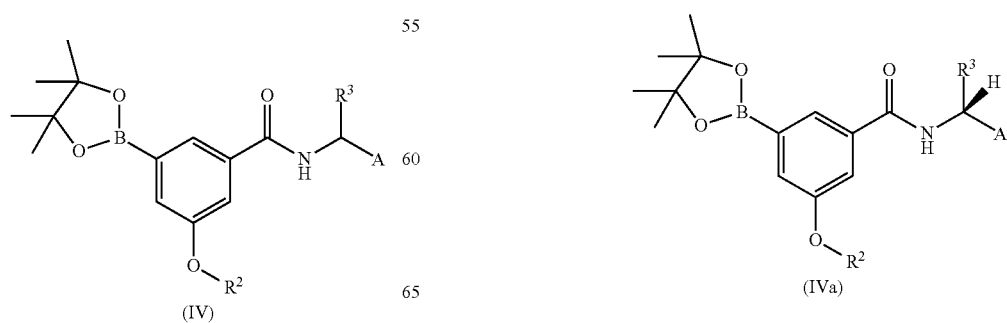

Scheme 4
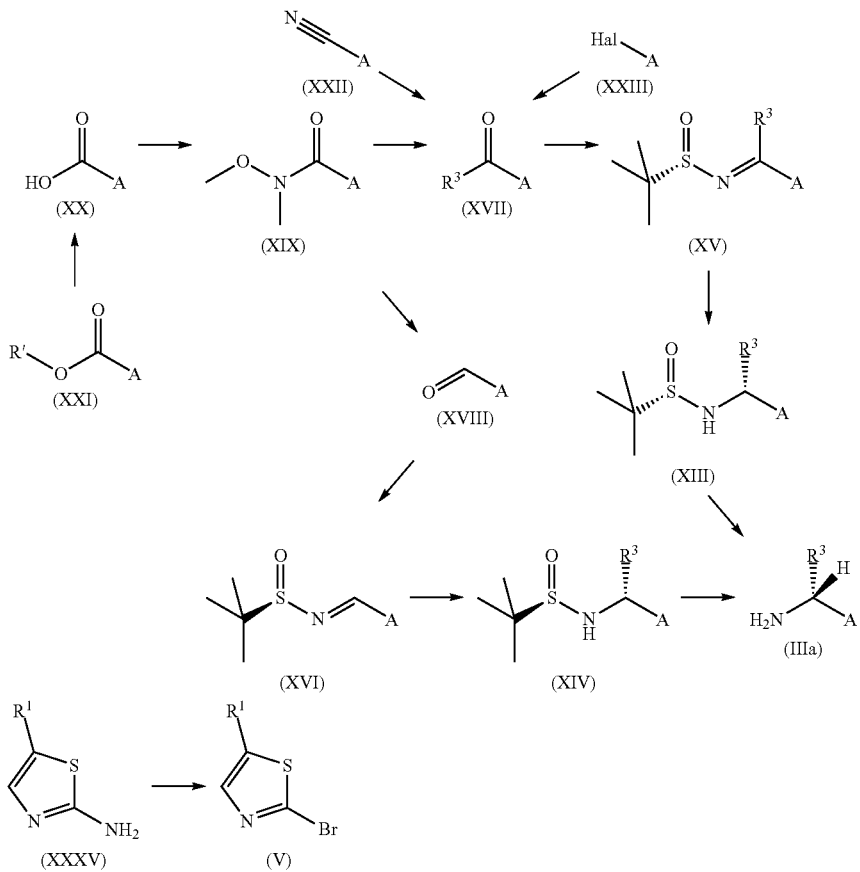
Scheme 5
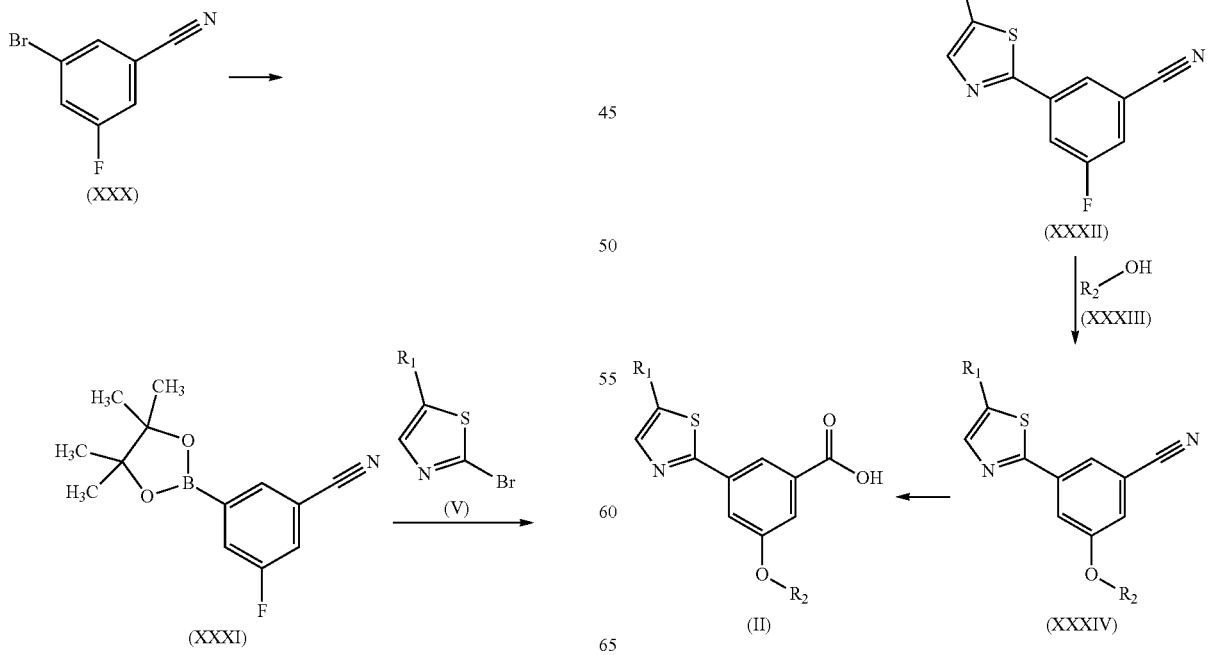

12 Experimental Section

The example testing experiments described herein serve to illustrate the present invention and the invention is not limited to the examples given.

The following table lists the abbreviations used in this paragraph, and in the examples section.

| Abbreviation | Meaning |
|---|---|
| $Cs_2CO_3$ | Cesium carbonate |
| Cu(I)Cl | Copper(I) chloride |
| ca. | circa |
| DCE | 1,2-Dichloroethane |
| DCM | Dichloromethane |
| DIAD | Diisopropyl azodicarboxylate |
| DIPEA | N-Ethyl-N-isopropylpropan-2-amine |
| DIAD | Diisopropyl azodicarboxylate |
| DMA | Dimethylacetamide |
| DMAP | N,N-Dimethylpyridin-4-amine |
| DMF | N,N-Dimethylformamide |
| DMSO | Dimethyl sulfoxide |
| DP | Desired product |
| EE | Ethyl acetate |
| EEDQ | N-Ethoxycarbonyl-2-ethoxy-1,2-dihydroquinoline |
| EtOAc | Ethyl acetate |
| EtOH | Ethanol |
| $Et_2O$ | Diethyl ether |
| h | Hour(s) |
| HATU | N-[(Dimethylamino)(3H-[1,2,3]triazolo[4,5-b]pyridin-3-yloxy)methylene]-N-methylmethanaminium hexafluorophosphate |
| HBr | Hydrogen bromide |
| HCl | Hydrochloric acid |
| HPLC | high performance liquid chromatography |
| IPA | 2-Propanol |
| IPC | In process check |
| $K_2CO_3$ | Potassium carbonate |
| KOtBu | Potassium 2-methylpropan-2-olate |
| LC-MS | liquid chromatography-mass spectrometry |
| LCMS | liquid chromatography-mass spectrometry |
| LiOH | Lithium hydroxide |
| M | Molar |
| μW | Microwave |
| MeCN | Acetonitrile |
| MeOH | Methanol |
| $MgSO_4$ | Magnesium sulfate |
| min | Minute(s) |
| N | Normal |
| $NaBH_4$ | Sodium tetrahydroborate |
| $Na_2CO_3$ | Sodium carbonate |
| NaH | Sodium hydride |
| $NaHCO_3$ | Sodium bicarbonate |
| NaI | Sodium iodide |
| NaOH | Sodium hydroxide |
| $Na_2SO_4$ | Sodium sulfate |
| $NH_4Cl$ | Ammonium chloride |
| NMP | N-Methyl-2-pyrrolidinone |
| NMR | nuclear magnetic resonance spectroscopy |
| $PdCl_2(PPh_3)_2$ | Bis(triphenylphosphine)palladium(II)dichloride |
| $Pd(dppf)Cl_2$ | [1,1'-Bis(diphenylphosphino)ferrocene]dichloropalladium(II) |
| $Pd(dppf)Cl_2 \cdot CH_2Cl_2$ | 1,1'-Bis(diphenylphosphino)ferrocene-palladium(II)dichloride dichloromethane complex |
| $PPh_3$ | Triphenylphosphine |
| ppm | parts per million |
| RT | Room temperature |
| rt | Retention time |
| Rt | Retention time |
| sat. | Saturated |
| SM | Starting material |
| STAB | Sodium triacetoxyborohydride |
| T3P | Propylphosphonic anhydride |
| TBAI | Tetra-N-butylammonium iodide |
| TBME | tert-Butyl methyl ether |
| TEA | Triethylamine |
| TFA | Trifluoroacetic acid |
| THF | Tetrahydrofuran |
| TMS-Br | Trimethylsilyl bromide |

Analysis Methods

LC-MS, Method A: Routine high throughput analysis

| Column | Supelco Ascentis Express |
|---|---|
|  | 2.1 × 30 mm, 2.7 μm |
| Available on | MS14, MS17, MS18 and MS19 |
| Column Temp | 40° C. |
| Mobile Phase | A, Water + 0.1% Formic acid |
|  | B, Acetonitrile + 0.1% Formic acid |

| Gradient | Time (mins) | % organic |
|---|---|---|
|  | 0 | 5 |
|  | 1.5 | 100 |
|  | 1.6 | 100 |
|  | 1.61 | 5 |

| Flow rate | 1 ml/min |
|---|---|
| Injection Vol | 3 μl |

Detection

| Signal | UV 215 |
|---|---|
| PDA Spectrum | Range: 210-420 nm step: 1 nm (Not MS14 this has single wavelength detector) |
| MSD Signal settings | Scan Pos (Shimadzu): 100-1000 Scan Pos (M514): 130-850 |

LC-MS, Method B: Routine high throughput analysis

| Column | Waters Atlantis dC18 |
|---|---|
|  | 2.1 × 50 mm, 3 μm |
| Available on | MS11, MS14, MS17, MS18 and MS19 |
| Column Temp | 40° C. |
| Mobile Phase | A, Water + 0.1% Formic acid |
|  | B, Acetonitrile + 0.1% Formic acid |

| Gradient | Time (mins) | % organic |
|---|---|---|
|  | 0.00 | 5 |
|  | 2.50 | 100 |
|  | 2.70 | 100 |
|  | 2.71 | 5 |
|  | 3.50 | 5 |

| Flow rate | 1 ml/min |
|---|---|
| Injection Vol | 3 μl |

Detection

| Signal | UV 215 |
|---|---|
| PDA Spectrum | Range: 210-420 nm step: 1 nm (Not MS14 this has single wavelength detector) |
| MSD Signal settings | Scan Pos (Shimadzu): 100-1000 Scan Pos (MS14): 130-850 |

LC-MS, Method C: Routine high throughput analysis at high pH

| Column | Phenomenex Gemini-NX C18 |
|---|---|
|  | 2.0 × 50 mm, 3 μm |
| Available on | MS10 |
| Column Temp | 40° C. |

-continued

| | |
|---|---|
| Mobile Phase | A, 2 mM amm. bicarbonate, buffered to pH10 |
| | B, Acetonitrile |

| Gradient | Time (mins) | % organic |
|---|---|---|
| | 0.00 | 1 |
| | 1.80 | 100 |
| | 2.10 | 100 |
| | 2.30 | 1 |
| | 3.50 | 1 |

| | |
|---|---|
| Flow rate | 1 ml/min |
| Injection Vol | 3 μl |
| Detection | |
| Signal | UV 215 |
| PDA Spectrum | Range: 210-420 nm step: 1 nm |
| MSD Signal settings | Scan Pos: 150-850 |

LC-MS, Analytical Method D:

| | |
|---|---|
| Column | Waters Atlantis dC18 |
| | 2.1 × 100 mm, 3 μm |
| Available on | MS11, MS17, MS18 and MS19 |
| Column Temp | 40° C. |
| Mobile Phase | A, Water + 0.1% Formic acid |
| | B, Acetonitrile + 0.1% Formic acid |

| Gradient | Time (mins) | % organic |
|---|---|---|
| | 0.00 | 5 |
| | 5.00 | 100 |
| | 5.40 | 100 |
| | 5.42 | 5 |
| | 7.00 | 5 |

| | |
|---|---|
| Flow rate | 0.6 ml/min |
| Injection Vol | 3 μl |
| Detection | |
| Signal | UV 215 |
| PDA Spectrum | Range: 210-420 nm step: 1 nm |
| MSD Signal settings | Scan Pos: 100-1000 |

LC-MS, Analytical Method E: High pH

| | |
|---|---|
| Column | Phenomenex Gemini -NX C18 |
| | 2.0 × 100 mm, 3 μm column |
| Available on | MS10 |
| Column Temp | 40° C. |
| Mobile Phase | A, 2mM amm. bicarbonate, buffered to pH10 |
| | B, Acetonitrile |

| Gradient | Time (mins) | % organic |
|---|---|---|
| | 0.00 | 5 |
| | 5.50 | 100 |
| | 5.90 | 100 |
| | 5.92 | 5 |
| | 7.00 | 5 |

| | |
|---|---|
| Flow rate | 0.5 ml/min |
| Injection Vol | 3 μl |
| Detection | |
| Signal | UV 215 |
| PDA Spectrum | Range: 210-420 nm step: 1 nm |
| MSD Signal settings | Scan Pos: 100-1000 |

LC-MS, Analytical Method F:

| | |
|---|---|
| Column | Phenomenex Kinetix-XB C18 |
| | 2.1 × 100 mm, 1.7 μm |
| Available on | MSQ1 |
| Column Temp | 40° C. |
| Mobile Phase | A, Water + 0.1% Formic acid |
| | B, Acetonitrile + 0.1% Formic acid |

| Gradient | Time (mins) | % organic |
|---|---|---|
| | 0.00 | 5 |
| | 5.30 | 100 |
| | 5.80 | 100 |
| | 5.82 | 5 |
| | 7.00 | 5 |

| | |
|---|---|
| Flow rate | 0.6 ml/min |
| Injection Vol | 1 μl |
| Detection | |
| Signal | UV 215 |
| PDA Spectrum | Range: 200-400 nm step: 1 nm |
| MSD Signal settings | Scan Pos: 150-850 |

Analytical LCMS Method 1, low pH:

Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Analytical LCMS Method 2, high pH:

Instrument: Waters Acquity UPLCMS SingleQuad; Colum: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Chiral Analysis Methods:

| Method | Column Type | Flow rate (ml/min) | Detector wavelength (nm) | Isocratic Conditions |
|---|---|---|---|---|
| 1 | Amy-C (4.6 mm × 250 mm, 5 μm) | 4 | 210-400 | 20:80 MeOH/CO$_2$ |
| 2 | Lux C3 (4.6 mm × 250 mm, 5 μm) | 4 | 210-400 | 2:8 MeOH/CO$_2$ (0.1% v/v NH$_3$) |
| 3 | Lux C4 (4.6 mm × 250 mm, 5 μm) | 4 | 210-400 | 25:75 MeOH/CO$_2$ |
| 4 | Lux C4 (4.6 mm × 250 mm, 5 μm) | 1 | 210-400 | 50:50 Heptane/IPA (DEA added as a modifier) |
| 5 | Amy-C (4.6 mm × 250 mm, 5 μm) | 4 | 210-400 | 25:75 EtOH/CO$_2$ (0.1% v/v NH$_3$) |
| 6 | Lux C1 (4.6 mm × 250 mm, 5 μm) | 4 | 210-280 | 3:7 MeOH/CO$_2$ (0.1% v/v DEA) |
| 7 | Amy-C (4.6 mm × 250 mm, 5 μm) | 21 | 210-400 | 25:75 MeOH/CO$_2$ (0.1% v/v NH$_3$) |

-continued

| Method | Column Type | Flow rate (ml/min) | Detector wavelength (nm) | Isocratic Conditions |
|---|---|---|---|---|
| 8 | Amy-C (4.6 mm × 250 mm, 5 μm) | 4 | 210-400 | 40:60 EtOH/CO$_2$ (0.1% v/v NH$_3$) |
| 9 | Amy-C (4.6 mm × 250 mm, 5 μm) | 1 | 254 | 60:40 Heptane/IPA (0.1% v/v NH$_3$) |
| 10 | Amy-C (4.6 mm × 250 mm, 5 μm) | 4 | 210-400 | 35:65 MeOH/CO$_2$ (0.1% v/v NH3) |
| 11 | Lux C1 (4.6 mm × 250 mm, 5 μm) | 1 | 220 | 70:30 Heptane/EtOH (0.1% v/v DEA) |
| 12 | Lux C1 (4.6 mm × 250 mm, 5 μm) | 1 | 220 | 40:60 Heptane/EtOH (0.1% v/v DEA) |
| 13 | Amy-C (4.6 mm × 250 mm, 5 μm) | 4 | 210-400 | 30:70 MeOH/CO$_2$ (0.1% v/v NH$_3$) |
| 14 | Amy-C (4.6 mm × 250 mm, 5 μm) | 4 | 210-400 | 20:80 MeOH/CO$_2$ (0.1% v/v NH$_3$) |
| 15 | Amy-C (4.6 mm × 250 mm, 5 μm) | 4 | 210-400 | 25:75 MeOH/CO$_2$ (0.1% v/v NH$_3$) |
| 16 | Amy-C (4.6 mm × 250 mm, 5 μm) | 4 | 210-400 | 10:90 to 50:50 MeOH/CO$_2$ (0.1% v/v NH$_3$) |

Analytical chiral HPLC Methods

Method A:

Instrument: Agilent HPLC 1260; Column: Chiralpak IE 3μ 100×4,6 mm; Eluent A: tert-butyl methyl ether+0.1 Vol-% diethylamine (99%); Eluent B: ethanol; isokratic: 95% A+5% D; flow 1.4 ml/min; temperature: 25° C.; DAD 325 nm Method B:

Instrument: Agilent: 1260, Aurora SFC-Modul; column: Chiralpak IF 5 μm 100×4.6 mm; eluent A: CO$_2$, eluent B: ethanol; isokratic: 16% B; flow 4.0 ml/min; temperature: 37.5° C.; BPR: 100 bar; MWD 254 nm Method C:

Instrument: Agilent HPLC 1260; column: Chiralpak IC 3μ 100×4,6 mm; eluent A: hexane; eluent B: 2-propanol; isokratic: 70% A+30% B; flow 1.0 ml/min; temperature: 25° C.; DAD @ 254 nm Method D:

Instrument: Agilent HPLC 1260; column: Chiralpak IC 3μ 100×4,6 mm; eluent A: hexane +0.1 Vol-% diethylamine (99%); eluent B: ethanol; isokratic: 80% A+20% B; flow 1.0 ml/min; temperature: 25° C.; DAD 254 nm Method E:

Instrument: Agilent HPLC 1260; column: Chiralpak IC 3μ 100×4,6 mm; eluent A: hexane +0.1 Vol-% diethylamine (99%); eluent B: ethanol; isokratic: 50% A+50% B; flow 1.4 ml/min; temperature: 25° C.; DAD 254 nm Method F:

Instrument: Agilent: 1260, Aurora SFC-Modul; column: LUNA HILIC 5 μm 100×4.6 mm; eluent A: CO$_2$, eluent B: methanol +0.2 Vol-% diethylamine (99%); isokratic: 20% B; flow 4.0 ml/min; temperature: 37.5° C.; BPR: 100 bar; MWD 254 nm Method G:

Instrument: Agilent HPLC 1260; column: Chiralpak IF 3μ 100×4.6 mm; Eluent A: water, Eluent B: acetonitrile; isocratic: 70% A +30% B; flow 1.4 ml/min; temperature: 25° C.; MWD @ 220 nm Purification Methods:

Biotage Isolera™ chromatography system using pre-packed silica and pre-packed modified silica cartridges.

Preparative HPLC, Method A: High pH

| Column | Waters Xbridge C18 30 × 100 mm, 10 μm |
|---|---|
| Available on Column Temp | Gilson 3 and Gilson 5 Room temperature |
| Mobile Phase | A, Water + 0.2% Ammonium hydroxide B, Acetonitrile + 0.2% Ammonium hydroxide |

| Gradient | Time (mins) | % organic |
|---|---|---|
| | 0 | 5 |
| | 2.5 | 5 |
| | 16.05 | 95 |
| | 18.2 | 95 |
| | 19.1 | 5 |
| | 20 | 5 |

| Flow rate | 40 mL/min |
|---|---|
| Injection Vol | 1500 μl |
| Detection | |
| Signal | UV 215 |

Preparative HPLC, Method B: Low pH

| Column | Waters Sunfire C18 30 × 100 mm, 10 μm |
|---|---|
| Available on Column Temp | Waters02 Room temperature |
| Mobile Phase | A, Water + 0.1% Formic acid B, Acetonitrile + 0.1% Formic acid |

| Gradient | Time (mins) | % organic |
|---|---|---|
| | 0 | 5 |
| | 2 | 5 |
| | 2.5 | 10 |
| | 14.5 | 100 |
| | 15.5 | 100 |
| | 16 | 5 |
| | 17 | 5 |

| Flow rate | 40 mL/min |
|---|---|
| Injection Vol | 1500 μl |
| Detection | |
| Signal | UV 215 |

Preparative HPLC Methods

Preparative HPLC, method 1:

System: Waters autopurification system: Pump 2545, Sample Manager 2767, CFO, DAD 2996, ELSD 2424, SQD; Column: XBrigde C18 5μ 100×30 mm; Solvent: A=H2O+0.1% Vol. formic acid (99%), B=acetonitrile; Gradient: 0-8 min 10-100% B, 8-10 min 100% B; Flow: 50 mL/min; temperature: room temp.; Solution: Max. 250 mg/max. 2.5 mL DMSO o. DMF; Injection: 1×2.5 mL; Detection: DAD scan range 210-400 nm; MS ESI+, ESI−, scan range 160-1000 m/z.

Preparative HPLC, method 2:

System: Waters autopurification system: Pump 2545, Sample Manager 2767, CFO, DAD 2996, ELSD 2424, SQD; Column: XBrigde C18 5μ 100×30 mm; Solvent: A=H2O+0.1% Vol. ammonia (99%), B=acetonitrile; Gradient: 0-8 min 10-100% B, 8-10 min 100% B; Flow: 50 mL/min; temperature: room temp.; Solution: Max. 250 mg/max. 2.5 mL DMSO o. DMF; Injection: 1×2.5 mL; Detection: DAD scan range 210-400 nm; MS ESI+, ESI−, scan range 160-1000 m/z.

Chiral Purification Methods:

| Method | Column Type | Flow rate (ml/min) | Detector wavelength (nm) | Isocratic Conditions |
|---|---|---|---|---|
| 1 | Amy-C (20 mm × 250 mm, 5 μm) | 50 | 210 | 20:80 MeOH/CO$_2$ |
| 2 | Lux C3 (21.2 mm × 250 mm, 5 μm) | 50 | 210 | 20:80 MeOH/CO$_2$ (0.1% v/v NH$_3$) |
| 3 | Lux C4 (20 mm × 250 mm, 5 μm) | 50 | 210 | 25:75 MeOH/CO$_2$ |
| 4 | Lux C4 (20 mm × 250 mm, 5 μm) | 21 | 212 | 50:50 Heptane/IPA (DEA added as a modifier) |
| 5 | Amy-C (20 mm × 250 mm, 5 μm) | 50 | 210 | 25:75 EtOH/CO$_2$ |
| 6 | Lux C1 (20 mm × 250 mm, 5 μm) | 50 | 215 | 25:75 MeOH/CO$_2$ (0.1% v/v DEA) |
| 7 | Amy-C (20 mm × 250 mm, 5 μm) | 50 | 210 | 25:75 MeOH/CO$_2$ (0.1% v/v NH$_3$) |
| 8 | Amy-C (20 mm × 250 mm, 5 μm) | 50 | 210 | 40:60 EtOH/CO$_2$ (0.1% v/v NH$_3$) |
| 9 | Amy-C (20 mm × 250 mm, 5 μm) | 42 | 210 | 70:30 Heptane/IPA (0.1% v/v NH$_3$) |
| 10 | Amy-C (20 mm × 250 mm, 5 μm) | 50 | 220 | 35:65 MeOH/CO$_2$ (0.1% v/v NH$_3$) |
| 11 | Lux C1 (20 mm × 250 mm, 5 μm) | 21 | 220 | 70:30 Heptane/EtOH (0.1% v/v DEA) |
| 12 | Lux C1 (20 mm × 250 mm, 5 μm) | 21 | 220 | 50:50 Heptane/EtOH (0.1% v/v DEA) |
| 13 | Amy-C (20 mm × 250 mm, 5 μm) | 50 | 210 | 25:75 MeOH/CO$_2$ (0.1% v/v NH$_3$) |
| 14 | Amy-C (20 mm × 250 mm, 5 μm) | 50 | 210 | 15:85 MeOH/CO$_2$ (0.1% v/v NH$_3$) |
| 15 | Amy-C (20 mm × 250 mm, 5 μm) | 50 | 215 | 25:75 MeOH/CO$_2$ (0.1% v/v NH$_3$) |

Preparative chiral HPLC Methods

Method A:

Instrument: Labomatic HD5000, Labocord-5000; Gilson GX-241, Labcol Vario 4000; column: Chiralpak IE 5μ 250×30 mm; eluent A: ethanol +0.1 Vol-% diethylamine (99%); eluent B: tert.-butyl methyl ether; isokratic: 5% A+95% B; flow 50.0 ml/min; UV 325 nm Method B:

Instrument: Sepiatec: Prep SFC100; column: Chiralpak IF 5 μm 250×30 mm; eluent A: CO$_2$, eluent B: ethanol; isokratic: 16% B; flow 100.0 ml/min; temperature: 40° C.; BPR: 150 bar; MWD @ 254 nm Method C:

Instrument: Agilent PrepHPLC 1200, column: Chiralpak IC 5μ 250×20 mm; eluent A: hexane; eluent B: 2-propanol; isokratic: 70% A+30% B; flow 15.0 ml/min; UV @ 254 nm Method D:

Instrument: Labomatic HD5000, Labocord-5000; Gilson GX-241, Labcol Vario 4000; column: Chiralpak IC 5μ 250×30 mm; eluent A: hexane +0.1 Vol-% diethylamine (99%); eluent B: ethanol; isokratic: 80% A+20% B; flow 50.0 ml/min; UV 254 nm Method E:

Instrument: Labomatic HD5000, Labocord-5000; Gilson GX-241, Labcol Vario 4000; column: Chiralpak IC 5μ 250×30 mm; eluent A: hexane +0.1 Vol-% diethylamine (99%); eluent B: ethanol; isokratic: 70% A+30% B; flow 50.0 ml/min; UV 254 nm Method F:

Instrument: Sepiatec: Prep SFC100; column: LUNA HILIC 5 μm 250×30 mm; eluent A CO$_2$, eluent B: methanol +0.5 Vol-% ammonia (32%); isokratic: 20% B; flow 100.0 ml/min temperature: 40° C.; BPR: 90 bar; MWD @ 254 nm

EXAMPLES

Chemical naming of the Examples and Intermediates was performed using ACD software by ACD/LABS or Marvin software by ChemAxon.

Reaction times are either specified explicitly in the protocols of the experimental section, or reactions were run until completion. Chemical reactions were monitored and their completion was judged using methods well known to the person skilled in the art, such as thin layer chromatography, e.g. on plates coated with silica gel, or by LCMS methods.

Intermediate 1: Methyl 3-bromo-5-hydroxybenzoate

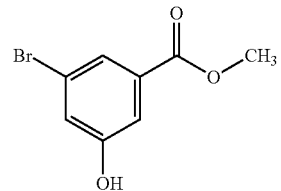

A solution of 3-bromo-5-hydroxybenzoic acid (47.7 g, 0.22 mot) and acetyl chloride (31.5 mL, 0.44 mol) in methanol (500 mL) was stirred under reflux for 16 h. TLC analysis indicated complete conversion to a single product. The solvent was removed under reduced pressure to give 49.9 g (98% yield) of the title compound as an off-white powder, used without further purification in the next step.

$^1$H NMR (250 MHz, Chloroform-d): δ [ppm] 7.74 (t, J=1.5 Hz, 1H), 7.46 (dd, J=2.4, 1.3 Hz, 1H), 7.25-7.16 (m, 1H), 5.57 (s, 1H), 3.92 (s, 3H).

Intermediate 2: Methyl 3-hydroxy-5-(4,4,5,5-tetramethyl-1,3,2-dioxaborolan-2-yl)benzoate

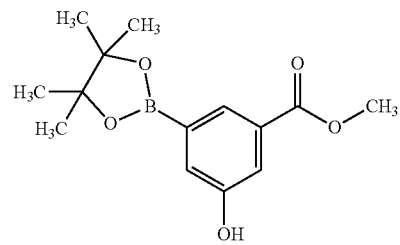

Methyl 3-bromo-5-hydroxybenzoate (26 g, 112.5 mmol), bis(pinacolato)diborane (31.4 g, 123.8 mmol) and potassium acetate (33.1 g, 337.6 mmol) were dissolved in 1,4-dioxane (450 mL) and the solution degassed with a stream of nitrogen for 10 min. Pd(dppf)Cl$_2$.CH$_2$Cl$_2$ (4.6 g, 5.62 mmol) was added and the resulting solution degassed with a stream of nitrogen for a further 5 min before the reaction mixture was stirred at 100° C. for 16 h. The reaction mixture was filtered through Celite® and concentrated in vacuo to give a brown solid. The crude material was purified by dry flash silica chromatography (eluting with 0-25% EtOAc in heptanes). Product containing fractions were concentrated, the material slurried in heptane and the solid collected by filtration to give the title compound 30.1 g (96% yield) as a cream powder.

¹H NMR (500 MHz, Chloroform-d): δ [ppm] 8.04 (s, 1H), 7.60 (dd, J=2.7, 1.5 Hz, 1H), 7.47-7.41 (m, 1H), 4.95 (s, 1H), 3.90 (s, 3H), 1.35 (s, 12H).

Intermediate 3: Methyl 3-hydroxy-5-(5-methyl-1,3-thiazol-2-yl)benzoate

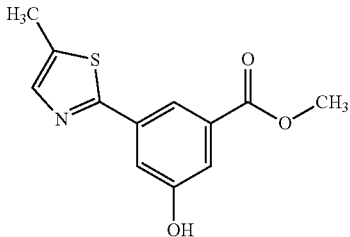 [SMILES: COC(=O)c1cc(O)cc(-c2ncc(C)s2)c1]

Intermediate 2 (1.0 g, 3.60 mmol) and 2-bromo-5-methyl-1,3-thiazole (0.451 mL, 4.32 mmol) were dissolved in 1M $K_2CO_3$ aqueous solution (8.63 mL) and THF (58.7 mL). The solution was degassed with a stream of nitrogen for 10 minutes, [1,1-Bis(diphenylphosphino)ferrocene]palladium (II) dichloride (395.3 mg, 0.539 mmol) was added and the reaction mixture heated at 90° C. for 17 h until reaction completion (monitored by TLC). The reaction mixture was diluted with water (100 mL) and extracted with EtOAc (3×100 mL). The combined organics were dried (over $MgSO_4$) and concentrated under reduced pressure. Crude material was purified by Biotage Isolera™ chromatography (eluting with 12-80% EtOAc in heptane on a 25 g pre-packed KP—SiO₂ column) to give 359.7 mg (40% yield) of the title compound as an off-white powder.

¹H NMR (250 MHz, Chloroform-d): δ [ppm] 8.06 (t, J=1.4 Hz, 1H), 7.67-7.62 (m, 1H), 7.54 (dd, J=2.5, 1.4 Hz, 1H), 7.52 (d, J=1.1 Hz, 1H), 5.84 (s, 2H), 3.93 (s, 3H), 2.53 (d, J=1.1 Hz, 3H).

Intermediate 3A: Methyl 3-(5-ethyl-1,3-thiazol-2-yl)-5-hydroxybenzoate

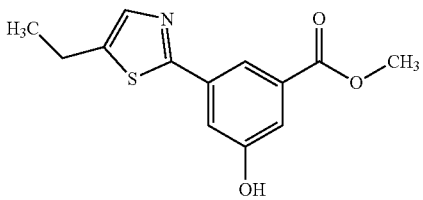 [SMILES: CCc1cnc(-c2cc(O)cc(C(=O)OC)c2)s1]

A mixture of Intermediate 2 (7.08 g, 25.5 mmol), 2-chloro-5-ethyl-1,3-thiazole (4.51 g, 30.5 mmol), [1,1,-Bis-(diphenylphosphino)-ferrocen]-palladium(II) dichloride (3.12 g, 3.82 mmol), and $K_2CO_3$ (31 ml, 2.0 M, 61 mmol) in THF (420 mL) was stirred at reflux until complete conversion. The solvent was evaporated under reduced pressure, water added and the mixture extracted with EtOAc. The combined organic layers were washed with saturated aqueous NaCl-solution and evaporated to dryness under reduced pressure. Crude material was purified by column chromatography (silica gel, hexane/EtOAc gradient) to give 2.54 g (38% yield) of the title compound.

¹H NMR (400 MHz, DMSO-d₆): δ [ppm] 1.26-1.32 (m, 3H) 2.89 (m, 2H) 3.87 (s, 3H) 7.39 (dd, 1H) 7.52 (dd, 1H) 7.66 (t, 1H) 7.87 (t, 1H) 10.24 (s, 1H).

Intermediate 3B: Methyl 3-(5-chloro-1,3-thiazol-2-yl)-5-hydroxybenzoate

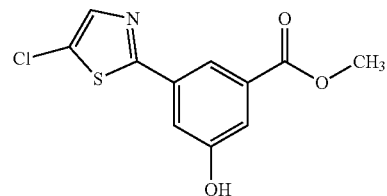 [SMILES: COC(=O)c1cc(O)cc(-c2ncc(Cl)s2)c1]

A mixture of Intermediate 2 (30.1 g, 50% purity, 54.2 mmol), 2-bromo-5-chloro-1,3-thiazole (14.0 g, 70.4 mmol), [1,1,-Bis-(diphenylphosphino)-ferrocen]-palladium(II) dichloride (6.63 g, 8.13 mmol), and $K_2CO_3$ (65 mL, 2.0 M, 130 mmol) in THF (890 mL) was stirred at reflux until complete conversion. The solvent was evaporated under reduced pressure, water added and the mixture extracted with EtOAc. The combined organic layers were washed with saturated aqueous NaCl-solution and evaporated to dryness under reduced pressure. Crude material was purified by column chromatography (silica gel, hexane/EtOAc gradient) to give 5.21 g (34% yield) of the title compound.

¹H NMR (400 MHz, DMSO-d₆): δ [ppm] 3.85-3.90 (m, 3H) 7.44 (dd, 1H) 7.51 (dd, 1H) 7.84 (t, 1H) 7.99 (s, 1H) 10.35 (br. s., 1H).

Intermediate 4A: Methyl 3-(cyclopropylmethoxy)-5-(5-methyl-1,3-thiazol-2-yl)benzoate

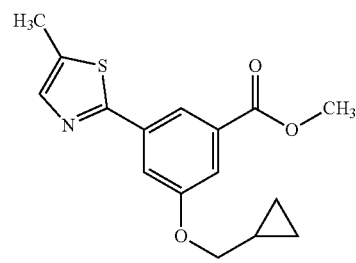 [SMILES: COC(=O)c1cc(OCC2CC2)cc(-c2ncc(C)s2)c1]

Intermediate 3 (500 mg, 2.0 mmol), (bromomethyl)cyclopropane (331 uL, 3.41 mmol) and potassium carbonate (554 mg, 4.01 mmol) were stirred in acetonitrile at 100° C. for 4 h. The reaction was re-treated with (bromomethyl) cyclopropane (331 uL, 3.41 mmol) and stirred at 100° C. for a further 4 h. The reaction mixture was filtered and the filtrate concentrated under vaccum. Crude material was purified by Biotage Isolera™ chromatography (eluting with 1-40% EtOAc in heptane on a 50 g pre-packed HP-SiO2 column) to give the title compound 498.4 mg (74% yield) as a pale yellow semi-crystalline solid.

¹H NMR (250 MHz, Chloroform-d): δ [ppm] 8.10 (t, J=1.4 Hz, 1H), 7.73-7.64 (m, 1H), 7.59 (dd, J=2.5, 1.4 Hz, 1H), 7.51 (d, J=1.1 Hz, 1H), 3.92 (d, J=6.9 Hz, 5H), 2.52 (d, J=1.1 Hz, 3H), 1.35-1.26 (m, 1H), 0.73-0.60 (m, 2H), 0.38 (q, J=4.7 Hz, 2H)

Intermediate 5A: 3—(Cyclopropylmethoxy)-5-(5-methyl-1,3-thiazol-2-yl)benzoic acid

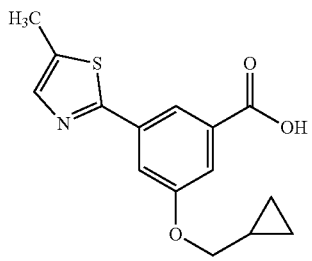 [SMILES: Cc1cnc(-c2cc(OCC3CC3)cc(C(=O)O)c2)s1]

Intermediate 4A (498.4 mg, 1.48 mMol) was dissolved in MeOH (5 mL) and THF (5 mL). 1M LiOH (2.2 mL) was added, and the reaction stirred at RT for 2 h. Further 1M LiOH (1 mL) was added and the reaction stirred for 1 h. The reaction mixture was concentrated to dryness and the residue taken up in water (5 mL) and washed with EtOAc (2×5 mL). The aqueous layer was acidified to pH 4 with 1M HCl and extracted with DCM (4×10 mL). The combined organics were dried (MgSO$_4$), filtered and concentrated to give the title compound 389.5 mg (91% yield) as a white powder.

$^1$H NMR (250 MHz, Chloroform-d): δ [ppm] 8.27 (s, 1H), 7.68 (d, J=1.5 Hz, 1H), 7.65 (d, J=1.3 Hz, 1H), 7.57 (d, J=1.1 Hz, 1H), 3.94 (d, J=6.9 Hz, 2H), 2.54 (d, J=1.0 Hz, 3H), 1.28 (d, J=14.7 Hz, 1H), 0.68 (q, J=6.1 Hz, 2H), 0.39 (q, J=4.8 Hz, 2H).

LC-MS (Analytical Method A) Rt=1.32 min, MS (ESI-pos): m/z=290 (M+H)$^+$.

Intermediate 6B: (3S)-Tetrahydrofuran-3-yl 4-methylbenzenesulfonate

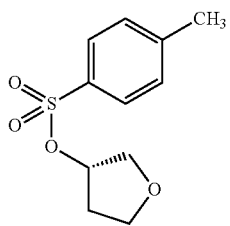 [SMILES: Cc1ccc(S(=O)(=O)O[C@H]2CCOC2)cc1]

A solution of (3S)-tetrahydrofuran-3-ol (23.6.0 g, 268 mmol), TEA (56 ml, 402 mmol) and trimethylamine hydrochloride (2.6 g, 27 mmol) were stirred in DCM (500 mL) and cooled to 0° C. 4-Methylbenzenesulfonyl chloride (63.8 g, 335 mmol) was added portionwise and the mixture stirred at RT for 4 h. TLC (50% EtOAc in heptane) indicated complete consumption of alcohol. Excess 4-methylbenzenesulfonyl chloride was reacted with N,N-dimethylethane-1,2-diamine (8.8 ml, 80 mmol). The crude reaction mixture was washed with 1 M HCl (2×500 mL) and the organic portion dried (MgSO$_4$), filtered and concentrated under reduced pressure to give the title compound 64.6 g (99% yield) of as orange viscous oil.

$^1$H NMR (500 MHz, Chloroform-d): δ [ppm] 7.79 (d, J=8.3 Hz, 2H), 7.35 (d, J=8.0 Hz, 2H), 5.11 (tt, J=4.7, 2.3 Hz, 1H), 3.91-3.78 (m, 4H), 2.45 (s, 3H), 2.12-2.07 (m, 2H).

Intermediate 7: Methyl 3-bromo-5-[(3R)-tetrahydrofuran-3-yloxy]benzoate

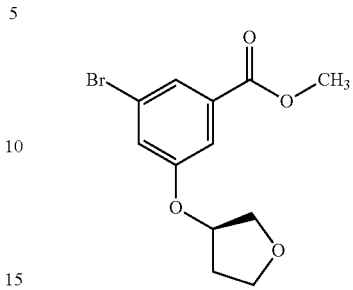

A mixture of Intermediate 1 (15 g, 4.33 mmol), Intermediate 6B (20.4 g, 84.4 mmol) and cesium carbonate (42.3 g, 129.8 mmol) were stirred in acetonitrile (250 mL) at 100° C. overnight. The cooled reaction mixture was filtered through celite, washed with EtOAc and the filtrate evaporated. The residue was dissolved in EtOAc (200 mL), washed with water (2×200 mL), brine (100 mL), dried (MgSO$_4$), filtered and concentrated at reduced pressure. Crude material was purified by Biotage Isolera™ chromatography (eluting with 1-50% EtOAc in heptane on a 340 g pre-packed HP-SiO$_2$ column) to give the title compound 18.12 g (92% yield) as colourless oil.

$^1$H NMR (250 MHz, Chloroform-d): δ [ppm] 7.77 (t, J=1.5 Hz, 1H), 7.44 (dd, J=2.4, 1.3 Hz, 1H), 7.23-7.19 (m, 1H), 4.96 (ddt, J=6.2, 4.2, 2.0 Hz, 1H), 4.06-3.86 (m, 7H), 2.33-2.19 (m, 1H), 2.18-2.05 (m, 1H).

Intermediate 8: Methyl 3-[(3R)-tetrahydrofuran-3-yl]oxy-5-(4,4,5,5-tetramethyl-1,3,2-dioxaborolan-2-yl)benzoate

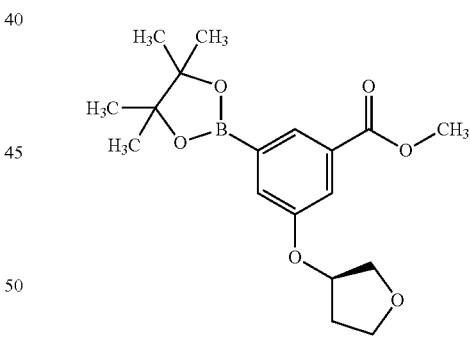

Intermediate 7 (18.1 g, 59.8 mmol), bis(pinacolato)diborane (16.7 g, 65.7 mmol) and potassium acetate (17.6 g, 179.3 mmol) were dissolved in 1,4-dioxane (200 mL) and the solution degassed with a stream of nitrogen for 10 min. Pd(dppf)Cl$_2$.CH$_2$Cl$_2$ (2.4 g, 2.99 mmol) was added and the resulting solution was degassed with a stream of nitrogen for a further 10 min before the reaction mixture was stirred at 100° C. for 2 h. The reaction mixture was cooled to RT then filtered through Celite® and concentrated in vacuo to give a brown solid. The crude material was purified by dry flash silica chromatography (eluting with 0-25% EtOAc in heptanes). The material was further purified by slurrying in heptane to give the title compound 16.57 g (80% yield) as an off-white solid.

LCMS (Analytical Method A): Rt=1.48 min, MS (ESI-pos): m/z=304 (M+H)$^+$.

¹H NMR (250 MHz, Chloroform-d): δ [ppm] 8.06 (d, J=1.0 Hz, 1H), 7.61 (dd, J=2.7, 1.5 Hz, 1H), 7.54-7.45 (m, 1H), 5.03 (ddt, J=6.4, 4.4, 2.0 Hz, 1H), 4.07-3.86 (m, 7H), 2.32-2.08 (m, 2H), 1.34 (s, 12H).

Intermediate 4B: Methyl 3-(5-methyl-1,3-thiazol-2-yl)-5-[(3R)-tetrahydrofuran-3-yloxy]benzoate

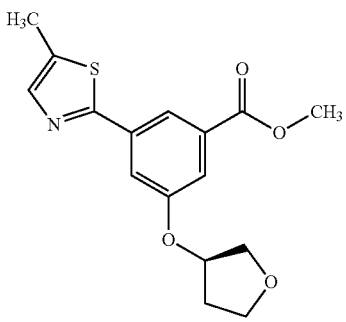 [SMILES: COC(=O)c1cc(O[C@@H]2CCOC2)cc(-c2ncc(C)s2)c1]

Intermediate 8 (5.2 g, 14.9 mmol), 2-bromo-5-methyl-1,3-thiazole (1.87 mL, 17.9 mmol) and cesium carbonate (12.2 g, 37.3 mmol) were dissolved in 4:1 1,4-dioxane/water (75 mL). The solution was degassed with a stream of nitrogen for 10 min. Tetrakis(triphenylphosphine)palladium(0) (517.7 mg, 0.45 mmol) was added and the reaction mixture heated at 100° C. overnight. The reaction mixture was diluted with water (100 mL) and extracted with DCM (2×100 mL). The combined organics were dried (MgSO₄), filtered and concentrated under reduced pressure. The crude material was purified by Biotage Isolera™ chromatography (eluting with 1-40% EtOAc in heptane on a 100 g KP—SiO2 column) to give the title compound 3.06 g (64% yield) as a yellow solid.

¹H NMR (250 MHz, Chloroform-d): δ [ppm] 8.11 (t, J=1.4 Hz, 1H), 7.67-7.63 (m, 1H), 7.55 (dd, J=2.5, 1.4 Hz, 1H), 7.52 (d, J=1.2 Hz, 1H), 5.07 (td, J=4.1, 2.2 Hz, 1H), 4.11-3.86 (m, 7H), 2.53 (d, J=1.1 Hz, 3H), 2.35-2.09 (m, 2H).

LCMS (Analytical Method A) Rt=1.34 min, MS (ESI-pos): m/z=320 (M+H)⁺.

Intermediate 5B: 3-(5-Methyl-1,3-thiazol-2-yl)-5-[(3R)-tetrahydrofuran-3-yloxy]benzoic acid

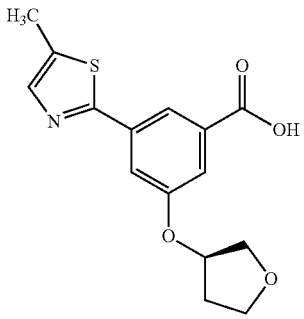 [SMILES: Cc1cnc(-c2cc(O[C@@H]3CCOC3)cc(C(=O)O)c2)s1]

In analogy to Intermediate 5A, reaction of 8 g (25.0 mmol) Intermediate 4B with 1M lithium hydroxide (20 mL) gave title compound 5.83 g (76% yield) as white powder.

¹H NMR (250 MHz, Chloroform-d): δ [ppm] 8.30 (s, 1H), 7.69-7.56 (m, 3H), 5.08 (s, 1H), 4.12-3.87 (m, 4H), 2.54 (s, 3H), 2.39-2.11 (m, 2H).

LCMS (Analytical Method A) Rt=1.16 min, MS (ESI-pos): m/z=305.9 (M+H)⁺.

Intermediate 6C: (3R)-Tetrahydrofuran-3-yl 4-methylbenzenesulfonate

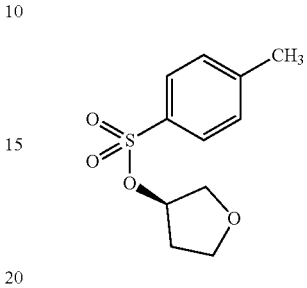

A solution of (3R)-tetrahydrofuran-3-ol (18.0 g, 204 mmol), TEA (43 mL, 306 mmol) and trimethylamine hydrochloride (1.95 g, 20 mmol) were stirred in DCM (625 mL) at RT. 4-Methylbenzenesulfonyl chloride (42.8 g, 2255 mmol) was added and the mixture stirred at RT for 20 h. Excess 4-methylbenzenesulfonyl chloride was reacted with N,N-dimethylethane-1,2-diamine (26 ml, 245 mmol). Water was added and the crude reaction mixture was extracted three times with DCM. The combined organic portions were concentrated under reduced pressure and purified via column chromatography (silica gel, hexane/EE gradient) to give 41 g (83% yield) of the title compound.

¹H NMR (400 MHz, DMSO-d₆) δ [ppm] 1.83-1.94 (m, 1H) 2.08 (dtd, J=14.29, 8.32, 8.32, 6.08 Hz, 1H) 2.43 (s, 3H) 3.61-3.80 (m, 4H) 5.12 (ddt, J=5.83, 3.87, 1.62, 1.62 Hz, 1H) 7.49 (d, J=8.11 Hz, 2H) 7.81 (d, J=8.36 Hz, 2H).

Intermediate 4C: Methyl 3-(5-methyl-1,3-thiazol-2-yl)-5-[(3S)-tetrahydrofuran-3-yloxy]benzoate

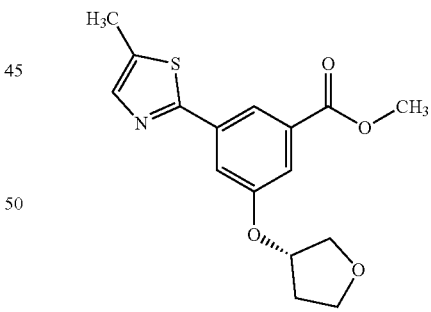

Intermediate 3 (4.5 g, 18.2 mmol), Intermediate 6C (5.3 g, 21.8 mmol) and caesium carbonate (8.9 g, 27.3 mmol) were stirred in DMF (100 mL) at 90° C. for 36 h. The reaction mixture was filtered and the filtrate concentrated under reduced pressure. Crude material was purified by column chromatography (silica gel, hexane/EE gradient) to give 3.9 g (67% yield) of the title compound.

¹H NMR (400 MHz, DMSO-d₆) δ [ppm] 1.96-2.05 (m, 1H) 2.20-2.31 (m, 1H) 3.74-3.82 (m, 1H) 3.82-3.94 (m, 6H) 5.19-5.26 (m, 1H) 7.48 (dd, J=2.41, 1.39 Hz, 1H) 7.61 (dd, J=2.28, 1.52 Hz, 1H) 7.66 (d, J=1.27 Hz, 1H) 8.00 (t, J=1.39 Hz, 1H).

Intermediate 5C: 3-(5-Methyl-1,3-thiazol-2-yl)-5-[(3S)-tetrahydrofuran-3-yloxy]benzoic acid

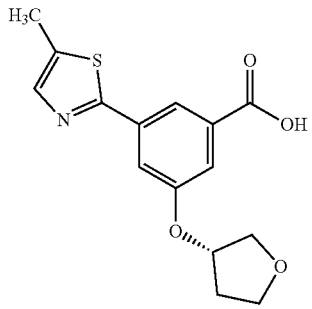 [SMILES: Cc1cnc(-c2cc(O[C@H]3CCOC3)cc(C(=O)O)c2)s1]

Intermediate 4C (3.9 g, 12.2 mmol) was dissolved in MeOH (200 mL). 2M NaOH (30.5 mL) was added, and the reaction stirred at RT for 3 days. The reaction mixture was neutralized with 2N HCl, the aqueous phase extracted with DCM and the combined organics concentrated to dryness under reduced pressure to give 2.3 g (62% yield) of the title compound.

$^1$H NMR (400 MHz, DMSO-d$_6$) δ [ppm] 1.95-2.05 (m, 1H) 2.19-2.30 (m, 1H) 3.73-3.94 (m, 4H) 5.20 (dd, J=5.96, 4.44 Hz, 1H) 7.46 (dd, J=2.41, 1.39 Hz, 1H) 7.58 (dd, J=2.41, 1.65 Hz, 1H) 7.65 (d, J=1.27 Hz, 1H) 7.98 (t, J=1.39 Hz, 1H) 13.06-13.46 (m, 1H).

Intermediate 4D: 3-(5-methyl-1,3-thiazol-2-yl)-5-(prop-2-yn-1-yloxy)benzoate

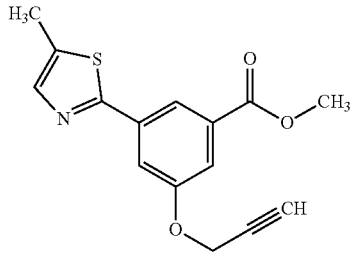 [SMILES: C#CCOc1cc(C(=O)OC)cc(-c2ncc(C)s2)c1]

To a solution of Intermediate 3 (300 mg, 1.203 mmol) in acetone (15 mL) was added K$_2$CO$_3$ (831.6 mg, 6.017 mmol) and 3-bromoprop-1-yne (201.1 µL, 1.805 mmol). The reaction mixture was stirred for 2 h under reflux then cooled to RT and evaporated to dryness. Crude material was taken up in DCM and washed with 1M NaOH (aq) and brine. The organic phase was evaporated to dryness to give a dark tan powder 489 mg (>100% yield). Purification by Biotage Isolera™ chromatography (on a pre-packed 10 g silica column eluting with EtOAC/heptanes 0-100%) gave the title compound 335 mg (97% yield) as a pale yellow powder.

$^1$H NMR (250 MHz, Chloroform-d): δ [ppm] 8.16 (t, J=1.4 Hz, 1H), 7.74 (dd, J=2.5, 1.6 Hz, 1H), 7.66 (dd, J=2.6, 1.4 Hz, 1H), 7.53 (d, J=1.2 Hz, 1H), 4.80 (d, J=2.4 Hz, 2H), 3.94 (s, 3H), 2.55 (t, J=2.4 Hz, 1H), 2.53 (d, J=1.1 Hz, 3H).

Intermediate 5D: 3-(5-methyl-1,3-thiazol-2-yl)-5-(prop-2-yn-1-yloxy)benzoic acid

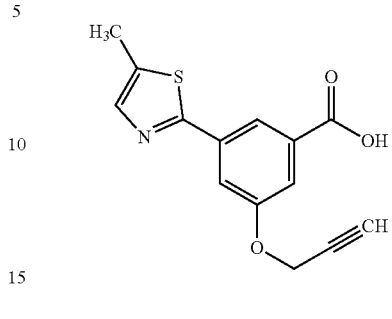

In analogy to Intermediate 5A, reaction of 300 mg (0.625 mmol) Intermediate 4D with 1M lithium hydroxide (0.9 mL) gave 159 mg (89% yield) of the title compound.

$^1$H NMR (250 MHz, DMSO-d6): δ [ppm] 8.07-7.94 (m, 1H), 7.74-7.60 (m, 2H), 7.56 (dd, J=2.4, 1.3 Hz, 1H), 4.96 (d, J=2.3 Hz, 2H), 3.63 (t, J=2.3 Hz, 1H), 2.50 (s, 3H).

Intermediate 4E: Methyl 3-(but-2-yn-1-yloxy)-5-(5-methyl-1,3-thiazol-2-yl)benzoate

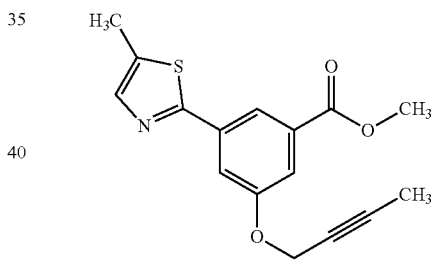

To a solution of Intermediate 3 (250 mg, 1.0 mmol) dissolved in acetone (10 mL) was added K$_2$CO$_3$ (693 mg, 5.0 mmol) and 1-bromo-2-butyne (175.4 µL, 2.0 mmol) and the reaction mixture stirred for 2 h at 60° C. in a sealed tube. The reaction mixture was cooled to RT, filtered and evaporated to dryness. The residue was taken up in DCM and washed with water. The organic phase was dried (over MgSO$_4$) and evaporated at reduced pressure to give 300.9 mg (98% yield) of the title compound as a tan powder.

$^1$H NMR (250 MHz, CDCl$_3$) δ [ppm] 8.15 (t, J=1.4 Hz, 1H), 7.74-7.70 (m, 1H), 7.65 (dd, J=2.5, 1.4 Hz, 1H), 7.54-7.50 (m, 1H), 4.75 (q, J=2.3 Hz, 2H), 3.94 (s, 3H), 2.53 (d, J=1.1 Hz, 3H), 1.87 (t, J=2.3 Hz, 3H).

LCMS (Analytical method A) Rt=1.43 min, MS (ESIpos): m/z=302 (M+H)$^+$.

Intermediate 5E: 3-(But-2-yn-1-yloxy)-5-(5-methyl-1,3-thiazol-2-yl)benzoic acid

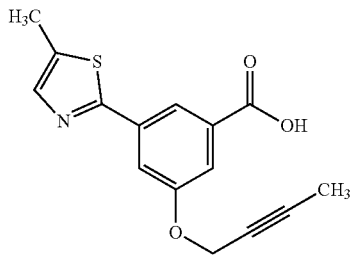 [SMILES: CC#CCOc1cc(C(=O)O)cc(-c2ncc(C)s2)c1]

To a solution of Intermediate 4E (300 mg, 1.00 mmol) in MeOH (5 mL) and THF (5 mL) was added 1M LiOH (2 mL) and the reaction stirred at RT for 2 h. The reaction mixture was concentrated and the residue taken up in water (5 mL) and washed with EtOAc (5 mL). The aqueous layer was acidified to pH 4 with 1M HCl and the precipitate collected by vacuum filtration and dried in the vacuum oven to give 245.1 mg (85% yield) of the title compound as a white powder.

$^1$H NMR (250 MHz, DMSO-d6): δ 8.00 (t, J=1.4 Hz, 1H), 7.65 (q, J=1.4 Hz, 2H), 7.54 (dd, J=2.5, 1.3 Hz, 1H), 4.89 (d, J=2.4 Hz, 2H), 1.84 (t, J=2.3 Hz, 3H).

Intermediate 4F: Methyl 3-(5-methyl-1,3-thiazol-2-yl)-5-(oxetan-3-yloxy)benzoate

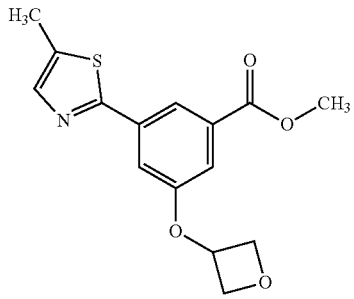 [SMILES: COC(=O)c1cc(OC2COC2)cc(-c2ncc(C)s2)c1]

Intermediate 3 (300 mg, 1.2 mmol), oxetan-3-yl tosylate (357 mg, 1.56 mmol) and cesium carbonate (588 mg, 1.81 mmol) were combined in acetonitrile (5 mL) and stirred at 100° C. in a sealed tube for 6 h, then at 110° C. for 4 h. The reaction mixture was cooled to RT and filtered through celite, washing with EtOAc. The filtrate was concentrated under reduced pressure and purified by Biotage Isolera™ chromatography (silica gel eluting with heptanes—ethyl acetate 9:1 to 2:3) to give 163.5 mg (43% yield) of the title compound as a colourless gum.

$^1$H NMR (500 MHz, Chloroform-d): δ [ppm]=8.12 (t, J=1.4 Hz, 1H), 7.52 (d, J=1.1 Hz, 1H), 7.51 (dd, J=2.5, 1.6 Hz, 1H), 7.37 (dd, J=2.5, 1.3 Hz, 1H), 5.33 (p, J=5.6 Hz, 1H), 5.07-4.98 (m, 2H), 4.78 (dd, J=7.9, 5.1 Hz, 2H), 3.94 (s, 3H), 2.53 (d, J=1.1 Hz, 3H).

LCMS (Analytical Method A) Rt=1.29 min, MS (ESI-pos): m/z=309.95 (M+H)$^+$.

Intermediate 5F: 3-(5-Methyl-1,3-thiazol-2-yl)-5-(oxetan-3-yloxy)benzoic acid

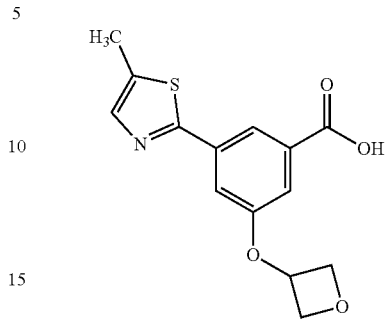

Methyl 3-(5-methyl-1,3-thiazol-2-yl)-5-(oxetan-3-yloxy)benzoate (163.5 mg, 0.52 mmol) was stirred in 1M LiOH (1 mL), THF (2 mL) and MeOH (2 mL) for 1 h. The organics were removed under reduced pressure and the residue taken up in water (5 mL) and acidified to pH 3 with 1 M HCl. The resulting precipitate was collected by vacuum filtration to give 151.8 mg (100% yield) of the title compound as a white powder.

$^1$H NMR (500 MHz, Chloroform-d): δ [ppm]=8.31 (t, J=1.4 Hz, 1H), 7.59 (d, J=1.1 Hz, 1H), 7.53 (dd, J=2.4, 1.7 Hz, 1H), 7.42 (dd, J=2.4, 1.3 Hz, 1H), 5.35 (p, J=5.6 Hz, 1H), 5.05 (t, J=6.9 Hz, 2H), 4.80 (dd, J=7.7, 5.1 Hz, 2H), 2.54 (d, J=1.0 Hz, 3H).

LCMS (Analytical Method A) Rt=1.12 min, MS (ESI-pos): m/z=219.95 (M+H)$^+$.

Intermediate 4G: Methyl 3-(5-methyl-1,3-thiazol-2-yl)-5-[(2S)-tetrahydrofuran-2-ylmethoxy]benzoate

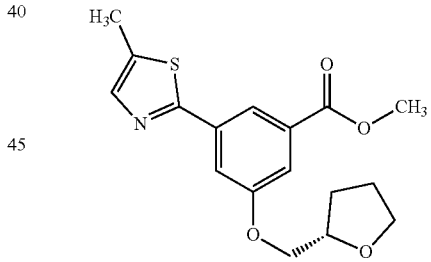

To a solution of Intermediate 3 (500 mg, 2.0 mmol), (2S)-tetrahydrofuran-2-ylmethanol (245 mg, 2.4 mmol) and PPh$_3$ (789 mg, 3.0 mmol) in DCM (20 mL) was added DIAD (0.6 mL, 3.0 mmol) and the resulting solution stirred for 18 h at RT. The reaction mixture was concentrated and purified by Biotage Isolera™ chromatography (silica gel, eluting with 20-60% EtOAc in heptanes) to give 550 mg (50% yield) of the title compound as a colourless gum.

$^1$H NMR (500 MHz, CDCl$_3$): δ [ppm] 8.11 (t, J=1.4 Hz, 1H), 7.70 (dd, J=2.5, 1.6 Hz, 1H), 7.61 (dd, J=2.5, 1.4 Hz, 1H), 7.51 (d, J=1.2 Hz, 1H), 4.36-4.23 (m, 1H), 4.12-4.03 (m, 2H), 3.99-3.91 (m, 4H), 3.88-3.81 (m, 1H), 2.52 (d, J=1.1 Hz, 3H), 2.13-2.05 (m, 1H), 2.03-1.89 (m, 2H), 1.84-1.74 (m, 1H).

LCMS (Analytical Method F): Rt=3.64 min, MS (ESI-pos); m/z=33 (M+H)$^+$.

Intermediate 5G: 3-(5-Methyl-1,3-thiazol-2-yl)-5-[(2S)-tetrahydrofuran-2-ylmethoxy]benzoic acid

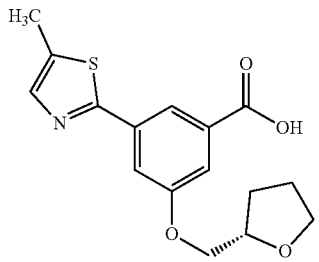 [SMILES: Cc1cnc(-c2cc(OC[C@@H]3CCCO3)cc(C(=O)O)c2)s1]

A mixture of methyl 3-(5-methyl-1,3-thiazol-2-yl)-5-[(2S)-tetrahydrofuran-2-ylmethoxy]benzoate (600 mg, 1.83 mmol) and 1M LiOH (10 mL, 10 mmol) in THF (20 mL) was stirred at RT for 18 h. The reaction was neutralised with 1M HCl (10 mL) at 0° C., prior to addition of 10 mL buffer (pH=6.5). The aqueous phase was extracted with CHCl$_3$/iPrOH (1:1, 4×5 mL) and the combined organic layer dried (over Na$_2$SO$_4$) and concentrated at reduced pressure. The crude material was purified by Biotage Isolera™ chromatography (silica gel, eluting with 50% EtOAc in heptane and then 10% MeOH in DCM) to give 520 mg (84% yield) of the title compound as a yellow gum.

$^1$H NMR (500 MHz, CDCl$_3$): δ [ppm] 8.24 (s, 1H), 7.67 (s, 2H), 7.54 (s, 1H), 4.31 (s, 1H), 4.15-3.77 (m, 4H), 2.50 (s, 3H), 2.13-1.66 (m, 4H).

LCMS (Analytical Method A): Rt=1.22 min, MS (ESI-pos); m/z=391 (M+H)$^+$.

Intermediate 4H: Methyl 3-(5-methyl-1,3-thiazol-2-yl)-5-[(2R)-tetrahydrofuran-2-ylmethoxy]benzoate

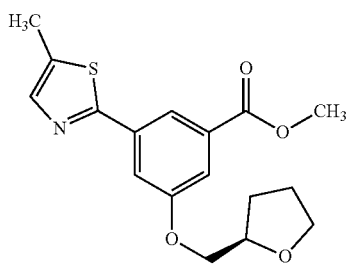 [SMILES: COC(=O)c1cc(OC[C@H]2CCCO2)cc(-c2ncc(C)s2)c1]

To a suspension of Intermediate 3 (600 mg, 2.4 mmol) in DCM (10 mL) was added (2R)-tetrahydrofuran-2-ylmethanol (295 mg, 2.9 mmol) and triphenylphosphine (950 mg, 3.6 mmol). DIAD (0.7 mL, 3.6 mmol) was added at ~10° C. and the resulting solution stirred at RT for 20 hours. The reaction mixture was concentrated and the residue dissolved in THF (10 mL) and retreated with (2R)-tetrahydrofuran-2-ylmethanol (150 mg, 1.4 mmol), triphenylphosphine (475 mg, 1.8 mmol), DIAD (0.7 mL, 3.6 mmol) and the resulting solution stirred at RT for 72 hours. The reaction mixture was concentrated under reduced pressure and the residue partitioned between water (20 mL) and EtOAc (20 mL). The aqueous layer was re-extracted with EtOAc (2×20 mL) and the combined organics dried (over MgSO$_4$) and concentrated under reduced pressure. The crude material was purified by Biotage Isolera™ chromatography (eluting with 12-100% EtOAc in heptane on a 55 g pre-packed KP—NH SiO$_2$ column) to give 973 mg (55% yield) of the title compound.

$^1$H NMR (250 MHz, CDCl$_3$): δ [ppm] 8.11 (t, J=1.4 Hz, 1H), 7.76-7.67 (m, 1H), 7.66-7.58 (m, 1H), 7.52 (d, J=1.1 Hz, 1H), 4.37-4.25 (m, 1H), 4.19-4.04 (m, 3H), 3.93 (s, 4H), 3.91-3.81 (m, 2H), 3.80-3.67 (m, 2H), 2.52 (d, J=1.0 Hz, 3H).

LCMS (Analytical Method A) Rt=1.39, MS (ESIpos): m/z=334.1 (M+H)$^+$.

Intermediate 5H: 3-(5-Methyl-1,3-thiazol-2-yl)-5-[[(2R)-tetrahydrofuran-2-yl]methoxy]benzoic acid

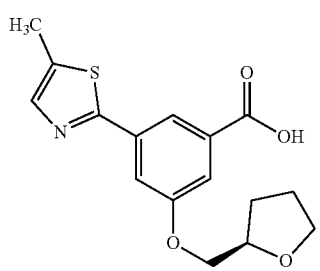 [SMILES: Cc1cnc(-c2cc(OC[C@H]3CCCO3)cc(C(=O)O)c2)s1]

To a solution of methyl 3-(5-methyl-1,3-thiazol-2-yl)-5-[(2R)-tetrahydrofuran-2-ylmethoxy]benzoate (973.mg, ~45% purity, 1.31 mmol) in THF (1.8 mL) and methanol (1.3 mL) was added 1M LiOH (1.84 mL, 1.84 mmol) and the solution stirred at RT for 2 h. The reaction mixture was concentrated under reduced pressure to remove organic solvents, diluted with 1M NaOH (13 mL) and washed with ethyl acetate (2×20 mL). The aqueous phase was acidified to pH 4 with 1M HCl and the resulting precipitate collected by filtration, washed with water and dried in the vacuum oven to give 258 mg (61% yield) of the title compound as a white powder.

$^1$H NMR (500 MHz, DMSO-d6): δ [ppm] 13.27 (s, 0.5H), 8.05-7.91 (m, 1H), 7.69-7.63 (m, 1H), 7.63-7.57 (m, 1H), 7.54-7.43 (m, 1H), 4.24-4.15 (m, 1H), 4.15-4.07 (m, 1H), 4.07-3.99 (m, 1H), 3.83-3.76 (m, 1H), 3.72-3.66 (m, 1H), 2.51 (s, 3H), 2.07-1.96 (m, 1H), 1.96-1.77 (m, 2H), 1.77-1.64 (m, 1H).

LCMS (Analytical Method A) Rt=1.24 min, MS (ESIpos): m/z=320 (M+H)$^+$.

Intermediate 4I: Methyl 3-(5-methyl-1,3-thiazol-2-yl)-5-[(3S)-tetrahydrofuran-3-ylmethoxy]benzoate

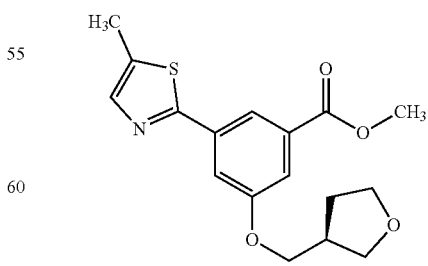

To a suspension of Intermediate 3 (300 mg, 1.2 mmol), (3R)-tetrahydrofuran-3-ylmethanol (185 mg, 1.8 mmol) and triphenylphosphine (475 mg, 1.8 mmol) in DCM (10 mL)

was added DIAD (355 μl, 1.8 mmol) and the resulting solution was stirred over the weekend (~65 hours) at RT. The reaction mixture was washed with water (20 mL) and the aqueous layer re-extracted with DCM (2×20 mL). The combined organics were dried (over MgSO$_4$) and concentrated under reduced. The crude material was purified by Biotage Isolera™ chromatography (silica gel, eluting with heptanes-EtOAc, 1:0 to 35:65) to give 700 mg (91% yield) of the title compound.

$^1$H NMR (500 MHz, Chloroform-d): δ [ppm]=8.09 (t, J=1.4 Hz, 1H), 7.71-7.67 (m, 1H), 7.58 (dd, J=2.5, 1.4 Hz, 1H), 7.52 (d, J=1.2 Hz, 1H), 4.05 (dd, J=8.9, 6.5 Hz, 1H), 4.02-3.97 (m, 1H), 3.94 (s, 3H), 3.96-3.88 (m, 5H), 3.83-3.77 (m, 1H), 3.72 (dd, J=8.9, 5.3 Hz, 1H), 2.77 (hept, J=6.8, 6.2 Hz, 1H), 2.53 (d, J=1.1 Hz, 3H), 2.13 (dtd, J=13.5, 8.1, 5.6 Hz, 1H), 1.76 (td, J=12.7, 6.9 Hz, 1H).

Intermediate 5I: 3-(5-Methyl-1,3-thiazol-2-yl)-5-[(3S)-tetrahydrofuran-3-ylmethoxy]benzoic acid

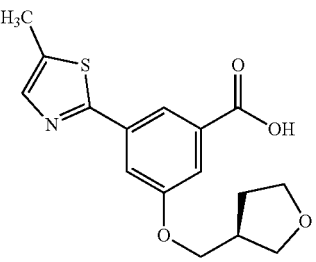 [SMILES: Cc1cnc(-c2cc(OC[C@H]3CCOC3)cc(C(=O)O)c2)s1]

To a solution of methyl 3-(5-methyl-1,3-thiazol-2-yl)-5-[(3S)-tetrahydrofuran-3-ylmethoxy]benzoate (939 mg, 1.41 mmol, ~50% purity) in THF (3 mL) was added 1M aqueous sodium hydroxide (3 mL). The reaction was stirred vigorously for 18 h at RT, an additional portion of 1M aqueous sodium hydroxide (1 mL) was added and the reaction was stirred vigorously for 4 h at RT. The reaction mixture was acidified to pH 3 with 1M HCl and extracted into EtOAc (3×30 mL) and the combined organics washed with 1M HCl (4×20 mL). The aqueous phase was concentrated (to ~20 mL) and extracted with DCM (4×20 mL). The combined DCM and EtOAc organics were dried (over MgSO$_4$) and concentrated to give 600 mg (86% yield) of the title compound.

$^1$H NMR (500 MHz, Chloroform-d): δ [ppm]=8.22 (t, J=1.4 Hz, 1H), 7.84 (s, 1H), 7.69 (dd, J=2.4, 1.3 Hz, 1H), 7.66-7.62 (m, 1H), 4.17-4.02 (m, 2H), 4.01-3.91 (m, 2H), 3.87-3.74 (m, 0H), 2.86-2.75 (m, 1H), 2.58 (d, J=0.8 Hz, 0H), 2.23-2.12 (m, 2H), 2.07 (s, 1H), 1.86-1.76 (m, 1H).

LCMS (Analytical Method A) R$_t$=1.20 min, MS (ESIpos) m/z=320 (M+H)$^+$.

Intermediate 4J: Methyl 3-(5-Methyl-1,3-thiazol-2-yl)-5-[[(3R)-tetrahydrofuran-3-yl]methoxy]benzoate

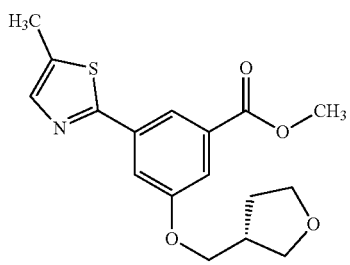 [SMILES: COC(=O)c1cc(OC[C@@H]2CCOC2)cc(-c2ncc(C)s2)c1]

To a stirred solution of PPh$_3$ (552 mg, 2.11 mmol) and DIAD (415 μL, 2.11 mmol) in THF (8 mL) was added Intermediate 3 (350 mg, 1.40 mmol) and (3S)-tetrahydrofuran-3-ylmethanol (215 mg, 2.11 mmol). The reaction mixture was stirred at RT for 16 h then concentrated in vacuo. The residue was taken up in DCM and washed with water, dried (over Na$_2$SO$_4$) and concentrated in vacuo to give an amber viscous oil. The crude material was purified by Biotage Isolera™ chromatography (on KP—NH silica gel, eluting with heptanes-DCM, 1:0 to 7:3) to give 566 mg (40% yield) of the title compound as an off white gum.

$^1$H NMR (500 MHz, Chloroform-d): δ [ppm]=8.08 (s, 1H), 7.71-7.63 (m, 5H), 7.60-7.50 (m, 4H), 7.46 (td, J=7.7, 2.8 Hz, 4H), 4.07-3.87 (m, 7H), 3.79 (q, J=7.7 Hz, 1H), 3.72 (dd, J=8.9, 5.3 Hz, 1H), 2.83-2.70 (m, J=7.2, 6.4 Hz, 1H), 2.52 (s, 3H), 2.13 (dtd, J=13.6, 8.1, 5.6 Hz, 1H), 1.76 (dq, J=12.9, 7.1 Hz, 1H), 1.36-1.17 (m, 3H), 0.87 (t, J=7.0 Hz, 1H).

LCMS (Analytical Method A) R$_t$=1.37 min, MS (ESIpos) m/z=334 (M+H)$^+$.

Intermediate 5J: 3-(5-methyl-1,3-thiazol-2-yl)-5-[(3R)-tetrahydrofuran-3-ylmethoxy]benzoic acid

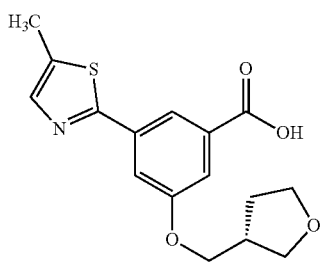 [SMILES: Cc1cnc(-c2cc(OC[C@@H]3CCOC3)cc(C(=O)O)c2)s1]

To a solution of methyl 3-(5-methyl-1,3-thiazol-2-yl)-5-[(3R)-tetrahydrofuran-3-ylmethoxy]benzoate (566 mg, 0.80 mmol, ~50% purity) in THF (1.2 mL) and methanol (0.5 mL) was added aqueous 1M lithium hydroxide (1.2 mL) and the reaction mixture stirred at RT for 2 h. The reaction mixture was diluted with water (3 mL) and washed with EtOAc (2×6 mL). The aqueous phase was acidified to pH ~4 leading to precipitation of a white solid. Filtration gave 264 mg (98% yield) of the title compound as a white solid.

LCMS (Analytical Method A) R$_t$=1.20 min, MS (ESIpos) m/z=320 (M+H)$^+$.

Intermediate 4K: Methyl 3-(5-Methyl-1,3-thiazol-2-yl)-5-tetrahydro-2H-pyran-4-yloxy-benzoate

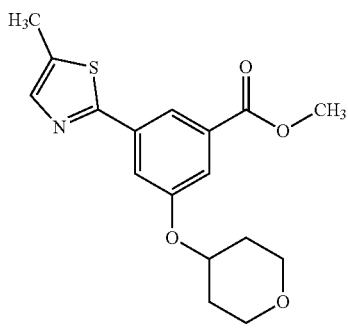 [SMILES: COC(=O)c1cc(OC2CCOCC2)cc(-c2ncc(C)s2)c1]

To a solution of Intermediate 3 (700 mg, 2.81 mmol), tetrahydro-2H-pyran-4-ol (0.386 mL, 3.65 mmol) and triphenylphosphine (957 mg, 3.65 mmol) in THF (10 mL) was slowly added DIAD (0.724 mL, 3.65 mmol) and the reaction mixture stirred at RT for 19 h. The reaction mixture was diluted with water (20 mL) and extracted with EtOAc (2×30 mL). The combined organic phases were washed with brine (10 mL), dried (over $Na_2SO_4$) and concentrated in vacuo. The resulting material was purified by chromatography using silica gel (gradient: hexane/EE) to give 571 mg (54% yield) of the title compound as a yellow oil. The impure fractions from chromatography were re-purified using the same conditions to give an additional 981 mg (25% yield) of title compound.

$^1$H NMR (500 MHz, $CDCl_3$): δ 8.11-8.06 (m, 1H), 7.72-7.68 (m, 1H), 7.60-7.58 (m, 1H), 7.53-7.48 (m, 1H), 4.69-4.60 (m, 1H), 4.02-3.96 (m, 2H), 3.94 (s, 3H), 3.66-3.57 (m, 2H), 2.53 (d, J=1.1 Hz, 3H), 2.10-2.00 (m, 2H), 1.87-1.77 (m, 2H).

Intermediate 5K: 3-(5-Methyl-1,3-thiazol-2-yl)-5-tetrahydro-2H-pyran-4-yloxy-benzoic acid

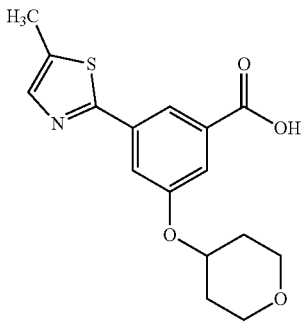 [SMILES: Cc1cnc(-c2cc(OC3CCOCC3)cc(C(=O)O)c2)s1]

To a solution of methyl 3-(5-Methyl-1,3-thiazol-2-yl)-5-tetrahydro-2H-pyran-4-yloxy-benzoate (565 mg, 1.49 mmol) in THF/MeOH (1:1, 6 mL) was added 1M LiOH (2.24 mL, 2.24 mmol) and the reaction mixture stirred at RT for 3 h. The reaction mixture was adjusted to pH~3 with 1 M HCl then extracted with EtOAc (2×15 mL). Combined organic phases were washed with brine (5 mL), dried (using Biotage phase separator) and concentrated in vacuo to give 516 mg (90% yield) of the title compound as an off-white solid.

$^1$H NMR (250 MHz, $CDCl_3$): δ [ppm] 8.36-8.21 (m, 1H), 7.73-7.63 (m, 2H), 7.61-7.57 (m, 1H), 4.75-4.58 (m, 1H), 4.08-3.94 (m, 2H), 3.71-3.54 (m, 2H), 2.54 (d, J=1.1 Hz, 3H), 2.17-1.99 (m, 2H), 1.94-1.73 (m, 2H).

LCMS (Analytical Method A) Rt=1.16 min, MS (ESI-pos): m/z=320 (M+H)$^+$.

Intermediate 4L: Methyl 3-(5-Methyl-1,3-thiazol-2-yl)-5-(tetrahydro-2H-pyran-4-ylmethoxy)benzoate

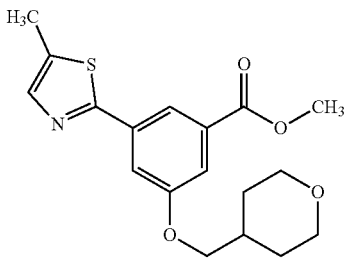 [SMILES: COC(=O)c1cc(OCC2CCOCC2)cc(-c2ncc(C)s2)c1]

To a stirred solution of Intermediate 3 (250 mg, 1 mmol) and 4-(bromomethyl)tetrahydro-2H-pyran (449 mg, 2.51 mmol) in anhydrous MeCN (7 mL) was added dipotassium carbonate (347 mg, 2.51 mmol). The reaction mixture was stirred overnight at 100° C., cooled to RT, filtered through Celite® and concentrated under reduced pressure. The resulting material was purified by chromatography using silica gel (gradient: hexane/EE) to give 1.0 g (76% yield) of the title compound as a colourless oil.

$^1$H NMR (500 MHz, $CDCl_3$): δ [ppm] 8.08 (t, J=1.4 Hz, 1H), 7.69-7.67 (m, 1H), 7.57 (dd, J=2.5, 1.4 Hz, 1H), 7.53-7.51 (m, 1H), 4.05-4.00 (m, 2H), 3.94 (s, 3H), 3.92 (d, J=6.5 Hz, 2H), 3.49-3.42 (m, 2H), 2.53-2.52 (m, 3H), 2.14-2.03 (m, 1H), 1.80-1.75 (m, 2H), 1.53-1.43 (m, 2H).

LCMS (Analytical Method A) Rt=1.45 min, MS (ESI-pos): m/z=348 (M+H)$^+$.

Intermediate 5L: 3-(5-Methyl-1,3-thiazol-2-yl)-5-(tetrahydro-2H-pyran-4-ylmethoxy)benzoic acid

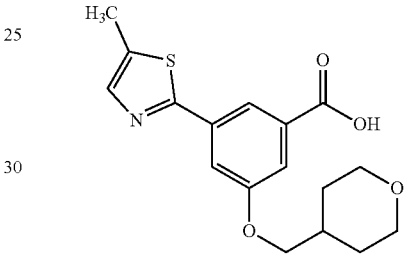

To a solution of methyl 3-(5-Methyl-1,3-thiazol-2-yl)-5-(tetrahydro-2H-pyran-4-ylmethoxy)benzoate (1 g, 2.88 mmol) in THF (6 mL) and MeOH (6 mL) was added 1M LiOH (4.3 mL) at RT and the resulting solution stirred overnight at RT. The reaction mixture was concentrated under reduced pressure, the residue taken up in water and acidified to pH 4 with 1M HCl resulting in precipitate formation. The precipitate was collected by vacuum filtration, washed with ethyl acetate and vacuum dried to give 179 mg (16% yield) of the title as a white solid. The filtrate was re-extracted with IPA/Chloroform 50:50, the combined organic layers washed with brine and dried (over $Na_2SO_4$) and concentrated to give 302 mg (27% yield) of a second batch of the title compound as a white solid.

$^1$H NMR (500 MHz, DMSO-d6): δ [ppm] 7.97 (s, 1H), 7.66-7.64 (m, 1H), 7.62-7.60 (m, 1H), 7.50 (s, 1H), 3.97 (d, J=6.4 Hz, 2H), 3.92-3.86 (m, 2H), 3.38-3.34 (m, 2H), 2.54-2.49 (m, 3H), 2.10-1.99 (m, 1H), 1.75-1.68 (m, 2H), 1.42-1.32 (m, 2H).

LCMS (Analytical Method A) Rt=1.24 min, MS (ESI-pos): m/z=334 (M+H)$^+$.

Intermediate 5M: 3-(5-methyl-1,3-thiazol-2-yl)-5-[(2-methylpyridin-4-yl)oxy]benzoic acid

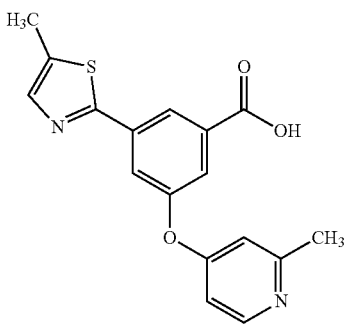 [SMILES: Cc1cc(Oc2cc(C(=O)O)cc(-c3ncc(C)s3)c2)ccn1]

A mixture of Intermediate 3 (1.0 g, 3.81 mmol), 4-fluoro-2-methylpyridine (0.63 g, 5.71 mmol) and Cs₂CO₃ (2.48 g, 7.6 mmol) in DMSO (10 mL) was heated at 100° C. for 6 h. The reaction mixture was treated with 1 M aqueous NaOH (5 mL) and stirred for 30 min. The solution was diluted with water (30 mL) and acidified to pH 4 with 1M aqueous HCl. On addition of EtOAc (40 mL) a precipitate formed that was collected by vacuum filtration to give 722 mg (56% yield) of the title compound as an orange powder.

$^1$H NMR (500 MHz, MeOH-d4): δ [ppm]=8.39 (t, J=1.5 Hz, 1H), 8.35 (d, J=6.0 Hz, 1H), 7.90-7.85 (m, 1H), 7.77 (dd, J=2.3, 1.4 Hz, 1H), 7.58 (d, J=1.2 Hz, 1H), 6.98 (d, J=2.4 Hz, 1H), 6.93 (dd, J=6.0, 2.5 Hz, 1H), 2.55 (d, J=1.1 Hz, 3H), 2.52 (s, 3H).

LCMS (Analytical Method A) Rt=0.96 min, MS (ESIpos) m/z=327 (M+H)⁺.

Intermediate 9: Methyl 3,5-dibromobenzoate

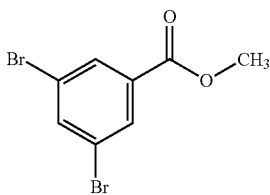

A solution of 3,5-dibromobenzoic acid (10.5 g, 37.5 mmol) and acetyl chloride (6.7 mL, 93.8 mmol) in methanol (212 mL) was stirred under reflux for 17 h. The solvent was removed under reduced pressure. The crude material was purified by column chromatography (silica gel, hexane/EE gradient) to give the title compound 11.0 g (99% yield).

Intermediate 10: Methyl 3-bromo-5-(5-methyl-1,3-thiazol-2-yl)benzoate

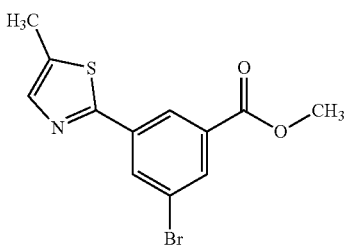 [SMILES: COC(=O)c1cc(Br)cc(-c2ncc(C)s2)c1]

Intermediate 9 (3.5 g, 11.91 mmol) and 5-methyl-2-(tributylstannanyl)-1,3-thiazole (4.62 g, 11.91 mmol) were dissolved in DMF (105 mL). The solution was degassed with a stream of nitrogen for 10 minutes, tetrakis(triphenylphosphine)palladium(0) (550 mg, 0.476 mmol) was added and the reaction mixture heated at 100° C. for 17 hours. The reaction mixture was concentrated under reduced pressure. Crude material was purified by column chromatography (silica gel, hexane/EE gradient) to afford the title compound 1.72 g (42% yield).

$^1$H NMR (400 MHz, DMSO-d₆) δ [ppm] 2.53 (d, J=1.27 Hz, 3H) 3.89-3.94 (m, 3H) 7.71 (d, J=1.27 Hz, 1H) 8.08-8.11 (m, 1H) 8.27 (t, J=1.77 Hz, 1H) 8.35 (t, J=1.52 Hz, 1H).

Intermediate 5N: 3-[(6-Methylpyridin-3-yl)oxy]-5-(5-methyl-1,3-thiazol-2-yl)benzoic acid

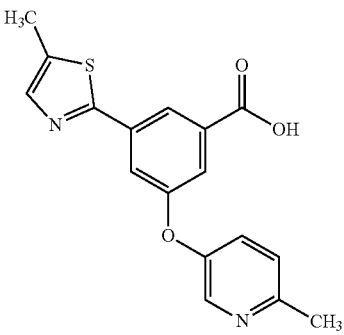 [SMILES: Cc1ccc(Oc2cc(C(=O)O)cc(-c3ncc(C)s3)c2)cn1]

Intermediate 10 (1.29 g, 4.14 mmol), 5-hydroxy-2-methylpyridine (903 mg, 8.28 mmol), 2,2,6,6-tetramethylheptane-3,5-dione (0.11 ml, 0.83 mmol), Cu(I)Cl (165 mg, 1.65 mmol) and Cs₂CO₃ (4.05 g, 12.4 mmol) in NMP (51 mL) were stirred at 220° C. for 20 minutes using a microwave. The reaction mixture was concentrated to dryness under reduced pressure and the crude material purified by column chromatography (silica gel, hexane/EE gradient) to give 1.0 g (70% purity, 52% yield) of the title compound.

$^1$H NMR (300 MHz, DMSO-d₆) δ [ppm] 7.31 (d, 1H) 7.45 (d, 1H) 7.49 (m, 2H) 7.58 (d, 1H) 8.08-8.16 (m, 1H) 8.31 (d, 1H).

Intermediate 40: Methyl 3-[(5-methyl-1,3,4-thiadiazol-2-yl)oxy]-5-(5-methyl-1,3-thiazol-2-yl)benzoate

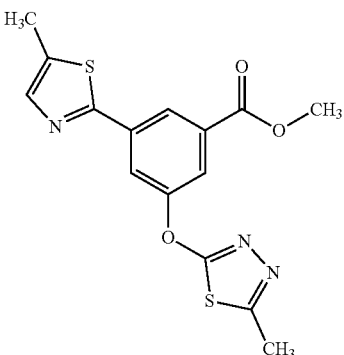

A solution of Intermediate 3 (250 mg, 1.0 mmol), 2-bromo-5-methyl-1,3,4-thiadiazole (270 mg, 1.5 mmol) and cesium carbonate (654 mg, 2.0 mmol) in DMF (5 mL) was heated in a sealed tube at 110° C. overnight. The cooled reaction mixture was concentrated under reduced pressure and the residue partitioned between water (10 mL) and DCM (10 mL). The aqueous layer was extracted with DCM (10 mL) and the combined organics dried (over $MgSO_4$) and concentrated under reduced pressure. The crude material was purified by Biotage Isolera™ chromatography (silica gel, eluting with heptanes—EtOAc, 4:1 to 3:7). Mixed fractions were re-purified by Biotage Isolera™ chromatography (eluting with heptanes—EtOAc, 1:0 to 3:7). Clean fractions from both purifications were combined and concentrated to give 204.9 mg (59% yield) of the title compound as an off-white solid.

$^1$H NMR (500 MHz, Chloroform-d): δ [ppm]=8.39 (t, J=1.4 Hz, 1H), 8.09 (dd, J=2.3, 1.7 Hz, 1H), 7.98 (dd, J=2.4, 1.4 Hz, 1H), 7.54 (d, J=1.1 Hz, 1H), 3.95 (s, 3H), 2.69 (s, 3H), 2.54 (d, J=1.0 Hz, 3H).

LCMS (Analytical Method A) Rt=1.33 min, MS (ESIpos) m/z=348 $(M+H)^+$.

Intermediate 50: 3-[(5-Methyl-1,3,4-thiadiazol-2-yl)oxy]-5-(5-methyl-1,3-thiazol-2-yl)benzoic acid

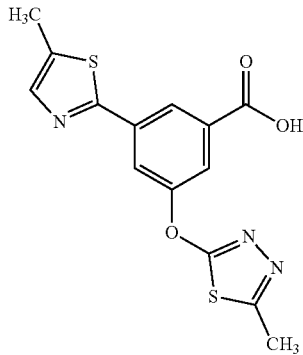 [SMILES: Cc1cnc(-c2cc(Oc3nnc(C)s3)cc(C(=O)O)c2)s1]

To a stirred solution of methyl 3-[(5-methyl-1,3,4-thiadiazol-2-yl)oxy]-5-(5-methyl-1,3-thiazol-2-yl)benzoate (204.9 mg, 0.59 mmol) in MeOH (2.5 mL) and THF (2.5 mL) was added 1M LiOH (2.5 mL). After 1 h the reaction mixture was concentrated under reduced pressure and the residue taken up in water (5 mL) and washed with EtOAc (5 mL). The aqueous layer was acidified with 1M HCl to pH ~3 to form a white precipitate that was collected by vacuum filtration to give 128.6 mg (58% yield) of the title compound as a white powder.

$^1$H NMR (500 MHz, DMSO-d6): δ [ppm]=8.29 (s, 1H), 8.10 (s, 1H), 7.90 (s, 1H), 7.69 (s, 1H), 2.64 (s, 3H), 2.52 (s, 3H).

LCMS (Analytical Method A) Rt=1.15 mins, MS (ESIpos) m/z=334 $(M+H)^+$.

Intermediate 5P: 3-(5-methyl-1,3-thiazol-2-yl)-5-(1,3-thiazol-2-yloxy)benzoic acid

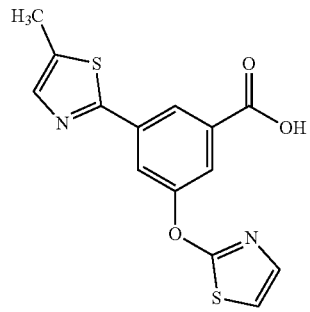 [SMILES: Cc1cnc(-c2cc(Oc3nccs3)cc(C(=O)O)c2)s1]

A solution of Intermediate 3 (250 mg, 1.0 mmol), 2-bromothiazole (246.7 mg, 1.5 mmol) and cesium carbonate (654 mg, 2.0 mmol) in DMF (5 mL) was heated in a sealed tube at 110° C. overnight. The cooled reaction mixture was treated with 1M LiOH (2 mL) and stirred at 110° C. for 1 h. The reaction mixture was concentrated under reduced pressure and the residue taken up in water (10 mL) and washed with EtOAc (2×10 mL). The aqueous layer was acidified to pH 3 with 1 M HCl and the solution extracted with DCM (3×10 mL). The combined organics were dried (over $MgSO_4$) and concentrated under reduced pressure to give 328.3 mg (86% yield) of the title compound as a brown powder.

$^1$H NMR (500 MHz, DMSO-d6): δ [ppm]=8.26 (d, J=1.3 Hz, 1H), 8.08-8.05 (m, 1H), 7.86 (dd, J=2.2, 1.4 Hz, 1H), 7.69-7.67 (m, 1H), 7.36 (d, J=3.8 Hz, 1H), 7.34 (d, J=3.8 Hz, 1H), 2.52 (s, 3H).

LCMS (Analytical Method A) Rt=1.23 min, MS (ESIpos) m/z=319 $(M+H)^+$.

Intermediate 11: Methyl 3-bromo-5-(2-hydroxy-2-methylpropoxy)benzoate

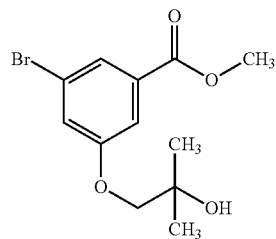 [SMILES: COC(=O)c1cc(Br)cc(OCC(C)(C)O)c1]

A mixture of Intermediate 1 (1.92 g, 8.33 mmol), 2,2-dimethyloxirane (3 g, 41.5 mmol) and $K_2CO_3$ (2.3 g, 16.6 mmol) in DMSO (23 mL) were stirred at 100° C. for 17 h. The reaction mixture was filtered, washed with DCM. The organics were washed with water and concentrated at reduced pressure. Crude material was purified by column chromatography (silica gel, hexane/EE gradient) to give the title compound 2.1 g (87% yield).

$^1$H NMR (400 MHz, DMSO-$d_6$) δ [ppm] 1.16-1.23 (m, 6H) 3.80 (s, 2H) 3.86 (s, 3H) 4.66 (s, 1H) 7.41-7.49 (m, 2H) 7.62 (t, J=1.52 Hz, 1H).

Intermediate 12: 3-Bromo-5-(2-methoxy-2-methylpropoxy)benzoic acid

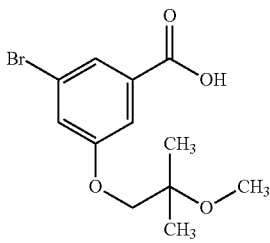 [SMILES: COC(C)(C)COc1cc(Br)cc(C(=O)O)c1]

637 mg NaH (60%, 15.9 mmol) were added to a solution of Intermediate 11 (1.92 g, 6.64 mmol) in THF (21 mL) at RT and stirred for 30 minutes before adding methyl iodide (1.24 ml, 19.9 mmol) at RT. The reaction mixture stirred at 50° C. for 1 hour and at RT overnight. The reaction mixture was diluted with water and extracted three times with DCM. The organics were concentrated at reduced pressure to give the title compound (2.9 g, >100% yield) which was used without further purification in the next step.

Intermediate 13: Methyl 3-bromo-5-(2-methoxy-2-methylpropoxy)benzoate

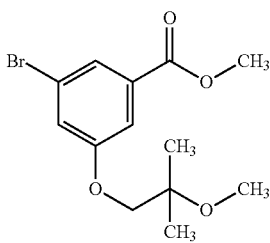 [SMILES: COC(=O)c1cc(Br)cc(OCC(C)(C)OC)c1]

A mixture of crude Intermediate 12 (2.9 g) and acetyl chloride (1.7 ml, 23.9 mmol) in MeOH (130 mL) were stirred at 90° C. The reaction mixture was concentrated at reduced pressure. Crude material was purified by column chromatography (silica gel, hexane/EE gradient) to give the title compound 1.66 g (79% yield over two steps from Intermediate 11).

$^1$H NMR (400 MHz, DMSO-$d_6$) δ [ppm] 1.21 (s, 6H) 3.15 (s, 3H) 3.86 (s, 3H) 3.94 (s, 2H) 7.45 (dd, J=2.40, 1.39 Hz, 1H) 7.49 (t, J=2.15 Hz, 1H) 7.63 (t, J=1.52 Hz, 1H).

Intermediate 14Q: Methyl 3-(2-methoxy-2-methyl-propoxy)-5-(4,4,5,5-tetramethyl-1,3,2-dioxaborolan-2-yl)benzoate

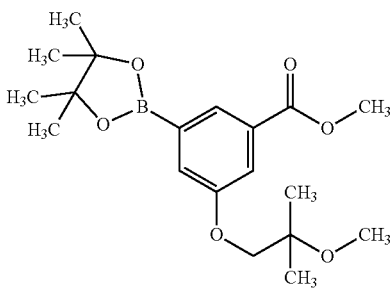

A mixture of Intermediate 13 (1.66 g, 5.23 mmol), bis(pinacolato)diborane (3.32 g, 13.08 mmol), potassium acetate (1.8 g, 18.3 mmol) and Pd(dppf)Cl$_2$ (383 mg, 0.52 mmol) in 1,4-dioxane (100 mL) was stirred at 90° C. for 17 hours. The reaction mixture was cooled to RT and concentrated in vacuo. The remaining crude reaction mixture was extracted three times with DCM and concentrated in vacuo again. Crude material was purified by column chromatography (silica gel, hexane/EE gradient) to give the title compound 1.2 g (63% yield).

$^1$H NMR (300 MHz, DMSO-$d_6$) δ [ppm] 1.22 (s, 6H) 1.31 (s, 12H) 3.16 (s, 3H) 3.86 (s, 3H) 3.92 (s, 2H) 7.41 (d, J=2.07 Hz, 1H) 7.56 (dd, J=2.64, 1.70 Hz, 1H) 7.85 (s, 1H).

Intermediate 15Q: Methyl 3-(5-chloro-1,3-thiazol-2-yl)-5-(2-methoxy-2-methylpropoxy)benzoate

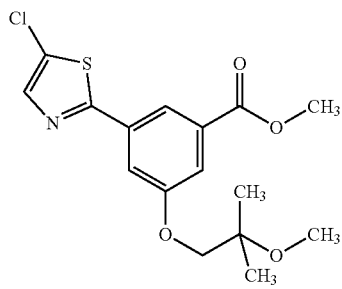 [SMILES: COC(=O)c1cc(OCC(C)(C)OC)cc(-c2ncc(Cl)s2)c1]

Intermediate 14Q (1.15 g, 3.16 mmol), 2-bromo-5-chloro-1,3-thiazole (752 mg, 3.79 mmol) and Pd(dppf)Cl$_2$ (347 mg, 0.47 mmol) were dissolved in 1M K$_2$CO$_3$ aqueous solution (7.58 mL) and THF (100 mL). The reaction mixture was stirred at RT for 4 days and for another day at 90° C. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 790 mg (70% yield).

Intermediate 5Q: 3-(5-Chloro-1,3-thiazol-2-yl)-5-(2-methoxy-2-methylpropoxy)benzoic acid

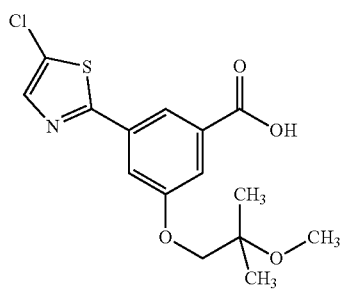 [SMILES: COC(C)(C)COc1cc(C(=O)O)cc(-c2ncc(Cl)s2)c1]

Intermediate 15Q (790 mg, 2.22 mmol) was dissolved in MeOH (40 mL). 2M NaOH (5.55 mL) was added, and the reaction stirred at RT overnight. The reaction mixture was neutralized with 2N HCl, the aqueous phase extracted with DCM and the combined organics concentrated to dryness under reduced pressure to give 460 mg (56% yield) of the title compound.

$^1$H NMR (300 MHz, DMSO-d$_6$) δ [ppm] 1.22-1.25 (m, 6H) 3.17 (s, 3H) 3.99 (s, 2H) 7.57 (dd, J=2.45, 1.32 Hz, 1H) 7.62-7.66 (m, 1H) 7.96-8.02 (m, 2H) 13.22-13.43 (m, 1H).

Intermediate 16: Methyl 3-bromo-5-(tetrahydro-2H-pyran-4-ylmethoxy)benzoate

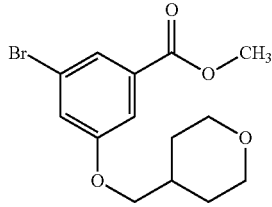 [SMILES: COC(=O)c1cc(Br)cc(OCC2CCOCC2)c1]

Intermediate 1 (5.1 g, 22.1 mmol), 4-(bromomethyl)tetrahydro-2H-pyran (4.35 g, 24.3 mmol) and caesium carbonate (36 g, 110 mmol) were stirred in DMF (150 mL) at 120° C. for 22 h. The reaction mixture was filtered and the filtrate concentrated under reduced pressure. Crude material (7.1 g) contained the title compound alongside with the corresponding carboxylic acid.

This mixture was stirred in methanol (150 mL) and acetyl chloride (4.23 g, 53.9 mmol) at 90° C. for 16 hours. The reaction mixture was filtered and the filtrate concentrated under reduced pressure. Crude material was purified by column chromatography (silica gel, hexane/EE gradient) to afford the title compound 6.02 g (83% yield).

$^1$H NMR (400 MHz, DMSO-d$_6$) δ [ppm] 1.26-1.39 (m, 2H) 1.66 (dd, J=12.80, 1.90 Hz, 2H) 1.94-2.06 (m, 1H) 3.29-3.37 (m, 2H) 3.85-3.90 (m, 5H) 3.92 (d, J=6.34 Hz, 2H) 7.42 (dd, J=2.41, 1.39 Hz, 1H) 7.46 (t, J=2.15 Hz, 1H) 7.62 (t, J=1.52 Hz, 1H).

Intermediate 14R: Methyl 3-(tetrahydro-2H-pyran-4-ylmethoxy)-5-(4,4,5,5-tetramethyl-1,3,2-dioxaborolan-2-yl)benzoate

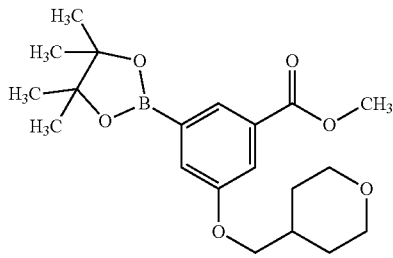 [SMILES: COC(=O)c1cc(OCC2CCOCC2)cc(B2OC(C)(C)C(C)(C)O2)c1]

A mixture of Intermediate 16 (6.2 g, 18.8 mmol), bis(pinacolato)diborane (11.96 g, 47.1 mmol), potassium acetate (6.47 g, 65.9 mmol) and Pd(dppf)Cl$_2$ (1.38 g, 1.88 mmol) in 1,4-dioxane (150 mL) was stirred at 90° C. for 17 hours. The reaction mixture was cooled to RT and concentrated in vacuo. The remaining crude reaction mixture was purified by column chromatography (silica gel, hexane/EE gradient) to give the title compound 9.2 g (quantitative yield).

$^1$H NMR (400 MHz, DMSO-d$_6$) δ [ppm] 1.29-1.41 (m, 14H) 1.64-1.72 (m, 2H) 1.93-2.06 (m, 1H) 3.33 (d, J=1.52 Hz, 2H) 3.84-3.94 (m, 7H) 7.38 (dd, J=2.79, 0.76 Hz, 1H) 7.53-7.55 (m, 1H) 7.83-7.85 (m, 1H).

Intermediate 15R: Methyl 3-(tetrahydro-2H-pyran-4-ylmethoxy)-5-[5-(trifluoromethyl)-1,3-thiazol-2-yl]benzoate

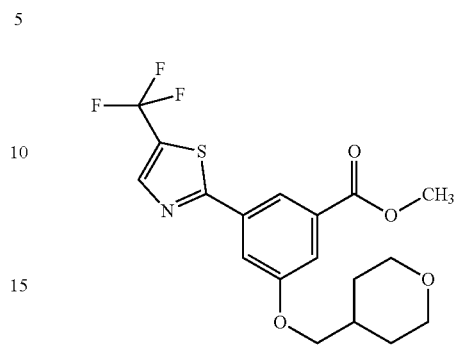

Intermediate 14R (717 mg, 1.9 mmol), 2-bromo-5-(trifluoromethyl)-1,3-thiazole (531 mg, 2.29 mmol) and Pd(dppf)Cl$_2$ (209 mg, 0.29 mmol) were dissolved in 1M K$_2$CO$_3$ aqueous solution (4.5 mL) and THF (30 mL). The reaction mixture was heated at 120° C. for 90 minutes in the microwave. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound in a mixture with unreacted boronic acid (300 mg).

Intermediate 5R: 3-(Tetrahydro-2H-pyran-4-ylmethoxy)-5-[5-(trifluoromethyl)-1,3-thiazol-2-yl]benzoic acid

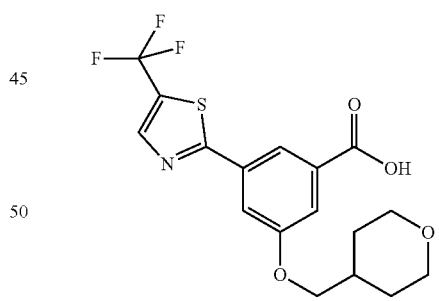

Intermediate 15R (300 mg, 0.75 mmol) was dissolved in MeOH (30 mL). 2M NaOH (1.87 mL) was added and the reaction stirred at RT. The reaction mixture was concentrated under reduced pressure, neutralized with 2N HCl, the aqueous phase extracted three times with DCM and the combined organics concentrated to dryness under reduced pressure to give 230 mg of the crude title compound (55% purity by LCMS), which was used without further purification.

Intermediate 15S: Methyl 3-(5-cyclobutyl-1,3-thiazol-2-yl)-5-(tetrahydro-2H-pyran-4-ylmethoxy)benzoate

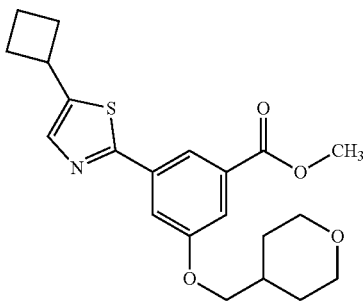 [SMILES: COC(=O)c1cc(OCC2CCOCC2)cc(-c2ncc(C3CCC3)s2)c1]

Intermediate 14R (667 mg, 1.77 mmol), 2-chloro-5-cyclobutyl-1,3-thiazole (369 mg, 2.13 mmol) and Pd(dppf)Cl$_2$ (194 mg, 0.27 mmol) were dissolved in 1M K$_2$CO$_3$ aqueous solution (4.25 mL) and THF (28 mL). The reaction mixture was stirred at 90° C. overnight. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 180 mg (26% yield).

$^1$H NMR (400 MHz, DMSO-d$_6$) δ [ppm] 1.33-1.43 (m, 2H) 1.70 (dd, J=12.67, 1.77 Hz, 2H) 1.85-1.95 (m, 1H) 1.96-2.05 (m, 2H) 2.15 (td, J=9.00, 2.53 Hz, 2H) 2.40-2.46 (m, 2H) 3.33-3.39 (m, 2H) 3.76-3.84 (m, 1H) 3.86-3.91 (m, 5H) 3.97 (d, J=6.34 Hz, 2H) 7.49 (dd, J=2.41, 1.39 Hz, 1H) 7.63 (dd, J=2.28, 1.52 Hz, 1H) 7.69 (d, J=0.76 Hz, 1H) 8.00 (t, J=1.52 Hz, 1H).

Intermediate 5S: 3-(5-Cyclobutyl-1,3-thiazol-2-yl)-5-(tetrahydro-2H-pyran-4-ylmethoxy)benzoic acid

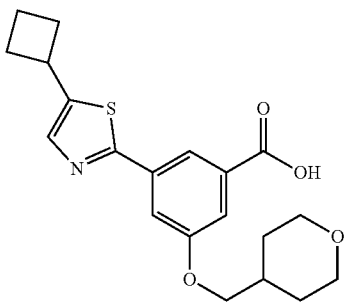 [SMILES: O=C(O)c1cc(OCC2CCOCC2)cc(-c2ncc(C3CCC3)s2)c1]

Intermediate 15S (180 mg, 0.46 mmol) was dissolved in MeOH (20 mL). 2M NaOH (1.16 mL) was added, and the reaction stirred at RT. The reaction mixture was concentrated under reduced pressure, neutralized with 2N HCl, the precipitated solid material filtered off to give 160 mg (92% yield) of the title compound.

$^1$H NMR (400 MHz, DMSO-d$_6$) δ [ppm] 1.27-1.44 (m, 2H) 1.62-1.74 (m, 2H) 1.83-1.94 (m, 1H) 1.95-2.07 (m, 2H) 2.08-2.20 (m, 2H) 2.38-2.45 (m, 2H) 3.31-3.38 (m, 2H) 3.81 (s, 1H) 3.88 (dd, J=11.37, 2.78 Hz, 2H) 3.96 (d, J=6.57 Hz, 2H) 7.48 (dd, J=2.40, 1.39 Hz, 1H) 7.61 (dd, J=2.40, 1.64 Hz, 1H) 7.68 (d, J=0.76 Hz, 1H) 7.98 (t, J=1.52 Hz, 1H) 13.17-13.32 (m, 1H).

Intermediate 17A: (3S)-Tetrahydrofuran-3-ylmethyl 4-methylbenzenesulfonate

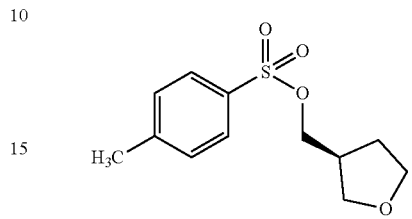

A solution of (3R)-tetrahydrofuran-3-ylmethanol (3.0 g, 29.4 mmol), TEA (6.1 mL, 44 mmol) and trimethylamine hydrochloride (281 mg, 2.9 mmol) were stirred in DCM (90 mL) at RT for 10 minutes and cooled to 0° C. 4-Methylbenzenesulfonyl chloride (6.16 g, 32 mmol) was added and the mixture stirred at RT for 17 h. The mixture was treated with N,N-dimethylethane-1,2-diamine (3.8 mL, 35 mmol) and water. The aqueous layer was extracted three times with DCM. The combined organic portions were concentrated under reduced pressure and purified via column chromatography (silica gel, hexane/EE gradient) to give 6.45 g (86% yield) of the title compound.

$^1$H NMR (300 MHz, DMSO-d$_6$) δ [ppm] 1.45 (td, J=13.09, 6.97 Hz, 1H) 1.79-1.96 (m, 1H) 1.83-1.83 (m, 1H) 2.43 (s, 3H) 3.27-3.36 (m, 1H) 3.48-3.68 (m, 3H) 3.88-4.01 (m, 2H) 7.49 (d, J=7.91 Hz, 2H) 7.75-7.84 (m, 2H).

Intermediate 18: Methyl 3-bromo-5-[(3S)-tetrahydrofuran-3-ylmethoxy]benzoate

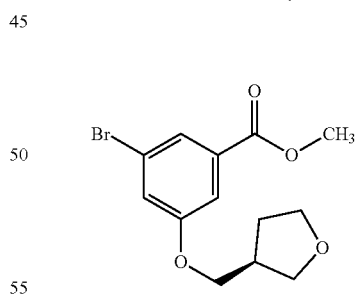

Intermediate 1 (4.85 g, 21 mmol), Intermediate 17A (6.45 g, 25.2 mmol) and caesium carbonate (10.2 g, 31.5 mmol) were stirred in DMF (81 mL) at 50° C. for 60 h. The reaction mixture was cooled to RT, filtered and the filtrate concentrated under reduced pressure to give the crude title compound (7.47 g) which was used in the next step without further purification.

Intermediate 14T: Methyl 3-[(3S)-tetrahydrofuran-3-ylmethoxy]-(4,4,5,5-tetramethyl-1,3,2-dioxaborolan-2-yl)benzoate

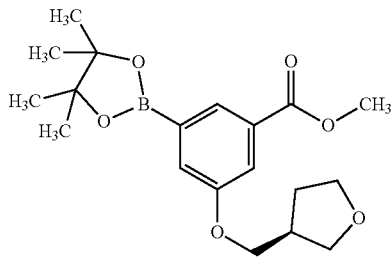

Intermediate 18 (7.47 g, 23.7 mmol), bis(pinacolato)diborane (15.05 g, 59.3 mmol), potassium acetate (8.14 g, 83 mmol) and Pd(dppf)Cl$_2$ (1.73 g, 2.37 mmol) in 1,4-dioxane (91 mL) were stirred at 90° C. for 80 hours. The reaction mixture was cooled to RT and concentrated in vacuo. The remaining crude reaction mixture was extracted with DCM, washed with water and the organic phase concentrated in vacuo. The crude material was purified by column chromatography (silica gel, hexane/EE gradient) to give the title compound 9.3 g (quantitative yield).

$^1$H NMR (400 MHz, DMSO-d$_6$) δ [ppm] 1.31 (s, 12H) 1.63-1.75 (m, 1H) 1.95-2.07 (m, 1H) 2.58-2.69 (m, 1H) 3.54 (dd, J=8.59, 5.56 Hz, 1H) 3.66 (d, J=6.82 Hz, 1H) 3.72-3.83 (m, 2H) 3.86 (s, 3H) 3.99 (dd, J=19.07, 7.20 Hz, 2H) 7.39 (dd, J=2.78, 0.76 Hz, 1H) 7.55 (dd, J=2.65, 1.64 Hz, 1H) 7.83-7.87 (m, 1H).

Intermediate 15T: Methyl 3-(5-cyclobutyl-1,3-thiazol-2-yl)-5-[(3S)-tetrahydrofuran-3-ylmethoxy]benzoate

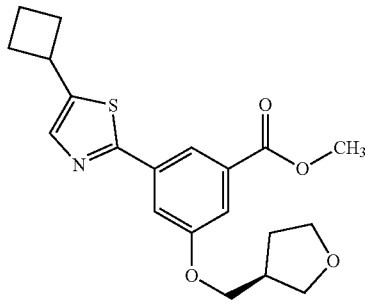 [SMILES: COC(=O)c1cc(OC[C@H]2CCOC2)cc(-c2ncc(C3CCC3)s2)c1]

Intermediate 14T (1 g, 2.76 mmol), 2-chloro-5-cyclobutyl-1,3-thiazole (623 mg, 3.59 mmol) and Pd(dppf)Cl$_2$.CH$_2$Cl$_2$ (338 mg, 0.41 mmol) were dissolved in 1M K$_2$CO$_3$ aqueous solution (6.63 mL) and THF (45 mL). The reaction mixture was heated under reflux for 2 hours. The reaction mixture was concentrated under reduced pressure. The crude material was purified by column chromatography (silica gel, hexane/EE gradient) to afford the title compound 770 mg (75% yield).

Intermediate 5T: 3-(5-Cyclobutyl-1,3-thiazol-2-yl)-5-[(3S)-tetrahydrofuran-3-ylmethoxy]benzoic acid

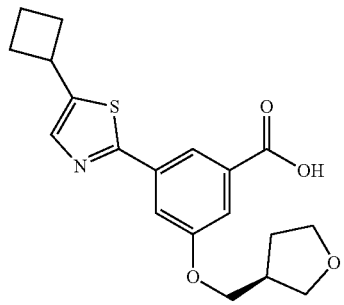 [SMILES: O=C(O)c1cc(OC[C@H]2CCOC2)cc(-c2ncc(C3CCC3)s2)c1]

Intermediate 15T (770 mg, 2.06 mmol) was dissolved in MeOH (20 mL) and THF (20 mL). 2M NaOH (4.12 mL) was added, and the reaction stirred at RT. The reaction mixture was concentrated under reduced pressure. Water was added and the aqueous phase adjusted to pH 2 with 2N HCl, extracted with EE and the organics concentrated under reduced pressure to give 765 mg (quantitative yield) of the title compound which was used without further purification.

Intermediate 15U: Methyl 3-(5-ethyl-1,3-thiazol-2-yl)-5-(tetrahydro-2H-pyran-4-ylmethoxy)benzoate

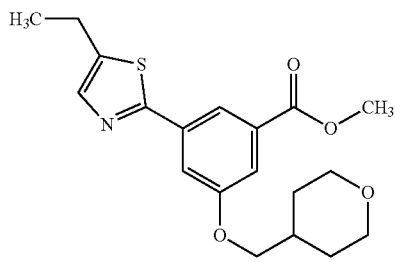 [SMILES: CCc1cnc(-c2cc(OCC3CCOCC3)cc(C(=O)OC)c2)s1]

Intermediate 14R (1.05 g, 2.79 mmol), 2-chloro-5-ethyl-1,3-thiazole (495 mg, 3.34 mmol) and Pd(dppf)Cl$_2$ (306 mg, 0.42 mmol) were dissolved in 1M K$_2$CO$_3$ aqueous solution (6.6 mL) and THF (42 mL). The reaction mixture was heated at 120° C. for 90 minutes in the microwave. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 450 mg (44% yield).

Intermediate 5U: 3-(5-Ethyl-1,3-thiazol-2-yl)-5-(tetrahydro-2H-pyran-4-ylmethoxy)benzoic acid

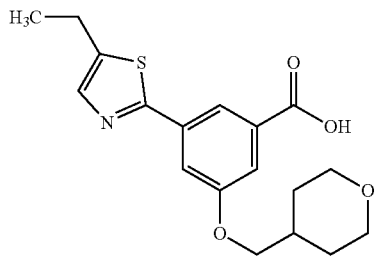 [SMILES: CCc1cnc(-c2cc(OCC3CCOCC3)cc(C(=O)O)c2)s1]

Intermediate 15U (450 mg, 1.25 mmol) was dissolved in MeOH (50 mL). 2M NaOH (3.1 mL) was added, and the reaction stirred at RT. The reaction mixture was concentrated under reduced pressure, neutralized with 2N HCl, the mixture extracted three times with EE and the combined organics concentrated under reduced pressure. The remaining material was purified by column chromatography (silica gel, hexane/EE gradient) to give 50 mg (12% yield) of the title compound.

¹H NMR (400 MHz, DMSO-d₆) δ [ppm] 1.29 (t, J=7.45 Hz, 3H) 1.31-1.43 (m, 2H) 1.65-1.75 (m, 2H) 1.97-2.08 (m, 1H) 2.90 (d, J=7.58 Hz, 2H) 3.31-3.38 (m, 2H) 3.84-3.92 (m, 2H) 3.95 (d, J=6.32 Hz, 2H) 7.50 (s, 1H) 7.55 (s, 1H) 7.66 (s, 1H) 7.98 (s, 1H).

Intermediate 15V: Methyl 3-(5-isopropyl-1,3-thiazol-2-yl)-5-(tetrahydro-2H-pyran-4-ylmethoxy)benzoate

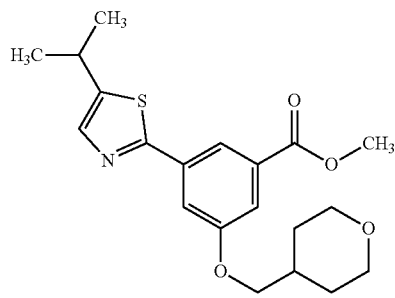 [SMILES: COC(=O)c1cc(OCC2CCOCC2)cc(-c2ncc(C(C)C)s2)c1]

Intermediate 14R (716 mg, 1.90 mmol), 2-chloro-5-(propan-2-yl)-1,3-thiazole (370 mg, 2.28 mmol) and Pd(dppf)Cl₂.CH₂Cl₂ (233 mg, 0.29 mmol) were dissolved in 1M K₂CO₃ aqueous solution (4.6 mL) and THF (28 mL). The reaction mixture was heated at 120° C. for 90 minutes in the microwave. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 330 mg (46% yield).

Intermediate 5V: 3-(5-Isopropyl-1,3-thiazol-2-yl)-5-(tetrahydro-2H-pyran-4-ylmethoxy)benzoic acid

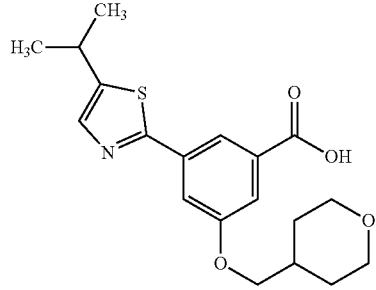 [SMILES: CC(C)c1cnc(-c2cc(OCC3CCOCC3)cc(C(=O)O)c2)s1]

Intermediate 15V (330 mg, 0.88 mmol) was dissolved in MeOH (50 mL). 2M NaOH (2.2 mL) was added, and the reaction stirred at RT. The reaction mixture was concentrated under reduced pressure, neutralized with 2N HCl, the mixture extracted three times with EE and the combined organics concentrated under reduced pressure. The remaining material was purified by column chromatography (silica gel, hexane/EE gradient) to give 140 mg (32% yield) of the title compound which was used without further purification.

Intermediate 17B: Tetrahydro-2H-pyran-4-yl 4-methylbenzenesulfonate

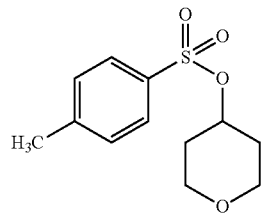 [SMILES: Cc1ccc(S(=O)(=O)OC2CCOCC2)cc1]

A solution of tetrahydro-2H-pyran-4-ol (25.0 g, 245 mmol), TEA (51 mL, 367 mmol) and trimethylamine hydrochloride (2.34 g, 24.5 mmol) were stirred in DCM (750 mL) at RT for 10 minutes and cooled to 0° C. 4-Methylbenzenesulfonyl chloride (51.3 g, 269 mmol) was added and the mixture stirred at RT for 17 h. The mixture was treated with N,N-dimethylethane-1,2-diamine (31.6 mL, 294 mmol) and water. The aqueous layer was extracted three times with DCM. The combined organic portions were concentrated under reduced pressure and purified via column chromatography (silica gel, hexane/EE gradient) to give 58.5 g (93% yield) of the title compound.

¹H NMR (400 MHz, DMSO-d₆) δ [ppm] 1.51-1.61 (m, 2H) 1.74 (dq, J=13.04, 3.65 Hz, 2H) 2.42 (s, 3H) 3.39 (ddd, J=11.75, 8.97, 3.03 Hz, 2H) 3.71 (dt, J=11.81, 4.71 Hz, 2H) 4.69 (tt, J=8.65, 4.23 Hz, 1H) 7.47 (d, J=8.08 Hz, 2H) 7.81 (d, J=8.34 Hz, 2H).

Intermediate 14W: Methyl 3-(tetrahydro-2H-pyran-4-yloxy)-5-(4,4,5,5-tetramethyl-1,3,2-dioxaborolan-2-yl)benzoate

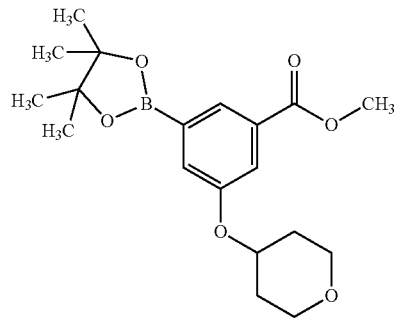

Intermediate 24 (0.85 g, 2.7 mmol), bis(pinacolato)diborane (1.71 g, 6.74 mmol), potassium acetate (0.93 g, 9.44 mmol) and Pd(dppf)Cl₂ (0.20 g, 0.27 mmol) in 1,4-dioxane (50 mL) was stirred at 80° C. until complete conversion. The reaction mixture was cooled to RT and concentrated in vacuo. The remaining crude reaction mixture was extracted with DCM, and the organic phase concentrated in vacuo.

The crude material was purified by column chromatography (silica gel, hexane/EE gradient) to give the title compound 1.06 g (quantitative yield).

$^1$H NMR (400 MHz, DMSO-d$_6$) δ [ppm] 1.27-1.33 (m, 12H) 1.60 (s, 2H) 1.89-1.98 (m, 2H) 3.51 (s, 2H) 3.78-3.87 (m, 5H) 4.66-4.74 (m, 1H) 7.42 (dd, J=2.76, 0.75 Hz, 1H) 7.58 (dd, J=2.51, 1.51 Hz, 1H) 7.83-7.86 (m, 1H).

Intermediate 1 5W: Methyl 3-(5-cyclobutyl-1,3-thiazol-2-yl)-5-(tetrahydro-2H-pyran-4-yloxy)benzoate

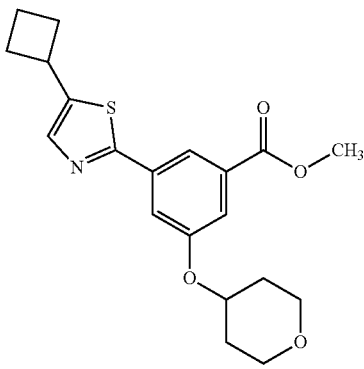 [SMILES: COC(=O)c1cc(OC2CCOCC2)cc(-c2ncc(C3CCC3)s2)c1]

Intermediate 14W (500 mg, 1.38 mmol), 2-chloro-5-cyclobutyl-1,3-thiazole (288 mg, 1.66 mmol), Pd(dppf)Cl$_2$ (151 mg, 0.21 mmol) were dissolved in 1M K$_2$CO$_3$ aqueous solution (3.3 mL) and THF (25 mL). The reaction mixture was heated at 90° C. until complete conversion. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 320 mg (62% yield).

$^1$H NMR (400 MHz, DMSO-d$_6$) δ [ppm] 1.55-1.69 (m, 2H) 1.91 (br. s., 1H) 1.95-2.04 (m, 3H) 2.12-2.21 (m, 2H) 2.43 (dt, J=8.27, 3.19 Hz, 2H) 3.53 (ddd, J=11.68, 9.03, 3.03 Hz, 2H) 3.81-3.91 (m, 6H) 4.79 (s, 1H) 7.53 (dd, J=2.40, 1.39 Hz, 1H) 7.64-7.72 (m, 2H) 8.00 (t, J=1.52 Hz, 1H).

Intermediate 5W: 3-(5-cyclobutyl-1,3-thiazol-2-yl)-5-(tetrahydro-2H-pyran-4-yloxy)benzoic acid

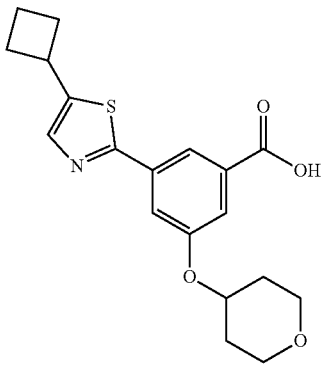 [SMILES: O=C(O)c1cc(OC2CCOCC2)cc(-c2ncc(C3CCC3)s2)c1]

Intermediate 15W (320 mg, 0.86 mmol) was dissolved in MeOH. 2M NaOH (2.1 mL) was added, and the reaction stirred at RT. The reaction mixture was concentrated under reduced pressure, adjusted to pH 2 with 2N HCl, extracted with EE and concentrated under reduced pressure to give 114 mg (37% yield) of the title compound, which was used without further purification.

Intermediate 15X: Methyl 3-(5-ethyl-1,3-thiazol-2-yl)-5-(tetrahydro-2H-pyran-4-yloxy)benzoate

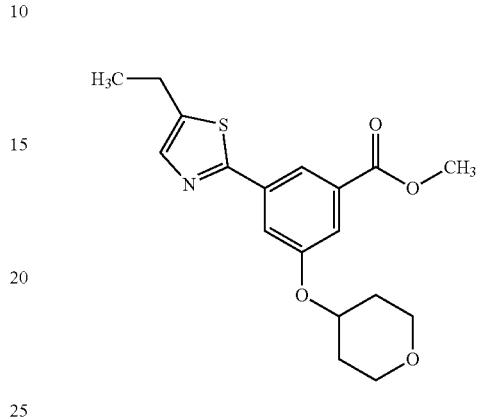

Intermediate 14W (500 mg, 1.38 mmol), 2-chloro-5-ethyl-1,3-thiazole (245 mg, 1.66 mmol) and Pd(dppf)Cl$_2$ (151 mg, 0.21 mmol) were dissolved in 1M K$_2$CO$_3$ aqueous solution (3.3 mL) and THF (25 mL). The reaction mixture was heated at 90° C. until complete conversion. The reaction mixture was concentrated under reduced pressure, the remaining material diluted with water and extracted three times with DCM. The combined organics were concentrated under reduced pressure. Crude material was purified by column chromatography (silica gel, hexane/EE gradient) to afford the title compound 320 mg (62% yield).

Intermediate 5X: 3-(5-Ethyl-1,3-thiazol-2-yl)-5-(tetrahydro-2H-pyran-4-yloxy)benzoic acid

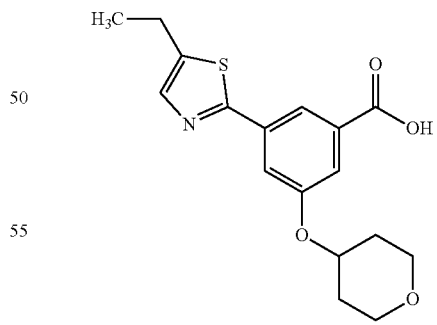

Intermediate 15X (450 mg, 1.29 mmol) was dissolved in MeOH. 2M NaOH (2.59 mL) was added, and the reaction stirred at RT. The reaction mixture was concentrated under reduced pressure, adjusted to pH 2 with 2N HCl, extracted with EE and concentrated under reduced pressure to give 251 mg (58% yield) of the title compound, which was used without further purification.

Intermediate 15Y: Methyl 3-bromo-5-(2-methoxyethoxy)benzoate

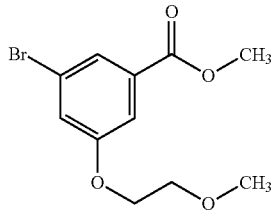 [SMILES: COCCOc1cc(Br)cc(C(=O)OC)c1]

A mixture of Intermediate 1 (300 g, 1.3 mol), 2-bromoethyl methyl ether (330 g, 2.37 mot), K₂CO₃ (330 g, 2.39 mot) and NaI (2 g) in acetonitrile (2500 mL) was refluxed for 12 h. The suspension was filtered, solid was washed with acetonitrile (1000 mL) and combined filtrate was evaporated under reduced pressure to give a dark oil. Petroleum ether (2500 mL) was added and the formed solution was filtered through a layer of aluminum oxide. The filtrate was evaporated under reduced pressure to give 250.3 g of the title compound (67% yield).

¹H NMR (300 MHz, DMSO-d₆) δ [ppm] 3.30 (s, 3H) 3.61-3.69 (m, 2H) 3.86 (s, 3H) 4.14-4.24 (m, 2H) 7.43 (dd, J=2.45, 1.32 Hz, 1H) 7.48 (t, J=2.17 Hz, 1H) 7.63 (t, J=1.51 Hz, 1H).

Intermediate 5Y: 3-Bromo-5-(2-methoxyethoxy)benzoic acid

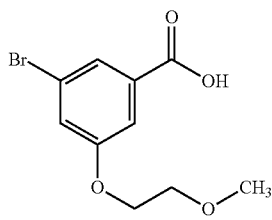

Intermediate 15Y (5.0 g, 17.3 mmol) was dissolved in MeOH (52 mL). 2M NaOH (17.3 mL) was added, and the reaction stirred at RT. The reaction mixture was adjusted to pH 3 with 1N HCl, extracted with EE, dried (Na₂SO₄) and concentrated under reduced pressure to give 5.12 g (>100%) of the title compound, which was used without further purification.

¹H NMR (300 MHz, DMSO-d₆) δ [ppm] 3.30 (s, 3H) 3.65 (dd, J=5.27, 3.58 Hz, 2H) 4.18 (dd, J=5.27, 3.58 Hz, 2H) 7.39-7.45 (m, 2H) 7.61 (t, J=1.51 Hz, 1H) 13.26-13.53 (m, 1H).

Intermediate 19Z: Tert-butyl 4-[3-(methoxycarbonyl)-5-(5-methyl-1,3-thiazol-2-yl)phenoxy]piperidine-1-carboxylate

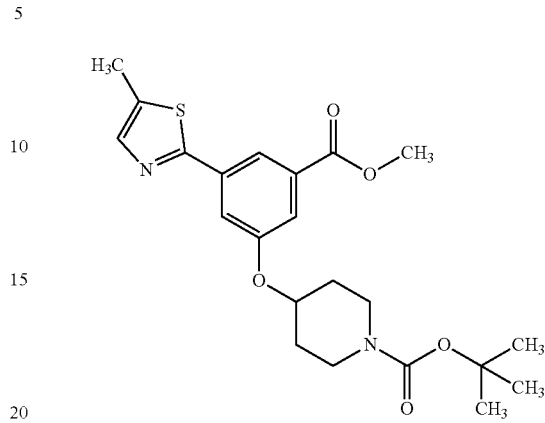

Intermediate 3 (500 mg, 2.0 mmol), tert-butyl 4-hydroxypiperidine-1-carboxylate (807 mg, 4.0 mmol) and triphenylphosphine (2104 mg, 8.0 mmol) were combined in THF and cooled to 0° C. in an ice bath. DIAD (0.788 mL, 4.0 mmol) was added dropwise and the reaction mixture stirred for 10 min before warming to RT. After stirring for 16 h the reaction mixture was concentrated in vacuo, taken up in EtOAc (10 mL), washed with brine (5 mL) and ammonium chloride solution (5 mL). The organic phase was separated, dried (over MgSO₄) and concentrated in vacuo to give a brown oil. Purification by Biotage Isolera™ chromatography (on a pre-packed 50 g SiO₂, eluting with EtOAc in heptane 0-100%) gave 1000 mg (92% yield) of the title compound as a colourless oil.

¹H NMR (250 MHz, Chloroform-d): δ [ppm]=8.08 (t, J=1.4 Hz, 1H), 7.69 (dd, J=2.4, 1.6 Hz, 1H), 7.58 (dd, J=2.5, 1.4 Hz, 1H), 7.51 (d, J=1.2 Hz, 1H), 4.62 (tt, J=6.9, 3.5 Hz, 1H), 3.93 (s, 3H), 3.77-3.62 (m, 2H), 3.47-3.31 (m, 2H), 2.52 (d, J=1.1 Hz, 3H), 2.03-1.88 (m, 3H), 1.87-1.55 (m, 5H), 1.48 (s, 9H).

LCMS (Analytical Method A) Rt=1.65 min, MS (ESI-pos): m/z=433 (M+H)⁺.

Intermediate 5Z: 3-{[1-(Tert-butoxycarbonyl)piperidin-4-yl]oxy}-5-(5-methyl-1,3-thiazol-2-yl)benzoic acid

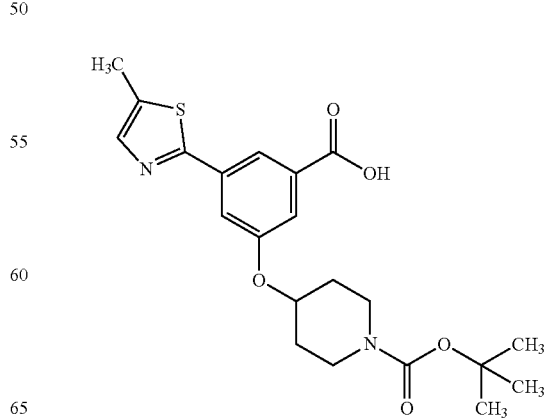

To a solution of tert-butyl 4-[3-(methoxycarbonyl)-5-(5-methyl-1,3-thiazol-2-yl)phenoxy]piperidine-1-carboxylate (1000 mg, 1.85 mmol) in THF (2.5 mL) was added 1M LiOH (2.7 mL) and the resulting solution stirred for 16 h at RT. The organic solvent was removed in vacuo and the aqueous phase acidified to pH ~4 with 1M HCl.

The resulting precipitate was collected by filtration and evaporated to give 682 mg (88% yield) of the title compound as a white solid.

LCMS (Analytical Method A) $R_t$=1.48 min, MS (ESIpos): m/z=419 (M+H)$^+$.

Intermediate 1 9AA: Methyl 3-[(3R)-1-methylpyrrolidin-3-yl]oxy-5-(5-methyl-1,3-thiazol-2-yl)benzoate

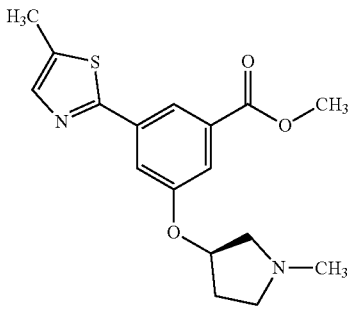 [SMILES: COC(=O)c1cc(O[C@@H]2CCN(C)C2)cc(-c2ncc(C)s2)c1]

To a solution of Intermediate 3 (150 mg, 0.60 mmol), (3S)-1-methylpyrrolidin-3-ol (121 mg, 1.20 mmol) and triphenylphosphine (631 mg, 2.41 mmol) in THF (3 mL) at 0° C. was added DIAD (236 µL, 1.20 mmol) dropwise. The solution was stirred for a further 5 mins at 0° C. then allowed to warm to RT and stirred for a further 16 h. The reaction mixture was concentrated in vacuo, taken up in DCM and washed with brine, saturated NaHCO$_3$, dried (over MgSO$_4$) and concentrated in vacuo to give a brown oil. The crude material was purified by Biotage Isolera™ chromatography (on a pre-packed KP—NH column, eluting with heptane-acetone 5:1 to 1:4) to give 143 mg (54% yield) of the title compound as a clear oil.

$^1$H NMR (250 MHz, Chloroform-d): δ [ppm]=8.10 (t, J=1.5 Hz, 1H), 7.62 (dd, J=2.5, 1.6 Hz, 1H), 7.56-7.48 (m, 2H), 4.99-4.89 (m, 1H), 3.93 (s, 3H), 2.95-2.76 (m, 3H), 2.52 (d, J=1.1 Hz, 3H), 2.40 (s, 5H), 2.12-1.95 (m, 1H), 1.69-1.57 (m, 1H)

LCMS (Analytical Method A) $R_t$=0.93 min, MS (ESIpos) m/z=534 (M+H)$^+$.

Intermediate 19AB: Methyl 3-(5-methyl-1,3-thiazol-2-yl)-5-[(3S)-pyrrolidin-3-yloxy]benzoate

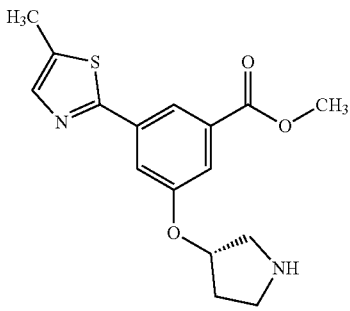 [SMILES: COC(=O)c1cc(O[C@H]2CCNC2)cc(-c2ncc(C)s2)c1]

To a 0° C. stirred solution of Intermediate 3 (150 mg, 0.60 mmol), tert-butyl (3R)-3-hydroxypyrrolidine-1-carboxylate (225 mg, 1.20 mmol) and triphenylphosphine (63 mg, 2.40 mmol) in THF (3 mL) was added DIAD (236 µL, 1.20 mmol) dropwise. The solution was stirred at 0° C. for 5 min then allowed to warm to RT and stirred for a further 16 h. The reaction mixture was concentrated in vacuo, taken up in DCM and washed with brine, saturated NaHCO$_3$, dried (over Mg2SO$_4$) and concentrated in vacuo to give a brown oil. Purification by Biotage Isolera™ chromatography (prepacked 10 g cartridge, eluting with heptane-EtOAc, 15:3 to 0:1) to give a colourless oil (620 mg). The oil was dissolved in DCM (1 mL) and TFA (1 mL) and the solution stirred for 1 h at RT. The reaction mixture was concentrated in vacuo, taken up in DCM (1 mL) and stirred for 15 mins in saturated sodium bicarbonate. The organic phase was collected and dried (over MgSO$_4$) and concentrated in vacuo to give 400 mg (34% yield) of the title compound as an amber oil.

$^1$H NMR (500 MHz, Chloroform-d): δ [ppm]=8.10 (t, J=1.3 Hz, 1H), 7.73-7.65 (m, 1H), 7.65-7.57 (m, 2H), 3.94 (s, 3H), 2.54 (d, J=1.0 Hz, 3H), 1.26 (s, 12H), 1.25 (s, 9H).

LCMS (Analytical Method A) $R_t$=0.96, MS (ESIpos) m/z=319 (M+H)$^+$.

Intermediate 20: Methyl 3-{[(3S)-1-methylpyrrolidin-3-yl]oxy}-5-(5-methyl-1,3-thiazol-2-yl)benzoate

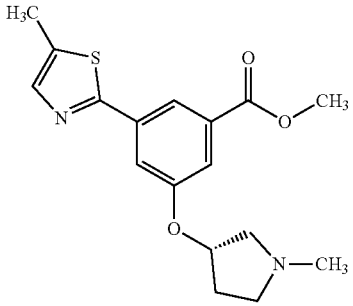 [SMILES: COC(=O)c1cc(O[C@H]2CCN(C)C2)cc(-c2ncc(C)s2)c1]

Methyl 3-(5-methyl-1,3-thiazol-2-yl)-5-[(3S)-pyrrolidin-3-yloxy]benzoate (420 mg, 0.40 mmol), formaldehyde (37% solution in water, 59 µL, 0.79 mmol) and formic acid (59 µL, 1.58 mmol) were combined in THF and heated at reflux for 4 h. The reaction mixture was concentrated in vacuo, taken up in sodium bicarbonate and extracted with DCM. The organic phase was dried (over MgSO$_4$) and concentrated in vacuo to give 65 mg (49% yield) of the title compound.

$^1$H NMR (500 MHz, Chloroform-d): δ [ppm]=8.12 (t, J=1.4 Hz, 1H), 7.64 (dd, J=2.4, 1.6 Hz, 1H), 7.55 (dd, J=2.5, 1.4 Hz, 6H), 7.53 (d, J=1.2 Hz, 1H), 5.06-4.93 (m, 6H), 3.95 (s, 3H), 2.92-2.82 (m, 3H), 2.54 (d, J=1.1 Hz, 3H), 2.51-2.36 (m, 5H), 2.10-2.00 (m, 2H).

Intermediate 21: Tert-butyl 3-[3-(methoxycarbonyl)-5-(5-methyl-1,3-thiazol-2-yl)phenoxy]azetidine-1-carboxylate

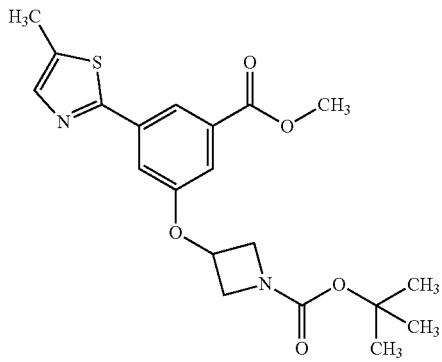 [SMILES: COC(=O)c1cc(OC2CN(C(=O)OC(C)(C)C)C2)cc(-c2ncc(C)s2)c1]

Intermediate 3 (300 mg, 1.20 mmol), tert-butyl 3-{[(4-methylphenyl)sulfonyl]oxy}azetidine-1-carboxylate (511 mg, 1.80 mmol) and cesium carbonate (780 mg, 2.39 mmol) were combined in dry dimethylformamide (3 mL) under an atmosphere of nitrogen and heated to 80° C. for 16 h. The room temperature reaction mixture was poured onto brine (3 mL) and extracted with ethyl acetate (10 mL). The organic phase was washed with brine (3 mL), dried (over MgSO$_4$) and concentrated in vacuo to give a brown oil. The crude material was purified by Biotage Isolera™ chromatography (silica gel, eluting with heptane-tertbutyl methyl ether, 3:1 to 0:1) to give 440 mg (81% yield) of the title compound as a colourless oil that crystallised on standing.

$^1$H NMR (250 MHz, CDCl3): δ [ppm]=1.45 (s, 9H), 2.52 (d, 3H), 3.94 (s, 3H), 4.02 (dd, 2H), 4.36 (dd, 2H), 5.00 (tt, 1H), 7.41 (dd, 1H), 7.48-7.58 (m, 2H), 8.12 (t, 1H).

Intermediate 22: Methyl 3-(azetidin-3-yloxy)-5-(5-methyl-1,3-thiazol-2-yl)benzoate

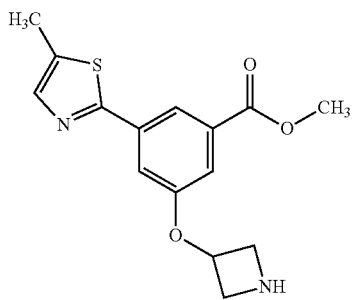 [SMILES: COC(=O)c1cc(OC2CNC2)cc(-c2ncc(C)s2)c1]

Tert-butyl 3-[3-(methoxycarbonyl)-5-(5-methyl-1,3-thiazol-2-yl)phenoxy]azetidine-1-carboxylate (440 mg, 0.98 mmol) was stirred in 4 M HCl in dioxane (2.5 mL) for 2 h. The reaction was concentrated to dryness and the resulting solid dissolved in saturated NaHCO$_3$ and extracted with DCM/Methanol (9:1, 2×25 mL). The organic phase was dried (over MgSO$_4$) and concentrated to dryness to give 259 mg (87% yield) of the title compound.

LCMS (Analytical Method A) R$_t$=0.92 min, MS (ESIpos) m/z=305 (M+H)$^+$.

Intermediate 23: Methyl 3-[(1-methylazetidin-3-yl)oxy]-5-(5-methyl-1,3-thiazol-2-yl)benzoate

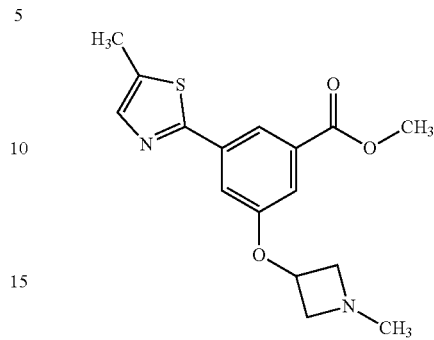

To a solution of methyl 3-(azetidin-3-yloxy)-5-(5-methyl-1,3-thiazol-2-yl)benzoate (255 mg, 0.84 mmol) in DCE (0.5 mL) was added formaldehyde (37% aqueous solution, 1 mL) and acetic acid (0.048 mL) and the resulting mixture stirred at RT for 30 min. Sodium triacetoxyborohydride (213 mg, 1.00 mmol) was added and the mixture stirred at RT for a further 16 h. The reaction mixture was concentrated in vacuo and the residue basified to pH 9 with saturated sodium bicarbonate solution and extracted into ethyl acetate. The organic phase was separated, dried (over MgSO$_4$) and concentrated in vacuo to give a brown oil. The crude material was purified by Biotage Isolera™ chromatography to give 80 mg (29% yield) of the title compound as a colourless oil.

$^1$H NMR (500 MHz, MeOD): δ [ppm]=2.53 (d, 3H), 3.27-3.31 (m, 2H), 3.83-3.90 (m, 2H), 3.93 (s, 3H), 4.92 (p, 1H), 7.44 (dd, 1H), 7.50-7.57 (m, 2H), 8.04 (t, 1H).

Intermediate 24: Methyl 3-bromo-5-(tetrahydro-2H-pyran-4-yloxy)benzoate

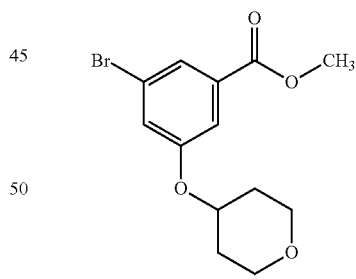

Intermediate 1 (1.5 g, 6.49 mmol), Intermediate 17B (2.5 g, 9.74 mmol) and caesium carbonate (3.17 g, 9.74 mmol) were stirred in DMF (25 mL) at RT until complete conversion. The reaction mixture was filtered and the filtrate concentrated under reduced pressure. The remaining material was purified via column chromatography (silica gel, hexane/EE gradient) to give the title compound, 0.85 g (42% yield).

$^1$H NMR (400 MHz, DMSO-d$_6$) δ [ppm] 1.59 (s, 2H) 1.92-1.99 (m, 2H) 3.49 (s, 2H) 3.80-3.86 (m, 5H) 4.65-4.81 (m, 1H) 7.45 (dd, J=2.41, 1.39 Hz, 1H) 7.52-7.54 (m, 1H) 7.62 (t, J=1.52 Hz, 1H).

Intermediate 4AC: Methyl 3-[(5-methyl-1,3,4-thiadiazol-2-yl)oxy]-5-(5-methyl-1,3-thiazol-2-yl)benzoate

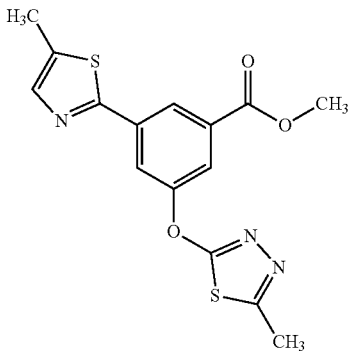 [SMILES: COC(=O)c1cc(Oc2nnc(C)s2)cc(-c2ncc(C)s2)c1]

A solution of Intermediate 3 (250 mg, 1.0 mmol), 2-bromo-5-methyl-1,3,4-thiadiazole (270 mg, 1.5 mmol) and cesium carbonate (654 mg, 2.0 mmol) in DMF (5 mL) was heated in the microwave at 120° C. for 1 h. The reaction mixture partitioned between brine (10 mL) and EtOAc (10 mL). The layers were separated and the aqueous layer was extracted with further EtOAc (2×10 mL). The combined organics were washed with brine (20 mL), dried over MgSO$_4$, filtered and concentrated under reduced pressure. The crude material was purified by Biotage Isolera™ chromatography (silica gel, eluting with heptane-EtOAc, 4:1 to 1:4) to afford 226.6 mg (65% yield) of the title compound as a yellow gum.

$^1$H NMR (500 MHz, Chloroform-d): δ [ppm] 8.39 (t, J=1.4 Hz, 1H), 8.09 (dd, J=2.3, 1.7 Hz, 1H), 7.98 (dd, J=2.4, 1.4 Hz, 1H), 7.54 (d, J=1.1 Hz, 1H), 3.95 (s, 3H), 2.69 (s, 3H), 2.54 (d, J=1.0 Hz, 3H).

LCMS (Analytical Method A) Rt=1.23 min, MS (ESI-pos): m/z=347.9 (M+H)$^+$.

Intermediate 5AC: 3-[(5-Methyl-1,3,4-thiadiazol-2-yl)oxy]-5-(5-methyl-1,3-thiazol-2-yl)benzoic acid

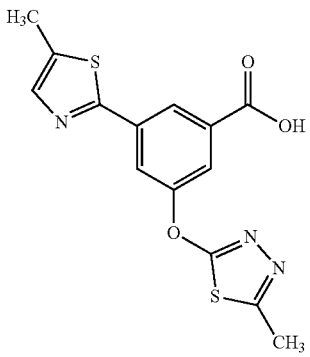 [SMILES: Cc1cnc(-c2cc(Oc3nnc(C)s3)cc(C(=O)O)c2)s1]

Intermediate 4AC (226 mg, 0.65 mmol) was stirred in MeOH (2.5 mL), THF (2.5 mL) and 1M LiOH (2.5 mL) for 1 h. The reaction mixture was concentrated under reduced pressure and the residue taken up in water (5 mL) and washed with EtOAc (5 mL). The aqueous layer was acidified with 1M HCl to pH ~3 and the precipitate formed was collected by vacuum filtration to afford 198.6 mg (92% yield) of the title compound as an off-white powder.

$^1$H NMR (250 MHz, DMSO-d6): δ [ppm] 8.30 (t, J=1.5 Hz, 1H), 8.13-8.10 (m, 1H), 7.94-7.89 (m, 1H), 7.70 (d, J=1.2 Hz, 1H), 2.65 (s, 3H).

LCMS (Analytical Method A) Rt=1.08 min, MS (ESI-pos): m/z=333.9 (M+H)$^+$.

Intermediate 4AD: Tert-butyl 3-[3-(methoxycarbonyl)-5-(5-methyl-1,3-thiazol-2-yl)phenoxy]azetidine-1-carboxylate

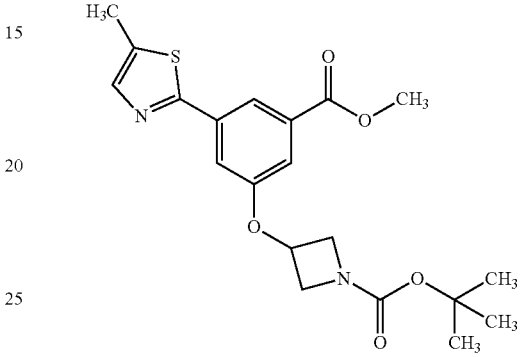

Intermediate 3 (300 mg, 1.20 mmol), tert-butyl 3-{[(4-methylphenyl)sulfonyl]oxy}azetidine-1-carboxylate (443 mg, 1.56 mmol) and caesium carbonate (784 mg, 2.04 mmol) were combined in MeCN (5 mL) and heated to 100° C. for 2 h. On cooling to RT the reaction mixture was diluted with EtOAc (5 mL) and filtered before being concentrated under reduced pressure. The crude material was purified by Biotage Isolera™ chromatography (silica gel, eluting with heptane-EtOAc, 1:0 to 3:2) to afford 303.7 mg (57% yield) of the title compound as an off-white solid.

$^1$H NMR (500 MHz, Chloroform-d): δ [ppm] 8.13 (t, J=1.3 Hz, 1H), 7.57-7.55 (m, 1H), 7.53 (d, J=1.1 Hz, 1H), 7.42 (dd, J=2.4, 1.3 Hz, 1H), 5.05-4.97 (m, 1H), 4.37 (dd, J=10.0, 6.6 Hz, 2H), 4.03 (dd, J=9.8, 3.9 Hz, 2H), 3.94 (s, 3H), 2.53 (d, J=0.9 Hz, 3H), 1.45 (s, 9H).

LCMS (Analytical Method A) Rt=1.37 min, MS (ESI-pos): m/z=405.05 (M+H)$^+$.

Intermediate 5AD: 3-{[1-(Tert-butoxycarbonyl)azetidin-3-yl]oxy}-5-(5-methyl-1,3-thiazol-2-yl)benzoic acid

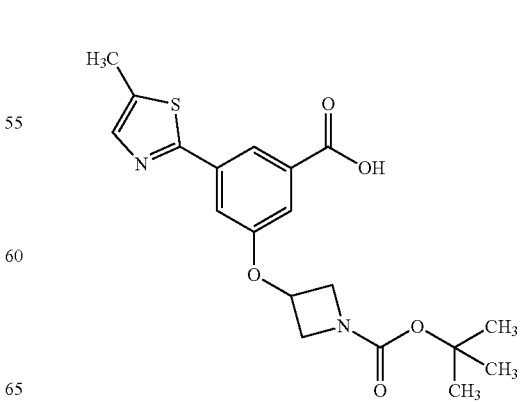

Intermediate 4AD (303 mg, 0.68 mmol) was dissolved in MeOH (5 mL) and THF (5 mL). 1M LiOH (2 mL) was added, and the reaction stirred at RT for 2 h. The reaction mixture was concentrated to remove MeOH/THF, and the residue taken up in water (5 mL) and washed with EtOAc (5 mL). The aqueous layer was acidified to pH 4 with 1M HCl and the solution extracted with DCM (3×5 mL) to afford 205.6 mg (77% yield) of the title compound as white powder.

$^{1}$H NMR (500 MHz, Chloroform-d): δ [ppm] 8.28 (s, 1H), 7.60-7.58 (m, 1H), 7.58-7.57 (m, 1H), 7.46 (dd, J=2.4, 1.3 Hz, 1H), 5.02 (ddd, J=10.4, 6.3, 4.1 Hz, 1H), 4.39 (dd, J=9.9, 6.5 Hz, 2H), 4.05 (dd, J=9.8, 4.0 Hz, 2H), 2.58-2.49 (m, 3H), 1.46 (s, 9H).

LCMS (Analytical Method A) Rt=1.19 min, MS (ESI-pos): m/z=391.00 (M+H)$^{+}$.

Intermediate 4AE: Tert-butyl (3S)-3-[3-(methoxycarbonyl)-5-(5-methyl-1,3-thiazol-2-yl)phenoxy]pyrrolidine-1-carboxylate

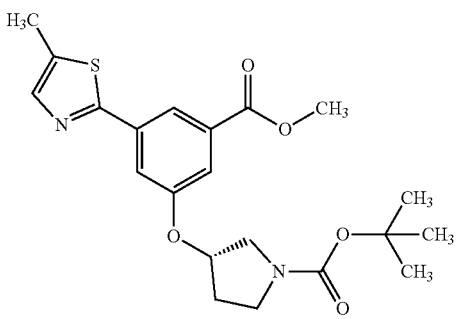 [SMILES: COC(=O)c1cc(O[C@H]2CCN(C(=O)OC(C)(C)C)C2)cc(-c2ncc(C)s2)c1]

To a solution of Intermediate 3 (250 mg, 1.0 mmol), tert-butyl (3R)-3-hydroxypyrrolidine-1-carboxylate (375 mg, 2 mmol) and triphenylphosphine (1.05 g, 4 mmol) in THF (5 mL) cooled to 0° C. was added DIAD (394 μL, 2 mmol) dropwise. The solution was stirred at 0° C. for 5 min then allowed to warm to RT and stirred for a further 72 h. The reaction mixture was then concentrated under reduced pressure and the crude material was purified by Biotage Isolera™ chromatography (silica gel, eluting with heptane-EtOAc, 20:1 to 2:3) to give 745 mg (88% yield, 50% purity) of the title compound as a colourless gum.

$^{1}$H NMR (500 MHz, Chloroform-d) δ [ppm] 8.11 (d, J=7.2 Hz, 1H), 7.68 (s, 1H), 7.56 (s, 1H), 7.53 (s, 1H), 5.04 (s, 1H), 3.94 (s, 3H), 3.68 (s, 3H), 3.30 (s, 1H), 2.53 (s, 3H), 2.26-2.09 (m, 2H), 1.27 (s, 9H).

LCMS (Analytical Method A) Rt=1.37 min, MS (ESI-pos): m/z=419.1 (M+H)$^{+}$.

Intermediate 5AE: 3-[(3S)-1-Tert-butoxycarbonylpyrrolidin-3-yl]oxy-5-(5-methylthiazol-2-yl)benzoic acid

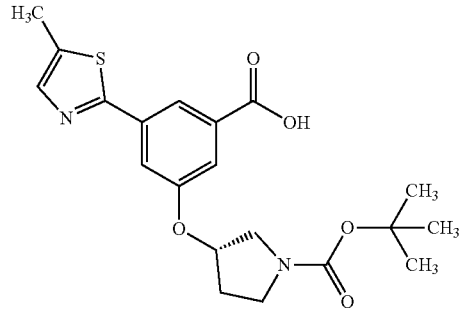 [SMILES: Cc1cnc(-c2cc(O[C@H]3CCN(C(=O)OC(C)(C)C)C3)cc(C(=O)O)c2)s1]

To a solution of Intermediate 4AE (745 mg, 50% purity, 0.89 mmol) dissolved in THF (2 mL) and MeOH (5 mL) was added 1 M LiOH (2.5 mL) and the resulting solution stirred at RT for 2 h. The reaction mixture was concentrated to remove MeOH/THF, and the residue taken up in water (5 mL) and washed with EtOAc (5 mL). The aqueous layer was acidified to pH 4 with 1M HCl then extracted with DCM (3×10 mL). The combined organics were dried over MgSO$_4$, filtered and concentrated under reduced pressure to afford 296.3 mg (82% yield) of the title compound as white powder.

$^{1}$H NMR (250 MHz, DMSO-d6): δ [ppm] 7.99 (t, J=1.4 Hz, 1H), 7.65 (d, J=1.2 Hz, 1H), 7.62-7.59 (m, 1H), 7.48 (dd, J=2.5, 1.3 Hz, 1H), 5.19 (s, 1H), 3.51 (dd, J=39.9, 10.7 Hz, 4H), 2.08 (s, 2H), 1.40 (s, 9H).

LCMS (Analytical Method A) Rt=1.21 min, MS (ESI-pos): m/z=405.10 (M+H)$^{+}$.

Intermediate 4AF: tert-butyl 3-[3-(methoxycarbonyl)-5-(5-methyl-1,3-thiazol-2-yl)phenoxy]piperidine-1-carboxylate

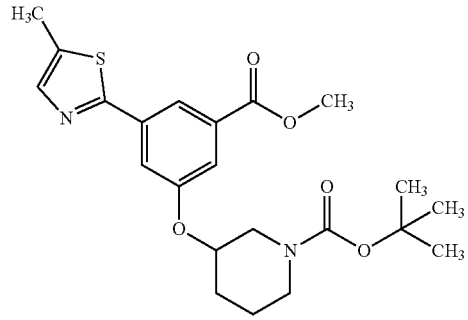 [SMILES: COC(=O)c1cc(OC2CCCN(C(=O)OC(C)(C)C)C2)cc(-c2ncc(C)s2)c1]

Intermediate 3 (1.3 g, 3.65 mmol, 70% purity), tert-butyl 4-hydroxypiperidine-1-carboxylate (1.47 g, 7.3 mmol) and triphenylphosphine (3.8 g, 14.6 mmol) were combined in THF (10 mL) and cooled to 0° C. in an ice bath. DIAD (1.43 mL, 7.3 mmol) was added dropwise and the reaction mixture stirred for 10 min then allowed to warm to RT and stirred for a further 16 h. The reaction mixture was concentrated under reduced pressure, taken up in DCM (20 mL) then washed with brine (10 mL) and ammonium chloride (10 mL). The organic phase was separated, dried over MgSO$_4$, filtered and concentrated under reduced pressure. The crude material was purified by Biotage Isolera™ chromatography (silica gel, eluting with heptane-EtOAc, 1:0 to 0:1) to afford 209 mg (15% yield) of the title compound as colourless oil.

$^1$H NMR (250 MHz, Chloroform-d): δ [ppm] 8.10 (t, J=1.4 Hz, 1H), 7.72-7.63 (m, 1H), 7.62-7.56 (m, 1H), 7.51 (d, J=1.1 Hz, 1H), 4.52-4.32 (m, 1H), 3.93 (s, 3H), 3.81-3.68 (m, 1H), 3.59-3.25 (m, 3H), 2.52 (d, J=1.1 Hz, 3H), 2.14-1.72 (m, 4H), 1.37 (s, 9H).

LCMS (Analytical Method A) Rt=1.60 min, m/z=433 (M+H)$^+$.

Intermediate 5AF: 3-{[1-(tert-butoxycarbonyl)piperidin-3-yl]oxy}-5-(5-methyl-1,3-thiazol-2-yl)benzoic acid

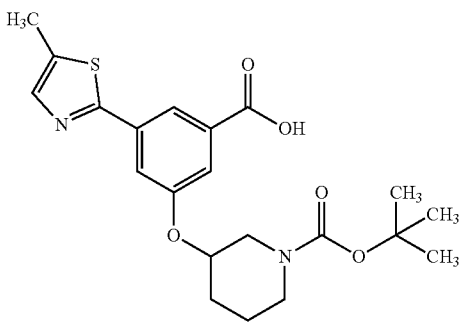 [SMILES: Cc1cnc(-c2cc(OC3CCCN(C(=O)OC(C)(C)C)C3)cc(C(=O)O)c2)s1]

To a solution of Intermediate 4AF (367 mg, 0.76 mmol, 90% purity) in THF (2 mL) was added 1 M LiOH (1.1 mL) and the reaction mixture stirred for 16 h at RT before concentrating under reduced pressure. The residue was taken up in water (~1 mL) and basified to pH 4 with 1 M HCl to precipitate a white solid that was extracted with EtOAc (2×5 mL). The combined organics were dried over MgSO$_4$, filtered and concentrated under reduced pressure to give a colourless gum that was freeze-dried to give 264 mg (77% yield) of the title compound as white powder.

LCMS (Analytical Method A) Rt=1.39, MS (ESIpos) m/z=419 (M+H)$^+$.

Intermediate 4AG: Methyl 3-[(1-acetylpiperidin-4-yl)oxy]-5-(5-methyl-1,3-thiazol-2-yl)benzoate

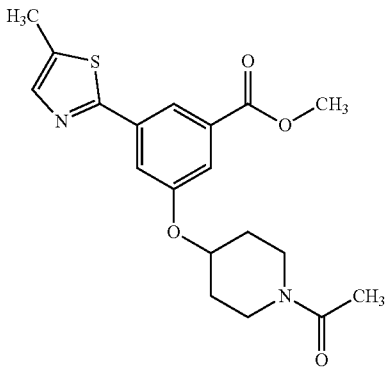 [SMILES: COC(=O)c1cc(OC2CCN(C(C)=O)CC2)cc(-c2ncc(C)s2)c1]

To a solution of Intermediate 3 (200 mg, 0.80 mmol), 1-(4-hydrompiperidin-1-yl)ethanone (126 mg, 0.88 mmol) and triphenylphosphine (630 mg, 2.40 mmol) in THF (2 mL) cooled to 0° C. was added DIAD (0.3 mL, 1.53 mmol) dropwise. The resulting solution was allowed to warm to RT and stirred for 16 h. LCMS analysis showed complete conversion to desired product thus the mixture was concentrated under reduced pressure. The residue was dissolved in DCM (10 mL) and washed with NH$_4$Cl (5 mL). The organic phase was separated, dried over MgSO$_4$, filtered and concentrated under reduced pressure. The crude material was purified by Biotage Isolera™ chromatography (silica gel, eluting with heptane-EtOAc, 1:4 to 0:1 followed by EtOAc-MeOH, 1:0 to 20:3) to give 182 mg (52% yield) of the title compound as yellow gum.

$^1$H NMR (250 MHz, Chloroform-d): δ [ppm] 8.08 (t, 1H), 7.70 (dd, 1H), 7.58 (dd, 1H), 7.51 (d, 1H), 4.69 (tt, 1H), 3.93 (s, 3H), 3.77-3.61 (m, 3H), 3.52-3.34 (m, 1H), 2.52 (d, 3H), 2.12 (s, 3H), 2.01-1.79 (m, 4H).

LCMS (Analytical Method A) Rt=1.28 min, MS (ESIpos): m/z=375.1 (M+H)$^+$.

Intermediate 5AG: 3-[(1-acetylpiperidin-4-yl)oxy]-5-(5-methyl-1,3-thiazol-2-yl)benzoic acid

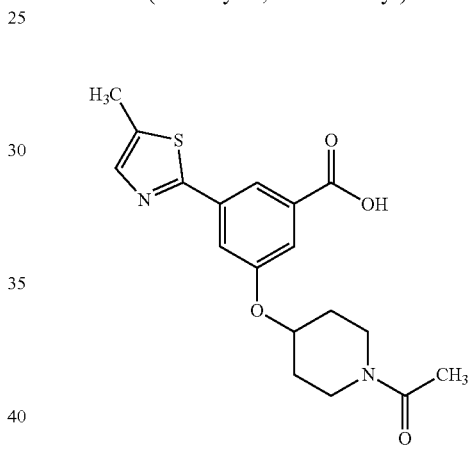

To a solution of Intermediate 4AG (182 mg, 0.44 mmol, 90% purity) in THF (1 mL) was added 1 M LiOH solution (0.65 mL) and the resulting mixture was stirred at RT for 2 h before being concentrated under reduced pressure. The residue was taken up in water (4 mL), acidified to pH 4 with 1 M HCl solution then extracted with 1:1 IPA/chloroform (2×20 mL). The combined organics were dried over MgSO$_4$, filtered and concentrated under reduced pressure to give 120 mg (76% yield) of the title compound as white solid.

$^1$H NMR (500 MHz, DMSO): δ [ppm] 7.96 (t, 1H), 7.65-7.63 (m, 2H), 7.53 (dd, 1H), 4.85-4.75 (m, 1H), 3.87-3.77 (m, 1H), 3.72-3.63 (m, 1H), 2.02 (s, 3H), 2.01-1.86 (m, 2H), 1.72-1.61 (m, 1H), 1.61-1.49 (m, 1H).

LCMS (Analytical Method A) Rt=1.13 min, MS (ESIpos) m/z=361 (M+H)$^+$.

Intermediate 4AH: Tert-butyl 6-[3-(methoxycarbonyl)-5-(5-methyl-1,3-thiazol-2-yl)phenoxy]-2-azaspiro[3.3]heptane-2-carboxylate

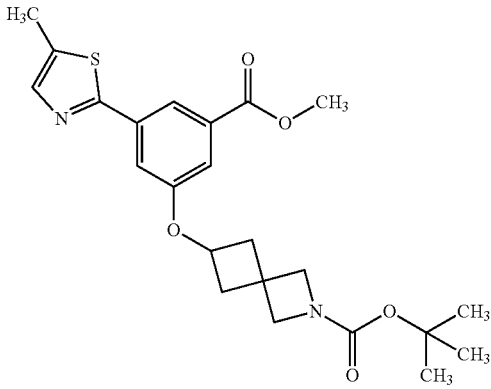 [SMILES: COC(=O)c1cc(OC2CC3(C2)CN(C(=O)OC(C)(C)C)C3)cc(-c2ncc(C)s2)c1]

A solution of Intermediate 3 (250 mg, 0.702 mmol, 70% purity), tert-butyl 6-hydroxy-2-azaspiro[3.3]heptane-2-carboxylate (225 mg, 1.06 mmol) and triphenylphosphine (735 mg, 2.80 mmol) in THF (3 mL) under an atmosphere of nitrogen was cooled to 0° C. in an ice bath and DIAD (0.2 mL, 1.07 mmol) was added dropwise. The resulting solution was allowed to warm to RT and stirred for 16 h. LCMS (Analytical Method A) showed approx. 50% conversion to product. A further portion of DIAD (0.1 mL, 0.54 mmol) was added and the mixture stirred for a further 24 h. LCMS (Analytical Method A) still showed incomplete conversion therefore a further portion of tert-butyl 6-hydroxy-2-azaspiro[3.3]heptane-2-carboxylate (40 mg, 0.19 mmol) and DIAD (0.1 mL, 0.54 mmol) was added and stirred for a further 16 h. The mixture was then concentrated under reduced pressure, and the residue triturated with heptane to precipitate triphenylphosphine oxide which was removed by filtration. The residue was concentrated under reduced pressure and the residue purified by Biotage Isolera™ chromatography (silica gel, eluting with heptane-EtOAc, 4:1 to 2:3) to give 250 mg (76% yield) of the title compound as a colourless gum.

$^1$H NMR (500 MHz, Chloroform-d): δ [ppm] 8.08 (t, J=1.4 Hz, 1H), 7.57-7.49 (m, 2H), 7.44 (dd, J=2.4, 1.4 Hz, 1H), 4.69 (p, J=6.6 Hz, 1H), 4.00 (s, 2H), 3.93 (d, J=3.7 Hz, 5H), 2.81-2.73 (m, 2H), 2.52 (d, J=1.0 Hz, 3H), 2.40-2.32 (m, 2H), 1.44 (s, 9H).

LCMS (Analytical Method A) Rt=1.64 min, MS (ESIpos) 445 (M+H)$^+$.

Intermediate 5AH: 3-{[2-(tert-butoxycarbonyl)-2-azaspiro[3.3]hept-6-yl]oxy}-5-(5-methyl-1,3-thiazol-2-yl)benzoic acid

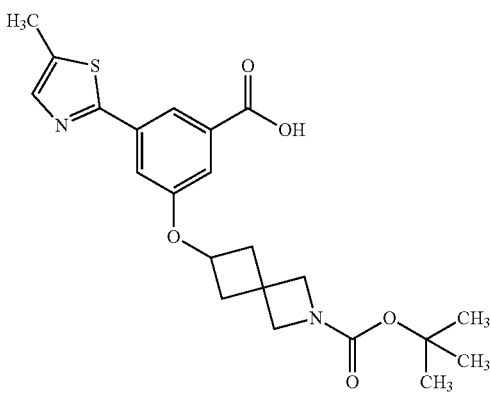 [SMILES: Cc1cnc(-c2cc(OC3CC4(C3)CN(C(=O)OC(C)(C)C)C4)cc(C(=O)O)c2)s1]

To a solution of Intermediate 4AH (250 mg, 0.534 mmol, 95% purity) in THF (1 mL) was added 1 M LiOH solution (0.8 mL) and the resulting solution stirred for 16 h before concentrating under reduced pressure. The residue was taken up in water (1 mL) and acidified to pH 5 with 1 M HCl to precipitate a white solid which was collected by filtration to afford 160 mg (66% yield) of the title compound as white powder.

$^1$H NMR (250 MHz, DMSO): δ [ppm] 7.96 (t, 1H), 7.64 (d, 1H), 7.54-7.44 (m, 1H), 7.37 (dd, 1H), 4.78 (q, 1H), 3.93 (s, 2H), 3.83 (s, 2H), 2.81-2.65 (m, 2H), 2.35-2.19 (m, 2H), 1.37 (s, 9H).

LCMS (MS17, 2 min) Rt=1.42 min, MS (ESIpos) m/z=431 (M+H)$^+$.

Intermediate 47: Methyl 3-({trans-3-[(tert-butoxycarbonyl)amino]cyclobutyl}oxy)-5-(5-methyl-1,3-thiazol-2-yl)benzoate

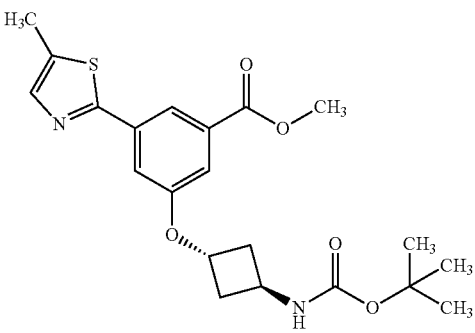 [SMILES: COC(=O)c1cc(O[C@H]2C[C@H](NC(=O)OC(C)(C)C)C2)cc(-c2ncc(C)s2)c1]

Intermediate 3 (500 mg, 2.00 mmol), cis-tert-butyl 3-hydroxycyclobutylcarbamate (488.2 mg, 2.6 mmol) and triphenylphosphine (2104 mg, 8.0 mmol) were combined in THF (10 mL) and cooled to 0° C. DIAD (0.79 mL, 4.0 mmol) was added dropwise and the reaction mixture stirred for 10 min then allowed to warm to RT and stirred for a further 96 h. The reaction mixture was concentrated under reduced pressure, and purified by Biotage Isolera™ chromatography (silica gel, eluting with heptane-EtOAc, 9:1 to 3:7) to afford 1.6 mg (74% yield) of the title compound as a colourless oil.

$^1$H NMR (500 MHz, Chloroform-d): δ [ppm] 8.09 (t, J=1.4 Hz, 1H), 7.54 (dd, J=2.4, 1.6 Hz, 1H), 7.51 (d, J=1.0 Hz, 1H), 7.44 (dd, J=2.5, 1.4 Hz, 1H), 4.94-4.87 (m, 1H), 4.31 (s, 1H), 3.93 (s, 3H), 2.63-2.53 (m, 2H), 2.52 (d, J=1.2 Hz, 3H), 2.48-2.39 (m, 2H), 1.45 (s, 9H).

LCMS (Analytical Method A) Rt=1.53 min, MS (ESIpos): m/z=419.05 (M+H)$^+$.

Intermediate 48: Methyl 3-[(trans-3-aminocyclobutyl)oxy]-5-(5-methyl-1,3-thiazol-2-yl)benzoate

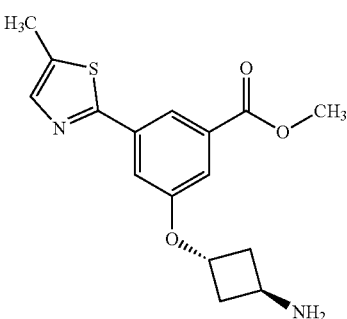

Intermediate 47 (1.6 g, 39% purity, 1.5 mmol) was stirred in hydrochloric acid (4M in 1,4-dioxane, 1.5 ml, 6.0 mmol) and DCM (10 mL) for 2 h. The reaction mixture was concentrated under reduced pressure and the residue taken up in water (15 mL) and washed with EtOAc (2×15 mL). The aqueous layer was basified to pH 8 with sat. NaHCO₃ solution and the mixture extracted with DCM (3×15 mL). The combined organics were dried over MgSO₄, filtered and concentrated under reduced pressure. The residue was loaded in methanol onto a pre-washed SCX-2 cartridge, which was washed with further methanol, followed by 2M NH₃ in MeOH to elute the product. The material was further purified by Biotage Isolera™ chromatography (silica gel, eluting with heptane-EtOAc, 1:3 to 0:1) afford 477 mg (80% yield) of the title compound.

¹H NMR (500 MHz, Chloroform-d): δ [ppm] 8.09 (t, J=1.5 Hz, 1H), 7.55 (dd, J=2.4, 1.6 Hz, 1H), 7.51 (d, J=1.2 Hz, 1H), 7.46 (dd, J=2.5, 1.4 Hz, 1H), 4.98-4.94 (m, 1H), 3.93 (s, 3H), 3.82 (tt, J=7.7, 5.2 Hz, 1H), 2.52 (d, J=1.1 Hz, 3H), 2.48 (ddt, J=10.8, 7.2, 3.4 Hz, 2H), 2.30-2.19 (m, 2H).

LCMS (Analytical Method A) Rt=0.95 min, MS (ESI-pos): m/z=319.0 (M+H)⁺.

Intermediate 49: Methyl 3-{[trans-3-(dimethyl-amino)cyclobutyl]oxy}-5-(5-methyl-1,3-thiazol-2-yl)benzoate

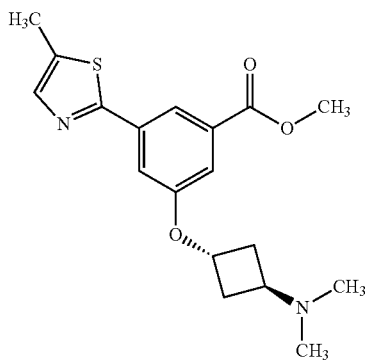 [SMILES: COC(=O)c1cc(O[C@H]2C[C@H](N(C)C)C2)cc(-c2ncc(C)s2)c1]

Intermediate 48 (477 mg, 80% purity, 1.19 mmol) was dissolved in methanol (10 mL) and acetic acid (0.5 mL). Formaldehyde (133 μl, 4.79 mmol) followed by STAB (762 mg, 3.60 mmol) was added, and the reaction stirred for 2 h. LCMS (Analytical Method A) showed incomplete conversion, hence the reaction was re-treated with formaldehyde (133 μl, 4.79 mmol) followed by STAB (762 mg, 3.60 mmol) and stirred for a further 4 h. LCMS (Analytical Method A) still showed incomplete conversion, hence the reaction was again re-treated with formaldehyde (266 μl, 9.58 mmol) followed by STAB (1.53 g, 7.2 mmol) and stirred over the weekend. The reaction mixture was concentrated under reduced pressure, and the residue taken up in sat. NaHCO₃ (30 mL), and the solution extracted with DCM (3×30 mL). The combined organics were dried over MgSO₄, filtered and concentrated under reduced pressure to afford 477.7 mg (92% yield) of the title compound as a colourless gum.

¹H NMR (250 MHz, Chloroform-d): δ [ppm] 8.09 (t, J=1.5 Hz, 1H), 7.55 (dd, J=2.5, 1.6 Hz, 1H), 7.51 (d, J=1.2 Hz, 1H), 7.46 (dd, J=2.5, 1.4 Hz, 1H), 4.87 (tt, J=6.7, 3.5 Hz, 1H), 3.93 (s, 3H), 3.01-2.89 (m, 1H), 2.52 (d, J=1.1 Hz, 3H), 2.48-2.30 (m, 4H), 2.18 (s, 7H).

LCMS (Analytical Method A) Rt=1.00 min, MS (ESI-pos): m/z=347.1 (M+H)⁺.

Intermediate 5AI: 3-{[Trans-3-(dimethylamino)cy-clobutyl]oxy}-5-(5-methyl-1,3-thiazol-2-yl)benzoic acid

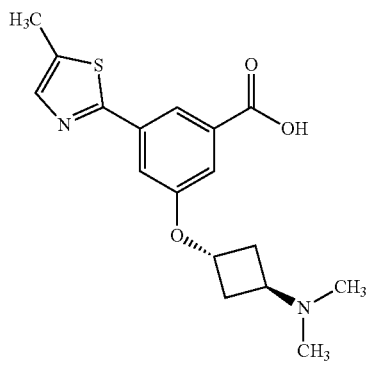 [SMILES: Cc1cnc(-c2cc(O[C@H]3C[C@H](N(C)C)C3)cc(C(=O)O)c2)s1]

Intermediate 49 (477 mg, 80% purity, 1.1 mmol) was dissolved in MeOH (5 mL) and THF (5 mL). 1M LiOH (2 mL) was added, and the reaction stirred at RT for 2 h. The reaction mixture was concentrated to remove MeOH/THF, and the residue taken up in water (5 mL) and washed with EtOAc (5 mL). The aqueous layer was acidified to pH 6 with 1M HCl and the solution extracted with 1:1 IPA/chloroform (3×5 mL). The combined organics were dried over MgSO₄, filtered and concentrated under reduced pressure. The residue was freeze-dried from acetonitrile/water to afford 230 mg (57% yield) of the title compound as a white solid.

¹H NMR (500 MHz, DMSO): δ [ppm] 8.00 (s, 1H), 7.62 (d, J=1.1 Hz, 1H), 7.40 (s, 2H), 4.85 (s, 1H), 2.88 (p, J=7.5 Hz, 1H), 2.43-2.33 (m, 2H), 2.24-2.16 (m, 2H), 2.10 (s, 6H). thiazole methyl group obscured by solvent.

LCMS (Analytical Method A) Rt=0.92 min, MS (ESI-pos): m/z=333.0 (M+H)⁺.

Intermediate 6AJ: Tert-butyl-3-fluoro-4-{[(4-meth-ylphenyl)sulfonyl]oxy}piperidine-1-carboxylate, as a mixture of 2 transisomers

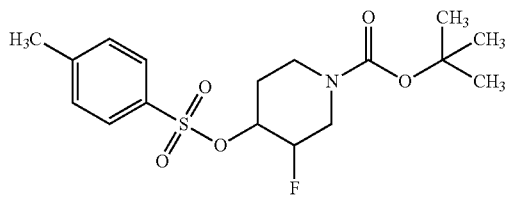 [SMILES: Cc1ccc(S(=O)(=O)OC2CCN(C(=O)OC(C)(C)C)CC2F)cc1]

Tert-butyl 3-fluoro-4-hydroxypiperidine-1-carboxylate (750 mg, 3.42 mmol), trimethylamine (0.72 mL, 5.13 mmol) and trimethylamine hydrochloride (33 mg, 0.34 mmol) were stirred in DCM (15 mL). 4-Methylbenzenesulfonyl chloride (815 mg, 4.28 mmol) was added. The reaction was stirred at RT for 4 h. TLC (50% EtOAc in heptane) showed complete reaction, hence, the reaction mixture was treated with N,N-dimethylethane-1,2-diamine (225 μL, 2.05 mmol) to consume the unreacted TsCl. The reaction mixture was washed with 1 M HCl (2×5 mL) before being dried over MgSO₄, filtered and concentrated under reduced pressure. The crude material was purified by Biotage Isolera™ chromatography (silica gel, eluting with heptane-EtOAc, 10:1 to 1:1) to afford 606.1 mg (47% yield) of the title compound as white powder.

$^1$H NMR (500 MHz, Chloroform-d): δ [ppm] 7.86-7.78 (m, 2H), 7.35 (d, J=8.0 Hz, 2H), 4.71 (d, J=10.0 Hz, 1H), 4.58 (d, J=48.3 Hz, 1H), 3.87 (d, J=52.6 Hz, 2H), 3.34 (s, 2H), 2.45 (s, 3H), 2.08 (s, 1H), 1.76-1.67 (m, 1H), 1.44 (s, 9H).

Intermediate 4AJ: Tert-butyl-3-fluoro-4-[3-(methoxycarbonyl)-5-(5-methyl-1,3-thiazol-2-yl)phenoxy]piperidine-1-carboxylate, as a mixture of 2 transisomers

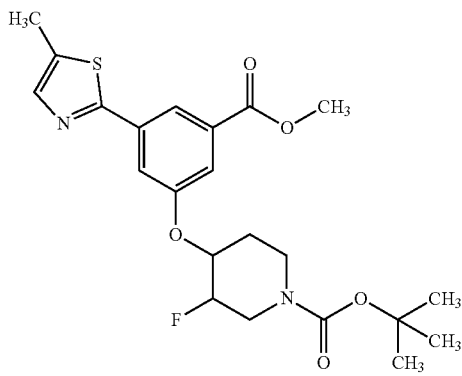 [SMILES: COC(=O)c1cc(OC2CCN(C(=O)OC(C)(C)C)CC2F)cc(-c2ncc(C)s2)c1]

Intermediate 3 (426 mg, 73% purity, 1.25 mmol), Intermediate 6AJ (606 mg, 1.62 mmol) and caesium carbonate (610 mg, 1.87 mmol) were combined in acetonitrile (5 mL) and stirred at 120° C. in the microwave for 3×30 min. The reaction mixture was diluted with EtOAc and filtered through Celite® before being concentrated at reduced pressure. The crude material was purified by Biotage Isolera™ chromatography (silica gel, eluting with heptane-EtOAc, 1:0 to 2:3) to afford 387.6 mg (57% yield) of the title compound as a colourless gum.

$^1$H NMR (500 MHz, Chloroform-d): δ [ppm] 8.12 (t, J=1.4 Hz, 1H), 7.74 (dd, J=2.4, 1.6 Hz, 1H), 7.62 (dd, J=2.5, 1.3 Hz, 1H), 7.52 (d, J=1.2 Hz, 1H), 4.72-4.52 (m, 2H), 3.95 (s, 3H), 3.92-3.77 (m, 1H), 3.66 (s, 1H), 3.58 (s, 1H), 3.46 (s, 1H), 2.53 (d, J=1.1 Hz, 3H), 2.20-2.10 (m, 1H), 1.84-1.75 (m, 1H), 1.70-1.59 (m, 1H), 1.48 (s, 9H).

LCMS (Analytical Method A) Rt=1.41 min, MS (ESI-pos): m/z=451.1 (M+H)$^+$.

Intermediate 5AJ: 3-{[-1-(tert-butoxycarbonyl)-3-fluoropiperidin-4-yl]oxy}-5-(5-methyl-1,3-thiazol-2-yl)benzoic acid, as a mixture of stereoisomers

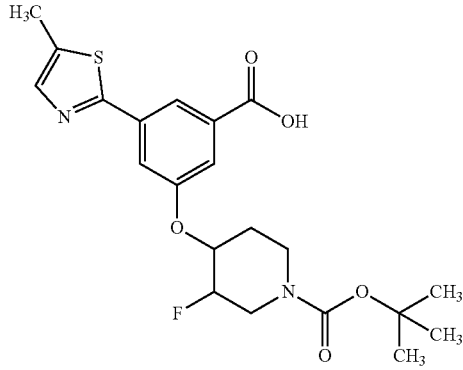 [SMILES: Cc1cnc(-c2cc(OC3CCN(C(=O)OC(C)(C)C)CC3F)cc(C(=O)O)c2)s1]

Intermediate 4AJ (387 mg, 83% purity, 0.71 mmol) was dissolved in MeOH (5 mL) and THF (5 mL). 1M LiOH (2 mL) was added, and the reaction stirred at RT for 2 h. The reaction mixture was concentrated to remove MeOH/THF, and the residue taken up in water (5 mL) and washed with EtOAc (5 mL). The aqueous layer was acidified to pH 4 with 1M HCl, and extracted with DCM (3×5 mL). The combined organics were dried over MgSO$_4$, filtered and concentrated under reduced pressure. The crude material was purified by Biotage Isolera™ chromatography (silica gel, eluting with heptane-EtOAc, 1:0 to 2:3) to afford 105.2 mg (34% yield) of the title compound as white powder.

$^1$H NMR (500 MHz, Chloroform-d): δ [ppm] 8.27-8.21 (m, 1H), 7.80-7.74 (m, 1H), 7.70-7.64 (m, 1H), 7.56 (d, J=1.2 Hz, 1H), 4.62 (d, J=22.8 Hz, 2H), 3.87 (d, J=58.5 Hz, 1H), 3.61 (s, 2H), 3.45 (s, 1H), 2.54 (d, J=1.0 Hz, 3H), 2.20-2.11 (m, 1H), 1.80 (s, 2H), 1.48 (s, 9H).

LCMS (Analytical Method A) Rt=1.16 min, MS (ESI-pos): m/z=437.15 (M+H)$^+$.

Intermediate 5AK: 3-[(6-Methylpyridazin-3-yl)oxy]-5-(5-methyl-1,3-thiazol-2-yl)benzoic acid

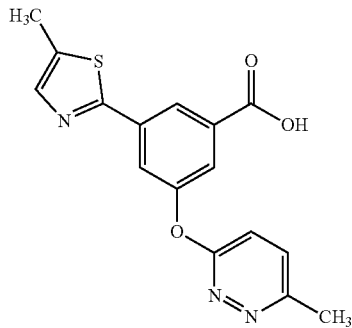 [SMILES: Cc1ccc(Oc2cc(C(=O)O)cc(-c3ncc(C)s3)c2)nn1]

A solution of Intermediate 3 (130 mg, 0.52 mmol), 3-bromo-6-methyl-pyridazine (135 mg, 0.78 mmol) and caesium carbonate (340 mg, 1.04 mmol) in DMF (2.5 mL) was heated in the microwave to 120° C. for 45 min, then for a further 20 min at the same temperature. The reaction mixture was concentrated under reduced pressure and the residue taken up in methanol (5 mL) and treated with 1M LiOH (2.5 mL). After 1.5 h, the reaction was concentrated to remove the organics, before being diluted with water (10 mL) and extracted with EtOAc (2×10 mL). The aqueous layer was acidified to ~pH 4 with 2M HCl, the extracted with DCM (3×10 mL). The combined organics were dried over MgSO$_4$, filtered and concentrated under reduced pressure to afford 143 mg (73% yield) of the title compound as brown gum.

$^1$H NMR (500 MHz, Chloroform-d): δ [ppm] 8.48 (s, 1H), 8.06 (s, 1H), 8.00-7.96 (m, 1H), 7.59 (s, 1H), 7.42 (d, J=9.0 Hz, 1H), 7.19 (d, J=9.0 Hz, 1H), 2.70 (d, J=7.7 Hz, 3H), 2.53 (s, 3H).

LCMS (Analytical Method A) Rt=1.01 min, MS (ESI-pos): m/z=328.05 (M+H)$^+$.

Intermediate 4AY: Methyl 3-({1-[(tert-butoxycarbonyl)amino]cyclopropyl}methoxy)-5-(5-methyl-1,3-thiazol-2-yl)benzoate

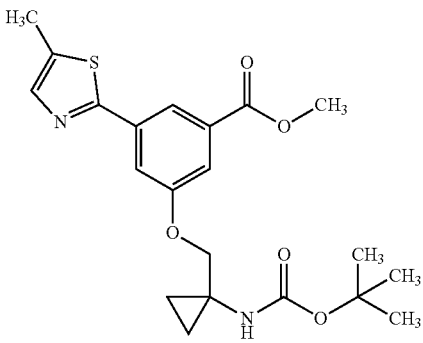 [SMILES: COC(=O)c1cc(OCC2(NC(=O)OC(C)(C)C)CC2)cc(-c2ncc(C)s2)c1]

Intermediate 3 (400 mg, 1.6 mmol), tert-butyl [1-(hydroxymethyl)cyclopropyl]carbamate (390.5 mg, 2.01 mmol) and triphenylphosphine (1683 mg, 6.4 mmol) were combined in THF (10 mL) and cooled to 0° C. in an ice bath. DIAD (0.63 mL, 3.2 mmol) was added dropwise and the reaction mixture stirred for 10 min before being allowed to warm to RT and stirred for a further 96 h. The reaction mixture was concentrated under reduced pressure, and purified by Biotage Isolera™ chromatography (silica gel, eluting with heptane-EtOAc, 1:0 to 1:1). A second purification by Biotage Isolera™ chromatography (silica gel, eluting with heptane-EtOAc, 20:3) afforded 208.9 mg (23% yield) of the title compound as a colourless oil.

LCMS (Analytical Method A) Rt=1.47 min, MS (ESI-pos): m/z=419 (M+H)$^+$.

Intermediate 5AY: 3-({1-[(Tert-butoxycarbonyl)amino]cyclopropyl}methoxy)-5-(5-methyl-1,3-thiazol-2-yl)benzoic acid

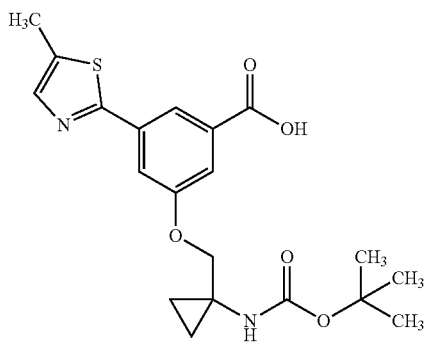 [SMILES: Cc1cnc(-c2cc(OCC3(NC(=O)OC(C)(C)C)CC3)cc(C(=O)O)c2)s1]

Intermediate 4AY (208.9 mg, 0.369 mmol) was stirred in methanol (5 mL) and 1M LiOH (2.5 mL) for 1 h. The organics were removed under reduced pressure, and the residue diluted with water (5 mL) and extracted with EtOAc (5 mL). The aqueous phase was acidified to pH 2 with 2M HCl, before being extracted with DCM (2×5 mL). The combined organics were dried over MgSO$_4$, filtered and concentrated under reduced pressure to afford 48.1 mg (32% yield) of the title compound as a colourless gum.

$^1$H NMR (500 MHz, Chloroform-d): δ [ppm] 8.20 (s, 1H), 7.70-7.67 (m, 1H), 7.64 (s, 1H), 7.57-7.53 (m, 1H), 5.19 (s, 1H), 4.09 (s, 2H), 2.53 (d, J=0.9 Hz, 3H), 1.43 (s, 9H), 0.94 (d, J=19.3 Hz, 4H).

LCMS (Analytical Method A) Rt=1.31 min, MS (ESI-pos): m/z=405 (M+H)$^+$.

Intermediate 30: 3-Hydroxy-5-(5-methyl-1,3-thiazol-2-yl)benzoic acid

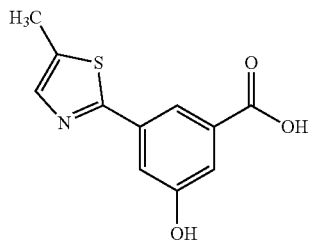 [SMILES: Cc1cnc(-c2cc(O)cc(C(=O)O)c2)s1]

To a solution of Intermediate 3 (500 mg, 2.0 mmol) dissolved in THF (5 mL) and MeOH (5 mL) was added 2M LiOH (2.5 mL, 5 mmol) and stirred for 50° C. for 2 h. The reaction mixture was cooled then concentrated to remove MeOH/THF, and the residue taken up in water (5 mL) and washed with EtOAc (5 mL). The aqueous layer was acidified to pH 4 with 1M HCl and the precipitate collected by vacuum filtration and dried in the vacuum oven to afford 281.1 mg (59% yield) of the title compound as an off-white powder.

$^1$H NMR (500 MHz, DMSO-d6): δ [ppm] 14.89 (s, 1H), 12.60 (t, J=1.5 Hz, 1H), 12.38 (d, J=1.2 Hz, 1H), 12.27-12.22 (m, 1H), 12.14 (dd, J=2.4, 1.4 Hz, 1H).

LCMS (Analytical Method A) Rt=0.94 min, MS (ESI-pos): m/z=235.95 (M+H)$^+$.

Intermediate 32: 3-Hydroxy-5-(5-methyl-1,3-thiazol-2-yl)-N-{(1R)-1-[2-(trifluoromethyl)pyrimidin-5-yl]ethyl}benzamide

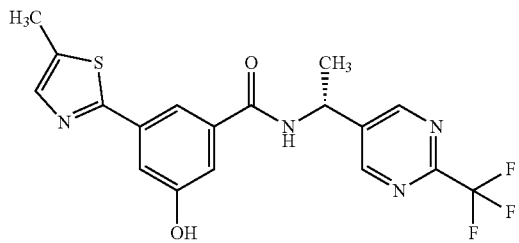 [SMILES: Cc1cnc(-c2cc(O)cc(C(=O)N[C@H](C)c3cnc(C(F)(F)F)nc3)c2)s1]

Intermediate 30 (486 mg, 1.86 mmol), Intermediate VI (465.5 mg, 2.05 mmol) and DIPEA (1.30 mL, 7.44 mmol)

were combined in DMF (10 mL) and HATU (848.3 mg, 2.23 mmol) was added. The reaction mixture was allowed to stir at room temperature overnight. The crude reaction was quenched by addition of water (~15 mL). The resultant emulsion was evaporated to a free-flowing oil. Water (~15 mL) was added and the resultant precipitate removed by filtration and washed with a further aliquot of water, then allowed to dry in air to give 660 mg (82% yield) of the title compound as an off-white powder.

$^1$H NMR (500 MHz, DMSO-d6): δ [ppm]=10.05 (s, 1H), 9.13-9.09 (m, 3H), 7.79 (t, J=1.4, 1H), 7.62 (d, J=1.2, 1H), 7.46-7.39 (m, 1H), 7.37-7.29 (m, 1H), 5.28 (m, 1H), 2.49 (s, 3H), 1.59 (d, J=7.1, 3H).

LCMS (Analytical Method F) Rt=2.87 min, MS (ESIpos): m/z=409.1 (M+H)$^+$.

Intermediate 63: 3-Hydroxybutan-2-yl]oxy}-5-(5-methyl-1,3-thiazol-2-yl)-N-{(1R)-1-[2-(trifluoromethyl)pyrimidin-5-yl]ethyl}benzamide, mixture of 2 transisomers

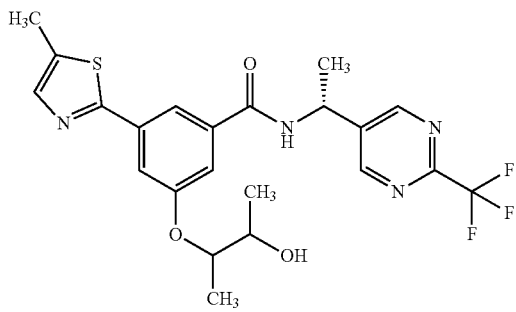

To a solution of 3-hydroxybutan-2-yl]oxy}-5-(5-methyl-1,3-thiazol-2-yl)benzoic acid (145 mg, 0.47 mmol), Intermediate VI (129 mg, 0.57 mmol) and DIPEA (0.25 mL, 1.42 mmol) in DCM (2 mL) was added HATU (269 mg, 0.71 mmol). The mixture was stirred for 2 h at RT then diluted with DCM and washed with water and saturated aqueous ammonium chloride solution. The organic phase was separated, dried (MgSO$_4$), filtered and concentrated at reduced pressure. The crude material was purified by by Biotage Isolera™ chromatography (eluting with 0-7% MeOH in DCM on a pre-packed KP—SiO$_2$ column) to give 222 mg (88% yield) of the title compound.

$^1$H NMR (250 MHz, Chloroform-d): δ [ppm] 8.94 (s, 2H), 7.79 (s, 1H), 7.55-7.43 (m, 2H), 7.35 (s, 1H), 6.92 (d, J=6.6 Hz, 1H), 5.36 (m, 1H), 4.45 (dt, J=6.4, 3.4 Hz, 1H), 4.04 (s, 1H), 2.79 (s, 6H), 2.53 (s, 3H), 1.71 (d, J=7.1 Hz, 4H), 1.32-1.23 (m, 6H).

LCMS (Analytical Method D) Rt=4.22 min, MS (ESIpos) m/z=481 (M+H)$^+$.

Intermediate 76: 3-(5-Chloro-1,3-thiazol-2-yl)-5-{[trans-3-hydroxybutan-2-yl]oxy}benzoic acid, as a mixture of transisomers

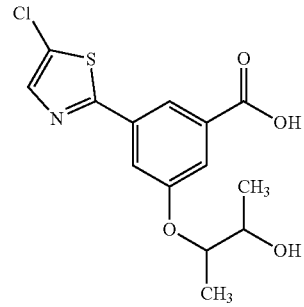 [SMILES: CC(O)C(C)Oc1cc(C(=O)O)cc(-c2ncc(Cl)s2)c1]

To a solution of methyl 3-hydroxy-5-(5-chloro-1,3-thiazol-2-yl)benzoate (500 mg, 1.67 mmol) and trans-2,3-epoxybutane (0.63 mL, 6.67 mmol) in DMSO (5 mL) was added caesium carbonate (2.17 g, 6.67 mmol). The mixture was heated to 100° C. for 16 h then diluted with water (10 mL) and washed with EtOAc (10 mL). The aqueous layer was acidified with conc. HCl and extracted into DCM (2×15 mL). The combined organics were dried over MgSO$_4$, filtered and concentrated under reduced pressure. The crude material was purified by Biotage Isolera™ chromatography (silica gel, eluting with DCM/MeOH, 1:0 to 4:1) followed by preparative HPLC (Method B) to afford 306 mg (56% yield) of the title compound as an off-white solid.

$^1$H NMR (250 MHz, DMSO-d6): δ [ppm] 8.00 (s, 1H), 7.94 (t, J=1.4 Hz, 1H), 7.64-7.60 (m, 1H), 7.55 (dd, J=2.4, 1.4 Hz, 1H), 4.82 (s, 1H), 4.47-4.32 (m, 1H), 3.85-3.69 (m, 1H), 1.24 (d, J=6.2 Hz, 3H), 1.14 (d, J=6.4 Hz, 3H).

LCMS (Analytical Method D) Rt=3.84 min, MS (ESIpos): m/z=327.97 (M+H)$^+$.

The mixture of trans isomers was separated using Chiral Purification (Method 1) to give Intermediate 77 (Trans Isomer 1) and Intermediate 78 (Trans Isomer 2)

Intermediate 77: Trans Isomer 1; 3-(5-chloro-1,3-thiazol-2-yl)-5-{[3-hydroxybutan-2-yl]oxy}benzoic acid SFC Chiral Purification (Method 1) on 296 mg of Intermediate 76 gave 98.4 mg of the title compound as an off-white solid.

SFC Chiral Analysis (Method 1): 96.2% e.e. Rt=2.71 min.

$^1$H NMR (250 MHz, DMSO-d6) δ [ppm]=7.99 (s, 1H), 7.94 (s, 1H), 7.61 (s, 1H), 7.55 (s, 1H), 4.82 (s, 1H), 4.52-4.28 (m, 1H), 3.75 (s, 1H), 1.23 (d, J=6.2 Hz, 3H), 1.13 (d, J=6.4 Hz, 3H).

Intermediate 78: Trans Isomer 2; 3-(5-chloro-1,3-thiazol-2-yl)-5-{[3-hydroxybutan-2-yl]oxy}benzoic acid SFC Chiral Purification (Method 1) on 296 mg of Intermediate 76 gave 93.2 mg of the title compound as an off-white solid.

SFC Chiral Analysis (Method 1): 97.2% e.e. Rt=3.18 min.

$^1$H NMR (250 MHz, DMSO-d6): δ [ppm] 8.00 (s, 1H), 7.97-7.88 (m, 1H), 7.64-7.59 (m, 1H), 7.56-7.51 (m, 1H), 4.83 (d, J=5.1 Hz, 1H), 4.49-4.33 (m, 1H), 3.85-3.70 (m, 1H), 1.23 (d, J=6.2 Hz, 3H), 1.13 (d, J=6.4 Hz, 3H).

Intermediate 87: 3-Hydroxybutan-2-yl]oxy}-5-(5-methyl-1,3-thiazol-2-yl)benzoic acid, as a mixture of transisomers

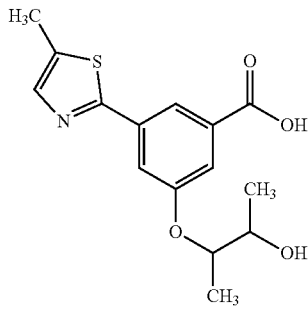 [SMILES: Cc1cnc(-c2cc(OC(C)C(C)O)cc(C(=O)O)c2)s1]

To a solution of Intermediate 3 (300 mg, 0.88 mmol) and trans-2,3-epoxybutane (0.32 mL, 3.51 mmol) in DMSO (3 mL) was added caesium carbonate (1145 mg, 3.51 mmol). The mixture heated to 100° C. for 16 h then diluted with water (10 mL) and acidified with conc. HCl to form a white precipitate which was extracted into IPA/CHCl3 (1:3) (2×25 mL). The combined organics were dried over MgSO$_4$, filtered and concentrated under reduced pressure. The residue was purified by preparative HPLC (Method B) to give 500 mg (57% yield) of the title compound as an off-white solid.

The mixture of trans isomers was separated using Chiral Purification (Method 1) to give Intermediate 88 (Trans Isomer 1) and Intermediate 89 (Trans Isomer 2)

Intermediate 88: Trans Isomer 1; 3-Hydroxybutan-2-yl]oxy}-5-(5-methyl-1,3-thiazol-2-yl)benzoic acid SFC Chiral Purification (Method 1) on 298.2 mg of Intermediate 87 gave 183.6 mg of the title compound as an off-white powder.

SFC Chiral Analysis (Method 1): 100% e.e. Rt=2.17 min.

$^1$H NMR (250 MHz, DMSO-d6): δ [ppm] 7.96-7.92 (m, 1H), 7.66-7.59 (m, 2H), 7.51-7.47 (m, 1H), 4.43-4.32 (m, 2H), 3.82-3.71 (m, 1H), 1.24 (d, J=6.2 Hz, 3H), 1.14 (d, J=6.4 Hz, 3H).

Intermediate 89: Trans Isomer 2; 3-Hydroxybutan-2-yl]oxy}-5-(5-methyl-1,3-thiazol-2-yl)benzoic acid SFC Chiral Purification (Method 1) on 298.2 mg of Intermediate 89 gave 46.7 mg of the title compound as an off-white powder.

SFC Chiral Analysis (Method 1): 100% e.e. Rt=2.41 min.

$^1$H NMR (250 MHz, DMSO-d6): δ [ppm] 13.25 (s, 1H), 7.97-7.91 (m, 1H), 7.67-7.58 (m, 2H), 7.53-7.47 (m, 1H), 4.81 (d, J=5.1 Hz, 1H), 4.43-4.31 (m, 1H), 3.82-3.70 (m, 1H), 1.24 (d, J=6.1 Hz, 3H), 1.14 (d, J=6.4 Hz, 3H.

Intermediate 92: 3-Hydroxybutan-2-yl]oxy}-5-(5-methyl-1,3-thiazol-2-yl)benzoic acid, as a mixture of cis isomers

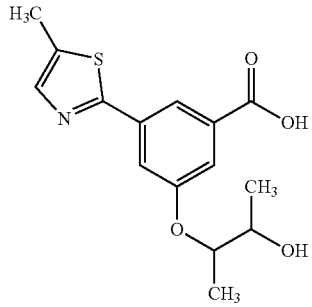 [SMILES: Cc1cnc(-c2cc(OC(C)C(C)O)cc(C(=O)O)c2)s1]

To a solution of Intermediate 3 (780 mg, 3.13 mmol) and cis-2,3-epoxybutane (1.09 mL, 12.5 mmol) in DMSO (10 mL) was added caesium carbonate (4.08 g, 12.5 mmol). The mixture heated to 100° C. for 16 h then diluted with water (30 mL) and acidified to pH 4 with 2N HCl to form a white precipiate which was extracted into IPA/CHCl3 (1:1) (30 mL). The combined organics were dried over MgSO$_4$, filtered and concentrated under reduced pressure. The residue was purified by Biotage Isolera™ chromatography (eluting with 0-80% EtOAc in heptane on a 50 g pre-packed KP—SiO$_2$ column) to give 565 mg (55% yield) of the title compound as an off-white powder.

Intermediate 25: 3-Fluoro-5-(4,4,5,5-tetramethyl-1,3,2-dioxaborolan-2-yl)benzonitrile

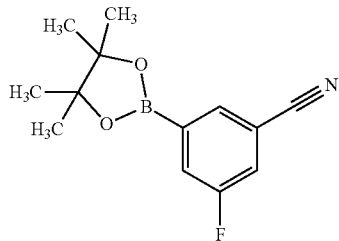 [SMILES: CC1(C)OB(c2cc(F)cc(C#N)c2)OC1(C)C]

3-Bromo-5-fluoro benzonitrile (30 g, 150 mmol), bis(pinacolato)diborane (41.9 g, 0.15 mol) and potassium acetate (44.2 g, 0.45 mol) were combined in 1,4-dioxane (300 mL) and degassed with N$_2$ for 10 mins. [1,1'-Bis(diphenylphosphino)ferrocene]palladium(II) dichloride (5.5 g, 7.5 mmol) was added and the mixture degassed with N$_2$ for a further 10 min before heating at 100° C. under an atmosphere of nitrogen for 18 h. The mixture was filtered through Celite® and the solids washed with ethyl acetate. The filtrate was washed with brine, the organic phase separated, dried over MgSO$_4$, filtered and concentrated under reduced pressure. The crude material was purified by filtration through a silica plug, eluting with EtOAc, and the resultant filtrate concentrated under reduced pressure to afford 43.7 g (quantitative yield assumed, 84% purity) of the title compound as brown oil $^1$H NMR (500 MHz, DMSO-d6): δ [ppm] 1.31 (s, 12H), 7.65-7.72 (m, 1H), 7.79-7.83 (m, 1H), 8.00 (ddd, J=8.8, 2.7, 1.4 Hz, 1H).

LCMS (Analytical Method A) Rt=0.91 min.

Intermediate 26:
3-Fluoro-5-(5-methyl-1,3-thiazol-2-yl)benzonitrile

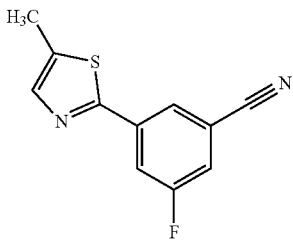

Intermediate 25 (15 g, 51 mmol), 2-bromo-5-methyl-1,3-thiazole (5.9 mL, 56 mmol) and potassium carbonate (17.6 g, 127.5 mmol) were dissolved in 4:1 1,4-dioxane/water (200 mL). The solution was with $N_2$ for 10 min. Tetrakis(triphenylphosphine)palladium(0) (1.2 g, 1.0 mmol) was added and the reaction mixture heated at 80° C. for 16 h. After this time the reaction mixture was partitioned between water and EtOAc. The organic phase was separated and the aqueous phase extracted with further EtOAc. The combined organics were washed with brine, dried ($MgSO_4$), filtered and concentrated under reduced pressure. The crude material was purified by Biotage Isolera™ chromatography (silica gel, eluting with heptanes-EtOAc, 1:0 to 4:1). The product containing fractions were combined and triturated with heptane and the precipitate collected and dried by vacuum filtration. The mother liqueur and mixed fractions were combined and concentrated.

The residue was re-purified by Biotage Isolera™ chromatography (silica gel, eluting with heptane-EtOAc, 1:0 to 4:1). The two batches were combined to afford 7.06 g (59% yield) of the title compound as white powder.

$^1$H NMR (250 MHz, Chloroform-d): δ [ppm] 7.96 (t, J=1.4 Hz, 1H), 7.86 (ddd, J=9.2, 2.4, 1.6 Hz, 1H), 7.57 (d, J=1.1 Hz, 1H), 7.35 (ddd, J=7.7, 2.5, 1.3 Hz, 1H), 2.55 (d, J=1.1 Hz, 3H).

LCMS (Analytical Method A) Rt=1.26 min, MS (ESI-pos): m/z=218.85 (M+H)$^+$.

Intermediate 29:
3-(5-Ethyl-1,3-thiazol-2-yl)-5-fluorobenzonitrile

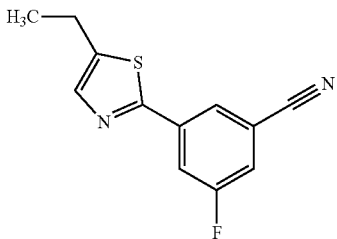 [SMILES: CCc1cnc(-c2cc(F)cc(C#N)c2)s1]

Intermediate 26 (5 g, 17 mmol), 2-chloro-5-ethyl-1,3-thiazole (3 g, 20 mmol) and cesium carbonate (14 g, 42.5 mmol) were dissolved in 4:1 1,4-dioxane/water (50 mL). The solution was degassed with a stream of nitrogen for 10 min. Tetrakis(triphenylphosphine)palladium(0) (982 mg, 0.85 mmol) was added and the reaction mixture stirred at 100° C. overnight. The reaction was diluted with water (20 mL) and extracted with DCM (2×50 mL). The combined organics were washed with brine (30 mL), dried over anhydrous $Na_2SO_4$, filtered and concentrated under reduced pressure. The crude material was purified by Biotage Isolera™ chromatography (silica gel, eluting with heptane-EtOAc, 1:0 to 3:1). The product containing fractions were concentrated and the residue crystallised from heptane to afford 2.5 g (63% yield) of the title compound as white crystalline solid.

$^1$H NMR (250 MHz, Chloroform-d): δ [ppm] 7.97 (d, J=1.3 Hz, 1H), 7.91-7.79 (m, 1H), 7.59 (s, 1H), 7.35 (ddd, J=7.7, 2.4, 1.3 Hz, 1H), 3.01-2.82 (m, 2H), 1.37 (t, J=7.5 Hz, 3H).

LCMS (Analytical Method A) Rt=1.34 min, MS (ESI-pos): m/z=232.9 (M+H)$^+$.

Intermediate 54: Tert-butyl (3-endo)-3-hydroxy-8-azabicyclo[3.2.1]octane-8-carboxylate

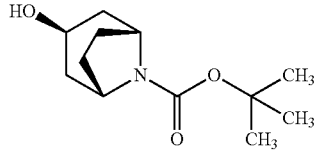

To a solution of (3-endo)-8-azabicyclo[3.2.1]octan-3-ol (3 g, 23.6 mmol) and triethylamine (5.1 mL, 36.6 mmol) in DCM (30 mL) was added di-tert-butyl dicarbonate (10.3 g, 47.2 mmol) portionwise and the resulting reaction mixture stirred at RT for 16 h. The reaction mixture was diluted with water then the organic layer was separated and washed with saturated citric acid (aq), water and brine. The organic layer was dried over $Na_2SO_4$, filtered and concentrated under reduced pressure then triturated with heptane to afford 4.16 g (77% yield) of the title compound as an off-white crystalline solid.

$^1$H NMR (250 MHz, DMSO-d6): δ [ppm] 1.38 (s, 9H), 1.61 (d, J=13.5 Hz, 2H), 1.70-1.96 (m, 4H), 2.12 (d, J=6.7 Hz, 2H), 3.94 (d, J=19.0 Hz, 3H), 4.56 (d, J=2.3 Hz, 1H).

Intermediate 27AL: Tert-butyl (3-endo)-3-[3-cyano-5-(5-methyl-1,3-thiazol-2-yl)phenoxy]-8-azabicyclo[3.2.1]octane-8-carboxylate

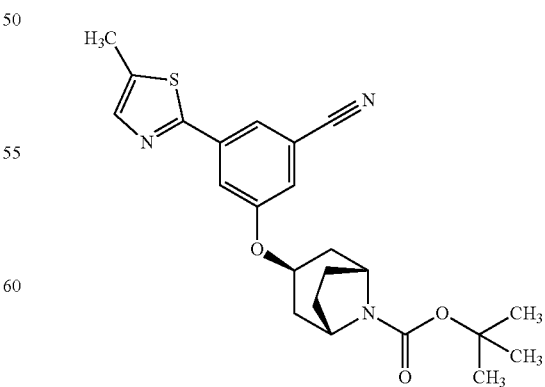

To a stirred solution of Intermediate 54 (1.56 g, 8.86 mmol) in dry DMF (10 mL) was added NaH (60% dispersion in mineral oil, 274 mg, 6.85 mmol). After the mixture was stirred for 15 min Intermediate 26 (1.0 g, 4.58 mmol) was added in one portion. The resulting mixture was stirred for 18 h. After this time the reaction mixture was quenched with brine and extracted with EtOAc. The organic phase was separated and washed with brine, dried over MgSO$_4$, filtered and evaporated under reduced pressure. The crude material was purified Biotage Isolera™ chromatography (silica gel, eluting with heptane-EtOAc, 1:0 to 1:1) to afford 1.25 g (58% yield) of the title compound.

$^1$H NMR (250 MHz, Chloroform-d): δ [ppm] 7.67 (t, J=1.4 Hz, 1H), 7.67-7.57 (m, 1H), 7.53 (d, J=1.2 Hz, 1H), 7.08 (dd, J=2.4, 1.3 Hz, 1H), 4.72 (t, J=4.7 Hz, 1H), 4.22 (s, 2H), 2.54 (d, J=1.1 Hz, 3H), 2.33-1.89 (m, 9H), 1.47 (d, J=4.7 Hz, 9H). LCMS (Analytical Method A) Rt=1.49 min, MS (ESIpos) m/z=426 (M+H)$^+$.

Intermediate 28AL: 3-{[(3-endo)-8-(tert-butoxycarbonyl)-8-azabicyclo[3.2.1]oct-3-yl]oxy}-5-(5-methyl-1,3-thiazol-2-yl)benzoic acid

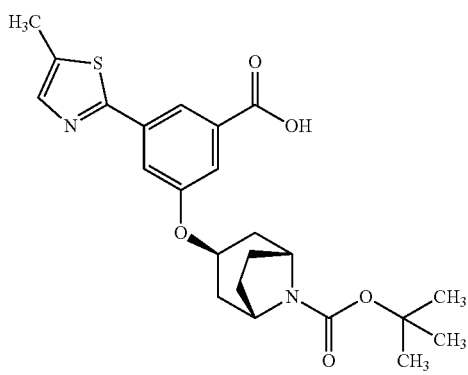 [SMILES: Cc1cnc(-c2cc(O[C@H]3C[C@H]4CC[C@@H](C3)N4C(=O)OC(C)(C)C)cc(C(=O)O)c2)s1]

To a solution of Intermediate 27AL (1.25 g, 2.64 mmol) in DMSO (5 mL) was added 2 M NaOH (2 mL) and the mixture stirred at 110° C. for 3 h. The mixture was slowly acidified with 2M HCl to pH ~5 to precipitate a white solid which was collected by filtration. The solids were dried in a vacuum oven, which resulted in melting of the compound, affording 290 mg (53% yield) of the title compound as a colourless gum. LCMS (Analytical Method A) Rt=1.32 min, MS (ESIpos) m/z=445 (M+H)$^+$.

Intermediate 63: Tert-butyl (3-exo)-3-hydroxy-8-azabicyclo[3.2.1]octane-8-carboxylate

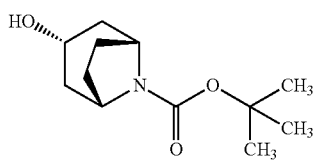 [SMILES: CC(C)(C)OC(=O)N1[C@@H]2CC[C@H]1C[C@H](O)C2]

To a solution of (3-exo)-8-azabicyclo[3.2.1]octan-3-ol (0.95 g, 7.5 mmol) and triethylamine (1.7 mL, 12.2 mmol) in DCM (10 mL) was added di-tert-butyl dicarbonate (3.27 g, 15.0 mmol) portionwise and the resulting reaction mixture stirred at RT for 16 h. The reaction mixture was diluted with water then the organic layer was separated and washed with saturated citric acid (aq), water and brine. The organic layer was dried over MgSO$_4$, filtered and concentrated under reduced pressure to afford 1.65 g (97% yield) of the title compound as an off white solid.

$^1$H NMR (250 MHz, Chloroform-d): δ [ppm] 4.41-3.95 (m, 3H), 2.00-1.53 (m, 9H), 1.45 (s, 9H).

Intermediate 27AM: Tert-butyl (3-exo)-3-[3-cyano-5-(5-methyl-1,3-thiazol-2-yl)phenoxy]-8-azabicyclo[3.2.1]octane-8-carboxylate

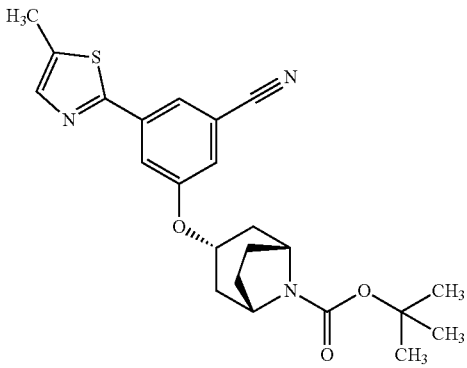 [SMILES: Cc1cnc(-c2cc(C#N)cc(O[C@@H]3C[C@H]4CC[C@@H](C3)N4C(=O)OC(C)(C)C)c2)s1]

To a stirred solution of Intermediate 63 (0.68 g, 2.98 mmol) in dry DMF (10 mL) was added NaH (60% dispersion in mineral oil, 120 mg, 3.00 mmol). After the mixture was stirred for 15 min Intermediate 26 (0.5 g, 2.29 mmol) was added as one portion. The resulting mixture was stirred at RT for 48 h. The reaction mixture was poured onto brine and extracted into EtOAc. The organic layer was washed with brine, separated, dried over MgSO$_4$, filtered and concentrated under reduced pressure to give brown oil. The crude material was purified by Biotage Isolera™ chromatography (silica gel, eluting with heptane-EtOAc, 1:0 to 0:1) to afford 531 mg (54% yield) of the title compound as an off-white powder.

$^1$H NMR (250 MHz, Chloroform-d): δ [ppm] 7.71 (t, J=1.4 Hz, 2H), 7.68-7.63 (m, 1H), 7.53 (d, J=1.2 Hz, 1H), 7.13 (dd, J=2.4, 1.3 Hz, 1H), 4.75 (tt, J=10.6, 5.9 Hz, 1H), 4.34 (s, 2H), 2.53 (d, J=1.1 Hz, 3H), 2.20-2.00 (m, 4H), 1.93-1.65 (m, 4H), 1.49 (s, 9H).

LCMS (Analytical Method A) Rt=1.46 min, MS (ESIpos): m/z=426.05 (M+H)$^+$.

Intermediate 28AM: 3-{[(3-exo)-8-(tert-butoxycarbonyl)-8-azabicyclo[3.2.1]oct-3-yl]oxy}-5-(5-methyl-1,3-thiazol-2-yl)benzoic acid

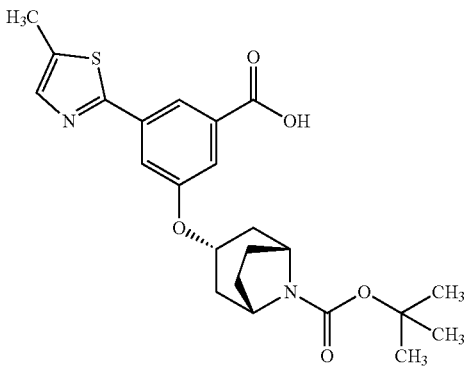 [SMILES: Cc1cnc(-c2cc(O[C@@H]3C[C@H]4CC[C@@H](C3)N4C(=O)OC(C)(C)C)cc(C(=O)O)c2)s1]

To a solution of Intermediate 27AL (1.25 g, 2.64 mmol) in DMSO (5 mL) was added 2 M aqueous sodium hydroxide (2 mL) and the mixture stirred at 110° C. for 3 h. The mixture was slowly acidified by 2 M aqueous HCl to pH ~5 to precipitate a white solid which was collected by filtration. The solids were dried in a vacuum oven to give 0.56 g (48% yield) of the title compound as an off-white powder.

LCMS (Analytical Method A) Rt=1.35 min, MS (ESIpos) m/z=445 (M+H)$^+$.

Intermediate 27AN: 3-[(3-methyloxetan-3-yl)oxy]-5-(5-methyl-1,3-thiazol-2-yl)benzonitrile

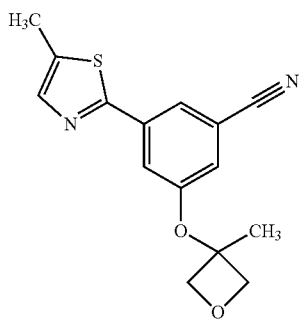 [SMILES: Cc1cnc(-c2cc(C#N)cc(OC3(C)COC3)c2)s1]

To a solution of 3-methyloxetan-3-ol (121 mg, 1.37 mmol) in dry DMF (2 mL) was added NaH (60% dispersion in mineral oil, 55 mg, 1.38 mmol) and the mixture stirred at RT for 1 h before addition of Intermediate 26 (200 mg, 0.92). The resulting mixture was stirred at RT for 3 h then partitioned between EtOAc and water. The organic phase was separated and the aqueous phase extracted with EtOAc. The combined organics were washed with brine, dried over MgSO$_4$, filtered and concentrated under reduced pressure. TLC analysis (EtOAc-heptane, 1:1) indicated incomplete consumption of SM. The residue was dissolved in DMF (1 mL) and added to a pre-stirred solution of 3-methyloxetan-3-ol (121 mg, 1.37 mmol) and NaH (60% dispersion in mineral oil, 55 mg, 1.38 mmol). The mixture was stirred at RT overnight at which point TLC analysis indicated consumption of starting material. The mixture was partitioned between EtOAc and water. The organic phase was separated and the aqueous phase extracted with EtOAc. The combined organics were washed with brine, dried over MgSO$_4$, filtered and concentrated under reduced pressure. The crude material was purified by Biotage Isolera™ chromatography (silica gel, eluting with heptane-EtOAc, 1:0 to 2:3) to give 140 mg (51% yield) of the title compound as brown oil.

$^1$H NMR (250 MHz, Chloroform-d): δ [ppm] 7.73 (t, J=1.4 Hz, 1H), 7.53 (d, J=1.2 Hz, 1H), 7.40 (dd, J=2.4, 1.5 Hz, 1H), 6.86 (dd, J=2.4, 1.3 Hz, 1H), 4.94 (d, J=6.6 Hz, 2H), 4.64 (d, J=7.3 Hz, 2H), 2.54 (d, J=1.1 Hz, 3H), 1.79 (s, 3H)

LCMS (Analytical Method A) Rt=1.18 min, MS (ESIpos) m/z=287 (M+H)$^+$.

Intermediate 28AN: 3-[(3-methyloxetan-3-yl)oxy]-5-(5-methyl-1,3-thiazol-2-yl)benzoic acid

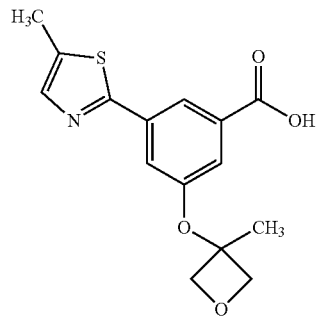 [SMILES: Cc1cnc(-c2cc(OC3(C)COC3)cc(C(=O)O)c2)s1]

Intermediate 27AN (140 mg, 0.46 mmol) was stirred in 2M NaOH (2.3 mL) and DMF (1 mL) at 110° C. for 14 h in a sealed tube. THF was added to aid dissolution and the resulting solution was heated for 16 h at 110° C. in a sealed tube. A further portion of 2 M NaOH solution (2 mL) was added and heated to 110° C. for 3 h. The mixture was acidified with 2M HCl to form a white precipitate that was extracted into EtOAc. The organic phase was separated, dried over MgSO$_4$, filtered and concentrated under reduced pressure to give 118 mg (75% yield) of the title compound as white powder.

LCMS (Analytical Method A) Rt=1.05 min, MS (ESIpos) m/z=306 (M+H)$^+$.

Intermediate 27AO: Tert-butyl (3S)-3-[3-cyano-5-(5-methyl-1,3-thiazol-2-yl)phenoxy]piperidine-1-carboxylate

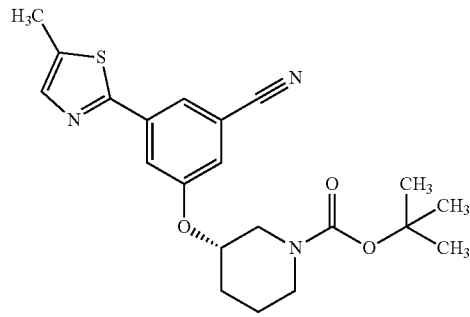 [SMILES: Cc1cnc(-c2cc(C#N)cc(O[C@H]3CCCN(C(=O)OC(C)(C)C)C3)c2)s1]

To a solution of tert-butyl (3S)-3-hydroxypiperidine-1-carboxylate (415 mg, 2.06 mmol) in dry DMF (3 mL) was added NaH (60% dispersion in mineral oil, 88 mg, 2.2 mmol) and the mixture stirred at RT for 1 h before addition of Intermediate 26 (300 mg, 1.38 mmol). The resulting mixture was stirred at RT for 16 h then partitioned between EtOAc and water. The organic phase was separated and the aqueous phase extracted with EtOAc. The combined organics were washed with brine, dried over MgSO$_4$, filtered and concentrated under reduced pressure. The crude material was purified by Biotage Isolera™ chromatography (silica gel, eluting with heptane-EtOAc, 4:1 to 1:4) to afford 510 mg (93% yield) of the title compound.

$^1$H NMR (500 MHz, Chloroform-d): δ [ppm] 7.72-7.68 (m, 1H), 7.68-7.63 (m, 1H), 7.53-7.49 (m, 1H), 7.16-7.12

(m, 1H), 4.36 (tt, J=6.8, 3.3 Hz, 1H), 3.96-3.11 (m, 4H), 2.51 (s, 3H), 2.07-1.96 (m, 1H), 1.91-1.72 (m, 2H), 1.60-1.50 (m, 1H), 1.48-1.26 (m, 9H).

Intermediate 57: 3-{[(3S)-1-methylpiperidin-3-yl]oxy}-5-(5-methyl-1,3-thiazol-2-yl)benzonitrile

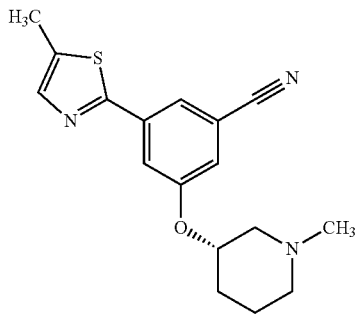

To a solution of Intermediate 27AO (510 mg, 1.28 mmol) in DCM (5 mL) was added TFA (0.5 mL, 6.49 mmol) and the mixture stirred at RT overnight. The mixture was diluted with DCM and poured onto saturated sodium bicarbonate solution. The organic phase was separated, and the aqueous phase extracted with DCM. The combined organics were dried over MgSO$_4$, filtered and concentrated under reduced pressure. The resulting solids were dissolved in DCE (3 mL) then formaldehyde, 37% solution in water (1 mL, 1.08 mmol) and acetic acid (0.1 mL, 1.04 mmol) were added. The solution was stirred at RT for 15 min before the addition of STAB (540 mg, 2.55 mmol) portionwise, which was subsequently stirred for 2 h. The reaction mixture was diluted with DCM and poured onto saturated sodium bicarbonate solution. The organic phase was separated and the aqueous extracted with further DCM. The combined organics were dried over MgSO$_4$, filtered and concentrated under reduced pressure. The crude material was purified by Biotage Isolera™ chromatography (silica gel, eluting with heptane-TBME, 2:3 to 0:1) to give 172 mg (43% yield) of the title compound.

LCMS (Analytical Method A) Rt=0.85 min, MS (ESIpos) m/z=314 (M+H)$^+$.

Intermediate 28AO: 3-{[(3S)-1-methylpiperidin-3-yl]oxy}-5-(5-methyl-1,3-thiazol-2-yl)benzoic acid

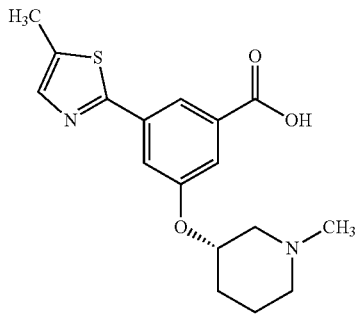

Intermediate 57 (172 mg, 0.55 mmol) and 2M NaOH (5.5 mL, 11.0 mmol) were heated together at 110° C. in a sealed tube for 6 h. On cooling to RT the mixture was acidified to pH 11 and extracted with IPA/CHCl3 (1:4) (3×15 mL). The combined organics were dried over MgSO$_4$ and concentrated under reduced pressure to give 130 mg (71% yield) of the title compound as white powder LCMS (Analytical Method A) Rt=0.80 min, MS (ESIpos) m/z=333 (M+H)$^+$.

Intermediate 27AP: Tert-butyl (3R)-3-[3-cyano-5-(5-methyl-1,3-thiazol-2-yl)phenoxy]piperidine-1-carboxylate

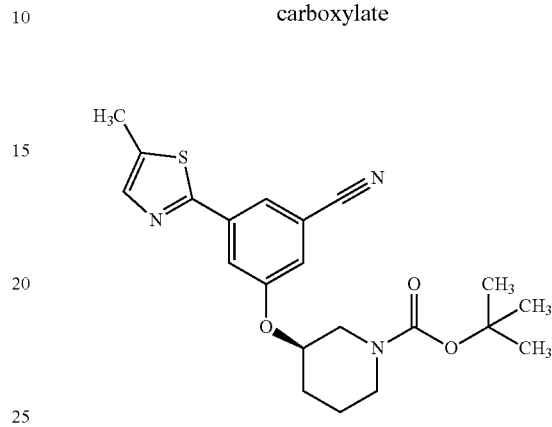

To a solution of tert-butyl (3S)-3-hydroxypiperidine-1-carboxylate (415 mg, 2.06 mmol) in dry DMF (3 mL) was added NaH (60% dispersion in mineral oil, 88 mg, 2.2 mmol) and the mixture stirred at RT for 1 h before addition of Intermediate 26 (300 mg, 1.38 mmol). The resulting mixture was stirred at RT for 16 h then partitioned between EtOAc and water. The organic phase was separated and the aqueous phase extracted with EtOAc. The combined organics were washed with brine, dried over MgSO$_4$, filtered and concentrated under reduced pressure. The crude material was purified by Biotage Isolera™ chromatography (silica gel, eluting with heptane-EtOAc, 4:1 to 1:4) to give 452 mg (82% yield) of the title compound.

$^1$H NMR (500 MHz, Chloroform-d): δ [ppm] 7.72 (t, J=1.3 Hz, 1H), 7.70-7.65 (m, 1H), 7.55-7.50 (m, 1H), 7.18-7.13 (m, 1H), 4.38 (tt, J=6.9, 3.4 Hz, 1H), 4.02-3.09 (m, 4H), 2.53 (d, J=0.9 Hz, 3H), 2.11-1.97 (m, 1H), 1.95-1.71 (m, 2H), 1.61-1.30 (m, 10H).

LCMS (Analytical Method A) Rt=1.38 min, MS (ESIpos) m/z=400 (M+H)$^+$.

Intermediate 58: 3-{[(3R)-1-methylpiperidin-3-yl]oxy}-5-(5-methyl-1,3-thiazol-2-yl)benzonitrile

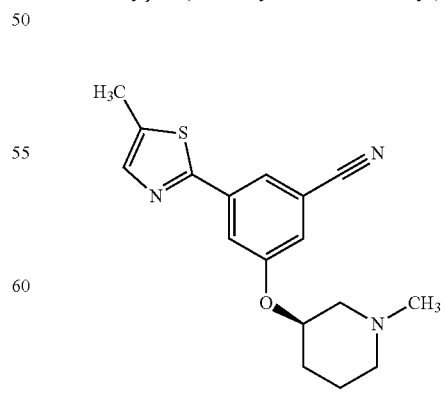

Intermediate 27AP (452 mg, 1.28 mmol) in DCM (5 mL) was added TFA (0.4 mL, 5.19 mmol) and the mixture stirred at RT overnight. The mixture was diluted with DCM and poured onto saturated aqueous sodium bicarbonate solution. The organic phase was separated, and the aqueous phase extracted with DCM. The combined organics were dried over MgSO$_4$, filtered and concentrated under reduced pressure. The resulting solids were dissolved in DCE (3 mL) then formaldehyde, 37% solution in water (0.4 mL, 5.33 mmol) and acetic acid (0.1 mL, 1.04 mmol) was added. The solution was stirred at RT for 15 min before the addition of STAB (480 mg, 2.27 mmol) portionwise, which was subsequently stirred for 2 h. The reaction mixture was diluted with DCM and poured onto saturated aqueous sodium bicarbonate solution. The organic phase was separated and the aqueous extracted with further DCM. The combined organics were dried over MgSO$_4$, filtered and concentrated under reduced pressure. The crude material was purified by Biotage Isolera™ chromatography (silica gel, eluting with heptane-TBME, 2:3 to 0:1) to give 183 mg (52% yield) of the title compound.

LCMS (Analytical Method A) Rt=0.84 min, MS (ESIpos) m/z=314 (M+H)$^+$.

Intermediate 28AP: 3-{[(3R)-1-methylpiperidin-3-yl]oxy}-5-(5-methyl-1,3-thiazol-2-yl)benzoic acid

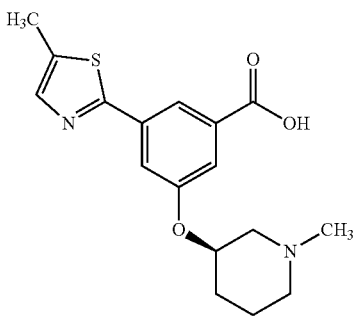

Intermediate 58 (183 mg, 0.58 mmol) and 2 M NaOH (5.8 mL, 11.6 mmol) were heated together at 110° C. in a sealed tube for 6 h. On cooling to RT the mixture was acidified to pH 11 and extracted with IPA/CHCl$_3$ (1:4) (3×15 mL). The combined organics were dried over MgSO$_4$, filtered and concentrated under reduced pressure to give 185 mg (95% yield) of the title compound as white powder.

LCMS (Analytical Method A) Rt=0.81 min, MS (ESIpos) m/z=333 (M+H)$^+$.

Intermediate 27AR: 3-[(3R)-1-Azabicyclo[2.2.2]oct-3-yloxy]-5-(5-methyl-1,3-thiazol-2-yl)benzonitrile

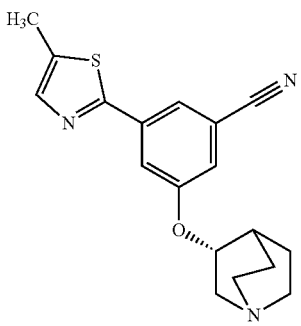 [SMILES: Cc1cnc(-c2cc(C#N)cc(O[C@H]3CN4CCC3CC4)c2)s1]

To a stirred solution of (3R)-1-azabicyclo[2.2.2]octan-3-ol hydrochloride (0.29 g, 1.79 mmol) in dry DMF (5 mL) was added NaH (60% dispersion in mineral oil, 137 mg, 3.44 mmol). After the mixture was stirred for 15 min Intermediate 26 (0.3 g, 1.38 mmol) was added as one portion. The resulting mixture was stirred at RT for 18 h. The reaction mixture was poured onto brine and extracted with EtOAc. The organic layer was washed with brine, separated, dried over MgSO$_4$, filtered and concentrated under reduced pressure. The crude material was purified by Biotage Isolera™ chromatography (silica gel, eluting with heptane-EtOAc, 3:2 to 0:1 followed by EtOAc-MeOH, 1:0 to 4:1) to afford 258.8 mg (51% yield) of the title compound as a yellow gum, which crystallised on standing.

$^1$H NMR (500 MHz, Chloroform-d): δ [ppm] 7.70 (t, J=1.4 Hz, 1H), 7.64 (dd, J=2.4, 1.6 Hz, 1H), 7.54 (d, J=1.2 Hz, 1H), 7.11 (dd, J=2.4, 1.3 Hz, 1H), 4.55-4.44 (m, 1H), 3.42-3.31 (m, 1H), 3.07-2.96 (m, 1H), 2.96-2.79 (m, 4H), 2.54 (d, J=1.1 Hz, 3H), 2.23-2.17 (m, 1H), 2.03-1.95 (m, 1H), 1.80 (ddt, J=14.0, 9.3, 4.3 Hz, 1H), 1.67-1.58 (m, 1H), 1.50-1.40 (m, 1H).

LCMS (Analytical Method A) Rt=0.94 min, MS (ESIpos): m/z=326 (M+H)$^+$.

Intermediate 28AR: 3-[(3R)-1-Azabicyclo[2.2.2]oct-3-yloxy]-5-(5-methyl-1,3-thiazol-2-yl)benzoic acid—formic acid

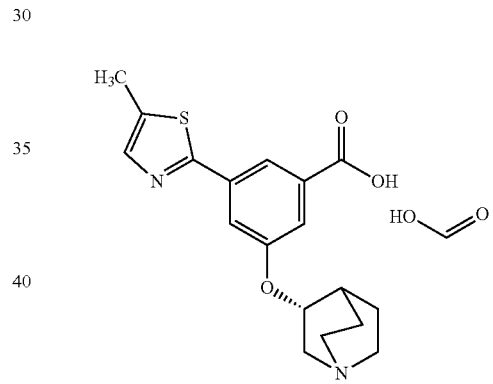

Intermediate 27AR (258 mg, 0.7 mmol) was stirred in 2 M NaOH (3.5 mL) and DMSO (3.5 mL) at 110° C. for 3 h. After cooling to RT the mixture was slowly acidified to pH ~2, before being concentrated under reduced pressure to afford the crude material in DMSO. The crude material was purified by preparative HPLC (Method A). The product containing fractions were concentrated and the residue freeze-dried from MeCN/water to afford 146.4 mg (53% yield) of the title compound as an off-white powder.

$^1$H NMR (250 MHz, DMSO-d6): δ [ppm] 8.21 (s, 1H), 7.96 (s, 1H), 7.64 (d, J=1.2 Hz, 1H), 7.55 (d, J=1.7 Hz, 1H), 7.48 (s, 1H), 4.71 (s, 1H), 3.44 (d, J=13.1 Hz, 1H), 3.04-2.77 (m, 4H), 2.21 (d, J=11.9 Hz, 1H), 1.94 (s, 1H), 1.74 (s, 2H), 1.51 (s, 1H).

LCMS (Analytical Method A) Rt=0.91 min, MS (ESIpos): m/z=345 (M+H)$^+$.

Intermediate 27AS: 3-(1-Azabicyclo[2.2.2]oct-4-yloxy)-5-(5-methyl-1,3-thiazol-2-yl)benzonitrile

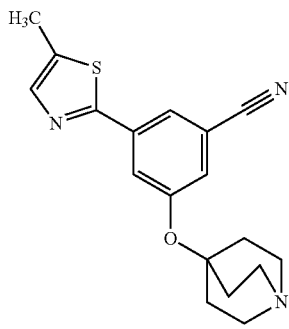 [SMILES: Cc1cnc(-c2cc(C#N)cc(OC34CCN(CC3)CC4)c2)s1]

To a stirred solution of quinuclidin-4-ol (250 mg, 1.97 mmol) in dry DMF (4 mL) was added NaH (60% dispersion in mineral oil, 78 mg, 1.95 mmol). After the mixture was stirred for 15 min Intermediate 26 (286 mg, 1.31 mmol) was added as one portion and the resulting mixture was stirred at RT for 24 h. A further portion of NaH (78 mg, 1.95 mmol) was added along with DBU (1 mL) and finally Intermediate 26 (286 mg, 1.31 mmol). The resulting mixture was stirred at RT for 16 h. The reaction mixture was quenched with saturated sodium bicarbonate solution and extracted into EtOAc. The organic phase was separated, dried over MgSO$_4$, filtered and concentrated under reduced pressure. The crude material was purified by preparative HPLC (Method A). The product containing fractions were concentrated and the residue freeze-dried from MeCN/water to afford 111 mg (26% yield) of the title compound as beige powder.

$^1$H NMR (250 MHz, Chloroform-d): δ [ppm] 7.86 (t, J=1.4 Hz, 1H), 7.72 (t, J=1.9 Hz, 1H), 7.58-7.49 (m, 1H), 7.25-7.21 (m, 1H), 3.11-2.97 (m, 6H), 2.53 (d, 3H), 1.90-1.76 (m, 6H).

LCMS (Analytical Method A) Rt=1.00 min, MS (ESIpos) m/z=326 (M+H)$^+$.

Intermediate 28AS: 3-(1-Azabicyclo[2.2.2]oct-4-yloxy)-5-(5-methyl-1,3-thiazol-2-yl)benzoic acid

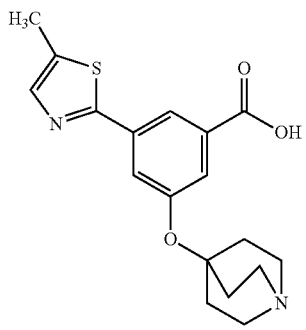 [SMILES: Cc1cnc(-c2cc(OC34CCN(CC3)CC4)cc(C(=O)O)c2)s1]

Intermediate 27AS (111 mg, 0.34 mmol) was suspended in 2 M NaOH (2.5 mL) and heated to 120° C. in a sealed tube for 1 h to give a yellow solution. The mixture was acidified to pH 6 and concentrated under reduced pressure to give 531 mg (>100% yield) of the title compound as pale yellow solid. The crude material was used in the next step without purification.

LCMS (Analytical Method A) Rt=0.90 min, MS (ESIpos) m/z=345 (M+H)$^+$.

Intermediate 65: Tert-butyl-4-hydroxy-2-(trifluoromethyl)piperidine-1-carboxylate, as a mixture of 2 cis isomers

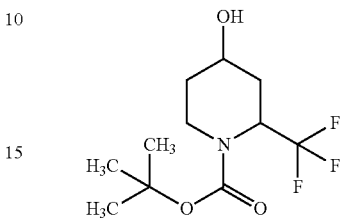

Sodium borohydride (71 mg, 1.87 mmol) was added at −10° C. to a solution of 1-boc-2-trifluoromethyl-piperidin-4-one (250 mg, 0.94 mmol) in MeOH (8 mL) and the reaction stirred at −10° C. for 1 h. Sat. aq. NH$_4$Cl (3 mL) was added, and the resulting mixture allowed to warm to RT. The MeOH was removed under reduced pressure, and the resulting aqueous layer extracted with DCM (4×5 mL). The combined organics were washed with brine, dried over MgSO$_4$, filtered and concentrated under reduced pressure to afford 247.6 mg (98% yield) of the title compound as colourless oil.

$^1$H NMR (250 MHz, Chloroform-d): δ [ppm] 4.84-4.62 (m, 1H), 4.15-3.95 (m, 2H), 3.39-3.18 (m, 1H), 2.10-2.00 (m, 1H), 1.91-1.57 (m, 3H), 1.47 (s, 9H).

Intermediate 27AT: Tert-butyl-4-[3-cyano-5-(5-methyl-1,3-thiazol-2-yl)phenoxy]-2-(trifluoromethyl)piperidine-1-carboxylate, as a mixture of 2 cis isomers

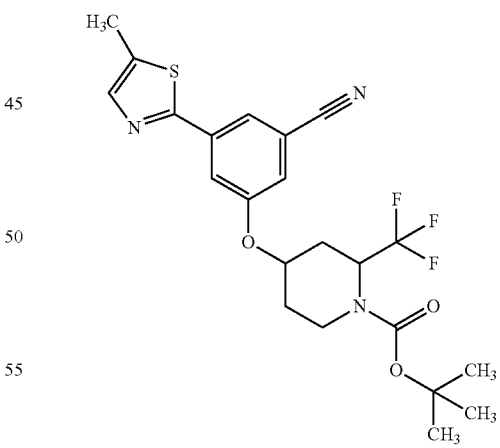

To a stirred solution of Intermediate 65 (125 mg, 0.467 mmol) in dry DMF (2 mL) was added NaH (60% dispersion in mineral oil, 19 mg, 0.49 mmol) to give a white precipitate. After the mixture was stirred for 15 min Intermediate 26 (85 mg, 0.39 mmol) was added as one portion. The resulting mixture was stirred for at RT for 18 h. The reaction mixture was poured onto brine and extracted into EtOAc. The organic layer was washed with brine, separated, dried over MgSO₄, filtered and concentrated under reduced pressure. The crude material was purified by Biotage Isolera™ chromatography (silica gel, eluting with heptane-EtOAc, 100:1 to 3:2) to afford 111.1 mg (61% yield) of the title compound as brown gum.

¹H NMR (500 MHz, Chloroform-d): δ [ppm] 7.71 (t, J=1.3 Hz, 1H), 7.68-7.65 (m, 1H), 7.54 (d, J=1.2 Hz, 1H), 7.14 (dd, J=2.3, 1.3 Hz, 1H), 4.78 (s, 1H), 4.76-4.72 (m, 1H), 4.15-4.06 (m, 1H), 3.36 (s, 1H), 2.54 (d, J=1.1 Hz, 3H), 2.36 (d, J=15.6 Hz, 1H), 2.13-1.97 (m, 3H), 1.90-1.81 (m, 1H), 1.49 (s, 9H).

LCMS (Analytical Method A) Rt=1.48 min, MS (ESIpos): m/z=468 (M+H)⁺.

Intermediate 28AT: 3-{[1-(tert-butoxycarbonyl)-2-(trifluoromethyl)piperidin-4-yl]oxy}-5-(5-methyl-1,3-thiazol-2-yl)benzoic acid, as a mixture of 2 cis isomers

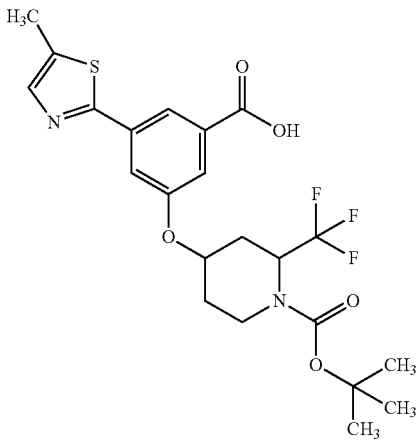 [SMILES: Cc1cnc(-c2cc(OC3CCN(C(=O)OC(C)(C)C)C(C(F)(F)F)C3)cc(C(=O)O)c2)s1]

Intermediate 27AT (111 mg, 0.22 mmol) was stirred in 2 M NaOH (1.5 mL) and DMSO (1.5 mL) at 130° C. for 3 h. After cooling to RT the organics were removed under reduced pressure, then the residue diluted with water (3 mL) and slowly acidified to pH ~4 with 1M HCl then extracted with EtOAc (3×10 mL). The combined organics were dried over MgSO₄, filtered and concentrated under reduced pressure to afford 104.8 mg (83% yield) of the title compound as colourless gum.

¹H NMR (500 MHz, Chloroform-d) d 8.19 (t, J=1.3 Hz, 1H), 7.73-7.68 (m, 1H), 7.62-7.59 (m, 1H), 7.56 (s, 1H), 4.85-4.70 (m, 2H), 4.07 (d, J=19.4 Hz, 1H), 3.38 (s, 1H), 2.53 (d, J=1.0 Hz, 3H), 2.38 (d, J=15.5 Hz, 1H), 2.14-2.07 (m, 2H), 2.06-1.97 (m, 2H), 1.89-1.80 (m, 1H), 1.49 (s, 9H).

LCMS (Analytical Method A) Rt=1.34 min, MS (ESIpos): m/z=487 (M+H)⁺.

Intermediate 27AU: 3-[(3S)-1-azabicyclo[2.2.2]oct-3-yloxy]-5-(5-methyl-1,3-thiazol-2-yl)benzonitrile

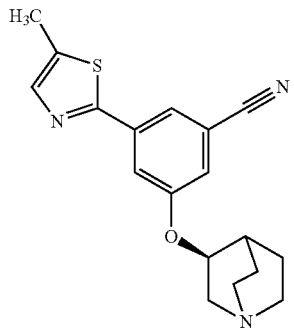 [SMILES: Cc1cnc(-c2cc(C#N)cc(O[C@@H]3CN4CCC3CC4)c2)s1]

(S)-Quinuclidin-3-ol (0.758 g, 5.96 mmol) was dissolved in DMF (15 mL) at RT with stirring. NaH, (60% dispersion in mineral oil, 458 mg, 11.46 mmol) was added and the mixture allowed to stir for 15 min. Intermediate 26 (1.0 g, 4.58 mmol) was added, and the mixture allowed to stir overnight. The reaction was quenched with water before being concentrated under reduced pressure. The crude material was purified by Biotage Isolera™ chromatography (silica gel, eluting with heptane-EtOAc, 1:0 to 0:1) to afford 386 mg (23% yield) of the title compound as an off-white powder.

¹H NMR (500 MHz, DMSO-d6): δ [ppm] 7.82 (t, J=1.3, 1H), 7.67 (d, J=1.2, 1H), 7.66-7.64 (m, 1H), 7.50 (dd, J=2.3, 1.3, 1H), 4.65 (dd, J=7.3, 3.3, 1H), 2.85-2.74 (m, 2H), 2.72-2.60 (m, 4H), 2.52 (d, J=0.9, 3H), 2.08 (q, J=2.9, 1H), 1.81 (dddt, J=12.5, 10.0, 5.1, 2.9, 1H), 1.70-1.52 (m, 2H), 1.35 (dtd, J=11.4, 8.1, 7.6, 2.9, 1H)

LCMS (Analytical Method F) Rt=1.91 min, MS (ESIpos): m/z=326 (M+H)⁺.

Intermediate 28AU: 3-[(3S)-1-azabicyclo[2.2.2]oct-3-yloxy]-5-(5-methyl-1,3-thiazol-2-yl)benzoic acid—chlorosodium (1:3)

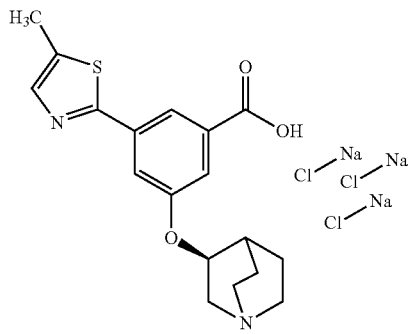

Intermediate 27AU (386 mg, 1.04 mmol, 88%) was dissolved in EtOH (5 mL) in a sealed tube at RT with stirring and 2M NaOH (1.57 mL, 3.13 mmol) was added. The reaction was stirred at 80° C. for 5h, followed by 100° C. for 24 h. The reaction mixture was quenched with 2M HCl (1.57 mL, 3.13 mmol) before being concentrated under reduced pressure to afford 449 mg (83% yield) of the title compound.

¹H NMR (500 MHz, DMSO-d6): δ [ppm] 7.87 (s, 1H), 7.57 (d, J=1.2 Hz, 1H), 7.45-7.42 (m, 1H), 7.33-7.30 (m, 1H), 4.52-4.44 (m, 1H), 3.26-3.18 (m, 1H), 2.84-2.59 (m, 5H), 2.49 (s, 3H), 2.05 (q, J=3.0, 1H), 1.89-1.79 (m, 1H), 1.70-1.60 (m, 1H), 1.55 (dddd, J=12.5, 8.9, 6.3, 2.8, 1H), 1.38-1.26 (m, 1H).

LCMS (Analytical Method A) Rt=0.93 min, MS (ESI-pos): m/z=345 (M+H)+.

Intermediate 27AV: 3-[(3R)-1-Azabicyclo[2.2.2]oct-3-yloxy]-5-(5-ethyl-1,3-thiazol-2-yl)benzonitrile

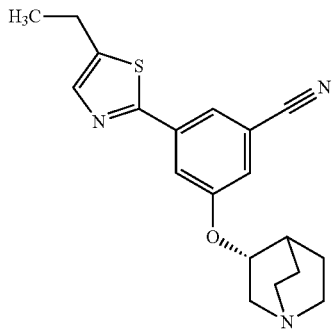 [SMILES: CCc1cnc(-c2cc(C#N)cc(O[C@H]3CN4CCC3CC4)c2)s1]

To a stirred solution of (3R)-1-azabicyclo[2.2.2]octan-3-ol hydrochloride (0.37 g, 2.24 mmol) in dry DMF (5 mL) was added NaH (60% dispersion in mineral oil, 172 mg, 4.3 mmol). After the mixture was stirred for 15 min Intermediate 29 (0.4 g, 1.72 mmol) was added as one portion. The resulting mixture was stirred at RT overnight. The reaction mixture was poured onto brine and extracted into EtOAc. The organic layer was washed with brine, separated, dried over MgSO₄, filtered and concentrated under reduced pressure. The crude material was purified by Biotage Isolera™ chromatography (silica gel, eluting with DCM-MeOH, 1:0 to 4:1) to afford 374.9 mg (64% yield) of the title compound as yellow gum.

¹H NMR (500 MHz, Chloroform-d): δ [ppm] 7.71 (t, J=1.3 Hz, 1H), 7.64 (dd, J=2.3, 1.6 Hz, 1H), 7.56 (s, 1H), 7.11 (dd, J=2.4, 1.3 Hz, 1H), 4.51-4.44 (m, 1H), 3.34 (ddd, J=14.3, 7.9, 2.0 Hz, 1H), 3.04-2.76 (m, 7H), 2.19 (q, J=3.1 Hz, 1H), 2.01-1.93 (m, 1H), 1.79 (ddt, J=14.0, 9.6, 4.3 Hz, 1H), 1.60 (dtd, J=13.4, 6.1, 3.0 Hz, 1H), 1.48-1.40 (m, 1H), 1.37 (t, J=7.5 Hz, 3H).

LCMS (Analytical Method A) Rt=1.03 min, MS (ESI-pos): m/z=340 (M+H)+.

Intermediate 28AV: 3-[(3R)-1-Azabicyclo[2.2.2]oct-3-yloxy]-5-(5-ethyl-1,3-thiazol-2-yl)benzoic acid—chlorosodium (1:3)

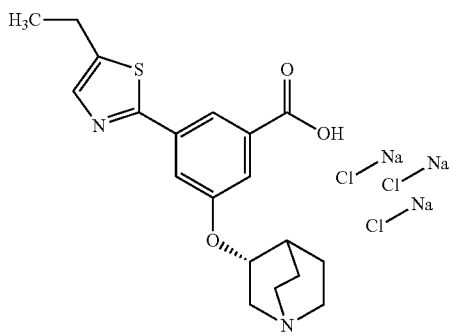

Intermediate 27AV (375 mg, 1.11 mmol) was dissolved in EtOH (5 mL) and 2M NaOH (1.7 mL) was added. The reactions were stirred at 80° C. in a sealed tube for 8 h. The reaction was quenched by addition of HCl (2M, 1.7 mL) and concentrated under reduced pressure to afford 602 mg (quantitative yield) of the title compound.

¹H NMR (250 MHz, DMSO-d6): δ [ppm] 7.97 (t, J=1.4 Hz, 1H), 7.65 (s, 1H), 7.53-7.44 (m, 2H), 4.81-4.69 (m, 1H), 3.56-3.38 (m, 2H), 3.04-2.80 (m, 6H), 2.28-2.15 (m, 1H), 2.13-1.92 (m, 1H), 1.87-1.68 (m, 2H), 1.62-1.42 (m, 1H), 1.28 (t, J=7.5 Hz, 3H).

LCMS (Analytical Method A) Rt=0.94 min, MS (ESI-pos): m/z=359 (M+H)+.

Intermediate 27AW: 3-[(3S)-1-Azabicyclo[2.2.2]oct-3-yloxy]-5-(5-ethyl-1,3-thiazol-2-yl)benzonitrile

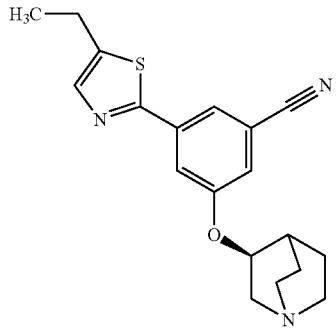 [SMILES: CCc1cnc(-c2cc(C#N)cc(O[C@@H]3CN4CCC3CC4)c2)s1]

To a stirred solution of (3S)-1-azabicyclo[2.2.2]octan-3-ol (0.29 g, 2.24 mmol) in dry DMF (5 mL) was added NaH 60% dispersion in mineral oil (103 mg, 2.6 mmol). After the mixture was stirred for 15 min Intermediate 29 (0.4 g, 1.72 mmol) was added as one portion. The resulting mixture was stirred at RT overnight. The reaction mixture was poured onto brine and extracted into EtOAc. The organic layer was washed with brine, separated, dried over MgSO₄, filtered and concentrated under reduced pressure. The crude material was purified by Biotage Isolera™ chromatography (silica gel, eluting with DCM-MeOH, 1:0 to 4:1) to afford 406 mg (69% yield) of the title compound as yellow gum.

¹H NMR (500 MHz, Chloroform-d): δ [ppm] 7.71 (t, J=1.3 Hz, 1H), 7.66-7.63 (m, 1H), 7.56 (s, 1H), 7.11 (dd, J=2.4, 1.3 Hz, 1H), 4.46 (dd, J=7.3, 3.4 Hz, 1H), 3.33 (ddd, J=14.4, 8.0, 2.0 Hz, 1H), 3.03-2.75 (m, 7H), 2.20-2.14 (m, 1H), 2.00-1.92 (m, 1H), 1.77 (ddt, J=14.1, 9.9, 4.3 Hz, 1H), 1.64-1.55 (m, 1H), 1.46-1.40 (m, 1H), 1.37 (t, J=7.5 Hz, 3H).

LCMS (Analytical Method A) Rt=1.03 min, MS (ESI-pos): m/z=340 (M+H)+.

Intermediate 28AW: 3-[(3S)-1-Azabicyclo[2.2.2]oct-3-yloxy]-5-(5-ethyl-1,3-thiazol-2-yl)benzoic acid—chlorosodium (1:3)

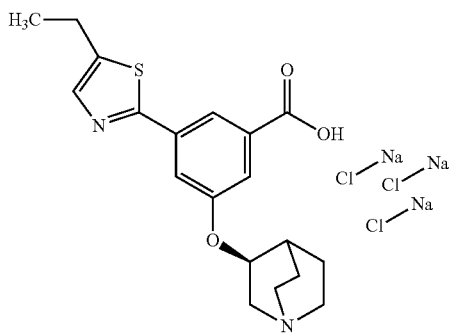

Intermediate 27AW (365 mg, 1.08 mmol) was dissolved in EtOH (5 mL) and 2M NaOH (1.6 mL) was added. The reactions were stirred at 80° C. in a sealed tube for 8 h. The reaction was quenched by addition of HCl (2M, 1.6 mL) and concentrated under reduced pressure to afford 502 mg (86% yield) of the title compound.

$^1$H NMR (250 MHz, DMSO-d6): δ [ppm] 7.97 (t, J=1.3 Hz, 1H), 7.65 (s, 1H), 7.57-7.44 (m, 2H), 4.82-4.67 (m, 1H), 3.49 (dd, J=13.6, 7.8 Hz, 1H), 3.08-2.79 (m, 7H), 2.28-2.17 (m, 1H), 2.08-1.87 (m, 1H), 1.86-1.70 (m, 2H), 1.61-1.43 (m, 1H), 1.28 (t, J=7.5 Hz, 3H).

LCMS (Analytical Method A) Rt=0.95 min, MS (ESI-pos): m/z=359 (M+H)$^+$.

Intermediate 6AX: 2-methyl-2-nitropropyl 4-methylbenzenesulfonate

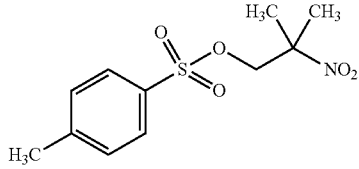 [SMILES: Cc1ccc(S(=O)(=O)OCC(C)(C)[N+](=O)[O-])cc1]

2-Methyl-2-nitropropan-1-ol (0.5 g, 4.2 mmol), triethylamine (0.878 ml, 6.3 mmol) and trimethylamine hydrochloride (40 mg, 0.42 mmol) were stirred in DCM (10 mL), and 4-methylbenzenesulfonyl chloride (1.2 g, 6.3 mmol) was added. The reaction was stirred at RT for 1.5 h. TLC (70% EtOAc in heptane) showed complete reaction, hence the reaction mixture was treated with N,N-dimethylethane-1,2-diamine (0.28 ml, 2.52 mmol) to consume the unreacted TsCl. The reaction mixture was washed with 1 M HCl (10 mL) then water (10 mL) before being dried over MgSO$_4$, filtered and concentrated under reduced pressure to afford 1.16 g (99% yield) of the title compound as a yellow crystalline solid $^1$H NMR (500 MHz, Chloroform-d): δ [ppm] 7.77 (d, J=8.3 Hz, 2H), 7.37 (d, J=8.0 Hz, 2H), 4.28 (s, 2H), 2.47 (s, 3H), 1.60 (s, 6H).

Intermediate 27AZ: Tert-butyl 5-[3-cyano-5-(5-methyl-thiazol-2-yl)phenoxy]-2-azabicyclo[2.2.1]heptane-2-carboxylate

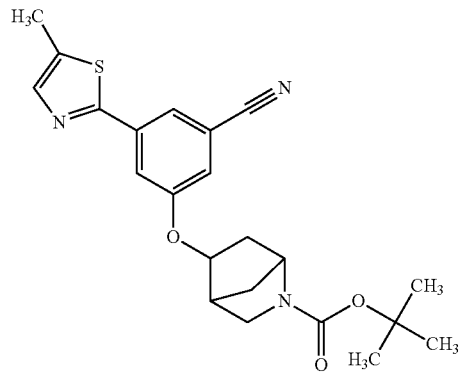 [SMILES: Cc1cnc(-c2cc(C#N)cc(OC3CC4CC3CN4C(=O)OC(C)(C)C)c2)s1]

To a stirred solution of tert-butyl 5-hydroxy-2-azabicyclo[2.2.1]heptane-2-carboxylate (254 mg, 1.19 mmol) in dry DMF (4 mL) was added NaH (60%, 55 mg, 1.37 mmol). After the mixture was stirred for 90 mins, Intermediate 26 (200 mg, 0.92 mmol) was added to the reaction in one portion. The resulting mixture was stirred overnight at RT. The reaction was stopped and poured onto brine and extracted using ethyl acetate. The organic layer was washed with brine, separated, dried over MgSO$_4$, filtered and concentrated under reduced pressure. The crude material was purified by Biotage Isolera™ chromatography (basic silica gel, eluting with heptane-EtOAc, 6:2 to 0:1 followed by EtOAc-MeOH, 1:0 to 4:1) to afford 388 mg (86% yield) of the title compound as a yellow gum.

$^1$H NMR (500 MHz, Chloroform-d): δ [ppm] 7.71 (s, 1H), 7.63 (s, 1H), 7.54 (d, J=1.1 Hz, 1H), 7.10 (s, 1H), 4.50 (d, J=6.1 Hz, 1H), 3.37-3.30 (m, 1H), 3.07-2.98 (m, 1H), 2.54 (d, J=1.1 Hz, 3H), 1.87 (d, J=10.0 Hz, 1H), 1.72-1.59 (m, 5H), 1.47 (s, 9H).

LCMS (Analytical Method A) Rt=1.47 min, MS (ESI-pos): m/z=356 (M+H)$^+$.

Intermediate 28AZ: 3-[(2-tert-butoxycarbonyl-2-azabicyclo[2.2.1]heptan-5-yl)oxy]-5-(5-methylthiazol-2-yl)benzoic acid

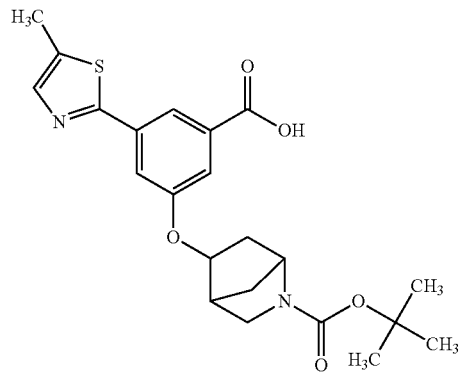 [SMILES: Cc1cnc(-c2cc(OC3CC4CC3CN4C(=O)OC(C)(C)C)cc(C(=O)O)c2)s1]

A stirred solution of Intermediate 27AZ (388 mg, 0.94 mmol) in 2M NaOH (4.71 mL) and DMSO (4.5 mL) was heated to 110° C. for 3 hours. After cooling to RT the mixture was slowly acidified to pH ~2, before being dried using the genevac to afford the crude material in residual DMSO. Crude material was taken up in minimal MeOH and the salt was removed by filtration. MeOH was removed and the material was purified by preparative HPLC (Method B) to afford 49 mg (12% yield) of the title compound as a colourless gum.

¹H NMR (500 MHz, Chloroform-d): δ [ppm] 8.24 (t, J=1.4 Hz, 1H), 7.65-7.58 (m, 3H), 4.63-4.54 (m, 1H), 4.30 (d, J=62.5 Hz, 1H), 3.36-3.30 (m, 1H), 3.08 (dd, J=54.7, 10.4 Hz, 1H), 2.82-2.78 (m, 1H), 2.54 (d, J=1.1 Hz, 3H), 2.42-2.30 (m, 1H), 1.92 (d, J=9.9 Hz, 1H), 1.74-1.66 (m, 2H), 1.48 (s, 9H).

LCMS (Analytical Method A) Rt=1.36 min, MS (ESI-pos): m/z=431 (M+H)⁺.

Intermediate 27BA: 3-(5-methylthiazol-2-yl)-5-[2-(1,2,4-triazol-1-yl)ethoxy]benzonitrile

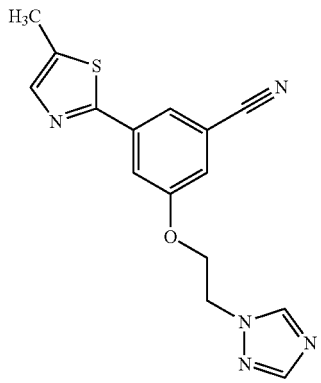 [SMILES: Cc1cnc(-c2cc(C#N)cc(OCCn3cncn3)c2)s1]

A solution of 2-(1H-1,2,4-triazol-1-yl)ethanol (465 mg, 4.11 mmol) and dry DMF (3 mL) was prepared. NaH (60% in mineral oil, 205 mg, 5.14 mmol) was added, and the solution was stirred for 90 mins, after which Intermediate 26 (747 mg, 3.42 mmol) was added. The resulting mixture was stirred over night at RT. Brine was then added to the reaction, and the reaction solution was extracted with ethyl acetate. The solution was washed with water and the organic layer was separated and dried over Na₂SO₄, filtered and concentrated under reduced pressure. Biotage Isolera™ chromatography (silica gel, eluting with DCM-MeOH, 1:0 to 4:1) gave 604 mg (48% yield) of the title compound as a waxy solid.

¹H NMR (500 MHz, Chloroform-d): δ [ppm] 8.22 (s, 1H), 7.97 (s, 1H), 7.73 (s, 1H), 7.65 (s, 1H), 7.56-7.50 (m, 1H), 7.15-7.06 (m, 1H), 4.61 (t, J=5.0 Hz, 2H), 4.44 (t, J=5.0 Hz, 2H), 2.53 (s, 3H).

LCMS (Analytical Method A) Rt=1.09 min, MS (ESI-pos): m/z=333.95 (M+H)⁺.

Intermediate 28BA: 3-(5-methylthiazol-2-yl)-5-[2-(1,2,4-triazol-1-yl)ethoxy]benzoic acid—chlorosodium (1:3)

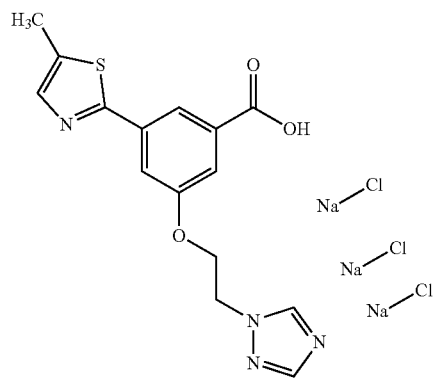

Intermediate 27BA (604 mg, 1.94 mmol) was dissolved in EtOH (4 mL) and 2M NaOH (2.91 mL) was added. The reaction was stirred in the microwave at 130° C. for 1 h. On completion, the reaction was quenched with 2M HCl (2.91 mL) and concentrated under reduced pressure to afford 572 mg (58% yield) of the title compound.

¹H NMR (500 MHz, DMSO-d6): δ [ppm] 8.60 (s, 1H), 8.41 (s, 2H), 7.98 (s, 1H), 7.92 (s, 1H), 7.44 (s, 1H), 4.60 (t, J=5.0 Hz, 2H), 4.41 (t, J=5.0 Hz, 2H). LCMS (Analytical Method A) Rt=1.00 min, MS (ESIpos): m/z=333 (M+H)⁺.

Intermediate 27BC: tert-butyl (4aS,7R,7aR)-7-[3-cyano-5-(5-methyl-1,3-thiazol-2-yl)phenoxy]-octahydrocyclopenta[b]morpholine-4-carboxylate

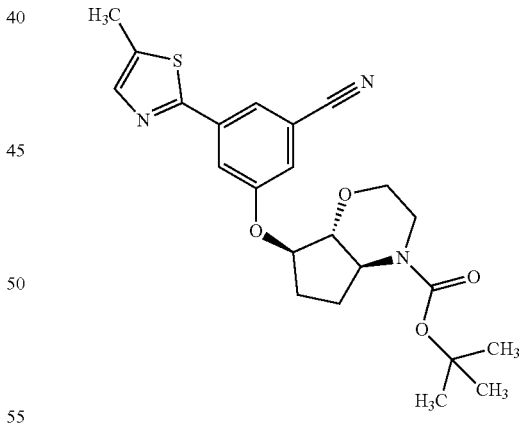

To a stirred solution of tert-butyl (4aS,7R,7aR)-7-hydroxy-octahydrocyclopenta[b]morpholine-4-carboxylate (215 mg, 0.88 mmol) in dry DMF (3 mL) in a three-necked heat-gun-dried flask under nitrogen, was added NaH 60% dispersion in mineral oil (37 mg, 0.92 mmol) and the mixture was stirred for 15 minutes before Intermediate 26 (161 mg, 0.74 mmol) was added as one portion. The resulting mixture was stirred at ambient temperature for 20 h. The reaction mixture was poured onto water and extracted with EtOAc (×2). The combined organic extracts were dried over MgSO₄, filtered and concentrated under reduced pressure. The crude material was purified by Biotage Isolera™ chromatography (silica gel, eluting with heptane/EtOAc, 1:0 to 3:2) to afford 262 mg (68% yield) of the title compound as brown oil.

$^1$H NMR (500 MHz, Chloroform-d): δ [ppm] 7.74 (t, J=1.3 Hz, 1H), 7.70-7.66 (m, 1H), 7.53 (d, J=1.1 Hz, 1H), 7.19 (dd, J=2.3, 1.3 Hz, 1H), 4.62 (ddd, J=9.3, 7.9, 4.6 Hz, 1H), 4.03 (ddd, J=11.6, 3.5, 1.5 Hz, 1H), 3.89 (d, J=13.1 Hz, 1H), 3.69 (td, J=11.8, 2.9 Hz, 1H), 3.58 (dd, J=10.2, 7.8 Hz, 1H), 3.07-2.78 (m, 2H), 2.58-2.54 (m, 1H), 2.53 (d, J=1.0 Hz, 3H), 2.32 (dq, J=14.3, 9.3 Hz, 1H), 2.16-1.94 (m, 1H), 1.79 (ddd, J=14.3, 10.6, 4.4 Hz, 1H), 1.47 (s, 9H).

LCMS (Analytical Method A) Rt=1.43 min, MS (ESI-pos): m/z=442.0 (M+H)$^+$.

Intermediate 28BC: 3-{[(447R,7aR)-4-[(tert-butoxy)carbonyl]-octahydrocyclopenta[b]morpholin-7-yl]oxy}-5-(5-methyl-1,3-thiazol-2-yl)benzoic acid

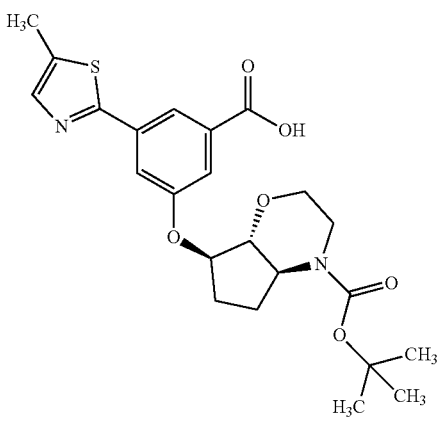 [SMILES: Cc1cnc(-c2cc(O[C@@H]3CC[C@H]4[C@H]3OCCN4C(=O)OC(C)(C)C)cc(C(=O)O)c2)s1]

Intermediate 27BC (258 mg, 2.01 mmol) was stirred in 2 M NaOH (2.8 mL) and DMSO (2.8 mL) at 110° C. for 3 h. The mixture was slowly acidified to pH ~4 with 2 M HCl, at which point off-pink precipitate formed. This was filtered and dried under vacuum filtration to afford 155 mg (58% yield) of the title compound as a pale pink solid.

$^1$H NMR (500 MHz, Chloroform-d): δ [ppm] 8.31 (s, 1H), 7.69-7.67 (m, 1H), 7.67-7.63 (m, 1H), 7.58 (d, J=0.9 Hz, 1H), 4.68 (td, J=9.0, 4.6 Hz, 1H), 4.09-3.99 (m, 1H), 3.90 (d, J=13.3 Hz, 1H), 3.72 (td, J=11.7, 2.8 Hz, 1H), 3.63 (dd, J=10.1, 7.9 Hz, 1H), 3.05-2.89 (m, 2H), 2.53 (s, 3H), 2.52-2.49 (m, 1H), 2.36 (dq, J=14.2, 9.1 Hz, 1H), 2.07 (dt, J=22.4, 10.3 Hz, 1H), 1.84-1.74 (m, 1H), 1.47 (s, 9H).

LCMS (Analytical Method A) Rt=1.28 min, MS (ESI-pos): m/z=461.1 (M+H)$^+$.

Intermediate 27BD: tert-butyl (4aS,7S,7aR)-7-[3-cyano-5-(5-methyl-1,3-thiazol-2-yl)phenoxy]-octahydrocyclopenta[b]morpholine-4-carboxylate

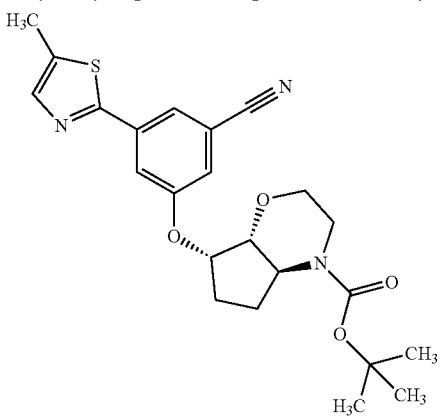

To a stirred solution of tert-butyl (4aS,7S,7aR)-7-hydroxy-octahydrocyclopenta[b]morpholine-4-carboxylate (215 mg, 0.88 mmol) in dry DMF (3 mL) in a three-necked heat-gun-dried flask under nitrogen, was added NaH 60% dispersion in mineral oil (37 mg, 0.92 mmol) and the mixture was stirred for 15 minutes before Intermediate 26 (161 mg, 0.74 mmol) was added as one portion. The resulting mixture was stirred at ambient temperature for 3.5 h. The reaction mixture was poured onto water and extracted with ethyl acetate twice. The combined organic extracts were dried over MgSO$_4$, filtered, concentrated under reduced pressure and purified by Biotage Isolera™ chromatography (silica gel, eluting with heptane-EtOAc, 1:0 to 3:2) to afford 338 mg (85% yield) of the title compound as pale pink solid.

$^1$H NMR (500 MHz, Chloroform-d): δ [ppm] 7.73 (d, J=1.2 Hz, 1H), 7.69-7.64 (m, 1H), 7.52 (d, J=1.1 Hz, 1H), 7.19 (dd, J=2.3, 1.3 Hz, 1H), 4.84-4.71 (m, 1H), 4.05 (ddd, J=11.6, 3.4, 1.6 Hz, 1H), 3.86 (d, J=13.5 Hz, 1H), 3.69 (td, J=11.7, 2.8 Hz, 1H), 3.46 (td, J=10.5, 6.8 Hz, 1H), 3.33 (dd, J=10.5, 4.6 Hz, 1H), 3.00 (ddd, J=13.6, 11.9, 3.6 Hz, 1H), 2.61-2.54 (m, 1H), 2.53 (d, J=0.9 Hz, 3H), 2.32-2.20 (m, 1H), 1.88-1.72 (m, 2H), 1.47 (s, 9H).

LCMS (Analytical Method A) Rt=1.40 min, MS (ESI-pos): m/z=442.0 (M+H)$^+$.

Intermediate 28BD: 3-{[(4a5,7S,7aR)-4-[(tert-butoxy)carbonyl]-octahydrocyclopenta[b]morpholin-7-yl]oxy}-5-(5-methyl-1,3-thiazol-2-yl)benzoic acid

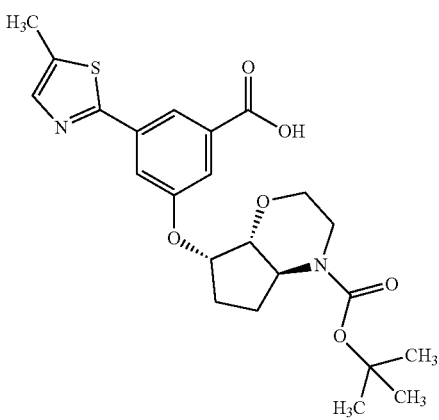 [SMILES: Cc1cnc(-c2cc(O[C@H]3CC[C@H]4[C@H]3OCCN4C(=O)OC(C)(C)C)cc(C(=O)O)c2)s1]

Intermediate 27BD (333 mg, 0.62 mmol) was dissolved in EtOH (3 mL) and 2M NaOH (1.2 mL) was added. The reaction was stirred at 80° C. for 24 h. The reaction was stopped, cooled to ambient temperature and ethanol was removed under reduced pressure. The resulting mixture was acidified to ~pH 4 by addition of 2M HCl, at which point a white precipitate formed. This was collected by filtration, washed with water and dried in vacuum oven to afford 244 mg (77% yield) of the title compound as an off-white solid.

$^1$H NMR (500 MHz, Chloroform-d): δ [ppm] 8.24 (s, 1H), 7.84 (s, 1H), 7.74 (s, 1H), 7.63 (s, 1H), 4.93 (t, J=5.4 Hz, 1H), 4.20-4.08 (m, 1H), 3.88 (d, J=13.4 Hz, 1H), 3.78-3.68 (m, 1H), 3.52 (td, J=10.5, 6.8 Hz, 1H), 3.38 (dd, J=10.6, 4.8 Hz, 1H), 3.05 (td, J=13.6, 3.6 Hz, 1H), 2.55 (s, 3H), 2.54-2.47 (m, 1H), 2.37 (dd, J=20.9, 10.1 Hz, 1H), 1.90-1.70 (m, 2H), 1.47 (s, 9H).

LCMS (Analytical Method A) Rt=1.26 min, MS (ESI-pos): m/z=461.1 (M+H)$^+$.

Intermediate 83: (2S)-2-[(benzyloxy)methyl]-1,4-dioxane

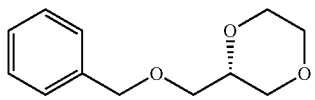 [SMILES: c1ccc(COC[C@H]2COCCO2)cc1]

To a solution of (2R)-3-(benzyloxy)propane-1,2-diol (2 g, 11 mmol) and tetra-n-butylammonium bromide (0.71 g, 2.2 mmol) in dichloroethane (52 mL) was added sodium hydroxide (26.3 g, 0.66 mot) as a solution in water (25 mL). The reaction mixture was then stirred at 50° C. for 16 h. Further dichloroethane (52 mL) and sodium hydroxide (26.3 g, 0.66 mot) as a solution in water (25 mL) was added and the reaction mixture stirred at 50° C. for a further 48 h. The reaction mixture was filtered under vacuum, washing with ethyl acetate. The filtrate was diluted with water and the layers separated. The organic layer was further washed with brine, dried over Na$_2$SO$_4$, filtered and concentrated under reduced pressure. The crude residue was purified by Biotage Isolera™ chromatography (silica gel, eluting with heptane-EtOAc, 1:0 to 1:1) to afford 1.25 g (54% yield) of the title compound as colourless oil.

$^1$H NMR (250 MHz, Chloroform-d): δ [ppm] 7.40-7.27 (m, 5H), 4.55 (s, 2H), 3.86-3.57 (m, 6H), 3.52-3.37 (m, 3H).

Intermediate 84: (2S)-1,4-dioxan-2-ylmethanol

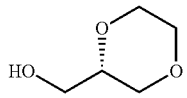

To a solution of Intermediate 83 (1.25 g, 4.74 mmol) in ethanol (20 mL) was added palladium, 10% on carbon (192 mg) and the reaction mixture stirred under an atmosphere of hydrogen for 18 h. The reaction mixture was filtered through a plug of Celite®, washing with EtOAc, and concentrated under reduced pressure to afford 630 mg (89% yield) of the title compound as pale yellow oil.

$^1$H NMR (500 MHz, Chloroform-d): δ [ppm] 3.85-3.67 (m, 5H), 3.66-3.57 (m, 2H), 3.55 (dd, J=11.7, 5.9 Hz, 1H), 3.46 (dd, J=11.1, 10.0 Hz, 1H), 1.75 (s, 1H).

Intermediate 27BE: 3-[(2R)-1,4-dioxan-2-yl-methoxy]-5-(5-methyl-1,3-thiazol-2-yl)benzonitrile

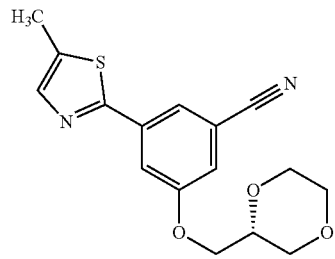 [SMILES: Cc1cnc(-c2cc(C#N)cc(OC[C@H]3COCCO3)c2)s1]

To a stirred solution of Intermediate 84 (250 mg, 1.76 mmol) in dry DMF (7 mL) was added NaH 60% dispersion in mineral oil (88 mg, 2.20 mmol). After the mixture was stirred for 15 min, Intermediate 26 (385 mg, 1.76 mmol) was added as one portion. The resulting mixture was stirred at ambient temperature for 1.5 h. The reaction mixture was then poured onto brine and extracted into EtOAc. The organic layer was washed with brine, dried over MgSO$_4$, filtered and concentrated under reduced pressure. The crude material was purified by Biotage Isolera™ chromatography (silica gel, eluting with heptane-EtOAc, 1:0 to 20:9) to afford 460 mg (82% yield) of the title compound as an off-white solid.

$^1$H NMR (500 MHz, Chloroform-d): δ [ppm] 7.75 (s, 1H), 7.71-7.67 (m, 1H), 7.55-7.49 (m, 1H), 7.18 (dd, J=2.3, 1.2 Hz, 1H), 4.11-4.05 (m, 1H), 4.05-3.98 (m, 2H), 3.93-3.85 (m, 2H), 3.82 (td, J=11.7, 11.1, 2.6 Hz, 1H), 3.78-3.72 (m, 1H), 3.68 (td, J=11.5, 3.2 Hz, 1H), 3.56 (dd, J=11.4, 9.3 Hz, 1H), 2.54 (s, 3H)

LCMS (Analytical Method A) Rt=1.17 min, MS (ESI-pos): m/z=317.0 (M+H)$^+$.

Intermediate 28BE: 3-[(2R)-1,4-dioxan-2-yl-methoxy]-5-(5-methyl-1,3-thiazol-2-yl)benzoic acid

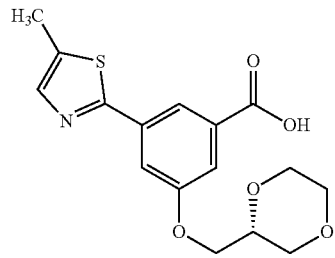 [SMILES: Cc1cnc(-c2cc(OC[C@H]3COCCO3)cc(C(=O)O)c2)s1]

Intermediate 27BE (455 mg, 1.44 mmol) was dissolved in EtOH (7 mL) and 2M NaOH (2.9 mL) was added. The reaction was stirred in a microwave at 130° C. for 1 h. The reaction was stopped, cooled to ambient temperature and ethanol was removed under reduced pressure. The resulting mixture was acidified to ~pH 4 by addition of 2M HCl, at which point a white precipitate formed. This was collected by filtration, washed with water and dried in vacuum oven overnight to afford 480 mg (99% yield) of the title compound as an off-white solid.

$^1$H NMR (500 MHz, Chloroform-d) δ 8.33 (s, 1H), 7.69 (s, 1H), 7.67 (s, 1H), 7.59 (s, 1H), 4.17-4.10 (m, 1H), 4.09-4.00 (m, 2H), 3.97-3.86 (m, 2H), 3.83 (td, J=11.7, 11.2, 2.5 Hz, 1H), 3.77 (d, J=11.0 Hz, 1H), 3.69 (td, J=11.3, 3.0 Hz, 1H), 3.59 (t, J=10.7 Hz, 1H), 2.54 (s, 3H).

LCMS (Analytical Method A) Rt=1.05 min, MS (ESI-pos): m/z=336.0 (M+H)+.

Intermediate 85:
(2R)-2-[(benzyloxy)methyl]-1,4-dioxane

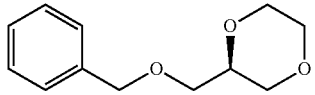 [SMILES: c1ccc(COC[C@@H]2COCCO2)cc1]

To a solution of (2S)-3-(benzyloxy)propane-1,2-diol (0.8 g, 4.4 mmol) and tetra-n-butylammonium bromide (283 mg, 0.88 mmol) in dichloroethane (21 mL) was added sodium hydroxide (10.5 g, 0.26 mot) as a solution in water (10 mL). The reaction mixture was then stirred at 50° C. for 16 h. Further dichloroethane (21 mL) and sodium hydroxide (10.5 g, 0.26 mot) as a solution in water (10 mL) was added and the reaction mixture stirred at 50° C. for a further 48 h. The reaction mixture was filtered under vacuum, washing with ethyl acetate. The filtrate was diluted with water and the layers separated. The organic layer was further washed with brine, dried over Na₂SO₄, filtered and concentrated under reduced pressure. The crude residue was purified by Biotage Isolera™ chromatography (silica gel, eluting with heptane-EtOAc, 1:1 to 1:1) to afford 560 mg (60% yield) of the title compound as colourless oil.

¹H NMR (250 MHz, Chloroform-d): δ [ppm] 7.40-7.27 (m, 5H), 4.55 (s, 2H), 3.86-3.60 (m, 6H), 3.52-3.38 (m, 3H).

Intermediate 86: (2R)-1,4-Dioxan-2-ylmethanol

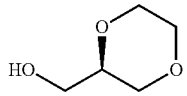

To a solution of Intermediate 85 (560 mg, 2.47 mmol) in ethanol (10 mL) was added palladium, 10% on carbon (100 mg) and the reaction mixture was stirred under an atmosphere of hydrogen for 18 h. The solution was filtered through a plug of Celite®, washing with EtOAc, and concentrated under reduced pressure to afford 260 mg (89% yield) of the title compound as pale yellow oil.

¹H NMR (500 MHz, Chloroform-d): δ [ppm] 3.87-3.66 (m, 5H), 3.65-3.58 (m, 2H), 3.54 (dd, J=11.7, 5.9 Hz, 1H), 3.46 (t, J=10.6 Hz, 1H), 1.95 (s, 1H).

Intermediate 27BF: 3-[(2S)-1,4-dioxan-2-yl-methoxy]-5-(5-methyl-1,3-thiazol-2-yl)benzonitrile

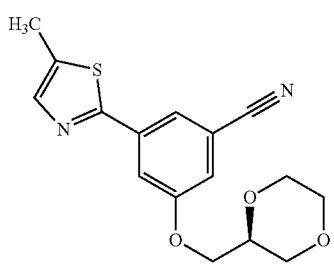 [SMILES: Cc1cnc(-c2cc(C#N)cc(OC[C@@H]3COCCO3)c2)s1]

To a stirred solution of Intermediate 86 (250 mg, 2.12 mmol) in dry DMF (7 mL) was added NaH 60% dispersion in mineral oil (88 mg, 2.20 mmol). After the mixture was stirred for 15 min, Intermediate 26 (385 mg, 1.76 mmol) was added as one portion. The resulting mixture was stirred at ambient temperature for 2.5 h. The reaction mixture was then poured onto brine and extracted into ethyl acetate. The organic layer was washed with brine, separated, dried over MgSO₄, filtered and concentrated under reduced pressure. The crude material was purified by Biotage Isolera™ chromatography (silica gel, eluting with heptane-EtOAc, 1:0 to 20:9) to afford 400 mg (72% yield) of the title compound as pale yellow solid.

¹H NMR (500 MHz, Chloroform-d): δ [ppm] 7.75 (s, 1H), 7.69 (s, 1H), 7.54 (s, 1H), 7.18 (s, 1H), 4.11-4.05 (m, 1H), 4.05-3.98 (m, 2H), 3.92-3.86 (m, 2H), 3.82 (td, J=11.7, 11.2, 2.6 Hz, 1H), 3.76 (d, J=12.1 Hz, 1H), 3.68 (td, J=11.3, 3.2 Hz, 1H), 3.56 (dd, J=11.4, 9.3 Hz, 1H), 2.54 (s, 3H).

LCMS (Analytical Method A) Rt=1.17 min, MS (ESI-pos): m/z=317.0 (M+H)+.

Intermediate 28BF: 3-[(2S)-1,4-dioxan-2-yl-methoxy]-5-(5-methyl-1,3-thiazol-2-yl)benzoic acid

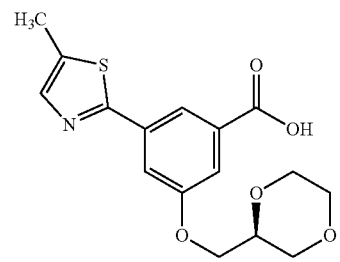 [SMILES: Cc1cnc(-c2cc(OC[C@@H]3COCCO3)cc(C(=O)O)c2)s1]

Intermediate 27BF (395 mg, 1.25 mmol) was dissolved in ethanol (6 mL) and 2M NaOH (2.5 mL) was added. The reaction was stirred in a microwave at 130° C. for 2 h. The reaction was stopped, cooled to ambient temperature and ethanol was removed under reduced pressure. The resulting mixture was acidified to ~pH 4 by addition of 2M HCl, at which point a white precipitate formed. This was collected by filtration, washed with water and dried in vacuum oven overnight to afford 380 mg (89% yield) of the title compound as an off-white solid.

¹H NMR (500 MHz, DMSO-d6): δ [ppm] 13.32 (s, 1H), 7.98 (s, 1H), 7.65 (s, 1H), 7.61 (s, 1H), 7.49 (s, 1H), 4.15-4.04 (m, 2H), 3.93-3.86 (m, 1H), 3.84 (d, J=11.4 Hz, 1H), 3.80-3.74 (m, 1H), 3.71-3.59 (m, 2H), 3.55-3.47 (m, 1H), 3.47-3.40 (m, 1H)

LCMS (Analytical Method A) Rt=1.05 min, MS (ESI-pos): m/z=336.0 (M+H)+.

Intermediate 34: tert-butyl 3-[3-(5-methyl-1,3-thiazol-2-yl)-5-({(1R)-1-[6-(trifluoromethyl)pyridazin-3-yl]ethyl}carbamoyl)phenoxy]azetidine-1-carboxylate

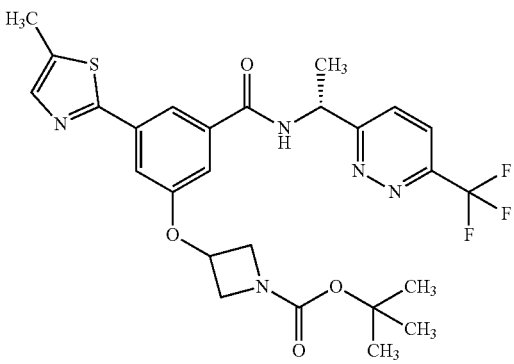 [SMILES: Cc1cnc(-c2cc(OC3CN(C(=O)OC(C)(C)C)C3)cc(C(=O)N[C@H](C)c3ccc(C(F)(F)F)nn3)c2)s1]

To a solution of Intermediate 5AD (185 mg, 0.47 mmol), Intermediate XVIII (130 mg, 0.57 mmol) and DIPEA (248 µL, 1.42 mmol) in DCM (1 mL) was added HATU (270 mg, 0.71 mmol) and the resulting mixture stirred at RT for 2 h. DCM (1 mL) was added and the crude reaction product washed with water (1 mL). The organic phase was separated, dried over MgSO$_4$, filtered and concentrated under reduced pressure. The crude material was purified by Biotage Isolera™ chromatography (silica gel, eluting with heptane-EtOAc, 9:1 to 1:9) to give 248 mg (63% yield) of the title compound as yellow oil.

$^1$H NMR (250 MHz, Chloroform-d): δ [ppm] 7.91 (t, J=1.4 Hz, 1H), 7.81 (s, 1H), 7.76 (s, 1H), 7.57 (d, J=7.3 Hz, 1H), 7.51 (d, J=1.2 Hz, 1H), 7.42 (dd, J=2.4, 1.4 Hz, 1H), 5.59 (m, 1H), 5.07-4.92 (m, 1H), 4.35 (dd, J=9.7, 6.4 Hz, 2H), 4.01 (dd, J=9.5, 3.7 Hz, 2H), 2.52 (d, J=1.1 Hz, 3H), 1.75 (d, J=7.0 Hz, 3H), 1.44 (s, 9H).

LCMS (Analytical Method A) Rt=1.49 min, MS (ESIpos): m/z=508.1 (M+H)$^+$.

In analogy to the procedure described for Intermediate 34, the following Intermediates were prepared using HATU and the appropriate carboxylic acid and amine starting materials.

| Int. | Structure | Name | Analytical Data |
|---|---|---|---|
| 35 | 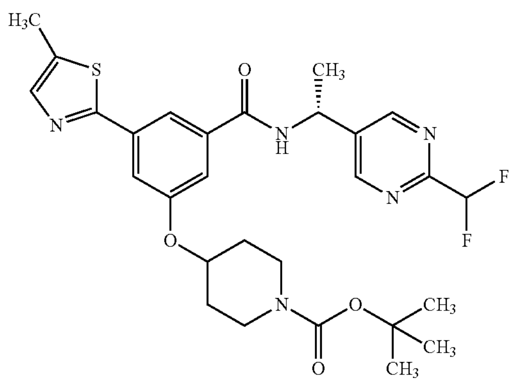 [SMILES: Cc1cnc(-c2cc(OC3CCN(C(=O)OC(C)(C)C)CC3)cc(C(=O)N[C@H](C)c3cnc(C(F)F)nc3)c2)s1] | Tert-butyl 4-[3-({(1R)-1-[2-(difluoromethyl)pyrimidin-5-yl]ethyl}carbamoyl)-5-(5-methyl-1,3-thiazol-2-yl)phenoxy]piperidine-1-carboxylate | $^1$H NMR (500 MHz, Chloroform-d): δ [ppm] 8.90 (s, 2H), 7.82 (s, 1H), 7.55-7.50 (m, 2H), 7.42-7.38 (m, 1H), 6.79-6.52 (m, 2H), 5.35 (m, 1H), 4.61 (tt, J = 7.3, 3.5 Hz, 1H), 3.75-3.66 (m, 2H), 3.39-3.30 (m, 2H), 2.53 (d, J = 1.0 Hz, 3H), 1.98-1.91 (m, 2H), 1.80-1.68 (m, 5H), 1.47 (s, 9H). LCMS (Analytical Method A) Rt = 1.30 min, m/z = 518 (M − tBu)$^+$. |
| 55 | 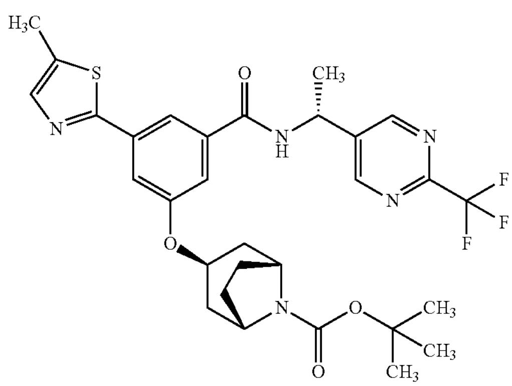 [SMILES: Cc1cnc(-c2cc(O[C@H]3C[C@H]4CC[C@@H](C3)N4C(=O)OC(C)(C)C)cc(C(=O)N[C@H](C)c3cnc(C(F)(F)F)nc3)c2)s1] | tert-butyl (3-endo)-3-[3-(5-methyl-1,3-thiazol-2-yl)-5-({(1R)-1-[2-(trifluoromethyl)pyrimidin-5-yl]ethyl}carbamoyl)phenoxy]-8-azabicyclo[3.2.1]octane-8-carboxylate | $^1$HNMR (250 MHz, Chloroform-d): δ [ppm] 8.93 (s, 2H), 7.82-7.74 (m, 1H), 7.56-7.49 (m, 1H), 7.44 (s, 1H), 7.31 (d, J = 1.5 Hz, 1H), 6.70 (d, J = 6.5 Hz, 1H), 5.36 (s, 1H), 4.77-4.69 (m, 1H), 4.31-4.09 (m, 2H), 2.57-2.49 (m, 3H), 2.35-1.88 (m, 8H + 1H impurity), 1.72 (d, J = 7.1 Hz, 3H), 1.47 (s, 9H). LCMS (Analytical Method A) Rt = 1.45 min, MS (ESIpos) m/z = 618 (M + H)$^+$. |

| Int. | Structure | Name | Analytical Data |
|---|---|---|---|
| 64 | 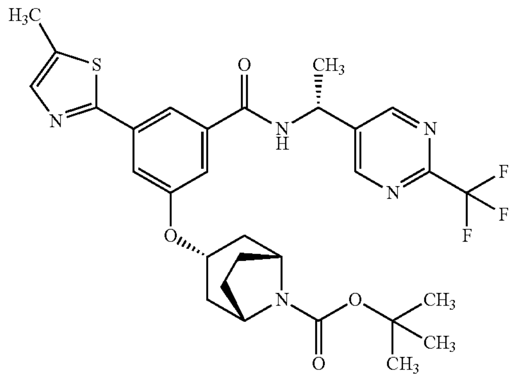 [SMILES: Cc1cnc(-c2cc(O[C@@H]3C[C@H]4CC[C@@H](C3)N4C(=O)OC(C)(C)C)cc(C(=O)N[C@H](C)c3cnc(C(F)(F)F)nc3)c2)s1] | Tert-butyl (3-exo)-3-[3-(5-methyl-1,3-thiazol-2-yl)-5-({(1R)-1-[2-(trifluoromethyl)pyrimidin-5-yl]ethyl}carbamoyl)phenoxy]-8-azabicyclo[3.2.1]octane-8-carboxylate | $^1$H NMR (500 MHz, Chloroform-d): δ [ppm] 8.86 (s, 2H), 7.77 (s, 1H), 7.47-7.41 (m, 2H), 7.35-7.31 (m, 1H), 6.58 (d, J = 6.4 Hz, 1H), 5.28 (m, 1H), 4.73 (td, J = 10.6, 5.4 Hz, 1H), 4.38-4.11 (m, 2H), 2.47 (d, J = 1.1 Hz, 3H), 2.15-2.02 (m, 2H), 2.00-1.93 (m, 2H), 1.82-1.60 (m, 7H), 1.49 (s, 9H). |
| 72 | 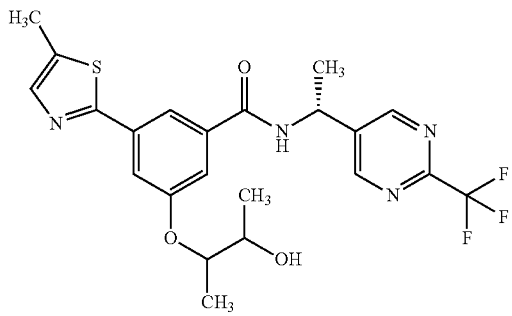 [SMILES: Cc1cnc(-c2cc(OC(C)C(C)O)cc(C(=O)N[C@H](C)c3cnc(C(F)(F)F)nc3)c2)s1] | 3-{[3-hydroxybutan-2-yl]oxy}-5-(5-methyl-1,3-thiazol-2-yl)-N-{(1S)-1-[2-(trifluoromethyl)pyrimidin-5-yl]ethyl}benzamide, as a mixture of trans isomers | $^1$H NMR (250 MHz, Chloroform-d): δ [ppm] 8.94 (s, 2H), 7.79 (s, 1H), 7.55-7.43 (m, 2H), 7.35 (s, 1H), 6.92 (d, J = 6.6 Hz, 1H), 5.36 (m, 1H), 4.45 (m, 1H), 4.04 (s, 1H), 2.79 (s, 6H), 2.53 (s, 3H), 1.71 (d, J = 7.1 Hz, 4H), 1.32-1.23 (m, 6H). LCMS (Analytical Method D) Rt = 4.22 min, MS (ESIpos) m/z = 481 (M + H)$^+$. |
| 79 | 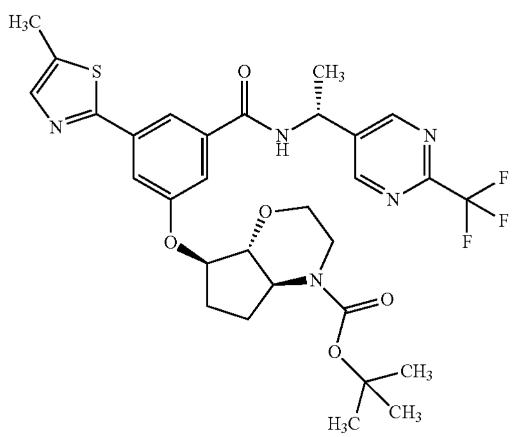 [SMILES: Cc1cnc(-c2cc(O[C@@H]3CC[C@H]4[C@H]3OCCN4C(=O)OC(C)(C)C)cc(C(=O)N[C@H](C)c3cnc(C(F)(F)F)nc3)c2)s1] | tert-Butyl-(4aS,7R,7aR)-7-[3-(5-methyl-1,3-thiazol-2-yl)-5-({(1R)-1-[2-(trifluoromethyl)pyrimidin-5-yl]ethyl}carbamoyl)phenoxy]hexahydrocyclopenta[b][1,4]oxazine-4(4aH)-carboxylate | $^1$H NMR (500 MHz, Chloroform-d): δ [ppm] 8.93 (s, 2H), 7.90-7.82 (m, 1H), 7.55 (s, 1H), 7.53-7.49 (m, 1H), 7.40 (s, 1H), 6.70 (d, J = 6.3 Hz, 1H), 5.35 (m, 1H), 4.65 (tt, J = 9.1, 4.6 Hz, 1H), 4.02 (d, J = 11.5 Hz, 1H), 3.89 (d, J = 12.0 Hz, 1H), 3.70 (t, J = 11.5 Hz, 1H), 3.59 (dd, J = 10.1, 7.9 Hz, 1H), 3.05-2.87 (m, 2H), 2.51 (s, 3H), 2.49-2.45 (m, 1H), 2.43-2.26 (m, 1H), 2.05 (m, 1H), 1.76 (tt, J = 9.4, 4.6 Hz, 1H), 1.70 (d, J = 7.1 Hz, 3H), 1.47 (s, 9H). LCMS (Analytical Method A) Rt = 1.41 min, MS (ESIpos): m/z = 634.2 (M + H)$^+$. |
| 81 | 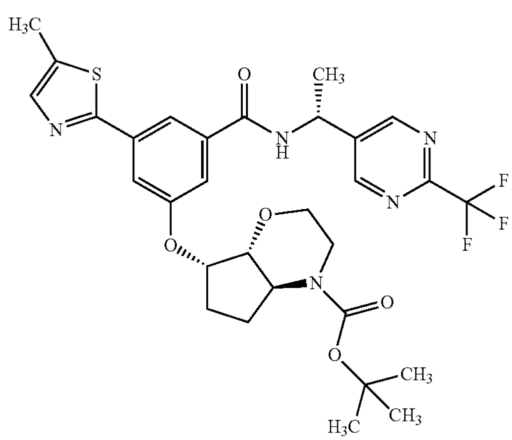 [SMILES: Cc1cnc(-c2cc(O[C@H]3CC[C@H]4[C@H]3OCCN4C(=O)OC(C)(C)C)cc(C(=O)N[C@H](C)c3cnc(C(F)(F)F)nc3)c2)s1] | tert-Butyl-(4aS,7S,7aR)-7-[3-(5-methyl-1,3-thiazol-2-yl)-5-({(1R)-1-[2-(trifluoromethyl)pyrimidin-5-yl]ethyl}carbamoyl)phenoxy]hexahydrocyclopenta[b][1,4]oxazine-4(4aH)-carboxylate | $^1$H NMR (500 MHz, Chloroform-d): δ [ppm] 8.93 (d, J = 3.6 Hz, 2H), 7.90 (d, J = 3.9 Hz, 1H), 7.55 (s, 1H), 7.53 (s, 1H), 7.41 (s, 1H), 6.73 (d, J = 6.2 Hz, 1H), 5.34 (m, 1H), 4.84 (m, 1H), 4.08 (d, J = 11.7 Hz, 1H), 3.87 (d, J = 13.6 Hz, 1H), 3.70 (t, J = 11.6 Hz, 1H), 3.56-3.42 (m, 1H), 3.33 (dd, J = 10.1, 4.3 Hz, 1H), 3.02 (td, J = 13.6, 3.6 Hz, 1H), 2.56-2.52 (m, 4H), 2.27 (t, J = 15.1 Hz, 1H), 1.85-1.75 (m, 2H), 1.71 (dd, J = 7.1, 1.8 Hz, 3H), 1.47 (s, 9H) LCMS (Analytical Method A) Rt = 1.37 min, MS (ESIpos): m/z = 634.2 (M + H)$^+$. |

| Int. | Structure | Name | Analytical Data |
|---|---|---|---|
| 93 | 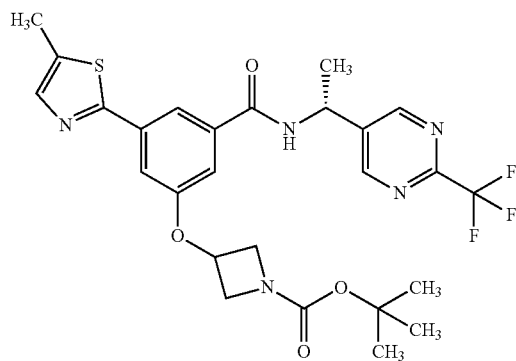 | 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide, as a mixture of 2 cis isomers | LCMS (MSQ1, 7 min) 82% @ Rt = 3.11 min, MS (ESIpos): m/z = 481.1 (M + H)+. |

Intermediate 33: Tert-butyl 3-[3-(5-methyl-1,3-thiazol-2-yl)-5-({(1R)-1-[2-(trifluoromethyl)pyrimidin-5-yl]ethyl}carbamoyl)phenoxy]azetidine-1-carboxylate Intermediate 5AD (205.6 mg, 0.527 mmol), Intermediate VI (121 mg, 0.632 mmol) and DIPEA (367 µL, 2.1 mmol) were combined in DCM (5 mL) and T3P (470 µL, 0.79 mmol) was added. The reaction mixture was stirred at RT for 2 h, then washed with saturated NaHCO₃ (5 mL). The layers were separated, and the aqueous layer extracted with DCM (2×5 mL). The combined organics were dried over MgSO₄, filtered and concentrated under reduced pressure. The crude material was purified by Biotage Isolera™ chromatography (silica gel, eluting with heptane-EtOAc, 4:1 to 1:4) to afford 226 mg (74% yield) of the title compound as colourless solid.

$^1$H NMR (500 MHz, Chloroform-d): δ [ppm] 8.94 (s, 2H), 7.90 (s, 1H), 7.54 (s, 1H), 7.40 (s, 1H), 7.22 (s, 1H), 6.69 (d, J=6.5 Hz, 1H), 5.36 (m, 1H), 4.98 (ddd, J=10.4, 6.4, 4.0 Hz, 1H), 4.35 (dd, J=9.6, 6.5 Hz, 2H), 4.00 (dd, J=9.7, 3.7 Hz, 2H), 2.54 (s, 3H), 1.72 (d, J=7.2 Hz, 3H), 1.45 (s, 9H).

LCMS (Analytical Method A) Rt=1.33 min, MS (ESIpos): m/z=508 (M−tBu)⁺.

In analogy to the procedure described for Intermediate 33, the following Intermediates were prepared using T3P and the appropriate carboxylic acid and amine starting materials.

| Int. | Structure | Name | Analytical Data |
|---|---|---|---|
| 37 | 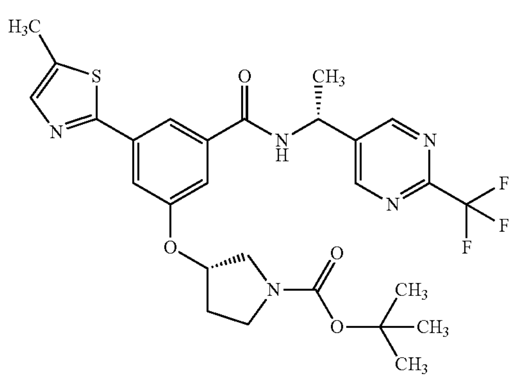 [SMILES: Cc1cnc(-c2cc(O[C@H]3CCN(C(=O)OC(C)(C)C)C3)cc(C(=O)N[C@H](C)c3cnc(C(F)(F)F)nc3)c2)s1] | Tert-butyl (3S)-3-[3-(5-methyl-1,3-thiazol-2-yl)-5-({(1R)-1-[2-(trifluoromethyl)pyrimidin-5-yl]ethyl}carbamoyl)phenoxy]pyrrolidine-1-carboxylate | $^1$H NMR (500 MHz, Chloroform-d): δ [ppm] 8.88 (s, 2H), 7.87 (d, J = 17.1 Hz, 1H), 7.48 (s, 1H), 7.43 (s, 1H), 7.31 (s, 1H), 6.70 (s, 1H), 5.29 (m, 1H), 4.96 (s, 1H), 3.62-3.39 (m, 4H), 2.48 (s, 3H), 2.11 (d, J = 9.2 Hz, 2H), 1.66 (d, J = 7.2 Hz, 3H), 1.39 (s, 9H). LCMS (Analytical Method D) Rt = 4.84 min, MS (ESIpos): m/z = 578.15 (M + H)⁺. |

| Int. | Structure | Name | Analytical Data |
|---|---|---|---|
| 41 | 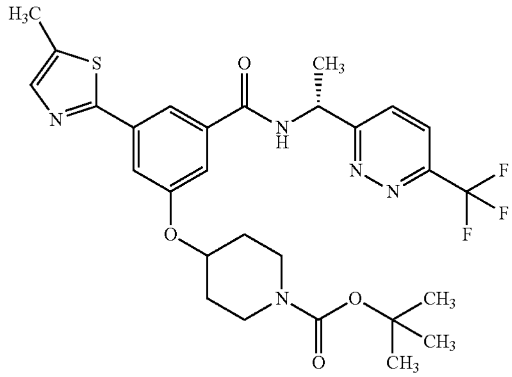 [SMILES: Cc1cnc(-c2cc(OC3CCN(C(=O)OC(C)(C)C)CC3)cc(C(=O)N[C@H](C)c3ccc(C(F)(F)F)nn3)c2)s1] | Tert-butyl 4-[3-(5-methyl-1,3-thiazol-2-yl)-5-({(1R)-1-[6-(trifluoromethyl)pyridazin-3-yl]ethyl}carbamoyl)phenoxy]piperidine-1-carboxylate | $^1$H NMR (500 MHz, Chloroform-d): δ [ppm] 7.87 (t, J = 1.4 Hz, 1H), 7.83 (d, J = 8.7 Hz, 1H), 7.74 (d, J = 8.7 Hz, 1H), 7.58 (dd, J = 2.4, 1.5 Hz, 1H), 7.52 (d, J = 1.2 Hz, 1H), 7.50-7.46 (m, 1H), 7.42 (dd, J = 2.3, 1.5 Hz, 1H), 5.60 (m, 1H), 4.62 (tt, J = 7.1, 3.4 Hz, 1H), 3.75-3.66 (m, 2H), 3.40-3.31 (m, 2H), 2.53 (d, J = 1.1 Hz, 3H), 2.01-1.90 (m, 2H), 1.76 (d, J = 7.0 Hz, 5H), 1.47 (s, 9H). LCMS (Analytical Method A) Rt = 1.55 min, MS (ESIpos): m/z = 592.2 (M + H)$^+$. |
| 50 | 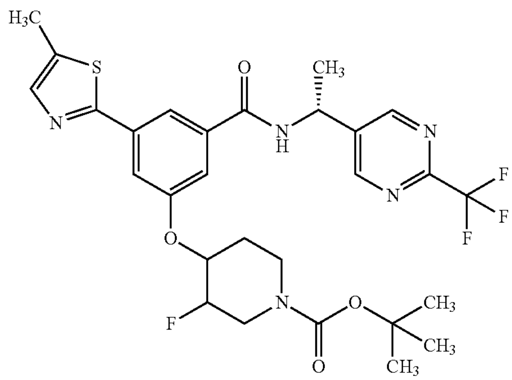 [SMILES: Cc1cnc(-c2cc(OC3CCN(C(=O)OC(C)(C)C)CC3F)cc(C(=O)N[C@H](C)c3cnc(C(F)(F)F)nc3)c2)s1] | Tert-butyl 3-fluoro-4-[3-(5-methyl-1,3-thiazol-2-yl)-5-{[(1R)-1-[2-(trifluoromethyl)pyrimidin-5-yl]ethyl]carbamoyl}phenoxy]piperidine-1-carboxylate, as a mixture of trans isomers | $^1$H NMR (500 MHz, Chloroform-d): δ [ppm] 8.94 (s, 2H), 7.86 (d, J = 1.4 Hz, 1H), 7.60-7.56 (m, 1H), 7.53 (d, J = 1.2 Hz, 1H), 7.44 (t, J = 3.5 Hz, 1H), 6.64 (d, J = 6.5 Hz, 1H), 5.36 (m, 1H), 4.59 (m, 2H), 3.68-2.97 (m, 4H), 2.54 (d, J = 1.1 Hz, 3H), 2.20-2.10 (m, 1H), 1.76 (s, 1H), 1.72 (d, J = 7.1 Hz, 3H), 1.48 (s, 9H). LCMS (Analytical Method A) Rt = 1.36 min, MS (ESIpos): m/z = 554 (M − tBu)$^+$. |
| 66 | 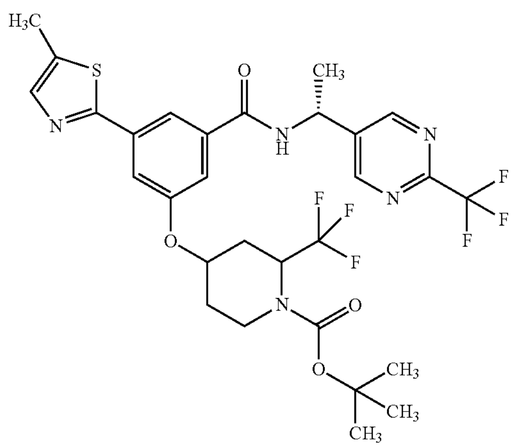 [SMILES: Cc1cnc(-c2cc(OC3CCN(C(=O)OC(C)(C)C)C(C(F)(F)F)C3)cc(C(=O)N[C@H](C)c3cnc(C(F)(F)F)nc3)c2)s1] | Tert-butyl 4-[3-(5-methyl-1,3-thiazol-2-yl)-5-({(1R)-1-[2-(trifluoromethyl)pyrimidin-5-yl]ethyl}carbamoyl)phenoxy]-2-(trifluoromethyl)piperidine-1-carboxylate, as a mixture of trans isomers | $^1$H NMR (500 MHz, Chloroform-d): δ [ppm] 8.94 (d, J = 1.2 Hz, 2H), 7.84 (d, J = 1.4 Hz, 1H), 7.53 (d, J = 1.1 Hz, 1H), 7.51 (s, 1H), 7.36 (q, J = 2.1 Hz, 1H), 6.61 (d, J = 6.5 Hz, 1H), 5.35 (m, 1H), 4.89-4.68 (m, 2H), 4.11-4.04 (m, 1H), 3.37 (t, J = 12.7 Hz, 1H), 2.54 (d, J = 1.0 Hz, 3H), 2.36 (dd, J = 15.5, 2.1 Hz, 1H), 2.08 (td, J = 8.0, 7.5, 4.3 Hz, 1H), 2.01 (d, J = 14.0 Hz, 1H), 1.90-1.78 (m, 1H), 1.73 (d, J = 7.2 Hz, 3H), 1.49 (s, 9H). LCMS (Analytical Method A) Rt = 1.49 min, MS (ESIpos): m/z = 604.00 (M − tBu)$^+$. |
| 68 | 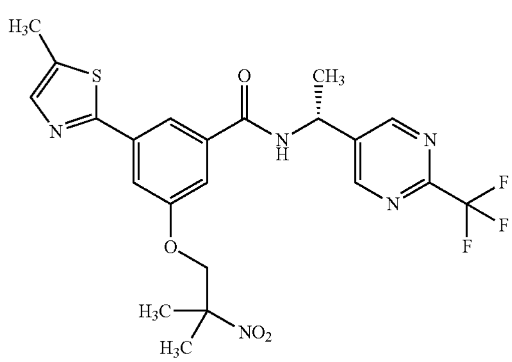 [SMILES: Cc1cnc(-c2cc(OCC(C)(C)[N+](=O)[O-])cc(C(=O)N[C@H](C)c3cnc(C(F)(F)F)nc3)c2)s1] | 3-(2-Methyl-2-nitropropoxy)-5-(5-methyl-1,3-thiazol-2-yl)-N-{(1R)-1-[2-(trifluoromethyl)pyrimidin-5-yl]ethyl}benzamide | 1H NMR (500 MHz, Chloroform-d): δ [ppm] 8.96 (s, 2H), 8.02 (s, 1H), 7.56-7.54 (m, 1H), 7.51-7.48 (m, 1H), 7.41-7.38 (m, 1H), 6.95 (s, 1H), 5.36 (m, 1H), 4.37 (q, J = 9.8 Hz, 2H), 2.55 (d, J = 0.9 Hz, 3H), 1.80-1.68 (m, 9H). LCMS (Analytical Method A) Rt = 1.44 min, MS (ESIpos): m/z = 510.0 (M + H)$^+$. |

| Int. | Structure | Name | Analytical Data |
|---|---|---|---|
| 69 | 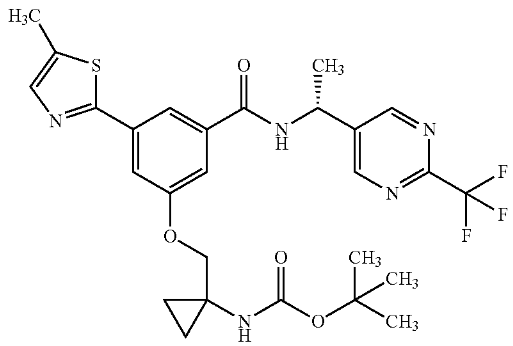 [SMILES: Cc1cnc(-c2cc(OCC3(NC(=O)OC(C)(C)C)CC3)cc(C(=O)N[C@H](C)c3cnc(C(F)(F)F)nc3)c2)s1] | Tert-butyl (1-{[3-(5-methyl-1,3-thiazol-2-yl)-5-({(1R)-1-[2-(trifluoromethyl)pyrimidin-5-yl]ethyl}carbamoyl)phenoxy]methyl}cyclopropyl)carbamate | 1H NMR (250 MHz, Chloroform-d) δ 8.95 (s, 2H), 7.84 (s, 1H), 7.51-7.40 (m, 3H), 6.96 (d, J = 6.6 Hz, 1H), 5.39 (m, 1H), 5.24 (s, 1H), 4.05 (s, 2H), 2.52 (d, J = 0.9 Hz, 3H), 1.73 (d, J = 7.2 Hz, 3H), 1.42 (s, 9H), 0.96-0.87 (m, 4H). LCMS (Analytical Method A) 100% @ Rt = 1.34 min, MS (ESIpos): m/z = 578.1 (M + H)+. |
| 73 | 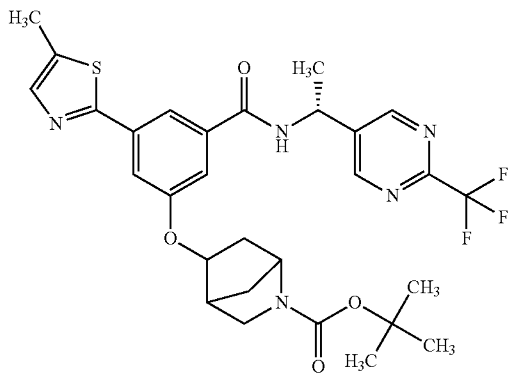 [SMILES: Cc1cnc(-c2cc(OC3CC4CC3CN4C(=O)OC(C)(C)C)cc(C(=O)N[C@H](C)c3cnc(C(F)(F)F)nc3)c2)s1] | Tert-butyl 5-[3-(5-methylthiazol-2-yl)-5-[[(1R)-1-[2-(trifluoromethyl)pyrimidin-5-yl]ethyl]carbamoyl]phenoxy]-2-azabicyclo[2.2.1]heptane-2-carboxylate | $^1$H NMR (500 MHz, Chloroform-d): δ [ppm] 8.92 (s, 2H), 7.81 (s, 1H), 7.50 (d, J = 1.2 Hz, 1H), 7.47-7.44 (m, 1H), 7.33 (br.s, 1H), 6.86 (d, J = 5.7 Hz, 1H), 5.39-5.32 (m, 1H), 4.53-4.47 (m, 1H), 4.25 (m, 1H), 3.28 (dd, J = 10.3, 3.6 Hz, 1H), 3.02-2.95 (m, 1H), 2.75 (br.s, 1H), 2.52 (d, J = 1.0 Hz, 3H), 2.33-2.20 (m, 1H), 1.89-1.83 (m, 1H), 1.70 (d, J = 7.2 Hz, 3H), 1.68-1.60 (m, 2H), 1.45 (s, 9H). LCMS (Analytical Method A) Rt = 1.53 min, MS (ESIpos): m/z = 548 (M + H)+. |

Intermediate 35: 3-(Azetidin-3-yloxy)-5-(5-methyl-1,3-thiazol-2-yl)-N-{(1R)-1-[2-(trifluoromethyl)pyrimidin-5-yl]ethyl}benzamide

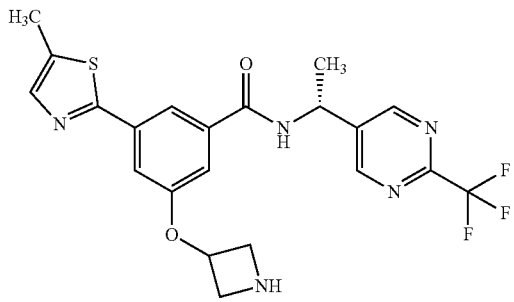 [SMILES: Cc1cnc(-c2cc(OC3CNC3)cc(C(=O)N[C@H](C)c3cnc(C(F)(F)F)nc3)c2)s1]

To a solution of Intermediate 33 (226 mg, 0.40 mmol) dissolved in DCM (5 mL) was added TFA (0.3 mL, 4.0 mmol) and the reaction stirred at RT until gas evolution ceased. The reaction mixture was neutralised with saturated NaHCO₃ solution, producing a precipitate. This was collected by filtration under reduced pressure and dried in the vacuum oven to afford 188.7 mg (quantitative yield) of the title compound as white powder.

$^1$H NMR (500 MHz, DMSO-d6): δ [ppm] 9.42-9.09 (m, 3H), 7.94 (s, 1H), 7.65 (s, 1H), 7.42 (m, 2H), 5.30 (m, 1H), 5.17-4.92 (m, 1H), 4.03-3.76 (m, 2H), 3.62-3.51 (m, 2H), 1.62 (d, J=7.1 Hz, 3H).

LCMS (Analytical Method A) Rt=0.94 min, MS (ESIpos): m/z=464.0 (M+H)+.

Intermediate 36: 3-(azetidin-3-yloxy)-5-(5-methyl-1,3-thiazol-2-yl)-N-{(1R)-1-[6-(trifluoromethyl)pyridazin-3-yl]ethyl}benzamide

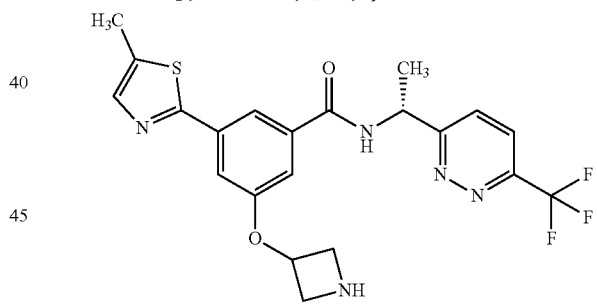

To a solution of Intermediate 34 (248 mg, 0.30 mmol, 68% purity) in DCM (1 mL) was added TFA (0.1 mL) then stirred for 4 h. The reaction mixture was concentrated under reduced pressure and the residue taken up in water and basified to pH ~4 with 10 M NaOH solution to give an off-white precipitate that was collected by filtration to afford 81 mg (53% yield) of the title compound as an off-white powder.

$^1$H NMR (500 MHz, DMSO-d6): δ [ppm] 9.35 (d, J=6.9 Hz, 1H), 8.24 (d, J=8.8 Hz, 1H), 8.06 (d, J=8.8 Hz, 1H), 7.99 (s, 1H), 7.65 (s, 1H), 7.43 (d, J=11.9 Hz, 2H), 5.52-5.45 (m, 1H), 5.17 (q, J=5.8 Hz, 1H), 3.92 (t, J=7.6 Hz, 2H), 3.65-3.61 (m, 2H), 1.66 (d, J=7.1 Hz, 3H).

LCMS (Analytical Method A) Rt=0.88 min, MS (ESIpos) m/z 464 (M+H+).

In analogy to the procedure described for Intermediate 36, the following Intermediates were prepared using TFA and the appropriate N-Boc protected amine starting materials.

| Int. | Structure | Name | Analytical Data |
|---|---|---|---|
| 40 | 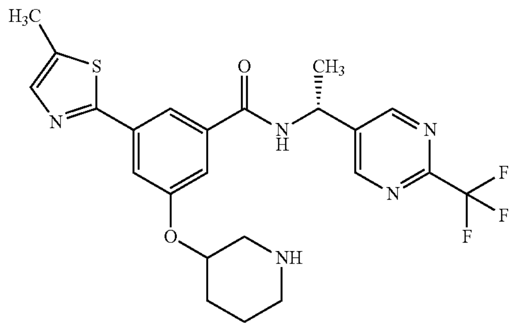 [SMILES: Cc1cnc(-c2cc(OC3CCCNC3)cc(C(=O)N[C@H](C)c3cnc(C(F)(F)F)nc3)c2)s1] | 3-(5-methyl-1,3-thiazol-2-yl)-5-[piperidin-3-yloxy]-N-{(1R)-1-[2-(trifluoromethyl)pyrimidin-5-yl]ethyl}benzamide, as a mixture of 2 diastereoisomers | $^1$H NMR (500 MHz, DMSO-d6): δ [ppm] 9.17 (d, J = 7.1 Hz, 1H), 9.11 (s, 2H), 7.91 (s, 1H), 7.64 (d, J = 1.2 Hz, 1H), 7.59-7.55 (m, 1H), 7.54-7.50 (m, 1H), 5.29 (m, 1H), 4.48 (dt, J = 7.5, 3.9 Hz, 1H), 3.15 (d, J = 12.2 Hz, 1H), 2.82 (dt, J = 11.8, 4.4 Hz, 1H), 2.62 (m, 2H), 2.02 (s, 1H), 1.77-1.67 (m, 1H), 1.61 (d, J = 7.1 Hz, 3H), 1.49 (ddt, J = 13.1, 9.3, 5.1 Hz, 1H). |
| 43 | 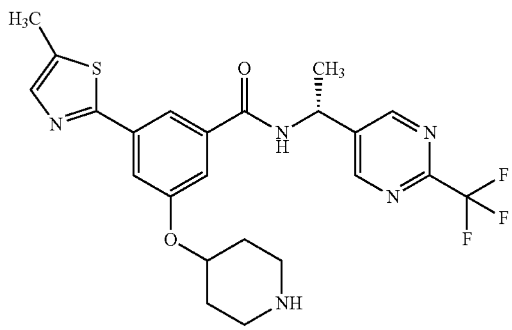 [SMILES: Cc1cnc(-c2cc(OC3CCNCC3)cc(C(=O)N[C@H](C)c3cnc(C(F)(F)F)nc3)c2)s1] | 3-(5-methyl-1,3-thiazol-2-yl)-5-(piperidin-4-yloxy)-N-{(1R)-1-[2-(trifluoromethyl)pyrimidin-5-yl]ethyl}benzamide | $^1$H NMR (500 MHz, Chloroform-d) δ 8.93 (s, 2H), 7.81 (s, 1H), 7.54-7.49 (m, 2H), 7.41-7.37 (m, 1H), 6.73 (d, J = 6.9 Hz, 1H), 5.35 (m, 1H), 4.51 (tt, J = 8.4, 3.8 Hz, 1H), 3.17-3.11 (m, 2H), 2.80-2.72 (m, 2H), 2.53 (s, 3H), 2.08-2.00 (m, 2H), 1.95 (s, 1H), 1.74-1.64 (m, 5H). LCMS (Analytical Method D) Rt = 3.12, MS (ESIpos): m/z = 493 (M + H)$^+$. |
| 46 | 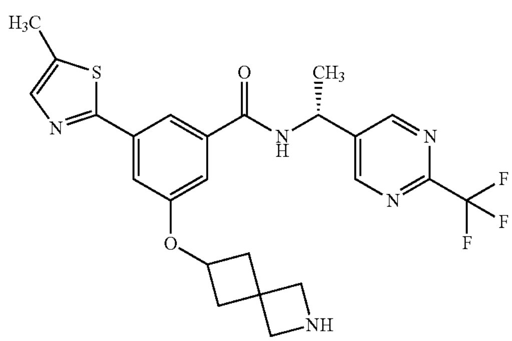 [SMILES: Cc1cnc(-c2cc(OC3CC4(CNC4)C3)cc(C(=O)N[C@H](C)c3cnc(C(F)(F)F)nc3)c2)s1] | 3-(2-azaspiro[3.3]hept-6-yloxy)-5-(5-methyl-1,3-thiazol-2-yl)-N-{(1R)-1-[2-(trifluoromethyl)pyrimidin-5-yl]ethyl}benzamide | 1H NMR (500 MHz, DMSO-d6): δ [ppm] 9.22 (d, J = 7.1 Hz, 1H), 9.11 (s, 2H), 7.93 (s, 1H), 7.66-7.62 (m, 1H), 7.41 (d, J = 10.2 Hz, 2H), 5.29 (m, 1H), 4.78 (p, J = 6.7 Hz, 1H), 4.03 (s, 2H), 3.93 (s, 2H), 3.17 (s, 3H), 2.81 (dd, J = 12.4, 6.8 Hz, 2H), 2.30 (dd, J = 13.2, 6.6 Hz, 2H), 1.61 (d, J = 7.1 Hz, 3H). LCMS (Analytical Method D) Rt = 3.20 min, MS (ESIpos): m/z = 504 (M + H)$^+$. |
| 51 | 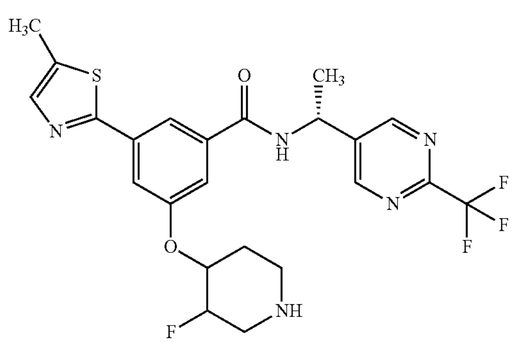 [SMILES: Cc1cnc(-c2cc(OC3CCNCC3F)cc(C(=O)N[C@H](C)c3cnc(C(F)(F)F)nc3)c2)s1] | 3-[(3-Fluoropiperidin-4-yl)oxy]-5-(5-methyl-1,3-thiazol-2-yl)-N-[(1R)-1-[2-(trifluoromethyl)pyrimidin-5-yl]ethyl]benzamide, as a mixture of trans isomers | $^1$H NMR (500 MHz, Chloroform-d): δ [ppm] 8.94 (s, 2H), 7.86 (d, J = 1.5 Hz, 1H), 7.61-7.57 (m, 1H), 7.53 (d, J = 1.2 Hz, 1H), 7.45 (s, 1H), 6.64 (d, J = 5.8 Hz, 1H), 5.35 (q, J = 7.1 Hz, 1H), 4.66-4.49 (m, 2H), 3.44-3.33 (m, 1H), 3.05 (d, J = 13.2 Hz, 1H), 2.88 (dd, J = 13.0, 7.4 Hz, 1H), 2.74 (dd, J = 12.6, 9.3 Hz, 1H), 2.54 (d, J = 1.0 Hz, 3H), 2.17 (d, J = 10.7 Hz, 1H), 1.71 (t, J = 7.3 Hz, 4H). LCMS (Analytical Method D) Rt = 3.28 min, MS (ESIpos): m/z = 510.0 (M + H)$^+$. |

-continued

| Int. | Structure | Name | Analytical Data |
|---|---|---|---|
| 67 | 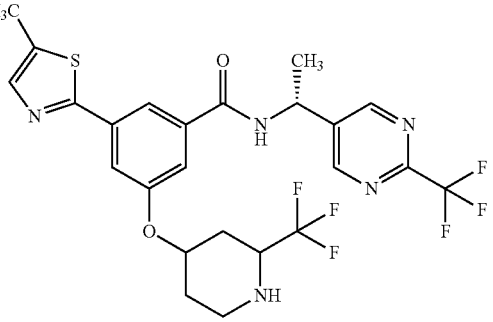 | 3-(5-methyl-1,3-thiazol-2-yl)-5-{[(2R,4S)-2-(trifluoromethyl)piperidin-4-yl]oxy}-N-{(1R)-1-[2-(trifluoromethyl)pyrimidin-5-yl]ethyl}benzamide, as a mixture of cis isomers | $^1$H NMR (500 MHz, Chloroform-d): δ [ppm] 8.94 (s, 2H), 7.86 (d, J = 1.4 Hz, 1H), 7.56-7.50 (m, 2H), 7.43-7.37 (m, 1H), 6.62 (d, J = 5.3 Hz, 1H), 5.35 (m, 1H), 4.44 (tt, J = 9.7, 4.2 Hz, 1H), 3.33-3.22 (m, 2H), 2.78 (t, J = 11.9 Hz, 1H), 2.54 (d, J = 1.0 Hz, 3H), 2.33 (dtt, J = 9.7, 4.7, 2.3 Hz, 1H), 2.23-2.15 (m, 1H), 1.72 (d, J = 7.2 Hz, 3H), 1.62-1.56 (m, 2H). LCMS (Analytical Method F) Rt = 2.59 min, MS (ESIpos): m/z = 560 (M + H)$^+$. |
| 70 | 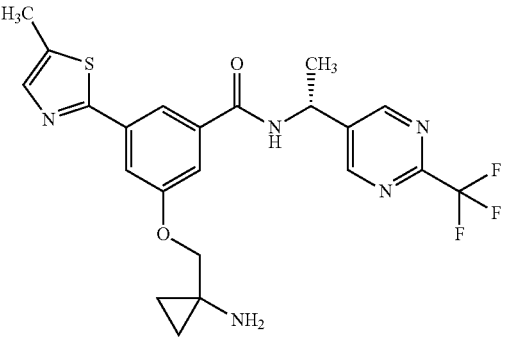 [SMILES: Cc1cnc(-c2cc(OCC3(N)CC3)cc(C(=O)N[C@H](C)c3cnc(C(F)(F)F)nc3)c2)s1] | 3-[(1-Aminocyclopropyl)methoxy]-5-(5-methyl-1,3-thiazol-2-yl)-N-{(1R)-1-[2-(trifluoromethyl)pyrimidin-5-yl]ethyl}benzamide | LCMS (Analytical Method A) Rt = 0.97 min, MS (ESIpos): m/z = 478 (M + H)$^+$. |
| 74 | 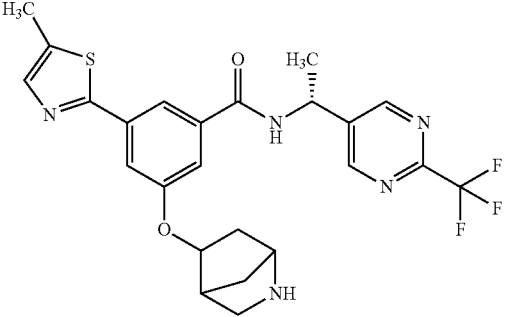 [SMILES: Cc1cnc(-c2cc(OC3CC4CC3CN4)cc(C(=O)N[C@H](C)c3cnc(C(F)(F)F)nc3)c2)s1] | 3-(2-azabicyclo[2.2.1]heptan-5-yloxy)-5-(5-methylthiazol-2-yl)-N-[(1R)-1-[2-(trifluoromethyl)pyrimidin-5-yl]ethyl]benzamide | LCMS (Analytical Method A) Rt = 0.95 min, MS (ESIpos): m/z = 504.3 (M + H)$^+$. |
| 76 | 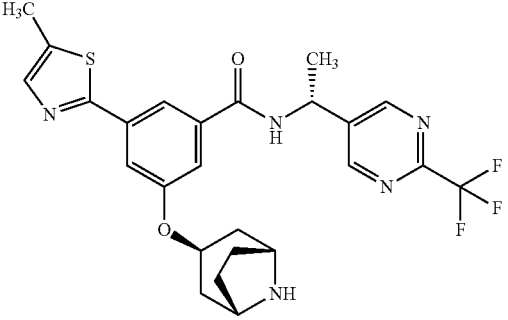 [SMILES: Cc1cnc(-c2cc(O[C@H]3C[C@H]4CC[C@@H](C3)N4)cc(C(=O)N[C@H](C)c3cnc(C(F)(F)F)nc3)c2)s1] | 3-[(1R,3S,5S)-8-azabicyclo[3.2.1]octan-3-yloxy]-5-(5-methyl-1,3-thiazol-2-yl)-N-[(1R)-1-[2-(trifluoromethyl)pyrimidin-5-yl]ethyl]benzamide | Used in the next step crude |

-continued

| Int. | Structure | Name | Analytical Data |
|---|---|---|---|
| 77 | 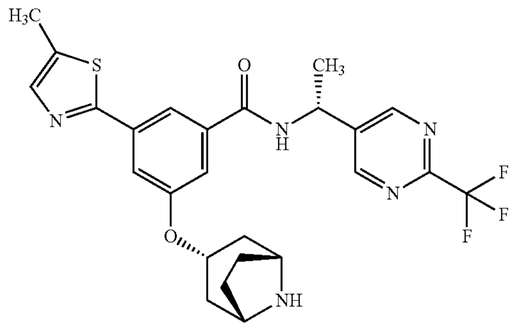 [SMILES: Cc1cnc(-c2cc(O[C@@H]3C[C@H]4CC[C@@H](C3)N4)cc(C(=O)N[C@H](C)c3cnc(C(F)(F)F)nc3)c2)s1] | 3-[(1R,3R,5S)-8-azabicyclo[3.2.1]octan-3-yloxy]-5-(5-methyl-1,3-thiazol-2-yl)-N-[(1R)-1-[2-(trifluoromethyl)pyrimidin-5-yl]ethyl]benzamide | Used in the next step crude |
| 80 | 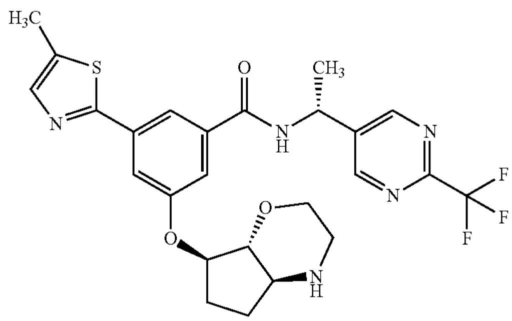 [SMILES: Cc1cnc(-c2cc(O[C@@H]3CC[C@@H]4NCCO[C@H]43)cc(C(=O)N[C@H](C)c3cnc(C(F)(F)F)nc3)c2)s1] | 3-(5-methyl-1,3-thiazol-2-yl)-5-[(4aS,7R,7aR)-octahydrocyclopenta[b][1,4]oxazin-7-yloxy]-N-{(1R)-1-[2-(trifluoromethyl)pyrimidin-5-yl]ethyl}benzamide | $^1$H NMR (500 MHz, Chloroform-d): δ [ppm] 8.93 (s, 2H), 7.90-7.82 (m, 1H), 7.56 (s, 1H), 7.51 (s, 1H), 7.41 (s, 1H), 6.68 (d, J = 4.8 Hz, 1H), 5.35 (m, 1H), 4.68 (dq, J = 9.5, 5.5 Hz, 1H), 3.97 (d, J = 11.4 Hz, 1H), 3.72 (t, J = 11.3 Hz, 1H), 3.54 (t, J = 8.8 Hz, 1H), 3.05-2.87 (m, 2H), 2.74 (td, J = 11.1, 6.6 Hz, 1H), 2.53 (s, 3H), 2.43-2.32 (m, 1H), 1.93-1.84 (m, 1H), 1.81-1.73 (m, 2H), 1.70 (d, J = 7.1 Hz, 4H). LCMS (Analytical Method A) Rt = 0.98 min, MS (ESIpos): m/z = 534.1 (M + H)$^+$. |
| 82 | 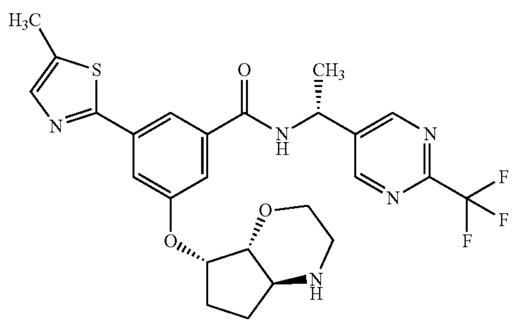 [SMILES: Cc1cnc(-c2cc(O[C@H]3CC[C@@H]4NCCO[C@H]43)cc(C(=O)N[C@H](C)c3cnc(C(F)(F)F)nc3)c2)s1] | 3-(5-methyl-1,3-thiazol-2-yl)-5-[(4aS,7S,7aR)-octahydrocyclopenta[b][1,4]oxazin-7-yloxy]-N-{(1R)-1-[2-(trifluoromethyl)pyrimidin-5-yl]ethyl}benzamide | $^1$H NMR (500 MHz, Chloroform-d): δ [ppm] 8.93 (d, J = 3.5 Hz, 2H), 7.85 (d, J = 3.9 Hz, 1H), 7.57 (s, 1H), 7.52-7.48 (m, 1H), 7.41 (s, 1H), 6.70 (d, J = 6.0 Hz, 1H), 5.34 (m, 1H), 4.85 (q, J = 4.8 Hz, 1H), 4.03 (d, J = 11.6 Hz, 1H), 3.74 (t, J = 11.8 Hz, 1H), 3.32 (dd, J = 9.8, 3.7 Hz, 1H), 3.30-3.20 (m, 1H), 3.06 (td, J = 12.1, 3.2 Hz, 1H), 2.94 (d, J = 11.7 Hz, 1H), 2.53 (s, 3H), 2.32-2.22 (m, 1H), 2.02-1.91 (m, 1H), 1.89-1.77 (m, 1H), 1.70 (dd, J = 7.1, 2.2 Hz, 3H), 1.50-1.34 (m, 1H). LCMS (Analytical Method A) Rt = 0.97 min, MS (ESIpos): m/z = 534.1 (M + H)$^+$. |

Intermediate 6AY: 1,1-Dioxidotetrahydro-2H-thiopyran-4-yl 4-methylbenzenesulfonate

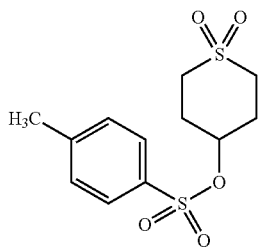 [SMILES: Cc1ccc(S(=O)(=O)OC2CCS(=O)(=O)CC2)cc1]

A mixture of tetrahydro-2H-thiopyran-4-ol 1,1-dioxide (660 mg, 4.39 mmol), 4-methylbenzenesulfonyl chloride (922 mg, 4.83 mmol), TEA (920 µl, 6.6 mmol), trimethylamine hydrochloride (42.0 mg, 439 µmol) in DCM (5.4 mL) was stirred at RT until complete conversion. DCM and water were added and the layers separated. The organic layer was evaporated to dryness under reduced pressure and the residue was purified by column chromatography to give 1.03 g (77% yield) of the title compound.

$^1$H NMR (400 MHz, DMSO-d$_6$) δ [ppm] 0.16-0.84 (m, 1H) 1.99-2.18 (m, 4H) 2.43 (s, 3H) 3.01-3.24 (m, 4H) 4.83 (dt, 1H) 7.49 (d, 2H) 7.85 (d, 2H).

Intermediate 4AZ: Methyl 3-[(1,1-dioxidotetrahydro-2H-thiopyran-4-yl)oxy]-5-(5-methyl-1,3-thiazol-2-yl)benzoate

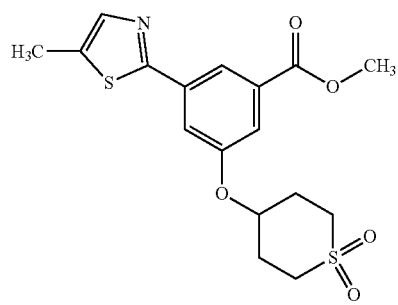 [SMILES: COC(=O)c1cc(OC2CCS(=O)(=O)CC2)cc(-c2ncc(C)s2)c1]

A mixture of Intermediate 3 (519 mg, 2.08 mmol), Intermediate 6AY (951 mg, 3.13 mmol), Cs₂CO₃ (1.02 g, 3.13 mmol) in DMF (15 mL) was stirred at 90° C. until complete conversion. The mixture was evaporated to dryness under reduced pressure and the residue purified by column chromatography (silica gel, hexane/EE gradient) to give 680 mg (86% yield) of the title compound.

LCMS, method 1, rt: 1.10 min, MS ES+m/z=382 (M+H)⁺.

Intermediate 5AZ: 3-[(1,1-Dioxidotetrahydro-2H-thiopyran-4-yl)oxy]-5-(5-methyl-1,3-thiazol-2-yl)benzoic acid

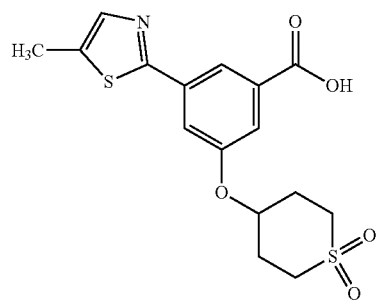 [SMILES: Cc1cnc(-c2cc(OC3CCS(=O)(=O)CC3)cc(C(=O)O)c2)s1]

A mixture of Intermediate 4AZ (680 mg, 1.78 mmol), an aqueous NaOH-solution (356 mg, 8.91 mmol, 2M) and MeOH (50 mL) was stirred at RT until complete conversion The solvent was evaporated under reduced pressure and an aqueous HU-solution (2M) was added to adjust the pH-value to pH: 6. The aqueous layer was separated and the organic layer was evaporated to dryness under reduced pressure. The residue was purified by column chromatography (silica gel) to give 288 mg (44% yield) of the title compound.

LCMS, method 1, rt: 0.92 min, MS ES+m/z=368 (M+H)⁺.

Intermediate 4BA: Methyl 3-(5-ethyl-1,3-thiazol-2-yl)-5-[(3R)-tetrahydrofuran-3-yloxy]benzoate

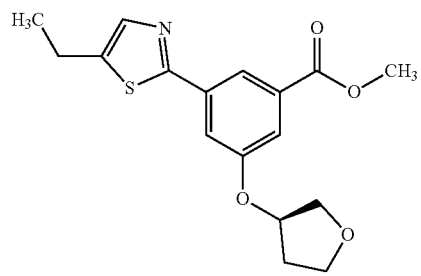 [SMILES: CCc1cnc(-c2cc(O[C@@H]3CCOC3)cc(C(=O)OC)c2)s1]

A mixture of Intermediate 8 (950 mg, 2.73 mmol), 2-bromo-5-ethyl-1,3-thiazole (681 mg, 3.55 mmol), [1,1,-Bis-(diphenylphosphino)-ferrocer]-palladium (II) dichloride (334 mg, 409 µmol), and K₂CO₃ (6.5 ml, 1.0 M, 6.5 mmol) in THF (45 mL) was stirred under reflux until complete conversion and evaporated to dryness under reduced pressure. The residue was purified by column chromatography (silica gel, hexane/EE/MeOH gradient) to give 265 mg (29% yield) of the title compound.

LCMS, method 1, rt: 1.33 min, MS ES+m/z=334 (M+H)⁺.

Intermediate 5BA: 3-(5-Ethyl-1,3-thiazol-2-yl)-5-[(3R)-tetrahydrofuran-3-yloxy]benzoic acid

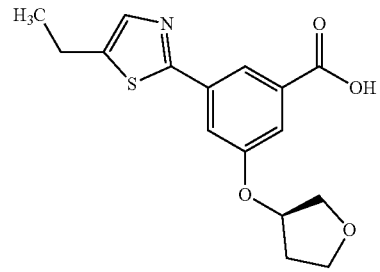 [SMILES: CCc1cnc(-c2cc(O[C@@H]3CCOC3)cc(C(=O)O)c2)s1]

A solution of intermediate 4BA (265 mg, 94% purity, 780 µmol) in MeOH (5 mL), THF (5 mL) and an aqueous NaOH-solution (780 µl, 2.0 M, 1.6 mmol) was stirred at RT until complete conversion. Water was added and the pH-value adjusted to pH: 2.

The aqueous phase was extracted with EE, the combined organic layers dried with Na₂SO₄, filtered and evaporated to dryness under reduced pressure to give 252 mg (100% yield) of the title compound which was used without further purification.

LCMS, method 1, MS ES+m/z=320 (M+H)⁺.

Intermediate 4BB: Methyl 3-(5-cyclobutyl-1,3-thiazol-2-yl)-5-[(3R)-tetrahydrofuran-3-yloxy]benzoate

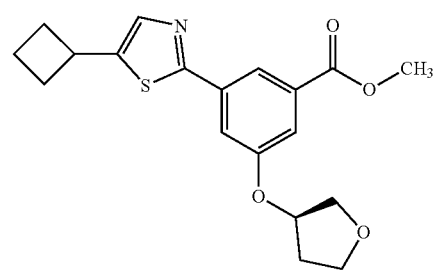 [SMILES: COC(=O)c1cc(O[C@@H]2CCOC2)cc(-c2ncc(C3CCC3)s2)c1]

A mixture of Intermediate 8 (870 mg, 2.50 mmol), 2-chloro-5-cyclobutyl-1,3-thiazole (564 mg, 3.25 mmol), [1,1,-Bis-(diphenylphosphino)-ferrocen]-palladium(II) dichloride (306 mg, 375 µmol) and K₂CO₃ (6.0 ml, 1.0 M, 6.0 mmol) in THF (41 mL) was stirred under reflux until complete conversion and evaporated to dryness under reduced pressure. The residue was purified by column chromatography (silica gel, hexane/EE gradient) to give 390 mg (43% yield) of the title compound.

LCMS, method 1, rt: 1.46 min, MS ES+m/z=360 (M+H)⁺.

Intermediate 5BB: 3-(5-Cyclobutyl-1,3-thiazol-2-yl)-5-[(3R)-tetrahydrofuran-3-yloxy]benzoic acid

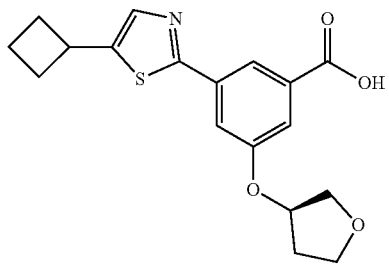 [SMILES: O=C(O)c1cc(O[C@@H]2CCOC2)cc(-c2ncc(C3CCC3)s2)c1]

A solution of Intermediate 4BB (390 mg, 94% purity, 1.02 mmol) in MeOH and an aqueous NaOH-solution (1.5 ml, 2.0 M, 3.1 mmol) was stirred at RT until complete conversion. Water was added and the pH-value adjusted to pH: 2. The aqueous phase was extracted with EE, the combined organic layers dried with $Na_2SO_4$, filtered and evaporated to dryness under reduced pressure to give 334 mg (95%) of the title compound which was used without further purification.

LCMS, method 1, rt: 1.23 min, MS ES+m/z=346 (M+H)$^+$.

Intermediate 4BC: Methyl 3-[5-(propan-2-yl)-1,3-thiazol-2-yl]-5-[(3R)-tetrahydrofuran-3-yloxy]benzoate

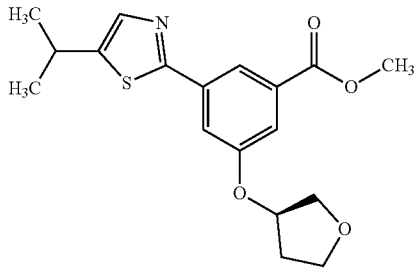 [SMILES: COC(=O)c1cc(O[C@@H]2CCOC2)cc(-c2ncc(C(C)C)s2)c1]

A mixture of Intermediate 8 (870 mg, 2.50 mmol), 2-bromo-5-(propan-2-yl)-1,3-thiazole (669 mg, 3.25 mmol), [1,1,-Bis-(diphenylphosphino)-ferrocer]-palladium(II) dichloride (306 mg, 375 µmol) and $K_2CO_3$ (6.0 ml, 1.0 M, 6.0 mmol) in THF (41 mL) was stirred under reflux until complete conversion and evaporated to dryness under reduced pressure. The residue was purified by column chromatography (silica gel, hexane/EE/MeOH gradient) to give 451 mg (52% yield) of the title compound.

LCMS, method 1, rt: 1.41 min, MS ES+: MS ES+m/z=348 (M+H)$^+$.

Intermediate 5BC: 3-[5-(Propan-2-yl)-1,3-thiazol-2-yl]-5-[(3R)-tetrahydrofuran-3-yloxy]benzoic acid

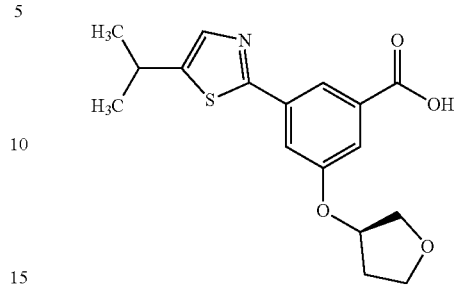

A solution of Intermediate 4BC (390 mg, 94% purity, 1.06 mmol) in MeOH and an aqueous NaOH-solution (1.6 ml, 2.0 M, 3.2 mmol) was stirred at RT until complete conversion. Water was added and the pH-value adjusted to pH: 2. The aqueous phase was extracted with EE, the combined organic layers dried with $Na_2SO_4$, filtered and evaporated to dryness under reduced pressure to give 400 mg of the title compound which was used without further purification.

LCMS, method 1, rt: 1.17 min, MS ES+m/z=334 (M+H)$^+$.

Intermediate 6AZ: (3R)-Tetrahydrofuran-3-yl 4-methylbenzenesulfonate

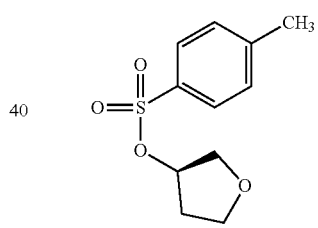

A mixture of (3R)-tetrahydrofuran-3-ol (18 g, 204 mmol), TEA (42.7 ml, 306 mmol), trimethylamine hydrochloride (1.95 g, 20.4 mmol) in DCM (626 mL) was stirred at RT for 20 min. 4-methylbenzenesulfonyl chloride (42.8 g, 225 mmol) was added and the reaction mixture stirred at RT until complete conversion. To the reaction mixture N,N-Dimethylethylenediamine (26.4 ml, 245 mmol) was added and stirred for 30 min to consume the unreacted 4-methylbenzenesulfonyl chloride. Water was added and the mixture was extracted with DCM (3×). The combined organic layers were evaporated to dryness under reduced pressure and the residue was purified by column chromatography (silica gel, hexane/EE/DCM/MeOH gradient) to give 41.0 g (83% yield) of the title compound.

$^1$H NMR (400 MHz, DMSO-d$_6$) δ [ppm] 1.79-1.95 (m, 1H) 2.08 (dtd, 1H) 2.43 (s, 3H) 3.57-3.81 (m, 4H) 5.12 (ddt, 1H) 7.49 (d, 2H) 7.81 (d, 2H).

Intermediate 95: Methyl 3-bromo-5-[(3S)-tetrahydrofuran-3-yloxy]benzoate

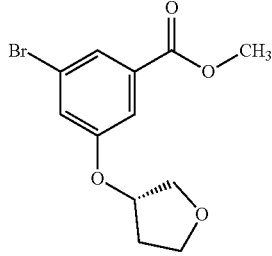 [SMILES: COC(=O)c1cc(Br)cc(O[C@H]2CCOC2)c1]

A mixture of Intermediate 1 (3.00 g, 13.0 mmol), Intermediate 6AZ (4.72 g, 19.5 mmol) and $Cs_2CO_3$ (6.35 g, 19.5 mmol) in DMF 25 ml was stirred at 80° C. until complete conversion. The reaction mixture was cooled to RT and the solid was filtered through Celite® and washed with DMF. The filtrate was evaporated and the residue purified by column chromatography (silica gel, hexane/EE gradient) to give 2.63 g (67% yield) of the title compound.

LCMS, method 1, rt: 1.17 min, MS ES+m/z=301 (M+H)+.

Intermediate 94: Methyl 3-[(3S)-tetrahydrofuran-3-yloxy]-5-(4,4,5,5-tetramethyl-1,3,2-dioxaborolan-2-yl)benzoate

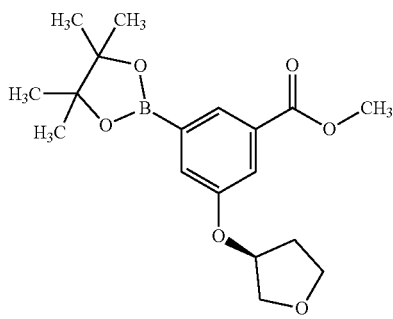

A mixture of Intermediate 95 (2.63 g, 8.73 mmol), 4,4,4',4',5,5,5',5'-octamethyl-2,2'-bi-1,3,2-dioxaborolane (5.54 g, 21.8 mmol), potassium acetate (3.00 g, 30.6 mmol) and [1,1,-Bis-(diphenylphosphino)-ferrocer]-palladium (II) dichloride (638 mg, 873 µmol) in 1,4-dioxane (50 mL) was stirred at 90° C. until complete conversion. The mixture was filtered through Celite® and the filtrate evaporated to dryness under reduced pressure. The residue was purified by column chromatography (silica gel, hexane/EE/MeOH gradient) to give 4.36 g of the title compound.

LCMS, method 1, rt: 1.31 min, MS ES+m/z=349 (M+H)+.

Intermediate 4BD: Methyl 3-(5-ethyl-1,3-thiazol-2-yl)-5-[(3S)-tetrahydrofuran-3-yloxy]benzoate

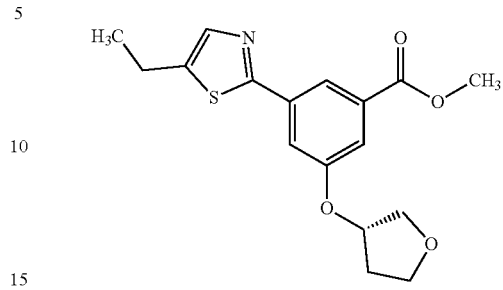

A mixture of Intermediate 94 (1.00 g, 2.87 mmol), 2-bromo-5-ethyl-1,3-thiazole (662 mg, 3.45 mmol), [1,1,-Bis-(diphenylphosphino)-ferrocer]-palladium (II) dichloride (352 mg, 431 µmol) and $K_2CO_3$ (6.9 ml, 1.0 M, 6.9 mmol) in THF (47 mL) was stirred under reflux until complete conversion and evaporated to dryness under reduced pressure. The residue was purified by column chromatography (silica gel, hexane/EE gradient) to give 327 mg (34% yield) of the title compound.

LCMS, method 1, rt: 1.33 min, MS ES+m/z=334 (M+H)+.

Intermediate 5BD: 3-(5-Ethyl-1,3-thiazol-2-yl)-5-[(3S)-tetrahydrofuran-3-yloxy]benzoic acid

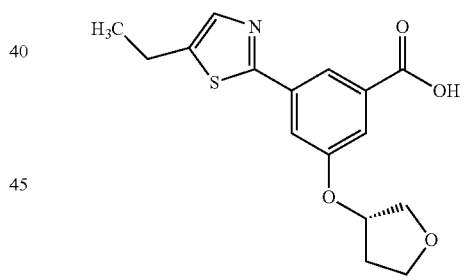

A solution of Intermediate 4BD (327 mg, 94% purity, 922 µmol) in MeOH (8.5 mL),

THF (8.5 mL) and an aqueous NaOH-solution (920 µl, 2.0 M, 1.8 mmol) was stirred at RT until complete conversion. Water was added and the pH-value adjusted to pH: 2. The aqueous phase was extracted with EE, the combined organic layers dried with $Na_2SO_4$, filtered and evaporated to dryness under reduced pressure to give 299 mg of the title compound which was used without further purification.

LCMS, method 1, rt: 1.10 min, MS ES+m/z=320 (M+H)+.

Intermediate 4BE: Methyl 3-(5-cyclobutyl-1,3-thiazol-2-yl)-5-[(3S)-tetrahydrofuran-3-yloxy]benzoate

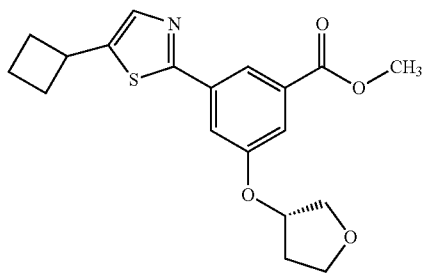 [SMILES: COC(=O)c1cc(O[C@H]2CCOC2)cc(-c2ncc(C3CCC3)s2)c1]

In analogy to the conversion of Intermediate 94 to Intermediate 4BD, reaction of Intermediate 94 (1.00 g, 2.87 mmol) with 2-chloro-5-cyclobutyl-1,3-thiazole (648 mg, 3.73 mmol) gave 410 mg (39% yield) of the title compound.
LCMS, method 1, rt: 1.46 min, MS ES+m/z=360 (M+H)$^+$.

Intermediate 5BE: 3-(5-Cyclobutyl-1,3-thiazol-2-yl)-5-[(3S)-tetrahydrofuran-3-yloxy]benzoic acid

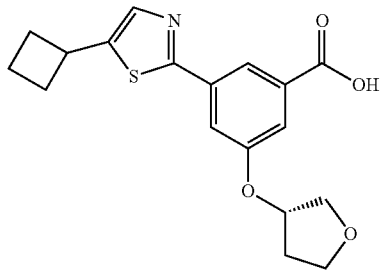 [SMILES: O=C(O)c1cc(O[C@H]2CCOC2)cc(-c2ncc(C3CCC3)s2)c1]

In analogy to the conversion of Intermediate 4BD to Intermediate 5BD, saponification of Intermediate 4BE (410 mg, 94% purity, 1.07 mmol) gave 413 mg of the title compound which was used without further purification.
LCMS, method 1, rt: 1.22 min, MS ES+m/z=346 (M+H)$^+$.

Intermediate 4BF: Methyl 3-[5-(propan-2-yl)-1,3-thiazol-2-yl]-5-[(3S)-tetrahydrofuran-3-yloxy]benzoate

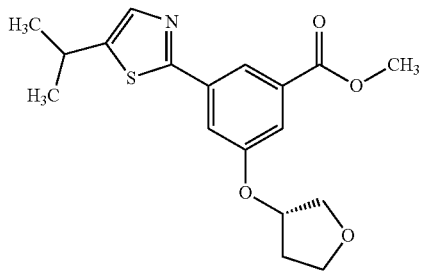 [SMILES: COC(=O)c1cc(O[C@H]2CCOC2)cc(-c2ncc(C(C)C)s2)c1]

In analogy to the conversion of Intermediate 94 to Intermediate 4BD, reaction of Intermediate 94 (1.00 g, 2.87 mmol) with 2-bromo-5-(propan-2-yl)-1,3-thiazole (710 mg, 3.45 mmol) gave 374 mg (37% yield) of the title compound.
LCMS, method 1, rt: 1.41 min, MS ES+m/z=348 (M+H)$^+$.

Intermediate 5BF: 3-[5-(Propan-2-yl)-1,3-thiazol-2-yl]-5-[(3S)-tetrahydrofuran-3-yloxy]benzoic acid

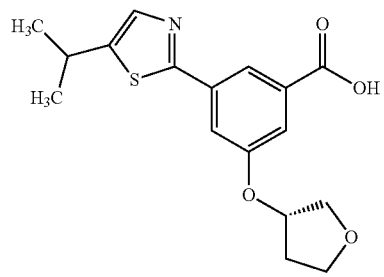 [SMILES: CC(C)c1cnc(-c2cc(O[C@H]3CCOC3)cc(C(=O)O)c2)s1]

In analogy to the conversion of Intermediate 4BD to Intermediate 5BD, saponification of Intermediate 4BF (374 mg, 94% purity, 1.01 mmol) gave 333 mg (99% yield) of the title compound which was used without further purification.
LCMS, method 1, rt: 1.17 min, MS ES+m/z=334 (M+H)$^+$.

Intermediate 4BG: Methyl 3-(5-chloro-1,3-thiazol-2-yl)-5-[(3S)-tetrahydrofuran-3-yloxy]benzoate

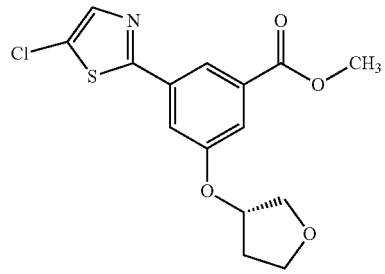 [SMILES: COC(=O)c1cc(O[C@H]2CCOC2)cc(-c2ncc(Cl)s2)c1]

In analogy to the conversion of Intermediate 94 to Intermediate 4BD, reaction of Intermediate 94 (500 mg, 1.44 mmol) with 2,5-dichloro-1,3-thiazole (288 mg, 1.87 mmol) gave 347 mg (71% yield) of the title compound.
LCMS, method 1, rt: 1.36 min, MS ES+m/z=340 (M+H)$^+$.

Intermediate 5BG: 3-(5-Chloro-1,3-thiazol-2-yl)-5-[(3S)-tetrahydrofuran-3-yloxy]benzoic acid

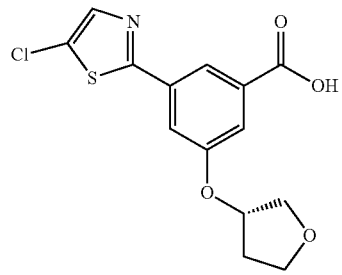 [SMILES: O=C(O)c1cc(O[C@H]2CCOC2)cc(-c2ncc(Cl)s2)c1]

In analogy to the conversion of Intermediate 4BD to Intermediate 5BD, saponification of Intermediate 4BG (347 mg, 1.02 mmol) gave 300 mg (90% yield) of the title compound which was used without further purification.
LCMS, method 1, rt: 1.12 min, MS ES+m/z=326 (M+H)$^+$.

Intermediate 4BH: Methyl 3-(5-chloro-1,3-thiazol-2-yl)-5-[(3R)-tetrahydrofuran-3-yloxy]benzoate

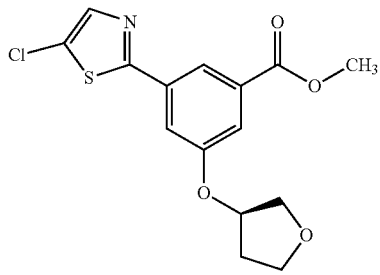 [SMILES: COC(=O)c1cc(O[C@@H]2CCOC2)cc(-c2ncc(Cl)s2)c1]

In analogy to the conversion of Intermediate 8 to Intermediate 4BA, reaction of Intermediate 8 (500 mg, 1.44 mmol) with 2,5-dichloro-1,3-thiazole (288 mg, 1.87 mmol) gave 249 mg (51% yield) of the title compound.
LCMS, method 1, rt: 1.36 min, MS ES+m/z=340 (M+H)+.

Intermediate 5BH: 3-(5-Chloro-1,3-thiazol-2-yl)-5-[(3R)-tetrahydrofuran-3-yloxy]benzoic acid

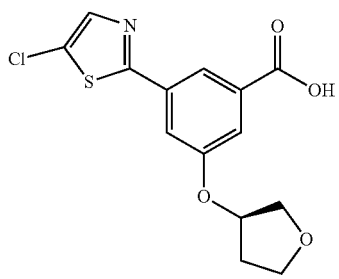 [SMILES: O=C(O)c1cc(O[C@@H]2CCOC2)cc(-c2ncc(Cl)s2)c1]

In analogy to the conversion of Intermediate 4BA to Intermediate SBA, saponification of Intermediate 4BH (239 mg, 703 µmol) gave 282 mg of the title compound which was used without further purification.
LCMS, method 1, rt: 1.11 min, MS ES+m/z=326 (M+H)+.

Intermediate 4BI: Methyl 3-(5-chloro-1,3-thiazol-2-yl)-5-(tetrahydro-2H-pyran-4-yloxy)benzoate

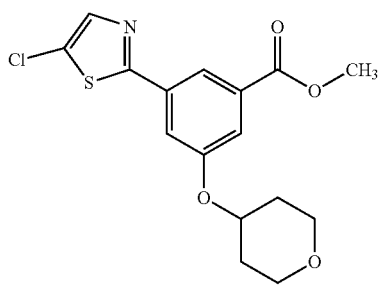 [SMILES: COC(=O)c1cc(OC2CCOCC2)cc(-c2ncc(Cl)s2)c1]

In analogy to the conversion of Intermediate 94 to Intermediate 4BD, reaction of Intermediate 14W (500 mg, 1.38 mmol) with 2,5-dichloro-1,3-thiazole (255 mg, 1.66 mmol) gave 380 mg (78% yield) of the title compound.
LCMS, method 1, rt: 1.42 min, MS ES+m/z=354 (M+H)+.

Intermediate 5BI: 3-(5-Chloro-1,3-thiazol-2-yl)-5-(tetrahydro-2H-pyran-4-yloxy)benzoic acid

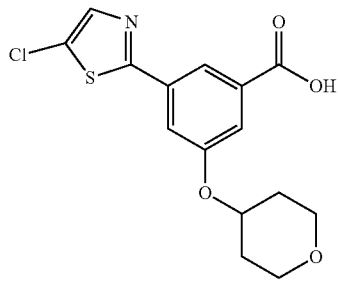 [SMILES: O=C(O)c1cc(OC2CCOCC2)cc(-c2ncc(Cl)s2)c1]

In analogy to the conversion of Intermediate 4BD to Intermediate 5BD, saponification of Intermediate 4BI (300 mg, 848 µmol) gave 353 mg of the title compound which was used without further purification.
LCMS, method 1, rt: 1.17 min, MS ES+m/z=340 (M+H)+.

Intermediate 6BA: (3R)-Tetrahydrofuran-3-ylmethyl 4-methylbenzenesulfonate

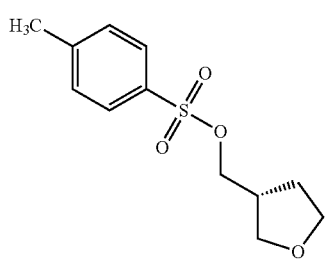 [SMILES: Cc1ccc(S(=O)(=O)OC[C@@H]2CCOC2)cc1]

In analogy to the synthesis of Intermediate 6AZ, reaction of (3S)-tetrahydrofuran-3-ylmethanol (5.4 g, 52.87 mmol) with 4-methylbenzenesulfonyl chloride (11.09 g, 58.16 mmol) gave 12.26 g (90% yield) of the title compound.
LCMS, method 1, rt: 1.02 min, MS ES+m/z=257 (M+H)+.

Intermediate 97: Methyl 3-bromo-5-[(3R)-tetrahydrofuran-3-ylmethoxy]benzoate

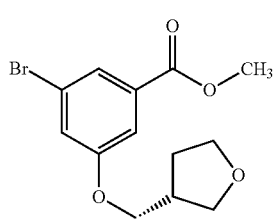

In analogy to the reaction of Intermediates 1 and 6AZ to Intermediate 95, reaction of Intermediate 1 (2.25 g, 9.75 mmol) with Intermediate 6BA (3.0 g, 11.7 mmol) gave 3.44 g of the title compound.
LCMS, method 1, rt: 1.25 min, MS ES+m/z=317 (M+H)+.

Intermediate 96: Methyl 3-[(3R)-tetrahydrofuran-3-ylmethoxy]-5-(4,4,5,5-tetramethyl-1,3,2-dioxaborolan-2-yl)benzoate

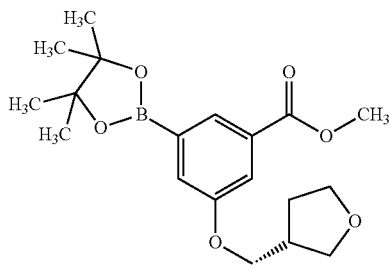

In analogy to the conversion of Intermediate 95 to Intermediate 94, reaction of Intermediate 97 (4.11 g, 13.0 mmol) with 4,4,4',4',5,5,5',5'-octamethyl-2,2'-bi-1,3,2-dioxaborolane (8.28 g, 32.6 mmol) gave 5.16 g of the title compound.

LCMS, method 1, rt: 1.43 min, MS ES+m/z=363 (M+H)+.

$^1$H NMR (400 MHz, DMSO-d$_6$) δ [ppm] 1.26-1.33 (m, 12H) 1.61-1.74 (m, 1H) 1.92-2.11 (m, 1H) 2.56-2.75 (m, 1H) 3.53 (dd, 1H) 3.65 (d, 1H) 3.71-3.82 (m, 2H) 3.85 (s, 3H) 3.96 (d, 1H) 4.00 (d, 1H) 7.38 (dd, 1H) 7.54 (dd, 1H) 7.84 (d, 1H).

Intermediate 4BJ: Methyl 3-(5-ethyl-1,3-thiazol-2-yl)-5-[(3R)-tetrahydrofuran-3-ylmethoxy]benzoate

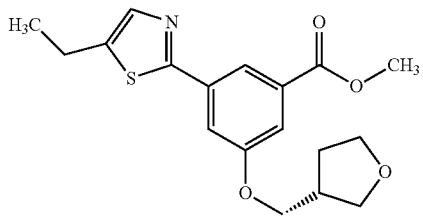

In analogy to the conversion of Intermediate 94 to Intermediate 4BD, reaction of Intermediate 96 (1.00 g, 2.76 mmol) with 2-bromo-5-ethyl-1,3-thiazole (583 mg, 3.04 mmol) gave 493 mg (51% yield) of the title compound.

LCMS, method 1, rt: 1.38 min, MS ES+m/z=348 (M+H)+.

Intermediate 5BJ: 3-(5-Ethyl-1,3-thiazol-2-yl)-5-[(3R)-tetrahydrofuran-3-ylmethoxy]benzoic acid

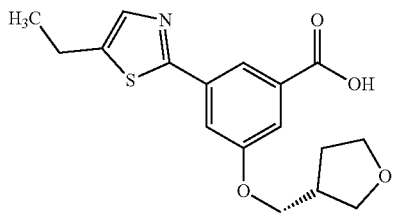

In analogy to the conversion of Intermediate 4BD to Intermediate 5BD, saponification of Intermediate 4BJ (490 mg, 94% purity, 1.33 mmol) gave 448 mg of the title compound which was used without further purification.

LCMS, method 1, rt: 1.15 min, MS ES+m/z=334 (M+H)+.

Intermediate 4BK: Methyl 3-[5-(propan-2-yl)-1,3-thiazol-2-yl]-5-[(3R)-tetrahydrofuran-3-ylmethoxy]benzoate

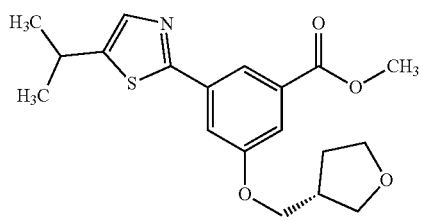 [SMILES: COC(=O)c1cc(OC[C@@H]2CCOC2)cc(-c2ncc(C(C)C)s2)c1]

In analogy to the conversion of Intermediate 94 to Intermediate 4BD, reaction of Intermediate 96 (1.00 g, 2.76 mmol) with 2-bromo-5-(propan-2-yl)-1,3-thiazole (626 mg, 3.04 mmol) gave 445 mg (45% yield) of the title compound.

LCMS, method 1, rt: 1.46 min, MS ES+m/z=362 (M+H)+.

Intermediate 5BK: 3-[5-(Propan-2-yl)-1,3-thiazol-2-yl]-5-[(3R)-tetrahydrofuran-3-ylmethoxy]benzoic acid

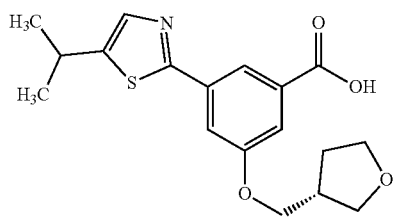 [SMILES: CC(C)c1cnc(-c2cc(OC[C@@H]3CCOC3)cc(C(=O)O)c2)s1]

In analogy to the conversion of Intermediate 4BD to Intermediate 5BD, saponification of Intermediate 4BK (450 mg, 94% purity, 1.17 mmol) gave 400 mg (98% yield) of the title compound which was used without further purification.

LCMS, method 1, rt: 1.23 min, MS ES+m/z=348 (M+H)+.

Intermediate 6BB: (2R)-Tetrahydrofuran-2-ylmethyl 4-methylbenzenesulfonate

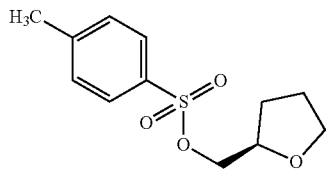 [SMILES: Cc1ccc(S(=O)(=O)OC[C@H]2CCCO2)cc1]

In analogy to the synthesis of Intermediate 6AZ, reaction of (2R)-tetrahydrofuran-2-ylmethanol (4.00 g, 39.2 mmol) with 4-methylbenzenesulfonyl chloride (8.21 g, 43.1 mmol) gave 10.1 g of the title compound.

LCMS, method 1, rt: 1.05 min, MS ES+m/z=257 (M+H)+.

Intermediate 99: Methyl 3-bromo-5-[(2R)-tetrahydrofuran-2-ylmethoxy]benzoate

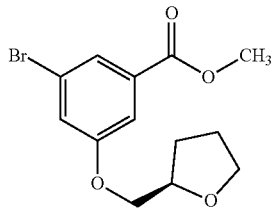 [SMILES: COC(=O)c1cc(Br)cc(OC[C@H]2CCCO2)c1]

In analogy to the reaction of Intermediates 1 and 6AZ to Intermediate 95, reaction of Intermediate 1 (4.94 g, 21.4 mmol) with Intermediate 6BB (6.58 g, 25.7 mmol) gave 6.26 g (93% yield) of the title compound.

Intermediate 98: Methyl 3-[(2R)-tetrahydrofuran-2-ylmethoxy]-5-(4,4,5,5-tetramethyl-1,3,2-dioxaborolan-2-yl)benzoate

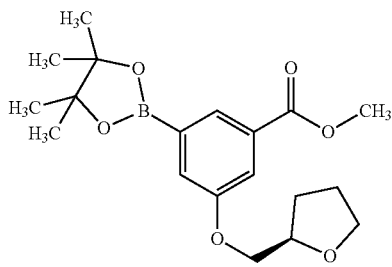

In analogy to the conversion of Intermediate 95 to Intermediate 94, reaction of Intermediate 99 (6.26 g, 19.9 mmol) with 4,4,4',4',5,5,5',5'-octamethyl-2,2'-bi-1,3,2-dioxaborolane (12.6 g, 49.7 mmol) gave 6.26 g (87% yield) of the title compound.

$^1$H NMR (400 MHz, DMSO-d$_6$) δ [ppm] 1.23-1.39 (m, 12H) 1.66-1.77 (m, 1H) 1.78-1.94 (m, 2H) 1.94-2.04 (m, 1H) 3.62-3.72 (m, 1H) 3.73-3.82 (m, 1H) 3.86 (s, 3H) 3.94-4.08 (m, 2H) 4.11-4.22 (m, 1H) 7.39 (dd, 1H) 7.55 (dd, 1H) 7.81-7.89 (m, 1H).

Intermediate 4BL: Methyl 3-(5-ethyl-1,3-thiazol-2-yl)-5-[(2R)-tetrahydrofuran-2-ylmethoxy]benzoate

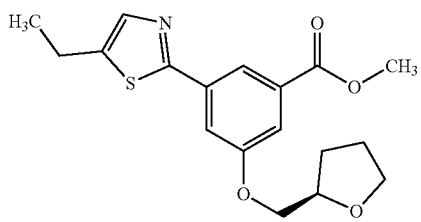 [SMILES: CCc1cnc(-c2cc(OC[C@H]3CCCO3)cc(C(=O)OC)c2)s1]

In analogy to the conversion of Intermediate 94 to Intermediate 4BD, reaction of Intermediate 98 (1.00 g, 2.76 mmol) with 2-bromo-5-ethyl-1,3-thiazole (583 mg, 3.04 mmol) gave 182 mg (19% yield) of the title compound.
LCMS, method 1, rt: 1.39 min, MS ES+m/z=348 (M+H)$^+$.

Intermediate 5BL: 3-(5-Ethyl-1,3-thiazol-2-yl)-5-[(2R)-tetrahydrofuran-2-ylmethoxy]benzoic acid

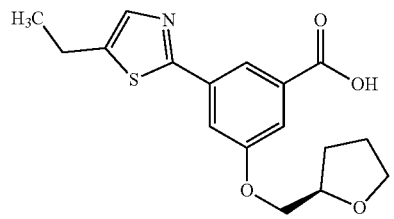 [SMILES: CCc1cnc(-c2cc(OC[C@H]3CCCO3)cc(C(=O)O)c2)s1]

In analogy to the conversion of Intermediate 4BD to Intermediate 5BD, saponification of Intermediate 4BL (188 mg, 94% purity, 509 µmol) gave 185 mg of the title compound which was used without further purification.
LCMS, method 1, rt: 1.17 min, MS ES+m/z=334 (M+H)$^+$.

Intermediate 4BM: Methyl 3-(5-cyclobutyl-1,3-thiazol-2-yl)-5-[(2R)-tetrahydrofuran-2-ylmethoxy]benzoate

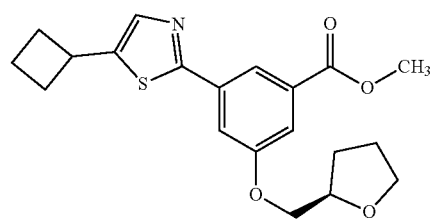 [SMILES: COC(=O)c1cc(OC[C@H]2CCCO2)cc(-c2ncc(C3CCC3)s2)c1]

In analogy to the conversion of Intermediate 94 to Intermediate 4BD, reaction of Intermediate 98 (1.00 g, 2.76 mmol) with 2-chloro-5-cyclobutyl-1,3-thiazole (527 mg, 3.04 mmol) gave 329 mg (32% yield) of the title compound.
LCMS, method 1, rt: 1.52 min, MS ES+m/z=374 (M+H)$^+$.

Intermediate 5BM: 3-(5-Cyclobutyl-1,3-thiazol-2-yl)-5-[(2R)-tetrahydrofuran-2-ylmethoxy]benzoic acid

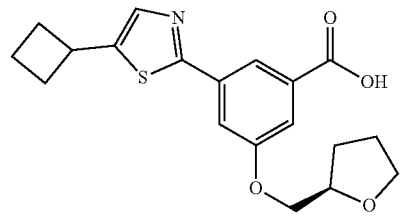 [SMILES: O=C(O)c1cc(OC[C@H]2CCCO2)cc(-c2ncc(C3CCC3)s2)c1]

In analogy to the conversion of Intermediate 4BD to Intermediate 5BD, saponification of Intermediate 4BM (329 mg, 94% purity, 828 µmol) gave 316 mg of the title compound which was used without further purification.
LCMS, method 1, rt: 1.30 min, MS ES+m/z=360 (M+H)$^+$.

Intermediate 4BN: Methyl 3-[5-(propan-2-yl)-1,3-thiazol-2-yl]-5-[(2R)-tetrahydrofuran-2-ylmethoxy]benzoate

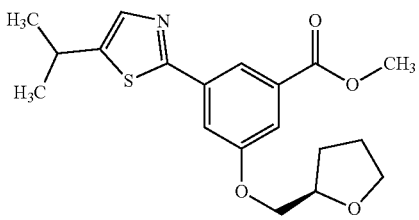 [SMILES: COC(=O)c1cc(OC[C@H]2CCCO2)cc(-c2ncc(C(C)C)s2)c1]

In analogy to the conversion of Intermediate 94 to Intermediate 4BD, reaction of Intermediate 98 (1.00 g, 2.76 mmol) with 2-bromo-5-(propan-2-yl)-1,3-thiazole (626 mg, 3.04 mmol) gave 386 mg (39% yield) of the title compound.

LCMS, method 1, rt: 1.47 min, MS ES+m/z=362 (M+H)+.

Intermediate 5BN: 3-[5-(Propan-2-yl)-1,3-thiazol-2-yl]-5-[(2R)-tetrahydrofuran-2-ylmethoxy]benzoic acid

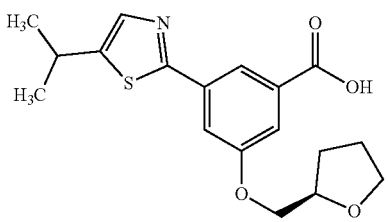 [SMILES: CC(C)c1cnc(-c2cc(OC[C@H]3CCCO3)cc(C(=O)O)c2)s1]

In analogy to the conversion of Intermediate 4BD to Intermediate 5BD, saponification of Intermediate 4BN (386 mg, 94% purity, 1.00 mmol) gave 401 mg of the title compound which was used without further purification.

LCMS, method 1, rt: 1.26 min, MS ES+m/z=348 (M+H)+.

Intermediate 101: Methyl 3-bromo-5-[(3S)-tetrahydrofuran-3-ylmethoxy]benzoate

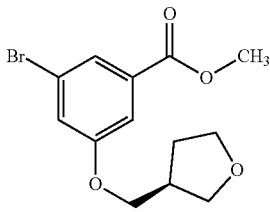 [SMILES: COC(=O)c1cc(Br)cc(OC[C@H]2CCOC2)c1]

In analogy to the reaction of Intermediates 1 and 6AZ to Intermediate 95, reaction of Intermediate 1 (4.85 g, 21.0 mmol) with Intermediate 17A (6.45 g, 25.2 mmol) gave 7.47 g of the title compound.

LCMS, method 1, rt: 1.25 min, MS ES+m/z=315 (M+H)+.

Intermediate 100: Methyl 3-[(3S)-tetrahydrofuran-3-ylmethoxy]-5-(4,4,5,5-tetramethyl-1,3,2-dioxaborolan-2-yl)benzoate

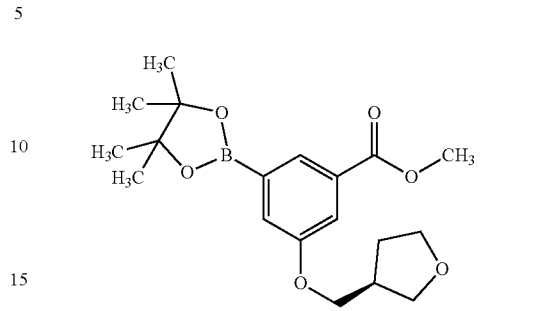

In analogy to the conversion of Intermediate 95 to Intermediate 94, reaction of Intermediate 101 (7.47 g, 23.7 mmol) with 4,4,4',4',5,5,5',5'-octamethyl-2,2'-bi-1,3,2-dioxaborolane (15.0 g, 59.3 mmol) gave 9.27 g of the title compound.

LCMS, method 1, rt: 1.36 min, MS ES+m/z=363 (M+H)+.
$^1$H NMR (400 MHz, DMSO-d$_6$) δ [ppm] 1.27-1.33 (m, 12H) 1.63-1.78 (m, 1H) 1.94-2.07 (m, 1H) 2.56-2.72 (m, 1H) 3.54 (dd, 1H) 3.66 (d, 1H) 3.73-3.83 (m, 2H) 3.86 (s, 3H) 3.99 (dd, 2H) 7.39 (dd, 1H) 7.55 (dd, 1H) 7.81-7.89 (m, 1H).

Intermediate 4BO: Methyl 3-(5-ethyl-1,3-thiazol-2-yl)-5-[(3S)-tetrahydrofuran-3-ylmethoxy]benzoate

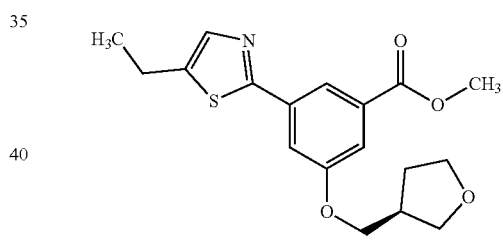

In analogy to the conversion of Intermediate 94 to Intermediate 4BD, reaction of Intermediate 100 (1.00 g, 2.76 mmol) with 2-bromo-5-ethyl-1,3-thiazole (583 mg, 3.04 mmol) gave 538 mg (56% yield) of the title compound.

LCMS, method 1, rt: 1.38 min, MS ES+m/z=348 (M+H)+.

Intermediate 5BO: 3-(5-Ethyl-1,3-thiazol-2-yl)-5-[(3S)-tetrahydrofuran-3-ylmethoxy]benzoic acid

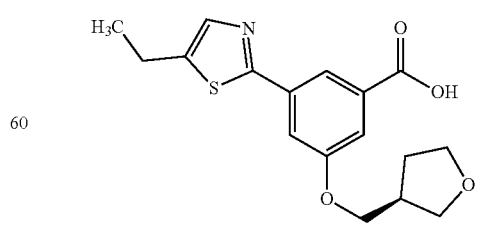

In analogy to the conversion of Intermediate 4BD to Intermediate 5BD, saponification of Intermediate 4BO (538 mg, 94% purity, 1.46 mmol) gave 525 mg of the title compound which was used without further purification.

LCMS, method 1, rt: 1.15 min, MS ES+m/z=334 (M+H)+.

Intermediate 4BP: Methyl 3-[5-(propan-2-yl)-1,3-thiazol-2-yl]-5-[(3S)-tetrahydrofuran-3-ylmethoxy]benzoate

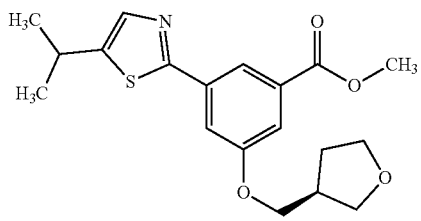

In analogy to the conversion of Intermediate 94 to Intermediate 4BD, reaction of Intermediate 100 (1.00 g, 2.76 mmol) with 2-bromo-5-(propan-2-yl)-1,3-thiazole (626 mg, 3.04 mmol) gave 570 mg (57% yield) of the title compound.

LCMS, method 1, rt: 1.46 min, MS ES+m/z=362 (M+H)+.

Intermediate 5BP: 3-[5-(Propan-2-yl)-1,3-thiazol-2-yl]-5-[(3S)-tetrahydrofuran-3-ylmethoxy]benzoic acid

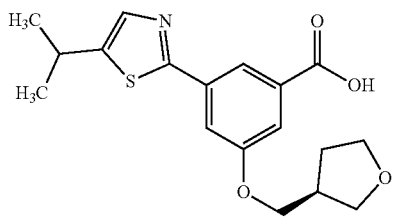 [SMILES: CC(C)c1cnc(-c2cc(OC[C@H]3CCOC3)cc(C(=O)O)c2)s1]

In analogy to the conversion of Intermediate 4BD to Intermediate 5BD, saponification of Intermediate 4BP (570 mg, 94% purity, 1.48 mmol) gave 534 mg of the title compound which was used without further purification.

LCMS, method 1, rt: 1.22 min, MS ES+m/z=348 (M+H)+.

Intermediate 4BQ: Methyl 3-(5-chloro-1,3-thiazol-2-yl)-5-[(3S)-tetrahydrofuran-3-ylmethoxy]benzoate

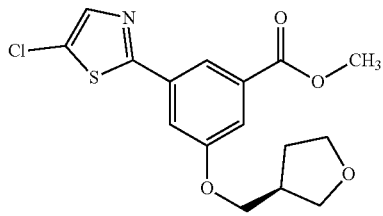 [SMILES: COC(=O)c1cc(OC[C@H]2CCOC2)cc(-c2ncc(Cl)s2)c1]

In analogy to the conversion of Intermediate 94 to Intermediate 4BD, reaction of Intermediate 100 (100 mg, 276 µmol) with 2,5-dichloro-1,3-thiazole (51.0 mg, 331 µmol) gave 77.8 mg (80% yield) of the title compound.

LCMS, method 1, rt: 1.42 min, MS ES+m/z=354 (M+H)+.

1H NMR (500 MHz, DMSO-d6) δ [ppm] 1.71 (d, 1H) 1.98-2.11 (m, 1H) 2.61-2.75 (m, 1H) 3.57 (dd, 1H) 3.67 (td, 1H) 3.73-3.85 (m, 2H) 3.89 (s, 3H) 3.98-4.05 (m, 1H) 4.06-4.16 (m, 1H) 7.55 (dd, 1H) 7.64 (dd, 1H) 7.96-8.06 (m, 2H).

Intermediate 5BQ: 3-(5-Chloro-1,3-thiazol-2-yl)-5-[(3S)-tetrahydrofuran-3-ylmethoxy]benzoic acid

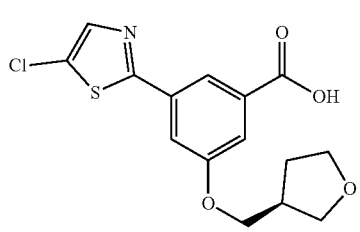 [SMILES: O=C(O)c1cc(OC[C@H]2CCOC2)cc(-c2ncc(Cl)s2)c1]

In analogy to the conversion of Intermediate 4BD to Intermediate 5BD, saponification of Intermediate 4BQ (347 mg, 981 µmol) gave 329 mg (99% yield) of the title compound which was used without further purification.

LCMS, method 1, rt: 1.18 min, MS ES+m/z=340 (M+H)+.

Intermediate 6BC: (2S)-Tetrahydrofuran-2-ylmethyl 4-methylbenzenesulfonate

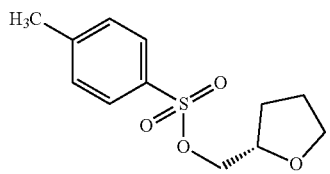 [SMILES: Cc1ccc(S(=O)(=O)OC[C@@H]2CCCO2)cc1]

In analogy to the synthesis of Intermediate 6AZ, reaction of (2S)-tetrahydrofuran-2-ylmethanol (3.00 g, 29.4 mmol) with 4-methylbenzenesulfonyl chloride (6.16 g, 32.3 mmol) gave 6.22 g (83% yield) of the title compound.

LCMS, method 1, rt: 1.06 min, MS ES+m/z=257 (M+H)+.

Intermediate 103: Methyl 3-bromo-5-[(2S)-tetrahydrofuran-2-ylmethoxy]benzoate

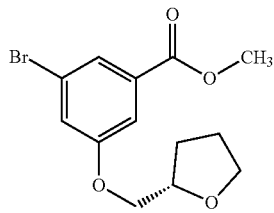 [SMILES: COC(=O)c1cc(Br)cc(OC[C@@H]2CCCO2)c1]

In analogy to the reaction of Intermediates 1 and 6AZ to Intermediate 95, reaction of Intermediate 1 (4.94 g, 21.4 mmol) with Intermediate 6BC (6.58 g, 25.7 mmol) gave 4.08 g (61% yield) of the title compound.

LCMS, method 1, rt: 1.26 min, MS ES+m/z=315 (M+H)+.

Intermediate 102: Methyl 3-[(2S)-tetrahydrofuran-2-ylmethoxy]-5-(4,4,5,5-tetramethyl-1,3,2-dioxaborolan-2-yl)benzoate

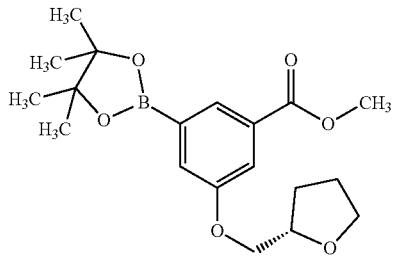

In analogy to the conversion of Intermediate 95 to Intermediate 94, reaction of Intermediate 103 (4.08 g, 12.9 mmol) with 4,4,4',4',5,5,5',5'-octamethyl-2,2'-bi-1,3,2-dioxaborolane (8.22 g, 32.4 mmol) gave 6.62 g (80% yield) of the title compound.

LCMS, method 1, rt: 1.40 min, MS ES-m/z=641 (M−H)⁻.

Intermediate 4BR: Methyl 3-(5-ethyl-1,3-thiazol-2-yl)-5-[(2S)-tetrahydrofuran-2-ylmethoxy]benzoate

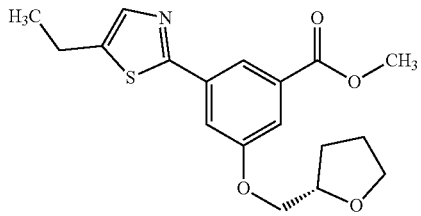 [SMILES: CCc1cnc(-c2cc(OC[C@@H]3CCCO3)cc(C(=O)OC)c2)s1]

In analogy to the conversion of Intermediate 94 to Intermediate 4BD, reaction of Intermediate 102 (1.00 g, 2.76 mmol) with 2-bromo-5-ethyl-1,3-thiazole (583 mg, 3.04 mmol) gave 480 mg (50% yield) of the title compound.

LCMS, method 1, rt: 1.40 min, MS ES+m/z=348 (M+H)⁺.

Intermediate 5BR: 3-(5-Ethyl-1,3-thiazol-2-yl)-5-[(2S)-tetrahydrofuran-2-ylmethoxy]benzoic acid

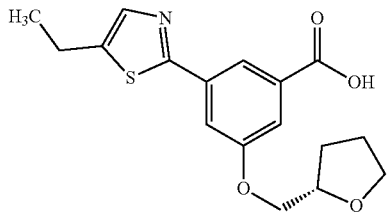 [SMILES: CCc1cnc(-c2cc(OC[C@@H]3CCCO3)cc(C(=O)O)c2)s1]

In analogy to the conversion of Intermediate 4BD to Intermediate 5BD, saponification of Intermediate 4BR (480 mg, 94% purity, 1.30 mmol) gave 552 mg of the title compound which was used without further purification.

LCMS, method 1, rt: 1.19 min, MS ES+m/z=334 (M+H)⁺.

Intermediate 4BS: Methyl 3-(5-cyclobutyl-1,3-thiazol-2-yl)-5-[(2S)-tetrahydrofuran-2-ylmethoxy]benzoate

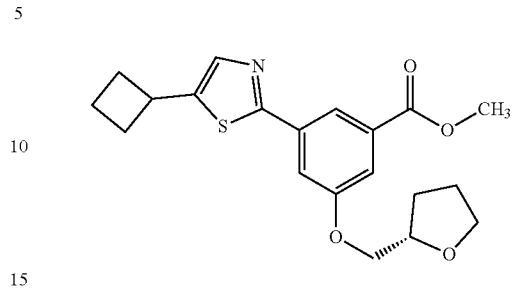

In analogy to the conversion of Intermediate 94 to Intermediate 4BD, reaction of Intermediate 102 (1.00 g, 2.76 mmol) with 2-chloro-5-cyclobutyl-1,3-thiazole (527 mg, 3.04 mmol) gave 590 mg (58% yield) of the title compound.

LCMS, method 1, rt: 1.52 min, MS ES+m/z=374 (M+H)⁺.

Intermediate 5BS: 3-(5-Cyclobutyl-1,3-thiazol-2-yl)-5-[(2S)-tetrahydrofuran-2-ylmethoxy]benzoic acid

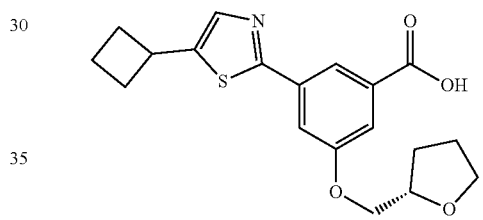

In analogy to the conversion of Intermediate 4BD to Intermediate 5BD, saponification of Intermediate 4BS (594 mg, 94% purity, 1.50 mmol) gave 634 mg of the title compound which was used without further purification.

LCMS, method 1, rt: 1.31 min, MS ES+m/z=360 (M+H)⁺.

Intermediate 4BT: Methyl 3-[5-(propan-2-yl)-1,3-thiazol-2-yl]-5-[(2S)-tetrahydrofuran-2-ylmethoxy]benzoate

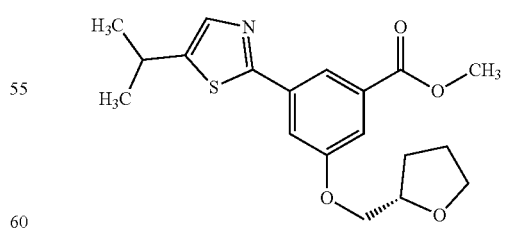

In analogy to the conversion of Intermediate 94 to Intermediate 4BD, reaction of Intermediate 102 (1.00 g, 2.76 mmol) with 2-bromo-5-(propan-2-yl)-1,3-thiazole (626 mg, 3.04 mmol) gave 485 mg (49% yield) of the title compound.

LCMS, method 1, rt: 1.47 min, MS ES+m/z=362 (M+H)⁺.

Intermediate 5BT: 3-[5-(Propan-2-yl)-1,3-thiazol-2-yl]-5-[(2S)-tetrahydrofuran-2-ylmethoxy]benzoic acid

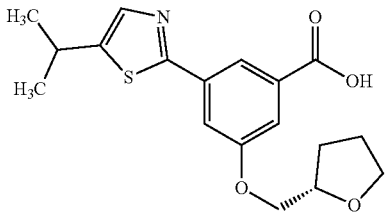 [SMILES: CC(C)c1cnc(-c2cc(OC[C@@H]3CCCO3)cc(C(=O)O)c2)s1]

In analogy to the conversion of Intermediate 4BD to Intermediate 5BD, saponification of Intermediate 4BT (490 mg, 94% purity, 1.27 mmol) gave 444 mg (100% yield) of the title compound which was used without further purification.

LCMS, method 1, rt: 1.25 min, MS ES+m/z=348 (M+H)+.

Intermediate 104: 1-(2,2,2-Trifluoroethyl)piperidin-4-ol

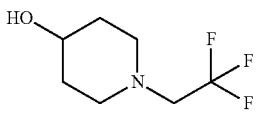

A mixture of 1-(2,2,2-trifluoroethyl)piperidin-4-one (2.40 g, 13.2 mmol), NaBH$_4$ (1.50 g, 39.7 mmol) in MeOH was stirred at rt for 16 hours. A saturated aqueous NaHCO$_3$-solution was added and the aqueous layer extracted with DCM (3 x). The combined organic layers were reduced to dryness under reduced pressure to give 2.14 g (88% yield) which was used without further purification.

Intermediate 6BD: 1-(2,2,2-Trifluoroethyl)piperidin-4-yl 4-methylbenzenesulfonate

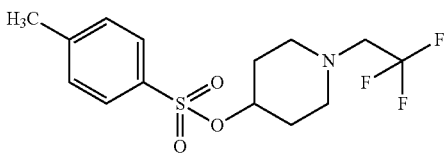 [SMILES: Cc1ccc(S(=O)(=O)OC2CCN(CC(F)(F)F)CC2)cc1]

In analogy to the synthesis of Intermediate 6AZ, reaction of Intermediate 104 (2.14 g, 11.7 mmol) with 4-methylbenzenesulfonyl chloride (2.45 g, 12.9 mmol) gave 3.70 g (94% yield) of the title compound.

$^1$H NMR (400 MHz, DMSO-d$_6$) δ [ppm] 1.59 (m, 2H) 1.65-1.79 (m, 2H) 2.42 (s, 3H) 2.70 (m, 2H) 3.14 (q, J=10.31 Hz, 2H) 4.52 (dt, 1H) 7.47 (d, 2H) 7.75-7.86 (m, 2H).

Intermediate 4BU: Methyl 3-(5-methyl-1,3-thiazol-2-yl)-5-{[1-(2,2,2-trifluoroethyl)piperidin-4-yl]oxy}benzoate

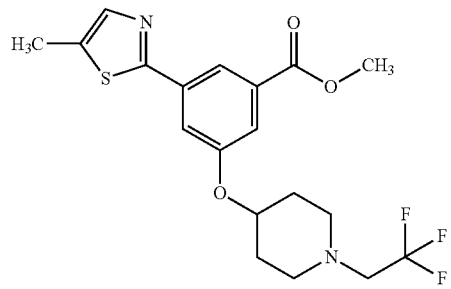 [SMILES: COC(=O)c1cc(OC2CCN(CC(F)(F)F)CC2)cc(-c2ncc(C)s2)c1]

In analogy to the reaction of Intermediates 3A with 6AY to Intermediate 4AZ, reaction of Intermediate 3 (1.89 g, 7.59 mmol) with Intermediate 6BD (3.7 g, 90% purity, 9.87 mmol) gave 2.0 g (64% yield) of the title compound.

$^1$H NMR (400 MHz, DMSO-d$_6$) δ [ppm] 1.69 (d, 2H) 1.93 (d, 2H) 2.58-2.69 (m, 2H) 2.78-2.92 (m, 2H) 3.13-3.27 (m, 2H) 3.89 (s, 3H) 4.55-4.69 (m, 1H) 7.51 (dd, 1H) 7.61-7.69 (m, 2H) 7.97 (t, 1H).

Intermediate 5BU: 3-(5-Methyl-1,3-thiazol-2-yl)-5-{[1-(2,2,2-trifluoroethyl)piperidin-4-yl]oxy}benzoic acid

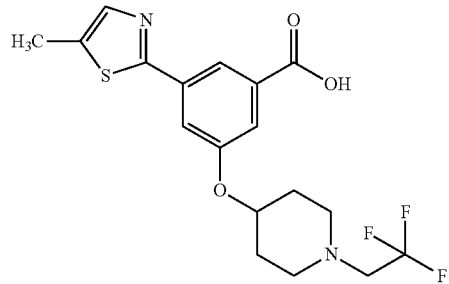 [SMILES: Cc1cnc(-c2cc(OC3CCN(CC(F)(F)F)CC3)cc(C(=O)O)c2)s1]

In analogy to the conversion of Intermediate 4BD to Intermediate 5BD, saponification of Intermediate 4BU (2.0 g, 4.83 mmol) gave 1.9 g (98% yield) of the title compound which was used without further purification.

$^1$H NMR (400 MHz, DMSO-d$_6$) δ [ppm] 1.58-1.77 (m, 2H) 1.95 (dd, 2H) 2.57-2.69 (m, 2H) 2.76-2.94 (m, 2H) 3.20 (q, 2H) 4.46-4.67 (m, 1H) 7.50 (dd, 1H) 7.53-7.69 (m, 2H) 7.95 (t, 1H).

Intermediate 105: 1-(2,2-Difluoroethyl)piperidin-4-ol

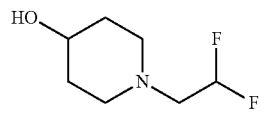

In analogy to the synthesis of Intermediate 104, reduction of 1-(2,2-difluoroethyl)piperidin-4-one (2.70 g, 16.5 mmol) gave 2.20 g (80% yield) of the title compound which was used without further purification.

Intermediate 6BE: 1-(2,2-Difluoroethyl)piperidin-4-yl 4-methylbenzenesulfonate

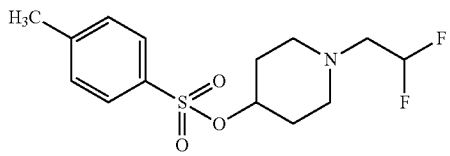 [SMILES: Cc1ccc(S(=O)(=O)OC2CCN(CC(F)F)CC2)cc1]

In analogy to the synthesis of Intermediate 6AZ, reaction of Intermediate 105 (2.20 g, 13.3 mmol) with 4-methylbenzenesulfonyl chloride (2.79 g, 14.7 mmol) gave 4.80 g of the title compound.

LCMS, method 1, rt: 0.86 min, MS ES+m/z=320 (M+H)⁺.

Intermediate 4BV: Methyl 3-{[1-(2,2-difluoroethyl)piperidin-4-yl]oxy}-5-(5-methyl-1,3-thiazol-2-yl)benzoate

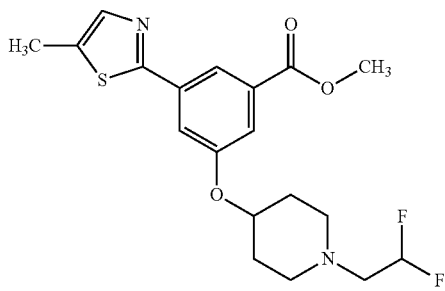 [SMILES: COC(=O)c1cc(OC2CCN(CC(F)F)CC2)cc(-c2ncc(C)s2)c1]

In analogy to the reaction of Intermediates 3A with 6AY to Intermediate 4AZ, reaction of Intermediate 3 (2.25 g, 9.02 mmol) with Intermediate 6BE (4.80 g, 90% purity, 13.5 mmol) gave 2.1 g (59% yield) of the title compound.

LCMS, method 1, rt: 0.94 min, MS ES+m/z=397 (M+H)⁺.

Intermediate 5BV: 3-{[1-(2,2-Difluoroethyl)piperidin-4-yl]oxy}-5-(5-methyl-1,3-thiazol-2-yl)benzoic acid

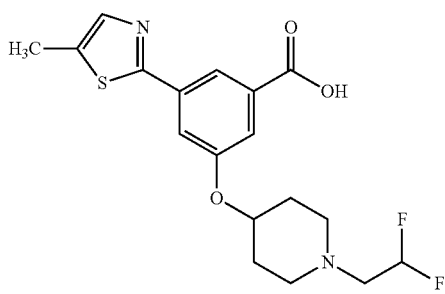 [SMILES: Cc1cnc(-c2cc(OC3CCN(CC(F)F)CC3)cc(C(=O)O)c2)s1]

In analogy to the conversion of Intermediate 4BD to Intermediate 5BD, saponification of Intermediate 4BV (2.10 g, 5.30 mmol) gave 600 mg (30% yield) of the title compound which was used without further purification.

LCMS, method 1, rt: 0.76 and 0.83 min, MS ES+m/z=383 (M+H)⁺.

Intermediate 6BF: (3-Methyloxetan-3-yl)methyl 4-methylbenzenesulfonate

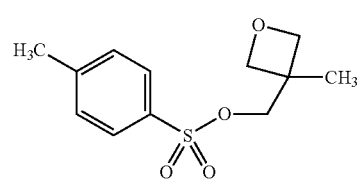

In analogy to the synthesis of Intermediate 6AZ, reaction of (3-methyloxetan-3-yl)methanol (630 mg, 6.17 mmol) with 4-methylbenzenesulfonyl chloride (1.29 g, 6.79 mmol) gave 1.20 g (76% yield) of the title compound.

¹H NMR (400 MHz, DMSO-d₆) δ ppm 1.13-1.23 (m, 3H) 2.43 (s, 3H) 4.11 (s, 2H) 4.15-4.20 (m, 2H) 4.22-4.28 (m, 2H) 7.50 (d, 2H) 7.77-7.86 (m, 2H).

Intermediate 4BW: Methyl 3-[(3-methyloxetan-3-yl)methoxy]-5-(5-methyl-1,3-thiazol-2-yl)benzoate

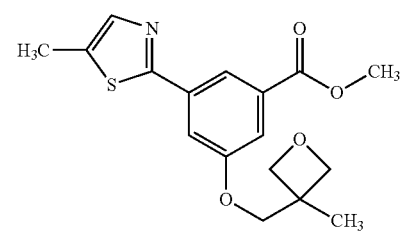

In analogy to the reaction of Intermediates 3A with 6AY to Intermediate 4AZ, reaction of Intermediate 3 (200 mg, 802 μmol) with Intermediate 6BF (308 mg, 1.20 mmol) gave 80.0 mg (30% yield) of the title compound.

LCMS, method 1, rt: 1.24 min, MS ES+m/z=334 (M+H)⁺.

Intermediate 5BW: 3-[(3-Methyloxetan-3-yl)methoxy]-5-(5-methyl-1,3-thiazol-2-yl)benzoic acid

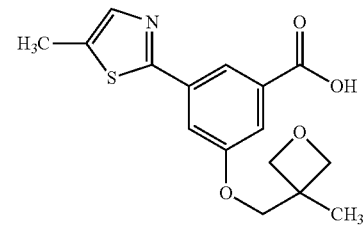

In analogy to the conversion of Intermediate 4BD to Intermediate 5BD, saponification of Intermediate 4BW (80.0 mg, 240 μmol) gave 75.0 mg (98% yield) of the title compound which was used without further purification.

LCMS, method 1, rt: 1.03 min, MS ES+m/z=320 (M+H)⁺.

Intermediate 6BG: (2-Methyltetrahydrofuran-2-yl)methyl 4-methylbenzenesulfonate, mixture of two enantiomers

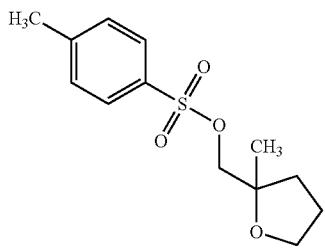 [SMILES: Cc1ccc(S(=O)(=O)OCC2(C)CCCO2)cc1]

In analogy to the synthesis of Intermediate 6AZ, reaction of racemic (2-methyltetrahydrofuran-2-yl)methanol (944 mg, 8.13 mmol) with 4-methylbenzenesulfonyl chloride (1.70 g, 8.94 mmol) gave 1.68 g (76% yield) of the title compound.

$^1$H NMR (400 MHz, DMSO-d6) δ [ppm] 0.99-1.12 (s, 3H) 1.47-1.65 (m, 1H) 1.66-1.89 (m, 3H) 2.37-2.47 (s, 3H) 3.49-3.63 (m, 1H) 3.63-3.74 (m, 1H) 3.78-3.92 (m, 2H) 7.49 (d, 2H) 7.72-7.96 (d, 2H).

Intermediate 5BX: 3-[(2-Methyltetrahydrofuran-2-yl)methoxy]-5-(5-methyl-1,3-thiazol-2-yl)benzoic acid, mixture of two enantiomers

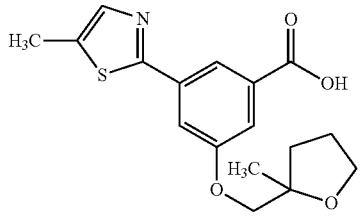 [SMILES: Cc1cnc(-c2cc(OCC3(C)CCCO3)cc(C(=O)O)c2)s1]

A mixture of Intermediate 3 (400 mg, 1.60 mmol), Intermediate 6BG (650 mg, 2.40 mmol) and Cs$_2$CO$_3$ (783 mg, 2.40 mmol) in DMF (12 mL) was stirred at 90° C. for 3 days. The mixture was filtrated and and the filtrate evaporated to dryness under reduced pressure to give 2.34 of the title compound which was used without further purification.

LCMS, method 1, rt: 1.18 min, MS ES+m/z=334 (M+H)$^+$.

Intermediate 6BH: (3-Methyltetrahydrofuran-3-yl]methyl 4-methylbenzenesulfonate, mixture of two enantiomers

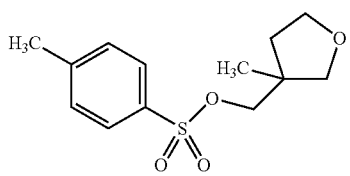 [SMILES: Cc1ccc(S(=O)(=O)OCC2(C)CCOC2)cc1]

In analogy to the synthesis of Intermediate 6AZ, reaction of racemic (3-methyltetrahydrofuran-3-yl)methanol (1.00 g, 8.61 mmol) with 4-methylbenzenesulfonyl chloride (1.81 g, 9.47 mmol) gave 2.00 g (82% yield) of the title compound.

$^1$H NMR (400 MHz, DMSO-d$_6$) δ [ppm] 0.93-1.05 (m, 3H) 1.54 (ddd, 1H) 1.69 (ddd, 1H) 2.37-2.47 (m, 3H) 3.22 (dl H) 3.45 (d, 1H) 3.59-3.73 (m, 2H) 3.81-3.92 (m, 2H) 7.50 (d, 2H) 7.80 (d, 2H).

Intermediate 4BY: Methyl 3-[(3-methyltetrahydrofuran-3-yl)methoxy]-5-(5-methyl-1,3-thiazol-2-yl)benzoate, mixture of two enantiomers

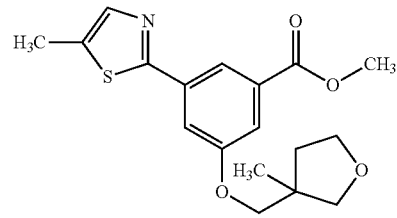

In analogy to the reaction of Intermediates 3A with 6AY to Intermediate 4AZ, reaction of Intermediate 3 (1.11 g, 4.44 mmol) with Intermediate 6BH (2.00 g, 90% purity, 6.66 mmol) gave 1.10 g (75% purity, 53% yield) of the title compound.

LCMS, method 1, rt: 1.37 min, MS ES+m/z=348 (M+H)$^+$.

Intermediate 5BY: 3-[(3-Methyltetrahydrofuran-3-yl)methoxy]-5-(5-methyl-1,3-thiazol-2-yl)benzoic acid, mixture of two enantiomers

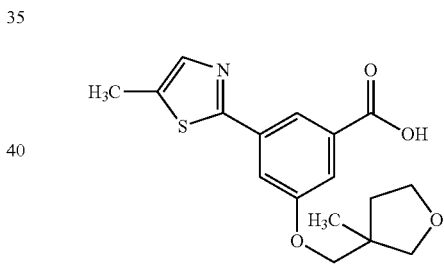

In analogy to the conversion of Intermediate 4BD to Intermediate 5BD, saponification of Intermediate 4BY (1.10 g, 3.17 mmol) gave 700 mg (63% yield) of the title compound which was used without further purification.

$^1$H NMR (400 MHz, DMSO-d$_6$) δ [ppm] 1.21 (s, 3H) 1.67 (ddd, 1H) 1.86-2.01 (m, 1H) 3.39 (d, 1H) 3.71 (d, 1H) 3.75-3.88 (m, 2H) 3.90-4.03 (m, 2H) 7.53 (dd, 1H) 7.56-7.67 (m, 2H) 7.98 (t, 1H).

Intermediate 4BI: 1-Methyl-6-oxopiperidin-3-yl 4-methylbenzenesulfonate, mixture of two enantiomers

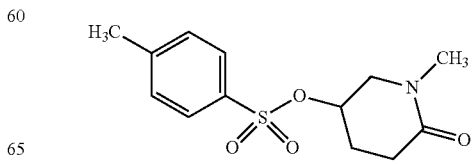

In analogy to the synthesis of Intermediate 6AZ, reaction of racemic 5-hydroxy-1-methylpiperidin-2-one (800 mg, 6.19 mmol) with 4-methylbenzenesulfonyl chloride (1.33 g, 6.81 mmol) gave 1.33 g (76% yield) of the title compound.

$^1$H NMR (400 MHz, DMSO-d$_6$) δ [ppm] 1.74-1.87 (m, 1H) 1.87-2.01 (m, 1H) 2.15-2.25 (m, 2H) 2.43 (s, 3H) 2.71 (s, 3H) 3.19-3.28 (m, 1H) 3.53 (dd, 1H) 4.88-5.02 (m, 1H) 7.49 (d, 2H) 7.79-7.91 (m, 2H).

Intermediate 4BZ: Methyl 3-[(1-methyl-6-oxopiperidin-3-yl)oxy]-5-(5-methyl-1,3-thiazol-2-yl)benzoate, mixture of two enantiomers

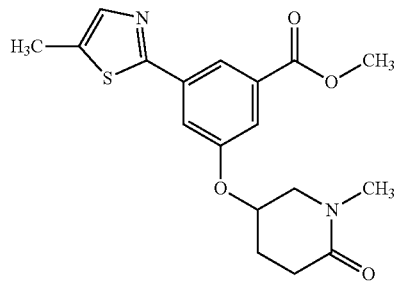 [SMILES: COC(=O)c1cc(OC2CCC(=O)N(C)C2)cc(-c2ncc(C)s2)c1]

In analogy to the reaction of Intermediates 3A with 6AY to Intermediate 4AZ, reaction of Intermediate 3 (702 mg, 2.82 mmol) with Intermediate 4BI (1.33 g, 90% purity, 4.22 mmol) gave 350 mg (34% yield) of the title compound.

$^1$H NMR (400 MHz, DMSO-d$_6$) δ [ppm] 2.06 (br. s., 2H) 2.20-2.30 (m, 1H) 2.31-2.42 (m, 1H) 2.81 (s, 3H) 3.41-3.46 (m, 1H) 3.65 (m, 1H) 3.89 (s, 3H) 4.99-5.13 (m, 1H) 7.57 (dd, 1H) 7.63-7.74 (m, 2H) 8.02 (t, 1H).

Intermediate 5BZ: 3-[(1-Methyl-6-oxopiperidin-3-yl)oxy]-5-(5-methyl-1,3-thiazol-2-yl)benzoic acid, mixture of two enantiomers

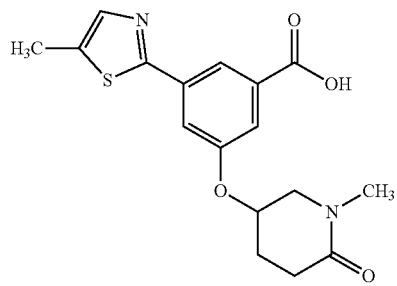 [SMILES: Cc1cnc(-c2cc(OC3CCC(=O)N(C)C3)cc(C(=O)O)c2)s1]

In analogy to the conversion of Intermediate 4BD to Intermediate 5BD, saponification of Intermediate 4BZ (350 mg, 971 μmol) gave 330 mg (98% yield) of the title compound which was used without further purification.

$^1$H NMR (400 MHz, DMSO-d$_6$) δ [ppm] 2.01-2.10 (m, 2H) 2.21-2.31 (m, 1H) 2.31-2.42 (m, 1H) 2.79-2.84 (m, 3H) 3.39-3.45 (m, 2H) 3.66 (dd, 1H) 5.05 (m, 1H) 7.55 (dd, 1H) 7.62-7.71 (m, 2H) 8.00 (t, 1H).

Intermediate 4CA: Methyl 3-[(2-hydroxycyclopentyl)oxy]-5-(5-methyl-1,3-thiazol-2-yl)benzoate, mixture of two trans stereoisomers

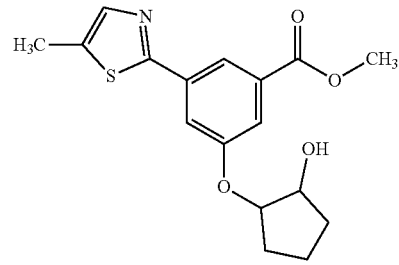

A mixture of Intermediate 3 (360 mg, 1.44 mmol), 6-oxabicyclo[3.1.0]hexane (182 mg, 2.17 mmol), KOtBu (16.2 mg, 144 μmol) in DMF (11 mL) was stirred at 130° C. for 6 hours. To this mixture was added water and DCM, and the phases were separated. The organic layer was extracted with DCM (3 x). The combined organic layers were evaporated to dryness and the residue was purified by column chromatography to give 800 mg of the title compound which was used without further purification.

LCMS, method 1, rt: 1.21 min, MS ES+m/z=334 (M+H)$^+$.

Intermediate 5CA: 3-[(2-Hydroxycyclopentyl)oxy]-5-(5-methyl-1,3-thiazol-2-yl)benzoic acid, mixture of two trans stereoisomers

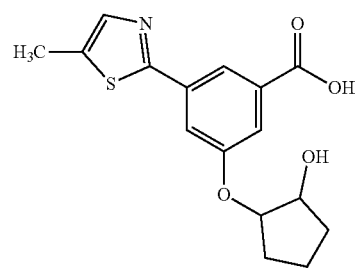 [SMILES: Cc1cnc(-c2cc(OC3CCCC3O)cc(C(=O)O)c2)s1]

In analogy to the conversion of Intermediate 4BD to Intermediate 5BD, saponification of Intermediate 4CA (500 mg, 1.50 mmol) gave 380 mg (79% yield) of the title compound which was used without further purification.

Intermediate 5CB: 3-[(3-Hydroxybutan-2-yl)oxy]-5-(5-methyl-1,3-thiazol-2-yl)benzoic acid, mixture of two trans stereoisomers

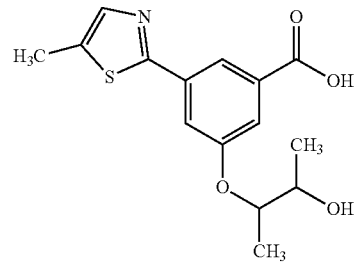 [SMILES: Cc1cnc(-c2cc(OC(C)C(C)O)cc(C(=O)O)c2)s1]

Intermediate 3 (600 mg, 2.4 mmol) and cis-2,3-epoxybutane (840 µl, 9.6 mmol) in THF (18.0 mL) were treated with NaOH (14.4 ml, 1.0 M, 14.4 mmol) and heated under reflux for 72 hours. The pH-value was adjusted to pH: 5, the reaction mixture extracted with ethyl acetate, the combined organic layers dried with $Na_2SO_4$, filtered and evaporated to dryness under reduced pressure to give 1.30 g of the title compound which was used without further purification.

LCMS, method 1, rt: 0.97 min, MS ES+m/z=308 (M+H)$^+$.

Intermediate 4CC: Methyl 3-(2-hydroxy-2-methyl-propoxy)-5-(5-methyl-1,3-thiazol-2-yl)benzoate

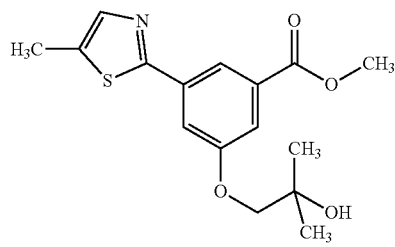

A mixture of Intermediate 3 (221 mg, 887 µmol), 2,2-dimethyloxirane (320 mg, 4.43 mmol) and $K_2CO_3$ (245 mg, 1.77 mmol) in DMSO (17 mL) was stirred for 3 hours at 130° C. The mixture was evaporated to dryness under reduced pressure and purified by column chromatography (silica gel) to give 230 mg (81% yield) of the title compound.

Intermediate 5CC: 3-(2-Hydroxy-2-methylpropoxy)-5-(5-methyl-1,3-thiazol-2-yl)benzoic acid

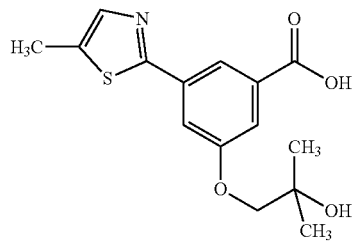 [SMILES: Cc1cnc(-c2cc(OCC(C)(C)O)cc(C(=O)O)c2)s1]

In analogy to the conversion of Intermediate 4BD to Intermediate 5BD, saponification of Intermediate 4CC (230 mg, 716 µmol) gave 180 mg (82% yield) of the title compound which was used without further purification.

Intermediate 106: Tert-butyl 9-[3-cyano-5-(5-methyl-1,3-thiazol-2-yl)phenoxy]-3-oxa-7-azabicyclo[3.3.1]nonane-7-carboxylate, mixture of two stereoisomers (syn/anti)

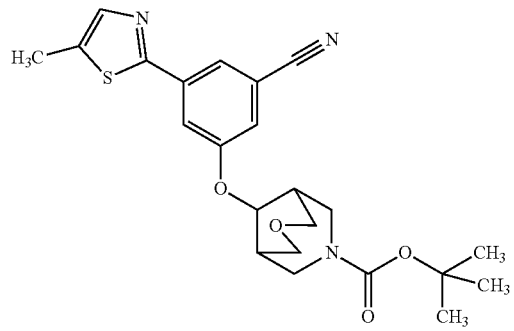 [SMILES: Cc1cnc(-c2cc(C#N)cc(OC3C4COCC3CN(C(=O)OC(C)(C)C)C4)c2)s1]

To a solution of tert-butyl 9-hydroxy-3-oxa-7-azabicyclo[3.3.1]nonane-7-carboxylate (mixture of two stereoisomers (syn/anti), 900 mg, 3.70 mmol) in DMF (12 mL) was added NaH (148 mg, 60% purity, 3.70 mmol) and the mixture was stirred at RT for 1 hour. Intermediate 26 was added (621 mg, 2.85 mmol) and the resulting mixture stirred for 17 hours at RT. Water was careful added, the mixture stirred for 30 min and extracted with EE. The combined organic layers were washed with water and saturated aqueous NaCl-solution, dried with $Na_2SO_4$, filters and evaporated to dryness under reduced pressure. The residue was purified by column chromatography to give 665 mg (53% yield) of the title compound.

LCMS, method 1, rt: 1.40 min, MS ES+m/z=442 (M+H)$^+$.

Intermediate 107: 3-{[7-(Tert-butoxycarbonyl)-3-oxa-7-azabicyclo[3.3.1]non-9-yl]oxy}-5-(5-methyl-1,3-thiazol-2-yl)benzoic acid, mixture of two stereoisomers (syn/anti)

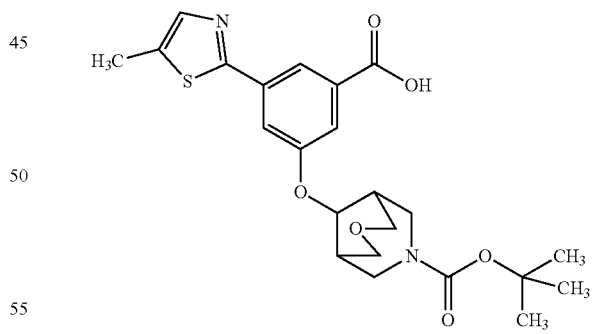

To a solution of Intermediate 106 (670 mg, 1.52 mmol) in DMSO (5 mL) was added sodium hydroxide (7.6 ml, 2.0 M, 15 mmol) and the mixture stirred at 110° C. for 3 hours. The mixture was acidified with 2 M aqueous HCl-solution and the pH-value adjusted to pH: 5. The solution was extracted with EE, the combined organic layers dried with $Na_2SO_4$, filtered and evaporated to dryness under reduced pressure to give 808 mg of the title compound which was used without further purification. LCMS, method 1, rt: 1.23 min, MS ES+m/z=461 (M+H)$^+$.

Intermediate 108: Tert-butyl 9-[3-(5-methyl-1,3-thiazol-2-yl)-5-({(1R)-1-[2-(trifluoromethyl)pyrimidin-5-yl]ethyl}carbamoyl)phenoxy]-3-oxa-7-azabicyclo[3.3.1]nonane-7-carboxylate, mixture of two stereoisomers (syn/anti)

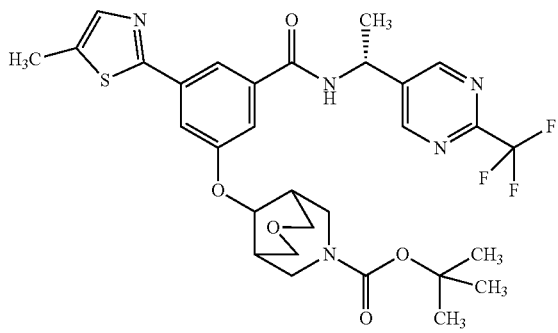 [SMILES: Cc1cnc(-c2cc(OC3C4COCC3CN(C(=O)OC(C)(C)C)C4)cc(C(=O)N[C@H](C)c3cnc(C(F)(F)F)nc3)c2)s1]

A mixture of Intermediate 107 (1.61 g, 3.50 mmol), Intermediate VI (1:1) (1.11 g, 4.89 mmol), HATU (3.19 g, 8.39 mmol) and DIPEA (3.0 ml, 17 mmol) in DMF (160 mL) was stirred at ambient temperature for 12 hours. The reaction mixture was evaporated to dryness under reduced pressure and the residue purified by column chromatography (silica gel) to give 1.35 g (58% yield) of the title compound.

LCMS, method 1, rt: 1.38 min, MS ES+m/z=634 (M+H)+.

Intermediate 109: 3-(5-Methyl-1,3-thiazol-2-yl)-5-(3-oxa-7-azabicyclo[3.3.1]non-9-yloxy)-N-{(1R)-1-[2-(trifluoromethyl)pyrimidin-5-yl]ethyl}benzamide, mixture of two stereoisomers (syn/anti)

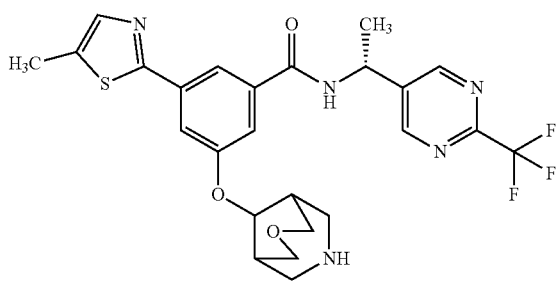 [SMILES: Cc1cnc(-c2cc(OC3C4CNCC3COC4)cc(C(=O)N[C@H](C)c3cnc(C(F)(F)F)nc3)c2)s1]

A mixture of Intermediate 108 (1.32 g, 2.08 mmol) and TFA (3.2 ml, 42 mmol) in DCM (110 mL) was stirred at RT for 17 hours. The mixture was evaporated to dryness under reduced pressure and purified by column chromatography to give (818 mg, 73% yield) of the title compound.

LCMS, method 1, rt: 0.90 min, MS ES+m/z=534 (M+H)+.

$^1$H NMR (500 MHz, DMSO-d$_6$) δ [ppm] 1.62 (d, 3H) 2.11-2.19 (m, 1H) 2.20-2.30 (m, 1H) 3.38-3.49 (m, 2H) 3.54-3.67 (m, 1H) 3.83-3.94 (m, 2H) 4.05-4.20 (m, 2H) 4.96-5.13 (m, 1H) 5.18-5.37 (m, 1H) 7.66 (m, 3H) 7.98 (s, 1H) 9.12 (d, 2H) 9.17-9.28 (m, 1H).

Intermediate 6CD: tert-butyl (2S)-2-({[(4-methylphenyl)sulfonyl]oxy}methyl) morpholine-4-carboxylate

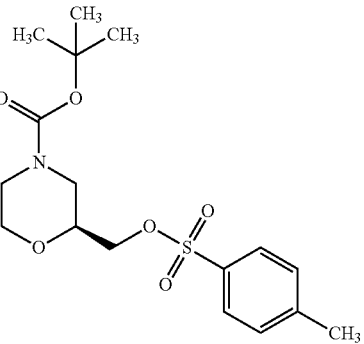

To tert-butyl (2S)-2-(hydroxymethyl)morpholine-4-carboxylate (5 g, 23 mmol), TEA (4.8 mL, 34.5 mmol) and trimethylamine hydrochloride (210 mg, 2.2 mmol) in DCM (60 mL) was added 4-methylbenzenesulfonyl chloride (6.6 g, 34.5 mmol) and the mixture stirred at RT overnight. The reaction mixture was treated with N,N-dimethylethane-1,2-diamine (1.5 mL, 13.8 mmol) to consume unreacted 4-methylbenzenesulfonyl chloride. The reaction mixture was washed with 1 M HCl and water. The organic fraction dried (sodium sulfate), filtered and concentrated under reduced pressure to give 10.1 g (99% yield) of the title compound as yellow oil, which solidified upon standing.

$^1$H NMR (250 MHz, DMSO-d6): δ [ppm] 1.38 (s, 9H), 2.43 (s, 3H), 2.55-2.71 (m, 1H), 2.71-2.89 (m, 1H), 3.24-3.41 (m, 1H), 3.52 (m, 1H), 3.59-3.84 (m, 3H), 3.92-4.14 (m, 2H), 7.49 (d, J=8.1 Hz, 2H), 7.79 (d, J=8.3 Hz, 2H).

Intermediate 110: (2R)-2-[(Benzyloxy)methyl]morpholine

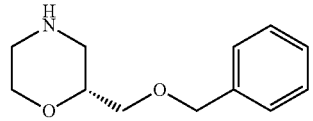 [SMILES: c1ccc(COC[C@H]2CNCCO2)cc1]

To a stirred mixture of (2R)-2-[(benzyloxy)methyl]oxirane (27.7 g, 0.17 mot) and NaOH (54.0 g, 1.3 mol) in water (130 mL) and MeOH (50 mL) was added 2-aminoethyl hydrogen sulfate (100 g, 0.7 mot) portionwise. After addition was complete, the reaction mixture was stirred at 40° C. for 2 h. On cooling, the mixture was treated with a further portion of NaOH (40.5 g, 1.0 mot), followed by toluene (200 mL) and stirred at 65° C. overnight. The mixture was cooled, diluted with toluene and water. The toluene layer was separated and the aqueous layer extracted with DCM (2×100 mL). The combined organic layers were concentrated to give the title compound, which was used in the next step without purification.

Intermediate 111: Tert-butyl (2R)-2-[(benzyloxy)methyl]morpholine-4-carboxylate

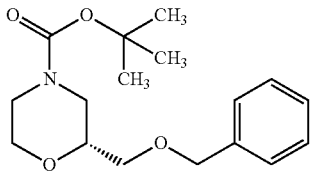 [SMILES: CC(C)(C)OC(=O)N1CCO[C@@H](COCc2ccccc2)C1]

A solution of Intermediate 110 in acetone (400 mL) and water (120 mL) was cooled to 0° C. and potassium carbonate (70 g, 0.5 mot) was added followed by di-tert-butyl dicarbonate (44 g, 0.2 mot). The reaction mixture was allowed to warm to ambient temperature and was stirred for 18 h. Acetone was removed under reduced pressure and the aqueous solution extracted twice with EtOAc. The combined organics were dried (MgSO$_4$), filtered and concentrated under reduced pressure. The crude material was purified by Biotage Isolera™ chromatography (eluting with 0-25% EtOAc in heptane on a pre-packed 340 g silica gel column) to give 19.8 g (38% yield) of the title compound as pale yellow oil.

$^1$H NMR (250 MHz, chloroform-d): δ [ppm] 7.39-7.27 (m, 5H), 4.56 (s, 2H), 4.03-3.73 (m, 3H), 3.69-3.34 (m, 4H), 3.05-2.86 (m, 1H), 2.84-2.65 (m, 1H), 1.46 (s, 9H)

LC-MS (Method A) Rt=1.27 min, MS (ESIpos): m/z=252 (M–tBu)$^+$.

Intermediate 112: Tert-butyl (2R)-2-(hydroxymethyl)morpholine-4-carboxylate

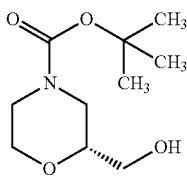

Intermediate 111 (19.8 g, 64.4 mmol) was stirred under an atmosphere of hydrogen in the presence of 10% Pd/C (1.98 g, 1.86 mmol) for 16 h. The catalyst was removed by vacuum filtration and the filtrate concentrated at reduced pressure to give 13.98 g (100% yield) of the title compound as a colourless viscous oil, which crystallised on standing.

$^1$H NMR (250 MHz, chloroform-d): δ [ppm] 3.98-3.75 (m, 3H), 3.73-3.41 (m, 4H), 3.03-2.83 (m, 1H), 2.82-2.65 (m, 1H), 2.12 (t, J=5.9 Hz, 1H), 1.45 (s, 9H).

Intermediate 6CE: Tert-butyl (2R)-2-({[(4-methylphenyl)sulfonyl]oxy}methyl) morpholine-4-carboxylate

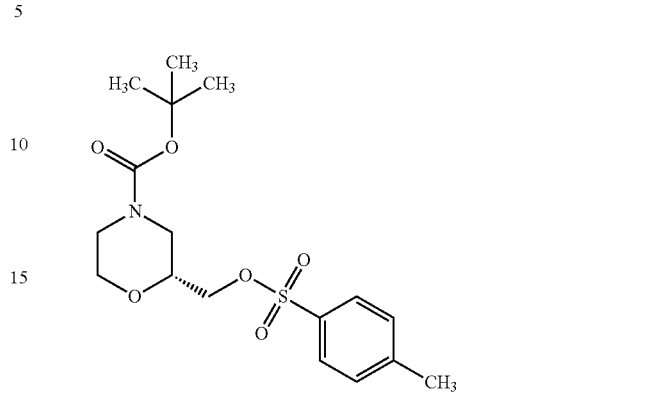

Intermediate 112 (5.96 g, 27.4 mmol), triethylamine (5.74 mL, 41.1 mmol) and trimethylamine hydrochloride (262 mg, 2.74 mmol) were stirred in dichloromethane (62 mL) then 4-toluenesulfonyl chloride (7.85 g, 41.1 mmol) was added. The reaction was stirred at ambient temperature for 2 h then treated with N,N-dimethylethane-1,2-diamine (1.81 mL, 16.5 mmol) to consume unreacted 4-toluenesulfonyl chloride. The reaction mixture was washed with 1 M HCl (2×100 mL) and water (50 mL). The organic fraction was dried (sodium sulfate), filtered and concentrated under reduced pressure to give the title compound (11.4 g, 100% yield) as yellow oil.

$^1$H NMR (500 MHz, chloroform-d): δ [ppm] 7.80 (d, J=8.3 Hz, 2H), 7.35 (d, J=8.0 Hz, 2H), 4.02 (qd, J=10.6, 5.0 Hz, 2H), 3.94-3.74 (m, 3H), 3.67-3.55 (m, 1H), 3.46 (td, J=11.6, 2.8 Hz, 1H), 2.98-2.81 (m, 1H), 2.75-2.57 (m, 1H), 2.45 (s, 3H), 1.45 (s, 9H).

LC-MS (Method A) Rt=1.28 min, MS (ESIpos): m/z=394 (M+Na)$^+$.

Intermediate 4CF: Tert-butyl 2-{[3-(methoxycarbonyl)-5-(5-methyl-1,3-thiazol-2-yl)phenoxy]methyl}morpholine-4-carboxylate

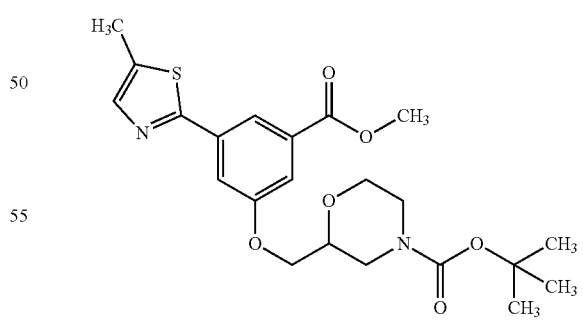

Intermediate 3 (300 mg, 1.2 mmol), tert-butyl 2-({[(4-methylphenyl)sulfonyl]oxy}methyl)morpholine-4-carboxylate (424.2 mg, 1.14 mmol) and cesium carbonate (439.4 mg, 1.32 mmol) were stirred in acetonitrile (5 mL) at 100° C. in a sealed tube for 6 h. The reaction mixture was cooled to RT and filtered through Celite®, washing with EtOAc. The filtrate was concentrated under reduced pressure and purified by Biotage Isolera™ chromatography (eluting with 5-70% EtOAc in heptane on a 25 g pre-packed KP—SiO₂ column) to give 331.1 mg (70% yield) of the title compound as a colourless gum.

¹H NMR (250 MHz, chloroform-d): δ [ppm] 8.13 (t, J=1.4 Hz, 1H), 7.72-7.68 (m, 1H), 7.61 (dd, J=2.5, 1.4 Hz, 1H), 7.52 (d, J=1.2 Hz, 1H), 4.18-4.05 (m, 2H), 3.93 (s, 5H), 3.88-3.76 (m, 2H), 3.67-3.55 (m, 1H), 3.07-2.80 (m, 2H), 2.52 (d, J=1.1 Hz, 3H), 1.48 (s, 9H).

Intermediate 4CE: Tert-butyl (2R)-2-{[3-(methoxycarbonyl)-5-(5-methyl-1,3-thiazol-2-yl)phenoxy]methyl}morpholine-4-carboxylate

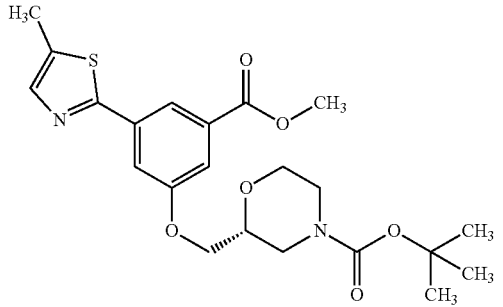 [SMILES: COC(=O)c1cc(OC[C@H]2CN(C(=O)OC(C)(C)C)CCO2)cc(-c2ncc(C)s2)c1]

Intermediate 3 (23.17 g, 70.6 mmol), Intermediate 6CE (28.9 g, 77.7 mmol) and cesium carbonate (34.52 g, 105.9 mmol) were combined in acetonitrile (300 mL) and stirred at 100° C. under nitrogen for 2.5 h. The cooled reaction mixture was filtered through Celite®, washing with EtOAc. The filtrate was concentrated under reduced pressure and purified by Biotage Isolera™ chromatography (eluting with 0-50% EtOAc in heptane on a 340 g pre-packed KP—SiO₂ column) to give 27.22 g (69% yield) of the title compound as viscous yellow oil.

¹H NMR (500 MHz, Chloroform-d): δ [ppm] 8.13 (t, J=1.4 Hz, 1H), 7.70 (s, 1H), 7.61 (dd, J=2.4, 1.3 Hz, 1H), 7.52 (d, J=1.1 Hz, 1H), 4.18-3.78 (m, 11H), 3.67-3.54 (m, 1H), 2.95 (m, 2H), 2.52 (d, J=1.0 Hz, 3H), 1.48 (s, 9H).

LCMS (Method A) Rt=1.40 min, MS (ESIpos): m/z=449 (M+H)⁺.

In analogy to the procedure described for Intermediate 4CE, the following Intermediates were prepared using the corresponding phenol and tosylate starting materials.

| Int. | Structure | Name | Analytical Data |
| --- | --- | --- | --- |
| 4CD | (structure) | Tert-butyl (2S)-2-{[3-(methoxycarbonyl)-5-(5-methyl-1,3-thiazol-2-yl)phenoxy]methyl}morpholine-4-carboxylate | ¹H NMR (250 MHz, chloroform-d): δ [ppm] 8.13 (t, J = 1.4 Hz, 1H), 7.73-7.66 (m, 1H), 7.61 (dd, J = 2.5, 1.4 Hz, 1H), 7.54-7.49 (m, 1H), 4.18-3.99 (m, 3H), 3.95-3.75 (m, 6H), 3.67-3.55 (m, 1H), 3.08-2.80 (m, 2H), 2.52 (d, J = 1.1 Hz, 3H), 1.48 (s, 9H). LC-MS (Method A) Rt = 1.36 min, MS (ESIpos) m/z = 449 (M+H)⁺. |
| 4CH | (structure) | Tert-butyl (2R)-2-{[3-(5-ethyl-1,3-thiazol-2-yl)-5-(methoxycarbonyl)phenoxy]methyl}morpholine-4-carboxylate | ¹H NMR (250 MHz, DMSO-d6): δ [ppm] 1.28 (t, J = 7.2 Hz, 3H), 1.41 (s, 9H), 2.72-3.02 (m, 4H), 3.38-3.56 (m, 1H), 3.61-3.80 (m, 2H), 3.80-4.02 (m, 5H), 4.07-4.29 (m, 2H), 7.52 (dd, J = 2.5, 1.4 Hz, 1H), 7.64-7.68 (m, 1H), 7.69 (s, 1H), 8.02 (t, J = 1.4 Hz, 1H). LC-MS (Method A) Rt = 1.51 min, MS (ESIpos): m/z = 463 (M + H)⁺. |

-continued

| Int. | Structure | Name | Analytical Data |
|---|---|---|---|
| 4CI | 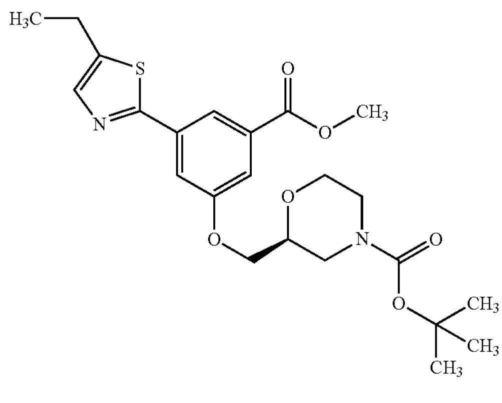 [SMILES: CCc1cnc(-c2cc(OC[C@@H]3CN(C(=O)OC(C)(C)C)CCO3)cc(C(=O)OC)c2)s1] | Tert-butyl (2S)-2-{[3-(5-ethyl-1,3-thiazol-2-yl)-5-(methoxycarbonyl)phenoxy]methyl}morpholine-4-carboxylate | LC-MS (Method A) Rt = 1.47 min, MS (ESIpos): m/z = 463 (M + H)+. |
| 4CJ | 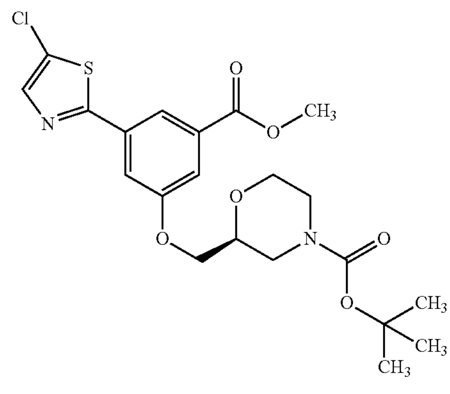 [SMILES: COC(=O)c1cc(OC[C@@H]2CN(C(=O)OC(C)(C)C)CCO2)cc(-c2ncc(Cl)s2)c1] | Tert-butyl (2S)-2-[[3-(5-chlorothiazol-2-yl)-5-methoxycarbonyl-phenoxy]methyl]morpholine-4-carboxylate | $^1$H NMR (250 MHz, chloroform-d): δ [ppm] 8.08 (t, J = 1.4 Hz, 1H), 7.71-7.53 (m, 3H), 4.22-3.74 (m, 9H), 3.70-3.53 (m, 1H), 3.13-2.78 (m, 2H), 1.48 (s, 9H). LC-MS (Method A) Rt = 1.50 min, MS (ESIpos): m/z = 491 (M + Na)+. |
| 4CK | 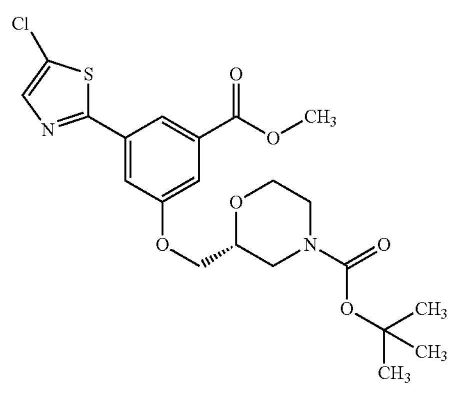 [SMILES: COC(=O)c1cc(OC[C@H]2CN(C(=O)OC(C)(C)C)CCO2)cc(-c2ncc(Cl)s2)c1] | Tert-butyl (2R)-2-[[3-(5-chlorothiazol-2-yl)-5-methoxycarbonyl-phenoxy]methyl]morpholine-4-carboxylate | $^1$H NMR (500 MHz, chloroform-d): δ [ppm] 8.08 (s, 1H), 7.71-7.59 (m, 3H), 4.14 (dd, J = 9.9, 5.4 Hz, 1H), 4.08 (dd, J = 9.9, 4.5 Hz, 1H), 4.06-3.99 (m, 1H), 3.99-3.96 (m, 1H), 3.94 (s, 3H), 3.92-3.88 (m, 1H), 3.86-3.78 (m, 1H), 3.66-3.53 (m, 1H), 3.09-2.96 (m, 1H), 2.97-2.76 (m, 1H), 1.48 (s, 9H). LC-MS (Method A) Rt = 1.53 min, MS (ESIpos): m/z = 491 (M + H)+. |

Intermediate 4CG: Tert-butyl 4-{[3-(methoxycarbonyl)-5-(5-methyl-1,3-thiazol-2-yl)phenoxy]methyl}piperidine-1-carboxylate

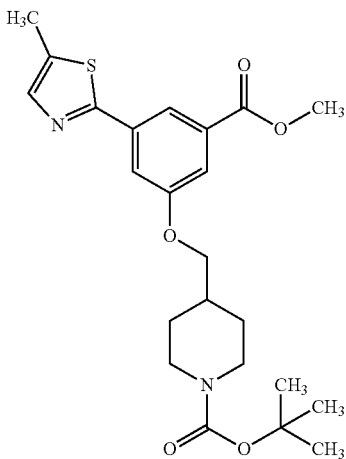 [SMILES: COC(=O)c1cc(OCC2CCN(C(=O)OC(C)(C)C)CC2)cc(-c2ncc(C)s2)c1]

Intermediate 3 (300 mg, 1.20 mmol), 1-Boc-4-bromomethylpiperidine (4.35 mg, 1.56 mmol) and cesium carbonate (784 mg, 2.04 mmol) were combined in MeCN (5 mL) and heated to 100° C. for 6 h. After cooling to room temperature the reaction mixture was diluted with EtOAc (5 mL), filtered and the filtrate concentrated under reduced pressure. The crude material was purified by Biotage Isolera™ chromatography (eluting with 0-40% EtOAc in heptane on a 25 g pre-packed KP—SiO$_2$ column) to give 272.2 mg (49% yield) of the title compound as colourless gum.

$^1$H NMR (500 MHz, chloroform-d): δ [ppm] 8.08 (s, 1H), 7.69 (s, 1H), 7.58 (s, 1H), 7.53 (s, 1H), 4.24-4.09 (m, 2H), 3.94 (s, 3H), 3.92 (d, J=6.4 Hz, 2H), 2.84-2.71 (m, 2H), 2.53 (s, 3H), 2.03-1.95 (m, 1H), 1.84 (d, J=11.5 Hz, 2H), 1.47 (s, 9H), 1.36-1.23 (m, 2H).

LC-MS (Method A) Rt=1.50 min, MS (ESIpos): m/z=447 (M+H)$^+$.

Intermediate 4CL: Tert-butyl 3-fluoro-3-{[3-(methoxycarbonyl)-5-(5-methyl-1,3-thiazol-2-yl)phenoxy]methyl}azetidine-1-carboxylate

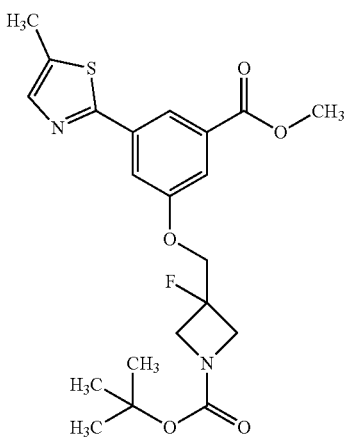 [SMILES: COC(=O)c1cc(OCC2(F)CN(C(=O)OC(C)(C)C)C2)cc(-c2ncc(C)s2)c1]

To a stirred 0° C. solution of Intermediate 3 (300 mg, 1.201 mmol), tert-butyl 3-fluoro-3-(hydroxymethyl)azetidine-1-carboxylate (321 mg, 1.56 mmol) and triphenylphosphine (1.26 g, 4.81 mmol) in anhydrous THF (3 mL) was added DIAD (472 μL, 2.41 mmol) dropwise. After 10 mins the reaction mixture was warmed to RT and stirred for 16 h. Additional DIAD (200 μL, 1.02 mmol) was added and the reaction stirred at RT for 24 h. Additional DIAD (200 μL, 1.02 mmol) was added and the reaction stirred at RT for 70 h. The reaction mixture was concentrated at reduced pressure and purified by Biotage Isolera™ chromatography (eluting with 0-100% gradient EtOAc in heptane on a pre-packed KP—SiO$_2$ column) to give 1.43 g (41% yield) of the title compound as colourless oil. The material was used without further purification.

LC-MS (Method A) Rt=1.37 min, MS (ESIpos): m/z=437 (M+H)$^+$.

Intermediate 6CV: Tert-butyl 3-({[(4-methylphenyl)sulfonyl]oxy}methyl)azetidine-1-carboxylate

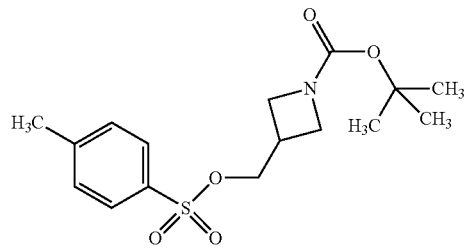 [SMILES: Cc1ccc(S(=O)(=O)OCC2CN(C(=O)OC(C)(C)C)C2)cc1]

A mixture of tert-butyl 3-(hydroxymethyl)azetidine-1-carboxylate (600 mg, 3.20 mmol), 4-methylbenzenesulfonyl chloride (672 mg, 3.52 mmol), TEA (670 μL, 4.8 mmol), trimethylammonium hydrochloride (30.6 mg, 320 μmol) in DCM (3.2 mL) was stirred at RT until complete conversion. The reaction mixture was evaporated to dryness. Crude material was purified by column chromatography (silica gel, hexane/EtOAc gradient) to give 800 mg (73% yield) of the title compound.

$^1$H NMR (400 MHz, DMSO-d$_6$): δ [ppm] 1.34 (s, 9H), 2.43 (s, 3H), 2.73-2.87 (m, 1H), 3.46 (br. s., 2H), 3.74-3.91 (m, 2H), 4.16 (d, 2H), 7.44-7.57 (m, 2H), 7.74-7.85 (m, 2H).

Intermediate 4CV: Tert-butyl 3-{[3-(methoxycarbonyl)-5-(5-methyl-1,3-thiazol-2-yl)phenoxy]methyl}azetidine-1-carboxylate

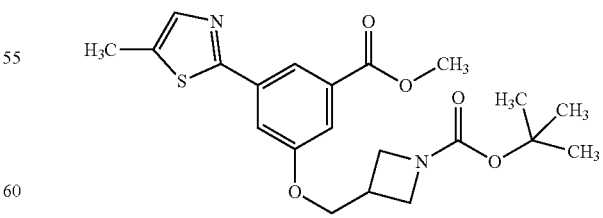

A mixture of Intermediate 3 (389 mg, 1.56 mmol), Intermediate 6CV (389 mg, 1.56 mmol) and Cs$_2$CO$_3$ in DMF (11 mL) was stirred at 90° C. until complete conversion. The DMF was evaporated under reduced pressure, water and DCM added, and the aqueous layer was extracted with DCM. The combined organics were evaporated to dryness. Crude material was purified by column chromatography (silica gel, hexane/EtOAc gradient) to give 300 mg (46% yield) of the title compound.

¹H NMR (400 MHz, DMSO-d₆): δ [ppm] 1.38-1.44 (m, 9H), 2.90-3.05 (m, 1H), 3.66-3.80 (m, 2H), 3.89 (s, 3H), 3.93-4.04 (m, 2H), 4.26 (d, 2H), 7.52 (dd, 1H), 7.60-7.69 (m, 2H), 8.00 (t, 1H).

Intermediate 149: N-[(2R)-1-(Benzyloxy)-3-hydroxypropan-2-yl]-2-chloroacetamide

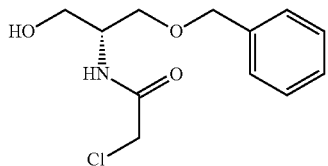 [SMILES: O=C(CCl)N[C@H](CO)COCc1ccccc1]

(2R)-2-Amino-3-(benzyloxy)propan-1-ol (5.00 g, 27.6 mmol) was dissolved in acetonitrile (87 mL) and MeOH (16 mL) and TEA (4.6 mL, 33 mmol) was added. The mixture was cooled to −10° C. and a solution of chloroacetyl chloride (2.4 mL, 30 mmol) in acetonitrile was added dropwise. The mixture was stirred for 20 hours at RT. The solvent was evaporated under reduced pressure and the residue purified by silica gel column chromatography (EtOAc/hexane gradient) to give 5.46 g (77% yield) of the title compound.

¹H NMR (400 MHz, CHLOROFORM-d): δ [ppm] 2.57 (br. s., 1H) 3.51-3.71 (m, 3H) 3.81 (dd, 1H) 3.95-4.10 (m, 3H) 4.42-4.52 (m, 2H) 7.16 (d, 1H) 7.21-7.35 (m, 5H).

Intermediate 150: (5S)-5-[(Benzyloxy)methyl]morpholin-3-one

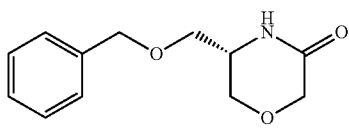 [SMILES: O=C1COC[C@H](COCc2ccccc2)N1]

To a solution of potassium tert-butoxide (980 mg, 8.73 mmol) in 2-methylbutan-2-ol was added dropwise a solution of the Intermediate 149 (2.25 g, 8.73 mmol) in 2-methylbutan-2-ol over two hours. After 12 hours, an additional 1 equivalent of potassium tert-butoxide was added and the reaction mixture stirred for 12 h. The solvent was distilled off under reduced pressure and the residue purified by silica gel column chromatography (EtOAc/EtOH gradient) to give 1.50 g (78% yield) of the title compound.

¹H NMR (400 MHz, CHLOROFORM-d): δ [ppm] 3.39-3.48 (m, 1H) 3.56 (dd, 1H) 3.63 (dd, 1H) 3.70-3.81 (m, 1H) 3.87 (dd, 1H) 4.16 (d, 2H) 4.55 (d, 2H) 6.33 (br. s., 1H) 7.29-7.42 (m, 5H).

Intermediate 151: (5S)-5-[(Benzyloxy)methyl]-4-methylmorpholin-3-one

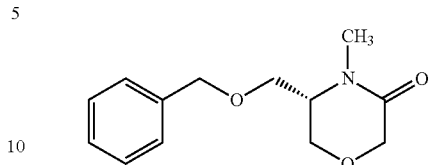

A solution of Intermediate 150 (619 mg, 2.8 mmol) in THF (25 mL) was added dropwise to a suspension of NaH (134 mg, 60%, 3.36 mmol) in THF (70 mL) at 0° C. The mixture was stirred for 30 minutes at RT then cooled to 0° C. and MeI (870 µL, 14 mmol) added. After 15 mins the reaction mixture was warmed to RT and stirred for 15 hours. A saturated aqueous solution of NH₄Cl (50 mL) was added at 0° C. and the solvent evaporated at reduced pressure. The residue was diluted with water, extracted with EtOAc and the organic layer dried over MgSO₄. The solvent was distilled off under reduced pressure to give 650 mg (99% yield) of the title compound, which was used without further purification.

LCMS, method 1, rt: 0.90 min, MS ES+m/z=236 (M+H)⁺.

Intermediate 152: (5S)-5-(Hydroxymethyl)-4-methylmorpholin-3-one

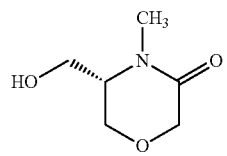

Intermediate 151 (617 mg, 2.62 mmol) was dissolved in EtOH, Pd(OH)₂ (92 mg, 20% on carbon, 131 µmol) was added and stirred for 10 h under hydrogen atmosphere.

Additional Pd(OH)₂ (0,025 eq.) was added and the mixture stirred for 3 h under hydrogen atmosphere. The reaction mixture was filtered through Celite® and washed with EtOH. The organic phase concentrated to dryness under reduced pressure to give 398 mg (100% yield) of the title compound.

¹H NMR (400 MHz, CHLOROFORM-d): δ [ppm] 1.96 (t, 1H) 3.06 (s, 3H) 3.29 (td, 1H) 3.79-3.96 (m, 3H) 4.08-4.28 (m, 3H).

Intermediate 6CX: [(3R)-4-Methyl-5-oxomorpholin-3-yl]methyl 4-methylbenzenesulfonate

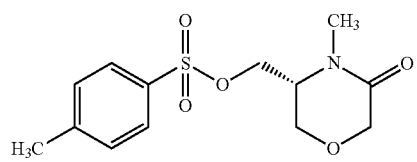 [SMILES: Cc1ccc(S(=O)(=O)OC[C@H]2COCC(=O)N2C)cc1]

A mixture of Intermediate 152 (322 mg, 2.22 mmol), TEA (460 µL, 3.3 mmol) and trimethylamine hydrochloride in DCM was cooled to 0° C. and stirred for 10 minutes.

4-Methylbenzenesulfonyl chloride (465 mg, 2.44 mmol) was added in 3 portions and the solution stirred at RT until complete conversion. The reaction mixture was treated with N,N-dimethylethylenediamine (290 μL, 2.7 mmol) to consume the unreacted 4-methylbenzenesulfonyl chloride. Water was added to the reaction mixture and the aqueous phase extracted with DCM. The organic phase was concentrated to dryness to give 505 mg (68% yield) of the title compound.

$^1$H NMR (400 MHz, DMSO-$d_6$): δ [ppm] 2.43 (s, 3H) 2.81 (s, 3H) 3.54-3.62 (m, 1H) 3.75 (d, 2H) 3.97 (s, 2H) 4.15-4.25 (m, 2H) 7.50 (d, 2H) 7.82 (d, 2H).

Intermediate 4CX: Methyl 3-{[(3R)-4-methyl-5-oxomorpholin-3-yl]methoxy}-5-(5-methyl-1,3-thiazol-2-yl)benzoate

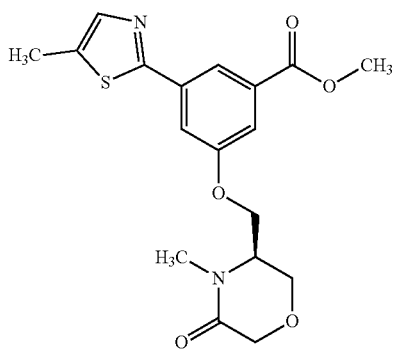

A mixture of Intermediate 3 (280 mg, 1.12 mmol), Intermediate 6CX (505 mg, 1.69 mmol) and Cs$_2$CO$_3$ (550 mg, 1.69 mmol) was stirred at 90° C. until complete conversion. The DMF was evaporated under reduced pressure, water and DCM added, and the aqueous layer extracted with DCM (three times). The combined organics were evaporated to dryness and the crude material purified by column chromatography (silica gel, hexane/EtOAc gradient) to give 530 mg of the title compound.

LCMS, method 1, rt: 1.09 min, MS ES+m/z=377 (M+H)$^+$.

Intermediate 153: (5S)-5-(Hydroxymethyl)morpholin-3-one

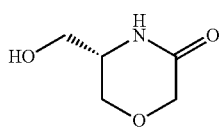

Intermediate 150 (650 mg, 2.94 mmol) was dissolved in MeOH (53 mL) and Pd(OH)$_2$ (103 mg, 20% on carbon, 147 μmol) added and stirred for 8 h under hydrogen atmosphere. The mixture was filtered through Celite®, washed with EtOH and the filtrate concentrated under reduced pressure to give 322 mg (74% yield) of the title compound, which was used without further purification.

$^1$H NMR (400 MHz, CHLOROFORM-d): δ [ppm] 2.88 (br. s., 1H) 3.59-3.79 (m, 4H) 3.82-3.97 (m, 1H) 4.06-4.25 (m, 2H) 7.18 (br. s., 1H).

Intermediate 6CY: [(3R)-5-Oxomorpholin-3-yl]methyl 4-methylbenzenesulfonate

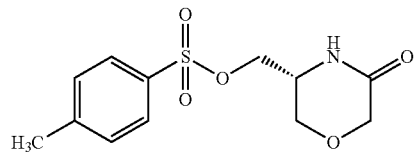 [SMILES: Cc1ccc(S(=O)(=O)OC[C@H]2COCC(=O)N2)cc1]

A mixture of Intermediate 153 (322 mg, 2.46 mmol), TEA (510 μL, 3.7 mmol) and trimethylamine hydrochloride (23.5 mg, 246 μmol) in DCM (7.2 mL) was cooled to 0° C. and stirred for 10 minutes. 4-Methylbenzenesulfonyl chloride (515 mg, 2.70 mmol) was added in 3 portions and the solution stirred at RT until complete conversion. The reaction mixture was treated with N,N-Dimethylethylenediamine (320 μL, 2.9 mmol) to consume unreacted 4-methylbenzenesulfonyl chloride. Water was added to the crude mixture and the collected aqueous phase was extracted with DCM (three times). The combined organic layers were concentrated to dryness to give 526 mg (42% yield) of the title compound, which was used without further purification.

LCMS, method 1, rt: 0.83 min, MS ES+m/z=286 (M+H)$^+$.

Intermediate 4CY: Methyl 3-(5-methyl-1,3-thiazol-2-yl)-5-{[(3R)-5-oxomorpholin-3-yl]methoxy}benzoate

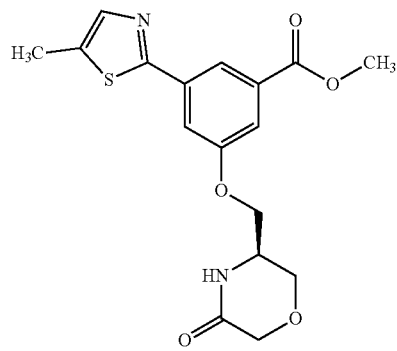

A mixture of Intermediate 3 (306 mg, 1.23 mmol), Intermediate 6CY (526 mg, 1.84 mmol) and Cs$_2$CO$_3$ (601 mg, 1.84 mmol) in DMF (120 mL) was stirred at 90° C. until complete conversion. DMF was evaporated under reduced pressure and the residue partitioned between water and DCM. The aqueous layer was extracted with DCM (three times) and the combined organic layers evaporated to dryness. Purification by column chromatography (silica gel, EtOAc/hexane gradient) gave 834 mg of the title compound.

LCMS, method 1, rt: 1.03 min, MS ES+m/z=363 (M+H)$^+$.

Intermediate 154: (2S)-3-[Benzyl(methyl)amino]propane-1,2-diol

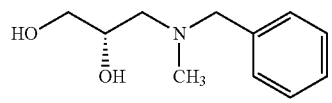

A solution of (2R)-oxiran-2-ylmethanol (4.71 g, 63.6 mmol) and N-methyl-1-phenylmethanamine (7.9 mL, 61 mmol) in MeOH (350 mL) was heated under reflux for 24 h, cooled to RT and evaporated to dryness under reduced pressure to give 12.6 g of the title compound, which was used without further purification.

LCMS, method 1, rt: 0.83 min, MS ES+m/z=196 (M+H)+.

Intermediate 155:
(2S)-3-(Methylamino)propane-1,2-diol

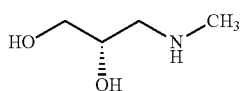

A mixture of Intermediate 154 (12.6 g, 64.5 mmol) and palladium on carbon (4.12 g, 5%, 1.94 mmol) in MeOH (78 mL) was hydrogenated at 5 bar for 18 h at 23° C. The mixture was filtered, washed with MeOH and the filtrate evaporated to dryness under reduced pressure to give 6.07 g (76% yield) of the title compound, which was used without further purification.

$^1$H NMR (400 MHz, CHLOROFORM-d): δ [ppm] 2.45 (s, 3H) 2.63-2.70 (m, 1H) 2.71-2.77 (m, 1H) 2.89-2.98 (m, 3H) 3.54-3.62 (m, 1H) 3.67-3.74 (m, 1H) 3.79 (ddt, 1H).

Intermediate 156: (5S)-5-(Hydroxymethyl)-3-methyl-1,3-oxazolidin-2-one

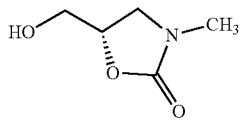

To a mixture of Intermediate 155 (3.25 g, 30.9 mmol) and diethyl carbonate (22 mL, 190 mmol) was added potassium tert-butoxide (173 mg, 1.55 mmol). The reaction mixture was stirred for 14 h at 100° C. and evaporated to dryness to give 1.44 g (31% yield) of the title compound, which was used without further purification.

$^1$H NMR (400 MHz, DMSO-d$_6$): δ [ppm] 2.72 (s, 3H) 3.27 (dd, 1H) 3.41-3.49 (m, 1H) 3.53 (t, 2H) 4.46 (ddd, 1H) 5.09 (s, 1H).

Intermediate 6CZ: [(5S)-3-Methyl-2-oxo-1,3-oxazolidin-5-yl]methyl 4-methylbenzenesulfonate

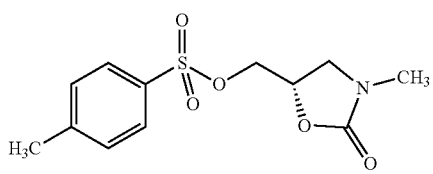

A mixture of Intermediate 156 (2.24 g, 17.1 mmol), TEA (3.6 mL, 26 mmol) and trimethylamine hydrochloride (163 mg, 1.71 mmol) in DCM (50 mL) was stirred at 0° C. for 10 minutes then treated with 4-methylbenzenesulfonyl chloride in 3 portions. The mixture was stirred at RT until complete conversion. The reaction mixture was treated with N,N-dimethylethylenediamine (2.2 mL, 20 mmol) to consume unreacted 4-methylbenzenesulfonyl chloride. Water was added, the aqueous phase extracted with DCM (three times) and the combined organic layers concentrated to dryness to give 4.67 g (91% yield) of the title compound.

$^1$H NMR (400 MHz, CHLOROFORM-d): δ [ppm] 2.47 (s, 3H) 2.87 (s, 3H) 3.44 (dd, 1H) 3.65 (t, 1H) 4.06-4.21 (m, 2H) 4.61-4.73 (m, 1H) 7.38 (d, 2H) 7.76-7.86 (m, 2H).

Analytical chiral HPLC, method G: retention time: 5.04 min (78.4%) and 5.48 min (21.6%), ee-value: 56.8%.

Intermediate 4CZ: Methyl 3-{[(5S)-3-methyl-2-oxo-1,3-oxazolidin-5-yl]methoxy}-5-(5-methyl-1,3-thiazol-2-yl)benzoate

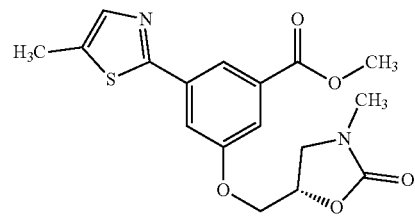 [SMILES: COC(=O)c1cc(OC[C@@H]2CN(C)C(=O)O2)cc(-c2ncc(C)s2)c1]

A mixture of Intermediate 3 (582 mg, 2.34 mmol), Intermediate 6CZ (1.00 g, 3.50 mmol) and Cs$_2$CO$_3$ (1.14 g, 3.50 mmol) in DMF (17 mL) was stirred at 90° C. until complete conversion. The DMF was evaporated under reduced pressure and the residue purified by column chromatography (silica gel, EtOAc/hexane gradient) to give 844 mg (94% yield) of the title compound.

LCMS, method 1, rt: 1.07 min, MS ES+m/z=363 (M+H)+.

Intermediate 157: (2R)-3-[Benzyl(methyl)amino]propane-1,2-diol

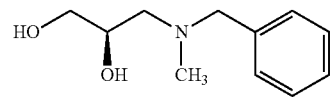

A solution of (2S)-oxiran-2-ylmethanol (3.77 g, 50.9 mmol) and N-methyl-1-phenylmethanamine (6.3 mL, 49 mmol) in MeOH (280 mL) was heated under reflux for 24 h, cooled to RT and evaporated to dryness under reduced pressure to give 9.72 g (98% yield) of the title compound, which was used without further purification.

LCMS, method 1, rt: 0.86 min, MS ES+m/z=196 (M+H)+.

Intermediate 158:
(2R)-3-(Methylamino)propane-1,2-diol

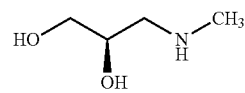

A mixture of Intermediate 157 (9.72 g, 49.8 mmol) and palladium on carbon ((3.18 g, 5%, 1.49 mmol) in MeOH (60 mL) was hydrogenated at 5 bar for 18 h at 23° C. The mixture was filtered, washed with MeOH and the filtrate evaporated to dryness under reduced pressure to give 5.35 g of the title compound, which was used without further purification.

¹H NMR (400 MHz, CHLOROFORM-d): δ [ppm] 2.43-2.47 (m, 3H) 2.64-2.71 (m, 1H) 2.72-2.79 (m, 1H) 2.91 (br. s., 3H) 3.57-3.63 (m, 1H) 3.68-3.75 (m, 1H) 3.76-3.83 (m, 1H).

Intermediate 159: (5R)-5-(Hydroxymethyl)-3-methyl-1,3-oxazolidin-2-one

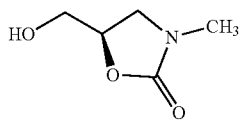

To a solution of Intermediate 158 (2.58 g, 24.5 mmol) in diethyl carbonate (18 mL, 150 mmol) was added potassium tert-butoxide (138 mg, 1.23 mmol). The reaction mixture was stirred for 24 h at 100° C. and evaporated to dryness. The residue was purified by column chromatography (silica gel, EtOAc/hexane gradient) to give 861 mg (27% yield) of the title compound.

¹H NMR (400 MHz, DMSO-d₆): δ [ppm] 2.72 (s, 3H) 3.27 (dd, 1H) 3.47 (dd, 1H) 3.49-3.58 (m, 2H) 4.40-4.51 (m, 1H) 5.10 (t, 1H).

Intermediate 6DA: [(5R)-3-Methyl-2-oxo-1,3-oxazolidin-5-yl]methyl 4-methylbenzenesulfonate

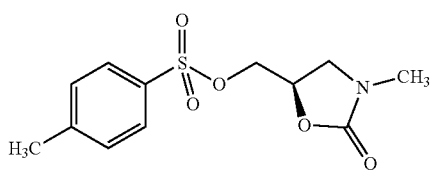

A mixture of Intermediate 159 (2.74 g, 20.9 mmol), TEA (4.4 mL, 31 mmol) and trimethylamine hydrochloride (200 mg, 2.09 mmol) in DCM (61 mL) was cooled to 0° C. and stirred for 10 minutes. 4-Methylbenzenesulfonyl chloride (4.38 g, 23.0 mmol) was added in 3 portions and the solution stirred at RT until complete conversion. The reaction mixture was treated with N,N-dimethylethylenediamine (2.7 mL, 25 mmol) to consume unreacted 4-methylbenzenesulfonyl chloride. Water was added, the aqueous phase extracted with DCM (three times) and the combined organic layers concentrated to dryness to give 5.97 g (94% yield) of the title compound, which was used without further purification.

¹H NMR (400 MHz, DMSO-d₆): δ ppm 2.43 (s, 3H) 2.66-2.73 (m, 3H) 3.17 (dd, 1H) 3.57 (t, 1H) 4.09-4.17 (m, 1H) 4.18-4.25 (m, 1H) 4.69 (dt, 1H) 7.47-7.55 (m, 2H) 7.75-7.85 (m, 2H).

Analytical chiral HPLC, method G: retention time: 5.46 min (88.0%) and 5.05 min (12.0%), ee-value: 76.0%.

Intermediate 4DA: Methyl 3-{[(5R)-3-methyl-2-oxo-1,3-oxazolidin-5-yl]methoxy}-5-(5-methyl-1,3-thiazol-2-yl)benzoate

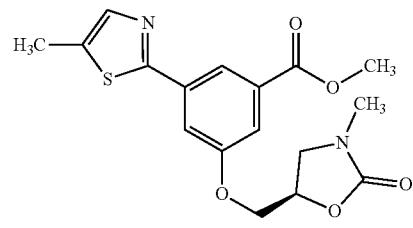 [SMILES: COC(=O)c1cc(OC[C@H]2CN(C)C(=O)O2)cc(-c2ncc(C)s2)c1]

A mixture of Intermediate 6DA (582 mg, 2.34 mmol), Intermediate 3 (1.00 g, 3.50 mmol) and Cs₂CO₃ (1.14 g, 3.50 mmol) in DMF (17 mL) was stirred at 90° C. until complete conversion. The DMF was evaporated under reduced pressure, water and DCM were added and the aqueous layer extracted with DCM (three times). The combined organic layers were evaporated to dryness under reduced pressure. The residue was purified by column chromatography (silica gel, EtOAc/hexane gradient) to give 609 mg (67% yield) of the title compound.

¹H NMR (400 MHz, DMSO-d₆): δ ppm 2.79 (s, 3H) 3.33 (s, 2H) 3.43 (dd, 1H) 3.70 (t, 1H) 3.89 (s, 3H) 4.22-4.31 (m, 1H) 4.32-4.40 (m, 1H) 4.82-4.93 (m, 1H) 7.53 (dd, 1H) 7.66 (q, 2H) 8.02 (t, 1H).

Intermediate 160: 2-Chloro-N-[(2R)-2,3-dihydroxypropyl]-N-methylacetamide

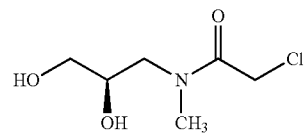

To a solution of Intermediate 158 (2.80 g, 26.6 mmol) in acetonitrile (84 mL) and MeOH (16 mL) was added TEA (4.5 mL, 32 mmol) and the mixture cooled to −10° C. A solution of chloroacetyl chloride (2.3 mL, 29 mmol) in acetonitrile was added dropwise and the mixture stirred for 20 hours at RT. The reaction solvent was distilled off to give 4.53 g (94% yield) of the title compound, which was used without further purification.

LCMS, method 1, rt: 0.45 min, MS ES+m/z=183 (M+H)⁺.

Intermediate 161: (6R)-6-(Hydroxymethyl)-4-methylmorpholin-3-one

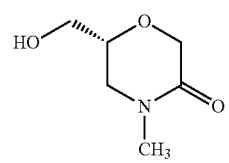

To a solution of potassium tert-butoxide (5.60 g, 49.9 mmol) in 2-methylbutan-2-ol was added dropwise a solution of the Intermediate 160 (4.53 g, 24.9 mmol) in 2-methylbutan-2-ol over two hours. After 4 hours conversion was complete. The solvent was distilled off under reduced pressure and the residue purified by silica gel column chromatography (EtOAc/EtOH gradient) to give 4.63 g of the title compound.

$^1$H NMR (400 MHz, DMSO-d$_6$): δ [ppm] 2.85 (s, 3H) 3.21-3.27 (m, 2H) 3.37-3.54 (m, 2H) 3.78 (dq, 1H) 4.01-4.06 (m, 2H) 4.91 (t, 1H).

Intermediate 6DB: [(2R)-4-Methyl-5-oxomorpholin-2-yl]methyl 4-methylbenzenesulfonate

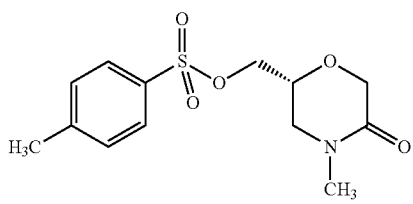

A mixture of Intermediate 161 (4.63 g, 31.9 mmol), TEA (6.7 mL, 48 mmol) and trimethylamine hydrochloride (305 mg, 3.19 mmol) in DCM (94 mL) was cooled to 0° C. and stirred for 10 minutes. After that 4-methylbenzenesulfonyl chloride (6.69 g, 35.1 mmol) was added in 3 portions. The solution was stirred at RT until complete conversion. The reaction mixture was treated with N,N-dimethylethylenediamine (4.2 mL, 38 mmol) to consume unreacted 4-methylbenzenesulfonyl chloride. Water was added, the aqueous phase extracted with DCM (three times) and the organic layer concentrated to dryness to give 3.43 g (36% yield) of the title compound, which was used without further purification.

LCMS, method 1, rt: 0.90 min, MS ES+m/z=300 (M+H)$^+$.

Intermediate 4DB: Methyl 3-{[(2R)-4-methyl-5-oxomorpholin-2-yl]methoxy}-5-(5-methyl-1,3-thiazol-2-yl)benzoate

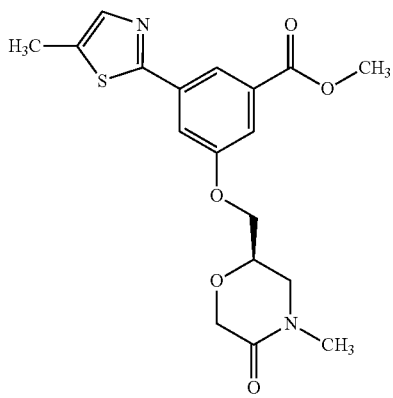

A mixture of Intermediate 3 (1.90 g, 7.64 mmol), Intermediate 6DB (3.43 g, 11.5 mmol), and Cs$_2$CO$_3$ (3.73 g, 11.5 mmol) in DMF (56 mL) was stirred at 90° C. until complete conversion. The DMF was evaporated under reduced pressure to give 2.76 g (96% yield) of the title compound, which was used without further purification.

LCMS, method 1, rt: 1.06 min, MS ES+m/z=377 (M+H)$^+$.

Intermediate 162: 2-Chloro-N-[(2S)-2,3-dihydroxypropyl]acetamide

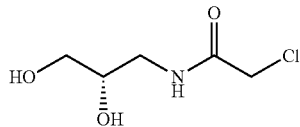

(2S)-3-Aminopropane-1,2-diol (5.00 g, 54.9 mmol) was dissolved in acetonitrile (170 mL) and MeOH (32 mL) and TEA (9.2 mL, 66 mmol) was added. The mixture was cooled to −10° C. and a solution of chloroacetyl chloride (4.8 mL, 60 mmol) in acetonitrile, was added dropwise, and the mixture was stirred for 21 hours at RT.

The reaction solvent was distilled off under reduced pressure and the remaining residue was purified by by column chromatography (silica gel, EtOAc/hexane/MeOH gradient) to give 10.5 g of the title compound.

Intermediate 163: (6S)-6-(Hydroxymethyl)morpholin-3-one

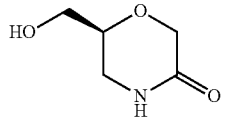

Potassium tert-butoxide (14.0 g, 125 mmol) was dissolved in 2-methylbutan-2-ol. A solution of the Intermediate 162 in 2-methylbutan-2-ol was added dropwise over two hours and the reaction mixture stirred until complete conversion. The solvent was distilled off under reduced pressure and the residue was purified by column chromatography (silica gel, EtOAc/hexane gradient) to give 7.46 g (27% yield).

Intermediate 6DC: [(2S)-5-Oxomorpholin-2-yl]methyl 4-methylbenzenesulfonate

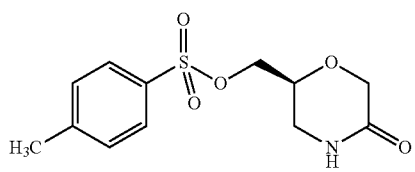 [SMILES: Cc1ccc(S(=O)(=O)OC[C@@H]2CNC(=O)CO2)cc1]

A mixture of Intermediate 163 (7.46 g, 56.9 mmol), TEA (12 mL, 85 mmol) and trimethylamine hydrochloride (544 mg, 5.69 mmol) in DCM was cooled to 0° C. and stirred for 10 minutes. After that 4-methylbenzenesulfonyl chloride (11.9 g, 62.6 mmol) was added in 3 portions. The solution was stirred at RT until complete conversion. The reaction mixture was treated with N,N-dimethylethylenediamine (7.5 mL, 68 mmol) to consume unreacted 4-methylbenzenesulfonyl chloride. Water was added, the aqueous phase extracted with DCM (three times) and the organic layer was concentrated to dryness under reduced pressure to give 5.23 g of the title compound, which was used without further purification.

LCMS, method 1, rt: 0.86 min, MS ES+m/z=286 (M+H)+.

Intermediate 4DC: Methyl 3-(5-methyl-1,3-thiazol-2-yl)-5-{[(2S)-5-oxomorpholin-2-yl]methoxy}benzoate

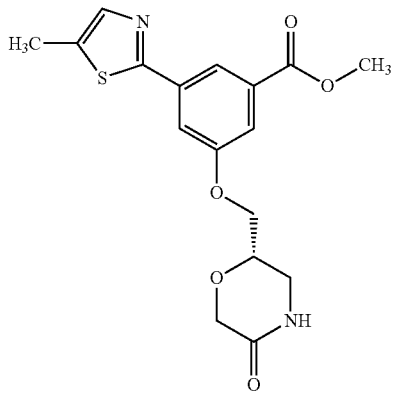

A mixture of Intermediate 3 (3.05 g, 12.2 mmol), Intermediate 6DC (5.23 g, 18.3 mmol), and Cs₂CO₃ (5.97 g, 18.3 mmol) in DMF (89 mL) was stirred at 90° C. until complete conversion. The DMF was evaporated and DCM and water was added. The mixture was extracted with DCM (three times), the combined organic layers evaporate to dryness under reduced pressure and the residue purified by silica gel column chromatography (EtOAc/EtOH gradient) to give 2.14 g (48% yield) of the title compound.

LCMS, method 1, rt: 1.00 min, MS ES+m/z=363 (M+H)+.

Intermediate 164: 2-Chloro-N-[(2S)-2,3-dihydroxypropyl]-N-methylacetamide

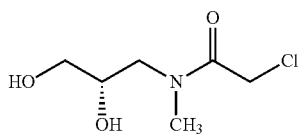

Intermediate 155 was dissolved in acetonitrile (84 mL) and MeOH (16 mL) and TEA (4.5 mL, 32 mmol) was added and the mixture was cooled to −10° C. A solution of chloroacetyl chloride (2.3 mL, 29 mmol) in acetonitrile was added dropwise and the mixture was stirred for 20 hours at RT. The solvent was distilled off under reduced pressure to give 8.64 g of the title compound, which was used without further purification.

Intermediate 165: (6S)-6-(Hydroxymethyl)-4-methylmorpholin-3-one

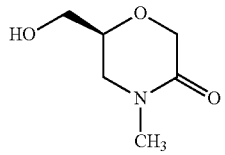

Potassium tert-butoxide (8.01 g, 71.4 mmol) was dissolved in 2-methylbutan-2-ol. A solution of Intermediate 164 in 2-methylbutan-2-ol was added dropwise over two hours. The mixture was stirred overnight and then the reaction solvent was distilled off under reduced pressure to give 3.63 g (53% yield) of the title compound, which was used without further purification.

Intermediate 6DD: [(2S)-4-Methyl-5-oxomorpholin-2-yl]methyl 4-methylbenzenesulfonate

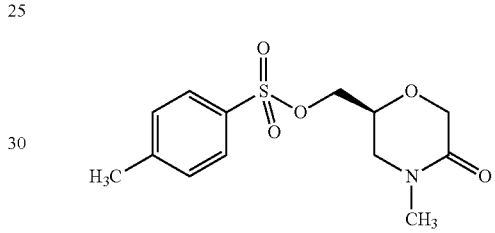

A mixture of Intermediate 165 (4.00 g, 27.6 mmol), TEA (5.8 mL, 41 mmol) and trimethylamine hydrochloride (263 mg, 2.76 mmol) in DCM (81 mL) was cooled to 0° C. and stirred for 10 minutes. After that 4-methylbenzenesulfonyl chloride (5.78 g, 30.3 mmol) was added in 3 portions. The solution was stirred at RT until complete conversion. The reaction mixture was treated with N,N-dimethylethylenediamine (3.6 mL, 33 mmol) to consume unreacted 4-methylbenzenesulfonyl chloride. Water was added, and the aqueous phase was extracted with DCM (three times) and the combined organic layers were concentrated to dryness. The residue was purified by column chromatography (silica gel, EtOAc/MeOH gradient) to give 2.55 g (31% yield) of the title compound.

LCMS, method 1, rt: 0.90 min, MS ES+m/z=300 (M+H)+.

Intermediate 4DD: Methyl 3-{[(2S)-4-methyl-5-oxomorpholin-2-yl]methoxy}-5-(5-methyl-1,3-thiazol-2-yl)benzoate

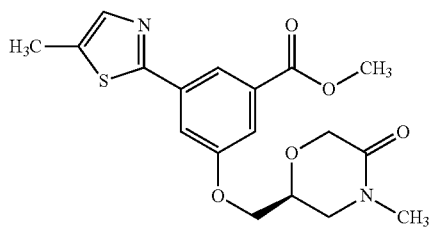

A mixture of Intermediate 3 (1.42 g, 5.68 mmol), Intermediate 6DD (2.55 g, 8.52 mmol), and $Cs_2CO_3$ (2.78 g, 8.52 mmol) in DMF (41 mL) was stirred at 90° C. until complete conversion. The DMF was distilled off under reduced pressure and the residue was purified by column chromatography (silica gel, EtOAc/hexane gradient) to give 1.57 g (73% yield) of the title compound.

LCMS, method 1, rt: 1.06 min, MS ES+m/z=377 (M+H)+.

Intermediate 166: N-[(2S)-1-(Benzyloxy)-3-hydroxypropan-2-yl]-2-chloroacetamide

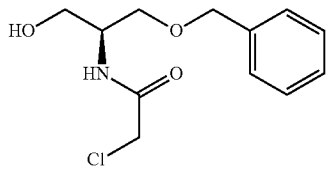 [SMILES: O=C(CCl)N[C@@H](CO)COCc1ccccc1]

(2S)-2-Amino-3-(benzyloxy)propan-1-ol (5.00 g, 27.6 mmol) was dissolved in acetonitrile (87 mL), MeOH (16 mL) and TEA (4.6 mL, 33 mmol) was added. The mixture was cooled to −10° C. and a solution of chloroacetyl chloride (2.4 mL, 30 mmol) in acetonitrile was added dropwise. The mixture was stirred for 20 hours at RT and the reaction solvents were distilled off to give 10.91 g of the title compound, which was used without further purification.

LCMS, method 1, rt: 0.83 min, MS ES+m/z=258 (M+H)+.

Intermediate 167: (5R)-5-[(Benzyloxy)methyl]morpholin-3-one

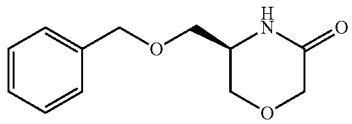 [SMILES: O=C1COC[C@@H](COCc2ccccc2)N1]

Potassium tert-butoxide (3.96 g, 35.3 mmol) was dissolved in 2-methylbutan-2-ol. A solution of the Intermediate 166 (5.68 g, 17.6 mmol) in 2-methylbutan-2-ol (160 mL in total) was added dropwise over two hours and the mixture was stirred until complete conversion. The reaction solvent was distilled off under reduced pressure and the residue was purified by silica gel column chromatography (EtOAc/EtOH gradient) to give 3.57 g (89% yield) of the title compound.

$^1$H NMR (400 MHz, CHLOROFORM-d): δ [ppm] 3.39-3.47 (m, 1H) 3.56 (dd, 1H) 3.63 (dd, 1H) 3.71-3.81 (m, 1H) 3.87 (dd, 1H) 4.09-4.24 (m, 2H) 4.49-4.60 (m, 2H) 6.39 (br. s., 1H) 7.29-7.43 (m, 5H).

Intermediate 168: (5R)-5-[(Benzyloxy)methyl]-4-methylmorpholin-3-one

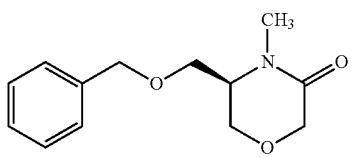 [SMILES: CN1C(=O)COC[C@H]1COCc1ccccc1]

A solution of Intermediate 167 (2.00 g, 9.04 mmol) in THF (25 mL) was added dropwise to a suspension of NaH (434 mg, 60% purity, 10.8 mmol) in THF (70 mL) at 0° C. The mixture was stirred for 30 minutes at RT. To the mixture, MeI (2.8 mL, 45 mmol) was added at 0° C., and the mixture was stirred for 15 hours at room temperature. A saturated aqueous solution (50 mL) of $NH_4Cl$ was added at 0° C., and the solvents were distilled off under reduced pressure. The residue was diluted with water and extracted with EtOAc (three times). The combined organic layers were dried over $MgSO_4$ and the solvent distilled off under reduced pressure to give 1.78 g (78% yield) of the title compound.

$^1$H NMR (500 MHz, CHLOROFORM-d): δ [ppm] 3.03 (s, 3H) 3.40 (ddd, 1H) 3.62-3.81 (m, 3H) 4.03-4.24 (m, 3H) 4.51-4.61 (m, 2H) 7.29-7.41 (m, 5H).

Intermediate 169: (5R)-5-(Hydroxymethyl)-4-methylmorpholin-3-one

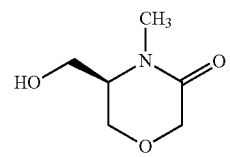

Intermediate 168 (1.78 g, 7.57 mmol) was dissolved in MeOH (140 mL), Pd(OH)$_2$ (266 mg, 20% on carbon, 378 μmol) was added and the mixture stirred for 10 hours under a hydrogen atmosphere. Another 0.0025 equivalents catalyst was added and and the mixture stirred for additional 3 hours under a hydrogen atmosphere. The reaction mixture was filtered through Celite® and washed with EtOH and the filtrate under reduced pressure to give 1.12 g of the title compound, which was used without further purification.

Intermediate 6DE: [(3S)-4-Methyl-5-oxomorpholin-3-yl]methyl 4-methylbenzenesulfonate

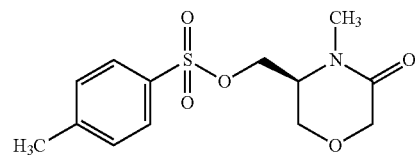 [SMILES: Cc1ccc(S(=O)(=O)OC[C@@H]2COCC(=O)N2C)cc1]

A mixture of Intermediate 169, TEA (1.6 mL, 12 mmol) and trimethylamine hydrochloride (73.7 mg, 772 μmol) in DCM (23 mL) was cooled to 0° C. and stirred for 10 minutes. After that 4-methylbenzenesulfonyl chloride (1.62 g, 8.49 mmol) was added in 3 portions. The solution was stirred at RT until complete conversion. The reaction mixture was treated with N,N-dimethylethylenediamine (1.0 mL, 9.3 mmol) to consume unreacted 4-methylbenzenesulfonyl chloride. Water was added to the mixture and the phases separated. The aqueous phase was extracted with DCM (three times) and the combined organic layers concentrated to dryness. The residue was purified by column chromatography (silica gel, EtOAc/hexane gradient) to give 917 mg (40% yield) of the title compound.

LCMS, method 1, rt: 0.89 min, MS ES+m/z=300 (M+H)+.

Intermediate 4DE: Methyl 3-{[(3S)-4-methyl-5-oxomorpholin-3-yl]methoxy}-5-(5-methyl-1,3-thiazol-2-yl)benzoate

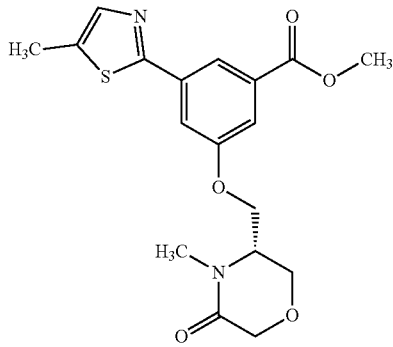

A mixture of Intermediate 3 (312 mg, 1.25 mmol), Intermediate 6DE (450 mg, 1.50 mmol) and Cs$_2$CO$_3$ (612 mg, 1.88 mmol) in DMF (6.3 mL) was stirred at 90° C. until complete conversion. The DMF was distilled off under reduced pressure, water and DCM was added and the layers separated. The aqueous layer was extracted with DCM (three times) and the combined organic layers were evaporated to dryness.

The residue was purified by column chromatography (silica gel, EtOAc/hexane gradient) to give 294 mg (58% yield) of the title compound.

$^1$H NMR (400 MHz, DMSO-d$_6$): δ [ppm] 3.00 (s, 3H) 3.71-3.79 (m, 1H) 3.83-3.92 (m, 4H) 4.01 (d, 1H) 4.08 (d, 2H) 4.29 (d, 1H) 4.33-4.42 (m, 1H) 7.57 (dd, 1H) 7.66 (d, 1H) 7.70 (dd, 1H) 8.02 (t, 1H).

Intermediate 170: (5R)-5-(Hydroxymethyl)morpholin-3-one

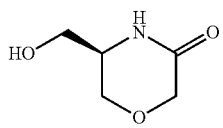

Intermediate 167 was dissolved in MeOH (120 mL), Pd(OH)$_2$ (244 mg, 20% on carbon, 348 μmol) added and stirred for 10 h under a hydrogen atmosphere. Another 0,025 equivalents catalyst was added and the mixture was stirred for additional 3 hours. The reaction mixture was filtered through Celite® and washed with EtOH. The filtrate was concentrated under reduced pressure to afford 1.16 g of the title compound, which was used without further purification.

Intermediate 6DF: [(3S)-5-Oxomorpholin-3-yl]methyl 4-methylbenzenesulfonate

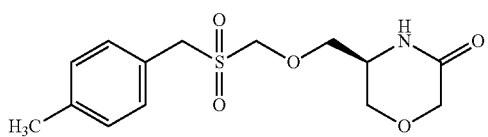 [SMILES: Cc1ccc(CS(=O)(=O)COC[C@@H]2COCC(=O)N2)cc1]

A mixture of Intermediate 170 (1.16 g, 8.85 mmol), TEA (1.8 mL, 13 mmol) and trimethylamine hydrochloride (84.5 mg, 885 μmol) in DCM (26 mL) was cooled to 0° C. and stirred for 10 minutes. After that 4-methylbenzenesulfonyl chloride (1.86 g, 9.73 mmol) was added in 3 portions. The solution was stirred at RT until complete conversion. The reaction mixture was treated with N,N-dimethylethylenediamine (1.2 mL, 11 mmol) to consume unreacted 4-methylbenzenesulfonyl chloride. Water was added to the mixture, the layers separated and the aqueous phase extracted with DCM (three times). The combined organic layers were concentrated to dryness and the residue was purified by silica gel column chromatography (hexane/EtOAc/MeOH gradient) to give 1.06 g (42% yield) of the title compound.

LCMS, method 1, rt: 0.83 min, MS ES+m/z=286 (M+H)$^+$.

Intermediate 4DF: Methyl 3-(5-methyl-1,3-thiazol-2-yl)-5-{[(3S)-5-oxomorpholin-3-yl]methoxy}benzoate

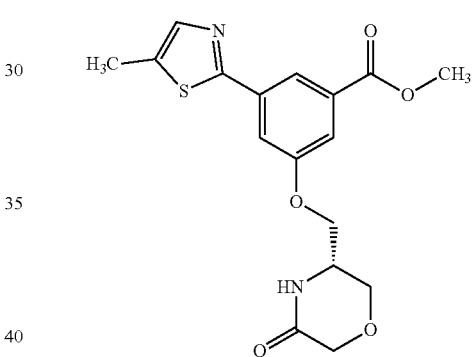

A mixture of Intermediate 3 (364 mg, 1.46 mmol), Intermediate 6DF (500 mg, 1.75 mmol) and Cs$_2$CO$_3$ (714 mg, 2.19 mmol) was stirred at 90° C. until complete conversion. The DMF was evaporated under reduced pressure, water and DCM was added and the layers separated. The aqueous layer was extracted with DCM (three times) and the combined organic layers were evaporated to dryness. The residue was purified by silica gel column chromatography (hexane/EtOAc/MeOH gradient) to give 349 mg (59% yield) of the title compound.

$^1$H NMR (400 MHz, DMSO-d$_6$): δ [ppm] 3.76 (d, 1H) 3.84-3.88 (m, 2H) 3.89 (s, 3H) 4.01 (s, 2H) 4.08 (dd, 1H) 4.20 (dd, 1H) 7.55 (dd, 1H) 7.63-7.72 (m, 2H) 7.98-8.05 (m, 1H) 8.30 (d, 1H).

Intermediate 6DJ: tert-Butyl 1-({[(4-methylphenyl)sulfonyl]oxy}methyl)-2-oxa-5-azabicyclo[2.2.1]heptane-5-carboxylate, as a mixture of two enantiomers

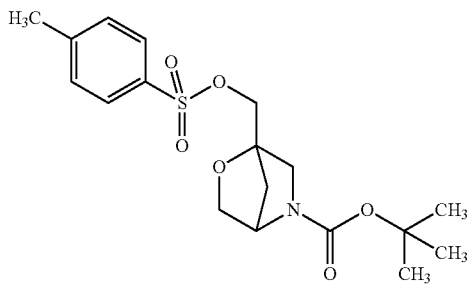 [SMILES: Cc1ccc(S(=O)(=O)OCC23CC(CO2)N(C(=O)OC(C)(C)C)C3)cc1]

A mixture of tert-butyl 1-(hydroxymethyl)-2-oxa-5-azabicyclo[2.2.1]heptane-5-carboxylate (1.00 g, 4.36 mmol), TEA (910 µL, 6.5 mmol) and trimethylamine hydrochloride (41.7 mg, 436 µmol) in DCM (13 mL) was cooled to 0° C. and stirred for 10 minutes. After that 4-methylbenzenesulfonyl chloride (915 mg, 4.80 mmol) was added in 3 portions and the solution stirred at RT overnight. The reaction mixture was treated with N,N-dimethylethylenediamine (570 µL, 5.2 mmol) to consume unreacted 4-methylbenzenesulfonyl chloride. Water was added to the mixture, the aqueous phase extracted with DCM (three times) and the combined organic layers concentrated to dryness under reduced pressure. The residue was purified by silica gel column chromatography (hexane/EtOAc/MeOH gradient) to give 1.41 g (84% yield) of the title compound.

$^1$H NMR (400 MHz, DMSO-$d_6$): δ [ppm] 1.38 (d, 9H) 1.63-1.82 (m, 2H) 2.43 (s, 3H) 3.04-3.24 (m, 2H) 3.66 (s, 2H) 4.37 (d, 3H) 7.49 (d, 2H) 7.75-7.85 (m, 2H).

Intermediate 4DG: tert-Butyl 1-{[3-(methoxycarbonyl)-5-(5-methyl-1,3-thiazol-2-yl)phenoxy]methyl}-2-oxa-5-azabicyclo[2.2.1]heptane-5-carboxylate, as a mixture of two enantiomers

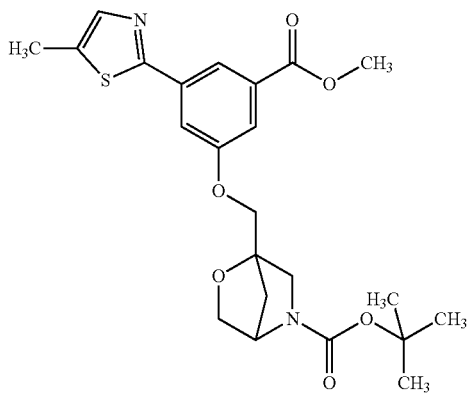 [SMILES: COC(=O)c1cc(OCC23CC(CO2)N(C(=O)OC(C)(C)C)C3)cc(-c2ncc(C)s2)c1]

A mixture of Intermediate 3 (450 mg, 1.81 mmol), Intermediate 6DJ, Cs2CO3 (882 mg, 2.71 mmol) and DMF (10 mL) was stirred at 90° C. until complete conversion. The DMF was evaporated under reduced pressure, the residue was dissolved in water and DCM and the phases separated. The aqueous layer was extracted twice with DCM. The combined organic layers were evaporated to dryness under reduced pressure and the residue was purified by silica gel column chromatography (hexane/EtOAc gradient) to give 635 mg (69% yield) of the title compound.

$^1$H NMR (400 MHz, DMSO-$d_6$): δ [ppm] 1.35-1.47 (m, 9H) 1.84-1.96 (m, 2H) 3.35-3.48 (m, 2H) 3.70-3.79 (m, 1H) 3.81-3.92 (m, 4H) 4.34-4.57 (m, 3H) 7.55 (dd, 1H) 7.64-7.72 (m, 2H) 8.01 (t, 1H).

Intermediate 171: Methyl 3-(5-methyl-1,3-thiazol-2-yl)-5-(2-oxa-5-azabicyclo[2.2.1]hept-1-ylmethoxy)benzoate, as a mixture of two enantiomers

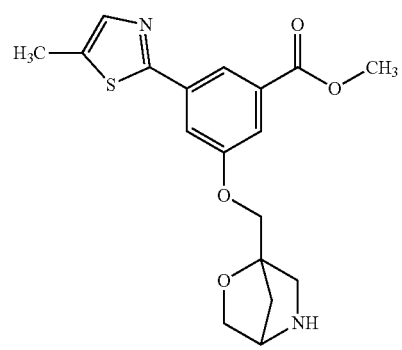

A mixture of Intermediate 4DG, TFA (4.4 mL, 57 mmol) and DCM (44 mL) was stirred at RT until complete conversion. The mixture was evaporated to dryness under reduced pressure to give 530 mg of the title compound, which was used without further purification.

$^1$H NMR (400 MHz, DMSO-$d_6$): δ [ppm] 2.02 (m, 1H) 2.12 (m, 1H) 3.35 (t, 2H) 3.85-3.93 (m, 4H) 3.97-4.18 (m, 2H) 4.45 (br. s., 1H) 4.50-4.67 (m, 2H) 7.56 (dd, 1H) 7.64-7.76 (m, 2H) 8.02 (t, 1H).

Intermediate 173: Methyl 3-[(5-methyl-2-oxa-5-azabicyclo[2.2.1]hept-1-yl)methoxy]-5-(5-methyl-1,3-thiazol-2-yl)benzoate, as a mixture of two enantiomers

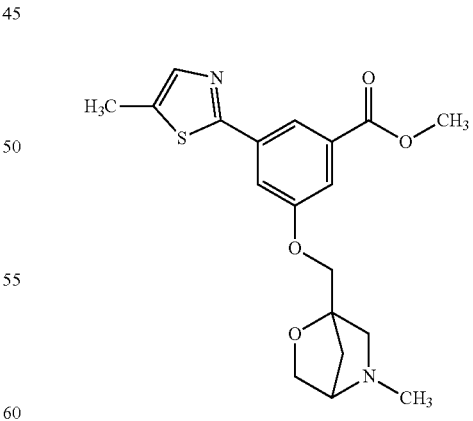

A mixture of Intermediate 171 (257 mg, 712 µmol), formaldehyde (530 µL, 37%, 7.1 mmol), acetic acid (410 µL, 100%, 7.1 mmol) and 1,2-dichlorethane (6.1 mL) was stirred at RT for 30 min. After that sodium triacetoxyborohydride was added (3.0 mL, 2.1 mmol) carefully and the mixture stirred at RT. Additional amounts of formaldehyde, acetic acid and sodium triacetoxyborohydride were added to drive the reaction to completion. A saturated aqueous NaHCO₃-solution was added and the aqueous layer extracted twice with DCM. The combined organic layers were evaporated to dryness under reduced pressure. The residue was purified by silica gel column chromatography (hexane/EtOAc gradient) to give 100 mg (38% yield) of the title compound.

¹H NMR (600 MHz, DMSO-d₆): δ [ppm] 1.68-1.75 (m, 1H) 1.84-1.92 (m, 1H) 2.34 (s, 3H) 2.90-2.97 (m, 1H) 3.36-3.41 (m, 1H) 3.62-3.68 (m, 1H) 3.89 (s, 3H) 3.96-4.01 (m, 1H) 4.37 (s, 1H) 4.41 (s, 1H) 7.48-7.57 (m, 1H) 7.66 (d, 2H) 8.01 (s, 1H).

Intermediate 174: Methyl 3-[(5-isopropyl-2-oxa-5-azabicyclo[2.2.1]hept-1-yl)methoxy]-5-(5-methyl-1,3-thiazol-2-yl)benzoate, as a mixture of two enantiomers

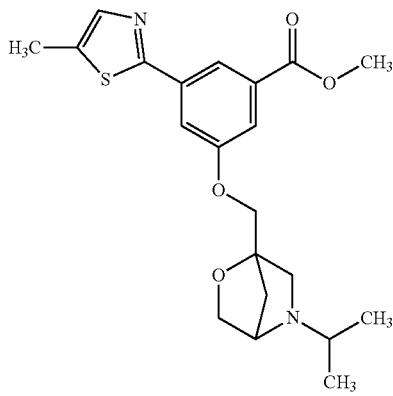 [SMILES: COC(=O)c1cc(OCC23CC(CO2)N(C(C)C)C3)cc(-c2ncc(C)s2)c1]

Intermediate 174 (150 mg, 54%) was synthesised from Intermediate 171 (250 mg, 694 µmol) and acetone (200 µL, 2.8 mmol) in analogy to the conversion of Intermediate 171 to Intermediate 173.

¹H NMR (500 MHz, DMSO-d₆) δ [ppm] 0.96-1.07 (m, 6H) 1.70-1.85 (m, 2H) 2.61-2.77 (m, 1H) 3.05-3.20 (m, 1H) 3.60-3.75 (m, 2H) 3.89 (s, 3H) 3.99 (d, 1H) 4.30-4.47 (m, 2H) 7.53 (dd, 1H) 7.63-7.70 (m, 2H) 8.00 (t, 1H).

Intermediate 5CF: 3-{[4-(Tert-butoxycarbonyl)morpholin-2-yl]methoxy}-5-(5-methyl-1,3-thiazol-2-yl)benzoic acid, as a mixture of enantiomers

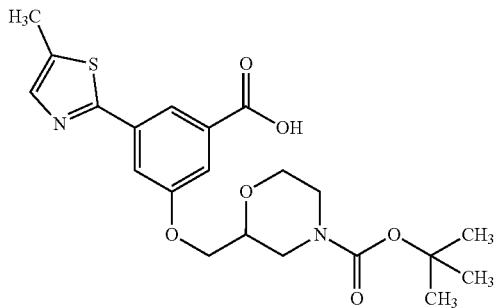 [SMILES: Cc1cnc(-c2cc(OCC3CN(C(=O)OC(C)(C)C)CCO3)cc(C(=O)O)c2)s1]

Intermediate 4CF (331 mg, 0.59 mmol) was dissolved in MeOH (5 mL) and THF (5 mL). 1M LiOH (2 mL) was added and the reaction stirred at RT for 2 h. The reaction mixture was concentrated to dryness and the residue taken up in water (5 mL) and washed with EtOAc (5 mL). The aqueous layer was acidified to pH 4 with 1M HCl and extracted with DCM (2×5 mL) and 1:1 IPA/CHCl₃ (2×5 mL). The combined organics were dried (MgSO₄), filtered and concentrated under reduced pressure. The residue was taken up in MeCN/water and freeze-dried to give 231.2 mg (85% yield) of the title compound as white powder.

¹H NMR (250 MHz, DMSO-d): δ [ppm] 7.99 (s, 1H), 7.67-7.63 (m, 1H), 7.63-7.59 (m, 1H), 7.53-7.48 (m, 1H), 4.24-4.07 (m, 2H), 3.99-3.81 (m, 2H), 3.79-3.65 (m, 2H), 3.53-3.40 (m, 1H), 3.00-2.79 (m, 2H), 1.41 (s, 9H).

LC-MS (Method A) Rt=1.36 min, MS (ESIpos): m/z=435 (M+H)⁺.

Intermediate 5CE: 3-{[(2R)-4-(tert-butoxycarbonyl)morpholin-2-yl]methoxy}-5-(5-methyl-1,3-thiazol-2-yl)benzoic acid

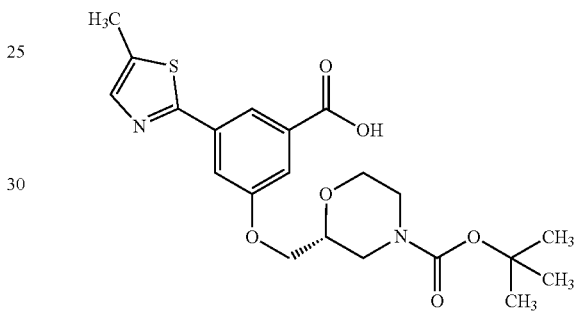

Intermediate 4CE (27.2 g, 48.6 mmol) was dissolved in THF (200 mL). 1M LiOH (100 mL, 100 mmol) was added and the reaction stirred at RT for 2 h. Further THF (50 mL), 1M LiOH (50 mL, 50 mmol) and methanol (20 mL) was added and the reaction mixture stirred at RT for 1 h. The reaction mixture was concentrated to remove MeOH/THF and the aqueous layer washed with EtOAc. The aqueous layer was acidified to pH 4 with conc. HCl and extracted with DCM (3×100 mL). The combined DCM and EtOAc organics were dried (MgSO₄), filtered and concentrated under reduced pressure to give 28.21 g (94% yield) of the title compound as yellow viscous oil.

¹H NMR (250 MHz, Chloroform-d): δ [ppm] 8.23 (s, 1H), 7.65 (s, 2H), 7.54 (s, 1H), 4.27-3.48 (m, 7H), 3.11-2.77 (m, 2H), 2.50 (s, 3H), 1.47 (s, 9H).

LCMS (Method A) Rt=1.23 min, MS (ESIpos): m/z=435 (M+H)⁺.

In analogy to the procedure described for Intermediate 5CF, the following Intermediates were prepared using the corresponding ester starting materials.

| Int. | Structure | Name | Analytical Data |
|---|---|---|---|
| 5CG | 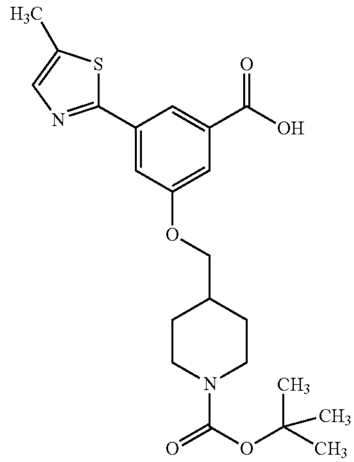 [SMILES: Cc1cnc(-c2cc(OCC3CCN(C(=O)OC(C)(C)C)CC3)cc(C(=O)O)c2)s1] | 3-{[1-(tert-butoxycarbonyl)piperidin-4-yl]methoxy}-5-(5-methyl-1,3-thiazol-2-yl)benzoic acid | $^1$H NMR (500 MHz, Chloroform-d): δ [ppm] 8.22 (t, J = 1.3, 1H), 7.74-7.68 (m, 1H), 7.63 (dd, J = 2.4, 1.3, 1H), 7.58 (d, J = 1.1, 1H), 4.17 (s, 2H), 3.94 (d, J = 6.4, 2H), 2.86-2.69 (m, 2H), 2.54 (d, J = 0.9, 3H), 2.04-1.95 (m, 1H), 1.91-1.79 (m, 2H), 1.48 (s, 9H), 1.38-1.25 (m, 2H). LC-MS (Method A) Rt = 1.29 min, MS (ESIpos): m/z = 433 (M + H)$^+$. |
| 5CD | 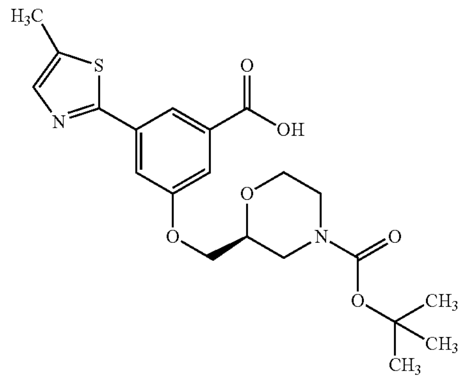 [SMILES: Cc1cnc(-c2cc(OC[C@@H]3CN(C(=O)OC(C)(C)C)CCO3)cc(C(=O)O)c2)s1] | 3-{[(2S)-4-(tert-butoxycarbonyl)morpholin-2-yl]methoxy}-5-(5-methyl-1,3-thiazol-2-yl)benzoic acid | LC-MS (Method A) Rt = 1.20 min, MS (ESIpos) m/z = 435 (M + H)$^+$. |
| 5CH | 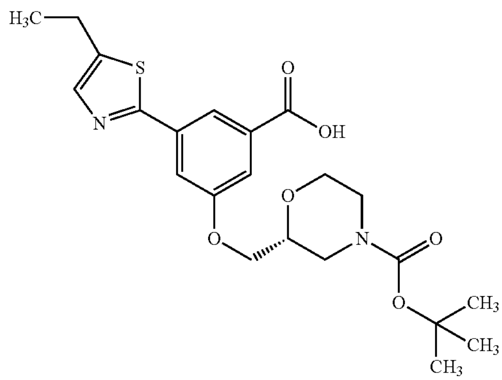 [SMILES: CCc1cnc(-c2cc(OC[C@H]3CN(C(=O)OC(C)(C)C)CCO3)cc(C(=O)O)c2)s1] | 3-{[(2R)-4-(tert-butoxycarbonyl)morpholin-2-yl]methoxy}-5-(5-ethyl-1,3-thiazol-2-yl)benzoic acid | $^1$H NMR (500 MHz, DMSO-d6): δ [ppm] 1.29 (t, J = 7.5 Hz, 3H), 1.41 (s, 9H), 2.73-3.00 (m, 4H), 3.46 (td, J = 11.6, 2.7 Hz, 1H), 3.67-3.76 (m, 2H), 3.82-3.96 (m, 2H), 4.11-4.22 (m, 2H), 7.51 (dd, J = 2.4, 1.3 Hz, 1H), 7.63-7.65 (m, 1H), 7.68-7.69 (m, 1H), 8.00 (t, J = 1.4 Hz, 1H), 13.23 (s, 1H). LC-MS (Method A) Rt = 1.31 min, MS (ESIpos): m/z = 449 (M + H)$^+$. |
| 5CI | 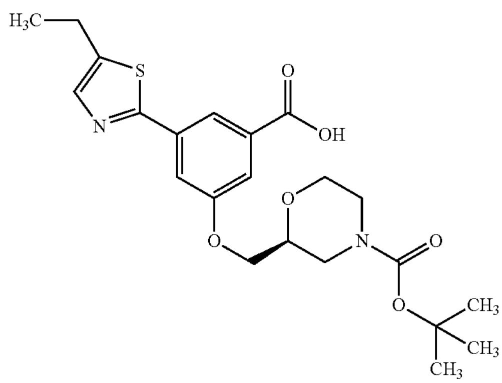 [SMILES: CCc1cnc(-c2cc(OC[C@@H]3CN(C(=O)OC(C)(C)C)CCO3)cc(C(=O)O)c2)s1] | 3-{[(2S)-4-(tert-butoxycarbonyl)morpholin-2-yl]methoxy}-5-(5-ethyl-1,3-thiazol-2-yl)benzoic acid | $^1$H NMR (500 MHz, DMSO-d6): δ [ppm] 1.29 (td, J = 7.5, 3.0 Hz, 3H), 1.41 (s, 9H), 2.90 (m, 4H), 3.46 (td, J = 11.6, 2.8 Hz, 1H), 3.66-3.78 (m, 2H), 3.82-3.98 (m, 2H), 4.11-4.23 (m, 2H), 7.51 (dd, J = 2.4, 1.4 Hz, 1H), 7.61-7.64 (m, 1H), 7.68 (s, 1H), 8.00 (t, J = 1.3 Hz, 1H), 13.27 (s, 1H). LC-MS (Method A) Rt = 1.33 min, MS (ESIpos): m/z = 449 (M + H)$^+$. |

| Int. | Structure | Name | Analytical Data |
|------|-----------|------|-----------------|
| 5CJ | 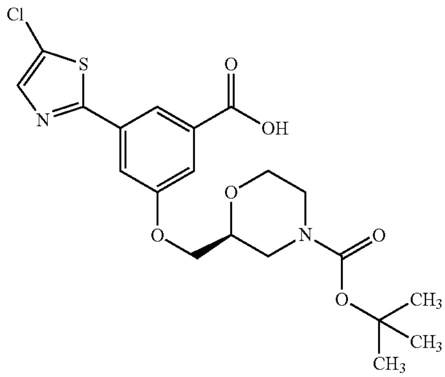 [SMILES: CC(C)(C)OC(=O)N1CCO[C@H](COc2cc(C(=O)O)cc(-c3ncc(Cl)s3)c2)C1] | 3-[[(2S)-4-tert-butoxycarbonylmorpholin-2-yl]methoxy]-5-(5-chlorothiazol-2-yl)benzoic acid | $^1$H NMR (500 MHz, chloroform-d): δ [ppm] 8.14 (s, 1H), 7.73-7.69 (m, 2H), 7.68 (s, 1H), 4.29-4.06 (m, 3H), 4.06-3.74 (m, 3H), 3.63 (td, J = 11.5, 2.3 Hz, 1H), 3.14-2.97 (m, 1H), 2.97-2.79 (m, 1H), 1.49 (s, 9H). LC-MS (Method A) Rt = 1.32 min, MS (ESIpos): m/z = 455 (M + H)$^+$. |
| 5CK | 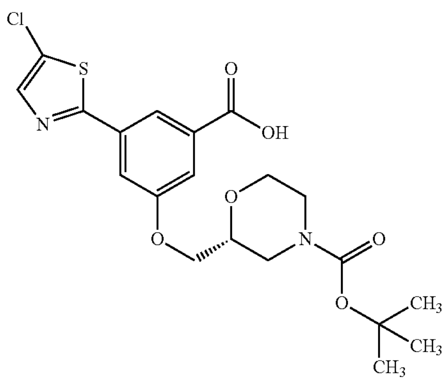 [SMILES: CC(C)(C)OC(=O)N1CCO[C@@H](COc2cc(C(=O)O)cc(-c3ncc(Cl)s3)c2)C1] | 3-[[(2R)-4-tert-butoxycarbonylmorpholin-2-yl]methoxy]-5-(5-chlorothiazol-2-yl)benzoic acid | $^1$H NMR (500 MHz, chloroform-d): δ [ppm] 8.14 (t, J = 1.4 Hz, 1H), 7.72-7.69 (m, 2H), 7.68 (s, 1H), 4.22-4.07 (m, 3H), 4.03-3.73 (m, 3H), 3.71-3.51 (m, 1H), 3.10-2.97 (m, 1H), 2.96-2.83 (m, 1H), 1.49 (s, 9H). LC-MS (Method A) Rt = 1.37 min, MS ESIpos): m/z = 455 (M + H)$^+$. |
| 5CL | 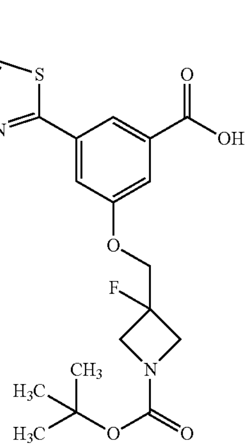 | 3-{[1-(tert-butoxycarbonyl)-3-fluoroazetidin-3-yl]methoxy}-5-(5-methyl-1,3-thiazol-2-yl)benzoic acid | $^1$H NMR (500 MHz, DMSO-d6): δ [ppm] 1.40 (s, 9H), 2.51 (s, 3H), 3.97-4.08 (m, 2H), 4.15 (dd, J = 18.1, 10.2 Hz, 2H), 4.53 (d, J = 22.0 Hz, 2H), 7.55 (dd, J = 2.5, 1.3 Hz, 1H), 7.63-7.67 (m, 2H), 8.02 (t, J = 1.4 Hz, 1H), 13.32 (s, 1H). LC-MS (Method A) Rt = 1.24 min, MS (ESIpos): m/z = 423 (M + H)$^+$. |

249

Intermediate 5CV: 3-{[1-(tert-Butoxycarbonyl)azetidin-3-yl]methoxy}-5-(5-methyl-1,3-thiazol-2-yl)benzoic acid

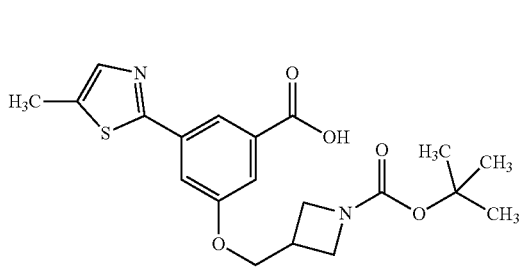 [SMILES: Cc1cnc(-c2cc(OCC3CN(C(=O)OC(C)(C)C)C3)cc(C(=O)O)c2)s1]

A mixture of Intermediate 4CV (100 mg, 239 μmol), NaOH (600 μL, 2.0 M, 1.2 mmol) in MeOH (20 mL) was stirred at RT until complete conversion. The MeOH was evaporated and aqueous HU-solution (2N) was added and the pH adjusted to pH 4. The aqueous layer was extracted with DCM. The combined organics were evaporated to dryness to give 95 mg (98% yield) of the title compound, which was used without further purification.

LCMS, method 1, rt: 1.28 min, MS ES+m/z=405 (M+H)+.

Intermediate 5CX: 3-{[(3R)-4-Methyl-5-oxomorpholin-3-yl]methoxy}-5-(5-methyl-1,3-thiazol-2-yl)benzoic acid

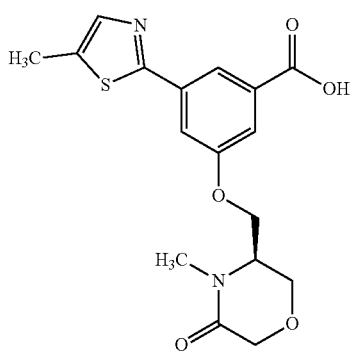 [SMILES: Cc1cnc(-c2cc(OC[C@H]3COCC(=O)N3C)cc(C(=O)O)c2)s1]

To a solution of Intermediate 4CX (530 mg, 1.41 mmol) in MeOH was added an aqueous NaOH-solution (1.8 mL, 2.0 M, 3.5 mmol). The mixture was stirred at RT until complete conversion. The reaction mixture was concentrated under reduced pressure and the pH adjusted to pH: 5. The mixture was extracted three times with EtOAc and the combined organic layers evaporated to dryness to give 417 mg (82% yield) of the title compound.

LCMS, method 1, rt: 0.90 min, MS ES+m/z=363 (M+H)+.

250

Intermediate 5CY: 3-(5-Methyl-1,3-thiazol-2-yl)-5-{[(3R)-5-oxomorpholin-3-yl]methoxy}benzoic acid

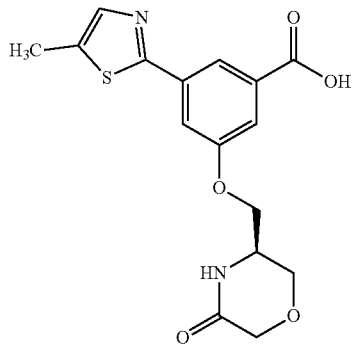 [SMILES: Cc1cnc(-c2cc(OC[C@H]3COCC(=O)N3)cc(C(=O)O)c2)s1]

To a solution of Intermediate 4CY (834 mg, 50% purity, 1.15 mmol) in MeOH was added an aqueous NaOH solution (1.4 mL, 2.0 M, 2.9 mmol). The mixture was stirred at RT for 15 h, another 1 mL aqueous NaOH solution (2.0 M) was added and the mixture stirred at RT until complete conversion. The reaction mixture was concentrated under reduced pressure and the pH adjusted to pH: 5. The mixture was extracted three times with EtOAc and the combined organic layers evaporated to dryness to give 466 mg of the title compound, which was used without further purification.

LCMS, method 1, rt: 0.84 min, MS ES+m/z=349 (M+H)+.

Intermediate 5CZ: 3-{[(5S)-3-Methyl-2-oxo-1,3-oxazolidin-5-yl]methoxy}-5-(5-methyl-1,3-thiazol-2-yl)benzoic acid

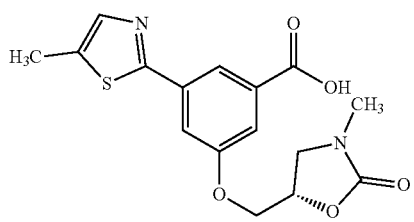 [SMILES: Cc1cnc(-c2cc(OC[C@@H]3CN(C)C(=O)O3)cc(C(=O)O)c2)s1]

To a mixture of Intermediate 4CZ in MeOH (15 mL) was added an aqueous NaOH solution (2.9 mL, 2.0 M, 5.8 mmol). The mixture was stirred at RT until complete conversion. The solvent was evaporated under reduced pressure and the pH adjusted to pH 5. The mixture was extracted three times with EtOAc and the organic layer evaporated to dryness to give 617 mg (83% yield) of the title compound, which was used without further purification.

LCMS, method 1, rt: 0.93 min, MS ES+m/z=349 (M+H)+.

Intermediate 5DA: 3-{[(5R)-3-Methyl-2-oxo-1,3-oxazolidin-5-yl]methoxy}-5-(5-methyl-1,3-thiazol-2-yl)benzoic acid

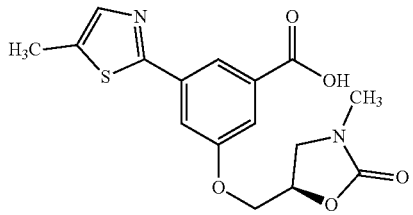 [SMILES: Cc1cnc(-c2cc(OC[C@H]3CN(C)C(=O)O3)cc(C(=O)O)c2)s1]

To a solution of Intermediate 4DA (609 mg, 1.68 mmol) in MeOH (6.4 mL) and THF (6.4 mL) was added an aqueous NaOH solution (2.1 mL, 2.0 M, 4.2 mmol). The mixture was stirred at RT until complete conversion. The mixture was concentrated under reduced pressure and the pH adjusted to pH: 3. Then the mixture was extracted three times with EtOAc and the organic layers evaporated to dryness under reduced pressure to give 518 mg (87% yield) of the title compound, which was used without further purification.

$^1$H NMR (400 MHz, DMSO-$d_6$): δ [ppm] 2.79 (s, 3H) 3.43 (dd, 1H) 3.70 (t, 1H) 4.22-4.30 (m, 1H) 4.31-4.38 (m, 1H) 4.82-4.93 (m, 1H) 7.53 (dd, 1H) 7.60-7.69 (m, 2H) 8.00 (t, 1H) 13.00-13.56 (m, 1H).

Intermediate 5DB: 3-{[(2R)-4-Methyl-5-oxomorpholin-2-yl]methoxy}-5-(5-methyl-1,3-thiazol-2-yl)benzoic acid

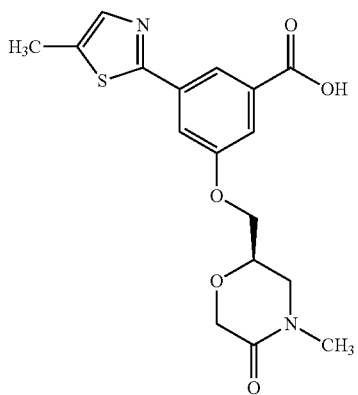

To a mixture of Intermediate 4DB in MeOH (28 mL) and THF (28 mL) was added an aqueous NaOH solution (9.2 mL, 2.0 M, 18 mmol). The mixture was stirred at RT until complete conversion. The mixture was concentrated under reduced pressure and the pH adjusted to pH: 3. The mixture was extracted three times with EtOAc, the combined organic layers were dried down under reduced pressure and the residue purified by column chromatography (silica gel, EtOAc/hexane gradient) to give 1.65 g (59% yield) of the title compound.

LCMS, method 1, rt: 0.91 min, MS ES+m/z=363 (M+H)$^+$.

Intermediate 5DC: 3-(5-Methyl-1,3-thiazol-2-yl)-5-{[(2S)-5-oxomorpholin-2-yl]methoxy}benzoic acid

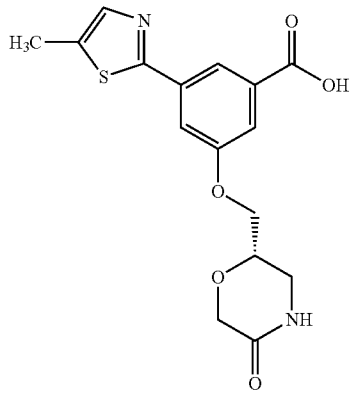 [SMILES: Cc1cnc(-c2cc(OC[C@@H]3CNC(=O)CO3)cc(C(=O)O)c2)s1]

To a mixture of Intermediate 4DC in MeOH (38 mL) and THF (38 mL) was added an aqueous NaOH solution (7.4 mL, 2.0 M, 15 mmol). The mixture was stirred at RT until complete conversion. The mixture was extracted with EtOAc and the phases separated. The aqueous layer was extracted three times with EtOAc and the combined organic layers were evaporated to dryness under reduced pressure to give 434 mg (21% yield) of the title compound LCMS, method 1, rt: 0.77 min, MS ES+m/z=349 (M+H)$^+$.

Intermediate 5DD: 3-{[(2S)-4-Methyl-5-oxomorpholin-2-yl]methoxy}-5-(5-methyl-1,3-thiazol-2-yl)benzoic acid

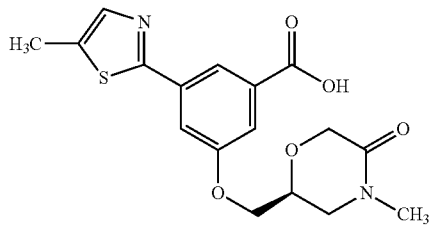

To a solution of Intermediate 4DD (1.57 g, 4.17 mmol) in MeOH (10 mL) and THF (10 mL) was added an aqueous NaOH solution (3.1 mL, 2.0 M, 6.3 mmol). The mixture was stirred at RT until complete conversion. The mixture was concentrated under reduced pressure and extracted three times with EtOAc. The combined organic layers were evaporated to dryness under reduced pressure to give 2.24 g of the title compound, which was used without further purification.

LCMS, method 1, rt: 0.87 min, MS ES+m/z=363 (M+H)$^+$.

Intermediate 5DE: 3-{[(3S)-4-Methyl-5-oxomorpholin-3-yl]methoxy}-5-(5-methyl-1,3-thiazol-2-yl)benzoic acid

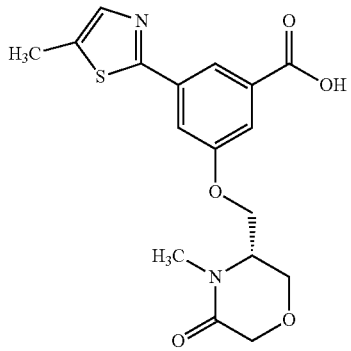 [SMILES: Cc1cnc(-c2cc(OC[C@@H]3COCC(=O)N3C)cc(C(=O)O)c2)s1]

To a mixture of Intermediate 4DE in MeOH was added an aqueous NaOH solution (980 μL, 2.0 M, 2.0 mmol). The mixture was stirred at RT until complete conversion. The pH was adjusted to pH: 5, the reaction mixture extracted with EtOAc, the organic layers dried with $Na_2SO_4$ and evaporated to dryness under reduced pressure to give 315 mg of the title compound, which was used without further purification.

LCMS, method 1, rt: 0.89 min, MS ES+m/z=363 (M+H)+.

Intermediate 5DF: 3-(5-Methyl-1,3-thiazol-2-yl)-5-{[(3S)-5-oxomorpholin-3-yl]methoxy}benzoic acid

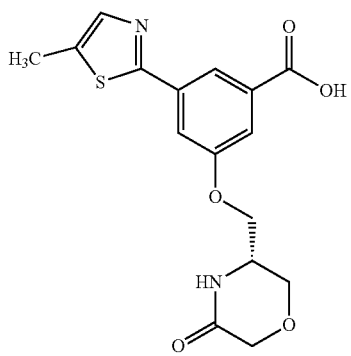 [SMILES: Cc1cnc(-c2cc(OC[C@@H]3COCC(=O)N3)cc(C(=O)O)c2)s1]

To a mixture of Intermediate 4DF in MeOH was added an aqueous NaOH solution (1.2 mL, 2.0 M, 2.4 mmol). The mixture was stirred at RT until complete conversion. The pH value was adjusted to pH: 5, and the reaction mixture extracted with EtOAc. The combined organic layers were dried with $Na_2SO_4$, filtered off and evaporated to dryness under reduced pressure to give 330 mg (98% yield) of the title compound, which was used without further purification.

LCMS, method 1, rt: 0.84 min, MS ES+m/z=349 (M+H)+.

Intermediate 172: 3-{[5-(tert-Butoxycarbonyl)-2-oxa-5-azabicyclo[2.2.1]hept-1-yl]methoxy}-5-(5-methyl-1,3-thiazol-2-yl)benzoic acid, as a mixture of two enantiomers

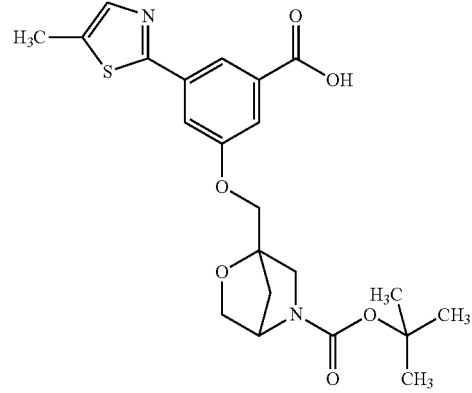 [SMILES: Cc1cnc(-c2cc(OCC34CC(CO3)N(C(=O)OC(C)(C)C)C4)cc(C(=O)O)c2)s1]

A mixture of Intermediate 4DG (630 mg, 1.37 mmol), aqueous NaOH solution (3.4 mL, 2.0 M, 6.8 mmol) and MeOH (20 mL) was stirred at RT until complete conversion.

The MeOH was evaporated under reduced pressure. DCM and water were added and the pH-value was adjusted to pH: 7 and the phases separated. The aqueous layer was extracted twice with DCM and the combined organic layers were evaporated to dryness to give 600 mg (98% yield) of the title compound, which was used without further purification.

$^1$H NMR (600 MHz, DMSO-$d_6$): δ [ppm] 1.36-1.49 (m, 9H) 1.82-2.01 (m, 2H) 3.32-3.47 (m, 2H) 3.71-3.80 (m, 1H) 3.81-3.92 (m, 1H) 4.36-4.55 (m, 3H) 7.54 (dd, 1H) 7.65 (d, 2H) 7.91-8.05 (m, 1H) 12.94-13.73 (m, 1H).

Intermediate 175: 3-[(5-Methyl-2-oxa-5-azabicyclo[2.2.1] hept-1-yl)methoxy]-5-(5-methyl-1,3-thiazol-2-yl)benzoic acid, as a mixture of two enantiomers

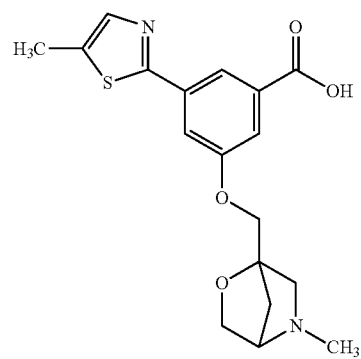

A mixture of Intermediate 173 (100 mg, 267 μmol), an aqueous NaOH solution (670 μL, 2.0 M, 1.3 mmol) in MeOH (10 mL) was stirred at RT until complete conversion. The solvent was evaporated under reduced pressure, DCM and water were added and the pH-value was adjusted to pH: 7. The aqueous layer was collected and evaporated to dryness to give 50 mg (52% yield) of the title compound.

LCMS, method 1, rt: 0.68 min, MS ES+m/z=361 (M+H)+.

Intermediate 176: 3-[(5-Isopropyl-2-oxa-5-azabicyclo[2.2.1]hept-1-yl)methoxy]-5-(5-methyl-1,3-thiazol-2-yl)benzoic acid, as a mixture of two enantiomers

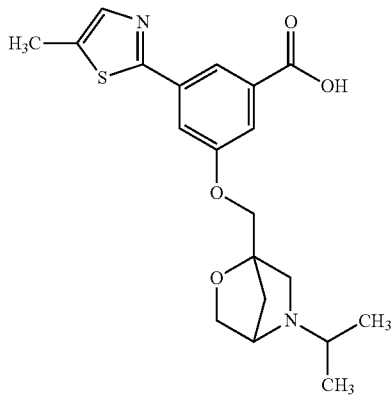 [SMILES: Cc1cnc(-c2cc(OCC34CC(CO3)N(C(C)C)C4)cc(C(=O)O)c2)s1]

A mixture of Intermediate 174 (150 mg, 373 μmol), an aqueous NaOH solution (930 μL, 2.0 M, 1.9 mmol) in MeOH (10 mL) was stirred at RT until complete conversion.

The solvent was evaporated under reduced pressure, DCM and water were added and the pH-value was adjusted to pH: 7. The layers were separated and the aqueous layer was extracted twice with DCM. The combined organic layers were evaporated to dryness and the residue purified by column chromatography to give 70.0 mg (48% yield) of the title compound.

LCMS, method 1, rt: 0.73 min, MS ES+m/z=389 (M+H)+.

Intermediate 114: Tert-butyl 2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate, as a mixture of diastereoisomers.

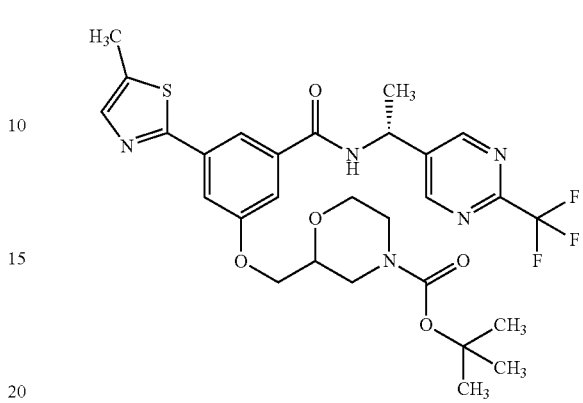

To a solution of Intermediate 5CF (497 mg, 0.995 mmol), Intermediate VI (228 mg, 1.19 mmol), DIPEA (693 μL, 3.98 mmol) in DCM (10 mL) was added T3P (889 μL, 1.49 mmol, 50% solution in EtOAc) and the mixture stirred at RT for 2 h. The reaction mixture was washed with saturated NaHCO₃ (5 mL). The organics were dried (MgSO₄), filtered and concentrated under reduced pressure. The crude material was purified by Biotage Isolera™ chromatography (eluting with 30-80% EtOAc in heptane on a 25 g pre-packed KP—SiO₂ column) to give 520.4 mg (86% yield) of the title compound as colourless gum.

¹H NMR (500 MHz, chloroform-d): δ [ppm] 8.94 (s, 2H), 7.89 (t, J=1.4 Hz, 1H), 7.56 (dd, J=2.3, 1.4 Hz, 1H), 7.53-7.51 (m, 1H), 7.40 (s, 1H), 6.78-6.71 (m, 1H), 5.41-5.32 (m, 1H), 4.18-4.02 (m, 3H), 3.99-3.77 (m, 3H), 3.65-3.55 (m, 1H), 3.13-2.73 (m, 2H), 2.53 (d, J=1.1 Hz, 3H), 1.71 (d, J=7.2 Hz, 3H), 1.48 (s, 9H)

LC-MS (Method A) Rt=1.32 min, MS (ESIpos): m/z=608 (M+H)+.

In analogy to the procedure described for Intermediate 114, the following Intermediates were prepared using T3P and the corresponding carboxylic acid and primary amine starting materials.

| Int. | Structure | Name | Analytical Data |
|---|---|---|---|
| 115 | (structure shown) | Tert-butyl 4-{[3-(5-methyl-1,3-thiazol-2-yl)-5-({(1R)-1-[2-(trifluoromethyl)pyrimidin-5-yl]ethyl}carbamoyl)phenoxy]methyl}piperidine-1-carboxylate | ¹H NMR (500 MHz, chloroform-d): δ [ppm] 8.94 (s, 2H), 7.86 (s, 1H), 7.54-7.52 (m, 1H), 7.52-7.49 (m, 1H), 7.38 (d, J = 1.6 Hz, 1H), 6.67 (d, J = 6.4 Hz, 1H), 5.36 (m, 1H), 3.90 (d, J = 6.3 Hz, 2H), 2.82-2.71 (m, 2H), 2.54 (s, 3H), 2.03-1.93 (m, 1H), 1.82 (d, J = 12.9 Hz, 2H), 1.72 (d, J = 7.2 Hz, 3H), 1.68-1.55 (m, 2H), 1.47 (s, 9H), 1.36-1.23 (m, 2H). LC-MS (Method A) Rt = 1.42 min, MS (ESIpos): m/z = 550 (M − ᵗBu)+. |

| Int. | Structure | Name | Analytical Data |
|---|---|---|---|
| 117 | 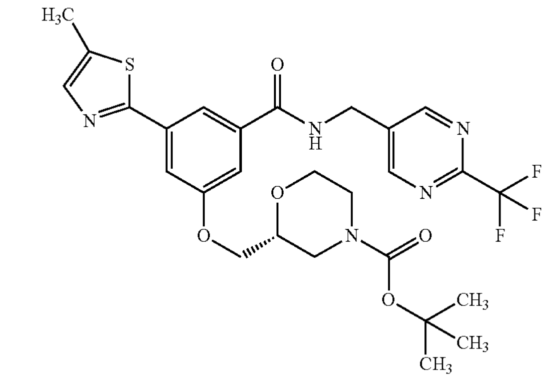 [SMILES: Cc1cnc(-c2cc(OC[C@H]3CN(C(=O)OC(C)(C)C)CCO3)cc(C(=O)NCc3cnc(C(F)(F)F)nc3)c2)s1] | Tert-butyl (2R)-2-{[3-(5-methyl-1,3-thiazol-2-yl)-5-({[2-(trifluoromethyl)pyrimidin-5-yl]methyl}carbamoyl)phenoxy]methyl}morpholine-4-carboxylate | $^1$H NMR (500 MHz, chloroform-d): δ [ppm] 8.94 (s, 2H), 7.93 (s, 1H), 7.60-7.55 (m, 1H), 7.52 (d, J = 1.1, 1H), 7.44 (s, 1H), 7.02 (s, 1H), 4.73 (d, J = 6.0, 2H), 4.10-4.04 (m, 2H), 4.01-3.76 (m, 4H), 3.64-3.54 (m, 1H), 3.06-2.95 (m, 1H), 2.95-2.76 (m, 1H), 2.53 (d, J = 1.0, 3H), 1.48 (s, 9H). LC-MS (Method A) Rt = 1.35 min, MS (ESIpos): m/z = 594 (M + H)$^+$. |
| 119 | 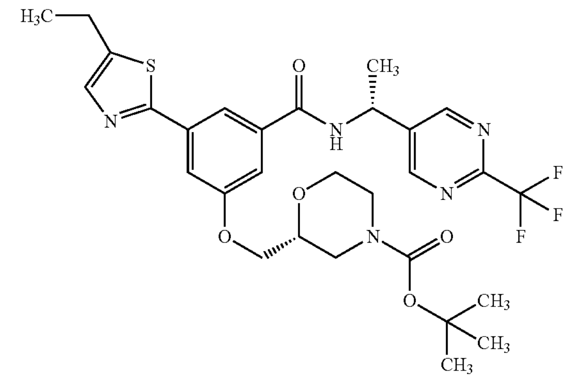 [SMILES: CCc1cnc(-c2cc(OC[C@H]3CN(C(=O)OC(C)(C)C)CCO3)cc(C(=O)N[C@H](C)c3cnc(C(F)(F)F)nc3)c2)s1] | Tert-butyl (2R)-2-{[3-(5-ethyl-1,3-thiazol-2-yl)-5-({(1R)-1-[2-(trifluoromethyl)pyrimidin-5-yl]ethyl}carbamoyl)phenoxy]methyl}morpholine-4-carboxylate | $^1$H NMR (500 MHz, DMSO-d6): δ [ppm] 1.30 (t, J = 7.5 Hz, 3H), 1.42 (s, 9H), 1.62 (d, J = 7.1 Hz, 3H), 2.73-3.01 (m, 4H), 3.47 (m, 1H), 3.70-3.78 (m, 2H), 3.83-3.99 (m, 2H), 4.12-4.23 (m, 2H), 5.31 (m, 1H), 7.51-7.62 (m, 2H), 7.69 (s, 1H), 7.96 (s, 1H), 9.13 (s, 2H), 9.16 (d, J = 7.1 Hz, 1H). LC-MS (Method A) Rt = 1.42 min, MS (ESIpos): m/z = 622 (M + H)$^+$. |
| 121 | 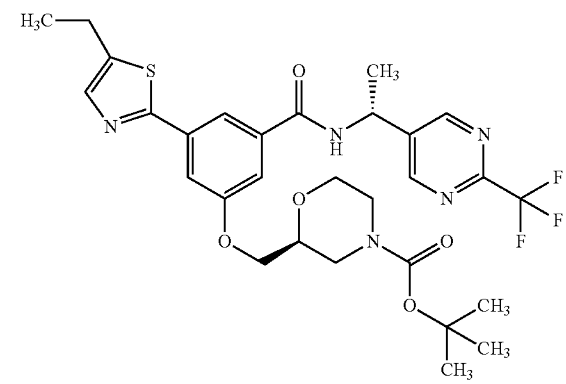 [SMILES: CCc1cnc(-c2cc(OC[C@@H]3CN(C(=O)OC(C)(C)C)CCO3)cc(C(=O)N[C@H](C)c3cnc(C(F)(F)F)nc3)c2)s1] | Tert-butyl (2S)-2-{[3-(5-ethyl-1,3-thiazol-2-yl)-5-({(1R)-1-[2-(trifluoromethyl)pyrimidin-5-yl]ethyl}carbamoyl)phenoxy]methyl}morpholine-4-carboxylate | $^1$H NMR (500 MHz, DMSO-d6): δ [ppm] 1.29 (t, J = 7.5 Hz, 3H), 1.41 (s, 9H), 1.61 (d, J = 7.1 Hz, 3H), 2.69-3.04 (m, 4H), 3.42-3.50 (m, 1H), 3.68-3.77 (m, 2H), 3.83-3.97 (m, 2H), 4.11-4.22 (m, 2H), 5.30 (m, 1H), 7.54-7.59 (m, 2H), 7.66-7.69 (m, 1H), 7.95 (t, J = 1.4 Hz, 1H), 9.09-9.13 (m, 2H), 9.15 (d, J = 7.1 Hz, 1H). LC-MS (Method A) Rt = 1.46 min, MS (ESIpos): m/z = 622 (M + H)$^+$. |
| 125 | 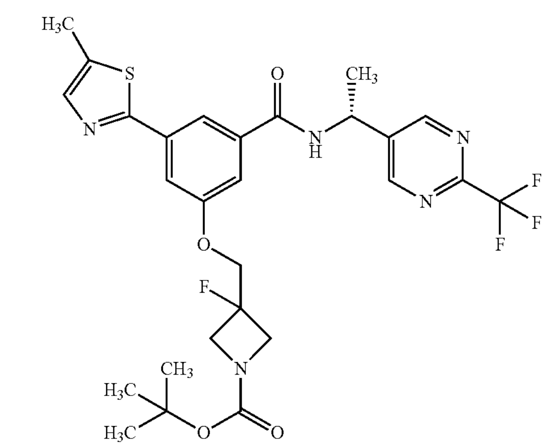 [SMILES: Cc1cnc(-c2cc(OCC3(F)CN(C(=O)OC(C)(C)C)C3)cc(C(=O)N[C@H](C)c3cnc(C(F)(F)F)nc3)c2)s1] | Tert-butyl 3-fluoro-3-{[3-(5-methyl-1,3-thiazol-2-yl)-5-({(1R)-1-[2-(trifluoromethyl)pyrimidin-5-yl]ethyl}carbamoyl)phenoxy]methyl}azetidine-1-carboxylate | $^1$H NMR (500 MHz, DMSO-d6): δ [ppm] 1.40 (s, 9H), 1.61 (d, J = 7.1 Hz, 3H), 2.51 (d, J = 1.0 Hz, 3H), 3.97-4.09 (m, 2H), 4.15 (dd, J = 18.4, 10.3 Hz, 2H), 4.52 (d, J = 22.0 Hz, 2H), 5.30 (m, 1H), 7.55-7.60 (m, 1H), 7.60-7.63 (m, 1H), 7.65 (d, J = 1.2 Hz, 1H), 7.96 (t, J = 1.4 Hz, 1H), 9.12 (s, 2H), 9.17 (d, J = 7.1 Hz, 1H). LC-MS (Method A) Rt = 1.35 min, MS (ESIpos): m/z = 596 (M + H)$^+$. |

-continued

| Int. | Structure | Name | Analytical Data |
|---|---|---|---|
| 119 | 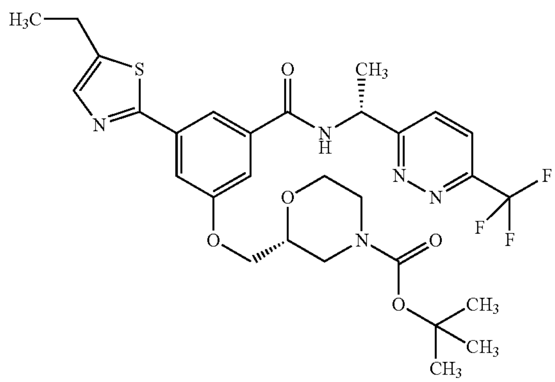 [SMILES: CCc1cnc(-c2cc(OC[C@H]3CN(C(=O)OC(C)(C)C)CCO3)cc(C(=O)N[C@H](C)c3ccc(C(F)(F)F)nn3)c2)s1] | Tert-butyl (2R)-2-{[3-(5-ethyl-1,3-thiazol-2-yl)-5-({(1R)-1-[6-(trifluoromethyl)pyridazin-3-yl]ethyl}carbamoyl)phenoxy]methyl}morpholine-4-carboxylate | $^1$H NMR (500 MHz, Chloroform-d): δ [ppm] 7.93-7.90 (m, 1H), 7.82 (d, J = 8.7 Hz, 1H), 7.74 (d, J = 8.7 Hz, 1H), 7.63-7.60 (m, 1H), 7.57-7.51 (m, 1H), 7.49-7.40 (m, 2H), 5.64-5.56 (m, 1H), 4.19-3.77 (m, 6H), 3.66-3.56 (m, 1H), 3.07-2.81 (m, 4H), 1.76 (d, J = 7.0 Hz, 3H), 1.48 (s, 9H), 1.36 (t, J = 7.5 Hz, 3H). LCMS (Method A) Rt = 1.42 min, MS (ESIpos): m/z = 622.15 (M + H)$^+$. |
| 121 | 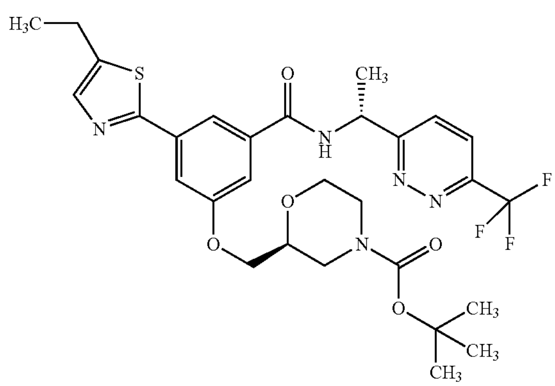 [SMILES: CCc1cnc(-c2cc(OC[C@@H]3CN(C(=O)OC(C)(C)C)CCO3)cc(C(=O)N[C@H](C)c3ccc(C(F)(F)F)nn3)c2)s1] | Tert-butyl (2S)-2-{[3-(5-ethyl-1,3-thiazol-2-yl)-5-({(1R)-1-[6-(trifluoromethyl)pyridazin-3-yl]ethyl}carbamoyl)phenoxy]methyl}morpholine-4-carboxylate | $^1$H NMR (500 MHz, Chloroform-d): δ [ppm] 7.92-7.90 (m, 1H), 7.82 (d, J = 8.7 Hz, 1H), 7.74 (d, J = 8.7 Hz, 1H), 7.62-7.59 (m, 1H), 7.55-7.53 (m, 1H), 7.49-7.41 (m, 2H), 5.66-5.52 (m, 1H), 4.18-3.77 (m, 6H), 3.61 (td, J = 11.6, 2.4 Hz, 1H), 3.08-2.85 (m, 4H), 1.76 (d, J = 7.0 Hz, 3H), 1.48 (s, 9H), 1.36 (t, J = 7.5 Hz, 3H). LCMS (Method A) Rt = 1.4 min, MS (ESIpos): m/z = 622.25 (M + H)$^+$. |
| 179 | 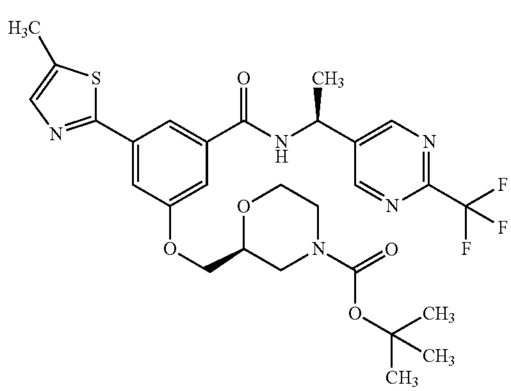 [SMILES: Cc1cnc(-c2cc(OC[C@@H]3CN(C(=O)OC(C)(C)C)CCO3)cc(C(=O)N[C@@H](C)c3cnc(C(F)(F)F)nc3)c2)s1] | Tert-butyl (2S)-2-{[3-(5-methyl-1,3-thiazol-2-yl)-5-({(1S)-1-[2-(trifluoromethyl)pyrimidin-5-yl]ethyl}carbamoyl)phenoxy]methyl}morpholine-4-carboxylate | $^1$H NMR (500 MHz, Chloroform-d): δ [ppm] 8.90 (s, 2H), 8.02-7.97 (m, 1H), 7.50-7.47 (m, 1H), 7.45 (d, J = 1.5 Hz, 1H), 7.42-7.37 (m, 1H), 7.22 (s, 1H), 5.34-5.26 (m, 1H), 4.10-3.69 (m, 6H), 3.56-3.48 (m, 1H), 2.97-2.71 (m, 2H), 2.47 (d, J = 1.0 Hz, 3H), 1.66 (d, J = 7.2 Hz, 3H), 1.41 (s, 9H). LCMS (Method A) Rt = 1.40 min, MS (ESIpos) m/z = 608 (M + H)$^+$. |

Intermediate 123: Tert-butyl (2S)-2-[[3-(5-chlorothiazol-2-yl)-5-[[(1R)-1-[2-(trifluoromethyl)pyrimidin-5-yl]ethyl]carbamoyl]phenoxy]methyl]morpholine-4-carboxylate Intermediate 148: Tert-butyl 3-{[3-(5-methyl-1,3-thiazol-2-yl)-5-({(1R)-1-[2-(trifluoromethyl)pyrimidin-5-yl]ethyl}carbamoyl)phenoxy]methyl}azetidine-1-carboxylate

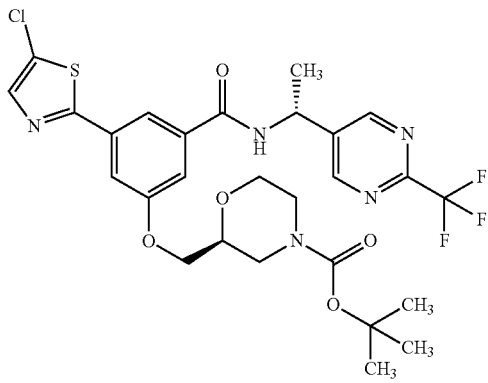 [SMILES: C[C@@H](NC(=O)c1cc(OC[C@@H]2CN(C(=O)OC(C)(C)C)CCO2)cc(-c2ncc(Cl)s2)c1)c1cnc(C(F)(F)F)nc1]

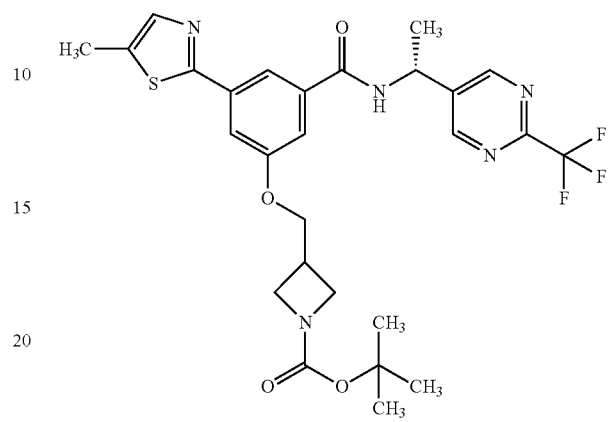

To a solution of Intermediate 5CJ (150 mg, 0.31 mmol) and DIPEA (0.16 mL, 0.94 mmol) in DCM (5 mL) was added Intermediate VI (86 mg, 0.38 mmol) followed by HATU (121 mg, 0.94 mmol) and the reaction mixture was stirred at ambient temperature for 2 h. The reaction mixture was washed with water (5 mL), dried (MgSO$_4$), filtered and concentrated under reduced pressure to give crude residue that was purified by Biotage Isolera™ chromatography (eluting with 25-100% EtOAc in heptane on a 25 g prepacked KP—SiO$_2$ column) to give 115 mg (56% yield) of the title compound as a solid.

$^1$H NMR (500 MHz, chloroform-d): δ [ppm] 8.94 (s, 2H), 7.83 (s, 1H), 7.67 (s, 1H), 7.61-7.49 (m, 1H), 7.42 (s, 1H), 6.62 (s, 1H), 5.36 (m, 1H), 4.20-4.01 (m, 3H), 4.00-3.83 (m, 2H), 3.86-3.74 (m, 1H), 3.60 (t, J=10.7 Hz, 1H), 3.09-2.91 (m, 1H), 2.95-2.72 (m, 1H), 1.73 (d, J=7.1 Hz, 3H), 1.48 (s, 9H).

LC-MS (Method A) Rt=1.47 min, MS (ESIpos): m/z=650 (M+H)$^+$.

In analogy to the procedure described for Intermediate 123, the following Intermediate was prepared using HATU and the corresponding carboxylic acid and primary amine starting materials.

A mixture of Intermediate 5CV (90.0 mg, 223 μmol), Intermediate VI (53.2 mg, 234 μmol), HATU (118 mg, 312 μmol) and DIPEA (150 μL, 890 μmol) in DMF (3 mL) was stirred at RT until complete conversion. The DMF was evaporated under reduced pressure, water and DCM added, and the aqueous layer was extracted with DCM. The combined organics were evaporated to dryness. Crude material was purified by column chromatography (silica gel, hexane/EtOAc gradient) to give 90 mg (70% yield) of the title compound.

LCMS, method 1, rt: 1.39 min, MS ES+m/z=578 (M+H)$^+$.

| Int. | Structure | Name | Analytical Data |
|---|---|---|---|
| 177 | (structure shown) | Tert-butyl (2R)-2-[[3-(5-chlorothiazol-2-yl)-5-[[(1R)-1-[2-(trifluoromethyl)pyrimidin-5-yl]ethyl]carbamoyl]phenoxy]methyl]morpholine-4-carboxylate | $^1$H NMR (500 MHz, chloroform-d): δ [ppm] 8.94 (s, 2H), 7.83 (t, J = 1.4 Hz, 1H), 7.67 (s, 1H), 7.57-7.49 (m, 1H), 7.42 (s, 1H), 6.64 (s, 1H), 5.36 (m, 1H), 4.20-4.01 (m, 3H), 4.00-3.85 (m, 2H), 3.85-3.74 (m, 1H), 3.60 (t, J = 11.2 Hz, 1H), 3.11-2.93 (m, 1H), 2.92-2.69 (m, 1H), 1.73 (d, J = 7.1 Hz, 3H), 1.48 (s, 9H). LC-MS (Method A) Rt = 1.45 min, MS (ESIpos): m/z = 650 (M + H)$^+$. |

Intermediate 116: 3-(5-Methyl-1,3-thiazol-2-yl)-5-(piperidin-4-ylmethoxy)-N-{(1R)-1-[2-(trifluoromethyl)pyrimidin-5-yl]ethyl}benzamide

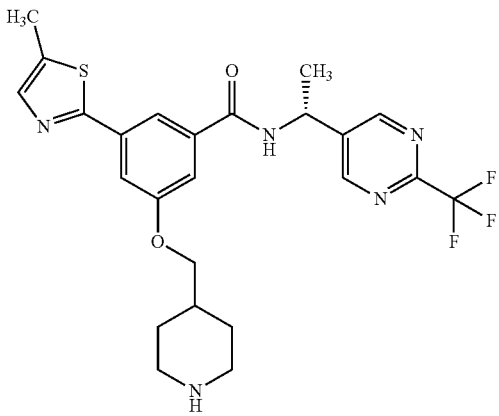 [SMILES: Cc1cnc(-c2cc(OCC3CCNCC3)cc(C(=O)N[C@H](C)c3cnc(C(F)(F)F)nc3)c2)s1]

To a solution of Intermediate 115 (206 mg, 0.34 mmol) dissolved in DCM (5 mL) was added TFA (0.26 mL, 3.4 mmol) and the reaction stirred at RT for 16 h. The reaction mixture was neutralised with saturated $NaHCO_3$ solution. The organic phase was separated and the aqueous phase extracted with DCM (2×5 mL). The combined organic phases were dried ($MgSO_4$), filtered and concentrated at reduced pressure. The residue was freeze-dried from MeCN/water to give 173.6 mg (100% yield) of the title compound as white powder.

$^1$H NMR (500 MHz, chloroform-d): δ [ppm] 8.98 (s, 2H), 7.83 (s, 1H), 7.55-7.44 (m, 2H), 7.38 (s, 1H), 5.47-5.31 (m, 1H), 3.99-3.81 (m, 2H), 3.47 (s, 2H), 2.91 (m, 2H), 2.56-2.40 (m, 3H), 2.08-1.90 (m, 3H), 1.73 (m, 5H).

LC-MS (Method A) Rt=0.94 min, MS (ESIpos): m/z=506 (M+H)$^+$.

In analogy to the procedure described for Intermediate 116, the following Intermediates were prepared using TFA and the corresponding N-Boc protected starting material.

| Int. | Structure | Name | Analytical Data |
|---|---|---|---|
| 118 | 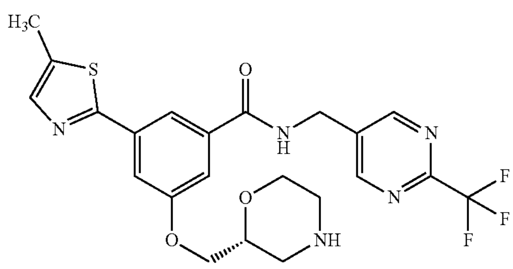 [SMILES: Cc1cnc(-c2cc(OC[C@H]3CNCCO3)cc(C(=O)NCc3cnc(C(F)(F)F)nc3)c2)s1] | 3-(5-Methyl-1,3-thiazol-2-yl)-5-[(2R)-morpholin-2-ylmethoxy]-N-{[2-(trifluoromethyl)pyrimidin-5-yl]methyl}benzamide | LC-MS (Method A) Rt = 1.01 min, MS (ESIpos): m/z = 494 (M + H)$^+$. |
| 120 | 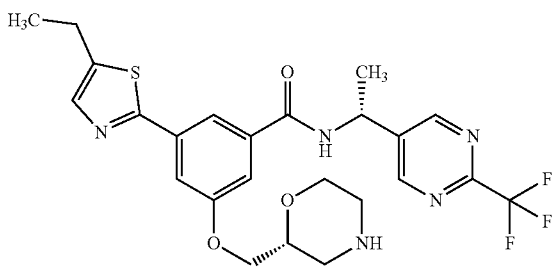 [SMILES: CCc1cnc(-c2cc(OC[C@H]3CNCCO3)cc(C(=O)N[C@H](C)c3cnc(C(F)(F)F)nc3)c2)s1] | 3-(5-Ethyl-1,3-thiazol-2-yl)-5-[(2R)-morpholin-2-ylmethoxy]-N-{(1R)-1-[2-(trifluoromethyl)pyrimidin-5-yl]ethyl}benzamide | $^1$H NMR (500 MHz, DMS0-d6): δ [ppm] 9.14 (d, J = 7.1 Hz, 1H), 9.12 (s, 2H), 7.97-7.91 (m, 1H), 7.67 (s, 1H), 7.58-7.51 (m, 2H), 5.30 (m, 1H), 4.06 (d, J = 5.1 Hz, 2H), 3.77-3.67 (m, 2H), 3.47 (td, J = 10.6, 3.7 Hz, 1H), 2.97-2.83 (m, 3H), 2.73-2.62 (m, 2H), 2.58-2.53 (m, 1H), 1.61 (d, J = 7.1 Hz, 3H), 1.29 (t, J = 7.5 Hz, 3H). LC-MS (Method A) Rt = 1.1 min, MS (ESIpos): m/z = 522 (M + H)$^+$. |
| 122 | 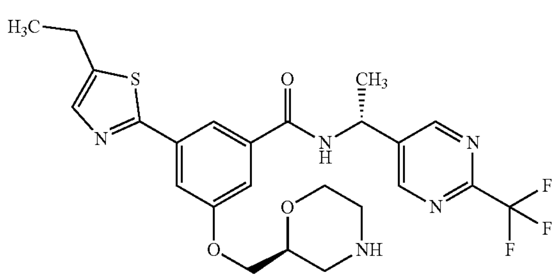 [SMILES: CCc1cnc(-c2cc(OC[C@@H]3CNCCO3)cc(C(=O)N[C@H](C)c3cnc(C(F)(F)F)nc3)c2)s1] | 3-(5-Ethyl-1,3-thiazol-2-yl)-5-[(2S)-morpholin-2-ylmethoxy]-N-{(1R)-1-[2-(trifluoromethyl)pyrimidin-5-yl]ethyl}benzamide | $^1$H NMR (500 MHz, DMSO-d6): δ [ppm] 1.29 (t, J = 7.5 Hz, 3H), 1.61 (d, J = 7.1 Hz, 3H), 2.52-2.58 (m, 1H), 2.61-2.73 (m, 2H), 2.85-2.95 (m, 3H), 3.43-3.53 (m, 1H), 3.68-3.79 (m, 2H), 4.06 (d, J = 4.9 Hz, 2H), 5.30 (m, 1H), 7.53-7.56 (m, 2H), 7.64-7.69 (m, 1H), 7.93 (t, J = 1.4 Hz, 1H), 9.08-9.18 (m, 3H). LC-MS (Method A) Rt = 1.07 min, MS (ESIpos): m/z = 522 (M + H)$^+$. |

-continued

| Int. | Structure | Name | Analytical Data |
|---|---|---|---|
| 124 | 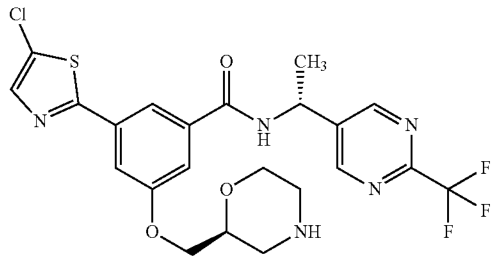 [SMILES: C[C@@H](NC(=O)c1cc(OC[C@@H]2CNCCO2)cc(-c2ncc(Cl)s2)c1)c1cnc(C(F)(F)F)nc1] | 3-(5-Chlorothiazol-2-yl)-5-[[(2S)-morpholin-2-yl]methoxy]-N-[(1R)-1-[2-(trifluoromethyl)pyrimidin-5-yl]ethyl]benzamide | $^1$H NMR (500 MHz, chloroform-d): δ [ppm] 8.95 (s, 2H), 7.80 (s, 1H), 7.65 (s, 1H), 7.57-7.45 (m, 1H), 7.46-7.35 (m, 1H), 6.80 (d, J = 6.5 Hz, 1H), 5.37 (m, 1H), 4.10 (dd, J = 9.8, 5.6 Hz, 1H), 4.05-3.90 (m, 3H), 3.77 (td, J = 11.5, 3.5 Hz, 1H), 3.11 (d, J = 11.7 Hz, 1H), 3.05-2.91 (m, 2H), 2.90-2.77 (m, 1H), 1.73 (d, J = 7.1 Hz, 3H). LC-MS (Method A) Rt = 1.07 min, MS (ESIpos): m/z = 528 (M + H)$^+$. |
| 178 | 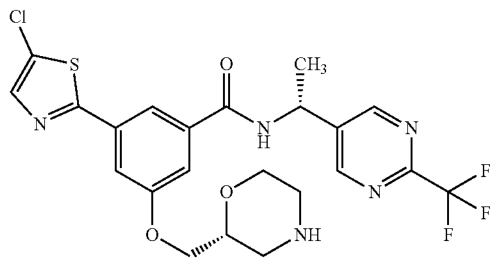 [SMILES: C[C@@H](NC(=O)c1cc(OC[C@H]2CNCCO2)cc(-c2ncc(Cl)s2)c1)c1cnc(C(F)(F)F)nc1] | 3-(5-Chlorothiazol-2-yl)-5-[[(2R)-morpholin-2-yl]methoxy]-N-[(1R)-1-[2-(trifluoromethyl)pyrimidin-5-yl]ethyl]benzamide | $^1$H NMR (500 MHz, chloroform-d): δ [ppm] 8.94 (s, 2H), 7.80 (s, 1H), 7.66 (s, 1H), 7.58-7.50 (m, 1H), 7.46-7.37 (m, 1H), 6.69 (d, J = 6.5 Hz, 1H), 5.36 (m, 1H), 4.09 (dd, J = 9.9, 6.0 Hz, 1H), 4.01 (dd, J = 9.9, 4.2 Hz, 1H), 3.99-3.86 (m, 2H), 3.72 (td, J = 11.3, 2.9 Hz, 1H), 3.11-3.02 (m, 1H), 3.01-2.85 (m, 2H), 2.80 (dd, J = 12.0, 10.4 Hz, 1H), 1.72 (d, J = 7.1 Hz, 3H). LC-MS (Method A) Rt = 1.08 min, MS (ESIpos): m/z = 528 (M + H)$^+$. |

Intermediate 126: [(3R)-4-Methylmorpholin-3-yl]methanol

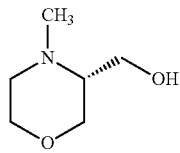

To a solution of 3-hydroxymethyl-morpholine-4-carboxylic acid tert-butyl ester (750 mg, 3.45 mmol) in anhydrous THF (16.5 mL) at 0° C. under nitrogen was added LiAlH$_4$ solution (2.4 M in THF, 8.6 mL). The reaction mixture was stirred for 20 minutes at 0° C. then warmed to RT and stirred for a further 2 h. The reaction mixture was cooled to 0° C. and quenched with dropwise addition of water (1 mL), 15% aqueous NaOH (1 mL) and water (3 mL). The inorganic by-products were removed by filtration through Celite®. The filtrate was concentrated under reduced pressure to give 475 mg (71% yield) of the title compound as colourless oil, which was used without further purification.

$^1$H NMR (250 MHz, chloroform-d): δ [ppm] 3.87-3.73 (m, 3H), 3.64-3.51 (m, 2H), 3.40 (dd, J=11.5, 1.7 Hz, 1H), 2.71 (dt, J=11.5, 1.9 Hz, 1H), 2.41 (td, J=11.4, 3.4 Hz, 1H), 2.33 (s, 3H), 2.25-2.15 (m, 1H).

In analogy to the procedure described for Intermediate 126, the following Intermediate was prepared using LiAlH$_4$ and the corresponding N-Boc protected starting material.

Intermediate 130: tert-Butyl-3-fluoro-3-(hydroxymethyl)piperidine-1-carboxylate, as a mixture of enantiomers

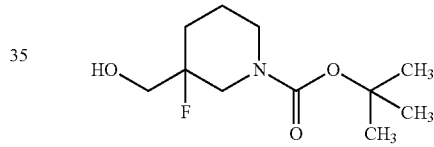

To a 0° C. solution of 1-Boc-3-fluoropiperidine-3-carboxylic acid (750 mg, 3.03 mmol) in anhydrous tetrahydrofuran (30 mL) under nitrogen atmosphere was added borane (1M in THF, 9.1 mL, 9.10 mmol) dropwise and the resulting reaction mixture warmed to RT and for stirred for 18 h. The reaction was quenched by careful addition of methanol and evaporated at reduced pressure. The residue was dissolved in ethyl acetate and washed with saturated sodium hydrogen carbonate solution. The organic layer was dried (MgSO$_4$), filtered and concentrated at reduced pressure. Purification by Biotage Isolera™ chromatography (eluting with 0-60% EtOAc in heptane on a 25 g pre-packed KP—SiO$_2$ column) gave 650 mg (95% yield) of the title compound as pale yellow viscous oil, which solidified on standing.

$^1$H NMR (500 MHz, chloroform-d): δ [ppm] 4.00-2.86 (m, 6H), 1.95-1.85 (m, 1H), 1.84-1.65 (m, 2H), 1.60-1.52 (m, 1H), 1.49 (s, 9H).

| Int. | Structure | Name | Analytical Data |
|---|---|---|---|
| 127 | 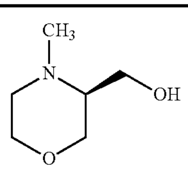 | [(3S)-4-Methylmorpholin-3-yl]methanol | $^1$H NMR (250 MHz, chloroform-d): δ [ppm] 3.80 (ddd, J = 12.1, 8.6, 3.9 Hz, 3H), 3.67-3.48 (m, 2H), 3.40 (dd, J = 11.5, 1.7 Hz, 1H), 2.78-2.65 (m, 1H), 2.41 (td, J = 11.5, 3.4 Hz, 1H), 2.32 (s, 3H), 2.28-2.12 (m, 1H). |

Intermediate 27CQ: tert-Butyl (2R)-2-{[3-cyano-5-(5-methyl-1,3-thiazol-2-yl)phenoxy]methyl}morpholine-4-carboxylate

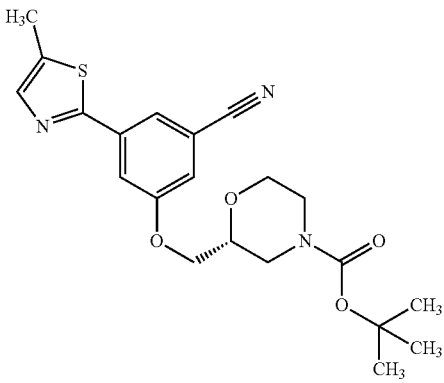 [SMILES: Cc1cnc(-c2cc(C#N)cc(OC[C@H]3CN(C(=O)OC(C)(C)C)CCO3)c2)s1]

To a stirred solution of Intermediate 112 (896 mg, 4.12 mmol) in dry DMF (7.5 mL) was added NaH 60% dispersion in mineral oil (172 mg, 4.30 mmol). After the mixture was stirred for 15 min Intermediate 26 (750 mg, 3.44 mmol) was added and the resulting mixture stirred at RT for 16 h. The reaction mixture was poured onto brine and extracted into EtOAc. The organic layer was washed with brine, dried (MgSO$_4$), filtered and concentrated at reduced pressure to give a brown oil. The crude material was purified by Biotage Isolera™ chromatography (eluting with 5-60% EtOAc in heptane on a 50 g pre-packed KP—SiO$_2$ column) to give 870.9 mg (59% yield) of the title compound as a colourless gum.

$^1$H NMR (250 MHz, chloroform-d): δ [ppm] 7.75 (t, J=1.4 Hz, 1H), 7.71-7.68 (m, 1H), 7.54 (d, J=1.2 Hz, 1H), 7.19 (dd, J=2.5, 1.3 Hz, 1H), 4.17-3.74 (m, 6H), 3.67-3.54 (m, 1H), 3.10-2.77 (m, 2H), 2.54 (d, J=1.1 Hz, 3H), 1.48 (s, 9H).

LC-MS (Method A) Rt=1.33 min, MS (ESIpos): m/z=416 (M+H)$^+$.

In analogy to the procedure described for Intermediate 27CQ, the following Intermediates were prepared using NaH and the corresponding fluoro-benzonitrile and alcohol starting materials.

| Int. | Structure | Name | Analytical Data |
|---|---|---|---|
| 27CM | 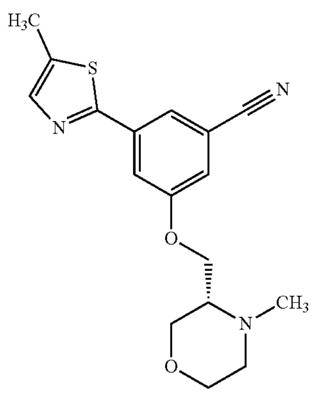 [SMILES: Cc1cnc(-c2cc(C#N)cc(OC[C@H]3COCCN3C)c2)s1] | 3-{[(3R)-4-Methylmorpholin-3-yl]methoxy}-5-(5-methyl-1,3-thiazol-2-yl)benzonitrile | $^1$H NMR (250 MHz, chloroform-d): δ [ppm] 7.73 (t, J = 1.3 Hz, 1H), 7.71-7.66 (m, 1H), 7.53 (d, J = 1.0 Hz, 1H), 7.16 (dd, J = 2.4, 1.3 Hz, 1H), 4.17-4.01 (m, 2H), 3.92 (dd, J = 11.3, 3.2 Hz, 1H), 3.83 (dt, J = 11.3, 3.1 Hz, 1H), 3.70 (m, 1H), 3.56 (m, 1H), 2.75 (m, 1H), 2.68-2.51 (m, 4H), 2.49-2.37 (m, 4H). |
| 27CN | 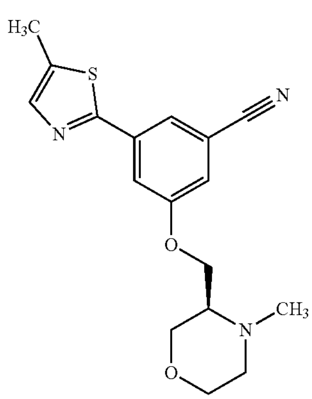 [SMILES: Cc1cnc(-c2cc(C#N)cc(OC[C@@H]3COCCN3C)c2)s1] | 3-{[(3S)-4-Methylmorpholin-3-yl]methoxy}-5-(5-methyl-1,3-thiazol-2-yl)benzonitrile | $^1$H NMR (250 MHz, chloroform-d): δ [ppm] 7.76 (t, J = 1.3 Hz, 1H), 7.74-7.69 (m, 1H), 7.56 (d, J = 1.1 Hz, 1H), 7.19 (dd, J = 2.4, 1.3 Hz, 1H), 4.20-4.04 (m, 2H), 3.95 (dd, J = 11.3, 3.2 Hz, 1H), 3.86 (dt, J = 11.2, 3.0 Hz, 1H), 3.73 (m, 1H), 3.59 (dd, J = 11.3, 9.2 Hz, 1H), 2.78 (dt, J = 11.8, 2.7 Hz, 1H), 2.69-2.58 (m, 1H), 2.56 (d, J = 1.0 Hz, 3H), 2.52-2.40 (m, 4H). |

| Int. | Name | Analytical Data |
|---|---|---|
| 27CO | Tert-butyl 3-{[3-cyano-5-(5-methyl-1,3-thiazol-2-yl)phenoxy]methyl}-3-fluoroazetidine-1-carboxylate | $^1$H NMR (250 MHz, chloroform-d): δ [ppm] 7.77 (t, J = 1.3 Hz, 1H), 7.75-7.71 (m, 1H), 7.55 (d, J = 1.2 Hz, 1H), 7.20 (dd, J = 2.4, 1.3 Hz, 1H), 4.32 (d, J = 19.2 Hz, 2H), 4.22-4.08 (m, 4H), 2.54 (d, J = 1.0 Hz, 3H), 1.47 (s, 9H). LC-MS (Method A) Rt = 1.34 min, MS (ESIpos): m/z = 404 (M + H)$^+$. |
| 27CP | tert-Butyl-3-{[3-cyano-5-(5-methyl-1,3-thiazol-2-yl)phenoxy]methyl}-3-fluoropiperidine-1-carboxylate, as a mixture of enantiomers | $^1$H NMR (250 MHz, chloroform-d): δ [ppm] 7.78 (s, 1H), 7.75-7.71 (m, 1H), 7.57 (d, J = 1.1 Hz, 1H), 7.22 (dd, J = 2.3, 1.3 Hz, 1H), 4.16 (s, 1H), 4.09 (s, 1H), 3.97 (s, 1H), 3.87-3.61 (m, 1H), 3.57-3.25 (m, 1H), 3.26-3.06 (m, 1H), 2.57 (d, J = 0.9 Hz, 3H), 2.12-1.79 (m, 3H), 1.70-1.60 (m, 1H), 1.48 (s, 9H). LC-MS (Method A) Rt = 1.48 min, MS (ESIpos): m/z = 432 (M + H)$^+$. |
| 27CR | tert-Butyl (2S)-2-{[3-cyano-5-(5-methyl-1,3-thiazol-2-yl)phenoxy]methyl}morpholine-4-carboxylate | $^1$H NMR (250 MHz, chloroform-d): δ [ppm] 7.75 (t, J = 1.3 Hz, 1H), 7.69 (d, J = 2.2 Hz, 1H), 7.53 (d, J = 1.1 Hz, 1H), 7.18 (dd, J = 2.4, 1.3 Hz, 1H), 4.20-3.75 (m, 6H [+EtOAc]), 3.60 (m, 2H), 3.10-2.76 (m, 1H [DMF]), 2.53 (d, J = 1.0 Hz, 3H), 1.48 (s, 9H). LC-MS (Method A) Rt = 1.34 min, MS (ESIpos) m/z = 416 (M + H)$^+$. |
| 27CS | tert-Butyl (2R)-2-{[3-cyano-5-(5-methyl-1,3-thiazol-2-yl)phenoxy]methyl}pyrrolidine-1-carboxylate | $^1$H NMR (250 MHz, chloroform-d): δ [ppm] 7.75-7.64 (m, 2H), 7.53 (s, 1H), 7.18 (s, 1H), 4.01 (m, 3H + EtOAc), 3.53-3.28 (m, 2H), 2.53 (s, 3H), 2.03-1.81 (m, 4H), 1.47 (s, 9H). |

| Int. | Structure | Name | Analytical Data |
|---|---|---|---|
| 27CT | 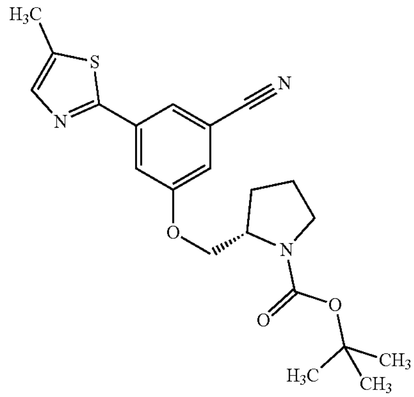 [SMILES: Cc1cnc(-c2cc(C#N)cc(OC[C@@H]3CCCN3C(=O)OC(C)(C)C)c2)s1] | tert-Butyl (2S)-2-{[3-cyano-5-(5-methyl-1,3-thiazol-2-yl)phenoxy]methyl}pyrrolidine-1-carboxylate | $^1$H NMR (250 MHz, chloroform-d): δ [ppm] 7.75-7.65 (m, 2H), 7.56-7.51 (m, 1H), 7.18 (s, 1H), 4.31-3.82 (m, 3H), 3.56-3.26 (m, 2H), 2.53 (d, J = 1.0 Hz, 3H), 2.04-1.79 (m, 4H), 1.47 (s, 9H). |
| 27CU | 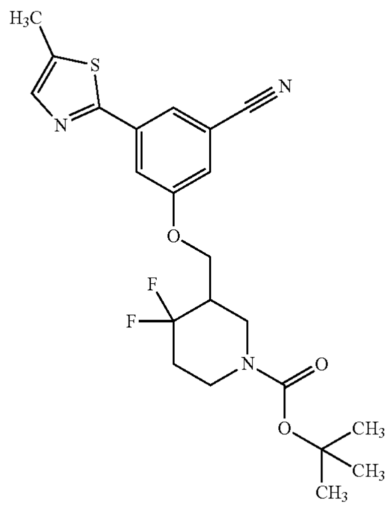 [SMILES: Cc1cnc(-c2cc(C#N)cc(OCC3CN(C(=O)OC(C)(C)C)CCC3(F)F)c2)s1] | Tert-butyl 3-{[3-cyano-5-(5-methyl-1,3-thiazol-2-yl)phenoxy]methyl}-4,4-difluoropiperidine-1-carboxylate, as a mixture of enantiomers | LC-MS (Method A) Rt = 1.45 min, MS (ESIpos): m/z = 450 (M + H)$^+$. |

Intermediate 5CE can also be synthesised from Intermediate 27CQ as illustrated below.

Intermediate 5CE: 3-{[(2R)-4-(Tert-butoxycarbonyl)morpholin-2-yl]methoxy}-5-(5-methyl-1,3-thiazol-2-yl)benzoic acid

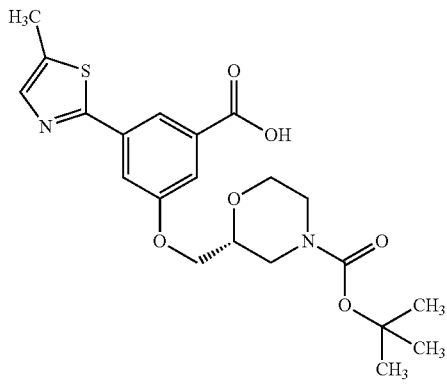 [SMILES: Cc1cnc(-c2cc(OC[C@H]3CN(C(=O)OC(C)(C)C)CCO3)cc(C(=O)O)c2)s1]

A stirred solution of Intermediate 27CQ (0.87 g, 2.01 mmol), DMSO (10 mL) and 2 M aqueous sodium hydroxide (10 mL) was heated at 110° C. for 3 h. After cooling to RT the mixture was slowly acidified to pH ~4, diluted with water (10 mL) and extracted with EtOAc (3×20 mL). The combined organics were washed with water (20 mL), brine (20 mL), dried (MgSO$_4$), filtered and concentrated under reduced pressure to give 672.1 mg (77% yield) of the title compound as a foam.

$^1$H NMR (500 MHz, chloroform-d): δ [ppm] 8.29 (t, J=1.4 Hz, 1H), 7.70 (s, 1H), 7.67 (dd, J=2.4, 1.3 Hz, 1H), 7.57 (d, J=1.1 Hz, 1H), 4.16 (dd, J=9.9, 5.5 Hz, 1H), 4.10 (dd, J=9.9, 4.5 Hz, 1H), 3.97 (d, J=10.7 Hz, 1H), 3.94-3.80 (m, 2H), 3.66-3.57 (m, 1H), 3.10-2.97 (m, 1H), 2.90 (s, 1H), 2.63 (s, 2H), 2.53 (d, J=1.0 Hz, 3H), 1.49 (s, 9H).

LC-MS (Method A) Rt=1.20 min, MS (ESIpos): m/z=435.55 (M+H)$^+$.

Intermediate 28CM: 3-{[(3R)-4-Methylmorpholin-3-yl]methoxy}-5-(5-methyl-1,3-thiazol-2-yl)benzoic acid—chlorosodium (1:3)

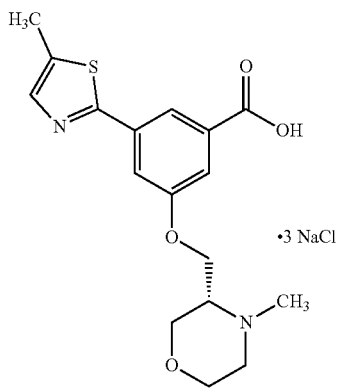 [SMILES: Cc1cnc(-c2cc(OC[C@H]3COCCN3C)cc(C(=O)O)c2)s1]

To a solution of Intermediate 27CM (304 mg, 0.83 mmol) in ethanol (2 mL) was added 2 M aqueous sodium hydroxide (1.24 mL) and the resultant mixture heated to 120° C. by microwave irradiation for 30 min. The cooled solution was diluted with water and washed with EtOAc. The aqueous phase was separated, neutralised with 1 M HCl (0.88 mL) and concentrated at reduced pressure. The residue was further dried in a vacuum oven to constant weight to give 381 mg (88% yield) of the title compound, which was used without further purification.

LC-MS (Method A) Rt=0.80 min, MS (ESIpos) m/z=349 (M+H)$^+$.

Intermediate 28CN: 3-{[(3S)-4-Methylmorpholin-3-yl]methoxy}-5-(5-methyl-1,3-thiazol-2-yl)benzoic acid hydrochloride (1:1)

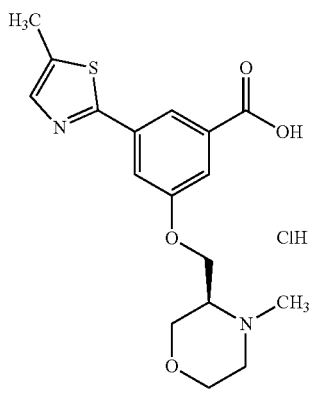 [SMILES: Cc1cnc(-c2cc(OC[C@@H]3COCCN3C)cc(C(=O)O)c2)s1 ; Cl]

To a stirred solution of Intermediate 27CN (200 mg, 0.53 mmol) in DMSO (3 mL) was added 2 M aqueous sodium hydroxide (3.5 mL) and the resultant mixture heated to 110° C. for 3 h. After cooling to RT the mixture was slowly acidified to pH ~2 with HCl and concentrated under reduced pressure to afford the crude material in DMSO. The residue was partitioned between water and chloroform/isopropanol (1:1). The organic layer was separated and the aqueous layer extracted twice with chloroform/isopropanol (1:1). The combined organic fraction was dried (magnesium sulfate), filtered and concentrated under reduced pressure. LC-MS (Method A) indicated product remained in the aqueous phase. The organic and aqueous layers were dried to remove residual DMSO, providing 75 mg (36% yield) and 100 mg (49% yield, not corrected for sodium chloride content). The combined fractions were used in the next step without further purification.

$^1$H NMR (500 MHz, DMSO-d6): δ [ppm] 10.76 (s, 1H), 8.03 (s, 1H), 7.74 (s, 1H), 7.72-7.57 (m, 2H), 7.61 (s, 1H), 4.52 (dd, J=11.1, 2.9 Hz, 1H), 4.44 (dd, J=11.3, 2.8 Hz, 1H), 4.15 (d, J=10.2 Hz, 1H), 4.02 (d, J=12.3 Hz, 1H), 3.86-3.79 (m, 1H), 3.78-3.68 (m, 2H), 3.29 (d, J=11.6 Hz, 1H), 2.92 (d, J=3.1 Hz, 3H), 2.53 (s, 3H).

LC-MS (Method A) Rt=0.94 min, MS (ESIpos): m/z=349 (M+H)$^+$.

Intermediate 28CP: 3-{[1-(Tert-butoxycarbonyl)-3-fluoropiperidin-3-yl]methoxy}-5-(5-methyl-1,3-thiazol-2-yl)benzoic acid, as a mixture of enantiomers

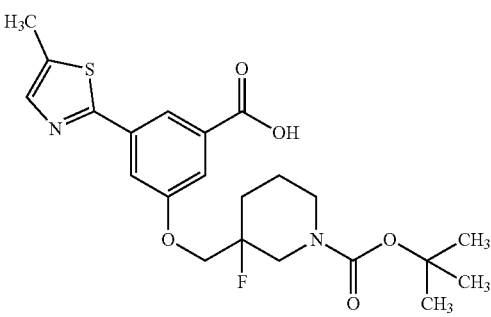 [SMILES: Cc1cnc(-c2cc(OCC3(F)CCCN(C(=O)OC(C)(C)C)C3)cc(C(=O)O)c2)s1]

To a stirred solution of Intermediate 27CP (400 mg, 0.83 mmol) in ethanol (5 mL) was added 2M sodium hydroxide (1.25 mL, 2.50 mmol) and the mixture heated to 80° C. for 18 h in a sealed tube. The reaction mixture was concentrated at reduced pressure and the aqueous residue washed with ethyl acetate. The aqueous layer was acidified to pH 4 with 2M HCl resulting in precipitation of white solid that was collected by filtration and dried to give 310 mg (80% yield) of the title compound as an off-white solid.

LC-MS (Method A) Rt=1.26 min, MS (ESIpos): m/z=451.6 (M+H)$^+$.

Intermediate 28CR: 3-{[(2S)-4-(Tert-butoxycarbonyl)morpholin-2-yl]methoxy}-5-(5-methyl-1,3-thiazol-2-yl)benzoic acid

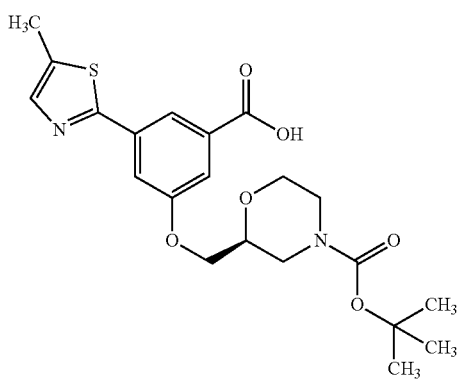 [SMILES: Cc1cnc(-c2cc(OC[C@@H]3CN(C(=O)OC(C)(C)C)CCO3)cc(C(=O)O)c2)s1]

A stirred solution of Intermediate 27CR (510 mg, 1.191 mmol) in EtOH (5 mL) and 2M NaOH (1.79 mL) was heated to 130° C. for 3 hours under microwave irradiation. The reaction was quenched by addition of HCl (2M, 1.79 mL) and concentrated under reduced pressure. The white residue was slurried in chloroform and inorganic material removed by filtration. The filtrate was evaporated at reduced pressure to give 571 mg (79% yield) of the title compound as white powder.

$^1$H NMR (500 MHz, chloroform-d): δ [ppm] 8.29-8.25 (m, 1H), 7.68 (s, 2H), 7.56 (d, 1H), 4.17-4.08 (m, 3H), 3.96 (d, J=11.1 Hz, 1H), 3.84 (br.s, 2H), 3.73 (q, J=7.0 Hz, 1H), 3.65-3.58 (m, 2H), 2.52 (s, 3H), 1.48 (s, 9H).

LC-MS (Method A) Rt=1.22 min, MS (ESIpos): m/z=434.95 (M+H)$^+$.

Intermediate 28CS: 3-{[(2R)-1-(Tert-butoxycarbonyl)pyrrolidin-2-yl]methoxy}-5-(5-methyl-1,3-thiazol-2-yl)benzoic acid

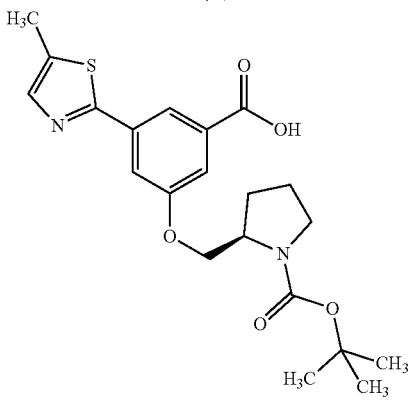

A stirred solution of Intermediate 27CS (0.348 g, 0.76 mmol) in ethanol (2 mL) and 2 M aqueous NaOH (1.0 mL, 2 mmol) was heated to 80° C. in a sealed tube for 3 h. A further portion of 2M aqueous NaOH (1.0 mL, 2 mmol) was added and the mixture heated to 80° C. in a sealed tube for 6 h. The reaction mixture was concentrated at reduced pressure and the residue taken up in water and acidified to form a white precipitate that was collected by filtration to give 0.31 g (81% yield) of the title compound.

LC-MS (Method A) Rt=1.34 min, MS (ESIpos) m/z=419 (M+H)$^+$.

Intermediate 28CT: 3-{[(2S)-1-(Tert-butoxycarbonyl)pyrrolidin-2-yl]methoxy}-5-(5-methyl-1,3-thiazol-2-yl)benzoic acid

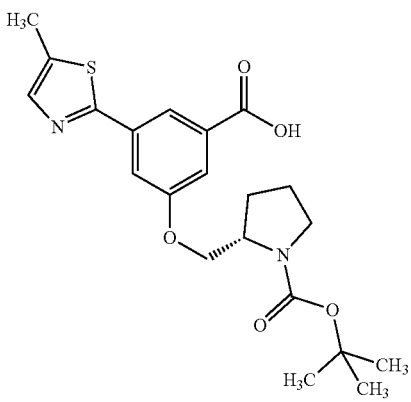 [SMILES: Cc1cnc(-c2cc(OC[C@@H]3CCCN3C(=O)OC(C)(C)C)cc(C(=O)O)c2)s1]

A stirred solution of Intermediate 27CT (0.318 g, 0.69 mmol) in ethanol (2 mL) and 2 M aqueous NaOH (1.0 mL, 2 mmol) was heated to 80° C. in a sealed tube for 3 h. The reaction mixture was concentrated at reduced pressure and the residue taken up in water and acidified to form a white precipitate that was collected by filtration to give 0.11 g (35% yield) of the title compound.

LC-MS (Method A) Rt=1.33 min, MS (ESIpos): m/z=419 (M+H)$^+$.

Intermediate 28CU: 3-{[1-(Tert-butoxycarbonyl)-4,4-difluoropiperidin-3-yl]methoxy}-5-(5-methyl-1,3-thiazol-2-yl)benzoic acid, as a mixture of enantiomers

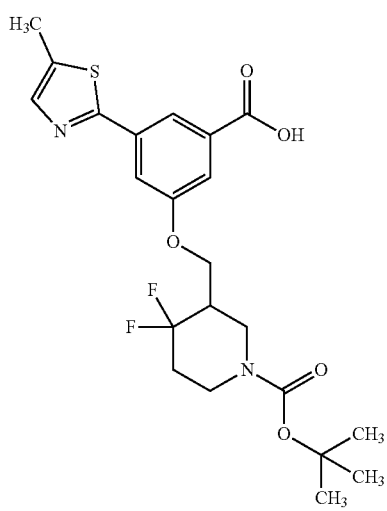 [SMILES: Cc1cnc(-c2cc(OCC3CN(C(=O)OC(C)(C)C)CCC3(F)F)cc(C(=O)O)c2)s1]

A stirred solution of Intermediate 27CU (340 mg, 0.68 mmol) in ethanol (1 mL) and 2 M aqueous sodium hydroxide (1 mL, 2 mmol) was heated by microwave irradiation to 120° C. for 1 h. The reaction mixture was acidified with conc. HCl to give a white precipitate that was extracted into ethyl acetate. The organic phase was separated, dried (MgSO$_4$), filtered and concentrated under reduced pressure to give 199 mg (62% yield) of the title compound.

LC-MS (Method A) Rt=1.31, MS (ESIpos): m/z=469 (M+H)$^+$.

Intermediate 128: 3-[(3-Fluoroazetidin-3-yl)methoxy]-5-(5-methyl-1,3-thiazol-2-yl)benzonitrile

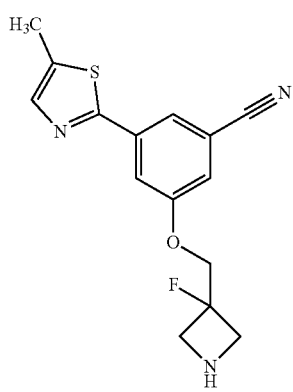 [SMILES: Cc1cnc(-c2cc(C#N)cc(OCC3(F)CNC3)c2)s1]

To a solution of Intermediate 27CO (330 mg, 0.8 mmol) in DCM (10 mL) was added TFA (4 mL) and the reaction stirred for 4 h at RT then neutralised with saturated aqeuous sodium bicarbonate solution. The organic layer was separated and the aqueous layer extracted with 1:1 IPA/CHCl$_3$ (2×20 mL). The combined organics were dried (MgSO$_4$), filtered and concentrated under reduced pressure to give 243.7 mg (95% yield) of the title compound as an off-white powder.

$^1$H NMR (250 MHz, Methanol-d4): δ [ppm] 7.85 (t, J=1.4 Hz, 1H), 7.83-7.79 (m, 1H), 7.62-7.59 (m, 1H), 7.46 (dd, J=2.5, 1.3 Hz, 1H), 4.46 (d, J=19.2 Hz, 2H), 4.16-3.94 (m, 4H), 2.55 (d, J=1.1 Hz, 3H).

mL). The combined organic phase was dried (MgSO$_4$), filtered and concentrated under reduced pressure to give 222.6 mg (83% yield) of the title compound as brown gum.

$^1$H NMR (500 MHz, chloroform-d): δ [ppm] 7.76 (t, J=1.4 Hz, 1H), 7.73 (dd, J=2.4, 1.5 Hz, 1H), 7.55-7.53 (m, 1H), 7.21 (dd, J=2.5, 1.3 Hz, 1H), 4.37 (d, J=23.0 Hz, 2H), 3.70-3.63 (m, 2H), 3.23 (dd, J=21.6, 9.5 Hz, 2H), 2.54 (d, J=1.1 Hz, 3H), 2.45 (s, 3H).

LC-MS (Method A) Rt=0.86 min, MS (ESIpos): m/z=318 (M+H)$^+$.

In analogy to the procedure described for Intermediate 28CM, the following Intermediate was prepared using NaOH and the corresponding benzonitrile starting material.

| Int. | Structure | Name | Analytical Data |
|---|---|---|---|
| 28CO | 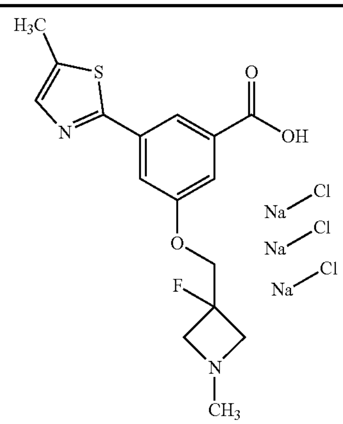 | 3-[(3-Fluoro-1-methylazetidin-3-yl)methoxy]-5-(5-methyl-1,3-thiazol-2-yl)benzoic acid-chlorosodium (1:3) | $^1$H NMR (250 MHz, DMSO-d6): δ [ppm] 8.02 (s, 1H), 7.66 (d, J = 1.3 Hz, 2H), 7.56 (s, 1H), 4.46 (d, J = 24.0 Hz, 2H), 3.66 (dd, J = 13.4, 9.8 Hz, 2H), 3.31-3.20 (m, 2H), 2.40 (s, 3H). LC-MS (Method A) Rt = 0.84 min, MS (ESIpos): m/z = 337 (M + H)$^+$. |

LC-MS (Method A) Rt=0.90 min, MS (ESIpos): m/z=304 (M+H)$^+$.

Intermediate 129: 3-[(3-Fluoro-1-methylazetidin-3-yl)methoxy]-5-(5-methyl-1,3-thiazol-2-yl)benzonitrile

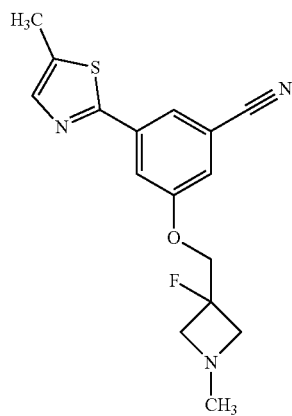 [SMILES: Cc1cnc(-c2cc(C#N)cc(OCC3(F)CN(C)C3)c2)s1]

Intermediate 128 (246 mg, 0.77 mmol), 37% formaldehyde solution in water (289 μL, 3.86 mmol) and acetic acid (5 μL) were combined in methanol (10 mL) and sodium triacetoxyborohydride (491 mg, 2.82 mmol) was added. The resulting solution was stirred at RT for 2 h before evaporating under reduced pressure. The residue was taken up in saturated NaHCO$_3$ (5 mL) and extracted with DCM (3×5 mL). The combined organic phase was dried (MgSO$_4$), filtered and concentrated under reduced pressure to give

Intermediate 131: tert-Butyl-3-fluoro-3-{[3-(5-methyl-1,3-thiazol-2-yl)-5-({(1R)-1-[2-(trifluoromethyl)pyrimidin-5-yl]ethyl}carbamoyl)phenoxy]methyl}piperidine-1-carboxylate, as a mixture of diastereoisomers To a stirred solution of Intermediate 28CP (150 mg, 0.33 mmol), Intermediate VI (91 mg, 0.40 mmol) and DIPEA (0.17 mL, 0.99 mmol) in dichloromethane (4 mL) was added HATU (189 mg, 0.50 mmol) and the reaction mixture stirred for 2 h at RT. The reaction mixture was washed with water (5 mL), dried (MgSO$_4$), filtered and concentrated at reduced pressure. Purification by Biotage Isolera™ chromatography (eluting with 25-90% EtOAc in heptane on a 25 g pre-packed KP—SiO$_2$ column) gave 162 mg (74% yield) of the title compound as white solid.

¹H NMR (250 MHz, DMSO-d6): δ [ppm] 9.09 (s, 2H), 8.94 (d, J=7.1 Hz, 1H), 8.01-7.84 (m, 1H), 7.67-7.57 (m, 2H), 7.57-7.53 (m, 1H), 5.33 (m, 1H), 4.35-4.16 (m, 2H), 4.12-3.95 (m, 1H), 3.85-3.64 (m, 1H), 3.46-3.16 (m, 1H), 1.94-1.87 (m, 1H), 1.81-1.49 (m, 6H), 1.40 (s, 9H).

LC-MS (Method A) Rt=1.44 min, MS (ESIpos) m/z=624 (M+H)⁺.

In analogy to the procedure described for Intermediate 131, the following Intermediates were prepared using HATU and the corresponding carboxylic acid and primary amine starting materials.

| Int. | Structure | Name | Analytical Data |
|---|---|---|---|
| 137 | 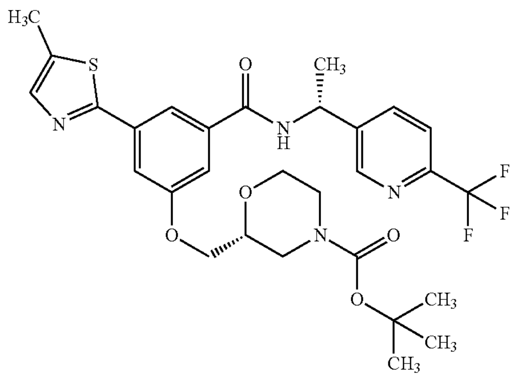 [SMILES: Cc1cnc(-c2cc(OC[C@H]3CN(C(=O)OC(C)(C)C)CCO3)cc(C(=O)N[C@H](C)c3ccc(C(F)(F)F)nc3)c2)s1] | tert-Butyl-(2R)-2-{[3-(5-methyl-1,3-thiazol-2-yl)-5-({(1R)-1-[6-(trifluoromethyl)pyridin-3-yl]ethyl}carbamoyl)phenoxy]-methyl}morpholine-4-carboxylate | ¹H NMR (250 MHz, chloroform-d): δ [ppm] 8.80 (d, J = 1.6 Hz, 1H), 7.95-7.84 (m, 2H), 7.69 (d, J = 8.1 Hz, 1H), 7.61-7.57 (m, 1H), 7.54 (d, J = 1.0 Hz, 1H), 7.46-7.40 (m, 1H), 6.63 (d, J = 7.1 Hz, 1H), 5.40 (m, 1H), 4.30-3.76 (m, 6H), 3.75-3.39 (m, 1H), 3.12-2.86 (m, 2H), 2.55 (s, 3H), 1.69 (d, J = 7.1 Hz, 3H), 1.50 (s, 9H). LC-MS (Method A) Rt = 1.40 min, MS (ESIpos): m/z = 607 (M + H)⁺. |
| 141 | 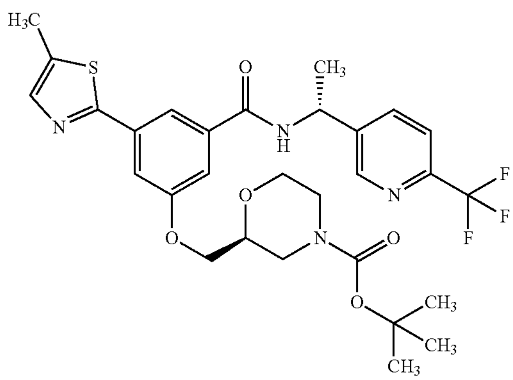 [SMILES: Cc1cnc(-c2cc(OC[C@@H]3CN(C(=O)OC(C)(C)C)CCO3)cc(C(=O)N[C@H](C)c3ccc(C(F)(F)F)nc3)c2)s1] | tert-Butyl-(2S)-2-{[3-(5-methyl-1,3-thiazol-2-yl)-5-({(1R)-1-[6-(trifluoromethyl)pyridin-3-yl]ethyl}carbamoyl)phenoxy]-methyl}morpholine-4-carboxylate | ¹H NMR (500 MHz, chloroform-d): δ [ppm] 8.80 (d, J = 1.3 Hz, 1H), 7.95-7.85 (m, 2H), 7.68 (d, J = 8.1 Hz, 1H), 7.58 (s, 1H), 7.56-7.51 (m, 1H), 7.42 (s, 1H), 6.71 (s, 1H), 5.40 (m, 1H), 4.24-4.05 (m, 3H), 4.03-3.85 (m, 2H), 3.82 (ddd, J = 10.2, 7.6, 4.9 Hz, 1H), 3.62 (m, 1H), 3.12-2.95 (m, 1H), 2.94-2.67 (m, 1H), 2.55 (s, 3H), 1.69 (d, J = 7.1 Hz, 3H), 1.50 (s, 9H). LC-MS (Method A) Rt = 1.38 min, MS (ESIpos): m/z = 607 (M + H)⁺. |
| 145 | 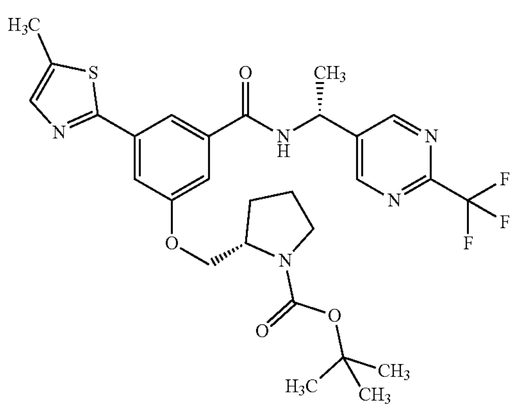 [SMILES: Cc1cnc(-c2cc(OC[C@@H]3CCCN3C(=O)OC(C)(C)C)cc(C(=O)N[C@H](C)c3cnc(C(F)(F)F)nc3)c2)s1] | Tert-butyl (2S)-2-{[3-(5-methyl-1,3-thiazol-2-yl)-5-({(1R)-1-[2-(trifluoromethyl)pyrimidin-5-yl]ethyl}carbamoyl)phenoxy]-methyl}pyrrolidine-1-carboxylate | ¹H NMR (250 MHz, chloroform-d): δ [ppm] 8.97 (s, 2H), 7.97 (s, 1H), 7.82 (s, 1H), 7.61 (s, 1H), 7.49 (s, 1H), 7.40-7.32 (m, 1H), 5.53-5.40 (m, 1H), 4.36-4.03 (m, 2H), 3.98-3.79 (m, 1H), 3.54-3.17 (m, 2H), 2.50 (s, 3H), 2.07-1.87 (m, 4H), 1.71 (d, J = 7.1 Hz, 3H), 1.40 (s, 9H). |

| Int. | Structure | Name | Analytical Data |
|---|---|---|---|
| 143 | 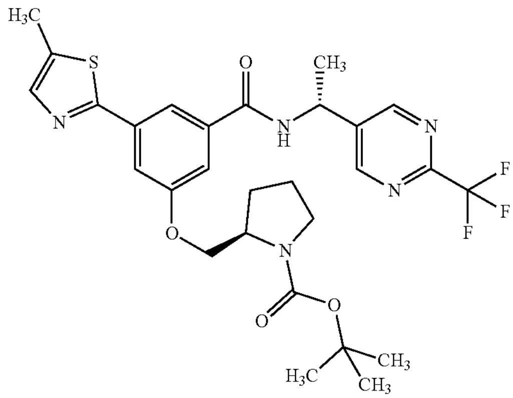 [SMILES: Cc1cnc(-c2cc(OC[C@H]3CCCN3C(=O)OC(C)(C)C)cc(C(=O)N[C@H](C)c3cnc(C(F)(F)F)nc3)c2)s1] | Tert-butyl (2R)-2-{[3-(5-methyl-1,3-thiazol-2-yl)-5-({(1R)-1-[2-(trifluoromethyl)pyrimidin-5-yl]ethyl}carbamoyl)phenoxy]methyl}pyrrolidine-1-carboxylate | ¹H NMR (250 MHz, chloroform-d): δ [ppm] 8.95 (s, 2H), 8.04-7.96 (m, 1H), 7.95-7.85 (m, 1H), 7.65 (s, 1H), 7.50 (s, 1H), 7.44-7.32 (m, 1H), 5.60-5.39 (m, 1H), 4.42-4.27 (m, 1H), 4.26-4.12 (m, 1H), 3.95-3.82 (m, 1H), 3.50-3.36 (m, 1H), 3.35-3.19 (m, 1H), 2.52 (s, 3H), 2.07-1.87 (m, 4H), 1.76 (d, J = 7.0 Hz, 3H), 1.42 (s, 9H). |

Intermediate 139: Tert-butyl (2R)-2-{[3-({(1R)-1-[6-(difluoromethyl)pyridin-3-yl]ethyl}carbamoyl)-5-(5-methyl-1,3-thiazol-2-yl)phenoxy]methyl}morpholine-4-carboxylate

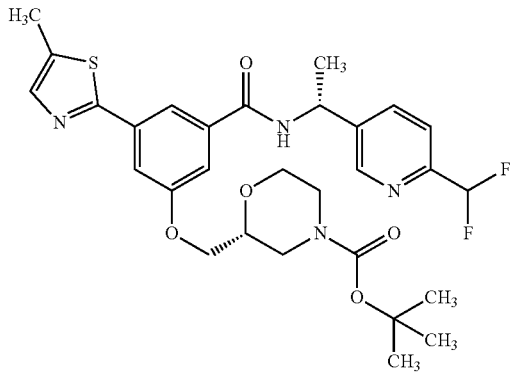

To a stirred solution of Intermediate 5CE (80 mg, 0.18 mmol), Intermediate LIV (46 mg, 0.17 mmol) and DIPEA (0.15 mL, 0.88 mmol) in DCM (2 mL) was added T3P (50% solution in EtOAc, 0.21 mL, 0.35 mmol). The reaction mixture was stirred at RT for 2 h then washed with saturated sodium bicarbonate solution (3 mL). The aqueous phase was re-extracted with DCM (3 mL) and the combined organics passed through a phase separator and concentrated under reduced pressure. The crude material was purified by Biotage Isolera™ chromatography (eluting with 0-2% MeOH in DCM on a 25 g pre-packed KP—SiO₂ column) to give 58 mg (53% yield) of the title compound as a colourless gum.

¹H NMR (500 MHz, chloroform-d): δ [ppm] 8.71 (d, J=1.7 Hz, 1H), 7.89 (s, 1H), 7.86 (dd, J=8.1, 2.2 Hz, 1H), 7.63 (d, J=8.1 Hz, 1H), 7.58-7.54 (m, 1H), 7.53-7.51 (m, 1H), 7.42 (s, 1H), 6.81-6.46 (m, 2H), 5.46-5.32 (m, 1H), 4.22-3.75 (m, 6H), 3.69-3.51 (m, 1H), 3.07-2.78 (m, 2H), 2.53 (d, J=1.0 Hz, 3H), 1.66 (d, J=7.1 Hz, 3H), 1.48 (s, 9H).

LC-MS (Method A) Rt=1.32 min, MS (ESIpos): m/z=589 (M+H)⁺.

In analogy to the procedure described for Intermediate 139, the following Intermediate was prepared using T3P and the corresponding carboxylic acid and primary amine starting materials.

| Int. | Structure | Name | Analytical Data |
|---|---|---|---|
| 146 | 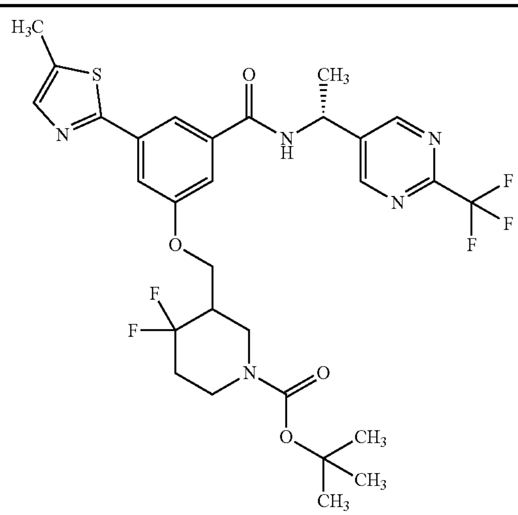 | Tert-butyl-4,4-difluoro-3-{[3-(5-methyl-1,3-thiazol-2-yl)-5-({(1R)-1-[2-(trifluoromethyl)pyrimidin-5-yl]ethyl}carbamoyl)phenoxy]methyl}piperidine-1-carboxylate, as a mixture of diastereoisomers | ¹H NMR (250 MHz, chloroform-d): δ [ppm] 8.95 (s, 2H), 7.88 (s, 1H), 7.58-7.47 (m, 2H), 7.37 (s, 1H), 6.92 (s, 1H), 5.36 (q, J = 6.9 Hz, 1H), 4.43-3.81 (m, 4H), 3.41-2.88 (m, 2H), 2.53 (d, J = 0.9 Hz, 3H), 2.50-2.31 (m, 1H), 2.13-1.80 (m, 2H), 1.73 (d, J = 7.1 Hz, 3H), 1.43 (s, 9H). LC-MS (Method A) Rt = 1.43 min, MS (ESIpos): m/z = 642 (M + H)⁺. |

Intermediate 138: 3-(5-Methyl-1,3-thiazol-2-yl)-5-[(2R)-morpholin-2-ylmethoxy]-N-{(1R)-1-[6-(trifluoromethyl)pyridin-3-yl]ethyl}benzamide

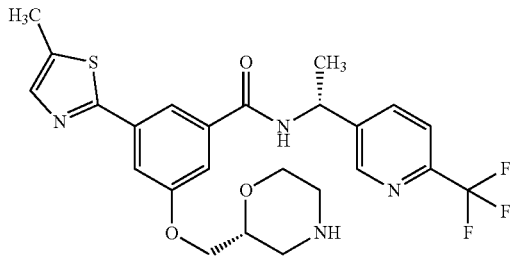

To a solution of Intermediate 137 (126 mg, 0.18 mmol) in dichloromethane (5 mL) was added trifluoroacetic acid (0.28 mL, 3.66 mmol) and the reaction mixture stirred at ambient temperature for 16 h. The reaction mixture was passed through an SCX cartridge (washing with methanol and eluting with 7N ammonia in methanol) to give 85 mg (92% yield) of the title compound as a glass solid.

$^1$H NMR (250 MHz, chloroform-d): δ [ppm] 8.80 (d, J=1.6 Hz, 1H), 7.97-7.82 (m, 2H), 7.68 (d, J=8.1 Hz, 1H), 7.61-7.55 (m, 1H), 7.53 (d, 1H), 7.49-7.36 (m, 1H), 6.68 (d, J=6.9 Hz, 1H), 5.40 (m, 1H), 4.21-3.82 (m, 4H), 3.73 (td, J=11.0, 3.5 Hz, 1H), 3.15-2.64 (m, 4H), 2.55 (s, 3H), 1.69 (d, J=7.1 Hz, 3H).

LC-MS (Method A) Rt=0.96 min, MS (ESIpos): m/z=507 (M+H)$^+$.

In analogy to the procedure described for Intermediate 138, the following Intermediates were prepared using TFA and the corresponding N-Boc protected starting materials.

| Int. | Structure | Name | Analytical Data |
|---|---|---|---|
| 412 | 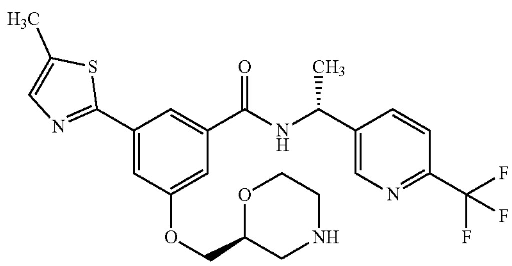 [SMILES: Cc1cnc(-c2cc(OC[C@@H]3CNCCO3)cc(C(=O)N[C@H](C)c3ccc(C(F)(F)F)nc3)c2)s1] | 3-(5-Methyl-1,3-thiazol-2-yl)-5-[(2S)-morpholin-2-ylmethoxy]-N-{(1R)-1-[6-(trifluoromethyl)pyridin-3-yl]ethyl}benzamide | $^1$H NMR (500 MHz, chloroform-d): δ [ppm] 8.81 (s, 1H), 7.95-7.80 (m, 2H), 7.68 (d, J = 8.1 Hz, 1H), 7.57 (s, 1H), 7.53 (s, 1H), 7.43 (s, 1H), 6.69 (d, J = 6.2 Hz, 1H), 5.40 (m, 1H), 4.10 (dd, J = 9.9, 5.9 Hz, 1H), 4.05 (dd, J = 9.9, 4.2 Hz, 1H), 4.01-3.87 (m, 2H), 3.74 (td, J = 11.3, 2.7 Hz, 1H), 3.07 (d, J = 11.7 Hz, 1H), 3.00-2.86 (m, 2H), 2.86-2.74 (m, 1H), 2.55 (s, 3H), 1.69 (d, J = 7.1 Hz, 3H). LC-MS (Method A) Rt = 0.99 min, MS (ESIpos): m/z = 507 (M + H)$^+$. |
| 132 | 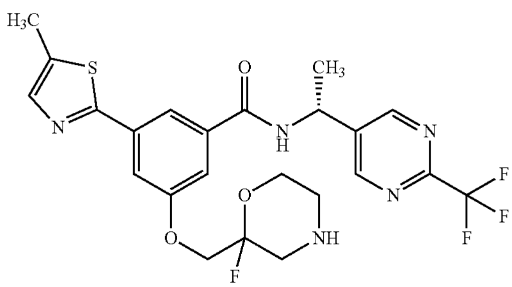 [SMILES: Cc1cnc(-c2cc(OCC3(F)CNCCO3)cc(C(=O)N[C@H](C)c3cnc(C(F)(F)F)nc3)c2)s1] | 3-(Fluoropiperidin-3-yl)methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers | $^1$H NMR (500 MHz, chloroform-d): δ [ppm] 8.95 (d, J = 1.1 Hz, 2H), 7.85 (s, 1H), 7.53 (s, 1H), 7.50 (s, 1H), 7.41 (d, J = 5.3 Hz, 1H), 6.99 (s, 1H), 5.36 (m, 1H), 4.19-3.94 (m, 2H), 3.33-3.17 (m, 1H), 3.06-3.00 (m, 1H), 2.90 (m, 1H), 2.68 (t, J = 10.9 Hz, 1H), 2.52 (s, 3H), 2.09-1.98 (m, 1H), 1.88-1.75 (m, 2H), 1.71 (d, J = 7.1 Hz, 3H), 1.65-1.52 (m, 1H). LC-MS (Analytical Method F) Rt = 2.17 min, MS (ESIpos): m/z = 524 (M + H)$^+$. |
| 140 | 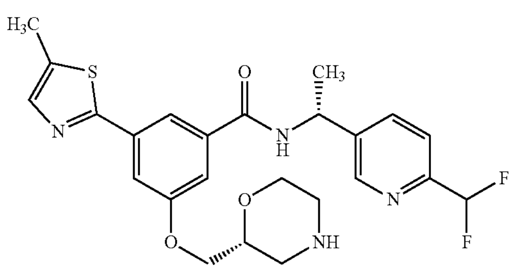 [SMILES: Cc1cnc(-c2cc(OC[C@H]3CNCCO3)cc(C(=O)N[C@H](C)c3ccc(C(F)F)nc3)c2)s1] | N-{(1R)-1-[6-(Difluoromethyl)pyridin-3-yl]ethyl}-3-(5-methyl-1,3-thiazol-2-yl)-5-[(2R)-morpholin-2-ylmethoxy]benzamide | $^1$H NMR (500 MHz, chloroform-d): δ [ppm] 8.75-8.67 (m, 1H), 7.88-7.83 (m, 2H), 7.62 (d, J = 8.1 Hz, 1H), 7.58-7.54 (m, 1H), 7.52-7.49 (m, 1H), 7.44-7.39 (m, 1H), 6.77-6.49 (m, 2H), 5.38 (m, 1H), 4.16-3.90 (m, 4H), 3.74 (td, J = 11.2, 3.2 Hz, 1H), 3.08 (d, J = 12.1 Hz, 1H), 3.03-2.68 (m, 3H), 2.52 (s, 3H), 1.66 (d, J = 7.1 Hz, 3H). LC-MS (Method A) Rt = 0.96 min, MS (ESIpos): m/z = 489 (M + H)$^+$. |
| 144 | 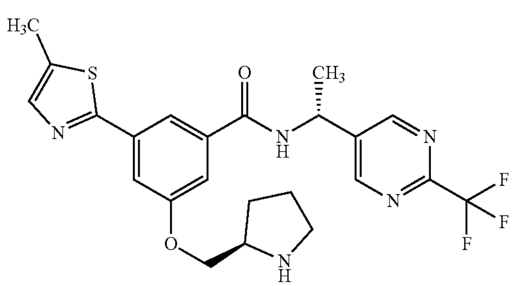 [SMILES: Cc1cnc(-c2cc(OC[C@H]3CCCN3)cc(C(=O)N[C@H](C)c3cnc(C(F)(F)F)nc3)c2)s1] | 3-(5-Methyl-1,3-thiazol-2-yl)-5-[(2R)-pyrrolidin-2-ylmethoxy]-N-{(1R)-1-[2-(trifluoromethyl)pyrimidin-5-yl]ethyl)benzamide | LC-MS (Method A) Rt = 0.94 min, MS (ESIpos): m/z = 492 (M + H)$^+$. |

Intermediate 133: 3-(5-Methyl-1,3-thiazol-2-yl)-5-[(2R)-morpholin-2-ylmethoxy]benzoic acid trifluoroacetate (1:1)

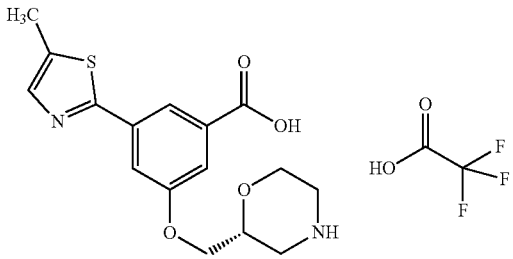 [SMILES: Cc1cnc(-c2cc(OC[C@H]3CNCCO3)cc(C(=O)O)c2)s1 ; O=C(O)C(F)(F)F]

To a solution of Intermediate 5CE (120 mg, 0.276 mmol) in DCM was added trifluoroacetic acid (2 mL, 25.96 mmol) and the reaction stirred at RT for 1 hour. The reaction was stopped and concentrated under reduced pressure to give 200 mg (quantitative yield; residual TFA present) of the title compound as pale yellow oil.

LC-MS (Method A) Rt=0.85 min, MS (ESIpos): M/Z=335 [M+H]$^+$.

Intermediate 134: 3-{[(2R)-4-Methylmorpholin-2-yl]methoxy}-5-(5-methyl-1,3-thiazol-2-yl)benzoic acid

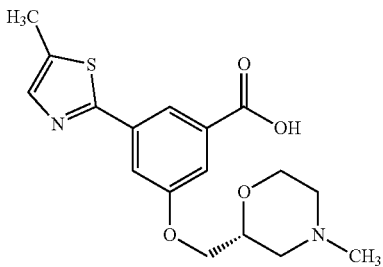 [SMILES: Cc1cnc(-c2cc(OC[C@H]3CN(C)CCO3)cc(C(=O)O)c2)s1]

To a solution of Intermediate 133 (200 mg, 0.45 mmol), formaldehyde (37% in water, 167.1 μL, 2.23 mmol) and acetic acid (38.3 μL, 1.05 mmol) in MeOH (2 mL) was added STAB (283.6 mg, 1.34 mmol) and mixture stirred at RT for 1 hour. The solvent was evaporated and the resulting residue basified to pH 8-9 using saturated NaHCO$_3$ and extracted in DCM (3×5 mL). The aqueous layer was neutralised to pH 7 with acid and concentrated under reduced pressure to give the title compound 859 mg (quantitative yield; inorganic salts present).

$^1$H NMR (500 MHz, DMSO-d6): δ [ppm] 7.92-7.91 (m, 1H), 7.57 (d, J=1.1 Hz, 1H), 7.47 (dd, 1H), 7.36-7.34 (m, 1H), 4.03-4.00 (m, 2H), 3.83-3.77 (m, 3H), 3.55 (td, J=11.2, 8.8 Hz, 3H), 2.81-2.77 (m, 1H), 2.62-2.58 (m, 1H), 2.20 (s, 3H), 2.00 (td, 1H), 1.90 (t, J=10.7 Hz, 1H).

LC-MS (Method A) Rt=0.93 min, MS (ESIpos): m/z=349 (M+H)$^+$.

Intermediate 147: 3-{[3-Fluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers

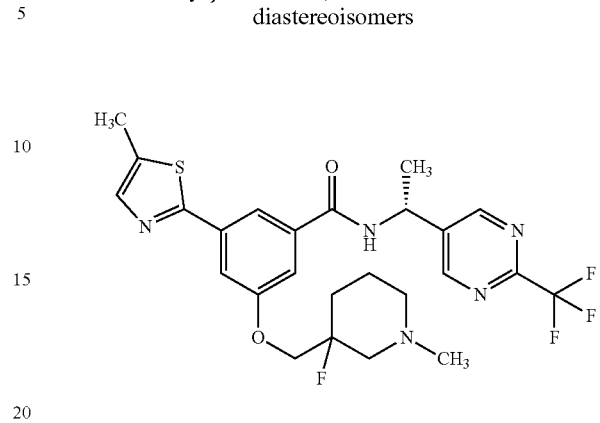

To a solution of Intermediate 132 (55 mg, 0.1 mmol) in methanol (1 mL) was added formaldehyde (37% in water, 16 uL, 0.21 mmol) and acetic acid (6 uL, 0.1 mmol) and the reaction stirred for 15 minutes at RT. STAB (33 mg, 0.16 mmol) was added and the reaction stirred for 1 h at RT. The reaction mixture was passed through an SCX cartridge (washing with methanol, eluting with 7N ammonia in methanol) and concentrated under reduced pressure to give 52 mg (91% yield) of the title compound as an off-white glass.

$^1$H NMR (500 MHz, DMSO-d6): δ [ppm] 9.17 (d, J=7.0 Hz, 1H), 9.12 (s, 2H), 7.93 (s, 1H), 7.64 (s, 1H), 7.60 (s, 1H), 7.56 (s, 1H), 5.30 (m, 1H), 4.27 (d, J=22.1 Hz, 2H), 2.62-2.53 (m, 2H), 2.39-2.31 (m, 1H), 2.29-2.22 (m, 1H), 2.19 (s, 3H), 1.87-1.77 (m, 1H), 1.75-1.67 (m, 2H), 1.61 (d, J=7.1 Hz, 3H), 1.58-1.48 (m, 1H).

LC-MS (Analytical Method F) Rt=2.19 min, MS (ESIpos): m/z=538 (M+H)$^+$.

Intermediate I: Ethyl 2-(trifluoromethyl)pyrimidine-5-carboxylate

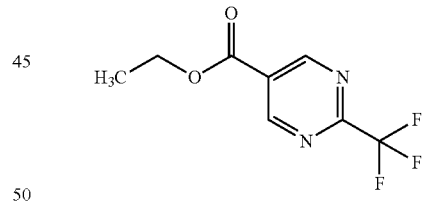

Note: The reaction was split into two 37.5 g batches, and the isolated product combined into one batch.

To a solution of ethyl 4-chloro-2-(trifluoromethyl)pyrimidine-5-carboxylate (37.5 g, 142.9 mmol) in ethanol (750 mL) was added DIPEA (68 mL, 392.3 mmol), 10% Pd/C (50% wet, 3 g) and the reaction mixture stirred under an atmosphere of hydrogen for 1 h. The reaction mixture was filtered through glass fibre filter paper and the filtrate concentrated under reduced pressure to give a yellow solid. The solid was taken up in EtOAc (500 mL), washed with water (500 mL), 1M aq HCl (500 mL), saturated aq. NaHCO$_3$ (500 mL), dried (over MgSO$_4$), filtered and concentrated under reduced pressure. The pale yellow solid was triturated with heptane and the solid collected by filtration. The filtrate was concentrated and trituration repeated with heptane. The mother liquors from both batches were combined and purified by Biotage Isolera™ chromatography (eluting with 1-30% EtOAc in heptane on a 100g KP—SiO$_2$ column). The product containing fractions were concentrated and the residue triturated with heptane. All the solids were combined to give 56.8 g (90% yield) of the title compound as yellow solid.

$^1$H NMR (250 MHz, Chloroform-d): δ [ppm] 9.43 (s, 2H), 4.50 (q, J=7.1 Hz, 2H), 1.45 (t, J=7.1 Hz, 3H).

LCMS (Analytical Method A) Rt=1.24 min, MS (ESI-pos): m/z=220.9 (M+H)$^+$.

Intermediate II: 2-(Trifluoromethyl)pyrimidine-5-carboxylic acid

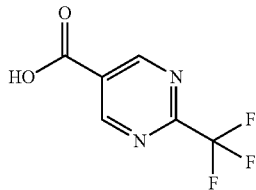 [SMILES: O=C(O)c1cnc(C(F)(F)F)nc1]

To a solution of ethyl 2-(trifluoromethyl)pyrimidine-5-carboxylate (56.8 g, 252.8 mmol) dissolved in THF (500 mL) was added 1M aq. LiOH (380 mL, 379.3 mmol). The reaction mixture was stirred at RT for 16 h, concentrated under vacuum to remove the organic solvent and the remaining aqueous acidified to pH 1 with conc. HCl. The resultant precipitate was collected by vacuum filtration to afford 44.4 g (91% yield) of the title compound as off-white powder.

$^1$H NMR (500 MHz, DMSO-d$_6$): δ [ppm] 9.44 (s, 2H).

LCMS (Analytical Method A) Rt=0.81 min, MS (ESIneg): m/z=190.9 (M)−.

Intermediate III: N-Methoxy-N-methyl-2-(trifluoromethyl)pyrimidine-5-carboxamide

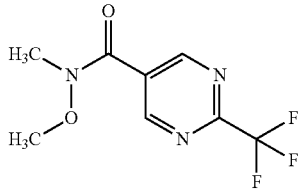 [SMILES: CON(C)C(=O)c1cnc(C(F)(F)F)nc1]

2-(Trifluoromethyl)pyrimidine-5-carboxylic acid (44.39 g, 231.1 mmol), methoxymethane hydrochloride (33.8 g, 346.6 mmol) and DIPEA (119.5 mL, 924.3 mmol) were combined in DCM (750 mL) then HATU (105.4 g, 277.3 mmol) was added and the mixture stirred at RT for 2 h. The reaction mixture was washed with water (3×300 mL), the organic phase collected, dried (over MgSO$_4$), filtered and concentrated in vacuo to give a viscous yellow oil. The crude material was purified by dry flash chromatography (eluting with 0-40% EtOAc in heptane) to give 54.2 g (95% yield) of the title compound as a free flowing pale yellow oil.

$^1$H NMR (500 MHz, Chloroform-d): δ [ppm] 9.22 (s, 2H), 3.61 (s, 3H), 3.43 (s, 3H).

LCMS (Analytical Method A) Rt=1.03 min, MS (ESI-pos): m/z=235.9 (M+H)$^+$.

Intermediate IV: 1-[2-(Trifluoromethyl)pyrimidin-5-yl]ethanone

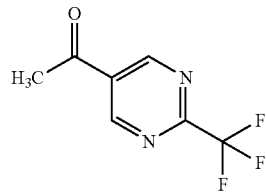

N-Methoxy-N-methyl-2-(trifluoromethyl)pyrimidine-5-carboxamide (54.9 g, 218.9 mmol) was dissolved in dry THF (550 mL) and cooled to 0° C. in an ice bath. Methyl magnesium bromide (1.4M in toluene/THF, 188 mL, 262.7 mmol) was added dropwise over 30 minutes. The reaction was stirred for a further 10 min at 0° C., quenched slowly with 1M HCl (260 mL) and stirred for another 30 mins before extracting with ethyl acetate (300 mL). The organic phase was separated, dried (over MgSO$_4$), filtered and concentrated in vacuo to give a yellow solid. LCMS and $^1$H NMR showed presence of ~20 mot % of unhydrolysed intermediate, hence the solid was stirred in a mixture of 2M HCl (200 mL) and DCM (200 mL) for 20 min. The layers were separated and the aqueous layer extracted with further DCM (2×100 mL). The combined organics were dried (over MgSO$_4$), filtered and concentrated under reduced pressure to afford 33.57 g (80% yield) of the title compound as yellow solid.

$^1$H NMR (500 MHz, Chloroform-d): δ [ppm] 9.36 (s, 2H), 2.72 (s, 3H).

LCMS (Analytical Method A) Rt=0.99 min, MS (ESI-pos): m/z=191.0 (M+H)$^+$.

Intermediate V: (S)-2-Methyl-N-{(1R)-1-[2-(trifluoromethyl)pyrimidin-5-yl]ethyl}propane-2-sulfinamide

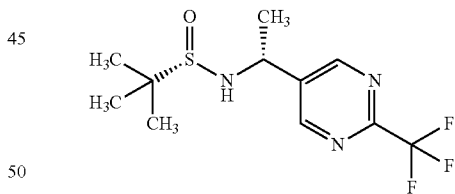

To a stirred solution of 1-[2-(trifluoromethyl)pyrimidin-5-yl]ethanone (20.65 g, 107.5 mmol) and titanium(IV) ethoxide (69.4 mL, 215.1 mmol) in Et$_2$O (1 L) was added (S)-2-t-butylsulfinamide (14.3 g, 118.3 mmol) and the resulting solution stirred at reflux overnight under nitrogen atmosphere. The reaction mixture was cooled to −78° C. and L-selectride (118.3 mL, 1M sol. in THF) added dropwise maintaining an internal temperature below −70° C. The reaction was stirred at −78° C. for a further 2h, after which time LCMS (Analytical Method A) showed residual imine intermediate. The reaction mixture was re-treated with L-selectride (12 mL, 1M sol. in THF) and stirred for 1 h. LCMS showed complete conversion of imine. The reaction was quenched by addition of brine (500 mL) and warmed to RT. The suspension was filtered through a plug of celite, washing with EtOAc. The filtrate was washed with brine (500 mL), and the aqueous layer re-extracted with EtOAc (2×300 mL). The combined organics were dried (over MgSO$_4$), filtered and concentrated under reduced pressure. The residue was triturated with Et$_2$O and the resulting precipitate collected by vacuum filtration to give 18.12 g (57% yield) of the title compound as off-white powder.

$^1$H NMR (500 MHz, Chloroform-d): δ [ppm] 8.88 (s, 2H), 4.75 (qd, J=6.8, 3.1 Hz, 1H), 3.43 (d, J=2.5 Hz, 1H), 1.64 (d, J=6.8 Hz, 3H), 1.24 (s, 9H).

LCMS (Analytical Method A) Rt=1.14 min, MS (ESI-pos): m/z=296.0 (M+H)$^+$.

Intermediate VI: (1R)-1-[2-(Trifluoromethyl)pyrimidin-5-yl]ethan-1-amine hydrochloride (1:1)

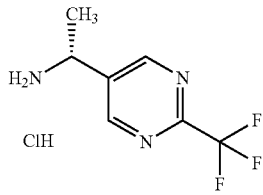

To a solution of (S)-2-methyl-N-[(1R)-1-[2-(trifluoromethyl)pyrimidin-5-yl]ethyl]propane-2-sulfinamide (14.37 g, 48.66 mmol) dissolved in methanol (140 mL) was added 4M HCl in dioxane (120 mL) and the resulting solution stirred for 1 h at RT. The reaction mixture was concentrated in vacuo, diethyl ether added to precipitate the title compound 10.06 g (91% yield) as an off-white solid after collection by vacuum filtration.

$^1$H NMR (250 MHz, DMSO-d6): δ [ppm] 9.28 (s, 2H), 8.96 (s, 2H), 4.67 (q, J=6.9 Hz, 1H), 1.64 (d, J=6.9 Hz, 3H).

Analytical HPLC: Column: Chiralpak AD-H 25 cm; Mobile phase: 90:10 Heptane: Ethanol; Flow rate: 0.3 ml/min; Detection: UV 254 nm.; Runtime: 70 mins; Rt=49.44 min; 100% ee.

Intermediate VII: (S)-2-Methyl-N-[(1R)-1-(6-methylpyridin-3-yl)ethyl]propane-2-sulfinamide

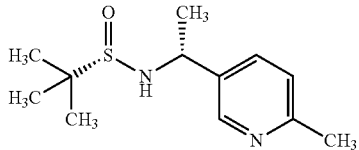 [SMILES: Cc1ccc([C@@H](C)N[S@@](=O)C(C)(C)C)cn1]

1-(6-Methylpyridin-3-yl)ethan-1-one (1.6 g, 11.8 mmol) and (S)-tert-butylsulfinamide (1.4 g, 11.8 mmol) were dissolved in THF (20 mL). Titanium(IV) ethoxide (containing 33% TiO$_2$) (6.1 g, 17.8 mmol) was added and the reaction mixture stirred at 80° C. for 2 hours. The reaction mixture was cooled to −78° C. and L-Selectride (1M soln in THF, 11.8 mL, 11.8 mmol) was added dropwise over 30 mins, maintaining in internal reaction temperature below −70° C. The reaction mixture was stirred at −78° C. for 1 hour and then quenched with MeOH (2 mL). The solution was allowed to warm to RT and diluted with water (50 mL). The resulting solid was removed via vacuum filtration, the filtrate collected and solvent removed in vacuo. The residue was taken up in brine (40 mL) and extracted with TBME (2×60 mL). The combined organics were dried (over Na$_2$SO$_4$), filtered and concentrated under reduced pressure. The crude material was purified by Biotage Isolera™ chromatography (eluting with 0-20% MeOH in DCM) to give 1.25 g (34% yield) of the title compound.

$^1$H NMR (500 MHz, Chloroform-d): δ [ppm] 8.46 (d, J=2.2, 1H), 7.53 (dd, J=8.0, 2.3, 1H), 7.13 (d, J=8.0, 1H), 4.57 (qd, J=6.7, 6.7, 6.7, 3.4, 1H), 2.55 (s, 3H), 1.54 (d, J=6.7, 3H), 1.18 (s, 9H).

Intermediate VIII: (1R)-1-(6-Methylpyridin-3-yl)ethanamine hydrochloride

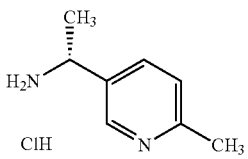

To a solution of (S)-2-methyl-N-[(1R)-1-(6-methylpyridin-3-yl)ethyl]propane-2-sulfinamide (1.25 g, 4.1 mmol) in 2-propanol (5 mL) cooled to 0° C. in an ice bath was added 5M HCl in 2-propanol (4 mL, 20 mmol). The mixture was allowed to warm to RT and stirred for 1 hour. Formation of a white precipitate was observed. The precipitate was collected by filtration and washed with TBME to give 616 mg (78% yield) of the title compound as a white solid.

$^1$H NMR (500 MHz, DMSO-d6): δ [ppm] 8.98 (s, 3H), 8.85 (d, J=2.0 Hz, 1H), 8.47 (dd, J=8.3, 2.0 Hz, 1H), 7.77 (d, J=8.3 Hz, 1H), 7.53-7.24 (m, 2H), 4.60 (s, 1H), 2.68 (s, 3H), 1.58 (d, J=6.9 Hz, 3H).

Intermediate IX: 1-(5-Methylpyrazin-2-yl)ethanone

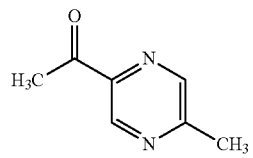

5-Methylpyrazine-2-carbonitrile (25.0 g, 210 mmol) was dissolved in diethyl ether (500 mL) and cooled to −15° C. To this was added methyl magnesium iodide (3M in THF, 84 mL, 241 mmol) dropwise over 1 hour and the internal temperature maintained below −10° C. A cloudy orange precipitate formed during reactant addition. The reaction was quenched by slowly pouring the mixture into 1M aq. HCl (250 mL) and crushed ice. The mixture was warmed to RT and basified with sat. aq, NaHCO$_3$. TBME (300 mL) was added and the organic layer collected. The aqueous layer was extracted with TBME (2×300 mL) and the combined organic layers were washed with brine (300 mL), dried (over Na$_2$SO$_4$), filtered and concentrated under reduced pressure to give 18.4 g (61% yield) of the title compound as a yellow solid.

$^1$H NMR (500 MHz, DMSO-d6): δ [ppm] 8.97 (d, J=1.2 Hz, 1H), 8.68 (s, 1H), 2.62 (s, 3H), 2.60 (s, 3H).

Intermediate X: (S)-2-Methyl-N-[(1R)-1-(5-methylpyrazin-2-yl)ethyl]propane-2-sulfinamide

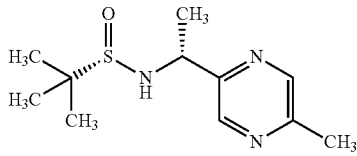

1-(5-Methylpyrazin-2-yl)ethanone (27.2 g, 200 mmol), (S)-tert-butylsulfinamide (24.24 g, 200 mmol) and titanium (IV) ethoxide (102 g, 300 mmol; containing 33% TiO₂) were heated in THF (1000 mL) at 80° C. for 1 hour then cooled to RT. TLC (EtOAc/acetone 1:1) indicated consumption of Intermediate IX. The mixture was cooled to −78° C. and L-Selectride (1m in THF, 200 mL, 200 mmol) added dropwise over 60 minutes with the internal temperature maintained below −70° C. The mixture was stirred at −78° C. for 1 hour then quenched by dropwise addition of MeOH (50 mL) and warmed to RT. Upon addition of water (100 mL) a white precipitate formed that was collected by filtration and washed with TBME (2 L). The aqueous layer of the filtrate was separated and washed with TBME (2×200 mL). The combined organics were washed with brine (100 mL), dried (over Na₂SO₄), filtered and concentrated under reduced pressure. The residue was purified by dry flash chromatography (silica gel, eluting with 0-60% acetone in EtOAc) to give 35.8 g (49% yield) of the title compound as a brown oil.

¹H NMR (500 MHz, DMSO-d6): δ [ppm] 8.57 (d, J=1.1 Hz, 1H), 8.45 (s, 1H), 5.56 (d, J=6.4 Hz, 1H), 5.29 (s, 1H), 4.56-4.44 (m, 1H), 2.47 (s, 3H), 1.51 (d, J=6.9 Hz, 3H), 1.11 (s, 9H), 1.08 (s, 5H).

Intermediate XI: (1R)-1-(5-Methylpyrazin-2-yl)ethanamine dihydrochloride

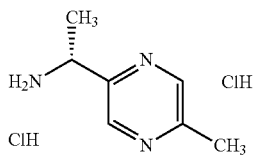

To a solution of (S)-2-methyl-N-[(1R)-1-(5-methylpyrazin-2-yl)ethyl]propane-2-sulfinamide (35 g, 63.7 mmol) in 2-propanol (200 mL) was added 5M HCl in 2-propanol (65 mL, 325 mmol) at 0° C. The mixture was warmed to RT, resulting in formation of a precipitate. After stirring for 1 hour the precipitate was collected by filtration. Recrystallisation from hot TBME (200 mL) gave 19.8 g (78% yield) of the title compound as a light brown solid.

¹H NMR (500 MHz, DMSO-d6) δ [ppm]: 8.70 (s, 4H), 8.59 (s, 1H), 4.57 (dq, J=12.2, 6.1 Hz, 1H), 2.52 (s, 3H), 1.53 (d, J=6.8 Hz, 3H).

Intermediate XII: 6-Methylpyridazine-3-carbonitrile

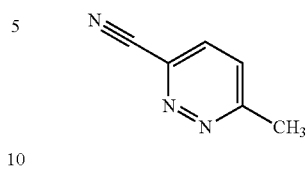

A solution of 3-chloro-6-methylpyridazine (50 g, 389 mmol) in DMA (1250 mL) was degassed under nitrogen for 10 minutes then zinc (II) cyanide (27.4 g, 233 mmol), zinc dust (1017 mg, 15.6 mmol) and Pd(dppf)Cl₂.DCM (12.7 g, 15.6 mmol) were added. The mixture was heated at 120° C. overnight. The reaction mixture was cooled to RT, diluted with DCM (1 L) and filtered through celite, washing with further DCM. The filtrate was concentrated under reduced pressure. The residue was purified by dry flash silica chromatography (eluting with TBME) to give 34.9 g (75% yield) of the title compound as an off-white solid.

¹H NMR (500 MHz, Chloroform-d): δ [ppm] 7.72 (d, J=8.6 Hz, 1H), 7.48 (d, J=8.6 Hz, 1H), 2.85 (s, 3H).

Intermediate XIII: 1-(6-Methylpyridazin-3-yl)ethan-1-one

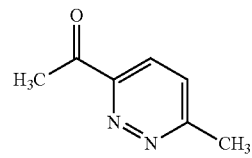

A solution of 6-methylpyridazine-3-carbonitrile (23.8 g, 200 mmol) in TBME (1.2 L) was stirred under nitrogen and cooled to −15° C. Methyl magnesium iodide (3M in Et₂O, 80 mL, 240 mmol) was added over ~20 min, keeping the internal temperature below −15° C. The reaction mixture was stirred for 1.5 h before quench by addition of 2M HCl (120 mL). The mixture was warmed to RT, the organic layer collected, dried (over Na₂SO₄), filtered and concentrated under reduced pressure to give a yellow solid. The aqueous layer was basified to pH 8-9 with NaHCO₃, extracted with DCM (4×200 mL) and the combined organics dried (over Na₂SO₄), filtered and concentrated under reduced pressure. The two batches were combined to give 26.2 g (67% yield) of the title compound as a yellow solid.

¹H NMR (500 MHz, Chloroform-d): δ [ppm] 8.02 (d, J=8.6 Hz, 1H), 7.46 (d, J=8.6 Hz, 1H), 2.87 (s, 3H), 2.81 (s, 3H).

Intermediate XIV: (S)-2-Methyl-N-[(1R)-1-[6-methylpyridazin-3-yl)ethyl]propane-2-sulfinamide

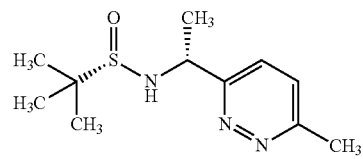 [SMILES: Cc1ccc([C@@H](C)N[S@@](=O)C(C)(C)C)nn1]

To a stirred solution of 1-(6-methylpyridazin-3-yl)ethan-1-one (26.2 g crude, 19.90 g purity corrected mass, 146.2 mmol) and titanium(IV) ethoxide (61.3 mL, 292.3 mmol) in dry THF (600 mL) was added (S)-2-t-butylsulfinamide (17.71 g, 146.2 mmol) and the resulting solution stirred at 80° C. for 60 min. The solution was cooled to −70° C. and L-Selectride (1M in THF, 146.2 mL, 142 mmol) added dropwise, whilst maintaining an internal temperature below −72° C. The reaction mixture was stirred at −78° C. for 30 min, quenched by slow addition of methanol (30 mL) and allowed to warm to room temperature. Ethyl acetate (800 mL) and water (800 mL) were added resulting in precipitation. The solid was collected by filtration, washed with ethyl acetate (3×400 mL). Each 3×~400 mL EtOAc filtrate was used to back-extract the aqueous layer. The combined organics were dried (over $Na_2SO_4$), filtered and concentrated under reduced pressure. The crude material was part-purified by dry flash silica chromatography (eluting with EtOAc followed by acetone). Re-purification by dry flash silica chromatography (eluting with 50% acetone in EtOAc) gave 21.4 g (44% yield) of the title compound as a brown viscous oil.

$^1$H NMR (250 MHz, Chloroform-d): δ 7.40 [ppm] (d, J=8.6 Hz, 1H), 7.30 (d, J=8.6 Hz, 1H), 4.84 (p, J=6.7 Hz, 1H), 3.97 (d, J=6.1 Hz, 1H), 3.71 (s, 1.3H), 2.70 (s, 3H), 1.68 (d, J=6.8 Hz, 3H), 1.22 (s, 6H), 1.20 (s, 9H).

Intermediate XV: (1R)-1-(6-Methylpyridazin-3-yl)ethan-1-amine hydrochloride

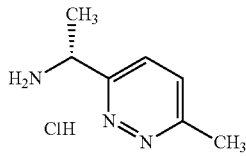

(S)-2-methyl-N-[(1R)-1-(6-methylpyridazin-3-yl)ethyl]propane-2-sulfinamide (21.3 g, 88.3 mmol) was dissolved in methanol (400 mL) and cooled to 0° C. prior to slow addition of 12M HCl in water (73.6 mL, 883 mmol). The reaction was stirred at room temperature for 1 hour before evaporation under vacuum. The residue was azeotroped twice with isopropanol (100 mL) and triturated with warm isopropanol (100 mL). After cooling to RT, the precipitate was collected by filtration and dried under vacuum to give 11.8 g (55% yield) of the title compound as an off-white powder.

$^1$H NMR (500 MHz, DMSO-d6): δ [ppm] 8.90 (s, 3H), 8.02 (d, J=8.7 Hz, 1H), 7.87 (d, J=8.7 Hz, 1H), 7.58-7.14 (m, 2H), 4.71 (dt, J=12.4, 6.1 Hz, 1H), 2.71 (s, 3H), 1.58 (d, J=6.9 Hz, 3H).

Analytical HPLC: Column: Chiralpak AD-H 25 cm; Mobile phase: 90:10 Heptane: Ethanol +1% DEA; Flow rate: 1 ml/min; Detection: UV 254 nm.; Runtime: 60 mins; Rt=28.64 min; 100% ee.

Intermediate XVI: 1-[6-(Trifluoromethyl)pyridazin-3-yl]ethanone

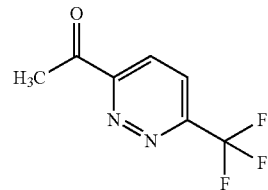

To a degassed solution of 3-chloro-6-(trifluoromethyl)pyridazine (17.26 g, 94.6 mmol) and tributyl(1-ethoxyethenyl)stannane (38.3 mL, 113.5 mmol) in DMF (400 mL) under $N_2$ was added $PdCl_2(PPh_3)_2$ (0.66 g, 0.95 mmol). The reaction was stirred at 100° C. for 3 h. The cooled reaction mixture was diluted with diethyl ether (800 mL) and treated with aqueous KF solution (27 g of KF in 800 mL water). The mixture was stirred vigorously for 1 h before filtering through celite. The filtrate was washed with saturated $NaHCO_3$ solution (400 mL) and brine (400 mL). The aqueous phase was re-extracted with EtOAc (500 mL) and the combined organics dried (over $MgSO_4$) and concentrated under reduced pressure. The crude material was suspended in THF (400 mL) and 2M HCl (400 mL) was added. The solution was stirred overnight at RT before being concentrated to remove THF and extracted with DCM (3×500 mL). The combined organics were dried (over $MgSO_4$) and concentrated under reduced pressure. The crude material was purified by dry flash silica chromatography (eluting with DCM) to give 11.2 g (61% yield) of the title compound as a white solid.

$^1$H NMR (500 MHz, CDCl$_3$): δ [ppm] 8.32 (d, J=8.7 Hz, 1H), 8.00 (d, J=8.7 Hz, 1H), 2.95 (s, 3H).

LCMS (Analytical Method A) Rt=1.01 min, MS (ESI-pos): m/z=190.9 (M+H)$^+$.

Intermediate XVII: (S)-2-Methyl-N-[(1R)-1-[6-(trifluoromethyl)pyridazin-3-yl]ethyl]propane-2-sulfinamide

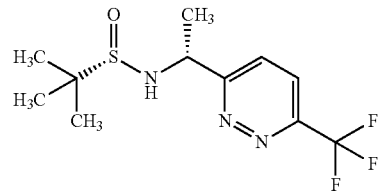 [SMILES: C[C@@H](N[S@@](=O)C(C)(C)C)c1ccc(C(F)(F)F)nn1]

To a stirred solution of 1-[6-(trifluoromethyl)pyridazin-3-yl]ethanone (1.27 g, 6.68 mmol) and titanium (IV) ethoxide (2.80 mL, 13.36 mmol) in dry THF (27.5 mL) was added (S)-2-t-butylsulfinamide (0.81 g, 6.68 mmol) and the resulting solution stirred at 80° C. for 60 mins. The reaction was cooled to below −70° C. and L-selectride (1M, 6.7 mL) added dropwise, keeping the internal temperature below −68° C. After the addition was complete, the reaction was stirred at this temperature for a further 60 minutes before being quenched by dropwise addition of methanol (1.4 mL), followed by EtOAc (40 mL) and water (40 mL). The organic layer was collected by decanting and the solid residue stirred with EtOAc (30 mL). The organic layer was collected by decantation and the process repeated three times. The combined organics were dried (over Na₂SO₄), filtered, diluted with heptane (20 mL) and evaporated onto silica (5 g). The material was purified by dry flash chromatography (eluting with TBME, followed by EtOAc then acetone) to give 1.09 g (51% yield) of the title compound as an off-white powder.

¹H NMR (500 MHz, CDCl₃) δ [ppm]=7.81 (d, J=8.7 Hz, 1H), 7.75 (d, J=8.7 Hz, 1H), 5.01 (p, J=6.7 Hz, 1H), 3.93 (d, J=5.8 Hz, 1H), 1.75 (d, J=6.9 Hz, 3H), 1.23 (s, 9H).

Intermediate XVIII: (1R)-1-[6-(Trifluoromethyl) pyridazin-3-yl]ethanamine hydrochloride (1:1)

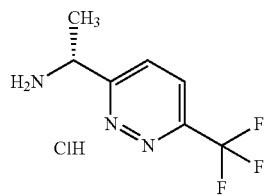

To a solution of (S)-2-methyl-N-[(1R)-1-[6-(trifluoromethyl)pyridazin-3-yl]ethyl]propane-2-sulfinamide (998 mg, 3.38 mmol) in methanol (12 mL) at 0° C. was added concentrated HCl (12 M, 2.8 mL, 883 mmol) and the reaction stirred for 1 h at RT. The reaction mixture was concentrated under reduced pressure and azeotroped with isopropanol (2×30 mL). The residue was triturated with dry acetone and the precipitate collected by vacuum filtration. The mother liqueur was concentrated and the residue triturated with EtOAc. The precipitate was collected by vacuum filtration and the batches combined to give 738 mg (89% yield) of the title compound as an off-white powder.

¹H NMR (500 MHz, DMSO-d6) δ [ppm]=8.95 (s, 3H), 8.42 (d, J=8.8 Hz, 1H), 8.27 (d, J=8.8 Hz, 1H), 4.88 (q, J=6.8 Hz, 1H), 1.63 (d, J=6.9 Hz, 3H).

Intermediate XIX: Tert-butyl [(2R)-1-(2-acetylhydrazinyl)-1-oxopropan-2-yl]carbamate

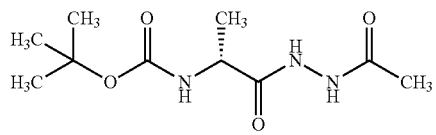

N-Boc-D-alanine (1 g, 5.29 mmol) was dissolved in DCM (15 mL). EEDQ (1.3 g, 5.29 mmol) was added in one portion, followed by acetic hydrazide (0.47 g, 6.34 mmol) and the solution stirred for 72 h. The reaction mixture was concentrated under reduced pressure and the resulting residue purified by Biotage Isolera™ chromatography (eluting with 20-100% acetone in heptane on a 25 g pre-packed KP—SiO₂ column) to give 917.7 mg (71% yield) of the title compound as a white solid.

¹H NMR (500 MHz, CDCl₃): δ [ppm] 8.95 (s, 1H), 8.29 (s, 1H), 5.06 (d, J=7.2 Hz, 1H), 4.30 (s, 1H), 2.06 (s, 3H), 1.45 (s, 9H), 1.40 (d, J=7.2 Hz, 3H).

Intermediate XX: Tert-butyl [(1R)-1-(5-methyl-1,3,4-thiadiazol-2-yl)ethyl]carbamate

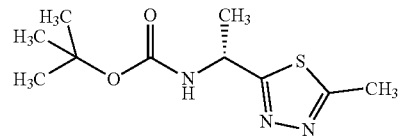 [SMILES: Cc1nnc([C@@H](C)NC(=O)OC(C)(C)C)s1]

Tert-butyl [(2R)-1-(2-acetylhydrazinyl)-1-oxopropan-2-yl]carbamate (917.7 mg, 3.74 mmol) was dissolved in dry THF (50 mL) and Lawesson's Reagent (1.66 g, 4.12 mmol) added in one portion. The resulting suspension was heated at reflux for 2 h and allowed to cool to RT overnight. The evaporated crude residue was part-purified by Biotage Isolera™ chromatography (eluting with 0-50% EtOAc in heptane on a 25 g pre-packed (solute Silica gel column) to give a yellow gum. Purification was performed by dissolving in EtOAc (20 mL) and stirring with decolourising charcoal (2×4 g) for 10 minutes. The filtrate was concentrated under reduced pressure to give 876.6 mg (96% yield) of the title compound as a clear gum that crystallised on standing.

¹H NMR (500 MHz, Chloroform-d): δ 5.32-5.04 (m, 2H), 2.75 (s, 3H), 1.65 (d, J=6.6 Hz, 3H), 1.45 (s, 9H).

LCMS (Analytical Method A) Rt=1.04 min, MS (ESI-pos): m/z=244.0 (M+H)⁺.

Intermediate XXI: (1R)-1-(5-Methyl-1,3,4-thiadiazol-2-yl)ethanamine hydrochloride

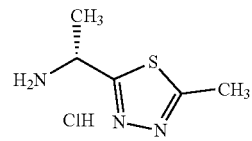

To a 0° C. solution of tert-butyl [(1R)-1-(5-methyl-1,3,4-thiadiazol-2-yl)ethyl]carbamate (876.6 mg, 3.6 mmol) in MeOH (12 mL) was added 4 M HCl in dioxane (9 mL, 36.0 mmol). After stirring for 4 h at RT the solvent was evaporated and the residue triturated from Et₂O. The precipitate was collected by filtration and dried in a vacuum oven to give 565 mg (81% yield) of the title compound as a white solid.

1H NMR (250 MHz, DMSO-d6): δ 7.21 (s, 3H), 4.77-4.63 (m, 1H), 2.71 (s, 3H), 1.51 (d, J=6.7 Hz, 3H).

Analytical HPLC: Column: YMC Amy-C (150 mm x 4.6 mm, 5 um); Mobile phase: Heptane/Ethanol (1:1) (DEA was added as a modifier); Flow rate: 1 ml/min; Detection: UV 254 nm.; Runtime: 10 mins; Rt=5.13 min; 92.1% ee.

Intermediate XXII: 2-(Trifluoromethyl)pyrimidine-5-carbaldehyde

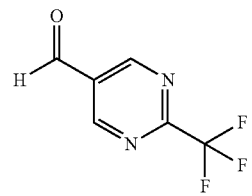 [SMILES: O=Cc1cnc(C(F)(F)F)nc1]

N-Methoxy-N-methyl-2-(trifluoromethyl)pyrimidine-5-carboxamide (1 g, 4.25 mmol) was dissolved in anhydrous THF (25 mL) under N₂ and cooled to −78° C. Lithium aluminium hydride (1M in THF, 2.66 mL, 6.34 mmol) was added dropwise and the reaction stirred for 30 mins. The reaction was quenched by addition of water (5 mL) and the reaction mixture allowed to warm to RT. EtOAc (10 mL) and 1M HCl (10 mL) were added and the mixture stirred for 30 mins. The aqueous layer was collected and extracted with EtOAc (10 mL). The combined organics were dried (over MgSO₄) and concentrated under reduced pressure to give 577.2 mg (77% yield) of the title compound as a colourless oil.

¹H NMR (250 MHz, CDCl₃): δ [ppm] 10.26 (s, 1H), 9.35 (s, 2H).

Intermediate XXIII: (R)-2-Methyl-N-{(E)-[2-(trifluoromethyl)pyrimidin-5-yl]methylidene}propane-2-sulfinamide

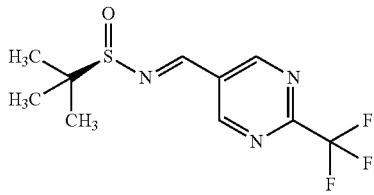 [SMILES: CC(C)(C)[S@@](=O)/N=C/c1cnc(C(F)(F)F)nc1]

To a solution of 2-(trifluoromethyl)pyrimidine-5-carbaldehyde (0.58 g, 3.28 mmol) in DCE (10 mL) was added (R)-(+)-2-methyl-2-propanesulfinamide (0.44 g, 3.60 mmol) and copper(II) sulfate (1.05 g, 6.55 mmol). The mixture was heated to 50° C. and stirred overnight. The reaction mixture was cooled and filtered through celite, washing with DCM. The filtrate was concentrated under reduced pressure to give 697.8 mg (76% yield) of the title compound as a brown gum.

¹H NMR (250 MHz, CDCl₃): δ 9.30 (s, 2H), 8.73 (s, 1H), 1.30 (s, 9H).

Intermediate XXIV: (R)-2-Methyl-N-{(1R)-1-[2-(trifluoromethyl)pyrimidin-5-yl]propyl}propane-2-sulfinamide

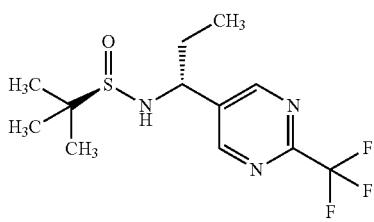 [SMILES: CC[C@@H](N[S@](=O)C(C)(C)C)c1cnc(C(F)(F)F)nc1]

To a solution of (R)-2-methyl-N-{(E)-[2-(trifluoromethyl)pyrimidin-5-yl]methylidene}propane-2-sulfinamide (697.8 mg, 2.5 mmol) in THF (10 mL) at −70° C. was added ethylmagnesium bromide (1M in THF, 2.75 mL, 2.75 mmol). The mixture was stirred at −70° C. for 15 mins. The mixture was quenched with saturated NH₄Cl and the reaction allowed to warm to RT. The solution was extracted with EtOAc (3×10 mL) and the combined organics dried (over MgSO₄) and concentrated under reduced pressure. The crude material was purified by Biotage Isolera™ chromatography (basic silica gel, eluting with 0-60% EtOAc in heptanes) to give 445.2 mg (52% yield) of the title compound as a yellow gum.

¹H NMR (500 MHz, CDCl₃): δ [ppm] 8.87 (s, 2H), 4.42 (q, J=6.2 Hz, 1H), 3.52 (d, J=5.4 Hz, 1H), 2.12 (tt, J=14.0, 7.3 Hz, 1H), 1.89 (dp, J=14.7, 7.4 Hz, 1H), 1.24 (s, 10H), 0.93 (t, J=7.4 Hz, 3H).

LCMS (Analytical Method A) Rt=1.19 min, MS (ESI-pos): m/z=310 (M+H)⁺.

Intermediate XXV: (1R)-1-[2-(Trifluoromethyl)pyrimidin-5-yl]propan-1-amine hydrochloride

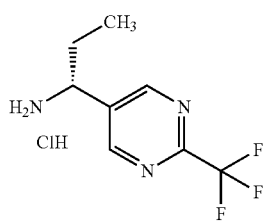

To a solution of (R)-2-methyl-N-{(1R)-1-[2-(trifluoromethyl)pyrimidin-5-yl]propyl}propane-2-sulfinamide (445.2 mg, 1.31 mmol) in diethyl ether (5 mL) was added hydrochloric acid (2M in Et₂O), 3.3 mL, 6.6 mmol) and the reaction stirred at RT for 1 h. The precipitate was collected by filtration and dried in the vacuum oven to give 283.0 mg (89% yield) of the title compound as a yellow powder.

¹H NMR (250 MHz, DMSO): δ [ppm] 9.26 (s, 2H), 8.81 (s, 3H), 4.45 (dd, J=8.5, 6.4 Hz, 1H), 2.19-1.89 (m, 2H), 0.85 (t, J=7.4 Hz, 3H).

Intermediate)XVI: (R)-2-Methyl-N-{(1S)-1-[2-(trifluoromethyl)pyrimidin-5-yl]ethyl}propane-2-sulfinamide

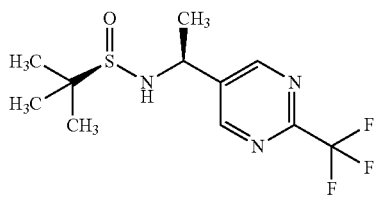 [SMILES: C[C@H](N[S@](=O)C(C)(C)C)c1cnc(C(F)(F)F)nc1]

To a stirred solution of 1-[2-(trifluoromethyl)pyrimidin-5-yl]ethanone (331 mg, 1.74 mmol) and titanium (IV) ethoxide (0.73 mL, 3.5 mmol) in THF (10 mL) was added (R)-2-t-butylsulfinamide (211 mg, 1.74 mmol) and the resulting solution stirred at 80° C. for 45 mins. The reaction mixture was cooled to −78° C. and L-selectride (1.74 mL, 1M solution in THF) added dropwise maintaining an internal temperature below −70° C. The reaction was stirred at −78° C. for a further 30 mins. The reaction was quenched by addition of MeOH (1 mL) and warmed to RT. Water (50 mL) then EtOAc (100 mL) was added and mixture filtered through glass fibre filter paper, washing with EtOAc (2×50 mL). The filtrate was separated and the aqueous layer extracted with EtOAc (2×50 mL). The combined organics combined were dried (over Na₂SO₄), filtered and concentrated under reduced pressure. The crude material was purified by Biotage Isolera™ chromatography (silica gel, eluting with 0-10% MeOH in EtOAc) followed by trituration from TBME to give 170 mg (28% yield) as an off-white powder.

¹H NMR (500 MHz, CDCl3) δ [ppm]=8.88 (s, 2H), 4.75 (qd, J=6.8, 3.6 Hz, 1H), 3.48-3.38 (m, 1H), 1.68-1.62 (m, 3H), 1.24 (s, 9H).

Intermediate XXVII: (1S)-1-[2-(Trifluoromethyl)pyrimidin-5-yl]ethanamine hydrochloride (1:1)

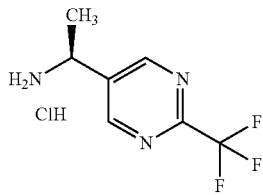

(R)-2-Methyl-N-[(1S)-1-[2-(trifluoromethyl)pyrimidin-5-yl]ethyl]propane-2-sulfinamide (0.17 g, 0.58 mmol) was dissolved in methanol (5 mL) and cooled to 0° C. Concentrated aqueous HCl (0.55 mL) was added dropwise and the reaction was stirred at room temperature for 1 hour before being concentrated under vacuum.

The yellow oil obtained was sonicated with diethyl ether to give a white solid that was collected by filtration to give 0.107 g (82% yield) of the title compound as a white solid.

¹H NMR (250 MHz, DMSO-d6) δ [ppm]=9.25 (s, 2H), 8.79 (s, 3H), 4.67 (q, J=6.9 Hz, 1H), 1.63 (d, J=6.9 Hz, 3H).

Analytical HPLC: Column: Chiralpak AD-H 25 cm; Mobile phase: 90:10 Heptane: Ethanol; Flow rate: 0.3 ml/min; Detection: UV 254 nm.; Runtime: 70 mins; Rt=37.79 min; 100% ee.

Intermediate XXVIII: (1R)-1-(2-Methylpyrimidin-5-yl)ethanamine

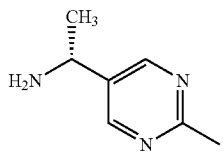

Intermediate XXVIII has been synthesized following the description in WO2008/130481.

Intermediate) XXXIX: 2-(Trifluoromethyl)pyrimidine-5-carbonitrile

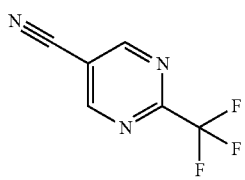 [SMILES: N#Cc1cnc(C(F)(F)F)nc1]

Intermediate II (1 g, 5.2 mmol), ammonium chloride (0.56, 10.4 mmol) and triethylamine (1.45 mL, 10.4 mmol) were suspended in 1,4-dioxane. T3P (50% in EtOAc, 7.3 mL, 12.5 mmol) was added and the reaction stirred at 100° C. for 24 h.

The reaction was re-treated with T3P (50% in EtOAc, 3.65 mL, 6.25 mmol) and heated for a further 6 h. The reaction was re-treated with ammonium chloride (0.56, 10.4 mmol) and triethylamine (1.45 mL, 10.4 mmol) and stirred at 100° C. for 18 h. The reaction mixture was diluted with water (20 mL) and extracted with EtOAc (3×20 mL). The combined organics were dried over MgSO4, filtered and concentrated under reduced pressure. The crude material was purified by Biotage Isolera™ chromatography (silica gel, eluting with heptane-EtOAc, 1:0 to 1:1) to afford 642 mg (71% yield) of the title compound as a colourless oil.

¹H NMR (250 MHz, Chloroform-d): δ [ppm] 9.19 (s, 2H). LCMS (Analytical Method A) Rt=0.96 min.

Intermediate XL: 1-[2-(Trifluoromethyl)pyrimidin-5-yl]methanamine hydrochloride

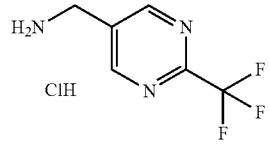 [SMILES: NCc1cnc(C(F)(F)F)nc1 ; Cl]

To a solution of Intermediate XXXIX (500 mg, 2.9 mmol) in ethanol (10 mL) was added 6 M hydrochloric acid (1 mL), Pd/C (10% wt. 50 mg, 10% by weight) and the resulting mixture stirred under an atmosphere of hydrogen at room temperature for 3 h. The catalyst was removed by filtration under reduced pressure and the solids washed with MeOH. The filtrate was concentrated under reduced pressure and the residue triturated with Et₂O to afford 381.3 mg (50% yield) of the title compound as an off-white powder.

¹H NMR (250 MHz, DMSO): δ [ppm] 9.22 (s, 2H), 8.71 (s, 3H), 4.22 (s, 2H), contains 19 wt % NH4Cl.

Intermediate XLI: 1-[6-(Trifluoromethyl)-3-pyridyl]ethanone

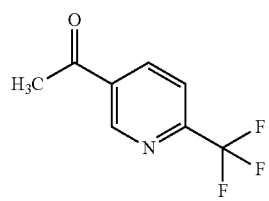

5-Bromo-2-(trifluoromethyl)pyridine (10.0 g, 44.3 mmol), water (40 mL), DMF (120 mL), potassium carbonate (12.2 g, 88.5 mmol), bis(triphenylphosphine)palladium(II) dichloride (621 mg, 2 mol %) and tributyl(1-ethoxyethenyl)stannane (19.2 g, 53.1 mmol) were stirred and heated to 110° C. under nitrogen for 1.5 h. The reaction mixture was cooled down, diluted with diethyl ether (120 mL) and KF (12.8 g in 50 mL of water) was added. The resulting reaction mixture was vigorously stirred for 1 h before being filtered through Celite®. The organic layer was then washed with saturated aqueous NaHCO3 followed by brine and was then dried over MgSO4, filtered and concentrated under reduced pressure.

The residue was taken up in THF (200 mL) and 2M HCl (60 mL) and the reaction was stirred at ambient temperature for 40 minutes. The organics were removed under reduced pressure and the aqueous layer was extracted with DCM (3×50 mL). The organic layers were combined, dried over MgSO$_4$, filtered and concentrated under reduced pressure. The crude material was purified by Biotage Isolera™ chromatography (silica gel, eluting with heptane-EtOAc, 1:0 to 10:1) to afford 4.90 g (56% yield) as a white crystalline solid.

$^1$H NMR (250 MHz, Chloroform-d): δ [ppm] 9.25 (d, J=1.3 Hz, 1H), 8.41 (dd, J=8.2, 1.6 Hz, 1H), 7.82 (d, J=8.2 Hz, 1H), 2.70 (s, 3H).

LCMS (Analytical Method A) Rt=1.15 min, MS (ESI-pos): m/z=190.0 (M+H)$^+$.

Intermediate XLII: 2-Methyl-N-[(1R)-1-[6-(trifluoromethyl)-3-pyridyl]ethyl]propane-2-sulfinamide

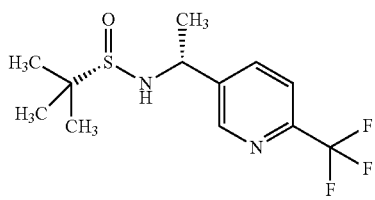 [SMILES: C[C@@H](N[S@@](=O)C(C)(C)C)c1ccc(C(F)(F)F)nc1]

To a stirred solution of Intermediate XLI (5.44 g, 28.8 mmol) and titanium(IV) ethoxide (18.6 mL, 57.5 mmol) in diethyl ether (120 mL) was added (S)-2-t-butylsulfinamide (3.85 g, 31.6 mmol) and the resulting solution was stirred at reflux under nitrogen for 3 h. The reaction mixture was cooled to room temperature and then to −78° C. and lithium tri-s-butylborohydride (1M in THF, 34.5 ml, 34.5 mmol) was added dropwise. The reaction was stirred at −78° C. for 30 minutes. The reaction was quenched by addition of brine (20 mL) and was allowed to warm up to room temperature prior to filtration through a plug of Celite® (washing with ethyl acetate). The filtrate was washed with brine (40 mL) and the aqueous layer was extracted once with ethyl acetate (40 mL). The organic layers were combined, dried over MgSO$_4$, filtered and concentrated under reduced pressure. The residue was triturated with Et$_2$O, and the solids collected by vacuum filtration to afford 5.15 g (61% yield) of the title compound as a white solid.

$^1$H NMR (500 MHz, Chloroform-d): δ [ppm] 8.71 (d, J=1.6, 1H), 7.83 (dd, J=8.1, 2.0, 1H), 7.66 (d, J=8.1, 1H), 4.70 (qd, J=6.7, 2.6, 1H), 3.44-3.39 (m, 1H), 1.58 (d, J=6.8, 3H), 1.21 (s, 9H).

LCMS (Analytical Method A) Rt=1.13 min, MS (ESI-pos): m/z=295.05 (M+H)$^+$.

Intermediate XLIII: (1R)-1-[6-(Trifluoromethyl)pyridin-3-yl]ethanamine hydrochloride

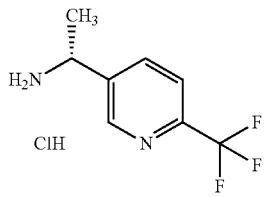

To a solution of Intermediate XLII (5.15 g, 17.5 mmol) in 2-propanol (20 mL) cooled to 0° C. in an ice bath, was added conc. HCl (5 mL, 60 mmol). The mixture was allowed to warm to room temperature and after 20 minutes methanol (5 mL) was added to aid solubility. The reaction was stirred for 3 hours. The solvent was removed under reduced pressure and the residue was triturated with diethyl ether and collected by vacuum filtration to afford 3.28 g (83% yield) of the title compound as a white powder.

$^1$H NMR (500 MHz, Chloroform-d): δ [ppm] 8.68 (s, 1H), 7.79 (dd, J=8.1, 2.1, 1H), 7.64 (d, J=8.1, 1H), 4.88 (s, 2H), 1.48 (d, J=6.7, 3H), 1.41 (s, 9H).

Intermediate XLIV: Tert-butyl {(1R)-1-[6-(trifluoromethyl)pyridin-3-yl]ethyl}carbamate

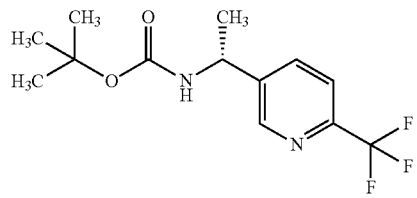 [SMILES: C[C@@H](NC(=O)OC(C)(C)C)c1ccc(C(F)(F)F)nc1]

To a solution of Intermediate XLIII in DCM (40 mL) was added di-tert-butyl dicarbonate (2.91 g, 13.3 mmol) and triethylamine (5.1 mL, 36.4 mmol). The reaction mixture was stirred at RT for 4 h before being washed with sat. NH$_4$Cl solution (40 mL). The aqueous phase was re-extracted with DCM (2×40 mL), and the combined organics were dried over MgSO$_4$, filtered and concentrated under reduced pressure to afford 3.7 g (100% yield) of the title compound as a white powder. 1H NMR (500 MHz, Chloroform-d): δ [ppm] 8.68 (s, 1H), 7.79 (dd, J=8.1, 2.1, 1H), 7.64 (d, J=8.1, 1H), 4.88 (s, 2H), 1.48 (d, J=6.7, 3H), 1.41 (s, 9H).

LCMS (Analytical Method A) Rt=1.37 min, MS (ESI-pos): m/z=290.95 (M+H)$^+$.

Intermediate XLVII: Ethyl (5-bromopyrimidin-2-yl)(difluoro)acetate

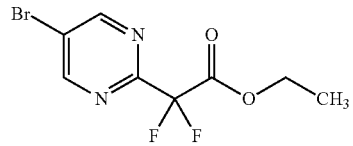

To a mixture of zinc powder (9.6 g, 147.4 mmol) in triglyme (100 mL) was added TMSBr (1.9 mL, 14.4 mmol) under N$_2$ and the reaction stirred at reflux for 90 minutes. The reaction was cooled to RT, ethyl bromo(difluoro)acetate (15.3 mL, 119.3 mmol) was added dropwise, and the mixture stirred for 30 minutes before being cooled to ~10° C. 5-Bromo-2-iodo-pyrimidine (10 g, 35.1 mmol) in DMA (100 mL) was added dropwise, then the reaction allowed to warm to RT. Copper(I) bromide (21.1 g, 147.4 mmol) was added portionwise over 40 minutes, then the reaction stirred at RT for a further 1 h. The reaction mixture was poured slowly into a cooled mixture of 10% NaCl (100 mL), 5M HCl (100 mL) and toluene (200 mL), and stirred for 30 minutes. The mixture was filtered, and the organic layer separated and dried over MgSO₄, filtered and concentrated under reduced pressure. The crude material was purified by Biotage Isolera™ chromatography (silica gel, eluting with heptane-EtOAc, 1:0 to 7:3) afford 10.34 g (82% yield, 78% purity) of the title compound as a colourless oil.

¹H NMR (500 MHz, Chloroform-d): δ [ppm] 8.92 (s, 2H), 4.41 (qd, J=7.1, 3.4 Hz, 2H), 1.34 (t, J=7.1 Hz, 3H).

LCMS (Analytical Method A) Rt=1.10 min, MS (ESI-pos): m/z=280.9/282.9 (M+H)⁺.

Intermediate XLVIII: Ethyl (5-acetylpyrimidin-2-yl)(difluoro)acetate

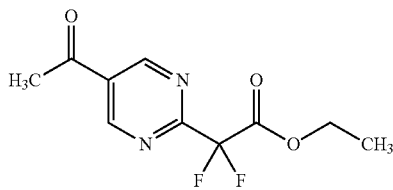 [SMILES: CCOC(=O)C(F)(F)c1ncc(C(C)=O)cn1]

To a degassed solution of Intermediate XLVII (4.5 g, 12.5 mmol) and tributyl(1-ethoxyethenyl)stannane (5.06 mL, 15.0 mmol) in dry DMF (45 mL) under N₂ was added PdCl₂(PPh₃)₂ (88 mg, 0.13 mmol). The reaction was stirred at 100° C. for 3 h. The reaction mixture was diluted with ether (90 mL) and treated with aqueous KF solution (7.26 mg of KF in 90 ml water). The mixture was stirred vigorously for 1 h before being filtered through glass fibre filter paper. The filtrate was washed with saturated NaHCO₃ solution followed by brine. The aqueous was extracted with EtOAc. The combined organics were dried over MgSO₄, filtered and concentrated under reduced pressure. The crude material was suspended in THF (90 mL) and 1M HCl (90 mL) was added. The solution was stirred for 2 h at RT, before being concentrated to remove THF, then extracted with DCM (3×90 mL). The combined organics were dried over MgSO₄, filtered and concentrated under reduced pressure. The crude material was purified by Biotage Isolera™ chromatography (silica gel, eluting with heptane-EtOAc, 3:2 to 1:1) to afford 1.37 g (45% yield) of the title compound as a colourless oil.

¹H NMR (500 MHz, Chloroform-d): δ [ppm] 9.32 (s, 2H), 4.41 (q, J=7.1 Hz, 2H), 2.70 (s, 3H), 1.35 (t, J=7.1 Hz, 3H).

LCMS (Analytical Method A) Rt=1.01 min, MS (ESI-pos): m/z=244.95 (M+H)⁺.

Intermediate XLIX: 1-[2-(Difluoromethyl)pyrimidin-5-yl]ethanone

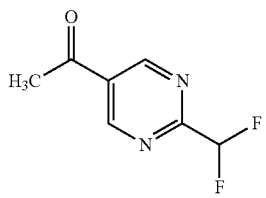

A mixture of Intermediate XLVIII (1.05 g, 4.3 mmol), KF (1.25 g, 21.5 mmol) and water (387.3 μL, 21.5 mmol) in DMF (20 mL) was stirred at 170° C. under N₂ for 3 h, then cooled to RT. Saturated NaHCO₃ solution (20 mL) was added and the mixture extracted with Et₂O (3×40 mL). The combined organics were dried over MgSO₄, filtered and concentrated under reduced pressure. The crude material was purified by Biotage Isolera™ chromatography (silica gel, eluting with heptane-EtOAc, 3:2) to afford 493 mg (67% yield) of the title compound as a yellow oil which crystallised on standing.

¹H NMR (250 MHz, Chloroform-d): δ [ppm] 9.33 (s, 2H), 6.71 (t, J=54.2 Hz, 1H), 2.70 (s, 3H).

LCMS (Analytical Method A) Rt=0.69 min, MS (ESI-pos): m/z=172.90 (M+H)⁺.

Intermediate L: (S)—N-[(1R)-1-[2-(Difluoromethyl)pyrimidin-5-yl]ethyl]-2-methylpropane-2-sulfinamide

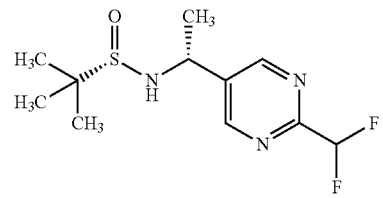 [SMILES: C[C@@H](N[S@@](=O)C(C)(C)C)c1cnc(C(F)F)nc1]

To a stirred solution of Intermediate XLIX (492 mg, 2.86 mmol) and titanium(IV) ethoxide (1.84 mL, 3.14 mmol) in Et₂O (20 mL) was added (S)-2-t-butylsulfinamide (381 mg, 3.14 mmol) and the resulting solution stirred at reflux for 2 h under nitrogen. The reaction mixture was cooled to RT and then to −78° C. and L-selectride (3.7 mL, 1M sol. in THF) was added dropwise. The reaction was stirred at −78° C. for a further 45 min, then the reaction was quenched by addition of brine (5 mL), before being allowed to warm to RT. The suspension was filtered through a plug of Celite®, washing with EtOAc. The filtrate was washed with brine (10 mL), and the aqueous layer re-extracted with EtOAc (2×10 mL). The combined organics were dried over MgSO₄, filtered and concentrated under reduced pressure. The residue was triturated with diethyl ether to afford 365.1 mg (45% yield) of the title compound as a white solid.

1H NMR (250 MHz, Chloroform-d): δ [ppm] 8.84 (s, 2H), 6.67 (t, J=54.5 Hz, 1H), 4.72 (qd, J=6.7, 3.1 Hz, 1H), 3.41 (d, J=2.6 Hz, 1H), 1.63 (d, J=6.8 Hz, 3H), 1.23 (s, 9H).

LCMS (Analytical Method A) Rt=0.90 min, MS (ESI-pos): m/z=277.95 (M+H)⁺.

Intermediate LI: (1R)-1-[2-(Difluoromethyl)pyrimidin-5-yl]ethanamine hydrochloride

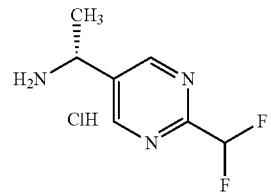

Intermediate L (982 mg, 3.54 mmol) was stirred in 1 M HCl in ether (35 mL) for 4 h to form a white precipitate. The material was collected by filtration and dried in a vacuum oven to afford 780 mg (90% yield) as a yellow glass.

¹H NMR (250 MHz, DMSO-d6): δ [ppm] 9.17 (s, 2H), 8.87 (s, 2H), 7.01 (t, J=53.9 Hz, 1H), 4.68-4.55 (m, 1H), 1.62 (d, J=6.9 Hz, 3H).

Intermediate LII: 1-[6-(Difluoromethyl)pyridin-3-yl]ethanone

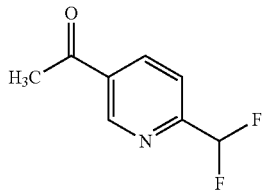

To a degassed solution of 5-bromo-2-(difluoromethyl)pyridine (1 g, 4.81 mmol) and tributyl(1-ethoxyethenyl)stannane (1.95 mL, 5.77 mmol) in DMF (20 mL) under N₂ was added PdCl₂(PPh₃)₂ (34 mg, 0.05 mmol). The reaction was stirred at 100° C. for 2.5 h. The reaction mixture was diluted with ether (40 mL) and treated with aqueous KF solution (1.4 g of KF in 40 mL water). The mixture was stirred vigorously for 1 h before being filtered through Celite®. The filtrate was diluted with ethyl acetate (50 mL), washed with saturated sodium bicarbonate solution, then brine, dried over MgSO₄, filtered and concentrated under reduced pressure. The crude material was suspended in THF (20 mL) and 2M HCl (20 mL) was added. The solution was stirred vigorously for 15 minutes at RT before being concentrated to remove THF, then extracted with DCM (3×50 mL). The combined organics were dried over MgSO₄, filtered and concentrated under reduced pressure. The crude material was purified by Biotage Isolera™ chromatography (silica gel, eluting with heptane-EtOAc, 1:0 to 4:1) to afford 730 mg (87% yield) of the title compound as a colourless oil.

¹H NMR (500 MHz, DMSO-d6): δ [ppm] 9.20 (d, J=1.6 Hz, 1H), 8.47 (dd, J=8.1, 2.1 Hz, 1H), 7.86 (d, J=8.1 Hz, 1H), 7.05 (t, J=54.6 Hz, 1H), 2.67 (s, 3H). LCMS (Analytical Method A) Rt=0.94 min, MS (ESIpos): m/z=171.9 (M+H)⁺.

Intermediate LIII: (S)—N-[(1R)-1-[6-(Difluoromethyl)pyridin-3-yl]ethyl]-2-methylpropane-2-sulfinamide

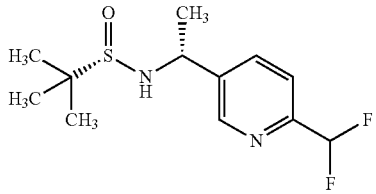 [SMILES: C[C@@H](N[S@@](=O)C(C)(C)C)c1ccc(C(F)F)nc1]

To a stirred solution of Intermediate LII (725 mg, 4.19 mmol) and titanium(IV) ethoxide (2.73 mL, 8.47 mmol) in diethyl ether (40 mL) was added (S)-2-t-butylsulfinamide (565 mg, 8.47 mmol) and the resulting solution stirred at reflux for 20 h under nitrogen. The reaction mixture was cooled to RT then further cooled to −78° C. and L-selectride (4.66 mL, 1M sol. in THF) was added dropwise. The reaction was stirred at −78° C. for a further 1 h then quenched by addition of brine (25 mL), before being allowed to warm to RT. The suspension was filtered through a plug of Celite®, washing with ethyl acetate. The filtrate was washed with brine (20 mL), and the aqueous layer re-extracted with EtOAc (30 mL). The combined organics were dried over MgSO₄, filtered and concentrated under reduced pressure. The crude yellow solid was triturated with diethyl ether to afford 525 mg (44% yield) of the title compound as a white solid.

¹H NMR (500 MHz, DMSO-d6): δ [ppm] 8.67 (d, J=1.7 Hz, 1H), 7.96 (dd, J=8.1, 2.0 Hz, 1H), 7.67 (d, J=8.1 Hz, 1H), 6.93 (t, J=55.0 Hz, 1H), 5.58 (d, J=5.6 Hz, 1H), 4.56 (m, 1H), 1.51 (d, J=6.8 Hz, 3H), 1.11 (s, 9H).

LCMS (Analytical Method A) Rt=0.99 min, MS (ESIpos): m/z=276.95 (M+H)⁺.

Intermediate LIV: (1R)-1-[6-(Difluoromethyl)pyridin-3-yl]ethanamine hydrochloride

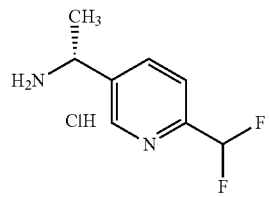

To a solution of Intermediate LIII (517 mg, 2.23 mmol) in methanol (2 mL) cooled to 0° C. in an ice bath, was added 5M HCl in 2-propanol (1.87 mL, 9.35 mmol). The mixture was allowed to warm to room temperature and was stirred for 1 hour. The solvent was removed under reduced pressure and the residue triturated in diethyl ether to afford 450 mg (97% yield) of the title compound as a white solid.

¹H NMR (500 MHz, DMSO-d6): δ [ppm] 8.84-8.79 (m, 1H), 8.65 (s, 3H), 8.18 (d, J=8.2 Hz, 1H), 7.79 (d, J=8.1 Hz, 1H), 6.98 (t, J=54.8 Hz, 1H), 4.57 (m, 1H), 1.57 (d, J=6.9 Hz, 3H).

Intermediate LV: Methyl (2R)-2-(tert-butoxycarbonylamino)propanoate

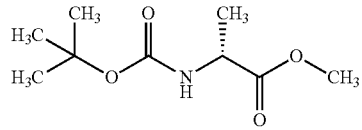

To a solution of D-alanine methyl ester hydrochloride (5 g, 35.8 mmol) and sodium hydrogen carbonate (9.0 g, 107 mmol) in water (100 mL) was added di-tert-butyl dicarbonate (11.7 g, 53.7 mmol) and the resulting solution was stirred at RT overnight. The reaction mixture was extracted with DCM (3×100 mL) and the combined organics were dried over MgSO₄, filtered and concentrated under reduced pressure. Crude NMR revealed large amounts of un-reacted di-tert-butyl dicarbonate, hence the material was taken up in DCM (50 mL) and treated with N,N-dimethyl ethylenediamine (5 mL), and stirred for 30 mins. The solution was washed with 1M HCl (50 mL), dried over MgSO₄, filtered and concentrated under reduced pressure to afford 5.35 g (73% yield) of the title compound as a colourless oil.

¹H NMR (500 MHz, Chloroform-d) δ 5.04 (s, 1H), 4.31 (m, 1H), 3.73 (s, 3H), 1.44 (s, 9H), 1.37 (d, J=7.2 Hz, 3H).

Intermediate LVI: Tert-butyl [(2R)-1-hydrazino-1-oxopropan-2-yl]carbamate

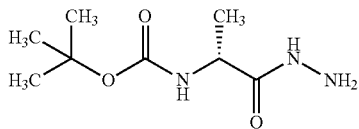

To a solution of Intermediate LV (5.35 g, 26.3 mmol) in ethanol (140 mL) was added hydrazine hydrate (19.8 mL) and the reaction was stirred at RT for 5 h. The reaction mixture was concentrated under reduced pressure and the residue was triturated with heptane. The resulting precipitate was collected by filtration and dried in the vacuum oven to afford 5.00 g (93% yield) of the title compound as a white crystalline powder.
¹H NMR (250 MHz, DMSO): δ [ppm] 8.96 (s, 1H), 6.81 (d, J=7.7 Hz, 1H), 4.17 (s, 2H), 4.03-3.81 (m, 1H), 1.36 (s, 9H), 1.14 (d, J=7.1 Hz, 3H).

Intermediate LVII: Tert-butyl {(2R)-1-oxo-1-[2-(trifluoroacetyl)hydrazino]propan-2-yl}carbamate

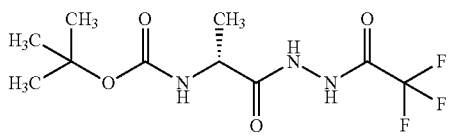 [SMILES: C[C@@H](NC(=O)OC(C)(C)C)C(=O)NNC(=O)C(F)(F)F]

To a solution of Intermediate LVI (3.96 g, 19.5 mmol) and DIPEA (4.07 mL, 23.4 mmol) in MeCN (100 mL) at −45° C. under N₂ was added trifluoroacetic anhydride (3.03 mL, 21.4 mmol). The reaction was gradually warmed to RT and further stirred for 30 mins. The solvent was removed by evaporation and the residue partitioned between H₂O (25 mL) and EtOAc (25 mL). The organic phase was separated and the aqueous phase was re-extracted with EtOAc (25 mL). The combined organic phases were washed with H₂O (30 mL), brine (30 mL), dried over MgSO₄ and evaporated, and the residue was purified by flash column chromatography (silica gel, eluting with heptane-EtOAc, 3:2) to afford 4.30 g (69% yield) of the title compound as a white solid foam.
¹H NMR (250 MHz, Chloroform-d): δ [ppm] 9.16 (s, 1H), 8.89 (s, 1H), 4.93 (s, 1H), 4.39-4.22 (m, 1H), 1.46 (s, 9H), 1.42 (d, J=7.1 Hz, 3H).
LCMS (Analytical Method A) Rt=0.90 min, MS (ESI-pos): m/z=321.95 (M+Na)⁺.

Intermediate LVIII: Tert-butyl {(1R)-1-[5-(trifluoromethyl)-1,3,4-thiadiazol-2-yl]ethyl}carbamate

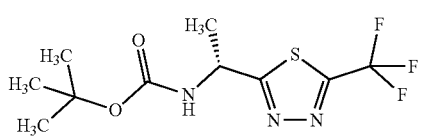

Intermediate LVII (1.25 g, 4.18 mmol) was dissolved in dry THF (50 mL) and Lawesson's Reagent (1.86 g, 4.6 mmol) was added in one portion. The resulting suspension was then heated to reflux for 2 h then concentrated under reduced pressure. The residue was purified by Biotage Isolera™ chromatography (eluting with 10-25% EtOAc in heptane on a pre-packed KP—SiO₂ column). The product containing fractions were combined and decolourised with ~5 g activated charcoal (stirring for 1 h). The mixture was filtered and concentrated under reduced pressure to give 0.63 g (51% yield) of the title compound as a white powder.
¹H NMR (250 MHz, Chloroform-d): δ [ppm] 5.30-5.21 (m, 1H), 5.17 (s, 1H), 1.74 (d, J=6.9 Hz, 3H), 1.46 (s, 9H).
LCMS (Analytical Method A) Rt=1.18 min, MS (ESI-pos): m/z=241.85 (M+H)⁺.

Intermediate LIX: (1R)-1-[5-(Trifluoromethyl)-1,3,4-thiadiazol-2-yl]ethanamine hydrochloride

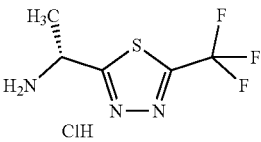

Intermediate LVIII (571 mg, 1.92 mmol) was stirred in hydrochloric acid, 4M in 1,4-dioxane (4.5 mL, 16 mmol) for 2 h. The solution was concentrated under reduced pressure, and the residue triturated with Et₂O to afford 384 mg (86% yield) of the title compound as a white powder.
¹H NMR (250 MHz, DMSO-d6): δ [ppm] 9.03 (s, 3H), 5.20 (q, J=6.8 Hz, 1H), 1.71 (d, J=6.8 Hz, 3H).

Example 1

3-(Cyclopropylmethoxy)-5-(5-methyl-1,3-thiazol-2-yl)-N-{(1R)-1-[2-(trifluoromethyl)pyrimidin-5-yl]ethyl}benzamide

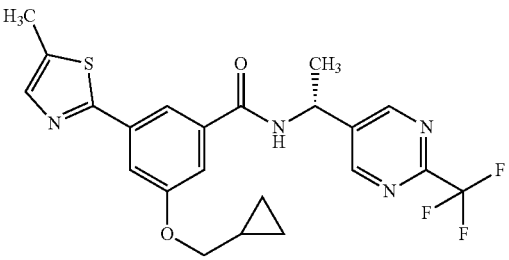 [SMILES: Cc1cnc(-c2cc(OCC3CC3)cc(C(=O)N[C@H](C)c3cnc(C(F)(F)F)nc3)c2)s1]

To a stirred solution of Intermediate 5A (46 mg, 0.16 mmol), Intermediate VI (40.1 mg, 0.176 mmol), DIPEA (0.111 mL, 0.64 mmol) and DMAP (3.9 mg, 0.032 mmol) in DCM (2 mL) was added HATU (73.0 mg, 0.192 mmol) at RT. After stirring for 2 h at RT, the reaction mixture was washed with water (3 mL) and the aqueous layer re-extracted with DCM (2×3 mL). The combined organics were dried (over MgSO₄) and evaporated at reduced pressure. Crude material was purified by crystallisation from acetonitrile to give 43.4 mg (59% yield) of the title compound as a white powder.

¹H NMR (500 MHz, Chloroform-d): δ [ppm] 8.93 (s, 2H), 7.84 (s, 1H), 7.55-7.53 (m, 1H), 7.53-7.51 (m, 1H), 7.42-7.35 (m, 1H), 6.62 (d, J=6.6 Hz, 1H), 5.36 (p, J=7.1 Hz, 1H), 3.91 (d, J=7.0 Hz, 2H), 2.53 (s, 3H), 1.71 (d, J=7.2 Hz, 3H), 1.36-1.22 (m, 1H), 0.71-0.63 (m, 2H), 0.37 (q, J=4.9 Hz, 2H).

Analytical LC-MS (Analytical Method D) 99% @ Rt=4.57, MH+=463.

Example 2

3-(Cyclopropylmethoxy)-N-[(6-methylpyridazin-3-yl)methyl]-5-(5-methyl-1,3-thiazol-2-yl)benzamide

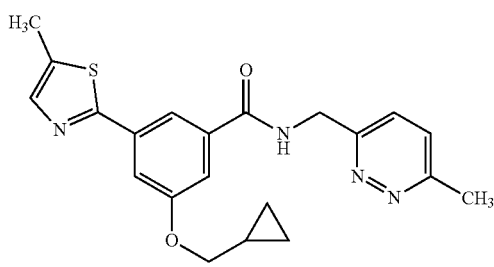 [SMILES: Cc1ccc(CNC(=O)c2cc(OCC3CC3)cc(-c3ncc(C)s3)c2)nn1]

In analogy to Example 1, reaction of 50 mg Intermediate 5A with 22 mg (0.18 mmol) 1-(6-methylpyridazin-3-yl)methanamine and subsequent purification by preparative HPLC (Method A) gave 38.2 mg (59% yield) of the title compound.

¹H NMR (500 MHz, Chloroform-d): δ [ppm] 7.92 (t, J=1.4 Hz, 1H), 7.65 (m, J=5.3 Hz, 1H), 7.62 (dd, J=2.4, 1.5 Hz, 1H), 7.54 (d+s, J=8.6 Hz, 2H), 7.47 (dd, J=2.3, 1.5 Hz, 1H), 7.40 (d, J=8.6 Hz, 1H), 4.95 (d, J=5.3 Hz, 2H), 3.95 (d, J=6.9 Hz, 2H), 2.76 (s, 3H), 2.54 (d, J=1.1 Hz, 3H), 1.36-1.28 (m, 1H), 0.72-0.66 (m, 2H), 0.40 (q, J=4.7 Hz, 2H).

Analytical LC-MS (Analytical Method F): 98.5% @ Rt=2.90, MH+=395.

Example 3

3—(Cyclopropylmethoxy)-N-[(5-methylpyrazin-2-yl)methyl]-5-(5-methyl-1,3-thiazol-2-yl)benzamide

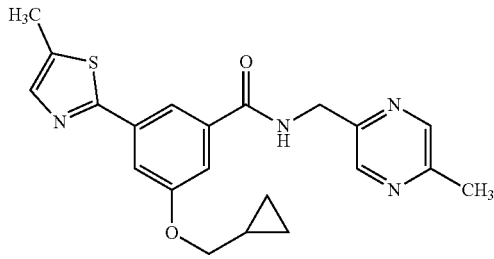 [SMILES: Cc1cnc(CNC(=O)c2cc(OCC3CC3)cc(-c3ncc(C)s3)c2)cn1]

To a suspension of sodium 3-(cyclopropylmethoxy)-5-(5-methyl-1,3-thiazol-2-yl)benzoate (50 mg, 0.16 mmol), 1-(5-methylpyrazin-2-yl)methanamine (22 mg, 0.18 mmol) and DMAP (4 mg, 0.03 mmol) in DCM (1 mL) was added DIPEA (84 µL, 0.48 mmol) and HATU (73 mg, 0.19 mmol) and the reaction stirred for 18 h. The reaction mixture was diluted with DCM (4 mL) and washed with saturated aq. NaHCO₃ (2×2 mL), brine (2 mL), dried (over MgSO₄) and concentrated in vacuo. The crude material was purified by preparative HPLC (Method A) to give 36 mg (55% yield) of the title compound.

¹H NMR (500 MHz, CDCl₃): δ [ppm]=8.57-8.51 (m, 1H), 8.40 (s, 1H), 7.87 (d, J=1.3 Hz, 1H), 7.58-7.55 (m, 1H), 7.50 (d, J=1.1 Hz, 1H), 7.44-7.41 (m, 1H), 7.29 (s, 1H), 4.76 (d, J=5.2 Hz, 2H), 3.91 (d, J=6.9 Hz, 2H), 2.57 (s, 3H), 2.51 (d, J=0.9 Hz, 3H), 1.29 (dqt, J=9.5, 7.1, 4.8 Hz, 1H), 0.69-0.64 (m, 2H), 0.37 (q, J=4.8 Hz, 2H).

LCMS (Analytical Method F) Rt=3.19 min, MS (ESIpos) m/z=395 (M+H)⁺.

Example 4

3-(Cyclopropylmethoxy)-N-[(1R)-1-(5-methylpyrazin-2-yl)ethyl]-5-(5-methyl-1,3-thiazol-2-yl)benzamide

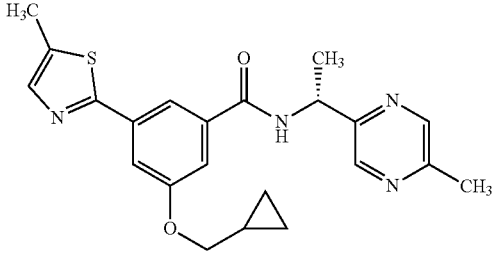 [SMILES: Cc1cnc([C@@H](C)NC(=O)c2cc(OCC3CC3)cc(-c3ncc(C)s3)c2)cn1]

To a suspension of sodium 3-(cyclopropylmethoxy)-5-(5-methyl-1,3-thiazol-2-yl)benzoate (50 mg, 0.16 mmol), (1R)-1-(5-methylpyrazin-2-yl)ethanamine hydrochloride (30 mg, 0.18 mmol) and DMAP (4 mg, 0.03 mmol) in DCM (1 mL) was added DIPEA (84 µL, 0.48 mmol) and HATU (73 mg, 0.19 mmol) and the reaction stirred for 18 h. The reaction mixture was diluted with DCM (4 mL) and washed with saturated aq. NaHCO₃ (2×2 mL), brine (2 mL), dried (over MgSO₄) and concentrated in vacuo. The crude material was purified by preparative HPLC (Method A) to give 43 mg (63% yield) of the title compound.

¹H NMR (500 MHz, CDCl₃): δ [ppm]=8.52 (d, J=1.3 Hz, 1H), 8.40 (s, 1H), 7.86 (d, J=1.3 Hz, 1H), 7.58-7.53 (m, 1H), 7.50 (d, J=1.1 Hz, 1H), 7.43-7.38 (m, 1H), 7.31 (d, J=7.5 Hz, 1H), 5.42 (p, J=6.9 Hz, 1H), 3.91 (d, J=7.0 Hz, 2H), 2.56 (s, 3H), 2.51 (d, J=0.9 Hz, 3H), 1.59 (d, J=6.8 Hz, 3H), 1.34-1.24 (m, 1H), 0.68-0.63 (m, 2H), 0.36 (q, J=4.8 Hz, 2H).

LCMS (Analytical Method F) Rt=3.42 min, MS (ESIpos) m/z=409 (M+H)⁺.

Example 5

N-[1-(3-Chloro-5-fluoropyridin-2-yl)ethyl]-3-(cyclopropylmethoxy)-5-(5-methyl-1,3-thiazol-2-yl)benzamide

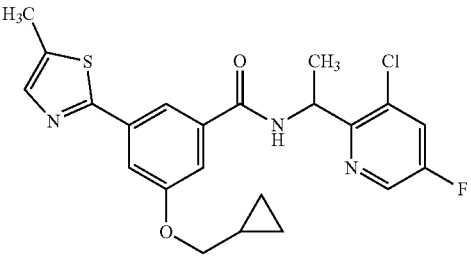 [SMILES: Cc1cnc(-c2cc(OCC3CC3)cc(C(=O)NC(C)c3ncc(F)cc3Cl)c2)s1]

To a suspension of sodium 3-(cyclopropylmethoxy)-5-(5-methyl-1,3-thiazol-2-yl)benzoate (47.5 mg, 0.15 mmol), 1-(3-chloro-5-fluoropyridin-2-yl)ethanamine hydrochloride (35 mg, 0.17 mmol) and DMAP (4 mg, 0.03 mmol) in DCM (1 mL) was added DIPEA (80 µL, 0.46 mmol) and HATU (70 mg, 0.18 mmol) and the reaction stirred for 2.5 h. The reaction mixture was diluted with DCM (4 mL) and washed with saturated aq. NaHCO₃ (2×2 mL), brine (2 mL), dried (over MgSO₄) and concentrated in vacuo. The crude material was purified by preparative HPLC (Method A) then triturated with diethylether to give 31 mg (59% yield) of the title compound as a mixture of two enantiomers.

$^1$H NMR (500 MHz, CDCl₃): δ [ppm]=8.39 (d, J=2.5 Hz, 1H), 7.90 (t, J=1.4 Hz, 1H), 7.64 (d, J=7.6 Hz, 1H), 7.58 (dd, J=2.4, 1.5 Hz, 1H), 7.54-7.49 (m, 2H), 7.44 (dd, J=2.4, 1.5 Hz, 1H), 5.76 (p, J=6.6 Hz, 1H), 3.93 (d, J=7.0 Hz, 2H), 2.53 (d, J=1.1 Hz, 3H), 1.53 (d, J=5.6 Hz, 3H), 1.30 (td, J=7.9, 4.0 Hz, 1H), 0.71-0.64 (m, 2H), 0.38 (q, J=4.8 Hz, 2H).

LCMS (Analytical Method F) Rt=4.18 min, MS (ESIpos) m/z=446 (M+H)⁺.

Example 6

N-[1-(5-Chloro-3-fluoropyridin-2-yl)ethyl]-3-(cyclopropylmethoxy)-5-(5-methyl-1,3-thiazol-2-yl)benzamide

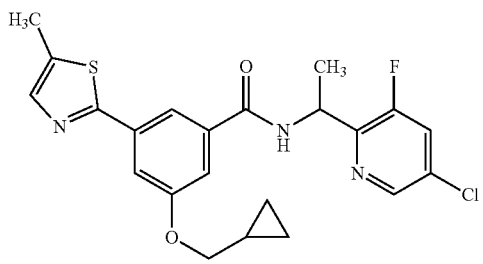 [SMILES: Cc1cnc(-c2cc(OCC3CC3)cc(C(=O)NC(C)c3ncc(Cl)cc3F)c2)s1]

To a suspension of sodium 3-(cyclopropylmethoxy)-5-(5-methyl-1,3-thiazol-2-yl)benzoate (47.5 mg, 0.15 mmol), 1-(5-chloro-3-fluoropyridin-2-yl)ethanamine hydrochloride (35 mg, 0.17 mmol) and DMAP (4 mg, 0.03 mmol) in DCM (1 mL) was added DIPEA (80 µL, 0.46 mmol) and HATU (70 mg, 0.17 mmol) and the reaction stirred for 2.5 h. The reaction mixture was diluted with DCM (4 mL) and washed with saturated aq. NaHCO₃ (2×2 mL), brine (2 mL), dried (over MgSO₄) and concentrated in vacuo. The crude material was purified by preparative HPLC (Method A) then triturated with acetonitrile to give 30 mg (43% yield) of the title compound as a mixture of two enantiomers.

$^1$H NMR (500 MHz, CDCl₃): δ [ppm]=8.38 (d, J=1.8 Hz, 1H), 7.89 (t, J=1.4 Hz, 1H), 7.58 (dd, J=2.4, 1.5 Hz, 1H), 7.57-7.51 (m, 2H), 7.47 (dd, J=8.9, 2.0 Hz, 1H), 7.43 (dd, J=2.4, 1.5 Hz, 1H), 5.70-5.62 (m, 1H), 3.93 (d, J=7.0 Hz, 2H), 2.53 (d, J=1.1 Hz, 3H), 1.55 (d, J=6.7 Hz, 3H), 1.31 (ddd, J=12.8, 8.0, 5.3 Hz, 1H), 0.70-0.64 (m, 2H), 0.38 (q, J=4.7 Hz, 2H).

LCMS (Analytical Method F) Rt=4.19 min, MS (ESIpos) m/z=446 (M+H)⁺.

Example 7

3-(Cyclopropylmethoxy)-N-[(1R)-1-(5-methyl-1,3,4-thiadiazol-2-yl)ethyl]-5-(5-methyl-1,3-thiazol-2-yl)benzamide

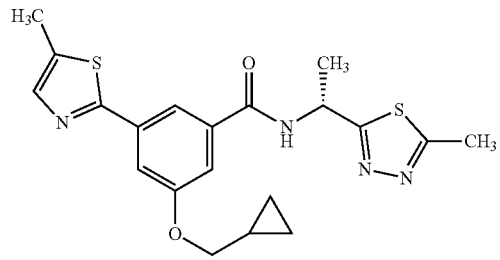 [SMILES: Cc1cnc(-c2cc(OCC3CC3)cc(C(=O)N[C@H](C)c3nnc(C)s3)c2)s1]

To a solution of 3-(cyclopropylmethoxy)-5-(5-methyl-1,3-thiazol-2-yl)benzoic acid (58 mg, 0.2 mmol), (1R)-1-(5-methyl-1,3,4-thiadiazol-2-yl)ethanamine hydrochloride (43 mg, 0.24 mmol) and DIPEA (0.174 mL, 1.0 mmol) in DCM (2 mL) was added T3P (0.23 mL, 0.4 mmol, 50% solution in EtOAc) and the reaction mixture stirred at RT for 2 h. The reaction mixture washed with 2M NaOH (2 mL) and the aqueous layer further extracted with DCM (2×2 mL). The combined organics were dried (over MgSO₄) and concentrated under reduced pressure. The material was triturated from Et₂O to give 46.8 mg (54% yield) of the title compound as a white powder.

$^1$H NMR (500 MHz, CDCl₃): δ [ppm]=7.84 (t, J=1.4 Hz, 1H), 7.57 (dd, J=2.4, 1.5 Hz, 1H), 7.51 (d, J=1.2 Hz, 1H), 7.41 (dd, J=2.3, 1.6 Hz, 1H), 6.99 (d, J=7.5 Hz, 1H), 5.68 (p, J=7.0 Hz, 1H), 3.92 (d, J=6.9 Hz, 2H), 2.76 (s, 3H), 2.52 (d, J=1.1 Hz, 3H), 1.79 (d, J=6.9 Hz, 3H), 1.35-1.24 (m, 1H), 0.70-0.63 (m, 2H), 0.37 (q, J=4.7 Hz, 2H).

LCMS (Analytical Method F) Rt=3.33 min, MS (ESIpos): m/z=415 (M+H)⁺.

Example 8

3-(Cyclopropylmethoxy)-N-[(1R)-1-(6-methylpyridazin-3-yl)ethyl]-5-(5-methyl-1,3-thiazol-2-yl)benzamide

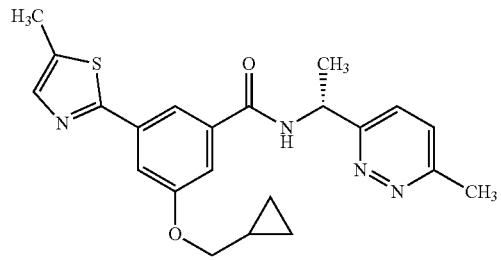 [SMILES: Cc1ccc([C@@H](C)NC(=O)c2cc(OCC3CC3)cc(-c3ncc(C)s3)c2)nn1]

To a solution of 3-(cyclopropylmethoxy)-5-(5-methyl-1,3-thiazol-2-yl)benzoic acid (46 mg, 0.16 mmol), (1R)-1-(6-methylpyridazin-3-yl)ethanamine hydrochloride (30.6 mg, 0.18 mmol), DIPEA (0.11 mL, 0.64 mmol) and DMAP (3.9 mg, 0.032 mmol) in DCM (2 mL) was added HATU (73.0 mg, 0.19 mmol) and the reaction stirred for 2 h at RT. The reaction mixture was diluted with water (3 mL) and the aqueous layer re-extracted with DCM (2×3 mL). The combined organics were dried (over MgSO₄) and concentrated under reduced pressure. The crude material was purified preparative HPLC (Method A) then triturated from Et₂O to give 29.7 mg (45% yield) of the title compound as a white powder.

¹H NMR (500 MHz, CDCl₃): δ [ppm]=7.90-7.86 (m, 1H), 7.73 (d, J=7.4 Hz, 1H), 7.60-7.57 (m, 1H), 7.51 (s, 1H), 7.44-7.42 (m, 1H), 7.40 (d, J=8.5 Hz, 1H), 7.33 (d, J=8.5 Hz, 1H), 5.46 (p, J=7.2 Hz, 1H), 3.92 (d, J=6.9 Hz, 2H), 2.73 (s, 3H), 2.52 (s, 3H), 1.68 (d, J=6.8 Hz, 3H), 1.35-1.23 (m, 1H), 0.71-0.61 (m, 2H), 0.37 (q, J=4.8 Hz, 2H).

LCMS (Analytical Method D) Rt=3.96 min, MS (ESIpos) m/z=409 (M+H)⁺.

Example 9

3-(Cyclopropylmethoxy)-5-(5-methyl-1,3-thiazol-2-yl)-N-{(1R)-1-[6-(trifluoromethyl)pyridazin-3-yl]ethyl}benzamide

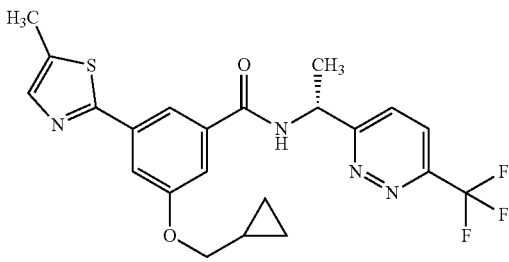 [SMILES: Cc1cnc(-c2cc(OCC3CC3)cc(C(=O)N[C@H](C)c3ccc(C(F)(F)F)nn3)c2)s1]

To a solution of 3-(cyclopropylmethoxy)-5-(5-methyl-1,3-thiazol-2-yl)benzoic acid (60 mg, 0.21 mmol), (1R)-1-[6-(trifluoromethyl)pyridazin-3-yl]ethanamine hydrochloride (51 mg, 0.22 mmol) and DIPEA (144 µL, 0.83 mmol) in DCM (1 mL) was added HATU (95 mg, 0.25 mmol) and the reaction mixture stirred at RT for 2 h. The mixture was diluted with DCM (1 mL) and washed with water (2×2 mL). The aqueous phase was re-extracted with DCM (2 mL) and the combined organics dried (over Na₂SO₄) and concentrated in vacuo. The crude product was purified by preparative HPLC (Method A) to give 61.2 mg (64% yield) of the title compound as a white powder.

¹H NMR (500 MHz, CDCl₃): δ [ppm]=7.88 (s, 1H), 7.82 (d, J=8.7 Hz, 1H), 7.74 (d, J=8.7 Hz, 1H), 7.59-7.54 (m, 1H), 7.51 (d, J=1.1 Hz, 1H), 7.48-7.38 (m, 2H), 5.60 (p, J=7.0 Hz, 1H), 3.91 (d, J=6.9 Hz, 2H), 2.52 (d, J=0.9 Hz, 3H), 2.00 (s, 1H), 1.76 (d, J=7.0 Hz, 3H), 1.29 (dtd, J=14.7, 7.4, 6.8, 4.7 Hz, 1H), 0.70-0.61 (m, 2H), 0.37 (q, J=4.8 Hz, 2H).

LCMS (Analytical Method F) Rt=3.84 min, MS (ESIpos) m/z=463 (M+H)⁺.

Example 10

3—(Cyclopropylmethoxy)-N-[(1R)-1-(2-methylpyrimidin-5-yl)ethyl]-5-(5-methyl-1,3-thiazol-2-yl)benzamide

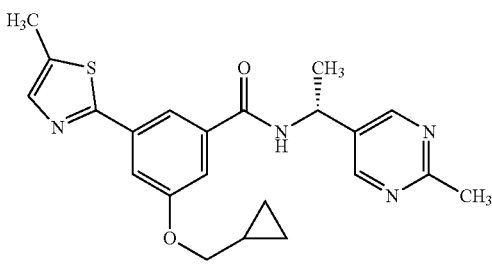 [SMILES: Cc1ncc([C@@H](C)NC(=O)c2cc(OCC3CC3)cc(-c3ncc(C)s3)c2)cn1]

To a suspension of sodium 3-(cyclopropylmethoxy)-5-(5-methyl-1,3-thiazol-2-yl)benzoate (50 mg, 0.16 mmol), (1R)-1-(2-methylpyrimidin-5-yl)ethanamine (24 mg, 0.18 mmol) and DMAP (4 mg, 0.03 mmol) in DCM (1 mL) was added DIPEA (85 µL, 0.48 mmol) and HATU (73 mg, 0.19 mmol) and the reaction stirred for 2 h. The reaction mixture was diluted with DCM (4 mL), washed with saturated aq. NaHCO₃ (2×2 mL), brine (2 mL) and the organic phase dried (over MgSO₄) and concentrated in vacuo to give 37.4 mg (56% yield) of the title compound. ¹H NMR (500 MHz, CDCl₃) δ [ppm]=8.69 (s, 2H), 7.85 (s, 1H), 7.56-7.48 (m, 2H), 7.39 (dd, J=2.3, 1.6 Hz, 1H), 6.53 (d, J=6.8 Hz, 1H), 5.30 (p, J=7.2 Hz, 1H), 3.91 (d, J=6.9 Hz, 2H), 2.73 (s, 3H), 2.53 (d, J=1.1 Hz, 3H), 1.66 (d, J=7.1 Hz, 3H), 1.34-1.24 (m, 1H), 0.69-0.62 (m, 2H), 0.39-0.33 (m, 2H).

LCMS (Analytical Method F) Rt=3.17 min, MS (ESIpos) m/z=409 (M+H)⁺.

Example 11

3-(5-Methyl-1,3-thiazol-2-yl)-5-[(3R)-tetrahydrofuran-3-yloxy]-N-{(1R)-1-[2-(trifluoromethyl)pyrimidin-5-yl]ethyl}benzamide

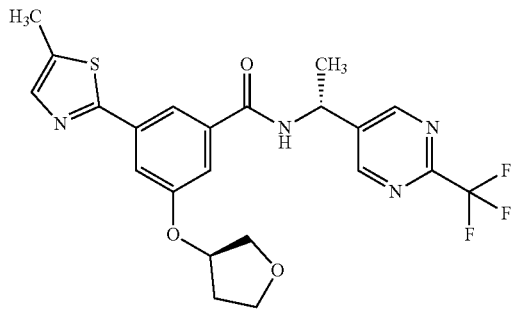

To a solution of 3-(5-methyl-1,3-thiazol-2-yl)-5-[(3R)-tetrahydrofuran-3-yloxy]benzoic acid, i.e. Intermediate 5B, (6.8 g, 22.3 mmol), Intermediate VI (6.8 g, 26.7 mmol) and DIPEA (15.5 mL, 89.1 mmol) in DCM (100 mL) was added T3P (19.5 mL, 33.4 mmol, 50% in EtOAc) and the reaction mixture stirred at RT for 2 h. The mixture was washed with 1M NaOH (100 mL) and the aqueous layer re-extracted with DCM (2×50 mL). The combined organics were dried (over MgSO₄) and concentrated under reduced pressure. The residue was triturated with Et₂O to give 7.51 g (70% yield) of the title compound as a white powder.

¹H NMR (500 MHz, CDCl₃): δ [ppm]=8.93 (s, 2H), 7.85 (t, J=1.4 Hz, 1H), 7.53-7.52 (m, 1H), 7.51 (dd, J=2.4, 1.5 Hz, 1H), 7.36 (t, J=2.4, 1.6 Hz, 1H), 6.64 (d, J=6.5 Hz, 1H), 5.36 (p, J=7.1 Hz, 1H), 5.08-5.03 (m, 1H), 4.05-3.97 (m, 3H), 3.91 (td, J=8.4, 4.3 Hz, 1H), 2.54 (d, J=1.1 Hz, 3H), 2.27 (dtd, J=14.4, 8.4, 6.1 Hz, 1H), 2.20-2.12 (m, 1H), 1.72 (d, J=7.2 Hz, 3H).

LCMS (Analytical Method D) Rt=4.16 min, MS (ESIpos) m/z=479 (M+H)⁺.

Example 12

N-[(5-methylpyrazin-2-yl)methyl]-3-(5-methyl-1,3-thiazol-2-yl)-5-[(3R)-tetrahydrofuran-3-yloxy]benzamide

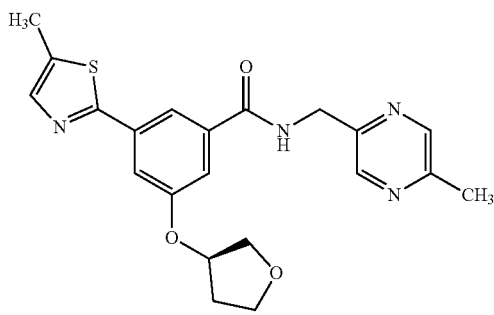 [SMILES: Cc1cnc(CNC(=O)c2cc(O[C@@H]3CCOC3)cc(-c3ncc(C)s3)c2)cn1]

To a solution of 3-(5-methyl-1,3-thiazol-2-yl)-5-[(3R)-tetrahydrofuran-3-yloxy]benzoic acid (40 mg, 0.13 mmol), 1-(5-methylpyrazin-2-yl)methanamine dihydrochloride (30.8 mg, 0.16 mmol) and DIPEA (91 µL, 0.52 mmol) in DCM (1 mL) was added HATU (74.7 mg, 0.20 mmol) and the reaction mixture stirred for 2 h at RT. The mixture was diluted with DCM (1 mL), washed with water (2×1 mL), dried (over a hydrophobic frit) and concentrated in vacuo to give yellow oil. The crude material was purified by preparative HPLC (Method A) to give 35.1 mg (65% yield) of the title compound as a yellow gum.

$^1$H NMR (500 MHz, CDCl$_3$): δ [ppm]=8.58 (d, J=1.1 Hz, 1H), 8.44 (s, 1H), 7.94 (s, 1H), 7.58 (dd, J=2.3, 1.5 Hz, 1H), 7.54 (d, J=1.2 Hz, 1H), 7.44 (dd, J=2.2, 1.5 Hz, 1H), 7.33 (s, 1H), 5.10 (ddt, J=5.9, 4.0, 2.0 Hz, 1H), 4.79 (d, J=5.1 Hz, 2H), 4.11-3.98 (m, 3H), 3.94 (td, J=8.4, 4.3 Hz, 1H), 2.60 (s, 3H), 2.55 (d, J=1.1 Hz, 3H), 2.36-2.26 (m, 1H), 2.24-2.14 (m, 1H).

LCMS (Analytical Method D) Rt=3.66 min, MS (ESIpos) m/z=411 (M+H)$^+$.

Example 13

N-[1-(3-chloro-5-fluoropyridin-2-yl)ethyl]-3-(5-methyl-1,3-thiazol-2-yl)-5-[(3R)-tetrahydrofuran-3-yloxy]benzamide

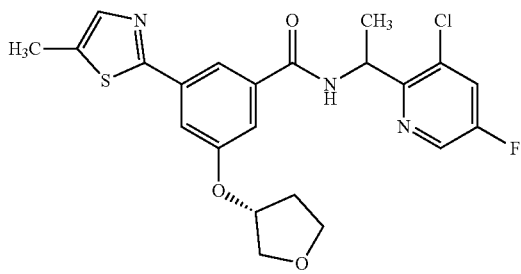 [SMILES: Cc1cnc(-c2cc(O[C@@H]3CCOC3)cc(C(=O)NC(C)c3ncc(F)cc3Cl)c2)s1]

Intermediate 5B (70 mg, 0.23 mmol), (+/-) 1-(3-chloro-5-fluoropyridin-2-yl)ethanamine (44 mg, 0.25 mmol), DIPEA (119 mg, 0.92 mmol) and HATU (123 mg, 0.32 mmol) were dissolved in DMF (3.1 mL). The reaction mixture was stirred at RT until complete conversion and evaporated to dryness. Crude material was purified by preparative HPLC (method 1, rt: 1.27 min) to afford the title compound 65 mg (60% yield) as a mixture of two diastereoisomers.

$^1$H NMR (400 MHz, DMSO-d$_6$) δ [ppm] 1.49 (d, J=6.84 Hz, 3H) 1.95-2.05 (m, 1H) 2.25 (d, J=7.86 Hz, 1H) 3.73-3.95 (m, 4H) 5.15-5.24 (m, 1H) 5.54 (t, J=6.97 Hz, 1H) 7.51 (d, J=1.52 Hz, 2H) 7.64 (d, J=1.27 Hz, 1H) 7.93 (q, J=1.27 Hz, 1H) 8.09 (dd, J=8.49, 2.66 Hz, 1H) 8.58 (d, J=2.53 Hz, 1H) 9.08 (d, J=7.35 Hz, 1H).

Example 14

N-[1-(5-chloro-3-fluoropyridin-2-yl)ethyl]-3-(5-methyl-1,3-thiazol-2-yl)-5-[(3R)-tetrahydrofuran-3-yloxy]benzamide

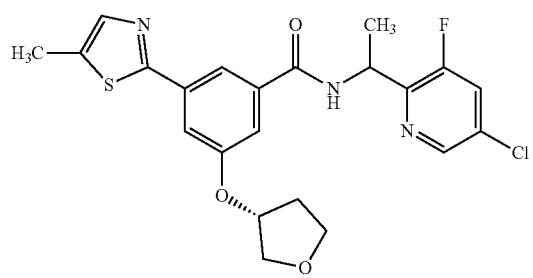 [SMILES: Cc1cnc(-c2cc(O[C@@H]3CCOC3)cc(C(=O)NC(C)c3ncc(Cl)cc3F)c2)s1]

Intermediate 58 (74 mg, 0.24 mmol), (+/-) 1-(5-chloro-3-fluoropyridin-2-yl)ethanamine (47 mg, 0.27 mmol), DIPEA (126 mg, 0.97 mmol) and HATU (130 mg, 0.34 mmol) were dissolved in DMF (3.2 mL). The reaction mixture was stirred at RT until complete conversion and evaporated to dryness. Crude material was purified by preparative HPLC (method 1, rt: 1.27 min) to afford the title compound 65 mg (57% yield) as a mixture of two diastereoisomers.

$^1$H NMR (400 MHz, DMSO-d$_6$) δ [ppm] 1.51 (d, J=7.10 Hz, 3H) 1.94-2.05 (m, 1H) 2.19-2.31 (m, 1H) 3.73-3.95 (m, 4H) 5.15-5.24 (m, 1H) 5.42 (t, J=6.97 Hz, 1H) 7.47-7.54 (m, 2H) 7.64 (d, J=1.27 Hz, 1H) 7.90-7.96 (m, 1H) 8.06 (dd, J=10.01, 1.90 Hz, 1H) 8.49 (d, J=1.77 Hz, 1H) 9.10 (d, J=7.10 Hz, 1H).

Example 15

N-[(1R)-1-(5-chloropyridin-2-yl)ethyl]-3-(5-methyl-1,3-thiazol-2-yl)-5-[(3R)-tetrahydrofuran-3-yloxy]benzamide

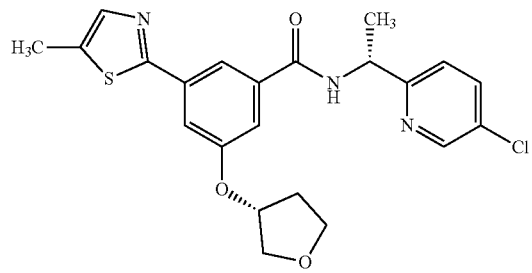 [SMILES: Cc1cnc(-c2cc(O[C@@H]3CCOC3)cc(C(=O)N[C@H](C)c3ccc(Cl)cn3)c2)s1]

Intermediate 58 (80 mg, 0.26 mmol), (1R)-1-(5-chloropyridin-2-yl)ethanamine hydrochloride (56 mg, 0.29 mmol), DIPEA (135 mg, 1.05 mmol) and HATU (139 mg, 0.37 mmol) were dissolved in DMF (3.5 mL). The reaction mixture was stirred at RT until complete conversion and evaporated to dryness. Crude material was purified by preparative HPLC (method 1, rt: 1.21 min) to afford the title compound 60 mg (51% yield).

$^1$H NMR (300 MHz, DMSO-d$_6$) δ [ppm] 1.52 (d, J=7.16 Hz, 3H) 1.94-2.06 (m, 1H) 2.26 (d, J=7.72 Hz, 1H) 3.75-3.95 (m, 4H) 5.15-5.26 (m, 2H) 7.46 (d, J=8.48 Hz, 1H) 7.53 (d, J=1.13 Hz, 2H) 7.65 (d, J=1.32 Hz, 1H) 7.90 (dd, J=8.48, 2.64 Hz, 1H) 7.93-7.98 (m, 1H) 8.58 (d, J=2.07 Hz, 1H) 9.08 (d, J=7.54 Hz, 1H).

Example 16

N-[(1R)-1-(5-methylpyrazin-2-yl)ethyl]-3-(5-methyl-1,3-thiazol-2-yl)-5-[(3R)-tetrahydrofuran-3-yloxy]benzamide

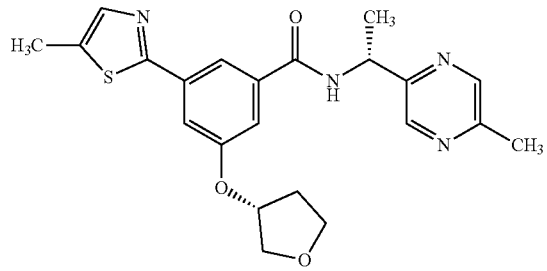

Intermediate 5B (80 mg, 0.26 mmol), (1R)-1-(5-methylpyrazin-2-yl)ethanamine (40 mg, 0.29 mmol), DIPEA (135 mg, 1.05 mmol) and HATU (139 mg, 0.37 mmol) were dissolved in DMF (3.5 mL). The reaction mixture was stirred at RT until complete conversion and evaporated to dryness. Crude material was purified by preparative HPLC (method 1, rt: 1.04 min) to afford the title compound 40 mg (35% yield).

$^1$H NMR (400 MHz, DMSO-d$_6$) δ [ppm] 1.54 (d, J=7.07 Hz, 3H) 1.96-2.05 (m, 1H) 2.20-2.31 (m, 1H) 2.47 (s, 3H) 3.75-3.94 (m, 4H) 5.18-5.26 (m, 2H) 7.52 (d, J=1.26 Hz, 2H) 7.64 (d, J=1.26 Hz, 1H) 7.94 (t, J=1.39 Hz, 1H) 8.48 (d, J=1.01 Hz, 1H) 8.56 (d, J=1.26 Hz, 1H) 9.08 (d, J=7.58 Hz, 1H).

Example 17

N-[(6-methylpyridazin-3-yl)methyl]-3-(5-methyl-1,3-thiazol-2-yl)-5-[(3R)-tetrahydrofuran-3-yloxy]benzamide

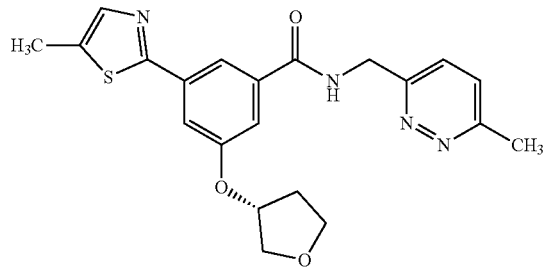

Intermediate 5B (77 mg, 0.25 mmol), 1-(6-methylpyridazin-3-yl)methanamine (34 mg, 0.28 mmol), DIPEA (130 mg, 1.0 mmol) and HATU (133 mg, 0.35 mmol) were dissolved in DMF (3.3 mL). The reaction mixture was stirred at RT until complete conversion and evaporated to dryness. Crude material was purified by preparative HPLC (method 1, rt: 0.91 min) to afford the title compound 50 mg (48% yield).

$^1$H NMR (400 MHz, DMSO-d$_6$) δ [ppm] 2.02 (d, J=6.84 Hz, 1H) 2.26 (dd, J=13.43, 6.08 Hz, 1H) 2.60 (s, 3H) 3.73-3.95 (m, 4H) 4.73 (d, J=5.83 Hz, 2H) 5.14-5.23 (m, 1H) 7.48-7.57 (m, 4H) 7.64 (d, J=1.01 Hz, 1H) 7.98 (t, J=1.39 Hz, 1H) 9.39 (t, J=5.83 Hz, 1H).

Example 18

N-[(1R)-1-(6-methylpyridazin-3-yl)ethyl]-3-(5-methyl-1,3-thiazol-2-yl)-5-[(3R)-tetrahydrofuran-3-yloxy]benzamide

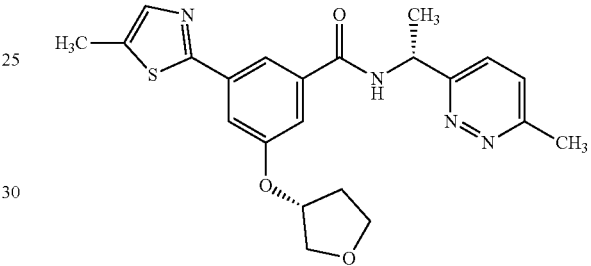

Intermediate 5B (69 mg, 0.23 mmol), Intermediate XV (43 mg, 0.25 mmol), DIPEA (117 mg, 0.9 mmol) and HATU (120 mg, 0.32 mmol) were dissolved in DMF (3 mL). The reaction mixture was stirred at RT until complete conversion and evaporated to dryness. Crude material was purified by preparative HPLC (method 1, rt: 0.95 min) to afford the title compound 30 mg (31% yield).

$^1$H NMR (400 MHz, DMSO-d$_6$) δ [ppm] 1.58 (d, J=7.10 Hz, 3H) 2.01 (d, J=6.59 Hz, 1H) 2.20-2.31 (m, 1H) 2.59 (s, 3H) 3.74-3.95 (m, 4H) 5.15-5.25 (m, 1H) 5.36 (t, J=7.22 Hz, 1H) 7.49-7.56 (m, 3H) 7.56-7.67 (m, 2H) 7.95 (t, J=1.39 Hz, 1H) 9.14 (d, J=7.35 Hz, 1H).

Example 19

3-(5-Methyl-1,3-thiazol-2-yl)-5-[(3R)-tetrahydrofuran-3-yloxy]-N-{(1R)-1-[6-(trifluoromethyl)pyridazin-3-yl]ethyl}benzamide

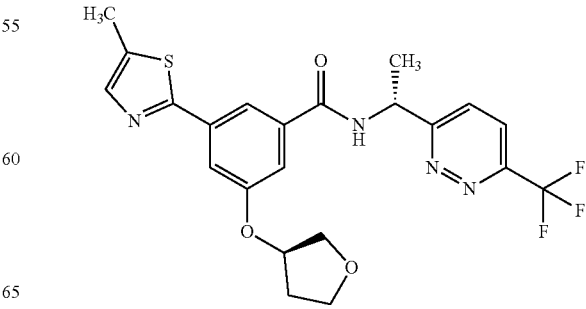

To a solution of 3-(5-methyl-1,3-thiazol-2-yl)-5-[(3R)-tetrahydrofuran-3-yloxy]benzoic acid (50 mg, 0.16 mmol), (1R)-1-[6-(trifluoromethyl)pyridazin-3-yl]ethanamine hydrochloride (48 mg, 0.21 mmol) and DIPEA (113 µL, 0.65 mmol) in DCM (1 mL) was added HATU (74 mg, 0.20 mmol). The reaction mixture was stirred at RT for 2 h then diluted with DCM (1 mL) and washed with water (2×2 mL). The aqueous phase was re-extracted with DCM (2 mL) and the combined organics dried (over $Na_2SO_4$) and concentrated in vacuo. The crude product was purified by preparative HPLC (Method A) to give 39.5 mg (51% yield) of the title compound as a white powder.

$^1$H NMR (500 MHz, Chloroform-d): δ [ppm]=7.88 (t, J=1.4 Hz, 1H), 7.82 (d, J=8.7 Hz, 1H), 7.74 (d, J=8.7 Hz, 1H), 7.54 (dd, J=2.4, 1.5 Hz, 1H), 7.51 (d, J=1.2 Hz, 2H), 7.37 (dd, J=2.3, 1.5 Hz, 1H), 5.60 (p, J=7.0 Hz, 1H), 5.06 (ddt, J=6.1, 4.0, 1.8 Hz, 1H), 4.06-3.95 (m, 3H), 3.91 (td, J=8.4, 4.2 Hz, 1H), 2.52 (d, J=1.1 Hz, 3H), 2.26 (dtd, J=14.4, 8.4, 6.1 Hz, 1H), 2.20-2.11 (m, 1H), 1.76 (d, J=7.0 Hz, 3H)

LCMS (Analytical Method F) Rt=3.32 min, MS (ESIpos) m/z=479 (M+H)$^+$.

Example 20

N-[(1R)-1-(5-methyl-1,3,4-thiadiazol-2-yl)ethyl]-3-(5-methyl-1,3-thiazol-2-yl)-5-[(3R)-tetrahydrofuran-3-yloxy]benzamide

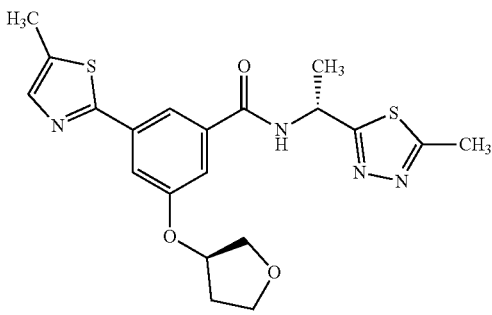 [SMILES: Cc1cnc(-c2cc(O[C@@H]3CCOC3)cc(C(=O)N[C@H](C)c3nnc(C)s3)c2)s1]

To a solution of 3-(5-methyl-1,3-thiazol-2-yl)-5-[(3R)-tetrahydrofuran-3-yloxy]benzoic acid (61 mg, 0.2 mmol), (1R)-1-(5-methyl-1,3,4-thiadiazol-2-yl)ethanamine hydrochloride (43 mg, 0.24 mmol) and DIPEA (0.174 mL, 1.0 mmol) in DCM (2 mL) was added T3P (0.23 mL, 0.4 mmol, 50% in EtOAc) and the reaction mixture stirred at RT for 2 h. The reaction mixture was washed with 2M NaOH (2 mL) and the aqueous layer further extracted with DCM (2×2 mL). The combined organic phase was dried (over $MgSO_4$), evaporated and the resulting material triturated from $Et_2O$ to give 42.0 mg (49% yield) of the title compound as a white powder.

$^1$H NMR (500 MHz, Chloroform-d): δ [ppm]=7.85 (t, J=1.4 Hz, 1H), 7.55 (dd, J=2.4, 1.5 Hz, 1H), 7.52 (d, J=1.2 Hz, 1H), 7.39 (dd, J=2.4, 1.5 Hz, 1H), 7.02 (d, J=7.5 Hz, 1H), 5.69 (p, J=7.0 Hz, 1H), 5.08 (td, J=4.2, 2.1 Hz, 1H), 4.07-3.97 (m, 3H), 3.92 (td, J=8.4, 4.2 Hz, 1H), 2.76 (s, 3H), 2.53 (d, J=1.1 Hz, 3H), 2.28 (dtd, J=14.4, 8.4, 6.1 Hz, 1H), 2.22-2.14 (m, 1H), 1.80 (d, J=7.0 Hz, 3H).

LCMS (Analytical Method F) Rt=2.72 min, MS (ESIpos): m/z=431 (M+H)$^+$.

Example 21

3-(5-Methyl-1,3-thiazol-2-yl)-5-[(3R)-tetrahydrofuran-3-yloxy]-N-{[6-(trifluoromethyl)pyridazin-3-yl]methyl}benzamide

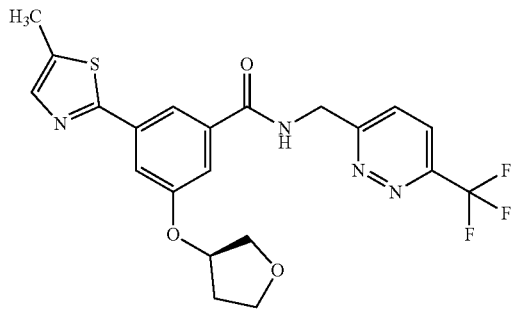 [SMILES: Cc1cnc(-c2cc(O[C@@H]3CCOC3)cc(C(=O)NCc3ccc(C(F)(F)F)nn3)c2)s1]

To a solution of 3-(5-methyl-1,3-thiazol-2-yl)-5-[(3R)-tetrahydrofuran-3-yloxy]benzoic acid (40 mg, 0.13 mmol), 1-[6-(trifluoromethyl)pyridazin-3-yl]methanamine monohydrochloride (31 mg, 0.14 mmol) and DIPEA (68 µL, 0.52 mmol) in DCM (1 mL) was added T3P (50% solution in EtOAc, 117 µL, 0.20 mmol) and the resulting solution stirred at RT for 2 h. The reaction mixture was diluted with DCM (1 mL), washed with water (1 mL), dried (over $MgSO_4$) and concentrated in vacuo. The crude material was purified by preparative HPLC (Method A) to give 13 mg (21% yield) of the title compound as a white powder.

$^1$H NMR (500 MHz, CDCl3) δ [ppm]=7.88 (s, 1H), 7.82 (d, J=2.2 Hz, 2H), 7.76 (t, J=5.3 Hz, 1H), 7.52 (s, 1H), 7.48 (s, 1H), 7.39 (s, 1H), 5.04 (d, J=5.5 Hz, 3H), 4.04-3.95 (m, 3H), 3.90 (td, J=8.4, 4.2 Hz, 1H), 2.50 (s, 3H), 2.30-2.20 (m, 1H), 2.19-2.10 (m, 1H).

LCMS (Analytical Method D) Rt=4.05, m/z=465 (M+H)$^+$.

Example 22

3-(5-Methyl-1,3-thiazol-2-yl)-5-[(3R)-tetrahydrofuran-3-yloxy]-N-{(1R)-1-[2-(trifluoromethyl)pyrimidin-5-yl]propyl}benzamide

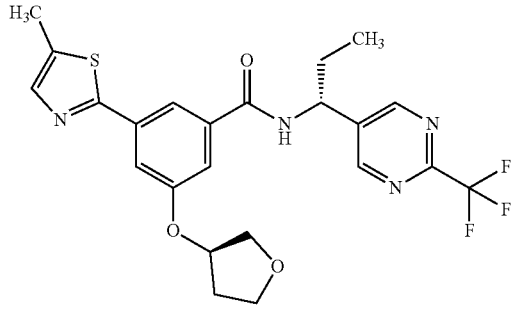 [SMILES: CC[C@@H](NC(=O)c1cc(O[C@@H]2CCOC2)cc(-c2ncc(C)s2)c1)c1cnc(C(F)(F)F)nc1]

To a solution of 3-(5-methyl-1,3-thiazol-2-yl)-5-[(3R)-tetrahydrofuran-3-yloxy]benzoic acid (61 mg, 0.2 mmol), (1R)-1-[2-(trifluoromethyl)pyrimidin-5-yl]propan-1-amine hydrochloride (58 mg, 0.24 mmol) and DIPEA (0.174 mL, 1.0 mmol) in DCM (2 mL) was added T3P (0.23 mL, 0.4 mmol, 50% in EtOAc) and the reaction stirred at RT for 4 h.

The reaction mixture was washed with saturated NaHCO$_3$ solution (2 mL) and the aqueous layer further extracted with DCM (2×2 mL). The combined organics were dried (over MgSO$_4$) and concentrated under reduced pressure. The crude material was purified by preparative HPLC (Method A) and freeze-dried from acetonitrile/water to give 70.6 mg (72% yield) of the title compound as a white powder.

$^1$H NMR (500 MHz, CDCl3): δ [ppm]=8.91 (s, 2H), 7.85 (s, 1H), 7.53 (d, J=1.1 Hz, 1H), 7.51 (dd, J=2.3, 1.4 Hz, 1H), 7.36-7.34 (m, 1H), 6.62 (d, J=6.8 Hz, 1H), 5.10 (q, J=7.3 Hz, 1H), 5.06 (d, J=2.4 Hz, 1H), 4.04-3.98 (m, 3H), 3.91 (td, J=8.4, 4.3 Hz, 1H), 2.54 (d, J=1.0 Hz, 3H), 2.32-2.23 (m, 1H), 2.20-2.11 (m, 1H), 2.10-1.96 (m, 2H), 1.08 (t, J=7.4 Hz, 3H).

LCMS (Analytical Method F) Rt=3.60 min, MS (ESIpos): m/z=493.3 (M+H)$^+$.

Example 23

N-[(1R)-1-(2-Methylpyrimidin-5-yl)ethyl]-3-(5-methyl-1,3-thiazol-2-yl)-5-[(3R)-tetrahydrofuran-3-yloxy]benzamide

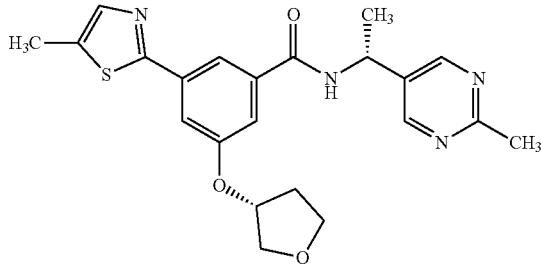

Intermediate 5B (70 mg, 0.23 mmol), (1R)-1-(2-methylpyrimidin-5-yl)ethanamine dihydrochloride (53 mg, 0.25 mmol), DIPEA (119 mg, 0.92 mmol) and HATU (122 mg, 0.32 mmol) were dissolved in DMF (3.05 mL). The reaction mixture was stirred at RT until complete conversion and evaporated to dryness. Crude material was purified by preparative HPLC (method 1, rt: 0.97 min) to afford the title compound 45 mg (45% yield).

$^1$H NMR (400 MHz, DMSO-d$_6$) δ [ppm] 1.54 (d, J=7.07 Hz, 3H) 1.96-2.05 (m, 1H) 2.25 (s, 1H) 2.59 (s, 3H) 3.74-3.95 (m, 4H) 5.12-5.23 (m, 2H) 7.48 (dd, J=2.27, 1.52 Hz, 1H) 7.50-7.53 (m, 1H) 7.64 (d, J=1.26 Hz, 1H) 7.91 (t, J=1.52 Hz, 1H) 8.72 (s, 2H) 9.04 (d, J=7.58 Hz, 1H).

Example 24

N-[(1R)-1-(6-Methylpyridin-3-yl)ethyl]-3-(5-methyl-1,3-thiazol-2-yl)-5-[(3R)-tetrahydrofuran-3-yloxy]benzamide

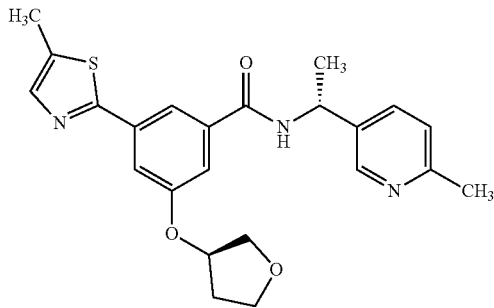 [SMILES: Cc1ccc([C@@H](C)NC(=O)c2cc(O[C@@H]3CCOC3)cc(-c3ncc(C)s3)c2)cn1]

To a solution of 3-(5-methyl-1,3-thiazol-2-yl)-5-[(3R)-tetrahydrofuran-3-yloxy]benzoic acid (61 mg, 0.2 mmol), (1R)-1-(6-methylpyridin-3-yl)ethanamine (33 mg, 0.24 mmol) and DIPEA (0.17 mL, 1.0 mmol) in DCM (2 mL) was added T3P (0.23 mL, 0.4 mmol, 50% in EtOAc) and the reaction mixture stirred at RT for 2 h. The reaction mixture was washed with 2M NaOH (2 mL) and the aqueous layer further extracted with DCM (2×2 mL). The combined organics were dried (over MgSO$_4$) and concentrated under reduced pressure. The material was triturated from Et$_2$O to give 50.7 mg (60% yield) of the title compound as an off-white powder.

$^1$H NMR (500 MHz, Chloroform-d): δ [ppm]=8.55 (d, J=2.3 Hz, 1H), 7.81 (t, J=1.3 Hz, 1H), 7.60 (dd, J=8.0, 2.4 Hz, 1H), 7.51 (d, J=1.2 Hz, 1H), 7.50 (dd, J=2.4, 1.5 Hz, 1H), 7.37 (dd, J=2.3, 1.5 Hz, 1H), 6.44 (d, J=7.4 Hz, 1H), 5.32 (p, J=7.0 Hz, 1H), 5.09-5.03 (m, 1H), 4.06-3.96 (m, 3H), 3.91 (td, J=8.4, 4.3 Hz, 1H), 2.55 (s, 3H), 2.53 (d, J=1.1 Hz, 3H), 2.32-2.22 (m, 1H), 2.19-2.12 (m, 1H), 1.63 (d, J=7.0 Hz, 4H).

LCMS (Analytical Method D) Rt=3.06, MS (ESIpos) m/z=424 (M+H)$^+$.

Example 25

N-[(1R)-1-(6-Methylpyridazin-3-yl)ethyl]-3-(5-methyl-1,3-thiazol-2-yl)-5-[(3S)-tetrahydrofuran-3-yloxy]benzamide

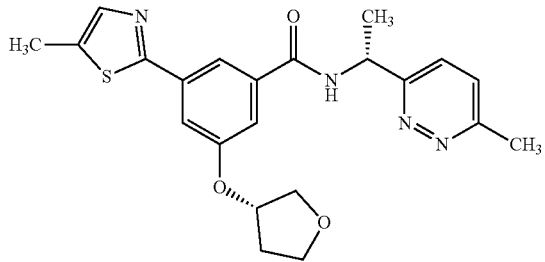

Intermediate 5C (240 mg, 0.79 mmol), Intermediate XV (191 mg, 1.1 mmol), TEA (0.22 mL, 1.57 mmol) and HATU (329 mg, 0.87 mmol) were dissolved in DMF (12 mL). The reaction mixture was stirred at RT until complete conversion and evaporated to dryness. Crude material was purified by preparative HPLC (System: Labomatic Vario 2000, HPLC pump HD-3000; Column: Chromatex C18 10μ 125×30 mm; flow rate: 150 ml/min; solvent: acetonitrile/water; A=85%, B=15% to A=0%, B=100%; rt: 6.26-6.77 min) to afford the title compound 150 mg (44% yield).

$^1$H NMR (400 MHz, DMSO-d$_6$) δ [ppm] 1.59 (d, J=7.07 Hz, 3H) 1.96-2.07 (m, 1H) 2.20-2.31 (m, 1H) 2.59 (s, 3H) 3.75-3.95 (m, 4H) 5.17-5.24 (m, 1H) 5.37 (t, J=7.20 Hz, 1H) 7.50-7.56 (m, 3H) 7.57-7.62 (m, 1H) 7.64 (d, J=1.26 Hz, 1H) 7.95 (t, J=1.39 Hz, 1H) 9.13 (d, J=7.58 Hz, 1H).

Example 26

3-(5-Methyl-1,3-thiazol-2-yl)-5-[(3S)-tetrahydrofuran-3-yloxy]-N-{(1R)-1-[2-(trifluoromethyl)pyrimidin-5-yl]ethyl}benzamide

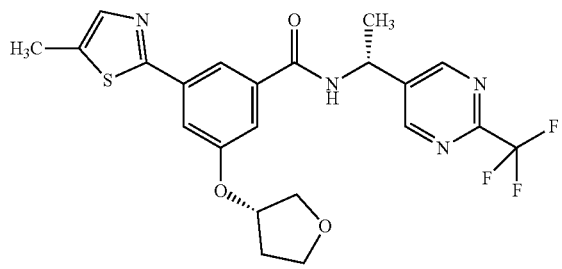 [SMILES: Cc1cnc(-c2cc(O[C@H]3CCOC3)cc(C(=O)N[C@H](C)c3cnc(C(F)(F)F)nc3)c2)s1]

Intermediate 5C (230 mg, 0.75 mmol), (1R)-1-[2-(trifluoromethyl)pyrimidin-5-yl]ethan-1-amine dihydrochloride (239 mg, 0.9 mmol), TEA (0.42 mL, 3.01 mmol) and HATU (430 mg, 1.13 mmol) were dissolved in DMF (6.9 mL). The reaction mixture was stirred at RT until complete conversion and evaporated to dryness. Crude material was purified by preparative HPLC (System: Labomatic Vario 2000, HPLC pump HD-3000; Column: Chromatex C18 10μ 125×30 mm; flow rate: 150 ml/min; solvent: acetonitrile/water; A=70%, B=30% to A=0%, B=100%; rt: 6.46-7.42 min) to afford the title compound 205 mg (57% yield).

$^1$H NMR (300 MHz, DMSO-$d_6$) δ [ppm] 1.61 (d, J=7.16 Hz, 3H) 2.02 (d, J=6.03 Hz, 1H) 2.19-2.33 (m, 1H) 3.74-3.96 (m, 4H) 5.15-5.36 (m, 2H) 7.47-7.55 (m, 2H) 7.65 (d, J=1.13 Hz, 1H) 7.93 (s, 1H) 9.09-9.20 (m, 3H).

Example 27

N-[(1R)-1-(5-Chloropyridin-2-yl)ethyl]-3-(5-methyl-1,3-thiazol-2-yl)-5-[(3S)-tetrahydrofuran-3-yloxy]benzamide

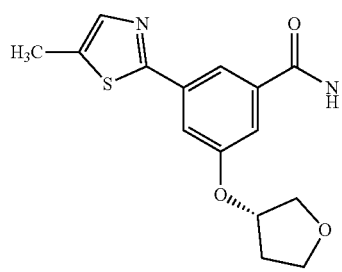

Intermediate 5C (120 mg, 0.39 mmol), (1R)-1-(5-chloropyridin-2-yl)ethanamine hydrochloride (106 mg, 0.55 mmol), TEA (0.16 mL, 1.18 mmol) and HATU (164 mg, 0.43 mmol) were dissolved in DMF (4.3 mL). The reaction mixture was stirred at 60° C. until complete conversion and evaporated to dryness. Crude material was purified by preparative HPLC (method 1, rt: 1.22 min) to afford the title compound 100 mg (57% yield).

$^1$H NMR (400 MHz, DMSO-$d_6$) δ [ppm] 1.53 (d, J=7.10 Hz, 3H) 1.97-2.07 (m, 1H) 2.20-2.32 (m, 1H) 3.76-3.95 (m, 4H) 5.14-5.26 (m, 2H) 7.47 (d, J=8.36 Hz, 1H) 7.51-7.56 (m, 2H) 7.65 (d, J=1.27 Hz, 1H) 7.91 (dd, J=8.62, 2.53 Hz, 1H) 7.96 (t, J=1.39 Hz, 1H) 8.58 (d, J=2.03 Hz, 1H) 9.08 (d, J=7.60 Hz, 1H).

Example 28

N-[(1R)-1-(5-Methylpyridin-2-yl)ethyl]-3-(5-methyl-1,3-thiazol-2-yl)-5-[(3S)-tetrahydrofuran-3-yloxy]benzamide

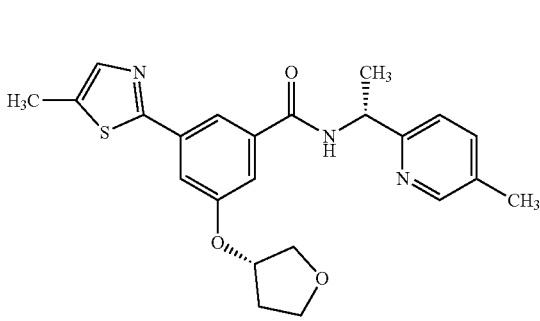

Intermediate 5C (120 mg, 0.39 mmol), (1R)-1-(5-methylpyridin-2-yl)ethanamine hydrochloride (95 mg, 0.55 mmol), TEA (0.08 mL, 0.59 mmol) and HATU (164 mg, 0.43 mmol) were dissolved in DMF (3.9 mL). The reaction mixture was stirred at RT until complete conversion and evaporated to dryness. Crude material was purified by preparative HPLC (method 2, rt: 1.15 min) to afford the title compound 93 mg (56% yield).

$^1$H NMR (400 MHz, DMSO-$d_6$) δ [ppm] 1.50 (d, J=7.10 Hz, 3H) 1.96-2.07 (m, 1H) 2.20-2.31 (m, 4H) 3.75-3.95 (m, 4H) 5.12-5.24 (m, 2H) 7.30 (d, J=7.86 Hz, 1H) 7.49-7.54 (m, 2H) 7.55-7.60 (m, 1H) 7.64 (d, J=1.27 Hz, 1H) 7.95 (t, J=1.39 Hz, 1H) 8.33-8.40 (m, 1H) 9.00 (d, J=7.86 Hz, 1H).

Example 29

N-[(1R)-1-(5-Methylpyrazin-2-yl)ethyl]-3-(5-methyl-1,3-thiazol-2-yl)-5-[(3S)-tetrahydrofuran-3-yloxy]benzamide

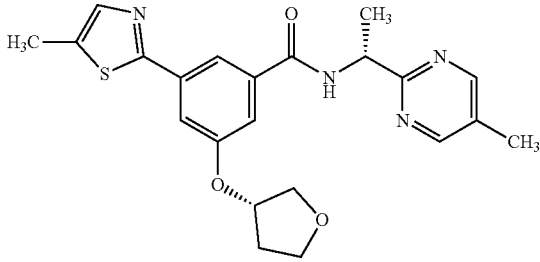

Intermediate 5C (120 mg, 0.39 mmol), ((1R)-1-(5-methylpyrazin-2-yl)ethanamine dihydrochloride (116 mg, 0.55 mmol), TEA (0.16 mL, 1.18 mmol) and HATU (164 mg, 0.43 mmol) were dissolved in DMF (4.3 mL). The reaction mixture was stirred at RT until complete conversion and evaporated to dryness. Crude material was purified by preparative HPLC (method 2, rt: 1.04 min) to afford the title compound 50 mg (30% yield).

$^1$H NMR (400 MHz, DMSO-$d_6$) δ [ppm] 1.54 (d, J=7.10 Hz, 3H) 1.97-2.06 (m, 1H) 2.25 (s, 1H) 2.47 (s, 3H) 3.75-3.94 (m, 4H) 5.17-5.28 (m, 2H) 7.49-7.54 (m, 2H) 7.64 (d, J=1.27 Hz, 1H) 7.94 (t, J=1.52 Hz, 1H) 8.49 (d, J=1.01 Hz, 1H) 8.56 (d, J=1.27 Hz, 1H) 9.09 (d, J=7.35 Hz, 1H).

In analogy to the procedure described for Example 7 the following example was prepared using the appropriate carboxylic acid and amine as starting materials.

| Ex. | Structure | Name | Analytical Data |
|---|---|---|---|
| 30 | 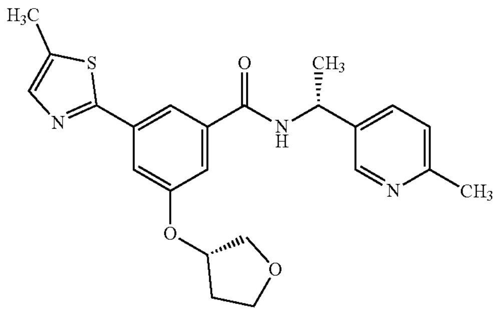 [SMILES: Cc1ccc([C@@H](C)NC(=O)c2cc(O[C@H]3CCOC3)cc(-c3ncc(C)s3)c2)cn1] | N-[(1R)-1-(6-Methylpyridin-3-yl)ethyl]-3-(5-methyl-1,3-thiazol-2-yl)-5-[(3S)-tetrahydrofuran-3-yloxy]benzamide | $^1$H NMR (500 MHz, CDCl$_3$): δ [ppm] = 8.56 (d, J = 2.2 Hz, 1H), 7.84 (t, J = 1.3 Hz, 1H), 7.61 (dd, J = 8.0, 2.3 Hz, 1H), 7.51 (d, J = 1.2 Hz, 2H), 7.50 (dd, J = 2.4, 1.5 Hz, 1H), 7.38 (dd, J = 2.3, 1.5 Hz, 1H), 7.14 (d, J = 8.0 Hz, 1H), 6.65 (d, J = 7.5 Hz, 1H), 5.33 (p, J = 7.1 Hz, 1H), 5.05 (ddd, J = 5.9, 3.8, 2.0 Hz, 1H), 4.04-3.97 (m, 3H), 3.92 (td, J = 8.4, 4.3 Hz, 1H), 2.55 (s, 3H), 2.53 (d, J = 1.1 Hz, 3H), 2.32-2.22 (m, 1H), 2.21-2.12 (m, 1H), 1.64 (d, J = 7.0 Hz, 3H). LCMS (Analytical Method F) Rt = 1.87 min, MS (ESIpos): m/z = 424.4 (M + H)$^+$. |

In analogy to the procedure described for Example 1 the following examples were prepared using the appropriate carboxylic acid and amine as starting materials.

| Ex. | Structure | Name | Analytical Data |
|---|---|---|---|
| 31 | 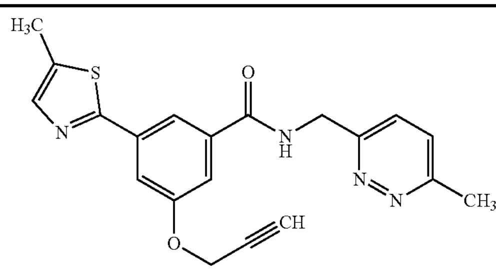 | N-[(6-Methylpyridazin-3-yl)methyl]-3-(5-methyl-1,3-thiazol-2-yl)-5-(prop-2-yn-1-yloxy)benzamide | $^1$H NMR (500 MHz, CDCl$_3$): δ [ppm] = 8.16 (t, J = 5.4 Hz, 1H), 7.93 (t, J = 1.4 Hz, 1H), 7.60 (dd, J = 2.4, 1.5 Hz, 1H), 7.53-7.49 (m, 2H), 7.46 (d, J = 1.2 Hz, 1H), 7.30 (d, J = 8.6 Hz, 1H), 4.87 (d, J = 5.5 Hz, 2H), 4.74 (d, J = 2.4 Hz, 2H), 2.66 (s, 3H), 2.54 (t, J = 2.4 Hz, 1H), 2.47 (d, J = 1.1 Hz, 3H). LCMS (Analytical Method F) Rt = 2.51 min, MS (ESIpos): m/z = 379.1 (M + H)$^+$. |
| 32 | 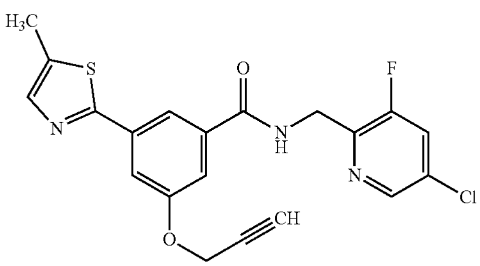 [SMILES: C#CCOc1cc(C(=O)NCc2ncc(Cl)cc2F)cc(-c2ncc(C)s2)c1] | N-[(5-Chloro-3-fluoropyridin-2-yl)methyl]-3-(5-methyl-1,3-thiazol-2-yl)-5-(prop-2-yn-1-yloxy)benzamide | $^1$H NMR (500 MHz, CDCl$_3$): δ [ppm] = 8.39 (d, J = 1.7 Hz, 1H), 7.98 (br s, 1H), 7.67 (dd, J = 2.4, 1.5 Hz, 1H), 7.56-7.52 (m, 2H), 7.51-7.46 (m, 2H), 4.83-4.81 (m, 4H), 2.57 (t, J = 2.4 Hz, 1H), 2.53 (d, J = 1.0 Hz, 3H). LCMS (Analytical Method F) Rt = 3.48 min, MS (ESIpos): m/z = 416.0 (M + H)$^+$. |
| 33 | 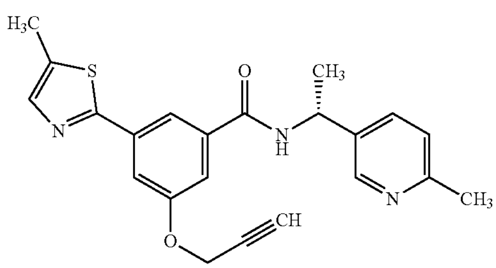 [SMILES: C#CCOc1cc(C(=O)N[C@H](C)c2ccc(C)nc2)cc(-c2ncc(C)s2)c1] | N-[(1R)-1-(6-Methylpyridin-3-yl)ethyl]-3-(5-methyl-1,3-thiazol-2-yl)-5-(prop-2-yn-1-yloxy)benzamide | $^1$H NMR (500 MHz, CDCl$_3$): δ [ppm] = 8.58 (d, J = 1.9 Hz, 1H), 7.87 (t, J = 1.3 Hz, 1H), 7.64 (dd, J = 8.0, 2.3 Hz, 1H), 7.59 (dd, J = 2.4, 1.4 Hz, 1H), 7.51 (d, J = 1.2 Hz, 1H), 7.49 (dd, J = 2.4, 1.5 Hz, 1H), 7.16 (d, J = 8.0 Hz, 1H), 6.59 (d, J = 7.0 Hz, 1H), 5.32 (p, 1H), 4.78 (d, J = 2.4 Hz, 2H), 2.56 (s, 3H), 2.55 (t, J = 2.4 Hz, 1H), 2.52 (d, J = 1.1 Hz, 3H), 1.63 (d, J = 7.0 Hz, 3H). LCMS (Analytical Method F) Rt = 1.99 min, MS (ESIpos): m/z = 392.1 (M + H)$^+$. |
| 34 | 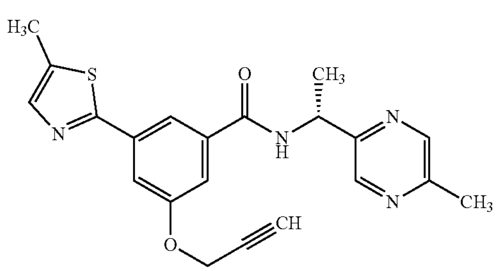 [SMILES: C#CCOc1cc(C(=O)N[C@H](C)c2cnc(C)cn2)cc(-c2ncc(C)s2)c1] | N-[(1R)-1-(5-Methylpyrazin-2-yl)ethyl]-3-(5-methyl-1,3-thiazol-2-yl)-5-(prop-2-yn-1-yloxy)benzamide | $^1$H NMR (500 MHz, Benzene-d6): δ [ppm] = 8.53 (d, J = 1.4 Hz, 1H), 8.41 (s, 1H), 7.95 (s, 1H), 7.63 (dd, J = 2.4, 1.5 Hz, 1H), 7.53 (d, J = 1.2 Hz, 1H), 7.50 (dd, J = 2.4, 1.5 Hz, 1H), 7.34 (d, J = 7.4 Hz, 1H), 5.43 (p, J = 6.9 Hz, 1H), 4.80 (d, J = 2.4 Hz, 2H), 2.57 (s, 3H), 2.56 (t, J = 2.4 Hz, 1H), 2.53 (d, J = 1.1 Hz, 3H), 1.60 (d, J = 6.8 Hz, 3H). LCMS (Analytical Method F) Rt = 3.00 min, MS (ESIpos): m/z = 393.1 (M + H)$^+$. |

| Ex. | Structure | Name | Analytical Data |
|---|---|---|---|
| 35 | 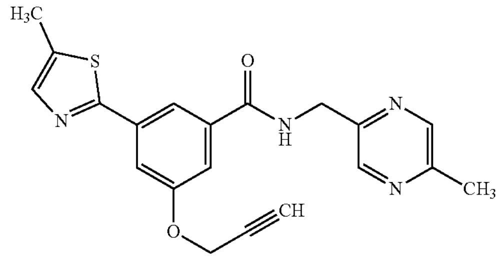 [SMILES: C#CCOc1cc(C(=O)NCc2cnc(C)cn2)cc(-c2ncc(C)s2)c1] | N-[(5-Methylpyrazin-2-yl)methyl]-3-(5-methyl-1,3-thiazol-2-yl)-5-(prop-2-yn-1-yloxy)benzamide | $^1$H NMR (500 MHz, CDCl$_3$): δ [ppm] = 8.56 (d, J = 1.2 Hz, 1H), 8.42 (s, 1H), 7.95 (t, J = 1.4 Hz, 1H), 7.65 (dd, J = 2.5, 1.5 Hz, 1H), 7.52 (dd, J = 2.4, 1.4 Hz, 2H), 7.27 (s, 1H), 4.80 (d, J = 2.4 Hz, 2H), 4.78 (d, J = 5.2 Hz, 2H), 2.58 (s, 3H), 2.56 (t, J = 2.4 Hz, 1H), 2.53 (d, J = 1.1 Hz, 3H). LCMS (Analytical Method F) Rt = 2.78 min, MS (ESIpos) m/z = 379 (M + H)$^+$. |
| 36 | 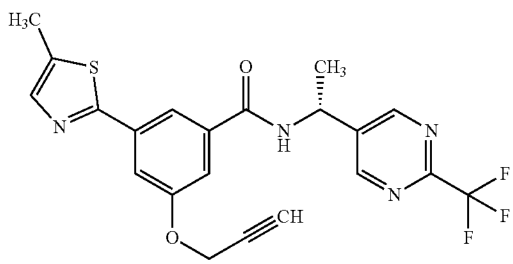 [SMILES: C#CCOc1cc(C(=O)N[C@H](C)c2cnc(C(F)(F)F)nc2)cc(-c2ncc(C)s2)c1] | 3-(5-Methyl-1,3-thiazol-2-yl)-5-(prop-2-yn-1-yloxy)-N-{(1R)-1-[2-(trifluoromethyl)pyrimidin-5-yl]ethyl}benzamide | $^1$H NMR (500 MHz, DMSO-d6): δ [ppm] = 9.17 (d, J = 7.1 Hz, 1H), 9.11 (s, 2H), 7.97 (t, J = 1.4 Hz, 1H), 7.65 (d, J = 1.2 Hz, 1H), 7.63 (dd, J = 2.4, 1.5 Hz, 1H), 7.56 (dd, J = 2.4, 1.5 Hz, 1H), 5.30 (p, J = 7.0 Hz, 1H), 4.95 (d, J = 2.3 Hz, 2H), 3.62 (t, J = 2.3 Hz, 1H), 3.31 (s, 3H), 1.61 (d, J = 7.1 Hz, 3H). LCMS (Analytical Method F) Rt = 3.54 min, MS (ESIpos) m/z = 447 (M + H)$^+$. |
| 37 | 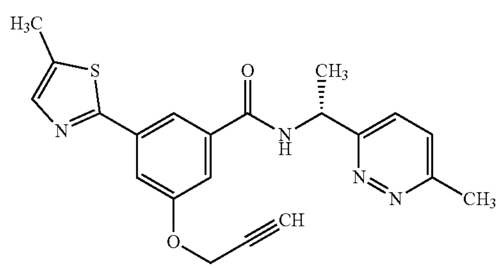 | N-[(1R)-1-(6-Methylpyridazin-3-yl)ethyl]-3-(5-methyl-1,3-thiazol-2-yl)-5-(prop-2-yn-1-yloxy)benzamide | $^1$H NMR (500 MHz, CDCl$_3$): δ [ppm] = 7.93 (t, J = 1.4 Hz, 1H), 7.78 (d, J = 7.2 Hz, 1H), 7.65 (dd, J = 2.4, 1.5 Hz, 1H), 7.53-7.48 (m, 2H), 7.39 (d, J = 8.6 Hz, 1H), 7.33 (d, J = 8.6 Hz, 1H), 5.46 (p, J = 6.9 Hz, 1H), 4.79 (d, J = 2.4 Hz, 2H), 2.72 (s, 3H), 2.56 (t, J = 2.4 Hz, 1H), 2.52 (d, J = 1.0 Hz, 3H), 1.68 (d, J = 6.8 Hz, 3H). LCMS (Analytical Method F) Rt = 2.64 min, MS (ESIpos) m/z = 437 (M + H)$^+$. |
| 38 | 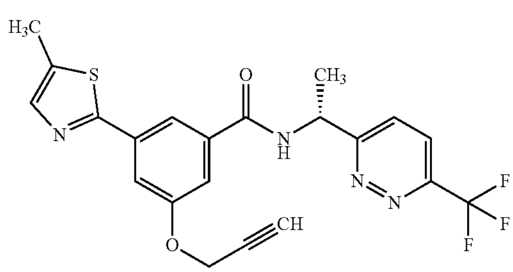 [SMILES: C#CCOc1cc(C(=O)N[C@H](C)c2ccc(C(F)(F)F)nn2)cc(-c2ncc(C)s2)c1] | 3-(5-Methyl-1,3-thiazol-2-yl)-5-(prop-2-yn-1-yloxy)-N-[(1R)-1-[6-(trifluoromethyl)-pyridazin-3-yl]ethyl]benzamide | $^1$H NMR (500 MHz, CDCl$_3$): δ [ppm] = 7.93 (t, J = 1.4 Hz, 1H), 7.82 (d, J = 8.7 Hz, 1H), 7.74 (d, J = 8.7 Hz, 1H), 7.63 (dd, J = 2.4, 1.4 Hz, 1H), 7.55-7.45 (m, 3H), 5.60 (p, J = 7.0 Hz, 1H), 4.78 (d, J = 2.4 Hz, 2H), 2.56 (t, J = 2.4 Hz, 1H), 2.52 (d, J = 1.1 Hz, 3H), 1.76 (d, J = 7.0 Hz, 3H). LCMS (Analytical Method D) Rt = 4.18 min, MS (ESIpos): m/z = 447 (M + H)$^+$. |
| 39 | 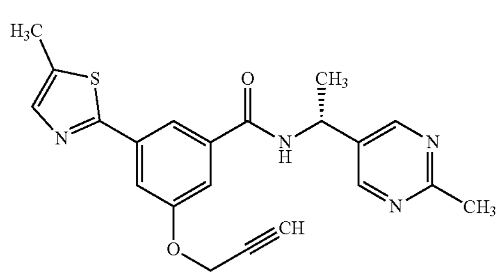 [SMILES: C#CCOc1cc(C(=O)N[C@H](C)c2cnc(C)nc2)cc(-c2ncc(C)s2)c1] | N-[(1R)-1-(2-Methylpyrimidin-5-yl)ethyl]-3-(5-methyl-1,3-thiazol-2-yl)-5-(prop-2-yn-1-yloxy)benzamide | $^1$H NMR (500 MHz, DMSO-d6): δ [ppm] = 9.06 (d, J = 7.5 Hz, 1H), 8.72 (s, 2H), 7.95 (t, J = 1.4 Hz, 1H), 7.65 (d, J = 1.2 Hz, 1H), 7.62 (dd, J = 2.4, 1.5 Hz, 1H), 7.54 (dd, J = 2.4, 1.4 Hz, 1H), 5.17 (p, J = 7.1 Hz, 1H), 4.94 (d, J = 2.3 Hz, 2H), 4.03 (s, 1H), 3.62 (t, J = 2.3 Hz, 1H), 3.31 (s, 3H), 2.59 (s, 3H), 1.55 (d, J = 7.1 Hz, 3H). LCMS (Analytical Method A) Rt = 1.17 min, MS (ESIpos): m/z = 393.1 (M + H)$^+$. |

In analogy to the procedure described for Example 7 the following examples were prepared using the appropriate carboxylic acid and amine as starting materials.

| Ex. | Structure | Name | Analytical Data |
|---|---|---|---|
| 40 | 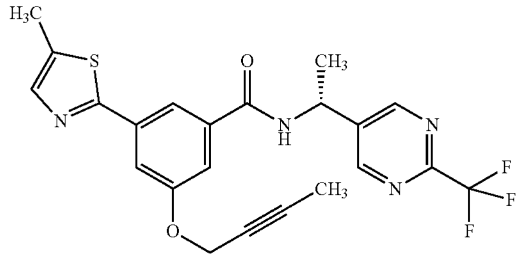 [SMILES: CC#CCOc1cc(C(=O)N[C@H](C)c2cnc(C(F)(F)F)nc2)cc(-c2ncc(C)s2)c1] | 3-(But-2-yn-1-yloxy)-5-(5-methyl-1,3-thiazol-2-yl)-N-[(1R)-1-[2-(trifluoromethyl)-pyrimidin-5-yl]ethyl]benzamide | ¹H NMR (500 MHz, CDCl₃): δ [ppm] = 8.94 (s, 2H), 7.90 (t, J = 1.4 Hz, 1H), 7.58 (dd, J = 2.4, 1.4 Hz, 1H), 7.55-7.51 (m, 1H), 7.48-7.44 (m, 1H), 6.66 (d, J = 7.0 Hz, 1H), 5.36 (p, J = 7.0 Hz, 1H), 4.74 (q, J = 2.3 Hz, 2H), 2.54 (d, J = 1.0 Hz, 3H), 1.87 (t, J = 2.3 Hz, 3H), 1.71 (d, J = 7.0 Hz, 3H). LCMS (Analytical Method F) Rt = 3.478 min, MS (ESIpos): m/z = 461.1 (M + H)⁺. |
| 41 | 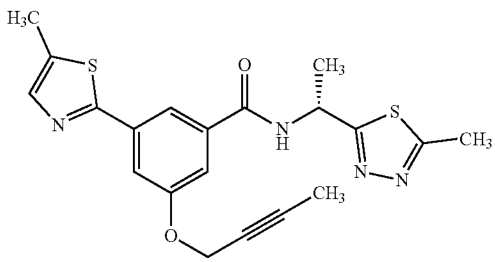 [SMILES: CC#CCOc1cc(C(=O)N[C@H](C)c2nnc(C)s2)cc(-c2ncc(C)s2)c1] | 3-(But-2-yn-1-yloxy)-N-[(1R)-1-(5-methyl-1,3,4-thiadiazol-2-yl)ethyl]-5-(5-methyl-1,3-thiazol-2-yl)benzamide | ¹H NMR (500 MHz, CDCl₃): δ [ppm] = 7.82 (s, 1H), 7.53 (s, 1H), 7.44 (s, 1H), 7.41 (s, 1H), 7.10 (d, J = 7.6 Hz, 1H), 5.61 (p, J = 7.0 Hz, 1H), 4.67 (d, J = 2.2 Hz, 2H), 2.68 (s, 3H), 2.45 (s, 3H), 1.80 (t, J = 2.1 Hz, 3H), 1.72 (d, J = 7.0 Hz, 3H). LCMS (Analytical Method D) Rt = 4.11 min, MS (ESIpos): m/z = 413 (M + H)⁺. |

Example 42

N-[(1R)-1-(5-Methylpyrazin-2-yl)ethyl]-3-(5-methyl-1,3-thiazol-2-yl)-5-(oxetan-3-yloxy)benzamide

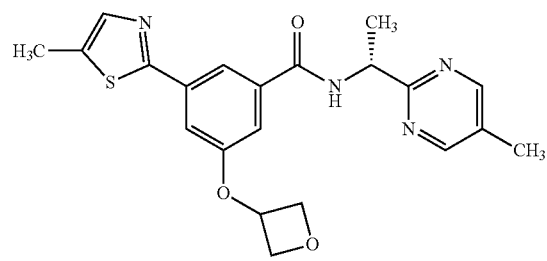

Intermediate 5F (81 mg, 0.28 mmol), (1R)-1-(5-methylpyrazin-2-yl)ethanamine (44 mg, 0.32 mmol), DIPEA (144 mg, 1.11 mmol) and HATU (148 mg, 0.39 mmol) were dissolved in DMF (3.7 mL). The reaction mixture was stirred at RT until complete conversion and evaporated to dryness. Crude material was purified by preparative HPLC (method 1, rt: 1.00 min) to afford the title compound 20 mg (18% yield).

¹H NMR (400 MHz, DMSO-d₆) δ [ppm] 1.54 (d, J=7.07 Hz, 3H) 2.48 (s, 3H) 4.55-4.63 (m, 2H) 4.95 (t, J=6.95 Hz, 2H) 5.23 (s, 1H) 5.46 (s, 1H) 7.37 (t, J=1.52 Hz, 2H) 7.65 (d, J=1.01 Hz, 1H) 7.98 (t, J=1.39 Hz, 1H) 8.49 (d, J=0.76 Hz, 1H) 8.56 (d, J=1.26 Hz, 1H) 9.10 (d, J=7.33 Hz, 1H).

Example 43

N-[(1R)-1-(2-Methylpyrimidin-5-yl)ethyl]-3-(5-methyl-1,3-thiazol-2-yl)-5-(oxetan-3-yloxy)benzamide

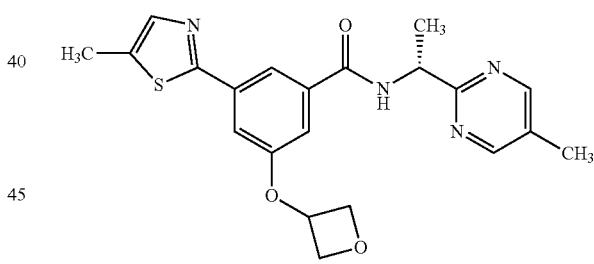

Intermediate 5F (73 mg, 0.25 mmol), (1R)-1-(2-methylpyrimidin-5-yl)ethanamine dihydrochloride (58 mg, 0.28 mmol), DIPEA (0.17 ml, 1.0 mmol) and HATU (133 mg, 0.35 mmol) were dissolved in DMF (3.3 mL). The reaction mixture was stirred at RT until complete conversion and evaporated to dryness. Crude material was purified by preparative HPLC (method 1, rt: 0.93 min) to afford the title compound 48 mg (47% yield).

¹H NMR (400 MHz, DMSO-d₆) δ [ppm] 1.55 (d, J=7.10 Hz, 3H) 2.59 (s, 3H) 4.55-4.62 (m, 2H) 4.91-4.99 (m, 2H) 5.16 (t, J=7.22 Hz, 1H) 5.41-5.50 (m, 1H) 7.31-7.40 (m, 2H) 7.65 (d, J=1.01 Hz, 1H) 7.95 (t, J=1.39 Hz, 1H) 8.72 (s, 2H) 9.07 (d, J=7.35 Hz, 1H).

Example 44

N-[1-(5-Chloro-3-fluoropyridin-2-yl)ethyl]-3-(5-methyl-1,3-thiazol-2-yl)-5-(oxetan-3-yloxy)benzamide

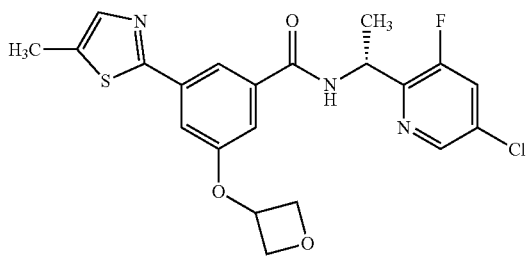 [SMILES: Cc1cnc(-c2cc(OC3COC3)cc(C(=O)N[C@H](C)c3ncc(Cl)cc3F)c2)s1]

Intermediate 5F (74 mg, 0.25 mmol), (+/−) 1-(5-chloro-3-fluoropyridin-2-yl)ethanamine (49 mg, 0.28 mmol), DIPEA (131 mg, 1.02 mmol) and HATU (136 mg, 0.36 mmol) were dissolved in DMF (3.4 mL). The reaction mixture was stirred at RT until complete conversion and evaporated to dryness. Crude material was purified by preparative HPLC (method 1, rt: 1.24 min) to afford the title compound 50 mg (43% yield).

$^1$H NMR (400 MHz, DMSO-$d_6$) δ [ppm] 1.52 (d, J=7.10 Hz, 3H) 4.54-4.62 (m, 2H) 4.95 (t, J=6.59 Hz, 2H) 5.36-5.49 (m, 2H) 7.33-7.39 (m, 2H) 7.64 (d, J=1.27 Hz, 1H) 7.96 (t, J=1.39 Hz, 1H) 8.07 (dd, J=9.89, 2.03 Hz, 1H) 8.50 (d, J=2.03 Hz, 1H) 9.12 (d, J=7.10 Hz, 1H).

Example 45

N-[(6-Methylpyridazin-3-yl)methyl]-3-(5-methyl-1,3-thiazol-2-yl)-5-(oxetan-3-yloxy)benzamide

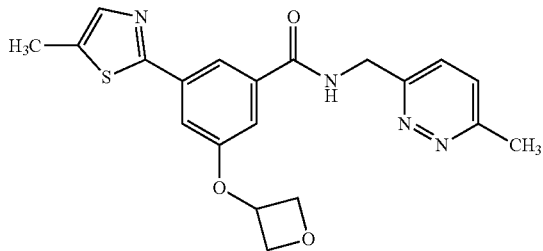

Intermediate 5F (73 mg, 0.25 mmol), 1-(6-methylpyridazin-3-yl)methanamine (34 mg, 0.27 mmol), DIPEA (129 mg, 1.0 mmol) and HATU (133 mg, 0.35 mmol) were dissolved in DMF (3.3 mL). The reaction mixture was stirred at RT until complete conversion and evaporated to dryness. Crude material was purified by preparative HPLC (method 1, rt: 0.87 min) to afford the title compound 40 mg (40% yield).

$^1$H NMR (400 MHz, DMSO-$d_6$) δ [ppm] 2.61 (s, 3H) 4.59 (dd, J=7.86, 4.82 Hz, 2H) 4.73 (d, J=5.83 Hz, 2H) 4.96 (t, J=6.84 Hz, 2H) 5.40-5.50 (m, 1H) 7.36 (dd, J=2.28, 1.52 Hz, 1H) 7.41 (dd, J=2.53, 1.52 Hz, 1H) 7.57 (s, 2H) 7.65 (d, J=1.27 Hz, 1H) 8.01 (t, J=1.39 Hz, 1H) 9.41 (t, J=5.96 Hz, 1H).

Example 46

N-[(1R)-1-(5-Chloropyridin-2-yl)ethyl]-3-(5-methyl-1,3-thiazol-2-yl)-5-(oxetan-3-yloxy)benzamide

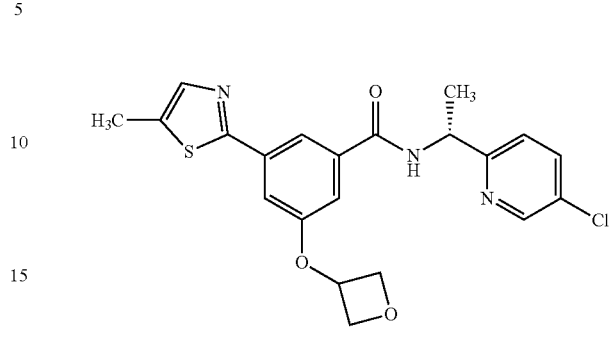

Intermediate 5F (81 mg, 0.28 mmol), (1R)-1-(5-chloropyridin-2-yl)ethanamine hydrochloride (59 mg, 0.31 mmol), DIPEA (144 mg, 1.11 mmol) and HATU (148 mg, 0.39 mmol) were dissolved in DMF (3.7 mL). The reaction mixture was stirred at RT until complete conversion and evaporated to dryness. Crude material was purified by preparative HPLC (method 2, rt: 1.17 min) to afford the title compound 20 mg (17% yield).

$^1$H NMR (400 MHz, DMSO-$d_6$) δ [ppm] 1.52 (d, J=7.10 Hz, 3H) 4.59 (ddd, J=7.16, 4.63, 2.66 Hz, 2H) 4.96 (t, J=6.59 Hz, 2H) 5.19 (t, J=7.22 Hz, 1H) 5.42-5.50 (m, 1H) 7.36-7.41 (m, 2H) 7.46 (d, J=8.62 Hz, 1H) 7.65 (d, J=1.27 Hz, 1H) 7.90 (dd, J=8.62, 2.53 Hz, 1H) 7.99 (t, J=1.39 Hz, 1H) 8.58 (d, J=2.03 Hz, 1H) 9.09 (d, J=7.35 Hz, 1H).

Example 47

N-[(1R)-1-(6-Methylpyridazin-3-yl)ethyl]-3-(5-methyl-1,3-thiazol-2-yl)-5-(oxetan-3-yloxy)benzamide

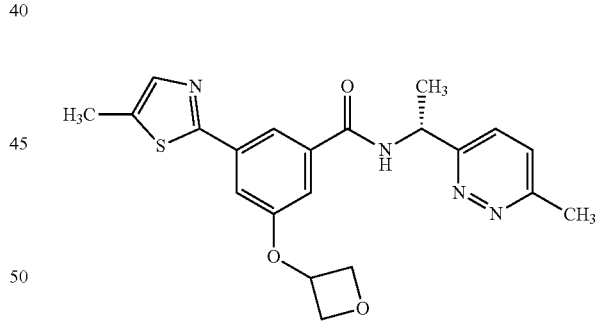

Intermediate 5F (72 mg, 0.25 mmol), (1R)-1-(6-methylpyridazin-3-yl)ethanamine hydrochloride (Intermediate XV, 47 mg, 0.27 mmol), DIPEA (128 mg, 0.99 mmol) and HATU (132 mg, 0.35 mmol) were dissolved in DMF (3.3 mL). The reaction mixture was stirred at RT until complete conversion and evaporated to dryness. Crude material was purified by preparative HPLC (method 1, rt: 0.92 min) to afford the title compound 30 mg (30% yield).

$^1$H NMR (400 MHz, DMSO-$d_6$) δ [ppm] 1.59 (d, J=7.10 Hz, 3H) 2.60 (s, 3H) 4.59 (ddd, J=7.10, 4.44, 2.91 Hz, 2H) 4.96 (t, J=6.72 Hz, 2H) 5.36 (t, J=7.35 Hz, 1H) 5.46 (t, J=5.32 Hz, 2H) 7.38 (d, J=1.52 Hz, 2H) 7.51-7.56 (m, 1H) 7.57-7.62 (m, 1H) 7.65 (d, J=1.01 Hz, 1H) 7.99 (t, J=1.27 Hz, 1H) 9.16 (d, J=7.60 Hz, 1H).

Example 48

3-(5-Methyl-1,3-thiazol-2-yl)-5-(oxetan-3-yloxy)-N-{(1R)-1-[2-(trifluoromethyl)pyrimidin-5-yl]ethyl}benzamide

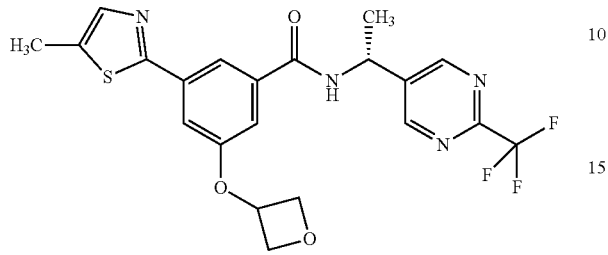

Intermediate 5F (76 mg, 0.26 mmol), Intermediate VI (65 mg, 0.29 mmol), DIPEA (135 mg, 1.04 mmol) and HATU (139 mg, 0.36 mmol) were dissolved in DMF (3.5 mL). The reaction mixture was stirred at RT until complete conversion and evaporated to dryness. Crude material was purified by column chromatography (silica, gel, hexane/EE gradient) to afford the title compound 80 mg (65% yield).

$^1$H NMR (400 MHz, DMSO-$d_6$) δ [ppm] 1.61 (d, J=7.10 Hz, 3H) 4.54-4.62 (m, 2H) 4.96 (t, J=6.59 Hz, 2H) 5.29 (s, 1H) 5.46 (t, J=4.94 Hz, 1H) 7.37 (d, J=1.01 Hz, 2H) 7.65 (d, J=1.01 Hz, 1H) 7.96 (t, J=1.39 Hz, 1H) 9.12 (s, 2H) 9.18 (d, J=7.10 Hz, 1H).

Example 49

N-[1-(3-Chloro-5-fluoropyridin-2-yl)ethyl]-3-(5-methyl-1,3-thiazol-2-yl)-5-(oxetan-3-yloxy)benzamide

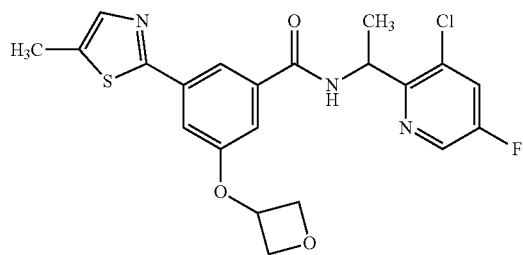 [SMILES: Cc1cnc(-c2cc(OC3COC3)cc(C(=O)NC(C)c3ncc(F)cc3Cl)c2)s1]

Intermediate 5F (79 mg, 0.27 mmol), (+/−) 1-(3-chloro-5-fluoropyridin-2-yl)ethanamine (52 mg, 0.30 mmol), DIPEA (140 mg, 1.08 mmol) and HATU (144 mg, 0.38 mmol) were dissolved in DMF (3.6 mL). The reaction mixture was stirred at RT until complete conversion and evaporated to dryness. Crude material was purified by preparative HPLC (method 1, rt: 1.24 min) to afford the title compound 60 mg (50% yield).

$^1$H NMR (400 MHz, DMSO-$d_6$) δ [ppm] 1.49 (d, J=7.07 Hz, 3H) 4.54-4.62 (m, 2H) 4.95 (t, J=6.82 Hz, 2H) 5.41-5.48 (m, 1H) 5.53 (m, 1H) 7.33-7.39 (m, 2H) 7.64 (d, J=1.26 Hz, 1H) 7.97 (t, J=1.52 Hz, 1H) 8.09 (dd, J=8.59, 2.53 Hz, 1H) 8.58 (d, J=2.78 Hz, 1H) 9.09 (d, J=7.07 Hz, 1H).

Example 50

N-[(1R)-1-(5-Methyl-1,3,4-thiadiazol-2-yl)ethyl]-3-(5-methyl-1,3-thiazol-2-yl)-5-(oxetan-3-yloxy)benzamide

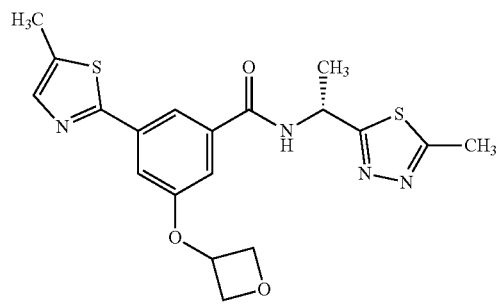 [SMILES: Cc1cnc(-c2cc(OC3COC3)cc(C(=O)N[C@H](C)c3nnc(C)s3)c2)s1]

3-(5-Methyl-1,3-thiazol-2-yl)-5-(oxetan-3-yloxy)benzoic acid (58.3 mg, 0.2 mmol), (1R)-1-(5-methyl-1,3,4-thiadiazol-2-yl)ethanamine hydrochloride (43 mg, 0.24 mmol) and DIPEA (0.174 mL, 1.0 mmol) were dissolved in DCM (2 mL). T3P (0.23 mL, 0.4 mmol, 50% solution in EtOAc) was added and the reaction mixture stirred at RT for 2 h. The reaction mixture washed with 2 M NaOH (2 mL) and the aqueous layer further extracted with DCM (2×2 mL). The crude material was purified by Biotage Isolera™ chromatography on silica gel (eluent: heptane-acetone, 0 to 1:1) to give 44.7 mg (54% yield) of the title compound as white powder.

$^1$H NMR (500 MHz, Chloroform-d): δ [ppm]=7.87 (t, J=1.3 Hz, 1H), 7.52 (d, J=1.1 Hz, 1H), 7.40 (dd, J=2.4, 1.4 Hz, 1H), 7.22 (dd, J=2.3, 1.5 Hz, 1H), 7.08 (d, J=7.5 Hz, 1H), 5.68 (p, J=7.0 Hz, 1H), 5.33 (p, J=5.5 Hz, 1H), 5.06-5.01 (m, 2H), 4.78 (dd, J=7.4, 5.4 Hz, 2H), 2.77 (s, 3H), 2.53 (d, J=1.1 Hz, 3H), 1.79 (d, J=6.9 Hz, 3H).

LCMS (Analytical Method D) Rt=3.61 min, MS (ESI-pos): m/z=417 (M+H)$^+$.

Example 51

N-[(1R)-1-(6-methylpyridin-3-yl)ethyl]-3-(5-methyl-1,3-thiazol-2-yl)-5-(oxetan-3-yloxy)benzamide

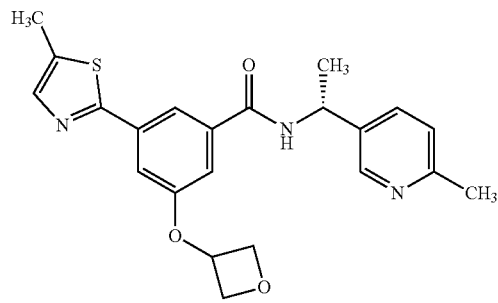 [SMILES: Cc1ccc([C@@H](C)NC(=O)c2cc(OC3COC3)cc(-c3ncc(C)s3)c2)cn1]

3-(5-Methyl-1,3-thiazol-2-yl)-5-(oxetan-3-yloxy)benzoic acid (210 mg, 0.72 mmol), (1R)-1-(6-methylpyridin-3-yl)ethanamine (37 mg, 0.27 mmol), DIPEA (191 μL, 1.1 mmol) and HATU (125 mg, 0.33 mmol) were dissolved in DCM (1 mL) and stirred at RT for 2 h. The reaction mixture was diluted with DCM (1 mL), washed with water (1 mL), dried (over Na$_2$SO$_4$) and concentrated in vacuo. The crude material was purified twice by preparative HPLC (Method A) to give 16.8 mg (6% yield) of the title compound as a white powder.

$^1$H NMR (500 MHz, Chloroform-d): δ [ppm]=8.55 (d, J=2.3 Hz, 1H), 7.83 (t, J=1.3 Hz, 1H), 7.59 (dd, J=8.0, 2.4 Hz, 1H), 7.51 (d, J=1.2 Hz, 1H), 7.36 (dd, J=2.4, 1.4 Hz, 1H), 7.21-7.11 (m, 2H), 6.48 (d, J=7.5 Hz, 1H), 5.36-5.26 (m, 2H), 5.02 (t, J=7.0 Hz, 2H), 4.76 (t, J=5.8 Hz, 2H), 2.54 (s, 3H), 2.53 (d, J=1.1 Hz, 3H), 1.63 (d, J=7.0 Hz, 3H).

LCMS (Analytical Method F) Rt=1.76 min, MS (ESIpos): m/z=409 (M+H)$^+$.

In analogy to the procedure described for Example 1 the following example was prepared using the appropriate carboxylic acid and amine as starting materials.

Example 54

N-[(6-Methylpyridazin-3-yl)methyl]-3-(5-methyl-1,3-thiazol-2-yl)-5-[(2S)-tetrahydrofuran-2-ylmethoxy]benzamide

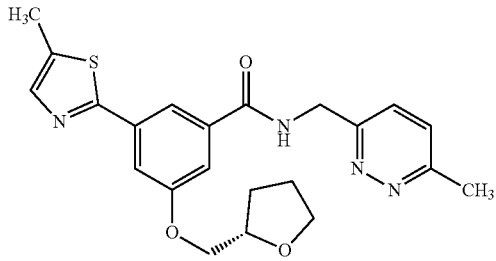 [SMILES: Cc1ccc(CNC(=O)c2cc(OC[C@@H]3CCCO3)cc(-c3ncc(C)s3)c2)nn1]

A mixture of 3-(5-methyl-1,3-thiazol-2-yl)-5-[(2S)-tetrahydrofuran-2-ylmethoxy]benzoic acid (100 mg, 0.313 mmol), (6-methylpyridazin-3-yl)methanamine (46 mg, 0.376 mmol), HATU (142 mg, 0.376 mmol) and DIPEA (60 mg, 0.47 mmol) in DCM (4 mL) were stirred at RT for 4 h. The solvent was removed in vacuo and the residue purified by Biotage Isolera™ chromatography (silica, eluting with 100% EtOAc followed by 1-6% MeOH in DCM) to give 110 mg (79% yield) of the title compound as an off-white gum.

$^1$H NMR (500 MHz, CDCl$_3$): δ [ppm] 7.89 (t, J=1.4 Hz, 1H), 7.76 (s, 1H), 7.63-7.55 (m, 1H), 7.50-7.42 (m, 3H), 7.31 (d, J=8.6 Hz, 1H), 4.89 (d, J=5.3 Hz, 2H), 4.29 (qd, J=6.8, 4.3 Hz, 1H), 4.04 (h, J=5.8 Hz, 2H), 3.97-3.88 (m, 1H), 3.87-3.79 (m, 1H), 2.69 (s, 3H), 2.50 (d, J=0.9 Hz, 3H), 2.07 (dtd, J=12.4, 7.6, 5.5 Hz, 1H), 2.01-1.91 (m, 2H), 1.76 (dq, J=12.2, 7.0 Hz, 1H).

| Ex. | Structure | Name | Analytical Data |
|---|---|---|---|
| 52 | (structure shown) | 3-(5-Methyl-1,3-thiazol-2-yl)-5-(oxetan-3-yloxy)-N-{[6-(trifluoromethyl)pyridazin-3-yl]methyl}benzamide | $^1$H NMR (500 MHz, CDCl$_3$): δ [ppm] = 7.91 (t, J = 1.3 Hz, 1H), 7.82 (s, 2H), 7.66 (t, J = 5.2 Hz, 1H), 7.50 (d, J = 1.1 Hz, 1H), 7.39 (dd, J = 2.3, 1.4 Hz, 1H), 7.23 (dd, J = 2.3, 1.5 Hz, 1H), 5.32 (p, J = 5.5 Hz, 1H), 5.06-4.99 (m, 4H), 4.77 (dd, J = 7.7, 5.1 Hz, 2H), 2.52 (d, J = 1.0 Hz, 3H). LCMS (Analytical Method D) Rt = 3.97, MS (ESIpos) m/z = 451 (M + H)$^+$. |

In analogy to the procedure described for Example 7 the following example was prepared using the appropriate carboxylic acid and amine as starting materials.

| Ex. | Structure | Name | Analytical Data |
|---|---|---|---|
| 53 | (structure shown) | 3-(5-Methyl-1,3-thiazol-2-yl)-5-(oxetan-3-yloxy)-N-[(1R)-1-[2-(trifluoromethyl)pyrimidin-5-yl]propyl]benzamide | $^1$H NMR (500 MHz, CDCl$_3$): δ [ppm] = 8.91 (s, 2H), 7.87 (s, 1H), 7.53 (d, J = 1.1 Hz, 1H), 7.38 (dd, J = 2.3, 1.4 Hz, 1H), 7.18-7.14 (m, 1H), 6.61 (d, J = 6.9 Hz, 1H), 5.31 (p, J = 5.5 Hz, 1H), 5.09 (q, J = 7.1 Hz, 1H), 5.05-5.00 (m, 2H), 4.77 (dd, J = 7.4, 5.2 Hz, 2H), 2.54 (d, J = 1.0 Hz, 3H), 2.12-1.97 (m, 2H), 1.08 (t, J = 7.4 Hz, 3H). LCMS (Analytical Method F) Rt = 3.48 min, MS (ESIpos): m/z = 479 (M + H)$^+$. |

Example 55

N-[(5-Chloro-3-fluoropyridin-2-yl)methyl]-3-(5-methyl-1,3-thiazol-2-yl)-5-[(2S)-tetrahydrofuran-2-ylmethoxy]benzamide

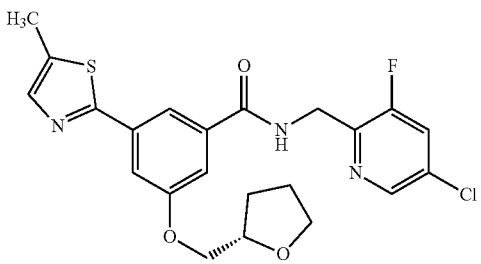 [SMILES: Cc1cnc(-c2cc(OC[C@@H]3CCCO3)cc(C(=O)NCc3ncc(Cl)cc3F)c2)s1]

A mixture of 3-(5-methyl-1,3-thiazol-2-yl)-5-[(2S)-tetrahydrofuran-2-ylmethoxy]benzoic acid (100 mg, 0.313 mmol), (5-chloro-3-fluoropyridin-2-yl)methanamine hydrochloride (74 mg, 0.376 mmol), HATU (143 mg, 0.376 mmol) and DIPEA (101 mg, 0.783 mmol) in DCM (4 mL) was stirred at RT for 3 h. The solvent was removed in vacuo and the residue purified by preparative HPLC (Method A) to give 95.2 mg (64% yield) of the title compound as an off-white solid.

$^1$H NMR (500 MHz, CDCl$_3$): δ [ppm] 8.39 (d, J=1.7 Hz, 1H), 7.92 (t, J=1.4 Hz, 1H), 7.63 (dd, J=2.4, 1.5 Hz, 1H), 7.56-7.41 (m, 4H), 4.81 (dd, J=4.7, 1.7 Hz, 2H), 4.32 (qd, J=7.0, 3.9 Hz, 1H), 4.13-4.04 (m, 2H), 3.95 (dt, J=8.2, 6.7 Hz, 1H), 3.89-3.83 (m, 1H), 2.53 (d, J=1.1 Hz, 3H), 2.14-2.06 (m, 1H), 2.03-1.91 (m, 2H), 1.77 (ddt, J=12.2, 8.4, 7.1 Hz, 1H).

LCMS (Analytical Method F) Rt=3.53 min, MS (ESIpos): m/z=461 (M+H)$^+$.

Example 56: N-[(5-Methylpyrazin-2-yl)methyl]-3-(5-methyl-1,3-thiazol-2-yl)-5-[(2S)-tetrahydrofuran-2-ylmethoxy]benzamide

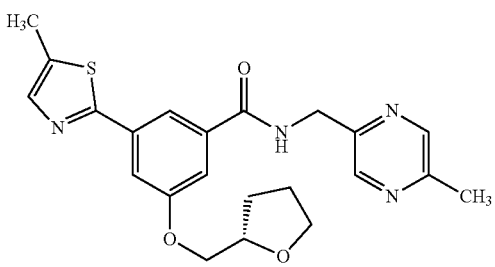 [SMILES: Cc1cnc(CNC(=O)c2cc(OC[C@@H]3CCCO3)cc(-c3ncc(C)s3)c2)cn1]

To a stirred solution of 3-(5-methyl-1,3-thiazol-2-yl)-5-[(2S)-tetrahydrofuran-2-ylmethoxy]benzoic acid (49 mg, 0.15 mmol), 1-(5-methylpyrazin-2-yl)methanamine hydrochloride (26.9 mg, 0.169 mmol), DIPEA (0.107 μL, 0.614 mmol) and DMAP (3.7 mg, 0.03 mmol) in DCM (2 mL) was added HATU (70.0 mg, 0.184 mmol) and the reaction stirred for 1.5 h at RT. The reaction mixture was diluted with water (3 mL) and the aqueous layer re-extracted with further DCM (2×3 mL). The combined organics were dried (over MgSO$_4$) and concentrated under reduced pressure. The crude material was purified by preparative HPLC (Method A) to give 39.8 mg (61% yield) of the title compound as a colourless glass.

$^1$H NMR (500 MHz, CDCl$_3$): δ [ppm] 8.55 (d, J=1.2 Hz, 1H), 8.42 (s, 1H), 7.90 (t, J=1.4 Hz, 1H), 7.61 (dd, J=2.4, 1.5 Hz, 1H), 7.51 (d, J=1.2 Hz, 1H), 7.47 (dd, J=2.4, 1.5 Hz, 1H), 7.25-7.21 (m, 1H), 4.77 (d, J=5.2 Hz, 2H), 4.31 (qd, J=6.9, 3.9 Hz, 1H), 4.11 (dd, J=9.7, 3.9 Hz, 1H), 4.06 (dd, J=9.7, 6.5 Hz, 1H), 3.95 (dt, J=8.2, 6.7 Hz, 1H), 3.88-3.82 (m, 1H), 2.58 (s, 3H), 2.52 (d, J=1.1 Hz, 3H), 2.15-2.05 (m, 1H), 2.03-1.90 (m, 2H), 1.82-1.72 (m, 1H).

LCMS (Analytical Method D) Rt=3.79 min, MS (ESIpos): m/z=425.1 (M$^+$H)+.

Example 57

N-[(1R)-1-(5-Methylpyrazin-2-yl)ethyl]-3-(5-methyl-1,3-thiazol-2-yl)-5-[(2S)-tetrahydrofuran-2-ylmethoxy]benzamide

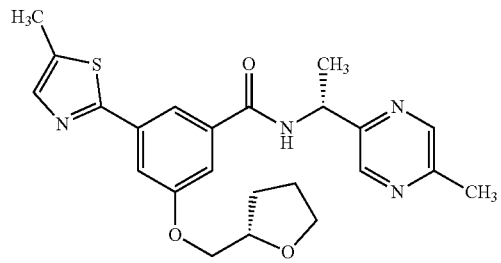 [SMILES: Cc1cnc([C@@H](C)NC(=O)c2cc(OC[C@@H]3CCCO3)cc(-c3ncc(C)s3)c2)cn1]

To a stirred solution of 3-(5-methyl-1,3-thiazol-2-yl)-5-[(2S)-tetrahydrofuran-2-ylmethoxy]benzoic acid (49 mg, 0.15 mmol), (1R)-1-(5-methylpyrazin-2-yl)ethanamine hydrochloride (29.3 mg, 0.169 mmol), DIPEA (0.107 μL, 0.614 mmol) and DMAP (3.7 mg, 0.03 mmol) in DCM (2 mL) was added HATU (70.0 mg, 0.184 mmol) and the reaction stirred for 1.5 h at RT. The reaction mixture was diluted with water (3 mL) and the aqueous layer re-extracted with further DCM (2×3 mL). The combined organics were dried (over MgSO$_4$) and concentrated under reduced pressure. The crude material was purified by preparative HPLC (Method A) to give 29.7 mg (44% yield) of the title compound as an orange glass.

$^1$H NMR (500 MHz, CDCl$_3$): δ [ppm] 8.53 (d, J=1.3 Hz, 1H), 8.41 (s, 1H), 7.90 (s, 1H), 7.60 (dd, J=2.4, 1.5 Hz, 1H), 7.52 (d, J=1.2 Hz, 1H), 7.45 (dd, J=2.4, 1.5 Hz, 1H), 7.31 (d, J=7.4 Hz, 1H), 5.42 (p, J=6.9 Hz, 1H), 4.31 (qd, J=7.0, 3.9 Hz, 1H), 4.10 (dd, J=9.7, 3.8 Hz, 1H), 4.05 (dd, J=9.7, 6.6 Hz, 1H), 3.95 (dt, J=8.3, 6.7 Hz, 1H), 3.88-3.83 (m, 1H), 2.57 (s, 3H), 2.53 (d, J=1.1 Hz, 3H), 2.09 (dtd, J=12.4, 7.7, 7.2, 5.5 Hz, 1H), 1.97 (tq, J=15.8, 6.0, 5.2 Hz, 2H), 1.76 (ddd, J=15.6, 12.3, 7.1 Hz, 1H), 1.60 (d, J=6.8 Hz, 3H).

LCMS (Analytical Method F) Rt=3.96 min, MS (ESIpos): m/z=439.1 (M+H)$^+$.

Example 58

3-(5-Methyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide

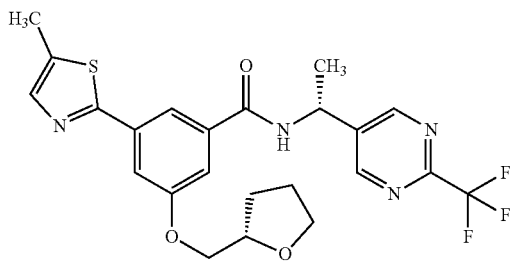 [SMILES: Cc1cnc(-c2cc(OC[C@@H]3CCCO3)cc(C(=O)N[C@H](C)c3cnc(C(F)(F)F)nc3)c2)s1]

To a stirred solution of 3-(5-methyl-1,3-thiazol-2-yl)-5-[(2S)-tetrahydrofuran-2-ylmethoxy]benzoic acid (49 mg, 0.15 mmol), Intermediate VI (38.4 mg, 0.169 mmol), DIPEA (0.107 μL, 0.614 mmol) and DMAP (3.7 mg, 0.03 mmol) in DCM (2 mL) was added HATU (70.0 mg, 0.184 mmol) and the reaction stirred for 1.5 h at RT. The reaction mixture was diluted with water (3 mL) and the aqueous layer re-extracted with further DCM (2×3 mL). The combined organics were dried (over MgSO$_4$) and concentrated under reduced pressure. The crude material was purified preparative HPLC (Method A). The material was further purified by trituration from acetonitrile to give 17.5 mg (23% yield) of the title compound as a white powder.

$^1$H NMR (500 MHz, CDCl$_3$): δ [ppm] 8.94 (s, 2H), 7.89 (s, 1H), 7.56 (dd, J=2.4, 1.5 Hz, 1H), 7.52 (d, J=1.2 Hz, 1H), 7.41 (dd, J=2.3, 1.5 Hz, 1H), 6.71 (d, J=6.6 Hz, 1H), 5.35 (p, J=7.0 Hz, 1H), 4.30 (qd, J=7.0, 3.7 Hz, 1H), 4.09 (dd, J=9.7, 3.7 Hz, 1H), 4.02 (dd, J=9.7, 6.6 Hz, 1H), 3.97-3.92 (m, 1H), 3.88-3.82 (m, 1H), 2.53 (d, J=1.1 Hz, 3H), 2.09 (dtd, J=12.3, 7.6, 7.2, 5.4 Hz, 1H), 1.97 (qt, J=12.1, 5.8 Hz, 2H), 1.79-1.74 (m, 1H), 1.72 (d, J=7.2 Hz, 3H).

LCMS (Analytical Method F) Rt=3.59 min, MS (ESIpos): m/z=493.1 (M+H)$^+$.

Example 59

N-[(1R)-1-(6-Methylpyridazin-3-yl)ethyl]-3-(5-methyl-1,3-thiazol-2-yl)-5-[(2S)-tetrahydrofuran-2-ylmethoxy]benzamide

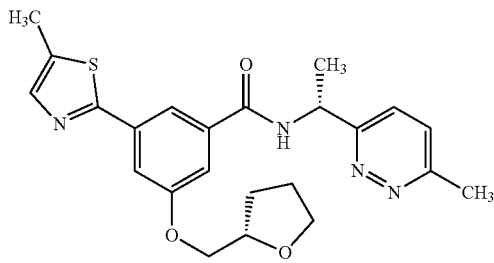 [SMILES: Cc1ccc([C@@H](C)NC(=O)c2cc(OC[C@@H]3CCCO3)cc(-c3ncc(C)s3)c2)nn1]

To a stirred solution of 3-(5-methyl-1,3-thiazol-2-yl)-5-[(2S)-tetrahydrofuran-2-ylmethoxy]benzoic acid (49 mg, 0.15 mmol), (1R)-1-(6-methylpyridazin-3-yl)ethanamine hydrochloride (29.3 mg, 0.169 mmol), DIPEA (0.107 μL, 0.614 mmol) and DMAP (3.7 mg, 0.03 mmol) in DCM (2 mL) was added HATU (70.0 mg, 0.184 mmol) and the reaction stirred for 1.5 h at RT. The reaction mixture was diluted with water (3 mL) and the aqueous layer re-extracted with further DCM (2×3 mL). The combined organics were dried (over MgSO$_4$) and concentrated under reduced pressure. The crude material was purified by preparative HPLC (Method A). The material was further purified by trituration from acetonitrile to give 31.9 mg (47% yield) of the title compound as a white powder.

$^1$H NMR (500 MHz, CDCl$_3$): δ [ppm] 7.90 (s, 1H), 7.71 (d, J=7.2 Hz, 1H), 7.63-7.60 (m, 1H), 7.51 (d, J=1.0 Hz, 1H), 7.46-7.43 (m, 1H), 7.40 (d, J=8.6 Hz, 1H), 7.33 (d, J=8.6 Hz, 1H), 5.46 (p, J=6.9 Hz, 1H), 4.35-4.26 (m, 1H), 4.08 (qd, J=9.7, 5.2 Hz, 2H), 4.00-3.91 (m, 1H), 3.88-3.79 (m, 1H), 2.72 (s, 3H), 2.52 (d, J=0.8 Hz, 3H), 2.15-2.05 (m, 1H), 1.97 (qt, J=12.3, 6.7 Hz, 2H), 1.85-1.74 (m, 1H), 1.68 (d, J=6.8 Hz, 3H).

LCMS (Analytical Method F) Rt=2.67 min, MS (ESIpos): m/z=439.1 (M+H)$^+$.

Example 60

3-(5-Methyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide

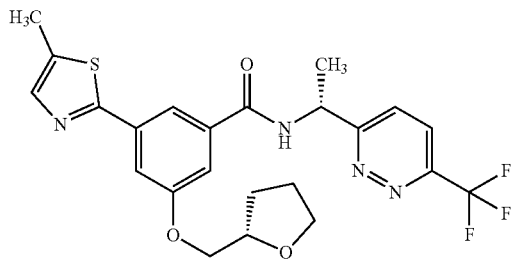 [SMILES: Cc1cnc(-c2cc(OC[C@@H]3CCCO3)cc(C(=O)N[C@H](C)c3ccc(C(F)(F)F)nn3)c2)s1]

To a stirred solution of 3-(5-methyl-1,3-thiazol-2-yl)-5-[(2S)-tetrahydrofuran-2-ylmethoxy]benzoic acid (50 mg, 0.157 mmol), (1R)-1-[6-(trifluoromethyl)pyridazin-3-yl]ethanamine hydrochloride (39 mg, 0.171 mmol) and DIPEA (109 μL, 0.626 mmol) in DCM (1 mL) was added HATU (71 mg, 0.187 mmol) and the reaction mixture stirred at RT for 2 h. The mixture was diluted with DCM (1 mL) and washed with water (2×2 mL). The aqueous phase was re-extracted with DCM (2 mL) and the combined organics dried (over Na$_2$SO$_4$) and concentrated in vacuo. The crude material was purified by preparative HPLC (Method A) to give 34.7 mg (45% yield) of the title compound as a white powder.

$^1$H NMR (500 MHz, CDCl$_3$): δ [ppm] 7.83 (s, 1H), 7.75 (d, J=8.7 Hz, 1H), 7.67 (d, J=8.7 Hz, 1H), 7.53 (dd, J=2.4, 1.5 Hz, 1H), 7.45 (d, J=1.2 Hz, 1H), 7.42-7.34 (m, 2H), 5.53 (p, J=7.0 Hz, 1H), 4.23 (qd, J=6.9, 4.0 Hz, 1H), 4.05-3.94 (m, 2H), 3.92-3.83 (m, 1H), 3.82-3.74 (m, 1H), 2.45 (d, J=1.1 Hz, 3H), 2.07-1.97 (m, 1H), 1.93-1.84 (m, 2H), 1.76-1.65 (m, 4H).

LCMS (Analytical Method F) Rt=3.50 min, MS (ESIpos): m/z=493.1 (M+H)$^+$.

Example 61

N-[(1R)-1-(6-methylpyridazin-3-yl)ethyl]-3-(5-methyl-1,3-thiazol-2-yl)-5-[(2R)-tetrahydrofuran-2-ylmethoxy]benzamide

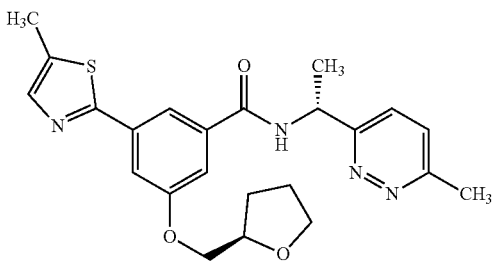 [SMILES: Cc1ccc([C@@H](C)NC(=O)c2cc(OC[C@H]3CCCO3)cc(-c3ncc(C)s3)c2)nn1]

To a solution of 3-(5-methyl-1,3-thiazol-2-yl)-5-[[(2R)-tetrahydrofuran-2-yl]methoxy]benzoic acid (40 mg, 0.125 mmol), (1R)-1-(6-methylpyridazin-3-yl)ethanamine hydrochloride (29 mg, 0.167 mmol) and DIPEA (87 µL, 0.499 mmol) in DCM (2 mL) was added HATU (60 mg, 0.158 mmol). The reaction mixture was stirred for 1 h at RT then diluted with DCM (10 mL) and water (10 mL). The aqueous layer was re-extracted with DCM (10 mL) and the combined organic layers dried (over $Na_2SO_4$) and concentrated under reduced pressure. The crude material was purified by preparative HPLC (Method A) to give 45 mg (78% yield) of the title compound as a white foam.

$^1$H NMR (500 MHz, $CDCl_3$): δ [ppm] 7.88 (s, 1H), 7.76 (d, J=7.3 Hz, 1H), 7.62-7.57 (m, 1H), 7.48 (s, 1H), 7.45-7.41 (m, 1H), 7.39 (d, J=8.6 Hz, 1H), 7.31 (d, J=8.6 Hz, 1H), 5.49-5.40 (m, 1H), 4.32-4.24 (m, 1H), 4.09-4.00 (m, 2H), 3.96-3.89 (m, 1H), 3.86-3.78 (m, 1H), 2.70 (s, 3H), 2.50 (s, 3H), 2.13-2.03 (m, 1H), 2.02-1.86 (m, 2H), 1.82-1.71 (m, 1H), 1.66 (d, J=6.9 Hz, 3H).

LCMS (Analytical Method D) Rt=3.66 min, MS (ESIpos): m/z=439.1 $(M+H)^+$.

Example 62

N-[(6-Methylpyridazin-3-yl)methyl]-3-(5-methyl-1,3-thiazol-2-yl)-5-[(2R)-tetrahydrofuran-2-ylmethoxy]benzamide

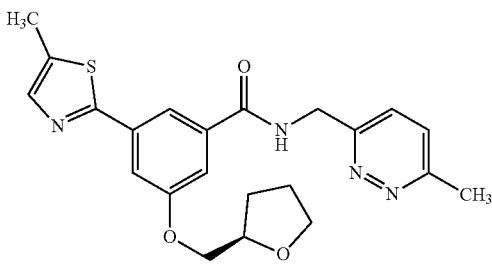 [SMILES: Cc1ccc(CNC(=O)c2cc(OC[C@H]3CCCO3)cc(-c3ncc(C)s3)c2)nn1]

To a solution of 3-(5-methyl-1,3-thiazol-2-yl)-5-[[(2R)-tetrahydrofuran-2-yl]methoxy]benzoic acid (40 mg, 0.125 mmol), 1-(6-methylpyridazin-3-yl)methanamine (25 mg, 0.203 mmol) and DIPEA (87 µL, 0.499 mmol) in DCM (2 mL) was added HATU (60 mg, 0.158 mmol). The reaction was stirred for 16 hours at RT then diluted with DCM (10 mL) and water (10 mL). The aqueous layer was re-extracted with DCM (10 mL) and the combined organic layers were dried (over $Na_2SO_4$) and concentrated under reduced pressure. The crude material was purified by preparative HPLC (Method A) to give 44 mg (79% yield) of the title compound as a yellow solid.

$^1$H NMR (500 MHz, $CDCl_3$): δ [ppm] 7.89 (s, 1H), 7.71 (t, J=5.0 Hz, 1H), 7.62-7.58 (m, 1H), 7.51-7.43 (m, 3H), 7.31 (d, J=8.6 Hz, 1H), 4.90 (d, J=5.3 Hz, 2H), 4.34-4.23 (m, 1H), 4.09-4.01 (m, 2H), 3.96-3.90 (m, 1H), 3.87-3.80 (m, 1H), 2.70 (s, 3H), 2.50 (s, 3H), 2.13-2.03 (m, 1H), 2.03-1.88 (m, 2H), 1.85-1.72 (m, 1H).

LCMS (Analytical Method F) Rt=2.55 min, MS (ESIpos): m/z=425.2 $(M+H)^+$.

Example 63

3-(5-Methyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide

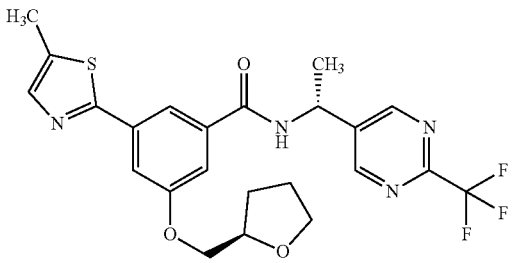 [SMILES: Cc1cnc(-c2cc(OC[C@H]3CCCO3)cc(C(=O)N[C@H](C)c3cnc(C(F)(F)F)nc3)c2)s1]

To a solution of 3-(5-methyl-1,3-thiazol-2-yl)-5-[[(2R)-tetrahydrofuran-2-yl]methoxy]benzoic acid (40 mg, 0.125 mmol), Intermediate VI (33 mg, 0.190 mmol) and DIPEA (87 µL, 0.499 mmol) in DCM (2 mL) was added HATU (60 mg, 0.158 mmol).

The reaction was stirred for 1 h at RT then diluted with DCM (10 mL) and water (10 mL). The aqueous layer was re-extracted with DCM (10 mL) and the combined organic layers dried (over $Na_2SO_4$) and concentrated under reduced pressure. The crude material was purified by preparative HPLC (Method A) to give 42 mg (65% yield) of the title compound as a white solid.

$^1$H NMR (500 MHz, $CDCl_3$): δ [ppm] 8.93 (s, 2H), 7.81 (s, 1H), 7.48 (s, 2H), 7.30 (s, 1H), 6.95 (s, 1H), 5.40-5.27 (m, 1H), 4.33-4.23 (m, 1H), 4.07-3.90 (m, 3H), 3.90-3.81 (m, 1H), 2.51 (s, 3H), 2.13-2.03 (m, 1H), 2.03-1.89 (m, J=7.3, 6.6 Hz, 2H), 1.76-1.64 (m, 4H).

LCMS (Analytical Method F) Rt=3.60 min, MS (ESIpos): m/z=493.1 $(M+H)^+$.

Example 64

N-[(1R)-1-(5-methylpyrazin-2-yl)ethyl]-3-(5-methyl-1,3-thiazol-2-yl)-5-[(2R)-tetrahydrofuran-2-ylmethoxy]benzamide

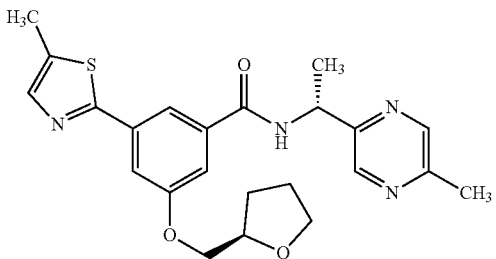 [SMILES: Cc1cnc([C@@H](C)NC(=O)c2cc(OC[C@H]3CCCO3)cc(-c3ncc(C)s3)c2)cn1]

To a solution of 3-(5-methyl-1,3-thiazol-2-yl)-5-[[(2R)-tetrahydrofuran-2-yl]methoxy]benzoic acid (40 mg, 0.125 mmol), (1R)-1-(5-methylpyrazin-2-yl)ethanamine hydrochloride (33 mg, 0.190 mmol) and DIPEA (87 µL, 0.499 mmol) in DCM (2 mL) was added HATU (60 mg, 0.158 mmol). The reaction was stirred for 1 h at RT then diluted with DCM (10 mL) and water (10 mL). The aqueous layer was re-extracted with DCM (10 mL) and the combined organic layers dried (over Na$_2$SO$_4$) and concentrated under reduced pressure. The crude material was purified by preparative HPLC (Method A) to give 49 mg (85% yield) of the title compound as a beige solid.

$^1$H NMR (500 MHz, CDCl$_3$) δ 8.52 (s, 1H), 8.40 (s, 1H), 7.90-7.84 (m, 1H), 7.62-7.56 (m, 1H), 7.50 (s, 1H), 7.46-7.41 (m, 1H), 7.30 (d, J=7.0 Hz, 1H), 5.42 (p, J=6.9 Hz, 1H), 4.38-4.22 (m, 1H), 4.11-4.01 (m, 2H), 3.98-3.91 (m, 1H), 3.88-3.81 (m, 1H), 2.56 (s, 3H), 2.51 (s, 3H), 2.14-2.04 (m, 1H), 2.03-1.88 (m, 2H), 1.81-1.69 (m, 1H), 1.59 (d, J=6.8 Hz, 3H).

LCMS (Analytical Method F) Rt=3.03 min, MS (ESIpos): m/z=439.1 (M+H)$^+$.

In analogy to the procedure described for Example 1 the following examples were prepared using the appropriate carboxylic acid and amine as starting materials.

| Ex. | Structure | Name | Analytical Data |
|---|---|---|---|
| 65 | 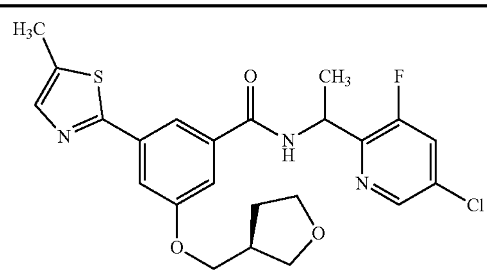 | N-[1-(5-Chloro-3-fluoropyridin-2-yl)ethyl]-3-(5-methyl-1,3-thiazol-2-yl)-5-[(3S)-tetrahydrofuran-3-ylmethoxy]benzamide | $^1$H NMR (500 MHz, CDCl$_3$): δ [ppm] = 8.38 (d, J = 1.8 Hz, 1H), 7.89 (t, J = 1.3 Hz, 1H), 7.58 (dd, J = 2.3, 1.5 Hz, 1H), 7.57-7.51 (m, 2H), 7.47 (dd, J = 8.9, 2.0 Hz, 1H), 7.42 (dd, J = 2.3, 1.5 Hz, 1H), 5.66 (p, J = 6.7 Hz, 1H), 4.06 (ddd, J = 9.0, 6.4, 2.7 Hz, 1H), 4.00 (td, J = 8.9, 8.4, 3.7 Hz, 1H), 3.97-3.88 (m, 2H), 3.83-3.77 (m, 1H), 3.72 (dd, J = 8.1, 5.4 Hz, 1H), 2.77 (dt, J = 14.1, 7.5 Hz, 1H), 2.54 (d, J = 1.1 Hz, 3H), 2.13 (dtd, J = 13.4, 8.1, 5.6 Hz, 1H), 1.76 (td, J = 12.7, 6.9 Hz, 1H), 1.56 (d, J = 6.8 Hz, 3H). LCMS (Analytical Method F) Rt = 3.79 min, MS (ESIpos): m/z = 476.1 (M + H)$^+$. |
| 66 | 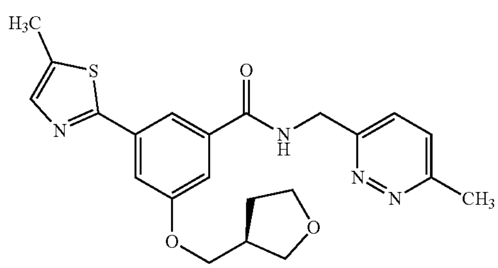 [SMILES: Cc1ccc(CNC(=O)c2cc(OC[C@H]3CCOC3)cc(-c3ncc(C)s3)c2)nn1] | N-[(6-Methylpyridazin-3-yl)methyl]-3-(5-methyl-1,3-thiazol-2-yl)-5-[(3S)-tetrahydrofuran-3-ylmethoxy]benzamide | $^1$H NMR (500 MHz, CDCl$_3$): δ [ppm] = 7.92 (t, J = 1.4 Hz, 1H), 7.68 (s, 1H), 7.63 (dd, J = 2.4, 1.5 Hz, 1H), 7.55-7.51 (m, 2H), 7.46 (dd, J = 2.4, 1.5 Hz, 1H), 7.40 (d, J = 8.6 Hz, 1H), 4.95 (d, J = 5.2 Hz, 2H), 4.08 (dd, J = 8.9, 6.5 Hz, 1H), 4.05-4.00 (m, 1H), 3.99-3.90 (m, 2H), 3.86-3.79 (m, 1H), 3.74 (dd, J = 8.9, 5.4 Hz, 1H), 2.83-2.77 (m, 1H), 2.76 (s, 3H), 2.55 (d, J = 1.1 Hz, 3H), 2.20-2.12 (m, 1H), 1.78 (td, J = 12.7, 6.9 Hz, 1H). LCMS (Analytical Method F) Rt = 2.50 min, MS (ESIpos): m/z = 425.1 (M + H)$^+$. |
| 67 | 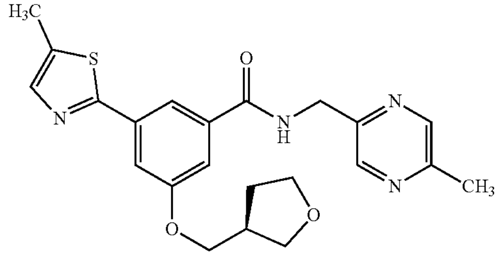 [SMILES: Cc1cnc(CNC(=O)c2cc(OC[C@H]3CCOC3)cc(-c3ncc(C)s3)c2)cn1] | N-[(5-Methylpyrazin-2-yl)methyl]-3-(5-methyl-1,3-thiazol-2-yl)-5-[(3S)-tetrahydrofuran-3-ylmethoxy]benzamide | $^1$H NMR (500 MHz, CDCl$_3$): δ [ppm] = 8.56 (d, J = 1.2 Hz, 1H), 8.42 (s, 1H), 7.88 (t, J = 1.4 Hz, 1H), 7.58 (dd, J = 2.4, 1.5 Hz, 1H), 7.52 (d, J = 1.2 Hz, 1H), 7.43 (dd, J = 2.4, 1.5 Hz, 1H), 7.22 (s, 1H), 4.78 (d, J = 5.2 Hz, 2H), 4.06 (dd, J = 9.0, 6.4 Hz, 1H), 4.03-3.96 (m, 1H), 3.96-3.85 (m, 2H), 3.85-3.76 (m, 1H), 3.72 (dd, J = 8.9, 5.3 Hz, 1H), 2.77 (dt, J = 14.3, 7.5 Hz, 1H), 2.58 (s, 3H), 2.53 (d, J = 1.1 Hz, 3H), 2.20-2.07 (m, 1H), 1.75 (td, J = 12.7, 6.9 Hz, 1H). LCMS (Analytical Method F) Rt = 2.77 min, MS (ESIpos): m/z = 425.1 (M + H)$^+$. |

-continued

| Ex. | Structure | Name | Analytical Data |
|---|---|---|---|
| 68 | 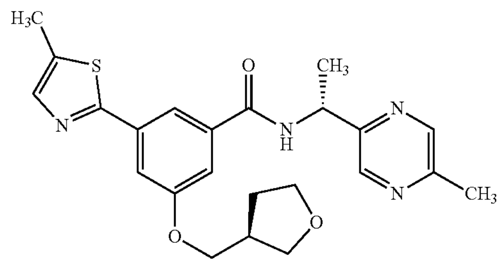 [SMILES: Cc1cnc([C@@H](C)NC(=O)c2cc(OC[C@H]3CCOC3)cc(-c3ncc(C)s3)c2)cn1] | N-[(1R)-1-(5-Methylpyrazin-2-yl)ethyl]-3-(5-methyl-1,3-thiazol-2-yl)-5-[(3S)-tetrahydrofuran-3-ylmethoxy]benzamide | $^1$H NMR (500 MHz, CDCl$_3$): δ [ppm] = 8.56 (d, J = 1.3 Hz, 1H), 8.44 (s, 1H), 7.91 (s, 1H), 7.59 (dd, J = 2.3, 1.5 Hz, 1H), 7.56 (d, J = 1.2 Hz, 1H), 7.46-7.41 (m, 1H), 7.33 (d, J = 7.5 Hz, 1H), 5.46 (p, J = 7.0 Hz, 1H), 4.08 (dd, J = 9.0, 6.4 Hz, 1H), 4.02 (dd, J = 10.3, 6.6 Hz, 1H), 3.98-3.90 (m, 2H), 3.82 (q, J = 7.8 Hz, 1H), 3.74 (dd, J = 8.9, 5.3 Hz, 1H), 2.79 (dt, J = 14.6, 7.6 Hz, 1H), 2.60 (s, 3H), 2.56 (d, J = 1.1 Hz, 3H), 2.15 (dtd, J = 13.6, 8.2, 5.6 Hz, 1H), 1.78 (td, J = 12.7, 6.9 Hz, 1H), 1.63 (d, J = 6.8 Hz, 3H). LCMS (Analytical Method F) Rt = 2.99 min, MS (ESIpos): m/z = 439.2 (M + H)$^+$. |
| 69 | 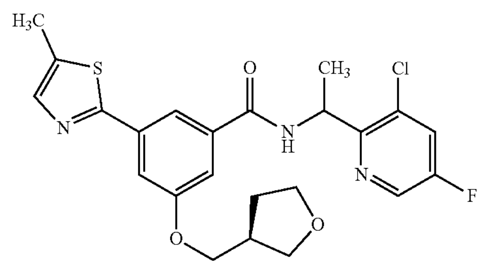 [SMILES: Cc1cnc(-c2cc(OC[C@H]3CCOC3)cc(C(=O)NC(C)c3ncc(F)cc3Cl)c2)s1] | N-[1-(3-Chloro-5-fluoropyridin-2-yl)ethyl]-3-(5-methyl-1,3-thiazol-2-yl)-5-[(3R)-tetrahydrofuran-3-ylmethoxy]benzamide | $^1$H NMR (500 MHz, CDCl$_3$): δ [ppm] = 8.39 (d, J = 2.5 Hz, 1H), 7.88 (t, J = 1.4 Hz, 1H), 7.63 (d, J = 7.7 Hz, 1H), 7.58 (dd, J = 2.3, 1.5 Hz, 1H), 7.54-7.49 (m, 2H), 7.43 (dd, J = 2.4, 1.5 Hz, 1H), 5.76 (p, J = 6.8 Hz, 1H), 4.06 (ddd, J = 9.4, 6.4, 3.1 Hz, 1H), 4.00 (td, J = 8.9, 8.4, 4.3 Hz, 1H), 3.97-3.88 (m, 2H), 3.84-3.77 (m, 1H), 3.72 (dd, J = 7.8, 5.3 Hz, 1H), 2.77 (dt, J = 14.3, 7.3 Hz, 1H), 2.53 (d, J = 1.1 Hz, 3H), 2.13 (dtd, J = 13.4, 8.2, 5.7 Hz, 1H), 1.76 (dq, J = 12.7, 6.8 Hz, 1H), 1.54 (d, J = 6.8 Hz, 3H). LCMS (Analytical Method F) Rt$_t$ = 3.79 min, MS (ESIpos): m/z = 476.1 (M + H)$^+$. |
| 70 | 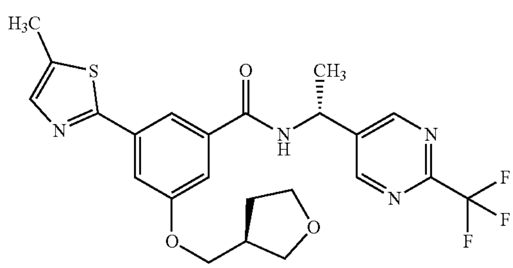 [SMILES: Cc1cnc(-c2cc(OC[C@H]3CCOC3)cc(C(=O)N[C@H](C)c3cnc(C(F)(F)F)nc3)c2)s1] | 3-(5-Methyl-1,3-thiazol-2-yl)-5-[(3S)-tetrahydrofuran-3-ylmethoxy]-N-[(1R)-1-[2-(trifluoromethyl)pyrimidin-5-yl]ethyl]benzamide | $^1$H NMR (500 MHz, CDCl$_3$): δ [ppm] = 8.91 (s, 2H), 7.81 (s, 1H), 7.53-7.43 (m, 2H), 7.34 (s, 1H), 6.91 (s, 1H), 5.34 (p, J = 7.0 Hz, 1H), 3.99 (dd, J = 8.6, 6.6 Hz, 1H), 3.96-3.84 (m, 3H), 3.77 (q, J = 7.8 Hz, 1H), 3.68 (dd, J = 8.9, 5.2 Hz, 1H), 2.73 (dt, J = 14.0, 7.4 Hz, 1H), 2.51 (s, 3H), 2.10 (dtd, J = 13.6, 8.1, 5.6 Hz, 1H), 1.72 (dd, J = 13.0, 7.1 Hz, 1H), 1.68 (d, J = 7.1 Hz, 3H). LCMS (Analytical Method F) Rt = 3.55 min, MS (ESIpos): m/z = 493.1 (M + H)$^+$. |
| 71 | 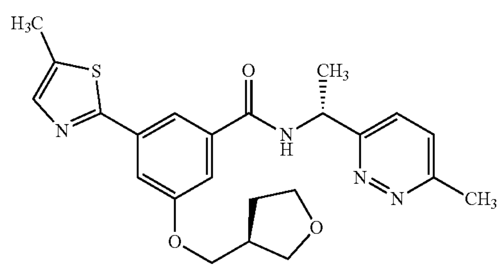 [SMILES: Cc1ccc([C@@H](C)NC(=O)c2cc(OC[C@H]3CCOC3)cc(-c3ncc(C)s3)c2)nn1] | N-[(1R)-1-(6-Methylpyridazin-3-yl)ethyl]-3-(5-methyl-1,3-thiazol-2-yl)-5-[(3S)-tetrahydrofuran-3-ylmethoxy]benzamide | $^1$H NMR (500 MHz, CDCl$_3$): δ [ppm] = 7.90 (s, 1H), 7.83 (d, J = 7.2 Hz, 1H), 7.62-7.57 (m, 1H), 7.52 (s, 1H), 7.48-7.40 (m, 2H), 7.37 (d, J = 8.6 Hz, 1H), 5.47 (p, J = 6.9 Hz, 1H), 4.08-3.86 (m, 4H), 3.80 (q, J = 7.8 Hz, 1H), 3.71 (dd, J = 8.9, 5.4 Hz, 1H), 2.74 (m, 4H), 2.53 (s, 3H), 2.13 (dtd, J = 13.5, 8.1, 5.6 Hz, 1H), 1.80-1.66 (m, 4H). LCMS (Analytical Method D) Rt = 3.55 min, MS (ESIpos): m/z = 439 (M + H)$^+$. |
| 72 | 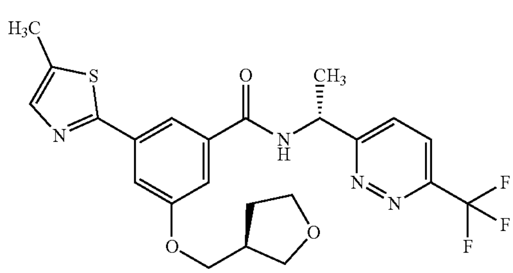 [SMILES: Cc1cnc(-c2cc(OC[C@H]3CCOC3)cc(C(=O)N[C@H](C)c3ccc(C(F)(F)F)nn3)c2)s1] | 3-(5-Methyl-1,3-thiazol-2-yl)-5-[(3S)-tetrahydrofuran-3-ylmethoxy]-N-[(1R)-1-[6-(trifluoromethyl)pyridazin-3-yl]ethyl]benzamide | $^1$H NMR (500 MHz, CDCl$_3$): δ [ppm] = 7.89 (s, 1H), 7.83 (d, J = 8.7 Hz, 1H), 7.74 (d, J = 8.7 Hz, 1H), 7.58 (dd, J = 2.3, 1.5 Hz, 1H), 7.52 (d, J = 1.1 Hz, 2H), 7.48 (t, J = 6.3 Hz, 1H), 7.42-7.37 (m, 1H), 5.61 (p, J = 7.0 Hz, 1H), 4.07-3.86 (m, 4H), 3.84-3.75 (m, 1H), 3.72 (dd, J = 8.9, 5.3 Hz, 1H), 2.76 (dq, J = 13.6, 6.9, 6.5 Hz, 1H), 2.53 (d, J = 1.0 Hz, 3H), 2.19-2.08 (m, 1H), 1.80-1.70 (m, 4H). LCMS (Analytical Method F) Rt = 3.46 min, MS (ESIpos): m/z = 493.1 (M + H)$^+$. |

-continued

| Ex. | Structure | Name | Analytical Data |
|---|---|---|---|
| 73 | 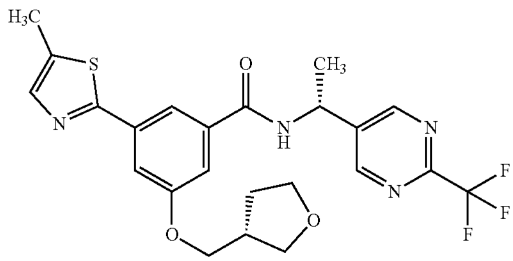 [SMILES: Cc1cnc(-c2cc(OC[C@@H]3CCOC3)cc(C(=O)N[C@H](C)c3cnc(C(F)(F)F)nc3)c2)s1] | 3-(5-Methyl-1,3-thiazol-2-yl)-5-[(3R)-tetrahydrofuran-3-ylmethoxy]-N-[(1R)-1-[2-(trifluoromethyl)pyrimidin-5-yl]ethyl]benzamide | $^1$H NMR (500 MHz, CDCl$_3$): δ [ppm] = 8.93 (s, 2H), 7.85 (d, J = 1.2 Hz, 1H), 7.54-7.48 (m, 2H), 7.40-7.35 (m, 1H), 6.75 (d, J = 6.6 Hz, 1H), 5.36 (p, J = 7.0 Hz, 1H), 4.06-3.85 (m, 4H), 3.79 (q, J = 7.8 Hz, 1H), 3.70 (dd, J = 8.9, 5.2 Hz, 1H), 2.75 (hept, J = 6.1 Hz, 1H), 2.53 (d, J = 1.0 Hz, 3H), 2.12 (dtd, J = 13.4, 8.1, 5.5 Hz, 1H), 1.84 (d, J = 7.2 Hz, OH), 1.79-1.68 (m, 4H). LCMS (Analytical Method D) Rt = 4.34 min, MS (ESIpos): m/z = 493 (M + H)$^+$. |
| 74 | 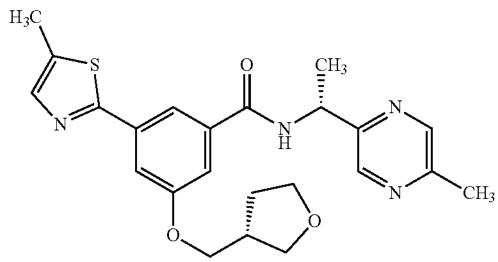 [SMILES: Cc1cnc([C@@H](C)NC(=O)c2cc(OC[C@@H]3CCOC3)cc(-c3ncc(C)s3)c2)cn1] | N-[(1R)-1-(5-Methylpyrazin-2-yl)ethyl]-3-(5-methyl-1,3-thiazol-2-yl)-5-[(3R)-tetrahydrofuran-3-ylmethoxy]benzamide | $^1$H NMR (500 MHz, CDCl$_3$): δ [ppm] = 8.53 (d, J = 1.3 Hz, 1H), 8.41 (s, 1H), 7.87 (s, 1H), 7.59-7.50 (m, 2H), 7.44-7.38 (m, 1H), 7.30 (d, J = 7.5 Hz, 1H), 5.43 (p, J = 6.9 Hz, 1H), 4.09-3.86 (m, 4H), 3.79 (q, J = 7.8 Hz, 1H), 3.71 (dd, J = 8.9, 5.3 Hz, 1H), 2.76 (hept, J = 6.4 Hz, 1H), 2.57 (s, 3H), 2.53 (d, J = 1.0 Hz, 3H), 2.12 (dtd, J = 13.5, 8.1, 5.6 Hz, 1H), 1.80-1.69 (m, 1H), 1.60 (d, J = 6.8 Hz, 3H). LCMS (Analytical Method D) Rt = 3.95 min, MS (ESIpos): m/z = 439 (M + H)$^+$. |
| 75 | 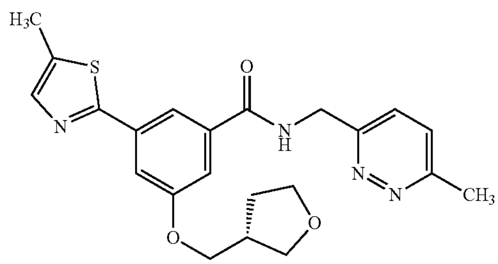 [SMILES: Cc1ccc(CNC(=O)c2cc(OC[C@@H]3CCOC3)cc(-c3ncc(C)s3)c2)nn1] | N-[(6-Methylpyridazin-3-yl)methyl]-3-(5-methyl-1,3-thiazol-2-yl)-5-[(3R)-tetrahydrofuran-3-ylmethoxy)benzamide | $^1$H NMR (500 MHz, CDCl$_3$): δ [ppm] = 7.96 (t, J = 5.0 Hz, 1H), 7.94-7.92 (m, 1H), 7.65-7.60 (m, 2H), 7.53 (d, J = 1.2 Hz, 1H), 7.49 (dd, J = 2.3, 1.5 Hz, 1H), 7.47-7.43 (m, 1H), 4.96 (d, J = 5.2 Hz, 2H), 4.12-3.88 (m, 4H), 3.85-3.78 (m, 1H), 3.73 (dd, J = 8.9, 5.4 Hz, 1H), 2.83-2.75 (m, 4H), 2.54 (d, J = 1.0 Hz, 3H), 2.20-2.10 (m, 1H), 1.82-1.73 (m, 1H). LCMS (Analytical Method D) Rt = 3.60 min, MS (ESIpos): m/z = 425 (M + H)$^+$. |
| 76 | 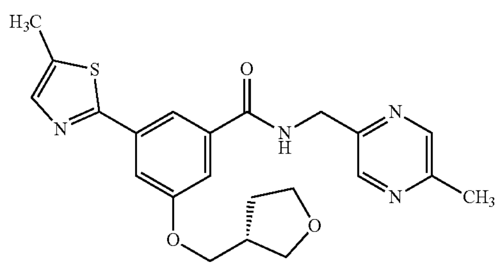 [SMILES: Cc1cnc(CNC(=O)c2cc(OC[C@@H]3CCOC3)cc(-c3ncc(C)s3)c2)cn1] | N-[(5-Methylpyrazin-2-yl)methyl]-3-(5-methyl-1,3-thiazol-2-yl)-5-[(3R)-tetrahydrofuran-3-ylmethoxy)benzamide | $^1$H NMR (500 MHz, CDCl$_3$): δ [ppm] = 8.56 (d, J = 1.1 Hz, 1H), 8.41 (s, 1H), 7.89 (s, 1H), 7.57 (dd, J = 2.4, 1.5 Hz, 1H), 7.51 (d, J = 1.2 Hz, 1H), 7.43 (dd, J = 2.3, 1.5 Hz, 1H), 7.30 (t, J = 5.1 Hz, 1H), 4.77 (d, J = 5.1 Hz, 2H), 4.08-3.86 (m, 4H), 3.83-3.75 (m, 1H), 3.71 (dd, J = 8.9, 5.3 Hz, 1H), 2.76 (hept, J = 6.2 Hz, 1H), 2.57 (s, 3H), 2.52 (d, J = 1.1 Hz, 3H), 2.12 (dtd, J = 13.3, 8.1, 5.6 Hz, 1H), 1.80-1.69 (m, 1H). LCMS (Analytical Method D) Rt = 3.81 min, MS (ESIpos): m/z = 425 (M + H)$^+$. |
| 77 | 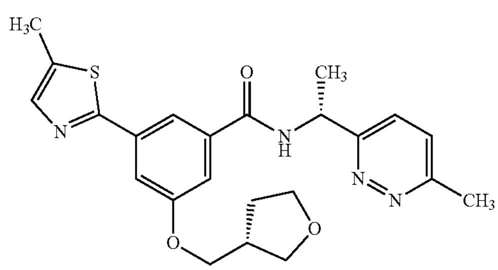 [SMILES: Cc1ccc([C@@H](C)NC(=O)c2cc(OC[C@@H]3CCOC3)cc(-c3ncc(C)s3)c2)nn1] | N-[(1R)-1-(6-Methylpyridazin-3-yl)ethyl]-3-(5-methyl-1,3-thiazol-2-yl)-5-[(3R)-tetrahydrofuran-3-ylmethoxy)benzamide | $^1$H NMR (500 MHz, CDCl$_3$): δ [ppm] = 8.02-7.96 (m, 2H), 7.67-7.58 (m, 2H), 7.55-7.45 (m, 3H), 5.50 (p, J = 7.0 Hz, 1H), 4.10-3.86 (m, 4H), 3.80 (q, J = 7.8 Hz, 1H), 3.71 (dd, J = 8.9, 5.4 Hz, 1H), 2.81-2.72 (m, 4H), 2.53 (s, 3H), 2.13 (dtd, J = 13.6, 8.1, 5.6 Hz, 1H), 1.81-1.68 (m, 4H). LCMS (Analytical Method D) Rt = 3.70 min, MS (ESIpos): m/z = 439 (M + H)$^+$. |

| Ex. | Name | Analytical Data |
|---|---|---|
| 78 | N-[1-(5-Chloro-3-fluoropyridin-2-yl)ethyl]-3-(5-methyl-1,3-thiazol-2-yl)-5-[(3R)-tetrahydrofuran-3-ylmethoxy]benzamide | $^1$H NMR (500 MHz, CDCl$_3$): δ [ppm] = 8.39 (d, J = 1.8 Hz, 1H), 7.90 (s, 1H), 7.61-7.52 (m, 3H), 7.50-7.41 (m, 2H), 5.66 (p, J = 6.9 Hz, 1H), 4.10-3.87 (m, 4H), 3.80 (q, J = 7.8 Hz, 1H), 3.72 (dd, J = 8.8, 5.3 Hz, 1H), 2.77 (hept, J = 6.2 Hz, 1H), 2.54 (s, 3H), 2.13 (dtd, J = 13.4, 8.1, 5.6 Hz, 1H), 1.76 (dq, J = 12.8, 7.0 Hz, 1H), 1.56 (d, J = 6.8 Hz, 3H). LCMS (Analytical Method D) Rt = 4.55 min, MS (ESIpos): m/z = 476 (M + H)$^+$. |
| 79 | 3-(5-Methyl-1,3-thiazol-2-yl)-5-[(3R)-tetrahydrofuran-3-ylmethoxy]-N-[(1R)-1-[6-(trifluoromethyl)pyridazin-3-yl]ethyl]benzamide | $^1$H NMR (500 MHz, CDCl$_3$): δ [ppm] = 7.88-7.79 (m, 2H), 7.74 (d, J = 8.7 Hz, 1H), 7.59-7.49 (m, 3H), 7.41-7.36 (m, 1H), 5.60 (p, J = 7.0 Hz, 1H), 4.07-3.86 (m, 4H), 3.79 (q, J = 7.8 Hz, 1H), 3.70 (dd, J = 8.9, 5.3 Hz, 1H), 2.75 (hept, J = 6.5 Hz, 1H), 2.52 (d, J = 0.9 Hz, 3H), 2.12 (dtd, J = 13.4, 8.1, 5.6 Hz, 1H), 1.77-1.69 (m, 4H). LCMS (Analytical Method F) Rt = 3.46 min, MS (ESIpos): m/z = 493.1 (M + H)$^+$. |
| 80 | N-[1-(3-Chloro-5-fluoropyridin-2-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.39 (d, J = 2.5 Hz, 1H), 7.90-7.85 (m, 1H), 7.67-7.61 (m, 1H), 7.60-7.56 (m, 1H), 7.55-7.49 (m, 2H), 7.47-7.43 (m, 1H), 5.81-5.71 (m, 1H), 4.70-4.61 (m, 1H), 4.04-3.95 (m, 2H), 3.64-3.55 (m, 2H), 2.53 (d, J = 1.1 Hz, 3H), 2.11-2.01 (m, 2H), 1.88-1.76 (m, 2H), 1.54 (d, J = 6.7 Hz, 3H). LCMS (Analytical Method F) Rt = 3.77 min, MS (ESIpos): m/z = 476.1 (M + H)$^+$. |
| 81 | N-[1-(5-Chloro-3-fluoropyridin-2-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.38 (d, J = 1.8 Hz, 1H), 7.89-7.85 (m, 1H), 7.61-7.58 (m, 1H), 7.57-7.51 (m, 2H), 7.50-7.46 (m, 1H), 7.45-7.42 (m, 1H), 5.71-5.61 (m, 1H), 4.70-4.61 (m, 1H), 4.04-3.95 (m, 2H), 3.64-3.55 (m, 2H), 2.53 (d, J = 1.1 Hz, 3H), 2.11-2.01 (m, 2H), 1.88-1.76 (m, 2H), 1.56 (d, J = 6.8 Hz, 3H). LCMS (Analytical Method F) Rt = 3.78 min, MS (ESIpos): m/z = 476.1 (M + H)$^+$. |
| 82 | N-[(6-Methylpyridazin-3-yl)methyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 7.89-7.85 (m, 1H), 7.67-7.62 (m, 1H), 7.62-7.59 (m, 1H), 7.52-7.48 (m, 1H), 7.48-7.43 (m, 2H), 7.34 (d, J = 8.6 Hz, 1H), 4.91 (d, J = 5.2 Hz, 2H), 4.69-4.61 (m, 1H), 4.03-3.94 (m, 2H), 3.64-3.56 (m, 2H), 2.72 (s, 3H), 2.52 (d, J = 1.1 Hz, 3H), 2.10-2.01 (m, 2H), 1.87-1.76 (m, 2H). LCMS (Analytical Method F) Rt = 2.48 min, MS (ESIpos): m/z = 425.2 (M + H)$^+$. |

-continued

| Ex. | Structure | Name | Analytical Data |
|---|---|---|---|
| 83 | 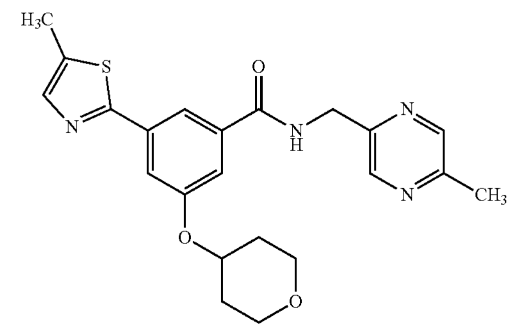 [SMILES: Cc1cnc(CNC(=O)c2cc(OC3CCOCC3)cc(-c3ncc(C)s3)c2)cn1] | N-[(5-Methylpyrazin-2-yl)methyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.58-8.54 (m, 1H), 8.44-8.40 (m, 1H), 7.88-7.84 (m, 1H), 7.61-7.56 (m, 1H), 7.53-7.49 (m, 1H), 7.49-7.43 (m, 1H), 7.26-7.23 (m, 1H), 4.77 (d, J = 5.2 Hz, 2H), 4.69-4.60 (m, 1H), 4.03-3.94 (m, 2H), 3.64-3.55 (m, 2H), 2.57 (s, 3H), 2.52 (d, J = 1.1 Hz, 3H), 2.10-2.01 (m, 2H), 1.87-1.76 (m, 2H). LCMS (Analytical Method F) Rt = 2727 min, MS (ESIpos): m/z = 425.1 (M + H)$^+$. |
| 84 | 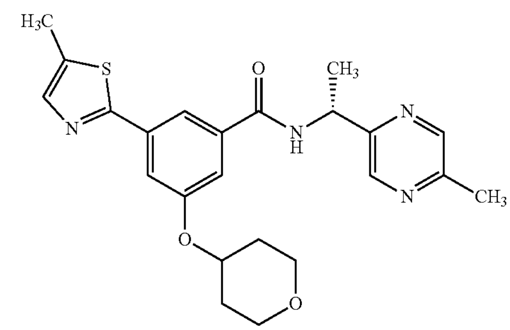 [SMILES: Cc1cnc([C@@H](C)NC(=O)c2cc(OC3CCOCC3)cc(-c3ncc(C)s3)c2)cn1] | N-[(1R)-1-(5-Methylpyrazin-2-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.56-8.51 (m, 1H), 8.44-8.39 (m, 1H), 7.87-7.83 (m, 1H), 7.60-7.55 (m, 1H), 7.53-7.51 (m, 1H), 7.45-7.41 (m, 1H), 7.32-7.27 (m, 1H), 5.48-5.38 (m, 1H), 4.69-4.60 (m, 1H), 4.03-3.94 (m, 2H), 3.64-3.55 (m, 2H), 2.57 (s, 3H), 2.53 (d, J = 1.1 Hz, 3H), 2.11-2.02 (m, 2H), 1.87-1.75 (m, 2H), 1.60 (d, J = 6.8 Hz, 3H). LCMS (Analytical Method F) Rt = 2.97 min, MS (ESIpos): m/z = 439.2 (M + H)$^+$. |
| 85 | 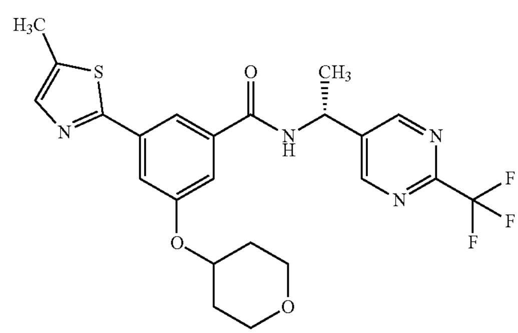 [SMILES: Cc1cnc(-c2cc(OC3CCOCC3)cc(C(=O)N[C@H](C)c3cnc(C(F)(F)F)nc3)c2)s1] | 3-(5-Methyl-1,3-thiazol-2-yl)-5-(tetrahydro-2H-pyran-4-yloxy)-N-{(1R)-1-[2-(trifluoromethyl)pyrimidin-5-yl]ethyl}benzamide | $^1$H NMR (500 MHz, CDCl$_3$): δ [ppm] = 8.93 (s, 2H), 7.86-7.81 (m, 1H), 7.56-7.50 (m, 2H), 7.43-7.38 (m, 1H), 6.65 (d, J = 6.5 Hz, 1H), 5.40-5.31 (m, 1H), 4.68-4.59 (m, 1H), 4.02-3.94 (m, 2H), 3.64-3.55 (m, 2H), 2.54 (d, J = 1.1 Hz, 3H), 2.09-2.02 (m, 2H), 1.86-1.75 (m, 2H), 1.72 (d, J = 7.2 Hz, 3H). LCMS (Analytical Method F) Rt = 3.52 min, MS (ESIpos): m/z = 493.1 (M + H)$^+$. |
| 86 | 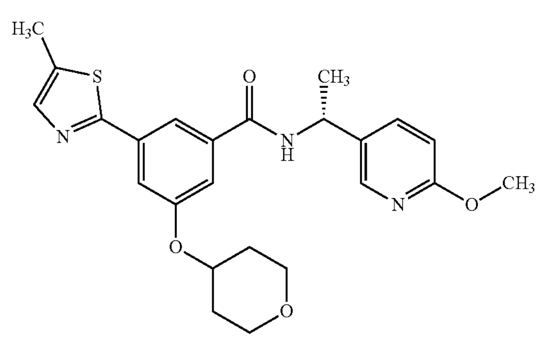 [SMILES: COc1ccc([C@@H](C)NC(=O)c2cc(OC3CCOCC3)cc(-c3ncc(C)s3)c2)cn1] | N-[(1R)-1-(6-Methoxypyridin-3-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.22 (d, J = 2.5 Hz, 1H), 7.78 (s, 1H), 7.61 (dd, J = 8.6, 2.5 Hz, 1H), 7.54-7.52 (m, 1H), 7.51 (d, J = 1.2 Hz, 1H), 7.44-7.41 (m, 1H), 6.74 (d, J = 8.6 Hz, 1H), 6.38 (d, J = 7.6 Hz, 1H), 5.35-5.26 (m, 1H), 4.64 (dt, J = 7.8, 3.8 Hz, 1H), 4.03-3.95 (m, 2H), 3.93 (s, 3H), 3.60 (t, J = 8.6 Hz, 2H), 2.53 (d, J = 1.1 Hz, 3H), 2.04 (s, 2H), 1.89-1.75 (m, 2H), 1.62 (d, J = 7.0 Hz, 3H). LCMS (Analytical Method F) Rt = 3.27 min, MS (ESIpos): m/z = 454.1 (M + H)$^+$. |

| Ex. | Structure | Name | Analytical Data |
|---|---|---|---|
| 87 | 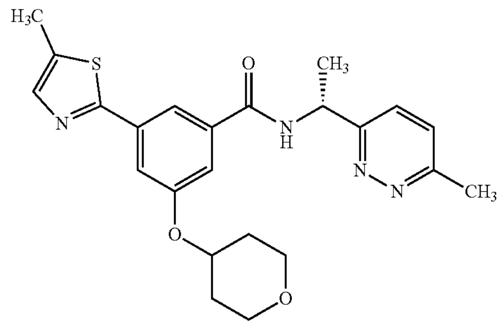 [SMILES: Cc1ccc([C@@H](C)NC(=O)c2cc(OC3CCOCC3)cc(-c3ncc(C)s3)c2)nn1] | N-[(1R)-1-(6-Methylpyridazin-3-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 7.87 (t, J = 1.4 Hz, 1H), 7.78 (d, J = 7.5 Hz, 1H), 7.62-7.58 (m, 1H), 7.51 (d, J = 1.2 Hz, 1H), 7.45-7.43 (m, 1H), 7.40 (d, J = 8.5 Hz, 1H), 7.34 (d, J = 8.6 Hz, 1H), 5.45 (q, J = 6.9 Hz, 1H), 4.65 (dt, J = 8.0, 4.0 Hz, 1H), 4.05-3.94 (m, 2H), 3.61 (ddt, J = 8.8, 5.5, 2.8 Hz, 2H), 2.73 (s, 3H), 2.53 (d, J = 1.1 Hz, 3H), 2.07 (d, J = 28.7 Hz, 2H), 1.82 (ddt, J = 12.6, 8.0, 4.1 Hz, 2H), 1.68 (d, J = 6.8 Hz, 3H). LCMS (Analytical Method F) Rt = 2.61 min, MS (ESIpos): m/z = 439.2 (M + H)$^+$. |
| 88 | 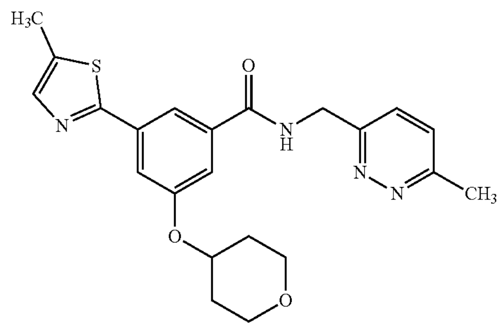 | N-[(6-Methoxypyridazin-3-yl)methyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 7.87 (t, J = 1.4 Hz, 1H), 7.63-7.60 (m, 1H), 7.51 (d, J = 1.2 Hz, 1H), 7.50-7.41 (m, 3H), 7.01 (d, J = 9.1 Hz, 1H), 4.86 (d, J = 5.1 Hz, 2H), 4.66 (dq, J = 7.6, 3.8 Hz, 1H), 4.14 (s, 3H), 4.05-3.96 (m, 2H), 3.61 (ddd, J = 11.6, 8.2, 3.2 Hz, 2H), 2.53 (d, J = 1.1 Hz, 3H), 2.12-2.02 (m, 2H), 1.82 (dtd, J = 12.0, 8.1, 3.8 Hz, 2H). LCMS (Analytical Method F) Rt = 2.82 min, MS (ESIpos): m/z = 441.1 (M + H)$^+$. |
| 89 | 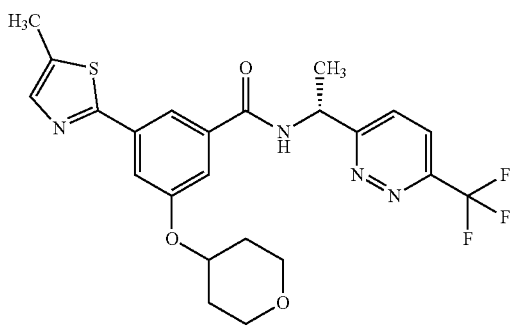 [SMILES: Cc1cnc(-c2cc(OC3CCOCC3)cc(C(=O)N[C@H](C)c3ccc(C(F)(F)F)nn3)c2)s1] | 3-(5-Methyl-1,3-thiazol-2-yl)-5-(tetrahydro-2H-pyran-4-yloxy)-N-{(1R)-1-[6-(trifluoromethyl)pyridazin-3-yl]ethyl}benzamide | $^1$H NMR (500 MHz, CDCl$_3$): δ [ppm] = 7.92 (s, 1H), 7.82 (d, J = 8.7 Hz, 1H), 7.75 (d, J = 8.7 Hz, 1H), 7.59 (dd, J = 2.3, 1.5 Hz, 1H), 7.54 (t, J = 2.4 Hz, 2H), 7.46-7.41 (m, 1H), 5.60 (p, J = 7.0 Hz, 1H), 4.64 (tt, J = 7.8, 3.8 Hz, 1H), 3.98 (dq, J = 9.9, 5.4, 4.9 Hz, 2H), 3.60 (ddt, J = 11.6, 6.2, 2.6 Hz, 2H), 2.54 (d, J = 1.1 Hz, 3H), 2.09-2.01 (m, 2H), 1.79 (dd, J = 28.1, 5.6 Hz, 5H). LCMS (Analytical Method F) Rt = 3.44 min, MS (ESIpos): m/z = 492.0 (M + H)$^+$. |

In analogy to the procedure described for Example 7 the following examples were prepared using the appropriate carboxylic acid and amine as starting materials.

| Ex. | Structure | Name | Analytical Data |
|---|---|---|---|
| 90 | 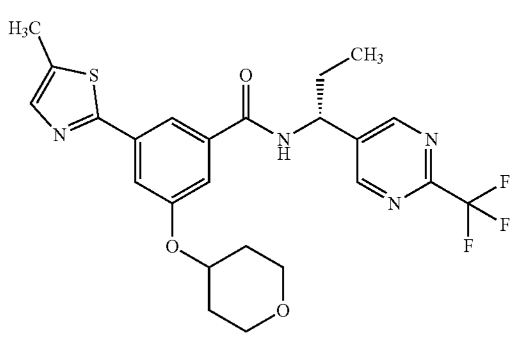 [SMILES: CC[C@@H](NC(=O)c1cc(OC2CCOCC2)cc(-c2ncc(C)s2)c1)c1cnc(C(F)(F)F)nc1] | 3-(5-Methyl-1,3-thiazol-2-yl)-5-(tetrahydro-2H-pyran-4-yloxy)-N-{(1R)-1-[2-(trifluoromethyl)pyrimidin-5-yl]propyl}benzamide | $^1$H NMR (500 MHz, CDCl$_3$): δ [ppm] = 8.91 (s, 2H), 7.83 (s, 1H), 7.57-7.53 (m, 1H), 7.53 (d, J = 1.1 Hz, 1H), 7.40 (d, J = 1.6 Hz, 1H), 6.61 (d, J = 6.9 Hz, 1H), 5.10 (q, J = 7.2 Hz, 1H), 4.63 (tt, J = 8.0, 3.8 Hz, 1H), 4.03-3.95 (m, 2H), 3.63-3.56 (m, 2H), 2.54 (d, J = 0.9 Hz, 3H), 2.10-1.97 (m, 4H), 1.81 (s, 2H), 1.08 (t, J = 7.4 Hz, 3H). LCMS (Analytical Method F) Rt = 3.74 min, MS (ESIpos): m/z = 507.3 (M + H)$^+$. |

-continued

| Ex. | Structure | Name | Analytical Data |
|---|---|---|---|
| 91 | 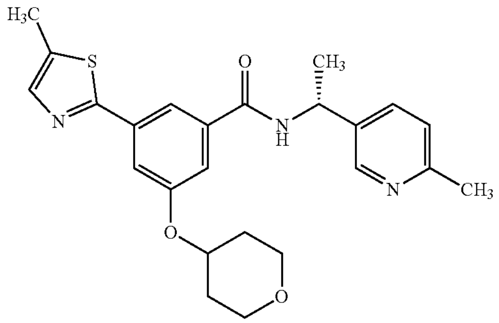 [SMILES: Cc1ccc([C@@H](C)NC(=O)c2cc(OC3CCOCC3)cc(-c3ncc(C)s3)c2)cn1] | N-[(1R)-1-(6-Methylpyridin-3-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 8.56 (d, J = 2.3 Hz, 1H), 7.79 (t, J = 1.4 Hz, 1H), 7.60 (dd, J = 8.0, 2.4 Hz, 1H), 7.53 (dd, J = 2.4, 1.5 Hz, 1H), 7.51 (d, J = 1.2 Hz, 1H), 7.44-7.40 (m, 1H), 7.14 (d, J = 8.0 Hz, 1H), 6.43 (d, J = 7.4 Hz, 1H), 5.32 (p, J = 7.0 Hz, 1H), 4.64 (tt, J = 7.9, 3.8 Hz, 1H), 3.98 (dt, J = 10.4, 4.5 Hz, 2H), 3.64-3.55 (m, 2H), 2.55 (s, 3H), 2.53 (d, J = 1.1 Hz, 3H), 2.09-2.02 (m, 2H), 1.81 (ddq, J = 12.8, 8.4, 4.0 Hz, 2H), 1.63 (d, J = 7.0 Hz, 3H). LCMS (Analytical Method D) Rt = 3.18 min, MS (ESIpos): m/z = 438.1 (M + H)$^+$. |
| 92 | 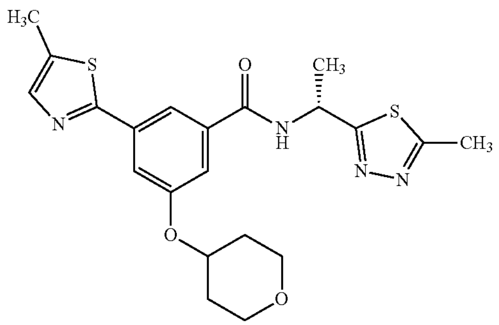 [SMILES: Cc1cnc(-c2cc(OC3CCOCC3)cc(C(=O)N[C@H](C)c3nnc(C)s3)c2)s1] | N-[(1R)-1-(5-Methyl-1,3,4-thiadiazol-2-yl)ethyl]-3-(5-methyl-1,3-thiazol-2-yl)-5-(tetrahydro-2H-pyran-4-yloxy)benzamide | $^1$H NMR (500 MHz, CDCl$_3$): δ [ppm] = 7.83 (t, J = 1.4 Hz, 1H), 7.59 (dd, J = 2.4, 1.5 Hz, 1H), 7.52 (d, J = 1.2 Hz, 1H), 7.45-7.42 (m, 1H), 7.01 (d, J = 7.6 Hz, 1H), 5.69 (p, J = 6.9 Hz, 1H), 4.65 (dt, J = 8.0, 4.1 Hz, 1H), 4.03-3.95 (m, 2H), 3.61 (ddd, J = 11.7, 8.4, 3.2 Hz, 2H), 2.77 (s, 3H), 2.53 (d, J = 1.1 Hz, 3H), 2.10-2.02 (m, 2H), 1.86-1.81 (m, 2H), 1.80 (d, J = 6.9 Hz, 3H). LCMS (Analytical Method F) 99% @ Rt = 2.87 min, MS (ESIpos): m/z = 445.2 (M + H)$^+$. |

In analogy to the procedure described for Example 1 the following examples were prepared using the appropriate carboxylic acid and amine as starting materials.

| Ex. | Structure | Name | Analytical Data |
|---|---|---|---|
| 93 | 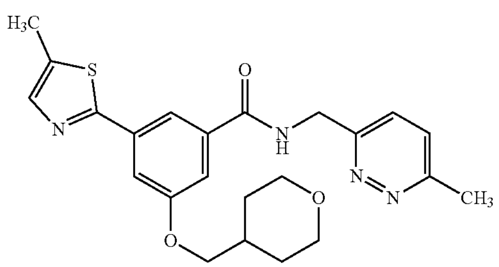 [SMILES: Cc1ccc(CNC(=O)c2cc(OCC3CCOCC3)cc(-c3ncc(C)s3)c2)nn1] | N-[(6-Methylpyridazin-3-yl)methyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 7.95-7.91 (m, 1H), 7.90 (s, 1H), 7.61-7.56 (m, 2H), 7.50 (d, J = 1.1 Hz, 1H), 7.45 (dd, J = 2.3, 1.4 Hz, 1H), 7.43-7.39 (m, 1H), 4.93 (d, J = 5.1 Hz, 2H), 4.05-3.99 (m, 2H), 3.92 (d, J = 6.5 Hz, 2H), 3.45 (td, J = 11.9, 2.0 Hz, 2H), 2.74 (s, 3H), 2.51 (d, J = 1.0 Hz, 3H), 2.15-2.03 (m, 1H), 1.81-1.73 (m, 2H), 1.46 (ddd, J = 12.1, 4.5 Hz, 2H). LCMS (Analytical Method F) Rt = 2.69 min, MS (ESIpos): m/z = 439.2 (M + H)$^+$. |
| 94 | 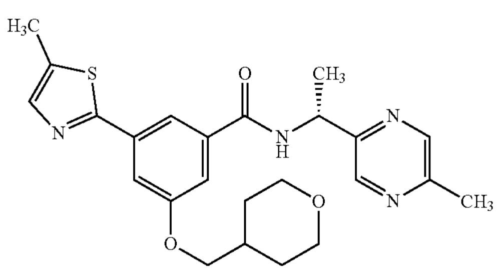 [SMILES: Cc1cnc([C@@H](C)NC(=O)c2cc(OCC3CCOCC3)cc(-c3ncc(C)s3)c2)cn1] | N-[(1R)-1-(5-Methylpyrazin-2-yl)ethyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 8.54 (d, J = 1.4 Hz, 1H), 8.42 (s, 1H), 7.89 (s, 1H), 7.56 (dd, J = 2.4, 1.5 Hz, 1H), 7.53 (d, J = 1.2 Hz, 1H), 7.41 (dd, J = 2.3, 1.5 Hz, 1H), 7.32 (d, J = 7.4 Hz, 1H), 5.43 (p, J = 6.9 Hz, 1H), 4.02 (dd, J = 11.4, 3.0 Hz, 2H), 3.92 (d, J = 6.4 Hz, 2H), 3.45 (td, J = 11.8, 2.0 Hz, 2H), 2.57 (s, 3H), 2.53 (d, J = 1.1 Hz, 3H), 2.15-2.04 (m, 1H), 1.77 (d, J = 12.5 Hz, 2H), 1.61 (d, J = 6.9 Hz, 3H), 1.48 (qd, J = 12.1, 4.5 Hz, 2H). LCMS (Analytical Method F) Rt = 3.18 min, MS (ESIpos): m/z = 453.2 (M + H)$^+$. |

| Ex. | Structure | Name | Analytical Data |
|---|---|---|---|
| 95 | 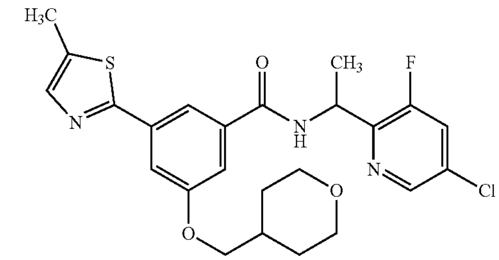 [SMILES: Cc1cnc(-c2cc(OCC3CCOCC3)cc(C(=O)NC(C)c3ncc(Cl)cc3F)c2)s1] | N-[1-(5-Chloro-3-fluoropyridin-2-yl)ethyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 8.38 (d, J = 1.8 Hz, 1H), 7.92 (s, 1H), 7.62-7.56 (m, 2H), 7.55 (d, J = 1.2 Hz, 1H), 7.47 (dd, J = 8.9, 2.0 Hz, 1H), 7.43 (dd, J = 2.3, 1.5 Hz, 1H), 5.66 (p, J = 6.7 Hz, 1H), 4.03 (dd, J = 11.4, 3.1 Hz, 2H), 3.94 (d, J = 6.4 Hz, 2H), 3.45 (td, J = 11.8, 2.0 Hz, 2H), 2.54 (d, J = 1.1 Hz, 3H), 2.15-2.05 (m, 1H), 1.82-1.74 (m, 2H), 1.56 (d, J = 6.8 Hz, 3H), 1.48 (qd, J = 12.2, 4.7 Hz, 2H). LCMS (Analytical Method D) Rt = 4.73 min, MS (ESIpos): m/z = 507 (M + H)$^+$. |
| 96 | 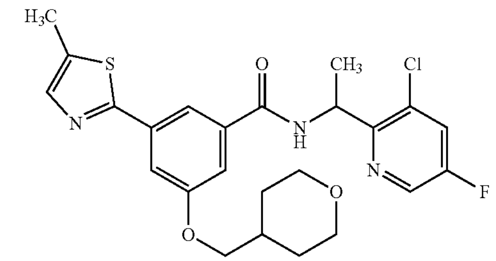 [SMILES: Cc1cnc(-c2cc(OCC3CCOCC3)cc(C(=O)NC(C)c3ncc(F)cc3Cl)c2)s1] | N-[1-(3-Chloro-5-fluoropyridin-2-yl)ethyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 8.39 (d, J = 2.5 Hz, 1H), 7.88 (t, J = 1.3 Hz, 1H), 7.65 (d, J = 7.6 Hz, 1H), 7.61-7.48 (m, 3H), 7.42 (dd, J = 2.4, 1.5 Hz, 1H), 5.75 (p, J = 6.7 Hz, 1H), 4.02 (dd, J = 11.4, 3.1 Hz, 2H), 3.93 (d, J = 6.4 Hz, 2H), 3.45 (td, J = 11.8, 2.0 hz, 2H), 2.53 (d, J = 1.1 Hz, 3H), 2.09 (tdd, J = 15.6, 6.8, 3.6 Hz, 1H), 1.80-1.74 (m, 2H), 1.53 (d, J = 6.7 Hz, 5H), 1.52-1.43 (m, 2H). LCMS (Analytical Method F) Rt = 3.97 min, MS (ESIpos): m/z = 490.1 (M + H)$^+$. |
| 97 | 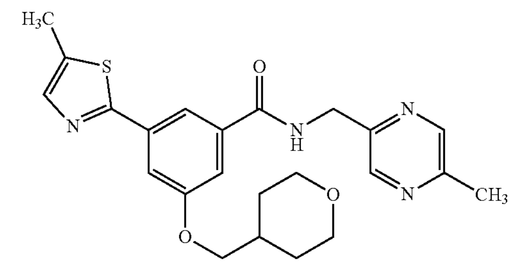 [SMILES: Cc1cnc(CNC(=O)c2cc(OCC3CCOCC3)cc(-c3ncc(C)s3)c2)cn1] | N-[(5-Methylpyrazin-2-yl)methyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 8.56 (d, J = 1.2 Hz, 1H), 8.42 (s, 1H), 7.87 (s, 1H), 7.57 (dd, J = 2.4, 1.5 Hz, 1H), 7.52 (d, J = 1.2 Hz, 1H), 7.43 (dd, J = 2.4, 1.5 Hz, 1H), 7.26-7.22 (m, 1H), 4.77 (d, J = 5.2 Hz, 2H), 4.06-4.00 (m, 2H), 3.93 (d, J = 6.5 Hz, 2H), 3.45 (td, J = 11.9, 2.0 Hz, 2H), 2.58 (s, 3H), 2.53 (d, J = 1.1 Hz, 3H), 2.15-2.04 (m, 1H), 1.81-1.74 (m, 2H), 1.48 (ddd, J = 12.1, 4.5 Hz, 2H). LCMS (Analytical Method F) Rt = 2.96 min, MS (ESIpos): m/z = 439.2 (M + H)$^+$. |
| 98 | 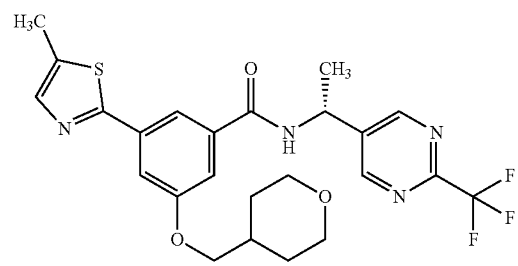 [SMILES: Cc1cnc(-c2cc(OCC3CCOCC3)cc(C(=O)N[C@H](C)c3cnc(C(F)(F)F)nc3)c2)s1] | 3-(5-Methyl-1,3-thiazol-2-yl)-5-(tetrahydro-2H-pyran-4-ylmethoxy)-N-[(1R)-1-[2-(trifluoromethyl)pyrimidin-5-yl]ethyl]benzamide | $^1$H NMR (500 MHz, CDCl$_3$): δ [ppm] = 8.93 (s, 2H), 7.86 (t, J = 1.3 Hz, 1H), 7.52 (d, J = 1.2 Hz, 1H), 7.50 (dd, J = 2.4, 1.5 Hz, 1H), 7.38 (dd, J = 2.3, 1.6 Hz, 1H), 6.76 (d, J = 6.6 Hz, 1H), 5.36 (p, J = 7.1 Hz, 1H), 4.02 (dd, J = 11.3, 3.1 Hz, 2H), 3.90 (d, J = 6.4 Hz, 2H), 3.45 (td, J = 11.8, 2.0 Hz, 2H), 2.53 (d, J = 1.1 Hz, 3H), 2.14-2.03 (m, 1H), 1.79-1.73 (m, 2H), 1.71 (d, J = 7.2 Hz, 3H), 1.47 (qd, J = 12.2, 4.6 Hz, 2H). LCMS (Analytical Method F) Rt = 3.72 min, MS (ESIpos): m/z = 507.1 (M + H)$^+$. |
| 99 | 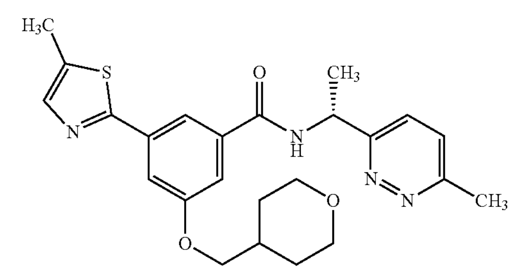 [SMILES: Cc1ccc([C@@H](C)NC(=O)c2cc(OCC3CCOCC3)cc(-c3ncc(C)s3)c2)nn1] | N-[(1R)-1-(6-Methylpyridazin-3-yl)ethyl]-3-(5-methyl-1,3-thiazol-2-yl)-5-(tetrahydro-2H-pyran-4-ylmethoxy)benzamide | $^1$H NMR (500 MHz, CDCl$_3$): δ [ppm] = 8.01-7.94 (m, 2H), 7.65-7.57 (m, 2H), 7.53 (s, 1H), 7.51-7.44 (m, 2H), 5.50 (p, J = 7.0 Hz, 1H), 4.02 (dd, J = 11.3, 3.4 Hz, 2H), 3.93 (d, J = 6.4 Hz, 2H), 3.45 (td, J = 11.8, 1.7 Hz, 2H), 2.78 (s, 3H), 2.53 (s, 3H), 2.13-2.04 (m, 1H), 1.81-1.67 (m, 5H), 1.47 (qd, J = 12.2, 4.4 Hz, 2H). LCMS (Analytical Method D) Rt = 3.84 min, MS (ESIpos): m/z = 453 (M + H)$^+$. |

| Ex. | Structure | Name | Analytical Data |
|---|---|---|---|
| 100 | 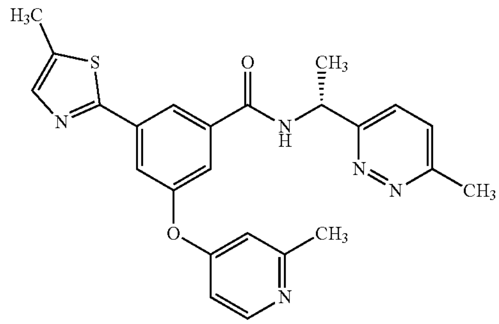 [SMILES: Cc1cc(Oc2cc(C(=O)N[C@H](C)c3ccc(C)nn3)cc(-c3ncc(C)s3)c2)ccn1] | N-[(1R)-1-(6-Methylpyridazin-3-yl)ethyl]-3-[(2-methyl pyridin-4-yl)oxy]-5-(5-methyl-1,3-thiazol-2-yl)benzamide | ¹H NMR (500 MHz, CDCl₃): δ [ppm] = 8.38 (d, J = 5.5 Hz, 1H), 8.18 (t, J = 1.4 Hz, 1H), 7.90 (d, J = 7.2 Hz, 1H), 7.79-7.75 (m, 1H), 7.61-7.57 (m, 1H), 7.53 (d, J = 1.1 Hz, 1H), 7.40 (d, J = 8.6 Hz, 1H), 7.34 (d, J = 8.6 Hz, 1H), 6.75-6.68 (m, 2H), 5.45 (p, J = 6.8 Hz, 1H), 2.73 (s, 3H), 2.53 (d, J = 0.9 Hz, 3H), 2.51 (s, 3H), 1.68 (d, J = 6.8 Hz, 3H). LCMS (Analytical Method D) Rt = 2.87 min, MS (ESIpos): m/z = 446 (M + H)⁺. |
| 101 | 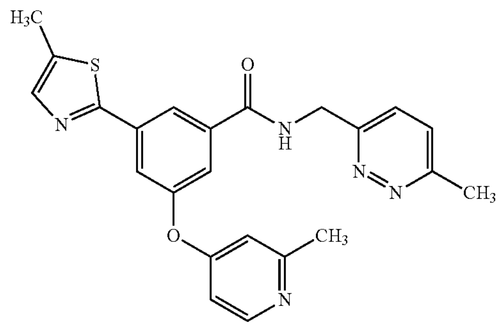 [SMILES: Cc1cc(Oc2cc(C(=O)NCc3ccc(C)nn3)cc(-c3ncc(C)s3)c2)ccn1] | N-[(6-Methylpyridazin-3-yl)methyl]-3-[(2-methyl pyridin-4-yl)oxy]-5-(5-methyl-1,3-thiazol-2-yl)benzamide | ¹H NMR (500 MHz, CDCl₃): δ [ppm] = 8.38 (d, J = 5.6 Hz, 1H), 8.18 (t, J = 1.5 Hz, 1H), 7.79-7.76 (m, 1H), 7.73 (t, J = 4.6 Hz, 1H), 7.63-7.59 (m, 1H), 7.52 (d, J = 1.1 Hz, 1H), 7.45 (d, J = 8.6 Hz, 1H), 7.35 (d, J = 8.6 Hz, 1H), 6.75-6.69 (m, 2H), 4.91 (d, J = 5.1 Hz, 2H), 2.72 (s, 3H), 2.53 (d, J = 1.0 Hz, 3H), 2.52 (s, 3H). LCMS (Analytical Method D) Rt = 2.80 min, MS (ESIpos): m/z = 432.1 (M + H)⁺. |
| 102 | 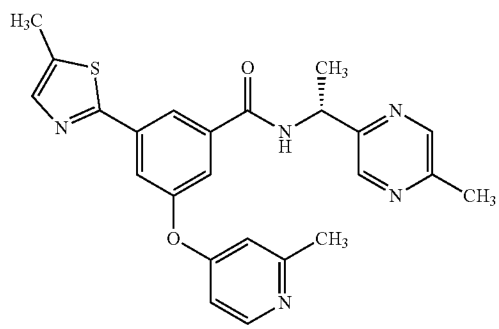 [SMILES: Cc1cnc([C@@H](C)NC(=O)c2cc(Oc3ccnc(C)c3)cc(-c3ncc(C)s3)c2)cn1] | N-[(1R)-1-(5-Methylpyrazin-2-yl)ethyl]-3-[(2-methylpyridin-4-yl)oxy]-5-(5-methyl-1,3-thiazol-2-yl)benzamide | ¹H NMR (500 MHz, CDCl₃): δ [ppm] = 8.56 (d, J = 1.4 Hz, 1H), 8.43 (s, 1H), 8.41 (d, J = 5.6 Hz, 1H), 8.18 (t, J = 1.5 Hz, 1H), 7.80-7.75 (m, 1H), 7.63-7.58 (m, 1H), 7.56 (d, J = 1.2 Hz, 1H), 7.37 (d, J = 7.4 Hz, 1H), 6.79-6.72 (m, 2H), 5.45 (p, J = 6.9 Hz, 1H), 2.60 (s, 3H), 2.56 (d, J = 1.1 Hz, 3H), 2.54 (s, 3H), 1.63 (d, J = 6.8 Hz, 3H). LCMS (Analytical Method D) Rt = 3.00 min, MS (ESIpos): m/z = 446.1 (M + H)⁺. |
| 103 | 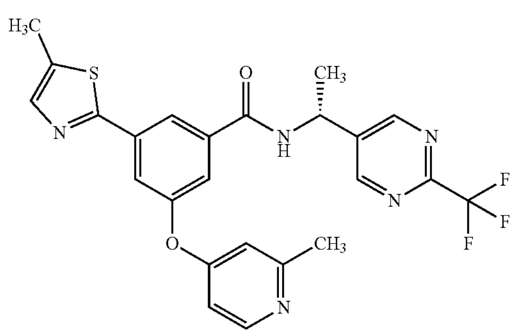 [SMILES: Cc1cc(Oc2cc(C(=O)N[C@H](C)c3cnc(C(F)(F)F)nc3)cc(-c3ncc(C)s3)c2)ccn1] | 3-[(2-Methylpyridin-4-yl)oxy]-5-(5-methyl-1,3-thiazol-2-yl)-N-{(1R)-1-[2-(trifluoromethyl)pyrimidin-5-yl]ethyl}benzamide | ¹H NMR (500 MHz, CDCl₃): δ [ppm] = 8.94 (s, 2H), 8.39 (d, J = 5.7 Hz, 1H), 8.13 (t, J = 1.5 Hz, 1H), 7.74-7.70 (m, 1H), 7.58-7.53 (m, 2H), 6.73 (d, J = 2.3 Hz, 1H), 6.71 (dd, J = 5.6, 2.3 Hz, 1H), 6.65 (d, J = 6.5 Hz, 1H), 5.37 (p, J = 7.0 Hz, 1H), 2.54 (d, J = 1.0 Hz, 3H), 2.52 (s, 3H), 1.73 (d, J = 7.1 Hz, 3H). LCMS (Analytical Method D) Rt = 3.28 min, MS (ESIpos): m/z = 500.1 (M + H)⁺. |

| Ex. | Structure | Name | Analytical Data |
|---|---|---|---|
| 104 | 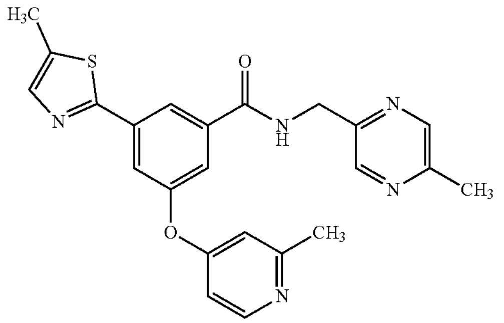 [SMILES: Cc1cnc(CNC(=O)c2cc(Oc3ccnc(C)c3)cc(-c3ncc(C)s3)c2)cn1] | N-[(5-Methylpyrazin-2-yl)methyl]-3-[(2-methylpyridin-4-yl)oxy]-5-(5-methyl-1,3-thiazol-2-yl)benzamide | $^1$H NMR (500 MHz, CDCl$_3$): δ [ppm] = 8.56 (d, J = 1.1 Hz, 1H), 8.42 (s, 1H), 8.39 (d, J = 5.6 Hz, 1H), 8.17 (t, J = 1.5 Hz, 1H), 7.78-7.73 (m, 1H), 7.61-7.57 (m, 1H), 7.53 (d, J = 1.1 Hz, 1H), 7.27 (s, 1H), 6.73 (dt, J = 8.1, 2.3 Hz, 2H), 4.78 (d, J = 5.1 Hz, 2H), 2.58 (s, 3H), 2.54 (d, J = 1.1 Hz, 3H), 2.52 (s, 3H). LCMS (Analytical Method D) Rt = 2.90 min, MS (ESIpos): m/z = 432.1 (M + H)$^+$. |
| 105 | 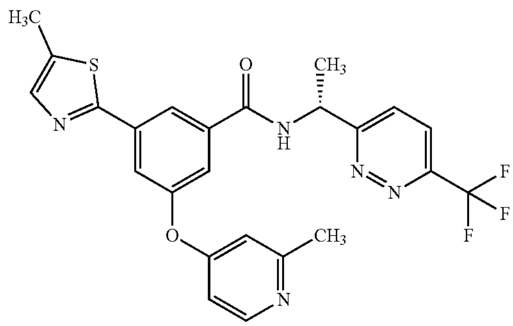 [SMILES: Cc1cc(Oc2cc(C(=O)N[C@H](C)c3ccc(C(F)(F)F)nn3)cc(-c3ncc(C)s3)c2)ccn1] | 3-[(2-Methylpyridin-4-yl)oxy]-5-(5-methyl-1,3-thiazol-2-yl)-N-{(1R)-1-[6-(trifluoromethyl)pyridazin-3-yl]ethyl}benzamide | $^1$H NMR (500 MHz, CDCl$_3$): δ [ppm] = 8.38 (dd, J = 5.3, 0.9 Hz, 1H), 8.17 (t, J = 1.5 Hz, 1H), 7.84 (d, J = 8.7 Hz, 1H), 7.78-7.72 (m, 2H), 7.69 (d, J = 7.3 Hz, 1H), 7.61-7.56 (m, 1H), 7.53 (d, J = 1.2 Hz, 1H), 6.77-6.71 (m, 2H), 5.60 (p, J = 7.0 Hz, 1H), 2.56-2.51 (m, 6H), 1.93 (d, J = 7.1 Hz, 0H), 1.76 (d, J = 7.0 Hz, 3H). LCMS (Analytical Method F) Rt = 2.16 min, MS (ESIpos): m/z = 499.0 (M + H)$^+$. |

Example 106

3-[(2-methylpyridin-4-yl)oxy]-N-[(1R)-1-(2-methylpyrimidin-5-yl)ethyl]-5-(5-methyl-1,3-thiazol-2-yl)benzamide

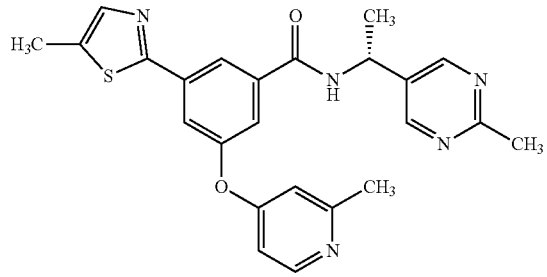

3-Bromo-5-[(2-methylpyridin-4-yl)oxy]benzoic acid

Intermediate 1 (2.3 g, 9.95 mmol), 4-bromo-2-methylpyridine (2.05 g, 11.95 mmol) and Cs$_2$CO$_3$ (19.5 g, 59.7 mmol) in DMF (150 mL) were stirred at 120° C. for 48 hours. The reaction mixture was cooled to RT, filtrated and evaporated to dryness. The crude material was purified by column chromatography (silica gel, hexane/EE gradient) to afford the title compound 1.1 g (36% yield).

3-Bromo-5-[(2-methylpyridin-4-yl)oxy]-N-[(1R)-1-(2-methylpyrimidin-5-yl)ethyl]benzamide 3-Bromo-5-[(2-methylpyridin-4-yl)oxy]benzoic acid (273 mg, 0.89 mmol), (1R)-1-(2-methylpyrimidin-5-yl) ethanamine dihydrochloride (205 mg, 0.97 mmol), DIPEA (0.76 ml, 4.4 mmol) and HATU (371 mg, 0.97 mmol) were dissolved in DMF. The reaction mixture was stirred overnight at RT. Additional (1R)-1-(2-methylpyrimidin-5-yl) ethanamine dihydrochloride (205 mg, 0.97 mmol), DIPEA (0.76 ml, 4.4 mmol) and HATU (371 mg, 0.97 mmol) was added and the reaction mixture was stirred at 60° C. until complete conversion and evaporated to dryness. The crude material was purified by column chromatography (silica gel, hexane/EE gradient) to afford the title compound.

$^1$H NMR (400 MHz, DMSO-d$_6$) δ [ppm] 1.52 (d, J=7.07 Hz, 3H) 2.43 (s, 3H) 2.58 (s, 3H) 5.13 (s, 1H) 6.78-6.82 (m, 1H) 6.87 (d, J=2.53 Hz, 1H) 7.63 (t, J=1.39 Hz, 2H) 7.99 (t, J=1.64 Hz, 1H) 8.36 (d, J=5.56 Hz, 1H) 8.69 (s, 2H) 9.03 (d, J=7.33 Hz, 1H).

(3-[(2-Methylpyridin-4-yl)oxy]-5-{[(1R)-1-(2-methylpyrimidin-5-yl)ethyl]carbamoyl}phenyl)boronic acid 3-Bromo-5-[(2-methylpyridin-4-yl)oxy]-N-[(1R)-1-(2-methylpyrimidin-5-yl)ethyl]benzamide (0.97 g, 77% purity, 1.75 mmol), bis(pinacolato)diborane (1.11 g, 4.37 mmol) and potassium acetate (0.58 g, 5.94 mmol) were dissolved in 1,4-dioxane. Pd(dppf)Cl$_2$.CH$_2$Cl$_2$ (80 mg, 0.1 mmol) was added and the reaction mixture was stirred at 100° C. for 12 hours. The reaction mixture was concentrated in vacuo and purified by column chromatography (silica gel, hexane/EE gradient) to afford the title compound 96 mg (14% yield).

3-[(2-Methylpyridin-4-yl)oxy]-N-[(1R)-1-(2-methylpyrimidin-5-yl)ethyl]-5-(5-methyl-1,3-thiazol-2-yl)benzamide (3-[(2-methylpyridin-4-yl)oxy]-5-{[(1R)-1-(2-methylpyrimidin-5-yl)ethyl]carbamoyl}phenyl)boronic acid (96 mg, 0.24 mmol) and 2-bromo-5-methyl-1,3-thiazole (65 mg, 0.37 mmol) were dissolved in 1M K$_2$CO$_3$ aqueous solution (0.59 mL) and THF (4 mL). Pd(dppf)Cl$_2$.CH$_2$Cl$_2$ (30 mg, 0.04 mmol) was added and the reaction mixture heated to reflux for 2 hours. The reaction mixture was concentrated under reduced pressure. Crude material was purified by preparative HPLC (method 2, rt: 1.03 min) to afford the title compound 27 mg (25% yield).

$^1$H NMR (300 MHz, DMSO-d$_6$) δ [ppm] 1.54 (d, J=7.16 Hz, 3H) 2.43 (s, 3H) 2.59 (s, 3H) 5.17 (s, 1H) 6.84 (dd, J=5.65, 2.45 Hz, 1H) 6.91 (d, J=2.26 Hz, 1H) 7.66 (d, J=1.13 Hz, 1H) 7.71-7.78 (m, 2H) 8.24 (s, 1H) 8.37 (d, J=5.65 Hz, 1H) 8.72 (s, 2H) 9.14 (d, J=7.35 Hz, 1H).

In analogy to the procedure described for Example 1 the following example was prepared using the appropriate carboxylic acid and amine as starting materials.

| Ex. | Structure | Name | Analytical Data |
|---|---|---|---|
| 107 | H$_3$C-thiazole-benzamide-pyridine-pyridine structure | N-[(1R)-1-(6-Methylpyridin-3-yl)ethyl]-3-[(2-methylpyridin-4-yl)oxy]-5-(5-methyl-1,3-thiazol-2-yl)benzamide | $^1$H NMR (500 MHz, CDCl$_3$): δ [ppm] = 8.50 (d, J = 2.4 Hz, 1H), 8.31 (d, J = 5.7 Hz, 1H), 8.11 (t, J = 1.5 Hz, 1H), 7.78 (t, J = 1.4 Hz, 0H), 7.70-7.65 (m, 1H), 7.60-7.53 (m, 2H), 7.49 (d, J = 1.2 Hz, 1H), 7.39-7.37 (m, 0H), 7.10 (d, J = 8.0 Hz, 1H), 7.00 (d, J = 7.6 Hz, 1H), 6.69-6.62 (m, 2H), 5.30 (dd, J = 14.5, 7.4 Hz, 1H), 2.50 (d, J = 1.2 Hz, 6H), 2.45 (s, 3H), 1.60 (d, J = 7.0 Hz, 3H). LCMS (Analytical Method F) Rt = 1.25 min, MS (ESIpos): m/z = 445.2 (M + H)$^+$. |

Example 108

3-[(6-Methylpyridin-3-yl)ont]-5-(5-methyl-1,3-thiazol-2-yl)-N-{(1R)-1-[2-(trifluoromethyl)pyrimidin-5-yl]ethyl}benzamide

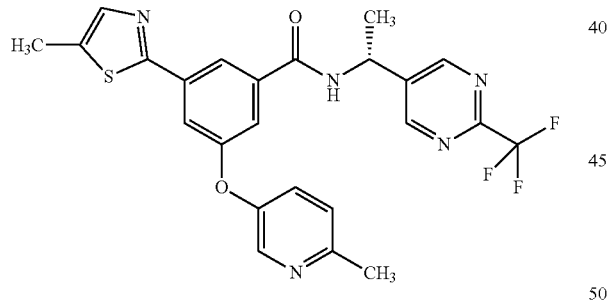

Intermediate 5N (375 mg, 1.15 mmol), Intermediate VI (242 mg, 1.26 mmol), DIPEA (0.8 ml, 4.6 mmol) and HATU (612 mg, 1.61 mmol) were dissolved in DMF (13.3 mL). The reaction mixture was stirred at RT until complete conversion and evaporated to dryness. The crude material was extracted three times with EE and evaporated to dryness again. The remaining crude material was purified by preparative HPLC (method 1, rt: 1.16 min) to afford the title compound 18.5 mg (3.2% yield).

$^1$H NMR (400 MHz, DMSO-d$_6$) δ [ppm] 1.61 (d, J=7.10 Hz, 3H) 5.24-5.33 (m, 1H) 7.35 (d, J=8.36 Hz, 1H) 7.51 (dd, J=8.49, 2.91 Hz, 1H) 7.60 (t, J=1.39 Hz, 2H) 7.64 (d, J=1.27 Hz, 1H) 8.12 (t, J=1.52 Hz, 1H) 8.36 (d, J=2.53 Hz, 1H) 9.11 (s, 2H) 9.23-9.29 (m, 1H).

In analogy to the procedure described for Example 7 the following examples were prepared using the appropriate carboxylic acid and amine as starting materials.

| Ex. | Structure | Name | Analytical Data |
|---|---|---|---|
| 109 | 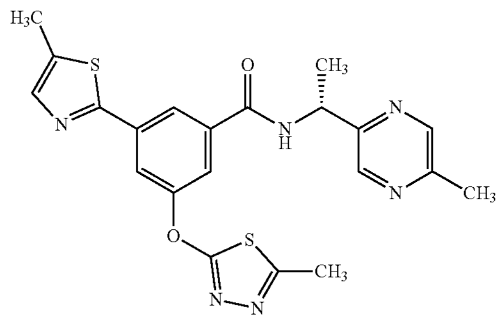 [SMILES: Cc1cnc([C@@H](C)NC(=O)c2cc(Oc3nnc(C)s3)cc(-c3ncc(C)s3)c2)cn1] | N-[(1R)-1-(5-Methylpyrazin-2-yl)ethyl]-3-[(5-methyl-1,3,4-thiadiazol-2-yl)oxy]-5-(5-methyl-1,3-thiazol-2-yl)benzamide | $^1$H NMR (500 MHz, CDCl$_3$): δ [ppm] = 8.53 (d, J = 1.2 Hz, 1H), 8.42 (s, 1H), 8.18 (s, 1H), 8.00-7.97 (m, 1H), 7.81-7.77 (m, 1H), 7.54 (d, J = 1.1 Hz, 1H), 7.36 (d, J = 7.5 Hz, 1H), 5.43 (p, J = 6.8 Hz, 1H), 2.69 (s, 3H), 2.58 (s, 3H), 2.54 (d, J = 0.9 Hz, 3H), 1.60 (d, J = 6.8 Hz, 3H). LCMS (Analytical Method F) Rt = 2.82 min, MS (ESIpos): m/z = 453.2 (M + H)$^+$. |
| 110 | 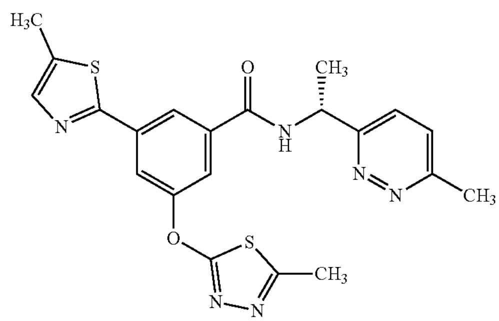 [SMILES: Cc1ccc([C@@H](C)NC(=O)c2cc(Oc3nnc(C)s3)cc(-c3ncc(C)s3)c2)nn1] | N-[(1R)-1-(6-Methylpyridazin-3-yl)ethyl]-3-[(5-methyl-1,3,4-thiadiazol-2-yl)oxy]-5-(5-methyl-1,3-thiazol-2-yl)benzamide | $^1$H NMR (500 MHz, CDCl$_3$): δ [ppm] = 8.21 (t, J = 1.4 Hz, 1H), 8.02-8.00 (m, 1H), 7.86 (d, J = 7.2 Hz, 1H), 7.82-7.79 (m, 1H), 7.53 (d, J = 1.1 Hz, 1H), 7.40 (d, J = 8.6 Hz, 1H), 7.34 (d, J = 8.6 Hz, 1H), 5.46 (p, J = 6.9 Hz, 1H), 2.73 (s, 3H), 2.68 (s, 3H), 2.53 (d, J = 1.0 Hz, 3H), 1.68 (d, J = 6.8 Hz, 3H). LCMS (Analytical Method F) Rt = 2.48 min, MS (ESIpos): m/z = 453.2 (M + H)$^+$. |
| 111 | 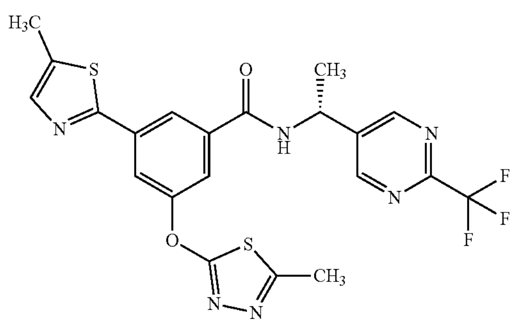 [SMILES: Cc1cnc(-c2cc(Oc3nnc(C)s3)cc(C(=O)N[C@H](C)c3cnc(C(F)(F)F)nc3)c2)s1] | 3-[(5-Methyl-1,3,4-thiadiazol-2-yl)oxy]-5-(5-methyl-1,3-thiazol-2-yl)-N-[(1R)-1-[2-(trifluoromethyl)pyrimidin-5-yl]ethyl]benzamide | $^1$H NMR (500 MHz, CDCl$_3$): δ [ppm] = 8.95 (s, 2H), 8.13 (s, 1H), 7.97-7.92 (m, 1H), 7.81-7.76 (m, 1H), 7.53 (d, J = 1.1 Hz, 1H), 6.97 (d, J = 6.6 Hz, 1H), 5.37 (p, J = 7.0 Hz, 1H), 2.69 (s, 3H), 2.54 (d, J = 0.9 Hz, 3H), 1.72 (d, J = 7.2 Hz, 3H). LCMS (Analytical Method F) Rt = 3.41 min, MS (ESIpos): m/z = 507.1 (M + H)$^+$. |
| 112 | 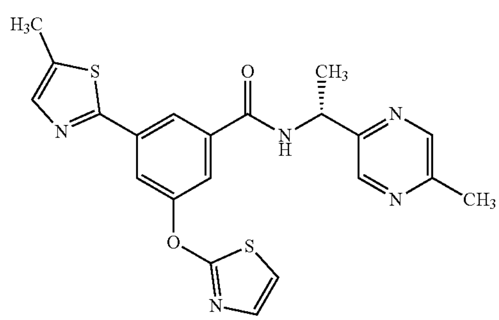 [SMILES: Cc1cnc([C@@H](C)NC(=O)c2cc(Oc3nccs3)cc(-c3ncc(C)s3)c2)cn1] | N-[(1R)-1-(5-Methylpyrazin-2-yl)ethyl]-3-(5-methyl-1,3-thiazol-2-yl)-5-(1,3-thiazol-2-yloxy)benzamide | $^1$H NMR (500 MHz, CDCl$_3$): δ [ppm] = 8.53 (d, J = 1.4 Hz, 1H), 8.41 (s, 1H), 8.17 (t, J = 1.5 Hz, 1H), 7.97 (dd, J = 2.3, 1.6 Hz, 1H), 7.78 (dd, J = 2.3, 1.6 Hz, 1H), 7.54 (d, J = 1.2 Hz, 1H), 7.33 (d, J = 7.2 Hz, 1H), 7.25 (d, J = 3.8 Hz, 1H), 6.88 (d, J = 3.8 Hz, 1H), 5.43 (p, J = 6.8 Hz, 1H), 2.58 (s, 3H), 2.54 (d, J = 1.1 Hz, 3H), 1.60 (d, J = 6.8 Hz, 3H). LCMS (Analytical Method D) Rt = 4.04 min, MS (ESIpos): m/z = 438.1 (M + H)$^+$. |
| 113 | 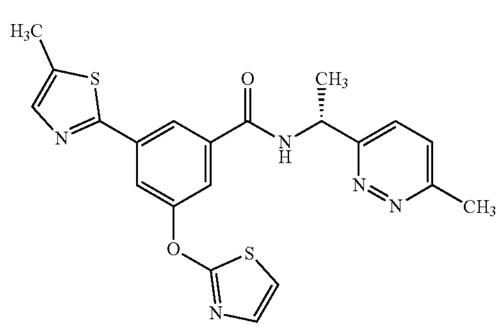 [SMILES: Cc1ccc([C@@H](C)NC(=O)c2cc(Oc3nccs3)cc(-c3ncc(C)s3)c2)nn1] | N-[(1R)-1-(6-Methylpyridazin-3-yl)ethyl]-3-(5-methyl-1,3-thiazol-2-yl)-5-(1,3-thiazol-2-yloxy)benzamide | $^1$H NMR (500 MHz, CDCl$_3$): δ [ppm] = 8.19 (t, J = 1.5 Hz, 1H), 8.00 (dd, J = 2.3, 1.5 Hz, 1H), 7.83 (d, J = 7.2 Hz, 1H), 7.80 (dd, J = 2.2, 1.6 Hz, 1H), 7.53 (d, J = 1.1 Hz, 1H), 7.39 (d, J = 8.6 Hz, 1H), 7.34 (d, J = 8.6 Hz, 1H), 7.25 (d, J = 3.8 Hz, 1H), 6.87 (d, J = 3.8 Hz, 1H), 5.50-5.43 (m, 1H), 2.73 (s, 3H), 2.53 (d, J = 1.1 Hz, 3H), 1.68 (d, J = 6.8 Hz, 3H). LCMS (Analytical Method D) Rt = 3.77 min, MS (ESIpos): m/z = 438.0 (M + H)$^+$. |

| Ex. | Structure | Name | Analytical Data |
|---|---|---|---|
| 114 | 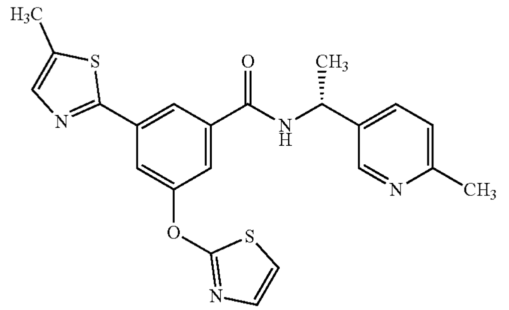 [SMILES: Cc1ccc([C@@H](C)NC(=O)c2cc(Oc3nccs3)cc(-c3ncc(C)s3)c2)cn1] | N-[(1R)-1-(6-Methylpyridin-3-yl)ethyl]-3-(5-methyl-1,3-thiazol-2-yl)-5-(1,3-thiazol-2-yloxy)benzamide | $^1$H NMR (500 MHz, CDCl$_3$): δ [ppm] = 8.56 (s, 1H), 8.11 (t, J = 1.5 Hz, 1H), 7.93 (dd, J = 2.3, 1.5 Hz, 1H), 7.80-7.74 (m, 1H), 7.60 (dd, J = 8.0, 2.3 Hz, 1H), 7.53 (d, J = 1.2 Hz, 1H), 7.24 (d, J = 3.8 Hz, 1H), 7.14 (d, J = 8.0 Hz, 1H), 6.88 (d, J = 3.8 Hz, 1H), 6.42 (d, J = 7.1 Hz, 1H), 5.33 (p, J = 7.2 Hz, 1H), 2.55 (s, 3H), 2.53 (d, J = 1.1 Hz, 3H), 1.64 (d, J = 7.0 Hz, 3H). LCMS (Analytical Method D) Rt = 3.24 min, MS (ESIpos): m/z = 437.0 (M + H)$^+$. |

Example 115

N-[(1R)-1-(5-Chloropyridin-2-yl)ethyl]-3-(5-chloro-1,3-thiazol-2-yl)-5-(2-methoxy-2-methylpropoxy)benzamide

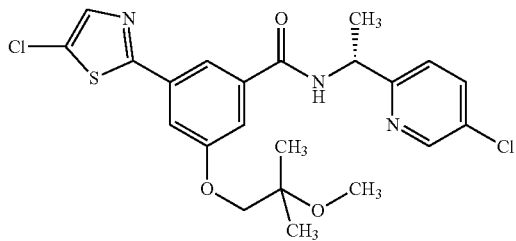 [SMILES: COC(C)(C)COc1cc(C(=O)N[C@H](C)c2ccc(Cl)cn2)cc(-c2ncc(Cl)s2)c1]

Intermediate 5Q (115 mg, 0.34 mmol), (1R)-1-(5-chloropyridin-2-yl)ethanamine dihydrochloride (77 mg, 0.34 mmol), DIPEA (0.23 mL, 1.35 mmol) and HATU (179 mg, 0.47 mmol) were dissolved in DMF (2.5 mL). The reaction mixture was stirred at RT until complete conversion and evaporated to dryness. The remaining crude material was purified by preparative HPLC (method 1, rt: 1.44 min) to afford the title compound 81 mg (50% yield).

$^1$H NMR (300 MHz, DMSO-d$_6$) δ [ppm] 1.25 (s, 6H) 1.53 (d, J=6.97 Hz, 3H) 3.18 (s, 3H) 3.99 (s, 2H) 5.19 (d, J=7.16 Hz, 1H) 7.46 (d, J=8.29 Hz, 1H) 7.56-7.61 (m, 1H) 7.62-7.66 (m, 1H) 7.90 (dd, J=8.48, 2.45 Hz, 1H) 7.96 (t, J=1.41 Hz, 1H) 8.01 (s, 1H) 8.58 (d, J=2.07 Hz, 1H) 9.10 (d, J=7.54 Hz, 1H).

Example 116

3-(5-Chloro-1,3-thiazol-2-yl)-5-(2-methoxy-2-methylpropoxy)-N-{(1R)-1-[2-(trifluoromethyl)pyrimidin-5-yl]ethyl}benzamide

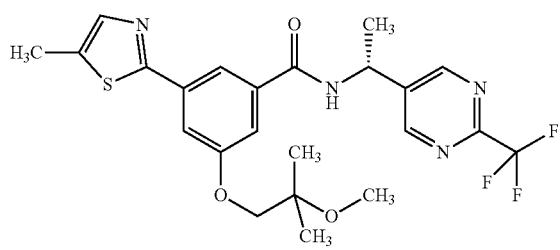 [SMILES: COC(C)(C)COc1cc(C(=O)N[C@H](C)c2cnc(C(F)(F)F)nc2)cc(-c2ncc(C)s2)c1]

Intermediate 5Q (115 mg, 0.34 mmol), Intermediate VI (77 mg, 0.34 mmol), DIPEA (0.23 mL, 1.35 mmol) and HATU (179 mg, 0.47 mmol) were dissolved in DMF (2.5 mL). The reaction mixture was stirred at RT until complete conversion and evaporated to dryness. The remaining crude material was purified by preparative HPLC (method 1, rt: 1.41 min) to afford the title compound 97 mg (56% yield).

$^1$H NMR (400 MHz, DMSO-d$_6$) δ [ppm] 1.22-1.25 (m, 6H) 1.61 (d, J=7.10 Hz, 3H) 3.17 (s, 3H) 3.99 (s, 2H) 5.30 (s, 1H) 7.57-7.63 (m, 2H) 7.93 (t, J=1.39 Hz, 1H) 8.01 (s, 1H) 9.12 (s, 2H) 9.18 (d, J=7.10 Hz, 1H).

Example 117

3-(5-Chloro-1,3-thiazol-2-yl)-5-(2-methoxy-2-methylpropoxy)-N-[(1R)-1-(5-methylpyrazin-2-yl)ethyl]benzamide

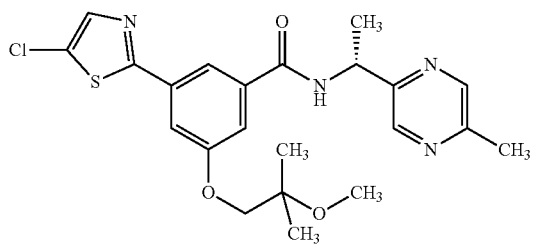 [SMILES: COC(C)(C)COc1cc(C(=O)N[C@H](C)c2cnc(C)cn2)cc(-c2ncc(Cl)s2)c1]

Intermediate 5Q (115 mg, 0.34 mmol), (1R)-1-(5-methylpyrazin-2-yl)ethanamine hydrochloride (58 mg, 0.34 mmol), DIPEA (0.23 mL, 1.35 mmol) and HATU (179 mg, 0.47 mmol) were dissolved in DMF (2.5 mL). The reaction mixture was stirred at RT until complete conversion and evaporated to dryness. The remaining crude material was purified by preparative HPLC (method 1, rt: 1.28 min) to afford the title compound 38 mg (23% yield).

$^1$H NMR (400 MHz, DMSO-d$_6$) δ [ppm] 1.23-1.25 (m, 6H) 1.55 (d, J=7.10 Hz, 3H) 2.47 (s, 3H) 3.17 (s, 3H) 3.99 (s, 2H) 5.19-5.28 (m, 1H) 7.56-7.59 (m, 1H) 7.62 (d, J=1.52 Hz, 1H) 7.95 (t, J=1.39 Hz, 1H) 8.00 (s, 1H) 8.49 (d, J=0.76 Hz, 1H) 8.56 (d, J=1.52 Hz, 1H) 9.08-9.14 (m, 1H).

Example 118

N-[(6-Methylpyridazin-3-yl)methyl]-3-(tetrahydro-2H-pyran-4-ylmethoxy)-5-[5-(trifluoromethyl)-1,3-thiazol-2-yl]benzamide

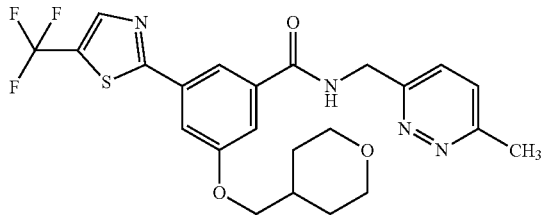 [SMILES: Cc1ccc(CNC(=O)c2cc(OCC3CCOCC3)cc(-c3ncc(C(F)(F)F)s3)c2)nn1]

Intermediate 5R (55% purity, 110 mg, 0.156 mmol), 1-(6-methylpyridazin-3-yl)methanamine (19 mg, 0.156 mmol), DIPEA (0.11 mL, 0.63 mmol) and HATU (83 mg, 0.22 mmol) were dissolved in DMF (2.5 mL). The reaction mixture was stirred at RT until complete conversion and evaporated to dryness. The remaining crude material was purified by preparative HPLC (method 1, rt: 1.19 min) to afford the title compound 14 mg (18% yield).

$^1$H NMR (400 MHz, DMSO-$d_6$) δ [ppm] 1.29-1.43 (m, 2H) 1.70 (br. s., 2H) 1.97-2.12 (m, 1H) 2.60 (s, 3H) 3.32-3.39 (m, 2H) 3.89 (dd, J=11.12, 3.28 Hz, 2H) 4.00 (d, J=6.32 Hz, 2H) 4.74 (d, J=5.81 Hz, 2H) 7.54 (s, 2H) 7.62-7.74 (m, 2H) 8.12 (t, J=1.39 Hz, 1H) 8.51-8.64 (m, 1H) 9.43 (s, 1H).

Example 119

3-(5-Cyclobutyl-1,3-thiazol-2-yl)-N-[(6-methylpyridazin-3-yl)methyl]-5-(tetrahydro-2H-pyran-4-ylmethoxy)benzamide

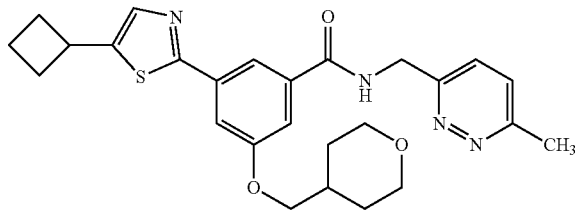 [SMILES: Cc1ccc(CNC(=O)c2cc(OCC3CCOCC3)cc(-c3ncc(C4CCC4)s3)c2)nn1]

Intermediate 5S (53 mg, 0.14 mmol), 1-(6-methylpyridazin-3-yl)methanamine (18 mg, 0.14 mmol), DIPEA (0.1 mL, 0.57 mmol) and HATU (76 mg, 0.2 mmol) were dissolved in DMF (2.5 mL). The reaction mixture was stirred at RT until complete conversion and evaporated to dryness. The remaining crude material was purified by preparative HPLC (method 1, rt: 1.22 min) to afford the title compound 31 mg (45% yield).

$^1$H NMR (400 MHz, DMSO-$d_6$) δ [ppm] 1.30-1.43 (m, 2H) 1.66-1.74 (m, 2H) 1.85-1.94 (m, 1H) 1.96-2.07 (m, 2H) 2.14 (d, J=2.53 Hz, 2H) 2.43 (d, J=8.11 Hz, 2H) 2.60 (s, 3H) 3.35 (d, J=1.77 Hz, 2H) 3.77-3.85 (m, 1H) 3.86-3.92 (m, 2H) 3.96 (d, J=6.59 Hz, 2H) 4.73 (d, J=5.83 Hz, 2H) 7.50-7.56 (m, 3H) 7.56-7.59 (m, 1H) 7.68 (d, J=0.76 Hz, 1H) 7.99 (t, J=1.39 Hz, 1H) 9.35-9.42 (m, 1H).

Example 120

3-(5-Cyclobutyl-1,3-thiazol-2-yl)-5-(tetrahydro-2H-pyran-4-ylmethoxy)-N-{(1R)-1-[2-(trifluoromethyl)pyrimidin-5-yl]ethyl}benzamide

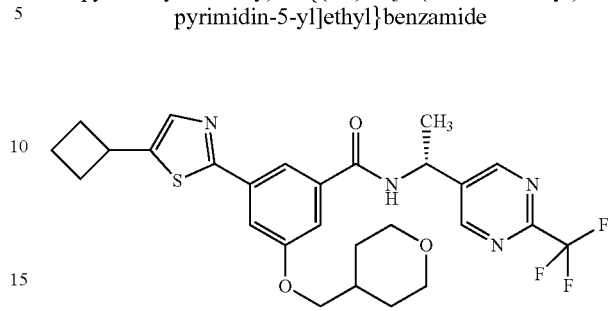

Intermediate 5S (53 mg, 0.14 mmol), Intermediate VI (27 mg, 0.14 mmol), DIPEA (0.1 mL, 0.57 mmol) and HATU (76 mg, 0.2 mmol) were dissolved in DMF (2.5 mL). The reaction mixture was stirred at RT until complete conversion and evaporated to dryness. The remaining crude material was purified by preparative HPLC (method 1, rt: 1.47 min) to afford the title compound 40 mg (52% yield).

$^1$H NMR (400 MHz, DMSO-$d_6$) δ [ppm] 1.31-1.44 (m, 2H) 1.61 (d, J=7.07 Hz, 3H) 1.67-1.75 (m, 2H) 1.86-1.96 (m, 1H) 1.97-2.08 (m, 2H) 2.09-2.20 (m, 2H) 2.39-2.47 (m, 2H) 3.35 (d, J=1.77 Hz, 2H) 3.77-3.85 (m, 1H) 3.86-3.92 (m, 2H) 3.97 (d, J=6.32 Hz, 2H) 5.25-5.35 (m, 1H) 7.49-7.53 (m, 1H) 7.55-7.58 (m, 1H) 7.68 (d, J=1.01 Hz, 1H) 7.94 (t, J=1.39 Hz, 1H) 9.12 (s, 2H) 9.13-9.16 (m, 1H).

Example 121

3-(5-Cyclobutyl-1,3-thiazol-2-yl)-N-[(1R)-1-(5-methylpyrazin-2-yl)ethyl]-5-[(3S)-tetrahydrofuran-3-ylmethoxy]benzamide

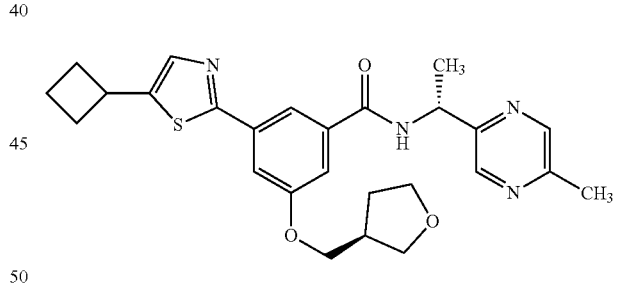

Intermediate 5T (150 mg, 0.42 mmol), (1R)-1-(5-methylpyrazin-2-yl)ethanamine dihydrochloride (105 mg, 0.5 mmol), TEA (0.09 mL, 0.63 mmol) and HATU (175 mg, 0.46 mmol) were dissolved in DMSO (4.2 mL). The reaction mixture was stirred at RT until complete conversion and evaporated to dryness. The remaining crude material was purified by preparative HPLC (method 2, rt: 1.31 min) to afford the title compound 38 mg (19% yield).

$^1$H NMR (400 MHz, DMSO-$d_6$) δ [ppm] 1.55 (d, J=7.10 Hz, 3H) 1.66-1.77 (m, 1H) 1.84-1.95 (m, 1H) 2.03 (dd, J=10.65, 9.38 Hz, 2H) 2.10-2.21 (m, 2H) 2.44 (dt, J=8.24, 3.11 Hz, 2H) 2.47-2.49 (m, 3H) 2.62-2.76 (m, 1H) 3.58 (dd, J=8.62, 5.58 Hz, 1H) 3.68 (d, J=7.10 Hz, 1H) 3.75-3.88 (m, 3H) 3.98-4.13 (m, 2H) 5.24 (s, 1H) 7.53-7.60 (m, 2H) 7.68 (d, J=1.01 Hz, 1H) 7.97 (t, J=1.39 Hz, 1H) 8.49 (d, J=0.76 Hz, 1H) 8.57 (d, J=1.52 Hz, 1H) 9.09 (d, J=7.35 Hz, 1H).

Example 122

3-(5-Cyclobutyl-1,3-thiazol-2-yl)-N-[(6-methylpyridazin-3-yl)methyl]-5-[(3S)-tetrahydrofuran-3-ylmethoxy]benzamide

Intermediate 5T (150 mg, 0.42 mmol), 1-(6-methylpyridazin-3-yl)methanamine hydrochloride (93 mg, 0.58 mmol), TEA (0.09 mL, 0.63 mmol) and HATU (175 mg, 0.46 mmol) were dissolved in DMF (4.5 mL). The reaction mixture was stirred at RT until complete conversion and evaporated to dryness. The remaining crude material was purified by preparative HPLC (method 2, rt: 1.19 min) to afford the title compound 13 mg (6% yield).

$^1$H NMR (400 MHz, DMSO-$d_6$) δ [ppm] 1.70 (dd, J=13.31, 5.96 Hz, 1H) 1.84-1.95 (m, 1H) 1.96-2.07 (m, 2H) 2.09-2.20 (m, 2H) 2.38-2.47 (m, 2H) 2.60 (s, 3H) 2.64-2.74 (m, 1H) 3.57 (dd, J=8.62, 5.58 Hz, 1H) 3.67 (q, J=7.69 Hz, 1H) 3.74-3.85 (m, 3H) 3.97-4.12 (m, 2H) 4.73 (d, J=5.83 Hz, 2H) 7.51-7.59 (m, 4H) 7.68 (s, 1H) 7.99 (s, 1H) 9.39 (t, J=5.83 Hz, 1H).

Example 123

3-(5-Cyclobutyl-1,3-thiazol-2-yl)-5-[(3S)-tetrahydrofuran-3-ylmethoxy]-N-{(1R)-1-[2-(trifluoromethyl)pyrimidin-5-yl]ethyl}benzamide

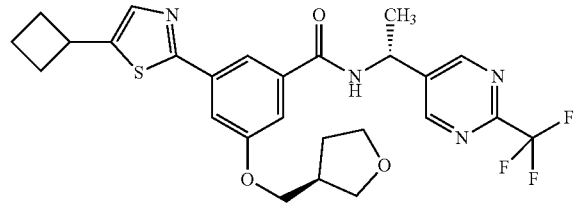 [SMILES: C[C@@H](NC(=O)c1cc(OC[C@H]2CCOC2)cc(-c2ncc(C3CCC3)s2)c1)c1cnc(C(F)(F)F)nc1]

Intermediate 5T (150 mg, 0.42 mmol), Intermediate VI (104 mg, 0.46 mmol), TEA (0.09 mL, 0.63 mmol) and HATU (175 mg, 0.46 mmol) were dissolved in DMSO (4.2 mL). The reaction mixture was stirred at RT until complete conversion and evaporated to dryness. The remaining crude material was purified by preparative HPLC (method 2, rt: 1.42 min) to afford the title compound 100 mg (45% yield).

$^1$H NMR (400 MHz, DMSO-$d_6$) δ [ppm] 1.61 (d, J=7.10 Hz, 3H) 1.66-1.76 (m, 1H) 1.84-1.94 (m, 1H) 2.02 (td, J=9.06, 1.90 Hz, 2H) 2.09-2.21 (m, 2H) 2.38-2.48 (m, 2H) 2.63-2.74 (m, 1H) 3.57 (dd, J=8.62, 5.58 Hz, 1H) 3.63-3.71 (m, 1H) 3.74-3.85 (m, 3H) 3.98-4.12 (m, 2H) 5.30 (s, 1H) 7.53 (dd, J=2.28, 1.52 Hz, 1H) 7.57 (dd, J=2.28, 1.52 Hz, 1H) 7.68 (d, J=1.01 Hz, 1H) 7.95 (t, J=1.39 Hz, 1H) 9.12 (s, 2H) 9.16 (d, J=7.10 Hz, 1H).

Example 124

3-(5-Cyclobutyl-1,3-thiazol-2-yl)-N-[(1R)-1-(2-methylpyrimidin-5-yl)ethyl]-5-(tetrahydro-2H-pyran-4-ylmethoxy)benzamide

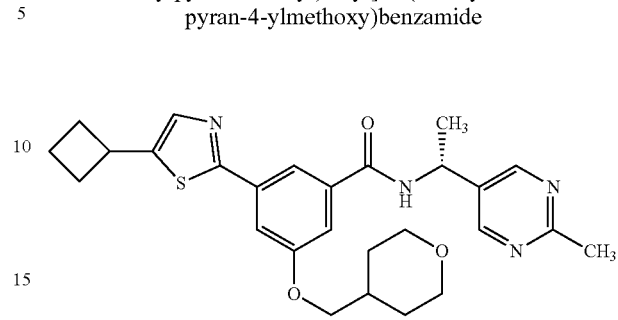

Intermediate 5S (53 mg, 0.14 mmol), (1R)-1-(2-methylpyrimidin-5-yl)ethanamine (20 mg, 0.14 mmol), DIPEA (0.1 mL, 0.57 mmol) and HATU (76 mg, 0.2 mmol) were dissolved in DMF (2.5 mL). The reaction mixture was stirred at RT until complete conversion and evaporated to dryness. The remaining crude material was purified by preparative HPLC (method 1, rt: 1.28 min) to afford the title compound 21 mg (29% yield).

$^1$H NMR (400 MHz, DMSO-$d_6$) δ [ppm] 1.31-1.44 (m, 2H) 1.55 (d, J=7.33 Hz, 3H) 1.66-1.75 (m, 2H) 1.86-1.96 (m, 1H) 1.96-2.07 (m, 2H) 2.15 (s, 2H) 2.42 (s, 2H) 2.59 (s, 3H) 3.35 (d, J=1.77 Hz, 2H) 3.77-3.85 (m, 1H) 3.85-3.92 (m, 2H) 3.96 (d, J=6.32 Hz, 2H) 5.13-5.23 (m, 1H) 7.48-7.51 (m, 1H) 7.55 (dd, J=2.40, 1.64 Hz, 1H) 7.68 (d, J=0.76 Hz, 1H) 7.93 (t, J=1.52 Hz, 1H) 8.72 (s, 2H) 9.01-9.06 (m, 1H).

Example 125

3-(5-Ethyl-1,3-thiazol-2-yl)-N-[(1R)-1-(2-methylpyrimidin-5-yl)ethyl]-5-(tetrahydro-2H-pyran-4-ylmethoxy)benzamide

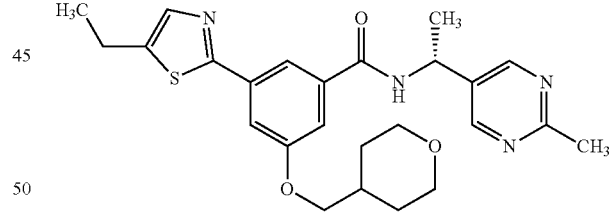

Intermediate 5U (50 mg, 0.14 mmol), (1R)-1-(2-methylpyrimidin-5-yl)ethanamine (20 mg, 0.14 mmol), DIPEA (0.1 mL, 0.58 mmol) and HATU (77 mg, 0.2 mmol) were dissolved in DMF (2.5 mL). The reaction mixture was stirred at RT until complete conversion and evaporated to dryness. The remaining crude material was purified by preparative HPLC (method 1, rt: 1.16 min) to afford the title compound 23 mg (34% yield).

$^1$H NMR (400 MHz, DMSO-$d_6$) δ [ppm] 1.29 (t, J=7.48 Hz, 3H) 1.37 (dd, J=12.55, 4.18 Hz, 2H) 1.55 (d, J=7.10 Hz, 3H) 1.65-1.76 (m, 2H) 1.96-2.10 (m, 1H) 2.59 (s, 3H) 2.84-2.95 (m, 2H) 3.33-3.39 (m, 2H) 3.89 (dd, J=11.15, 3.04 Hz, 2H) 3.96 (d, J=6.34 Hz, 2H) 5.17 (t, J=7.22 Hz, 1H) 7.47-7.51 (m, 1H) 7.53-7.56 (m, 1H) 7.67 (s, 1H) 7.91 (t, J=1.27 Hz, 1H) 8.72 (s, 2H) 9.04 (d, J=7.35 Hz, 1H).

Example 126

N-[(1R)-1-(2-Methylpyrimidin-5-yl)ethyl]-3-[5-(propan-2-yl)-1,3-thiazol-2-yl]-5-(tetrahydro-2H-pyran-4-ylmethoxy)benzamide

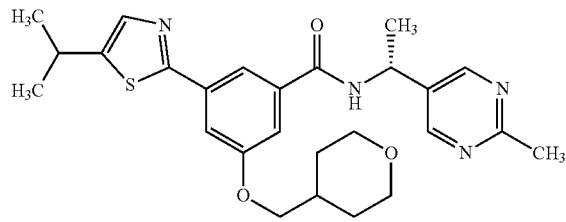 [SMILES: Cc1ncc([C@@H](C)NC(=O)c2cc(OCC3CCOCC3)cc(-c3ncc(C(C)C)s3)c2)cn1]

Intermediate 5V (70 mg, 0.19 mmol), (1R)-1-(2-methylpyrimidin-5-yl)ethanamine (27 mg, 0.19 mmol), DIPEA (0.14 mL, 0.78 mmol) and HATU (103 mg, 0.27 mmol) were dissolved in DMF (2.5 mL). The reaction mixture was stirred at RT until complete conversion and evaporated to dryness. The remaining crude material was purified by preparative HPLC (method 1, rt: 1.23 min) to afford the title compound 11 mg (11% yield).

$^1$H NMR (400 MHz, DMSO-$d_6$) δ [ppm] 1.33 (d, J=6.84 Hz, 6H) 1.37 (d, J=8.62 Hz, 2H) 1.55 (d, J=7.10 Hz, 3H) 1.70 (d, J=10.65 Hz, 2H) 1.97-2.10 (m, 1H) 2.57-2.60 (m, 3H) 3.24-3.30 (m, 1H) 3.34-3.39 (m, 2H) 3.89 (dd, J=11.41, 2.28 Hz, 2H) 3.96 (d, J=6.34 Hz, 2H) 5.10-5.23 (m, 1H) 7.47-7.57 (m, 2H) 7.68 (d, J=1.01 Hz, 1H) 7.92 (t, J=1.27 Hz, 1H) 8.72 (s, 2H) 8.99-9.09 (m, 1H).

Example 127

3-(5-Cyclobutyl-1,3-thiazol-2-yl)-N-[(1R)-1-(6-methylpyridazin-3-yl)ethyl]-5-(tetrahydro-2H-pyran-4-yloxy)benzamide

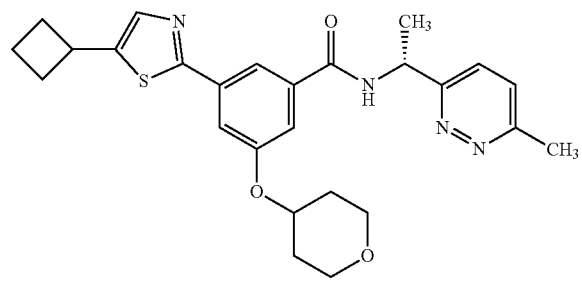 [SMILES: Cc1ccc([C@@H](C)NC(=O)c2cc(OC3CCOCC3)cc(-c3ncc(C4CCC4)s3)c2)nn1]

Intermediate 5W (57 mg, 0.16 mmol), (1R)-1-(6-methylpyridazin-3-yl)ethanamine dihydrochloride (37 mg, 0.17 mmol), TEA (0.03 mL, 0.24 mmol) and HATU (66 mg, 0.17 mmol) were dissolved in DMSO (1.6 mL). The reaction mixture was stirred at RT until complete conversion and evaporated to dryness. The remaining crude material was purified by column chromatography (silica gel, hexane/EE gradient) to afford the title compound 27 mg (36% yield).

$^1$H NMR (400 MHz, DMSO-$d_6$) δ [ppm] 1.56-1.69 (m, 5H) 1.85-1.94 (m, 1H) 1.95-2.06 (m, 3H) 2.09-2.21 (m, 2H) 2.38-2.48 (m, 2H) 2.59 (s, 3H) 3.48-3.58 (m, 2H) 3.76-3.91 (m, 3H) 4.76 (s, 1H) 5.32-5.41 (m, 1H) 7.50-7.62 (m, 4H) 7.68 (d, J=0.76 Hz, 1H) 7.96 (t, J=1.39 Hz, 1H) 9.12 (d, J=7.33 Hz, 1H).

Example 128

3-(5-Ethyl-1,3-thiazol-2-yl)-N-[(1R)-1-(6-methylpyridazin-3-yl)ethyl]-5-(tetrahydro-2H-pyran-4-yloxy)benzamide

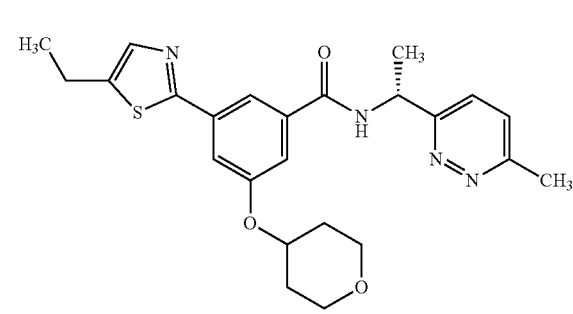 [SMILES: CCc1cnc(-c2cc(OC3CCOCC3)cc(C(=O)N[C@H](C)c3ccc(C)nn3)c2)s1]

Intermediate 5X (62 mg, 0.19 mmol), (1R)-1-(6-methylpyridazin-3-yl)ethanamine dihydrochloride (43 mg, 0.21 mmol), TEA (0.04 mL, 0.28 mmol) and HATU (78 mg, 0.21 mmol) were dissolved in DMSO (1.9 mL). The reaction mixture was stirred at RT until complete conversion and evaporated to dryness. The remaining crude material was purified by column chromatography (silica gel, hexane/EE gradient) to afford the title compound 12 mg (14% yield).

$^1$H NMR (400 MHz, DMSO-$d_6$) δ [ppm] 1.29 (t, J=7.48 Hz, 3H) 1.55-1.69 (m, 5H) 2.00 (d, J=11.15 Hz, 2H) 2.59 (s, 3H) 2.85-2.96 (m, 2H) 3.48-3.58 (m, 2H) 3.81-3.91 (m, 2H) 4.76 (s, 1H) 5.36 (t, J=7.22 Hz, 1H) 7.50-7.62 (m, 4H) 7.67 (s, 1H) 7.92-7.97 (m, 1H) 9.13 (d, J=7.60 Hz, 1H).

Example 129

3-(5-Ethyl-1,3-thiazol-2-yl)-5-(tetrahydro-2H-pyran-4-yloxy)-N-{(1R)-1-[2-(trifluoromethyl)pyrimidin-5-yl]ethyl}benzamide

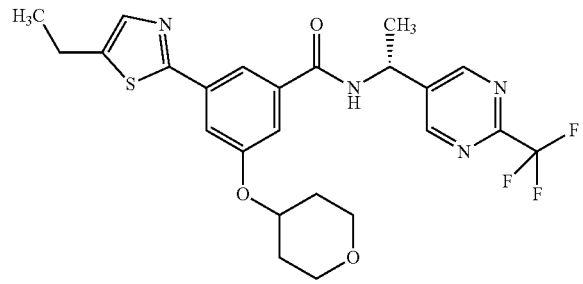 [SMILES: CCc1cnc(-c2cc(OC3CCOCC3)cc(C(=O)N[C@H](C)c3cnc(C(F)(F)F)nc3)c2)s1]

Intermediate 5X (62 mg, 0.19 mmol), Intermediate VI (47 mg, 0.21 mmol), TEA (0.04 mL, 0.28 mmol) and HATU (78 mg, 0.21 mmol) were dissolved in DMSO (1.9 mL). The reaction mixture was stirred at RT until complete conversion and evaporated to dryness. The remaining crude material was purified by column chromatography (silica gel, hexane/EE gradient) to afford the title compound 15 mg (16% yield).

¹H NMR (400 MHz, DMSO-d₆) δ [ppm] 1.29 (t, J=7.48 Hz, 3H) 1.57-1.68 (m, 5H) 2.00 (dd, J=12.42, 2.53 Hz, 2H) 2.90 (qd, J=7.48, 0.89 Hz, 2H) 3.47-3.57 (m, 2H) 3.81-3.90 (m, 2H) 4.71-4.81 (m, 1H) 5.29 (t, J=7.10 Hz, 1H) 7.54 (dd, J=2.28, 1.52 Hz, 1H) 7.57-7.61 (m, 1H) 7.68 (t, J=1.01 Hz, 1H) 7.93 (t, J=1.39 Hz, 1H) 9.12 (s, 2H) 9.15 (d, J=7.10 Hz, 1H).

Example 130

N-[(1R)-1-(2-Methylpyrimidin-5-yl)ethyl]-3-(5-methyl-1,3-thiazol-2-yl)-5-[(3S)-tetrahydrofuran-3-yloxy]benzamide

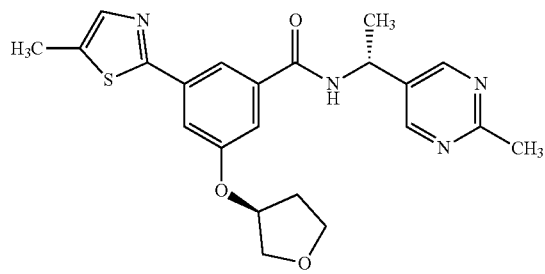

Intermediate 5C (120 mg, 0.39 mmol), (1R)-1-(2-methylpyrimidin-5-yl)ethanamine hydrochloride (96 mg, 0.55 mmol), TEA (0.08 mL, 0.59 mmol) and HATU (1.79 g, 4.72 mmol) were dissolved in DMF (4.3 mL). The reaction mixture was stirred at 60° C. until complete conversion and evaporated to dryness. Crude material was purified by preparative HPLC (method 1, rt: 0.98 min) to afford the title compound 87 mg (52% yield).

¹H NMR (400 MHz, DMSO-d₆) δ [ppm] 1.54 (d, J=7.10 Hz, 3H) 1.95-2.05 (m, 1H) 2.25 (s, 1H) 2.59 (s, 3H) 3.77-3.93 (m, 4H) 5.12-5.23 (m, 2H) 7.48 (dd, J=2.28, 1.52 Hz, 1H) 7.50-7.53 (m, 1H) 7.65 (d, J=1.01 Hz, 1H) 7.91 (t, J=1.39 Hz, 1H) 8.72 (s, 2H) 9.05 (d, J=7.60 Hz, 1H).

Example 131

N-[(1R)-1-(5-methylpyrazin-2-yl)ethyl]-3-[(6-methylpyridin-3-yl)oxy]-5-(5-methyl-1,3-thiazol-2-yl)benzamide

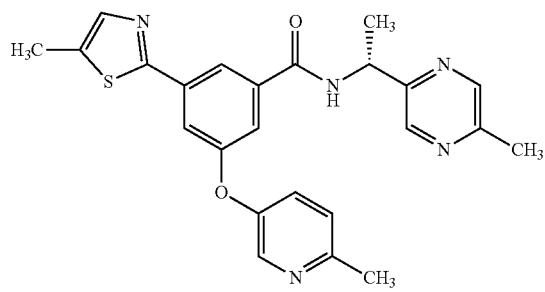

Intermediate 5N (375 mg, 1.15 mmol), (1R)-1-(5-methylpyrazin-2-yl)ethanamine hydrochloride (219 mg, 1.26 mmol), DIPEA (0.8 mL, 4.6 mmol) and HATU (612 mg, 1.61 mmol) were dissolved in DMF (13.3 mL). The reaction mixture was stirred at RT until complete conversion and evaporated to dryness. The crude material was extracted three times with EE and evaporated to dryness again. The remaining crude material was purified by preparative HPLC (method 1, rt: 0.97 min) to afford the title compound 13 mg (2.5% yield).

¹H NMR (400 MHz, DMSO-d₆) δ [ppm] 1.53 (d, J=7.07 Hz, 3H) 2.47 (s, 3H) 5.22 (s, 1H) 7.37 (d, J=8.34 Hz, 1H) 7.54 (d, J=2.78 Hz, 1H) 7.58-7.65 (m, 3H) 8.13 (t, J=1.39 Hz, 1H) 8.38 (d, J=2.78 Hz, 1H) 8.48 (s, 1H) 8.55 (d, J=1.26 Hz, 1H) 9.17 (d, J=7.58 Hz, 1H).

Example 132

N-[1-(3-Chloro-5-fluoropyridin-2-yl)ethyl]-3-(5-methyl-1,3-thiazol-2-yl)-5-[(3S)-tetrahydrofuran-3-yloxy]benzamide

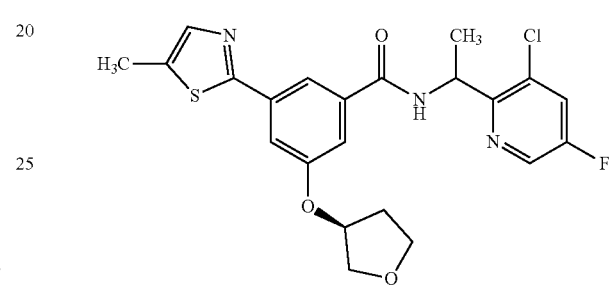

Intermediate 5C (120 mg, 0.39 mmol), (+/-) 1-(3-chloro-5-fluoropyridin-2-yl)ethanamine (96 mg, 0.55 mmol), TEA (0.08 mL, 0.59 mmol) and HATU (164 mg, 0.43 mmol) were dissolved in DMF (3.9 mL). The reaction mixture was stirred at 60° C. until complete conversion and evaporated to dryness. Crude material was purified by preparative HPLC (method 1, rt: 1.28 min) to afford the title compound 95 mg (52% yield) as a mixture of two diastereoisomers.

¹H NMR (400 MHz, DMSO-d₆) δ [ppm] 1.49 (d, J=6.84 Hz, 3H) 1.95-2.05 (m, 1H) 2.18-2.31 (m, 1H) 3.75-3.94 (m, 4H) 5.20 (d, J=1.52 Hz, 1H) 5.54 (t, J=6.97 Hz, 1H) 7.51 (d, J=1.27 Hz, 2H) 7.64 (d, J=1.27 Hz, 1H) 7.93 (q, J=1.44 Hz, 1H) 8.09 (dd, J=8.62, 2.53 Hz, 1H) 8.58 (d, J=2.79 Hz, 1H) 9.08 (d, J=7.10 Hz, 1H).

Example 133

N-[(6-Methylpyridazin-3-yl)methyl]-3-(5-methyl-1,3-thiazol-2-yl)-5-[(3S)-tetrahydrofuran-3-yloxy]benzamide

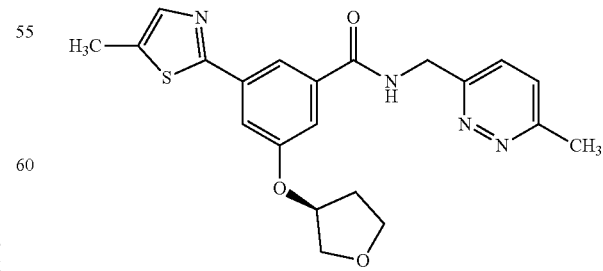

Intermediate 5C (120 mg, 0.39 mmol), 1-(6-methylpyridazin-3-yl)methanamine hydrochloride (88 mg, 0.55 mmol), TEA (0.08 mL, 0.59 mmol) and HATU (164 mg, 0.43 mmol) were dissolved in DMF (4.3 mL). The reaction mixture was stirred at 60° C. until complete conversion and evaporated to dryness. Crude material was purified by preparative HPLC (method 1, rt: 0.91 min) to afford the title compound 70 mg (42% yield).

$^1$H NMR (400 MHz, DMSO-$d_6$) δ [ppm] 2.03 (br. s., 1H) 2.21-2.31 (m, 1H) 2.61 (s, 3H) 3.77-3.94 (m, 4H) 4.73 (d, J=5.83 Hz, 2H) 5.16-5.23 (m, 1H) 7.53 (dt, J=6.72, 2.09 Hz, 2H) 7.57 (s, 2H) 7.64 (d, J=1.27 Hz, 1H) 7.98 (t, J=1.39 Hz, 1H) 9.40 (t, J=5.83 Hz, 1H).

Example 134

N-[1-(5-Chloro-3-fluoropyridin-2-yl)ethyl]-3-(5-methyl-1,3-thiazol-2-yl)-5-[(3S)-tetrahydrofuran-3-yloxy]benzamide

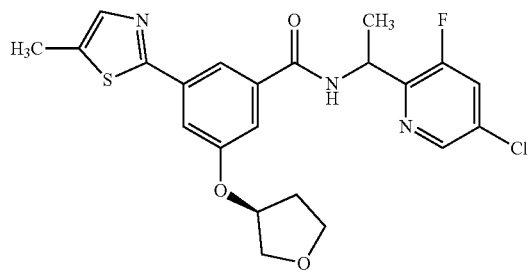 [SMILES: Cc1cnc(-c2cc(O[C@H]3CCOC3)cc(C(=O)NC(C)c3ncc(Cl)cc3F)c2)s1]

Intermediate 5C (120 mg, 0.39 mmol), (+/−) 1-(5-chloro-3-fluoropyridin-2-yl)ethanamine (96 mg, 0.55 mmol), TEA (0.08 mL, 0.59 mmol) and HATU (164 mg, 0.43 mmol) were dissolved in DMF (4.3 mL). The reaction mixture was stirred at 60° C. until complete conversion and evaporated to dryness. Crude material was purified by preparative HPLC (method 1, rt: 1.28 min) to afford the title compound 75 mg (41% yield) as a mixture of two diastereoisomers.

$^1$H NMR (400 MHz, DMSO-$d_6$) δ [ppm] 1.51 (d, J=7.10 Hz, 3H) 1.94-2.05 (m, 1H) 2.24 (s, 1H) 3.77-3.93 (m, 4H) 5.19 (d, J=1.52 Hz, 1H) 5.42 (s, 1H) 7.49-7.53 (m, 2H) 7.64 (d, J=1.27 Hz, 1H) 7.93 (q, J=1.27 Hz, 1H) 8.06 (dd, J=9.89, 2.03 Hz, 1H) 8.49 (d, J=1.52 Hz, 1H) 9.10 (d, J=7.10 Hz, 1H).

Example 135

3-(5-Cyclobutyl-1,3-thiazol-2-yl)-N-[(1R)-1-(6-methylpyridazin-3-yl)ethyl]-5-[(3S)-tetrahydrofuran-3-ylmethoxy]benzamide

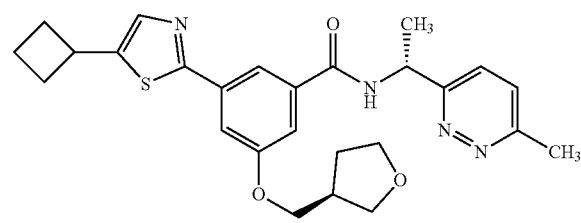 [SMILES: Cc1ccc([C@@H](C)NC(=O)c2cc(OC[C@H]3CCOC3)cc(-c3ncc(C4CCC4)s3)c2)nn1]

Intermediate 5T (150 mg, 0.42 mmol), (1R)-1-(6-methylpyridazin-3-yl)ethanamine dihydrochloride (96 mg, 0.46 mmol), TEA (0.09 mL, 0.63 mmol) and HATU (175 mg, 0.46 mmol) were dissolved in DMSO (4.2 mL). The reaction mixture was stirred at RT until complete conversion and evaporated to dryness. The remaining crude material was purified by preparative HPLC (method 2, rt: 1.24 min) to afford the title compound 57 mg (29% yield).

$^1$H NMR (400 MHz, DMSO-$d_6$) δ [ppm] 1.59 (d, J=7.10 Hz, 3H) 1.71 (d, J=7.60 Hz, 1H) 1.91 (d, J=0.76 Hz, 1H) 1.96-2.07 (m, 2H) 2.09-2.20 (m, 2H) 2.38-2.48 (m, 2H) 2.59 (s, 3H) 2.68 (d, J=6.84 Hz, 1H) 3.58 (dd, J=8.62, 5.58 Hz, 1H) 3.63-3.72 (m, 1H) 3.74-3.88 (m, 3H) 3.98-4.12 (m, 2H) 5.37 (t, J=7.22 Hz, 1H) 7.50-7.62 (m, 4H) 7.68 (d, J=0.76 Hz, 1H) 7.97 (t, J=1.39 Hz, 1H) 9.14 (d, J=7.60 Hz, 1H).

Example 136

3-(2-Methoxyethoxy)-N-[(1R)-1-(2-methylpyrimidin-5-yl)ethyl]-5-(5-methyl-1,3-thiazol-2-yl)benzamide

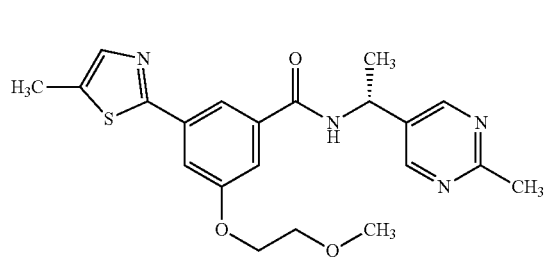

3-Bromo-5-(2-methoxyethoxy)-N-[(1R)-1-(2-methylpyrimidin-5-yl)ethyl]benzamide

Intermediate 5Y (5.12 g, 18.6 mmol), (1R)-1-(2-methylpyrimidin-5-yl)ethanamine dihydrochloride (5.08 g, 24.2 mmol), DIPEA (16.2 mL, 93 mmol) and HATU (7.78 g, 20.5 mmol) were dissolved in DMF (25 mL) at 60° C. Water and EE were added, the phases separated, the organic phase washed with water, dried (Na$_2$SO$_4$) and evaporated to dryness. The crude material was purified by column chromatography (silica gel, hexane/EE gradient) to afford the title compound 5.45 g (74% yield).

$^1$H NMR (300 MHz, DMSO-$d_6$) δ [ppm] 1.51 (d, J=7.16 Hz, 3H) 2.59 (s, 3H) 3.30 (s, 3H) 3.61-3.69 (m, 2H) 4.13-4.20 (m, 2H) 5.12 (s, 1H) 7.34 (s, 1H) 7.43 (s, 1H) 7.61 (s, 1H) 8.69 (s, 2H) 8.95 (d, J=7.16 Hz, 1H).

3-(2-Methoxyethoxy)-N-[(1R)-1-(2-methy(pyrimidin-5-yl)ethyl]-5-(4,4,5,5-tetramethyl-1,3,2-dioxaborolan-2-yl)benzamide 3-Bromo-5-(2-methoxyethoxy)-N-[(1R)-1-(2-methylpyrimidin-5-yl)ethyl]benzamide (5.3 g, 13.4 mmol), bis(pinacolato)diborane (6.83 g, 26.9 mmol) and potassium acetate (4.62 g, 47 mmol) were dissolved in 1,4-dioxane and the mixture degasse with nitrogen for 20 minutes at RT. Pd(dppf)Cl$_2$ (984 mg, 1.34 mmol) was added and the reaction mixture was degassed for another 5 minutes and then stirred at 90° C. for 16 hours. The reaction mixture was portioned between EE and water. The aqueous phase was extracted with EE, the combined organics dried (Na$_2$SO$_4$) and concentrated in vacuo. Purification by column chromatography (silica gel, hexane/EE gradient) afforded the title compound 2.51 g (42% yield).

3-(2-Methoxyethoxy)-N-[(1R)-1-(2-methy(pyrimidin-5-yl)ethyl]-5-(5-methyl-1,3-thiazol-2-yl)benzamide 3-(2-Methoxyethoxy)-N-[(1R)-1-(2-methylpyrimidin-5-yl)ethyl]-5-(4,4,5,5-tetramethyl-1,3,2-dioxaborolan-2-yl)benzamide (150 mg, 0.34 mmol) and 2-bromo-5-methyl-1,3-thiazole (91 mg, 0.51 mmol) were dissolved in 1M K$_2$CO$_3$ aqueous solution (0.84 mL) and THF. Pd(dppf)Cl$_2$.CH$_2$Cl$_2$ (42 mg, 0.05 mmol) was added and the reaction mixture heated to reflux overnight. The reaction mixture was concentrated under reduced pressure. Crude material was purified by preparative HPLC (Method 1) to afford the title compound 80 mg (57% yield).

$^1$H NMR (300 MHz, DMSO-d$_6$) δ [ppm] 1.54 (d, J=7.16 Hz, 3H) 2.59 (s, 3H) 3.32 (s, 3H) 3.69 (dd, J=5.18, 3.67 Hz, 2H) 4.19-4.25 (m, 2H) 5.17 (t, J=7.16 Hz, 1H) 7.50-7.56 (m, 2H) 7.64 (d, J=1.32 Hz, 1H) 7.91 (s, 1H) 8.72 (s, 2H) 9.05 (d, J=7.54 Hz, 1H).

Example 137 tert-Butyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate

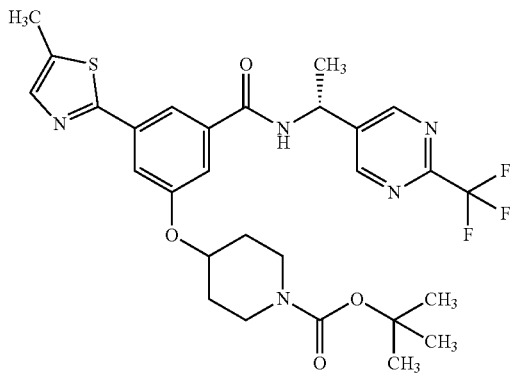 [SMILES: Cc1cnc(-c2cc(OC3CCN(C(=O)OC(C)(C)C)CC3)cc(C(=O)N[C@H](C)c3cnc(C(F)(F)F)nc3)c2)s1]

To a solution of 3-{[1-(tert-butoxycarbonyl)piperidin-4-yl]oxy}-5-(5-methyl-1,3-thiazol-2-yl)benzoic acid (682 mg, 1.63 mmol), Intermediate VI (408 mg, 1.79 mmol) and DIPEA (1.14 mL, 6.52 mmol) in DCM (6 mL) was added T3P (1.43 mL, 2.44 mmol) and the resulting solution stirred for 2 h at RT. The reaction mixture was diluted with DCM (6 mL) and washed with sodium bicarbonate. The organic phase was separated, dried (over MgSO$_4$) and concentrated in vacuo. The crude material was purified by Biotage Isolera™ chromatography (pre-packed SiO$_2$ column eluting with EtOAc) to give the title compound 130 mg (46% yield) as a colourless oil.

$^1$H NMR (250 MHz, CDCl3): δ [ppm]=8.93 (s, 2H), 7.83 (s, 1H), 7.58-7.47 (m, 2H), 7.44-7.34 (m, 1H), 6.83 (d, J=6.7 Hz, 1H), 5.35 (p, J=8.0, 7.6 Hz, 1H), 4.59 (dt, J=7.2, 3.6 Hz, 1H), 3.76-3.61 (m, 2H), 3.41-3.25 (m, 2H), 2.53 (d, J=0.9 Hz, 3H), 2.01-1.85 (m, 2H), 1.82-1.70 (m, 5H), 1.46 (s, 9H).

LCMS (Analytical Method D) Rt=5.13, MS (ESIpos) m/z=592 (M+H)$^+$.

Example 138

3-(5-Methyl-1,3-thiazol-2-yl)-5-(piperidin-4-yloxy)-N-{(1R)-1-[2-(trifluoromethyl)pyrimidin-5-yl]ethyl}benzamide

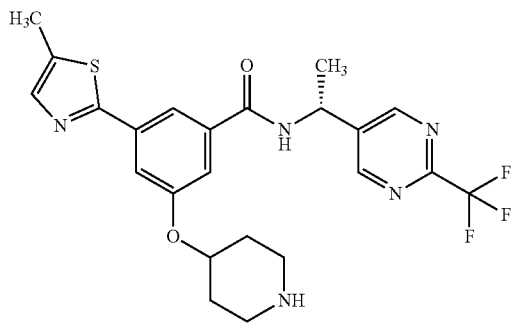 [SMILES: Cc1cnc(-c2cc(OC3CCNCC3)cc(C(=O)N[C@H](C)c3cnc(C(F)(F)F)nc3)c2)s1]

To a solution of tert-butyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate (100 mg, 0.169 mmol) in DCM (1 mL) was added TFA (0.13 mL, 1.69 mmol) and the reaction stirred at RT until gas evolution ceased. The reaction mixture was concentrated in vacuo and the residue taken up in DCM and neutralised with saturated NaHCO$_3$ solution. The organic phase was separated, dried (over MgSO$_4$) and concentrated in vacuo to give the title compound 72 mg (85% yield) as a white solid.

$^1$H NMR (500 MHz, Chloroform-d): δ [ppm]=8.95 (s, 2H), 7.89 (s, 1H), 7.57-7.53 (m, 2H), 7.52 (d, J=1.1 Hz, 1H), 7.42 (d, J=1.5 Hz, 1H), 7.00 (d, J=6.7 Hz, 1H), 5.37 (p, J=7.1 Hz, 1H), 4.73-4.69 (m, 1H), 3.34-3.26 (m, 2H), 3.10-3.03 (m, 2H), 2.53 (d, J=0.9 Hz, 3H), 2.19-2.12 (m, 4H), 2.03-1.97 (m, 2H), 1.72 (d, J=7.1 Hz, 3H).

LCMS (Analytical Method D) Rt=3.14, MS (ESIpos) m/z=491 (M+H)$^+$.

Example 139

3-[(1-Methylpiperidin-4-yl)oxy]-5-(5-methyl-1,3-thiazol-2-yl)-N-{(1R)-1-[2-(trifluoromethyl)pyrimidin-5-yl]ethyl}benzamide

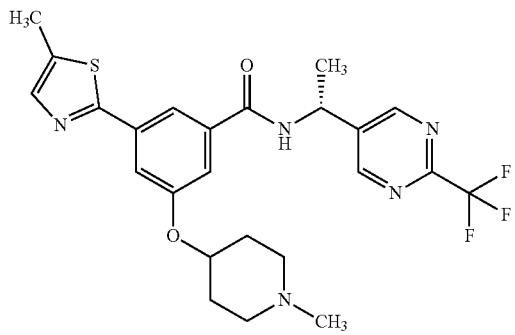 [SMILES: Cc1cnc(-c2cc(OC3CCN(C)CC3)cc(C(=O)N[C@H](C)c3cnc(C(F)(F)F)nc3)c2)s1]

To 3-(5-methyl-1,3-thiazol-2-yl)-5-(piperidin-4-yloxy)-N-{(1R)-1-[2-(trifluoromethyl)pyrimidin-5-yl]ethyl}benzamide hydrochloride (80 mg, 0.15 mmol) suspended in DCE (1 mL) was added 37% formaldehyde solution in water (0.045 mL, 0.61 mmol) and the resulting mixture stirred for 30 min. Sodium triacetoxyborohydride (38 mg, 0.18 mmol) was added and the reaction mixture stirred for 16 h. LCMS (Method A) indicated unreacted starting material. The reaction was retreated with 37% formaldehyde solution (1 mL) and 3 drops of acetic acid and stirred for 30 min. Sodium triacetoxyborohydride (38 mg, 0.18 mmol) was added and the mixture stirred for 8 h. LCMS (Method A) indicated complete conversion to product. The organic solvent was removed under reduced pressure and the remaining aqueous basified to pH ~8-9 and extracted into EtOAc (2 mL). The organic phase was separated, dried (over MgSO$_4$), concentrated and purified by preparative HPLC (Method A) to give the title compound 39.6 mg (52% yield) as a white powder.

$^1$H NMR (500 MHz, Chloroform-d): δ [ppm]=8.93 (s, 2H), 7.83 (s, 1H), 7.54-7.49 (m, 2H), 7.41-7.37 (m, 1H), 6.70 (d, J=6.5 Hz, 1H), 5.35 (p, J=7.0 Hz, 1H), 4.48-4.43 (m, 1H), 2.74-2.63 (m, 2H), 2.53 (d, J=0.9 Hz, 3H), 2.34-2.25 (m, 5H), 2.07-2.01 (m, 2H), 2.00 (s, 0H), 1.90-1.81 (m, 2H), 1.71 (d, J=7.2 Hz, 3H).

LCMS (Analytical Method D) Rt=3.23, MS (ESIpos) m/z=506 (M+H)$^+$.

Example 140

3-(5-Methyl-1,3-thiazol-2-yl)-5-{[1-(propan-2-yl) piperidin-4-yl]oxy}-N-{(1R)-1-[2-(trifluoromethyl) pyrimidin-5-yl]ethyl}benzamide

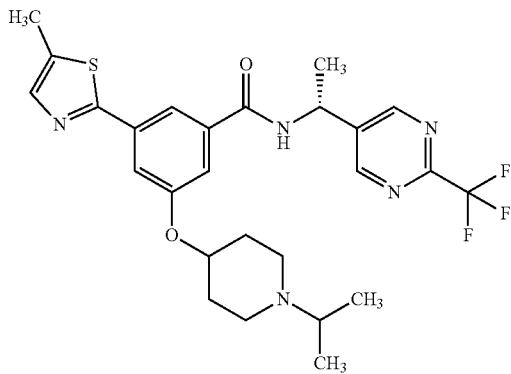

To a stirred solution of 3-(5-methyl-1,3-thiazol-2-yl)-5-(piperidin-4-yloxy)-N-{(1R)-1-[2-(trifluoromethyl)pyrimidin-5-yl]ethyl}benzamide hydrochloride (80 mg, 50% purity, 0.076 mmol) in DCE (1 mL) was added acetone (1 mL). After stirring at RT for 30 min, STAB (20 mg, 0.094 mmol) was added and the reaction mixture stirred for a further 4 h. LCMS (Method A) indicated ~20% conversion. A further portion of acetone (1 mL) and STAB (20 mg, 0.094 mmol) were added and the reaction mixture stirred for 16 h at 40° C. LCMS (Method A) indicated ~50% conversion. The reaction mixture was concentrated in vacuo and basified with 10 M NaOH to form a white precipitate that was extracted into EtOAc. The organic phase was concentrated in vacuo and purified by preparative HPLC (Method A) to give the title compound 20 mg (49% yield) as a tan powder.

$^1$H NMR (500 MHz, Chloroform-d): δ [ppm]=8.93 (s, 2H), 7.82 (t, J=1.4 Hz, 1H), 7.53-7.49 (m, 2H), 7.41-7.36 (m, 1H), 6.76 (d, J=6.6 Hz, 1H), 5.35 (t, J=7.0 Hz, 1H), 4.42 (dt, J=7.9, 4.0 Hz, 1H), 2.81-2.70 (m, 3H), 2.52 (d, J=1.1 Hz, 3H), 2.40 (t, J=8.9 Hz, 2H), 2.07-2.00 (m, 2H), 1.87-1.77 (m, 2H), 1.70 (d, J=7.2 Hz, 3H), 1.05 (d, J=6.6 Hz, 6H).

LCMS (Analytical Method D) Rt=3.36, MS (ESIpos) m/z=534 (M+H)$^+$.

Example 141

3-{[(3R)-1-Methylpyrrolidin-3-yl]oxy}-5-(5-methyl-1,3-thiazol-2-yl)-N-{(1R)-1-[2-(trifluoromethyl) pyrimidin-5-yl]ethyl}benzamide

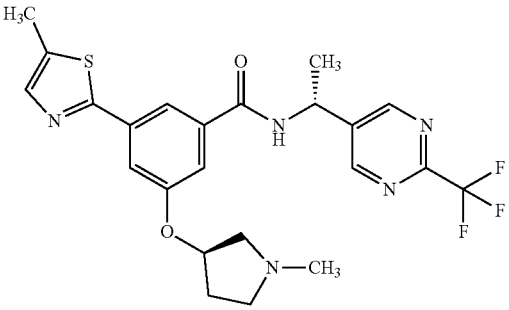 [SMILES: Cc1cnc(-c2cc(O[C@@H]3CCN(C)C3)cc(C(=O)N[C@H](C)c3cnc(C(F)(F)F)nc3)c2)s1]

To a solution of methyl 3-{[(3R)-1-methylpyrrolidin-3-yl]oxy}-5-(5-methyl-1,3-thiazol-2-yl)benzoate (143 mg, 0.32 mmol) in THF (1 mL) was added 1M lithium hydroxide (0.48 mL) and stirred for 16 h at RT. The organic solvent was removed under reduced pressure and the aqueous phase acidified to pH 4 then concentrated to dryness. The reaction residue, [Intermediate VI (88 mg, 0.39 mmol)] and DIPEA (0.23 mL, 1.29 mmol) were combined in DCM (1 mL) and T3P (50% in EtOAc, 0.14 mL, 0.48 mmol) was added and the resulting solution stirred for 16 h at RT. The mixture was diluted with DCM (1 mL), washed with brine (1 mL), dried (over Na$_2$SO$_4$) and concentrated in vacuo to give a yellow oil. The crude material was purified by preparative HPLC (Method A) to give the title compound 42 mg (26% yield) as a white powder.

$^1$H NMR (500 MHz, Chloroform-d): δ [ppm]=8.95 (s, 2H), 7.86 (t, J=1.4 Hz, 1H), 7.53 (d, J=1.2 Hz, 1H), 7.51 (dd, J=2.4, 1.5 Hz, 1H), 7.37-7.34 (m, 1H), 7.28 (s, 1H), 6.74 (d, J=6.5 Hz, 1H), 5.37 (p, J=7.0 Hz, 1H), 5.00-4.91 (m, 1H), 2.94-2.88 (m, 2H), 2.77 (dd, J=10.7, 5.7 Hz, 1H), 2.55 (d, J=1.1 Hz, 3H), 2.45-2.35 (m, 5H), 2.07-1.98 (m, 1H), 1.72 (d, J=7.2 Hz, 3H).

LCMS (Analytical Method D) Rt=3.16, MS (ESIpos) m/z=492 (M+H)$^+$.

Example 142

3-{[(3S)-1-Methylpyrrolidin-3-yl]oxy}-5-(5-methyl-1,3-thiazol-2-yl)-N-{(1R)-1-[2-(trifluoromethyl) pyrimidin-5-yl]ethyl}benzamide

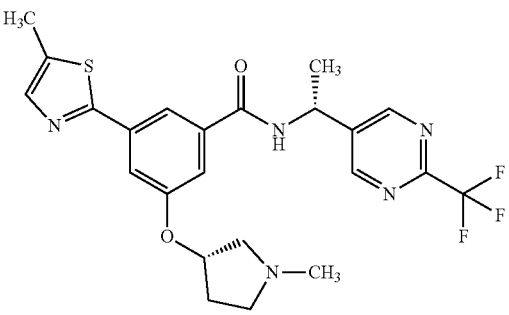 [SMILES: Cc1cnc(-c2cc(O[C@H]3CCN(C)C3)cc(C(=O)N[C@H](C)c3cnc(C(F)(F)F)nc3)c2)s1]

To methyl 3-{[(3S)-1-methylpyrrolidin-3-yl]oxy}-5-(5-methyl-1,3-thiazol-2-yl)benzoate (64 mg, 0.19 mmol) in THF was added 1 M lithium hydroxide (0.3 mL) and the resulting solution stirred at RT for 4 h. The reaction mixture was concentrated in vacuo, the residue acidified with 2M HCl and concentrated to dryness. The residue was dissolved in DCM and Intermediate VI (48 mg, 0.21 mmol), DIPEA (0.13 mL, 0.77 mmol) and HATU (110 mg, 0.29 mmol) were added and the mixture stirred at RT for 2 h. The reaction mixture was diluted with DCM (1 mL), washed with water (1 mL) and dried (over MgSO$_4$) and concentrated in vacuo. The crude material was purified by preparative HPLC (Method A) to give the title compound 23.9 mg (25% yield) as an off white solid.

$^1$H NMR (500 MHz, Chloroform-d): δ [ppm]=8.93 (s, 2H), 7.86 (t, J=1.4 Hz, 1H), 7.51 (d, J=1.2 Hz, 1H), 7.49 (dd, J=2.3, 1.5 Hz, 1H), 7.37-7.32 (m, 1H), 6.75 (d, J=6.6 Hz, 1H), 5.35 (p, J=7.0 Hz, 1H), 4.97-4.90 (m, 1H), 2.93-2.84 (m, 2H), 2.75 (dd, J=10.8, 5.7 Hz, 1H), 2.53 (d, J=1.1 Hz, 3H), 2.43-2.32 (m, 5H), 2.06-1.96 (m, 1H), 1.70 (d, J=7.2 Hz, 3H).

LCMS (Analytical Method D) Rt=3.18 min, MS (ESIpos) m/z=492 (M+H)$^+$.

Example 143

3-[(1-Methylazetidin-3-yl)oxy]-5-(5-methyl-1,3-thiazol-2-yl)-N-{(1R)-1-[2-(trifluoromethyl)pyrimidin-5-yl]ethyl}benzamide

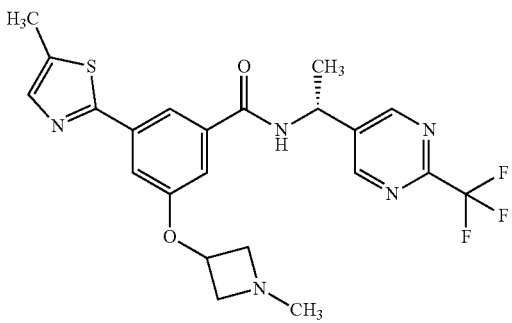 [SMILES: Cc1cnc(-c2cc(OC3CN(C)C3)cc(C(=O)N[C@H](C)c3cnc(C(F)(F)F)nc3)c2)s1]

To methyl 3-[(1-methylazetidin-3-yl)oxy]-5-(5-methyl-1,3-thiazol-2-yl)benzoate (80 mg, 0.25 mmol) in THF (1 mL) was added 1M lithium hydroxide solution (0.37 mL) and the resulting solution stirred at RT for 3 h. The reaction mixture was concentrated in vacuo and the residue acidified to pH 5 with 1 M HCl then concentrated to dryness. The residue was dissolved in DCM (1 mL) and Intermediate VI (67 mg, 0.29 mmol), DIPEA (0.17 mL, 0.99 mmol) and HATU (140 mg, 0.37 mmol) were added and the mixture stirred at RT for 2 h. The mixture was diluted with DCM (1 mL), washed with water (1 mL), dried (over MgSO$_4$) and concentrated in vacuo. The residue was purified by preparative HPLC (Method A) to give the title compound 41.3 mg (35% yield) as a white powder.

$^1$H NMR (500 MHz, CDCl$_3$): δ [ppm]=1.69 (d, 3H), 2.39 (s, 3H), 2.52 (d, 3H), 3.11-3.18 (m, 2H), 3.78-3.85 (m, 2H), 4.82 (p, 1H), 5.34 (p, 1H), 6.87 (d, 1H), 7.20-7.25 (m, 1H), 7.37 (dd, 1H), 7.49 (d, 1H), 7.85 (s, 1H), 8.92 (s, 2H).

LCMS (Analytical Method F) Rt=2.03 min, MS (ESIpos) m/z=478 (M+H)$^+$.

Example 144

3-(5-Methyl-1,3-thiazol-2-yl)-5-(prop-2-yn-1-yloxy)-N-{(1S)-1-[2-(trifluoromethyl)pyrimidin-5-yl]ethyl}benzamide

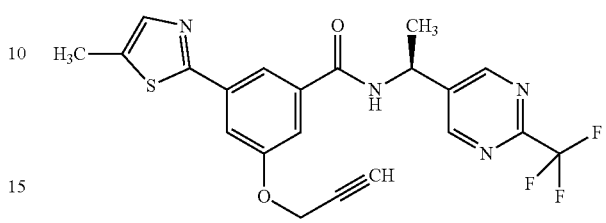

Intermediate 5D (540 mg, 1.98 mmol), (1S)-1-[2-(trifluoromethyl)pyrimidin-5-yl]ethanamine (415 mg, 2.17 mmol), TEA (0.41 mL, 2.96 mmol) and HATU (826 mg, 2.17 mmol) were dissolved in DMSO (20 mL). The reaction mixture was stirred at RT until complete conversion and evaporated to dryness. The remaining crude material was purified by column chromatography (silica gel, hexane/EE gradient) to afford the title compound 600 mg (68% yield).

$^1$H NMR (300 MHz, DMSO-d$_6$) δ [ppm] 1.61 (d, J=7.16 Hz, 3H) 3.64 (t, J=2.35 Hz, 1H) 4.95 (d, J=2.26 Hz, 2H) 5.30 (t, J=7.06 Hz, 1H) 7.53-7.58 (m, 1H) 7.61-7.64 (m, 1H) 7.66 (d, J=1.13 Hz, 1H) 7.97 (s, 1H) 9.12 (s, 2H) 9.19 (d, J=7.16 Hz, 1H).

Example 145

3-(5-Methyl-1,3-thiazol-2-yl)-5-(tetrahydro-2H-pyran-4-yloxy)-N-{(1S)-1-[2-(trifluoromethyl)pyrimidin-5-yl]ethyl}benzamide

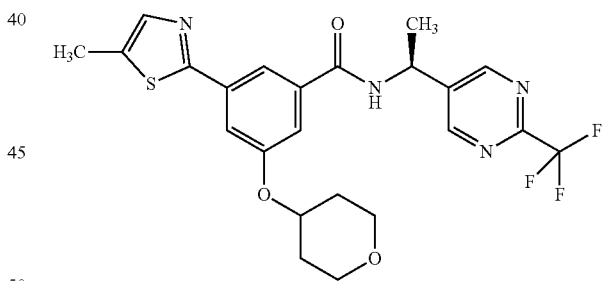

Intermediate 5K (530 mg, 1.66 mmol), (1S)-1-[2-(trifluoromethyl)pyrimidin-5-yl]ethanamine (349 mg, 1.83 mmol), TEA (0.35 mL, 2.49 mmol) and HATU (694 mg, 1.83 mmol) were dissolved in DMSO (17 mL). The reaction mixture was stirred at RT until complete conversion and evaporated to dryness. The remaining crude material was purified by column chromatography (silica gel, hexane/EE gradient) to afford the title compound 600 mg (73% yield).

$^1$H NMR (300 MHz, DMSO-d$_6$) δ [ppm] 1.54-1.70 (m, 5H) 1.93-2.07 (m, 2H) 3.46-3.59 (m, 2H) 3.80-3.91 (m, 2H) 4.69-4.82 (m, 1H) 5.29 (t, J=7.06 Hz, 1H) 7.51-7.55 (m, 1H) 7.56-7.61 (m, 1H) 7.64 (d, J=1.13 Hz, 1H) 7.91 (t, J=1.32 Hz, 1H) 9.12 (s, 2H) 9.16 (d, J=7.16 Hz, 1H).

In analogy to the procedure described for Example 1, the following examples were prepared using HATU and the appropriate carboxylic acid and amine starting materials.

| Ex. | Structure | Name | Analytical Data |
|---|---|---|---|
| 146 | 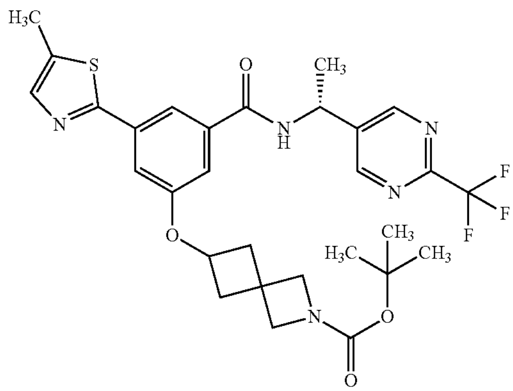 [SMILES: Cc1cnc(-c2cc(OC3CC4(C3)CN(C(=O)OC(C)(C)C)C4)cc(C(=O)N[C@H](C)c3cnc(C(F)(F)F)nc3)c2)s1] | tert-butyl 6-[3-(5-methyl-1,3-thiazol-2-yl)-5-({(1R)-1-[2-(trifluoromethyl)pyrimidin-5-yl]ethyl}carbamoyl)phenoxy]-2-azaspiro[3.3]heptane-2-carboxylate | $^1$H NMR (500 MHz, MeOD): δ [ppm] 9.01 (s, 2H), 7.90 (t, 1H), 7.56 (d, 1H), 7.50 (dd, 1H), 7.35 (dd, 1H), 5.34 (q, 1H), 4.74 (m, 1H), 4.01 (s, 2H), 3.92 (s, 2H), 2.80 (dd, 2H), 2.54 (d, 3H), 2.37-2.29 (m, 2H), 1.70 (d, 3H), 1.43 (s, 9H). LCMS (Analytical Method D) Rt = 5.05 min, MS (ESIpos): 604 (M + H)$^+$. |
| 147 | 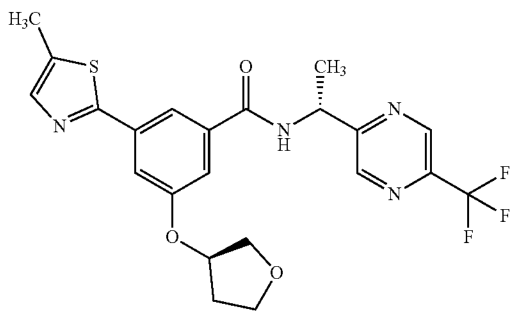 [SMILES: Cc1cnc(-c2cc(O[C@@H]3CCOC3)cc(C(=O)N[C@H](C)c3cnc(C(F)(F)F)cn3)c2)s1] | 3-(5-methyl-1,3-thiazol-2-yl)-5-[(3R)-tetrahydrofuran-3-yloxy]-N-{(1R)-1-[5-(trifluoromethyl)pyrazin-2-yl]ethyl}benzamide | $^1$H NMR (250 MHz, MeOD): δ [ppm] 9.03-8.94 (m, 1H), 8.86 (s, 1H), 7.92 (t, 1H), 7.58 (dd, 1H), 7.55 (d, 1H), 7.45 (dd, 1H), 5.42 (q, 1H), 5.14 (ddt, 1H), 4.09-3.81 (m, 4H), 3.72 (ddd, 1H), 2.53 (d, 3H), 2.42-2.05 (m, 2H), 1.68 (d, 3H). LCMS (Analytical Method D) Rt = 4.44 min, MS (ESIpos): m/z = 479 (M + H)$^+$. |
| 148 | 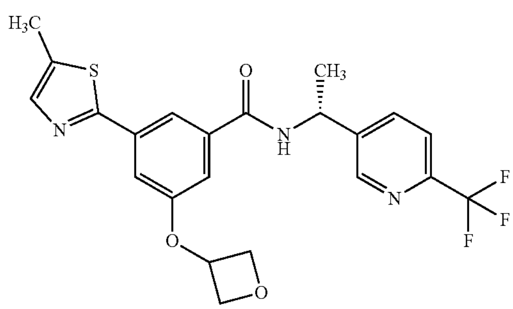 [SMILES: Cc1cnc(-c2cc(OC3COC3)cc(C(=O)N[C@H](C)c3ccc(C(F)(F)F)nc3)c2)s1] | 3-(5-methyl-1,3-thiazol-2-yl)-5-(oxetan-3-yloxy)-N-{(1R)-1-[6-(trifluoromethyl)pyridin-3-yl]ethyl}benzamide | $^1$H NMR (500 MHz, Chloroform-d): δ [ppm] 8.76 (d, J = 1.7 Hz, 1H), 7.89-7.84 (m, 2H), 7.65 (d, J = 8.1 Hz, 1H), 7.50 (d, J = 1.1 Hz, 1H), 7.34 (dd, J = 2.4, 1.4 Hz, 1H), 7.19-7.14 (m, 1H), 6.78 (d, J = 7.0 Hz, 1H), 5.35 (m, 1H), 5.31-5.25 (m, 1H), 5.00 (t, J = 6.7 Hz, 2H), 4.74 (dd, J = 7.4, 5.2 Hz, 2H), 2.52 (d, J = 1.0 Hz, 3H), 1.64 (d, J = 7.1 Hz, 3H). LCMS (Analytical Method D) Rt = 3.36 min, MS (ESIpos): m/z = 464 (M + H)$^+$. |
| 149 | 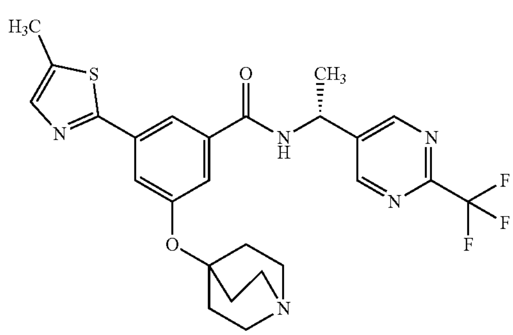 [SMILES: Cc1cnc(-c2cc(OC34CCN(CC3)CC4)cc(C(=O)N[C@H](C)c3cnc(C(F)(F)F)nc3)c2)s1] | 3-(1-azabicyclo[2.2.2]oct-4-yloxy)-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.85 (s, 2H), 7.90 (t, J = 1.4 Hz, 1H), 7.48-7.45 (m, 1H), 7.43 (d, J = 1.1 Hz, 1H), 7.39-7.34 (m, 1H), 6.85 (d, J = 6.6 Hz, 1H), 5.27 (m, 1H), 2.95-2.88 (m, 6H), 2.45 (d, J = 0.9 Hz, 3H), 1.76-1.69 (m, 6H), 1.62 (d, J = 7.2 Hz, 3H). LCMS (Analytical Method F) Rt = 2.15 min, MS (ESIpos): m/z = 518 (M + H)$^+$. |

| Ex. | Name | Analytical Data |
|---|---|---|
| 150 | 3-[(1-acetylpiperidin-4-yl)oxy]-5-(5-methyl-1,3-thiazol-2-yl)-N-{(1R)-1-[2-(trifluoromethyl)pyrimidin-5-yl]ethyl}benzamide | $^1$H NMR (250 MHz, DMSO-d6): δ [ppm] 9.09 (s, 2H), 8.91 (d, J = 7.1 Hz, 1H), 7.92 (t, J = 1.4 Hz, 1H), 7.65-7.56 (m, 2H), 7.56-7.50 (m, 1H), 5.32 (m, 1H), 4.76 (tt, J = 7.5, 3.8 Hz, 1H), 3.91-3.65 (m, 2H), 3.38 (ddd, J = 13.1, 8.3, 3.7 Hz, 2H), 2.09-1.88 (m, 5H), 1.75-1.55 (m, 5H). LCMS (Analytical Method D) Rt = 4.23 min, MS (ESIpos): m/z = 534 (M + H)$^+$. |
| 151 | N-{(1R)-1-[2-(difluoromethyl)pyrimidin-5-yl]ethyl}-3-(5-methyl-1,3-thiazol-2-yl)-5-[(3S)-tetrahydrofuran-3-yloxy]benzamide | $^1$H NMR (500 MHz, Chloroform-d): δ [ppm] 8.90 (s, 2H), 7.85 (s, 1H), 7.54-7.48 (m, 2H), 7.36 (s, 1H), 6.78-6.53 (m, 2H), 5.35 (m, 1H), 5.07-5.03 (m, 1H), 4.05-3.96 (m, 3H), 3.91 (td, J = 8.4, 4.3 Hz, 1H), 2.53 (s, 3H), 2.33-2.22 (m, 1H), 2.20-2.11 (m, 1H), 1.70 (d, J = 7.1 Hz, 3H). LCMS (Analytical Method F) Rt = 2.95 min, MS (ESIpos): m/z = 461 (M + H)$^+$. |
| 152 | N-{(1R)-1-[2-(difluoromethyl)pyrimidin-5-yl]ethyl}-3-(5-methyl-1,3-thiazol-2-yl)-5-(oxetan-3-yloxy)benzamide | $^1$H NMR (500 MHz, Chloroform-d): δ [ppm] 8.88 (s, 2H), 7.85 (s, 1H), 7.51 (s, 1H), 7.36 (s, 1H), 7.16 (s, 1H), 6.79-6.53 (m, 2H), 5.38-5.25 (m, 2H), 5.01 (t, J = 6.7 Hz, 2H), 4.75 (dd, J = 7.1, 5.3 Hz, 2H), 2.53 (s, 3H), 1.69 (d, J = 7.1 Hz, 3H). LCMS (Analytical Method F) Rt = 2.93 min, MS (ESIpos): m/z = 447 (M + H)$^+$. |
| 153 | N-{(1R)-1-[2-(difluoromethyl)pyrimidin-5-yl]ethyl}-3-(5-methyl-1,3-thiazol-2-yl)-5-[(3R)-tetrahydrofuran-3-yloxy]benzamide | $^1$H NMR (500 MHz, Chloroform-d): δ [ppm] 8.89 (s, 2H), 7.85 (s, 1H), 7.54-7.47 (m, 2H), 7.38-7.33 (m, 1H), 6.78-6.53 (m, 2H), 5.34 (m, 1H), 5.08-5.01 (m, 1H), 4.05-3.96 (m, 3H), 3.91 (td, J = 8.4, 4.3 Hz, 1H), 2.53 (d, J = 1.0 Hz, 3H), 2.32-2.21 (m, 1H), 2.19-2.10 (m, 1H), 1.70 (d, J = 7.1 Hz, 3H). LCMS (Analytical Method F) Rt = 2.94 min, MS (ESIpos): m/z = 461 (M + H)$^+$. |

-continued

| Ex. | Structure | Name | Analytical Data |
|---|---|---|---|
| 154 | 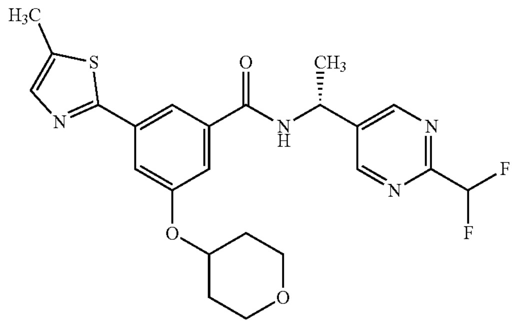 [SMILES: Cc1cnc(-c2cc(OC3CCOCC3)cc(C(=O)N[C@H](C)c3cnc(C(F)F)nc3)c2)s1] | N-{(1R)-1-[2-(difluoromethyl)pyrimidin-5-yl]ethyl}-3-(5-methyl-1,3-thiazol-2-yl)-5-(tetrahydro-2H-pyran-4-yloxy)benzamide | $^1$H NMR (500 MHz, Chloroform-d): δ [ppm] 8.88 (s, 2H), 7.81 (t, J = 1.2 Hz, 1H), 7.51 (dd, J = 2.3, 1.5 Hz, 1H), 7.50 (d, J = 1.1 Hz, 1H), 7.41-7.37 (m, 1H), 6.80 (d, J = 6.8 Hz, 1H), 6.65 (t, J = 54.5 Hz, 1H), 5.33 (m, 1H), 4.60 (tt, J = 7.9, 3.9 Hz, 1H), 4.00-3.93 (m, 2H), 3.57 (ddd, J = 11.5, 8.6, 2.7 Hz, 2H), 2.52 (d, J = 1.0 Hz, 3H), 2.07-2.00 (m, 2H), 1.84-1.73 (m, 2H), 1.68 (d, J = 7.1 Hz, 3H). LCMS (Analytical Method F) Rt = 3.09 min, MS (ESIpos): m/z = 474 (M + H)$^+$. |
| 155 | 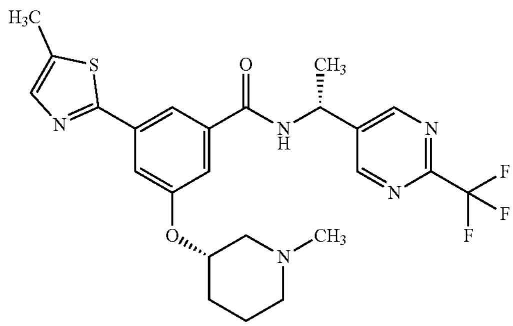 [SMILES: Cc1cnc(-c2cc(O[C@H]3CCCN(C)C3)cc(C(=O)N[C@H](C)c3cnc(C(F)(F)F)nc3)c2)s1] | 3-{[(3S)-1-methylpiperidin-3-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.89 (s, 2H), 7.81 (t, J = 1.4 Hz, 1H), 7.52 (dd, J = 2.3, 1.5 Hz, 1H), 7.45 (d, J = 1.2 Hz, 1H), 7.40-7.36 (m, 1H), 6.98 (d, J = 6.7 Hz, 1H), 5.32 (m, 1H), 4.48 (dq, J = 7.2, 3.6 Hz, 1H), 2.74 (d, J = 10.2 Hz, 1H), 2.48 (d, J = 1.1 Hz, 4H), 2.37-2.33 (m, 1H), 2.26 (s, 4H), 1.90-1.79 (m, 2H), 1.65 (d, J = 7.2 Hz, 3H), 1.62-1.54 (m, 2H). LCMS (Analytical Method D) Rt = 3.28 min, MS (ESIpos): m/z = 506 (M + H)$^+$. |
| 156 | 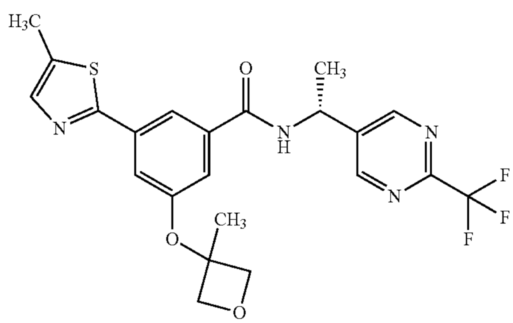 [SMILES: Cc1cnc(-c2cc(OC3(C)COC3)cc(C(=O)N[C@H](C)c3cnc(C(F)(F)F)nc3)c2)s1] | 3-[(3-methyloxetan-3-yl)oxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.90 (s, 2H), 7.83 (t, J = 1.4 Hz, 1H), 7.48 (d, J = 1.2 Hz, 1H), 7.25 (dd, J = 2.4, 1.4 Hz, 1H), 7.06 (dd, J = 2.3, 1.5 Hz, 1H), 6.93 (d, J = 6.6 Hz, 1H), 5.32 (m, 1H), 4.91 (dd, J = 6.5, 1.9 Hz, 2H), 4.62 (dd, J = 6.6, 3.4 Hz, 2H), 2.51 (d, J = 1.1 Hz, 3H), 1.75 (s, 3H), 1.67 (d, J = 7.2 Hz, 3H). LCMS (Analytical Method D) Rt = 4.32 min, MS (ESIpos): m/z = 478 (M + H)$^+$. |
| 157 | 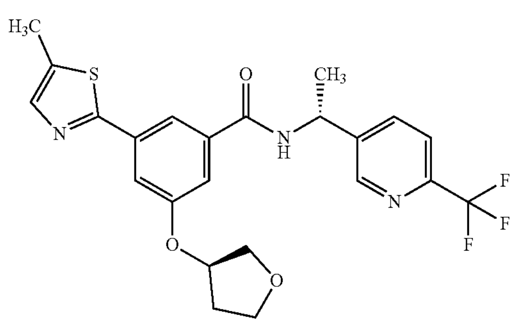 [SMILES: Cc1cnc(-c2cc(O[C@@H]3CCOC3)cc(C(=O)N[C@H](C)c3ccc(C(F)(F)F)nc3)c2)s1] | 3-(5-methyl-1,3-thiazol-2-yl)-5-[(3R)-tetrahydrofuran-3-yloxy]-N-{(1R)-1-[6-(trifluoromethyl)pyridin-3-yl]ethyl}benzamide | $^1$H NMR (500 MHz, Chloroform-d): δ [ppm] 8.81 (s, 1H), 8.02-7.82 (m, 2H), 7.69 (d, J = 8.1 Hz, 1H), 7.54 (d, J = 11.9 Hz, 2H), 7.40 (s, 1H), 6.63 (d, J = 6.7 Hz, 1H), 5.40 (m, 1H), 5.20-4.96 (m, 1H), 4.10-3.98 (m, 3H), 3.93 (td, J = 8.4, 4.3 Hz, 1H), 2.56 (s, 3H), 2.29 (td, J = 14.2, 8.3 Hz, 1H), 2.18 (dt, J = 11.9, 4.9 Hz, 1H), 1.70 (d, J = 7.1 Hz, 3H). LCMS (Analytical Method F) Rt = 3.42 min, MS (ESIpos): m/z = 478.0 (M + H)$^+$. |

-continued

| Ex. | Structure | Name | Analytical Data |
|---|---|---|---|
| 158 | 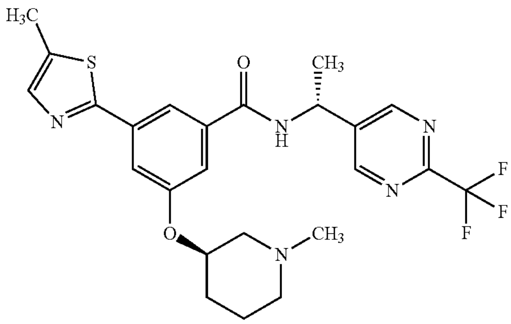 [SMILES: Cc1cnc(-c2cc(O[C@@H]3CCCN(C)C3)cc(C(=O)N[C@H](C)c3cnc(C(F)(F)F)nc3)c2)s1] | 3-{[(3R)-1-methylpiperidin-3-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.88 (s, 2H), 7.79 (s, 1H), 7.53-7.48 (m, 1H), 7.46-7.42 (m, 1H), 7.36 (d, J = 1.5 Hz, 1H), 6.99 (d, J = 6.1 Hz, 1H), 5.31 (m, 1H), 4.47 (dt, J = 7.1, 3.5 Hz, 1H), 2.73 (d, J = 10.2 Hz, 1H), 2.50-2.43 (m, 4H), 2.34 (s, 1H), 2.26 (s, 4H), 1.89-1.78 (m, 2H), 1.64 (d, J = 7.2 Hz, 3H), 1.62-1.51 (m, 2H). LCMS (Analytical Method D) Rt = 3.32 min, MS (ESIpos): m/z = 506 (M + H)$^+$. |
| 159 | 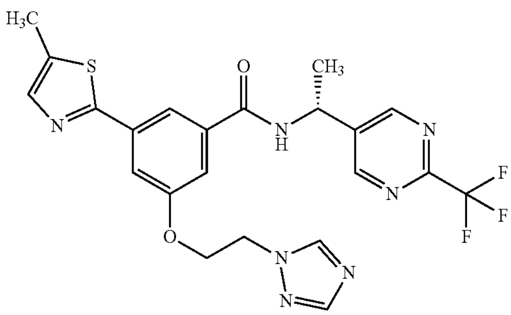 [SMILES: Cc1cnc(-c2cc(OCCn3cncn3)cc(C(=O)N[C@H](C)c3cnc(C(F)(F)F)nc3)c2)s1] | 3-(5-methyl-1,3-thiazol-2-yl)-5-[2-(1H-1,2,4-triazol-1-yl)ethoxy]-N-{(1R)-1-[2-(trifluoromethyl)pyrimidin-5-yl]ethyl}benzamide | $^1$H NMR (500 MHz, Chloroform-d): δ [ppm] 8.94 (s, 2H), 8.25 (s, 1H), 7.95 (m, 2H), 7.54 (d, J = 1.2 Hz, 1H), 7.50-7.46 (m, 1H), 7.36 (s, 1H), 6.71 (s, 1H), 5.36 (m, 1H), 4.67-4.56 (m, 2H), 4.45 (dd, J = 7.1, 3.0 Hz, 2H), 2.54 (d, J = 1.1 Hz, 3H), 1.73 (d, J = 7.2 Hz, 3H). LCMS (Analytical Method F) Rt = 2.87 min, MS (ESIpos): m/z = 505.1 (M + H)$^+$. |
| 160 | 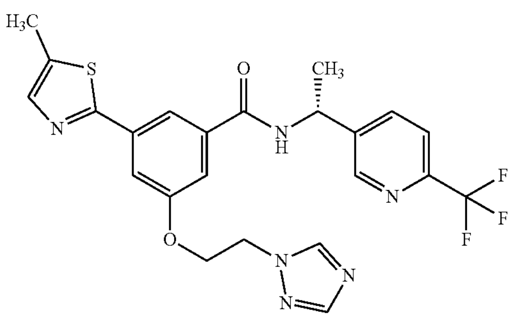 [SMILES: Cc1cnc(-c2cc(OCCn3cncn3)cc(C(=O)N[C@H](C)c3ccc(C(F)(F)F)nc3)c2)s1] | 3-(5-methyl-1,3-thiazol-2-yl)-5-[2-(1H-1,2,4-triazol-1-yl)ethoxy]-N-{(1R)-1-[6-(trifluoromethyl)pyridin-3-yl]ethyl}benzamide | $^1$H NMR (500 MHz, Chloroform-d): δ [ppm] 8.79 (d, J = 1.6 Hz, 1H), 8.27 (s, 1H), 7.97 (s, 1H), 7.92-7.83 (m, 2H), 7.67 (d, J = 8.1 Hz, 1H), 7.52 (d, J = 1.2 Hz, 1H), 7.50-7.45 (m, 1H), 7.35 (s, 1H), 6.61 (d, J = 6.8 Hz, 1H), 5.38 (m, 1H), 4.61 (t, J = 4.9 Hz, 2H), 4.48-4.41 (m, 2H), 2.53 (d, J = 1.1 Hz, 3H), 1.68 (d, J = 7.1 Hz, 3H) LCMS (Analytical Method F) Rt = 2.96 min, MS (ESIpos): m/z = 503.1 (M + H)$^+$. |
| 161 | 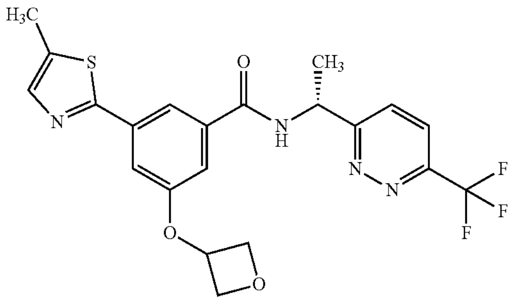 [SMILES: Cc1cnc(-c2cc(OC3COC3)cc(C(=O)N[C@H](C)c3ccc(C(F)(F)F)nn3)c2)s1] | 3-(5-methyl-1,3-thiazol-2-yl)-5-(oxetan-3-yloxy)-N-{(1R)-1-[6-(trifluoromethyl)pyridazin-3-yl]ethyl}benzamide | $^1$H NMR (500 MHz, Chloroform-d): δ [ppm] 7.90 (t, J = 1.4 Hz, 1H), 7.83 (d, J = 8.7 Hz, 1H), 7.74 (d, J = 8.7 Hz, 1H), 7.56 (d, J = 7.3 Hz, 1H), 7.52 (d, J = 1.2 Hz, 1H), 7.39 (dd, J = 2.4, 1.4 Hz, 1H), 7.21 (dd, J = 2.4, 1.5 Hz, 1H), 5.59 (m, 1H), 5.36-5.28 (m, 1H), 5.06-4.98 (m, 2H), 4.80-4.73 (m, 2H), 2.53 (d, J = 1.1 Hz, 3H), 1.76 (d, J = 7.0 Hz, 3H). LCMS (Analytical Method D) Rt = 4.12 min, MS (ESIpos): m/z = 465 (M + H)$^+$. |

Intermediate 63 was formed as a mixture of two trans isomers. Chiral Purification (Method 2) provided Example 162 (Trans Isomer 1) and Example 163 (Trans Isomer 2).

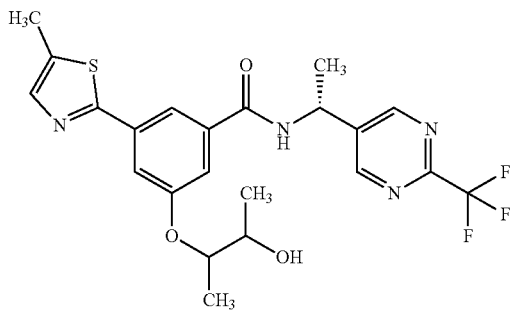

Example 162

Trans Isomer 1; 3-{[3-hydroxybutan-2-yl]oxy}-5-(5-methyl-1,3-thiazol-2-yl)-N-{(1R)-1-[2-(trifluoromethyl)pyrimidin-5-yl]ethyl}benzamide Chiral Purification (Method 2) on 189 mg of Intermediate 63 gave 72 mg of the title compound.
SFC Chiral Analysis (Method 2): 100% e.e., Rt=1.25 min.

$^1$H NMR (500 MHz, Chloroform-d): δ [ppm] 8.94 (s, 2H), 7.76 (s, 1H), 7.50 (s, 1H), 7.44 (s, 1H), 7.31 (s, 1H), 6.95 (d, J=6.4 Hz, 1H), 5.35 (m, 1H), 4.43 (qd, J=6.2, 3.3 Hz, 1H), 4.02 (qd, J=6.4, 3.3 Hz, 1H), 2.52 (s, 3H), 1.72 (s, 3H), 1.27 (d, J=6.3 Hz, 3H), 1.25 (d, J=6.5 Hz, 3H).
LCMS (Analytical Method D) Rt=4.14 min, MS (ESIpos) m/z=481 (M+H)$^+$.

Example 163

Trans Isomer 2; 3-{[3-hydroxybutan-2-yl]oxy}-5-(5-methyl-1,3-thiazol-2-yl)-N-{(1R)-1-[2-(trifluoromethyl)pyrimidin-5-yl]ethyl}benzamide Chiral Purification (Method 2) on 189 mg of Intermediate 63 gave 77.2 mg of the title compound.
SFC Chiral Analysis (Method 2): 99.4% e.e., Rt=1.42 min.

$^1$H NMR (500 MHz, Chloroform-d): δ [ppm] 8.94 (s, 2H), 7.80 (s, 1H), 7.54-7.49 (m, 1H), 7.47 (s, 1H), 7.38-7.33 (m, 1H), 6.82 (d, J=6.5 Hz, 1H), 5.35 (m, 1H), 4.47 (qd, J=6.3, 3.3 Hz, 1H), 4.03 (qd, J=6.4, 3.3 Hz, 1H), 2.53 (d, J=0.9 Hz, 3H), 1.71 (d, J=7.2 Hz, 3H), 1.29 (d, J=6.3 Hz, 3H), 1.27 (d, J=6.5 Hz, 3H).
LCMS (Analytical Method D) Rt=4.15 min, MS (ESIpos) m/z=481 (M+H)$^+$.

In analogy to the procedure described for Example 7, the following examples were prepared using T3P and the appropriate carboxylic acid and amine starting materials.

| Ex. | Structure | Name | Analytical Data |
|---|---|---|---|
| 164 | 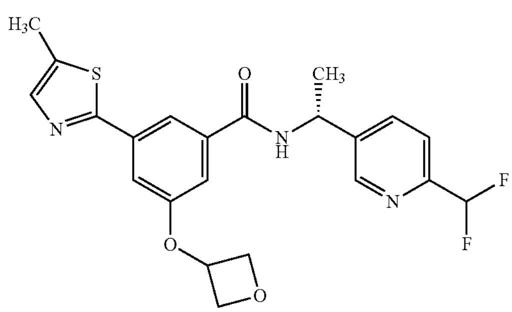 [SMILES: Cc1cnc(-c2cc(OC3COC3)cc(C(=O)N[C@H](C)c3ccc(C(F)F)nc3)c2)s1] | N-{(1R)-1-[6-(difluoromethyl)pyridin-3-yl]ethyl}-3-(5-methyl-1,3-thiazol-2-yl)-5-(oxetan-3-yloxy)benzamide | $^1$H NMR (500 MHz, Chloroform-d): δ [ppm] 8.71 (d, J = 1.6 Hz, 1H), 7.90-7.80 (m, 2H), 7.63 (d, J = 8.1 Hz, 1H), 7.53 (d, J = 1.1 Hz, 1H), 7.37 (dd, J = 2.4, 1.4 Hz, 1H), 7.20-7.18 (m, 1H), 6.76-6.49 (m, 2H), 5.41-5.28 (m, 2H), 5.05-4.99 (m, 2H), 4.77 (dd, J = 7.4, 5.1 Hz, 2H), 2.54 (d, J = 1.0 Hz, 3H), 1.67 (d, J = 7.1 Hz, 3H). LCMS (Analytical Method F) Rt = 3.02 min, MS (ESIpos): m/z = 446.0 (M + H)$^+$. |
| 165 | 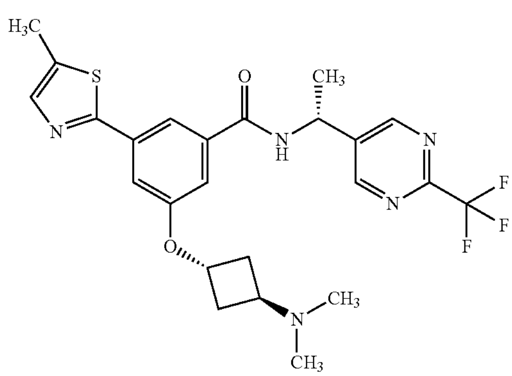 [SMILES: Cc1cnc(-c2cc(O[C@H]3C[C@H](N(C)C)C3)cc(C(=O)N[C@H](C)c3cnc(C(F)(F)F)nc3)c2)s1] | 3-{[trans-3-(dimethylamino)cyclobutyl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.93 (s, 2H), 7.84 (t, J = 1.4 Hz, 1H), 7.52 (d, J = 1.2 Hz, 1H), 7.40 (dd, J = 2.3, 1.5 Hz, 1H), 7.30-7.25 (m, 3H), 6.68 (d, J = 6.6 Hz, 1H), 5.35 (m, 1H), 4.85 (tt, J = 6.7, 3.4 Hz, 1H), 2.93 (ddd, J = 13.7, 7.6, 6.1 Hz, 1H), 2.53 (d, J = 1.1 Hz, 3H), 2.46-2.38 (m, 2H), 2.34-2.27 (m, 2H), 2.16 (s, 6H), 1.71 (d, J = 7.2 Hz, 3H). LCMS (Analytical Method F) Rt = 2.17 min, MS (ESIpos): m/z = 506.2 (M + H)$^+$. |

| Ex. | Structure | Name | Analytical Data |
|---|---|---|---|
| 166 | 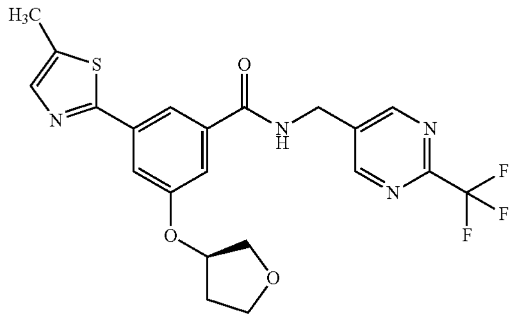 [SMILES: Cc1cnc(-c2cc(O[C@@H]3CCOC3)cc(C(=O)NCc3cnc(C(F)(F)F)nc3)c2)s1] | 3-(5-methyl-1,3-thiazol-2-yl)-5-[(3R)-tetrahydrofuran-3-yloxy]-N-{[2-(trifluoromethyl)pyrimidin-5-yl]methyl}benzamide | $^1$H NMR (500 MHz, Chloroform-d): δ [ppm] 8.94 (s, 2H), 7.86 (t, J = 1.4 Hz, 1H), 7.53-7.49 (m, 2H), 7.39 (dd, J = 2.3, 1.6 Hz, 1H), 6.95 (t, J = 5.8 Hz, 1H), 5.06 (ddt, J = 5.9, 4.0, 1.9 Hz, 1H), 4.72 (d, J = 6.1 Hz, 2H), 4.06-3.97 (m, 3H), 3.92 (td, J = 8.4, 4.3 Hz, 1H), 2.53 (d, J = 1.1 Hz, 3H), 2.28 (dtd, J = 14.4, 8.4, 6.1 Hz, 1H), 2.21-2.12 (m, 1H). LCMS (Analytical Method F) Rt = 3.23 min, MS (ESIpos): m/z = 465.1 (M + H)$^+$. |
| 167 | 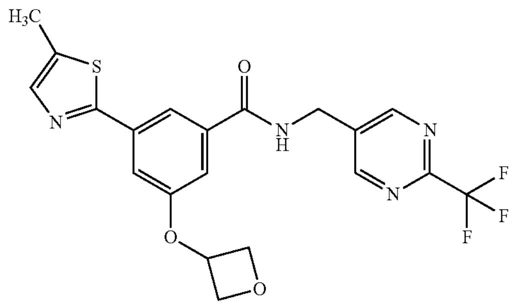 [SMILES: Cc1cnc(-c2cc(OC3COC3)cc(C(=O)NCc3cnc(C(F)(F)F)nc3)c2)s1] | 3-(5-methyl-1,3-thiazol-2-yl)-5-(oxetan-3-yloxy)-N-{[2-(trifluoromethyl)pyrimidin-5-yl]methyl}benzamide | $^1$H NMR (500 MHz, Chloroform-d): δ [ppm] 8.94 (s, 2H), 7.88 (t, J = 1.4 Hz, 1H), 7.51 (d, J = 1.2 Hz, 1H), 7.39 (dd, J = 2.4, 1.4 Hz, 1H), 7.20 (dd, J = 2.4, 1.5 Hz, 1H), 6.92 (s, 1H), 5.33 (m, 1H), 5.04 (t, J = 7.0 Hz, 2H), 4.77 (dd, J = 8.0, 5.0 Hz, 2H), 4.73 (d, J = 6.0 Hz, 2H), 2.53 (d, J = 1.1 Hz, 3H). LCMS (Analytical Method D) Rt = 4.10 min, MS (ESIpos): m/z = 451.0 (M + H)$^+$. |
| 168 | 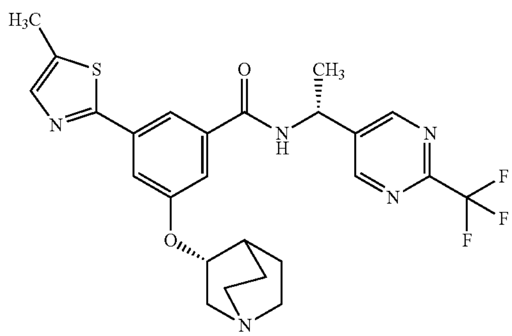 [SMILES: Cc1cnc(-c2cc(O[C@H]3CN4CCC3CC4)cc(C(=O)N[C@H](C)c3cnc(C(F)(F)F)nc3)c2)s1] | 3-[(3R)-1-azabicyclo[2.2.2]oct-3-yloxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.97 (s, 2H), 7.85 (s, 1H), 7.52 (dd, J = 4.5, 1.6 Hz, 2H), 7.38 (s, 1H), 6.85 (s, 1H), 5.37 (m, 1H), 4.61-4.55 (m, 1H), 3.52-3.43 (m, 1H), 3.09-3.00 (m, 1H), 2.99-2.83 (m, 4H), 2.53 (d, J = 1.1 Hz, 3H), 2.28-2.21 (m, 1H), 2.09-2.01 (m, 1H), 1.84-1.75 (m, 1H), 1.73 (d, J = 7.2 Hz, 3H), 1.66 (s, 1H), 1.53-1.42 (m, 1H). LCMS (Analytical Method F) Rt = 2.22 min, MS (ESIpos): m/z = 518.1 (M + H)$^+$. |
| 169 | 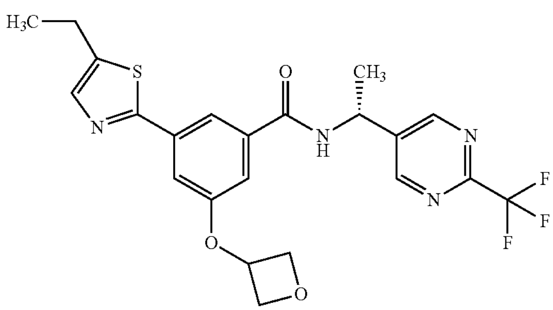 [SMILES: CCc1cnc(-c2cc(OC3COC3)cc(C(=O)N[C@H](C)c3cnc(C(F)(F)F)nc3)c2)s1] | 3-(5-ethyl-1,3-thiazol-2-yl)-5-(oxetan-3-yloxy)-N-{(1R)-1-[2-(trifluoromethyl)pyrimidin-5-yl]ethyl}benzamide | $^1$H NMR (500 MHz, Chloroform-d): δ [ppm] 8.93 (s, 2H), 7.87 (s, 1H), 7.56 (s, 1H), 7.39 (dd, J = 2.3, 1.4 Hz, 1H), 7.20-7.16 (m, 1H), 6.60 (d, J = 6.4 Hz, 1H), 5.39-5.29 (m, 2H), 5.03 (t, J = 6.7 Hz, 2H), 4.77 (dd, J = 7.4, 5.1 Hz, 2H), 2.92 (q, J = 7.5 Hz, 2H), 1.72 (d, J = 7.2 Hz, 3H), 1.37 (t, J = 7.5 Hz, 3H). LCMS (Analytical Method F) Rt = 4.42 min, MS (ESIpos): m/z = 479.05 (M + H)$^+$. |
| 170 | 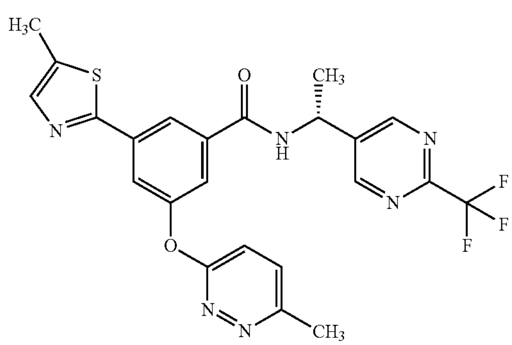 [SMILES: Cc1ccc(Oc2cc(C(=O)N[C@H](C)c3cnc(C(F)(F)F)nc3)cc(-c3ncc(C)s3)c2)nn1] | 3-[(6-methylpyridazin-3-yl)oxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 8.06 (s, 1H), 7.80 (s, 1H), 7.67 (s, 1H), 7.47 (s, 1H), 7.38 (d, J = 9.0 Hz, 1H), 7.15 (d, J = 8.9 Hz, 1H), 5.37-5.30 (m, 1H), 2.63 (s, 3H), 2.50 (s, 3H), 1.65 (s, 3H). LCMS (Analytical Method D) Rt = 4.16 min, MS (ESIpos): m/z = 501.1 (M + H)$^+$. |

| Ex. | Structure | Name | Analytical Data |
|---|---|---|---|
| 171 | 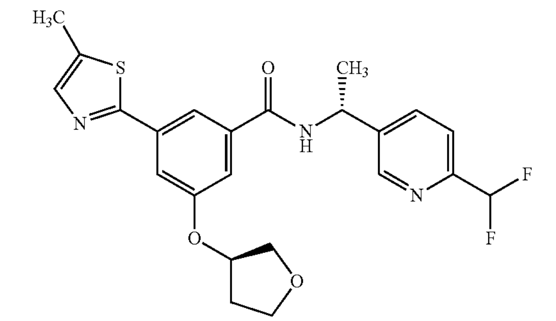 [SMILES: Cc1cnc(-c2cc(O[C@@H]3CCOC3)cc(C(=O)N[C@H](C)c3ccc(C(F)F)nc3)c2)s1] | N-{(1R)-1-[6-(difluoromethyl)pyridin-3-yl]ethyl}-3-(5-methyl-1,3-thiazol-2-yl)-5-[(3R)-tetrahydrofuran-3-yloxy]benzamide | $^1$H NMR (500 MHz, Chloroform-d): δ [ppm] 8.71 (d, J = 1.8 Hz, 1H), 7.91-7.81 (m, 2H), 7.63 (d, J = 8.1 Hz, 1H), 7.53 (d, J = 1.1 Hz, 1H), 7.50 (dd, J = 2.3, 1.5 Hz, 1H), 7.43-7.31 (m, 1H), 6.76-6.51 (m, 2H), 5.37 (m, 1H), 5.12-5.00 (m, 1H), 4.07-3.99 (m, 3H), 3.91 (td, J = 8.4, 4.3 Hz, 1H), 2.54 (d, J = 1.0 Hz, 3H), 2.34-2.22 (m, 1H), 2.20-2.12 (m, 1H), 1.67 (d, J = 7.1 Hz, 3H).<br>LCMS (Analytical Method F) Rt = 3.13 min, MS (ESIpos): m/z = 460.1 (M + H)$^+$. |
| 172 | 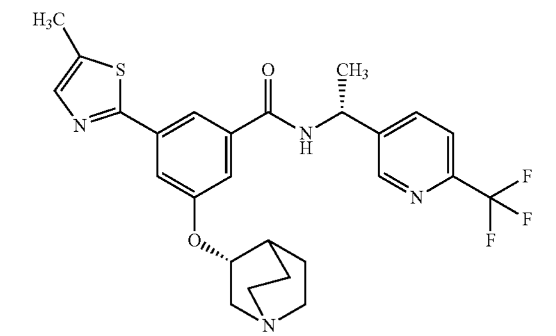 [SMILES: Cc1cnc(-c2cc(O[C@H]3CN4CCC3CC4)cc(C(=O)N[C@H](C)c3ccc(C(F)(F)F)nc3)c2)s1] | 3-[(3R)-1-azabicyclo[2.2.2]oct-3-yloxy]-5-(5-methyl-1,3-thiazol-2-yl)-N-{(1R)-1-[6-(trifluoromethyl)pyridin-3-yl]ethyl}benzamide | $^1$H NMR (500 MHz, DMSO-d6): δ [ppm] = 9.14 (d, J = 7.4, 1H), 8.82 (d, J = 1.7, 1H), 8.08 (dd, J = 8.2, 1.8, 1H), 7.92-7.88 (m, 2H), 7.64 (d, J = 1.2, 1H), 7.51-7.49 (m, 1H), 7.49-7.46 (m, 1H), 5.28 (dq, J = 7.0, 1H), 4.60 (dt, J = 6.8, 2.8, 1H), 3.26 (ddd, J = 14.1, 7.9, 1.6, 1H), 2.84-2.60 (m, 5H), 2.51 (s, 3H), 2.10-2.03 (m, 1H), 1.89-1.79 (m, 1H), 1.71-1.61 (m, 1H), 1.61-1.52 (m, 4H), 1.39-1.29 (m, 1H)<br>LCMS (Analytical Method F) Rt = 2.30 min, MS (ESIpos): m/z = 517.1 (M + H)$^+$. |
| 173 | 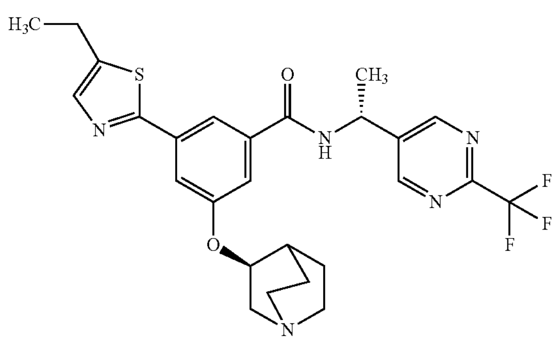 [SMILES: CCc1cnc(-c2cc(O[C@@H]3CN4CCC3CC4)cc(C(=O)N[C@H](C)c3cnc(C(F)(F)F)nc3)c2)s1] | 3-[(3S)-1-azabicyclo[2.2.2]oct-3-yloxy]-5-(5-ethyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.96 (s, 2H), 7.83 (s, 1H), 7.57 (s, 1H), 7.53 (dd, J = 2.3, 1.5 Hz, 1H), 7.39-7.36 (m, 1H), 6.64 (d, J = 6.6 Hz, 1H), 5.38 (m, 1H), 4.57-4.49 (m, 1H), 3.35 (ddd, J = 14.3, 8.0, 1.9 Hz, 1H), 3.06-2.76 (m, 7H), 2.24-2.16 (m, 1H), 2.06-1.94 (m, 1H), 1.85-1.77 (m, 1H), 1.74 (d, J = 7.2 Hz, 3H), 1.65-1.57 (m, 1H), 1.48-1.42 (m, 1H), 1.39 (t, J = 7.5 Hz, 3H).<br>LCMS (Analytical Method D) Rt = 3.60 min, MS (ESIpos): m/z = 532.0 (M + H)$^+$. |
| 174 | 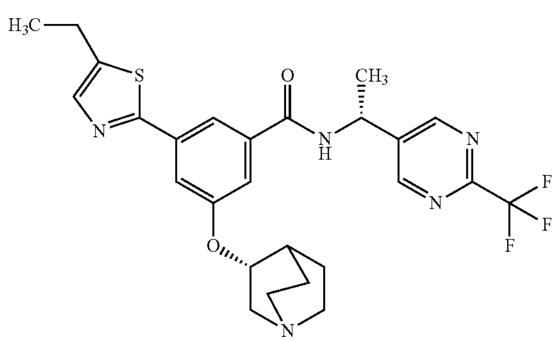 [SMILES: CCc1cnc(-c2cc(O[C@H]3CN4CCC3CC4)cc(C(=O)N[C@H](C)c3cnc(C(F)(F)F)nc3)c2)s1] | 3-[(3R)-1-azabicyclo[2.2.2]oct-3-yloxy]-5-(5-ethyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.81 (s, 1H), 7.55 (s, 1H), 7.50 (dd, J = 2.2, 1.5 Hz, 1H), 7.37-7.33 (m, 1H), 6.63 (d, J = 6.5 Hz, 1H), 5.36 (m, 1H), 4.58-4.46 (m, 1H), 3.34 (ddd, J = 14.3, 7.9, 1.8 Hz, 1H), 3.03-2.74 (m, 7H), 2.22-2.14 (m, 1H), 2.05-1.93 (m, 1H), 1.80-1.74 (m, 1H), 1.72 (d, J = 7.2 Hz, 3H), 1.62-1.54 (m, 1H), 1.47-1.39 (m, 1H), 1.37 (t, J = 7.5 Hz, 3H).<br>LCMS (Analytical Method D) Rt = 3.61 min, MS (ESIpos): m/z = 532.1 (M + H)$^+$. |

| Ex. | Structure | Name | Analytical Data |
|---|---|---|---|
| 175 | 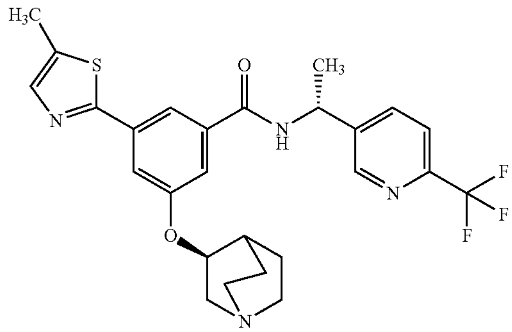 [SMILES: Cc1cnc(-c2cc(O[C@@H]3CN4CCC3CC4)cc(C(=O)N[C@H](C)c3ccc(C(F)(F)F)nc3)c2)s1] | 3-[(3S)-1-azabicyclo[2.2.2]oct-3-yloxy]-5-(5-methyl-1,3-thiazol-2-yl)-N-{(1R)-1-[6-(trifluoromethyl)pyridin-3-yl]ethyl}benzamide | $^1$H NMR (500 MHz, DMSO-d6): δ [ppm] = 9.13 (d, J = 7.4, 1H), 8.82 (d, J = 1.6, 1H), 8.08 (dd, J = 8.1, 1.8, 1H), 7.93-7.86 (m, 2H), 7.64 (d, J = 1.2, 1H), 7.49 (dt, J = 11.1, 2.2, 2H), 5.28 (dq, J = 7.2, 1H), 4.60 (dt, J = 6.7, 2.8, 1H), 3.30-3.21 (m, 1H), 2.85-2.60 (m, 5H), 2.51 (s, 3H), 2.07 (q, J = 2.8, 1H), 1.84 (dddd, J = 15.5, 7.3, 5.3, 3.4, 1H), 1.66 (ddt, J = 13.3, 9.4, 4.9, 1H), 1.63-1.53 (m, 4H), 1.40-1.30 (m, 1H) LCMS (Analytical Method F) Rt = 2.28 min, MS (ESIpos): m/z = 517.2 (M + H)$^+$. |
| 176 | 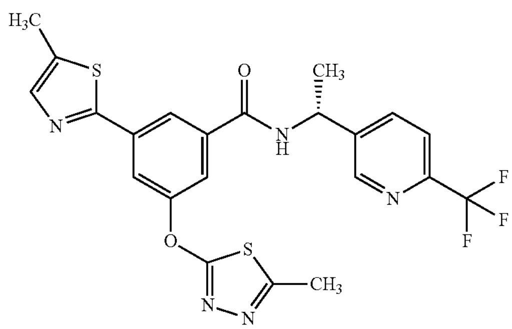 [SMILES: Cc1cnc(-c2cc(Oc3nnc(C)s3)cc(C(=O)N[C@H](C)c3ccc(C(F)(F)F)nc3)c2)s1] | 3-[(5-methyl-1,3,4-thiadiazol-2-yl)oxy]-5-(5-methyl-1,3-thiazol-2-yl)-N-{(1R)-1-[6-(trifluoromethyl)pyridin-3-yl]ethyl}benzamide | $^1$H NMR (500 MHz, Chloroform-d): δ [ppm] 8.78 (d, J = 1.8 Hz, 1H), 8.14 (t, J = 1.3 Hz, 1H), 7.95 (dd, J = 2.3, 1.5 Hz, 1H), 7.89 (dd, J = 8.1, 2.0 Hz, 1H), 7.82-7.76 (m, 1H), 7.67 (d, J =8.1 Hz, 1H), 7.53 (d, J = 1.1 Hz, 1H), 6.76 (d, J = 7.0 Hz, 1H), 5.38 (m, 1H), 2.68 (s, 3H), 2.53 (d, J = 1.0 Hz, 3H), 1.68 (d, J = 7.1 Hz, 3H). LCMS (Analytical Method D) Rt = 4.40 min, MS (ESIpos): m/z = 506.0 (M + H)$^+$. |
| 177 | 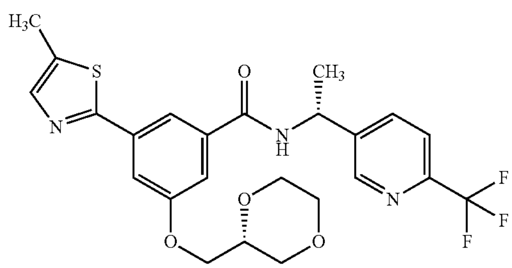 [SMILES: Cc1cnc(-c2cc(OC[C@H]3COCCO3)cc(C(=O)N[C@H](C)c3ccc(C(F)(F)F)nc3)c2)s1] | 3-[(2R)-1,4-dioxan-2-ylmethoxy]-5-(5-methyl-1,3-thiazol-2-yl)-N-{(1R)-1-[6-(trifluoromethyl)pyridin-3-yl]ethyl}benzamide | $^1$H NMR (500 MHz, Chloroform-d): δ [ppm] 8.81-8.74 (m, 1H), 7.88 (s, 2H), 7.66 (d, J = 8.1 Hz, 1H), 7.55 (s, 1H), 7.52 (s, 1H), 7.41 (s, 1H), 6.59 (d, J = 6.9 Hz, 1H), 5.38 (m, 1H), 4.13-4.06 (m, 1H), 4.06-3.98 (m, 2H), 3.88 (td, J = 11.8, 2.3 Hz, 2H), 3.82 (td, J = 11.7, 1.1, 2.6 Hz, 1H), 3.78-3.72 (m, 1H), 3.67 (td, J = 11.3, 3.1 Hz, 1H), 3.59-3.51 (m, 1H), 2.53 (s, 3H), 1.67 (d, J = 7.1 Hz, 3H). LCMS (Analytical Method F) Rt = 3.36 min, MS (ESIpos): m/z = 508.1 (M + H)$^+$. |
| 178 | 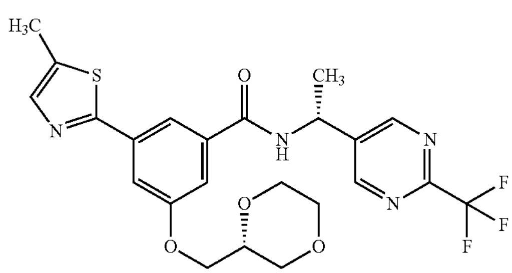 [SMILES: Cc1cnc(-c2cc(OC[C@H]3COCCO3)cc(C(=O)N[C@H](C)c3cnc(C(F)(F)F)nc3)c2)s1] | 3-[(2R)-1,4-dioxan-2-ylmethoxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 7.90 (s, 1H), 7.82 (d, J = 8.7 Hz, 1H), 7.73 (d, J = 8.7 Hz, 1H), 7.59 (s, 1H), 7.52 (s, 1H), 7.45 (d, J = 7.3 Hz, 1H), 7.42 (s, 1H), 5.60 (m, 1H), 4.14-4.07 (m, 1H), 4.06-3.97 (m, 2H), 3.94-3.85 (m, 2H), 3.82 (td, J = 11.7, 11.1, 2.6 Hz, 1H), 3.78-3.73 (m, 1H), 3.68 (td, J = 11.2, 3.2 Hz, 1H), 3.57 (dd, J = 11.3, 9.9 Hz, 1H), 2.53 (s, 3H), 1.76 (d, J = 7.0 Hz, 3H). LCMS (Analytical Method F) Rt = 3.14 min, MS (ESIpos): m/z = 509.1 (M + H)$^+$. |
| 179 | 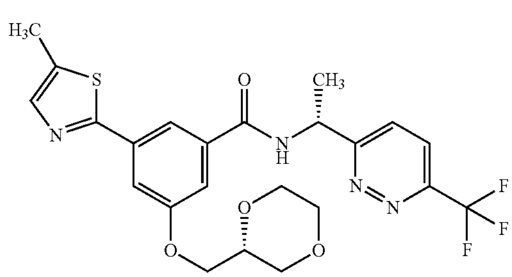 [SMILES: Cc1cnc(-c2cc(OC[C@H]3COCCO3)cc(C(=O)N[C@H](C)c3ccc(C(F)(F)F)nn3)c2)s1] | 3-[(2R)-1,4-dioxan-2-ylmethoxy]-5-(5-methyl-1,3-thiazol-2-yl)-N-{(1R)-1-[6-(trifluoromethyl)pyridazin-3-yl]ethyl}benzamide | $^1$H NMR (500 MHz, Chloroform-d): δ [ppm] 8.93 (s, 2H), 7.87 (s, 1H), 7.56 (d, J = 2.0 Hz, 1H), 7.53-7.48 (m, 1H), 7.43-7.34 (m, 1H), 6.64 (d, J = 6.5 Hz, 1H), 5.36 (m, 1H), 4.13-4.07 (m, 1H), 4.06-3.96 (m, 2H), 3.88 (td, J = 12.3, 11.8, 2.2 Hz, 2H), 3.82 (td, J = 11.7, 11.1, 2.6 Hz, 1H), 3.78-3.71 (m, 1H), 3.67 (td, J = 11.2, 3.1 Hz, 1H), 3.56 (dd, J = 11.4, 9.7 Hz, 1H), 2.53 (s, 3H), 1.71 (d, J = 7.1 Hz, 3H). |

| Ex. | Structure | Name | Analytical Data |
|---|---|---|---|
| | | | LCMS (Analytical Method F) Rt = 3.28 min, MS (ESIpos): m/z = 509 (M + H)⁺. |
| 180 | 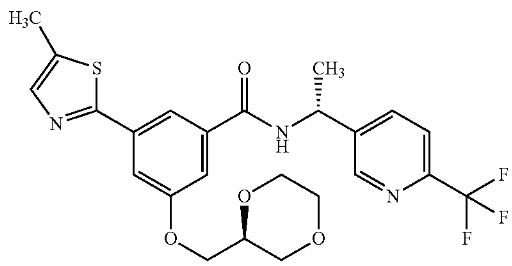 | 3-[(2S)-1,4-dioxan-2-ylmethoxy]-5-(5-methyl-1,3-thiazol-2-yl)-N-{(1R)-1-[6-(trifluoromethyl)pyridin-3-yl]ethyl}benzamide | ¹H NMR (500 MHz, Chloroform-d): δ [ppm] 8.78 (s, 1H), 7.93-7.85 (m, 2H), 7.66 (d, J = 8.1 Hz, 1H), 7.53 (d, J = 11.1 Hz, 2H), 7.41 (s, 1H), 6.65 (d, J = 6.8 Hz, 1H), 5.38 (m, 1H), 4.12-4.06 (m, 1H), 4.06-3.96 (m, 2H), 3.88 (td, J = 12.1, 2.3 Hz, 2H), 3.81 (td, J = 11.7, 11.2, 2.6 Hz, 1H), 3.78-3.70 (m, 1H), 3.67 (td, J = 11.3, 3.1 Hz, 1H), 3.59-3.50 (m, 1H), 2.53 (s, 3H), 1.67 (d, J = 7.1 Hz, 3H). LCMS (Analytical Method F) Rt = 3.36 min, MS (ESIpos): m/z = 508 (M + H)⁺. |
| 181 | 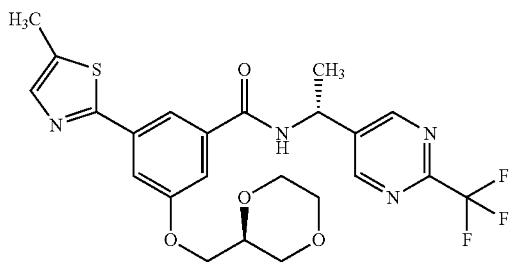 [SMILES: Cc1cnc(-c2cc(OC[C@@H]3COCCO3)cc(C(=O)N[C@H](C)c3cnc(C(F)(F)F)nc3)c2)s1] | 3-[(2S)-1,4-dioxan-2-ylmethoxy]-5-(5-methyl-1,3-thiazol-2-yl)-N-{(1R)-1-[2-(trifluoromethyl)pyrimidin-5-yl]ethyl}benzamide | ¹H NMR (500 MHz, Chloroform-d): δ [ppm] 8.93 (s, 2H), 7.87 (s, 1H), 7.55 (dd, J = 2.2, 1.4 Hz, 1H), 7.53-7.49 (m, 1H), 7.41-7.37 (m, 1H), 6.69 (d, J = 6.6 Hz, 1H), 5.36 (m, 1H), 4.13-4.06 (m, 1H), 4.05-3.97 (m, 2H), 3.88 (td, J = 12.0, 2.4 Hz, 2H), 3.81 (td, J = 11.7, 11.1, 2.6 Hz, 1H), 3.78-3.71 (m, 1H), 3.67 (td, J = 11.2, 3.1 Hz, 1H), 3.56 (dd, J = 11.3, 10.0 Hz, 1H), 2.57-2.46 (m, 3H), 1.71 (d, J = 7.1 Hz, 3H). LCMS (Analytical Method F) Rt = 3.28 min, MS (ESIpos): m/z = 509 (M + H)⁺. |
| 182 | 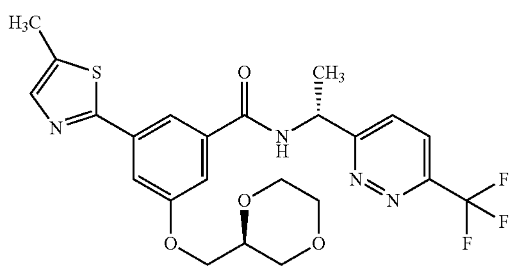 | 3-[(2S)-1,4-dioxan-2-ylmethoxy]-5-(5-methyl-1,3-thiazol-2-yl)-N-{(1R)-1-[6-(trifluoromethyl)pyridazin-3-yl]ethyl}benzamide | ¹H NMR (500 MHz, Chloroform-d): δ [ppm] 7.92 (s, 1H), 7.82 (d, J = 8.7 Hz, 1H), 7.74 (d, J = 8.7 Hz, 1H), 7.63-7.57 (m, 1H), 7.55-7.50 (m, 1H), 7.48 (d, J = 7.3 Hz, 1H), 7.43 (d, J = 1.5 Hz, 1H), 5.60 (m, 1H), 4.13-4.07 (m, 1H), 4.07-3.96 (m, 2H), 3.93-3.85 (m, 2H), 3.82 (td, J = 11.7, 11.1, 2.6 Hz, 1H), 3.78-3.72 (m, 1H), 3.68 (td, J = 11.2, 3.1 Hz, 1H), 3.57 (dd, J = 11.4, 9.8 Hz, 1H), 2.53 (s, 3H), 1.76 (d, J = 7.0 Hz, 3H). LCMS (Analytical Method F) Rt = 3.14 min, MS (ESIpos): m/z = 509 (M + H)⁺. |
| 183 | 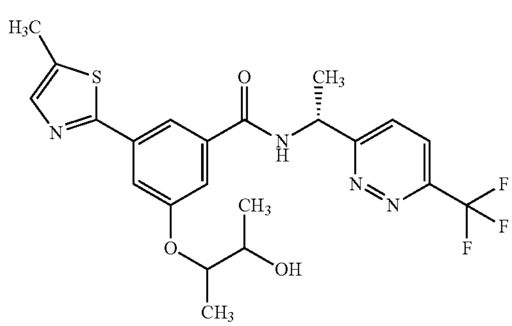 [SMILES: Cc1cnc(-c2cc(OC(C)C(C)O)cc(C(=O)N[C@H](C)c3ccc(C(F)(F)F)nn3)c2)s1] | Trans Isomer 1; 3-{[3-hydroxybutan-2-yl]oxy}-5-(5-methyl-1,3-thiazol-2-yl)-N-{(1R)-1-[6-(trifluoromethyl)pyridazin-3-yl]ethyl}benzamide | ¹H NMR (500 MHz, Chloroform-d): δ [ppm] 7.87 (t, J = 1.3 Hz, 1H), 7.83 (d, J = 8.7 Hz, 1H), 7.74 (d, J = 8.7 Hz, 1H), 7.60-7.59 (m, 1H), 7.52 (d, J = 1.1 Hz, 1H), 7.50-7.46 (m, 1H), 7.43-7.41 (m, 1H), 5.60 (m, 1H), 4.52-4.47 (m, 1H), 4.08-4.03 (m, 1H), 2.53 (d, J = 1.0 Hz, 3H), 2.00 (d, J = 4.9 Hz, 1H), 1.76 (d, J = 7.0 Hz, 3H), 1.30 (d, J = 6.3 Hz, 3H), 1.27 (d, J = 6.5 Hz, 3H). LCMS (Analytical Method F) Rt = 3.07 min, MS (ESIpos): m/z = 481 (M + H)⁺. |

| Ex. | Structure | Name | Analytical Data |
|---|---|---|---|
| 184 | 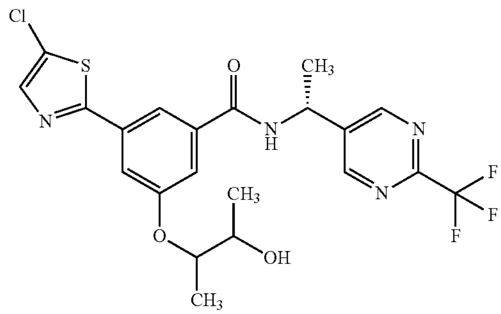 [SMILES: CC(O)C(C)Oc1cc(C(=O)N[C@H](C)c2cnc(C(F)(F)F)nc2)cc(-c2ncc(Cl)s2)c1] | Trans Isomer 1; 3-(5-chloro-1,3-thiazol-2-yl)-5-{[3-hydroxybutan-2-yl]oxy}-N-[(1R)-1-[2-(trifluoromethyl)pyrimidin-5-yl]ethyl}benzamide | $^1$H NMR (500 MHz, Chloroform-d): δ [ppm] 8.94 (s, 2H), 7.77 (t, J = 1.4 Hz, 1H), 7.67 (s, 1H), 7.50 (dd, J = 2.4, 1.5 Hz, 1H), 7.41 (dd, J = 2.4, 1.5 Hz, 1H), 6.57 (d, J = 6.5 Hz, 1H), 5.36 (m, 1H), 4.48 (qd, J = 6.3, 3.3 Hz, 1H), 4.09-4.00 (m, 1H), 1.98 (d, J = 5.0 Hz, 1H), 1.73 (d, J = 7.2 Hz, 3H), 1.31 (d, J = 6.3 Hz, 3H), 1.27 (d, J = 6.5 Hz, 3H). LCMS (Analytical Method D) Rt = 4.39 min, MS (ESIpos): m/z = 501 (M + H)$^+$. |
| 185 | 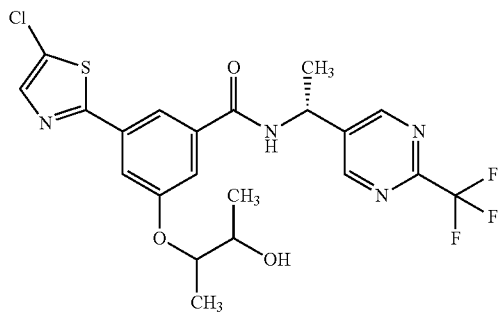 | Cis Isomer 1; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide | $^1$H NMR (500 MHz, DMSO-d6) δ [ppm] 9.16 (d, J = 7.1 Hz, 1H), 9.11 (s, 2H), 8.00 (s, 1H), 7.91-7.88 (m, 1H), 7.60-7.55 (m, 2H), 5.35-5.23 (m, 1H), 4.84 (d, J = 4.8 Hz, 1H), 4.49-4.39 (m, 1H), 3.81-3.73 (m, 1H), 1.61 (d, J = 7.1 Hz, 3H), 1.21 (d, J = 6.2 Hz, 3H), 1.11 (d, J = 6.4 Hz, 3H). LCMS (Analytical Method F) Rt = 3.56 min, MS (ESIpos): m/z = 501.1 (M + H)$^+$. |
| 186 | 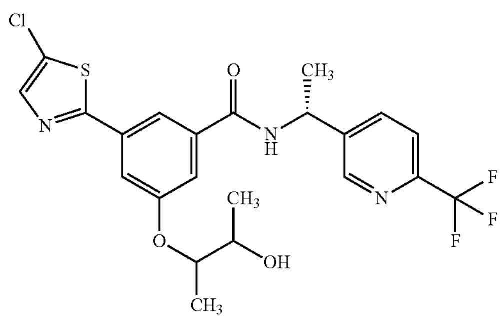 [SMILES: CC(O)C(C)Oc1cc(C(=O)N[C@H](C)c2ccc(C(F)(F)F)nc2)cc(-c2ncc(Cl)s2)c1] | Trans Isomer 1; 3-(5-chloro-1,3-thiazol-2-yl)-5-{[3-hydroxybutan-2-yl]oxy}-N-[(1R)-1-[6-(trifluoromethyl)pyridin-3-yl]ethyl}benzamide | $^1$H NMR (500 MHz, Chloroform-d): δ [ppm] 8.79 (d, J = 1.9 Hz, 1H), 7.89 (dd, J = 8.1, 2.2 Hz, 1H), 7.77 (d, J = 1.4 Hz, 1H), 7.70-7.66 (m, 2H), 7.51 (dd, J = 2.4, 1.5 Hz, 1H), 7.43 (dd, J = 2.3, 1.5 Hz, 1H), 6.50 (d, J = 7.0 Hz, 1H), 5.38 (m, 1H), 4.48 (qd, J = 6.3, 3.4 Hz, 1H), 4.09-4.01 (m, 1H), 1.94 (d, J = 4.9 Hz, 1H), 1.69 (d, J = 7.1 Hz, 3H), 1.31 (d, J = 6.3 Hz, 3H), 1.27 (d, J = 6.5 Hz, 3H). LCMS (Analytical Method D) Rt = 4.46 min, MS (ESIpos): m/z = 499.95 (M + H)$^+$. |
| 187 | 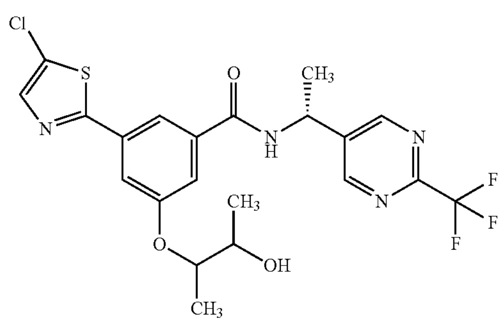 [SMILES: CC(O)C(C)Oc1cc(C(=O)N[C@H](C)c2cnc(C(F)(F)F)nc2)cc(-c2ncc(Cl)s2)c1] | Cis Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide | $^1$H NMR (500 MHz, Chloroform-d) δ 8.94 (s, 2H), 7.77 (t, 1H), 7.67 (s, 1H), 7.51-7.49 (m, 1H), 7.42-7.41 (m, 1H), 6.66 (d, J = 6.6 Hz, 1H), 5.36 (p, J = 7.0 Hz, 1H), 4.31 (p, J = 6.2 Hz, 1H), 3.88 (p, J = 6.5 Hz, 1H), 2.43 (s, 1H), 1.73 (d, J = 7.2 Hz, 3H), 1.29 (dd, J = 11.5, 6.3 Hz, 6H). LCMS (Analytical Method F) Rt = 3.54 min, MS (ESIpos): m/z = 501 (M + H)$^+$. |
| 188 | 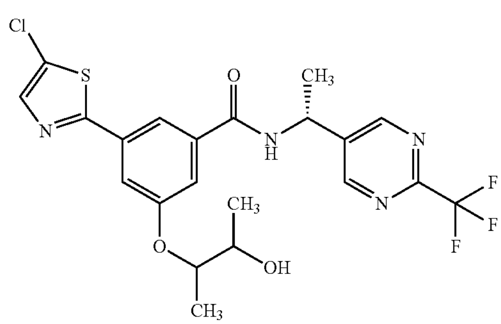 | Trans Isomer 2; 3-(5-chloro-1,3-thiazol-2-yl)-5-{[3-hydroxybutan-2-yl]oxy}-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.76 (t, J = 1.4 Hz, 1H), 7.67 (s, 1H), 7.50 (dd, J = 2.4, 1.5 Hz, 1H), 7.41 (dd, J = 2.4, 1.5 Hz, 1H), 6.58 (d, J = 6.6 Hz, 1H), 5.36 (m, 1H), 4.47 (qd, J = 6.3, 3.4 Hz, 1H), 4.09-3.96 (m, 1H), 1.98 (d, J = 4.9 Hz, 1H), 1.73 (d, J = 7.2 Hz, 3H), 1.31 (d, J = 6.3 Hz, 3H), 1.27 (d, J = 6.5 Hz, 3H). LCMS (Analytical Method D) Rt = 4.38 min, MS (ESIpos): m/z = 501 (M + H)$^+$. |

| Ex. | Structure | Name | Analytical Data |
|---|---|---|---|
| 189 | 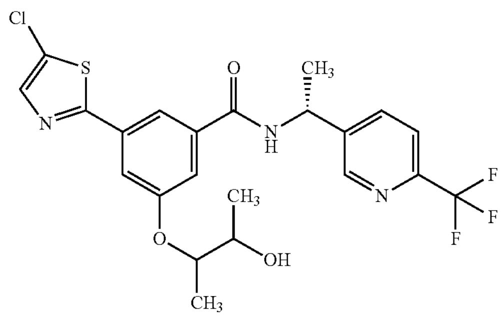 [SMILES: CC(O)C(C)Oc1cc(C(=O)N[C@H](C)c2ccc(C(F)(F)F)nc2)cc(-c2ncc(Cl)s2)c1] | Trans Isomer 2; 3-(5-chloro-1,3-thiazol-2-yl)-5-{[3-hydroxybutan-2-yl]oxy}-N-{(1R)-1-[6-(trifluoromethyl)pyridin-3-yl]ethyl}benzamide | $^1$H NMR (500 MHz, Chloroform-d): δ [ppm] 8.78 (d, J = 1.9 Hz, 1H), 7.88 (dd, J = 8.1, 2.1 Hz, 1H), 7.77 (t, J = 1.4 Hz, 1H), 7.69-7.65 (m, 2H), 7.50 (dd, J = 2.4, 1.5 Hz, 1H), 7.44-7.38 (m, 1H), 6.51 (d, J = 6.9 Hz, 1H), 5.38 (m, 1H), 4.47 (qd, J = 6.3, 3.4 Hz, 1H), 4.09-4.01 (m, 1H), 1.96 (d, J = 4.9 Hz, 1H), 1.68 (d, J = 7.1 Hz, 3H), 1.31 (d, J = 6.3 Hz, 3H), 1.27 (d, J = 6.5 Hz, 3H). LCMS (Analytical Method D) Rt = 4.46 min, MS (ESIpos): m/z = 499.95 (M + H)$^+$. |

Example 190 tert-Butyl (3R)-3-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate, as a mixture of diastereoisomers

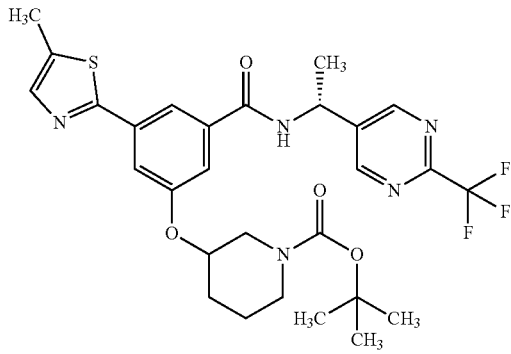 [SMILES: Cc1cnc(-c2cc(OC3CCCN(C(=O)OC(C)(C)C)C3)cc(C(=O)N[C@H](C)c3cnc(C(F)(F)F)nc3)c2)s1]

To a solution of Intermediate 5AF (200 mg, 0.44 mmol), Intermediate VI (121 mg, 0.53 mmol) and DIPEA (0.231 mL, 1.33 mmol) in DCM (1 mL) was added T3P (50% solution in EtOAc, 0.198 mL, 0.66 mmol) and the resulting solution stirred at RT for 16 h. LCMS analysis indicated incomplete consumption of starting material. HATU (50 mg, 0.13 mmol) was added and the mixture stirred at RT for 2 h then diluted with DCM (1 mL) and washed with water (1 mL). The organic phase was dried (MgSO$_4$), filtered and concentrated at reduced pressure. Purification by Biotage Isolera™ chromatography (eluting with 0-80% EtOAc in heptane on a pre-packed KP—SiO$_2$ column) gave a colourless oil that was freeze-dried to give 195 mg (71% yield) of the title compound as white powder.

$^1$H NMR (250 MHz, DMSO-d6): δ [ppm] 9.08 (s, 2H), 8.92 (d, J=7.1 Hz, 1H), 7.94 (t, J=1.4 Hz, 1H), 7.65-7.47 (m, 3H), 5.33 (m, 1H), 4.53 (d, J=3.1 Hz, 1H), 3.68-3.23 (m, 4H), 2.07-1.59 (m, 6H), 1.60-1.41 (m, 1H), 1.30 (d, J=2.4 Hz, 9H).

LCMS (Analytical Method F) Rt=4.27 min, MS (ESIpos): m/z=592 (M+H)$^+$.

In analogy to the procedure described for Example 190, the following examples were prepared using both T3P and HATU with the appropriate carboxylic acid and amine starting materials.

| Ex. | Structure | Name | Analytical Data |
|---|---|---|---|
| 191 | 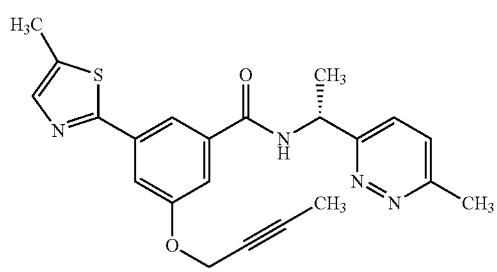 [SMILES: CC#CCOc1cc(C(=O)N[C@H](C)c2ccc(C)nn2)cc(-c2ncc(C)s2)c1] | 3-(but-2-yn-1-yloxy)-N-[(1R)-1-(6-methylpyridazin-3-yl)ethyl]-5-(5-methyl-1,3-thiazol-2-yl)benzamide | $^1$H NMR (500 MHz, Chloroform-d): δ [ppm] 7.94 (t, J = 1.4 Hz, 1H), 7.89 (d, J = 7.4 Hz, 1H), 7.60 (dd, J = 2.4, 1.5 Hz, 1H), 7.52-7.46 (m, 2H), 7.41 (d, J = 8.6 Hz, 1H), 7.32 (d, J = 8.6 Hz, 1H), 5.46 (m, 1H), 4.73 (q, J = 2.3 Hz, 2H), 2.70 (s, 3H), 2.51 (d, J = 1.1 Hz, 3H), 1.86 (t, J = 2.3 Hz, 3H), 1.68 (d, J = 6.9 Hz, 3H). LCMS (Analytical Method D) Rt = 3.93 min, MS (ESIpos): m/z = 407 (M + H)$^+$. |

| Ex. | Structure | Name | Analytical Data |
|---|---|---|---|
| 192 | 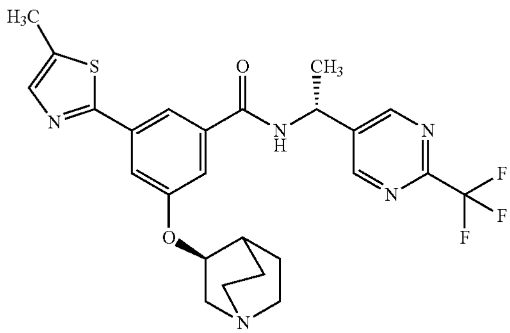 [SMILES: Cc1cnc(-c2cc(O[C@@H]3CN4CCC3CC4)cc(C(=O)N[C@H](C)c3cnc(C(F)(F)F)nc3)c2)s1] | 3-[(3S)-1-azabicyclo[2.2.2]oct-3-yloxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.81 (t, J = 1.3 Hz, 1H), 7.52 (d, J = 1.2 Hz, 1H), 7.50-7.48 (m, 1H), 7.36-7.33 (m, 1H), 6.65 (d, J = 6.5 Hz, 1H), 5.36 (m, 1H), 4.54-4.48 (m, 1H), 3.37-3.29 (m, 1H), 3.03-2.94 (m, 1H), 2.93-2.75 (m, 4H), 2.54 (d, J = 1.0 Hz, 3H), 2.21-2.16 (m, 1H), 2.02-1.93 (m, 1H), 1.80-1.74 (m, 1H), 1.72 (d, J = 7.2 Hz, 3H), 1.63-1.55 (m, 1H), 1.45-1.37 (m, 1H). LCMS (Analytical Method F) Rt = 2.15 min, MS (ESIpos): m/z = 518.1 (M + H)$^+$. |

Examples 193 to 200 were prepared using T3P and the appropriate carboxylic acid and amine starting materials. The isomeric mixtures were separated by the given methods into single isomers.

Example 193 (Enantiomer 1) and Example 194 (Enantiomer 2)

3-(5-Methyl-1,3-thiazol-2-yl)-5-(oxetan-3-yloxy)-N-{1-[5-(trifluoromethyl)-1,3,4-thiadiazol-2-yl]ethyl}benzamide, formed as a mixture of 2 enantiomers

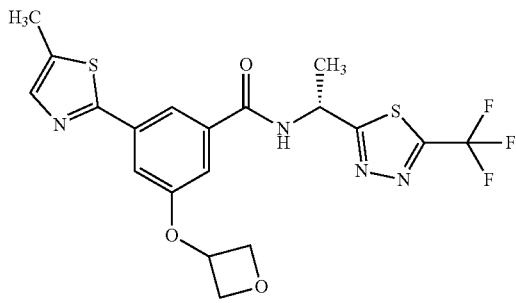 [SMILES: Cc1cnc(-c2cc(OC3COC3)cc(C(=O)N[C@H](C)c3nnc(C(F)(F)F)s3)c2)s1]

Intermediate 5F (40 mg, 0.14 mmol), 1-[5-(trifluoromethyl)-1,3,4-thiadiazol-2-yl]ethanamine (38 mg, 0.17 mmol) and DIPEA (0.12 mL, 0.69 mmol) were dissolved in DCM (2 mL). T3P (0.16 mL, 0.28 mmol, 50% in EtOAc) was added and the reaction mixture stirred at RT for 2 h. The reaction mixture washed with saturated NaHCO$_3$ (3 mL) and the aqueous layer further extracted with DCM (2×2 mL). The crude material was purified by Biotage Isolera™ chromatography (eluting with 10-70% EtOAc in heptane on a 10 g pre-packed KP—SiO$_2$ column) to give 31 mg (48% yield) of the title compound as a colourless gum.

$^1$H NMR (500 MHz, CDCl3): δ [ppm] 7.88 (t, J=1.4 Hz, 1H), 7.53 (d, J=1.2 Hz, 1H), 7.40 (dd, J=2.4, 1.4 Hz, 1H), 7.22 (dd, J=2.4, 1.5 Hz, 1H), 6.93 (d, J=7.4 Hz, 1H), 5.74 (m, 1H), 5.34 (m, 1H), 5.07-5.02 (m, 2H), 4.78 (ddd, J=7.4, 5.0, 2.8 Hz, 2H), 2.54 (d, J=1.1 Hz, 3H), 1.91 (d, J=7.0 Hz, 3H).

LCMS (Analytical Method F) Rt=3.37 min, MS (ESIpos): m/z=471.1 (M+H)$^+$.

Example 193

Enantiomer 1; 3-(5-Methyl-1,3-thiazol-2-yl)-5-(oxetan-3-yloxy)-N-{1-[5-(trifluoromethyl)-1,3,4-thiadiazol-2-yl]ethyl}benzamide SFC Chiral Purification (Method 3) was performed on 28.7 mg of Enantiomer 1 (Example 193) and Enantiomer 2 (Example 194) mixture to give 8.9 mg of the title compound.

SFC Chiral Analysis (Method 3): 100% e.e. Rt=2.21 min.

$^1$H NMR (500 MHz, CDCl3): δ [ppm] 7.87 (s, 1H), 7.53 (d, J=1.1 Hz, 1H), 7.42-7.39 (m, 1H), 7.23-7.21 (m, 1H), 6.87 (d, J=7.5 Hz, 1H), 5.78-5.71 (m, 1H), 5.34 (t, J=5.4 Hz, 1H), 5.04 (t, J=6.7 Hz, 2H), 4.78 (t, J=7.6 Hz, 2H), 2.54 (d, J=1.1 Hz, 3H), 1.91 (d, J=7.0 Hz, 3H).

LCMS (Analytical Method D) Rt=4.39 min, MS (ESIpos): m/z=471.1 (M+H)$^+$.

Example 194

Enantiomer 2; 3-(5-Methyl-1,3-thiazol-2-yl)-5-(oxetan-3-yloxy)-N-{1-[5-(trifluoromethyl)-1,3,4-thiadiazol-2-yl]ethyl}benzamide SFC Chiral Purification (Method 3) was performed on 28.7 mg of Enantiomer 1 (Example 193) and Enantiomer 2 (Example 194) mixture to give 11.7 mg of the title compound.

SFC Chiral Analysis (Method 3): 99.2% e.e. Rt=2.53 min.

$^1$H NMR (500 MHz, CDCl3): δ [ppm] 7.88 (s, 1H), 7.53 (s, 1H), 7.40 (s, 1H), 7.22 (s, 1H), 6.91-6.85 (m, 1H), 5.78-5.71 (m, 1H), 5.37-5.31 (m, 1H), 5.04 (t, J=6.7 Hz, 2H), 4.81-4.76 (m, 2H), 2.54 (s, 3H), 1.91 (d, J=7.1 Hz, 3H).

LCMS (Analytical Method D) Rt=4.40 min, MS (ESIpos): m/z=471.0 (M+H)$^+$.

Example 195 (Enantiomer 1) and Example 196 (Enantiomer 2)

3-(5-methyl-1,3-thiazol-2-yl)-5-(tetrahydro-2H-pyran-4-yloxy)-N-{1-[5-(trifluoromethyl)-1,3,4-thiadiazol-2-yl]ethyl}benzamide, formed as a mixture of 2 enantiomers

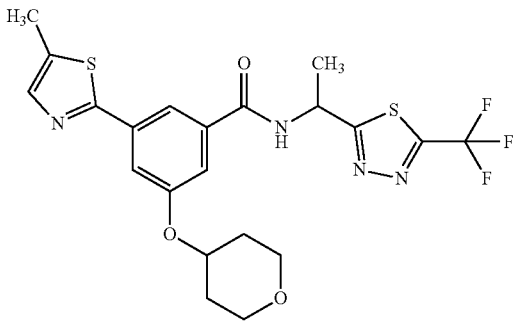 [SMILES: Cc1cnc(-c2cc(OC3CCOCC3)cc(C(=O)NC(C)c3nnc(C(F)(F)F)s3)c2)s1]

Intermediate 5K (96 mg, 0.3 mmol), 1-[5-(trifluoromethyl)-1,3,4-thiadiazol-2-yl]ethanamine (84 mg, 0.36 mmol) and DIPEA (0.261 mL, 1.5 mmol) were dissolved in DCM (3 mL). T3P (0.35 mL, 0.6 mmol, 50% in EtOAc) was added and the reaction mixture stirred at RT for 2 h. The reaction mixture washed with saturated NaHCO$_3$ (3 mL) and the aqueous layer further extracted with DCM (2×2 mL). The combined organics were dried over MgSO$_4$, filtered and concentrated under reduced pressure. The crude material was triturated with Et$_2$O to give 112 mg (75% yield) of the title compound as white powder.

$^1$H NMR (500 MHz, CDCl3): δ [ppm] 7.84 (d, J=1.4 Hz, 1H), 7.60-7.57 (m, 1H), 7.53 (d, J=1.1 Hz, 1H), 7.45-7.42 (m, 1H), 6.89 (d, J=7.4 Hz, 1H), 5.74 (m, 1H), 4.65 (dq, J=7.7, 3.8 Hz, 1H), 4.03-3.96 (m, 2H), 3.61 (ddd, J=11.6, 8.3, 3.2 Hz, 2H), 2.54 (d, J=1.0 Hz, 3H), 2.11-2.03 (m, 2H), 1.91 (d, J=7.0 Hz, 3H), 1.82 (dtd, J=12.4, 8.1, 3.6 Hz, 2H).

LCMS (Analytical Method F) Rt=3.64 min, MS (ESIpos): m/z=499.1 (M+H)$^+$.

Example 195

Enantiomer 1; 3-(5-methyl-1,3-thiazol-2-yl)-5-(tetrahydro-2H-pyran-4-yloxy)-N-{1-[5-(trifluoromethyl)-1,3,4-thiadiazol-2-yl]ethyl}benzamide SFC Chiral Purification (Method 3) was performed on 112 mg of Enantiomer 1 (Example 195) and Enantiomer 2 (Example 196) mixture to give 47.8 mg of the title compound.

SFC Chiral Analysis (Method 3): 100% e.e. Rt=2.21 min.

$^1$H NMR (500 MHz, Chloroform-d): δ [ppm] 7.84 (s, 1H), 7.60-7.57 (m, 1H), 7.53 (d, J=1.1 Hz, 1H), 7.45-7.41 (m, 1H), 6.87 (d, J=7.1 Hz, 1H), 5.74 (m, 1H), 4.70-4.61 (m, 1H), 4.03-3.96 (m, 2H), 3.61 (ddd, J=11.6, 8.3, 3.2 Hz, 2H), 2.54 (d, J=1.1 Hz, 3H), 2.12-2.03 (m, 2H), 1.91 (d, J=7.0 Hz, 3H), 1.86-1.77 (m, 2H).

LCMS (Analytical Method D) Rt=4.62 min, MS (ESIpos): m/z=499.1 (M+H)$^+$.

Example 196

Enantiomer 2; 3-(5-methyl-1,3-thiazol-2-yl)-5-(tetrahydro-2H-pyran-4-yloxy)-N-{1-[5-(trifluoromethyl)-1,3,4-thiadiazol-2-yl]ethyl}benzamide SFC Chiral Purification (Method 3) was performed on 112 mg of Enantiomer 1 (Example 195) and Enantiomer 2 (Example 196) mixture to give 49.6 mg of the title compound.

SFC Chiral Analysis (Method 3): 100% e.e. Rt=2.70 min.

$^1$H NMR (500 MHz, Chloroform-d): δ [ppm] 7.85 (s, 1H), 7.59-7.57 (m, 1H), 7.53 (d, J=1.2 Hz, 1H), 7.45-7.42 (m, 1H), 6.89 (d, J=7.0 Hz, 1H), 5.74 (m, 1H), 4.71-4.62 (m, 1H), 4.04-3.94 (m, 2H), 3.61 (ddd, J=11.7, 8.4, 3.2 Hz, 2H), 2.54 (d, J=1.1 Hz, 3H), 2.11-2.03 (m, 2H), 1.91 (d, J=7.0 Hz, 3H), 1.87-1.78 (m, 2H).

LCMS (Analytical Method D) Rt=4.62 min, MS (ESIpos): m/z=499.2 (M+H)$^+$.

Example 197

(Diastereoisomer 1) and Example 198 (Diastereoisomer 2): 3-(5-methyl-1,3-thiazol-2-yl)-5-[(3R)-tetrahydrofuran-3-yloxy]-N-{1-[5-(trifluoromethyl)-1,3,4-thiadiazol-2-yl]ethyl}benzamide, formed as a mixture of 2 diastereoisomers

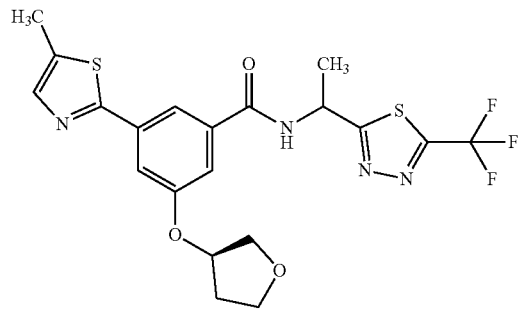 [SMILES: Cc1cnc(-c2cc(O[C@@H]3CCOC3)cc(C(=O)NC(C)c3nnc(C(F)(F)F)s3)c2)s1]

Intermediate 5B (92 mg, 0.3 mmol), 1-[5-(trifluoromethyl)-1,3,4-thiadiazol-2-yl]ethanamine (84 mg, 0.36 mmol) and DIPEA (0.261 mL, 1.5 mmol) were dissolved in DCM (3 mL). T3P (0.35 mL, 0.6 mmol, 50% in EtOAc) was added and the reaction mixture stirred at RT for 2 h. The reaction mixture washed with saturated NaHCO$_3$ (3 mL) and the aqueous layer further extracted with DCM (2×2 mL). The combined organics were dried over MgSO$_4$, filtered and concentrated under reduced pressure. The crude material was purified by Biotage Isolera™ chromatography (eluting with 10-70% EtOAc in heptane on a 10 g pre-packed KP—SiO$_2$ column) to give 86.1 mg (59% yield) of the title compound as white powder.

$^1$H NMR (500 MHz, CDCl3): δ [ppm] 7.86 (s, 1H), 7.54 (dd, J=2.3, 1.5 Hz, 1H), 7.52 (d, J=1.1 Hz, 1H), 7.39 (q, J=2.2 Hz, 1H), 6.91 (d, J=7.3 Hz, 1H), 5.74 (m, 1H), 5.13-5.03 (m, 1H), 4.07-3.97 (m, 3H), 3.92 (td, J=8.4, 4.2 Hz, 1H), 2.54 (d, J=1.0 Hz, 3H), 2.34-2.23 (m, 1H), 2.23-2.14 (m, 1H), 1.91 (d, J=7.0 Hz, 3H).

LCMS (Analytical Method F) Rt=3.49 min, MS (ESIpos): m/z=485 (M+H)$^+$.

Example 197

Diastereoisomer 1; 3-(5-methyl-1,3-thiazol-2-yl)-5-[(3R)-tetrahydrofuran-3-yloxy]-N-{1-[5-(trifluoromethyl)-1,3,4-thiadiazol-2-yl]ethyl}benzamide SFC Chiral Purification (Method 3) was performed on 86 mg of Diastereoisomer 1 (Example 197) and Diastereoisomer 2 (Example 198) mixture to give 34.6 mg of the title compound.
SFC Chiral Analysis (Method 3): 100% e.e. Rt=2.39 min.
$^1$H NMR (500 MHz, Chloroform-d): δ [ppm] 7.87 (s, 1H), 7.60-7.50 (m, 2H), 7.40 (s, 1H), 6.88 (d, J=6.6 Hz, 1H), 5.78-5.70 (m, 1H), 5.10-5.06 (m, 1H), 4.06-3.98 (m, 3H), 3.93 (td, J=8.4, 4.3 Hz, 1H), 2.54 (s, 3H), 2.29 (td, J=14.4, 8.4 Hz, 1H), 2.21-2.14 (m, 1H), 1.91 (d, J=7.0 Hz, 3H).
LCMS (Analytical Method D) Rt=4.49 min, MS (ESI-pos): m/z=485 (M+H)$^+$.

Example 198

Diastereoisomer 2; 3-(5-methyl-1,3-thiazol-2-yl)-5-[(3R)-tetrahydrofuran-3-yloxy]-N-{1-[5-(trifluoromethyl)-1,3,4-thiadiazol-2-yl]ethyl}benzamide SFC Chiral Purification (Method 3) was performed on 86 mg of Diastereoisomer 1 (Example 197) and Diastereoisomer 2 (Example 198) mixture to give 36.9 mg of the title compound.
SFC Chiral Analysis (Method 3): 99.8% e.e. Rt=2.75 min.
$^1$H NMR (500 MHz, Chloroform-d): δ [ppm] 7.87 (s, 1H), 7.58-7.51 (m, 2H), 7.40 (s, 1H), 6.88 (d, J=6.6 Hz, 1H), 5.81-5.69 (m, 1H), 5.08 (d, J=1.9 Hz, 1H), 4.07-3.99 (m, 2H), 3.93 (td, J=8.3, 4.2 Hz, 1H), 2.54 (s, 3H), 2.37-2.23 (m, 1H), 2.23-2.09 (m, 1H), 1.91 (d, J=7.0 Hz, 3H).
LCMS (Analytical Method D) Rt=4.49 min, MS (ESI-pos): m/z=485 (M+H)$^+$.

Example 199

(Diastereoisomer 1) and Example 200 (Diastereoisomer 2): 3-(5-methyl-1,3-thiazol-2-yl)-5-[(3S)-tetrahydrofuran-3-yloxy]-N-{1-[5-(trifluoromethyl)-1,3,4-thiadiazol-2-yl]ethyl}benzamide, formed as a mixture of 2 Diastereoisomers

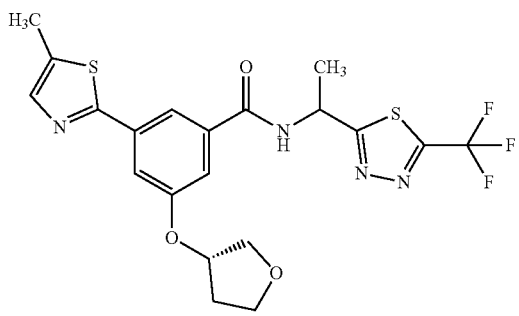 [SMILES: Cc1cnc(-c2cc(O[C@H]3CCOC3)cc(C(=O)NC(C)c3nnc(C(F)(F)F)s3)c2)s1]

Intermediate 5C (61 mg, 0.2 mmol), 1-[5-(trifluoromethyl)-1,3,4-thiadiazol-2-yl]ethanamine (56 mg, 0.24 mmol) and DIPEA (0.174 mL, 1 mmol) were dissolved in DCM (3 mL). T3P (0.234 mL, 0.4 mmol, 50% in EtOAc) was added and the reaction mixture stirred at RT for 2 h. The reaction mixture washed with saturated NaHCO$_3$ (3 mL) and the aqueous layer further extracted with DCM (2×2 mL). The combined organics were dried over MgSO$_4$, filtered and concentrated under reduced pressure. The crude material was purified by Biotage Isolera™ chromatography (eluting with 20-80% EtOAc in heptane on a 10 g pre-packed KP—SiO$_2$ column) to give 41.1 mg (42% yield) of the title compound as an off-white solid.
$^1$H NMR (500 MHz, CDCl3): δ [ppm] 8.00 (s, 1H), 7.56 (s, 1H), 7.53 (s, 1H), 7.43 (s, 1H), 7.05 (s, 1H), 5.75 (m, 1H), 5.08 (d, J=1.9 Hz, 1H), 4.09-3.97 (m, 3H), 3.93 (td, J=8.4, 4.3 Hz, 1H), 2.55 (d, J=0.9 Hz, 3H), 2.30 (td, J=14.3, 8.3 Hz, 1H), 2.24-2.13 (m, 1H), 1.92 (d, J=7.0 Hz, 3H).
LCMS (Analytical Method D) Rt=4.43 min, MS (ESI-pos): m/z=485.95 (M+H)$^+$.

Example 199

Diastereoisomer 1; 3-(5-methyl-1,3-thiazol-2-yl)-5-[(3S)-tetrahydrofuran-3-yloxy]-N-{1-[5-(trifluoromethyl)-1,3,4-thiadiazol-2-yl]ethyl}benzamide SFC Chiral Purification (Method 3) was performed on 41 mg of Diastereoisomer 1 (Example 199) and Diastereoisomer 2 (Example 200) mixture to give 13.1 mg of the title compound.
SFC Chiral Analysis (Method 3): 100% e.e. Rt=1.74 min.
$^1$H NMR (500 MHz, Chloroform-d): δ [ppm] 7.86 (s, 1H), 7.56-7.53 (m, 1H), 7.53-7.52 (m, 1H), 7.41-7.38 (m, 1H), 6.90 (d, J=7.2 Hz, 1H), 5.74 (m, 1H), 5.10-5.05 (m, 1H), 4.07-3.98 (m, 3H), 3.93 (td, J=8.4, 4.3 Hz, 1H), 2.54 (s, 3H), 2.33-2.25 (m, 1H), 2.21-2.14 (m, 1H), 1.91 (d, J=7.0 Hz, 3H).
LCMS (Analytical Method D) Rt=4.45 min, MS (ESI-pos): m/z=485.05 (M+H)$^+$.

Example 200

Diastereoisomer 2; 3-(5-methyl-1,3-thiazol-2-yl)-5-[(3S)-tetrahydrofuran-3-yloxy]-N-{1-[5-(trifluoromethyl)-1,3,4-thiadiazol-2-yl]ethyl}benzamide SFC Chiral Purification (Method 3) was performed on 41 mg of Diastereoisomer 1 (Example 199) and Diastereoisomer 2 (Example 200) mixture to give 16.1 mg of the title compound.
SFC Chiral Analysis (Method 3): 100% e.e. Rt=2.81 min.
$^1$H NMR (500 MHz, Chloroform-d): δ [ppm] 7.86 (s, 1H), 7.54 (s, 1H), 7.53 (s, 1H), 7.42-7.38 (m, 1H), 6.89 (d, J=7.1 Hz, 1H), 5.74 (m, 1H), 5.11-5.03 (m, 1H), 4.06-3.99 (m, 3H), 3.93 (td, J=8.4, 4.3 Hz, 1H), 2.54 (s, 3H), 2.35-2.24 (m, 1H), 2.22-2.14 (m, 1H), 1.91 (d, J=7.0 Hz, 3H).
LCMS (Analytical Method D) Rt=4.45 min, MS (ESI-pos): m/z=485.0 (M+H)$^+$.

Example 201

3-(5-methyl-1,3-thiazol-2-yl)-5-(piperidin-4-yloxy)-N-{(1R)-1-[6-(trifluoromethyl)pyridazin-3-yl]ethyl}benzamide

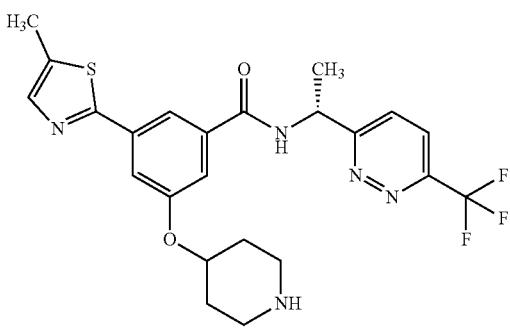 [SMILES: Cc1cnc(-c2cc(OC3CCNCC3)cc(C(=O)N[C@H](C)c3ccc(C(F)(F)F)nn3)c2)s1]

To a solution of Intermediate 41 (178 mg, 0.30 mmol) in DCM (5 mL) was added TFA (0.23 mL, 3.0 mmol) and the resulting mixture stirred at RT for 16 h. The reaction was quenched with 1M NaOH (5 mL), and the layers separated. The aqueous layer was extracted with DCM (2×5 mL), and the combined organics were dried over MgSO$_4$, filtered and concentrated under reduced pressure. The crude material was purified by Biotage Isolera™ chromatography (silica gel, eluting with heptanes-EtOAc, 1:4 to 0:1 followed by EtOAc-MeOH, 1:0 to 4:1). The product containing fractions were concentrated and the residue freeze-dried from MeCN/water to give 101.3 mg (69% yield) of the title compound as white powder.

$^1$H NMR (500 MHz, Chloroform-d): δ [ppm] 7.86 (t, J=1.4 Hz, 1H), 7.82 (d, J=8.7 Hz, 1H), 7.74 (d, J=8.7 Hz, 1H), 7.58 (dd, J=2.3, 1.5 Hz, 1H), 7.52 (d, J=1.2 Hz, 1H), 7.46 (d, J=7.4 Hz, 1H), 7.43-7.40 (m, 1H), 5.60 (m, 1H), 4.53 (tt, J=8.0, 3.8 Hz, 1H), 3.19-3.10 (m, 2H), 2.80-2.71 (m, 2H), 2.53 (d, J=1.1 Hz, 3H), 2.09-1.99 (m, 2H), 1.76 (d, J=7.0 Hz, 3H), 1.74-1.65 (m, 2H).

LCMS (Analytical Method F) Rt=2.02 min, MS (ESIpos): m/z=492.2 (M+H)$^+$.

In analogy to the procedure described for Example 201, the following examples were prepared using TFA and the appropriate N-Boc-protected amine starting materials.

| Ex. | Structure | Name | Analytical Data |
|---|---|---|---|
| 202 | 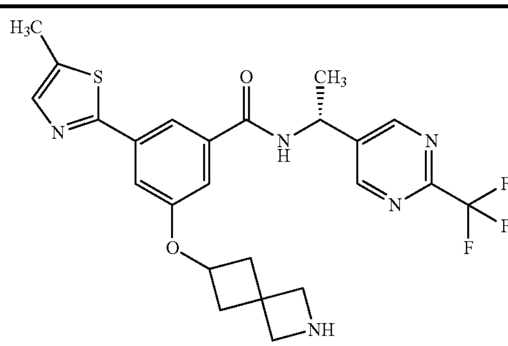 | 3-(2-azaspiro[3.3]hept-6-yloxy)-5-(5-methyl-1,3-thiazol-2-yl)-N-{(1R)-1-[2-(trifluoromethyl)pyrimidin-5-yl]ethyl}benzamide | $^1$H NMR (500 MHz, DMSO-d6): δ [ppm] 9.22 (d, J = 7.1 Hz, 1H), 9.11 (s, 2H), 7.93 (s, 1H), 7.66-7.62 (m, 1H), 7.41 (d, J = 10.2 Hz, 2H), 5.29 (p, J = 7.0 Hz, 1H), 4.78 (m, 1H), 4.03 (s, 2H), 3.93 (s, 2H), 3.17 (s, 3H), 2.81 (dd, J = 12.4, 6.8 Hz, 2H), 2.30 (dd, J = 13.2, 6.6 Hz, 2H), 1.61 (d, J = 7.1 Hz, 3H). LCMS (Analytical Method D) Rt = 3.20 min, MS (ESIpos): m/z = 504 (M + H)$^+$. |
| 203 | 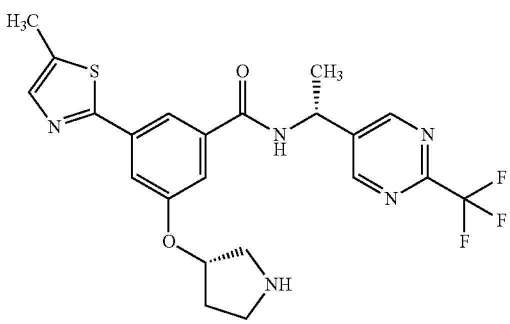 [SMILES: Cc1cnc(-c2cc(O[C@H]3CCNC3)cc(C(=O)N[C@H](C)c3cnc(C(F)(F)F)nc3)c2)s1] | 3-(5-methyl-1,3-thiazol-2-yl)-5-[(3S)-pyrrolidin-3-yloxy]-N-{(1R)-1-[2-(trifluoromethyl)pyrimidin-5-yl]ethyl}benzamide | $^1$H NMR (500 MHz, Chloroform-d): δ [ppm] 8.96 (s, 2H), 7.86 (s, 1H), 7.54-7.52 (m, 1H), 7.52-7.51 (m, 1H), 7.45-7.42 (m, 1H), 6.89 (d, J = 6.4 Hz, 1H), 5.37 (m, 1H), 5.06-4.94 (m, 1H), 3.30-3.20 (m, 2H), 3.18-2.99 (m, 2H), 2.61-2.50 (m, 3H), 2.23-2.12 (m, 1H), 2.10-2.02 (m, 1H), 1.72 (d, J = 7.1 Hz, 3H). LCMS (Analytical Method F) Rt = 2.03 min, MS (ESIpos): m/z = 478.1 (M + H)$^+$. |
| 204 | 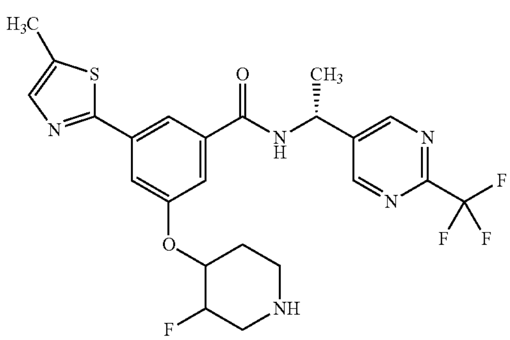 [SMILES: Cc1cnc(-c2cc(OC3CCNCC3F)cc(C(=O)N[C@H](C)c3cnc(C(F)(F)F)nc3)c2)s1] | 3-{[3-fluoropiperidin-4-yl]oxy}-5-(5-methyl-1,3-thiazol-2-yl)-N-{(1R)-1-[2-(trifluoromethyl)pyrimidin-5-yl]ethyl}benzamide, as a mixture of cis isomers | $^1$H NMR (500 MHz, Chloroform-d): δ [ppm] 8.94 (s, 2H), 7.86 (d, J = 1.5 Hz, 1H), 7.61-7.57 (m, 1H), 7.53 (d, J = 1.2 Hz, 1H), 7.45 (s, 1H), 6.64 (d, J = 5.8 Hz, 1H), 5.35 (q, J = 7.1 Hz, 1H), 4.66-4.49 (m, 2H), 3.44-3.33 (m, 1H), 3.05 (d, J = 13.2 Hz, 1H), 2.88 (dd, J = 13.0, 7.4 Hz, 1H), 2.74 (dd, J = 12.6, 9.3 Hz, 1H), 2.54 (d, J = 1.0 Hz, 3H), 2.17 (d, J = 10.7 Hz, 1H), 1.71 (t, J = 7.3 Hz, 4H). LCMS (Analytical Method D) Rt = 3.28 min, MS (ESIpos): m/z = 510 (M + H)$^+$. |

Example 205 (Diastereoisomer 1) and Example 206 (Diastereoisomer 2)

3-(5-methyl-1,3-thiazol-2-yl)-5-(piperidin-3-yloxy)-N-{(1R)-1-[2-(trifluoromethyl)pyrimidin-5-yl]ethyl}benzamide, formed as a mixture of 2 diastereoisomers

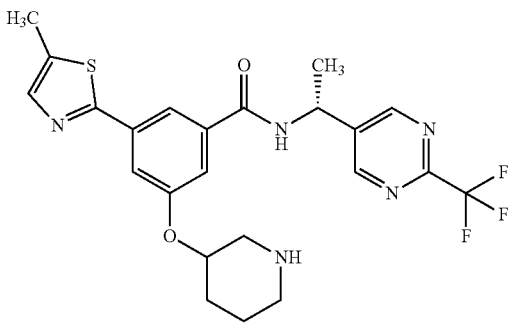 [SMILES: Cc1cnc(-c2cc(OC3CCCNC3)cc(C(=O)N[C@H](C)c3cnc(C(F)(F)F)nc3)c2)s1]

To a solution of Example 190 (189 mg, 0.32 mmol) in DCM (1 mL) was added TFA (0.25 mL, 3.19 mmol) and the resulting mixture stirred at RT for 16 h. The mixture was concentrated at reduced pressure and the residue taken up in water (1 mL) and basified to pH 12 with 10 M NaOH solution to give a white precipitate. The precipitate was dissolved and extracted with EtOAc (2×5 mL). The combined organics were dried over MgSO$_4$, filtered and concentrated at reduced pressure to give 160 mg (quantitative yield) of the title compound as white powder.

$^1$H NMR (500 MHz, DMSO-d6): δ [ppm] 9.17 (d, J=7.1 Hz, 1H), 9.11 (s, 2H), 7.91 (s, 1H), 7.64 (d, J=1.2 Hz, 1H), 7.59-7.55 (m, 1H), 7.54-7.50 (m, 1H), 5.29 (m, 1H), 4.48 (dt, J=7.5, 3.9 Hz, 1H), 3.15 (d, J=12.2 Hz, 1H), 2.82 (dt, J=11.8, 4.4 Hz, 1H), 2.62 (dt, J=30.0, 8.9 Hz, 2H), 2.02 (s, 1H), 1.77-1.67 (m, 1H), 1.61 (d, J=7.1 Hz, 3H), 1.49 (ddt, J=13.1, 9.3, 5.1 Hz, 1H).

Example 205

Diastereoisomer 1; 3-(5-methyl-1,3-thiazol-2-yl)-5-(piperidin-3-yloxy)-N-{(1R)-1-[2-(trifluoromethyl)pyrimidin-5-yl]ethyl}benzamide HPLC Chiral Purification (Method 4) was performed on 60 mg of Diastereoisomer 1 (Example 205) and Diastereoisomer 2 (Example 206) mixture to give 24.6 mg of the title compound.

HPLC Chiral Analysis (Method 4): 100% e.e. Rt=10.2 min.

$^1$H NMR (500 MHz, DMSO): δ [ppm] 9.18 (d, 1H), 9.12 (s, 2H), 7.91 (t, 1H), 7.64 (d, 1H), 7.58-7.55 (m, 1H), 7.55-7.51 (m, 1H), 5.30 (m, 1H), 4.48 (tt, 1H), 3.18-3.11 (m, 1H), 2.85-2.77 (m, 1H), 2.67-2.54 (m, 2H), 2.06-1.99 (m, 1H), 1.75-1.69 (m, 1H), 1.64-1.44 (m, 5H).

LCMS (Analytical Method F) Rt=2.08 min, MS (ESIpos): m/z=492 (MH)$^+$.

Example 206

Diastereoisomer 2; 3-(5-methyl-1,3-thiazol-2-yl)-5-(piperidin-3-yloxy)-N-{(1R)-1-[2-(trifluoromethyl)pyrimidin-5-yl]ethyl}benzamide HPLC Chiral Purification (Method 4) was performed on 60 mg of Diastereoisomer 1 (Example 205) and Diastereoisomer 2 (Example 206) mixture to give 24.6 mg of the title compound.

HPLC Chiral Analysis (Method 4): 96% e.e. Rt=12.4 min.

$^1$H NMR (500 MHz, DMSO-d6): δ [ppm] 9.17 (d, J=7.1 Hz, 1H), 9.11 (s, 2H), 7.90 (s, 1H), 7.64 (d, J=1.1 Hz, 1H), 7.57-7.54 (m, 2H), 7.54-7.50 (m, 1H), 5.29 (m, 1H), 4.42 (dt, J=8.2, 4.2 Hz, 1H), 3.16-3.07 (m, 1H), 2.85-2.74 (m, 1H), 2.60-2.52 (m, 2H), 2.08-2.00 (m, 1H), 1.74-1.65 (m, 1H), 1.64-1.41 (m, 5H).

LCMS (Analytical Method F) Rt=2.08 min, MS (ESIpos): m/z=492 (MH)$^+$.

Intermediate 67 was formed as a mixture of two cis isomers. SFC Chiral Purification (Method 5) provided Example 207 (Cis Isomer 1) and Example 208 (Cis Isomer 2).

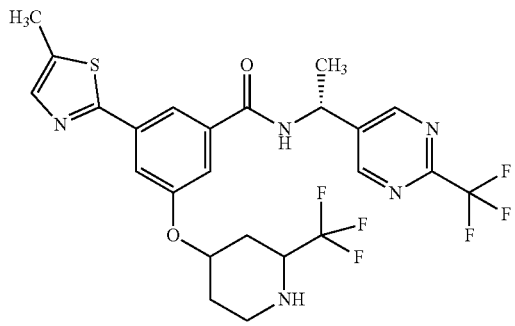 [SMILES: Cc1cnc(-c2cc(OC3CCNC(C(F)(F)F)C3)cc(C(=O)N[C@H](C)c3cnc(C(F)(F)F)nc3)c2)s1]

Example 207

Cis Isomer 1; 3-(5-methyl-1,3-thiazol-2-yl)-5-{[2-(trifluoromethyl)piperidin-4-yl]oxy}-N-{(1R)-1-[2-(trifluoromethyl)pyrimidin-5-yl]ethyl}benzamide SFC Chiral Purification (Method 5) on 46.9 mg of Intermediate 67 gave 15.3 mg of the title compound.

SFC Chiral Analysis (Method 2): 99.6% e.e., Rt=1.66 min.

$^1$H NMR (500 MHz, Chloroform-d): δ [ppm] 8.96 (s, 2H), 7.88 (s, 1H), 7.59-7.53 (m, 2H), 7.45-7.41 (m, 1H), 6.63 (d, J=6.5 Hz, 1H), 5.38 (m, 1H), 4.47 (ddd, J=15.5, 11.0, 4.4 Hz, 1H), 3.36-3.23 (m, 2H), 2.80 (td, J=12.6, 2.4 Hz, 1H), 2.57 (d, J=1.0 Hz, 3H), 2.41-2.33 (m, 1H), 2.27-2.18 (m, 1H), 1.75 (d, J=7.2 Hz, 3H), 1.68-1.60 (m, 3H).

LCMS (Analytical Method D) Rt=3.69 min, MS (ESIpos): m/z=560 (M+H)$^+$.

Example 208

Cis Isomer 2; 3-(5-methyl-1,3-thiazol-2-yl)-5-{[2-(trifluoromethyl)piperidin-4-yl]oxy}-N-{(1R)-1-[2-(trifluoromethyl)pyrimidin-5-yl]ethyl}benzamide Chiral Purification (Method 5) on 46.9 mg of Intermediate 67 gave 14.1 mg of the title compound.

SFC Chiral Analysis (Method 5): 99.6% e.e., Rt=1.87 min.

$^1$H NMR (500 MHz, Chloroform-d): δ [ppm] 8.94 (s, 2H), 7.85 (s, 1H), 7.55-7.51 (m, 2H), 7.44-7.38 (m, 1H), 6.61 (d, J=6.4 Hz, 1H), 5.35 (m, 1H), 4.48-4.38 (m, 1H), 3.32-3.19 (m, 2H), 2.78 (td, J=12.6, 2.3 Hz, 1H), 2.54 (d, J=0.9 Hz, 3H), 2.35-2.29 (m, 1H), 2.23-2.15 (m, 1H), 1.72 (d, J=7.2 Hz, 3H), 1.67-1.59 (m, 3H).

LCMS (Analytical Method D) Rt=3.70 min, MS (ESIpos): m/z=560 (M+H)$^+$.

Example 209

3-{[2-methyl-2-azabicyclo[2.2.1]hept-5-yl]oxy}-5-(5-methyl-1,3-thiazol-2-yl)-N-{(1R)-1-[2-(trifluoromethyl)pyrimidin-5-yl]ethyl}benzamide

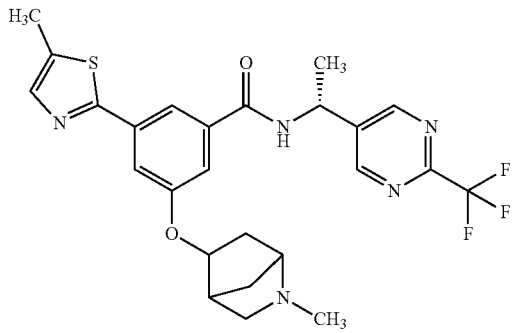 [SMILES: Cc1cnc(-c2cc(OC3CC4CC3CN4C)cc(C(=O)N[C@H](C)c3cnc(C(F)(F)F)nc3)c2)s1]

Intermediate 74 (30 mg, 0.06 mmol), formaldehyde (37% in water) (22.32 µL, 0.3 mmol) and acetic acid (5.12 µL, 0.09 mmol) were combined in MeOH (2 mL) and STAB (37.88 mg, 0.18 mmol) was added. The resulting solution was stirred at RT for 1 hour before concentrating under reduced pressure. The resulting residue was taken up in saturated NaHCO$_3$ (5 mL) and extracted with DCM (3×5 mL). The combined organics were washed with water and dried over MgSO$_4$, filtered and concentrated under reduced pressure. The crude material was purified by preparative HPLC (Method A) and freeze-dried from MeCN/water to give 13.7 mg (44% yield) of the title compound as white powder.

$^1$H NMR (500 MHz, Chloroform-d): δ [ppm] 8.93 (s, 2H), 7.82 (t, J=1.3 Hz, 1H), 7.52 (d, J=1.2 Hz, 1H), 7.49-7.47 (m, 1H), 7.37-7.35 (m, 1H), 6.60 (d, J=6.0 Hz, 1H), 5.36 (m, 1H), 4.38 (d, J=6.1 Hz, 1H), 3.21 (s, 1H), 2.84 (m, 1H), 2.60 (d, J=3.4 Hz, 1H), 2.53 (d, J=1.1 Hz, 3H), 2.43-2.37 (m, 1H), 2.33 (s, 3H), 2.15-2.09 (m, 1H), 1.77 (d, J=10.0 Hz, 1H), 1.71 (d, J=7.2 Hz, 3H), 1.48 (d, J=13.8 Hz, 1H).

LCMS (Analytical Method F) Rt=2.21 min, MS (ESIpos): m/z=518.1 (M+H)$^+$.

In analogy to the procedure described for Example 220/Example 221, the following examples were prepared using STAB and the appropriate amine starting materials.

| Ex. | Structure | Name | Analytical Data |
|---|---|---|---|
| 210 | 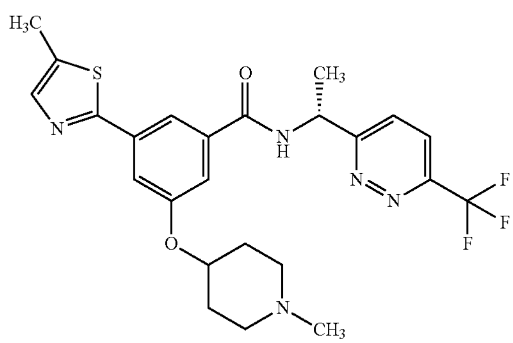 [SMILES: Cc1cnc(-c2cc(OC3CCN(C)CC3)cc(C(=O)N[C@H](C)c3ccc(C(F)(F)F)nn3)c2)s1] | 3-[(1-methylpiperidin-4-yl)oxy]-5-(5-methyl-1,3-thiazol-2-yl)-N-{(1R)-1-[6-(trifluoromethyl)pyridazin-3-yl]ethyl}benzamide | $^1$H NMR (500 MHz, Chloroform-d): δ [ppm] 7.86 (t, J = 1.4 Hz, 1H), 7.82 (d, J = 8.7 Hz, 1H), 7.74 (d, J = 8.7 Hz, 1H), 7.59-7.56 (m, 1H), 7.52 (d, J = 1.2 Hz, 1H), 7.45 (d, J = 7.1 Hz, 1H), 7.42-7.39 (m, 1H), 5.60 (m, 1H), 4.53-4.45 (m, 1H), 2.76-2.63 (m, 2H), 2.53 (d, J = 1.1 Hz, 3H), 2.40-2.27 (m, 5H), 2.10-2.00 (m, 2H), 1.94-1.84 (m, 2H), 1.76 (d, J = 7.0 Hz, 3H). LCMS (Analytical Method F) Rt = 2.06 min, MS (ESIpos): m/z = 506.3 (M + H)$^+$. |
| 211 | 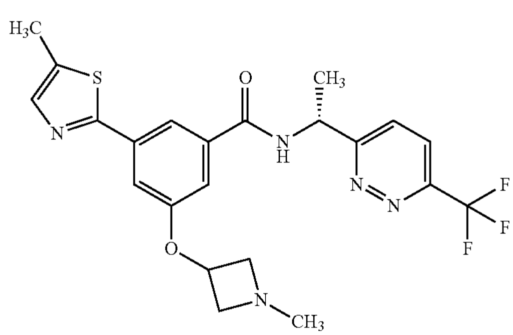 [SMILES: Cc1cnc(-c2cc(OC3CN(C)C3)cc(C(=O)N[C@H](C)c3ccc(C(F)(F)F)nn3)c2)s1] | 3-[(1-methylazetidin-3-yl)oxy]-5-(5-methyl-1,3-thiazol-2-yl)-N-{(1R)-1-[6-(trifluoromethyl)pyridazin-3-yl]ethyl}benzamide | $^1$H NMR (250 MHz, Chloroform-d): δ [ppm] 7.88 (s, 3H), 7.82 (d, J = 8.7 Hz, 1H), 7.74 (d, J = 8.7 Hz, 1H), 7.62-7.36 (m, 3H), 7.27 (d, J = 1.6 Hz, 1H), 5.59 (m, 1H), 4.84 (p, J = 5.6 Hz, 1H), 3.84 (td, J = 6.0, 2.4 Hz, 2H), 3.14 (dt, J = 7.2, 3.3 Hz, 2H), 2.51 (d, J = 1.0 Hz, 3H), 2.40 (s, 3H), 1.74 (d, J = 7.0 Hz, 3H). LCMS (Analytical Method F) Rt = 1.90 min, MS (ESIpos): m/z = 478 (M + H)$^+$. |

| Ex. | Structure | Name | Analytical Data |
|---|---|---|---|
| 212 | 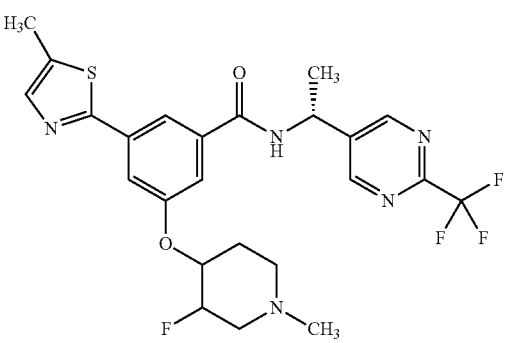 [SMILES: Cc1cnc(-c2cc(OC3CCN(C)CC3F)cc(C(=O)N[C@H](C)c3cnc(C(F)(F)F)nc3)c2)s1] | 3-[(3-fluoro-1-methylpiperidin-4-yl)oxy]-5-(5-methyl-1,3-thiazol-2-yl)-N-{(1R)-1-[2-(trifluoromethyl)pyrimidin-5-yl]ethyl}benzamide, as a single unknown isomer | $^1$H NMR (500 MHz, Chloroform-d): δ [ppm] 8.94 (s, 2H), 7.88-7.83 (m, 1H), 7.58 (dt, J = 2.6, 1.4 Hz, 1H), 7.52 (d, J = 1.2 Hz, 1H), 7.46-7.42 (m, 1H), 6.63 (d, J = 6.3 Hz, 1H), 5.35 (m, 1H), 4.71 (dtd, J = 49.1, 8.0, 4.4 Hz, 1H), 4.44 (tt, J = 11.3, 5.8 Hz, 1H), 3.04 (t, J = 12.4 Hz, 1H), 2.70 (d, J = 11.5 Hz, 1H), 2.54 (d, J = 1.1 Hz, 3H), 2.35 (s, 4H), 2.28-2.15 (m, 2H), 1.80 (tdd, J = 13.6, 10.0, 3.8 Hz, 1H), 1.72 (d, J = 7.1 Hz, 3H).<br>LCMS (Analytical Method F) Rt = 2.12 min, MS (ESIpos): m/z = 524.2 (M + H)$^+$. |
| 213 | 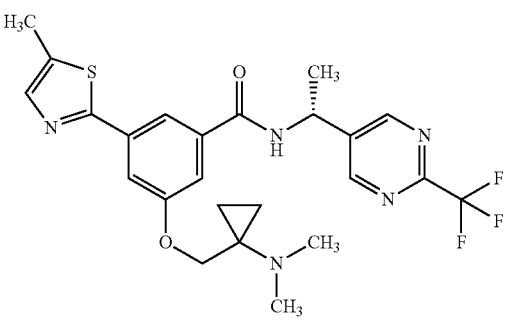 [SMILES: Cc1cnc(-c2cc(OCC3(N(C)C)CC3)cc(C(=O)N[C@H](C)c3cnc(C(F)(F)F)nc3)c2)s1] | 3-{[1-(dimethylamino)cyclopropyl]methoxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.82 (s, 1H), 7.56-7.50 (m, 2H), 7.39-7.34 (m, 1H), 6.63 (d, J = 6.2 Hz, 1H), 5.37 (m, 1H), 4.07 (s, 2H), 2.57-2.52 (m, 3H), 2.51 (s, 6H), 1.72 (d, J = 7.1 Hz, 3H), 0.81 (s, 2H), 0.75-0.68 (m, 2H).<br>LCMS (Analytical Method D) Rt = 3.46 min, MS (ESIpos): m/z = 506.0 (M + H)$^+$. |
| 214 | 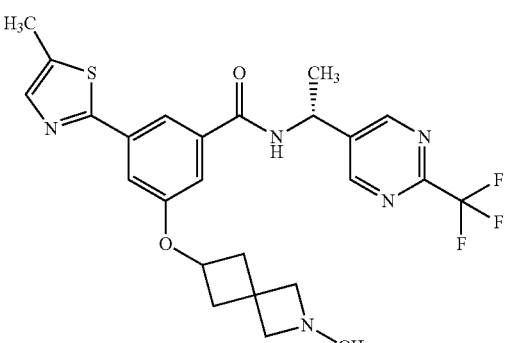 | 3-[(2-methyl-2-azaspiro[3.3]hept-6-yl)oxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.89 (s, 2H), 7.81 (t, 1H), 7.45 (d, 1H), 7.34 (dd, 1H), 7.25-7.20 (m, 1H), 7.08 (d, 1H), 5.31 (m, 1H), 4.60 (p, 1H), 3.25-3.20 (m, 2H), 3.20-3.15 (m, 2H), 2.72-2.62 (m, 2H), 2.48 (d, 3H), 2.27-2.20 (m, 5H), 1.64 (d, 3H).<br>LCMS (Analytical Method D) Rt = 3.21 min, MS (ESIpos): m/z = 518 (M + H)$^+$. |
| 215 | 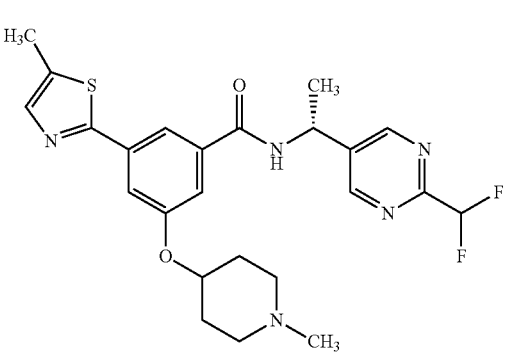 [SMILES: Cc1cnc(-c2cc(OC3CCN(C)CC3)cc(C(=O)N[C@H](C)c3cnc(C(F)F)nc3)c2)s1] | N-{(1R)-1-[2-(difluoromethyl)pyrimidin-5-yl]ethyl}-3[(1-methylpiperidin-4-yl)oxy]-5-(5-methyl-1,3-thiazol-2-yl)benzamide | $^1$H NMR (500 MHz, Chloroform-d): δ [ppm] 8.89 (s, 2H), 7.80 (s, 1H), 7.53-7.48 (m, 2H), 7.40-7.36 (m, 1H), 6.78-6.52 (m, 2H), 5.34 (m, 1H), 4.47-4.42 (m, 1H), 2.73-2.64 (m, 2H), 2.52 (d, J = 1.0 Hz, 3H), 2.35-2.25 (m, 5H), 2.06-1.98 (m, 2H), 1.90-1.79 (m, 2H), 1.69 (d, J = 7.1 Hz, 3H).<br>LCMS (Analytical Method F) Rt = 1.85 min, MS (ESIpos): m/z = 488.2 (M + H)$^+$. |

-continued

| Ex. | Structure | Name | Analytical Data |
|---|---|---|---|
| 216 | 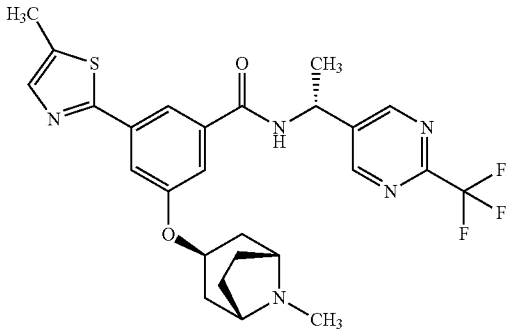 [SMILES: Cc1cnc(-c2cc(O[C@H]3C[C@H]4CC[C@@H](C3)N4C)cc(C(=O)N[C@H](C)c3cnc(C(F)(F)F)nc3)c2)s1] | 3-{[(3-endo)-8-methyl-8-azabicyclo[3.2.1]oct-3-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.78 (t, J = 1.3 Hz, 1H), 7.52 (d, J = 1.2 Hz, 1H), 7.43 (dd, J = 2.2, 1.5 Hz, 1H), 7.34-7.29 (m, 1H), 6.73 (d, J = 6.5 Hz, 1H), 5.36 (m, 1H), 4.64 (t, J = 4.9 Hz, 1H), 3.17 (s, 2H), 2.53 (d, J = 1.1 Hz, 3H), 2.32 (s, 3H), 2.25-2.18 (m, 2H), 2.10-2.01 (m, 4H), 1.95 (d, J = 14.6 Hz, 2H), 1.72 (d, J = 7.2 Hz, 3H). LCMS (Analytical Method D) Rt = 3.43 min, MS (ESIpos) m/z = 532.1 (M + H)$^+$. |
| 217 | 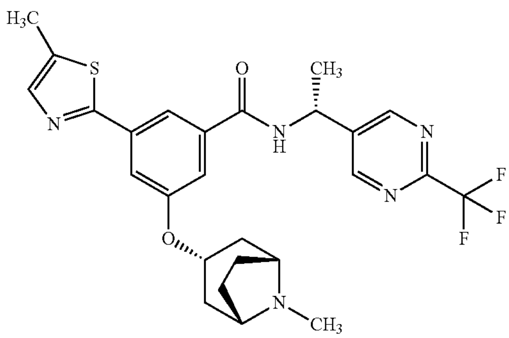 [SMILES: Cc1cnc(-c2cc(O[C@@H]3C[C@H]4CC[C@@H](C3)N4C)cc(C(=O)N[C@H](C)c3cnc(C(F)(F)F)nc3)c2)s1] | 3-{[(3-exo)-8-methyl-8-azabicyclo[3.2.1]oct-3-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.92 (s, 2H), 7.81 (t, J = 1.3 Hz, 1H), 7.50 (d, J = 1.2 Hz, 1H), 7.47 (dd, J = 2.3, 1.5 Hz, 1H), 7.39-7.34 (m, 1H), 6.75 (d, J = 6.5 Hz, 1H), 5.34 (m, 1H), 4.60 (ddd, J = 16.6, 10.6, 6.1 Hz, 1H), 3.28-3.24 (m, 2H), 2.52 (d, J = 1.1 Hz, 3H), 2.36 (s, 3H), 2.11-2.04 (m, 2H), 2.02-1.96 (m, 2H), 1.84 (t, J = 11.9 Hz, 2H), 1.70 (d, J = 7.2 Hz, 3H), 1.68-1.63 (m, 2H). LCMS (Analytical Method D) Rt = 3.36 min, MS (ESIpos) m/z = 532.1 (M + H)$^+$. |
| 218 | 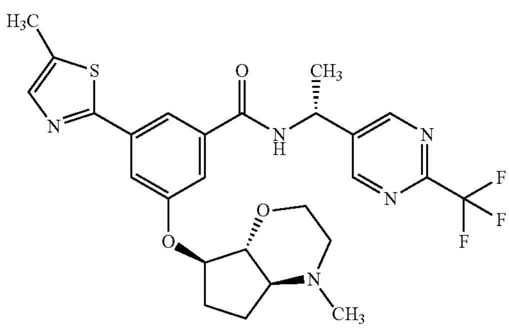 [SMILES: Cc1cnc(-c2cc(O[C@@H]3CC[C@H]4[C@H]3OCCN4C)cc(C(=O)N[C@H](C)c3cnc(C(F)(F)F)nc3)c2)s1] | 3-{[(4aS,7R,7aR)-4-methyloctahydrocyclopenta[b][1,4]oxazin-7-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.93 (s, 2H), 7.90-7.78 (m, 1H), 7.56 (s, 1H), 7.52-7.49 (m, 1H), 7.40 (s, 1H), 6.70 (s, 1H), 5.34 (m, 1H), 4.80-4.56 (m, 1H), 3.98 (d, J = 11.7 Hz, 1H), 3.90-3.76 (m, 1H), 3.73-3.57 (m, 1H), 2.84-2.67 (m, 1H), 2.52 (s, 3H), 2.42-2.35 (m, 1H), 2.31 (s, 3H), 2.24 (s, 1H), 1.97 (s, 2H), 1.82-1.73 (m, 1H), 1.70 (d, J = 7.1 Hz, 3H), 1.70-1.55 (m, 1H). LCMS (Analytical Method F) Rt = 2.19 min, MS (ESIpos): m/z = 548.2 (M + H)$^+$. |
| 219 | 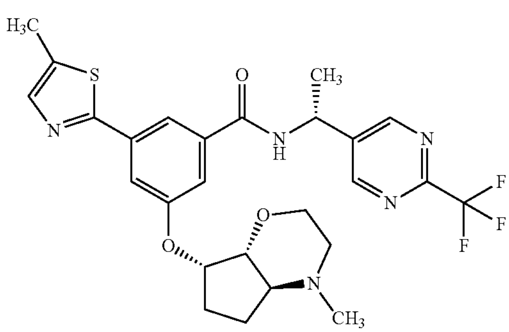 [SMILES: Cc1cnc(-c2cc(O[C@H]3CC[C@H]4[C@H]3OCCN4C)cc(C(=O)N[C@H](C)c3cnc(C(F)(F)F)nc3)c2)s1] | 3-{[(4aS,7S,7aR)-4-methyloctahydrocyclopenta[b][1,4]oxazin-7-yl]oxy}-5-(5-methyl-1,3-thiazol-2-yl)-N-{(1R)-1-[2-(trifluoromethyl)pyrimidin-5-yl]ethyl}benzamide | $^1$H NMR (500 MHz, DMSO-d6): δ [ppm] 9.16 (d, J = 7.1 Hz, 1H), 9.11 (s, 2H), 7.88 (s, 1H), 7.66-7.63 (m, 1H), 7.53 (s, 1H), 7.52-7.49 (m, 1H), 5.29 (m, 1H), 4.92 (s, 1H), 3.93-3.74 (m, 1H), 3.67-3.54 (m, 1H), 3.28 (m, 1H), 2.71-2.58 (m, 1H), 2.33-1.84 (m, 7H), 1.68 (dt, J = 15.5, 8.6 Hz, 1H), 1.60 (d, J = 7.1 Hz, 3H), 1.41-1.17 (m, 1H), thiazole CH$_3$ peak obscured by solvent. LCMS (Analytical Method F) Rt = 2.18 min, MS (ESIpos): m/z = 548.1 (M + H)$^+$. |

Example 220 (Diastereoisomer 1) and Example 221 (Diastereoisomer 2)

3-[(1-methylpiperidin-3-yl)oxy]-5-(5-methyl-1,3-thiazol-2-yl)-N-{(1R)-1-[2-(trifluoromethyl)pyrimidin-5-yl]ethyl}benzamide, formed as a mixture of 2 diastereoisomers

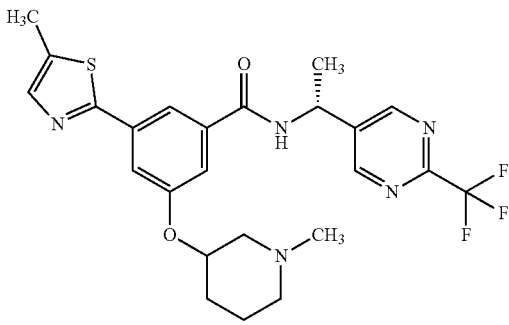

Intermediate 40 (93 mg, 0.189 mmol), 37% formaldehyde solution in water (0.07 mL, 0.946 mmol) and acetic acid (0.02 mL, 0.378 mmol) were combined in methanol (1 mL) and STAB (60 mg, 0.28 mmol) was added portionwise. The resulting solution was stirred at RT for 2 h before concentrating at reduced pressure. The residue was taken up in water (1 mL) and basified to pH 5 with 10 M sodium hydroxide solution and extracted with EtOAc. The organic phase was separated, dried (MgSO$_4$), filtered, evaporated at reduced pressure and freeze dried to give 59 mg (62% yield) of the title compound as white solid.

$^1$H NMR (500 MHz, DMSO-d6): δ [ppm] 9.17 (d, J=7.1 Hz, 1H), 9.11 (s, 2H), 7.91 (s, 1H), 7.64 (d, J=1.2 Hz, 1H), 7.59-7.55 (m, 1H), 7.54-7.50 (m, 1H), 5.29 (m, 1H), 4.48 (dt, J=7.5, 3.9 Hz, 1H), 3.15 (d, J=12.2 Hz, 1H), 2.82 (dt, J=11.8, 4.4 Hz, 1H), 2.62 (dt, J=30.0, 8.9 Hz, 2H), 2.02 (s, 1H), 1.77-1.67 (m, 1H), 1.61 (d, J=7.1 Hz, 3H), 1.49 (ddt, J=13.1, 9.3, 5.1 Hz, 1H).

Example 220

Diastereoisomer 1; 3-[(1-methylpiperidin-3-yl)oxy]-5-(5-methyl-1,3-thiazol-2-yl)-N-{(1R)-1-[2-(trifluoromethyl)pyrimidin-5-yl]ethyl}benzamide SFC Chiral Purification (Method 6) on 56 mg of Diastereoisomer 1 (Example 220) and Diastereoisomer 2 (Example 221) mixture gave 29 mg of the title compound.

SFC Chiral Analysis (Method 6): 99.8% e.e., Rt=2.01 min.

$^1$H NMR (500 MHz, Chloroform-d): δ [ppm] 8.93 (s, 2H), 7.86 (t, J=1.4 Hz, 1H), 7.57 (dd, J=2.3, 1.5 Hz, 1H), 7.50 (d, J=1.2 Hz, 1H), 7.45-7.40 (m, 1H), 6.80 (d, J=6.6 Hz, 1H), 5.35 (m, 1H), 4.54 (dt, J=7.2, 3.7 Hz, 1H), 2.78 (d, J=10.4 Hz, 1H), 2.52 (d, J=1.1 Hz, 4H), 2.39 (s, 1H), 2.29 (s, 4H), 1.95-1.83 (m, 2H), 1.70 (d, J=7.2 Hz, 3H), 1.63 (dd, J=10.6, 5.5 Hz, 2H).

LCMS (Analytical Method D) Rt=3.16 min, MS (ESI-pos): m/z=506 (M+H)$^+$.

Example 221

Diastereoisomer 2; 3-[(1-methylpiperidin-3-yl)oxy]-5-(5-methyl-1,3-thiazol-2-yl)-N-{(1R)-1-[2-(trifluoromethyl)pyrimidin-5-yl]ethyl}benzamide SFC Chiral Purification (Method 6) on 56 mg of Diastereoisomer 1 (Example 220) and Diastereoisomer 2 (Example 221) mixture gave 20.1 mg of the title compound.

SFC Chiral Analysis (Method 6): 95.1% e.e., Rt=2.19 min.

$^1$H NMR (250 MHz, MeOD): δ [ppm] 9.01 (s, 2H), 7.91 (t, 1H), 7.67-7.59 (m, 1H), 7.54 (d, 1H), 7.51-7.45 (m, 1H), 5.34 (q, 1H), 4.64-4.53 (m, 1H), 2.90 (d, 1H), 2.67-2.29 (m, 9H), 2.06-1.82 (m, 2H), 1.75-1.57 (m, 5H).

LCMS (Analytical Method D) Rt=3.15 min, MS (ESI-pos): m/z=506 (M+H)$^+$.

Example 222 (Cis Isomer 1) and Example 223 (Cis Isomer 2): 3-(5-methyl-1,3-thiazol-2-yl)-5-{[1-methyl-2-(trifluoromethyl)piperidin-4-yl]oxy}-N-{(1R)-1-[2-(trifluoromethyl)pyrimidin-5-yl]ethyl}benzamide, formed as a mixture of cis-isomers

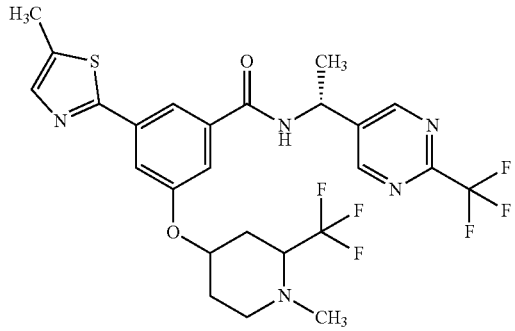 [SMILES: Cc1cnc(-c2cc(OC3CCN(C)C(C(F)(F)F)C3)cc(C(=O)N[C@H](C)c3cnc(C(F)(F)F)nc3)c2)s1]

Intermediate 67 (50 mg, 0.09 mmol), 37% formaldehyde solution in water (33 μL, 0.45 mmol) and acetic acid (5 μL) were combined in methanol (3 mL) and STAB (57 mg, 0.27 mmol) was added and the reaction was stirred for 2 h. LCMS showed incomplete conversion. The reaction mixture was re-treated with 37% formaldehyde solution in water (33 μL, 0.45 mmol) and STAB (57 mg, 0.27 mmol) and stirred for a further 1 h. The reaction required five further re-treatments to drive to completion. The crude reaction mixture was concentrated under reduced pressure, the resulting residue taken up in saturated NaHCO$_3$ (2 mL) solution and extracted with DCM (3×2 mL). The combined organic phase was dried (MgSO$_4$), filtered, concentrated at reduced pressure and freeze-dried from MeCN/water to give 46.6 mg (86% yield) of the title compound as white powder.

$^1$H NMR (500 MHz, Chloroform-d): δ [ppm] 8.93 (s, 2H), 7.85 (d, J=1.3 Hz, 1H), 7.55-7.49 (m, 2H), 7.39 (s, 1H), 6.61 (d, J=4.7 Hz, 1H), 5.35 (m, 1H), 4.39 (dq, J=9.9, 4.8, 4.2 Hz, 1H), 3.03 (dt, J=12.2, 3.5 Hz, 1H), 2.80-2.71 (m, 1H), 2.56-2.50 (m, 3H), 2.45 (s, 3H), 2.41 (d, J=12.6 Hz, 1H), 2.36-2.28 (m, 1H), 2.17-2.08 (m, 1H), 1.88-1.74 (m, 2H), 1.72 (d, J=7.2 Hz, 3H).

LCMS (Analytical Method F) Rt=3.31 min, MS (ESIpos): m/z=574.1 (M+H)$^+$.

Example 222

Cis Isomer 1; 3-(5-methyl-1,3-thiazol-2-yl)-5-{[1-methyl-2-(trifluoromethyl)piperidin-4-yl]oxy}-N-{(1R)-1-[2-(trifluoromethyl)pyrimidin-5-yl]ethyl}benzamide SFC Chiral Purification (Method 7) on 43.9 mg of Cis Isomer 1 (Example 222) and Cis Isomer 2 (Example 223) mixture gave 11.7 mg of the title compound.

SFC Chiral Analysis (Method 7): 98.2% e.e., Rt=1.51 min $^1$H NMR (500 MHz, Chloroform-d): δ [ppm] 8.96 (s, 2H), 7.88 (s, 1H), 7.58-7.52 (m, 2H), 7.46-7.37 (m, 1H), 6.63 (d, J=6.3 Hz, 1H), 5.38 (m, 1H), 4.49-4.35 (m, 1H), 3.09-3.02 (m, 1H), 2.78 (s, 1H), 2.56 (d, J=0.9 Hz, 3H), 2.47 (s, 3H), 2.46-2.40 (m, 1H), 2.35 (d, J=11.0 Hz, 1H), 2.14 (d, J=12.3 Hz, 1H), 1.89-1.76 (m, 2H), 1.75 (d, J=7.2 Hz, 3H).

LCMS (Analytical Method D) Rt=4.26 min, MS (ESIpos): m/z=574 (M+H)$^+$.

Example 223

Cis Isomer 2; 3-(5-methyl-1,3-thiazol-2-yl)-5-{[1-methyl-2-(trifluoromethyl)piperidin-4-yl]oxy}-N-{(1R)-1-[2-(trifluoromethyl)pyrimidin-5-yl]ethyl}benzamide SFC Chiral purification (Method 7) on 43.9 mg of Cis Isomer 1 (Example 222) and Cis Isomer 2 (Example 223) mixture gave 9.5 mg of the title compound.

SFC Chiral Analysis (Method 7): 98.6% e.e., Rt=1.76 min $^1$H NMR (500 MHz, Chloroform-d): δ [ppm] 8.94 (s, 2H), 7.85 (s, 1H), 7.55-7.51 (m, 2H), 7.39 (s, 1H), 6.61 (d, J=6.4 Hz, 1H), 5.35 (m, 1H), 4.40 (dt, J=10.5, 5.9 Hz, 1H), 3.06-3.00 (m, 1H), 2.82-2.68 (m, 1H), 2.54 (s, 3H), 2.45 (s, 3H), 2.41 (d, J=11.7 Hz, 1H), 2.31 (d, J=12.5 Hz, 1H), 2.13 (d, J=13.4 Hz, 1H), 1.80 (p, J=12.4 Hz, 2H), 1.72 (d, J=7.2 Hz, 3H).

LCMS (Analytical Method D) Rt=4.27 min, MS (ESIpos): m/z=574 (M+H)$^+$.

Example 224

3-(5-Methyl-1,3-thiazol-2-yl)-5-{[1-(propan-2-yl)piperidin-4-yl]oxy}-N-{(1R)-1-[6-(trifluoromethyl)pyridazin-3-yl]ethyl}benzamide

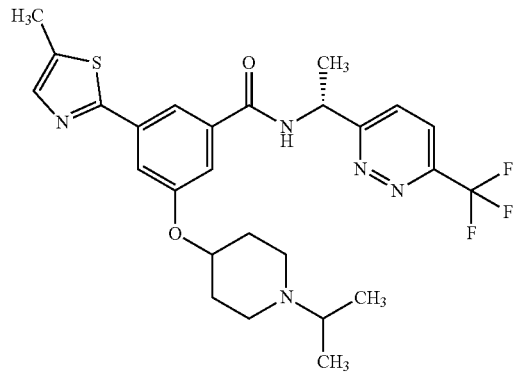 [SMILES: Cc1cnc(-c2cc(OC3CCN(C(C)C)CC3)cc(C(=O)N[C@H](C)c3ccc(C(F)(F)F)nn3)c2)s1]

Example 201 (50 mg, 0.1 mmol) in DCE (1 mL), acetone (1 mL) and acetic acid (50 μL) was stirred at RT for 30 min. STAB (65 mg, 0.3 mmol) was added and the reaction stirred overnight. The reaction mixture was re-treated with acetone (1 mL) and STAB (65 mg, 0.3 mmol) and stirred overnight. The reaction was again re-treated with acetone (3 mL) and STAB (130 mg, 0.6 mmol) and stirred for 4 h. The reaction mixture was concentrated under reduced pressure and the residue taken up in saturated NaHCO$_3$ (5 mL) and extracted with DCM (3×5 mL). The combined organics were dried over MgSO$_4$, filtered and concentrated under reduced pressure. The compound was freeze-dried from acetonitrile/water to give 48.0 mg (88% yield) of the title compound as white powder.

$^1$H NMR (500 MHz, Chloroform-d): δ [ppm] 7.87-7.84 (m, 1H), 7.82 (d, J=8.7, 1H), 7.74 (d, J=8.7, 1H), 7.57 (dd, J=2.3, 1.5, 1H), 7.53-7.51 (m, 1H), 7.44 (d, J=7.2, 1H), 7.41 (dd, J=2.3, 1.6, 1H), 5.64-5.55 (m, 1H), 4.51-4.42 (m, 1H), 2.84-2.72 (m, 3H), 2.53 (d, J=1.1, 3H), 2.50-2.38 (m, 2H), 2.11-1.99 (m, 2H), 1.91-1.80 (m, 2H), 1.76 (d, J=7.0, 3H), 1.07 (d, J=6.5, 6H).

LCMS (Analytical Method D) Rt=3.22 min, MS (ESIpos): m/z=534.2 (M+H)$^+$.

In analogy to the procedure described for Example 224, the following example was prepared using STAB and the appropriate ketone and amine starting materials.

| Ex. | Structure | Name | Analytical Data |
|---|---|---|---|
| 225 | 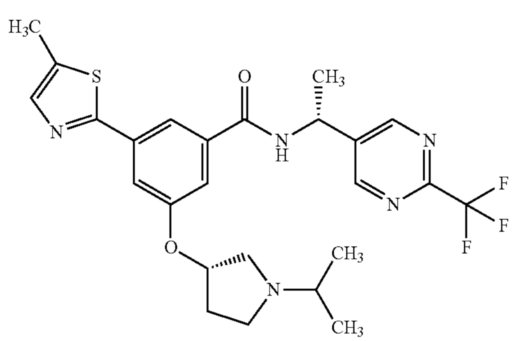 [SMILES: Cc1cnc(-c2cc(O[C@H]3CCN(C(C)C)C3)cc(C(=O)N[C@H](C)c3cnc(C(F)(F)F)nc3)c2)s1] | 3-(5-methyl-1,3-thiazol-2-yl)-5-{[(3S)-1-(propan-2-yl)pyrrolidin-3-yl]oxy}-N-{(1R)-1-[2-(trifluoromethyl)pyrimidin-5-yl]ethyl}benzamide | $^1$H NMR (250 MHz, Chloroform-d): δ [ppm] 8.94 (s, 2H), 7.85 (s, 1H), 7.57-7.46 (m, 2H), 7.40 (s, 1H), 6.77 (s, 1H), 5.36 (m, 1H), 5.03-4.90 (m, 1H), 3.08-2.91 (m, 3H), 2.69-2.56 (m, 1H), 2.56-2.45 (m, 4H), 2.45-2.28 (m, 1H), 2.13-1.98 (m, 1H), 1.71 (d, J = 7.1 Hz, 3H), 1.17 (d, J = 3.6 Hz, 3H), 1.14 (d, J = 3.6 Hz, 3H). LCMS (Analytical Method D) Rt = 3.35 min, MS (ESIpos): m/z = 520 (M + H)$^+$. |

Example 226

Methyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate

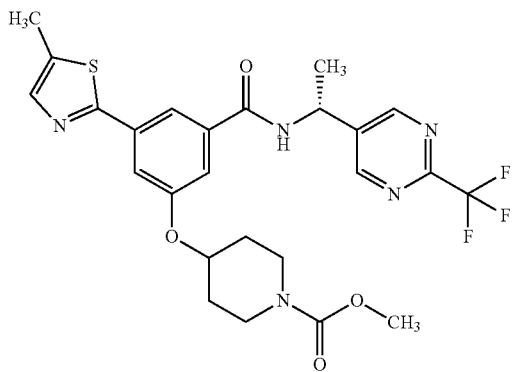 [SMILES: COC(=O)N1CCC(Oc2cc(C(=O)N[C@H](C)c3cnc(C(F)(F)F)nc3)cc(-c3ncc(C)s3)c2)CC1]

To a solution of Example 138 (60 mg, 0.12 mmol) and DIPEA (0.11 mL, 0.61 mmol) in DCM (1 mL) was added methyl carbonochloridate (0.028 mL, 0.37 mmol) and the resulting solution stirred at RT for 3 h. The solution was diluted with DCM (5 mL) and washed with water (2 mL). The organic phase was dried (MgSO$_4$), filtered and concentrated at reduced pressure and the crude material purified by Biotage Isolera™ chromatography (on pre-packed KP—SiO$_2$ column, eluting with heptane-EtOAc). The purified material was freeze-dried from MeCN/water to give 53 mg (79% yield) of the title compound as white powder.

$^1$H NMR (500 MHz, Chloroform-d): δ [ppm] 8.93 (s, 2H), 7.82 (s, 1H), 7.55-7.49 (m, 2H), 7.39 (s, 1H), 6.75 (d, J=6.6 Hz, 1H), 5.36 (m, 1H), 4.62 (tt, J=6.9, 3.4 Hz, 1H), 3.76-3.68 (m, 5H), 3.45-3.38 (m, 2H), 2.53 (s, 3H), 1.99-1.90 (m, 2H), 1.81-1.73 (m, 2H), 1.71 (d, J=7.2 Hz, 3H).

LCMS (Analytical Method D) Rt=4.53, MS (ESIpos) m/z=550 (M+H)$^+$.

Example 227

Ethyl 4-[3-(5-methyl-1,3-thiazol-2-yl)-5-({(1R)-1-[2-(trifluoromethyl)pyrimidin-5-yl]ethyl}carbamoyl)phenoxy]piperidine-1-carboxylate

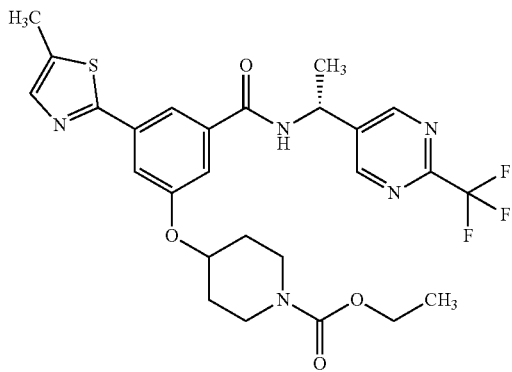 [SMILES: CCOC(=O)N1CCC(Oc2cc(C(=O)N[C@H](C)c3cnc(C(F)(F)F)nc3)cc(-c3ncc(C)s3)c2)CC1]

To a solution of Example 138 (60 mg, 0.12 mmol) and DIPEA (0.11 mL, 0.61 mmol) in DCM (1 mL) was added ethyl carbonochloridate (0.035 mL, 0.37 mmol) and the resulting solution stirred at RT for 3 h. The solution was diluted with DCM (5 mL) and washed with water (2 mL). The organic phase was dried (MgSO$_4$), filtered and concentrated at reduced pressure and the crude material purified by Biotage Isolera™ chromatography (on pre-packed KP—SiO$_2$ column, eluting with heptane-EtOAc). The purified material was freeze-dried from MeCN/water to give 53 mg (79% yield) of the title compound as white powder.

$^1$H NMR (500 MHz, Chloroform-d): δ [ppm] 8.93 (s, 2H), 7.82 (t, J=1.3 Hz, 1H), 7.53 (dd, J=2.3, 1.5 Hz, 1H), 7.52 d, J=1.1 Hz, 1H), 7.42-7.37 (m, 1H), 6.74 (d, J=6.6 Hz, 1H), 5.36 (m, 1H), 4.66-4.58 (m, 1H), 4.14 (q, J=7.1 Hz, 2H), 3.77-3.68 (m, 2H), 3.45-3.36 (m, 2H), 2.53 (d, J=1.0 Hz, 3H), 1.99-1.90 (m, 2H), 1.81-1.73 (m, 2H), 1.71 (d, J=7.2 Hz, 3H), 1.27 (t, J=7.1 Hz, 3H).

LCMS (Analytical Method D) Rt=4.70, MS (ESIpos) m/z=564 (M+H)$^+$.

Example 228

Ethyl (3S)-3-[3-(5-methyl-1,3-thiazol-2-yl)-5-({(1R)-1-[2-(trifluoromethyl)pyrimidin-5-yl]ethyl}carbamoyl)phenoxy]pyrrolidine-1-carboxylate

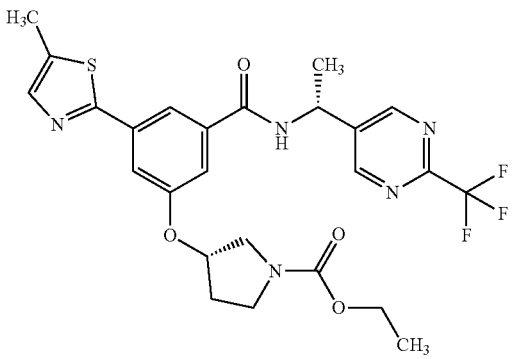 [SMILES: CCOC(=O)N1CC[C@H](Oc2cc(C(=O)N[C@H](C)c3cnc(C(F)(F)F)nc3)cc(-c3ncc(C)s3)c2)C1]

To a solution of Example 203 (40 mg, 0.08 mmol) and DIPEA (73 μL, 0.42 mmol) in DCM (1 mL) was added ethyl carbonochloridate (24 μL, 0.25 mmol) and the resulting solution stirred at RT for 3 h. The solution was diluted with DCM (5 mL) and washed with water (2 mL). The organic phase was dried (MgSO$_4$), filtered and concentrated at reduced pressure and the crude material purified by Biotage Isolera™ chromatography (on pre-packed KP—SiO$_2$ column, eluting with heptane-EtOAc, 3:2 to 0:1). The purified material was freeze-dried from MeCN/water to give 32.5 mg (71% yield) of the title compound as white powder.

$^1$H NMR (250 MHz, Chloroform-d): δ [ppm] 8.95 (s, 2H), 7.91 (s, 1H), 7.54 (s, 1H), 7.52-7.48 (m, 1H), 7.37 (s, 1H), 6.75 (d, J=6.8 Hz, 1H), 5.44-5.25 (m, 1H), 5.03 (m, 1H), 4.23-4.07 (m, 2H), 3.65 (s, 4H), 2.54 (s, 3H), 2.21 (m, 2H), 1.73 (d, J=7.1 Hz, 3H), 1.26 (m, 3H).

LCMS (Analytical Method D) Rt=4.52 min, MS (ESIpos): m/z=550.15 (M+H)$^+$.

Example 229

3-(5-Methyl-1,3-thiazol-2-yl)-5-{[1-(propan-2-yl)azetidin-3-yl]oxy}-N-{(1R)-1-[2-(trifluoromethyl)pyrimidin-5-yl]ethyl}benzamide

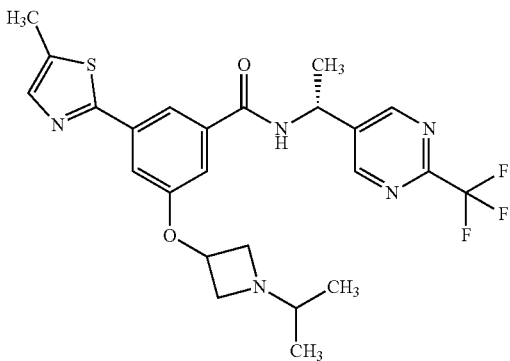 [SMILES: Cc1cnc(-c2cc(OC3CN(C(C)C)C3)cc(C(=O)N[C@H](C)c3cnc(C(F)(F)F)nc3)c2)s1]

A solution of Intermediate 35 (20 mg, 0.043 mmol), 2-bromopropane (6.1 μL, 0.065 mmol) and potassium carbonate (11.9 mg, 0.086 mmol) in acetonitrile (0.5 mL) was heated in the microwave at 60° C. for 10 mins then at 100° C. for 30 mins. The reaction was re-treated with excess 2-bromopropane (~50 μL) and heated at 100° C. for 2 h. The reaction mixture was filtered and concentrated under reduced pressure. The crude material was purified by prep-TLC, eluting with 1% NH3 in 5% MeOH in DCM. The material was then freeze-dried from MeCN/water to give 12.9 mg (59% yield) of the title compound as white powder.

$^1$H NMR (500 MHz, Chloroform-d): δ [ppm] 8.95 (s, 2H), 7.88 (s, 1H), 7.52 (d, J=1.1 Hz, 1H), 7.46-7.40 (m, 1H), 7.31 (s, 1H), 6.81 (s, 1H), 5.37 (m, 1H), 5.02-4.89 (m, 1H), 3.99 (s, 2H), 3.29 (s, 2H), 2.58 (s, 1H), 2.53 (d, J=1.0 Hz, 3H), 1.72 (d, J=7.2 Hz, 3H), 1.05 (d, J=6.2 Hz, 6H).

LCMS (Analytical Method D) Rt=3.34 min, MS (ESIpos): m/z=506.1 (M+H)$^+$.

Intermediate 93 was formed as a mixture of cis-isomers. SFC Chiral Purification (Method 10) provided Example 230 (Cis Isomer 1) and Example 231 (Cis Isomer 2).

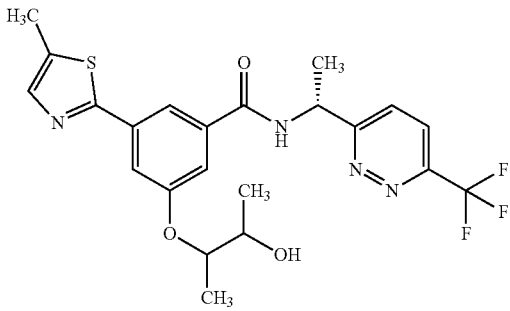 [SMILES: Cc1cnc(-c2cc(OC(C)C(C)O)cc(C(=O)N[C@H](C)c3ccc(C(F)(F)F)nn3)c2)s1]

Example 230

Cis Isomer 1; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide SFC Chiral Purification (Method 10) on 243 mg of Intermediate 93 gave 45.8 mg of the title compound as a white powder.

SFC Chiral Analysis (Method 10): 100% e.e., Rt=1.59 min $^1$H NMR (500 MHz, DMSO-d6): δ [ppm] 9.27 (d, J=7.0, 1H), 8.24 (d, J=8.8, 1H), 8.03 (d, J=8.8, 1H), 7.96-7.89 (m, 1H), 7.64 (d, J=1.2, 1H), 7.59-7.52 (m, 2H), 5.54-5.41 (m, 1H), 4.85 (d, J=4.7, 1H), 4.50-4.36 (m, 1H), 3.84-3.71 (m, 1H), 2.54-2.51 (m, 3H), 1.65 (d, J=7.2, 3H), 1.21 (d, J=6.2, 3H), 1.12 (d, J=6.4, 3H).

LCMS (Analytical Method F) Rt=3.11 min, MS (ESIpos): m/z=481.1 (M+H)$^+$.

Example 231

Cis Isomer 2; 3-[(-3-hydroxybutan-2-yl)oxy]-5-(5-methyl-1,3-thiazol-2-yl)-N-{(1R)-1-[6-(trifluoromethyl)pyridazin-3-yl]ethyl}benzamide SFC Chiral Purification (Method 10) on 243 mg of Intermediate 93 gave 43.8 mg of the title compound as a white powder.

SFC Chiral Analysis (Method 10): 100% e.e., Rt=2.51 min $^1$H NMR (500 MHz, DMSO-d6): δ [ppm] 9.27 (d, J=7.0, 1H), 8.24 (d, J=8.8, 1H), 8.03 (d, J=8.8, 1H), 7.95-7.90 (m, 1H), 7.64 (d, J=1.2, 1H), 7.59-7.52 (m, 2H), 5.52-5.45 (m, 1H), 4.84 (d, J=4.8, 1H), 4.47-4.39 (m, 1H), 3.83-3.75 (m, 1H), 2.54-2.51 (m, 3H), 1.65 (d, J=7.2, 3H), 1.22 (d, J=6.2, 3H), 1.11 (d, J=6.4, 3H).

LCMS (Analytical Method F) Rt=3.10 min, MS (ESIpos): m/z=481.1 (M+H)$^+$.

Example 232

3-[(1,1-dioxidotetrahydro-2H-thiopyran-4-yl)oxy]-5-(5-methyl-1,3-thiazol-2-yl)-N-{(1R)-1-[2-(trifluoromethyl)pyrimidin-5-yl]ethyl}benzamide

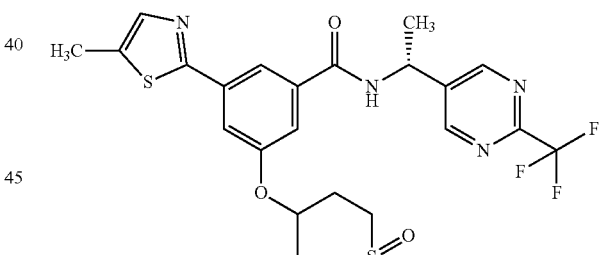

A mixture of Intermediate 5AZ (158 mg, 430 μmol), Intermediate VI (103 mg, 451 μmol), HATU (229 mg, 602 μmol) and DIPEA (300 μl, 1.7 mmol) in DMF (3.0 mL) was stirred at RT until complete conversion. The reaction mixture was evaporated to dryness under reduced pressure and the remaining material purified by preparative HPLC (method 1) to give 90 mg (39% yield) of the title compound.

LCMS (method 1): rt: 1.14 min, MS ES+m/z=541 (M+H)$^+$.

$^1$H NMR (400 MHz, DMSO-d$_6$) δ [ppm] 1.62 (d, 3H) 2.25 (d, 4H) 3.08-3.32 (m, 4H) 4.93 (br. s., 1H) 5.30 (t, 1H) 7.55-7.61 (m, 1H) 7.63-7.74 (m, 2H) 7.95 (s, 1H) 9.05-9.25 (m, 3H).

In analogy to the procedure described for the preparation of Example 232 the following derivatives have been prepared:

| Ex. | Structure | Name | Analytical Data |
|---|---|---|---|
| 233 | 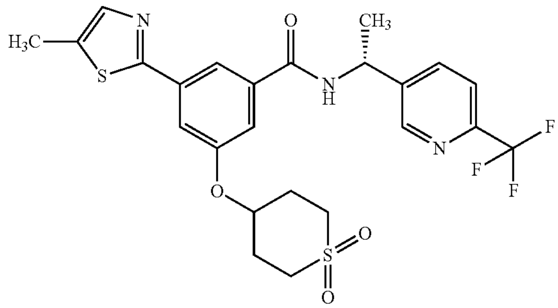 [SMILES: Cc1cnc(-c2cc(OC3CCS(=O)(=O)CC3)cc(C(=O)N[C@H](C)c3ccc(C(F)(F)F)nc3)c2)s1] | 3-[(1,1-dioxidotetrahydro-2H-thiopyran-4-yl)oxy]-5-(5-methyl-1,3-thiazol-2-yl)-N-{(1R)-1-[6-(trifluoromethyl)pyridin-3-yl]ethyl}benzamide | $^1$H NMR (400 MHz, DMSO-d$_6$) δ [ppm] 1.61 (d, 3 H) 2.24 (m, 4 H) 3.10-3.31 (m, 4 H) 4.92 (t, 1 H) 5.30 (t, 1 H) 7.53-7.74 (m, 3 H) 7.95 (t, 1 H) 9.05-9.24 (m, 3 H). LCMS (method 1): Rt = 1.16 min, MS ES+ m/z = 540 (M + H)$^+$. |
| 234 | 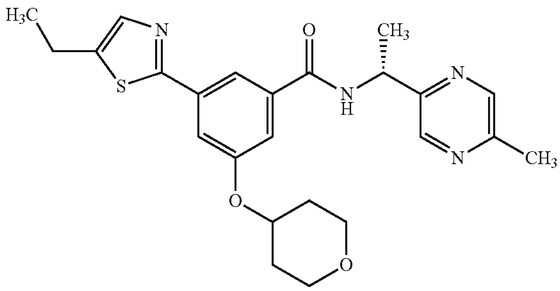 [SMILES: CCc1cnc(-c2cc(OC3CCOCC3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-(tetrahydro-2H-pyran-4-yloxy)benzamide | LCMS (method 1): rt: 1.18 min, MS ES+ m/z = 453 (M + H)$^+$. $^1$H NMR (400 MHz, DMSO-d$_6$) δ [ppm] 1.29 (t, 3 H) 1.54 (d, 3 H) 1.58-1.70 (m, 2 H) 1.91-2.08 (m, 2 H) 2.47 (s, 3 H) 2.90 (dd, 2 H) 3.52 (m, 2 H) 3.85 (m, 2 H) 4.67-4.81 (m, 1 H) 5.12-5.31 (m, 1 H) 7.52-7.61 (m, 2 H) 7.67 (t, 1 H) 7.94 (t, 1 H) 8.44-8.59 (m, 2 H) 9.02-9.14 (m, 1 H). |
| 235 | 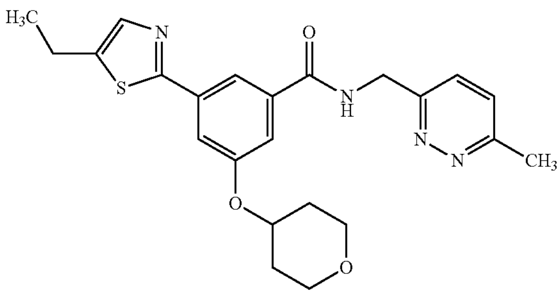 [SMILES: CCc1cnc(-c2cc(OC3CCOCC3)cc(C(=O)NCc3ccc(C)nn3)c2)s1] | 3-(5-ethyl-1,3-thiazol-2-yl)-N-[(6-methylpyridazin-3-yl)methyl]-5-(tetrahydro-2H-pyran-4-yloxy)benzamide | $^1$H NMR (400 MHz, METHANOL-d$_4$) δ [ppm] 1.38 (t, 3 H) 1.72-1.87 (m, 2 H) 2.06-2.21 (m, 2 H) 2.69 (s, 3 H) 2.96 (dd, 2 H) 3.65 (s, 2 H) 3.94-4.06 (m, 2 H) 4.66-4.81 (m, 1 H) 4.87 (s, 2 H) 7.55 (dd, 1 H) 7.59-7.65 (m, 2 H) 7.66-7.76 (m, 2 H) 7.97 (t, 1 H). |
| 236 | 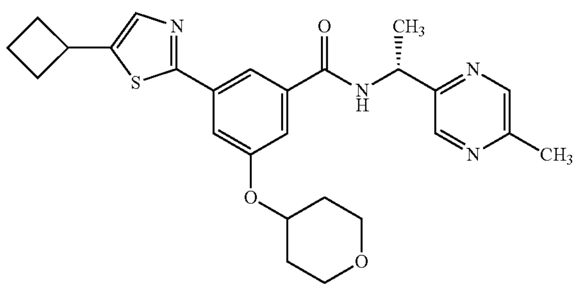 [SMILES: Cc1cnc([C@@H](C)NC(=O)c2cc(OC3CCOCC3)cc(-c3ncc(C4CCC4)s3)c2)cn1] | 3-(5-cyclobutyl-1,3-thiazol-2-yl)-N-[(1R)-1-(5-methylpyrazin-2-yl)ethyl]-5-(tetrahydro-2H-pyran-4-yloxy)benzamide | LCMS (method 1): rt: 1.31 min, MS ES+ m/z = 479 (M + H)$^+$. $^1$H NMR (400 MHz, DMSO-d$_6$) δ [ppm] 1.54 (d, 3 H) 1.64 (m, 2 H) 1.85-1.94 (m, 1 H) 1.95-2.05 (m, 3 H) 2.08-2.20 (m, 2 H) 2.43 (m, 2 H) 2.47 (s, 3 H) 3.44-3.59 (m, 2 H) 3.76-3.91 (m, 3 H) 4.76 (s, 1 H) 5.23 (s, 1 H) 7.48-7.63 (m, 2 H) 7.68 (d, 1 H) 7.95 (t, 1 H) 8.45-8.60 (m, 2 H) 9.09 (d, 1 H). |
| 237 | 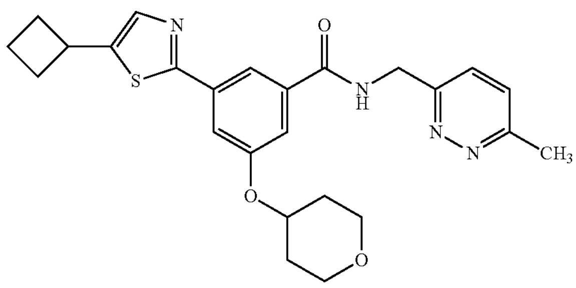 [SMILES: Cc1ccc(CNC(=O)c2cc(OC3CCOCC3)cc(-c3ncc(C4CCC4)s3)c2)nn1] | 3-(5-cyclobutyl-1,3-thiazol-2-yl)-N-[(6-methylpyridazin-3-yl)methyl]-5-(tetrahydro-2H-pyran-4-yloxy)benzamide | $^1$H NMR (400 MHz, DMSO-d$_6$) δ [ppm] 1.64 (s, 2 H) 1.82-1.94 (m, 1 H) 2.00 (m, 3 H) 2.13 (m, 2 H) 2.43 (m, 2 H) 2.60 (s, 3 H) 3.43-3.60 (m, 2 H) 3.74-3.93 (m, 3 H) 4.73 (m, 3 H) 7.48-7.64 (m, 4 H) 7.68 (d, 1 H) 7.98 (t, 1 H) 9.38 (s, 1 H). |

-continued

| Ex. | Structure | Name | Analytical Data |
|---|---|---|---|
| 238 | 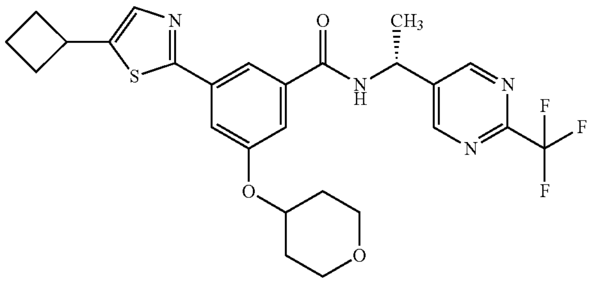 [SMILES: C[C@@H](NC(=O)c1cc(OC2CCOCC2)cc(-c2ncc(C3CCC3)s2)c1)c1cnc(C(F)(F)F)nc1] | 3-(5-cyclobutyl-1,3-thiazol-2-yl)-5-(tetrahydro-2H-pyran-4-yloxy)-N-{(1R)-1-[2-(trifluoromethyl)pyrimidin-5-yl]ethyl}benzamide | LCMS (method 1): rt: 1.42 min, MS ES+ m/z = 533 (M + H)+. 1H NMR (400 MHz, DMSO-d6) δ [ppm] 1.52-1.71 (m, 5 H) 1.81-1.94 (m, 1 H) 1.95-2.06 (m, 3 H) 2.08-2.21 (m, 2 H) 2.35-2.47 (m, 2 H) 3.52 (m, 2 H) 3.72-3.95 (m, 3 H) 4.69-4.84 (m, 1 H) 5.29 (s, 1 H) 7.53 (dd, 1 H) 7.57-7.63 (m, 1 H) 7.68 (d, 1 H) 7.94 (t, 1 H) 9.06-9.20 (m, 3 H). |
| 239 | 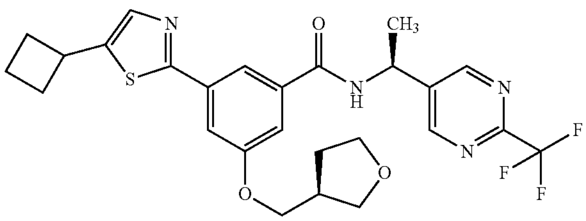 [SMILES: C[C@H](NC(=O)c1cc(OC[C@H]2CCOC2)cc(-c2ncc(C3CCC3)s2)c1)c1cnc(C(F)(F)F)nc1] | 3-(5-cyclobutyl-1,3-thiazol-2-yl)-5-[(3S)-tetrahydrofuran-3-ylmethoxy]-N-{(1S)-1-[2-(trifluoromethyl)pyrimidin-5-yl]ethyl}benzamide | LCMS (method 2): rt: 1.42 min, MS ES+ m/z = 533 (M + H)+. 1H NMR (400 MHz, DMSO-d6) δ ppm 1.61 (d, 3 H) 1.66-1.78 (m, 1 H) 1.81-1.95 (m, 1 H) 1.95-2.08 (m, 2 H) 2.09-2.23 (m, 2 H) 2.43 (dt, 2 H) 2.62-2.75 (m, 1 H) 3.51-3.71 (m, 2 H) 3.73-3.90 (m, 3 H) 3.95-4.17 (m, 2 H) 5.30 (s, 1 H) 7.50-7.61 (m, 2 H) 7.68 (d, 1 H) 7.95 (t, 1 H) 9.07-9.20 (m, 3 H). |
| 240 | 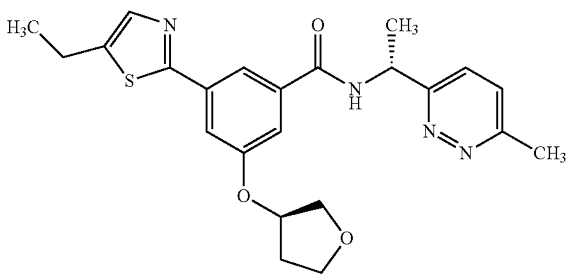 [SMILES: CCc1cnc(-c2cc(O[C@@H]3CCOC3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(3R)-tetrahydrofuran-3-yloxy]benzamide | LCMS (method 1): rt: 1.04 min, MS ES+ m/z = 439 (M + H)+. 1H NMR (400 MHz, DMSO-d6) δ [ppm] 1.29 (t, 3 H) 1.59 (d, 3 H) 1.93-2.09 (m, 1 H) 2.18-2.31 (m, 1 H) 2.59 (s, 3 H) 2.90 (dd, 2 H) 3.71-4.00 (m, 4 H) 5.21 (d, 1 H) 5.37 (m, 1 H) 7.46-7.56 (m, 3 H) 7.56-7.63 (m, 1 H) 7.68 (t, 1 H) 7.97 (t1 H) 9.14 (d, 1 H). |
| 241 | 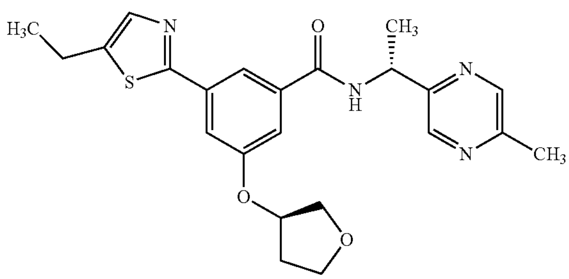 [SMILES: CCc1cnc(-c2cc(O[C@@H]3CCOC3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(3R)-tetrahydrofuran-3-yloxy]benzamide | LCMS (method 1): rt: 1.14 min, MS ES+ m/z = 439 (M + H)+. 1H NMR (400 MHz, DMSO-d6) δ [ppm] 1.29 (t, 3 H) 1.54 (d, 3 H) 1.95-2.05 (m, 1 H) 2.16-2.32 (m, 1 H) 2.47 (s, 3 H) 2.85-2.99 (m, 2 H) 3.72-3.97 (m, 4 H) 5.14-5.29 (m, 2 H) 7.44-7.57 (m, 1 H) 7.68 (t, 1 H) 7.96 (t, 1 H) 8.49 (d, 1 H) 8.56 (d, 1 H) 9.10 (d, 1 H). |
| 242 | 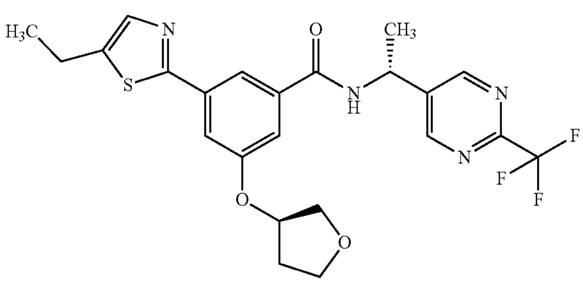 [SMILES: CCc1cnc(-c2cc(O[C@@H]3CCOC3)cc(C(=O)N[C@H](C)c3cnc(C(F)(F)F)nc3)c2)s1] | 3-(5-ethyl-1,3-thiazol-2-yl)-5-[(3R)-tetrahydrofuran-3-yloxy]-N-{(1R)-1-[2-(trifluoromethyl)pyrimidin-5-yl]ethyl}benzamide | LCMS (method 1): rt: 1.28 min, MS ES+ m/z = 493 (M + H)+. 1H NMR (400 MHz, DMSO-d6) δ [ppm] 1.29 (t, 3 H) 1.61 (d, 3 H) 1.93-2.07 (m, 1 H) 2.26 (m, 1 H) 2.83-2.98 (m, 2 H) 3.72-3.97 (m, 4 H) 5.21 (d, 1 H) 5.30 (t, 1 H) 7.52 (m, 2 H) 7.68 (s, 1 H) 7.94 (t, 1 H) 9.07-9.22 (m, 3 H). |

| Ex. | Name | Analytical Data |
|---|---|---|
| 243 | 3-(5-cyclobutyl-1,3-thiazol-2-yl)-N-[(1R)-1-(6-methylpyridazin-3-yl)ethyl]-5-[(3R)-tetrahydrofuran-3-yloxy]benzamide | LCMS (method 1): rt: 1.17 min, MS ES+ m/z = 465 (M + H)+. $^1$H NMR (400 MHz, DMSO-$d_6$) δ [ppm] 1.59 (d, 3 H) 1.79-2.07 (m, 3 H) 2.09-2.31 (m, 3 H) 2.36-2.48 (m, 2 H) 2.59 (s, 3 H) 3.69-3.98 (m, 5 H) 5.21 (d, 1 H) 5.37 (t, 1 H) 7.46-7.64 (m, 4 H) 7.69 (d, 1 H) 7.98 (t, 1 H) 9.14 (d, 1 H). |
| 244 | 3-(5-cyclobutyl-1,3-thiazol-2-yl)-N-[(1R)-1-(5-methylpyrazin-2-yl)ethyl]-5-[(3R)-tetrahydrofuran-3-yloxy]benzamide | LCMS (method 1): rt: 1.26 min, MS ES+ m/z = 465 (M + H)+. $^1$H NMR (400 MHz, DMSO-$d_6$) δ [ppm] 1.55 (d, 3 H) 1.84-2.07 (m, 3 H) 2.08-2.31 (m, 3 H) 2.39-2.46 (m, 2 H) 2.47 (s, 3 H) 3.72-3.98 (m, 5 H) 5.13-5.30 (m, 2 H) 7.53 (dt, 2 H) 7.68 (d, 1 H) 7.97 (t, 1 H) 8.49 (d, 1 H) 8.56 (d, 1 H) 9.08 (d, 1 H). |
| 245 | 3-(5-cyclobutyl-1,3-thiazol-2-yl)-5-[(3R)-tetrahydrofuran-3-yloxy]-N-{(1R)-1-[2-(trifluoromethyl)pyrimidin-5-yl]ethyl}benzamide | LCMS (method 1): rt: 1.39 min, MS ES+ m/z = 519 (M + H)+. $^1$H NMR (400 MHz, DMSO-$d_6$) δ [ppm] 1.61 (d, 3 H) 1.81-2.07 (m, 3 H) 2.08-2.35 (m, 3 H) 2.44 (dt, 2 H) 3.72-3.98 (m, 5 H) 5.21 (d, 1 H) 5.30 (t, 1 H) 7.45-7.59 (m, 2 H) 7.69 (d, 1 H) 7.95 (t, 1 H) 9.05-9.21 (m, 3 H). |
| 246 | N-[(1R)-1-(6-methylpyridazin-3-yl)ethyl]-3-[5-(propan-2-yl)-1,3-thiazol-2-yl]-5-[(3R)-tetrahydrofuran-3-yloxy]benzamide | LCMS (method 1): rt: 1.12 min, MS ES+ m/z = 453 (M + H)+. $^1$H NMR (400 MHz, DMSO-$d_6$) δ [ppm] 1.33 (d, 6 H) 1.59 (d, 3 H) 1.90-2.07 (m, 1 H) 2.25 (s, 1 H) 2.59 (s, 3 H) 3.28 (d, 1 H) 3.70-3.99 (m, 4 H) 5.21 (d, 1 H) 5.37 (t, 1 H) 7.48-7.64 (m, 4 H) 7.69 (d, 1 H) 7.97 (s, 1 H) 9.13 (d, 1 H). |
| 247 | N-[(1R)-1-(5-methylpyrazin-2-yl)ethyl]-3-[5-(propan-2-yl)-1,3-thiazol-2-yl]-5-[(3R)-tetrahydrofuran-3-yloxy]benzamide | LCMS (method 1): rt: 1.21 min, MS ES+ m/z = 453 (M + H)+. $^1$H NMR (400 MHz, DMSO-$d_6$) δ [ppm] 1.33 (d, 6 H) 1.55 (d, 3 H) 1.95-2.06 (m, 1 H) 2.26 (m, 1 H) 2.47 (s, 3 H) 3.28 (m, 1 H) 3.71-4.00 (m, 4 H) 5.15-5.32 (m, 2 H) 7.53 (m, 2 H) 7.69 (d, 1 H) 7.96 (t, 1 H) 8.49 (s, 1 H) 8.56 (d, 1 H) 9.08 (d, 1 H). |

-continued

| Ex. | Structure | Name | Analytical Data |
|---|---|---|---|
| 248 | 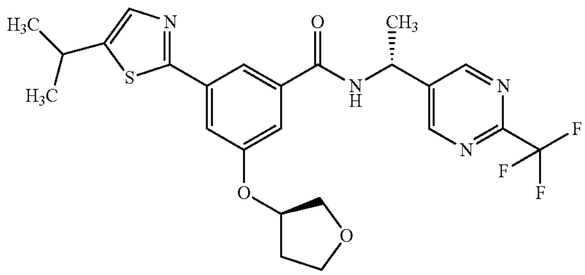 [SMILES: CC(C)c1cnc(-c2cc(O[C@@H]3CCOC3)cc(C(=O)N[C@H](C)c3cnc(C(F)(F)F)nc3)c2)s1] | 3-[5-(propan-2-yl)-1,3-thiazol-2-yl]-5-[(3R)-tetrahydrofuran-3-yloxy]-N-{(1R)-1-[2-(trifluoromethyl)pyrimidin-5-yl]ethyl}benzamide | LCMS (method 1): rt: 1.34 min, MS ES+ m/z = 507 (M + H)+. $^1$H NMR (400 MHz, DMSO-$d_6$) d [ppm] 1.33 (d, 6 H) 1.61 (d, 3 H) 1.93-2.07 (m, 1 H) 2.25 (m, 1 H) 3.28 (m, 1 H) 3.67-4.01 (m, 4 H) 5.21 (d, 1 H) 5.30 (t, 1 H) 7.45-7.59 (m, 2 H) 7.69 (d, 1 H) 7.95 (t, 1 H) 9.06-9.20 (m, 3 H). |
| 249 | 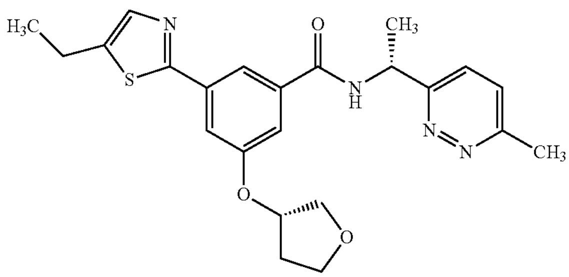 [SMILES: CCc1cnc(-c2cc(O[C@H]3CCOC3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(3S)-tetrahydrofuran-3-yloxy]benzamide | LCMS (method 1): rt: 1.04 min, MS ES+ m/z = 439 (M + H)+. $^1$H NMR (400 MHz, DMSO-$d_6$) δ [ppm] 1.29 (t, 3 H) 1.59 (d, 3 H) 1.95-2.07 (m, 1 H) 2.18-2.31 (m, 1 H) 2.59 (s, 3 H) 2.81-2.98 (m, 2 H) 3.71-3.97 (m, 4 H) 5.21 (d, 1 H) 5.37 (t, 1 H) 7.49-7.63 (m, 4 H) 7.68 (t, 1 H) 7.97 (t, 1 H) 9.14 (d, 1 H). |
| 250 | 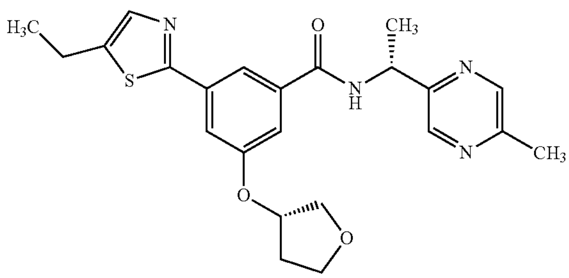 [SMILES: CCc1cnc(-c2cc(O[C@H]3CCOC3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(3S)-tetrahydrofuran-3-yloxy]benzamide | LCMS (method 1): rt: 1.13 min, MS ES+ m/z = 439 (M + H)+. $^1$H NMR (400 MHz, DMSO-$d_6$) δ [ppm] 1.29 (t, 3 H) 1.54 (d, 3 H) 2.02 (m, 1 H) 2.19-2.31 (m, 1 H) 2.47 (s, 3 H) 2.82-2.99 (m, 2 H) 3.70-4.00 (m, 4 H) 5.13-5.31 (m, 2 H) 7.53 (m, 2 H) 7.68 (s, 1 H) 7.96 (t, 1 H) 8.45-8.61 (m, 2 H) 9.08 (d, 1 H). |
| 251 | 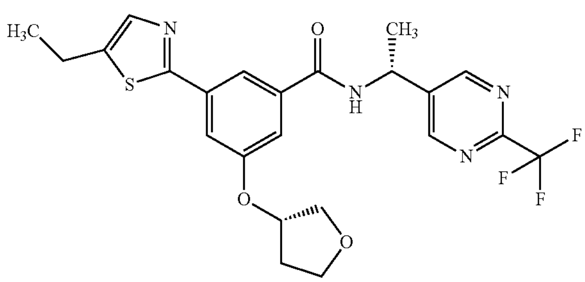 [SMILES: CCc1cnc(-c2cc(O[C@H]3CCOC3)cc(C(=O)N[C@H](C)c3cnc(C(F)(F)F)nc3)c2)s1] | 3-(5-ethyl-1,3-thiazol-2-yl)-5-[(3S)-tetrahydrofuran-3-yloxy]-N-{(1R)-1-[2-(trifluoromethyl)pyrimidin-5-yl]ethyl}benzamide | LCMS (method 1): rt: 1.28 min, MS ES+ m/z = 493 (M + H)+. $^1$H NMR (400 MHz, DMSO-$d_6$) δ [ppm] 1.29 (t, 3 H) 1.61 (d, 3 H) 1.89-2.09 (m, 1 H) 2.25 (m, 1 H) 2.90 (q, 2 H) 3.69-3.99 (m, 4 H) 5.21 (d, 1 H) 5.30 (t, 1 H) 7.43-7.58 (m, 2 H) 7.68 (s, 1 H) 7.89-8.00 (m, 1 H) 9.06-9.20 (m, 3 H). |
| 252 | 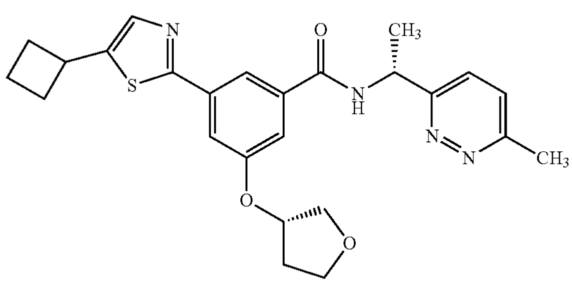 [SMILES: Cc1ccc([C@@H](C)NC(=O)c2cc(O[C@H]3CCOC3)cc(-c3ncc(C4CCC4)s3)c2)nn1] | 3-(5-cyclobutyl-1,3-thiazol-2-yl)-N-[(1R)-1-(6-methylpyridazin-3-yl)ethyl]-5-[(3S)-tetrahydrofuran-3-yloxy]benzamide | LCMS (method 1): rt: 1.17 min, MS ES+ m/z = 465 (M + H)+. $^1$H NMR (400 MHz, DMSO-$d_6$) d [ppm] 1.59 (d, 3 H) 1.84-2.08 (m, 3 H) 2.09-2.34 (m, 3 H) 2.44 (m, 2 H) 2.59 (s, 3 H) 3.74-3.95 (m, 5 H) 5.21 (d, 1 H) 5.37 (m, 1 H) 7.50-7.63 (m, 4 H) 7.68 (d, 1 H) 7.98 (t, 1 H) 9.13 (d, 1 H). |

| Ex. | Name | Analytical Data |
|---|---|---|
| 253 | 3-(5-cyclobutyl-1,3-thiazol-2-yl)-N-[(1R)-1-(5-methylpyrazin-2-yl)ethyl]-5-[(3S)-tetrahydrofuran-3-yloxy]benzamide | LCMS (method 1): rt: 1.26 min, MS ES+ m/z = 465 (M + H)+. $^1$H NMR (400 MHz, DMSO-d$_6$) δ [ppm] 1.55 (d, 3 H) 1.83-2.07 (m, 3 H) 2.08-2.31 (m, 3 H) 2.39-2.46 (m, 2 H) 2.47 (s, 3 H) 3.73-3.97 (m, 5 H) 5.13-5.31 (m, 2 H) 7.45-7.58 (m, 2 H) 7.68 (d, 1 H) 7.97 (t, 1 H) 8.43-8.62 (m, 2 H) 9.08 (d, 1 H). |
| 254 | 3-(5-cyclobutyl-1,3-thiazol-2-yl)-5-[(3S)-tetrahydrofuran-3-yloxy]-N-{(1R)-1-[2-(trifluoromethyl)pyrimidin-5-yl]ethyl}benzamide | LCMS (method 1): rt: 1.39 min, MS ES+ m/z = 519 (M + H)+. $^1$H NMR (400 MHz, DMSO-d$_6$) δ [ppm] 1.61 (d, 3 H) 1.79-2.06 (m, 3 H) 2.08-2.36 (m, 3 H) 2.36-2.47 (m, 2 H) 3.66-3.98 (m, 5 H) 5.21 (d, 1 H) 5.30 (t, 1 H) 7.44-7.59 (m, 2 H) 7.69 (d, 1 H) 7.95 (t, 1 H) 9.08-9.22 (m, 3 H). |
| 255 | N-[(1R)-1-(6-methylpyridazin-3-yl)ethyl]-3-[5-(propan-2-yl)-1,3-thiazol-2-yl]-5-[(3S)-tetrahydrofuran-3-yloxy]benzamide | LCMS (method 1): rt: 1.12 min, MS ES+ m/z = 453 (M + H)+. $^1$H NMR (400 MHz, DMSO-d$_6$) δ [ppm] 1.33 (d, 6 H) 1.59 (d, 3 H) 1.92-2.09 (m, 1 H) 2.17-2.31 (m, 1 H) 2.59 (s, 3 H) 3.28 (m, 1 H) 3.70-3.98 (m, 4 H) 5.13-5.26 (m, 1 H) 5.37 (m, 1 H) 7.48-7.63 (m, 4 H) 7.69 (d, 1 H) 7.97 (t, 1 H) 9.14 (d, 1 H). |
| 256 | N-[(1R)-1-(5-methylpyrazin-2-yl)ethyl]-3-[5-(propan-2-yl)-1,3-thiazol-2-yl]-5-[(3S)-tetrahydrofuran-3-yloxy]benzamide | LCMS (method 1): rt: 1.21 min, MS ES+ m/z = 453 (M + H)+. $^1$H NMR (400 MHz, DMSO-d$_6$) δ [ppm] 1.33 (d, 6 H) 1.54 (d, 3 H) 1.92-2.09 (m, 1 H) 2.17-2.32 (m, 1 H) 2.47 (s, 3 H) 3.28 (m, 1 H) 3.70-3.99 (m, 4 H) 5.15-5.31 (m, 2 H) 7.44-7.58 (m, 2 H) 7.69 (d, 1 H) 7.96 (t, 1 H) 8.43-8.60 (m, 2 H) 9.09 (d, 1 H). |
| 257 | 3-[5-(propan-2-yl)-1,3-thiazol-2-yl]-5-[(3S)-tetrahydrofuran-3-yloxy]-N-{(1R)-1-[2-(trifluoromethyl)pyrimidin-5-yl]ethyl}benzamide | LCMS (method 1): rt: 1.34 min, MS ES+ m/z = 507 (M + H)+. $^1$H NMR (400 MHz, DMSO-d$_6$) δ [ppm] 1.33 (d, 6 H) 1.61 (d, 3 H) 1.93-2.08 (m, 1 H) 2.26 (m, 1 H) 3.28 (m, 1 H) 3.71-3.97 (m, 4 H) 5.16-5.24 (m, 1 H) 5.30 (t, 1 H) 7.43-7.61 (m, 2 H) 7.69 (d, 1 H) 7.95 (t, 1 H) 9.07-9.24 (m, 3 H). |

| Ex. | Structure | Name | Analytical Data |
|---|---|---|---|
| 258 | 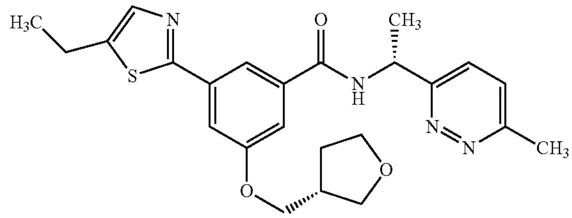 [SMILES: CCc1cnc(-c2cc(OC[C@@H]3CCOC3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(3R)-tetrahydrofuran-3-ylmethoxy]benzamide | LCMS (method 1): rt: 1.10 min, MS ES+ m/z = 453 (M + H)+. 1H NMR (400 MHz, DMSO-d6) δ [ppm] 1.29 (t, 3 H) 1.59 (d, 3 H) 1.64-1.79 (m, 1 H) 1.95-2.13 (m, 1 H) 2.59 (s, 3 H) 2.63-2.76 (m, 1 H) 2.85-2.98 (m, 2 H) 3.58 (dd, 1 H) 3.68 (m, 1 H) 3.73-3.87 (m, 2 H) 4.05 (m, 2 H) 5.37 (t, 1 H) 7.46-7.63 (m, 4 H) 7.67 (s, 1 H) 7.96 (s, 1 H) 9.12 (d, 1 H). |
| 259 | 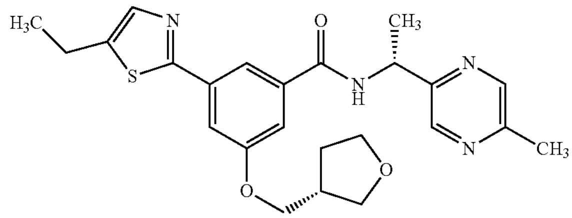 [SMILES: CCc1cnc(-c2cc(OC[C@@H]3CCOC3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(3R)-tetrahydrofuran-3-ylmethoxy]benzamide | LCMS (method 1): rt: 1.18 min, MS ES+ m/z = 453 (M + H)+. 1H NMR (400 MHz, DMSO-d6) δ [ppm] 1.29 (t, 3 H) 1.55 (d, 3 H) 1.72 (m, 1 H) 1.95-2.11 (m, 1 H) 2.47 (s, 3 H) 2.60-2.77 (m, 1 H) 2.81-2.97 (m, 2 H) 3.58 (dd, 1 H) 3.62-3.71 (m, 1 H) 3.73-3.89 (m, 2 H) 3.94-4.16 (m, 2 H) 5.23 (t, 1 H) 7.51-7.60 (m, 2 H) 7.67 (s, 1 H) 7.95 (t, 1 H) 8.43-8.60 (m, 2 H) 9.07 (d, 1 H). |
| 260 | 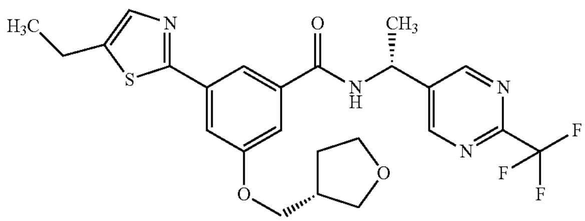 [SMILES: CCc1cnc(-c2cc(OC[C@@H]3CCOC3)cc(C(=O)N[C@H](C)c3cnc(C(F)(F)F)nc3)c2)s1] | 3-(5-ethyl-1,3-thiazol-2-yl)-5-[(3R)-tetrahydrofuran-3-ylmethoxy]-N-{(1R)-1-[2-(trifluoromethyl)pyrimidin-5-yl]ethyl}benzamide | LCMS (method 1): rt: 1.32 min, MS ES+ m/z = 507 (M + H)+. 1H NMR (400 MHz, DMSO-d6) δ [ppm] 1.29 (t, 3 H) 1.61 (d, 3 H) 1.65-1.78 (m, 1 H) 1.95-2.13 (m, 1 H) 2.60-2.77 (m, 1 H) 2.90 (dd, 2 H) 3.57 (dd, 1 H) 3.67 (d, 1 H) 3.74-3.88 (m, 2 H) 4.05 (dd, 2 H) 5.30 (m, 1 H) 7.55 (dt, 2 H) 7.67 (s, 1 H) 7.94 (t, 1 H) 9.07-9.21 (m, 3 H). |
| 261 | 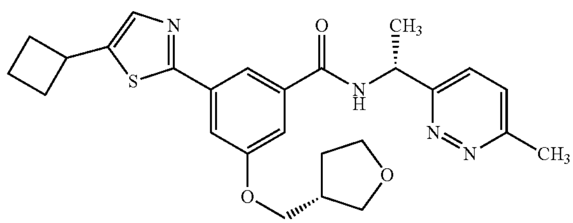 [SMILES: Cc1ccc([C@@H](C)NC(=O)c2cc(OC[C@@H]3CCOC3)cc(-c3ncc(C4CCC4)s3)c2)nn1] | 3-(5-cyclobutyl-1,3-thiazol-2-yl)-N-[(1R)-1-(6-methylpyridazin-3-yl)ethyl]-5-[(3R)-tetrahydrofuran-3-ylmethoxy]benzamide | LCMS (method 1): rt: 1.22 min, MS ES+ m/z = 479 (M + H)+. 1H NMR (400 MHz, DMSO-d6) δ [ppm] 1.59 (d, 3 H) 1.64-1.76 (m, 1 H) 1.82-1.95 (m, 1 H) 1.96-2.22 (m, 4 H) 2.35-2.48 (m, 2 H) 2.59 (s, 3 H) 2.63-2.74 (m, 1 H) 3.58 (dd, 1 H) 3.67 (d, 1 H) 3.74-3.90 (m, 3 H) 3.96-4.16 (m, 2 H) 5.37 (m, 1 H) 7.45-7.62 (m, 4 H) 7.68 (d, 1 H) 7.97 (t, 1 H) 9.12 (d, 1 H). |
| 262 | 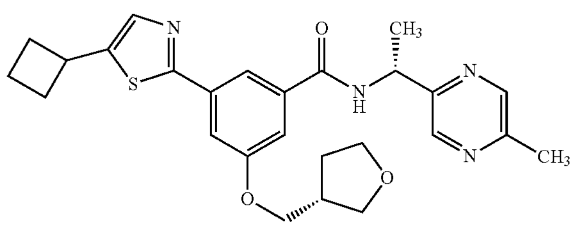 [SMILES: Cc1cnc([C@@H](C)NC(=O)c2cc(OC[C@@H]3CCOC3)cc(-c3ncc(C4CCC4)s3)c2)cn1] | 3-(5-cyclobutyl-1,3-thiazol-2-yl)-N-[(1R)-1-(5-methylpyrazin-2-yl)ethyl]-5-[(3R)-tetrahydrofuran-3-ylmethoxy]benzamide | LCMS (method 1): rt: 1.31 min, MS ES+ m/z = 479 (M + H)+. 1H NMR (400 MHz, DMSO-d6) δ [ppm] 1.55 (d, 3 H) 1.65-1.76 (m, 1 H) 1.84-2.21 (m, 5 H) 2.43 (m, 2 H) 2.47 (s, 3 H) 2.62-2.73 (m, 1 H) 3.58 (dd, 1 H) 3.67 (d, 1 H) 3.73-3.90 (m, 3 H) 3.95-4.14 (m, 2 H) 5.16-5.30 (m, 1 H) 7.52-7.61 (m, 2 H) 7.67 (d, 1 H) 7.96 (t, 1 H) 8.44-8.61 (m, 2 H) 9.07 (d, 1 H). |
| 263 | 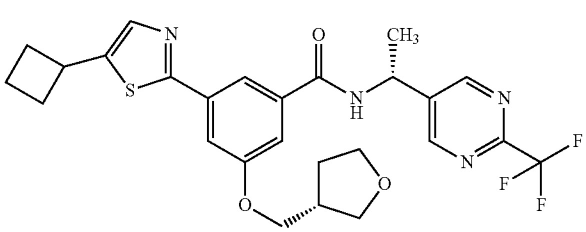 [SMILES: C[C@@H](NC(=O)c1cc(OC[C@@H]2CCOC2)cc(-c2ncc(C3CCC3)s2)c1)c1cnc(C(F)(F)F)nc1] | 3-(5-cyclobutyl-1,3-thiazol-2-yl)-5-[(3R)-tetrahydrofuran-3-ylmethoxy]-N-{(1R)-1-[2-(trifluoromethyl)pyrimidin-5-yl]ethyl}benzamide | LCMS (method 1): rt: 1.43 min, MS ES+ m/z = 533 (M + H)+. 1H NMR (400 MHz, DMSO-d6) δ [ppm] 1.61 (d, 3 H) 1.66-1.77 (m, 1 H) 1.84-2.21 (m, 5 H) 2.43 (m, 2 H) 2.61-2.75 (m, 1 H) 3.57 (dd, 1 H) 3.67 (d, 1 H) 3.73-3.89 (m, 3 H) 3.96-4.13 (m, 2 H) 5.30 (m, 1 H) 7.55 (dt, 2 H) 7.68 (s, 1 H) 7.95 (s, 1 H) 9.06-9.21 (m, 3 H). |

| Ex. | Structure | Name | Analytical Data |
|---|---|---|---|
| 264 | 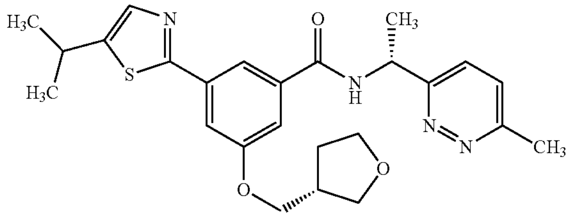 [SMILES: Cc1ccc([C@@H](C)NC(=O)c2cc(OC[C@@H]3CCOC3)cc(-c3ncc(C(C)C)s3)c2)nn1] | N-[(1R)-1-(6-methylpyridazin-3-yl)ethyl]-3-[5-(propan-2-yl)-1,3-thiazol-2-yl]-5-[(3R)-tetrahydrofuran-3-ylmethoxy]benzamide | LCMS (method 1): rt: 1.17 min, MS ES+ m/z = 467 (M + H)+. 1H NMR (400 MHz, DMSO-d6) δ [ppm] 1.33 (d, 6 H) 1.59 (d, 3 H) 1.64-1.78 (m, 1 H) 1.97-2.11 (m, 1 H) 2.59 (s, 3 H) 2.63-2.75 (m, 1 H) 3.27 (m, 1 H) 3.58 (dd, 1 H) 3.67 (d, 1 H) 3.74-3.88 (m, 2 H) 3.96-4.14 (m, 2 H) 5.37 (t, 1 H) 7.45-7.64 (m, 4 H) 7.68 (d, 1 H) 7.97 (t, 1 H) 9.12 (d, 1 H). |
| 265 | 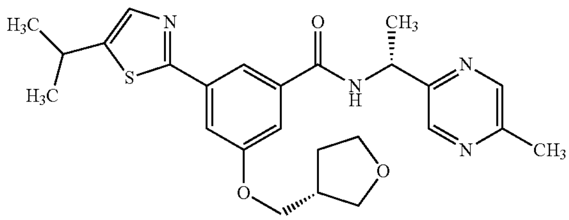 [SMILES: Cc1cnc([C@@H](C)NC(=O)c2cc(OC[C@@H]3CCOC3)cc(-c3ncc(C(C)C)s3)c2)cn1] | N-[(1R)-1-(5-methylpyrazin-2-yl)ethyl]-3-[5-(propan-2-yl)-1,3-thiazol-2-yl]-5-[(3R)-tetrahydrofuran-3-ylmethoxy]benzamide | LCMS (method 1): rt: 1.26 min, MS ES+ m/z = 467 (M + H)+. 1H NMR (400 MHz, DMSO-d6) δ [ppm] 1.33 (d, 6 H) 1.55 (d, 3 H) 1.63-1.79 (m, 1 H) 1.94-2.12 (m, 1 H) 2.47 (s, 3 H) 2.59-2.79 (m, 1 H) 3.28 (m, 1 H) 3.58 (dd, 1 H) 3.67 (d, 1 H) 3.73-3.88 (m, 2 H) 4.05 (m, 2 H) 5.24 (m, 1 H) 7.55 (dt, 2 H) 7.68 (d, 1 H) 7.96 (t, 1 H) 8.42-8.60 (m, 2 H) 9.07 (d, 1 H). |
| 266 | 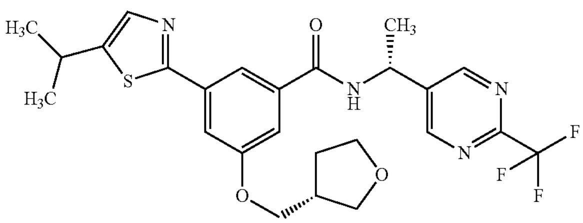 [SMILES: CC(C)c1cnc(-c2cc(OC[C@@H]3CCOC3)cc(C(=O)N[C@H](C)c3cnc(C(F)(F)F)nc3)c2)s1] | 3-[5-(propan-2-yl)-1,3-thiazol-2-yl]-5-[(3R)-tetrahydrofuran-3-ylmethoxy]-N-{(1R)-1-[2-(trifluoromethyl)pyrimidin-5-yl]ethyl}benzamide | LCMS (method 1): rt: 1.38 min, MS ES+ m/z = 521 (M + H)+. 1H NMR (400 MHz, DMSO-d6) δ [ppm] 1.33 (d, 6 H) 1.61 (d, 3 H) 1.71 (m, 1 H) 1.96-2.12 (m, 1 H) 2.68 (m, 1 H) 3.24-3.30 (m, 1 H) 3.57 (dd, 1 H) 3.61-3.71 (m, 1 H) 3.72-3.86 (m, 2 H) 3.96-4.15 (m, 2 H) 5.30 (t, 1 H) 7.55 (dt, 2 H) 7.68 (d, 1 H) 7.94 (t, 1 H) 9.07-9.21 (m, 3 H). |
| 267 | 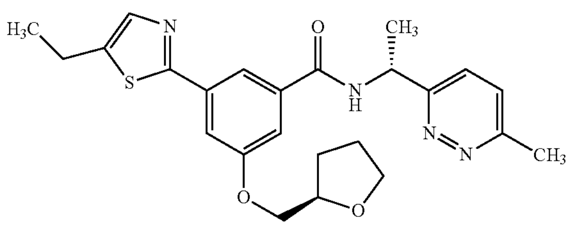 [SMILES: CCc1cnc(-c2cc(OC[C@H]3CCCO3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(2R)-tetrahydrofuran-2-ylmethoxy]benzamide | LCMS (method 1): rt: 1.11 min, MS ES+ m/z = 453 (M + H)+. 1H NMR (400 MHz, DMSO-d6) δ [ppm] 1.29 (t, 3 H) 1.59 (d, 3 H) 1.67-1.78 (m, 1 H) 1.79-1.95 (m, 2 H) 1.96-2.10 (m, 1 H) 2.59 (s, 3 H) 2.90 (m, 2 H) 3.63-3.73 (m, 1 H) 3.75-3.86 (m, 1 H) 3.97-4.13 (m, 2 H) 4.15-4.27 (m, 1 H) 5.37 (t, 1 H) 7.47-7.62 (m, 4 H) 7.67 (t, 1 H) 7.96 (t, 1 H) 9.14 (d, 1 H). |
| 268 | 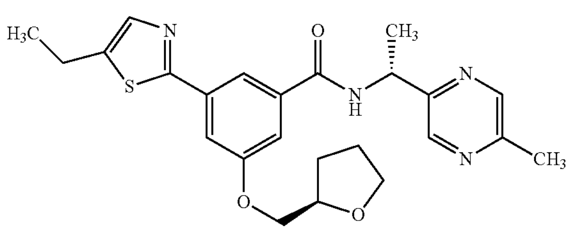 [SMILES: CCc1cnc(-c2cc(OC[C@H]3CCCO3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(2R)-tetrahydrofuran-2-ylmethoxy]benzamide | LCMS (method 1): rt: 1.20 min, MS ES+ m/z = 453 (M + H)+. 1H NMR (400 MHz, DMSO-d6) δ [ppm] 1.29 (t, 3 H) 1.54 (d, 3 H) 1.67-1.77 (m, 1 H) 1.78-1.95 (m, 2 H) 1.96-2.07 (m, 1 H) 2.47 (s, 3 H) 2.90 (m, 2 H) 3.60-3.74 (m, 1 H) 3.75-3.85 (m, 1 H) 3.98-4.14 (m, 2 H) 4.14-4.28 (m, 1 H) 5.23 (m, 1 H) 7.55 (d, 2 H) 7.67 (t, 1 H) 7.95 (t, 1 H) 8.43-8.61 (m, 2 H) 9.09 (d, 1 H). |
| 269 | 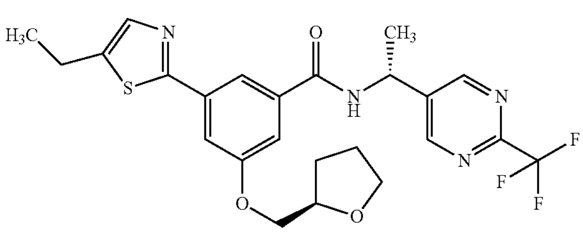 | 3-(5-ethyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide | LCMS (method 1): rt: 1.34 min, MS ES+ m/z = 507 (M + H)+. 1H NMR (400 MHz, DMSO-d6) δ [ppm] 1.29 (t, 3 H) 1.61 (d, 3 H) 1.75 (m, 1 H) 1.85 (m, 2 H) 1.96-2.08 (m, 1 H) 2.90 (m, 2 H) 3.62-3.74 (m, 1 H) 3.75-3.85 (m, 1 H) 4.00-4.14 (m, 2 H) 4.14-4.25 (m, 1 H) 5.30 (t, 1 H) 7.48-7.60 (m, 2 H) 7.68 (t, 1 H) 7.93 (t, 1 H) 9.07-9.20 (m, 3 H). |

| Ex. | Structure | Name | Analytical Data |
|---|---|---|---|
| 270 | 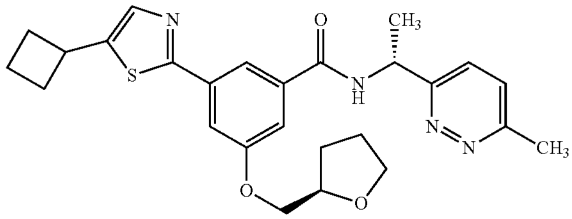 [SMILES: Cc1ccc([C@@H](C)NC(=O)c2cc(OC[C@H]3CCCO3)cc(-c3ncc(C4CCC4)s3)c2)nn1] | 3-(5-cyclobutyl-1,3-thiazol-2-yl)-N-[(1R)-1-(6-methylpyridazin-3-yl)ethyl]-5-[(2R)-tetrahydrofuran-2-ylmethoxy]benzamide | LCMS (method 1): rt: 1.24 min, MS ES+ m/z = 479 (M + H)+. 1H NMR (400 MHz, DMSO-d6) δ [ppm] 1.59 (d, 3 H) 1.75 (m, 1 H) 1.80-1.94 (m, 3 H) 1.96-2.07 (m, 2 H) 2.08-2.23 (m, 2 H) 2.37-2.47 (m, 2 H) 2.59 (s, 3 H) 3.64-3.74 (m, 1 H) 3.75-3.87 (m, 2 H) 3.98-4.14 (m, 2 H) 4.15-4.26 (m, 1 H) 5.37 (t, 1 H) 7.45-7.63 (m, 4 H) 7.68 (d, 1 H) 7.97 (t, 1 H) 9.13 (d, 1 H). |
| 271 | 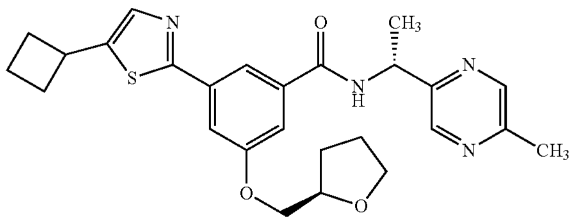 [SMILES: Cc1cnc([C@@H](C)NC(=O)c2cc(OC[C@H]3CCCO3)cc(-c3ncc(C4CCC4)s3)c2)cn1] | 3-(5-cyclobutyl-1,3-thiazol-2-yl)-N-[(1R)-1-(5-methylpyrazin-2-yl)ethyl]-5-[(2R)-tetrahydrofuran-2-ylmethoxy]benzamide | LCMS (method 1): rt: 1.32 min, MS ES+ m/z = 479 (M + H)+. 1H NMR (400 MHz, DMSO-d6) δ [ppm] 1.55 (d, 3 H) 1.75 (m, 1 H) 1.79-1.94 (m, 3 H) 1.96-2.07 (m, 2 H) 2.08-2.22 (m, 2 H) 2.38-2.46 (m, 2 H) 2.46-2.48 (s, 3 H) 3.64-3.75 (m, 1 H) 3.76-3.88 (m, 2 H) 4.01-4.13 (m, 2 H) 4.14-4.26 (m, 1 H) 5.23 (t, 1 H) 7.51-7.60 (m, 2 H) 7.68 (d, 1 H) 7.96 (t, 1 H) 8.46-8.58 (m, 2 H) 9.08 (d, 1 H). |
| 272 | 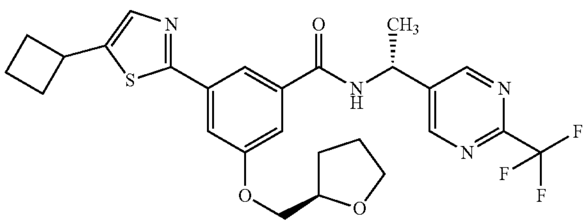 [SMILES: C[C@@H](NC(=O)c1cc(OC[C@H]2CCCO2)cc(-c2ncc(C3CCC3)s2)c1)c1cnc(C(F)(F)F)nc1] | 3-(5-cyclobutyl-1,3-thiazol-2-yl)-5-[(2R)-tetrahydrofuran-2-ylmethoxy]-N-{(1R)-1-[2-(trifluoromethyl)pyrimidin-5-yl]ethyl}benzamide | LCMS (method 1): rt: 1.44 min, MS ES+ m/z = 533 (M + H)+. 1H NMR (400 MHz, DMSO-d6) δ [ppm] 1.61 (d, 3 H) 1.67-1.78 (m, 1 H) 1.79-2.07 (m, 5 H) 2.08-2.21 (m, 2 H) 2.37-2.46 (m, 2 H) 3.64-3.74 (m, 1 H) 3.76-3.89 (m, 2 H) 4.02-4.13 (m, 2 H) 4.14-4.25 (m, 1 H) 5.30 (m, 1 H) 7.50-7.59 (m, 2 H) 7.68 (d, 1 H) 7.95 (t, 1 H) 9.08-9.19 (m, 3 H). |
| 273 | 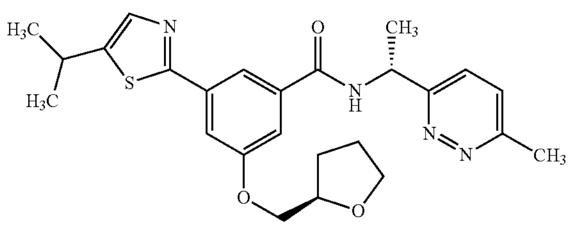 [SMILES: Cc1ccc([C@@H](C)NC(=O)c2cc(OC[C@H]3CCCO3)cc(-c3ncc(C(C)C)s3)c2)nn1] | N-[(1R)-1-(6-methylpyridazin-3-yl)ethyl]-3-[5-(propan-2-yl)-1,3-thiazol-2-yl]-5-[(2R)-tetrahydrofuran-2-ylmethoxy]benzamide | LCMS (method 1): rt: 1.19 min, MS ES+ m/z = 467 (M + H)+. 1H NMR (400 MHz, DMSO d6) δ [ppm] 1.30-1.37 (m, 6 H) 1.59 (d, 3 H) 1.66-2.10 (m, 4 H) 2.59 (s, 3 H) 3.28 (m, 1 H) 3.69 (m, 1 H) 3.79 (m, 1 H) 4.00-4.14 (m, 2 H) 4.15-4.26 (m, 1 H) 5.37 (m, 1 H) 7.48-7.63 (m, 4 H) 7.68 (d, 1 H) 7.96 (t, 1 H) 9.13 (d, 1 H). |
| 274 | 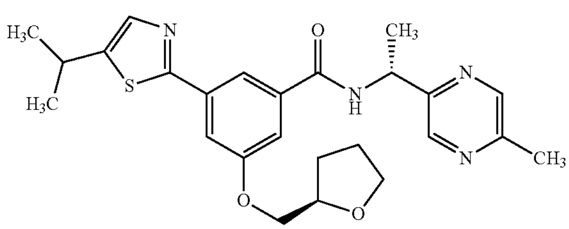 [SMILES: Cc1cnc([C@@H](C)NC(=O)c2cc(OC[C@H]3CCCO3)cc(-c3ncc(C(C)C)s3)c2)cn1] | N-[(1R)-1-(5-methylpyrazin-2-yl)ethyl]-3-[5-(propan-2-yl)-1,3-thiazol-2-yl]-5-[(2R)-tetrahydrofuran-2-ylmethoxy]benzamide | LCMS (method 1): rt: 1.27 min, MS ES+ m/z = 467 (M + H)+. 1H NMR (400 MHz, DMSO-d6) δ [ppm] 1.30-1.38 (m, 6 H) 1.55 (d, 3 H) 1.67-1.77 (m, 1 H) 1.80-1.95 (m, 2 H) 1.96-2.08 (m, 1 H) 2.47 (s, 3 H) 3.28 (m, 1 H) 3.63-3.74 (m, 1 H) 3.75-3.85 (m, 1 H) 4.02-4.13 (m, 2 H) 4.15-4.26 (m, 1 H) 5.23 (m, 1 H) 7.52-7.60 (m, 2 H) 7.68 (d, 1 H) 7.96 (t, 1 H) 8.49 (d, 1 H) 8.56 (d, 1 H) 9.08 (d, 1 H). |

| Ex. | Structure | Name | Analytical Data |
|---|---|---|---|
| 275 | 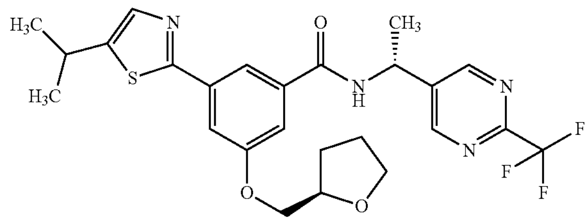 [SMILES: CC(C)c1cnc(-c2cc(OC[C@H]3CCCO3)cc(C(=O)N[C@H](C)c3cnc(C(F)(F)F)nc3)c2)s1] | 3-[5-(propan-2-yl)-1,3-thiazol-2-yl]-5-[(2R)-tetrahydrofuran-2-ylmethoxy]-N-{(1R)-1-[2-(trifluoromethyl)pyrimidin-5-yl]ethyl}benzamide | LCMS (method 1): rt: 1.40 min, MS ES+ m/z = 521 (M + H)+. $^1$H NMR (400 MHz, DMSO-d$_6$) δ [ppm] 1.33 (d, 6 H) 1.61 (d, 3 H) 1.68-1.78 (m, 1 H) 1.79-1.95 (m, 2 H) 1.96-2.07 (m, 1 H) 3.28 (m, 1 H) 3.65-3.73 (m, 1 H) 3.76-3.84 (m, 1 H) 4.01-4.13 (m, 2 H) 4.19 (m, 1 H) 5.30 (m, 1 H) 7.50-7.60 (m, 2 H) 7.69 (d, 1 H) 7.94 (t, 1 H) 9.08-9.19 (m, 3 H). |
| 276 | 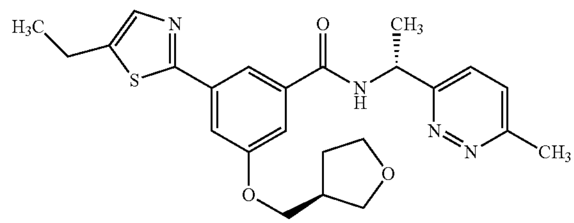 [SMILES: CCc1cnc(-c2cc(OC[C@H]3CCOC3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(3S)-tetrahydrofuran-3-ylmethoxy]benzamide | LCMS (method 1): rt: 1.10 min, MS ES+ m/z = 453 (M + H)+. $^1$H NMR (400 MHz, DMSO-d$_6$) δ [ppm] 1.29 (t, 3 H) 1.59 (d, 3 H) 1.64-1.81 (m, 1 H) 1.96-2.12 (m, 1 H) 2.59 (s, 3 H) 2.63-2.77 (m, 1 H) 2.84-2.98 (m, 2 H) 3.58 (dd, 1 H) 3.67 (m, 1 H) 3.74-3.88 (m, 2 H) 3.96-4.14 (m, 2 H) 5.37 (m, 1 H) 7.49-7.63 (m, 4 H) 7.67 (t, 1 H) 7.96 (t, 1 H) 9.12 (d, 1 H). |
| 277 | 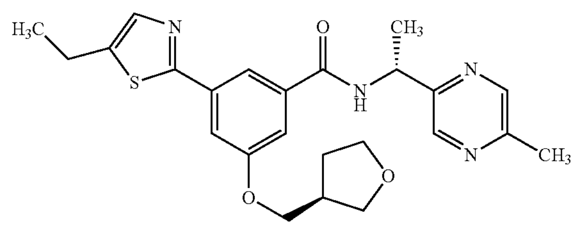 [SMILES: CCc1cnc(-c2cc(OC[C@H]3CCOC3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(3S)-tetrahydrofuran-3-ylmethoxy]benzamide | LCMS (method 1): rt: 1.18 min, MS ES+ m/z = 453 (M + H)+. $^1$H NMR (400 MHz, DMSO-d$_6$) δ [ppm] 1.29 (t, 3 H) 1.55 (d, 3 H) 1.72 (m, 1 H) 1.99-2.12 (m, 1 H) 2.47 (s, 3 H) 2.60-2.77 (m, 1 H) 2.90 (m, 2 H) 3.58 (dd, 1 H) 3.62-3.72 (m, 1 H) 3.74-3.89 (m, 2 H) 3.95-4.14 (m, 2 H) 5.23 (m, 1 H) 7.49-7.61 (m, 2 H) 7.67 (t, 1 H) 7.95 (t, 1 H) 8.48 (d, 1 H) 8.56 (d, 1 H) 9.07 (d, 1 H). |
| 278 | 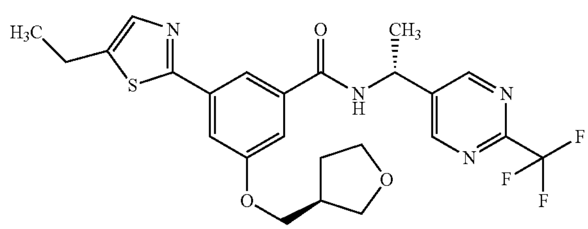 [SMILES: CCc1cnc(-c2cc(OC[C@H]3CCOC3)cc(C(=O)N[C@H](C)c3cnc(C(F)(F)F)nc3)c2)s1] | 3-(5-ethyl-1,3-thiazol-2-yl)-5-[(3S)-tetrahydrofuran-3-ylmethoxy]-N-{(1R)-1-[2-(trifluoromethyl)pyrimidin-5-yl]ethyl}benzamide | LCMS (method 1): rt: 1.32 min, MS ES+ m/z = 507 (M + H)+. $^1$H NMR (400 MHz, DMSO-d$_6$) δ [ppm] 1.29 (t, 3 H) 1.61 (d, 3 H) 1.65-1.81 (m, 1 H) 1.95-2.13 (m, 1 H) 2.60-2.77 (m, 1 H) 2.90 (m, 2 H) 3.58 (dd, 1 H) 3.67 (m, 1 H) 3.72-3.88 (m, 2 H) 4.05 (m, 2 H) 5.30 (m, 1 H) 7.46-7.60 (m, 2 H) 7.67 (t, 1 H) 7.94 (t, 1 H) 9.06-9.21 (m, 3 H). |
| 279 | 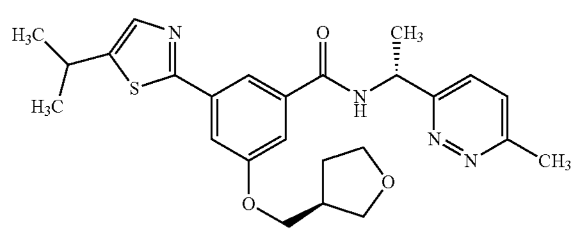 [SMILES: Cc1ccc([C@@H](C)NC(=O)c2cc(OC[C@H]3CCOC3)cc(-c3ncc(C(C)C)s3)c2)nn1] | N-[(1R)-1-(6-methylpyridazin-3-yl)ethyl]-3-[5-(propan-2-yl)-1,3-thiazol-2-yl]-5-[(3S)-tetrahydrofuran-3-ylmethoxy]benzamide | LCMS (method 1): rt: 1.17 min, MS ES+ m/z = 467 (M + H)+. $^1$H NMR (400 MHz, DMSO-d$_6$) δ [ppm] 1.33 (d, 6 H) 1.59 (d, 3 H) 1.64-1.79 (m, 1 H) 1.94-2.12 (m, 1 H) 2.59 (s, 3 H) 2.63-2.75 (m, 1 H) 3.28 (m, 1 H) 3.58 (dd, 1 H) 3.67 (m, 1 H) 3.73-3.90 (m, 2 H) 4.02 (m, 2 H) 5.37 (m, 1 H) 7.45-7.62 (m, 4 H) 7.68 (d, 1 H) 7.97 (t, 1 H) 9.12 (d, 1 H). |

| Ex. | Structure | Name | Analytical Data |
|---|---|---|---|
| 280 | 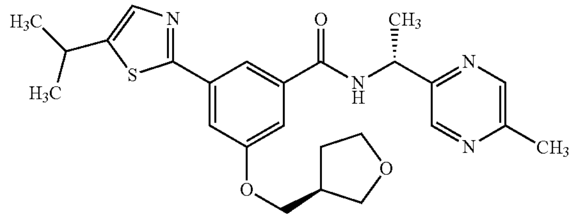 [SMILES: Cc1cnc([C@@H](C)NC(=O)c2cc(OC[C@H]3CCOC3)cc(-c3ncc(C(C)C)s3)c2)cn1] | N-[(1R)-1-(5-methylpyrazin-2-yl)ethyl]-3-[5-(propan-2-yl)-1,3-thiazol-2-yl]-5-[(3S)-tetrahydrofuran-3-ylmethoxy]benzamide | LCMS (method 1): rt: 1.26 min, MS ES+ m/z = 467 (M + H)+. $^1$H NMR (400 MHz, DMSO-d$_6$) δ [ppm] 1.33 (d, 6 H) 1.55 (d, 3 H) 1.64-1.82 (m, 1 H) 1.95-2.12 (m, 1 H) 2.47 (s, 3 H) 2.60-2.76 (m, 1 H) 3.28 (m, 1 H) 3.58 (dd, 1 H) 3.67 (m, 1 H) 3.81 (m, 2 H) 4.05 (m, 2 H) 5.24 (m, 1 H) 7.49-7.61 (m, 2 H) 7.68 (d, 1 H) 7.96 (t, 1 H) 8.49 (d, 1 H) 8.56 (d, 1 H) 9.07 (d, 1 H). |
| 281 | 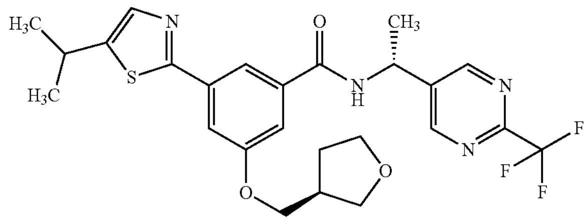 [SMILES: CC(C)c1cnc(-c2cc(OC[C@H]3CCOC3)cc(C(=O)N[C@H](C)c3cnc(C(F)(F)F)nc3)c2)s1] | 3-[5-(propan-2-yl)-1,3-thiazol-2-yl]-5-[(3S)-tetrahydrofuran-3-ylmethoxy]-N-{(1R)-1-[2-(trifluoromethyl)pyrimidin-5-yl]ethyl}benzamide | LCMS (method 1): rt: 1.38 min, MS ES+ m/z = 521 (M + H)+. $^1$H NMR (400 MHz, DMSO-d$_6$) δ [ppm] 1.33 (d, 6 H) 1.61 (d, 3 H) 1.66-1.78 (m, 1 H) 1.98-2.11 (m, 1 H) 2.61-2.76 (m, 1 H) 3.27 (m, 1 H) 3.57 (dd, 1 H) 3.67 (m, 1 H) 3.73-3.86 (m, 2 H) 4.05 (m, 2 H) 5.30 (m, 1 H) 7.53 (dd, 1 H) 7.57 (dd, 1 H) 7.68 (d, 1 H) 7.94 (t, 1 H) 9.07-9.18 (m, 3 H). |
| 282 | 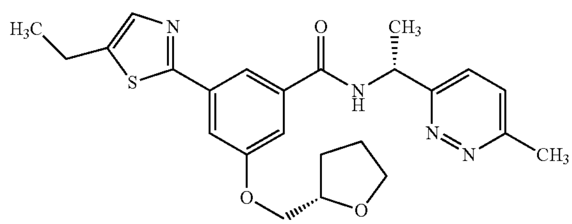 [SMILES: CCc1cnc(-c2cc(OC[C@@H]3CCCO3)cc(C(=O)N[C@H](C)c3ccc(C)nn3)c2)s1] | 3-(5-ethyl-1,3-thiazol-2-yl)-N-[(1R)-1-(6-methylpyridazin-3-yl)ethyl]-5-[(2S)-tetrahydrofuran-2-ylmethoxy]benzamide | LCMS (method 1): rt: 1.11 min, MS ES+ m/z = 453 (M + H)+. $^1$H NMR (400 MHz, DMSO-d$_6$) δ [ppm] 1.29 (t, 3 H) 1.59 (d, 3 H) 1.66-1.78 (m, 1 H) 1.79-1.95 (m, 2 H) 1.96-2.11 (m, 1 H) 2.59 (s, 3 H) 2.90 (m, 2 H) 3.61-3.73 (m, 1 H) 3.75-3.85 (m, 1 H) 3.98-4.14 (m, 2 H) 4.15-4.28 (m, 1 H) 5.37 (m, 1 H) 7.44-7.63 (m, 4 H) 7.67 (t, 1 H) 7.96 (t, 1 H) 9.14 (d, 1 H). |
| 283 | 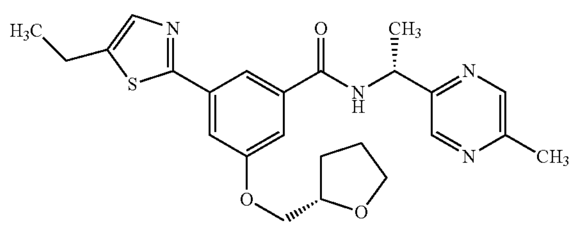 [SMILES: CCc1cnc(-c2cc(OC[C@@H]3CCCO3)cc(C(=O)N[C@H](C)c3cnc(C)cn3)c2)s1] | 3-(5-ethyl-1,3-thiazol-2-yl)-N-[(1R)-1-(5-methylpyrazin-2-yl)ethyl]-5-[(2S)-tetrahydrofuran-2-ylmethoxy]benzamide | LCMS (method 1): rt: 1.20 min, MS ES+ m/z = 453 (M + H)+. $^1$H NMR (400 MHz, DMSO-d$_6$) δ [ppm] 1.29 (t, 3 H) 1.54 (d, 3 H) 1.65-1.78 (m, 1 H) 1.80-1.94 (m, 2 H) 1.97-2.09 (m, 1 H) 2.47 (s, 3 H) 2.90 (m, 2 H) 3.70 (m, 1 H) 3.79 (m, 1 H) 3.99-4.14 (m, 2 H) 4.15-4.26 (m, 1 H) 5.23 (m, 1 H) 7.55 (d, 2 H) 7.67 (t, 1 H) 7.95 (t, 1 H) 8.49 (d, 1 H) 8.56 (d, 1 H) 9.09 (d, 1 H). |
| 284 | 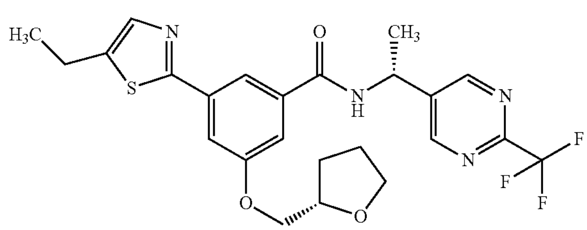 [SMILES: CCc1cnc(-c2cc(OC[C@@H]3CCCO3)cc(C(=O)N[C@H](C)c3cnc(C(F)(F)F)nc3)c2)s1] | 3-(5-ethyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide | LCMS (method 1): rt: 1.34 min, MS ES+ m/z = 507 (M + H)+. $^1$H NMR (400 MHz, DMSO-d$_6$) δ [ppm] 1.29 (t, 3 H) 1.61 (d, 3 H) 1.66-1.77 (m, 1 H) 1.78-1.95 (m, 2 H) 1.96-2.09 (m, 1 H) 2.90 (m, 2 H) 3.64-3.73 (m, 1 H) 3.79 (m, 1 H) 3.99-4.14 (m, 2 H) 4.15-4.25 (m, 1 H) 5.30 (m, 1 H) 7.49-7.60 (m, 2 H) 7.68 (t, 1 H) 7.93 (t, 1 H) 9.07-9.22 (m, 3 H). |

-continued

| Ex. | Structure | Name | Analytical Data |
|---|---|---|---|
| 285 | 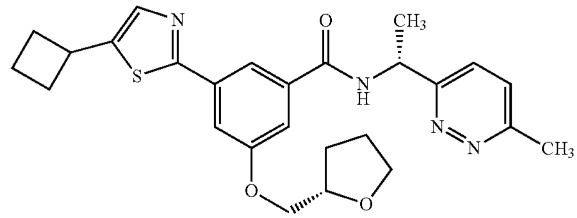 [SMILES: Cc1ccc([C@@H](C)NC(=O)c2cc(OC[C@@H]3CCCO3)cc(-c3ncc(C4CCC4)s3)c2)nn1] | 3-(5-cyclobutyl-1,3-thiazol-2-yl)-N-[(1R)-1-(6-methylpyridazin-3-yl)ethyl]-5-[(2S)-tetrahydrofuran-2-ylmethoxy]benzamide | LCMS (method 1): rt: 1.24 min, MS ES+ m/z = 479 (M + H)+. 1H NMR (400 MHz, DMSO-d6) δ [ppm] 1.59 (d, 3 H) 1.66-1.78 (m, 1 H) 1.90 (m, 3 H) 1.96-2.07 (m, 2 H) 2.08-2.21 (m, 2 H) 2.36-2.48 (m, 2 H) 2.59 (s, 3 H) 3.69 (m, 1 H) 3.80 (m, 2 H) 3.99-4.14 (m, 2 H) 4.15-4.25 (m, 1 H) 5.37 (m, 1 H) 7.49-7.63 (m, 4 H) 7.68 (d, 1 H) 7.97 (t, 1 H) 9.14 (d, 1 H). |
| 286 | 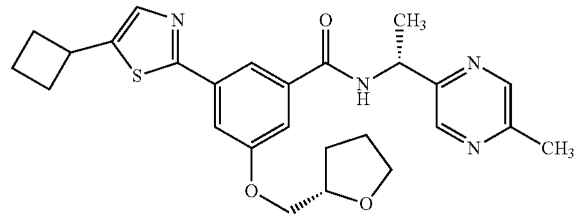 | 3-(5-cyclobutyl-1,3-thiazol-2-yl)-N-[(1R)-1-(5-methylpyrazin-2-yl)ethyl]-5-[(2S)-tetrahydrofuran-2-ylmethoxy]benzamide | LCMS (method 1): rt: 1.32 min, MS ES+ m/z = 479 (M + H)+. 1H NMR (400 MHz, DMSO-d6) d [ppm] 1.54 (d, 3 H) 1.67-1.78 (m, 1 H) 1.90 (m, 3 H) 1.96-2.07 (m, 2 H) 2.08-2.21 (m, 2 H) 2.43 (m, 2 H) 2.47 (s, 3 H) 3.69 (m, 1 H) 3.76-3.88 (m, 2 H) 3.97-4.14 (m, 2 H) 4.14-4.27 (m, 1 H) 5.23 (m, 1 H) 7.51-7.60 (m, 2 H) 7.68 (d, 1 H) 7.96 (t, 1 H) 8.49 (d, 1 H) 8.56 (d, 1 H) 9.10 (d, J = 7.35 Hz, 1 H). |
| 287 | 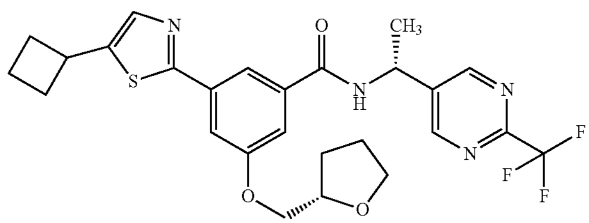 [SMILES: C[C@@H](NC(=O)c1cc(OC[C@@H]2CCCO2)cc(-c2ncc(C3CCC3)s2)c1)c1cnc(C(F)(F)F)nc1] | 3-(5-cyclobutyl-1,3-thiazol-2-yl)-5-[(2S)-tetrahydrofuran-2-ylmethoxy]-N-{(1R)-1-[2-(trifluoromethyl)pyrimidin-5-yl]ethyl}benzamide | LCMS (method 1): rt: 1.44 min, MS ES+ m/z = 533 (M + H)+. 1H NMR (400 MHz, DMSO-d6) δ [ppm] 1.61 (d, 3 H) 1.66-1.78 (m, 1 H) 1.80-1.94 (m, 3 H) 2.00 (m, 2 H) 2.14 (m, 2 H) 2.43 (m, 2 H) 3.70 (m, 1 H) 3.74-3.91 (m, 2 H) 3.98-4.13 (m, 2 H) 4.14-4.27 (m, 1 H) 5.19-5.37 (m, 1 H) 7.44-7.61 (m, 2 H) 7.68 (d, 1 H) 7.95 (t, 1 H) 9.05-9.23 (m, 3 H). |
| 288 | 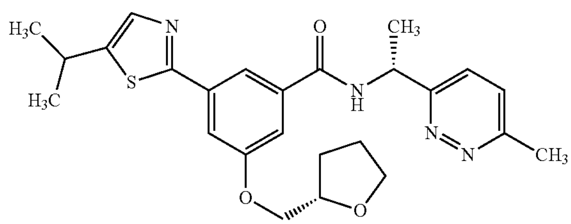 [SMILES: Cc1ccc([C@@H](C)NC(=O)c2cc(OC[C@@H]3CCCO3)cc(-c3ncc(C(C)C)s3)c2)nn1] | N-[(1R)-1-(6-methylpyridazin-3-yl)ethyl]-3-[5-(propan-2-yl)-1,3-thiazol-2-yl]-5-[(2S)-tetrahydrofuran-2-ylmethoxy]benzamide | LCMS (method 1): rt: 1.19 min, MS ES+ m/z = 467 (M + H)+. 1H NMR (400 MHz, DMSO-d6) δ [ppm] 1.33 (d, 6 H) 1.59 (d, 3 H) 1.66-1.77 (m, 1 H) 1.79-1.95 (m, 2 H) 1.96-2.09 (m, 1 H) 2.59 (s, 3 H) 3.21-3.31 (m, 1 H) 3.70 (m, 1 H) 3.79 (m, 1 H) 4.08 (m, 2 H) 4.15-4.26 (m, 1 H) 5.37 (m, 1 H) 7.46-7.63 (m, 4 H) 7.69 (d, 1 H) 7.97 (t, 1 H) 9.14 (d, 1 H). |
| 289 | 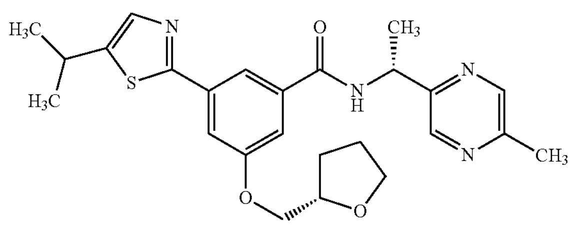 [SMILES: Cc1cnc([C@@H](C)NC(=O)c2cc(OC[C@@H]3CCCO3)cc(-c3ncc(C(C)C)s3)c2)cn1] | N-[(1R)-1-(5-methylpyrazin-2-yl)ethyl]-3-[5-(propan-2-yl)-1,3-thiazol-2-yl]-5-[(2S)-tetrahydrofuran-2-ylmethoxy]benzamide | LCMS (method 1): rt: 1.28 min, MS ES+ m/z = 467 (M + H)+. 1H NMR (400 MHz, DMSO-d6) δ [ppm] 1.33 (d, 6 H) 1.54 (d, 3 H) 1.65-1.77 (m, 1 H) 1.79-1.95 (m, 2 H) 1.96-2.10 (m, 1 H) 2.47 (s, 3 H) 3.28 (m, 1 H) 3.70 (m, 1 H) 3.79 (m, 1 H) 3.98-4.14 (m, 2 H) 4.15-4.26 (m, 1 H) 5.23 (m, 1 H) 7.49-7.61 (m, 2 H) 7.68 (d, 1 H) 7.96 (t, 1 H) 8.49 (d, 1 H) 8.56 (d, 1 H) 9.09 (d, 1 H). |

| Ex. | Structure | Name | Analytical Data |
|---|---|---|---|
| 290 | 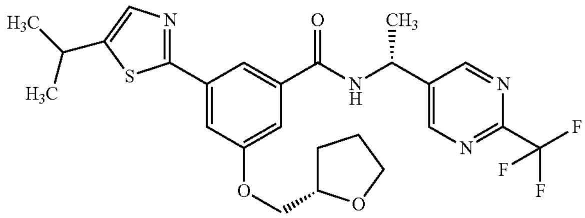 [SMILES: CC(C)c1cnc(-c2cc(OC[C@@H]3CCCO3)cc(C(=O)N[C@H](C)c3cnc(C(F)(F)F)nc3)c2)s1] | 3-[5-(propan-2-yl)-1,3-thiazol-2-yl]-5-[(2S)-tetrahydrofuran-2-ylmethoxy]-N-{(1R)-1-[2-(trifluoromethyl)pyrimidin-5-yl]ethyl}benzamide | LCMS (method 1): rt: 1.40 min, MS ES+ m/z = 521 (M + H)+. $^1$H NMR (400 MHz, DMSO-d$_6$) δ [ppm] 1.33 (d, 6 H) 1.61 (d, 3 H) 1.66-1.77 (m, 1 H) 1.78-1.94 (m, 2 H) 1.96-2.10 (m, 1 H) 3.28 (m, 1 H) 3.64-3.74 (m, 1 H) 3.75-3.86 (m, 1 H) 3.98-4.14 (m, 2 H) 4.15-4.27 (m, 1 H) 5.30 (m, 1 H) 7.49-7.61 (m, 2 H) 7.69 (d, 1 H) 7.94 (t, 1 H) 9.04-9.22 (m, 3 H). |
| 291 | 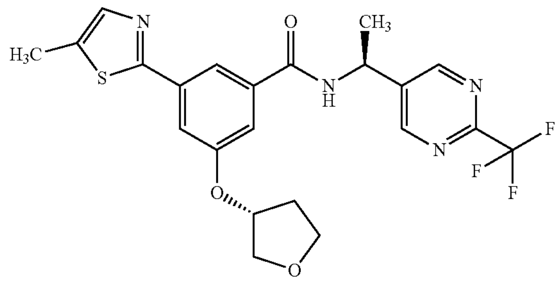 [SMILES: Cc1cnc(-c2cc(O[C@@H]3CCOC3)cc(C(=O)N[C@@H](C)c3cnc(C(F)(F)F)nc3)c2)s1] | 3-(5-methyl-1,3-thiazol-2-yl)-5-[(3R)-tetrahydrofuran-3-yloxy]-N-{(1S)-1-[2-(trifluoromethyl)pyrimidin-5-yl]ethyl}benzamide | LCMS (method 1): rt: 1.20 min, MS ES+ m/z = 479 (M + H)+. $^1$H NMR (400 MHz, DMSO-d$_6$) d [ppm] 1.60 (d, 3 H) 1.93-2.09 (m, 1 H) 2.18-2.31 (m, 1 H) 3.72-3.97 (m, 4 H) 5.13-5.37 (m, 2 H) 7.46-7.58 (m, 2 H) 7.65 (d, 1 H) 7.93 (t, 1 H) 9.05-9.25 (m, 3 H). |
| 292 | 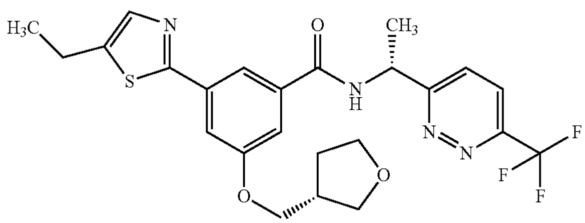 [SMILES: CCc1cnc(-c2cc(OC[C@@H]3CCOC3)cc(C(=O)N[C@H](C)c3ccc(C(F)(F)F)nn3)c2)s1] | 3-(5-ethyl-1,3-thiazol-2-yl)-5-[(3R)-tetrahydrofuran-3-ylmethoxy]-N-{(1R)-1-[6-(trifluoromethyl)pyridazin-3-yl]ethyl}benzamide | LCMS (method 1): rt: 1.29 min, MS ES+ m/z = 507 (M + H)+. $^1$H NMR (400 MHz, DMSO-d$_6$) δ [ppm] 1.29 (t, 3 H) 1.57-1.78 (m, 4 H) 1.95-2.13 (m, 1 H) 2.61-2.79 (m, 1 H) 2.90 (m, 2 H) 3.58 (dd, 1 H) 3.63-3.72 (m, 1 H) 3.73-3.88 (m, 2 H) 3.94-4.19 (m, 2 H) 5.49 (m, 1 H) 7.57 (m, 2 H) 7.68 (t, 1 H) 7.92-8.11 (m, 2 H) 8.25 (d, 1 H) 9.29 (d, 1 H). |
| 293 | 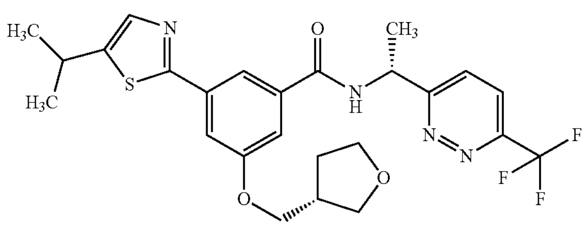 [SMILES: CC(C)c1cnc(-c2cc(OC[C@@H]3CCOC3)cc(C(=O)N[C@H](C)c3ccc(C(F)(F)F)nn3)c2)s1] | 3-[5-(propan-2-yl)-1,3-thiazol-2-yl]-5-[(3R)-tetrahydrofuran-3-ylmethoxy]-N-{(1R)-1-[6-(trifluoromethyl)pyridazin-3-yl]ethyl}benzamide | LCMS (method 1): rt: 1.35 min, MS ES+ m/z = 521 (M + H)+. $^1$H NMR (400 MHz, DMSO-d$_6$) δ [ppm] 1.33 (d, 6 H) 1.65 (m, 4 H) 1.95-2.15 (m, 1 H) 2.62-2.78 (m, 1 H) 3.28 (m, 1 H) 3.51-3.61 (m, 1 H) 3.67 (m, 1 H) 3.73-3.89 (m, 2 H) 3.95-4.17 (m, 2 H) 5.49 (m, 1 H) 7.50-7.64 (m, 2 H) 7.69 (d, 1 H) 7.91-8.10 (m, 2 H) 8.25 (d, 1 H) 9.29 (d, 1 H). |
| 294 | 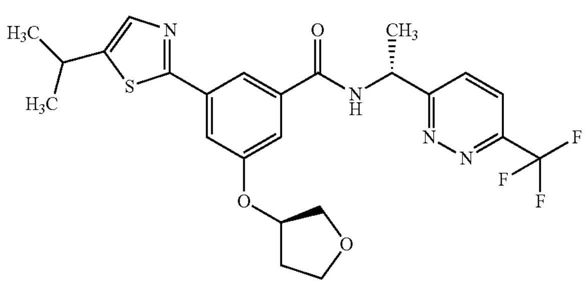 [SMILES: CC(C)c1cnc(-c2cc(O[C@@H]3CCOC3)cc(C(=O)N[C@H](C)c3ccc(C(F)(F)F)nn3)c2)s1] | 3-[5-(propan-2-yl)-1,3-thiazol-2-yl]-5-[(3R)-tetrahydrofuran-3-yloxy]-N-{(1R)-1-[6-(trifluoromethyl)pyridazin-3-yl]ethyl}benzamide | LCMS (method 1): rt: 1.31 min, MS ES+ m/z = 507 (M + H)+. $^1$H NMR (400 MHz, DMSO-d$_6$) δ [ppm] 1.33 (d, 6 H) 1.65 (d, 3 H) 1.93-2.10 (m, 1 H) 2.18-2.31 (m, 1 H) 3.28 (m, 1 H) 3.67-4.01 (m, 4 H) 5.13-5.28 (m, 1 H) 5.49 (m, 1 H) 7.48-7.62 (m, 2 H) 7.70 (d, 1 H) 7.94-8.10 (m, 2 H) 8.25 (d, 1 H) 9.29 (d, 1 H). |

-continued

| Ex. | Structure | Name | Analytical Data |
|---|---|---|---|
| 295 | 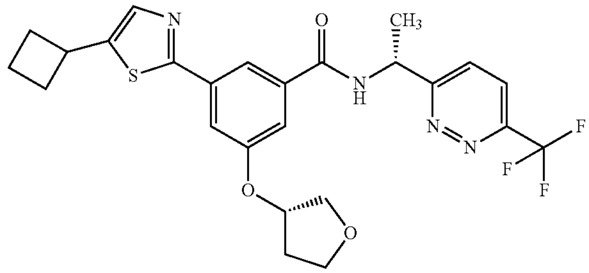 [SMILES: C[C@@H](NC(=O)c1cc(O[C@H]2CCOC2)cc(-c2ncc(C3CCC3)s2)c1)c1ccc(C(F)(F)F)nn1] | 3-(5-cyclobutyl-1,3-thiazol-2-yl)-5-[(3S)-tetrahydrofuran-3-yloxy]-N-{(1R)-1-[6-(trifluoromethyl)pyridazin-3-yl]ethyl}benzamide | LCMS (method 1): rt: 1.35 min, MS ES+ m/z = 519 (M + H)+. 1H NMR (400 MHz, DMSO-d6) δ [ppm] 1.65 (d, 3 H) 1.82-2.06 (m, 3 H) 2.07-2.31 (m, 3 H) 2.43 (m, 2 H) 3.70-3.99 (m, 5 H) 5.22 (m, 1 H) 5.49 (m, 1 H) 7.47-7.60 (m, 2 H) 7.69 (d, 1 H) 7.94-8.14 (m, 2 H) 8.25 (d, 1 H) 9.29 (d, 1 H). |
| 296 | 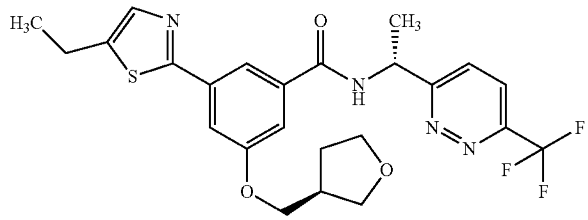 [SMILES: CCc1cnc(-c2cc(OC[C@H]3CCOC3)cc(C(=O)N[C@H](C)c3ccc(C(F)(F)F)nn3)c2)s1] | 3-(5-ethyl-1,3-thiazol-2-yl)-5-[(3S)-tetrahydrofuran-3-ylmethoxy]-N-{(1R)-1-[6-(trifluoromethyl)pyridazin-3-yl]ethyl}benzamide | LCMS (method 1): rt: 1.29 min, MS ES+ m/z = 507 (M + H)+. 1H NMR (400 MHz, DMSO-d6) δ [ppm] 1.29 (t, 3 H) 1.65 (m, 4 H) 1.91-2.12 (m, 1 H) 2.61-2.78 (m, 1 H) 2.90 (m, 2 H) 3.58 (dd, 1 H) 3.67 (m, 1 H) 3.73-3.88 (m, 2 H) 3.94-4.17 (m, 2 H) 5.49 (m, 1 H) 7.57 (m, 2 H) 7.68 (t, 1 H) 7.92-8.10 (m, 2 H) 8.25 (d, 1 H) 9.29 (d, 1 H). |
| 297 | 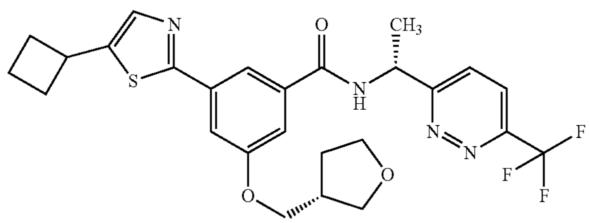 [SMILES: C[C@@H](NC(=O)c1cc(OC[C@@H]2CCOC2)cc(-c2ncc(C3CCC3)s2)c1)c1ccc(C(F)(F)F)nn1] | 3-(5-cyclobutyl-1,3-thiazol-2-yl)-5-[(3R)-tetrahydrofuran-3-ylmethoxy]-N-{(1R)-1-[6-(trifluoromethyl)pyridazin-3-yl]ethyl}benzamide | LCMS (method 1): rt: 1.39 min, MS ES+ m/z = 533 (M + H)+. 1H NMR (400 MHz, DMSO-d6) δ ppm 1.65 (m, 4 H) 1.83-1.95 (m, 1 H) 1.96-2.09 (m, 2 H) 2.10-2.23 (m, 2 H) 2.35-2.48 (m, 2 H) 2.61-2.78 (m, 1 H) 3.58 (dd, 1 H) 3.67 (m, 1 H) 3.73-3.89 (m, 3 H) 3.94-4.15 (m, 2 H) 5.49 (m, 1 H) 7.52-7.62 (m, 2 H) 7.68 (d, 1 H) 7.93-8.09 (m, 2 H) 8.25 (d, 1 H) 9.29 (d, 1 H). |
| 298 | 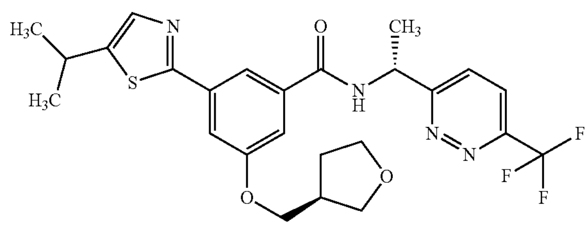 [SMILES: CC(C)c1cnc(-c2cc(OC[C@H]3CCOC3)cc(C(=O)N[C@H](C)c3ccc(C(F)(F)F)nn3)c2)s1] | 3-[5-(propan-2-yl)-1,3-thiazol-2-yl]-5-[(3S)-tetrahydrofuran-3-ylmethoxy]-N-{(1R)-1-[6-(trifluoromethyl)pyridazin-3-yl]ethyl}benzamide | LCMS (method 1): rt: 1.35 min, MS ES+ m/z = 521 (M + H)+. 1H NMR (400 MHz, DMSO-d6) δ [ppm] 1.33 (d, 6 H) 1.65 (m, 4 H) 1.96-2.12 (m, 1 H) 2.60-2.76 (m, 1 H) 3.20-3.31 (m, 1 H) 3.51-3.61 (m, 1 H) 3.62-3.72 (m, 1 H) 3.73-3.89 (m, 2 H) 3.93-4.16 (m, 2 H) 5.37-5.57 (m, 1 H) 7.49-7.62 (m, 2 H) 7.69 (d, 1 H) 7.93-8.09 (m, 2 H) 8.25 (d, 1 H) 9.18-9.36 (m, 1 H). |
| 299 | 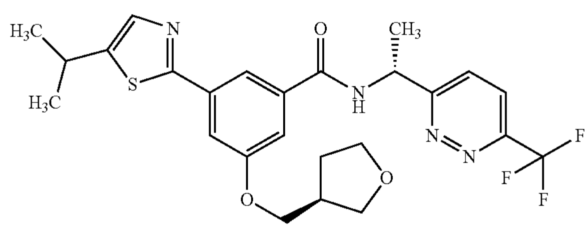 [SMILES: CC(C)c1cnc(-c2cc(OC[C@H]3CCOC3)cc(C(=O)N[C@H](C)c3ccc(C(F)(F)F)nn3)c2)s1] | 3-[5-(propan-2-yl)-1,3-thiazol-2-yl]-5-[(2R)-tetrahydrofuran-2-ylmethoxy]-N-{(1R)-1-[6-(trifluoromethyl)pyridazin-3-yl]ethyl}benzamide | LCMS (method 1): rt: 1.37 min, MS ES+ m/z = 521 (M + H)+. 1H NMR (400 MHz, DMSO-d6) δ [ppm] 1.33 (d, 6 H) 1.65 (d, 3 H) 1.69-1.78 (m, 1 H) 1.79-1.95 (m, 2 H) 1.96-2.09 (m, 1 H) 3.28 (m, 1 H) 3.69 (m, 1 H) 3.79 (m, 1 H) 3.98-4.13 (m, 2 H) 4.14-4.29 (m, 1 H) 5.49 (m, 1 H) 7.51-7.62 (m, 2 H) 7.69 (d, 1 H) 7.94-8.09 (m, 2 H) 8.25 (d, 1 H) 9.28 (d, 1 H). |

| Ex. | Structure | Name | Analytical Data |
|---|---|---|---|
| 300 | 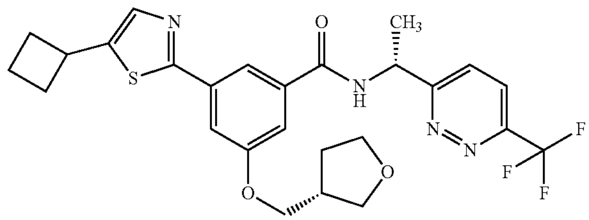 [SMILES: C[C@@H](NC(=O)c1cc(OC[C@@H]2CCOC2)cc(-c2ncc(C3CCC3)s2)c1)c1ccc(C(F)(F)F)nn1] | 3-(5-cyclobutyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide | LCMS (method 1): rt: 1.41 min, MS ES+ m/z = 533 (M + H)+. 1H NMR (400 MHz, DMSO-d6) δ [ppm] 1.65 (d, 3 H) 1.75 (m, 1 H) 1.80-1.95 (m, 3 H) 1.95-2.06 (m, 2 H) 2.08-2.22 (m, 2 H) 2.36-2.48 (m, 2 H) 3.61-3.73 (m, 1 H) 3.75-3.90 (m, 2 H) 3.96-4.14 (m, 2 H) 4.15-4.27 (m, 1 H) 5.49 (m, 1 H) 7.51-7.62 (m, 2 H) 7.68 (d, 1 H) 7.93-8.10 (m, 2 H) 8.25 (d, 1 H) 9.29 (d, 1 H). |
| 301 | 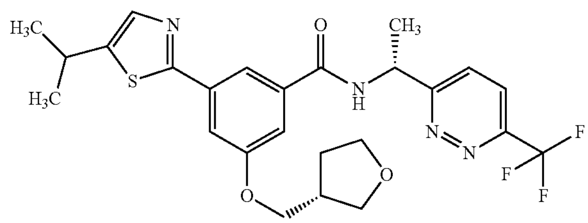 [SMILES: CC(C)c1cnc(-c2cc(OC[C@@H]3CCOC3)cc(C(=O)N[C@H](C)c3ccc(C(F)(F)F)nn3)c2)s1] | 3-[5-(propan-2-yl)-1,3-thiazol-2-yl]-5-[(2S)-tetrahydrofuran-2-ylmethoxy]-N-{(1R)-1-[6-(trifluoromethyl)pyridazin-3-yl]ethyl}benzamide | LCMS (method 1): rt: 1.37 min, MS ES+ m/z = 521 (M + H)+. 1H NMR (400 MHz, DMSO-d6) δ [ppm] 1.33 (d, 6 H) 1.65 (d, 3 H) 1.69-1.77 (m, 1 H) 1.80-1.95 (m, 2 H) 1.97-2.11 (m, 1 H) 3.20-3.32 (m, 1 H) 3.70 (m, 1 H) 3.79 (m, 1 H) 3.98-4.13 (m, 2 H) 4.16-4.26 (m, 1 H) 5.49 (m, 1 H) 7.57 (m, 2 H) 7.69 (d, 1 H) 7.92-8.11 (m, 2 H) 8.25 (d, 1 H) 9.28 (d, 1 H). |
| 302 | 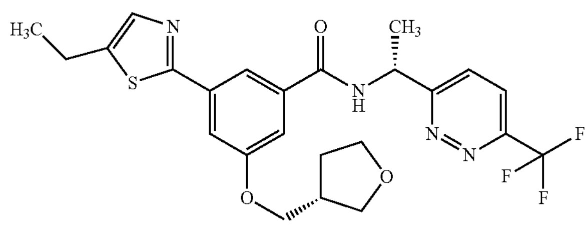 [SMILES: CCc1cnc(-c2cc(OC[C@@H]3CCOC3)cc(C(=O)N[C@H](C)c3ccc(C(F)(F)F)nn3)c2)s1] | 3-(5-ethyl-1,3-thiazol-2-yl)-5-[(2S)-tetrahydrofuran-2-ylmethoxy]-N-{(1R)-1-[6-(trifluoromethyl)pyridazin-3-yl]ethyl}benzamide | LCMS (method 1): rt: 1.30 min, MS ES+ m/z = 507 (M + H)+. 1H NMR (400 MHz, DMSO-d6) δ ppm 1.29 (t, 3 H) 1.65 (d, 3 H) 1.69-1.80 (m, 1 H) 1.80-1.95 (m, 2 H) 1.95-2.09 (m, 1 H) 2.90 (m, 2 H) 3.60-3.75 (m, 1 H) 3.79 (m, 1 H) 3.98-4.13 (m, 2 H) 4.15-4.28 (m, 1 H) 5.37-5.59 (m, 1 H) 7.57 (m, 2 H) 7.68 (t, 1 H) 7.92-8.09 (m, 2 H) 8.25 (d, 1 H) 9.29 (d, 1 H). |
| 303 | 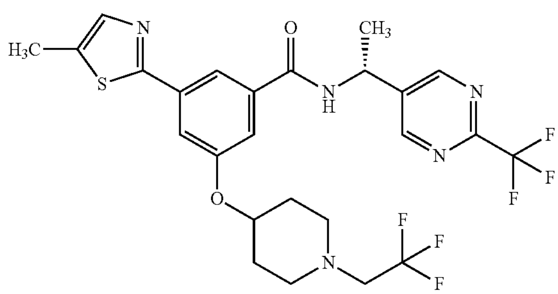 [SMILES: Cc1cnc(-c2cc(OC3CCN(CC(F)(F)F)CC3)cc(C(=O)N[C@H](C)c3cnc(C(F)(F)F)nc3)c2)s1] | 3-(5-methyl-1,3-thiazol-2-yl)-5-{[1-(2,2,2-trifluoroethyl)piperidin-4-yl]oxy}-N-{(1R)-1-[2-(trifluoromethyl)pyrimidin-5-yl]ethyl}benzamide | LCMS (method 1): rt: 1.39 min, MS ES+ m/z = 574 (M + H)+. 1H NMR (400 MHz, DMSO-d6) δ [ppm] 1.61 (d, 3 H) 1.69 (m, 2 H) 1.94 (m, 2 H) 2.55-2.66 (m, 2 H) 2.79-2.94 (m, 2 H) 3.12-3.27 (m, 2 H) 4.52-4.67 (m, 1 H) 5.29 (m, 1 H) 7.46-7.59 (m, 2 H) 7.64 (d, 1 H) 7.90 (t, 1 H) 9.05-9.21 (m, 3 H). |
| 304 | 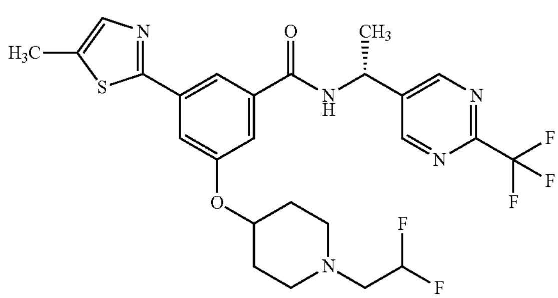 [SMILES: Cc1cnc(-c2cc(OC3CCN(CC(F)F)CC3)cc(C(=O)N[C@H](C)c3cnc(C(F)(F)F)nc3)c2)s1] | 3-{[1-(2,2-difluoroethyl)piperidin-4-yl]oxy}-5-(5-methyl-1,3-thiazol-2-yl)-N-{(1R)-1-[2-(trifluoromethyl)pyrimidin-5-yl]ethyl}benzamide | LCMS (method 1): rt: 0.97 min, MS ES+ m/z = 556 (M + H)+. 1H NMR (400 MHz, DMSO-d6) δ [ppm] 1.61 (m, 5 H) 1.84-2.10 (m, 2 H) 2.62-3.01 (m, 4 H) 4.42-4.73 (m, 1 H) 5.29 (m, 1 H) 5.85-6.42 (m, 1 H) 7.42-7.70 (m, 3 H) 7.91 (s, 1 H) 9.12 (m, 3 H). |

| Ex. | Structure | Name | Analytical Data |
|---|---|---|---|
| 305 | 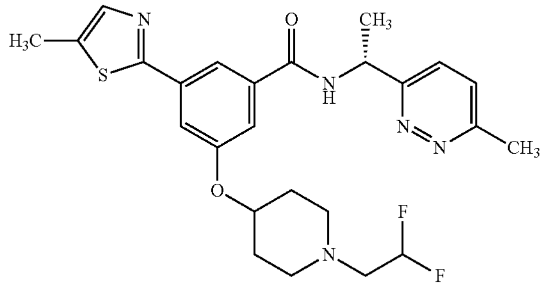 | 3-{[1-(2,2-difluoroethyl)piperidin-4-yl]oxy}-N-[(1R)-1-(6-methylpyridazin-3-yl)ethyl]-5-(5-methyl-1,3-thiazol-2-yl)benzamide | LCMS (method 1): rt: 0.77 min, MS ES+ m/z = 502 (M + H)+. 1H NMR (400 MHz, DMSO-d6) δ [ppm] 1.58 (d, 3 H) 1.62-1.75 (m, 2 H) 1.88-2.03 (m, 2 H) 2.59 (s, 3 H) 2.70-2.89 (m, 4 H) 3.33 (s, 2 H) 4.50-4.67 (m, 1 H) 5.36 (m, 1 H) 6.14 (m, 1 H) 7.48-7.69 (m, 5 H) 7.92 (t, 1 H) 9.14 (d, 1 H). |
| 306 | 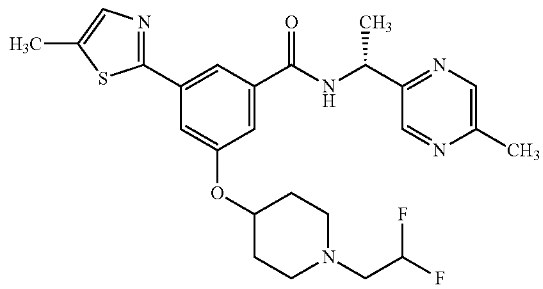 | 3-{[1-(2,2-difluoroethyl)piperidin-4-yl]oxy}-N-[(1R)-1-(5-methylpyrazin-2-yl)ethyl]-5-(5-methyl-1,3-thiazol-2-yl)benzamide | LCMS (method 1): rt: 0.84 min, MS ES+ m/z = 502 (M + H)+. 1H NMR (400 MHz, DMSO-d6) δ [ppm] 1.54 (d, 3 H) 1.69 (br. s., 2 H) 1.94 (br. s., 2 H) 2.47 (s, 3 H) 2.68-2.86 (m, 4 H) 3.21-3.46 (m, 2 H) 4.48-4.66 (m, 1 H) 5.22 (m, 1 H) 6.14 (m, 1 H) 7.48-7.57 (m, 2 H) 7.64 (d, 1 H) 7.91 (t, 1 H) 8.44-8.60 (m, 2 H) 9.10 (d, 1 H). |
| 307 | 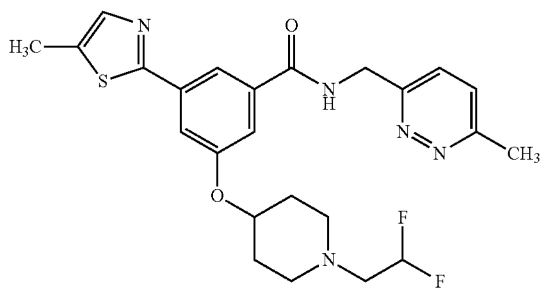 | 3-{[1-(2,2-difluoroethyl)piperidin-4-yl]oxy}-N-[(6-methylpyridazin-3-yl)methyl]-5-(5-methyl-1,3-thiazol-2-yl)benzamide | LCMS (method 2): rt: 1.09 min, MS ES+ m/z = 488 (M + H)+. 1H NMR (400 MHz, DMSO-d6) δ [ppm] 1.68 (m, 2 H) 1.88-2.04 (m, 2 H) 2.55-2.64 (s, 3 H) 2.69-2.85 (m, 4 H) 3.33 (s, 2 H) 4.56 (m, 1 H) 4.73 (d, 2 H) 6.14 (m, 1 H) 7.43-7.58 (m, 4 H) 7.64 (d, 1 H) 7.95 (t, 1 H) 9.39 (s, 1 H). |
| 308 | 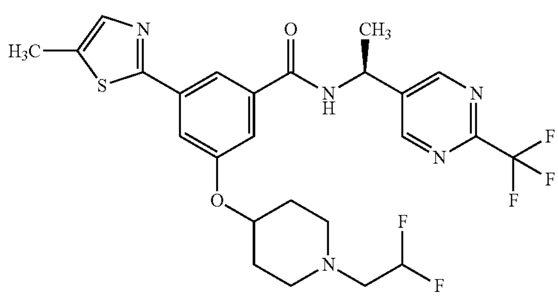 [SMILES: Cc1cnc(-c2cc(OC3CCN(CC(F)F)CC3)cc(C(=O)N[C@@H](C)c3cnc(C(F)(F)F)nc3)c2)s1] | 3-{[1-(2,2-difluoroethyl)piperidin-4-yl]oxy}-5-(5-methyl-1,3-thiazol-2-yl)-N-{(1S)-1-[2-(trifluoromethyl)pyrimidin-5-yl]ethyl}benzamide | LCMS (method 1): rt: 0.98 min, MS ES+ m/z = 556 (M + H)+. 1H NMR (400 MHz, DMSO-d6) δ [ppm] 1.61 (m, 5 H) 1.86-2.18 (m, 2 H) 2.61-3.05 (m, 4 H) 4.35-4.80 (m, 1 H) 5.29 (m, 1 H) 5.85-6.45 (m, 1 H) 7.44-7.71 (m, 3 H) 7.91 (s, 1 H) 9.03-9.27 (m, 3 H). |
| 309 | 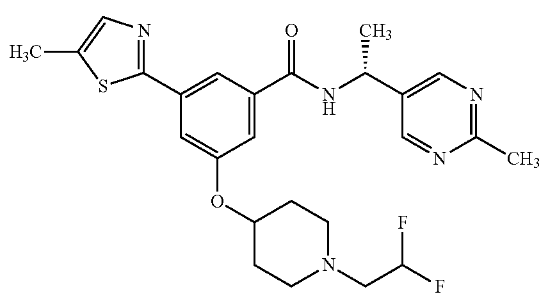 | 3-{[1-(2,2-difluoroethyl)piperidin-4-yl]oxy}-N-[(1R)-1-(2-methylpyrimidin-5-yl)ethyl]-5-(5-methyl-1,3-thiazol-2-yl)benzamide | LCMS (method 1): rt: 0.78 min, MS ES+ m/z = 502 (M + H)+. 1H NMR (400 MHz, DMSO-d6) δ ppm 1.54 (d, 3 H) 1.67 (m, 2 H) 1.94 (m, 2 H) 2.59 (s, 3 H) 2.69-2.84 (m, 4 H) 3.33 (br. s., 2 H) 4.50-4.65 (m, 2 H) 5.09-5.24 (m, 1 H) 6.14 (m, 1 H) 7.52 (m, 2 H) 7.64 (d, 1 H) 7.89 (t, 1 H) 8.71 (s, 2 H) 9.05 (d, 1 H). |

| Ex. | Structure | Name | Analytical Data |
|---|---|---|---|
| 310 | 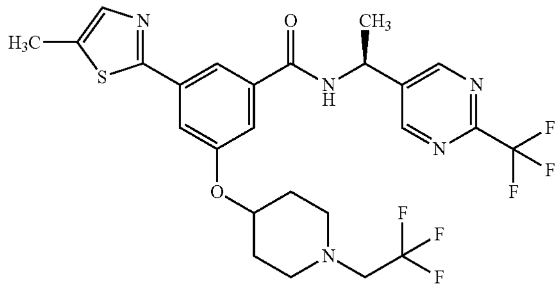 | 3-(5-methyl-1,3-thiazol-2-yl)-5-{[1-(2,2,2-trifluoroethyl)piperidin-4-yl]oxy}-N-{(1S)-1-[2-(trifluoromethyl)pyrimidin-5-yl]ethyl}benzamide | LCMS (method 1): rt: 1.39 min, MS ES+ m/z = 502 (M + H)+. 1H NMR (400 MHz, DMSO-d6) d [ppm] 1.60 (d, 3 H) 1.69 (br. s., 2 H) 1.88-2.03 (m, 2 H) 2.62 (br. s., 2 H) 2.80-2.94 (m, 2 H) 3.10-3.26 (m, 2 H) 4.51-4.70 (m, 1 H) 5.29 (m, 1 H) 7.54 (m, 2 H) 7.64 (d, 1 H) 7.90 (t, 1 H) 9.04-9.24 (m, 3 H). |
| 311 | 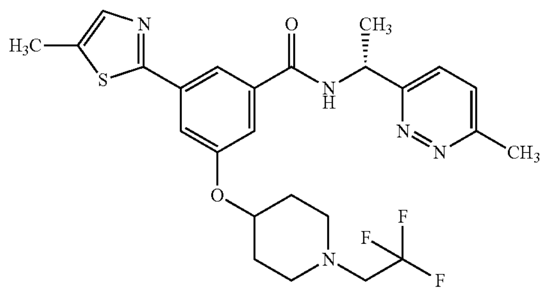 | N-[(1R)-1-(6-methylpyridazin-3-yl)ethyl]-3-(5-methyl-1,3-thiazol-2-yl)-5-{[1-(2,2,2-trifluoroethyl)piperidin-4-yl]oxy}benzamide | LCMS (method 1): rt: 1.15 min, MS ES+ m/z = 52 (M + H)+. 1H NMR (400 MHz, DMSO-d6) δ [ppm] 1.58 (d, 3 H) 1.64-1.79 (m, 2 H) 1.95 (br. s., 2 H) 2.55-2.68 (m, 5 H) 2.85 (m, 2 H) 3.10-3.28 (m, 2 H) 4.51-4.67 (m, 1 H) 5.36 (m, 1 H) 7.45-7.69 (m, 5 H) 7.93 (t, 1 H) 9.14 (d, 1 H). |
| 312 | 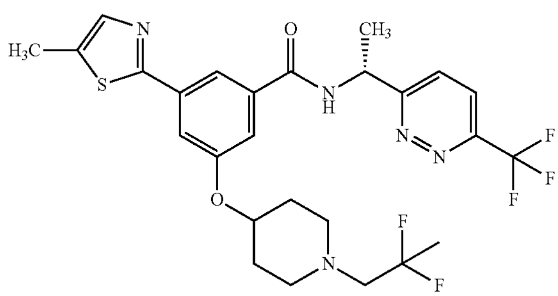 | 3-(5-methyl-1,3-thiazol-2-yl)-5-{[1-(2,2,2-trifluoroethyl)piperidin-4-yl]oxy}-N-{(1R)-1-[6-(trifluoromethyl)pyridazin-3-yl]ethyl}benzamide | LCMS (method 1): rt: 1.35 min, MS ES+ m/z = 574 (M + H)+. 1H NMR (400 MHz, DMSO-d6) δ [ppm] 1.65 (m, 5 H) 1.86-2.05 (m, 2 H) 2.62 (br. s., 2 H) 2.86 (br. s., 2 H) 3.21 (m, 2 H) 4.51-4.67 (m, 1 H) 5.48 (m, 1 H) 7.50-7.69 (m, 3 H) 7.94 (t, 1 H) 8.04 (d, 1 H) 8.25 (d, 1 H) 9.29 (d, 1 H). |
| 313 | 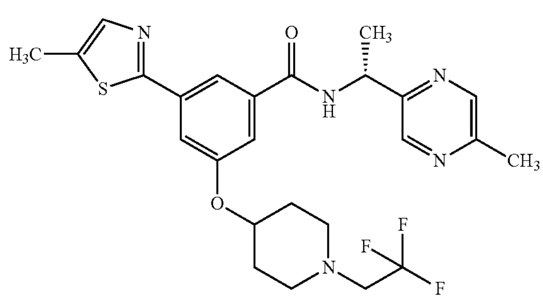 | N-[(1R)-1-(5-methylpyrazin-2-yl)ethyl]-3-(5-methyl-1,3-thiazol-2-yl)-5-{[1-(2,2,2-trifluoroethyl)piperidin-4-yl]oxy}benzamide | LCMS (method 1): rt: 1.25 min, MS ES+ m/z = 520 (M + H)+. 1H NMR (400 MHz, DMSO-d6) δ [ppm] 1.54 (d, 3 H) 1.69 (m, 2 H) 1.94 (br. s., 2 H) 2.47 (s, 3 H) 2.56-2.70 (m, 2 H) 2.80-2.94 (m, 2 H) 3.20 (q, 2 H) 4.50-4.66 (m, 1 H) 5.22 (m, 1 H) 7.45-7.57 (m, 2 H) 7.64 (d, 1 H) 7.92 (t, 1 H) 8.48 (d, 1 H) 8.56 (d, 1 H) 9.09 (d, 1 H). |
| 314 | 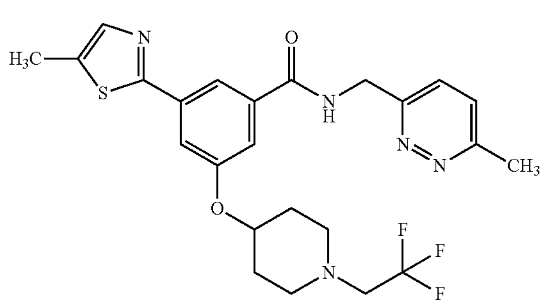 | N-[(6-methylpyridazin-3-yl)methyl]-3-(5-methyl-1,3-thiazol-2-yl)-5-{[1-(2,2,2-trifluoroethyl)piperidin-4-yl]oxy}benzamide | LCMS (method 1): rt: 1.11 min, MS ES+ m/z = 506 (M + H)+. 1H NMR (400 MHz, DMSO-d6) δ [ppm] 1.58-1.77 (m, 2 H) 1.88-2.07 (m, 2 H) 2.56-2.70 (m, 5 H) 2.79-2.94 (m, 2 H) 3.12-3.29 (m, 2 H) 4.51-4.65 (m, 1 H) 4.73 (d, 2 H) 7.48-7.58 (m, 4 H) 7.64 (d, 1 H) 7.95 (t, 1 H) 9.39 (s, 1 H). |

| Ex. | Structure | Name | Analytical Data |
| --- | --- | --- | --- |
| 315 | 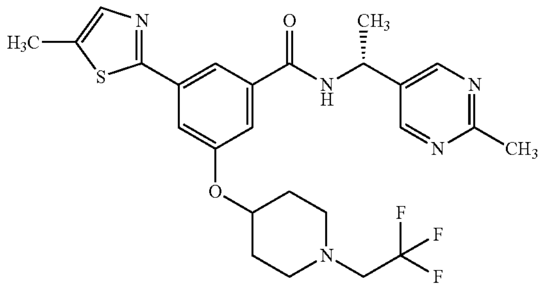 | N-[(1R)-1-(2-methylpyrimidin-5-yl)ethyl]-3-(5-methyl-1,3-thiazol-2-yl)-5-{[1-(2,2,2-trifluoroethyl)piperidin-4-yl]oxy}benzamide | LCMS (method 1): rt: 1.17 min, MS ES+ m/z = 520 (M + H)+. 1H NMR (400 MHz, DMSO-d6) δ [ppm] 1.54 (d, 3 H) 1.68 (m, 2 H) 1.94 (m, 2 H) 2.55-2.70 (m, 5 H) 2.78-2.94 (m, 2 H) 3.12-3.28 (m, 2 H) 4.59 (br. s., 1 H) 5.16 (m, 1 H) 7.42-7.58 (m, 2 H) 7.64 (d, 1 H) 7.89 (t, 1 H) 8.71 (s, 2 H) 9.05 (d, 1 H). |
| 316 | 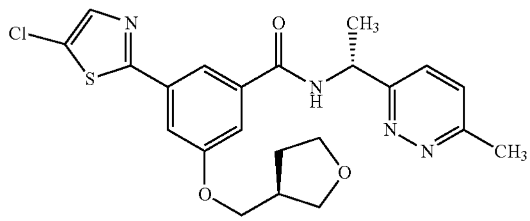 [SMILES: Cc1ccc([C@@H](C)NC(=O)c2cc(OC[C@H]3CCOC3)cc(-c3ncc(Cl)s3)c2)nn1] | 3-(5-chloro-1,3-thiazol-2-yl)-N-[(1R)-1-(6-methylpyridazin-3-yl)ethyl]-5-[(3S)-tetrahydrofuran-3-ylmethoxy]benzamide | LCMS (method 1): rt: 1.11 min, MS ES+ m/z = 459 (M + H)+. 1H NMR (400 MHz, DMSO-d6) δ [ppm] 1.59 (d, 3 H) 1.64-1.79 (m, 1 H) 1.97-2.14 (m, 1 H) 2.59 (s, 3 H) 2.63-2.77 (m, 1 H) 3.57 (dd, 1 H) 3.67 (m, 1 H) 3.81 (td, 2 H) 4.06 (dd, 2 H) 5.36 (m, 1 H) 7.42-7.69 (m, 4 H) 7.90-8.06 (m, 2 H) 9.17 (d, 1 H). |
| 317 | 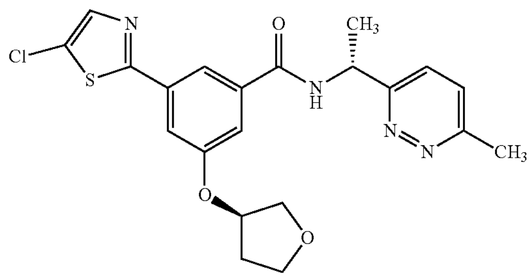 [SMILES: Cc1ccc([C@@H](C)NC(=O)c2cc(O[C@@H]3CCOC3)cc(-c3ncc(Cl)s3)c2)nn1] | 3-(5-chloro-1,3-thiazol-2-yl)-N-[(1R)-1-(6-methylpyridazin-3-yl)ethyl]-5-[(3R)-tetrahydrofuran-3-yloxy]benzamide | LCMS (method 1): rt: 1.06 min, MS ES+ m/z = 445 (M + H)+. 1H NMR (400 MHz, DMSO-d6) δ [ppm] 1.59 (d, J = 7.07 Hz, 3 H) 1.91-2.08 (m, 1 H) 2.15-2.31 (m, 1 H) 2.56-2.63 (s, 3 H) 3.71-3.97 (m, 4 H) 5.22 (m, 1 H) 5.36 (m, 1 H) 7.51-7.67 (m, 4 H) 7.91-8.07 (m, 2 H) 9.17 (d, 1 H). |
| 318 | 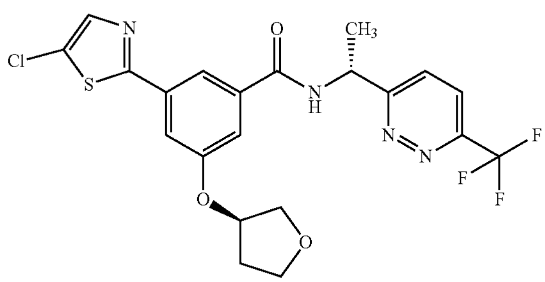 [SMILES: C[C@@H](NC(=O)c1cc(O[C@@H]2CCOC2)cc(-c2ncc(Cl)s2)c1)c1ccc(C(F)(F)F)nn1] | 3-(5-chloro-1,3-thiazol-2-yl)-5-[(3R)-tetrahydrofuran-3-yloxy]-N-{(1R)-1-[6-(trifluoromethyl)pyridazin-3-yl]ethyl}benzamide | LCMS (method 1): rt: 1.26 min, MS ES+ m/z = 499 (M + H)+. 1H NMR (400 MHz, DMSO-d6) δ [ppm] 1.65 (d, 3 H) 1.93-2.08 (m, 1 H) 2.18-2.32 (m, 1 H) 3.67-4.01 (m, 4 H) 5.23 (m, 1 H) 5.48 (m, 1 H) 7.49-7.66 (m, 2 H) 7.90-8.09 (m, 3 H) 8.25 (d, 1 H) 9.31 (d, 1 H). |
| 319 | 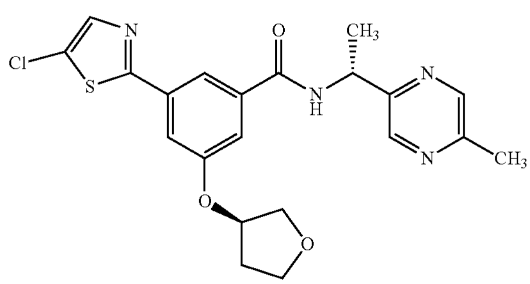 [SMILES: Cc1cnc([C@@H](C)NC(=O)c2cc(O[C@@H]3CCOC3)cc(-c3ncc(Cl)s3)c2)cn1] | 3-(5-chloro-1,3-thiazol-2-yl)-N-[(1R)-1-(5-methylpyrazin-2-yl)ethyl]-5-[(3R)-tetrahydrofuran-3-yloxy]benzamide | LCMS (method 1): rt: 1.15 min, MS ES+ m/z = 445 (M + H)+. 1H NMR (400 MHz, DMSO-d6) δ [ppm] 1.54 (d, 3 H) 1.91-2.06 (m, 1 H) 2.25 (m, 1 H) 2.47 (s, 3 H) 3.70-3.97 (m, 4 H) 5.13-5.30 (m, 2 H) 7.51-7.66 (m, 2 H) 7.90-8.06 (m, 2 H) 8.49 (d, 1 H) 8.56 (d, 1 H) 9.12 (d, 1 H). |

| Ex. | Structure | Name | Analytical Data |
|---|---|---|---|
| 320 | 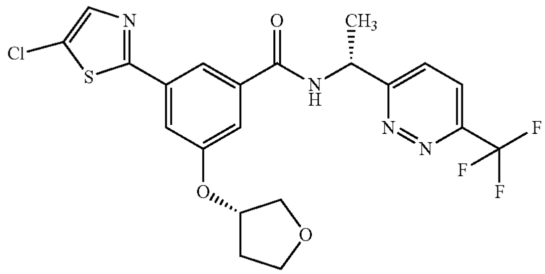 [SMILES: C[C@@H](NC(=O)c1cc(O[C@H]2CCOC2)cc(-c2ncc(Cl)s2)c1)c1ccc(C(F)(F)F)nn1] | 3-(5-chloro-1,3-thiazol-2-yl)-5-[(3S)-tetrahydrofuran-3-yloxy]-N-{(1R)-1-[6-(trifluoromethyl)pyridazin-3-yl]ethyl}benzamide | LCMS (method 1): rt: 1.26 min, MS ES+ m/z = 499 (M + H)+. $^1$H NMR (400 MHz, DMSO-$d_6$) δ [ppm] 1.65 (d, 3 H) 1.89-2.10 (m, 1 H) 2.26 (m, 1 H) 3.69-3.99 (m, 4 H) 5.23 (m, 1 H) 5.48 (m, 1 H) 7.58 (dt, 2 H) 7.90-8.12 (m, 3 H) 8.25 (d, 1 H) 9.31 (d, 1 H). |
| 321 | 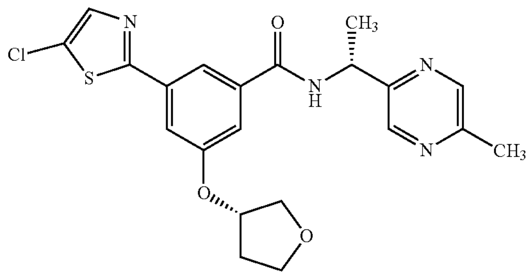 [SMILES: Cc1cnc([C@@H](C)NC(=O)c2cc(O[C@H]3CCOC3)cc(-c3ncc(Cl)s3)c2)cn1] | 3-(5-chloro-1,3-thiazol-2-yl)-N-[(1R)-1-(5-methylpyrazin-2-yl)ethyl]-5-[(3S)-tetrahydrofuran-3-yloxy]benzamide | LCMS (method 1): rt: 1.16 min, MS ES+ m/z = 445 (M + H)+. $^1$H NMR (400 MHz, DMSO-$d_6$) δ [ppm] 1.54 (d, 3 H) 1.94-2.09 (m, 1 H) 2.17-2.33 (m, 1 H) 2.47 (s, 3 H) 3.71-3.97 (m, 4 H) 5.12-5.29 (m, 2 H) 7.56 (dt, 2 H) 7.91-8.04 (m, 2 H) 8.49 (d, 1 H) 8.56 (d, 1 H) 9.12 (d, 1 H). |
| 322 | 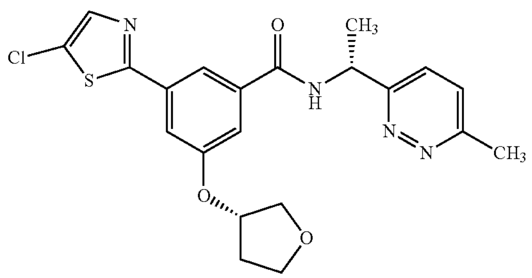 [SMILES: Cc1ccc([C@@H](C)NC(=O)c2cc(O[C@H]3CCOC3)cc(-c3ncc(Cl)s3)c2)nn1] | 3-(5-chloro-1,3-thiazol-2-yl)-N-[(1R)-1-(6-methylpyridazin-3-yl)ethyl]-5-[(3S)-tetrahydrofuran-3-yloxy]benzamide | LCMS (method 1): rt: 1.06 min, MS ES+ m/z = 445 (M + H)+. $^1$H NMR (400 MHz, DMSO-$d_6$) δ [ppm] 1.59 (d, 3 H) 1.93-2.12 (m, 1 H) 2.26 (m, 1 H) 2.59 (s, 3 H) 3.71-3.98 (m, 4 H) 5.23 (m, 1 H) 5.36 (m, 1 H) 7.48-7.66 (m, 4 H) 7.92-8.06 (m, 2 H) 9.17 (d, 1 H). |
| 323 | 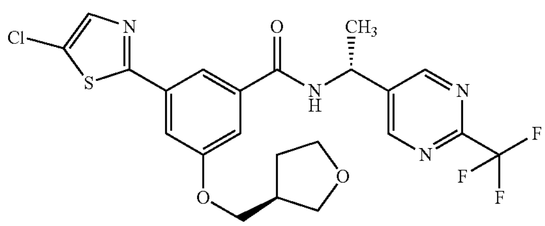 [SMILES: C[C@@H](NC(=O)c1cc(OC[C@H]2CCOC2)cc(-c2ncc(Cl)s2)c1)c1cnc(C(F)(F)F)nc1] | 3-(5-chloro-1,3-thiazol-2-yl)-5-[(3S)-tetrahydrofuran-3-ylmethoxy]-N-{(1R)-1-[2-(trifluoromethyl)pyrimidin-5-yl]ethyl}benzamide | LCMS (method 1): rt: 1.31 min, MS ES+ m/z = 513 (M + H)+. $^1$H NMR (400 MHz, CHLOROFORM-d) δ [ppm] 1.69 (m, 4 H) 1.98-2.17 (m, 1 H) 2.59-2.78 (m, 1 H) 3.59-3.79 (m, 2 H) 3.80-4.03 (m, 4 H) 5.43-5.63 (m, 1 H) 7.36 (dd, 1 H) 7.47 (dd, 2 H) 7.60 (s, 1 H) 7.64-7.72 (m, 1 H) 7.74-7.82 (m, 2 H). |
| 324 | 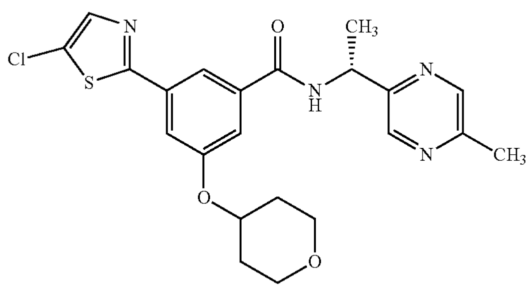 [SMILES: Cc1cnc([C@@H](C)NC(=O)c2cc(OC3CCOCC3)cc(-c3ncc(Cl)s3)c2)cn1] | 3-(5-chloro-1,3-thiazol-2-yl)-N-[(1R)-1-(5-methylpyrazin-2-yl)ethyl]-5-(tetrahydro-2H-pyran-4-yloxy)benzamide | LCMS (method 1): rt: 1.21 min, MS ES+ m/z = 459 (M + H)+. $^1$H NMR (400 MHz, DMSO-$d_6$) d [ppm] 1.54 (d, 3 H) 1.62 (m, 2 H) 2.00 (m, 2 H) 2.47 (s, 3 H) 3.44-3.60 (m, 2 H) 3.76-3.93 (m, 2 H) 4.77 (m, 1 H) 5.22 (m, 1 H) 7.51-7.67 (m, 2 H) 7.88-8.06 (m, 2 H) 8.43-8.60 (m, 2 H) 9.11 (d, 1 H). |

| Ex. | Structure | Name | Analytical Data |
|---|---|---|---|
| 325 | 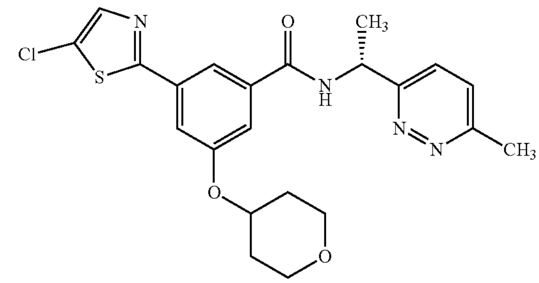 [SMILES: Cc1ccc([C@@H](C)NC(=O)c2cc(OC3CCOCC3)cc(-c3ncc(Cl)s3)c2)nn1] | 3-(5-chloro-1,3-thiazol-2-yl)-N-[(1R)-1-(6-methylpyridazin-3-yl)ethyl]-5-(tetrahydro-2H-pyran-4-yloxy)benzamide | LCMS (method 1): rt: 1.11 min, MS ES+ m/z = 459 (M + H)+. 1H NMR (400 MHz, DMSO-d6) δ [ppm] 1.59 (m, 5 H) 1.91-2.06 (m, 2 H) 2.59 (s, 3 H) 3.52 (m, 2 H) 3.86 (m, 2 H) 4.73-4.85 (m, 1 H) 5.36 (m, 1 H) 7.51-7.65 (m, 4 H) 7.90-8.07 (m, 2 H) 9.16 (d, 1 H). |
| 326 | 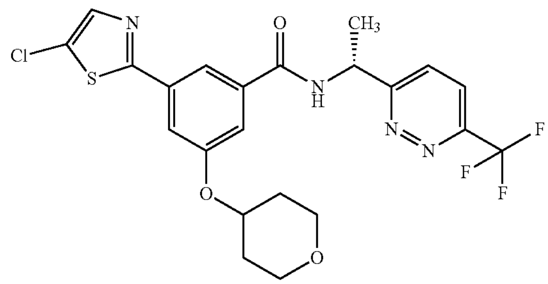 [SMILES: C[C@@H](NC(=O)c1cc(OC2CCOCC2)cc(-c2ncc(Cl)s2)c1)c1ccc(C(F)(F)F)nn1] | 3-(5-chloro-1,3-thiazol-2-yl)-5-(tetrahydro-2H-pyran-4-yloxy)-N-{(1R)-1-[6-(trifluoromethyl)pyridazin-3-yl]ethyl}benzamide | LCMS (method 1): rt: 1.31 min, MS ES+ m/z = 513 (M + H)+. 1H NMR (400 MHz, DMSO-d6) δ [ppm] 1.65 (m, 5 H) 1.99 (m, 2 H) 3.52 (m, 2 H) 3.86 (m, 2 H) 4.69-4.85 (m, 1 H) 5.48 (m, 1 H) 7.57-7.68 (m, 2 H) 7.90-8.10 (m, 3 H) 8.25 (d, 1 H) 9.30 (d, 1 H). |
| 327 | 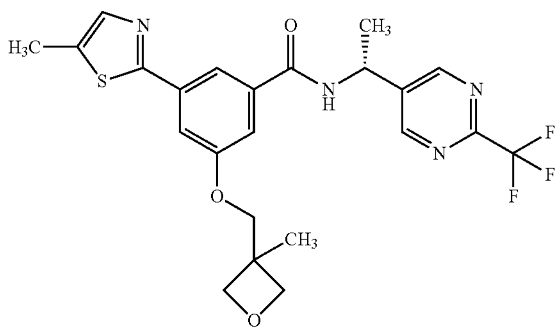 [SMILES: Cc1cnc(-c2cc(OCC3(C)COC3)cc(C(=O)N[C@H](C)c3cnc(C(F)(F)F)nc3)c2)s1] | 3-[(3-methyloxetan-3-yl)methoxy]-5-(5-methyl-1,3-thiazol-2-yl)-N-{(1R)-1-[2-(trifluoromethyl)pyrimidin-5-yl]ethyl}benzamide | LCMS (method 1): rt: 1.25 min, MS ES+ m/z = 493 (M + H)+. 1H NMR (400 MHz, DMSO-d6) δ [ppm] 1.39 (s, 3 H) 1.61 (d, 3 H) 4.19 (s, 2 H) 4.33 (d, 2 H) 4.54 (d, 2 H) 5.30 (s, 1 H) 7.52-7.72 (m, 3 H) 7.94 (t, 1 H) 9.12 (s, 2 H) 9.19 (d, 1 H). |
| 328 | 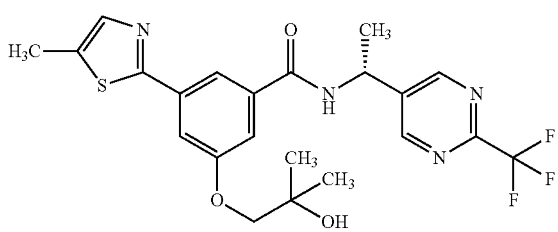 [SMILES: Cc1cnc(-c2cc(OCC(C)(C)O)cc(C(=O)N[C@H](C)c3cnc(C(F)(F)F)nc3)c2)s1] | 3-(2-hydroxy-2-methylpropoxy)-5-(5-methyl-1,3-thiazol-2-yl)-N-{(1R)-1-[2-(trifluoromethyl)pyrimidin-5-yl]ethyl}benzamide | LCMS (method 1): rt: 1.18 min, MS ES+ m/z = 481 (M + H)+. 1H NMR (400 MHz, DMSO-d6) δ [ppm] 1.23 (s, 6 H) 1.61 (d, 3 H) 3.84 (s, 2 H) 4.70 (s, 1 H) 5.30 (m, 1 H) 7.46-7.59 (m, 2 H) 7.64 (d, 1 H) 7.92 (t, 1 H) 9.12 (s, 2 H) 9.19 (d, 1 H). |

Example 329

3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide, as a mixture of two diastereoisomers

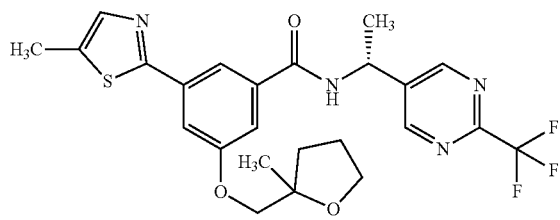 [SMILES: Cc1cnc(-c2cc(OCC3(C)CCCO3)cc(C(=O)N[C@H](C)c3cnc(C(F)(F)F)nc3)c2)s1]

Example 329 (69 mg) was prepared from Intermediate 5BX in analogy to the procedure described for Example 232.

LCMS (method 1): rt: 1.30 min, MS ES+m/z=507 (M+H)+.

1H NMR (400 MHz, DMSO-d6) δ [ppm] 1.24-1.32 (s, 3H) 1.61 (d, 3H) 1.65-1.74 (m, 1H) 1.93 (m, 3H) 3.70-3.84 (m, 2H) 3.95 (s, 2H) 5.20-5.40 (m, 1H) 7.49-7.59 (m, 2H) 7.64 (d, 1H) 7.92 (t, 1H) 9.06-9.23 (m, 3H).

Example 329 (54.5 mg, 108 μmol) was separated into two diastereoisomers by preparative chiral HPLC (method A, 54.5 mg in 2.5 ml ethanol) to give Example 330 (Diastereoisomer 1, 16 mg, rt: 5.6-7.4 min) and Example 331 (Diastereoisomer 2, 16 mg, rt: 8.0-10.1 min).

Example 330

Diastereoisomer 1; 3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide Analytical chiral HPLC, method A, rt: 2.61 min
$^1$H NMR (500 MHz, DMSO-$d_6$) δ [ppm] 1.28 (s, 3H) 1.61 (d, 3H) 1.65-1.75 (m, 1H) (m, 3H) 3.70-3.85 (m, 2H) 3.95 (d, 2H) 5.30 (m, 1H) 7.55 (m, 2H) 7.64 (d, 1H) 7.92 (t, 1H) 9.07-9.23 (m, 3H).

Example 331

Diastereoisomer 2; 3-[(2-methyltetrahydrofuran-2-yl)methoxy]-5-(5-methyl-1,3-thiazol-2-yl)-N-{(1R)-1-[2-(trifluoromethyl)pyrimidin-5-yl]ethyl}benzamide Analytical chiral HPLC, method A, rt: 3.16 min
$^1$H NMR (500 MHz, DMSO-$d_6$) δ [ppm] 1.28 (s, 3H) 1.61 (d, 3H) 1.65-1.77 (m, 1H) 1.93 (m, 3H) 3.70-3.86 (m, 2H) 3.95 (s, 2H) 5.30 (m, 1H) 7.55 (m, 2H) 7.64 (d, 1H) 7.92 (t, 1H) 9.05-9.24 (m, 3H).

Example 332

3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide, as a mixture of two diastereoisomers

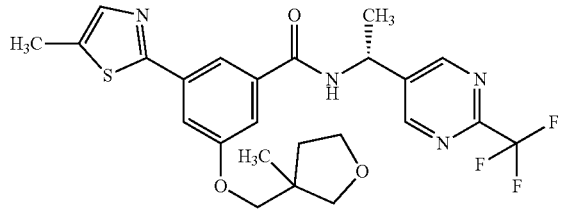 [SMILES: Cc1cnc(-c2cc(OCC3(C)CCOC3)cc(C(=O)N[C@H](C)c3cnc(C(F)(F)F)nc3)c2)s1]

Example 332 (1070 mg) was prepared from Intermediate 5BY in analogy to the procedure described for Example 232.
LCMS (method 1): rt: 1.32 min, MS ES+m/z=507 (M+H)$^+$.
$^1$H NMR (400 MHz, DMSO-$d_6$) δ [ppm] 1.21 (s, 3H) 1.55-1.74 (m, 4H) 1.93 (m, 1H) 3.39 (d, 1H) 3.71 (d, 1H) 3.74-3.88 (m, 2H) 3.96 (s, 2H) 5.30 (m, 1H) 7.47-7.71 (m, 3H) 7.92 (t, 1H) 9.07-9.25 (m, 3H).

Example 332 (1000 mg, 1.97 mmol) was separated into two diastereoisomers by preparative chiral HPLC (method B, 1000 mg in 7 ml DCM/methanol (1:1)) to give Example 333 (Diastereoisomer 1, 294 mg, rt: 6.0-8.0 min) and Example 334 (Diastereoisomer 2, 276 mg, rt: 9.0-10.0 min).

Example 333

Diastereoisomer 1; 3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide Analytical chiral HPLC, method B, rt: 2.89 min
$^1$H NMR (500 MHz, DMSO-$d_6$) δ [ppm] 1.21 (s, 3H) 1.61 (m, 4H) 1.88-2.03 (m, 1H) 3.39 (d, 1H) 3.71 (d, 1H) 3.81 (td, 2H) 3.96 (s, 2H) 5.30 (m, 1H) 7.48-7.60 (m, 2H) 7.64 (d, 1H) 7.92 (t, 1H) 9.04-9.24 (m, 3H).

Example 334

Diastereoisomer 2; 3-[(3-methyltetrahydrofuran-3-yl)methoxy]-5-(5-methyl-1,3-thiazol-2-yl)-N-{(1R)-1-[2-(trifluoromethyl)pyrimidin-5-yl]ethyl}benzamide Analytical chiral HPLC, method B, rt: 4.26 min
$^1$H NMR (500 MHz, DMSO-$d_6$) δ [ppm] 1.21 (s, 3H) 1.51-1.74 (m, 4H) 1.86-2.01 (m, 1H) 3.39 (d, 1H) 3.71 (d, 1H) 3.80 (td, 2H) 3.96 (s, 2H) 5.30 (m, 1H) 7.46-7.59 (m, 2H) 7.64 (d, 1H) 7.92 (t, 1H) 9.06-9.25 (m, 3H).

Example 335

3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide, as a mixture of two diastereoisomers

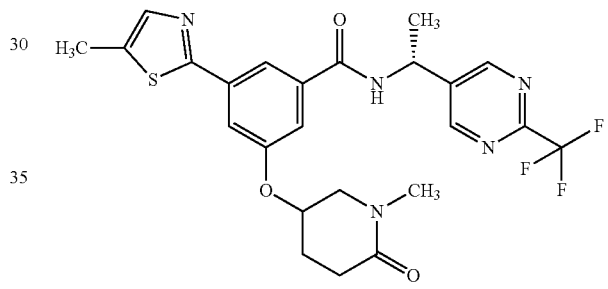

Example 335 (760 mg) was prepared from Intermediate 5BZ in analogy to the procedure described for example 232.
LCMS (method 1): rt: 1.09 min, MS ES+m/z=520 (M+H)$^+$.
$^1$H NMR (400 MHz, DMSO-$d_6$) δ [ppm] 1.60 (d, 3H) 2.07 (m, 2H) 2.18-2.43 (m, 2H) 2.82 (s, 3H) 3.37-3.51 (m, 1H) 3.60-3.75 (m, 1H) 4.96-5.13 (m, 1H) 5.20-5.36 (m, 1H) 7.52-7.70 (m, 3H) 7.94 (t, 1H) 9.04-9.23 (m, 3H).

Example 335 (700 mg, 1.35 mmol) was separated into two diastereoisomers by preparative chiral HPLC (method E, 700 mg in 6 ml DCM/methanol (1:1)) to give Example 336 (Diastereoisomer 1, 150 mg, rt: 7.00-9.00 min) and Example 337 (Diastereoisomer 2, 140 mg, rt: 10.00-12.60 min).

Example 336

Diastereoisomer 1; 3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide Analytical chiral HPLC, method E, rt: 2.11 min
$^1$H NMR (600 MHz, DMSO-$d_6$) δ [ppm] 1.61 (d, 3H) 2.07 (m, 2H) 2.21-2.32 (m, 1H) 2.33-2.43 (m, 1H) 2.82 (s, 3H) 3.39-3.50 (m, 1H) 3.64-3.75 (m, 1H) 5.05 (m, 1H) 5.30 (m, 1H) 7.56-7.72 (m, 3H) 7.94 (s, 1H) 9.06-9.23 (m, 3H).

Example 337

Diastereoisomer 2; 3-[(1-methyl-6-oxopiperidin-3-yl)oxy]-5-(5-methyl-1,3-thiazol-2-yl)-N-{(1R)-1-[2-(trifluoromethyl)pyrimidin-5-yl]ethyl}benzamide Analytical chiral HPLC, method E, rt: 2.88 min
$^1$H NMR (600 MHz, DMSO-d$_6$) δ [ppm] 1.61 (d, 3H) 2.01-2.14 (m, 2H) 2.21-2.30 (m, 1H) 2.33-2.42 (m, 1H) 2.82 (s, 3H) 3.37-3.49 (m, 1H) 3.63-3.74 (m, 1H) 4.95-5.12 (m, 1H) 5.22-5.37 (m, 1H) 7.55-7.71 (m, 3H) 7.94 (t, 1H) 9.12 (s, 3H).

Example 338

3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide, as a mixture of cis isomers

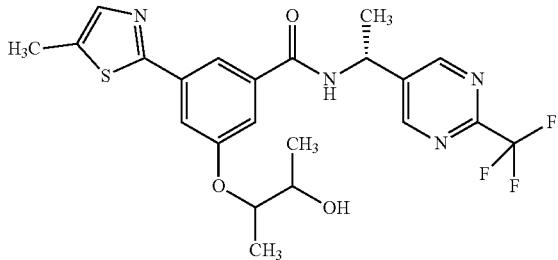 [SMILES: Cc1cnc(-c2cc(OC(C)C(C)O)cc(C(=O)N[C@H](C)c3cnc(C(F)(F)F)nc3)c2)s1]

Example 338 (154 mg) was prepared from Intermediate 5CB in analogy to the procedure described for example 232.
LCMS (method 1): rt: 1.18 min, MS ES+m/z=481 (M+H)$^+$.
$^1$H NMR (400 MHz, DMSO-d$_6$) δ [ppm] 1.11 (d, 3H) 1.21 (dd, 3H) 1.61 (d, 3H) 3.68-3.86 (m, 1H) 4.34-4.48 (m, 1H) 4.87 (dd, 1H) 5.20-5.38 (m, 1H) 7.53 (m, 2H) 7.64 (d, 1H) 7.89 (s, 1H) 9.06-9.22 (m, 3H).
Example 338 (646 mg, 1.34 mmol) was separated into two diastereoisomers by preparative chiral HPLC (method D, 646 mg in 5 ml DCM/methanol (1:1)) to give
Example 339 (Cis Isomer 1, 197 mg, rt: 9.7-10.8 min) and Example 340 (Cis Isomer 2, 198 mg, rt: 11.7-13.4 min).

Example 339

Cis Isomer 1; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide Analytical chiral HPLC, method D, rt: 5.73 min
$^1$H NMR (400 MHz, DMSO-d$_6$) δ [ppm] 1.09-1.12 (m, 6H) 1.21 (d, 3H) 1.61 (d, J=7.35 Hz, 3H) 3.69-3.85 (m, 1H) 4.43 (m, 1H) 4.86 (d, 1H) 5.29 (m, 1H) 7.47-7.58 (m, 2H) 7.64 (d, 1H) 7.89 (t, 1H) 9.05-9.22 (m, 3H).

Example 340

Cis Isomer 2; 3-[(3-hydroxybutan-2-yl)oxy]-5-(5-methyl-1,3-thiazol-2-yl)-N-{(1R)-1-[2-(trifluoromethyl)pyrimidin-5-yl]ethyl}benzamide Analytical chiral HPLC, method D, rt: 6.97 min
$^1$H NMR (400 MHz, DMSO-d$_6$) δ [ppm] 1.09-1.14 (m, 3H) 1.20 (d, 3H) 1.61 (d, 3H) 3.64-3.87 (m, 1H) 4.33-4.50 (m, 1H) 4.87 (d, 1H) 5.18-5.38 (m, 1H) 7.53 (m, 2H) 7.64 (d, 1H) 7.89 (t1H) 9.05-9.24 (m, 3H).

Example 341

3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide, as a mixture of two stereoisomers

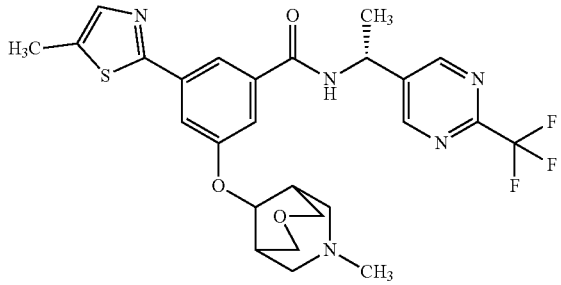 [SMILES: Cc1cnc(-c2cc(OC3C4COCC3CN(C)C4)cc(C(=O)N[C@H](C)c3cnc(C(F)(F)F)nc3)c2)s1]

A mixture of Intermediate 109 (100 mg, 187 μmol), formaldehyde (140 μl, 37% solution, 1.9 mmol), acetic acid (107 μl, 100%, 1.9 mmol) in 1,2-dichlorethane (1.5 mL) was stirred at RT for 30 min. Sodium triacetoxyborohydride (113 mg, 1.9 mmol) was added and the mixture stirred at RT for 17 h. A saturated aquous NaHCO$_3$-solution was added and the aqueous layer extracted twice with DCM. The combined organic layers were evaporated to dryness under reduced pressure and the residue purified by column chromatography to give 57 mg (55% yield) of the title compound.
LCMS (method 1): rt: 0.92 min, MS ES+m/z=548 (M+H)$^+$.
$^1$H NMR (400 MHz, DMSO-d$_6$) δ [ppm] 1.61 (d, 6H) 1.91 (br. s., 2H) 1.96-2.05 (m, 2H) 2.16 (s, 6H) 2.55-2.64 (m, 2H) 2.71-2.86 (m, 2H) 2.96-3.09 (m, 2H) 3.58-3.70 (m, 2H) 3.72-3.86 (m, 2H) 3.90-4.05 (m, 4H) 4.58-4.69 (m, 1H) 4.71-4.85 (m, 1H) 5.20-5.37 (m, 2H) 7.51-7.69 (m, 6H) 7.94 (s, 2H) 9.12 (s, 4H) 9.17-9.25 (m, 2H).
Example 341 (281 mg, 0.51 mmol) was separated into two stereoisomers by preparative HPLC (method F, 281 mg in 4 ml DMSO) to give Example 342 (stereoisomer 1, 125 mg, rt: 7.0-8.0 min) and Example 343 (stereoisomer 2, 100 mg, rt: 9.0-11.0 min).

Example 342

Stereoisomer 1; 3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide Analytical HPLC, method F, rt: 2.38 min
$^1$H NMR (400 MHz, DMSO-d$_6$) δ [ppm] 1.61 (d, 3H) 1.91 (br. s., 2H) 2.17 (s, 3H) 3.05 (d, 2H) 3.65 (d, 2H) 3.98 (d, 2H) 4.63 (br. s., 1H) 5.29 (m, 1H) 7.51-7.70 (m, 3H) 7.94 (t, 1H) 9.12 (s, 2H) 9.19 (d, 1H).

Example 343

Stereoisomer 2; 3-[(7-methyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide Analytical HPLC, method F, rt: 2.89 min
$^1$H NMR (400 MHz, DMSO-d$_6$) δ [ppm] 1.62 (d, 3H) 2.00 (br. s., 2H) 2.14 (s, 3H) 2.54-2.64 (m, 2H) 2.69-2.82 (m, 2H) 3.80 (m, 2H) 3.95 (m, 2H) 4.77 (br. s., 1H) 5.21-5.38 (m, 1H) 7.49-7.72 (m, 3H) 7.94 (t, 1H) 9.13 (s, 2H) 9.17-9.26 (m, 1H).

Example 344

3-[(7-isopropyl-3-oxa-7-azabicyclo[3.3.1]non-9-yl)oxy]-5-(5-methyl-1,3-thiazol-2-yl)-N-{(1R)-1-[2-(trifluoromethyl)pyrimidin-5-yl]ethyl}benzamide, as a mixture of two stereoisomers

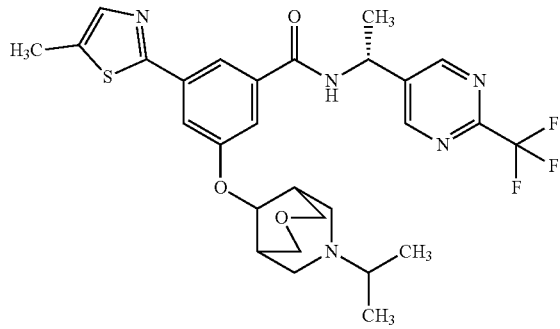 [SMILES: Cc1cnc(-c2cc(OC3C4COCC3CN(C(C)C)C4)cc(C(=O)N[C@H](C)c3cnc(C(F)(F)F)nc3)c2)s1]

Example 344 (66.7 mg) was prepared from Intermediate 109 (100 mg, 187 μmol) in analogy to the procedure described for Example 341.

LCMS (method 1): rt: 0.95 min, MS ES+m/z=576 (M+H)$^+$.

$^1$H NMR (400 MHz, DMSO-d$_6$) δ [ppm] 0.99 (m, 12H) 1.61 (d, 6H) 1.92 (br. s., 2H) 1.96-2.05 (m, 2H) 2.60-2.78 (m, 6H) 2.93-3.08 (m, 2H) 3.62 (m, 2H) 3.80 (m, 2H) 3.91 (m, 4H) 4.54-4.67 (m, 1H) 4.71-4.84 (m, 1H) 5.29 (m, 2H) 7.50-7.67 (m, 6H) 7.93 (s, 2H) 9.12 (s, 4H) 9.17-9.30 (m, 2H).

Example 345 methyl 9-[3-(5-methyl-1,3-thiazol-2-yl)-5-({(1R)-1-[2-(trifluoro-methyl)pyrimidin-5-yl]ethyl}carbamoyl)phenoxy]-3-oxa-7-azabicycle[3.3.1]nonane-7-carboxylate, as a mixture of two stereoisomers

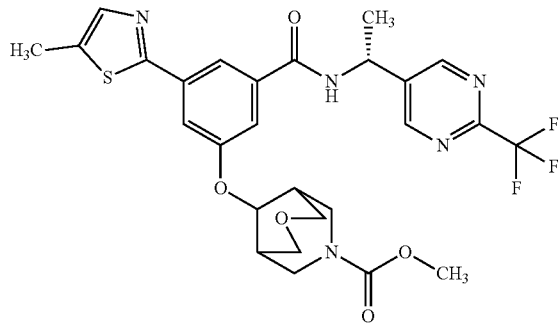 [SMILES: COC(=O)N1CC2COCC(C1)C2Oc1cc(C(=O)N[C@H](C)c2cnc(C(F)(F)F)nc2)cc(-c2ncc(C)s2)c1]

To a mixture of Intermediate 109 (100 mg, 187 μmol) and DIPEA (160 μl, 940 μmol) in DCM (4.6 mL) was added methyl carbonochloridate (43 μl, 560 μmol), and the mixture was stirred at RT for 17 h. Water and DCM were added, the phases separated and the aqueous layer extracted with DCM. The combined organice layers dried with Na$_2$SO$_4$, filtered and evaporated to dryness under reduced pressure and the residue purified by column chromatography to give 75 mg (68% yield) of the title compound.

LCMS (method 1): rt: 1.20 min, MS ES+m/z=592 (M+H)$^+$.

$^1$H NMR (400 MHz, DMSO-d$_6$) δ [ppm] 1.61 (d, 6H) 1.81-1.95 (m, 2H) 1.99 (m, 2H) 3.21-3.32 (m, 2H) 3.35-3.46 (m, 2H) 3.58 (d, 6H) 3.64-3.81 (m, 4H) 3.97 (m, 6H) 4.16-4.43 (m, 2H) 4.84-4.99 (m, 2H) 5.21-5.37 (m, 2H) 7.54-7.72 (m, 6H) 7.95 (d, 2H).

Example 346

Tert-butyl (2R)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate

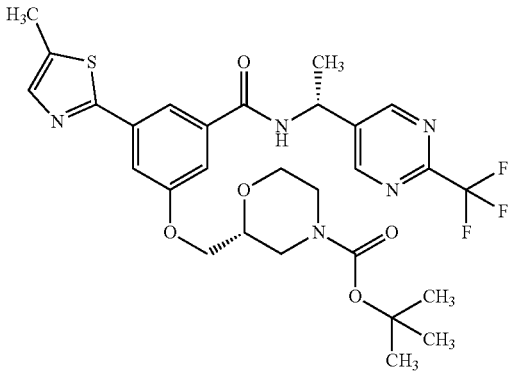

To a solution of Intermediate 5CE (28.21 g, 45.4 mmol), Intermediate VI (11.4 g, 50.0 mmol) and DIPEA (31.6 mL, 181.8 mmol) in ethyl acetate (400 mL) was added T3P (32 mL, 54.5 mmol). The reaction mixture was stirred at RT for 15 h. Further Intermediate VI (1 g, 4.55 mmol), DIPEA (3 mL, 17.7 mmol) and T3P (4 mL, 6.82 mmol) were added and the reaction mixture stirred at RT for 1 h. The reaction mixture was washed with saturated NaHCO$_3$, brine and the organic layer dried (MgSO$_4$), filtered and concentrated at reduced pressure. The crude product was purified by Biotage Isolera™ chromatography (eluting with 0-100% EtOAc in heptane on a pre-packed KP—SiO$_2$ column) to give 14.8 g (49% yield) of the title compound as white foam.

$^1$H NMR (500 MHz, Chloroform-d): δ [ppm] 8.94 (s, 2H), 7.96-7.88 (m, 1H), 7.58-7.53 (m, 1H), 7.54-7.52 (m, 1H), 7.42-7.39 (m, 1H), 6.79 (br s, 1H), 5.43-5.31 (m, 1H), 4.15-3.76 (m, 6H), 3.64-3.54 (m, 1H), 3.07-2.77 (m, 2H), 2.53 (d, J=1.1 Hz, 3H), 1.72 (d, J=7.2 Hz, 3H), 1.48 (s, 9H).

LCMS (Analytical Method F) Rt=4.02 min, MS (ESIpos): m/z=608 (M+H)$^+$.

Example 347

3-(5-Methyl-1,3-thiazol-2-yl)-5-[(2R)-morpholin-2-ylmethoxy]-N-{(1R)-1-[2-(trifluoromethyl)pyrimidin-5-yl]ethyl}benzamide

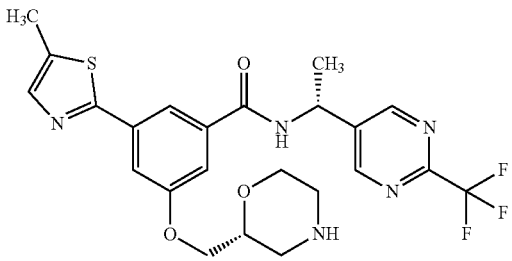

To a solution of Example 346 (14.7 g, 22.3 mmol) in DCM (100 mL) was added TFA (17.1 mL). The resulting solution was stirred for 16 h at RT. The reaction mixture was basified with 2M sodium hydroxide (100 mL) then saturated aqueous sodium bicarbonate solution to pH 8. The organic layer was separated and the aqueous layer extracted with further DCM. The combined organics were washed with brine, dried (sodium sulfate), filtered and concentrated at reduced pressure to give 10.5 g (93% yield) of the title compound as pale yellow solid. The bulk sample was used to prepare Example 348 without further purification.

$^1$H NMR (250 MHz, Chloroform-d): δ [ppm] 8.96 (s, 2H), 7.83-7.79 (m, 1H), 7.47 (dd, J=2.3, 1.5 Hz, 1H), 7.46-7.45 (m, 1H), 7.40-7.37 (m, 1H), 7.33-7.28 (m, 1H), 5.42-5.32 (m, 1H), 4.14-3.53 (m, 6H), 3.21-3.13 (m, 1H), 3.02-2.93 (m, 2H), 2.86-2.74 (m, 1H), 2.49 (d, J=1.0 Hz, 3H), 1.70 (d, J=7.2 Hz, 3H).

LCMS (Method A) Rt=1.04 min, MS (ESIpos): m/z=508 (M+H)$^+$.

An aliquot of Example 347 (150 mg) was further purified by SCX chromatography eluting with methanol then 7N ammonia in methanol. The relevant fractions were concentrated at reduced pressure then lyophilised from acetonitrile/water to give 145 mg of the title compound for profiling and chiral analysis.

HPLC Chiral Analysis (Method 11): 99.3% e.e. Rt=10.51 min.

$^1$H NMR (250 MHz, Chloroform-d): δ [ppm] 8.94 (s, 2H), 7.94-7.80 (m, 1H), 7.55 (dd, J=2.4, 1.5 Hz, 1H), 7.52-7.49 (m, 1H), 7.41 (dd, J=2.3, 1.5 Hz, 1H), 6.78 (d, J=6.6 Hz, 1H), 5.47-5.27 (m, 1H), 4.16-3.64 (m, 5H), 3.13-2.69 (m, 4H), 2.52 (d, J=1.1 Hz, 3H), 1.71 (d, J=7.1 Hz, 3H).

LCMS (Analytical Method F) Rt=2.16 min, MS (ESIpos): m/z=508 (M+H)$^+$.

Example 348

3-{[(2R)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide

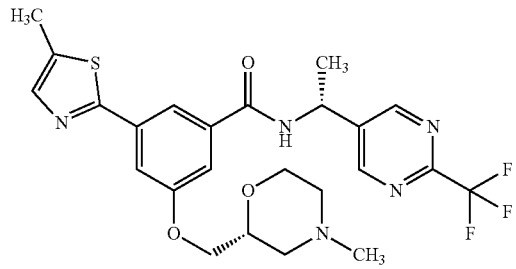 [SMILES: Cc1cnc(-c2cc(OC[C@H]3CN(C)CCO3)cc(C(=O)N[C@H](C)c3cnc(C(F)(F)F)nc3)c2)s1]

Example 347 (10.3 g, 19.3 mmol), formaldehyde (7.2 mL, 37% solution in water, 96.4 mmol) and acetic acid (1.10 mL) were combined in methanol (250 mL) and STAB (12.3 g, 57.8 mmol) was added portionwise. The resulting solution was stirred at RT for 2 h then concentrated under reduced pressure. The residue was taken up in saturated NaHCO$_3$ (100 mL) solution and extracted with DCM (3×100 mL). The combined organic phase was dried (MgSO$_4$), filtered and concentrated at reduced pressure. The crude material was purified by Biotage Isolera™ chromatography (eluting with 0-10% MeOH in DCM on a 340 g pre-packed KP—SiO$_2$ column). The relevant fractions were concentrated then lyophilised from acetonitrile/water to give 6.75 g (67% yield) of the title compound as white solid.

HPLC Chiral Analysis (Method 12): 100% e.e. Rt=5.09 min.

$^1$H NMR (500 MHz, Chloroform-d): δ [ppm] 8.93 (s, 2H), 7.87-7.85 (m, 1H), 7.57 (dd, J=2.4, 1.4 Hz, 1H), 7.52-7.50 (m, 1H), 7.40 (dd, J=2.3, 1.6 Hz, 1H), 6.67 (d, J=6.5 Hz, 1H), 5.42-5.29 (m, 1H), 4.12 (dd, J=9.9, 6.1 Hz, 1H), 4.04 (dd, J=9.9, 4.1 Hz, 1H), 4.00-3.93 (m, 2H), 3.79-3.72 (m, 1H), 2.85-2.80 (m, 1H), 2.72-2.65 (m, 1H), 2.53 (d, J=1.1 Hz, 3H), 2.33 (s, 3H), 2.24-2.15 (m, 1H), 2.08-2.00 (m, 1H), 1.71 (d, J=7.2 Hz, 3H).

LCMS (Analytical Method F) Rt=2.15 min, MS (ESIpos) m/z=522 (M+H)$^+$.

Example 349

Tert-butyl (2S)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate

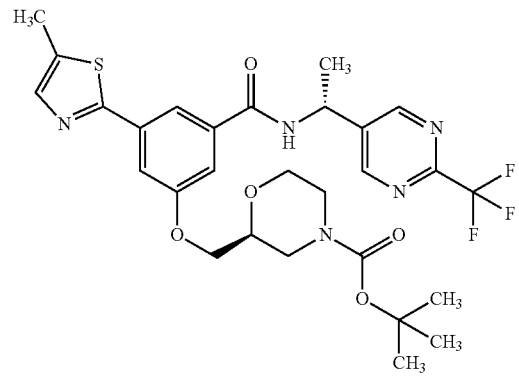 [SMILES: Cc1cnc(-c2cc(OC[C@@H]3CN(C(=O)OC(C)(C)C)CCO3)cc(C(=O)N[C@H](C)c3cnc(C(F)(F)F)nc3)c2)s1]

Intermediate 5CD (800 mg, 1.84 mmol), Intermediate VI (460 mg, 2.02 mmol) and DIPEA (0.96 mL, 5.51 mmol) were combined in DCM (7 mL) and HATU (1050 mg, 2.76 mmol) was added. The reaction mixture was stirred at RT for 2 h then diluted with DCM and washed with water. The aqueous phase was extracted with further DCM and the combined organics dried (MgSO$_4$), filtered and concentrated at reduced pressure. The crude material was purified by Biotage Isolera™ chromatography (eluting with 0-10% MeOH in DCM on a 50 g pre-packed KP—SiO$_2$ column) to give 1.6 g (100% yield) of the title compound as a colourless viscous oil.

$^1$H NMR (250 MHz, Chloroform-d): δ [ppm] 8.94 (s, 2H), 7.88 (s, 1H), 7.55 (d, J=2.2 Hz, 1H), 7.49 (d, J=1.1 Hz, 1H), 7.37 (s, 1H), 7.11 (d, J=6.1 Hz, 1H), 5.45-5.30 (m, 1H), 4.21-3.49 (m, 10H), 2.51 (d, J=0.9 Hz, 3H), 1.71 (d, J=7.1 Hz, 3H), 1.47 (s, 9H).

LC-MS (Method A) Rt=1.32 min, MS (ESIpos) m/z=608 (M+H)$^+$.

Example 350

3-(5-Methyl-1,3-thiazol-2-yl)-5-[(2S)-morpholin-2-ylmethoxy]-N-{(1R)-1-[2-(trifluoromethyl)pyrimidin-5-yl]ethyl}benzamide

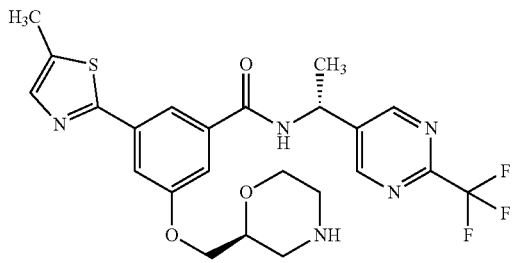 [SMILES: Cc1cnc(-c2cc(OC[C@@H]3CNCCO3)cc(C(=O)N[C@H](C)c3cnc(C(F)(F)F)nc3)c2)s1]

To a solution of Example 349 (1.6 g, 1.98 mmol) in DCM (16 mL) was added TFA (3 mL). The resulting solution was stirred for 4 h at RT then neutralised with saturated aqueous sodium bicarbonate solution. The organic layer was separated and the aqueous layer extracted with further DCM. The combined organics were dried (MgSO$_4$), filtered and concentrated at reduced pressure to give 0.87 g (87% yield) of the title compound as pale yellow solid.

HPLC Chiral Analysis (Method 11): 100% e.e. Rt=9.04 min.

$^1$H NMR (500 MHz, Chloroform-d): δ 8.93 (s, 2H), 7.86 (s, 1H), 7.56-7.53 (m, 2H), 7.52-7.48 (m, 1H), 7.42-7.37 (m, 1H), 6.81 (d, J=6.6 Hz, 1H), 5.40-5.31 (m, 1H), 4.07 (dd, J=9.9, 6.0 Hz, 1H), 4.01 (dd, J=9.9, 4.2 Hz, 2H), 3.98-3.86 (m, 2H), 3.75-3.66 (m, 1H), 3.06-2.99 (m, 1H), 2.98-2.90 (m, 1H), 2.90-2.84 (m, 1H), 2.78 (dd, J=11.9, 10.4 Hz, 1H), 2.52 (s, 3H), 1.71 (d, J=7.2 Hz, 3H).

LCMS (Analytical Method F) Rt=2.14 min, MS (ESIpos) m/z=508 (M+H)$^+$.

Example 351

3-{[(2S)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide

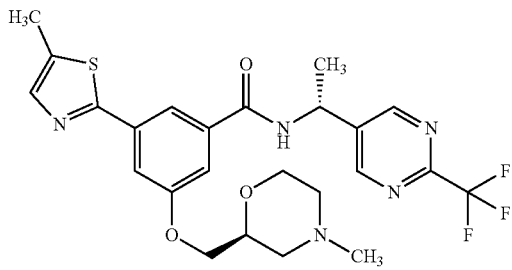 [SMILES: Cc1cnc(-c2cc(OC[C@@H]3CN(C)CCO3)cc(C(=O)N[C@H](C)c3cnc(C(F)(F)F)nc3)c2)s1]

Example 350 (238 mg, 0.47 mmol), formaldehyde (37% aqueous solution, 0.07 mL, 0.94 mmol) and acetic acid (0.03 mL, 0.47 mmol) in DCE (3 mL) were stirred for 15 min before addition of STAB (149 mg, 0.70 mmol) portionwise. The reaction mixture was stirred at RT for 2 h then diluted with DCM and washed with saturated aqueous sodium bicarbonate. The organic phase was separated, dried (MgSO$_4$), filtered and concentrated at reduced pressure. The crude material was purified by high pH preparative HPLC (Method A) to give 144 mg (59% yield) of the title compound, which was freeze-dried to a white powder.

HPLC Chiral Analysis (Method 12): 92.4% e.e. Rt=4.5 min.

$^1$H NMR (250 MHz, Chloroform-d): δ [ppm] 8.94 (s, 2H), 7.86 (s, 1H), 7.56 (d, J=1.4 Hz, 1H), 7.51 (d, J=1.2 Hz, 1H), 7.41 (s, 1H), 6.71 (d, J=6.1 Hz, 1H), 5.43-5.30 (m, 1H), 4.17-3.90 (m, 4H), 3.80-3.65 (m, 1H), 3.10-2.75 (m, 4H), 2.53 (d, J=1.0 Hz, 3H), 1.72 (d, J=7.1 Hz, 3H).

LC-MS (Analytical Method F) Rt=2.06 min, MS (ESIpos) 522 (M+H)$^+$.

Example 347 and Example 350 can also be prepared as a mixture of diastereoisomers (Example 352) and subsequently separated by HPLC Chiral Purification (Method 11).

Example 352

3-(5-Methyl-1,3-thiazol-2-yl)-5-[morpholin-2-ylmethoxy]-N-{(1R)-1-[2-(trifluoromethyl)pyrimidin-5-yl]ethyl}benzamide, formed as a mixture of Example 347 (Diastereoisomer 1) and Example 350 (Diastereoisomer 2)

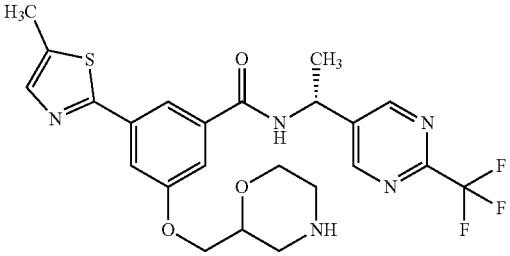

To a solution of Intermediate 114 (197 mg, 0.30 mmol) dissolved in DCM (5 mL) was added TFA (0.5 mL, 6.0 mmol) and the reaction stirred at RT overnight. The reaction mixture was neutralised with saturated NaHCO$_3$ solution. The organic phase was collected and the aqueous phase extracted with DCM (2×5 mL). The combined organic phases were dried (MgSO$_4$), filtered and concentrated at reduced pressure to give 177.0 mg (100% yield) of the title compound as a foam.

$^1$H NMR (500 MHz, CDCl$_3$): δ [ppm] 8.91-8.87 (m, 2H), 7.74-7.69 (m, 1H), 7.40-7.31 (m, 3H), 7.26-7.22 (m, 1H), 5.34-5.26 (m, 1H), 4.13-3.97 (m, 3H), 3.96-3.80 (m, 2H), 3.36-3.26 (m, 1H), 3.19-3.01 (m, 2H), 3.00-2.90 (m, 1H), 2.44-2.40 (m, 3H), 1.66-1.62 (m, 3H).

LC-MS (Method A) Rt=0.98 min, MS (ESIpos): m/z=508 (M+H)$^+$.

Example 347

3-(5-Methyl-1,3-thiazol-2-yl)-5-[(2R)-morpholin-2-ylmethoxy]-N-{(1R)-1-[2-(trifluoromethyl)pyrimidin-5-yl]ethyl}benzamide HPLC Chiral Purification (Method 11) was performed on 60 mg of Example 352 diastereoisomer mixture to give 22 mg of the title compound.

HPLC Chiral Analysis (Method 11): 95.4% e.e. Rt=10.81 min.

$^1$H NMR (500 MHz, Chloroform-d): δ [ppm] 8.92 (s, 2H), 7.85 (t, J=1.3 Hz, 1H), 7.53 (dd, J=2.3, 1.5 Hz, 2H), 7.50-7.48 (m, 1H), 7.40-7.35 (m, 1H), 6.90 (d, J=6.6 Hz, 1H), 5.39-5.29 (m, 1H), 4.06 (dd, J=9.9, 6.1 Hz, 1H), 3.98 (dd, J=9.9, 4.2 Hz, 3H), 3.96-3.91 (m, 1H), 3.91-3.85 (m, 1H), 3.73-3.64 (m, 1H), 3.04-2.97 (m, 1H), 2.96-2.82 (m, 2H), 2.76 (dd, J=12.0, 10.4 Hz, 1H), 2.51 (d, J=1.0 Hz, 3H), 1.68 (d, J=7.2 Hz, 3H).

LCMS (Analytical Method F) Rt=2.08 min, MS (ESIpos): m/z=508 (M+H)⁺.

Example 350

3-(5-Methyl-1,3-thiazol-2-yl)-5-[(2S)-morpholin-2-ylmethoxy]-N-{(1R)-1-[2-(trifluoromethyl)pyrimidin-5-yl]ethyl}benzamide HPLC Chiral Purification (Method 11) was performed on 60 mg of Example 352 diastereoisomer mixture to give 13.8 mg of the title compound.
HPLC Chiral Analysis (Method 11): 100% e.e. Rt=9.39 min.
¹H NMR (500 MHz, Chloroform-d): δ [ppm] 8.93 (s, 2H), 7.87-7.83 (m, 1H), 7.52 (dd, J=2.3, 1.5 Hz, 2H), 7.50-7.48 (m, 1H), 7.40-7.35 (m, 1H), 6.93 (d, J=6.7 Hz, 1H), 5.39-5.30 (m, 1H), 4.06 (dd, J=9.9, 6.0 Hz, 4H), 4.00 (dd, J=9.9, 4.2 Hz, 1H), 3.97-3.92 (m, 1H), 3.92-3.86 (m, 1H), 3.74-3.65 (m, 1H), 3.05-2.98 (m, 1H), 2.97-2.83 (m, 2H), 2.77 (dd, J=11.9, 10.5 Hz, 1H), 2.51 (d, J=1.0 Hz, 3H), 1.69 (d, J=7.2 Hz, 3H).
LCMS (Analytical Method F) Rt=2.08 min, MS (ESIpos): m/z=508 (M+H)⁺.

Example 348 and Example 351 can also be prepared as a mixture of diastereoisomers (Example 353) and subsequently separated by HPLC Chiral Purification (Method 12).

Example 353

3-{[4-methylmorpholin-2-yl]methoxy}-5-(5-methyl-1,3-thiazol-2-yl)-N-{(1R)-1-[2-(trifluoromethyl)pyrimidin-5-yl]ethyl}benzamide, formed as a mixture of Example 348 (Diastereoisomer 2) and Example 351 (Diastereoisomer 1)

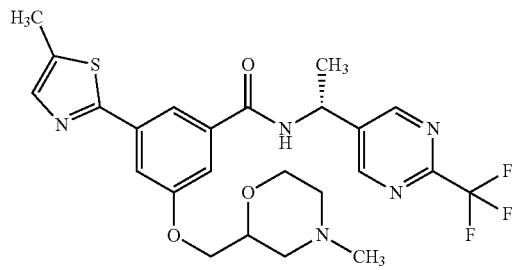 [SMILES: Cc1cnc(-c2cc(OCC3CN(C)CCO3)cc(C(=O)N[C@H](C)c3cnc(C(F)(F)F)nc3)c2)s1]

The Example 347 and Example 350 mixture (94.4 mg, 0.19 mmol), formaldehyde (37% solution in water, 70 µL, 0.93 mmol) and acetic acid (100 µL) were combined in methanol (2 mL) and STAB (118 mg, 0.56 mmol) was added. The resulting solution was stirred at RT for 2 h before being concentrated at reduced pressure. The residue was taken up in saturated NaHCO₃ (5 mL) solution then extracted with DCM (3×5 mL). The combined organic phase was dried (MgSO₄), filtered and concentrated at reduced pressure. The compound was freeze-dried from acetonitrile/water to give 78.7 mg (81% yield) of the title compound as white powder.
¹H NMR (500 MHz, CDCl₃): δ [ppm] 8.93 (s, 2H), 7.88-7.84 (m, 1H), 7.57 (dd, J=2.4, 1.4 Hz, 1H), 7.54-7.50 (m, 1H), 7.42-7.38 (m, 1H), 6.62 (d, J=6.4 Hz, 1H), 5.40-5.31 (m, 1H), 4.16-4.08 (m, 1H), 4.08-4.01 (m, 1H), 4.00-3.92 (m, 2H), 3.80-3.71 (m, 1H), 2.86-2.79 (m, 1H), 2.71-2.65 (m, 1H), 2.53 (d, J=1.1 Hz, 3H), 2.33 (s, 3H), 2.24-2.15 (m, 1H), 2.09-2.00 (m, 1H), 1.71 (d, J=7.2 Hz, 3H).

LC-MS (Analytical Method D) Rt=3.17 min, MS (ESIpos): m/z=522 (M+H)⁺.

Example 348

3-{[(2R)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide HPLC Chiral Purification (Method 12) was performed on 52.4 mg of Example 353 diastereoisomer mixture to give 22.9 mg (44% yield) of the title compound.
HPLC Chiral Analysis (Method 11): 96.4% e.e. Rt=5.15 min.
¹H NMR (500 MHz, Chloroform-d): δ [ppm] 8.94 (s, 2H), 7.87 (s, 1H), 7.58 (dd, J=2.4, 1.4 Hz, 1H), 7.52 (d, J=1.1 Hz, 1H), 7.41 (s, 1H), 6.71 (s, 1H), 5.36 (m, 1H), 4.17-4.10 (m, 1H), 4.09-4.02 (m, 2H), 3.97 (dd, J=11.6, 1.6 Hz, 1H), 3.82 (t, J=11.0 Hz, 1H), 2.91 (d, J=10.9 Hz, 1H), 2.76 (d, J=10.7 Hz, 1H), 2.53 (d, J=1.1 Hz, 3H), 2.39 (s, 3H), 2.28 (s, 1H), 2.14 (s, 1H), 1.72 (d, J=7.2 Hz, 3H).
LCMS (Analytical Method F) Rt=2.11 min, MS (ESIpos): m/z=522 (M+H)⁺.

Example 351

3-{[(2S)-4-methylmorpholin-2-yl]methoxy}-5-(5-methyl-1,3-thiazol-2-yl)-N-{(1R)-1-[2-(trifluoromethyl)pyrimidin-5-yl]ethyl}benzamide HPLC Chiral Purification (Method 12) was performed on 52.4 mg of Example 353 diastereoisomer mixture to give 21.6 mg (41% yield) of the title compound.
HPLC Chiral Analysis (Method 11): 100% e.e. Rt=4.58 min.
¹H NMR (500 MHz, Chloroform-d): δ [ppm] 8.94 (s, 2H), 7.87 (s, 1H), 7.58 (dd, J=2.3, 1.4 Hz, 1H), 7.52 (d, J=1.1 Hz, 1H), 7.41 (s, 1H), 6.71 (s, 1H), 5.36 (m, 1H), 4.16-4.01 (m, 3H), 4.00-3.93 (m, 1H), 3.81 (t, J=11.0 Hz, 1H), 2.91 (d, J=11.0 Hz, 1H), 2.76 (d, J=10.5 Hz, 1H), 2.53 (d, J=1.0 Hz, 3H), 2.39 (s, 3H), 2.28 (s, 1H), 2.15 (s, 1H), 1.72 (d, J=7.2 Hz, 3H).
LCMS (Analytical Method D) Rt=3.31 min, MS (ESIpos): m/z=522 (M+H)⁺.

Intermediate 132 was formed as a mixture of two diastereoisomers. SFC Chiral Purification (Method 13) provided diastereoisomer 1 (Example 354) and diastereoisomer 2 (Example 355).

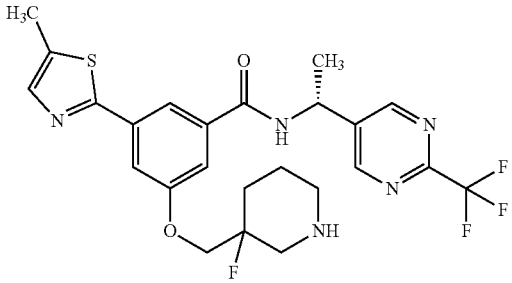 [SMILES: Cc1cnc(-c2cc(OCC3(F)CCCNC3)cc(C(=O)N[C@H](C)c3cnc(C(F)(F)F)nc3)c2)s1]

Example 354: Diastereoisomer 1; 3-(Fluoropiperidin-3-yl)methoxy}-5-(5-methyl-1,3-thiazol-2-yl)-N-{(1R)-1-[2-(trifluoromethyl)pyrimidin-5-yl]ethyl}benzamide SFC Chiral Purification (Method 13) on 55.2 mg of Intermediate 132 followed by SCX-2 cartridge purification gave 14 mg of the title compound.

SFC Chiral Analysis (Method 13): 100% e.e. Rt=2.17 min.
¹H NMR (500 MHz, Chloroform-d): δ [ppm] 8.97 (s, 2H), 7.84 (s, 1H), 7.53 (s, 1H), 7.50 (s, 1H), 7.44 (s, 1H), 7.02 (s, 1H), 5.36 (q, J=7.0 Hz, 1H), 4.23-3.99 (m, 2H), 3.43-3.22 (m, 1H), 3.09 (d, J=12.8 Hz, 1H), 2.95 (dd, J=29.1, 13.9 Hz, 1H), 2.73 (s, 1H), 2.52 (s, 3H), 2.09-2.02 (m, 1H), 1.94-1.78 (m, 3H), 1.73 (d, J=7.1 Hz, 3H), 1.67-1.60 (m, 1H).
LCMS (Analytical Method F) Rt=2.14 min, MS (ESIpos): m/z=524.4 (M+H)⁺.

Example 355

Diastereoisomer 2; 3-(Fluoropiperidin-3-yl)methoxy}-5-(5-methyl-1,3-thiazol-2-yl)-N-{(1R)-1-[2-(trifluoromethyl)pyrimidin-5-yl]ethyl}benzamide SFC Chiral Purification (Method 13) on 55.2 mg of Intermediate 132 followed by SCX-2 cartridge purification gave 15 mg of the title compound.
SFC Chiral Analysis (Method 13): 98.2% e.e. Rt=3.26 min.
¹H NMR (500 MHz, Chloroform-d): δ [ppm] 8.90 (s, 2H), 7.74 (s, 1H), 7.42 (s, 1H), 7.41 (s, 1H), 7.37 (s, 1H), 6.97 (s, 1H), 5.40-5.20 (m, 1H), 4.15-3.90 (m, 2H), 3.38-3.19 (m, 1H), 3.06 (d, J=11.3 Hz, 1H), 2.88 (dd, J=29.9, 13.7 Hz, 1H), 2.68 (t, J=11.1 Hz, 1H), 2.43 (s, 3H), 2.05-1.90 (m, 2H), 1.87-1.73 (m, 2H), 1.65 (d, J=7.0 Hz, 3H), 1.60-1.55 (m, 1H).
LCMS (Analytical Method F) Rt=2.12 min, MS (ESIpos): m/z=524.4 (M+H)⁺.

Intermediate 147 was formed as a mixture of two diastereoisomers. SFC Chiral Purification (Method 14) provided diastereoisomer 1 (Example 356) and diastereoisomer 2 (Example 357).

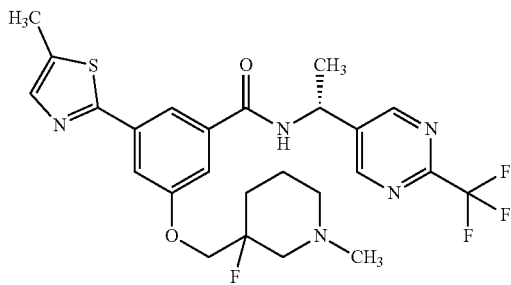 [SMILES: Cc1cnc(-c2cc(OCC3(F)CCCN(C)C3)cc(C(=O)N[C@H](C)c3cnc(C(F)(F)F)nc3)c2)s1]

Example 356

Diastereoisomer 1; 3-{[3-fluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide SFC Chiral Purification (Method 14) on 46 mg of Intermediate 147 gave 11 mg of the title compound.
SFC Chiral Analysis (Method 14): 100% e.e. Rt=2.56 min.
¹H NMR (500 MHz, Methanol-d4): δ [ppm] 9.02 (s, 2H), 7.95 (s, 1H), 7.66 (s, 1H), 7.57 (s, 1H), 7.53 (s, 1H), 5.34 (q, J=7.1 Hz, 1H), 4.31-4.11 (m, 2H), 3.03-2.88 (m, 1H), 2.70 (d, J=11.0 Hz, 1H), 2.54 (s, 3H), 2.43 (dd, J=26.8, 12.3 Hz, 1H), 2.31 (s, 3H), 2.22 (t, J=10.6 Hz, 1H), 2.00-1.86 (m, 2H), 1.77 (d, J=11.8 Hz, 1H), 1.70 (d, J=7.1 Hz, 3H), 1.68-1.63 (m, 1H).
LCMS (Analytical Method F) Rt=2.18 min, MS (ESIpos): m/z=538 (M+H)⁺.

Example 357

Diastereoisomer 2; 3-{[3-fluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide SFC Chiral Purification (Method 14) on 46 mg of Intermediate 147 followed by SCX-2 cartridge purification gave 10 mg of the title compound.
SFC Chiral Analysis (Method 14): 97.6% e.e. Rt=3.06 min.
¹H NMR (500 MHz, Methanol-d4): δ [ppm] 9.02 (s, 2H), 7.96 (s, 1H), 7.69-7.63 (m, 1H), 7.57 (d, J=1.1 Hz, 1H), 7.55-7.50 (m, 1H), 5.34 (q, J=7.1 Hz, 1H), 4.34-4.06 (m, 2H), 3.09 (s, 1H), 2.80 (d, J=10.2 Hz, 1H), 2.61-2.47 (m, 4H), 2.39 (s, 3H), 2.32 (t, J=10.1 Hz, 1H), 2.05-1.88 (m, 2H), 1.83-1.66 (m, 5H).
LCMS (Analytical Method F) Rt=2.15 min, MS (ESIpos): m/z=538.4 (M+H)⁺.

In analogy to the procedure described for Example 346, the following examples were prepared using TFA and the corresponding N-Boc protected amine starting materials.

| Ex. | Structure | Name | Analytical Data |
|---|---|---|---|
| 358 | ![structure] | 3-[(3-fluoroazetidin-3-yl)methoxy]-5-(5-methyl-1,3-thiazol-2-yl)-N-{(1R)-1-[2-(trifluoromethyl)pyrimidin-5-yl]ethyl}benzamide | ¹H NMR (500 MHz, DMSO-d6): δ [ppm] 9.18 (d, J = 7.1 Hz, 1H), 9.13 (s, 2H), 7.96 (s, 1H), 7.66 (d, J = 1.2 Hz, 1H), 7.64-7.60 (m, 2H), 5.31 (m, 1H), 4.49 (d, J = 23.7 Hz, 2H), 3.71 (m, 2H), 3.60 (m, 2H), 1.62 (d, J = 7.1 Hz, 3H). LCMS (Analytical Method D) Rt = 3.26 min, MS (ESIpos): m/z = 496 (M + H)⁺. |

| Ex. | Structure | Name | Analytical Data |
|---|---|---|---|
| 359 | 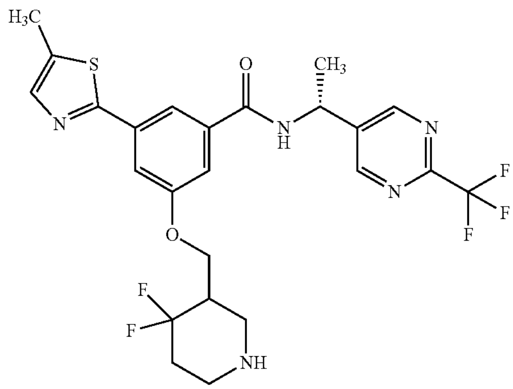 [SMILES: Cc1cnc(-c2cc(OCC3CNCCC3(F)F)cc(C(=O)N[C@H](C)c3cnc(C(F)(F)F)nc3)c2)s1] | 3-{[4,4-difluoropiperidin-3-yl]methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers | ¹H NMR (500 MHz, Chloroform-d): δ [ppm] 8.94 (s, 2H), 7.84 (s, 1H), 7.51 (s, 2H), 7.40-7.36 (m, 1H), 6.89 (d, J = 6.5 Hz, 1H), 5.36 (m, 1H), 4.40 (dt, J = 9.2, 3.2 Hz, 1H), 4.04 (dt, J = 9.2, 4.9 Hz, 1H), 3.37 (d, J = 12.5 Hz, 1H), 3.11 (d, J = 12.4 Hz, 1H), 2.95-2.87 (m, 1H), 2.84-2.75 (m, 1H), 2.52 (s, 3H), 2.50-2.37 (m, 1H), 2.16-2.05 (m, 1H), 1.96-1.82 (m, 1H), 1.71 (d, J = 7.1 Hz, 3H). LCMS (Analytical Method F) Rt = 2.26 min, MS (ESIpos) m/z = 542 (M + H)⁺. |

Example 360

3-{[(3R)-4-methylmorpholin-3-yl]methoxy}-5-(5-methyl-1,3-thiazol-2-yl)-N-{(1R)-1-[2-(trifluoromethyl)pyrimidin-5-yl]ethyl}benzamide

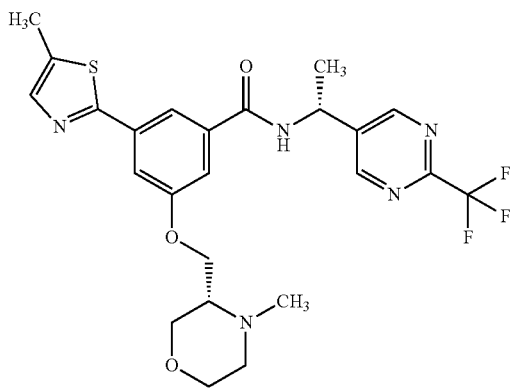

To a stirred solution of Intermediate 28CM (129 mg, 0.37 mmol), Intermediate VI (92.7 mg, 0.41 mmol) and DIPEA (128.98 μL, 0.74 mmol) in N,N-Dimethylformamide (1 mL) at RT was added HATU (211.17 mg, 0.56 mmol) and the reaction stirred at RT for 16 h. The material was dissolved in MeCN, water and DMSO and purified by preparative HPLC (Method A). Pure fractions were evaporated before freeze drying to give 107 mg (54.9% yield) of the title compound as a white flocculent solid.

¹H NMR (500 MHz, Chloroform-d): δ [ppm] 8.93 (s, 2H), 7.86 (t, J=1.3 Hz, 1H), 7.56 (dd, J=2.4, 1.4 Hz, 1H), 7.52 (d, J=1.2 Hz, 1H), 7.41-7.39 (m, 1H), 6.60 (d, J=6.5 Hz, 1H), 5.36 (m, 1H), 4.14-4.10 (m, 2H), 3.93 (dd, J=11.2, 3.0 Hz, 1H), 3.83 (dt, J=11.4, 2.8 Hz, 1H), 3.71 (td, J=10.9, 2.5 Hz, 1H), 3.60 (dd, J=11.3, 9.4 Hz, 1H), 2.77 (dt, J=11.8, 2.5 Hz, 1H), 2.61-2.55 (m, 1H), 2.54 (d, J=1.1 Hz, 3H), 2.46-2.42 (m, 1H), 2.41 (s, 3H), 1.72 (d, J=7.2 Hz, 3H).
LCMS (Analytical Method F) Rt=2.09 min, MS (ESIpos): m/z=522.1 (M+H)⁺.

In analogy to the procedure described for Example 360, the following examples were prepared using HATU and the corresponding carboxylic acid and primary amine starting material.

| Ex. | Structure | Name | Analytical Data |
|---|---|---|---|
| 361 | 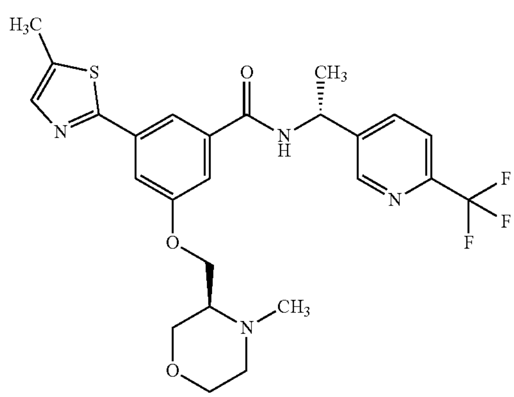 [SMILES: Cc1cnc(-c2cc(OC[C@@H]3COCCN3C)cc(C(=O)N[C@H](C)c3ccc(C(F)(F)F)nc3)c2)s1] | 3-{[(3S)-4-methylmorpholin-3-yl]methoxy}-5-(5-methyl-1,3-thiazol-2-yl)-N-{(1R)-1-[6-(trifluoromethyl)pyridin-3-yl]ethyl}benzamide | ¹H NMR (500 MHz, Chloroform-d): δ [ppm] 8.81 (s, 1H), 7.96-7.83 (m, 2H), 7.69 (d, J = 8.1 Hz, 1H), 7.59 (s, 1H), 7.54 (s, 1H), 7.47 (s, 1H), 6.64 (s, 1H), 5.41 (m, 1H), 4.29-4.07 (m, 2H), 4.00-3.93 (m, 1H), 3.87 (d, J = 11.2 Hz, 1H), 3.77 (t, J = 10.5 Hz, 1H), 3.66 (t, J = 10.3 Hz, 1H), 2.84 (d, J = 10.7 Hz, 1H), 2.72-2.61 (m, 1H), 2.56 (s, 3H), 2.53-2.49 (m, 1H), 2.47 (s, 3H), 1.70 (d, J = 7.0 Hz, 3H). LCMS (Analytical Method F) 2.20 min, MS (ESIpos): m/z = 521.1 (M + H)⁺. |

| Ex. | Structure | Name | Analytical Data |
|---|---|---|---|
| 362 | 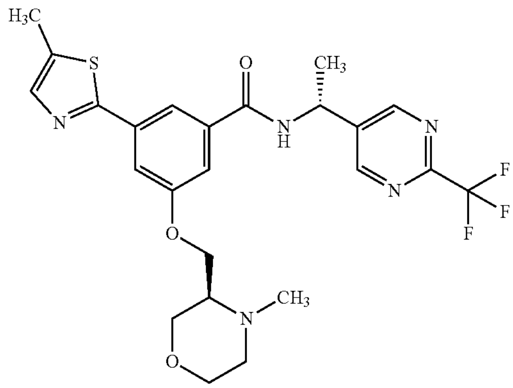 [SMILES: Cc1cnc(-c2cc(OC[C@@H]3COCCN3C)cc(C(=O)N[C@H](C)c3cnc(C(F)(F)F)nc3)c2)s1] | 3-{[(3S)-4-methylmorpholin-3-yl]methoxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.86 (s, 2H), 7.79 (s, 1H), 7.51-7.46 (m, 1H), 7.45-7.42 (m, 1H), 7.35 (s, 1H), 6.59 (d, J = 5.8 Hz, 1H), 5.28 (m, 1H), 4.06 (d, J = 4.9 Hz, 2H), 3.86 (dd, J = 11.2, 3.2 Hz, 1H), 3.76 (d, J = 11.4 Hz, 1H), 3.70-3.61 (m, 1H), 3.54 (dd, J = 11.2, 9.6 Hz, 1H), 2.71 (d, J = 11.8 Hz, 1H), 2.54 (d, J = 4.6 Hz, 1H), 2.49-2.44 (m, 3H), 2.41-2.37 (m, 1H), 2.35 (s, 3H), 1.64 (d, J = 7.2 Hz, 3H). LCMS (Analytical Method F) Rt = 2.07 min, MS (ESIpos): m/z = 522.0 (M + H)$^+$. |
| 363 | 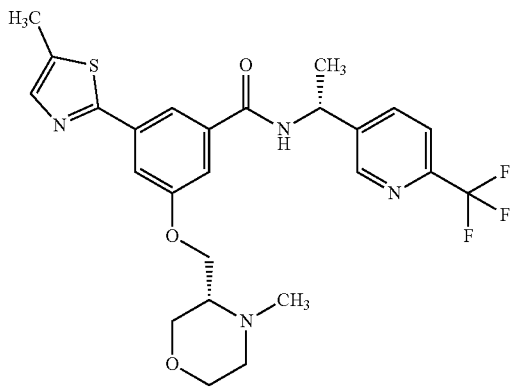 [SMILES: Cc1cnc(-c2cc(OC[C@H]3COCCN3C)cc(C(=O)N[C@H](C)c3ccc(C(F)(F)F)nc3)c2)s1] | 3-{[(3R)-4-methylmorpholin-3-yl]methoxy}-5-(5-methyl-1,3-thiazol-2-yl)-N-{(1R)-1-[6-(trifluoromethyl)pyridin-3-yl]ethyl}benzamide | $^1$H NMR (500 MHz, Chloroform-d): δ [ppm] 8.77 (d, J = 1.9 Hz, 1H), 7.91-7.83 (m, 2H), 7.66 (d, J = 8.1 Hz, 1H), 7.55 (dd, J = 2.4, 1.4 Hz, 1H), 7.51 (d, J = 1.2 Hz, 1H), 7.40 (dd, J = 2.4, 1.5 Hz, 1H), 6.64 (d, J = 7.0 Hz, 1H), 5.37 (m, 1H), 4.10 (d, J = 4.5 Hz, 2H), 3.92 (dd, J = 11.3, 2.9 Hz, 1H), 3.82 (dt, J = 11.4, 2.8 Hz, 1H), 3.70 (td, J = 11.3, 10.9, 2.5 Hz, 1H), 3.59 (dd, J = 11.3, 9.4 Hz, 1H), 2.75 (dt, J = 11.8, 2.6 Hz, 1H), 2.56 (m, 1H), 2.52 (d, J = 1.1 Hz, 3H), 2.45-2.39 (m, 4H), 1.66 (d, J = 7.1 Hz, 3H). LCMS (Analytical Method D) Rt = 3.32 min, MS (ESIpos): 521 (M + H)$^+$. |
| 364 | 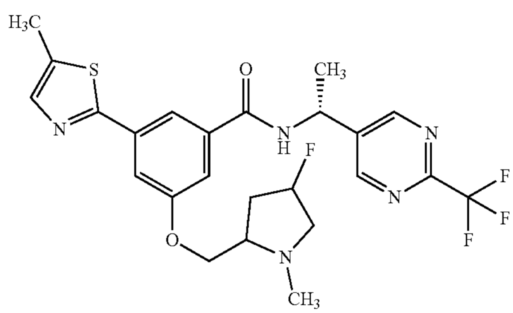 [SMILES: Cc1cnc(-c2cc(OCC3CC(F)CN3C)cc(C(=O)N[C@H](C)c3ccc(C(F)(F)F)nc3)c2)s1] | 3-{[4-fluoro-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide, as a mixture of stereoisomers | $^1$H NMR (500 MHz, Chloroform-d): δ [ppm] 8.94 (s, 2H), 7.87 (s, 1H), 7.60-7.55 (m, 1H), 7.52 (d, J = 1.1 Hz, 1H), 7.46 (s, 1H), 6.77 (s, 1H), 5.36 (m, 1H), 5.16 (dt, J = 54.2, 4.6 Hz, 1H), 4.21 (dd, J = 9.5, 5.4 Hz, 1H), 4.10 (dd, J = 9.5, 5.4 Hz, 1H), 3.42 (dd, J = 17.3, 12.5 Hz, 1H), 2.82 (s, 1H), 2.60-2.37 (m, 8H), 2.09 (ddd, J = 30.6, 15.2, 6.7 Hz, 1H), 1.72 (d, J = 7.2 Hz, 3H). LCMS (Analytical Method F) Rt = 2.13 min, MS (ESIpos): m/z = 524 (M + H)$^+$. |
| 365 | 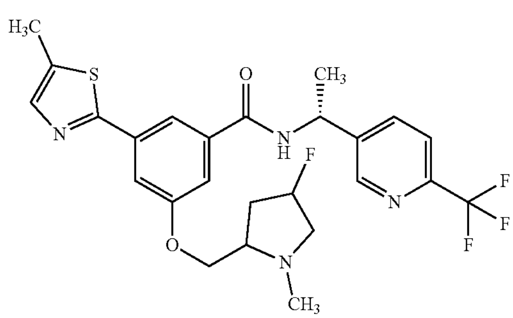 | 3-{[4-fluoro-1-methylpyrrolidin-2-yl]methoxy}-5-(5-methyl-1,3-thiazol-2-yl)-N-{(1R)-1-[6-(trifluoromethyl)pyridin-3-yl]ethyl}benzamide, as a mixture of stereoisomers | $^1$H NMR (500 MHz, Chloroform-d): δ [ppm] 8.79 (d, J = 1.7 Hz, 1H), 7.90 (dd, J = 8.1, 1.9 Hz, 1H), 7.87 (s, 1H), 7.67 (d, J = 8.1 Hz, 1H), 7.58-7.55 (m, 1H), 7.51 (d, J = 1.1 Hz, 1H), 7.47 (s, 1H), 6.67 (s, 1H), 5.39 (m, 1H), 5.16 (dt, J = 54.0, 4.3 Hz, 1H), 4.21 (dd, J = 9.3, 5.5 Hz, 1H), 4.10 (dd, J = 9.4, 5.4 Hz, 1H), 3.42 (dd, J = 18.1, 11.8 Hz, 1H), 2.81 (s, 1H), 2.63-2.37 (m, 8H), 2.09 (ddd, J = 30.4, 14.9, 6.6 Hz, 1H), 1.67 (d, J = 7.1 Hz, 3H). LCMS (Analytical Method F) Rt = 2.22 min, MS (ESIpos): m/z = 523 (M + H)$^+$. |

Example 366

3-{[(2R)-4-methylmorpholin-2-yl]methoxy}-5-(5-methyl-1,3-thiazol-2-yl)-N-{(1R)-1-[6-(trifluoromethyl)pyridin-3-yl]ethyl}benzamide

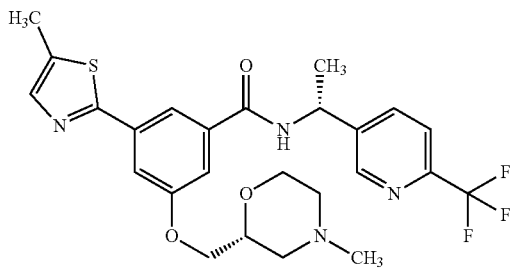

To a solution of Intermediate 138 (82 mg, 0.16 mmol) in methanol (2 mL) was added formaldehyde (37% aqueous solution, 0.02 mL, 0.32 mmol) and acetic acid (0.009 mL, 0.16 mmol) and the reaction was stirred at RT for 15 minutes. Sodium triacetoxyborohydride (51 mg, 0.24 mmol) was added and the reaction stirred for 1.5 hours. The reaction mixture was passed through an SCX cartridge (washing with methanol, eluting with 7N ammonia in methanol) and concentrated under reduced pressure. The resulting residue was triturated with water, filtered and dried in a high vacuum oven to give 37 mg (44% yield) of the title compound as beige solid.

$^1$H NMR (500 MHz, DMSO-d6): δ [ppm] 9.13 (d, J=7.3 Hz, 1H), 8.83 (s, 1H), 8.12-8.05 (m, 1H), 7.94 (s, 1H), 7.90 (d, J=8.1 Hz, 1H), 7.65 (s, 1H), 7.55 (s, 2H), 5.29 (m, 1H), 4.12 (d, J=4.9 Hz, 2H), 3.83 (d, J=10.4 Hz, 2H), 3.64-3.45 (m, 1H), 2.80 (d, J=11.0 Hz, 1H), 2.67-2.57 (m, 1H), 2.21 (s, 3H), 2.02 (td, J=11.2, 3.0 Hz, 1H), 1.94 (t, J=10.6 Hz, 1H), 1.57 (d, J=7.1 Hz, 3H).

LCMS (Analytical Method F) Rt=2.18 min, MS (ESIpos): m/z=521.2 (M+H)$^+$.

In analogy to the procedure described for Example 366, the following examples were prepared using STAB and the corresponding amine and aldehyde or ketone starting materials.

| Ex. | Structure | Name | Analytical Data |
|---|---|---|---|
| 367 | 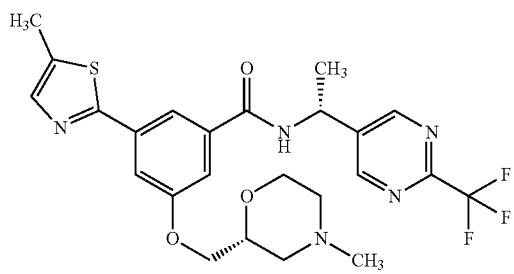 | 3-(5-chloro-1,3-thiazol-2-yl)-5-{[(2R)-4-methylmorpholin-2-yl]methoxy}-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.82 (s, 1H), 7.67 (s, 1H), 7.59-7.51 (m, 1H), 7.43 (s, 1H), 6.62 (s, 1H), 5.36 (m, 1H), 4.13 (dd, J = 9.8, 5.9 Hz, 1H), 4.09-3.99 (m, 2H), 3.99-3.93 (m, 1H), 3.79 (t, J = 11.0 Hz, 1H), 2.88 (d, J = 10.2 Hz, 1H), 2.73 (d, J = 11.4 Hz, 1H), 2.37 (s, 3H), 2.25 (t, J = 10.5 Hz, 1H), 2.11 (t, J = 9.5 Hz, 1H), 1.72 (d, J = 7.1 Hz, 3H). LCMS (Analytical Method F) Rt = 2.28 min, MS (ESIpos): m/z = 542.0 (M + H)$^+$. |
| 368 | 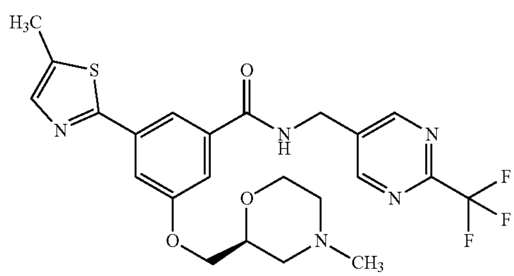 [SMILES: Cc1cnc(-c2cc(OC[C@@H]3CN(C)CCO3)cc(C(=O)NCc3cnc(C(F)(F)F)nc3)c2)s1] | 3-{[(2S)-4-methylmorpholin-2-yl]methoxy}-5-(5-methyl-1,3-thiazol-2-yl)-N-{[2-(trifluoromethyl)pyrimidin-5-yl]methyl}benzamide | $^1$H NMR (500 MHz, Chloroform-d): δ [ppm] 8.86 (s, 2H), 7.80 (t, J = 1.3 Hz, 1H), 7.50 (dd, J = 2.3, 1.5 Hz, 1H), 7.42 (d, J = 1.1 Hz, 1H), 7.37-7.32 (m, 1H), 6.95 (t, J = 5.8 Hz, 1H), 4.65 (d, J = 6.0 Hz, 2H), 4.05 (dd, J = 9.9, 5.9 Hz, 1H), 3.98 (dd, J = 9.9, 4.2 Hz, 1H), 3.96-3.85 (m, 2H), 3.70 (td, J = 11.4, 2.4 Hz, 1H), 2.80 (d, J = 11.2 Hz, 1H), 2.64 (d, J = 11.5 Hz, 1H), 2.45 (d, J = 1.0 Hz, 3H), 2.29 (s, 3H), 2.16 (td, J = 11.4, 3.3 Hz, 1H), 2.02 (t, J = 10.7 Hz, 1H). LCMS (Analytical Method F) Rt = 1.99 min, MS (ESIpos) m/z = 508 (M + H)$^+$. |
| 369 | 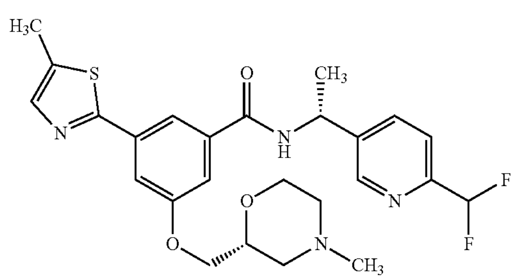 [SMILES: Cc1cnc(-c2cc(OC[C@H]3CN(C)CCO3)cc(C(=O)N[C@H](C)c3ccc(C(F)F)nc3)c2)s1] | N-{(1R)-1-[6-(difluoromethyl)pyridin-3-yl]ethyl}-3-{[(2R)-4-methylmorpholin-2-yl]methoxy}-5-(5-methyl-1,3-thiazol-2-yl)benzamide | $^1$H NMR (500 MHz, Chloroform-d): δ [ppm] 8.73-8.65 (m, 1H), 7.87-7.83 (m, 2H), 7.62 (d, J = 8.1 Hz, 1H), 7.56 (s, 1H), 7.51 (s, 1H), 7.41 (s, 1H), 6.75-6.51 (m, 2H), 5.37 (m, 1H), 4.17-3.94 (m, 4H), 3.89-3.75 (m, 1H), 2.97-2.85 (m, 1H), 2.83-2.71 (m, 1H), 2.52 (s, 3H), 2.47-2.33 (m, 3H), 2.34-2.25 (m, 1H), 2.22-2.11 (m, 1H), 1.66 (d, J = 7.1 Hz, 3H). LCMS (Analytical Method F) Rt = 2.01 min, MS (ESIpos): m/z = 503.1 (M + H)$^+$. |

| Ex. | Structure | Name | Analytical Data |
|---|---|---|---|
| 370 | 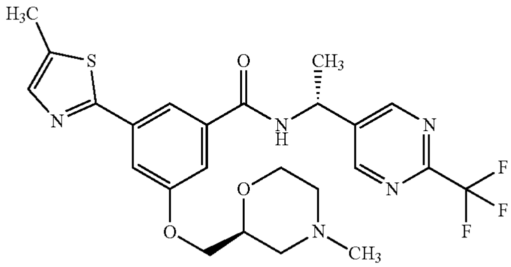 [SMILES: Cc1cnc(-c2cc(OC[C@@H]3CN(C)CCO3)cc(C(=O)N[C@H](C)c3cnc(C(F)(F)F)nc3)c2)s1] | 3-{[(2S)-4-methylmorpholin-2-yl]methoxy}-5-(5-methyl-1,3-thiazol-2-yl)-N-{(1R)-1-[6-(trifluoromethyl)pyridin-3-yl]ethyl}benzamide | $^1$H NMR (500 MHz, DMSO-d6): δ [ppm] 9.13 (d, J = 7.3 Hz, 1H), 8.83 (d, J = 1.5 Hz, 1H), 8.09 (dd, J = 8.2, 1.7 Hz, 1H), 7.94 (s, 1H), 7.90 (d, J = 8.1 Hz, 1H), 7.65 (d, J = 1.1 Hz, 1H), 7.55 (s, 2H), 5.29 (m, 1H), 4.12 (d, J = 5.0 Hz, 2H), 3.88-3.74 (m, 2H), 3.56 (td, J = 11.2, 2.4 Hz, 1H), 2.80 (d, J = 11.1 Hz, 1H), 2.68-2.60 (m, 1H), 2.21 (s, 3H), 2.02 (td, J = 11.3, 3.2 Hz, 1H), 1.93 (t, J = 10.6 Hz, 1H), 1.57 (d, J = 7.1 Hz, 3H). LCMS (Analytical Method F) Rt = 2.21 min, MS (ESIpos): m/z = 521.1 (M + H)$^+$. |
| 371 | 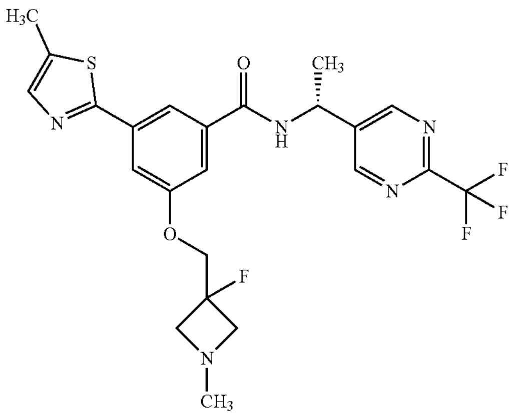 [SMILES: Cc1cnc(-c2cc(OCC3(F)CN(C)C3)cc(C(=O)N[C@H](C)c3cnc(C(F)(F)F)nc3)c2)s1] | 3-[(3-fluoro-1-methylazetidin-3-yl)methoxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.89 (t, J = 1.3 Hz, 1H), 7.59 (dd, J = 2.4, 1.4 Hz, 1H), 7.52 (d, J = 1.2 Hz, 1H), 7.46-7.43 (m, 1H), 6.69 (d, J = 6.6 Hz, 1H), 5.37 (m, 1H), 4.38 (d, J = 22.9 Hz, 2H), 3.73-3.61 (m, 2H), 3.30-3.15 (m, 2H), 2.53 (d, J = 1.1 Hz, 3H), 2.45 (s, 3H), 1.72 (d, J = 7.2 Hz, 3H). LCMS (Analytical Method D) Rt = 3.44 min, MS (ESIpos): m/z = 510.00 (M + H)$^+$. |
| 372 | 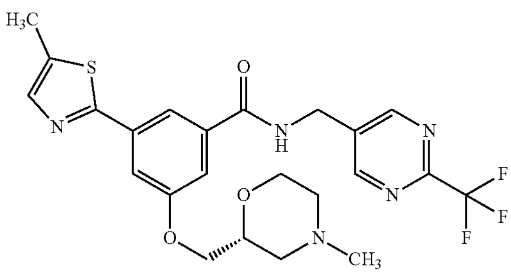 [SMILES: Cc1cnc(-c2cc(OC[C@H]3CN(C)CCO3)cc(C(=O)NCc3cnc(C(F)(F)F)nc3)c2)s1] | 3-{[(2R)-4-methylmorpholin-2-yl]methoxy}-5-(5-methyl-1,3-thiazol-2-yl)-N-{[2-(trifluoromethyl)pyrimidin-5-yl]methyl}benzamide | $^1$H NMR (500 MHz, Chloroform-d): δ [ppm] 8.93 (s, 2H), 7.86 (t, J = 1.4 Hz, 1H), 7.57 (dd, J = 2.3, 1.5 Hz, 1H), 7.50 (d, J = 1.2 Hz, 1H), 7.43 (dd, J = 2.3, 1.6 Hz, 1H), 6.88 (t, J = 5.8 Hz, 1H), 4.72 (d, J = 6.0 Hz, 2H), 4.12 (dd, J = 9.9, 6.0 Hz, 1H), 4.05 (dd, J = 9.9, 4.2 Hz, 1H), 4.01-3.93 (m, 2H), 3.75 (td, J = 11.4, 2.4 Hz, 1H), 2.83 (d, J = 11.2 Hz, 1H), 2.68 (d, J = 10.0 Hz, 1H), 2.52 (d, J = 1.0 Hz, 3H), 2.33 (s, 3H), 2.19 (td, J = 11.4, 3.3 Hz, 1H), 2.09-2.02 (m, 1H). LCMS (Analytical Method F) Rt = 2.00 min, MS (ESIpos): m/z = 508.0 (M + H)$^+$. |
| 373 | 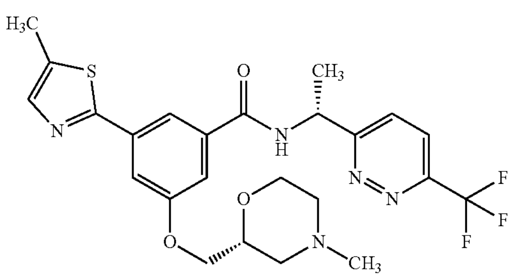 | 3{[(2R)-4-methylmorpholin-2-yl]methoxy}-5-(5-methyl-1,3-thiazol-2-yl)-N-{(1R)-1-[6-(trifluoromethyl)pyridazin-3-yl]ethyl}benzamide | $^1$H NMR (500 MHz, Chloroform-d): δ [ppm] 7.93 (t, J = 1.4 Hz, 1H), 7.84 (d, J = 8.7 Hz, 1H), 7.76 (d, J = 8.7 Hz, 1H), 7.62 (dd, J = 2.3, 1.5 Hz, 1H), 7.54 (d, J = 1.2 Hz, 1H), 7.49-7.42 (m, 2H), 5.62 (m, 1H), 4.15 (ddd, J = 8.6, 5.9, 2.7 Hz, 1H), 4.08 (dt, J = 9.8, 4.7 Hz, 1H), 4.03-3.94 (m, 2H), 3.78 (td, J = 11.4, 2.4 Hz, 1H), 2.86 (d, J = 11.1 Hz, 1H), 2.70 (d, J = 11.4 Hz, 1H), 2.55 (d, J = 1.1 Hz, 3H), 2.36 (s, 3H), 2.22 (td, J = 11.5, 3.3 Hz, 1H), 2.08 (td, J = 10.8, 3.8 Hz, 1H), 1.78 (d, J = 7.0 Hz, 3H). LCMS (Analytical Method F) Rt = 2.07 min, MS (ESIpos): m/z = 522 (M + H)$^+$. |

| Ex. | Structure | Name | Analytical Data |
|---|---|---|---|
| 374 | 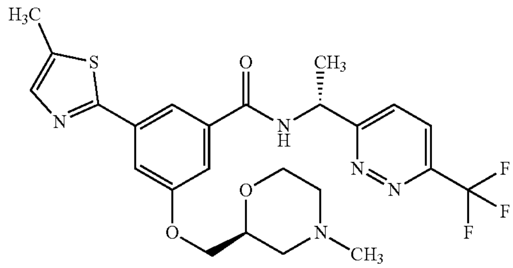 | 3-{[(2S)-4-methylmorpholin-2-yl]methoxy}-5-(5-methyl-1,3-thiazol-2-yl)-N-{(1R)-1-[6-(trifluoromethyl)pyridazin-3-yl]ethyl}benzamide | $^1$H NMR (500 MHz, Chloroform-d): δ [ppm] 7.90 (s, 1H), 7.82 (d, J = 8.7 Hz, 1H), 7.74 (d, J = 8.7 Hz, 1H), 7.62-7.58 (m, 1H), 7.53-7.49 (m, 1H), 7.46 (d, J = 7.3 Hz, 1H), 7.44-7.40 (m, 1H), 5.60 (m, 1H), 4.17-4.10 (m, 1H), 4.09-4.04 (m, 1H), 4.04-3.99 (m, 1H), 3.97 (d, J = 11.5 Hz, 1H), 13.80 (t, J = 11.1 Hz, 1H), 2.88 (d, J = 11.1 Hz, 1H), 2.73 (d, J = 11.0 Hz, 1H), 2.52 (s, 3H), 2.37 (s, 3H), 2.30-2.20 (m, 1H), 2.18-2.06 (m, 1H), 1.76 (d, J = 7.0 Hz, 3H). LCMS (Analytical Method F) Rt = 2.10 min, MS (ESIpos): m/z = 522 (M + H)$^+$. |
| 375 | 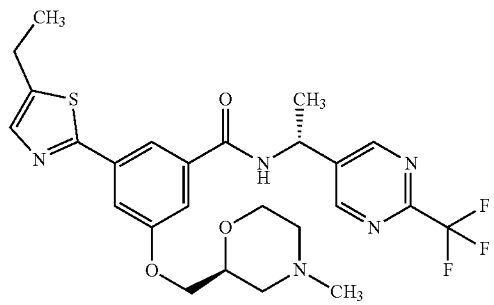 [SMILES: CCc1cnc(-c2cc(OC[C@@H]3CN(C)CCO3)cc(C(=O)N[C@H](C)c3cnc(C(F)(F)F)nc3)c2)s1] | 3-(5-ethyl-1,3-thiazol-2-yl)-5-{[(2S)-4-methylmorpholin-2-yl]methoxy}-N-{(1R)-1-[2-(trifluoromethyl)pyrimidin-5-yl]ethyl}benzamide | $^1$H NMR (500 MHz, DMSO-d6): δ [ppm] 9.14 (d, J = 7.1 Hz, 1H), 9.12 (s, 2H), 7.94 (t, J = 1.3 Hz, 1H), 7.68 (s, 1H), 7.61-7.50 (m, 2H), 5.30 (m, 1H), 4.11 (d, J = 5.0 Hz, 2H), 3.88-3.74 (m, 2H), 3.55 (td, J = 11.2, 2.4 Hz, 1H), 2.90 (q, J = 7.5 Hz, 2H), 2.83-2.76 (m, 1H), 2.63-2.58 (m, 1H), 2.20 (s, 3H), 2.01 (td, J = 11.3, 3.2 Hz, 1H), 1.93 (t, J = 10.6 Hz, 1H), 1.61 (d, J = 7.1 Hz, 3H), 1.29 (t, J = 7.5 Hz, 3H). LCMS (Analytical Method F) Rt = 2.28 min, MS (ESIpos): m/z = 536.1 (M + H)$^+$. |
| 376 | 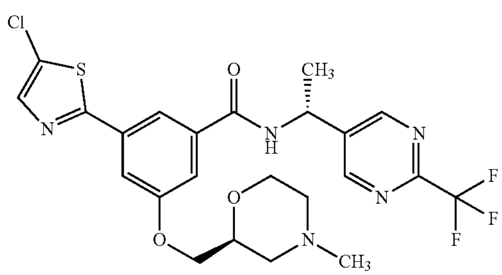 [SMILES: C[C@@H](NC(=O)c1cc(OC[C@@H]2CN(C)CCO2)cc(-c2ncc(Cl)s2)c1)c1cnc(C(F)(F)F)nc1] | 3-(5-chloro-1,3-thiazol-2-yl)-5-{[(2S)-4-methylmorpholin-2-yl]methoxy}-N-{(1R)-1-[2-(trifluoromethyl)pyrimidin-5-yl]ethyl}benzamide | $^1$H NMR (500 MHz, Chloroform-d): δ [ppm] 8.94 (s, 2H), 7.82 (s, 1H), 7.67 (s, 1H), 7.60-7.52 (m, 1H), 7.44 (s, 1H), 6.62 (s, 1H), 5.36 (m, 1H), 4.18-4.06 (m, 2H), 4.06-4.00 (m, 1H), 3.97 (d, J = 11.6 Hz, 1H), 3.80 (t, J = 10.6 Hz, 1H), 2.89 (d, J = 10.4 Hz, 1H), 2.74 (d, J = 10.6 Hz, 1H), 2.38 (s, 3H), 2.33-2.19 (m, 1H), 2.19-2.09 (m, 1H), 1.73 (d, J = 7.1 Hz, 3H). LCMS (Analytical Method F) Rt = 2.28 min, MS (ESIpos): m/z = 542.0 (M + H)$^+$. |
| 377 | 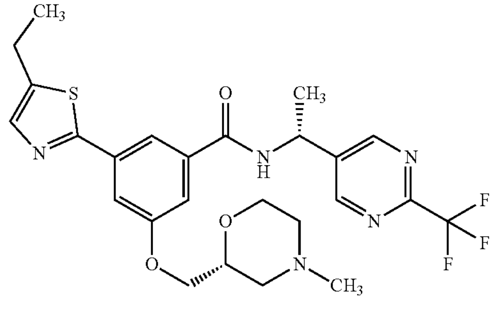 [SMILES: CCc1cnc(-c2cc(OC[C@H]3CN(C)CCO3)cc(C(=O)N[C@H](C)c3cnc(C(F)(F)F)nc3)c2)s1] | 3-(5-ethyl-1,3-thiazol-2-yl)-5-{[(2R)-4-methylmorpholin-2-yl]methoxy}-N-{(1R)-1-[2-(trifluoromethyl)pyrimidin-5-yl]ethyl}benzamide | $^1$H NMR (500 MHz, DMSO-d6): δ [ppm] 9.20-9.06 (m, 3H), 7.94 (t, J = 1.3 Hz, 1H), 7.68 (s, 1H), 7.55 (dt, J = 8.2, 2.3 Hz, 2H), 5.30 (m, 1H), 4.18-4.06 (m, 2H), 3.89-3.73 (m, 2H), 3.55 (td, J = 11.2, 2.4 Hz, 1H), 2.90 (q, J = 7.5 Hz, 2H), 2.83-2.74 (m, 1H), 2.70-2.56 (m, 1H), 2.20 (s, 3H), 2.01 (td, J = 11.3, 3.3 Hz, 1H), 1.93 (t, J = 10.6 Hz, 1H), 1.61 (d, J = 7.1 Hz, 3H), 1.29 (t, J = 7.5 Hz, 3H). LCMS (Analytical Method F) Rt = 2.29 min, MS (ESIpos): m/z = 536.1 (M + H)$^+$. |

| Ex. | Structure | Name | Analytical Data |
|---|---|---|---|
| 378 | 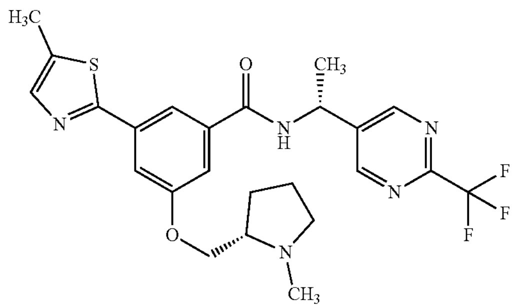 [SMILES: Cc1cnc(-c2cc(OC[C@@H]3CCCN3C)cc(C(=O)N[C@H](C)c3cnc(C(F)(F)F)nc3)c2)s1] | 3-{[(2S)-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide | $^1$H NMR (250 MHz, Chloroform-d): δ [ppm] 8.93 (s, 2H), 7.83 (s, 1H), 7.60-7.47 (m, 2H), 7.44-7.35 (m, 1H), 6.64 (d, J = 6.5 Hz, 1H), 5.36 (m, 1H), 4.02 (m, 2H), 3.12 (t, J = 7.4 Hz, 1H), 2.74-2.58 (m, 1H), 2.53 (d, J = 0.8 Hz, 3H), 2.47 (s, 3H), 2.40-2.21 (m, 1H), 2.10-1.75 (m, 4H), 1.70 (d, J = 7.2 Hz, 3H). LCMS (Analytical Method D) Rt = 3.41 min, MS (ESIpos) m/z = 506 (M + H)$^+$. |
| 379 | 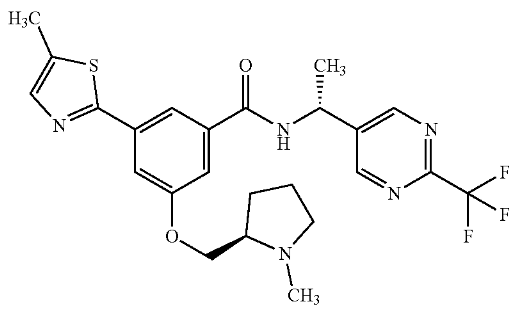 [SMILES: Cc1cnc(-c2cc(OC[C@H]3CCCN3C)cc(C(=O)N[C@H](C)c3cnc(C(F)(F)F)nc3)c2)s1] | 3-{[(2R)-1-methylpyrrolidin-2-yl]methoxy}-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.92 (s, 2H), 7.82 (s, 1H), 7.55-7.52 (m, 1H), 7.51-7.48 (m, 1H), 7.41-7.37 (m, 1H), 6.74 (d, J = 6.6 Hz, 1H), 5.35 (m, 1H), 4.04 (dd, J = 9.3, 5.2 Hz, 1H), 3.99 (dd, J = 9.3, 5.1 Hz, 1H), 3.15-3.08 (m, 1H), 2.69-2.60 (m, 1H), 2.54-2.50 (m, 3H), 2.47 (s, 3H), 2.34-2.25 (m, 1H), 2.07-1.97 (m, 1H), 1.90-1.71 (m, 3H), 1.69 (d, J = 7.2 Hz, 3H). LCMS (Analytical Method D) Rt = 3.41 min, MS (ESIpos) m/z = 506 (M + H)$^+$. |
| 380 | 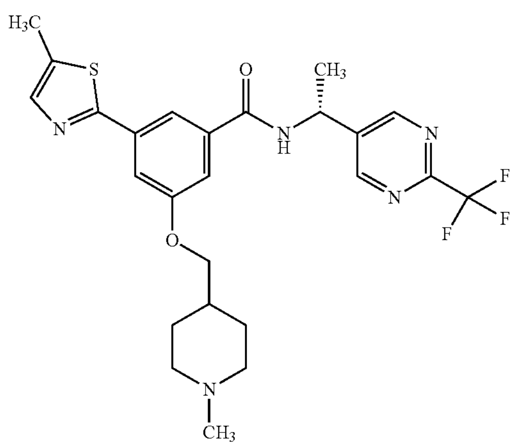 [SMILES: Cc1cnc(-c2cc(OCC3CCN(C)CC3)cc(C(=O)N[C@H](C)c3cnc(C(F)(F)F)nc3)c2)s1] | 3-[(1-methylpiperidin-4-yl)methoxy]-5-(5-methyl-1,3-thiazol-2-yl)-N-{(1R)-1-[2-(trifluoromethyl)pyrimidin-5-yl]ethyl}benzamide | $^1$H NMR (500 MHz, Chloroform-d): δ [ppm] 8.95 (s, 2H), 7.83 (t, J = 1.4 Hz, 1H), 7.52 (dt, J = 4.6, 1.3 Hz, 2H), 7.42-7.36 (m, 1H), 6.74 (s, 1H), 5.36 (m, 1H), 3.93 (d, J = 5.8 Hz, 2H), 2.98 (d, J = 10.8 Hz, 2H), 2.53 (d, J = 1.1 Hz, 3H), 2.36 (s, 3H), 2.08 (t, J = 11.3 Hz, 2H), 1.90-1.80 (m, 3H), 1.72 (d, J = 7.2 Hz, 3H), 1.63-1.49 (m, 2H). LCMS (Analytical Method F): Rt = 2.23 min, MS (ESIpos): m/z = 520 (M + H)$^+$. |
| 381 | 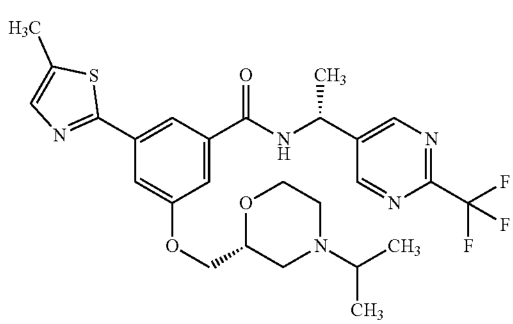 [SMILES: Cc1cnc(-c2cc(OC[C@H]3CN(C(C)C)CCO3)cc(C(=O)N[C@H](C)c3cnc(C(F)(F)F)nc3)c2)s1] | 3-(5-methyl-1,3-thiazol-2-yl)-5-{[(2R)-4-(propan-2-yl)morpholin-2-yl]methoxy}-N-{(1R)-1-[2-(trifluoromethyl)pyrimidin-5-yl]ethyl}benzamide | $^1$H NMR (500 MHz, Chloroform-d): δ [ppm] 8.96 (s, 2H), 7.89 (s, 1H), 7.60 (s, 1H), 7.52 (d, J = 1.2 Hz, 1H), 7.41 (s, 1H), 5.38 (m, 1H), 4.14 (s, 1H), 4.11-4.05 (m, 1H), 4.05-3.70 (m, 3H), 2.85 (s, 4H), 2.53 (d, J = 1.1 Hz, 3H), 1.73 (d, J = 7.1 Hz, 3H), 1.43-0.99 (m, 7H). LCMS (Analytical Method D) Rt = 3.40 min, MS (ESIpos): m/z = 550 (M + H)$^+$. |

| Ex. | Structure | Name | Analytical Data |
|---|---|---|---|
| 382 | (structure) | 3-(5-methyl-1,3-thiazol-2-yl)-5-{[(2S)-4-(propan-2-yl)morpholin-2-yl]methoxy}-N-{(1R)-1-[2-(trifluoromethyl)pyrimidin-5-yl]ethyl}benzamide | $^1$H NMR (500 MHz, DMSO-d6): δ [ppm] 1.00 (d, J = 6.5, 6H), 1.62 (d, J = 7.1, 3H), 2.14 (t, J = 10.6, 1H), 2.19-2.29 (m, 1H), 2.53 (s, 3H), 2.58-2.68 (m, 2H), 2.79-2.88 (m, 1H), 3.47-3.59 (m, 1H), 3.75-3.82 (m, 1H), 3.82-3.88 (m, 1H), 4.06-4.17 (m, 2H), 5.26-5.35 (m, 1H), 7.56 (s, 2H), 7.65 (d, J = 1.2, 1H), 7.93 (s, 1H), 9.12 (s, 2H), 9.15 (d, J = 7.1, 1H). LCMS (Analytical Method F) Rt = 2.23 min, MS (ESIpos): m/z = 550 (M + H)$^+$. |
| 383 | (structure) | 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide, as a mixture of 2 diastereoisomers | $^1$H NMR (500 MHz, Chloroform-d): δ [ppm] 8.87 (s, 2H), 7.80-7.76 (m, 1H), 7.48-7.43 (m, 2H), 7.32 (s, 1H), 6.63 (d, J = 6.5 Hz, 1H), 5.30 (m, 1H), 4.32 (dt, J = 9.1, 3.2 Hz, 1H), 4.02-3.94 (m, 1H), 2.95 (d, J = 9.3 Hz, 1H), 2.71-2.65 (m, 1H), 2.56-2.48 (m, 1H), 2.46 (d, J = 0.6 Hz, 3H), 2.33-2.24 (m, 4H), 2.19 (t, J = 9.9 Hz, 1H), 2.06 -1.94 (m, 2H), 1.65 (d, J = 7.1 Hz, 3H). LCMS (Analytical Method F) Rt = 2.29 min, MS (ESIpos) m/z = 556 (M + H)$^+$. |

Example 383 was formed as a mixture of two diastereoisomers. SFC Chiral Purification (Method 15) provided diastereoisomer 1 (Example 384) and diastereoisomer 2 (Example 385).

Example 384

Diastereoisomer 1; 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide SFC Chiral Purification (Method 15) on 90.3 mg of Example 383 gave 32.9 mg of the title compound as white solid.

SFC Chiral Analysis (Method 15): 99.2% e.e. Rt=1.71 min.

$^1$H NMR (500 MHz, Chloroform-d): δ [ppm] 8.94 (s, 2H), 7.84 (t, J=1.4 Hz, 1H), 7.54 (dd, J=2.4, 1.4 Hz, 1H), 7.54-7.52 (m, 1H), 7.39 (dd, J=2.3, 1.6 Hz, 1H), 6.58 (d, J=6.4 Hz, 1H), 5.37 (m, 1H), 4.39 (dd, J=9.4, 3.8 Hz, 1H), 4.06 (t, J=9.2 Hz, 1H), 3.03 (d, J=10.4 Hz, 1H), 2.79-2.72 (m, 1H), 2.65-2.56 (m, 1H), 2.54 (d, J=1.1 Hz, 3H), 2.41-2.31 (m, 4H), 2.31-2.20 (m, 1H), 2.14-2.00 (m, 2H), 1.72 (d, J=7.2 Hz, 3H).

LC-MS (Analytical Method F) Rt=2.32 min, MS (ESIpos): m/z=556 (M+H)$^+$.

Example 385

Diastereoisomer 2; 3-{[4,4-difluoro-1-methylpiperidin-3-yl]methoxy}-5-(5-methyl-1,3-thiazol-2-yl)-N-{(1R)-1-[2-(trifluoromethyl)pyrimidin-5-yl]ethyl}benzamide SFC Chiral Purification (Method 15) on 90.3 mg of Example 383 gave 27 mg of the title compound.

SFC Chiral Analysis (Method 15): 99.9% e.e. Rt=2.06 min.

$^1$H NMR (500 MHz, Chloroform-d): δ [ppm] 8.94 (s, 2H), 7.84 (t, J=1.4 Hz, 1H), 7.55 (dd, J=2.4, 1.4 Hz, 1H), 7.53 (d, J=1.2 Hz, 1H), 7.39 (dd, J=2.3, 1.6 Hz, 1H), 6.57 (d, J=6.5 Hz, 1H), 5.37 (m, 1H), 4.40 (dd, J=9.4, 3.8 Hz, 1H), 4.06 (t, J=9.2 Hz, 1H), 3.02 (d, J=10.4 Hz, 1H), 2.75 (d, J=11.2 Hz, 1H), 2.65-2.55 (m, 1H), 2.54 (d, J=1.1 Hz, 3H), 2.39-2.31 (m, 4H), 2.26 (t, J=10.1 Hz, 1H), 2.07 (m, 2H), 1.72 (d, J=7.2 Hz, 3H).

LC-MS (Analytical Method F) Rt=2.32 min, MS (ESIpos): m/z=556 (M+H)$^+$.

In analogy to the procedure described for Example 346, the following examples were prepared using T3P and the corresponding carboxylic acid and primary amine starting materials.

| Ex. | Name | Analytical Data |
|---|---|---|
| 386 | 3-[(3-fluoro-1-methylazetidin-3-yl)methoxy]-5-(5-methyl-1,3-thiazol-2-yl)-N-{(1R)-1-[6-(trifluoromethyl)pyridin-3-yl]ethyl}benzamide | ¹H NMR (500 MHz, Chloroform-d): δ [ppm] 8.79 (d, J = 1.7 Hz, 1H), 7.93-7.85 (m, 2H), 7.67 (d, J = 8.1 Hz, 1H), 7.59 (dd, J = 2.3, 1.5 Hz, 1H), 7.52 (d, J = 1.1 Hz, 1H), 7.47-7.44 (m, 1H), 6.62 (d, J = 7.0 Hz, 1H), 5.39 (m, 1H), 4.38 (d, J = 22.7 Hz, 2H), 3.74-3.58 (m, 2H), 3.25 (dd, J = 21.7, 9.5 Hz, 2H), 2.53 (d, J = 1.0 Hz, 3H), 2.46 (s, 3H), 1.67 (d, J = 7.1 Hz, 3H). LCMS (Method A) Rt = 3.49 min, MS (ESIpos): m/z = 509.05 (M + H)⁺. |
| 387 | 3-(5-ethyl-1,3-thiazol-2-yl)-5-[(3-fluoro-1-methylazetidin-3-yl)methoxy]-N-{(1R)-1-[6-(trifluoromethyl)pyridin-3-yl]ethyl}benzamide | ¹H NMR (500 MHz, Chloroform-d): δ [ppm] 8.81 (s, 1H), 7.95-7.88 (m, 2H), 7.69 (d, J = 8.1 Hz, 1H), 7.62 (s, 1H), 7.57 (s, 1H), 7.52 (s, 1H), 6.74 (s, 1H), 5.41 (m, 1H), 4.50-4.31 (m, 2H), 3.75 (t, J = 9.7 Hz, 2H), 3.30 (dd, J = 21.5, 8.7 Hz, 2H), 2.93 (q, J = 7.6 Hz, 2H), 2.50 (s, 3H), 1.70 (d, J = 7.1 Hz, 3H), 1.39 (t, J = 7.5 Hz, 3H). LCMS (Analytical Method F) Rt = 2.39 min, MS (ESIpos): m/z = 523 (M + H)⁺. |
| 388 | 3-{[(3R)-4-methylmorpholin-3-yl]methoxy}-5-(5-methyl-1,3-thiazol-2-yl)-N-{(1R)-1-[6-(trifluoromethyl)pyridazin-3-yl]ethyl}benzamide | ¹H NMR (500 MHz, Chloroform-d): δ [ppm] 7.90 (s, 1H), 7.82 (d, J = 8.7 Hz, 1H), 7.74 (d, J = 8.7 Hz, 1H), 7.61-7.59 (m, 1H), 7.52 (d, 1H), 7.49-7.45 (m, 1H), 7.44 (s, 1H), 5.61 (m, 1H), 4.21-4.15 (m, 1H), 4.12 (dd, J = 9.8, 5.2 Hz, 1H), 3.95 (dd, J = 11.4, 2.7 Hz, 1H), 3.88-3.83 (m, 1H), 3.80-3.72 (m, 1H), 3.64 (t, J = 10.0 Hz, 1H), 2.81 (d, J = 10.8 Hz, 1H), 2.66 (s, 1H), 2.53 (s, 3H), 2.46 (m, 4H), 1.76 (d, J = 7.0 Hz, 3H). LCMS (Analytical Method F) Rt = 2.04 min, MS (ESIpos): m/z = 522 (M + H)⁺. |
| 389 | 3-{[(3S)-4-methylmorpholin-3-yl]methoxy}-5-(5-methyl-1,3-thiazol-2-yl)-N-{(1R)-1-[6-(trifluoromethyl)pyridazin-3-yl]ethyl}benzamide | ¹H NMR (500 MHz, Chloroform-d): [ppm] 7.90 (s, 1H), 7.82 (d, J = 8.7 Hz, 1H), 7.74 (d, J = 8.7 Hz, 1H), 7.62-7.58 (m, 1H), 7.52 (d, J = 1.0 Hz, 1H), 7.49-7.45 (m, 1H), 7.45-7.43 (m, 1H), 5.61 (m, 1H), 4.22-4.15 (m, 1H), 4.15-4.09 (m, 1H), 3.95 (dd, J = 11.3, 2.9 Hz, 1H), 3.88-3.82 (m, 1H), 3.80-3.72 (m, 1H), 3.64 (t, J = 10.3 Hz, 1H), 2.81 (d, J = 9.9 Hz, 1H), 2.66 (s, 1H), 2.53 (d, 3H), 2.46 (m, 4H), 1.76 (d, J = 7.0 Hz, 3H). LCMS (Analytical Method F) Rt = 2.03 min, MS (ESIpos): m/z = 522 (M + H)⁺. |

Example 390

3-{[(2R)-4-ethylmorpholin-2-yl]methoxy}-5-(5-methyl-1,3-thiazol-2-yl)-N-{(1R)-1-[2-(trifluoromethyl)pyrimidin-5-yl]ethyl}benzamide

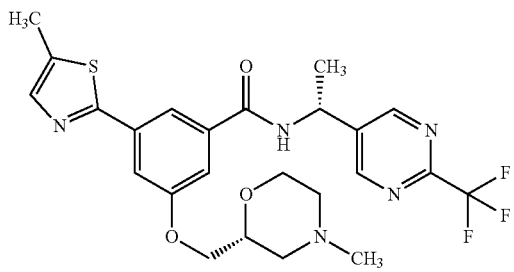

A solution of Example 347 (80 mg, 0.15 mmol), iodoethane (14.5 μL, 0.18 mmol) and potassium carbonate (31 mg, 0.23 mmol) in acetonitrile (2 mL) was stirred for 1 h at RT. The reaction mixture was then heated to 80° C. by microwave irradiation for 20 mins. The reaction was re-treated with iodoethane (14.5 μL, 0.18 mmol) and heated to 80° C. by microwave irradiation for a further 20 mins. The reaction mixture was filtered through Celite® and concentrated under reduced pressure. The crude material was purified by preparative HPLC (Method A) and freeze-dried from MeCN/water to afford 40.4 mg (50% yield) of the title compound as white powder.

$^1$H NMR (500 MHz, Chloroform-d): δ [ppm] 8.93 (s, 2H), 7.87 (t, J=1.4 Hz, 1H), 7.57 (dd, J=2.4, 1.5 Hz, 1H), 7.52 (d, J=1.2 Hz, 1H), 7.41 (dd, J=2.3, 1.6 Hz, 1H), 6.63 (d, J=6.5 Hz, 1H), 5.36 (m, 1H), 4.12 (dd, J=9.9, 6.0 Hz, 1H), 4.05 (dd, J=9.9, 4.1 Hz, 1H), 4.01-3.94 (m, 2H), 3.76 (td, J=11.4, 2.4 Hz, 1H), 2.91 (d, J=11.1 Hz, 1H), 2.77 (d, J=11.5 Hz, 1H), 2.53 (d, J=1.1 Hz, 3H), 2.46 (q, J=7.2 Hz, 2H), 2.17 (td, J=11.4, 3.3 Hz, 1H), 2.03 (t, J=10.7 Hz, 1H), 1.71 (d, J=7.2 Hz, 3H), 1.11 (t, J=7.2 Hz, 3H).

LCMS (Analytical Method F) Rt=2.17 min, MS (ESIpos): m/z=536 (M+H)$^+$.

Example 391

3-{[(2R)-4-(2,2-difluoroethyl)morpholin-2-yl]methoxy}-5-(5-methyl-1,3-thiazol-2-yl)-N-{(1R)-1-[2-(trifluoromethyl)pyrimidin-5-yl]ethyl}benzamide

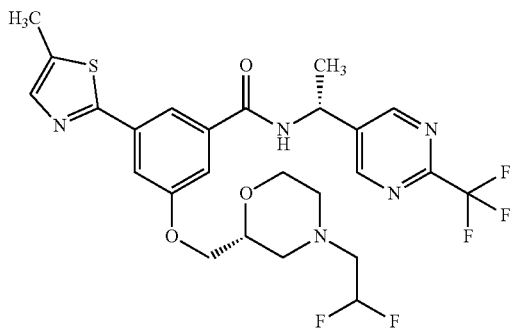 [SMILES: Cc1cnc(-c2cc(OC[C@H]3CN(CC(F)F)CCO3)cc(C(=O)N[C@H](C)c3cnc(C(F)(F)F)nc3)c2)s1]

A stirred mixture of Example 347 (100 mg, 0.19 mmol), 1,1-difluoro-2-iodoethane (20 μL, 0.21 mmol) and potassium carbonate (40 mg, 0.29 mmol) in anhydrous acetonitrile (3 mL) was heated to 80° C. by microwave irradiation for 20 mins. Additional 1,1-difluoro-2-iodoethane (40 μL, 0.42 mmol) and potassium carbonate (40 mg, 0.29 mmol) was added and the reaction mixture heated to 100° C. by microwave irradiation for 20 mins. A further quantity of 1,1-difluoro-2-iodoethane (100 μL, 2.1 mmol) was added and the reaction mixture heated to 100° C. for 3 h by microwave irradiation. Further 1,1-difluoro-2-iodoethane (100 μL, 2.1 mmol) was added and the reaction mixture heated to 100° C. for 2 h by microwave irradiation. The reaction mixture was filtered, concentrated under reduced pressure and purified by preparative HPLC (Method B) then lyophilised from acetonitrile/water to give 64 mg (58% yield) of the title compound as white solid.

$^1$H NMR (500 MHz, Chloroform-d): δ [ppm] 8.93 (s, 2H), 7.87 (s, 1H), 7.56 (dd, J=2.3, 1.4 Hz, 1H), 7.52 (d, J=1.1 Hz, 1H), 7.43-7.35 (m, 1H), 6.62 (d, J=6.3 Hz, 1H), 5.92 (t, J=55.9 Hz, 1H), 5.36 (m, 1H), 4.11 (dd, J=9.8, 5.7 Hz, 1H), 4.04 (dd, J=9.8, 4.4 Hz, 1H), 4.01-3.96 (m, 1H), 3.96-3.92 (m, 1H), 3.81-3.72 (m, 1H), 2.94 (d, J=11.1 Hz, 1H), 2.84-2.74 (m, 3H), 2.53 (d, J=0.9 Hz, 3H), 2.48 (td, J=11.3, 2.7 Hz, 1H), 2.35 (t, J=10.6 Hz, 1H), 1.71 (d, J=7.2 Hz, 3H).

LC-MS (Analytical Method F) Rt=3.24 min, MS (ESIpos): m/z=572 (M+H)$^+$.

Example 392

Methyl (2R)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate

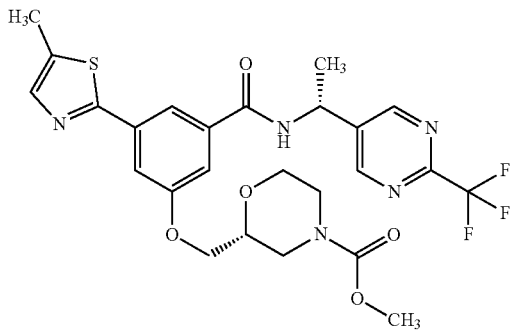 [SMILES: COC(=O)N1CCO[C@@H](COc2cc(C(=O)N[C@H](C)c3cnc(C(F)(F)F)nc3)cc(-c3ncc(C)s3)c2)C1]

To a solution of Example 347 (35 mg, 69.0 μmol) in DCM (1 mL) was added DIPEA (24 μL, 138 μmol) and methyl chloroformate (8.0 μL, 103 μmol) at RT. The reaction was stirred for 1 h then diluted with DCM (3 mL) and washed with saturated NaHCO$_3$ (3 mL). The aqueous layer was extracted with DCM (2×3 mL). The combined DCM layers were dried (MgSO$_4$), filtered and concentrated under reduced pressure. The crude material was purified by Biotage Isolera™ chromatography (eluting with 0-20% MeOH in DCM on a 10 g pre-packed KP—SiO$_2$ column) and the product freeze-dried from MeCN/water to give 31.8 mg (82% yield) of the title compound as white powder.

$^1$H NMR (500 MHz, Chloroform-d): δ [ppm] 8.94 (s, 2H), 7.88 (s, 1H), 7.57 (dd, J=2.4, 1.4 Hz, 1H), 7.53 (d, J=1.1 Hz, 1H), 7.42-7.39 (m, 1H), 6.64 (d, J=5.8 Hz, 1H), 5.36 (m, 1H), 4.21-4.09 (m, 2H), 4.07 (dd, J=9.9, 4.7 Hz, 1H), 4.02-3.87 (m, 2H), 3.86-3.78 (m, 1H), 3.74 (s, 3H), 3.61 (t, J=11.6 Hz, 1H), 3.07 (s, 1H), 2.93 (s, 1H), 2.54 (d, J=1.1 Hz, 3H), 1.72 (d, J=7.2 Hz, 3H).

LCMS (Analytical Method D) Rt=4.31 min, MS (ESIpos): m/z=566 (M+H)$^+$.

In analogy to the procedure described for Example 392, the following example was prepared from the corresponding secondary amine and chloroformate starting materials.

| Ex. | Structure | Name | Analytical Data |
|---|---|---|---|
| 393 | 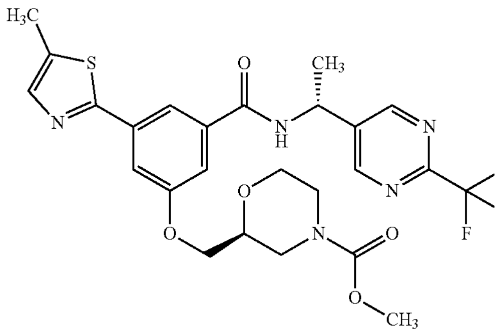 | Methyl (2S)-2-{[3-(5-methyl-1,3-thiazol-2-yl)-5-({(1R)-1-[2-(trifluoromethyl)pyrimidin-5-yl]ethyl}carbamoyl)phenoxy]methyl}morpholine-4-carboxylate | $^1$H NMR (500 MHz, DMSO-d6): δ [ppm] 1.61 (d, J = 7.1, 3H), 2.52 (s, 3H), 2.79-3.08 (m, 2H), 3.49 (td, J = 11.6, 2.8, 1H), 3.63 (s, 3H), 3.73-3.83 (m, 2H), 3.88 (d, J = 11.2, 1H), 3.94- 4.05 (m, 1H), 4.11-4.22 (m, 2H), 5.25-5.35 (m, 1H), 7.52-7.59 (m, 2H), 7.64 (d, J = 1.2, 1H), 7.93 (t, J = 1.3, 1H), 9.12 (s, 2H), 9.15 (d, J = 7.1, 1H). LCMS (Analytical Method F) Rt = 3.38 min, MS (ESIpos): m/z = 566 (M + H)$^+$. |

Example 394

3-(Azetidin-3-ylmethoxy)-5-(5-methyl-1,3-thiazol-2-yl)-N-{(1R)-1-[2-(trifluoromethyl)pyrimidin-5-yl]ethyl}benzamide

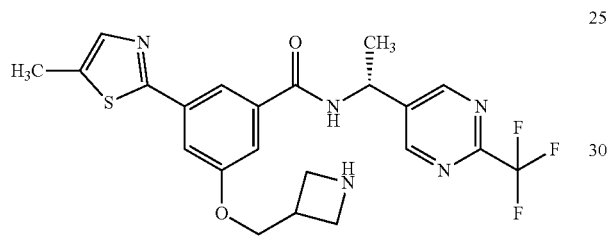

A mixture of Intermediate 148 (90.0 mg, 156 μmol), TFA (60 μL, 780 μmol) in DCM was stirred at RT for 18 h. The mixture was evaporated to dryness and the residue purified by preparative HPLC (method 1, LCMS, Rt: 0.85 min) to give 15.0 mg (18% yield) of the title compound.

$^1$H NMR (400 MHz, DMSO-d$_6$): δ [ppm] 1.61 (d, 3H) 3.10-3.21 (m, 1H) 3.63-3.78 (m, 2H) 3.93 (s, 2H) 4.27 (d, 2H) 5.19-5.39 (m, 1H) 7.49-7.70 (m, 3H) 7.88-7.99 (m, 1H) 9.12 (s, 2H) 9.20-9.33 (m, 1H).

LCMS, method 1, rt: 0.85 min, MS ES+m/z=478 (M+H)$^+$.

Example 395

3-{[(3R)-4-methyl-5-oxomorpholin-3-yl]methoxy}-5-(5-methyl-1,3-thiazol-2-yl)-N-{(1R)-1-[2-(trifluoromethyl)pyrimidin-5-yl]ethyl}benzamide

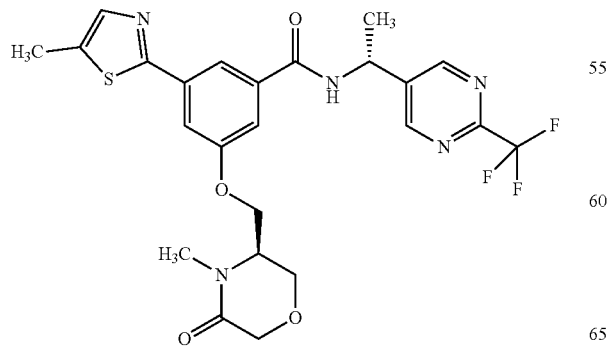

A mixture of Intermediate 5CX (417 mg, 1.15 mmol), Intermediate VI (367 mg, 1.61 mmol), HATU (1.05 g, 2.76 mmol) and DIPEA (980 µL, 5.8 mmol) in DMF (52 mL) was stirred at 60° C. for 12 h. The mixture was evaporated to dryness under reduced pressure and the residue purified by column chromatography (silica gel, hexane/EE gradient) to give 313 mg (49% yield) of the title compound.

$^1$H NMR (400 MHz, DMSO-d$_6$): δ [ppm] 1.61 (d, 3H) 3.01 (s, 3H) 3.70-3.81 (m, 1H) 3.89 (d, 1H) 3.96-4.12 (m, 3H) 4.22-4.41 (m, 2H) 5.30 (s, 1H) 7.50-7.70 (m, 3H) 7.96 (t, 1H) 9.06-9.27 (m, 3H).

LCMS, method 1, rt: 1.15 min, MS ES+m/z=536 (M+H)$^+$.

In analogy to the synthesis procedure described for Example 395, the following examples were prepared from the respective starting materials:

| Ex. | Structure | Name | Analytical Data |
|---|---|---|---|
| 396 | 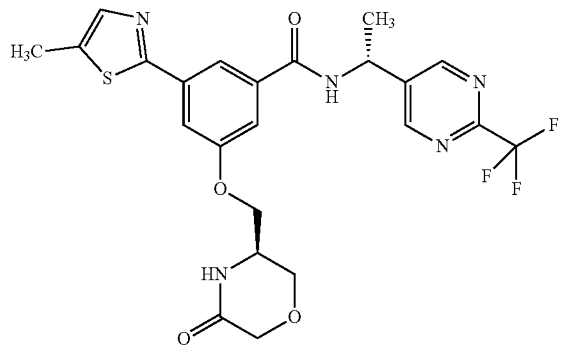 [SMILES: Cc1cnc(-c2cc(OC[C@H]3COCC(=O)N3)cc(C(=O)N[C@H](C)c3cnc(C(F)(F)F)nc3)c2)s1] | 3-(5-methyl-1,3-thiazol-2-yl)-5-{[(3R)-5-oxomorpholin-3-yl]methoxy}-N-{(1R)-1-[2-(trifluoromethyl)pyrimidin-5-yl]ethyl}benzamide | LCMS, method 1, rt: 1.06 min, MS ES+ m/z = 522 (M + H)$^+$; $^1$H NMR (400 MHz, DMSO-d$_6$): δ [ppm] 1.61 (d, 3 H) 3.70-3.80 (m, 1 H) 3.86 (t, 2H) 3.97-4.12 (m, 3 H) 4.17 (d, 1 H) 5.30 (s, 1 H) 7.50-7.70 (m, 3 H) 7.91-8.01 (m, 1 H) 8.30 (d, 1 H) 9.12 (s, 2 H) 9.20 (d, 1 H) |
| 397 | 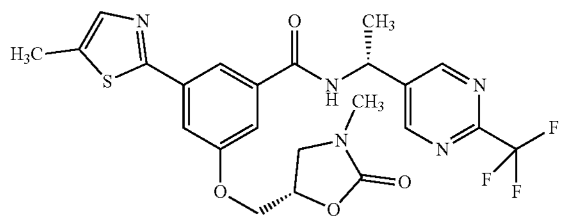 [SMILES: Cc1cnc(-c2cc(OC[C@@H]3CN(C)C(=O)O3)cc(C(=O)N[C@H](C)c3cnc(C(F)(F)F)nc3)c2)s1] | 3-{[(5S)-3-methyl-2-oxo-1,3-oxazolidin-5-yl]methoxy}-5-(5-methyl-1,3-thiazol-2-yl)-N-{(1R)-1-[2-(trifluoromethyl)pyrimidin-5-yl]ethyl}benzamide | LCMS, method 1, rt: 1.11 min, MS ES+ m/z = 522 (M + H)$^+$; $^1$H NMR (400 MHz, DMSO-d$_6$): δ [ppm] 1.61 (d, 3 H) 2.79 (s, 3 H) 3.43 (dd, 1 H) 3.70 (t, 1 H) 4.18-4.41 (m, 2 H) 4.79-4.97 (m, 1 H) 5.30 (s, 1 H) 7.52-7.71 (m, 3 H) 7.95 (t, 1 H) 9.12 (s, 2 H) 9.20 (d, 1 H) |
| 398 | 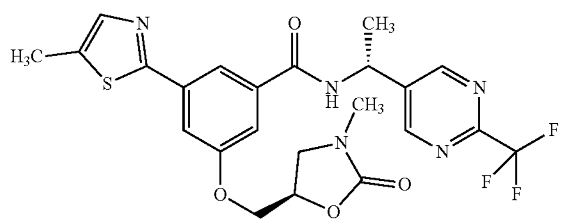 [SMILES: Cc1cnc(-c2cc(OC[C@H]3CN(C)C(=O)O3)cc(C(=O)N[C@H](C)c3cnc(C(F)(F)F)nc3)c2)s1] | 3-{[(5R)-3-methyl-2-oxo-1,3-oxazolidin-5-yl]methoxy}-5-(5-methyl-1,3-thiazol-2-yl)-N-{(1R)-1-[2-(trifluoromethyl)pyrimidin-5-yl]ethyl}benzamide | LCMS, method 1, rt: 1.11 min, MS ES+ m/z = 522 (M + H)$^+$; $^1$H NMR (400 MHz, DMSO-d$_6$): δ [ppm] 1.61 (d, 3 H) 2.79 (s, 3 H) 3.38-3.49 (m, 1 H) 3.70 (s, 1 H) 4.19-4.40 (m, 2 H) 4.82-4.96 (m, 1 H) 5.30 (s, 1 H) 7.49-7.71 (m, 3 H) 7.95 (t, 1 H) 9.12 (s, 2 H) 9.19 (d, 1 H) |
| 399 | 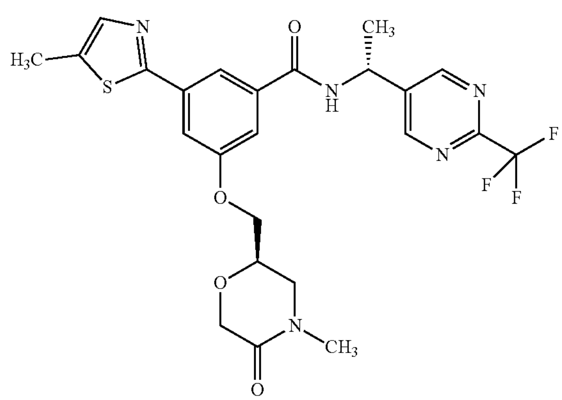 [SMILES: Cc1cnc(-c2cc(OC[C@H]3CN(C)C(=O)CO3)cc(C(=O)N[C@H](C)c3cnc(C(F)(F)F)nc3)c2)s1] | 3-{[(2R)-4-methyl-5-oxomorpholin-2-yl]methoxy}-5-(5-methyl-1,3-thiazol-2-yl)-N-{(1R)-1-[2-(trifluoromethyl)pyrimidin-5-yl]ethyl}benzamide | LCMS, method 1, rt: 1.09 min, MS ES+ m/z = 536 (M + H)$^+$; $^1$H NMR (500 MHz, DMSO-d$_6$): δ [ppm] 1.61 (d, 3 H) 2.89 (s, 3 H) 3.35-3.39 (m, 1 H) 3.42-3.54 (m, 1 H) 4.13 (s, 2H) 4.23 (s, 3 H) 5.21-5.37 (m, 1 H) 7.50-7.69 (m, 3 H) 7.88-7.99 (m, 1 H) 9.12 (s, 3 H) |

| Ex. | Structure | Name | Analytical Data |
|---|---|---|---|
| 400 | 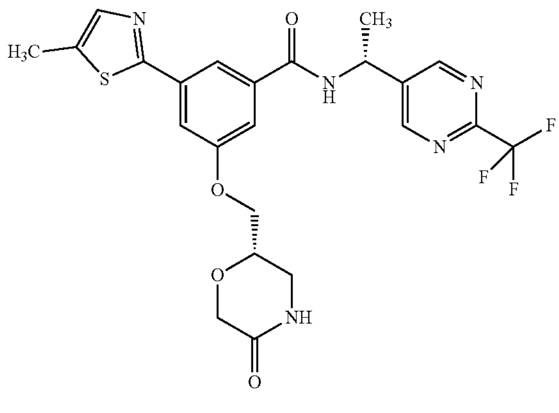 [SMILES: Cc1cnc(-c2cc(OC[C@@H]3CNC(=O)CO3)cc(C(=O)N[C@H](C)c3cnc(C(F)(F)F)nc3)c2)s1] | 3-(5-methyl-1,3-thiazol-2-yl)-5-{[(2S)-5-oxomorpholin-2-yl]methoxy}-N-{(1R)-1-[2-(trifluoromethyl)pyrimidin-5-yl]ethyl}benzamide | LCMS, method 1, rt: 1.04 min, MS ES+ m/z = 522 (M + H)+; 1H NMR (400 MHz, DMSO-d6): δ [ppm] 1.60 (d, 3 H) 3.31 (s, 2 H) 4.09 (s, 3 H) 4.15-4.28 (m, 2 H) 5.21-5.37 (m, 1 H) 7.50-7.68 (m, 3 H) 7.94 (s, 1 H) 8.02-8.13 (m, 1 H) 9.12 (s, 3 H) |
| 401 | 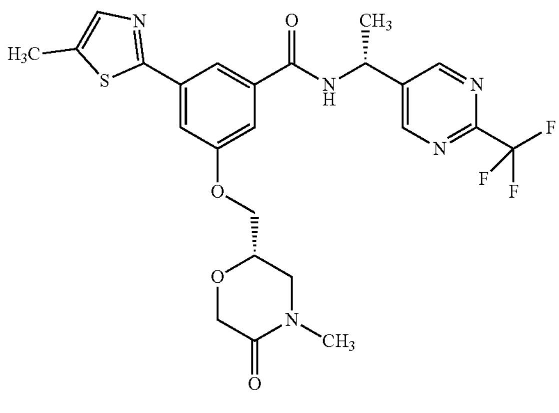 [SMILES: Cc1cnc(-c2cc(OC[C@@H]3CN(C)C(=O)CO3)cc(C(=O)N[C@H](C)c3cnc(C(F)(F)F)nc3)c2)s1] | 3-{[(2S)-4-methyl-5-oxomorpholin-2-yl]methoxy}-5-(5-methyl-1,3-thiazol-2-yl)-N-{(1R)-1-[2-(trifluoromethyl)pyrimidin-5-yl]ethyl}benzamide | LCMS, method 1, rt: 1.09 min, MS ES+ m/z = 536 (M + H)+; 1H NMR (400 MHz, DMSO-d6): δ [ppm] 1.61 (d, 3 H) 2.89 (s, 3 H) 3.35-3.41 (m, 1 H) 3.48 (s, 1 H) 4.13 (s, 2 H) 4.18-4.31 (m, 3 H) 5.30 (s, 1 H) 7.54-7.61 (m, 2 H) 7.65 (d, 1 H) 7.94 (t, 1 H) 9.06-9.25 (m, 3 H) |
| 402 | 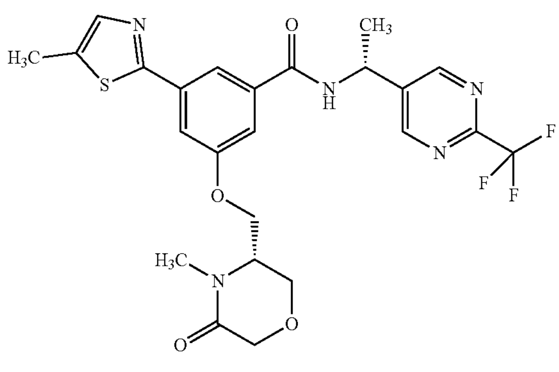 [SMILES: Cc1cnc(-c2cc(OC[C@@H]3COCC(=O)N3C)cc(C(=O)N[C@H](C)c3cnc(C(F)(F)F)nc3)c2)s1] | 3-{[(3S)-4-methyl-5-oxomorpholin-3-yl]methoxy}-5-(5-methyl-1,3-thiazol-2-yl)-N-{(1R)-1-[2-(trifluoromethyl)pyrimidin-5-yl]ethyl}benzamide | LCMS, method 1, rt: 1.11 min, MS ES+ m/z = 536 (M + H)+; 1H NMR (500 MHz, DMSO-d6): δ [ppm] 1.61 (d, 3 H) 3.00 (s, 3 H) 3.70-3.81 (m, 1 H) 3.88 (s, 1 H) 3.97-4.12 (m, 3 H) 4.29 (d, 2 H) 5.30 (s, 1 H) 7.51-7.69 (m, 3 H) 7.96 (t, 1 H) 9.12 (s, 2 H) 9.19 (d, 1 H) |
| 403 | 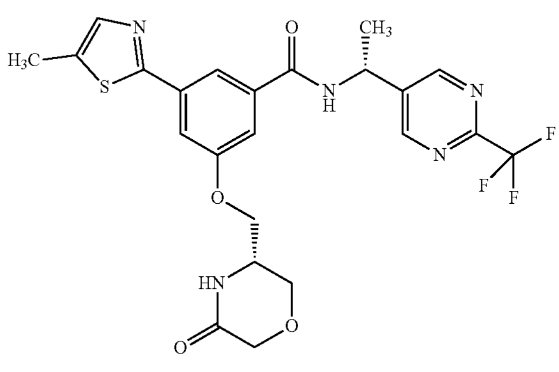 [SMILES: Cc1cnc(-c2cc(OC[C@@H]3COCC(=O)N3)cc(C(=O)N[C@H](C)c3cnc(C(F)(F)F)nc3)c2)s1] | 3-(5-methyl-1,3-thiazol-2-yl)-5-{[(3S)-5-oxomorpholin-3-yl]methoxy}-N-{(1R)-1-[2-(trifluoromethyl)pyrimidin-5-yl]ethyl}benzamide | LCMS, method 1, rt: 1.06 min, MS ES+ m/z = 522 (M + H)+; 1H NMR (500 MHz, DMSO-d6): δ [ppm] 1.61 (d, 3 H) 3.71-3.79 (m, 1 H) 3.86 (t, 2 H) 4.02 (s, 2 H) 4.08 (d, 1 H) 4.14-4.24 (m, 1 H) 5.30 (s, 1 H) 7.51-7.70 (m, 3 H) 7.95 (t, 1 H) 8.30 (d, 1 H) 9.12 (s, 2 H) 9.20 (d, 1 H) |

| Ex. | Structure | Name | Analytical Data |
|---|---|---|---|
| 404 | 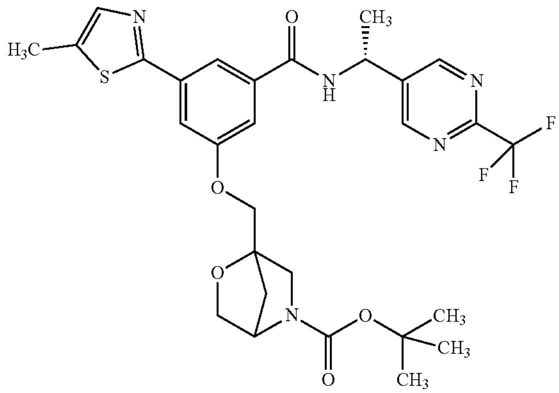 [SMILES: Cc1cnc(-c2cc(OCC34CC(CO3)N(C(=O)OC(C)(C)C)C4)cc(C(=O)N[C@H](C)c3cnc(C(F)(F)F)nc3)c2)s1] | tert-butyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers | LCMS, method 1, rt: 1.37 min, MS ES+ m/z = 620 (M + H)+; 1H NMR (400 MHz, DMSO-d6): δ [ppm] 1.41 (d, 9 H) 1.61 (d, 3 H) 1.84-2.00 (m, 2 H) 3.34-3.48 (m, 2 H) 3.72-3.79 (m, 1 H) 3.81-3.91 (m, 1 H) 4.44 (br. s., 3 H) 5.21-5.37 (m, 1 H) 7.52-7.72 (m, 3 H) 7.94 (t, 1 H) 9.12 (s, 3 H) |
| 405 | 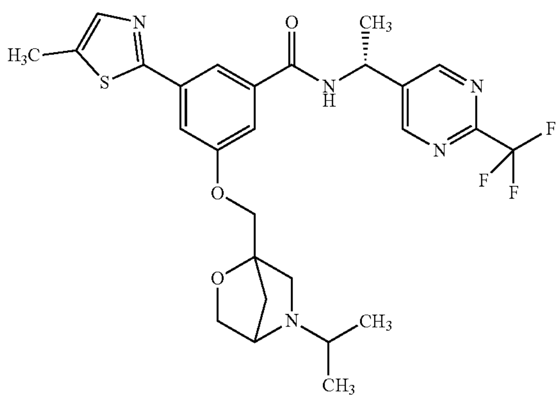 [SMILES: Cc1cnc(-c2cc(OCC34CC(CO3)N(C(C)C)C4)cc(C(=O)N[C@H](C)c3cnc(C(F)(F)F)nc3)c2)s1] | 3-[(5-isopropyl-2-oxa-5-azabicyclo[2.2.1]hept-1-yl)methoxy]-5-(5-methyl-1,3-thiazol-2-yl)-N-{(1R)-1-[2-(trifluoromethyl)pyrimidin-5-yl]ethyl}benzamide, as a mixture of 2 diastereoisomers | LCMS, method 1, rt: 0.94 min, MS ES+ m/z = 562 (M + H)+; 1H NMR (400 MHz, DMSO-d6): δ [ppm] 1.00 (t, 6 H) 1.61 (d, 3 H) 1.69-1.86 (m, 2 H) 2.61-2.76 (m, 1 H) 3.13 (d, J1 H) 3.60-3.72 (m, 2 H) 3.99 (d, 1 H) 4.27-4.46 (m, 2 H) 5.30 (s, 1 H) 7.50-7.69 (m, 3 H) 7.92 (t, 1 H) 9.07-9.23 (m, 3 H) |
| 406 | 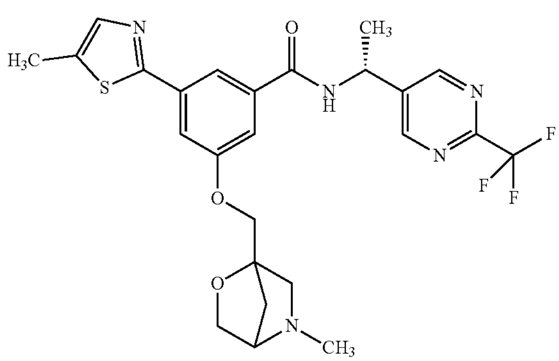 [SMILES: Cc1cnc(-c2cc(OCC34CC(CO3)N(C)C4)cc(C(=O)N[C@H](C)c3cnc(C(F)(F)F)nc3)c2)s1] | 3-[(5-methyl-2-oxa-5-azabicyclo[2.2.1]hept-1-yl)methoxy]-5-(5-methyl-1,3-thiazol-2-yl)-N-{(1R)-1-[2-(trifluoromethyl)pyrimidin-5-yl]ethyl}benzamide, as a mixture of 2 diastereoisomers | LCMS, method 1, rt: 0.89 min, MS ES+ m/z = 534 (M + H)+; 1H NMR (400 MHz, DMSO-d6): δ [ppm] 1.61 (d, 3 H) 1.74 (d, 1 H) 1.90 (s, 1 H) 2.38 (s, 3 H) 2.59 (s, 1 H) 2.97 (d, 1 H) 3.46 (s, 2 H) 3.67 (dd, 1 H) 4.01 (d, 1 H) 4.28-4.49 (m, 2 H) 5.30 (s, 1 H) 7.50-7.71 (m, 3 H) 7.93 (s, 1 H) 9.06-9.24 (m, 1 H) |

Example 407

3-(5-Methyl-1,3-thiazol-2-yl)-5-[2-oxa-5-azabicyclo[2.2.1]hept-1-ylmethoxy]-N-{(1R)-1-[2-(trifluoromethyl)pyrimidin-5-yl]ethyl}benzamide, as a mixture of 2 diastereoisomers

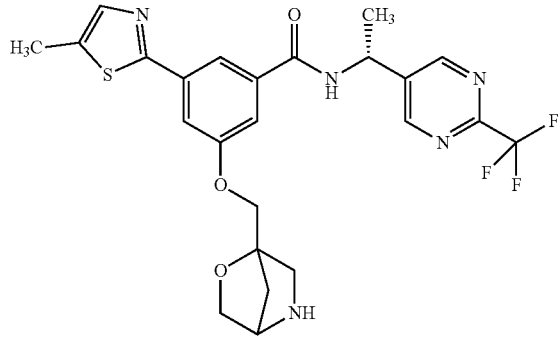 [SMILES: Cc1cnc(-c2cc(OCC34CNC(CO3)C4)cc(C(=O)N[C@H](C)c3cnc(C(F)(F)F)nc3)c2)s1]

A mixture of Example 404 (610 mg, 984 µmol), TFA (5.0 mL, 65 mmol) in DCM (50 mL) was stirred at until complete conversion. The mixture was evaporated to dryness under reduced pressure. Water, saturated aqueous NaHCO₃ and DCM were added and the phases separated. The aqueous layer was extracted twice with DCM. The combined organic layers were evaporated to dryness and purified by preparative HPLC (method 1, LCMS, Rt: 0.90 min) to give 480.0 mg (94% yield) of the title compound.

¹H NMR (500 MHz, DMSO-d₆): δ [ppm] 1.61 (d, 3H) 1.67-1.80 (m, 2H) 2.92-3.03 (m, 2H) 3.62-3.84 (m, 3H) 4.36-4.53 (m, 2H) 5.30 (t, 1H) 7.52-7.67 (m, 3H) 7.93 (t, 1H) 9.08-9.24 (m, 3H).

LCMS, method 1, rt: 0.88 min, MS ES+m/z=520 (M+H)⁺.

In analogy to the synthesis procedure described for Example 366, the following examples were prepared using STAB and the corresponding amine and aldehyde or ketone starting materials and purified by preparative HPLC (method 1):

Example 409

Methyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers

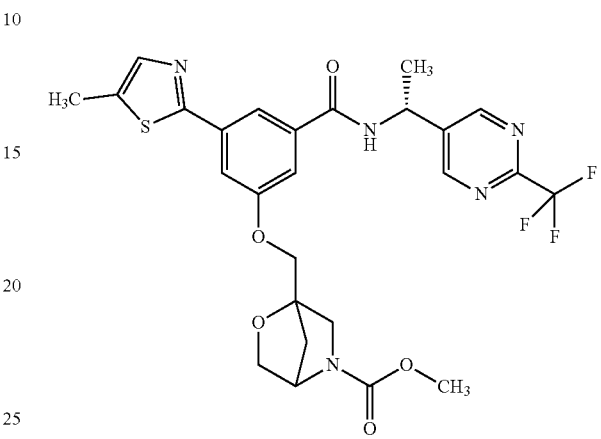

To a mixture of Example 407 (105 mg, 202 µmol), DIPEA (180 µL, 1.0 mmol) in DCM (5 mL) was added methyl carbonochloridate (47 µL, 610 µmol), and the mixture was stirred at until complete conversion. Water and DCM were added and the layers evaporated. The aqueous layer was extracted with DCM and the combined organic layers were evaporated to dryness. The residue was purified via preparative HPLC (method 1, LCMS, Rt: 1.19 min) to give 70.0 mg (60% yield) of the title compound.

¹H NMR (400 MHz, DMSO-d₆): δ [ppm] 1.61 (d, 3H) 1.92 (s, 2H) 3.34-3.54 (m, 2H) 3.61 (d, 3H) 3.73-3.93 (m, 2H) 4.39-4.61 (m, 3H) 5.30 (s, 1H) 7.53-7.70 (m, 3H) 7.94 (t, 1H) 9.07-9.26 (m, 3H).

LCMS, method 1, rt: 1.19 min, MS ES+m/z=578 (M+H)⁺.

| Ex. | Structure | Name | Analytic |
|---|---|---|---|
| 408 | 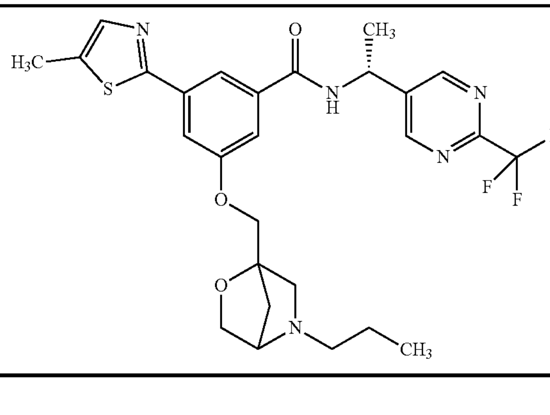 | 3-(5-methyl-1,3-thiazol-2-yl)-5-[(5-propyl-2-oxa-5-azabicyclo[2.2.1]hept-1-yl)methoxy]-N-{(1R)-1-[2-(trifluoromethyl)pyrimidin-5-yl]ethyl}benzamide, as a mixture of 2 diastereoisomers | LCMS, method 1, rt: 0.93 min, MS ES+ m/z = 562 (M + H)⁺; ¹H NMR (400 MHz, DMSO-d₆): δ [ppm] 0.88 (t, 3 H) 1.32-1.47 (m, 2 H) 1.61 (d, 3 H) 1.68-1.75 (m, 1 H) 1.80-1.89 (m, 1 H) 2.96-3.04 (m, 1 H) 3.48-3.51 (m, 1 H) 3.62-3.70 (m, 1 H) 3.92-4.03 (m, 1 H) 4.38 (d, 2 H) 5.23-5.35 (m, 1 H) 7.52-7.68 (m, 3 H) 7.92 (s, 1 H) 9.12 (s, 3 H) |

Example 410

Ethyl 1-{[3-(5-methyl-1,3-thiazol-2-yl)-5-({(1R)-1-[2-(trifluoromethyl)pyrimidin-5-yl]ethyl}carbamoyl)phenoxy]methyl}-2-oxa-5-azabicyclo[2.2.1]heptane-5-carboxylate, as a mixture of 2 diastereoisomers

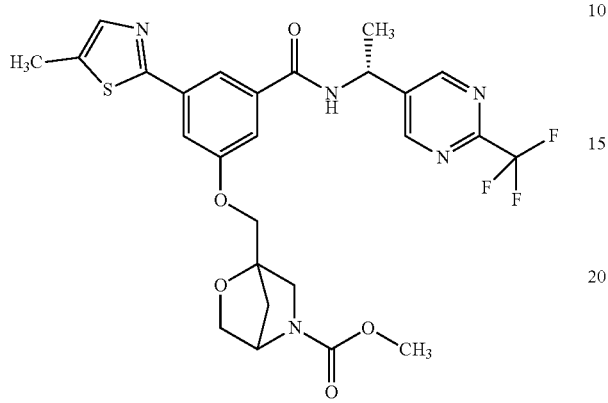

To a mixture of Example 407 (50.0 mg, 96.2 µmol), DIPEA (84 µL, 480 µmol) in DCM (2.4 mL) was added ethyl carbonochloridate (31.3 mg, 289 µmol), and the mixture was stirred at until complete conversion. Water and DCM were added and the layers evaporated. The aqueous layer was extracted with DCM and the combined organic layers were evaporated to dryness. The residue was purified via preparative HPLC (method 1, LCMS, Rt: 1.25 min) to give 40.0 mg (70% yield) of the title compound.

$^1$H NMR (400 MHz, DMSO-d$_6$): δ [ppm] 1.19 (q, 3H) 1.61 (d, 3H) 1.91 (br. s., 2H) 3.35-3.57 (m, 2H) 3.71-3.91 (m, 2H) 3.99-4.14 (m, 2H) 4.38-4.58 (m, 3H) 5.30 (s, 1H) 7.51-7.71 (m, 3H) 7.94 (t, 1H) 9.07-9.24 (m, 3H).

LCMS, method 1, rt: 1.25 min, MS ES+m/z=592 (M+H)$^+$.

Example 411

3-{[(2S)-4-ethylmorpholin-2-yl]methoxy}-5-(5-methyl-1,3-thiazol-2-yl)-N-{(1R)-1-[2-(trifluoromethyl)pyrimidin-5-yl]ethyl}benzamide

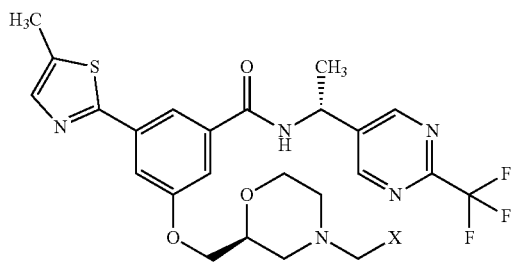

Example 350 (50 mg, 0.10 mmol) was dissolved in DCE (1 mL) at RT. Acetaldehyde (55 µL) and acetic acid (5 µL) were added and the reaction mixture stirred at RT for 30 minutes. STAB (63 mg, 0.30 mmol) was added and the reaction stirred overnight. The reaction mixture was neutralised with saturated NaHCO$_3$ (2 mL) and extracted with DCM (2×2 mL). The combined organics were dried over magnesium sulphate, filtered and evaporated to give crude product. Purification by preparative HPLC (Method A) in two injections gave 11 mg (20% yield) of the title compound.

$^1$H NMR (500 MHz, DMSO-d6): δ [ppm] 1.01 (t, J=7.2, 3H), 1.61 (d, J=7.1, 3H), 1.93 (t, J=10.6, 1H), 2.01 (td, J=11.3, 3.2, 1H), 2.35 (q, J=7.2, 2H), 2.51 (s, 3H), 2.66-2.74 (m, 1H), 2.85-2.92 (m, 1H), 3.55 (td, J=11.2, 2.4, 1H), 3.77-3.86 (m, 2H), 4.07-4.15 (m, 2H), 5.25-5.34 (m, 1H), 7.54 (d, J=1.3, 2H), 7.64 (d, J=1.2, 1H), 7.92 (t, J=1.4, 1H), 9.12 (s, 2H), 9.15 (d, J=7.1, 1H).

LC-MS (Analytical Method A) Rt=2.17 min, MS (ESI-pos): m/z=536.1 (M+H)$^+$.

In analogy to the procedure described for Example 346, the following example was prepared using T3P and the corresponding carboxylic acid and primary amine starting materials.

| Ex. | Structure | Name | Analytical Data |
|---|---|---|---|
| 412 | 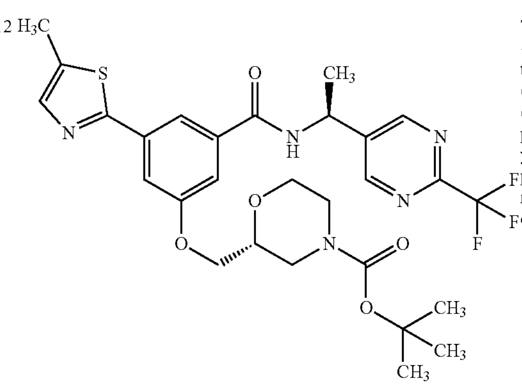 | Tert-butyl (2R)-2-{[3-(5-methyl-1,3-thiazol-2-yl)-5-({(1S)-1-[2-(trifluoromethyl)pyrimidin-5-yl]ethyl}carbamoyl)phenoxy]methyl}morpholine-4-carboxylate | $^1$H NMR (500 MHz, Chloroform-d): δ [ppm] 8.94 (s, 2H), 7.90-7.86 (m, 1H), 7.55-7.51 (m, 2H), 7.50-7.48 (m, 1H), 7.40-7.32 (m, 1H), 7.23-6.94 (m, 1H), 5.41-5.31 (m, 1H), 4.15-3.80 (m, 5H), 3.80-3.73 (m, 1H), 3.62-3.51 (m, 1H), 3.09-2.63 (m, 2H), 2.53-2.49 (m, 3H), 1.70 (d, J = 7.1 Hz, 3H), 1.47 (s, 9H). LCMS (Analytical Method F) Rt = 4.02 min, MS (ESIpos) m/z = 608 (M + H)$^+$. |

In analogy to the procedure described for Example 347, the following examples were prepared using TFA and the corresponding N-Boc protected amine starting materials.

| Ex. | Structure | Name | Analytical Data |
|---|---|---|---|
| 413 | 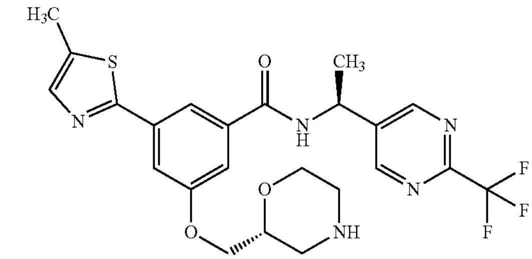 [SMILES: Cc1cnc(-c2cc(OC[C@H]3CNCCO3)cc(C(=O)N[C@@H](C)c3cnc(C(F)(F)F)nc3)c2)s1] | 3-(5-methyl-1,3-thiazol-2-yl)-5-[(2R)-morpholin-2-ylmethoxy]-N-{(1S)-1-[2-(trifluoromethyl)pyrimidin-5-yl]ethyl}benzamide | $^1$H NMR (500 MHz, Chloroform-d): δ [ppm] 8.93 (s, 2H), 7.84 (s, 1H), 7.54-7.49 (m, 1H), 7.50-7.46 (m, 1H), 7.40-7.35 (m, 1H), 6.99 (d, J = 6.7 Hz, 1H), 5.39-5.30 (m, 1H), 4.05 (dd, J = 9.9, 5.9 Hz, 1H), 3.99 (dd, J = 9.9, 4.2 Hz, 2H), 3.97-3.86 (m, 2H), 3.75-3.65 (m, 1H), 3.06-2.99 (m, 1H), 2.97-2.84 (m, 2H), 2.77 (dd, J = 12.0, 10.4 Hz, 1H), 2.50 (d, 3H), 1.69 (d, J = 7.2 Hz, 3H). LCMS (Analytical Method D) Rt = 3.17 min, MS (ESIpos) m/z = 508 (M + H)$^+$. |
| 414 | 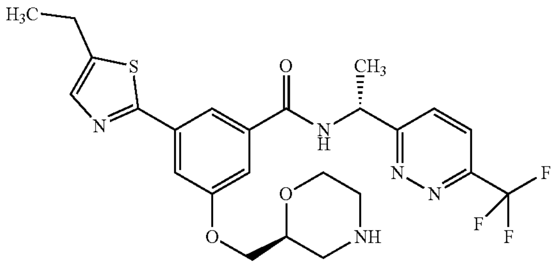 [SMILES: CCc1cnc(-c2cc(OC[C@@H]3CNCCO3)cc(C(=O)N[C@H](C)c3ccc(C(F)(F)F)nn3)c2)s1] | 3-(5-ethyl-1,3-thiazol-2-yl)-5-[(2S)-morpholin-2-ylmethoxy]-N-{(1R)-[6-(trifluoromethyl)pyridazin-3-yl]ethyl}benzamide | 1H NMR (500 MHz, Chloroform-d): δ [ppm] 7.92-7.89 (m, 1H), 7.82 (d, J = 8.7 Hz, 1H), 7.74 (d, J = 8.7 Hz, 1H), 7.63-7.57 (m, 1H), 7.56-7.52 (m, 1H), 7.46 (d, J = 7.1 Hz, 1H), 7.44-7.42 (m, 1H), 5.65-5.54 (m, 1H), 4.15-4.00 (m, 2H), 3.98-3.87 (m, 2H), 3.70 (td, J = 11.3, 2.7 Hz, 1H), 3.07-3.01 (m, 1H), 2.98-2.75 (m, 5H), 1.76 (d, J = 7.0 Hz, 3H), 1.36 (t, J = 7.5 Hz, 3H). LCMS (Analytical Method F) Rt = 2.24 min, MS (ESIpos): m/z = 522.2 (M + H)$^+$. |
| 415 | 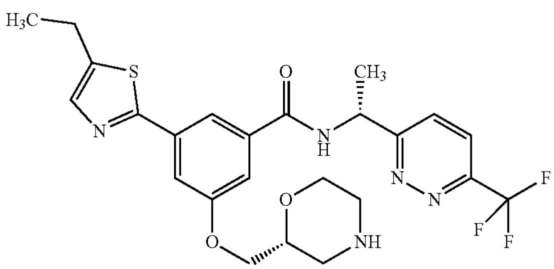 [SMILES: CCc1cnc(-c2cc(OC[C@H]3CNCCO3)cc(C(=O)N[C@H](C)c3ccc(C(F)(F)F)nn3)c2)s1] | 3-(5-ethyl-1,3-thiazol-2-yl)-5-[(2R)-morpholin-2-ylmethoxy]-N-{(1R)-[6-(trifluoromethyl)pyridazin-3-yl]ethyl}benzamide | $^1$H NMR (500 MHz, Chloroform-d): δ [ppm] 7.91-7.89 (m, 1H), 7.82 (d, J = 8.7 Hz, 1H), 7.74 (d, J = 8.7 Hz, 1H), 7.62-7.58 (m, 1H), 7.55-7.52 (m, 1H), 7.47-7.42 (m, 2H), 5.66-5.53 (m, 1H), 4.13-4.00 (m, 2H), 3.97-3.86 (m, 2H), 3.70 (td, J = 11.3, 2.7 Hz, 1H), 3.07-3.01 (m, 1H), 2.99-2.74 (m, 5H), 1.76 (d, J = 7.0 Hz, 3H), 1.36 (t, J = 7.5 Hz, 3H). LCMS (Analytical Method F) Rt = 2.21 min, MS (ESIpos): m/z = 522.3 (M + H)$^+$. |

In analogy to the procedure described for Example 366, the following examples were prepared using STAB and the corresponding amine and aldehyde or ketone starting materials.

| Ex. | Structure | Name | Analytical Data |
|---|---|---|---|
| 416 | 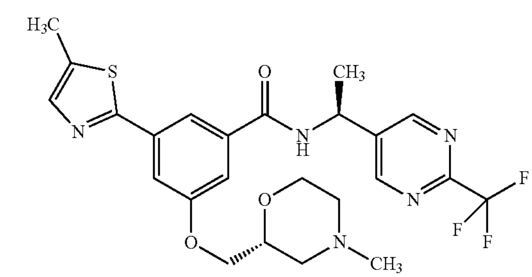 [SMILES: Cc1cnc(-c2cc(OC[C@H]3CN(C)CCO3)cc(C(=O)N[C@@H](C)c3cnc(C(F)(F)F)nc3)c2)s1] | 3-{[(2R)-4-methylmorpholin-2-yl]methoxy}-5-(5-methyl-1,3-thiazol-2-yl)-N-{(1S)-1-[2-(trifluoromethyl)pyrimidin-5-yl]ethyl}benzamide | SFC Chiral Analysis (Method 16): 99.8% e.e. Rt = 4.06 min. $^1$H NMR (500 MHz, Chloroform-d): δ [ppm] 8.93 (s, 2H), 7.88-7.84 (m, 1H), 7.57-7.52 (m, 1H), 7.50 (d, J = 1.0 Hz, 1H), 7.41-7.36 (m, 1H), 6.82 (d, J = 6.6 Hz, 1H), 5.40-5.30 (m, 1H), 4.10 (dd, J = 9.9, 5.9 Hz, 1H), 4.04 (dd, J = 9.9, 4.1 Hz, 1H), 4.01-3.91 (m, 2H), 3.81-3.72 (m, 1H), 2.87-2.81 (m, 1H), 2.73-2.67 (m, 1H), 2.54-2.50 (m, 3H), 2.34 (s, 3H), 2.26-2.17 (m, 1H), 2.11-2.05 (m, 1H), 1.70 (d, J = 7.2 Hz, 3H). LCMS (Analytical Method F) Rt = 2.16 min, MS (ESIpos) 522 (M + H)$^+$. |

-continued

| Ex. | Structure | Name | Analytical Data |
|---|---|---|---|
| 417 | 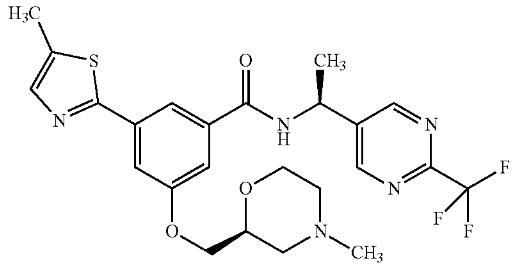 [SMILES: Cc1cnc(-c2cc(OC[C@@H]3CN(C)CCO3)cc(C(=O)N[C@@H](C)c3cnc(C(F)(F)F)nc3)c2)s1] | 3-{[(2S)-4-methylmorpholin-2-yl]methoxy}-5-(5-methyl-1,3-thiazol-2-yl)-N-{(1S)-1-[2-(trifluoromethyl)pyrimidin-5-yl]ethyl}benzamide | SFC Chiral Analysis (Method 16): 100% e.e. Rt = 3.71 min. $^1$H NMR (500 MHz, Chloroform-d): δ [ppm] 8.94 (s, 2H), 7.89-7.85 (m, 1H), 7.58-7.54 (m, 1H), 7.53-7.49 (m, 1H), 7.42-7.38 (m, 1H), 6.79 (d, J = 6.3 Hz, 1H), 5.40-5.31 (m, 1H), 4.12 (dd, J = 9.6, 5.6 Hz, 1H), 4.08-3.99 (m, 2H), 3.99-3.93 (m, 1H), 3.84-3.75 (m, 1H), 2.91-2.85 (m, 1H), 2.77-2.70 (m, 1H), 2.54-2.50 (m, 3H), 2.37 (s, 3H), 2.29-2.21 (m, 1H), 2.14-2.07 (m, 1H), 1.71 (s, 3H). LCMS (Analytical Method F) Rt = 2.16 min, MS (ESIpos) 522 (M + H)$^+$. |
| 418 | 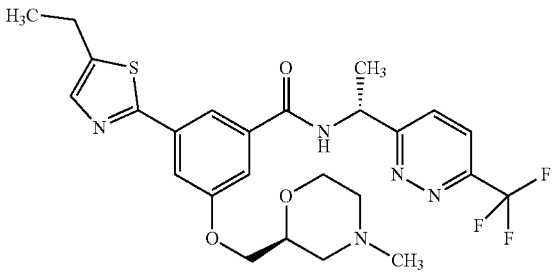 [SMILES: CCc1cnc(-c2cc(OC[C@@H]3CN(C)CCO3)cc(C(=O)N[C@H](C)c3ccc(C(F)(F)F)nn3)c2)s1] | 3-(5-Ethyl-1,3-thiazol-2-yl)-5-{[(2S)-4-methylmorpholin-2-yl]methoxy}-N-{(1R)-1-[6-(trifluoromethyl)pyridazin-3-yl]ethyl}benzamide | 1H NMR (500 MHz, Chloroform-d): δ [ppm] 7.92-7.89 (m, 1H), 7.82 (d, J = 8.7 Hz, 1H), 7.74 (d, J = 8.7 Hz, 1H), 7.61 (dd, J = 2.4, 1.5 Hz, 1H), 7.54-7.52 (m, 1H), 7.46 (d, J = 7.3 Hz, 1H), 7.43 (dd, J = 2.3, 1.6 Hz, 1H), 5.65-5.48 (m, 1H), 4.15-4.10 (m, 1H), 4.09-4.03 (m, 1H), 4.00-3.93 (m, 2H), 3.79-3.72 (m, 1H), 2.90 (qd, J = 7.5, 0.9 Hz, 2H), 2.87-2.80 (m, 1H), 2.71-2.65 (m, 1H), 2.34 (s, 3H), 2.25-2.16 (m, 1H), 2.12-2.03 (m, 1H), 1.76 (d, J = 7.0 Hz, 3H), 1.36 (t, J = 7.5 Hz, 3H). LCMS (Analytical Method F) Rt = 2.27 min, MS (ESIpos): m/z = 536.3 (M + H)$^+$. |
| 419 | 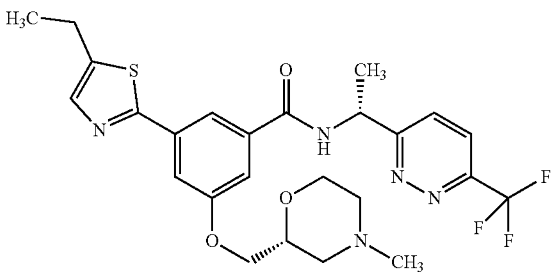 [SMILES: CCc1cnc(-c2cc(OC[C@H]3CN(C)CCO3)cc(C(=O)N[C@H](C)c3ccc(C(F)(F)F)nn3)c2)s1] | 3-(5-ethyl-1,3-thiazol-2-yl)-5-{[(2R)-4-methylmorpholin-2-yl]methoxy}-N-{(1R)-1-[6-(trifluoromethyl)pyridazin-3-yl]ethyl}benzamide | $^1$H NMR (500 MHz, Chloroform-d): δ [ppm] 7.84-7.83 (m, 1H), 7.75 (d, J = 8.7 Hz, 1H), 7.67 (d, J = 8.7 Hz, 1H), 7.54 (dd, J = 2.2, 1.5 Hz, 1H), 7.48-7.45 (m, 1H), 7.39 (d, J = 7.4 Hz, 1H), 7.36 (dd, J = 2.3, 1.5 Hz, 1H), 5.59-5.49 (m, 1H), 4.08-4.03 (m, 1H), 4.01-3.96 (m, 1H), 3.93-3.86 (m, 2H), 3.72-3.66 (m, 1H), 2.86-2.81 (m, 2H), 2.80-2.76 (m, 1H), 2.64-2.60 (m, 1H), 2.27 (s, 3H), 2.17-2.08 (m, 1H), 2.04-1.96 (m, 1H), 1.69 (d, J = 7.0 Hz, 3H), 1.29 (t, J = 7.5 Hz, 3H). LCMS (Analytical Method F) Rt = 2.27 min, MS (ESIpos): m/z = 536.3 (M + H)$^+$. |

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically acceptable carriers well known in the art using any effective conventional dosage unit forms, including immediate, slow and timed release preparations, orally, parenterally, topically, nasally, ophthalmic, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known in the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxylpropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et at., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et at., "Excipients and Their Use in Injectable Products" PDA Journal of Pharmaceutical Science Et Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, DEtC Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol); solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate); tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of the present invention can be administered as the sole pharmaceutical agent or in combination with one or more other pharmaceutical agents where the combination causes no unacceptable adverse effects. The present invention relates also to such combinations.

For example, the compounds of the present invention can be combined with known hormonal therapeutic agents.

In particular, the compounds of the present invention can be administered in combination or as comedication with hormonal contraceptives. Hormonal contraceptives can be administered via oral, subcutan, transdermal, intrauterine or intravaginal route, for example as Combined Oral Contraceptives (COCs) or Progestin-Only-Pills (POPs) or hormone-containing devices like implants, patches or intravaginal rings.

COCs include but are not limited to birth control pills or a birth control method that includes a combination of an estrogen (estradiol) and a progestogen (progestin). The estrogenic part is in most of the COCs ethinyl estradiol. Some COCs contain estradiol or estradiol valerate.

Said COCs contain the progestins norethynodrel, norethindrone, norethindrone acetate, ethynodiol acetate, norgestrel, levonorgestrel, norgestimate, desogestrel, gestodene, drospirenone, dienogest, or nomegestrol acetate.

Birth control pills include for example but are not limited to Yasmin, Yaz, both containing ethinyl estradiol and drospirenone; Microgynon or Miranova containing levonorgestrel and ethinyl estradiol; Marvelon containing ethinyl estradiol and desogestrel; Valette containing ethinyl estradiol and dienogest; Belara and Enriqa containing ethinyl estradiol and chlormadinonacetate; Qtaira containing estradiol valerate and dienogest as active ingredients; and Zoely containing estradiol and normegestrol.

POPs are contraceptive pills that contain only synthetic progestogens (progestins) and do not contain estrogen. They are colloquially known as mini pills.

POPs include but are not limited to Cerazette containing desogestrel; Microlut containing levonorgestrel and Micronor containing norethindrone.

Other Progeston-Only forms are intrauterine devices (IUDs), for example Mirena containing levonorgestrel or injectables, for example Depo-Provera containing medroxyprogesterone acetate, or implants, for example Implanon containing etonogestrel.

Other hormone-containing devices with contraceptive effect which are suitable for a combination with the compounds of the present invention are vaginal rings like Nuvaring containing ethinyl estradiol and etonogestrel or transdermal systems like a contraceptive patch, for example Ortho-Evra or Apleek (Lisvy) containing ethinyl estradiol and gestodene.

A preferred embodiment of the present invention is the administration of a compound of general formula (I) in combination with a COC or a POP or other Progestin-Only forms as well as vaginal rings or contraceptive patches as mentioned above.

The compounds of the present invention can be combined with therapeutic agents or active ingredients, that are already approved or that are still under development for the treatment and/or prophylaxis of diseases which are related to or mediated by P2X3 receptor.

For the treatment and/or prophylaxis of urinary tract diseases, the compounds of the present invention can be administered in combination or as comedication with any substance that can be applied as therapeutic agent in the following indications:

Urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular interstitial cystitis; idiopathic bladder hypersensitivity.

For the treatment and/or prophylaxis of overactive bladder and symptoms related to overactive bladder, the compounds of the present invention can be administered in combination or as comedication, independently or in addition to behavioral therapy like diet, lifestyle or bladder training, with anticholinergics like oxybutynin, tolterodine, propiverine, solifenacin, darifenacin, trospium, fesoterdine; β-3 agonists like mirabegron; neurotoxins like onabutolinumtoxin A; or antidepressants like imipramine, duloxetine.

For the treatment and/or prophylaxis of interstitial cystitis, the compounds of the present invention can be administered in combination or as comedication, independently or in addition to behavioral therapy like diet, lifestyle or bladder training, with pentosans like elmiron; NSAIDS (Non-Steroidal Antiinflammatory Drugs), either unselective NSAIDS like ibuprofen, diclofenac, aspirin, naproxen, ketoprofen, indomethacin; as well as Cox-2 selective NSAIDS like Parecoxib, Etoricoxib, Celecoxib; antidepressants like amitriptyline, imipramine; or antihistamines like loratadine.

For the treatment and/or prophylaxis of gynaecological diseases, the compounds of the present invention can be administered in combination or as comedication with any substance that can be applied as therapeutic agent in the following indications:

dysmenorrhea, including primary and secondary dysmenorrhea; dyspareunia; endometriosis; endometriosis-associated pain; endometriosis-associated symptoms, wherein said symptoms are in particular dysmenorrhea, dyspareunia, dysuria, or dyschezia.

For the treatment and/or prophylaxis of dysmenorrhea, including primary and secondary dysmenorrhea; dyspareunia; endometriosis and endometriosis-associated pain, the compounds of the present invention can be administered in combination or as comedication with pain medicaments, in particular NSAIDS like ibuprofen, diclofenac, aspirin, naproxen, ketoprofen, indomethacin; as well as Cox-2 selective NSAIDS like Parecoxib, Etoricoxib, Celecoxib; or in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases which are associated with pain, or pain syndromes, the compounds of the present invention can be administered in combination or as comedication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, trigeminal neuralgia, small fiber neuropathy, diabetic neuropathy, chronic arthritis and related neuralgias, HIV and HIV treatment-induced neuropathy.

The compounds of the present invention can be combined with other pharmacological agents and compounds that are intended to treat inflammatory diseases, inflammatory pain or general pain conditions.

In addition to well-known medicaments which are already approved and on the market, the compounds of the present invention can be administered in combination with inhibitors of PTGES (prostaglandin E synthase), with inhibitors of IRAK4 (interleukin-1 receptor-associated kinase 4) and with antagonists of the prostanoid EP4 receptor (prostaglandin E2 receptor 4).

In particular, the compounds of the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-keto-reductase1C3 (AKR1C3) and with functional blocking antibodies of the prolactin receptor.

For the treatment and/or prophylaxis of chronic cough and symptoms related to chronic cough, the compounds of the present invention can be administered in combination or as comedication with cough suppressants like dextromethorphan, benzonatate, codeine or hydrocodone; with inhalative agents to treat eosinophilic bronchitis, COPD or asthma like budesonide, beclomethasone, fluticasone, theophylline, ipatropiumbromid, montelukast or salbutamol; with drugs like proton pump inhibitors which are used to treat acid reflux, for example omeprazole, esomeprazole, lansoprazole, ranitidine, famotidine, cimetidine; and promotility agents such as metoclopramide; with nasal or topical glucocorticoids like fluticasone or mometasone or triamcinolone; or with oral antihistamines like loratadine, fexofenadine or cetirizine.

The compounds of the present invention can be combined with other pharmacological agents and compounds that are intended for the treatment, prevention or management of cancer.

In particular, the compounds of the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevuli nate, amrubici n, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin +estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine di hydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone +pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone +sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc—HYNIC-[Tyr3]-octreotide, tegafur, tegafur +gimeracil +oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine +tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Furthermore, the compounds of the present invention can be combined with active ingredients, which are well known for the treatment of cancer-related pain and chronic pain. Such combinations include, but are not limited to NSAIDS (either unselective NSAIDS like ibuprofen, diclofenac, aspirin, naproxen, ketoprofen and indomethacin; and Cox-2 selective NSAIDS like Parecoxib, Etoricoxib and Celecoxib), step II opiods like codeine phosphate, dextropropoxyphene, dihydro-codeine, Tramadol), step III opiods like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrhythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

Methods of Treating

The present invention relates to a method for using the compounds of the present invention and compositions thereof, to inhibit the P2X3 receptor.

The present invention also provides a method for using the compounds of the present invention and compositions thereof, to selectively inhibit the P2X3 receptor over the P2X2/3 receptor which means at least 3-fold selectivity over the P2X2/3 receptor.

The present invention also provides a method for using the preferred compounds of the present invention and compositions thereof, to selectively inhibit the P2X3 receptor over the P2X2/3 receptor with at least 10-fold selectivity over the P2X2/3 receptor. In addition to that, the present invention also provides a method of treating mammalian including human disorders and diseases using the more preferred compounds of the present invention which show further advantageous properties that are beneficial for their use as medicaments, such as desirable pharmacokinetic profiles that provide suitable metabolic stability and oral bioavailability. In addition to that, a method of treating mammalian including human disorders and diseases is provided using even more preferred compounds of the present invention which show further advantageous properties that are beneficial for their use as medicaments, such as desirable pharmacokinetic profiles that provide suitable metabolic stability and oral bioavailability, and at least one additional advantageous property chosen from an advantageous cardiovascular profile and a suitable CYP inhibition profile.

The present invention relates to a method for using the compounds of the present invention and compositions thereof, to treat mammalian including human disorders and diseases which include but are not limited to:

genitourinary, gastrointestinal, respiratory, and pain-related diseases, conditions and disorders;

gynecological diseases including dysmenorrhea (primary and secondary dysmenorrhea), dyspareunia, endometriosis, and adenomyosis; endometriosis-associated pain; endometriosis-associated symptoms, wherein said symptoms are in particular dysmenorrhea, dyspareunia, dysuria, or dyschezia; endometriosis-associated proliferation; pelvic hypersensitivity;

urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive urinary bladder and symptoms related to overactive urinary bladder wherein said symptoms are in particular increased urinary frequency, nocturia, urinary urgency or urge incontinence;

pelvic hypersensitivity; urethritis; prostatitis; prostatodynia; cystitis, in particular Interstitial cystitis; idiopathic bladder hypersensitivity;

cancer-related pain;

Epilepsy, partial and generalized seizures;

respiratory disorders including asthma, chronic obstructive pulmonary disease, pulmonary fibrosis, acute cough, chronic cough including chronic idiopathic and chronic refractory cough, bronchospasm;

gastrointestinal disorders including irritable bowel syndrome (IBS), inflammatory bowel disease (IBD), biliary colic and other biliary disorders, renal colic, diarrhea-dominant IBS; gastroesophageal reflux, gastrointestinal distension, Crohn's disease and the like;

neurodegenerative disorders such as Alzheimer's disease, Multiple Sclerosis, Parkinson's disease, Brain ischemia and traumatic brain injury;

pruritus.

The present invention relates to a method for using the compounds of the present invention and compositions thereof, to treat pain-associated mammalian including human disorders and diseases which include but not limited to pain-associated diseases or disorders selected from the group consisting of hyperalgesia, allodynia, functional bowel disorders (such as irritable bowel syndrome), gout, arthritis (such as osteoarthritis, rheumatoid arthritis and ankylosing spondylitis), burning mouth syndrome, burns, migraine or cluster headaches, nerve injury, traumatic nerve injury, post-traumatic injuries (including fractures and sport injuries), neuritis, neuralgias, poisoning, ischemic injury, interstitial cystitis, cancer, trigeminal neuralgia, small fiber neuropathy, diabetic neuropathy, chronic arthritis and related neuralgias, HIV and HIV treatment-induced neuropathy, pruritus; impaired wound healing and disease of the skeleton like degeneration of the joints.

The present invention relates to a method for using the compounds of the present invention and compositions thereof, to treat mammalian, including human disorders and diseases which are associated with pain, or pain syndromes which are in particular:

pain syndromes (including acute, chronic, inflammatory and neuropathic pain), preferably inflammatory pain, low back pain surgical pain, visceral pain, dental pain, periodontitis, premenstrual pain, endometriosis-associated pain, pain associated with fibrotic diseases, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, cancer pain, pain due to viral, parasitic or bacterial infections, pain due to traumatic nerve-injury, pain due to post-traumatic injuries (including fractures and sport injuries), pain due to trigeminal neuralgia, pain associated with small fiber neuropathy, pain associated with diabetic neuropathy, postherpetic neuralgia, chronic lower back pain, neck pain phantom limb pain, pelvic pain syndrome, chronic pelvic pain, neuroma pain, complex regional pain syndrome, pain associated with gastrointestinal distension, chronic arthritic pain and related neuralgias, and pain associated with cancer, Morphine-resistant pain, pain associated with chemotherapy, HIV and HIV treatment-induced neuropathy; and pain associated with diseases or disorders selected from the group consisting of hyperalgesia, allodynia, functional bowel disorders (such as irritable bowel syndrome) and arthritis (such as osteoarthritis, rheumatoid arthritis and ankylosing spondylitis).

The present invention relates to a method for using the compounds of the present and compositions thereof to treat inflammation, in particular neurogenic inflammation. The term "inflammation" is also understood to include any inflammatory disease, disorder or condition per se, any condition that has an inflammatory component associated with it, and/or any condition characterized by inflammation as a symptom, including, inter alia, acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this invention, inflammatory pain, pain generally and/or fever. The present invention relates to a method for using the compounds of the present invention and compositions thereof to treat fibromyalgia, myofascial disorders, viral infections (e.g. influenza, common cold, herpes zoster, hepatitis C and AIDS), bacterial infections, fungal infections, surgical or dental procedures, arthritis, osteoarthritis, juvenile arthritis, rheumatoid arthritis, juvenile onset rheumatoid arthritis, rheumatic fever, ankylosing spondylitis, Hodgkin's disease, systemic lupus erythematosus, vasculitis, pancreatitis, nephritis, bursitis, conjunctivitis, iritis, scleritis, uveitis, wound healing, dermatitis, eczema, stroke, autoimmune diseases, allergic disorders, rhinitis, ulcers, mild to moderately active ulcerative colitis, familial adenomatous polyposis, coronary heart disease, sarcoidosis and any other disease with an inflammatory component. The present invention relates to a method for using the compounds of the present invention and compositions thereof to treat mammalian, including human disorders and diseases which are not linked to inflammatory mechanisms, such as in the reduction of bone loss in a subject. Diseases that may be mentioned in this regard include osteoporosis, osteoarthritis, Paget's disease and/or periodontal diseases.

Based on the P2X3 receptor inhibitory activity of compounds of the present invention, the present invention relates to a method for using the compounds of the present invention and compositions thereof to treat pain, fever and inflammation of a variety of conditions including rheumatic fever, symptoms associated with influenza or other viral infections, common cold, low back and neck pain, dysmenorrhea, headache, migraine (acute and prophylactic treatment), toothache, sprains and strains, myositis, neuralgia, synovitis, arthritis, including rheumatoid arthritis, juvenile rheumatoid arthritis, degenerative joint diseases (osteoarthritis), acute gout and ankylosing spondylitis, acute, subacute and chronic musculoskeletal pain syndromes such as bursitis, burns, injuries, and pain following surgical (post-operative pain) and dental procedures as well as the preemptive treatment of surgical pain. The pain may be mild pain, moderate pain, severe pain, musculoskeletal pain, complex regional pain syndrome, neuropathic pain, back pain such as visceral pain including acute visceral pain, neuropathies, acute trauma, chemotherapy-induced mononeuropathy pain states, polyneuropathy pain states (such as diabetic peripheral neuropathy and/or chemotherapy induced neuropathy), autonomic neuropathy pain states, pheriphaeral nervous system (PNS) lesion or central nervous system (CNS) lesion or disease related pain states, polyradiculopathies of cervical, lumbar or sciatica type, cauda equina syndrome, piriformis syndrome, paraplegia, quadriplegia, pain states related to various Polyneuritis conditions underlying various infections, chemical injuries, radiation exposure, underlying disease or deficiency conditions (such as beriberi, vitamin deficiencies, hypothyroidism, porphyria, cancer, HIV, autoimmune disease such as multiple sclerosis and spinal-cord injury, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, overactive bladder, pelvic hypersensitivity, urinary incontinence, cystitis, stomach, duodenal ulcer, muscle pain, pain due to colicky and referred pain. The present invention relates to a method for using the compounds of the present invention and compositions thereof to treat hemophilic arthropathy and Parkinson's disease.

A preferred embodiment of the present invention relates to a method for using the compounds of the present invention and compositions thereof, to treat a gynaecological disease, preferably dysmenorrhea, dyspareunia or endometriosis, endometriosis-associated pain, or other endometriosis-associated symptoms, wherein said symptoms are in particular dysmenorrhea, dyspareunia, dysuria, or dyschezia.

Another preferred embodiment of the present invention relates to a method for using the compounds of the present invention and compositions thereof, to treat a urinary tract disease, in particular overactive bladder or cystitis, preferably interstitial cystitis.

Another preferred embodiment of the present invention relates to a method for using the compounds of the present invention and compositions thereof, to treat a respiratory disorder, preferably cough, in particular chronic cough.

Another preferred embodiment of the present invention relates to a method for using the compounds of the present invention and compositions thereof, to treat arthritis, in particular rheumatoid arthritis and ankylosing spondylitis.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving a condition, disease or disorder such as a gynaecological disease, urinary tract disease, respiratory disorder or arthritis.

Dose and Administration

Based upon standard laboratory techniques known to evaluate compounds useful for the treatment of disorders and/or disease which are mediated by the P2X3 receptor, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, preferably from about 0.01 mg/kg to about 20 mg/kg body weight per day. A preferred administration of the compound of the present invention includes but is not limited to 0.1 mg/kg to about 10 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. A preferred oral unit dosage for an administration of the compounds of the present invention includes but is not limited to 0.1 mg/kg to about 10 mg/kg body weight one to three times a day to once a week. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases treated with said method are gynaecological disorders, more preferably dysmenorrhea, dyspareunia or endometriosis, endometriosis-associated pain, or other endometriosis-associated symptoms, wherein said symptoms are in particular dysmenorrhea, dyspareunia, dysuria, or dyschezia. Further diseases which can be treated with said method are osteoarthritis, diabetic neuropathy, burning mouth syndrome, gastroesophageal reflux, migraine disorders, chronic cough, asthma, pruritus, irritable bowel disease, overactive urinary bladder, prostatic hyperplasia, interstitial cystitis.

Preferably, the method of treating the diseases mentioned above is not limited to the treatment of said disease but also includes the treatment of pain related to or associated with said diseases.

The compounds of the present invention can be used in particular in therapy and prevention, i.e. prophylaxis, of genitourinary, gastrointestinal, respiratory or pain-related disease, condition or disorder.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. Unless stated otherwise, when tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Intracellular Calcium Measurement to Assess Antagonist Activity at Human P2X3 and Human P2X2/3 Receptors A fluorescent imaging plate reader (FLEX/FLIPR station; Molecular Devices) was used to monitor intracellular calcium levels using the calcium chelating dye Fluo-4 (Molecular Probes). The excitation and emission wavelengths used to monitor fluorescence were 470-495 nm and 515-575 nm, respectively. Cells expressing purinergic receptors P2X3 (human) or P2X2/3 (human) were plated at a density of 15,000 cells/well in collagen-coated 384-well plates approximately 20 hours before beginning the assay. On the day of the assay, 20 µl of loading buffer (Hank's balanced salt solution, 20 mM HEPES, 0.5 mM $CaCl_2$, 0.5 mM $MgCl_2$, 0.1% BSA, 5 mM probenecid, 10 mM D-glucose monohydrate, 2 µM Fluo-4, and 5 units/mL, hexokinase, pH=7.4) was added and cells dye-loaded for 90 min at 37° C. The dye supernatant was removed and replaced with 45 µl probenecid buffer (Hank's balanced salt solution, 20 mM HEPES, 0.5 mM $CaCl_2$, 0.5 mM $MgCl_2$, 0.1% BSA, 5 mM probenecid, 10 mM D-glucose monohydrate, pH=7.4). The test compound was added in a volume of 5 µl and allowed to incubate for 30 min at 37° C. The final assay DMS0 concentration is 1%. The agonist, α,β-Me-ATP, was added in a volume of 2Op1 at a concentration representing the $EC_{80}$ value. The fluorescence was measured for an interval of 90 sec at 2 sec intervals and analyzed based on the increase in peak relative fluorescence units (RFU) compared to the basal fluorescence. Peak fluorescence was used to determine the response to agonist obtained at each concentration of test compound by the following equation:

% Response=100*($RFU_{(test\ compound)}$−$RFU_{(control)}$)/($RFU_{(DMSO)}$−$RFU_{(control)}$)

The Examples were tested in triplicates per plate and mean values were plotted in Excel XLFit to determine $IC_{50}$ values at the human P2X3 and human P2X21 3 receptors, percentage of maximal inhibition and the Hill coefficients.

| Patent Example | hP2X3 $IC_{50}$ (nM) | hP2X2/3 $IC_{50}$ (nM) |
|---|---|---|
| 1 | 4 | 76 |
| 2 | 19 | 251 |
| 3 | 26 | 1106 |
| 4 | 9 | 98 |
| 5 | 16 | 346 |
| 6 | 4 | 38 |
| 7 | 8 | 106 |
| 8 | 3 | 90 |
| 9 | 7 | 145 |
| 10 | 7 | 185 |
| 11 | 8 | 163 |
| 12 | 283 | 10000 |
| 13 | 21 | 1102 |
| 14 | 8 | 88 |
| 15 | 6 | 147 |
| 16 | 38 | 1707 |
| 17 | 35 | 1005 |
| 18 | 34 | 427 |
| 19 | 19 | 749 |
| 20 | 35 | 486 |
| 21 | 71 | 445 |
| 22 | 132 | 987 |
| 23 | 30 | 1106 |
| 24 | 36 | 332 |
| 25 | 39 | 975 |
| 26 | 8 | 297 |
| 27 | 25 | 280 |
| 28 | 48 | 121 |
| 29 | 79 | 580 |
| 30 | 38 | 485 |
| 31 | 173 | 10000 |
| 32 | 24 | 1781 |
| 33 | 29 | 912 |
| 34 | 111 | 2124 |
| 35 | 460 | 10000 |
| 36 | 14 | 306 |
| 37 | 55 | 1176 |
| 38 | 55 | 1145 |
| 39 | 81 | 1646 |
| 40 | 16 | 383 |
| 41 | 130 | 1592 |
| 42 | 129 | 1565 |
| 43 | 50 | 2688 |
| 44 | 11 | 370 |
| 45 | 212 | 1510 |
| 46 | 10 | 389 |
| 47 | 82 | 621 |
| 48 | 14 | 451 |
| 49 | 132 | 1525 |
| 50 | 77 | 982 |
| 51 | 74 | 1389 |
| 52 | 194 | 564 |
| 53 | 318 | 2740 |
| 54 | 66 | 10000 |
| 55 | 8 | 325 |
| 56 | 148 | 10000 |
| 57 | 25 | 2840 |
| 58 | 4 | 461 |
| 59 | 13 | 507 |
| 60 | 11 | 578 |
| 61 | 14 | 428 |
| 62 | 85 | 1436 |
| 63 | 4 | 118 |
| 64 | 53 | 984 |
| 65 | 3 | 54 |
| 66 | 35 | 6295 |
| 67 | 186 | 10000 |
| 68 | 44 | 1617 |
| 69 | 15 | 937 |
| 70 | 3 | 78 |
| 71 | 15 | 315 |
| 72 | 11 | 330 |
| 73 | 4 | 101 |
| 74 | 14 | 1107 |
| 75 | 38 | 6638 |
| 76 | 201 | 5789 |
| 77 | 10 | 183 |
| 78 | 6 | 83 |
| 79 | 9 | 413 |
| 80 | 12 | 339 |
| 81 | 3 | 34 |
| 82 | 28 | 380 |
| 83 | 125 | 1164 |
| 84 | 26 | 527 |
| 85 | 10 | 36 |
| 86 | 12 | 144 |
| 87 | 15 | 119 |
| 88 | 30 | 217 |
| 89 | 11 | 199 |
| 90 | 111 | 710 |
| 91 | 19 | 133 |
| 92 | 24 | 317 |
| 93 | 8 | 385 |
| 94 | 7 | 132 |
| 95 | 2 | 129 |
| 96 | 18 | 1077 |
| 97 | 15 | 1687 |
| 98 | 1 | 19 |
| 99 | 2 | 27 |
| 100 | 6 | 16 |
| 101 | 15 | 60 |
| 102 | 10 | 57 |
| 103 | 2 | 14 |
| 104 | 51 | 377 |
| 105 | 6 | 39 |
| 106 | 16 | 41 |
| 107 | 9 | 17 |
| 108 | 11 | 83 |
| 109 | 235 | 2412 |
| 110 | 114 | 1451 |
| 111 | 16 | 380 |
| 112 | 61 | 772 |
| 113 | 43 | 387 |
| 114 | 38 | 414 |
| 115 | 15 | 187 |
| 116 | 210 | 6430 |
| 117 | 36 | 883 |
| 118 | 198 | 1134 |
| 119 | 24 | 190 |
| 120 | 14 | 104 |
| 121 | 79 | 279 |
| 122 | 106 | 1167 |
| 123 | 46 | 164 |
| 124 | 27 | 165 |

| Patent Example | hP2X3 IC$_{50}$ (nM) | hP2X2/3 IC$_{50}$ (nM) |
|---|---|---|
| 125 | 3 | 27 |
| 126 | 34 | 532 |
| 127 | 111 | 536 |
| 128 | 10 | 91 |
| 129 | 3 | 33 |
| 130 | 74 | 1349 |
| 131 | 134 | 730 |
| 132 | 75 | 2051 |
| 133 | 177 | 10000 |
| 134 | 15 | 210 |
| 135 | 35 | 209 |
| 136 | 196 | 2780 |
| 137 | 26 | 328 |
| 138 | 11 | 559 |
| 139 | 8 | 962 |
| 140 | 33 | 1295 |
| 141 | 43 | 2201 |
| 142 | 6 | 222 |
| 143 | 84 | 3047 |
| 144 | 825 | 10000 |
| 145 | 271 | 4461 |
| 146 | 45 | 159 |
| 147 | 6 | 132 |
| 148 | 33 | 794 |
| 149 | 21 | 936 |
| 150 | 12 | 83 |
| 151 | 31 | 333 |
| 152 | 45 | 523 |
| 153 | 27 | 304 |
| 154 | 18 | 130 |
| 155 | 40 | 2267 |
| 156 | 5 | 163 |
| 157 | 17 | 534 |
| 158 | 21 | 1939 |
| 159 | 28 | 1233 |
| 160 | 28 | 1007 |
| 161 | 32 | 632 |
| 162 | 5 | 74 |
| 163 | 5 | 83 |
| 164 | 60 | 1107 |
| 165 | 81 | 1923 |
| 166 | 40 | 461 |
| 167 | 72 | 893 |
| 168 | 19 | 1600 |
| 169 | 9 | 70 |
| 170 | 165 | 2020 |
| 171 | 26 | 573 |
| 172 | 31 | 2107 |
| 173 | 5 | 311 |
| 174 | 11 | 790 |
| 175 | 23 | 1274 |
| 176 | 29 | 607 |
| 177 | 14 | 887 |
| 178 | 39 | 1880 |
| 179 | 13 | 703 |
| 180 | 31 | 1399 |
| 181 | 19 | 1181 |
| 182 | 63 | 1943 |
| 183 | 7 | 398 |
| 184 | 6 | 128 |
| 185 | 4 | 123 |
| 186 | 10 | 247 |
| 187 | 7 | 218 |
| 188 | 5 | 164 |
| 189 | 8 | 258 |
| 190 | 7 | 207 |
| 191 | 61 | 364 |
| 192 | 12 | 910 |
| 193 | 2705 | 10000 |
| 194 | 46 | 579 |
| 195 | 380 | 10000 |
| 196 | 19 | 293 |
| 197 | 1152 | 10000 |
| 198 | 30 | 245 |
| 199 | 1544 | 10000 |
| 200 | 30 | 546 |
| 201 | 16 | 1854 |
| 202 | 42 | 1710 |
| 203 | 36 | 1561 |
| 204 | 7 | 82 |
| 205 | 4 | 272 |
| 206 | 31 | 1676 |
| 207 | 5 | 87 |
| 208 | 2 | 89 |
| 209 | 30 | 1470 |
| 210 | 12 | 1012 |
| 211 | 395 | 10000 |
| 212 | 4 | 46 |
| 213 | 5 | 81 |
| 214 | 47 | 3392 |
| 215 | 16 | 992 |
| 216 | 14 | 928 |
| 217 | 25 | 1750 |
| 218 | 7 | 281 |
| 219 | 2 | 199 |
| 220 | 62 | 2502 |
| 221 | 26 | 1358 |
| 222 | 4 | 108 |
| 223 | 3 | 109 |
| 224 | 9 | 569 |
| 225 | 16 | 1145 |
| 226 | 6 | 59 |
| 227 | 13 | 161 |
| 228 | 5 | 54 |
| 229 | 44 | 2276 |
| 230 | 2 | 209 |
| 231 | 6 | 706 |
| 232 | 13 | 759 |
| 233 | 16 | 753 |
| 234 | 7 | 152 |
| 235 | 18 | 70 |
| 236 | 76 | 1012 |
| 237 | 177 | 537 |
| 238 | 38 | 397 |
| 239 | 1420 | 2171 |
| 240 | 12 | 35 |
| 241 | 12 | 533 |
| 242 | 2 | 22 |
| 243 | 117 | 259 |
| 244 | 75 | 555 |
| 245 | 34 | 142 |
| 246 | 266 | 982 |
| 247 | 205 | 963 |
| 248 | 44 | 273 |
| 249 | 11 | 57 |
| 250 | 15 | 299 |
| 251 | 5 | 38 |
| 252 | 75 | 275 |
| 253 | 99 | 598 |
| 254 | 28 | 116 |
| 255 | 254 | 449 |
| 256 | 136 | 1494 |
| 257 | 47 | 324 |
| 258 | 4 | 38 |
| 259 | 10 | 102 |
| 260 | 2 | 14 |
| 261 | 45 | 317 |
| 262 | 85 | 383 |
| 263 | 33 | 170 |
| 264 | 81 | 530 |
| 265 | 104 | 696 |
| 266 | 41 | 367 |
| 267 | 14 | 173 |
| 268 | 14 | 392 |
| 269 | 2 | 35 |
| 270 | 25 | 100 |
| 271 | 45 | 230 |
| 272 | 19 | 128 |
| 273 | 28 | 254 |
| 274 | 75 | 873 |

| Patent Example | hP2X3 IC$_{50}$ (nM) | hP2X2/3 IC$_{50}$ (nM) |
|---|---|---|
| 275 | 21 | 191 |
| 276 | 10 | 76 |
| 277 | 6 | 96 |
| 278 | 2 | 23 |
| 279 | 115 | 956 |
| 280 | 51 | 682 |
| 281 | 26 | 198 |
| 282 | 8 | 209 |
| 283 | 10 | 379 |
| 284 | 4 | 57 |
| 285 | 113 | 760 |
| 286 | 87 | 1234 |
| 287 | 35 | 275 |
| 288 | 150 | 1314 |
| 289 | 192 | 1768 |
| 290 | 31 | 368 |
| 291 | 1320 | 10000 |
| 292 | 6 | 52 |
| 293 | 63 | 1155 |
| 294 | 101 | 1060 |
| 295 | 55 | 557 |
| 296 | 6 | 133 |
| 297 | 56 | 933 |
| 298 | 62 | 781 |
| 299 | 37 | 575 |
| 300 | 78 | 820 |
| 301 | 91 | 1714 |
| 302 | 6 | 145 |
| 303 | 5 | 38 |
| 304 | 7 | 27 |
| 305 | 9 | 44 |
| 306 | 42 | 464 |
| 307 | 16 | 103 |
| 308 | 153 | 2586 |
| 309 | 8 | 70 |
| 310 | 116 | 1678 |
| 311 | 8 | 35 |
| 312 | 9 | 83 |
| 313 | 11 | 200 |
| 314 | 8 | 192 |
| 315 | 8 | 160 |
| 316 | 21 | 250 |
| 317 | 45 | 952 |
| 318 | 32 | 476 |
| 319 | 76 | 1324 |
| 320 | 33 | 627 |
| 321 | 120 | 1447 |
| 322 | 49 | 498 |
| 323 | 25 | 411 |
| 324 | 46 | 552 |
| 325 | 26 | 235 |
| 326 | 21 | 378 |
| 327 | 10 | 239 |
| 328 | 12 | 274 |
| 329 | 5 | 120 |
| 330 | 5 | 170 |
| 331 | 7 | 191 |
| 332 | 4 | 174 |
| 333 | 4 | 122 |
| 334 | 4 | 132 |
| 335 | 13 | 541 |
| 336 | 14 | 443 |
| 337 | 13 | 257 |
| 338 | 4 | 72 |
| 339 | 5 | 251 |
| 340 | 3 | 103 |
| 341 | 41 | 1242 |
| 342 | 40 | 1892 |
| 343 | 135 | 10000 |
| 344 | 34 | 987 |
| 345 | 7 | 99 |
| 346 | 13 | 334 |
| 347 | 9 | 1521 |
| 348 | 7 | 760 |
| 349 | 23 | 545 |
| 350 | 14 | 1162 |
| 351 | 16 | 690 |
| 352 | 18 | 1139 |
| 353 | 7 | 427 |
| 354 | 25 | 1034 |
| 355 | 9 | 956 |
| 356 | 29 | 643 |
| 357 | 5 | 310 |
| 358 | 57 | 1441 |
| 359 | 6 | 200 |
| 360 | 10 | 455 |
| 361 | 14 | 1254 |
| 362 | 8 | 1014 |
| 363 | 12 | 717 |
| 364 | 16 | 943 |
| 365 | 21 | 1049 |
| 366 | 18 | 977 |
| 367 | 13 | 506 |
| 368 | 84 | 1094 |
| 369 | 11 | 328 |
| 370 | 41 | 1007 |
| 371 | 24 | 1173 |
| 372 | 19 | 1211 |
| 373 | 21 | 2827 |
| 374 | 55 | 2557 |
| 375 | 11 | 185 |
| 376 | 32 | 898 |
| 377 | 5 | 273 |
| 378 | 60 | 3752 |
| 379 | 42 | 2755 |
| 380 | 32 | 2880 |
| 381 | 16 | 954 |
| 382 | 13 | 432 |
| 383 | 2 | 35 |
| 384 | 3 | 75 |
| 385 | 3 | 28 |
| 386 | 24 | 811 |
| 387 | 19 | 461 |
| 388 | 18 | 1353 |
| 389 | 18 | 1614 |
| 390 | 17 | 804 |
| 391 | 19 | 840 |
| 392 | 11 | 411 |
| 393 | 24 | 1033 |
| 394 | 82 | 3983 |
| 395 | 30 | 1312 |
| 396 | 22 | 1803 |
| 397 | 15 | 1362 |
| 398 | 17 | 1795 |
| 399 | 69 | 1722 |
| 400 | 59 | 1477 |
| 401 | 30 | 1466 |
| 402 | 21 | 1251 |
| 403 | 56 | 2108 |
| 404 | 44 | 533 |
| 405 | 17 | 1558 |
| 406 | 26 | 2026 |
| 407 | 15 | 1681 |
| 408 | 32 | 1710 |
| 409 | 22 | 976 |
| 410 | 22 | 906 |
| 411 | 20 | 697 |
| 412 | 687 | 10000 |
| 413 | 597 | 10000 |
| 414 | 29 | 2272 |
| 415 | 10 | 2177 |
| 416 | 227 | 10000 |
| 417 | 434 | 10000 |
| 418 | 23 | 1556 |
| 419 | 9 | 1136 |

Solubility Assays

The aqueous solubility of a drug substance is an important physicochemical parameter that has a significant role in various physical and biological processes. In vivo, inadequate solubility of the desired dose results in incomplete absorption of orally administered drugs and causes low oral bioavailability. Solubility data are used to assess absorption, distribution, metabolism and elimination parameters and to develop formulations for safety screens, pre-clinical and early clinical use.

High Throughput determination of aqueous test compound solubility (100 mmolar in DMSO)

The assay was run in a 96-well plate format. Each well was filled with an individual compound.

All pipetting steps were performed using a robot platform. 100 µl of a 10 mmolar solution of test compound in DMSO were concentrated by vacuum evaporation and resolved in 10 µl DMSO to gain a 100 mmolar DMSO solution. 990 µl 0.1 M phosphate buffer pH 6.5 were added. The content of DMSO amounts to 1%. The multititer plate was put on a shaker and mixed for 24 hrs at room temperature. 150 µl of the suspension were transferred to a filtration plate. After filtration using a vacuum manifold the filtrate was diluted 1:400 and 1:8000. A second microtiter plate with 20 µl of a 10 mM solution of test compound in DMSO served for calibration. Two concentrations (0.005 µM and 0.0025 µM) were prepared by dilution in DMSO/water 1:1 and used for calibration. Filtrate and calibration plates were quantified by HPLC-MS/MS.

Chemicals:
Preparation of 0.1 M phosphate buffer pH 6.5:
61.86 g NaCl and 39.54 mg $KH_2PO_4$ were solved in water and filled up to 1 l. The mixture was diluted 1:10 with water and the pH adjusted to 6.5 by NaOH.
Materials: Millipore MultiScreen$_{HTS}$-HV Plate 0.45 µm
Chromatographic conditions were as follows:
HPLC column: Ascentis Express C18 2.7µ 4.6×30 mm
Injection volume: 1 µl
Flow: 1.5 ml/min
Mobile phase: acidic gradient
 A: Water/0.05% HCOOH
 B: Acetonitrile/0.05% HCOOH
 0 min→95% A 5% B
 0.75 min→5% A 95% B
 2.75 min→5% A 95% B
 2.76 min→95% A 5% B
 3 min→95% A 5% B The areas of sample- and calibration injections were determined by using a mass spectrometry (AB Sciex Triple Quad 6500) software (AB SCIEX: Discovery Quant 2.1.3. and Analyst 1.6.1). The solubility value (in mg/l) was calculated from the sample- and calibration curves.

Equilibrium Shake Flask Solubility Assay

Thermodynamic solubility was determined by an equilibrium shake flask method [Literature: Edward H. Kerns and Li Di (2008) Solubility Methods in: Drug-like Properties: Concepts, Structure Design and Methods, p276-286. Burlington, Mass.: Academic Press].

A saturated solution of the test compound in 0.1 M phosphate buffer (pH 6.5) was prepared and the solution was mixed for 24 h to ensure that equilibrium has been reached. The solution was centrifuged to remove the insoluble fraction and the concentration of the compound in solution was determined by HPLC-UV using a standard calibration curve.

To prepare the sample, 1.5 mg solid compound was weighed in a 4 ml glass vial. 1 ml 0.1 M phosphate buffer (pH 6.5) was added. The suspension was put on a stirrer and mixed for 24 hrs at room temperature. The solution was centrifuged afterwards. To prepare the sample for the standard calibration, 0.6 mg solid sample was dissolved in 19 ml acetonitrile/water 1:1. After sonification the solution was filled up with acetonitrile/water 1:1 to 20 ml.

Sample and standards were quantified by HPLC with UV-detection. For each sample two injection volumes (5 and 50 µl) in triplicates were made. Three injection volumes (5 µl, 10 µl and 20 µl) were made for the standard.

Chemicals
Preparation of 0.1 M phosphate buffer pH 6.5:
61.86 g NaCl and 39.54 mg $KH_2PO_4$ were solved in water and filled up to 1 l. The mixture was diluted 1:10 with water and the pH adjusted to 6.5 by NaOH.
Chromatographic conditions were as follows:
HPLC column: Xterra MS C18 2.5µ 4.6×30 mm
Injection volume: Sample: 3×5 µl and 3×50 µl
 Standard: 5 µl, 10 µl, 20 µl
Flow: 1.5 ml/min
Mobile phase: acidic gradient
 A: Water/0.01% TFA
 B: Acetonitrile
 0 min→95% A 5% B
 0-3 min→35% A 65% B, linear gradient
 3-5 min→35% A 65% B, isocratic
 5-6 min→95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

Bidirectional Caco-2 Cell Permeability Assay

Caco-2 cells (purchased from DSMZ Braunschweig, Germany) were seeded at a density of $4.5 \times 10^4$ cell per well on 24 well insert plates, 0.4 µm pore size, and grown for 15 days in Dulbecco's modified Eagle medium supplemented with 10% fetal bovine serum, 1% GlutaMAX (100×, purchased from GIBCO), 100 U/ml penicillin, 100 µg/ml streptomycin (purchased from GIBCO) and 1% non-essential amino acids (100×). Cells were maintained at 37° C. in a humidified 5% $CO_2$ atmosphere. Medium was changed every 2-3 days. Before running the permeability assay, the culture medium was replaced by a serum free hepes-carbonate transport buffer (pH 7.2). Test compounds were dissolved in DMSO and added to the donor chamber representing either the apical or basolateral compartment in a final concentration of 2 µM. Before and after 2 h incubation at 37° C. samples were taken from both compartments (donor and receiver chamber). Analysis of compound concentrations was done after precipitation with methanol. Analysis was performed by high-pressure liquid chromatography and a tandem mass spectrometric detector using an Agilent 1200 liquid chromatography system and an AB Sciex API4000 triple-quadrupole mass spectrometer applying the parameters, which were optimized to achieve maximum signal intensity of the corresponding test compound. Permeability (Papp) was calculated in the apical to basolateral (A→B) and basolateral to apical (B→A) directions. The apparent permeability was calculated using following equation: $P_{app} = (V_r/P_o) \cdot (1/S) \cdot (P_2/t)$ where $V_r$ is the volume of medium in the receiver chamber; $P_o$ is the measured peak area of the test compound in the donor chamber at t=0 h; S the surface area of the monolayer; $P_2$ is the measured peak area of the test compound in the acceptor chamber after 2 h of incubation; and t is the incubation time. The efflux ratio basolateral (B) to apical (A) was calculated by dividing the $P_{app}$ B-A by the $P_{app}$ A-B.

The bidirectional Caco-2 cell permeability assay is a well-established method for predicting the in vivo absorption of drugs across the gut wall by measuring the rate of transport of a compound across the Caco-2 monolayer. Since differentiated Caco-2 cells express functional efflux transport proteins like P-gp, they are also used for identification of compounds with efflux liabilities. Intestinal efflux can decrease systemic plasma concentrations of an orally dosed compound by affecting intestinal absorption of a compound. Preferred examples of the present invention show permeability Papp A-B>50 nm/s and efflux ratio <5. More preferred examples of the present invention show permeability Papp A-B>80 nm/s and efflux ratio <2.

TABLE 1

Bidirectional Caco-2 cell permeability assay of test compounds

| Example | Papp A-B (nm/s) | Papp B-A (nm/s) | Efflux ratio |
|---|---|---|---|
| 11 | 155 | 216 | 1.4 |
| 19 | 249 | 163 | 0.65 |
| 48 | 180 | 212 | 1.2 |
| 185 | 102 | 181 | 1.8 |
| 339 | 153 | 214 | 1.4 |
| 348 | 135 | 190 | 1.4 |
| 347 | 5.8 | 209 | 36 |
| 419 | 104 | 175 | 1.7 |

In Vitro Metabolic Stability Assays

Determination of in vitro metabolic stability in microsomes (including calculation of hepatic in vivo blood clearance (CL) and of maximal oral bioavailability ($F_{max}$))

The in vitro metabolic stability of test compounds was determined by incubating them at 1 µM in a suspension liver microsomes in 100 mM phosphate buffer, pH 7.4 ($NaH_2PO_4 \times H_2O + Na_2HPO_4 \times 2H_2O$) and at a protein concentration of 0.5 mg/mL at 37° C. The microsomes were activated by adding a co-factor mix containing 8 mM Glucose-6-Phosphate, 4 mM $MgCl_2$; 0.5 mM NADP and 1 G-6-P-Dehydrogenase in phosphate buffer, pH 7.4. The metabolic assay was started shortly afterwards by adding the test compound to the incubation at a final volume of 1 mL. Organic solvent in the incubations was limited to 0.01% dimethylsulfoxide (DMSO) and 1')/0 acetonitrile. During incubation, the microsomal suspensions were continuously shaken at 580 rpm and aliquots were taken at 2, 8, 16, 30, 45 and 60 min, to which equal volumes of cold methanol were immediately added. Samples were frozen at −20° C. overnight, subsequently centrifuged for 15 minutes at 3000 rpm and the supernatant was analyzed with an Agilent 1200 HPLC-system with LCMS/MS detection.

The half-life of a test compound was determined from the concentration-time plot.

From the half-life (kel: slope of concentration-time plot; half-life=ln 2/kel) the intrinsic clearances were calculated. Together with the additional parameters liver blood flow, specific liver weight and microsomal protein content the hepatic in vivo blood clearance (CL) and the maximal oral bioavailability (Fmax) were calculated for the different species. The hepatic in vivo blood clearance (CLblood) and the maximal oral bioavailability (Fmax) was calculated using the following formulae: CL'intrinsic [ml/(min*kg)]=kel [1/min]/((mg protein/volume of incubation [ml])*fu,inc)*(mg protein/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L(h*kg)]); Fmax=1-CLblood/QH and using the following parameter values: Liver blood flow (QH) −1.32 L/h/kg (human), 2.1 L/h/kg (dog), 4.2 L/h/kg (rat); specific liver weight −21 g/kg (human), 39 g/kg (dog), 32 g/kg (rat); microsomal protein content −40 mg/g.; fu,inc and fu,blood is taken as 1.

Determination of in vitro metabolic stability in rat hepatocytes (including calculation of hepatic in vivo blood clearance (CL))

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold Williams' medium E (WME). The resulting cell suspension was filtered through sterile gaze in 50 mL falcon tubes and centrifuged at 50×g for 3 min at room temperature. The cell pellet was resuspended in 30 mL WME and centrifuged through a Percoll® gradient for 2 times at 100×g. The hepatocytes were washed again with WME and resuspended in medium containing 5% FCS. Cell viability was determined by trypan blue exclusion.

For the metabolic stability assay liver cells were distributed in WME containing 5% FCS to glass vials at a density of $1.0 \times 10^6$ vital cells/mL. The test compound was added to a final concentration of 1 µM. During incubation, the hepatocyte suspensions were continuously shaken at 580 rpm and aliquots were taken at 2, 8, 16, 30, 45 and 90 min, to which equal volumes of cold methanol were immediately added. Samples were frozen at −20° C. overnight, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life (kel: slope of concentration-time plot; half-life=ln 2/kel) the intrinsic clearances were calculated. Together with the additional parameters liver blood flow, amount of liver cells in vivo and in vitro. The hepatic in vivo blood clearance (CLblood) and the maximal oral bioavailability (Fmax) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L/(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow (QH) −4.2 L/h/kg rat; specific liver weight −32 g/kg rat body weight; liver cells in vivo-$1.1 \times 10^8$ cells/g liver, liver cells in vitro-$1.0 \times 10^6$/ml; fu,inc and fu,blood is taken as Investigation of In Vitro Metabolic Stability In Cryopreserved Human Hepatocytes (Including Calculation of Hepatic In Vivo Blood Clearance (CL))

Cryopreserved Hepatocytes (e.g. from Celsis InVitro-Technologies) were briefly thawed, washed with 45 mL pre-warmed in vitro GRO HT medium and centrifuged for 5 min at 50×g. The cell pellet was resuspended in 5 mL of Krebs-Henseleit Butter (KHB). Cell viability was determined by trypan blue exclusion.

For the metabolic stability assay liver cells were distributed in Williams' medium E (WME) containing 5% FCS to glass vials at a density of $0.5 \times 10^6$ vital cells/mL. The test compound was added to a final concentration of 1 µM. During incubation, the hepatocyte suspensions were continuously shaken at 580 rpm and aliquots were taken at 2, 8, 16, 30, 45 and 90 min, to which equal volumes of cold methanol were immediately added. Samples were frozen at −20° C. overnight, subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life (kel: slope of concentration-time plot; half-life=ln 2/kel) the intrinsic clearances were calculated. Together with the additional parameters liver blood flow, amount of liver cells in vivo and in vitro. The hepatic in vivo blood clearance (CL) and the maximal oral bioavailability (Fmax) was calculated. The hepatic in vivo blood clearance (CLblood) and the maximal oral bioavailability (Fmax) was calculated using the following formulae: CL'intrinsic [ml/(min*kg)]=kel [1/min]/((cellno/volume of incubation [ml])*fu,inc)*(cellno/liver weight [g])*(specific liver weight [g liver/kg body weight]); CLblood well-stirred [L/(h*kg)]=(QH [L(h*kg)]*fu,blood*CL'intrinsic [L/(h*kg)])/(QH [L/(h*kg)]+fu,blood*CL'intrinsic [L/(h*kg)]); Fmax=1-CLblood/QH and using the following parameter values: Liver blood flow-1.32 L/h/kg human; specific liver weight-21 g/kg rat body weight; liver cells in vivo-$1.1 \times 10^8$ cells/g liver, liver cells in vitro-$1.0 \times 10^6$/ml.; fu,inc and fu, blood is taken as 1.

Liver Microsomal and Hepatocytes Stability Assays

Metabolic instability is often the main clearance mechanism of xenobiotica leading to a high CL and low bioavailability which may eventually result in a short half-life and a low exposure after oral administration. Thus, reducing the susceptibility of metabolic degradation usually leads to a more favourable pharmacokinetic profile. When using liver microsomes as incubation matrix main phase I metabolic reactions, typically oxidoreductive reactions by cytochrome P450 enzymes and flavin mono-oxygenases (FMO) and hydrolytic reactions by esterases/amidases/epoxidhydrolases, are described. When the incubation of the test compound is performed in a hepatocyte matrix all potential hepatic metabolic processes (phase I and phase II) are covered. Preferred examples of the present invention show metabolic stability (given as Fmax) of 40% Fmax in human liver microsome as well as in human and rat hepatocyte preparations. More preferred examples of the present invention show metabolic stability (given as Fmax) of 50% Fmax in human liver microsome as well as in human and rat hepatocyte preparations.

TABLE 2

In vitro metabolic stability values of test compounds

| Example | In vitro metabolic stability | |
|---|---|---|
| | Human liver microsome Fmax (%) | Rat hepatocyte Fmax (%) |
| 11 | 57 | 52 |
| 26 | 67 | 56 |
| 48 | 99 | 68 |
| 163 | 100 | 53 |
| 183 | 74 | 43 |
| 185 | 77 | 58 |
| 188 | 68 | 56 |
| 339 | 94 | 52 |
| 340 | 90 | 64 |
| 348 | 54 | 58 |
| 419 | 74 | 51 |

Human Liver Cytosol Stability Assay

The use of human liver cytosol to evaluate the metabolic stability of a new drug candidate shows effectively its susceptibility to non-CYP mediated oxidative biotransformation. If a compound is a strong substrate of aldehyde oxidase or xanthine oxidase, metabolic clearance via this pathway can lead to a low bioavailability in human. As both enzymes are active in human liver cytosol, susceptibility of test compounds to aldehyde or xanthine oxidase mediated metabolism can be predicted and compared by determination of turnover of test compound as well as formation of the corresponding oxidised metabolite after incubation in human liver cytosol. More preferred examples of the present invention have <15% turnover after 4 hrs incubation time in human liver cytosol preparations.

Method description: Human liver cytosol (pooled, >30 male and female donors) was incubated with individual test compounds in order to compare the extent of depletion of test compound and formation of the respective oxidised metabolite. The incubation medium consisted of 50 mM potassium phosphate buffer (pH 7.4) and 1 mg/mL human liver cytosolic protein. An incubation volume of 1000 µL was used. The test compound was added from a stock solution in acetonitrile at 1 or 10 µM concentration in the incubation. Incubations were performed at 37° C. Reactions were stopped at 0 h and 4 h after incubation by addition of 100 µL acetonitrile to 250 pL of incubation mixture. Precipitated proteins were removed by centrifugation at approximately 3000 rpm. The supernatants were stored at approximately −20° C. until they were analysed. The determination of depletion of the test compound and formation of the metabolites was performed by chromatographic separation (Aquity BEH300 C4 50×2.1 mm, 1.7 µm, gradient: 10 mM ammonium acetate/acetonitrile) and simultaneous UV and mass spectrometric detection using an Accela UPLC pump and UV detector coupled to a LTQ-FT mass spectrometer (Thermo Fisher Scientific, Bremen, Germany).

Data analysis: The depletion of the test compound and formation of the corresponding metabolites were determined by decrease or increase of the corresponding peak area in the chromatogram after UV detection at approximately 300 nm 4 h after incubation compared to that at 0 h after incubation. The identity of the analytes under the peaks were confirmed by LC-MS/MS.

TABLE 3

Stability of test compound in human liver cytosol

| | [%] | |
|---|---|---|
| Example | Test compound turnover after 4 h | Formation of oxidised metabolites after 4h |
| 333 (WO2009110985) | 55 | 48 |
| 11 | 0.9 | 3.9 |
| 26 | 0.9 | 2.5 |
| 48 | 0.9 | 2.3 |
| 348 | 5.6 | 5.6 |

CYP Inhibition and Pre-Incubation CYP Inhibition Assays

Use of in vitro assays to evaluate the inhibition potential of new drug candidates towards CYP-mediated metabolism has been shown to be effective as part of a strategy to minimise the chances of drug interactions with co-administered drugs. The inhibitory potency of the test compound towards 5 human cytochrome P450 isoforms (CYP1A2, 2C8, 2C9, 2D6, and 3A4) was determined. More preferred examples of the present invention have CYP inhibition $IC_{50} \geq 10$ µM.

For CYP3A4 time dependent inhibitory potential was also tested by applying a 30 min pre-incubation time of the test compound in metabolically active incubation system. If a time-dependent inhibition of CYP3A4 is observed, this is a hint of an irreversible mechanism-based inhibition of the CYP3A4 activity by the test compound. More preferred examples of the present invention have pre-incubation CYP inhibition $IC_{50} \geq 20$ µM.

Method Description CYP Inhibition Assay

Human liver microsomes (pooled, >30 male and female donors) were incubated with individual CYP isoform-selective standard probes (phenacetin for CYP1A2, amodiquine for CYP2C8, diclofenac for CYP2C9, dextromethorphan for CYP2D6 and midazolam for CYP3A4) in the absence and presence of increasing concentrations of the test compound in order to compare the extent of formation of the respective metabolite. In addition, a set of incubation in the absence of test compound was used as a negative control. Furthermore, the inhibitory potency of standard inhibitors was included as positive controls (fluvoxamine for CYP1A2, montelukast for CYP2C8, sulfaphenazole for CYP2C9, fluoxetine for CYP2D6, ketoconazole for CYP3A4 and mibefradil for CYP3A4-preincubation). Incubation conditions (protein and probe substrate concentration, incubation time) were optimised with regard to linearity and metabolite turnover. Incubation medium consisted of 50 mM potassium phosphate buffer (pH 7.4) containing 1 mM EDTA, NADPH regenerating system (1 mM NADP, 5 mM glucose 6-phosphate, glucose 6-phosphate dehydrogenase (1.5 U/mL). Sequential dilutions and incubations were performed on a Genesis Workstation (Tecan, Crailsheim, FRG) in 96-well plates at 37° C. A final incubation volume of 200 µL was used. Reactions were stopped by addition of 100 µL acetonitrile containing the respective internal standard. Precipitated proteins were removed by centrifugation of the well plate, supernatants were combined and analyses were performed by LC-MS/MS. The LC-MS/MS quantification of the metabolites paracetamol (CYP1A2), desethylamodiaquine (CYP2C8), 4-hydroxydiclofenac (CYP2C9), dextrorphan (CYP2D6), and 1-hydroxymidazolam (CYP3A4) was performed with a PE SCIEX API 3000 LC/MS/MS system (Applied Biosystems, MDS Sciex, Concord, Ontario, Canada).

Data analysis: The CYP-mediated activities in the presence of inhibitors were expressed as percentages of the corresponding control values. A sigmoid-shaped curve was fitted to the data, and the enzyme inhibition parameter $IC_{50}$ was calculated using a nonlinear least-squares regression analysis of the plot of percent control activity versus concentration of the test inhibitor.

140, KCl 4, $CaCl_2$ 2, $MgCl_2$ 1, glucose 5, HEPES 10, pH 7.4 (NaOH); composition of intracellular solution (in mmol/L): NaCl 10, KCl 50, KF 60, EGTA 20, HEPES 10, pH 7.2 (KOH). The effects of test compound were compared to predrug control values (i.e. no test compound present) and to those induced by the positive control E-4031, a potent and selective hERG $K^+$ channel blocker (Sanguinetti M C, Jurkiewicz N K. Two components of cardiac delayed rectifier K+current. Differential sensitivity to block by class III antiarrhythmic agents. *J. Gen. Physio.* (1990; 96:195-215).

Exposure of HEK293 cells stably transfected with the hERG $K^+$ channel to test compound was associated with concentration-dependent inhibition of the hERG-mediated tail current amplitude. The concentration (µM) of test compound that reached half-maximal inhibitory concentrations ($IC_{50}$) was used to evaluate whether test compound has an intrinsic effect on the hERG K+ current. More preferred examples of the present invention have hERG $IC_{50}$>5 µM.

TABLE 4

Inhibitory effect of test compounds to CYP enzymes

| | $IC_{50}$ [µM] | | | | | |
|---|---|---|---|---|---|---|
| Example | CYP1A2 | CYP2C8 | CYP2C9 | CYP2D6 | CYP3A4 | CYP3A4 with preincubation |
| 333 (WO20091109 85) | >20 | >20 | 19.8 | >20 | >20 | 18 |
| 11 | >20 | >20 | >20 | >20 | >20 | >20 |
| 19 | >20 | >20 | >20 | >20 | >20 | >20 |
| 26 | >20 | >20 | >20 | >20 | >20 | >20 |
| 48 | >20 | >20 | >20 | >20 | >20 | >20 |
| 163 | >20 | >20 | >20 | >20 | >20 | >20 |
| 185 | >20 | 19 | >20 | >20 | >20 | >20 |
| 339 | >20 | >20 | >20 | >20 | >20 | >20 |
| 348 | 18 | >20 | >20 | >20 | >20 | >20 |

Patch-Clamp hERG Channel Electrophysiology Assay

Malfunction of cardiac ion channels can, in some cases, lead to cardiac arrhythmias. Investigation of the effects of compounds on cardiac ion channels is therefore recommended or mandatory (hERG) under safety pharmacology guidelines[1]. The hERG potassium channel is the most prominent target for drug-induced QT-prolongation[2,3], an unwanted side effect which can lead to the life-threatening torsade de pointes type arrhythmias.

[1] The ICH Steering Committee, The nonclinical evaluation of the potential for delayed ventricular repolarizaiton (QT interval prolongation) by human pharmaceuticals, S7B, 10 June 2004
[2] Roden, D M., *New England Journal of Medicine*, 350 10; 2004: 1013-1022.
[3] Netzer, R., Ebneth, A., Bischoff, U., Pongs, O., *Drug Discovery Today*, 2001, 6, 78-84.

The objective of this assay was to evaluate whether test compound has an intrinsic effect on the hERG $K^+$ current in stably transfected HEK293 cells. Test compound was evaluated in vitro at concentrations of 0.1, 1 and 10 µmol/L (approximately 5-6 minutes per concentration).

The whole-cell voltage-clamp technique (automated 8-channel system: Patchliner, Nanion, Germany) was used with PatchControlHT software (Nanion) to control the Patchliner system and to handle data aquisition and analysis. Voltage-clamp control was provided by two EPC-10 quadro amplifiers under control of the PatchMasterPro software (both: HEKA Elektronik, Lambrecht, Germany) and with NPC-16 medium resistance (~2 MW) chips (Nanion) serving as planar substrate at room temperature. hERG-mediated inward tail currents were elicited by hyperpolarizing voltage steps from +20 mV to −120 mV (duration 500 ms); holding potential was −80 mV, activating potential was +20 mV (duration 1000 ms), clamp protocol was repeated every 12 s. Composition of extracellular solution (in mmol/L): NaCl Rat CFA In Vivo Model Male Sprague Dawley rats were used. Mechanical hyperalgesia was induced by injecting 25 µl of Complete Freund's Adjuvant (CFA) into the plantar surface of one hind paw. Mechanical hyperalgesia was measured using the Pressure Application Measurement apparatus (Ugo Basile, Gemonio, Italy). Briefly, a linearly increasing pressure was applied to an area of ~50 mm2 of the plantar side of the hind paw until a behavioural response (paw withdrawal) was observed or until the pressure reached 1000 gf. The pressure at which the behavioural response occurred was recorded as the "Paw Withdrawal Threshold" (PWT). Both CFA-injected and contralateral PWTs were determined for each rat, in each treatment group and at each time point of the studies. Mechanical hyperalgesia testing was performed before injecting CFA, 22 hours after CFA treatment (pre-drug baseline) and 2, 4 and 6 hours after compound dosing. Compounds were dosed 24 hours after CFA injection. Data were expressed as the mean PWT for each treatment group and at each time point. Data were analysed by performing a repeated measures two way ANOVA (time x treatment). Planned comparison of means (each versus vehicle) was performed by using a Dunnett's post hoc test, provided that a main effect was detected. For p values less than 0.05 the results were deemed to be statistically significant.

Preclinical in vivo efficacy models, such as the rat CFA in vivo model, are used in drug discovery to evaluate efficacy response and demonstrate desirable duration of action of new drug candidates. More preferred examples of the present invention show rat CFA in vivo efficacy in the 'Paw withdrawal threshold 6 hours post drug' measure when dosed at 3 mg/kg p.o.

TABLE 5

Rat CFA in vivo model PWT data for test compounds

| Example | human P2X3 receptor IC$_{50}$ | Paw withdrawal threshold 6 hour-post vehicle | Dose, p.o. | Paw withdrawal threshold 6 hour-post drug |
|---|---|---|---|---|
| 11 | 8 nM | 514 ± 34 gf | 3 mg/kg | 639 ± 48 gf (*) |
| 48 | 14 nM | 430 ± 22 gf | 3 mg/kg | 817 ± 69 gf (****) |
| 185 | 4 nM | 489 ± 22 gf | 3 mg/kg | 630 ± 81 (*) |
| 348 | 7 nM | 512 ± 15 gf | 3 mg/kg | 633 ± 59 gf (*) |
| 333 (W02009110985) | 14 nM | 426 ± 20 gf | 3 mg/kg | 565 ± 74 gf (ns) |
| 333 (W02009110985) | 14 nM | 452 ± 23 gf | 3 mg/kg | 549 ± 42 (ns) |

*p < 0.05, ****p < 0.0001, Dunnett's post-hoc test, different from vehicle group, ns: not significant

TABLE 6

Rat CFA in vivo model PWT data for Example 348 at lower dose

| Example | human P2X3 receptor IC$_{50}$ | Paw withdrawal threshold 6 hour-post vehicle | Dose, p.o. | Paw withdrawal threshold 6 hour-post drug |
|---|---|---|---|---|
| 348 | 7 nM | 512 ± 15 gf | 3 mg/kg | 633 ± 59 gf (*) |
| 348 | 7 nM | 512 ± 15 gf | 1 mg/kg | 601 ± 28 gf (**) |
| 348 | 7 nM | 512 ± 15 gf | 0.3 mg/kg | 599 ± 47 gf (*) |

*p < 0.05, **p < 0.01, Dunnett's post-hoc test, different from vehicle group, ns: not significant Mouse CFA In Vivo Model Female C57BL/6 mice were used to assess the effects of P2X3 receptor antagonists on CFA-induced mechanical hyperalgesia. 30 µL of Complete Freud's Adjuvant (CFA, 1 mg/mL) were injected into the plantar surface of one hind paw. Mechanical hyperalgesia was measured using von Frey filaments. Briefly, von Frey filaments were being used to stimulate the animal's hindpaw and a behavioural response was measured depending on the strength of the von Frey filament used. The strength of the filament was expressed in [g] and the threshold was recorded when a response of the animal was observed. Both CFA-injected and contralateral response thresholds were determined for each mouse and in each treatment group 72 hrs after CFA-injection. Compound application was done p.o. b.i.d., starting one hour before CFA injection. Data were expressed as the mean threshold for each treatment group. Data were analysed by performing a one way ANOVA over the different dose groups. Planned comparison of means (each versus vehicle) was performed by using a Dunnett's post hoc test, provided that a main effect was detected. For p values less than 0.05 the results were deemed to be statistically significant.

| Example | Dose | Efficacy mouse CFA model |
|---|---|---|
| Vehicle | | 0.179 g ± 0.044 |
| 11 | 25 mg/kg, p.o. | 0.682 g ± 0.122 (*) |

*p < 0.05 different from vehicle group

Rat Dyspareunia Model

Dyspareunia was surgically induced in female Sprague Dawley rats by autotransplanting on abdominal arteries small pieces of uterine horn, that grow into vascularized cysts. The visceromotor response (VMR) to vaginal distension was used in conscious animals as an objective measure of vaginal sensitivity.

Briefly, animals in estrus phase were surgically implanted with biopsies of left uterine horn (3×3 mm) around alternate cascade mesenteric arteries that supply the small intestine (4 pieces) and on the wall of the distal colon (2 pieces). To measure VMR response, 2 Teflon-coated wire electrodes were sutured in the external oblique abdominal muscle, and tunneled subcutaneously to be exteriorized at the base of the neck for future access. On the day of VMR assessment, a lubricated small balloon (1 cm length) was inserted into the mid-vaginal canal. The balloon catheter was secured to the base of the tail and connected to a volume controller/timing device (infusion pump) for balloon distension. The vaginal balloon was inflated to ramp intensities of distension (0.05 ml increments every 20 sec.) to a maximal volume of 0.8 ml. The electrodes were connected to an amplifier (Animal Bio. Amp., ADInstruments), and the abdominal electromyographic signal was recorded using a data acquisition system (PowerLab, ADInstruments) for off-line analysis using LabChart version 7. The number of abdominal muscle contractions was counted manually for each 0.1 ml distension step, as an index of vaginal pain. Example 11 or vehicle were dosed orally, twice daily (b.i.d.), during 2 consecutive weeks, from week 4 to week 5 post-implantation of uterine horn pieces. Example 11 was dosed at 15 mg/kg b.i.d., and vehicle (tween 80/0.5% carboxymethylcellulose in water (5/95, vol/vol)), was dosed at 5 ml/kg b.i.d. VMR/vaginal distension testing were then performed 5 (on-drug) and 6 (off-drug) weeks post-implantation, when the animals were in proestrus phase.

Statistical Analysis

All data were expressed as mean±standard deviation (s.d.), for the number (n) of measured rats per group. Analyses were done by running the GraphPad Prism 6.03 software. Two (2) parameters were analyzed for each animal: 1) the cumulative number of abdominal contractions was calculated and plotted against vaginal distension volume; 2) the corresponding area under the curve (AUC) was calculated using GraphPad Prism version 6.03. A Grubbs' test was performed on individual AUC values to reveal potential outliers. Repeated measures 2-Way-Analysis of Variance (ANOVA) was used to analyze the cumulative number of contractions (distension volume×treatment). Planned comparison of means (matched-volume versus vehicle) was performed using a Bonferroni post hoc test, provided that a main effect was detected. A non-parametric Mann-Whitney t test was used to compare AUC means versus vehicle. For p values less than 0.05, the results were considered statistically significant.

Results

In vehicle-treated animals (5 ml/kg oral, b.i.d.), the cumulative number of abdominal contractions increased as a function of vaginal distension volume, 5 and 6 weeks post-implantation of uterine horn pieces, confirming the existence of vaginal hyperalgesia. Example 11-treated animals (15 mg/kg oral, b.i.d. during 2 weeks) presented a decreased vaginal hyperalgesia compared to vehicle-treated animals. Indeed, a decrease in the cumulative number of abdominal contractions was observed in response to matched-distension volume, associated with a significant decrease in corresponding AUC (see table below). This decrease in vaginal hyperalgesia was observed 5 weeks post-implantation (p<0.05), while the animals were still on-drug treatment, and 6 weeks later (p<0.01), while the animals were off-drug treatment.

| Time post-implantation | Treatment group | |
|---|---|---|
| | Vehicle (5 ml/kg oral, b.i.d. for 2 weeks) | Example 11 (15 mg/kg oral, b.i.d. for 2 weeks) |
| 5 weeks | 4.56 ± 3.20 (14) | 2.08 ± 1.63* (14) |
| 6 weeks | 3.83 ± 2.54 (15) | 1.64 ± 1.53** (17) |

Effect of Example 11 on areas under the curve (AUC, plot of individual cumulative number of abdominal contractions against vaginal distension volume) 5 and 6 weeks post-implantation of uterine horn pieces. Data represent mean ± s.d. (n in each group). *p < 0.05, **p < 0.01 different from Vehicle group.

In Vivo Pharmacokinetics In Rats, Dogs and Monkeys

For in vivo pharmacokinetic experiments test compounds were administered to male Wistar rats, Beagle dogs or Cynomolgus monkeys intravenously at doses of 0.3 to 1 mg/kg and intragastral at doses of 0.5 to 10 mg/kg formulated as solutions using solubilizers such as PEG400 in well-tolerated amounts.

In the rat also cassette administrations of up to 3 compounds given together in low doses were performed.

For pharmacokinetics after intravenous administration test compounds were given in the male rat as i.v. bolus and in dogs and monkeys as short term infusion (15 min). Blood samples were taken e.g. at 2 min, 8 min, 15 min, 30 min, 45 min, 1 h, 2 h, 4 h, 6 h, 8 h and 24 h after dosing from the vena jugularis (rat) or vena saphena (dog, monkey). For pharmacokinetics after intragastral administration test compounds were given intragastral to fasted rats, dogs and monkeys. Blood samples were taken e.g. at 5 min, 15 min, 30 min, 45 min, 1 h, 2 h, 4 h, 6 h, 8 h and 24 h after dosing. Blood was collected into Lithium-Heparintubes (Monovetten®, Sarstedt) and centrifuged for 15 min at 3000 rpm. An aliquot of 100 µL from the supernatant (plasma) was taken and precipitated by addition of 400 µL cold acetonitril and frozen at −20° C. over night. Samples were subsequently thawed and centrifuged at 3000 rpm, 4° C. for 20 minutes. Aliquots of the supernatants were taken for analytical testing using an Agilent HPLC-system with LCMS/MS detection. PK parameters were calculated by non-compartmental analysis using a PK calculation software, (e.g. Phoenix WinNonLin®, Certara USA, Inc.).

PK parameters derived from concentration-time profiles after i.v.: CLplasma (in L/kg/h): Total plasma clearance of test compound calculated by dose (in µg/kg) divided by area under the concentration-time curve from t=0 h to infinity (extrapolated) (AUCinf in pg*h/L); CLblood: Total blood clearance of test compound: CLplasma*Cp/Cb (in L/kg/h) with Cp/Cb being the ratio of test compound concentrations in plasma and blood. PK parameters directly taken or calculated from concentration time profiles after i.g.: Cmax: Maximal plasma concentration (directly taken from the profile in mg/L); Cmaxnorm: Cmax divided by the administered dose (in kg/L); Tmax: Time point at which Cmax was observed (in h). Parameters calculated from both, i.v. and i.g. concentration-time profiles: AUCnorm: Area under the concentration-time curve from t=0 h to infinity (extrapolated) divided by the administered dose (in kg*h/L); AUC(0-tlast) norm: Area under the concentration-time curve from t=0 h to the last time point for which plasma concentrations could be measured divided by the administered dose (in kg*h/L); t1/2: terminal half-life (in h); F: oral bioavailability: AUCnorm after intragastral administration divided by AUCnorm after intravenous administration (in %).

Pharmacokinetics describes the relationship between the dose and the unbound drug concentration at the site of action, and the time course of drug concentration in the body. Drug disposition is a broad term that covers all the processes by which the body handles foreign chemicals (including drugs). These are absorption, distribution, metabolism and excretion (ADME).

The terminal half-life (t1/2) after oral and intravenous dosing and bioavailability (BA) are important pharmacokinetic properties of drugs. Preferred examples of the present invention show elimination half-life 6 hours and bioavailability 50% in dog. More preferred examples of the present invention have elimination half-life 7 hours and bioavailability 70% in dog.

TABLE 7

Dog pharmacokinetic properties of test compounds

| Example | Dose, p.o. | Dose, i.v. | Dog t1/2 p.o. [hour] | Dog t1/2 i.v. [hour] | Dog Bioavailability (BA) [%] |
|---|---|---|---|---|---|
| 11 | 1 mg/kg | 0.5 mg/kg | 12 | 8.8 | 70 |
| 348 | 1 mg/kg | 0.5 mg/kg | 9.4 | 11 | 74 |

Cyclophosphamide-induced overactive bladder (rats)/Cyclophosphamide-induced cystitis (rats)

The aim of this study is to test the efficacy on P2X3 receptor antagonists on overactive bladder as well as on cystitis in cyclophosphamide-treated rats.

The experimental setup is adapted to a previous descripted protocol (Lecci A et at, Br. J. Pharmacol. 130: 331-38, 2000).

Briefly, female Sprague Daley rats (~200 g) are housed under normal conditions for laboratory rats in a 12:12-h light:dark cycle. The test compound is administrated by oral gavage (30 mg/kg) one hour before application of cyclophosphamide (100 mg/kg) by i.v. injection. Additional 1.5 hours after cyclophosphamide administration each rat is transferred to metabolic cage and voiding frequency is recorded for the next 15 hours. The micturition/per hour is recorded and the AUC during the plateau phase of the micturition (4-10 hours after transfer to metabolic cages) is calculated for each animal with GraphPad Prism 6 programme.

The invention claimed is:

1. A compound of formula (I):

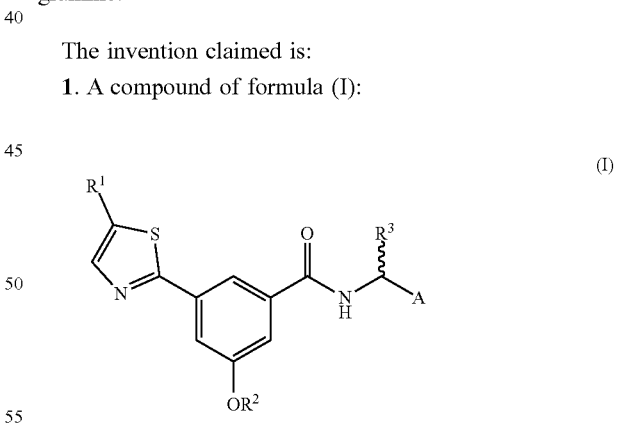

wherein:

$R^1$ is $C_1$-$C_4$-alkyl;

$R^2$ is unsubstituted tetrahydrofuran-3-yl;

$R^3$ is $C_1$-$C_4$-alkyl; and

A is $CF_3$-pyrimidinyl;

or an enantiomer, diastereomer, racemate, hydrate, solvate, or salt thereof, or a mixture of the foregoing.

2. The compound according to claim 1, or salt thereof, which is of formula (Ia):

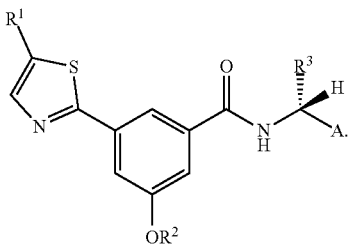

(Ia)

3. The compound according to claim 2, or a salt thereof, wherein $R^1$ is methyl or ethyl.

4. The compound according to claim 2, or a salt thereof, wherein $R^3$ is methyl.

5. The compound according to claim 2, or a salt thereof, wherein A is 2-$CF_3$-pyrimidin-5-yl.

6. The compound according to claim 2, or a salt thereof, wherein $R^1$ is unsubstituted (3R)-tetrahydrofuran-3-yl or (3S)-tetrahydrofuran-3-yl.

7. The compound of claim 2, or a salt thereof, wherein $R^2$ is unsubstituted (3R)-tetrahydrofuran-3-yl.

8. A method of treating a disease, condition, or disorder in a patient in need thereof, comprising administering an effective amount of the compound according to claim 2, or a salt thereof, to the patient, wherein the disease, condition, or disorder is associated with a pain syndrome.

9. The method of claim 8, wherein the disease, condition, or disorder associated with a pain syndrome is acute, chronic, inflammatory or neuropathic pain.

10. The method of claim 8, wherein the disease, condition, or disorder associated with a pain syndrome is inflammatory pain, surgical pain, visceral pain, dental pain, premenstrual pain, endometriosis-induced pain, central pain, pain due to burning mouth syndrome, pain due to burns, pain due to migraine, cluster headaches, pain due to nerve injury, pain due to neuritis, neuralgias, pain due to poisoning, pain due to ischemic injury, pain due to interstitial cystitis, pain due to viral, parasitic or bacterial infections, pain due to traumatic nerve-injury, pain due to post-traumatic injuries, pain due to factures and sport injuries, pain due to small fiber neuropathy, pain due to diabetic neuropathy, chronic lower back pain, phantom limb pain, chronic pelvic pain, neuroma pain, complex regional pain syndrome, pain due to gastrointestinal distension, pain due to cancer, pain due to chemotherapy, neuropathy induced by HIV or by HIV treatment hyperalgesia, allodynia, functional bowel disorders, or arthritis.

11. The method of claim 8, wherein the disease, condition, or disorder associated with a pain syndrome is pain due to trigeminal neuralgia, chronic arthritic pain and related neuralgias, pelvic pain syndrome, irritable bowel syndrome, osteoarthritis, or rheumatoid arthritis.

12. The method of claim 8, wherein the compound is:
3-(5-Methyl-1,3-thiazol-2-yl)-5-[(3R)-tetrahydrofuran-3-yloxy]-N-{(1R)-1-[2-(trifluoromethyl)pyrimidin-5-yl]ethyl}benzamide;
3-(5-Methyl-1,3-thiazol-2-yl)-5-[(3 S)-tetrahydrofuran-3-yloxy]-N-{(1R)-1-[2-(trifluoromethyl)pyrimidin-5-yl]ethyl}benzamide;
3-(5-Ethyl-1,3-thiazol-2-yl)-5-[(3R)-tetrahydrofuran-3-yloxy]-N-{(1R)-1-[2-(trifluoromethyl)pyrimidin-5-yl]ethyl}benzamide; or
3-(5-Ethyl-1,3-thiazol-2-yl)-5-[(3 S)-tetrahydrofuran-3-yloxy]-N-{(1R)-1-[2-(trifluoromethyl)pyrimidin-5-yl]ethyl}benzamide,
or a salt thereof.

13. The method according to claim 12, wherein the compound is:
3-(5-methyl-1,3-thiazol-2-yl)-5-[(3R)-tetrahydrofuran-3-yloxy]-N-{(1R)-1-[2-(trifluoromethyl)pyrimidin-5-yl]ethyl}benzamide; or
3-(5-methyl-1,3-thiazol-2-yl)-5-[(3 S)-tetrahydrofuran-3-yloxy]-N-{(1R)-1-[2-(trifluoromethyl)pyrimidin-5-yl]ethyl}benzamide,
or a salt thereof.

14. The method according to claim 12, wherein the compound is:
3-(5-methyl-1,3-thiazol-2-yl)-5-[(3R)-tetrahydrofuran-3-yloxy]-N-{(1R)-1-[2-(trifluoromethyl)pyrimidin-5-yl]ethyl}benzamide, or a salt thereof.

15. The method of claim 14, wherein the disease, condition, or disorder associated with a pain syndrome is neuralgia, pain due to traumatic nerve-injury, pain due to post-traumatic injuries, pain due to diabetic neuropathy, pain due to cancer, pain due to chemotherapy, or functional bowel disorder.

16. A compound or a salt thereof, wherein the compound is 3-(5-methyl-1,3-thiazol-2-yl)-5-[(3R)-tetrahydrofuran-3-yloxy]-N-{(1R)-1-[2-(trifluoromethyl)pyrimidin-5-yl]ethyl}benzamide.

* * * * *